(12) United States Patent
Gaillard et al.

(10) Patent No.: US 9,073,940 B2
(45) Date of Patent: Jul. 7, 2015

(54) TRICYCLIC PYRAZOL AMINE DERIVATIVES

(75) Inventors: Pascale Gaillard, Collonge-sous-Saleve (FR); Isabelle Jeanclaude-Etter, Bellevue (CH); Vincent Pomel, Groisy (FR); Eric Sebille, Le Poizat (FR); Seenisamy Jeyaprakashnarayanan, Bangalore (IN); Mathilde Muzerelle, Gaillard (FR)

(73) Assignee: MERCK SERONO SA, Coinsins, Vaud (CH)

( * ) Notice: Subject to any disclaimer, the term of this patent is extended or adjusted under 35 U.S.C. 154(b) by 273 days.

(21) Appl. No.: 13/509,291

(22) PCT Filed: Nov. 12, 2010

(86) PCT No.: PCT/EP2010/067412
§ 371 (c)(1),
(2), (4) Date: May 11, 2012

(87) PCT Pub. No.: WO2011/058149
PCT Pub. Date: May 19, 2011

(65) Prior Publication Data
US 2012/0238545 A1    Sep. 20, 2012

Related U.S. Application Data

(60) Provisional application No. 61/261,854, filed on Nov. 17, 2009.

(30) Foreign Application Priority Data

Nov. 13, 2009 (EP) ..................... 09175933

(51) Int. Cl.
*C07D 495/04* (2006.01)
*C07D 495/14* (2006.01)

(52) U.S. Cl.
CPC ............ *C07D 495/04* (2013.01); *C07D 495/14* (2013.01)

(58) Field of Classification Search
CPC ............................ C07D 495/04; C07D 495/14
USPC ........................................ 544/140; 514/232.5
See application file for complete search history.

(56) References Cited

U.S. PATENT DOCUMENTS

| 4,816,467 A | 3/1989 | Doria et al. |
| 8,232,286 B2 | 7/2012 | Breitfelder et al. |

FOREIGN PATENT DOCUMENTS

| JP | S 63-174988 | 7/1988 |
| JP | H08-027131 | 1/1996 |
| JP | 2008-515852 | 5/2008 |
| WO | WO 2004/056820 | 7/2004 |
| WO | WO 2009/010824 | 1/2009 |
| WO | WO 2009/071895 | * 6/2009 |
| WO | WO 2009/123971 | 10/2009 |

OTHER PUBLICATIONS

Ali, K. et al. "Essential role for the p110δ phosphoinositide 3-kinase in the allergic response" *Nature*, Oct. 21, 2004, pp. 1007-1011, vol. 431.
Cantley, L. C. "The Phosphoinositide 3-Kinase Pathway" *Science*, May 31, 2002, pp. 1655-1657, vol. 296.
Fruman, D. A. et al. "Phosphoinositide Kinases" *Annual Review of Biochemistry*, 1998, pp. 481-507, vol. 67.
Gerard, C. et al. "Chemokines and disease" *Nature Immunology*, Feb. 2001, pp. 108-115, vol. 2, No. 2.
Grant, S. "Targeted Therapies in Cancer—Second International Congress" *IDrugs*, 2003, pp. 946-948, vol. 6, No. 10.
Jou, S.-T. et al. "Essential, Nonredundant Role for the Phosphoinositide 3-Kinase p110δ in Signaling by the B-Cell Receptor Complex" *Molecular and Cellular Biology*, Dec. 2002, pp. 8580-8591, vol. 22, No. 24.
Laffargue, M. et al. "Phosphoinositide 3-Kinase γ is an Essential Amplifier of Mast Cell Function" *Immunity*, Mar. 2002, pp. 441-451, vol. 16.
Lawlor, M. A. et al. "PKB/Akt: a key mediator of cell proliferation, survival and insulin responses?" *Journal of Cell Science*, 2001, pp. 2903-2910, vol. 114, No. 16.
Parker, P. J. et al. "PI 3-kinase puts GTP on the Rac" *Current Biology*, 1995, pp. 577-579, vol. 5, No. 6.
Stein, R. C. et al. "PI3-kinase inhibition: a target for drug development?" *Molecular Medicine Today*, Sep. 2000, pp. 347-357, vol. 6.
Thelen, M. et al. "Wortmannin binds specifically to 1-phosphatidylinositol 3-kinase while inhibiting guanine nucleotide-binding protein-coupled receptor signaling in neutrophil leukocytes" *Proceedings of the National Academy of Sciences USA*, May 1994, pp. 4960-4964, vol. 91.
Theoharides, T. C. et al. "Critical role of mast cells in inflammatory diseases and the effect of acute stress" *Journal of Neuroimmunology*, 2004, pp. 1-12, vol. 146.

(Continued)

*Primary Examiner* — Rebecca Anderson
(74) *Attorney, Agent, or Firm* — Saliwanchik, Lloyd & Eisenschenk

(57) ABSTRACT

This invention relates to compounds of Formula (I*) as Pi3k inhibitors for treating autoimmune diseases, inflammatory disorders, multiple sclerosis and other diseases like cancers.

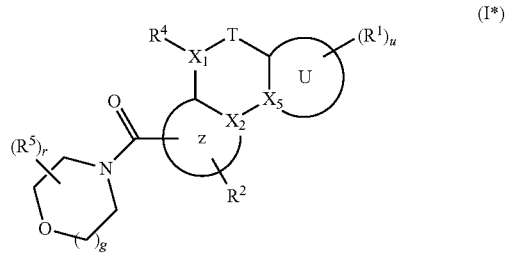

(I*)

15 Claims, No Drawings

(56) References Cited

OTHER PUBLICATIONS

Toker, A. "Phosphoinositides and signal transduction" *Cellular and Molecular Life Sciences*, 2002, pp. 761-779, vol. 59.

Vanhaesebroeck, B. et al. "Synthesis and Function of 3-Phosphorylated Inositol Lipids" *Annual Review of Biochemistry*, 2001, pp. 535-602, vol. 70.

Vanhaesebroeck, B. et al. "Signalling by PI3K isoforms: insights from gene-targeted mice" *Trends in Biochemical Sciences*, Apr. 2005, pp. 194-204, vol. 30, No. 4.

Wymann, M. P. et al. "Lipids on the move: phosphoinositide 3-kinases in leukocyte function" *Trends Immunology Today*, Jun. 2000, pp. 260-264, vol. 21, No. 6.

Yao, R. et al. "Requirement for Phosphatidylinositol-3 Kinase in the Prevention of Apoptosis by Nerve Growth Factor" *Science*, pp. 2003-2006, Mar. 31, 1995, vol. 267.

Written Opinion in International Application No. PCT/EP2010/067412, Feb. 14, 2011, pp. 1-6.

Database CA [Online] Chemical Abstracts Service, Registry No. 931714-28-2, Apr. 22, 2007, p. 1.

Database CA [Online] Chemical Abstracts Service, Registry No. 931355-99-6, Apr. 20, 2007, p. 1.

\* cited by examiner

TRICYCLIC PYRAZOL AMINE DERIVATIVES

CROSS-REFERENCE TO RELATED APPLICATIONS

This application is the U.S. national stage application of International Patent Application No. PCT/EP2010/067412, filed Nov. 12, 2010, which claims the benefit of U.S. Provisional Patent Application No. 61/261,854, filed Nov. 17, 2009.

The invention relates to compounds of formula (I) and related formulae, their use as medicament and their use for treating autoimmune diseases, inflammatory disorders, multiple sclerosis and other diseases like cancers.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, Science, 296, 1655-1657).

The term PI3K is given to a family of lipid kinases which, in mammals, consists in eight identified PI3Ks that are divided into three sub-families according to their structure and their substrate specificity.

Class I group of PI3Ks consists in two sub-groups, Class IA and Class IB.

Class IA are a family of heterodimeric lipid kinases consisting in a 85 kDa regulatory unit (responsible for protein-protein interactions via the interaction of Src homology 2 (SH2) domain with phosphotyrosine residues of other proteins) and a catalytic sub-unit of 110 kDa that generate second messenger signals downstream of tyrosine kinases, thereby controlling cell metabolism, growth, proliferation, differentiation, motility and survival. Three catalytic forms (p110α, p110β and p110δ) and five regulatory isoforms (p85α, p85β, p55γ, p55α and p50α) exist for this class.

Class IB are stimulated by G protein βγ sub-units of heterodimeric G proteins. The only characterized member of Class IB is PI3Kγ (p110γ catalytic sub-unit complex with a 101-kDa regulatory protein, p101).

Class 1A PI3Ks comprises α, β and δ isoforms, which are approximately of 110 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 2001, Annu. Rev. Biochem., 70, 535-602). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example. Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)P2), respectively generating three lipid products, namely phosphatidylinositol 3-monophosphate (PI(3)P), phosphatidylinositol 3,4-bisphosphate (PI(3,4)P2) and phosphatidylinositol 3,4,5-trisphosphate (PI(3,4,5)P3.

The preferred substrate for Class I PI3Ks is PI(4,5)P2. Class II PIKs have a strong preference for PtdIns as substrate over PI(4)P and PI(4,5)P2. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimidiation, transactivation by heterologous receptor (e.g. receptor tyrosine kinase) to a G-protein linked transmembrane receptor integrated into the plasma membrane resulting in the activation of PI3Ks.

Once activated, PI3Ks convert the membrane phospholipid PI(4,5)P2 into PI(3,4,5)P3 which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, Cell Mol. Life Sci. 59(5) 761-79).

The second messengers of phosphorylated products of PtdIns is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, Mol. Med. Today 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, Immunol Today 21(6) 260-4 and Gerard et al., 2001, Nat Immunol. 2(2) 108-15).

PI3-kinase activation is therefore believed to be involved in a range of cellular responses including cell growth, differentiation, migration and apoptosis (Parker et al., 1995, Current Biology, 5, 577-99; Yao et al., 1995, Science, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen. These effects are linked to increases in the transcription of a number of genes including interleukin-2 (IL-2), an important T cell growth factor (Fraser et al., 1991, Science, 251, 313-16). Mutation of CD28 such that it can no longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFa-mediated neutrophil priming and superoxide generation, and leukocyte migration and adhesion to endothelial cells.

Recently, it has been described that PI3Kγ relays inflammatory signals through various G(i)-coupled receptors (Laffargue et al., 2002, Immunity 16(3) 441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, J. Cell. Sci., 114 (Pt 16) 2903-10).

Two compounds, LY294002 and Wortmannin (cf.hereinafter), have been widely used as PI3-kinase inhibitors. These compounds are non-specific PI3K inhibitors, as they do not distinguish among the four members of Class I PI3-kinases.

IC50 values of Wortmannin against each of the various Class I PI3-kinases are in the range of 1-10 nM and IC50 values for LY294002 against each of these PI3-kinases are about 15-20 μM (Fruman et al., 1998, Ann. Rev. Biochem., 67, 481-507), also 5-10 μM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, Proc. Natl. Acad. Sci. USA, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using Wortmannin, there is evidence that P13-kinase function is also required for some aspects of leukocyte signalling through G-protein coupled receptors (Thelen et al., 1994, above). Moreover, it has been shown that Wortmannin and LY294002 block neutrophil migration and superoxide release.

Some results have indicated that PI3K inhibitors, for example, LY294002, can increase the in vivo antitumor activity of certain cytotoxic agents (e.g. paclitaxel) (Grant, 2003, Current Drugs, 6(10), 946-948).

However, these compounds are not selective for a particular isoforms of PI3K, it remains unclear which particular PI3K isoform or isoforms are involved in these phenomena. Specific inhibitors against individual members of a family of enzymes provide valuable tools for deciphering functions of each enzyme as depending on the disease application, varying the degree of selectivity for PI3K isoforms can be of interest.

p110δ is expressed predominantly in cells of hemopoeitic origin such as leukocytes.

To assess the role of the delta isoform of the p110 catalytic subunit of PI3Ks, PI3Kδ-null mice have been developed (Jou et al., 2002, Molecular and Cellular biology, 22(4), 8580-8591) and their specific immunological phenotype has been well characterized (Vanhaesebroeck et al., 2005, Trends in Biochemical Sciences, 30(4), 194-204). These experiments show that the PI3Kδ-null animals are viable and that a deficiency in PI3Kδ results in a very specific loss of the function of the B-cell antigen specific receptor complex, while signalling through the cytokine receptor complexes is unaffected (Jou et al., 2002, above).

It has been also shown that the inactivation of the p110δ isoform of PI3K in mast cells leads to defective stem cell factor-mediated in vitro proliferation, adhesion and migration and to impaired allergen-IgE-induced degranualtion and cytokine release. Inactivation of p110δ protects mice against anaphylactic allergic responses, suggesting p110δ as a target for therapeutic intervention in allergy and mast-cell-related pathologies (Ali. et al., 2004, Nature, 431, 1007-1010).

Mast cells have emerged as a unique immune cell that could participate in a variety of inflammatory diseases in the nervous system (e.g. multiple sclerosis), skin, joints as well as cardiopulmonary, intestinal and urinary systems (Theoharides et al., 2004, J. of Neuroimmunology, 146, 1-12).

The high relevance of the PI3K pathway in some widely spread diseases stresses the need to develop inhibitors, including selective inhibitors, of PI3K isozymes, in order that the functions of each isozyme can be better characterized.

PI3K inhibitors have been developed: thiazole derivatives (WO 2005/021519; and WO 04/078754), thiazolidine derivatives (WO 2004/007491 and WO 2004/056820) and Quinazolinones derivatives (WO 03/035075).

Dihydrochromenopyrazole derivatives have been disclosed (WO2009/010824, WO2007/075772, and WO2008/035356). The present invention provides new tricyclic pyrazol derivatives and their used as Pi3K modulators.

SUMMARY OF THE INVENTION

According to one aspect of the invention, are provided compounds of Formula (I). According to another aspect of the invention, are provided compounds of Formula (I) which are suitable for the treatment and/or prevention of disorders related to phosphoinositide-3-kinases, PI3Ks, such as PI3K alpha or PI3K gamma or PI3K delta or PI3K beta.

According to another aspect of the invention, are provided thichromane compounds, which are able to modulate, especially inhibit the activity or function of phosphoinositide-3-kinases, PI3Ks in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective of the delta isoform of PI3K over the other isoforms.

According to another aspect of the invention is provided a kit or a set comprising at least one compound of Formula (I), preferably in combination with immunomodulating agents.

Preferably, the kit consists of separate packs of:
(a) an effective amount of a compound of the formula (I) and/or pharmaceutically usable derivatives, solvates, salts, hydrates and stereoisomers thereof, including mixtures thereof in all ratios, and
(b) an effective amount of a further medicament active ingredient.

According to another aspect of the invention, is provided a process for the synthesis of compounds of Formulae (I) and (I*).

DETAILED DESCRIPTION OF THE INVENTION

The present invention provides compounds of Formula (I*)

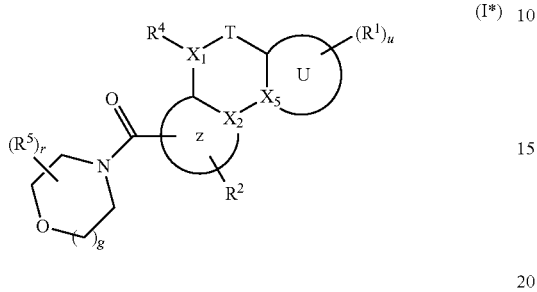

(I*)

wherein
$X_1$ denotes a nitrogen atom or $CR^3$,
$X_2$, $X_5$ are independently from one another nitrogen or carbon atoms,
U denotes an aromatic 6-membered ring having optionally 1, 2 or 3 nitrogen atoms, including $X_5$, or an unsaturated or aromatic 5-membered ring having 1 to 3 heteroatoms selected from N, S or O, including the meaning of $X_5$,
Z denotes an unsaturated or aromatic 5-membered heterocyclic ring having 2 nitrogen atoms, including the meaning of $X_2$.
T denotes S, SO or $SO_2$,
$R^1$ denotes H, A, Hal, CN, $NO_2$, $N(R^6)_2$, $OR^6$, Ar, Het, Y, $-NR^6COR^6$, $CON(R^6)_2$, $-NR^6COAr$, $NR^6COHet$, COHet, $-NR^6SO_2R^6$, $CO_2R^6$, including $CO_2Y$,
$R^2$ denotes H, Ar, Het, A, Cyc,
$R^3$ denotes H, Y,
$R^4$ denotes H, Y, $(CH_2)_nAr$, $(CH_2)_nCyc$, $(CH_2)_nHet$, $(CH_2)_nOY$, $(CH_2)_nNHY$, $(CH_2)_nNH_2$, or if $X_1$ is $CR^3$, also Hal,
$R^5$ denotes H, Y or Ar, when $R^5$ is Y and r is 2, two $R^5$ groups may be linked together to provide with the morpholine group to which they are linked, a bridged system.
$R^6$ is H, A, Cyc or Ar.
u is 0, 1, 2, 3, or 4, preferably 0 or 1,
r is 0, 1 or 2,
g is 1 or 2,
Ar denotes a monocyclic or fused bicyclic, unsaturated or aromatic carbocyclic ring having 6 to 14 carbon atoms, which is unsubstituted or monosubstituted, disubstituted or trisubstituted by Hal, $OCF_3$, $NO_2$, CN, perfluoroalkyl, A, $OR^6$, $N(R^6)_2$, $COR^6$, $-CO_2R^6$, $CON(R^6)_2$, COHet, $-NHCOR^6$, $-NHSO_2A$, $-NHSO_2Ar$, $-NHSO_2-N(R^6)_2$, $N(H)_{1-q}A_qCOR^6$, $N(H)_{1-q}A_qSO_2-N(H)_{2-m}(A)_m$, $-N(H)_{1-q}A_qCON(H)_{2-m}(A)_m$, $-SO_2A$, $-SO_2Ar$, $-SO_2N(H)_{2-m}(A)_m$, $-SO_2Het$, $-(CH_2)_n-N(R^6)_2$, $-(CH_2)_n-OR^6$, $-(CH_2)_n-N(R^6)SO_2A$, $-(CH_2)_n-N(R^6)SO_2R^6$, $Het^2$, $-(CH_2)_n$-$Het^2$, $-(CHY)_n$-$Het^2$;
Het denotes a monocyclic or bicyclic saturated, unsaturated or aromatic heterocyclic ring having 1, 2, 3 or 4 N, O and/or S atoms and eventually comprising a $SO_2$ or a CO group, which is unsubstituted or monosubstituted, disubstituted or trisubstituted by Hal, $OCF_3$, $NO_2$, CN, perfluoroalkyl, A, $OR^6$, $N(R^6)_2$, $COR^6$, $-CO_2R^6$, $CON(R^6)_2$, $-NHCOR^6$, $-NHSO_2A$, $-NHSO_2R^6$, $-NHSO_2-N(H)_{2-m}(A)_m$, $N(H)_{1-q}A_qCOR^6$, $N(H)_{1-q}$ $A_qSO_2-N(H)_{2-m}(A)_m$, $-N(H)_{1-q}A_qCON(H)_{2-m}(A)_m$, $-SO_2A$, $-SO_2Ar$, $-SO_2N(H)_{2-m}(A)_m$, COHet, $-SO_2Het$, $-(CH_2)_n-N(H)_{2-m}(A)_m$, $-(CH_2)_n-OR^6$, $-(CH_2)_n-N(R^6)SO_2A$, $-(CH_2)_n-N(R^6)SO_2R^6$, $Het^2$, $-(CH_2)_n$-$Het^2$; $-(CHY)_n$-$Het^2$;

$Het^2$ denotes

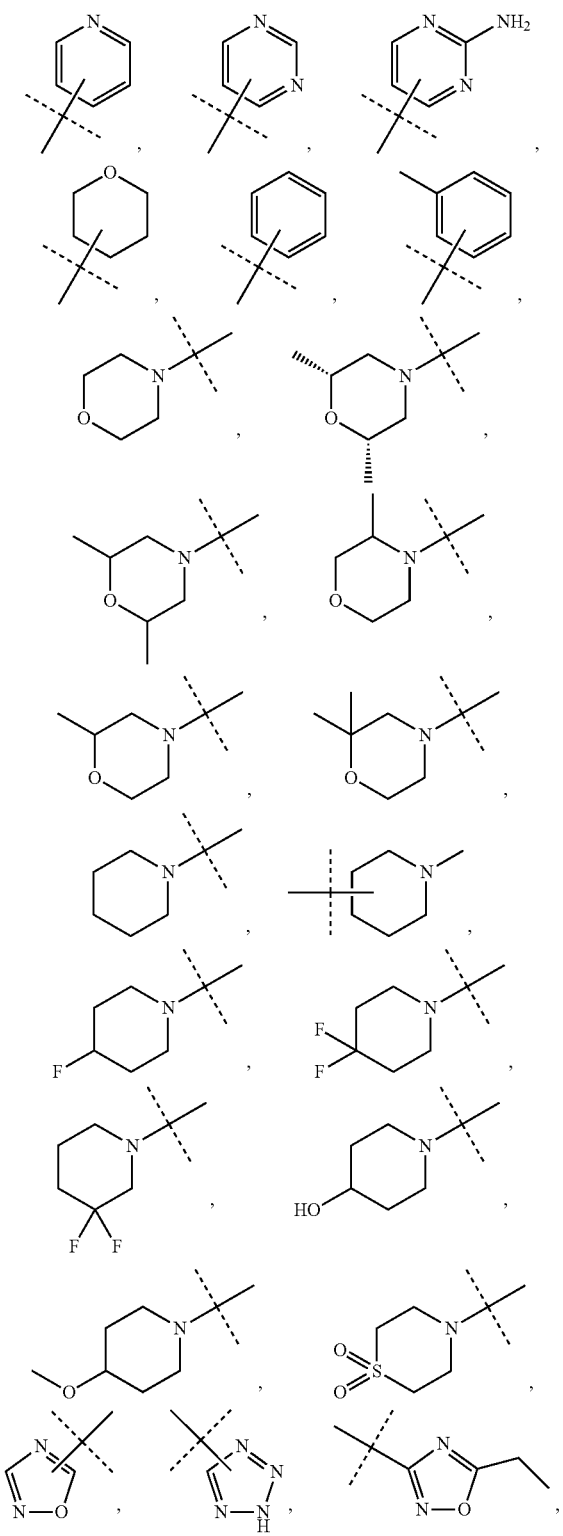

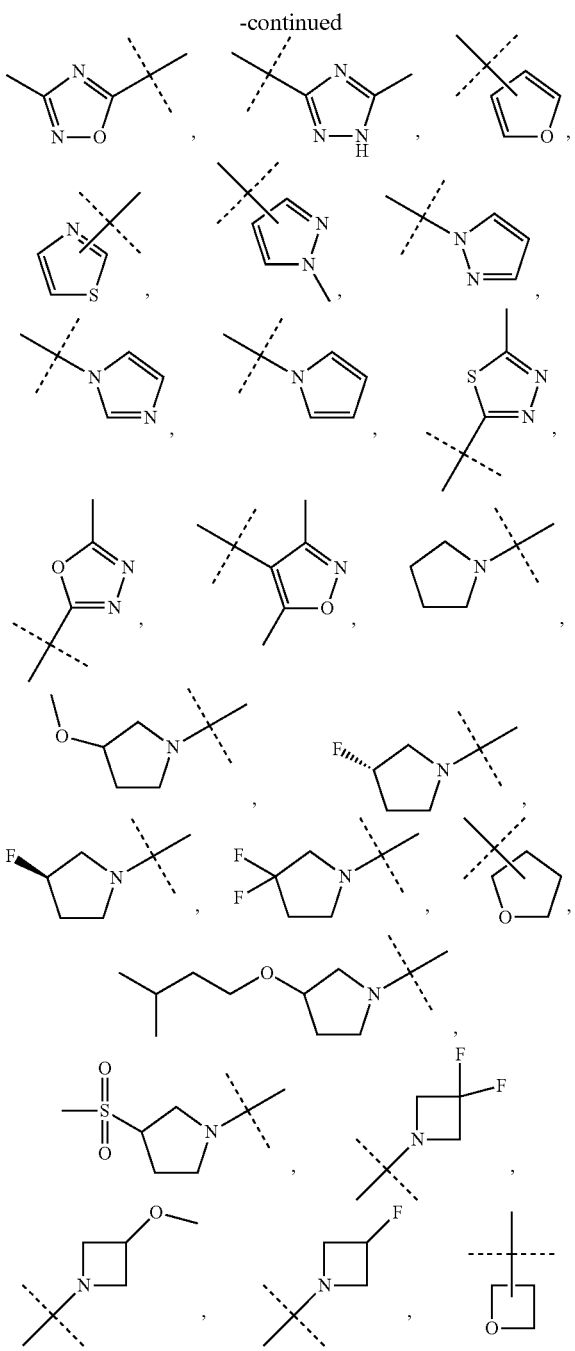

Cyc denotes a saturated or unsaturated carbocyclic ring having 3 to 8 carbon atoms, which is unsubstituted, mono-substituted, di-substituted or tri-substituted by Hal, $OCF_3$, $NO_2$, CN, perfluoroalkyl, A, $OR^6$, $N(R^6)_2$, $COR^6$, $CON(R^6)_2$, —$NHCOR^6$, —$NHSO_2A$, —$NHSO_2R^6$, —$NHSO_2$—$N(H)_{2-m}(A)_m$, $N(H)_{1-q}A_q$-$COR^6$, $N(H)_{1-q}A_qSO_2$—$N(H)_{2-q}(A)_m$, —$N(H)_{1-q}A_q$-$CON(H)_{2-m}(A)_m$, —$COOR^6$, —$SO_2A$, —$SO_2Ar$, —$SO_2N(H)_{2-m}(A)_m$, —$SO_2Het$, —$(CH_2)_p$—$N(H)_{2-m}(A)_m$, —$(CH_2)_n$—$OR^6$, —$(CH_2)_n$—$N(R^6)SO_2A$, —$(CH_2)_n$—$N(R^6)SO_2R^6$, $Het^2$, —$(CH_2)_n$-$Het^2$; —$(CHY)_n$-$Het^2$;

A is a branched or linear alkyl having 1 to 12 C-atoms, wherein one or more, preferably 1 to 7 H-atoms may be replaced by Hal, Ar, Het, Cyc, $OR^6$, —CN, —$CO_2Y$, $CO_2H$ or $N(R^6)_2$ and wherein one or more, preferably 1 to 7 non-adjacent $CH_2$-groups may be replaced by O, $NR^6$, CO, $CONR^6$, $NR^6CO$, OCO,—and/or by —CH=CH— or —C≡C— groups, or denotes cycloalkyl or cycloalkylalkylen having 3-7 ring C atoms;

Y denotes a branched or linear alkyl having 1 to 8 carbon atoms.

Hal denotes F, Cl, Br or I, q is 0 or 1, m is 0, 1 or 2, n is 1, 2, 3, or 4 and pharmaceutically acceptable derivatives, solvates, tautomers, salts, hydrates and stereoisomers thereof, including mixtures thereof in all ratios.

In a specific embodiment, U is an aromatic 6-membered ring having optionally 1 or 2 nitrogen atoms, including the meaning of $X_5$, In another specific embodiment, $X_5$ is a carbon atom, In another specific embodiment, $X_2$ is a carbon atom, In another specific embodiment, $X_2$ and $X_5$ are carbon atoms, U is an aromatic 6-membered ring having optionally 1 or 2 nitrogen atoms, Z is an unsaturated or aromatic 5-membered heterocyclic ring having 2 nitrogen atoms.

In another embodiment, $X_1$ is $CR^3$ wherein $R^3$ is as defined above.

In another embodiment, T is $SO_2$.

In another embodiment, $X_2$ and $X_5$ are carbon atoms, U is an aromatic 6-membered ring having optionally 1 nitrogen atoms, Z is an unsaturated or aromatic 5-membered heterocyclic ring having 2 nitrogen atoms, T is $SO_2$, and $X_1$ is $CR^3$ wherein $R^3$ is as defined above.

In a more specific embodiment, the moiety:

in Formula (I*) is selected from the following groups:

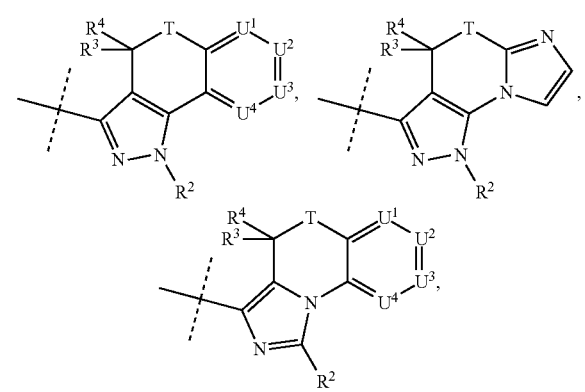

-continued

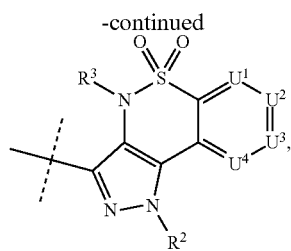

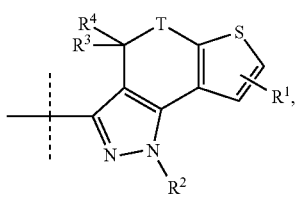

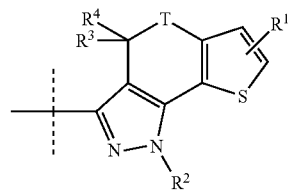

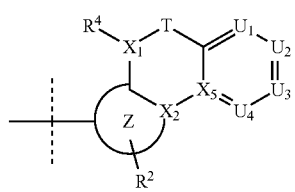

Wherein R¹, R², R³, R⁴, T, are as defined above.
And wherein
U¹, U², U³, and U⁴ denote CR¹ or one or two of U¹, U², U³ and U⁴ are independently N, and the remaining are CR¹, or one of U¹ and U⁴ is S, U²-U³ form together a group CR¹ and the remaining is CR¹, or one of U¹ and U⁴ is S, U²-U³ form together a group CR¹ and the remaining is N,
or denotes the following group:

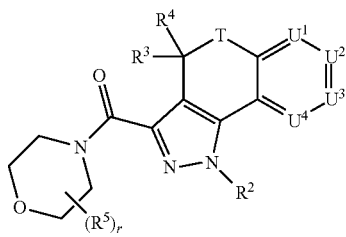

wherein U¹ denotes N, U²-U³ form together a group CR¹, U⁴ is CR¹, X₅ is N, and Z, X¹, X², R², T, are as above defined.
In a specific embodiment R² is Ar.
In another specific embodiment, R² is Het or Cyc.
In another specific embodiment, R² contains 1 or 2 chiral centers.
In a preferred embodiment, the present invention provides compounds of Formula (Ia*)

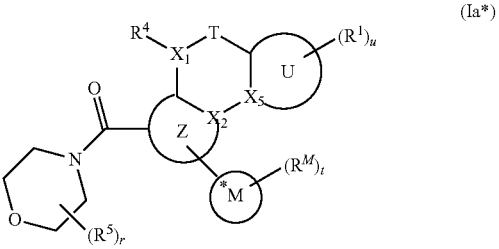

Wherein, $X_1$, $X_2$, $X_5$, $R^4$, T, $R^1$, Z, U, r and u are as defined above and
wherein
M denotes a saturated or unsaturated 4-, 5-, 6-, 7- or 8-membered ring optionally containing 1 to 3 heteroatoms selected from N, S and O,
The sign * denotes a chiral center,
$R^M$ denotes Hal, $OCF_3$, $NO_2$, CN, perfluoroalkyl, A, $OR^6$, $N(R^6)_2$, $COR^6$, $-CO_2R^6$, $CON(R^6)_2$, $-NHCOR^6$, $-NHSO_2A$, $-NHSO_2R^6$, $-NHSO_2-N(H)_{2-m}(A)_m$, $N(H)_{1-q}A_qCOR^6$, $N(H)_{1-q}A_qSO_2-N(H)_{2-m}(A)_m$, $-N(H)_{1-q}A_qCON(H)_{2-m}(A)_m$, $-SO_2A$, $-SO_2Ar$, $-SO_2N(H)_{2-m}(A)_m$, COHet, $-SO_2Het$, $-(CH_2)_n-N(H)_{2-m}(A)_m$, $-(CH_2)_n-OR^6$, $-(CH_2)_n-N(R^6)SO_2A$, $-(CH_2)_n-N(R^6)SO_2R^6$, $Het^2$, $-(CH_2)_n-Het^2$; or $-(CHY)_n-Het^2$;
t is 0, 1, 2, 3 or 4, preferably 0 or 1.
In a more specific embodiment, the invention provides compounds of Formula (I):

(I)

Wherein U¹, U², U³, and U⁴ are a above defined
R² denotes H, Ar, Het, A, Cyc,
R⁴ denotes H, Hal, Y, $(CH_2)_nAr$, $(CH_2)_nCyc$, $(CH_2)_nHet$, $(CH_2)_nOY$, $(CH_2)_nNHY$, $(CH_s)_nNH_2$,
R³ denotes H, Y,
R⁵ denotes H, Y or Ar, when R⁵ is Y and r is 2, two R⁵ groups may be linked together to provide with the morpholine group a bridged system.
R¹ denotes H, A, Hal, CN, $NO_2$, $N(R^6)_2$, $OR^6$, Ar, Het, Y, $-NR^6COR^6$, $CON(R^6)_2$, $-NR^6COAr$, $NR^6COHet$, COHet, $-NR^6SO_2R^6$, $CO_2R^6$, including $CO_2Y$,
T denotes S, SO or $SO_2$.
r denotes 0, 1 or 2,
Ar denotes a monocyclic or fused bicyclic, unsaturated or aromatic carbocyclic ring having 6 to 14 carbon atoms, which is unsubstituted or monosubstituted, disubstituted or trisubstituted by Hal, $OCF_3$, $NO_2$, CN, perfluoroalkyl, A, $OR^6$, $N(R^6)_2$, $COR^6$, $-CO_2R^6$, $CON(R^6)_2$, COHet, $-NHCOR^6$, $-NHSO_2A$, $-NHSO_2Ar$, $-NHSO_2-N(R^6)_2$, $N(H)_{1-q}A_qCOR^6$, $N(H)_{1-q}A_qSO_2-N(H)_{2-m}(A)_m$, $-N(H)_{1-q}A_qCON(H)_{2-m}(A)m$, $-SO_2A$, $-SO_2Ar$, $-SO_2N(H)_{2-m}(A)_m$, $-SO_2Het$, —(CH$_2$)$_n$—N(R$^6$)$_2$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$-Het$^2$; or —(CHY)$_n$-Het$^2$;

Het denotes a monocyclic or bicyclic saturated, unsaturated or aromatic heterocyclic ring having 1, 2, 3 or 4 N, O and/or S atoms which is unsubstituted or monosubstituted, disubstituted or trisubstituted by Hal, OCF$_3$, NO$_2$, CN, perfluoroalkyl, A, OR$^6$, N(R$^6$)$_2$, COR$^6$, —CO$_2$R$^6$, CON(R$^6$)$_2$, —NHCOR$^6$, —NHSO$_2$A, —NHSO$_2$R$^6$, —NHSO$_2$—N(H)$_{2-m}$(A)$_m$N(H)$_{1-q}$A$_q$COR$^6$, N(H)$_{1-q}$A$_q$SO$_2$—N(H)$_{2-m}$(A)$_m$, —N(H)$_{1-q}$A$_q$CON(H)$_{2-m}$(A)$_m$, —SO$_2$A, —SO$_2$Ar, —SO$_2$N(H)$_{2-m}$(A)$_m$, COHet, —SO$_2$Het, —(CH$_2$)$_n$—N(H)$_{2-m}$(A)$_m$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$-Het$^2$; or —(CHY)$_n$-Het$^2$;

Cyc denotes a saturated or unsaturated carbocyclic ring having 3 to 8 carbon atoms, which is unsubstituted, mono-substituted, di-substituted or tri-substituted by Hal, OCF$_3$, NO$_2$, CN, perfluoroalkyl, A, OR$^6$, N(R$^6$)$_2$, COR$^6$, CON(R$^6$)$_2$, —NHCOR$^6$, —NHSO$_2$A, —NHSO$_2$R$^6$, —NHSO$_2$—N(H)$_{2-m}$(A)$_m$, N(H)$_{1-q}$A$_q$COR$^6$, N(H)$_{1-q}$A$_q$SO$_2$—N(H)$_{2-m}$(A)$_m$, —N(H)$_{1-q}$A$_q$CON(H)$_{2-m}$(A)$_m$, —COOR$^6$, —SO$_2$A, —SO$_2$Ar, —SO$_2$N(H)$_{2-m}$(A)$_m$, —SO$_2$Het, —(CH$_2$)$_p$—N(H)$_{2-m}$(A)$_m$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$-Het$^2$; or —(CHY)$_n$-Het$^2$;

A is a branched or linear alkyl having 1 to 12 C-atoms, wherein one or more, preferably 1 to 7 H-atoms may be replaced by Hal, Ar, Het, Cyc, OR$^6$, —CN, —CO$_2$Y or N(R$^6$)$_2$ and wherein one or more, preferably 1 to 7 non-adjacent CH$_2$— groups may be replaced by O, NR$^6$, CONR$^6$— and/or by —CH=CH— or —C≡C— groups, or denotes cycloalkyl or cycloalkylalkylen having 3-7 ring C atoms;

Y denotes a branched or linear alkyl having 1 to 8 carbon atoms.

R$^6$ is H, A, Cyc or Ar.

Hal denotes F, Cl, Br or I, q is 0 or 1, m is 0, 1 or 2, n is 1, 2, 3, or 4

In another embodiment, the present invention provides compounds of Formula (I) wherein U$^1$, U$^2$, U$^3$, and U$^4$ denote CR$^1$ wherein 2 or 3 of the R$^1$ groups are H, preferably 3 R$^1$ groups are H.

In another embodiment, the present invention provides compounds of Formula (I) wherein U$^1$, U$^2$, U$^3$, and U$^4$ denote CH.

In another embodiment, the present invention provides compounds of Formula (I) wherein one of U$^1$ and U$^4$ is S, U$^2$-U$^3$ form together a group CR$^1$ and the remaining is CR$^1$.

In another embodiment, the present invention provides compounds of Formula (I*) or (I) wherein R$^2$ denotes H, Ar, Het, A, Cyc, R$^3$, R$^4$ denote independently from one another H, Y, (CH$_2$)$_n$Ar (CH$_2$)$_n$Cyc, (CH$_2$)$_n$Het R$^5$ denotes H, Y or Ar, U$^1$, U$^2$, U$^3$, and U$^4$ denote CR$^1$ or one or two of U$^1$, U$^2$, U$^3$ and U$^4$ are independently N, and the remaining are CR$^1$ R$^1$ denotes H, A, Hal, CN, NO$_2$, N(R$^6$)$_2$, OR$^6$, Ar, Het, Y, —NR$^6$COR$^6$, CON(R$^6$)$_2$ T denotes S, —SO or —SO$_2$.

r denotes 0, 1 or 2,

Ar denotes a monocyclic or fused bicyclic, unsaturated or aromatic carbocyclic ring having 6 to 14 carbon atoms, which is unsubstituted or monosubstituted, disubstituted or trisubstituted by Hal, OCF$_3$, NO$_2$, CN, perfluoroalkyl, A, OR$^6$, N(R$^6$)$_2$, COR$^6$, —CO$_2$R$^6$, CON(R$^6$)$_2$, COHet, —NHCOR$^6$, —NHSO$_2$A, —NHSO$_2$Ar, —NHSO$_2$—N(R$^6$)$_2$, N(H)$_{1-q}$A$_q$COR$^6$, N(H)$_{1-q}$A$_q$SO$_2$—N(H)$_{2-m}$(A)$_m$, —N(H)$_{1-q}$A$_q$CON(H)$_{2-m(A)m}$, —SO$_2$A, —SO$_2$Ar, —SO$_2$N(H)$_{2-m}$(A)$_m$, —SO$_2$Het, —(CH$_2$)$_n$—N(R$^6$)$_2$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$-Het$^2$; or —(CHY)$_n$-Het$^2$;

Het denotes a monocyclic or bicyclic saturated, unsaturated or aromatic heterocyclic ring having 1, 2, 3 or 4 N, O and/or S atoms which is unsubstituted or monosubstituted, disubstituted or trisubstituted by Hal, OCF$_3$, NO$_2$, CN, perfluoroalkyl, A, OR$^6$, N(R$^6$)$_2$, COR$^6$, —CO$_2$R$^6$, CON(R$^6$)$_2$, —NHCOR$^6$, —NHSO$_2$A, —NHSO$_2$R$^6$, —NHSO$_2$—N(H)$_{2-m}$(A)$_m$, N(H)$_{1-q}$A$_q$COR$^6$, N(H)$_{1-q}$A$_q$SO$_2$—N(H)$_{2-m}$(A)$_m$, —N(H)$_{1-q}$A$_q$CON(H)$_{2-m}$(A)$_m$, —SO$_2$A, —SO$_2$Ar, —SO$_2$N(H)$_{2-m}$(A)$_m$, COHet, —SO$_2$Het, —(CH$_2$)$_n$—N(H)$_{2-m}$(A)$_m$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$-Het$^2$; or —(CHY)$_n$-Het$^2$;

Cyc denotes a saturated carbocyclic ring having 1 to 8 carbon atoms, which is unsubstituted, mono-substituted, di-substituted or tri-substituted by Hal, OCF$_3$, NO$_2$, CN, perfluoroalkyl, A, OR$^6$, N(R$^6$)$_2$, COR$^6$, CON(R$^6$)$_2$, —NHCOR$^6$, —NHSO$_2$A, —NHSO$_2$R$^6$, —NHSO$_2$—N(H)$_{2-m}$(A)$_m$, N(H)$_{1-q}$A$_q$COR$^6$, N(H)$_{1-q}$A$_q$SO$_2$—N(H)$_{2-m}$(A)$_m$, —N(H)$_{1-q}$A$_q$CON(H)$_{2-m}$(A)$_m$, —COOR$^6$, —SO$_2$A, —SO$_2$Ar, —SO$_2$N(H)$_{2-m}$(A)$_m$, —SO$_2$Het, —(CH$_2$)$_p$—N(H)$_{2-m}$(A)$_m$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$-Het$^2$; or —(CHY)$_n$-Het$^2$;

A is a branched or linear alkyl having 1 to 12 C-atoms, wherein one or more, preferably 1 to 7 H-atoms may be replaced by Hal, Ar, Het, Cyc, OR$^6$, —CN, —CO$_2$Y or N(R$^6$)$_2$ and wherein one or more, preferably 1 to 7 non-adjacent CH$_2$-groups may be replaced by O, NR$^6$, CONR$^6$— and/or by —CH=CH— or —C≡C— groups, or denotes cycloalkyl or cycloalkylalkylen having 3-7 ring C atoms;

Y denotes a branched or linear alkyl having 1 to 8 carbon atoms.

R$^6$ is H, A, Cyc or Ar.

Hal denotes F, Cl, Br or I, q is 0 or 1, m is 0, 1 or 2, n is 1, 2, 3, or 4 and pharmaceutically acceptable derivatives, solvates, tautomers, salts, hydrates and stereo-isomers thereof, including mixtures thereof in all ratios.

In the compounds of Formulae (I) and related Formulae, wherein a substituent occurs more than once, such as R$^5$, each of them has the meaning hereby defined, independently from one another.

In another embodiment, the invention relates to compounds of formula (A1)

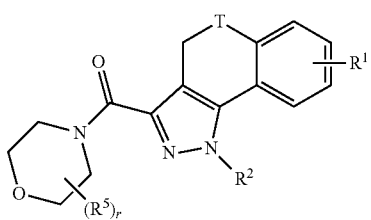

(A1)

Wherein $R^1$, $R^2$, $R^5$, r and T are as above defined, and pharmaceutically acceptable derivatives, solvates, tautomers, salts, hydrates and stereoisomers thereof, including mixtures thereof in all ratios.

In a second embodiment, the invention relates to compounds of formula (A2)

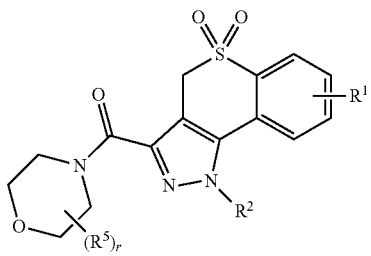

(A2)

Wherein $R^1$, $R^2$, $R^5$ and r are as above defined, and pharmaceutically acceptable derivatives, solvates, tautomers, salts and stereoisomers thereof, including mixtures thereof in all ratios.

In another embodiment, the invention relates to the compounds of formula (A3),

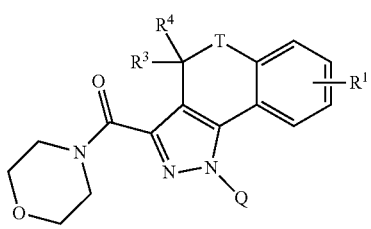

(A3)

wherein Q is Ar, Cyc, alkyl having 1 to 8 carbon atoms, or Het, and wherein $R^1$, $R^3$, $R^4$, and T are as above defined, and pharmaceutically acceptable derivatives, solvates, tautomers, salts, hydrates and stereoisomers thereof, including mixtures thereof in all ratios.

In another embodiment, the invention relates to the compounds of formula (A4),

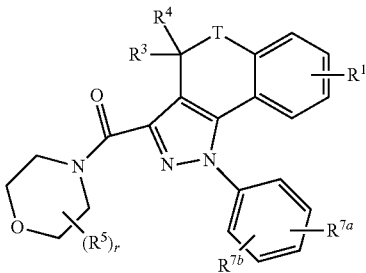

(A4)

wherein $R^1$, $R^3$, $R^4$, $R^5$, T and r are as above defined, and wherein $R^{7a}$ and $R^{7b}$ are independently from one another selected from H, Y, A, Hal, $NO_2$, CN, $OR^6$, $N(R^6)_2$, $COR^6$, —$CO_2R^6$, $CON(R^6)_2$, COHet, —NHCOA, —$NHSO_2A$, —$NHSO_2$—$N(R^6)_2$, $N(H)_{1-q}A_qCOA$, $N(H)_{1-q}A_qSO_2$—N$(H)_{2-m}(A)_m$, —$N(H)_{1-q}A_qCON(H)_{2-m}(A)_m$, —$SO_2A$, —$SO_2N(H)_{2-m}(A)_m$, —$SO_2$Het, —$(CH_2)_n$—$N(R^6)_2$, —$(CH_2)_n$—$OR^6$, —$(CH_2)_n$—$N(R^6)SO_2A$, and pharmaceutically acceptable derivatives, solvates, tautomers, salts, hydrates and stereoisomers thereof, including mixtures thereof in all ratios.

In another embodiment, the invention relates to compounds of Formula (A5):

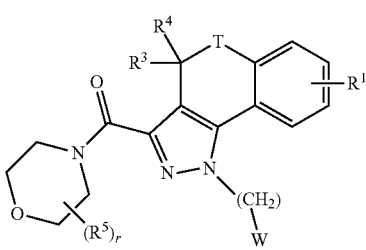

(A5)

wherein $R^1$, $R^2$, $R^3$, $R^4$, $R^5$, T and r are as above defined and wherein W is H, Y, Q, —$(CH_2)_pQ$, —$(CH_2)_pN(R^6)_2$, —$(CH_2)_pOR^6$, whereby p is 1, 2 or 3 and Q is Ar, Cyc, or Het;

In another preferred embodiment, the present invention provides compounds of Formula (A6) or (A7):

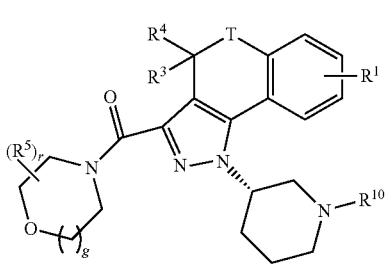

(A6)

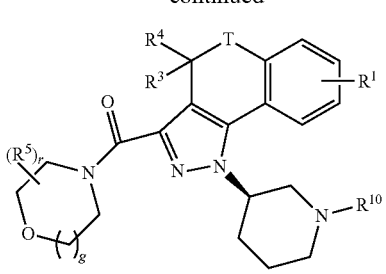

(A7)

As well as a mixture of (A6) and (A7) in all ratios,
wherein $R^1$, $R^3$, $R^4$, $R^5$, T, g, and r are as above defined and
wherein
$R^{10}$ denotes perfluoroalkyl, A, $COR^6$, —$CO_2R^6$, $CON(R^6)_2$, COHet, —$SO_2A$, —$SO_2Ar$, —$SO_2N(H)_{2-m}(A)_m$, —$SO_2$Het, —$(CH_2)_n$—$N(R^6)_2$, —$(CH_2)_n$—$OR^6$, —$(CH_2)_n$—$N(R^6)SO_2A$, —$(CH_2)_n$—$N(R^6)SO_2R^6$, $Het^2$, —$(CH_2)_n$-$Het^2$, —$(CHY)_n$-$Het^2$;
Wherein $R^6$, Y, A, m, n, Het and $Het^2$ are as above defined.

Preferrably $R^{10}$ denotes A, $Het^2$, —$(CH_2)_n$-$Het^2$, or —$(CHY)_n$-$Het^2$.

More preferably, $R^{10}$ denotes a branched or linear alkyl having 1 to 6 C-atoms, wherein one or more, preferably 1 to 3 H-atoms may be replaced by Hal, Ar, Het, Cyc, $OR^6$, —CN, wherein $R^6$ is a linear or branched alkyl having 1 to 6 carbon atoms.
and pharmaceutically acceptable derivatives, solvates, tautomers, salts, hydrates and stereoisomers thereof, including mixtures thereof in all ratios.

The following compound B1, referenced under the Registry Number 931355-99-6, is commercially available from ChemDiv Company. This compound was not used for any pharmaceutical or medical indication.

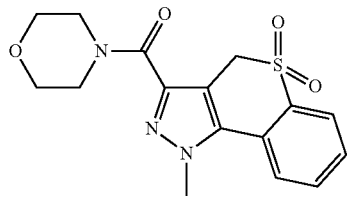

B1

In a preferred embodiment, the compound B1 is excluded from the compounds of the invention.

Above and below, Me refers to a methyl group, Et refers to an ethyl group.

The formula (I), (I*) and related formulae also encompasses mixtures of the compounds of the formula (I), (I*) and related Formulae, for example mixtures of two diastereomers or enantiomers, for example in the ratio 1:1, 1:2, 1:3, 1:4, 1:5, 1:10, 1:100 or 1:1000.

"Alkyl" denotes a carbon chain having 1, 2, 3, 4, 5, 6, 7, 8, 9, 10, 11, or 12 carbon atoms. Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl, pentafluoroethyl or 1,1,1-trifluoroethyl.

"Cycloalkylalkylene" or "cycloalkylalylen group" denotes a carbon chain having 1 to 6 carbon atoms wherein 1 H atom is substituted by a cycloalkyl group. Cycloalkylalkylene preferably denotes cyclopropylmethylene, cyclobutylmethylene, cyclopentylmethylene, cyclo-hexylmethylene or cycloheptylmethylene.

"Perfluoroalkyl" denotes an alkyl chain having 1 to 8 carbon atoms, preferably 1 to 6 carbon atoms, and wherein all the hydrogen atoms are replaced by F atoms. Perfluoroalkyl more preferably denotes $CF_3$.

Hal preferably denotes F, Cl or Br.

"Amino" or "amino group" denotes the group —NR'R" where each R', R" is independently hydrogen, Y, Ar, Het, Cyc or A. R' and R", together with the nitrogen atom to which they are attached, can optionally form a Het group. R' and R", together with the nitrogen atom to which they are attached, preferably form a 5-membered unsaturated or aromatic heterocyclic ring having 1, 2, 3, or 4, heteroatoms selected in the group of N, O, and S.

Ar preferably denotes a monocyclic or bicyclic, aromatic carbocyclic ring having 6 to 14 carbon atoms, which is unsubstituted or monosubstituted, disubstituted or trisubstituted by F, Cl, Br, $CF_3$, $OCF_3$, $NO_2$, CN, A, $OR^6$, $N(H)_{2-m}(A)_m$, —$CON(R^6)_2$, COHet, —NHCOA, $CO_2A$, —$SO_2A$, —$SO_2N(H)_{2-m}(A)_m$, —$SO_2$Het, —$(CH_2)_n$—$N(R^6)SO_2A$, More particularly, Ar is

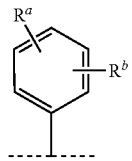

where $R^a$ and $R^b$ denote independently from one another H, Hal, $NO_2$, A, CN, $N(R^6)_2$, —$NR^6COA$, —$NR^6CO_2A$, —$OR^6$, —$CO_2A$, —$CON(R^6)_2$, —COHet, —$SO_2N(H)_{2-m}(A)_m$, —$NHSO_2A$, —$(CH_2)_n$—$N(R^6)SO_2A$, —$SO_2A$, —$SO_2$Het, Het, Ar, or Cyc,
wherein $R^6$, A, Ar, Het, Cyc and m are as above defined.

Examples of the preferred Ar groups are selected from the following groups:

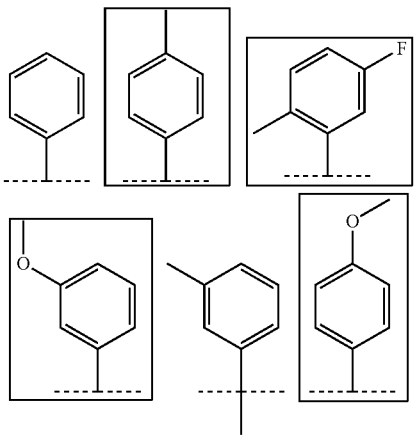

17
-continued

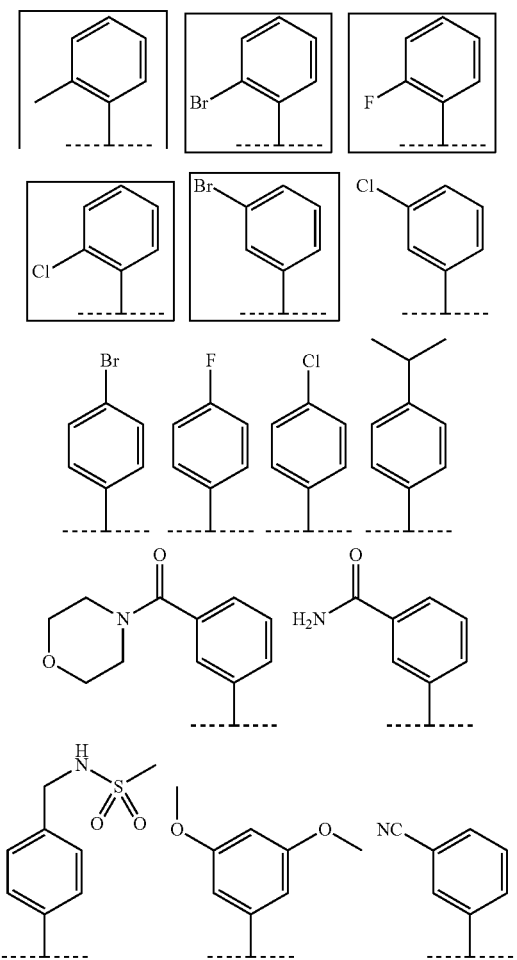

Het preferably denotes monocyclic or bicyclic saturated, unsaturated or aromatic heterocyclic ring having 1 or 2 heteroatoms selected from N, O and S, which is unsubstituted or monosubstituted, disubstituted or trisubstituted by alkyl having 1 to 8 carbon atoms, Hal, $CF_3$, $OCF_3$, $NO_2$, CN, $OR^6$, $N(R^6)_2$, $CON(R^6)_2$, $—CO_2A$, $—SO_2A$, $—SO_2N(H)_{2-m}(A)_m$, COHet, $—SO_2Het$, $—(CH_2)_n—OR^6$, $—(CH_2)_n—N(R^6)_2$.

In one embodiment, Het is preferably the group

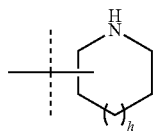

wherein h is 0, 1 or 2, preferably 1, and which is optionally substituted by Hal, $OCF_3$, $NO_2$, CN, perfluoroalkyl, A, $OR^6$, $N(R^6)_2$, $COR^6$, $—CO_2R^6$, $CON(R^6)_2$, $—NHCOR^6$, $—NHSO_2A$, $—NHSO_2R^6$, $—NHSO_2—N(H)_{2-m}(A)_m$, $N(H)_{1-q}NCOR^6$, $N(H)_{1-q}A_qSO_2—N(H)_{2-m}(A)_m$, $—N(H)_{1-q}NCON(H)_{2-m}(A)_m$, $—SO_2A$, $—SO_2Ar$, $—SO_2N(H)_{2-m}(A)_m$, COHet, $—SO_2Het$, $—(CH_2)_n—N(H)_{2-m}(A)_m$, $—(CH_2)_n—OR^6$, $—(CH_2)_n—N(R^6)SO_2A$, $—(CH_2)_n—N(R^6)SO_2R^6$, $Het^2$, $—(CH_2)_n-Het^2$; $—(CHY)_n-Het^2$;

18
Het more preferably denotes one of the following groups:

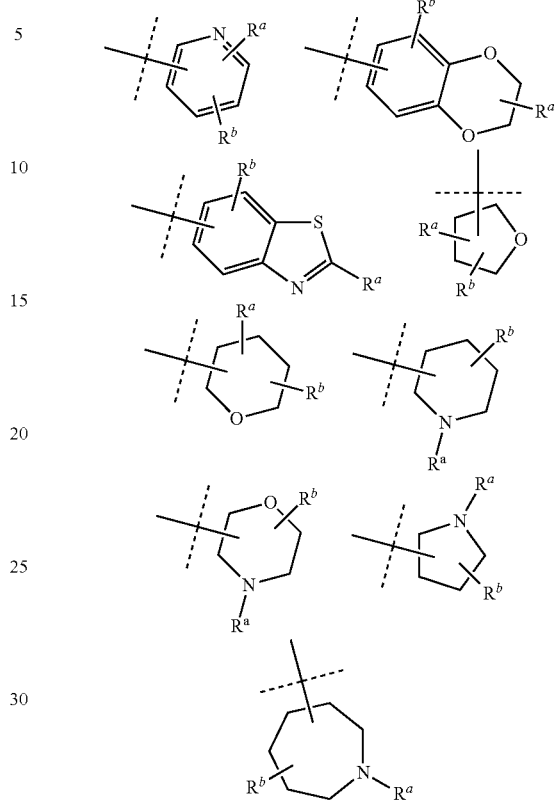

wherein $R^a$ and $R^b$ are as above defined.

Preferably, $R^a$ and $R^b$ denote independently from one another one of the following groups:
Y, H, Hal, $NO_2$, CN, $—(CH_2)_n—NH—SO_2Y$, $—O(CH_2)_n—N(H)_{2-m}(Y)_m$, $—NH(CH_2)_n—N(H)_{2-m}(Y)_m$, $—NH(CH_2)_n—OH$, $—NH(CH_2)_n—OY$, $—O—(CH_2)_n—OH$, $—O—(CH_2)_n—OY$, OH, OY, $—(CH_2)_n—OY$, $—(CH_2)_n—OH$, $—(CH_2)_n—N(H)_{2-m}(Y)_m$, $—NHCOY$, $—NHCO_2Y$, $—CF_3$, $Het^2$, $—(CH_2)_n-Het^2$; $—(CHY)_n-Het^2$;
whereby Y, m, and n are as above defined.

The group $—(CH_2)_n-Het^2$ preferably denotes

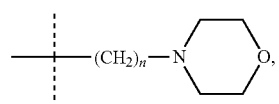

wherein n is as above defined. Preferably n is 2.
Y preferably denotes a branched or linear alkyl having 1 to 6 carbon atoms.
T preferably denotes SO or $SO_2$.
Cyc preferably denotes a saturated carbocyclic ring having 1 to 8 carbon atoms, which is unsubstituted, mono-substituted, or di-substituted by alkyl having 1 to 8 carbon atoms, alkoxy having 1 to 8 carbon atoms, Hal, $CF_3$, $OCF_3$, $NO_2$, CN, perfluoroalkyl, OH, $NH_2$, COH, $CO_2H$, $CONH_2$, $—(CH_2)_n—OR^6$, whereby $R^6$ and n are as above defined.
Most preferably, Cyc denotes cyclopropyl, cyclobutyl, cyclopentyl, cyclohexyl and cycloheptyl.
$R^3$ and $R^4$ preferably denote H or Y.
Most preferably, both $R^3$ and $R^4$ denote H.

Alternatively, R³ also denotes (CH₂)ₙAr, (CH₂)ₙCyc, (CH₂)ₙHet, (CH₂)ₙOY, (CH₂)ₙNHY, (CH₂)ₙNH₂.

In case X₁ is a nitrogen atom, R⁴ is preferably Y, (CH₂)ₙAr, (CH₂)ₙCyc, (CH₂)ₙHet, (CH₂)ₙOY, (CH₂)ₙNHY, (CH₂)ₙNH₂, R¹ preferably denotes H, OR⁶, Hal, CN, NO₂, —(CH₂)ₙ—N(R⁶)₂, —O(CH₂)ₙ—N(R⁶)₂, —NR⁶—(CH₂)ₙ—N(R⁶)₂, —NR⁶—(CH₂)ₙ—OR⁶, —NR⁶—CO₂R⁶, —NR⁶—COR⁶.

More preferably, R¹ is H or Hal.

R² is preferably selected from H, a linear or branched C₁-C₆-alkyl or one of the following groups:

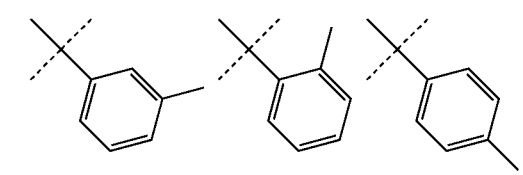
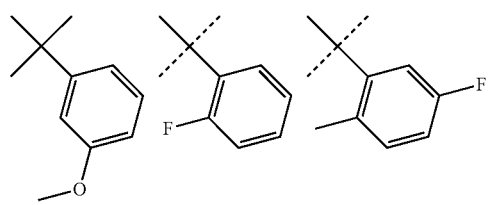
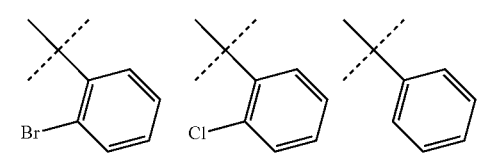
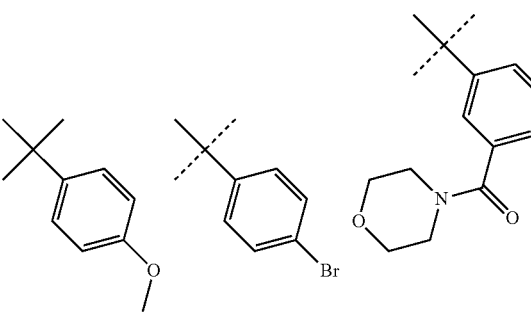
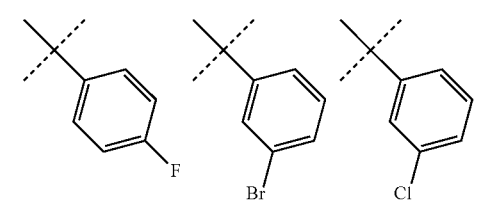
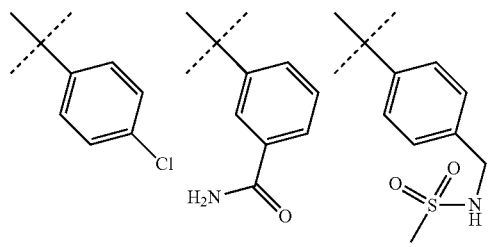
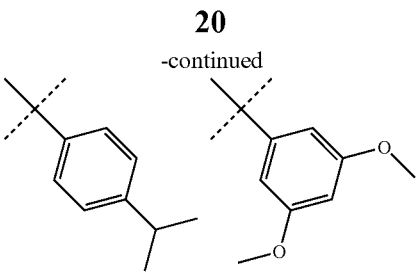
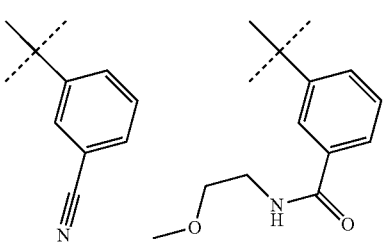
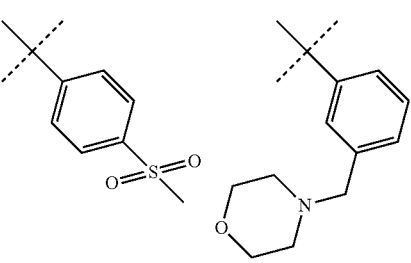
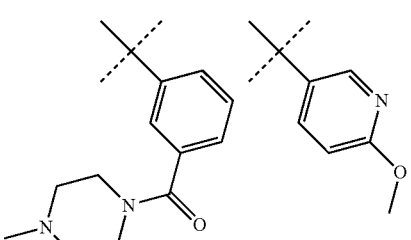
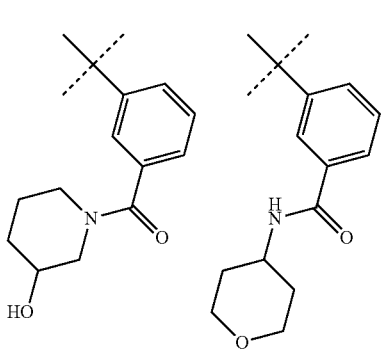
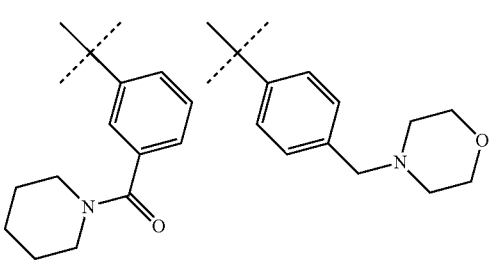

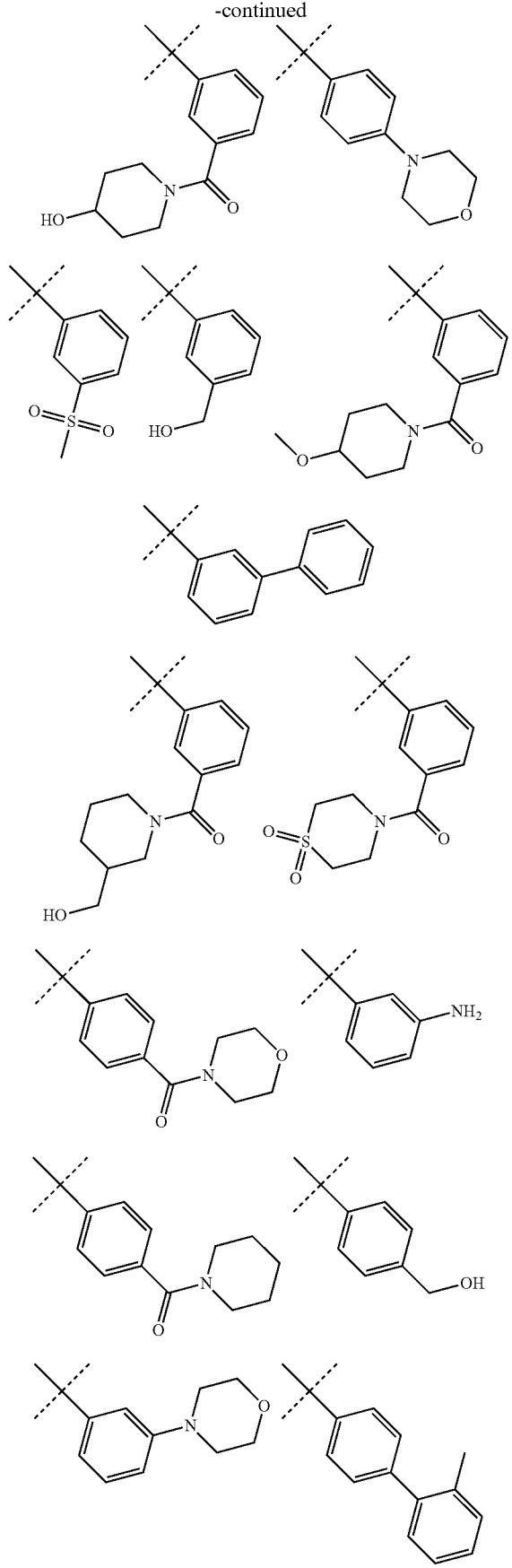
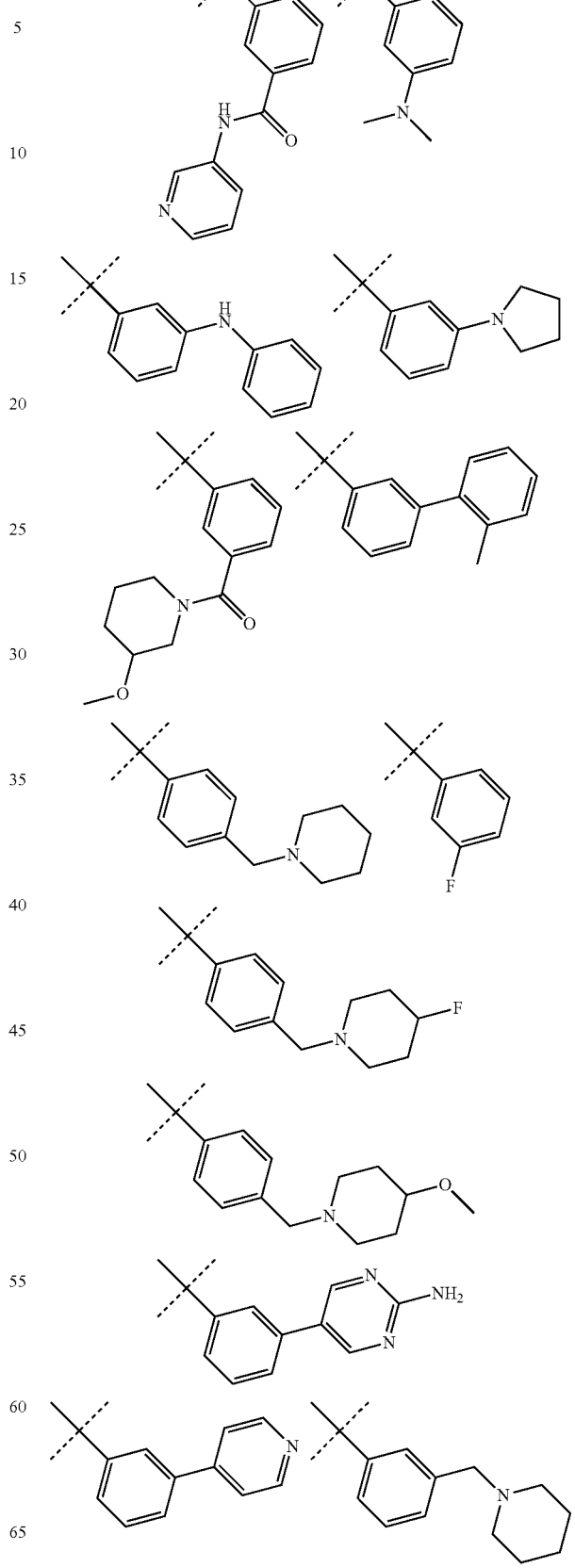

-continued
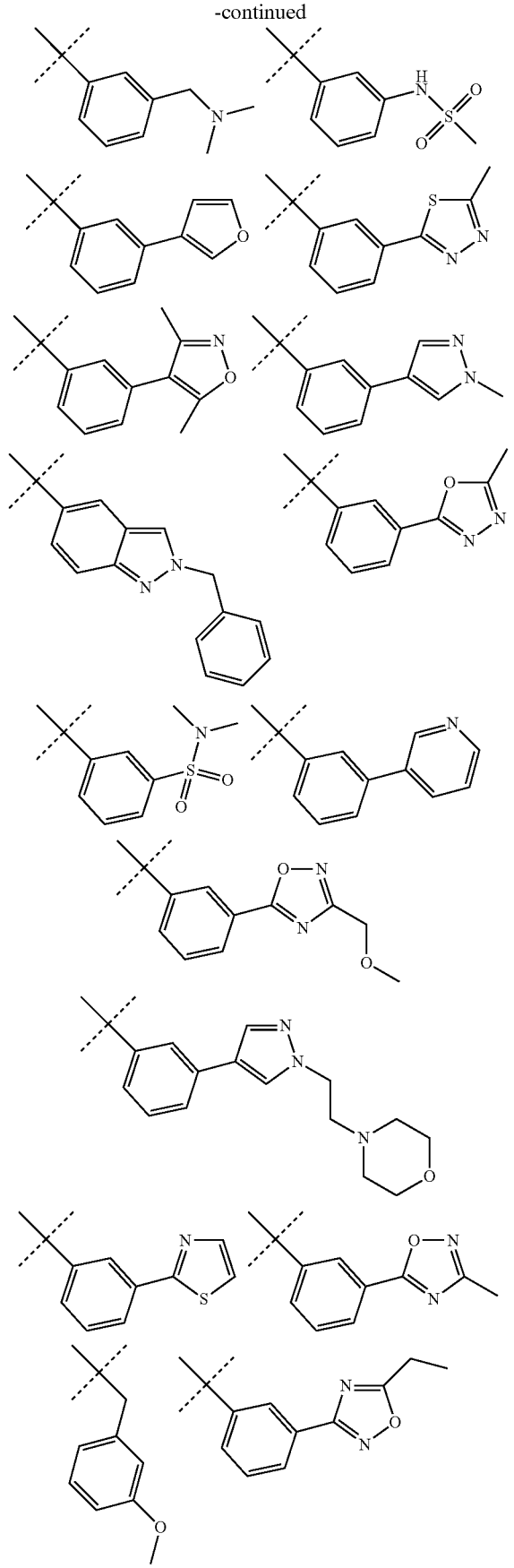
-continued
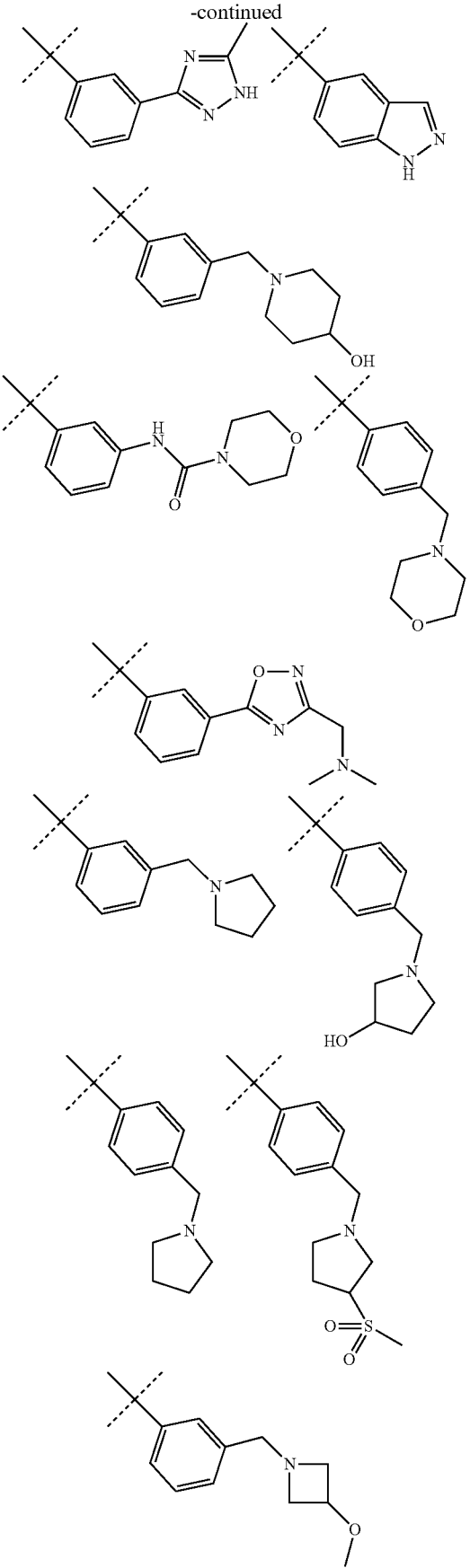

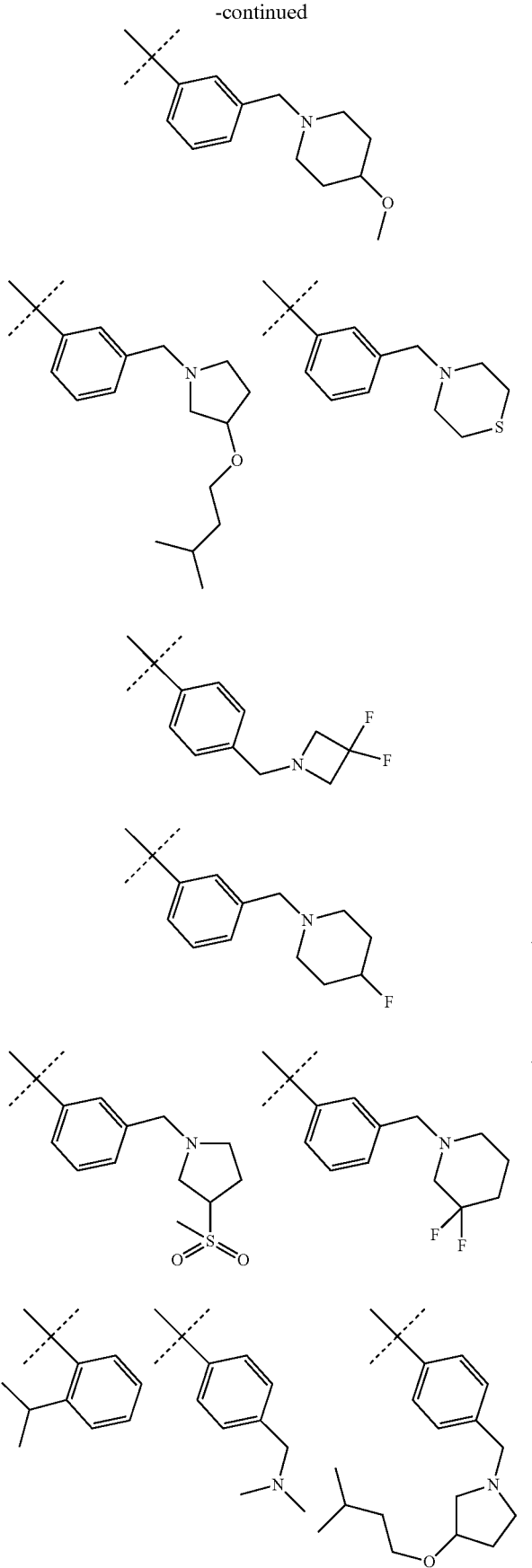
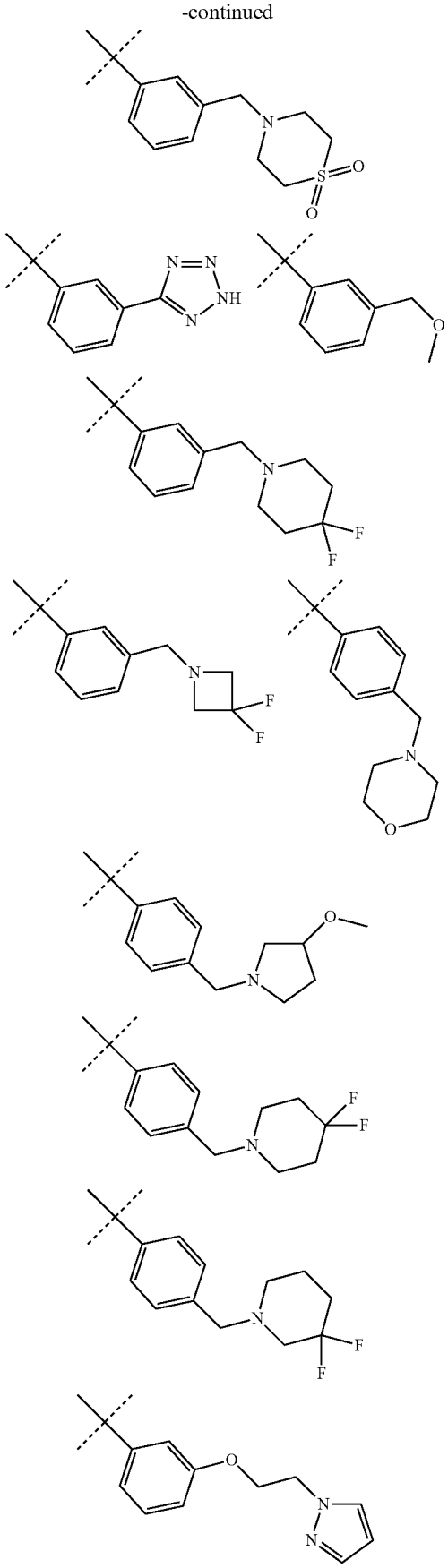

-continued
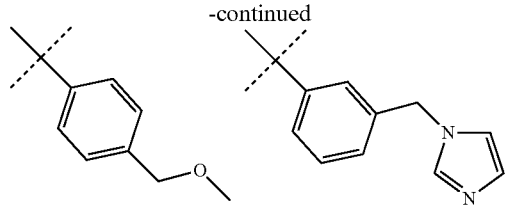
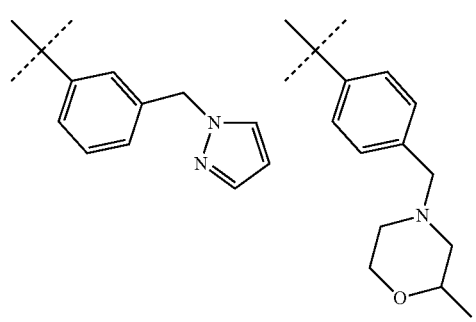
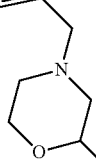
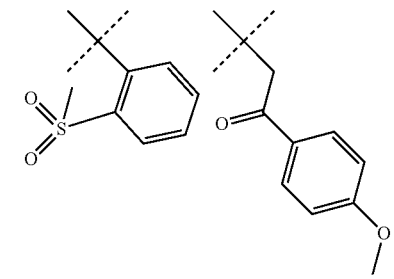
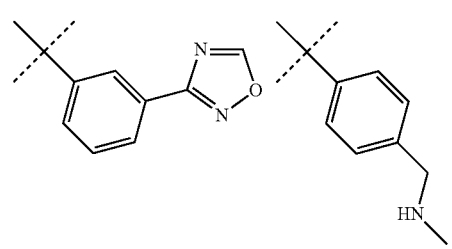
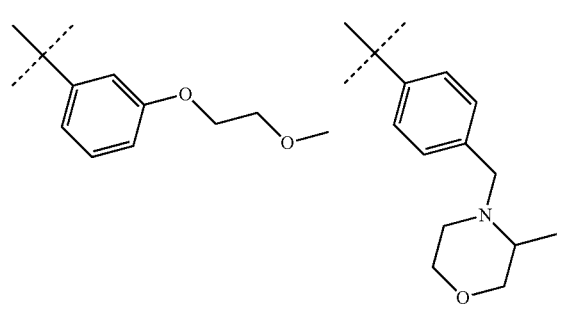
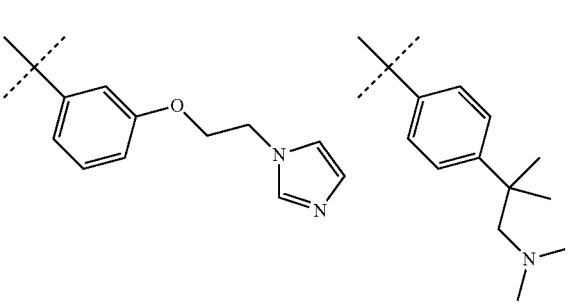
-continued
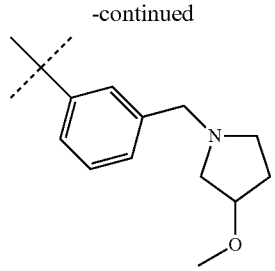
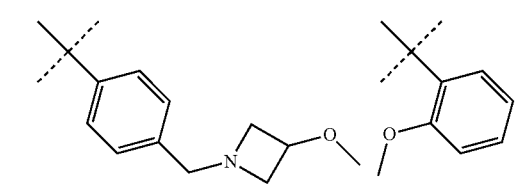
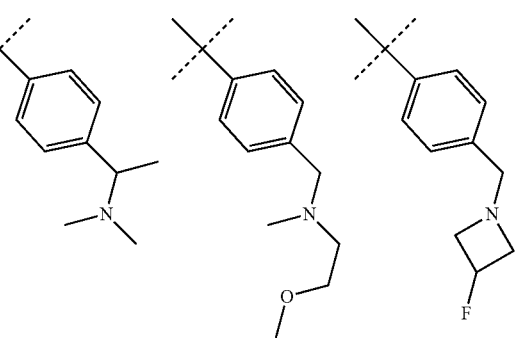
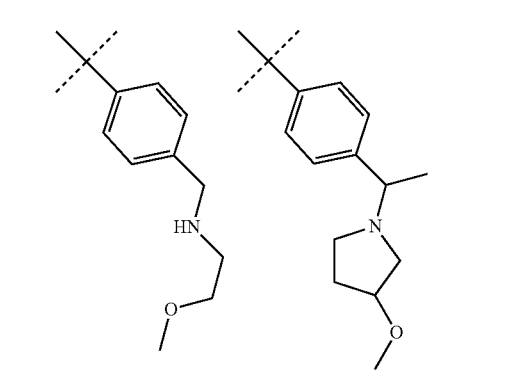
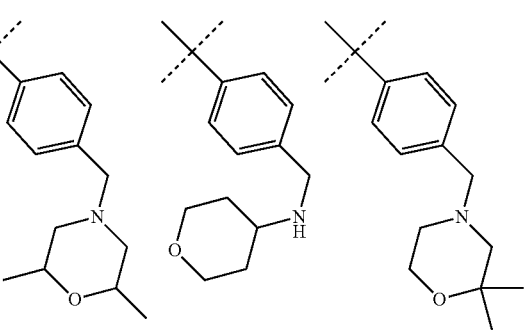

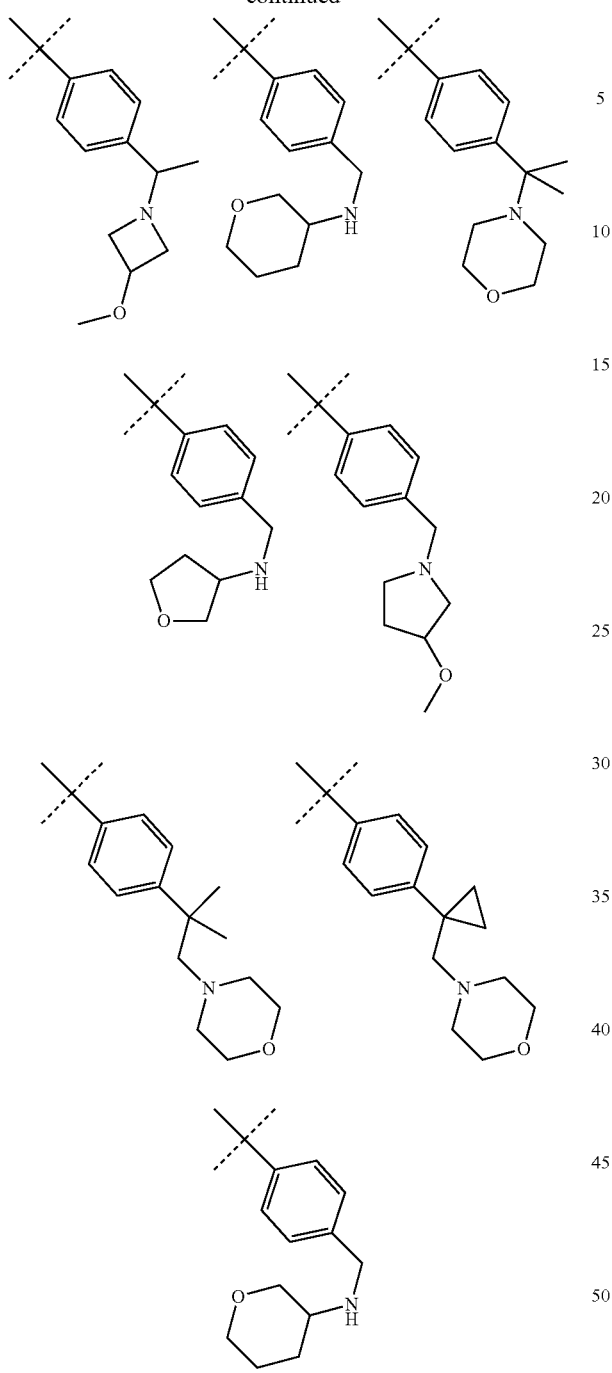
In another embodiment R² denotes one of the following groups:
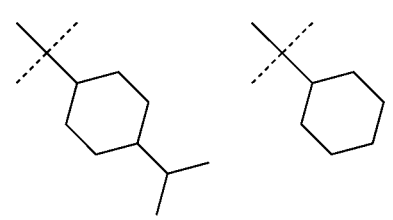
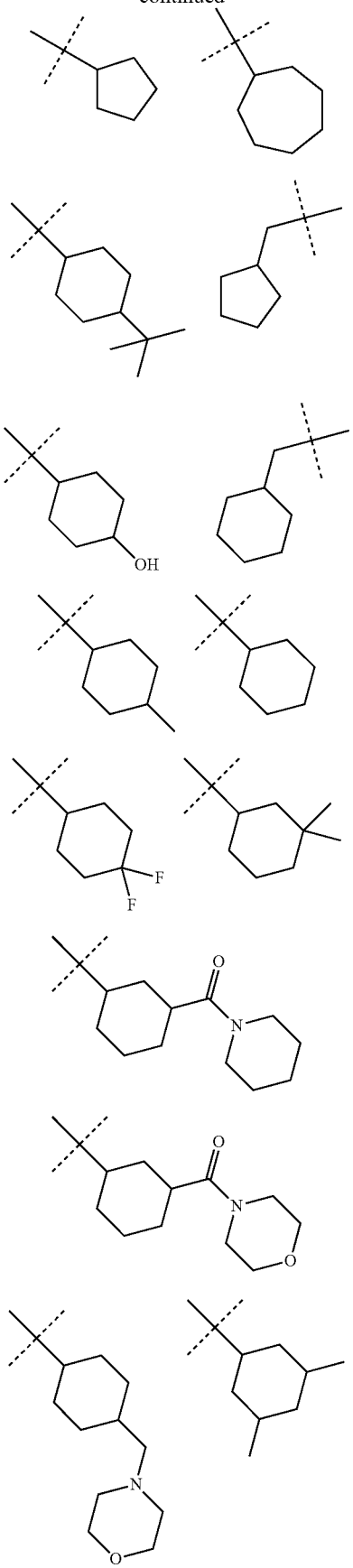

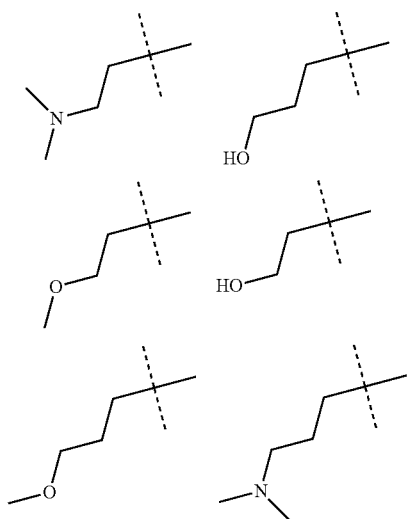
In another preferred embodiment, $R^2$ denotes one of the following groups:
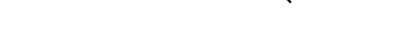

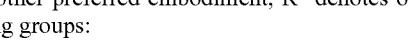
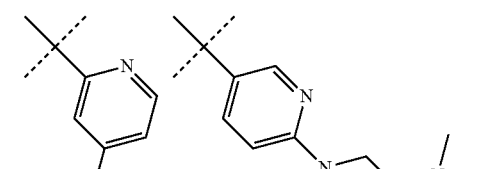

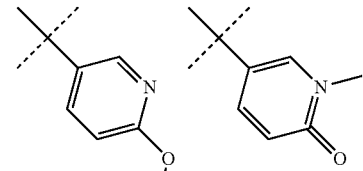
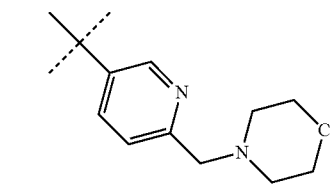
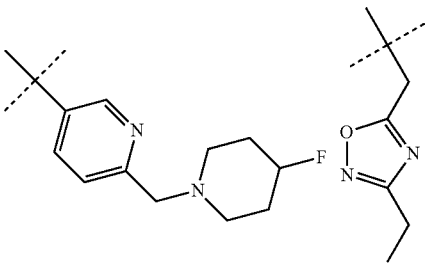
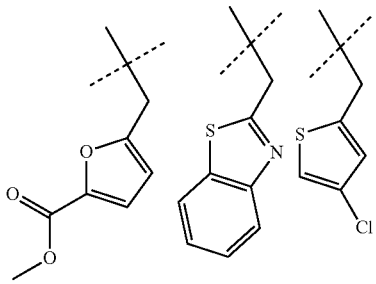
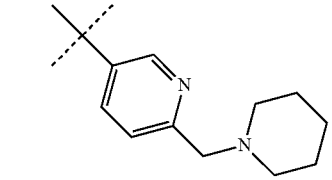
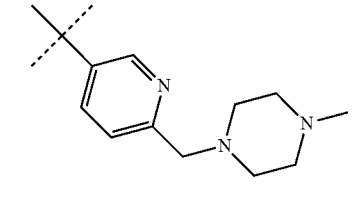
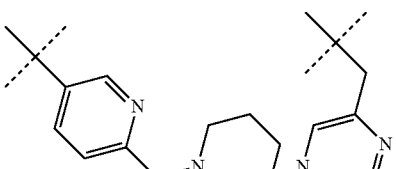
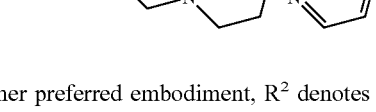
In another preferred embodiment, $R^2$ denotes one of the following groups:

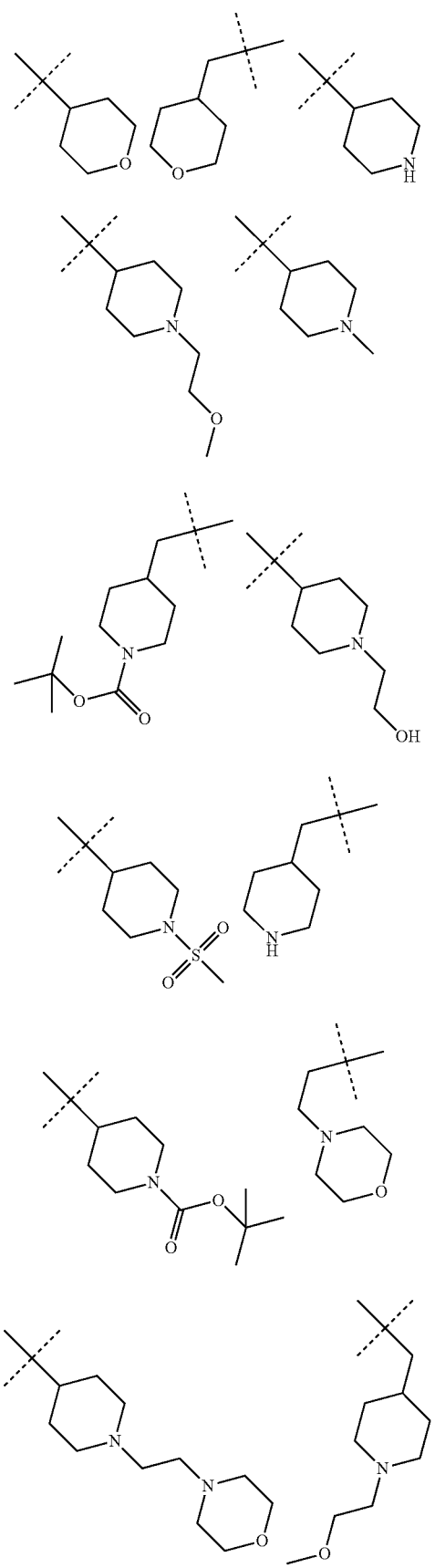
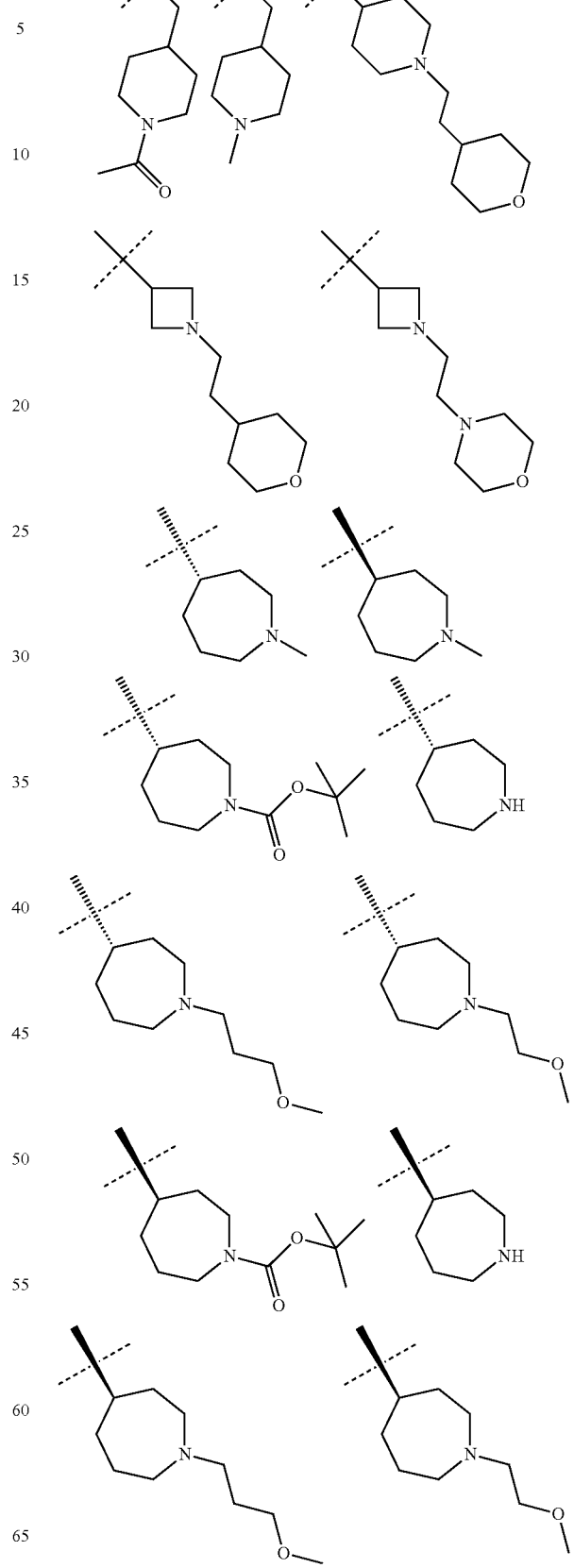

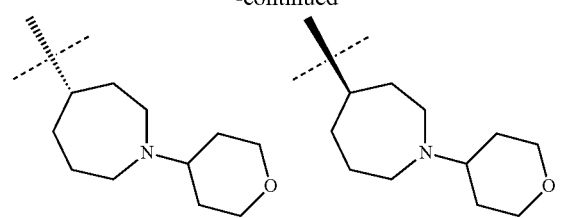
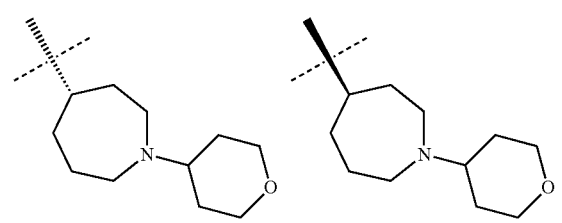
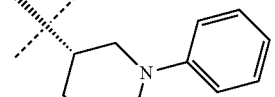
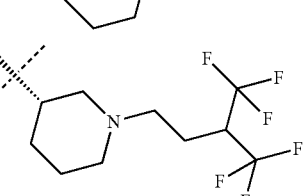
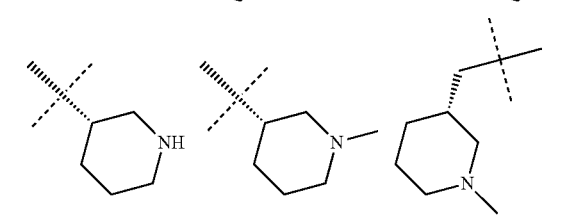
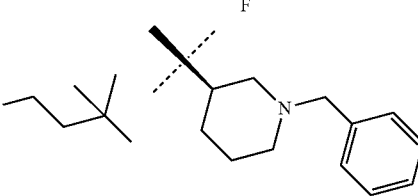
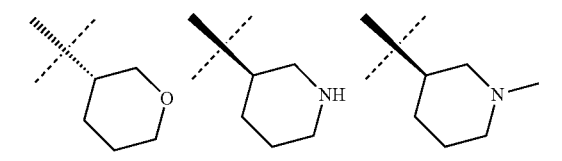
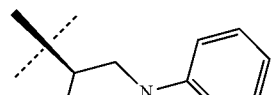

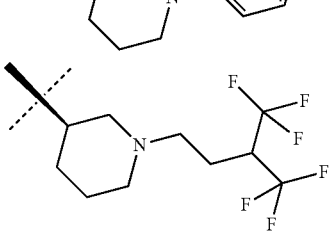
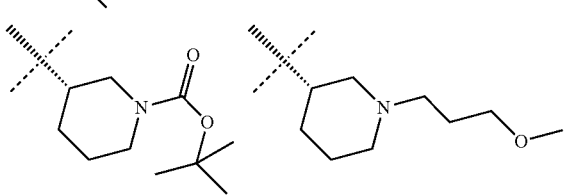
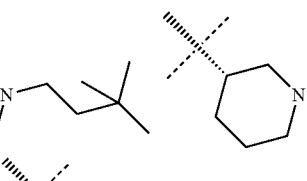
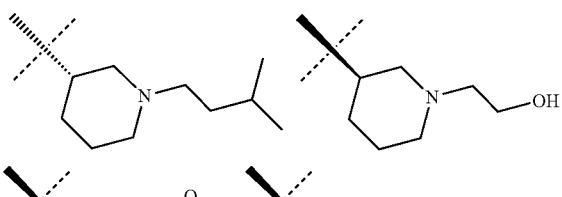
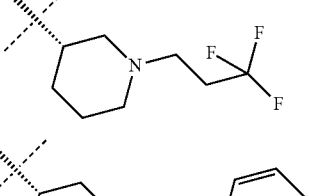
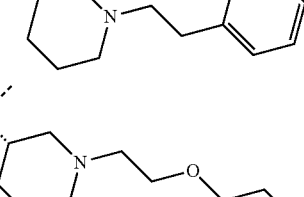
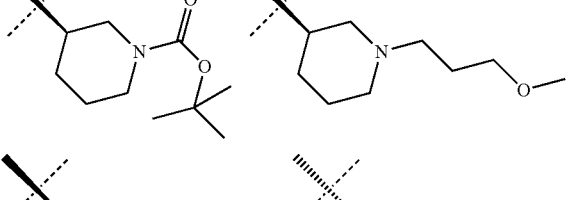
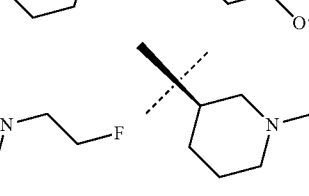
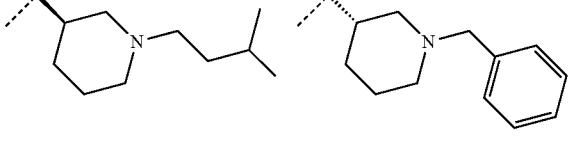
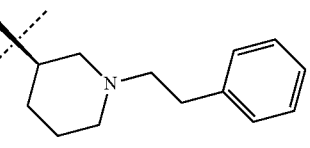

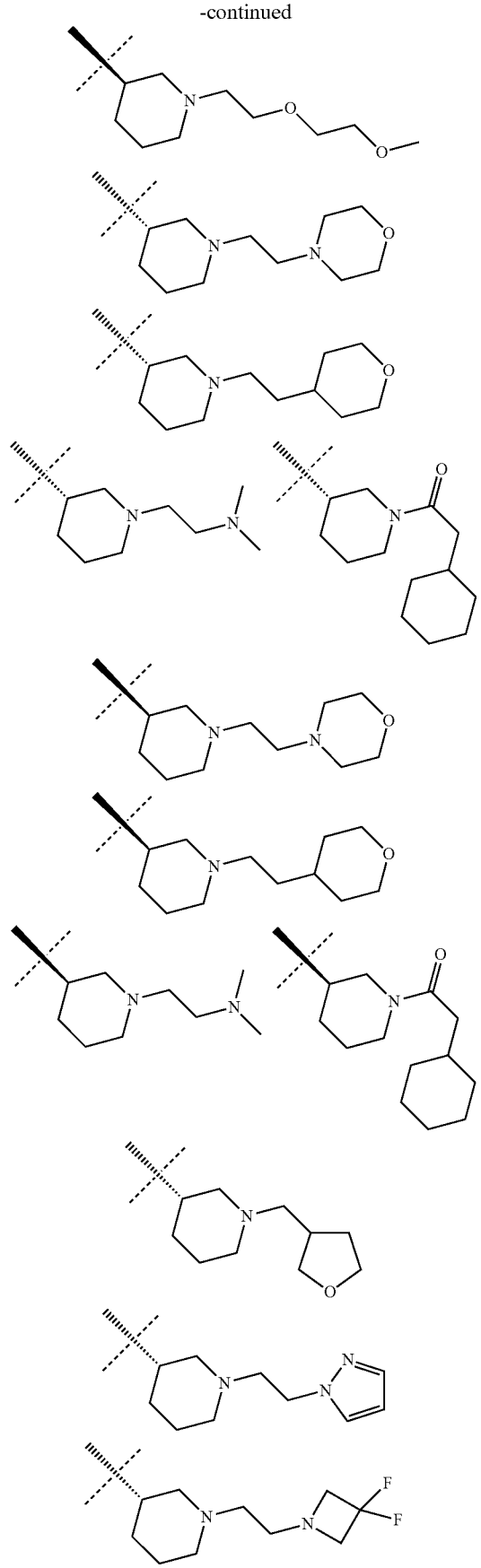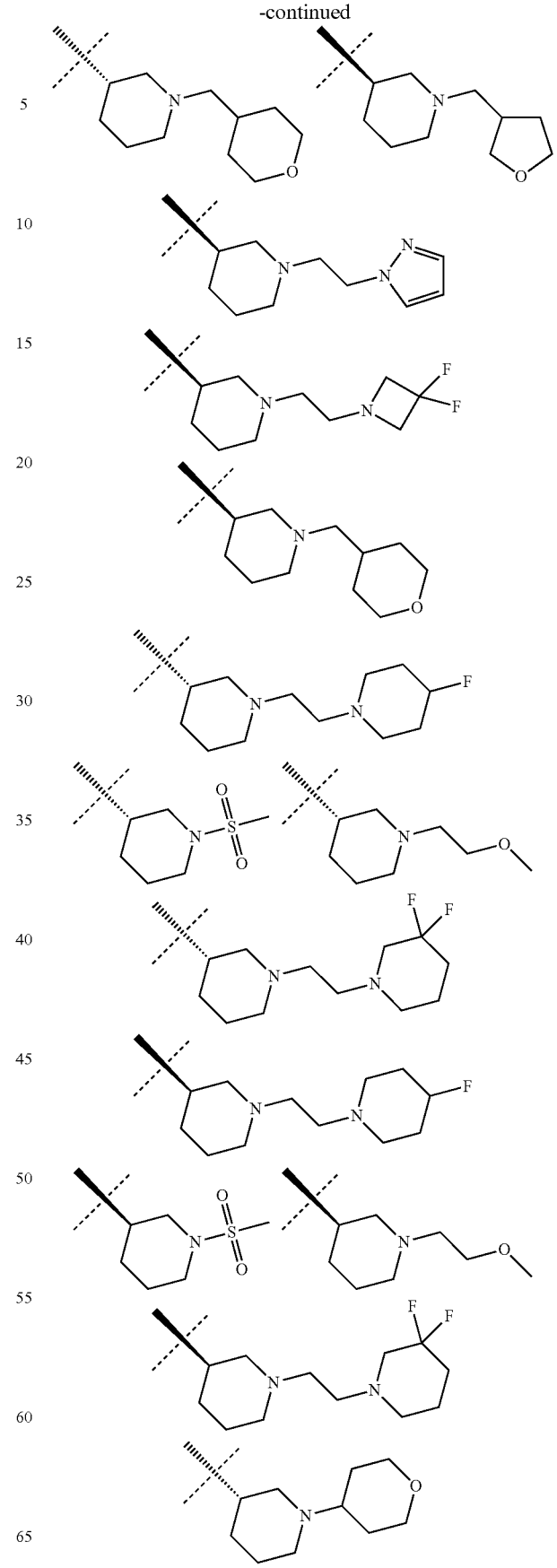

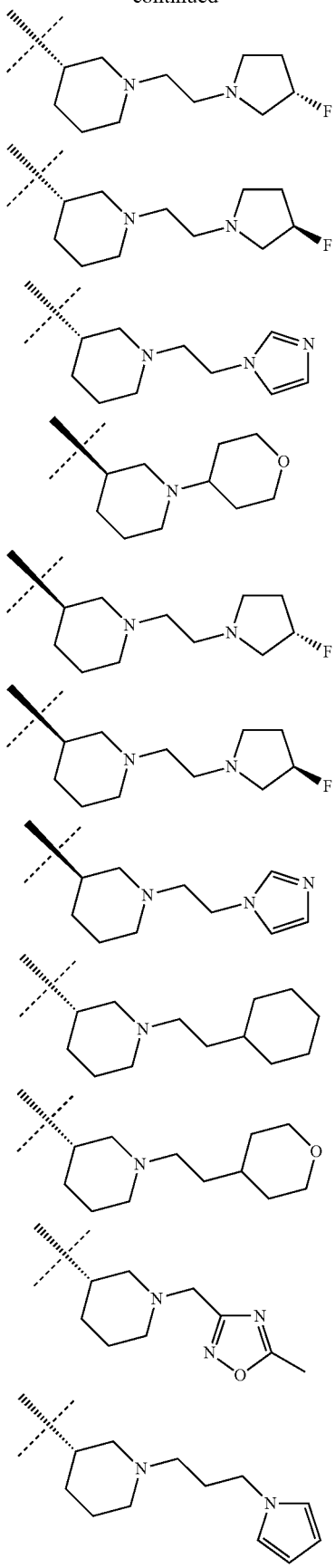
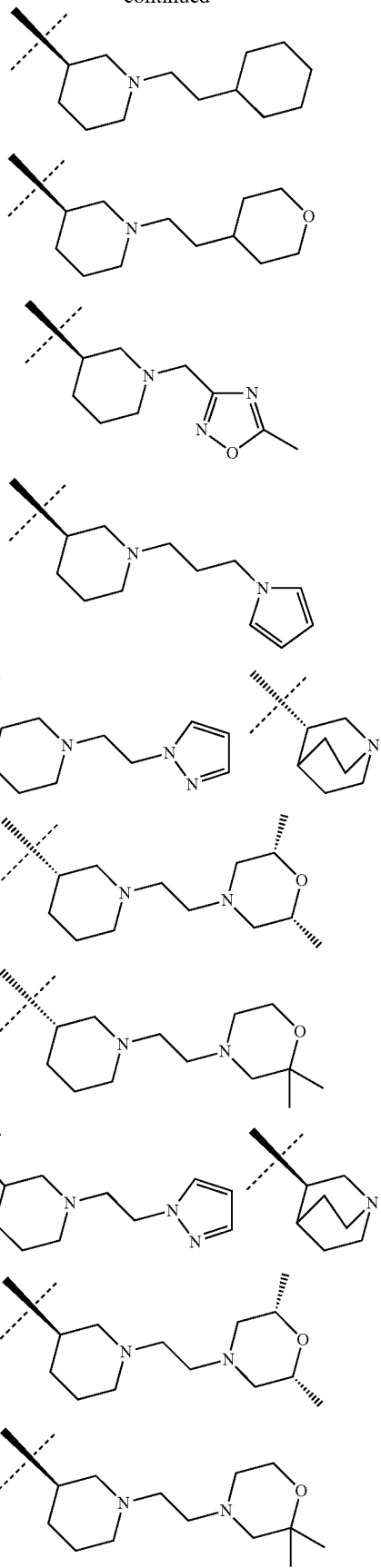

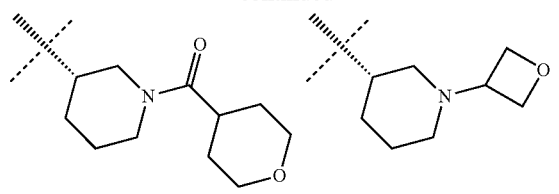
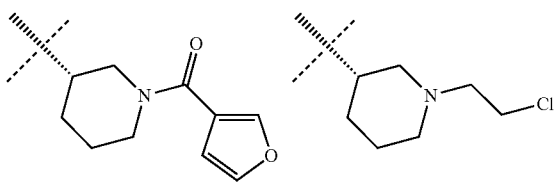
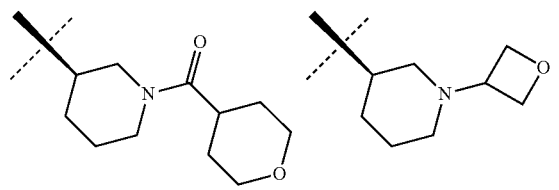
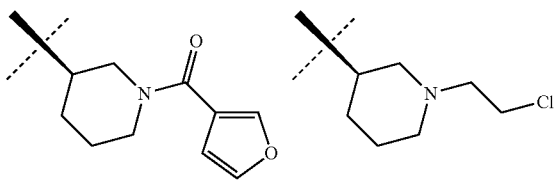
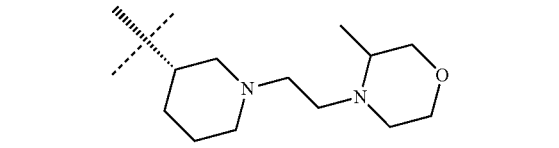
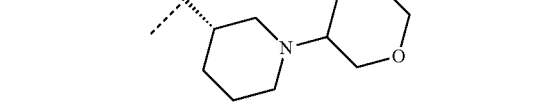
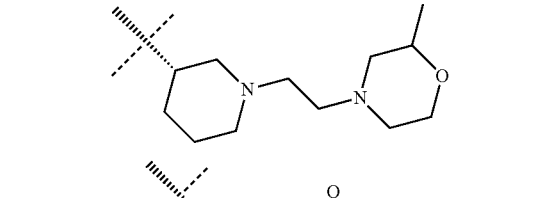
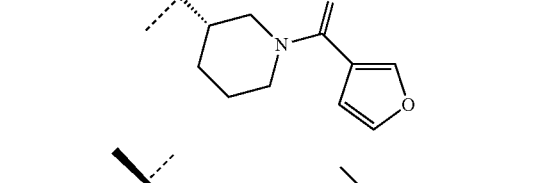
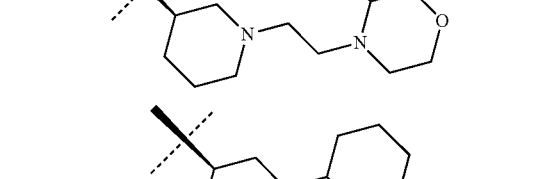
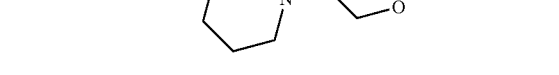
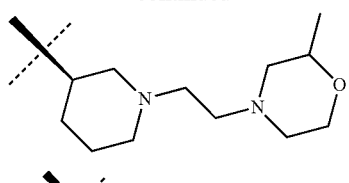
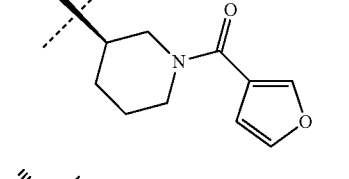
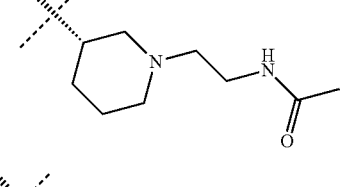
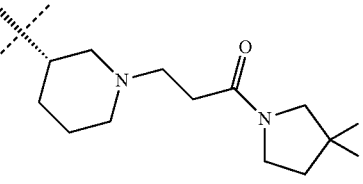
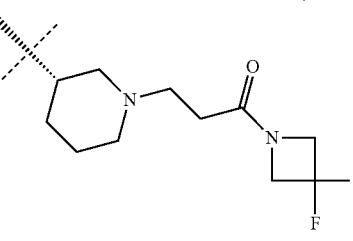
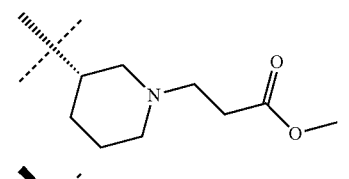
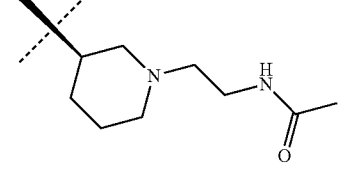
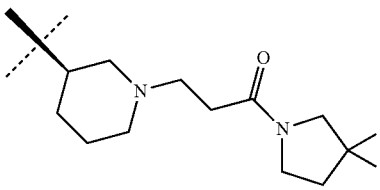
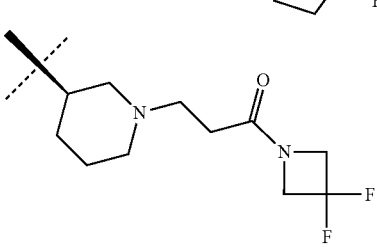


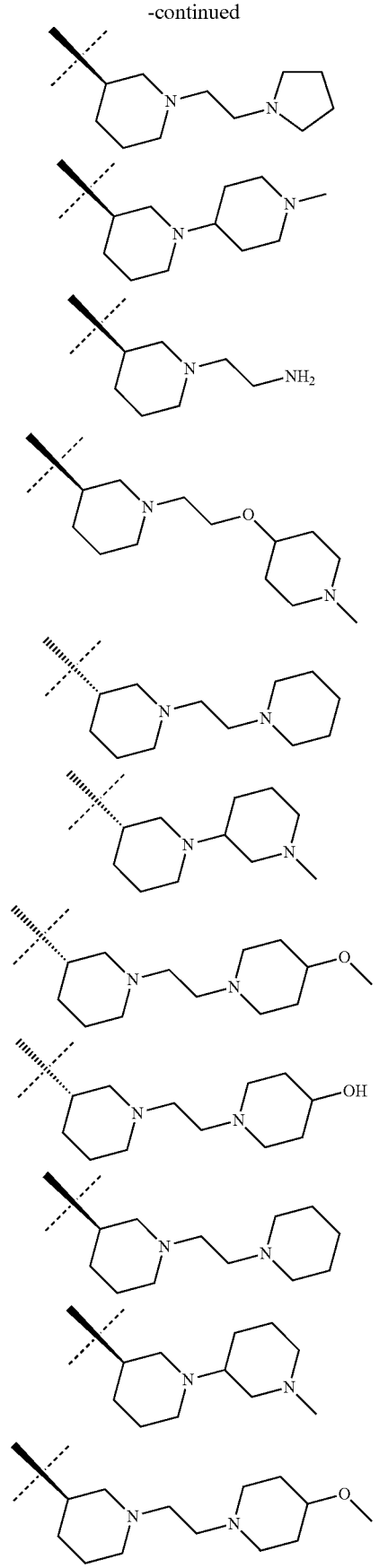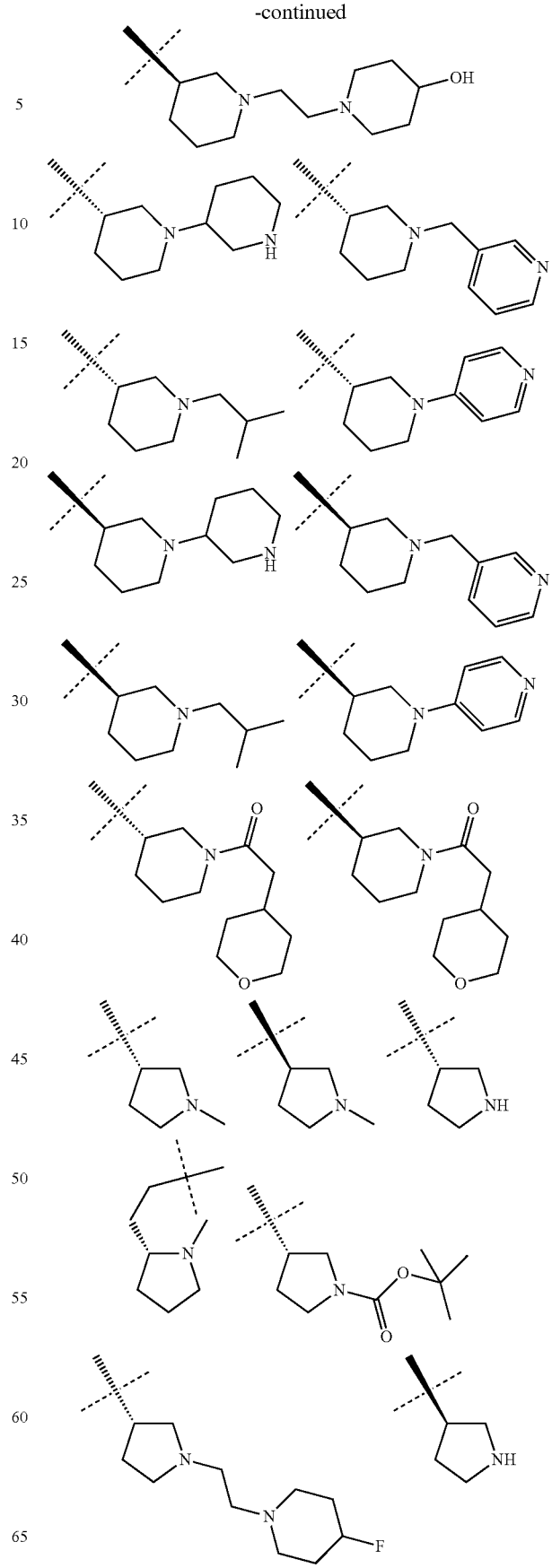

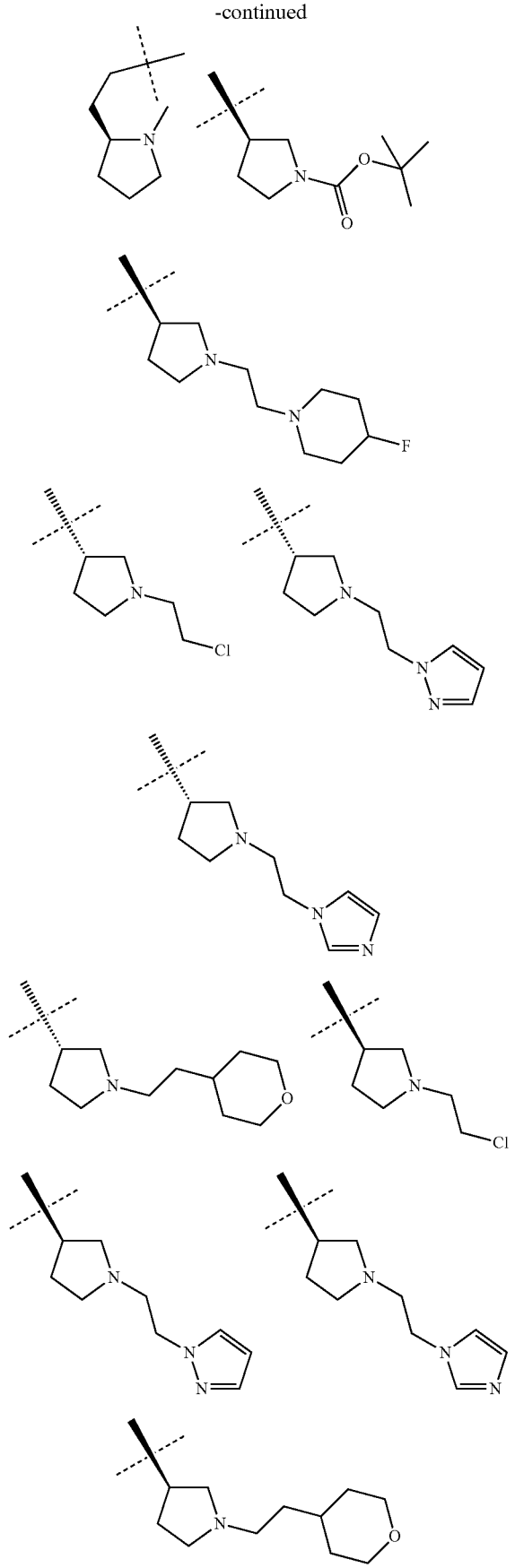
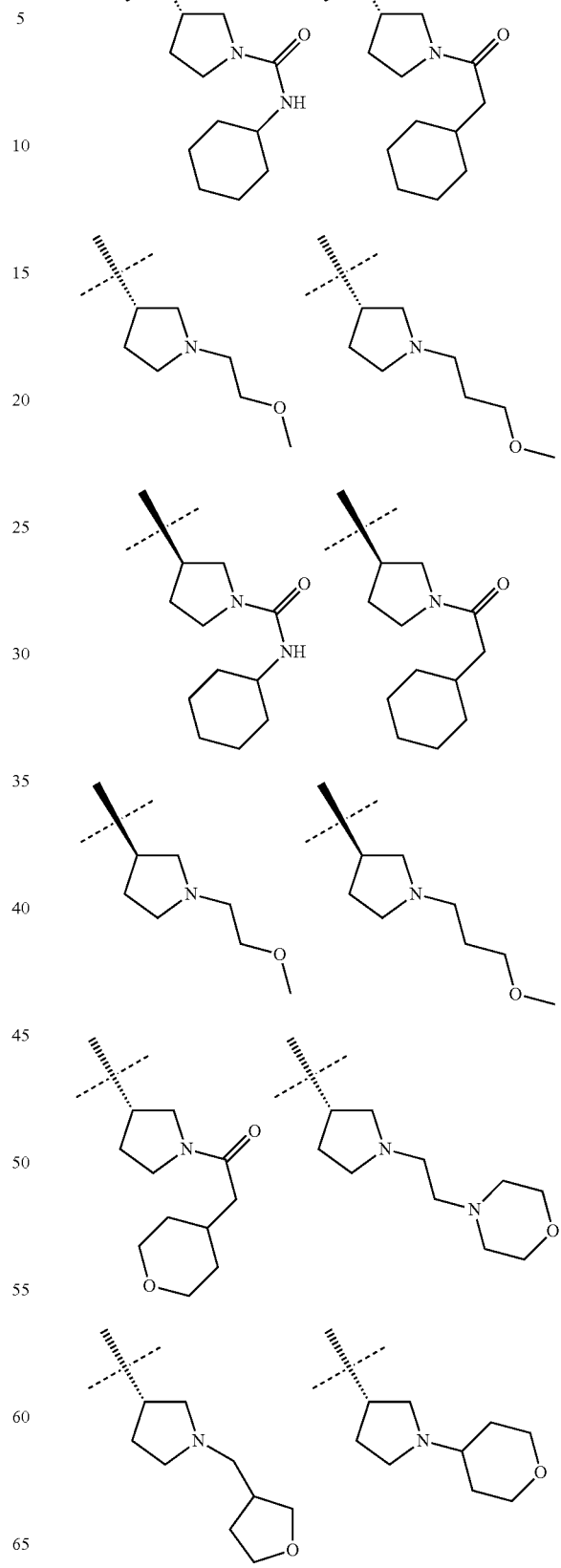

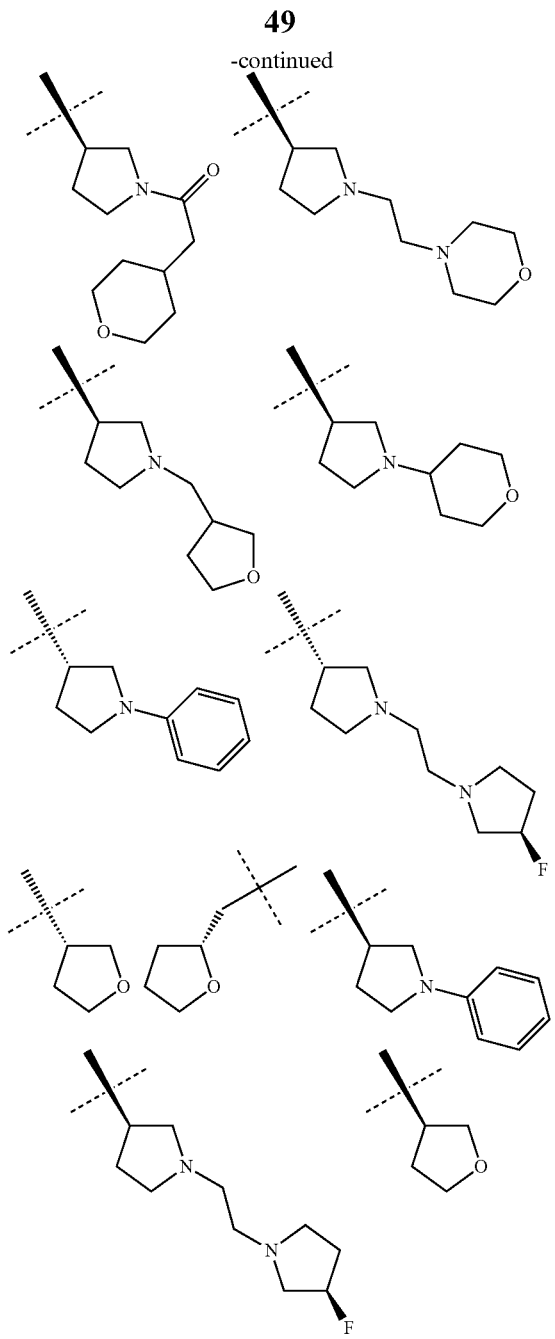

More preferably, $R^6$ denotes H or A.

More preferably, the group A denotes a branched or linear alkyl having 1 to 8 C-atoms, wherein one or more, preferably 1 to 3 H-atoms may be replaced by Hal, Ar, Het, Cyc, $OR^6$, —CN, —$CO_2Y$ or $N(R^6)_2$ and wherein one or more, preferably 1 to 3 non-adjacent $CH_2$-groups may be replaced by O, $NR^6$, $CONR^6$— and/or by —CH=CH— or —C≡C— groups, or denotes cycloalkyl or cycloalkylalkylen having 3-7 ring C atoms;

In a preferred embodiment, the invention provides compounds of Formula (I) wherein $R^5$ is H.

In another preferred embodiment, the invention provides compounds of formula (I) wherein one of $U^1$, $U^2$, $U^3$ and $U^4$ is N and the remaining are $CR^1$ whereby $R^1$ is as above defined.

In another preferred embodiment, the invention provides compounds of formula (I) wherein $R^2$ denotes H, Y, Ar, Het or Cyc, $R^3$ and $R^4$ are both H.

In another preferred embodiment, the present invention provides compounds of Formula (I) wherein $R^2$ denotes H, Y, Ar, Het or Cyc, $R^3$ and $R^4$ are both H, T is $SO_2$.

In another preferred embodiment, the present invention provides compounds of Formula (I) wherein $R^2$ denotes H, Y, Ar, Het or Cyc, $R^3$ and $R^4$ are both H, T is $SO_2$, and $U_1$, $U_2$, $U_3$ and $U_4$ are $CR^1$.

Most preferably, the invention relates to compounds of Formula (I), (I*) and related Formulae, selected from the following group. In the table below, in case the structures contain one or more stereogenic centers, the respective structure is depicted in an arbitrary absolute configuration. These structures also include the respective structure having the opposite stereochemistry and the corresponding racemate:

| Example No | structures |
|---|---|
| 1 | ![structure] |

-continued
| Example No | structures |
|---|---|
| 2 | 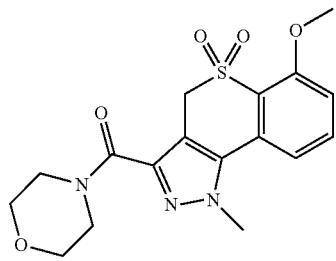 [SMILES: COc1cccc2c1S(=O)(=O)Cc1c(C(=O)N3CCOCC3)nn(C)c1-2] |
| 3 | 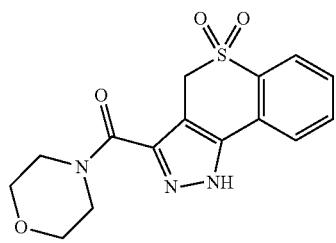 [SMILES: O=C(c1n[nH]c2c1CS(=O)(=O)c1ccccc1-2)N1CCOCC1] |
| 4 | 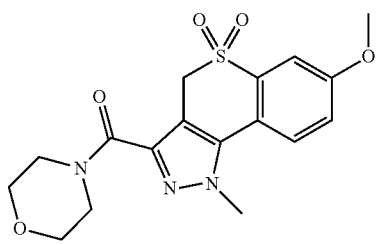 [SMILES: COc1ccc2c(c1)S(=O)(=O)Cc1c(C(=O)N3CCOCC3)nn(C)c1-2] |
| 5 | 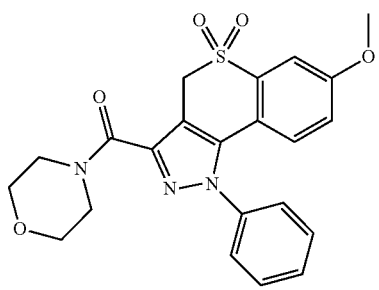 [SMILES: COc1ccc2c(c1)S(=O)(=O)Cc1c(C(=O)N3CCOCC3)nn(-c3ccccc3)c1-2] |
| 6 | 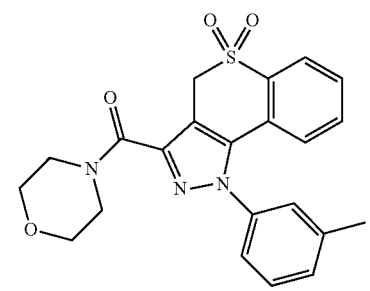 [SMILES: Cc1cccc(-n2nc(C(=O)N3CCOCC3)c3c2-c2ccccc2S(=O)(=O)C3)c1] |

-continued
| Example No | structures |
|---|---|
| 7 | 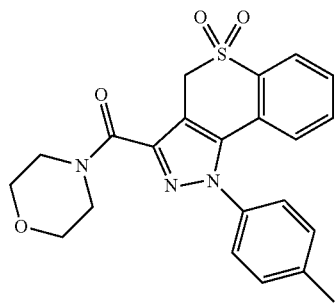 [SMILES: Cc1ccc(-n2nc(C(=O)N3CCOCC3)c3c2-c2ccccc2S(=O)(=O)C3)cc1] |
| 8 | 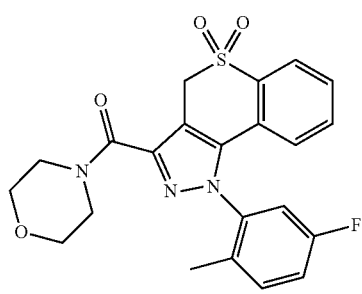 [SMILES: Cc1ccc(F)cc1-n1nc(C(=O)N2CCOCC2)c2c1-c1ccccc1S(=O)(=O)C2] |
| 9 | 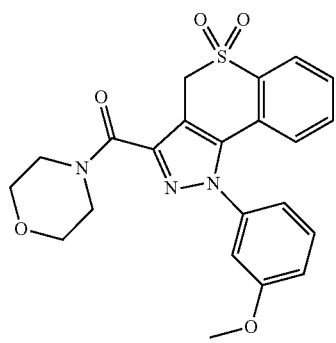 [SMILES: COc1cccc(-n2nc(C(=O)N3CCOCC3)c3c2-c2ccccc2S(=O)(=O)C3)c1] |
| 10 | 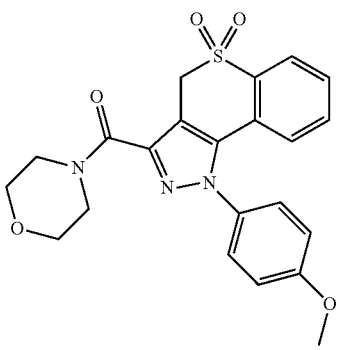 [SMILES: COc1ccc(-n2nc(C(=O)N3CCOCC3)c3c2-c2ccccc2S(=O)(=O)C3)cc1] |
| 11 | 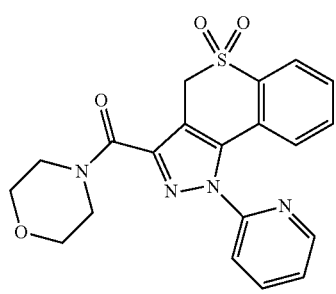 [SMILES: O=C(c1nn(-c2ccccn2)c2c1CS(=O)(=O)c1ccccc1-2)N1CCOCC1] |

-continued
| Example No | structures |
|---|---|
| 12 | 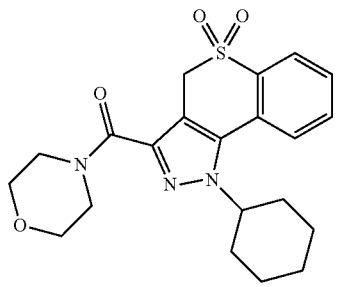 [SMILES: O=C(c1nn(C2CCCCC2)c2c1CS(=O)(=O)c1ccccc1-2)N1CCOCC1] |
| 13 | 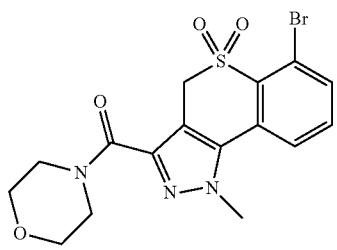 [SMILES: Cn1nc(C(=O)N2CCOCC2)c2c1-c1cccc(Br)c1S(=O)(=O)C2] |
| 14 | 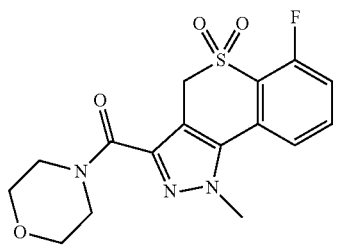 [SMILES: Cn1nc(C(=O)N2CCOCC2)c2c1-c1cccc(F)c1S(=O)(=O)C2] |
| 15 | 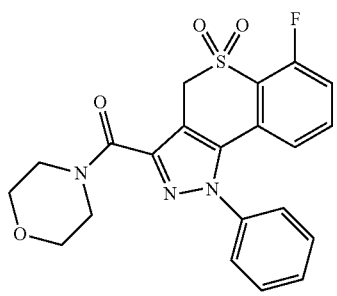 [SMILES: O=C(c1nn(-c2ccccc2)c2c1CS(=O)(=O)c1c(F)cccc1-2)N1CCOCC1] |
| 16 | 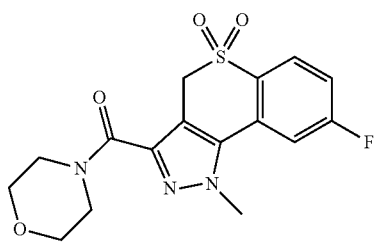 [SMILES: Cn1nc(C(=O)N2CCOCC2)c2c1-c1cc(F)ccc1S(=O)(=O)C2] |

-continued
| Example No | structures |
|---|---|
| 17 | 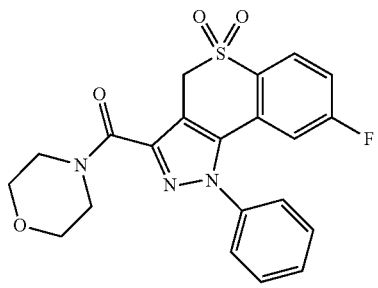 [SMILES: O=C(c1nn(-c2ccccc2)c2c1CS(=O)(=O)c1ccc(F)cc1-2)N1CCOCC1] |
| 18 | 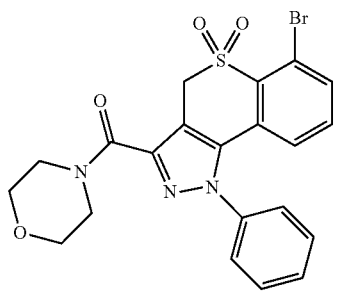 [SMILES: O=C(c1nn(-c2ccccc2)c2c1CS(=O)(=O)c1c(Br)cccc1-2)N1CCOCC1] |
| 19 | 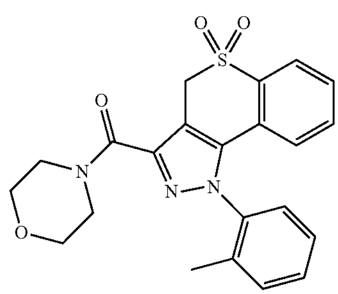 [SMILES: Cc1ccccc1-n1nc(C(=O)N2CCOCC2)c2c1-c1ccccc1S(=O)(=O)C2] |
| 20 | 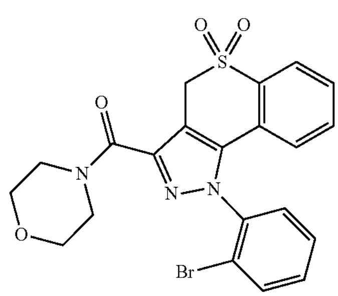 [SMILES: O=C(c1nn(-c2ccccc2Br)c2c1CS(=O)(=O)c1ccccc1-2)N1CCOCC1] |
| 21 | 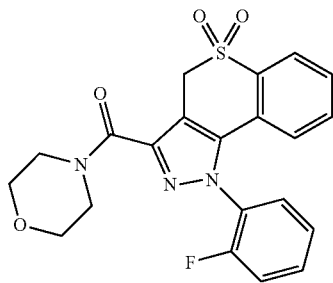 |

-continued

| Example No | structures |
|---|---|
| 22 | 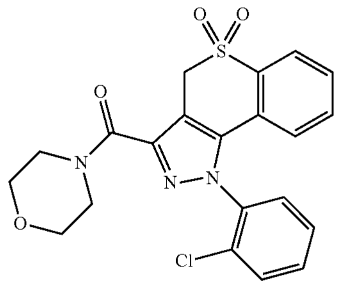 [SMILES: O=C(c1nn(-c2ccccc2Cl)c2c1CS(=O)(=O)c1ccccc1-2)N1CCOCC1] |
| 23 | 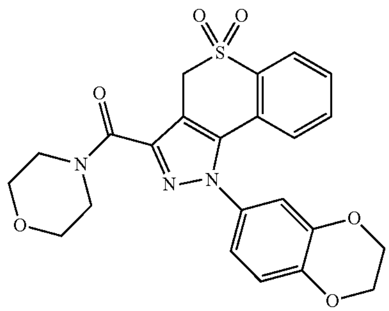 [SMILES: O=C(c1nn(-c2ccc3c(c2)OCCO3)c2c1CS(=O)(=O)c1ccccc1-2)N1CCOCC1] |
| 24 | 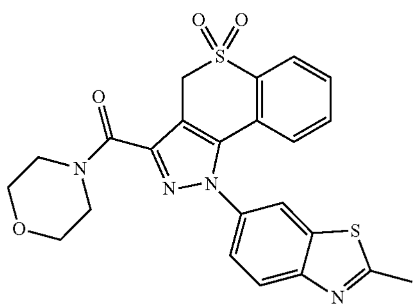 [SMILES: Cc1nc2ccc(-n3nc(C(=O)N4CCOCC4)c4c3-c3ccccc3S(=O)(=O)C4)cc2s1] |
| 25 | 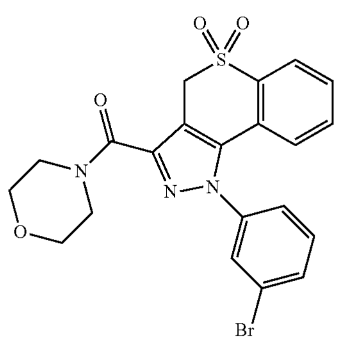 [SMILES: O=C(c1nn(-c2cccc(Cl)c2)c2c1CS(=O)(=O)c1ccccc1-2)N1CCOCC1] |
| 26 | 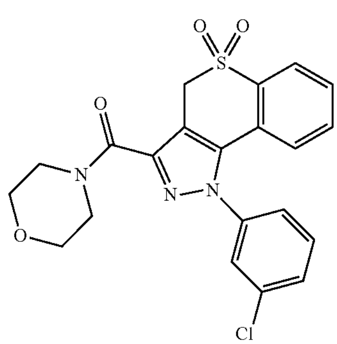 |

-continued
| Example No | structures |
|---|---|
| 27 | 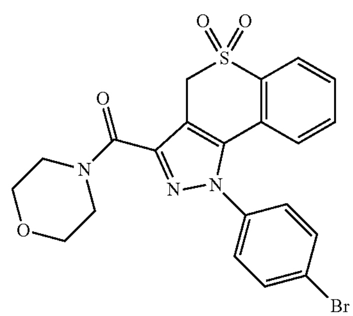 [SMILES: O=C(c1nn(-c2ccc(Br)cc2)c2c1CS(=O)(=O)c1ccccc1-2)N1CCOCC1] |
| 28 | 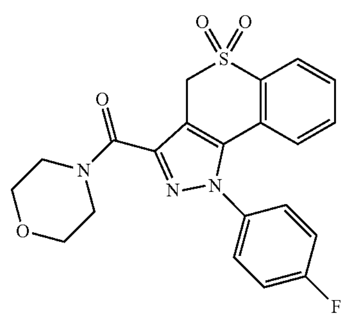 [SMILES: O=C(c1nn(-c2ccc(F)cc2)c2c1CS(=O)(=O)c1ccccc1-2)N1CCOCC1] |
| 29 | 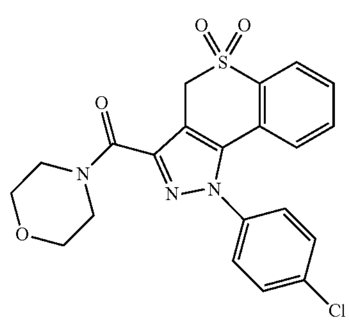 [SMILES: O=C(c1nn(-c2ccc(Cl)cc2)c2c1CS(=O)(=O)c1ccccc1-2)N1CCOCC1] |
| 30 | 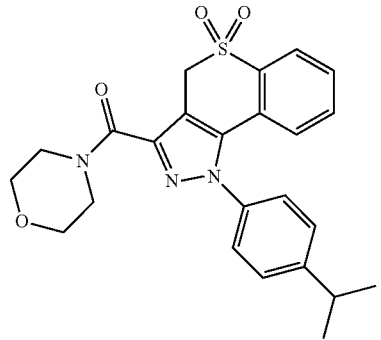 [SMILES: CC(C)c1ccc(-n2nc(C(=O)N3CCOCC3)c3c2-c2ccccc2S(=O)(=O)C3)cc1] |

-continued
| Example No | structures |
|---|---|
| 31 | 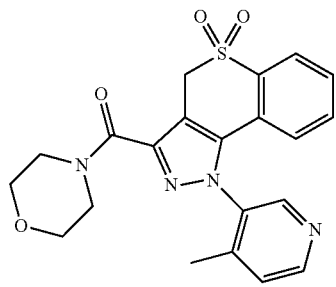 [SMILES: Cc1ccncc1-n1nc(C(=O)N2CCOCC2)c2c1-c1ccccc1S(=O)(=O)C2] |
| 32 | 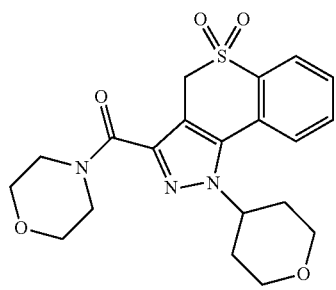 [SMILES: O=C(c1nn(C2CCOCC2)c2c1CS(=O)(=O)c1ccccc1-2)N1CCOCC1] |
| 33 | 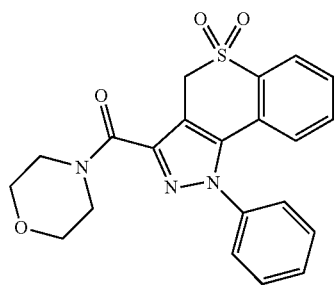 [SMILES: O=C(c1nn(-c2ccccc2)c2c1CS(=O)(=O)c1ccccc1-2)N1CCOCC1] |
| 34 | 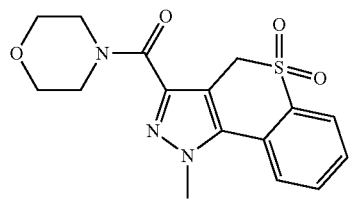 [SMILES: Cn1nc(C(=O)N2CCOCC2)c2c1-c1ccccc1S(=O)(=O)C2] |
| 35 | 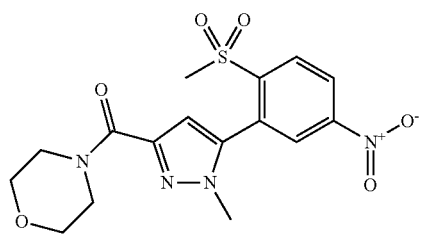 [SMILES: Cn1nc(C(=O)N2CCOCC2)cc1-c1cc([N+](=O)[O-])ccc1S(C)(=O)=O] |

-continued
| Example No | structures |
|---|---|
| 36 | 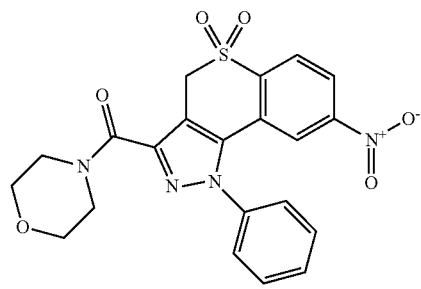 [SMILES: O=C(c1nn(-c2ccccc2)c2c1CS(=O)(=O)c1ccc([N+](=O)[O-])cc1-2)N1CCOCC1] |
| 37 | 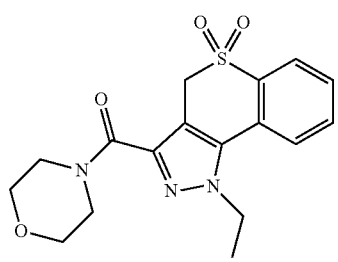 [SMILES: CCn1nc(C(=O)N2CCOCC2)c2c1-c1ccccc1S(=O)(=O)C2] |
| 38 | 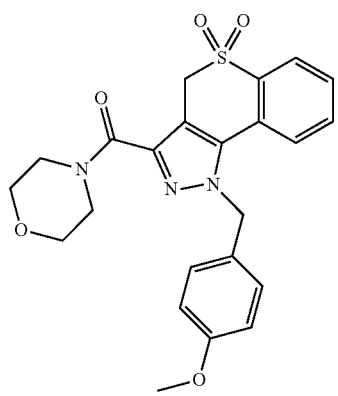 [SMILES: COc1ccc(Cn2nc(C(=O)N3CCOCC3)c3c2-c2ccccc2S(=O)(=O)C3)cc1] |
| 39 | 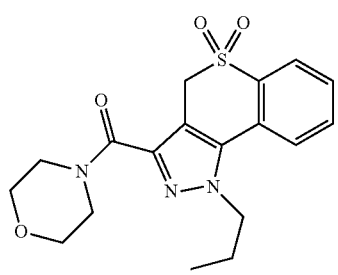 [SMILES: CCCn1nc(C(=O)N2CCOCC2)c2c1-c1ccccc1S(=O)(=O)C2] |
| 40 | 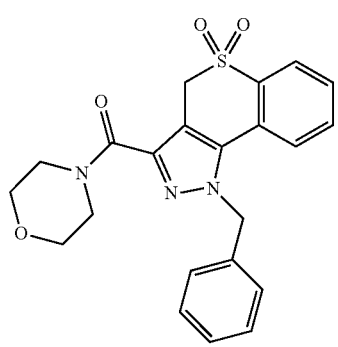 [SMILES: O=C(c1nn(Cc2ccccc2)c2c1CS(=O)(=O)c1ccccc1-2)N1CCOCC1] |

-continued
| Example No | structures |
|---|---|
| 41 | 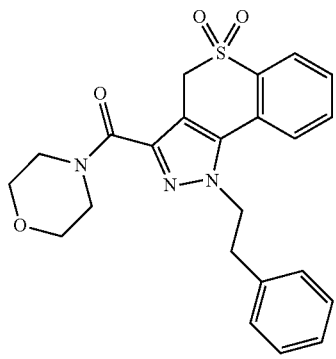 [SMILES: O=C(c1nn(CCc2ccccc2)c2c1CS(=O)(=O)c1ccccc1-2)N1CCOCC1] |
| 42 | 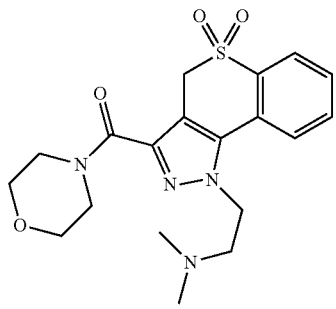 [SMILES: CN(C)CCn1nc(C(=O)N2CCOCC2)c2c1-c1ccccc1S(=O)(=O)C2] |
| 43 | 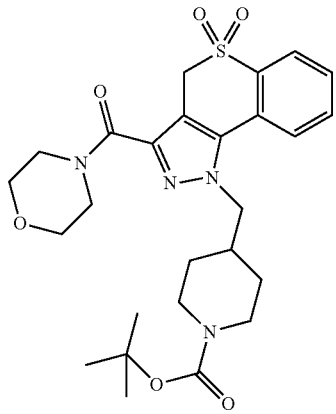 [SMILES: CC(C)(C)OC(=O)N1CCC(Cn2nc(C(=O)N3CCOCC3)c3c2-c2ccccc2S(=O)(=O)C3)CC1] |
| 44 | 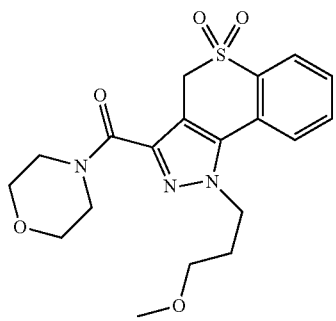 [SMILES: COCCCn1nc(C(=O)N2CCOCC2)c2c1-c1ccccc1S(=O)(=O)C2] |

-continued
| Example No | structures |
|---|---|
| 45 | 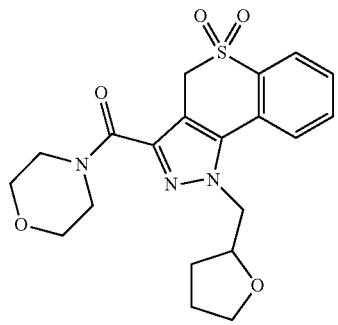 [SMILES: O=C(c1nn(CC2CCCO2)c2c1CS(=O)(=O)c1ccccc1-2)N1CCOCC1] |
| 46 | 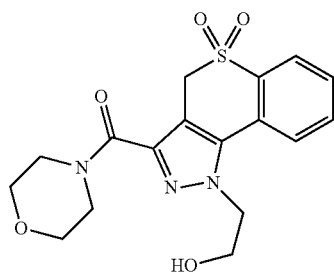 [SMILES: O=C(c1nn(CCO)c2c1CS(=O)(=O)c1ccccc1-2)N1CCOCC1] |
| 47 | 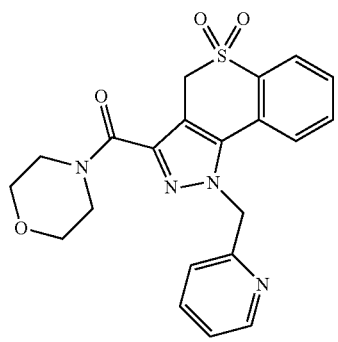 [SMILES: O=C(c1nn(Cc2ccccn2)c2c1CS(=O)(=O)c1ccccc1-2)N1CCOCC1] |
| 48 | 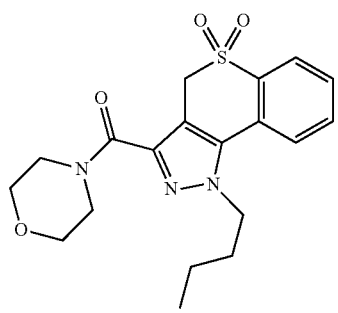 [SMILES: CCCCn1nc(C(=O)N2CCOCC2)c2c1-c1ccccc1S(=O)(=O)C2] |
| 49 | 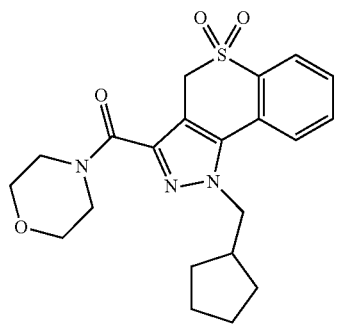 [SMILES: O=C(c1nn(CC2CCCC2)c2c1CS(=O)(=O)c1ccccc1-2)N1CCOCC1] |

| Example No | structures |
|---|---|
| 50 | 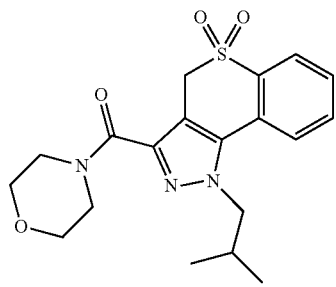 [SMILES: CC(C)Cn1nc(C(=O)N2CCOCC2)c2c1-c1ccccc1S(=O)(=O)C2] |
| 51 | 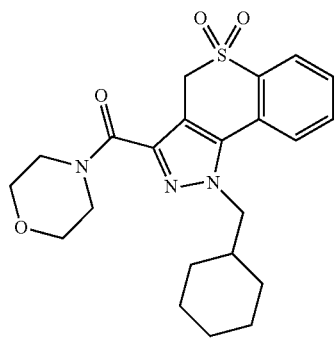 [SMILES: O=C(c1nn(CC2CCCCC2)c2c1CS(=O)(=O)c1ccccc1-2)N1CCOCC1] |
| 52 | 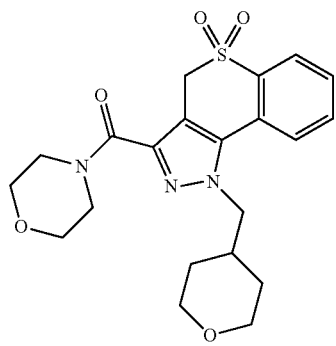 [SMILES: O=C(c1nn(CC2CCOCC2)c2c1CS(=O)(=O)c1ccccc1-2)N1CCOCC1] |
| 53 | 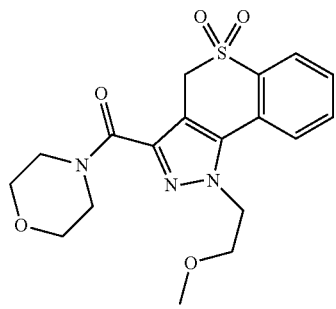 |

-continued
| Example No | structures |
|---|---|
| 54 | 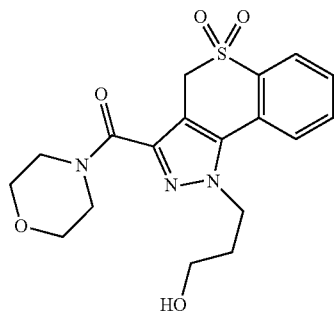 [SMILES: O=C(c1nn(CCCO)c2c1CS(=O)(=O)c1ccccc1-2)N1CCOCC1] |
| 55 | 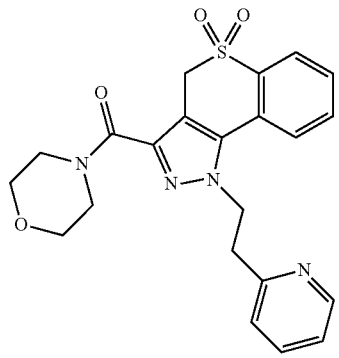 [SMILES: O=C(c1nn(CCc2ccccn2)c2c1CS(=O)(=O)c1ccccc1-2)N1CCOCC1] |
| 56 | 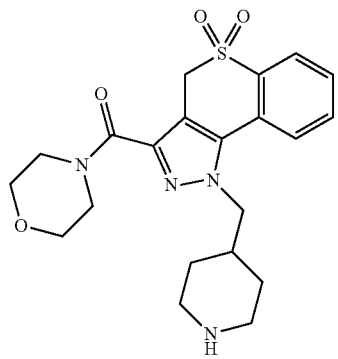 [SMILES: O=C(c1nn(CC2CCNCC2)c2c1CS(=O)(=O)c1ccccc1-2)N1CCOCC1] |
| 57 | 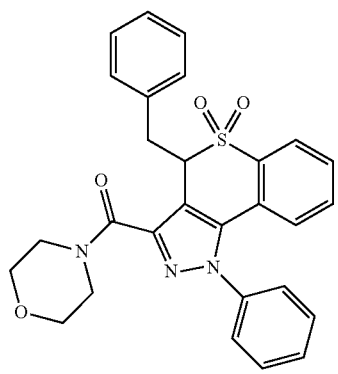 [SMILES: O=C(c1nn(-c2ccccc2)c2c1C(Cc1ccccc1)S(=O)(=O)c1ccccc1-2)N1CCOCC1] |

| Example No | structures |
|---|---|
| 58 | 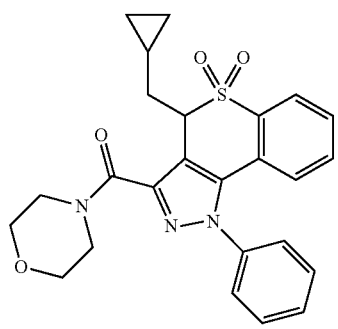 [SMILES: O=C(c1nn(-c2ccccc2)c2c1C(CC1CC1)S(=O)(=O)c1ccccc1-2)N1CCOCC1] |
| 59 | 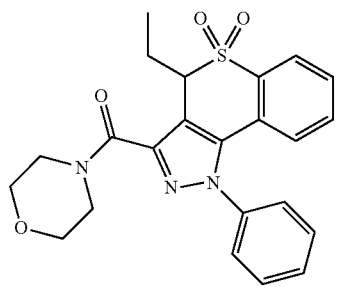 [SMILES: CCC1c2c(C(=O)N3CCOCC3)nn(-c3ccccc3)c2-c2ccccc2S1(=O)=O] |
| 60 | 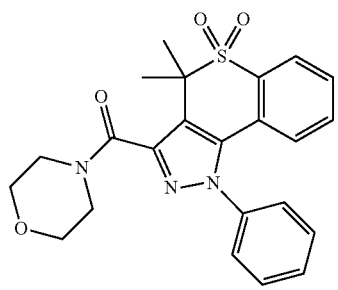 [SMILES: CC1(C)c2c(C(=O)N3CCOCC3)nn(-c3ccccc3)c2-c2ccccc2S1(=O)=O] |
| 61 | 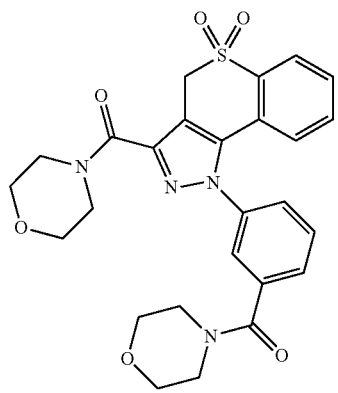 [SMILES: O=C(c1cccc(-n2nc(C(=O)N3CCOCC3)c3c2-c2ccccc2S(=O)(=O)C3)c1)N1CCOCC1] |

-continued

| Example No | structures |
|---|---|
| 62 | 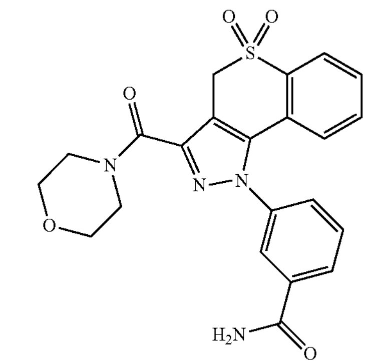 [SMILES: NC(=O)c1cccc(-n2nc(C(=O)N3CCOCC3)c3c2-c2ccccc2S(=O)(=O)C3)c1] |
| 63 | 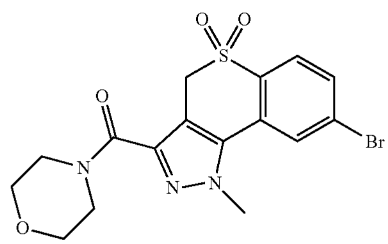 [SMILES: Cn1nc(C(=O)N2CCOCC2)c2c1-c1cc(Br)ccc1S(=O)(=O)C2] |
| 64 | 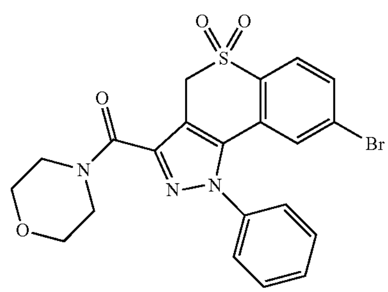 [SMILES: O=C(c1nn(-c2ccccc2)c2c1CS(=O)(=O)c1ccc(Br)cc1-2)N1CCOCC1] |
| 65 | 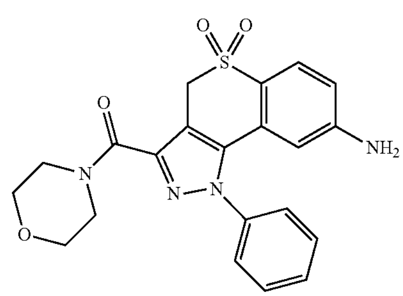 |
| 66 | 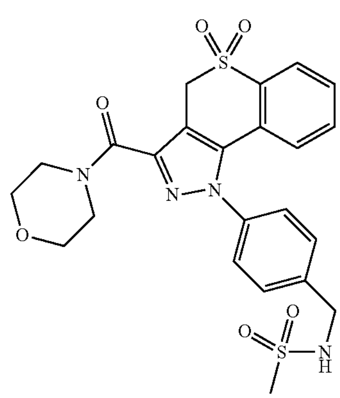 [SMILES: CS(=O)(=O)NCc1ccc(-n2nc(C(=O)N3CCOCC3)c3c2-c2ccccc2S(=O)(=O)C3)cc1] |

| Example No | structures |
|---|---|
| 67 | 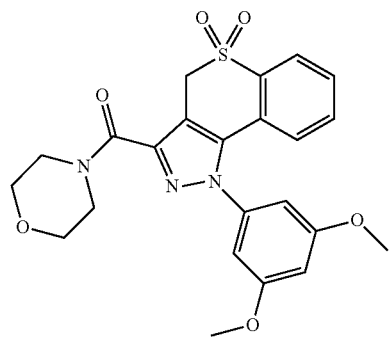 [SMILES: COc1cc(OC)cc(-n2nc(C(=O)N3CCOCC3)c3c2-c2ccccc2S(=O)(=O)C3)c1] |
| 68 | 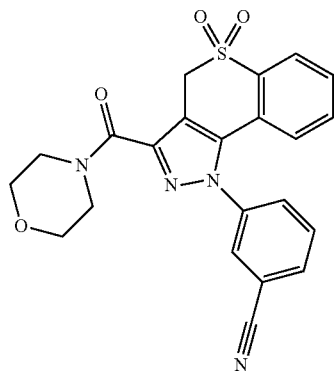 [SMILES: N#Cc1cccc(-n2nc(C(=O)N3CCOCC3)c3c2-c2ccccc2S(=O)(=O)C3)c1] |
| 69 | 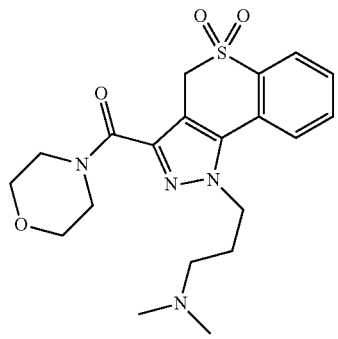 [SMILES: CN(C)CCCn1nc(C(=O)N2CCOCC2)c2c1-c1ccccc1S(=O)(=O)C2] |
| 70 | 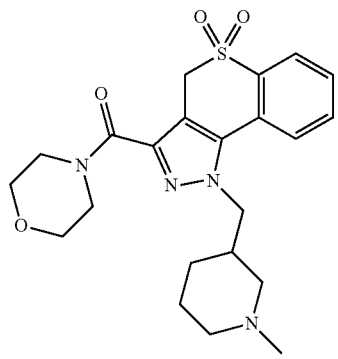 [SMILES: CN1CCCC(Cn2nc(C(=O)N3CCOCC3)c3c2-c2ccccc2S(=O)(=O)C3)C1] |

-continued
| Example No | structures |
|---|---|
| 71 | 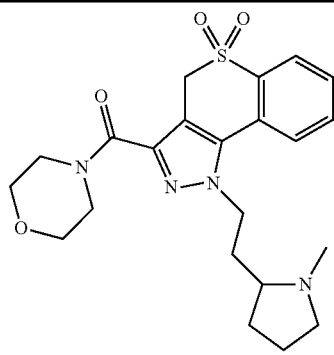 |
| 72 | 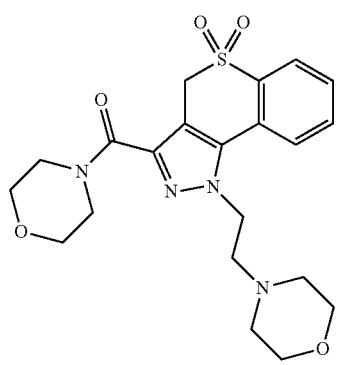 [SMILES: O=C(c1nn(CCN2CCOCC2)c2c1CS(=O)(=O)c1ccccc1-2)N1CCOCC1] |
| 73 | 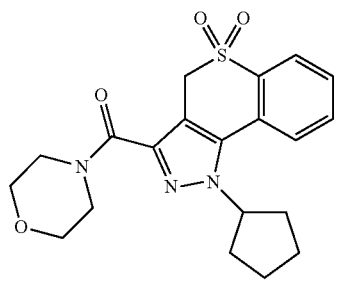 [SMILES: O=C(c1nn(C2CCCC2)c2c1CS(=O)(=O)c1ccccc1-2)N1CCOCC1] |
| 74 | 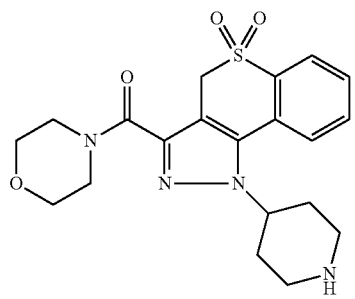 [SMILES: O=C(c1nn(C2CCNCC2)c2c1CS(=O)(=O)c1ccccc1-2)N1CCOCC1] |
| 75 | 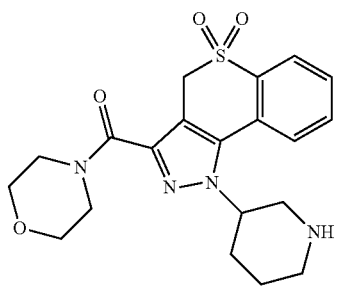 |

-continued
| Example No | structures |
|---|---|
| 76 | 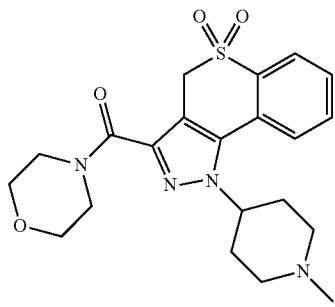 [SMILES: CN1CCC(n2nc(C(=O)N3CCOCC3)c3c2-c2ccccc2S(=O)(=O)C3)CC1] |
| 77 | 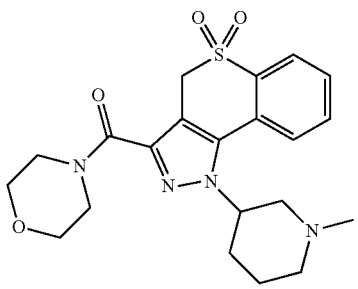 [SMILES: CN1CCCC(n2nc(C(=O)N3CCOCC3)c3c2-c2ccccc2S(=O)(=O)C3)C1] |
| 78 | 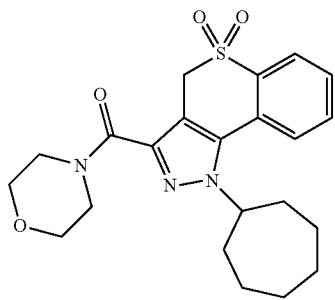 [SMILES: O=C(c1nn(C2CCCCCC2)c2c1CS(=O)(=O)c1ccccc1-2)N1CCOCC1] |
| 79 | 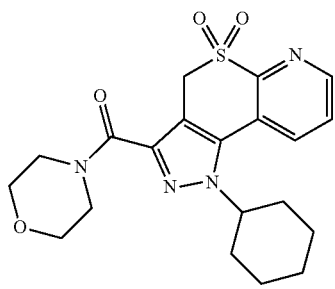 [SMILES: O=C(c1nn(C2CCCCC2)c2c1CS(=O)(=O)c1ncccc1-2)N1CCOCC1] |
| 80 | 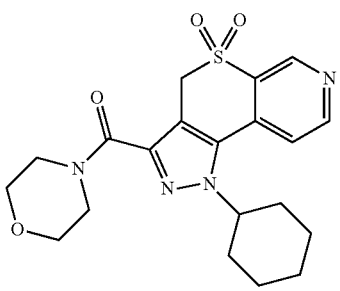 |

-continued
| Example No | structures |
|---|---|
| 81 | 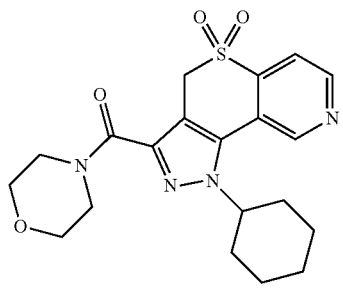 [SMILES: O=C(c1nn(C2CCCCC2)c2c1CS(=O)(=O)c1ccncc1-2)N1CCOCC1] |
| 82 | 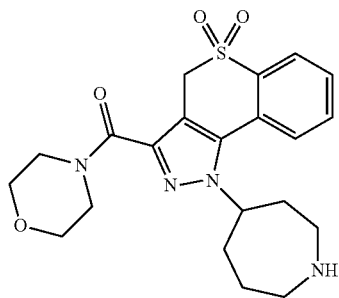 [SMILES: O=C(c1nn(C2CCCNCC2)c2c1CS(=O)(=O)c1ccccc1-2)N1CCOCC1] |
| 83 | 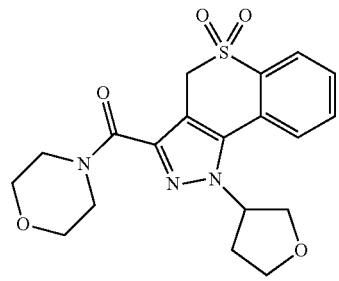 [SMILES: O=C(c1nn(C2CCOC2)c2c1CS(=O)(=O)c1ccccc1-2)N1CCOCC1] |
| 84 | 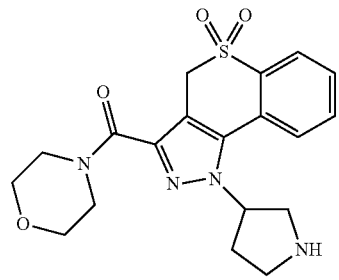 |
| 85 | 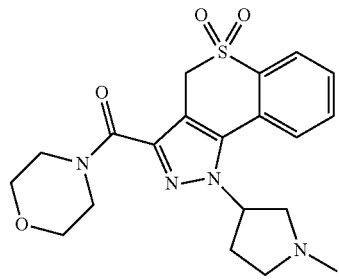 [SMILES: CN1CCC(n2nc(C(=O)N3CCOCC3)c3c2-c2ccccc2S(=O)(=O)C3)C1] |

-continued
| Example No | structures |
|---|---|
| 86 | 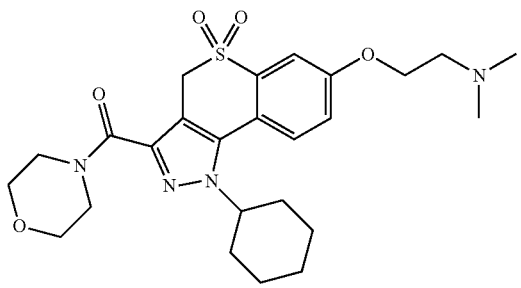 |
| 87 | 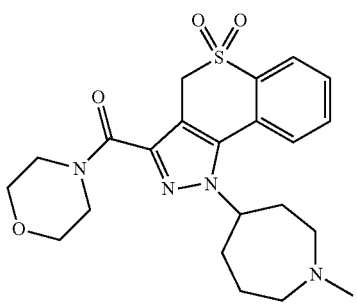 [SMILES: CN1CCCC(n2nc(C(=O)N3CCOCC3)c3c2-c2ccccc2S(=O)(=O)C3)CC1] |
| 88 | 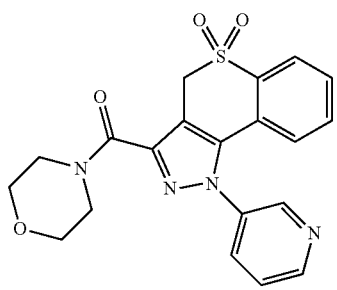 [SMILES: O=C(c1nn(-c2cccnc2)c2c1CS(=O)(=O)c1ccccc1-2)N1CCOCC1] |
| 89 | 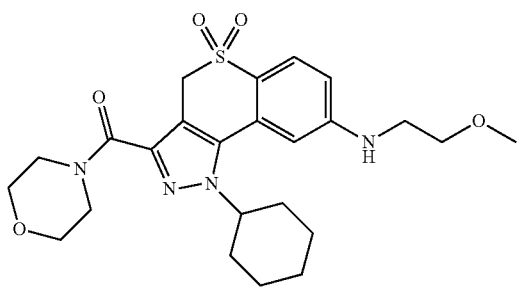 [SMILES: COCCNc1ccc2c(c1)-c1c(c(C(=O)N3CCOCC3)nn1C1CCCCC1)CS2(=O)=O] |
| 90 | 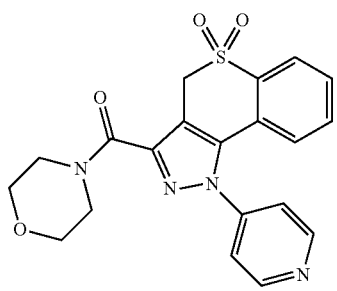 [SMILES: O=C(c1nn(-c2ccncc2)c2c1CS(=O)(=O)c1ccccc1-2)N1CCOCC1] |

-continued
| Example No | structures |
|---|---|
| 91 | 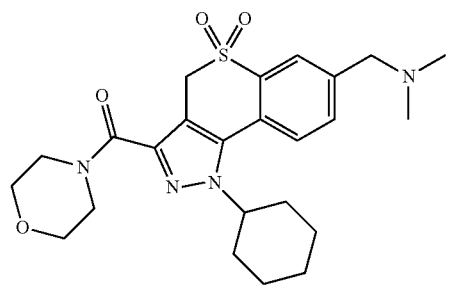 [SMILES: CN(C)Cc1ccc2c(c1)S(=O)(=O)Cc1c(C(=O)N3CCOCC3)nn(C3CCCCC3)c1-2] |
| 92 | 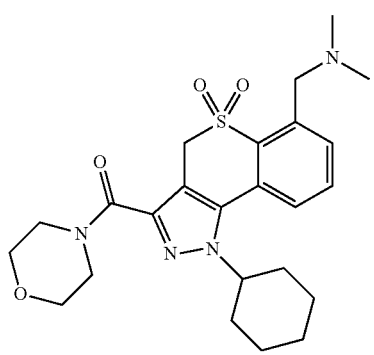 [SMILES: CN(C)Cc1cccc2c1S(=O)(=O)Cc1c(C(=O)N3CCOCC3)nn(C3CCCCC3)c1-2] |
| 93 | 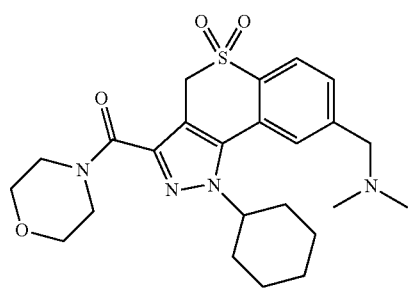 [SMILES: CN(C)Cc1ccc2c(c1)-c1c(c(C(=O)N3CCOCC3)nn1C1CCCCC1)CS2(=O)=O] |
| 94 | 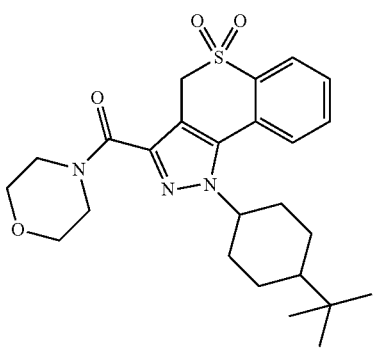 [SMILES: CC(C)(C)C1CCC(n2nc(C(=O)N3CCOCC3)c3c2-c2ccccc2S(=O)(=O)C3)CC1] |

-continued
| Example No | structures |
|---|---|
| 95 | 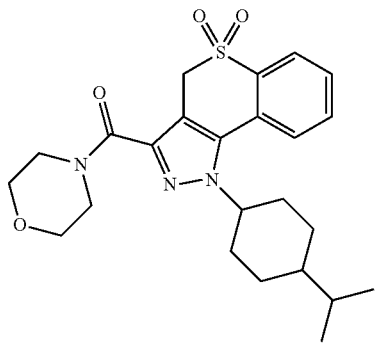 [SMILES: CC(C)C1CCC(n2nc(C(=O)N3CCOCC3)c3c2-c2ccccc2S(=O)(=O)C3)CC1] |
| 96 | 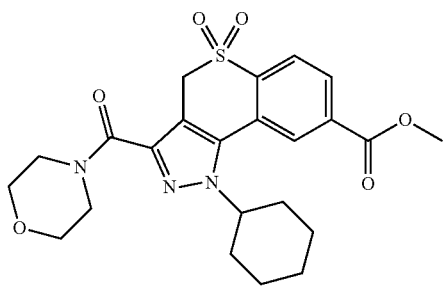 [SMILES: COC(=O)c1ccc2c(c1)-c1c(c(C(=O)N3CCOCC3)nn1C1CCCCC1)CS2(=O)=O] |
| 97 | 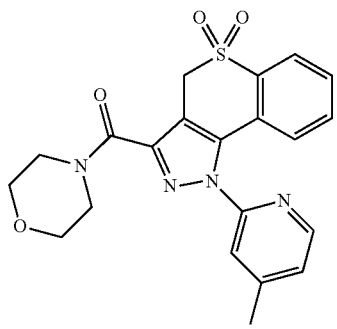 [SMILES: Cc1ccnc(-n2nc(C(=O)N3CCOCC3)c3c2-c2ccccc2S(=O)(=O)C3)c1] |
| 98 | 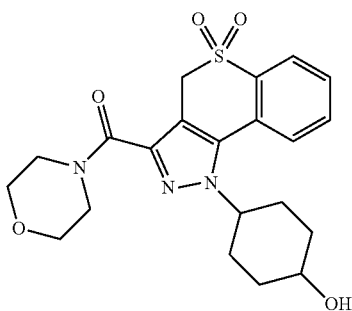 [SMILES: O=C(c1nn(C2CCC(O)CC2)c2c1CS(=O)(=O)c1ccccc1-2)N1CCOCC1] |
| 99 | 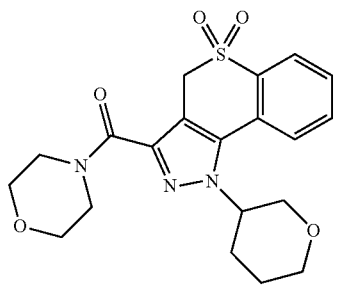 |

| Example No | structures |
|---|---|
| 100 | 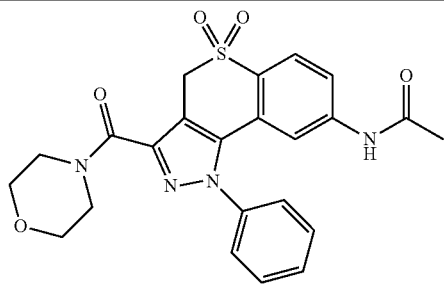 |
| 101 | 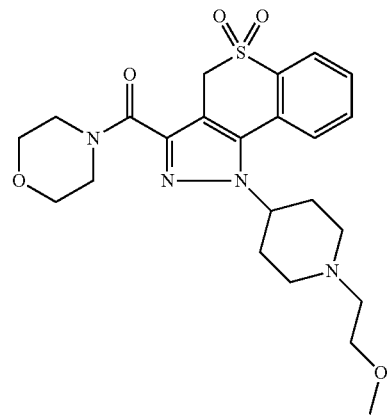 [SMILES: COCCN1CCC(n2nc(C(=O)N3CCOCC3)c3c2-c2ccccc2S(=O)(=O)C3)CC1] |
| 102 | 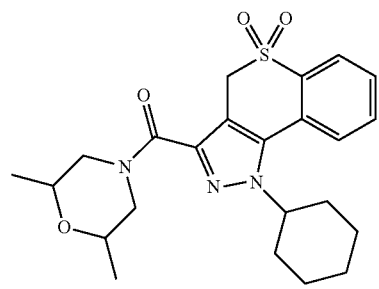 [SMILES: CC1CN(C(=O)c2nn(C3CCCCC3)c3c2CS(=O)(=O)c2ccccc2-3)CC(C)O1] |
| 103 | 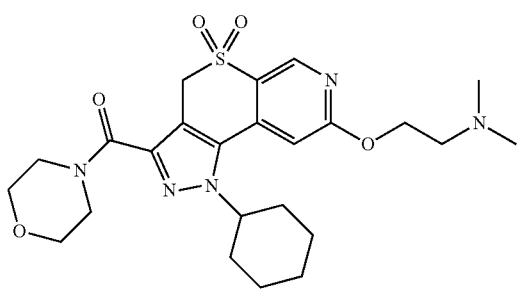 [SMILES: CN(C)CCOc1cc2c(cn1)S(=O)(=O)Cc1c(C(=O)N3CCOCC3)nn(C3CCCCC3)c1-2] |
| 104 | 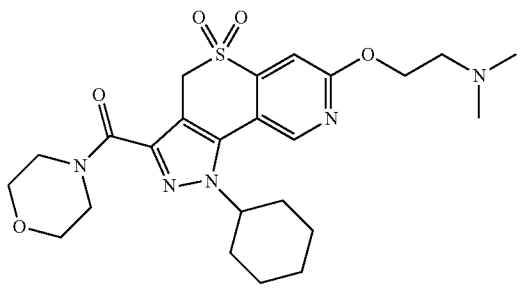 [SMILES: CN(C)CCOc1cc2c(cn1)-c1c(c(C(=O)N3CCOCC3)nn1C1CCCCC1)CS2(=O)=O] |

-continued

| Example No | structures |
|---|---|
| 105 | 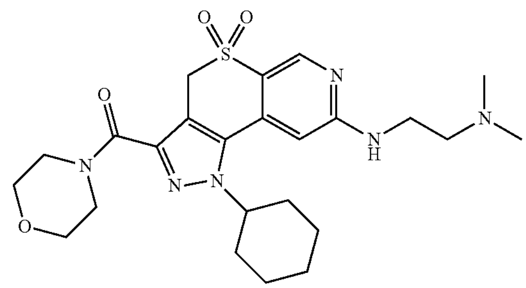 [SMILES: CN(C)CCNc1cc2c(cn1)S(=O)(=O)Cc1c(C(=O)N3CCOCC3)nn(C3CCCCC3)c1-2] |
| 106 | 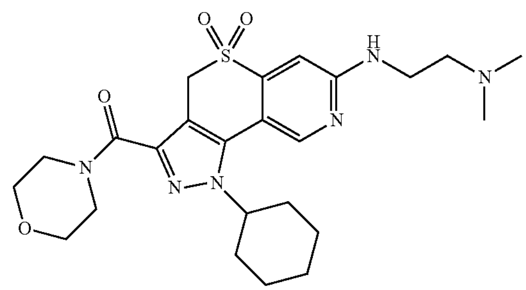 [SMILES: CN(C)CCNc1cc2c(cn1)-c1c(c(C(=O)N3CCOCC3)nn1C1CCCCC1)CS2(=O)=O] |
| 107 | 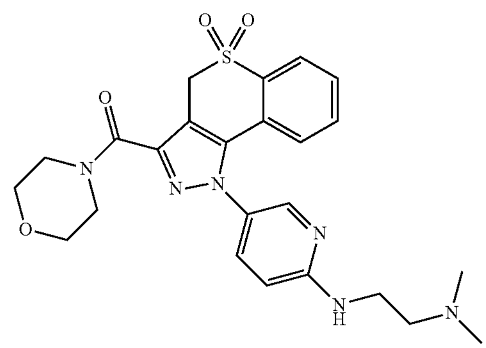 [SMILES: CN(C)CCNc1ccc(-n2nc(C(=O)N3CCOCC3)c3c2-c2ccccc2S(=O)(=O)C3)cn1] |
| 108 | 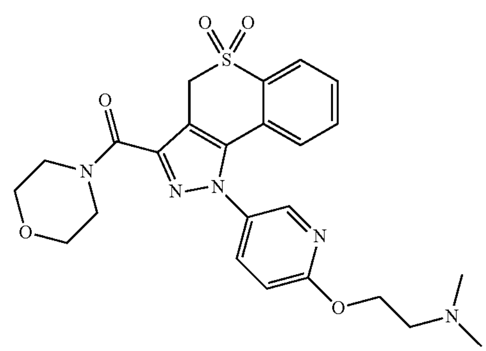 [SMILES: CN(C)CCOc1ccc(-n2nc(C(=O)N3CCOCC3)c3c2-c2ccccc2S(=O)(=O)C3)cn1] |
| 109 | 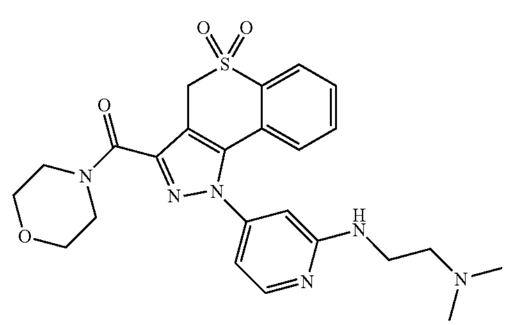 [SMILES: CN(C)CCNc1cc(-n2nc(C(=O)N3CCOCC3)c3c2-c2ccccc2S(=O)(=O)C3)ccn1] |

-continued
| Example No | structures |
|---|---|
| 110 | 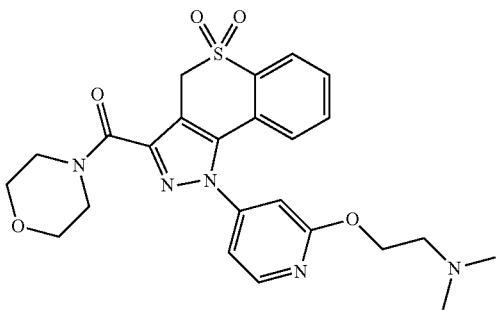 [SMILES: CN(C)CCOc1cc(-n2nc(C(=O)N3CCOCC3)c3c2-c2ccccc2S(=O)(=O)C3)ccn1] |
| 111 | 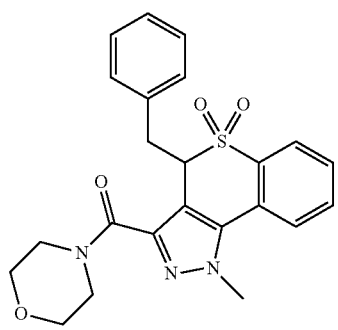 [SMILES: Cn1nc(C(=O)N2CCOCC2)c2c1-c1ccccc1S(=O)(=O)C2Cc1ccccc1] |
| 112 | 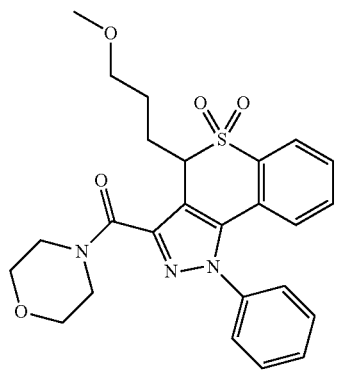 [SMILES: COCCCC1c2c(C(=O)N3CCOCC3)nn(-c3ccccc3)c2-c2ccccc2S1(=O)=O] |
| 113 | 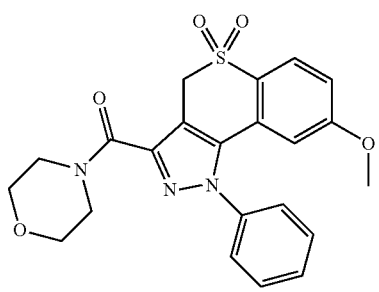 [SMILES: COc1ccc2c(c1)-c1c(c(C(=O)N3CCOCC3)nn1-c1ccccc1)CS2(=O)=O] |

-continued
| Example No | structures |
|---|---|
| 114 | 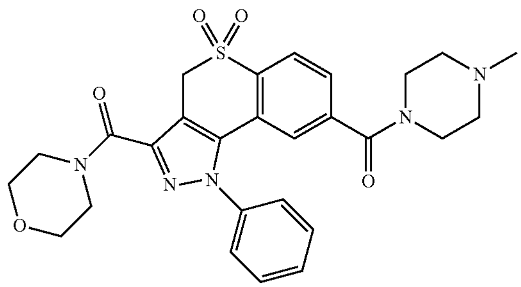 [SMILES: CN1CCN(C(=O)c2ccc3c(c2)-c2c(c(C(=O)N4CCOCC4)nn2-c2ccccc2)CS3(=O)=O)CC1] |
| 115 | 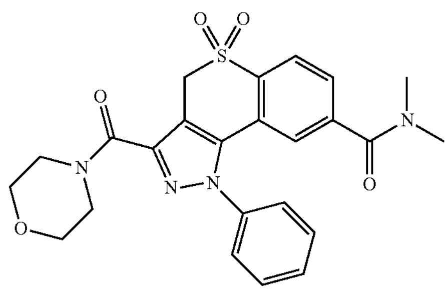 [SMILES: CN(C)C(=O)c1ccc2c(c1)-c1c(c(C(=O)N3CCOCC3)nn1-c1ccccc1)CS2(=O)=O] |
| 116 | 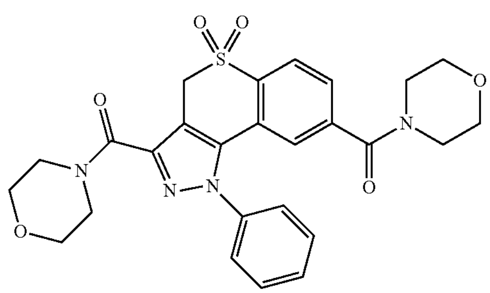 [SMILES: O=C(c1ccc2c(c1)-c1c(c(C(=O)N3CCOCC3)nn1-c1ccccc1)CS2(=O)=O)N1CCOCC1] |
| 117 | 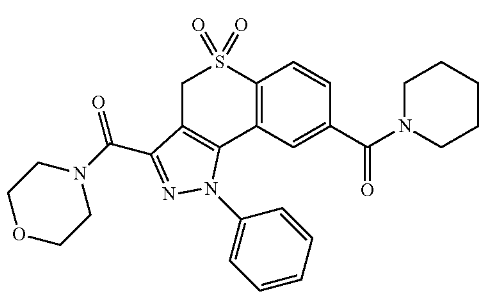 [SMILES: O=C(c1ccc2c(c1)-c1c(c(C(=O)N3CCOCC3)nn1-c1ccccc1)CS2(=O)=O)N1CCCCC1] |
| 118 | 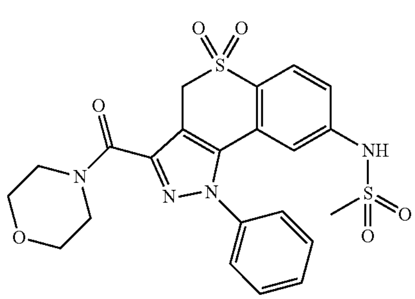 [SMILES: CS(=O)(=O)Nc1ccc2c(c1)-c1c(c(C(=O)N3CCOCC3)nn1-c1ccccc1)CS2(=O)=O] |

| Example No | structures |
|---|---|
| 119 | 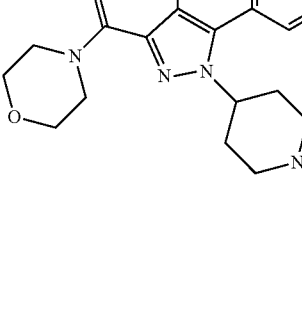 |
| 120 | 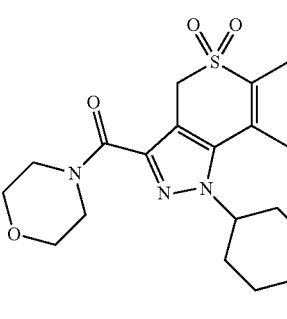 |
| 121 | 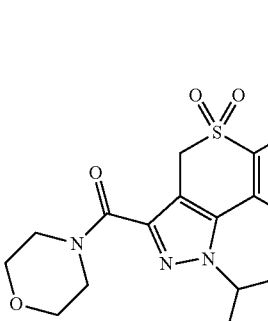 |
| 122 | 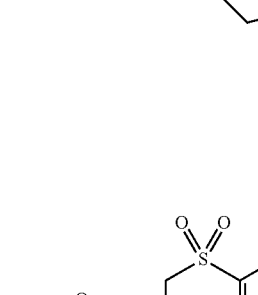 |

| Example No | structures |
|---|---|
| 123 | 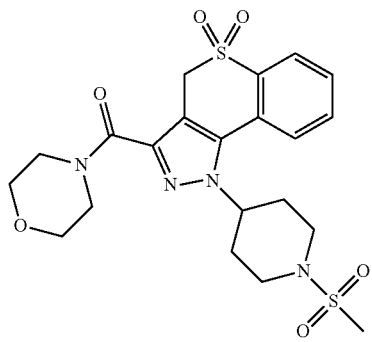 [SMILES: CS(=O)(=O)N1CCC(n2nc(C(=O)N3CCOCC3)c3c2-c2ccccc2S(=O)(=O)C3)CC1] |
| 124 | 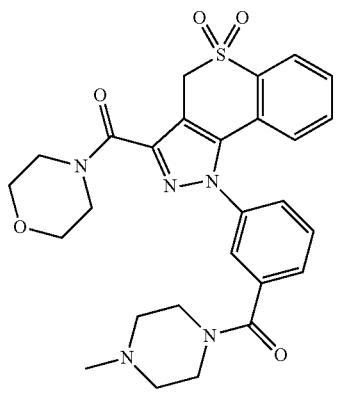 [SMILES: CN1CCN(C(=O)c2cccc(-n3nc(C(=O)N4CCOCC4)c4c3-c3ccccc3S(=O)(=O)C4)c2)CC1] |
| 125 | 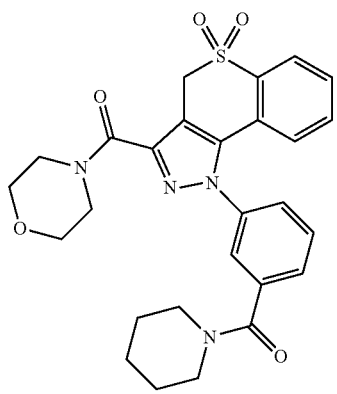 |
| 126 | 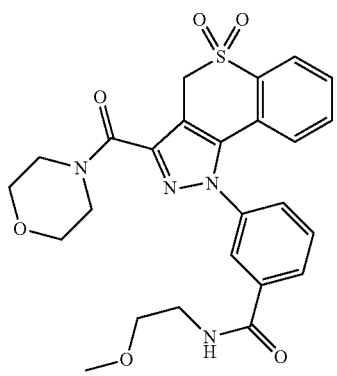 [SMILES: COCCNC(=O)c1cccc(-n2nc(C(=O)N3CCOCC3)c3c2-c2ccccc2S(=O)(=O)C3)c1] |

-continued
| Example No | structures |
|---|---|
| 127 | 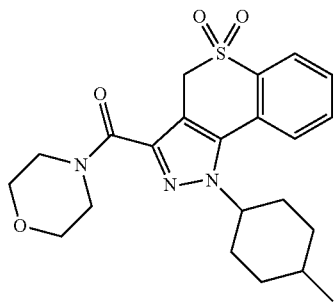 [SMILES: CC1CCC(n2nc(C(=O)N3CCOCC3)c3c2-c2ccccc2S(=O)(=O)C3)CC1] |
| 128 | 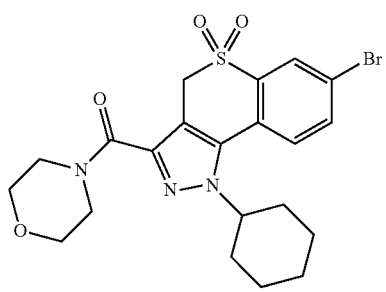 [SMILES: O=C(c1nn(C2CCCCC2)c2c1CS(=O)(=O)c1cc(Br)ccc1-2)N1CCOCC1] |
| 129 | 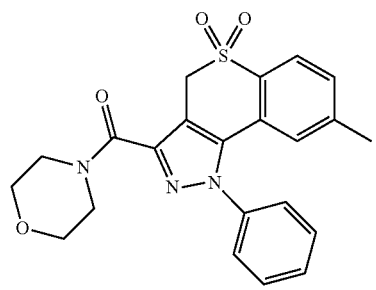 [SMILES: Cc1ccc2c(c1)-c1c(c(C(=O)N3CCOCC3)nn1-c1ccccc1)CS2(=O)=O] |
| 130 | 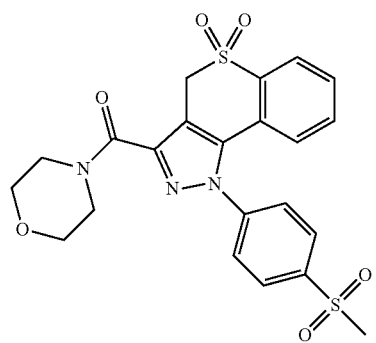 [SMILES: CS(=O)(=O)c1ccc(-n2nc(C(=O)N3CCOCC3)c3c2-c2ccccc2S(=O)(=O)C3)cc1] |
| 131 | 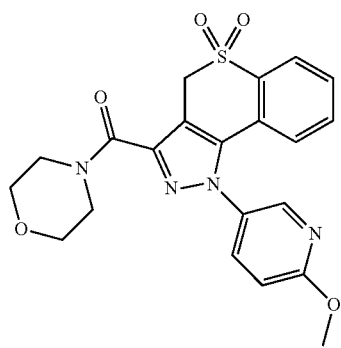 [SMILES: COc1ccc(-n2nc(C(=O)N3CCOCC3)c3c2-c2ccccc2S(=O)(=O)C3)cn1] |

-continued
| Example No | structures |
|---|---|
| 132 | 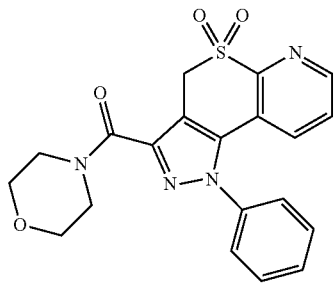 [SMILES: O=C(c1nn(-c2ccccc2)c2c1CS(=O)(=O)c1ncccc1-2)N1CCOCC1] |
| 133 | 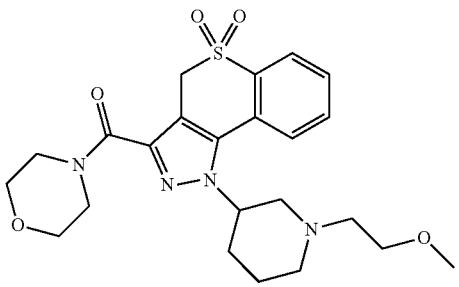 [SMILES: COCCN1CCCC(n2nc(C(=O)N3CCOCC3)c3c2-c2ccccc2S(=O)(=O)C3)C1] |
| 134 | 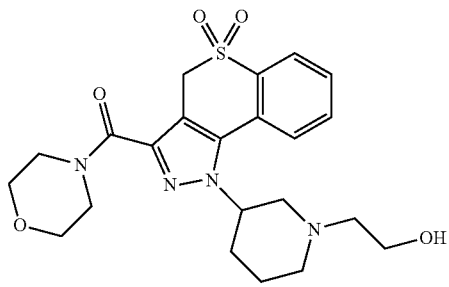 [SMILES: O=C(c1nn(C2CCCN(CCO)C2)c2c1CS(=O)(=O)c1ccccc1-2)N1CCOCC1] |
| 135 | 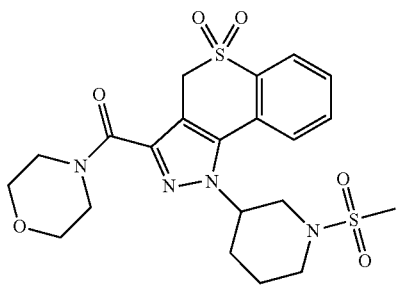 [SMILES: CS(=O)(=O)N1CCCC(n2nc(C(=O)N3CCOCC3)c3c2-c2ccccc2S(=O)(=O)C3)C1] |
| 136 | 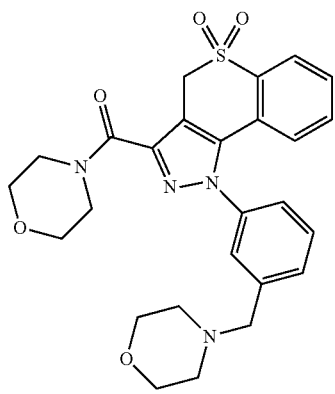 [SMILES: O=C(c1nn(-c2cccc(CN3CCOCC3)c2)c2c1CS(=O)(=O)c1ccccc1-2)N1CCOCC1] |

-continued
| Example No | structures |
|---|---|
| 137 | 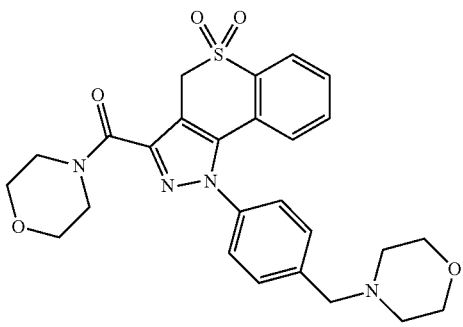 |
| 138 | 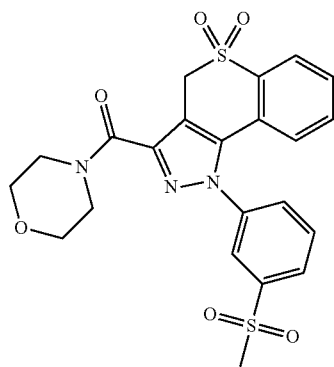 [SMILES: CS(=O)(=O)c1cccc(-n2nc(C(=O)N3CCOCC3)c3c2-c2ccccc2S(=O)(=O)C3)c1] |
| 139 | 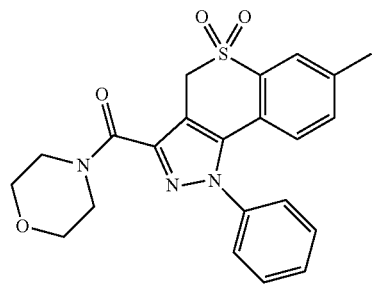 [SMILES: Cc1ccc2c(c1)S(=O)(=O)Cc1c(C(=O)N3CCOCC3)nn(-c3ccccc3)c1-2] |
| 140 | 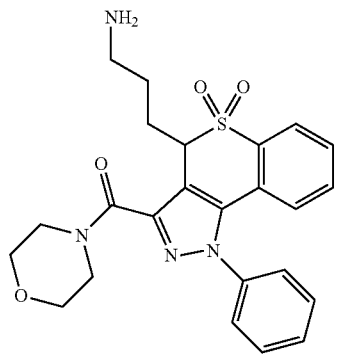 [SMILES: NCCCC1c2c(C(=O)N3CCOCC3)nn(-c3ccccc3)c2-c2ccccc2S1(=O)=O] |

-continued
| Example No | structures |
|---|---|
| 141 | 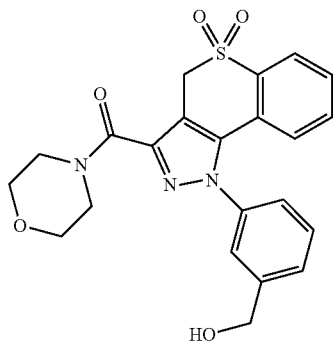 [SMILES: O=C(c1nn(-c2cccc(CO)c2)c2c1CS(=O)(=O)c1ccccc1-2)N1CCOCC1] |
| 142 | 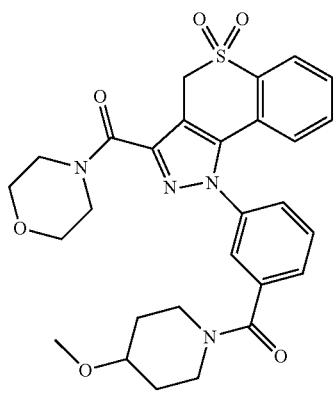 [SMILES: COC1CCN(C(=O)c2cccc(-n3nc(C(=O)N4CCOCC4)c4c3-c3ccccc3S(=O)(=O)C4)c2)CC1] |
| 143 | 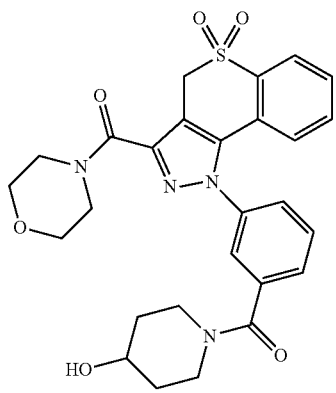 [SMILES: O=C(c1cccc(-n2nc(C(=O)N3CCOCC3)c3c2-c2ccccc2S(=O)(=O)C3)c1)N1CCC(O)CC1] |
| 144 | 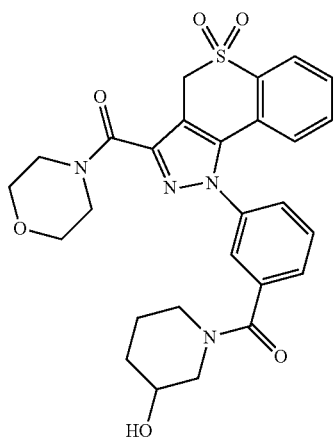 [SMILES: O=C(c1cccc(-n2nc(C(=O)N3CCOCC3)c3c2-c2ccccc2S(=O)(=O)C3)c1)N1CCCC(O)C1] |

| Example No | structures |
|---|---|
| 145 | 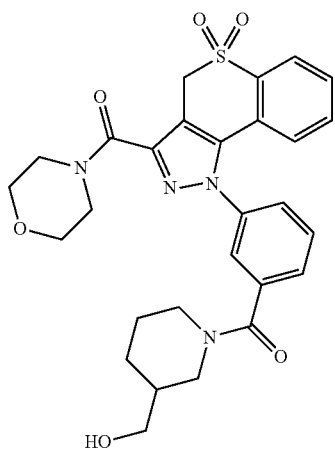 [SMILES: O=C(c1cccc(-n2nc(C(=O)N3CCOCC3)c3c2-c2ccccc2S(=O)(=O)C3)c1)N1CCCC(CO)C1] |
| 146 | 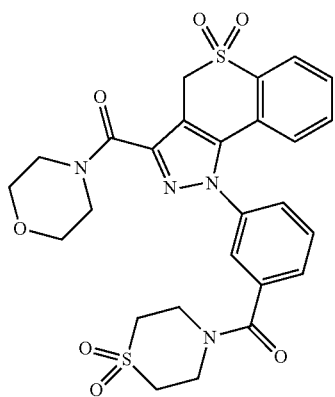 [SMILES: O=C(c1cccc(-n2nc(C(=O)N3CCOCC3)c3c2-c2ccccc2S(=O)(=O)C3)c1)N1CCS(=O)(=O)CC1] |
| 147 | 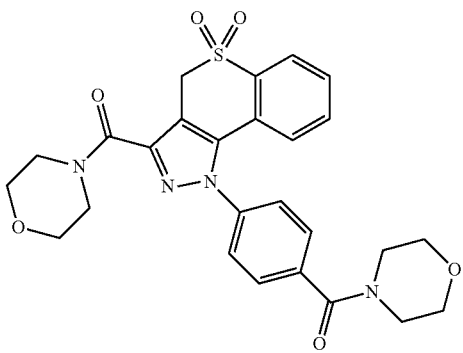 [SMILES: O=C(c1ccc(-n2nc(C(=O)N3CCOCC3)c3c2-c2ccccc2S(=O)(=O)C3)cc1)N1CCOCC1] |

| Example No | structures |
|---|---|
| 148 | 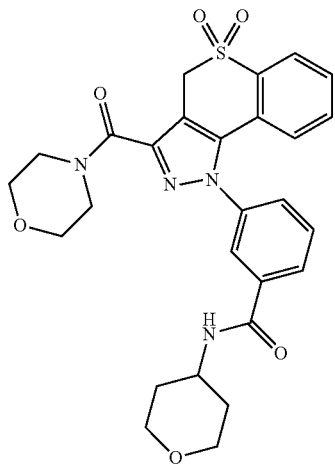 [SMILES: O=C(NC1CCOCC1)c1cccc(-n2nc(C(=O)N3CCOCC3)c3c2-c2ccccc2S(=O)(=O)C3)c1] |
| 149 | 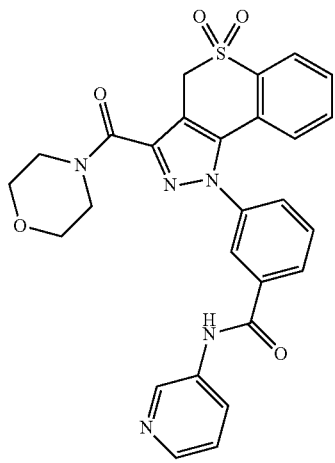 [SMILES: O=C(Nc1cccnc1)c1cccc(-n2nc(C(=O)N3CCOCC3)c3c2-c2ccccc2S(=O)(=O)C3)c1] |
| 150 | 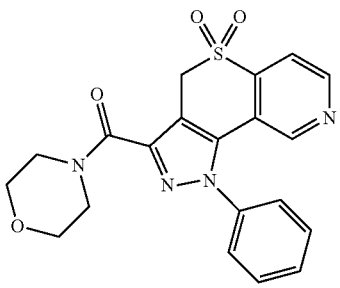 [SMILES: O=C(c1nn(-c2ccccc2)c2c1CS(=O)(=O)c1ccncc1-2)N1CCOCC1] |
| 151 | 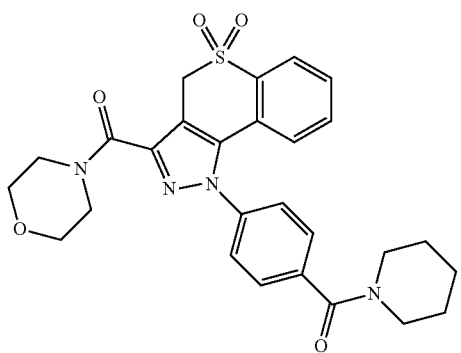 [SMILES: O=C(c1ccc(-n2nc(C(=O)N3CCOCC3)c3c2-c2ccccc2S(=O)(=O)C3)cc1)N1CCCCC1] |

-continued
| Example No | structures |
|---|---|
| 152 | 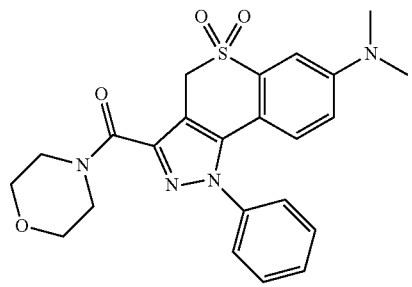 [SMILES: CN(C)c1ccc2c(c1)S(=O)(=O)Cc1c(C(=O)N3CCOCC3)nn(-c3ccccc3)c1-2] |
| 153 | 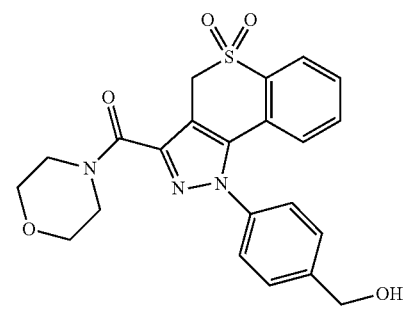 [SMILES: O=C(c1nn(-c2ccc(CO)cc2)c2c1CS(=O)(=O)c1ccccc1-2)N1CCOCC1] |
| 154 | 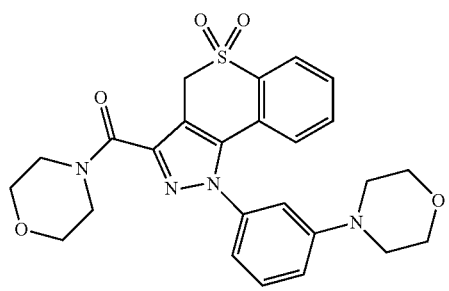 [SMILES: O=C(c1nn(-c2cccc(N3CCOCC3)c2)c2c1CS(=O)(=O)c1ccccc1-2)N1CCOCC1] |
| 155 | 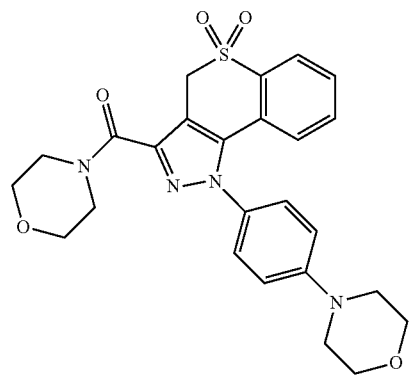 [SMILES: O=C(c1nn(-c2ccc(N3CCOCC3)cc2)c2c1CS(=O)(=O)c1ccccc1-2)N1CCOCC1] |
| 156 | 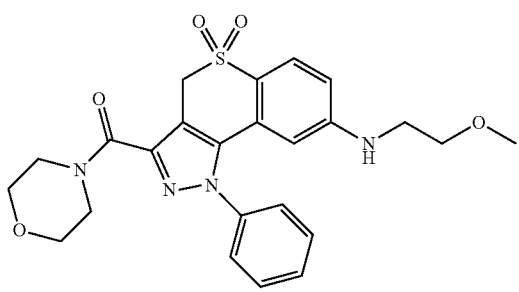 [SMILES: COCCNc1ccc2c(c1)-c1c(c(C(=O)N3CCOCC3)nn1-c1ccccc1)CS2(=O)=O] |

-continued
| Example No | structures |
|---|---|
| 157 | 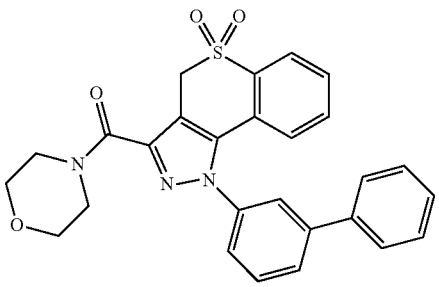 [SMILES: O=C(c1nn(-c2cccc(-c3ccccc3)c2)c2c1CS(=O)(=O)c1ccccc1-2)N1CCOCC1] |
| 158 | 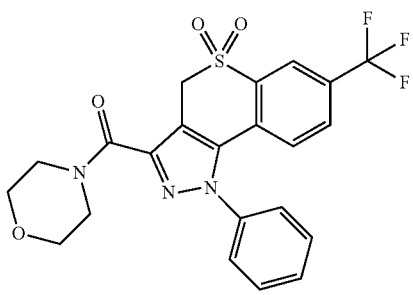 [SMILES: O=C(c1nn(-c2ccccc2)c2c1CS(=O)(=O)c1cc(C(F)(F)F)ccc1-2)N1CCOCC1] |
| 159 | 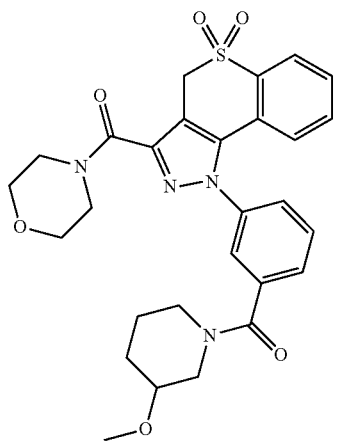 [SMILES: COC1CCCN(C(=O)c2cccc(-n3nc(C(=O)N4CCOCC4)c4c3-c3ccccc3S(=O)(=O)C4)c2)C1] |
| 160 | 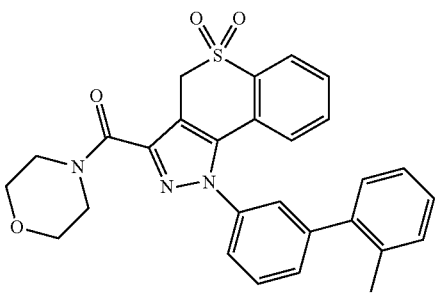 [SMILES: Cc1ccccc1-c1cccc(-n2nc(C(=O)N3CCOCC3)c3c2-c2ccccc2S(=O)(=O)C3)c1] |

-continued
| Example No | structures |
|---|---|
| 161 | 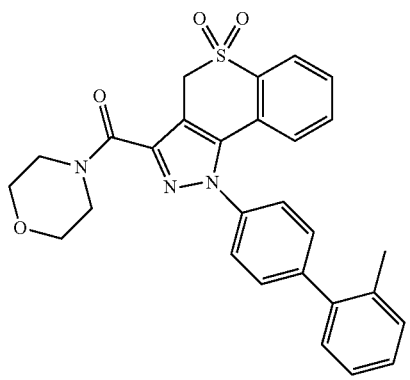 [SMILES: Cc1ccccc1-c1ccc(-n2nc(C(=O)N3CCOCC3)c3c2-c2ccccc2S(=O)(=O)C3)cc1] |
| 162 | 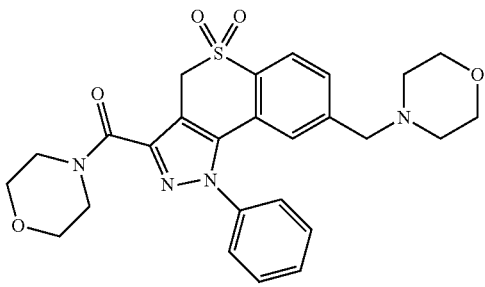 [SMILES: O=C(c1nn(-c2ccccc2)c2c1CS(=O)(=O)c1ccc(CN3CCOCC3)cc1-2)N1CCOCC1] |
| 163 | 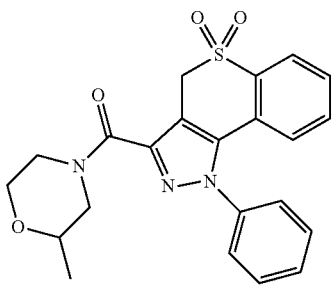 [SMILES: CC1CN(C(=O)c2nn(-c3ccccc3)c3c2CS(=O)(=O)c2ccccc2-3)CCO1] |
| 164 | 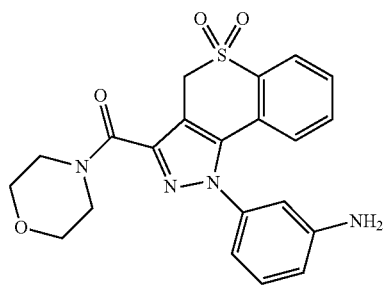 [SMILES: Nc1cccc(-n2nc(C(=O)N3CCOCC3)c3c2-c2ccccc2S(=O)(=O)C3)c1] |
| 165 | 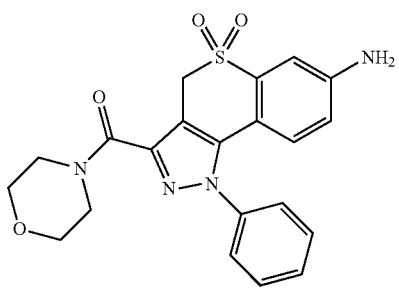 [SMILES: Nc1ccc2c(c1)S(=O)(=O)Cc1c(C(=O)N3CCOCC3)nn(-c3ccccc3)c1-2] |

-continued
| Example No | structures |
|---|---|
| 166 | 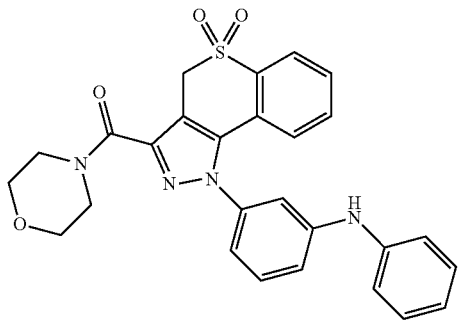 [SMILES: O=C(c1nn(-c2cccc(Nc3ccccc3)c2)c2c1CS(=O)(=O)c1ccccc1-2)N1CCOCC1] |
| 167 | 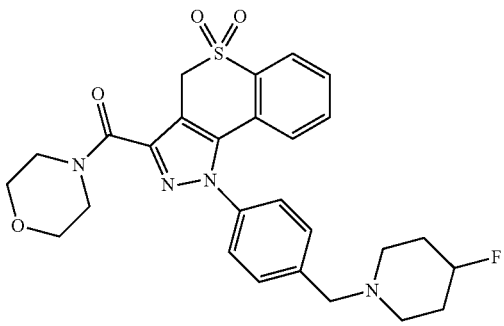 |
| 168 | 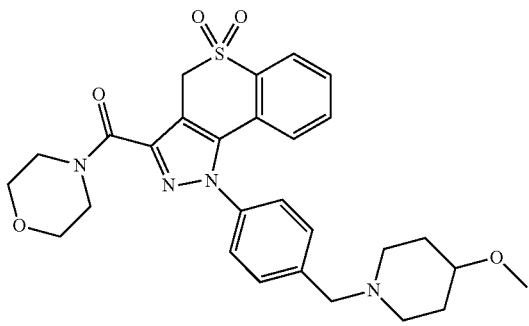 [SMILES: COC1CCN(Cc2ccc(-n3nc(C(=O)N4CCOCC4)c4c3-c3ccccc3S(=O)(=O)C4)cc2)CC1] |
| 169 | 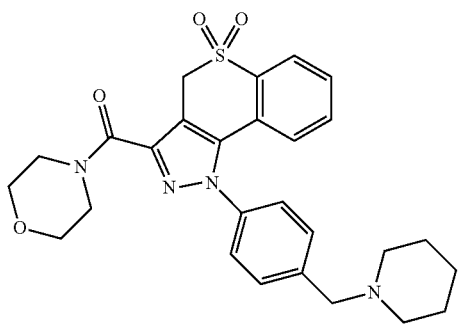 |

| Example No | structures |
|---|---|
| 170 | 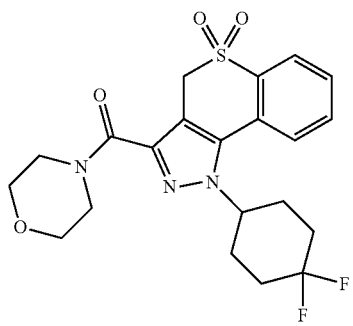 [SMILES: O=C(c1nn(C2CCC(F)(F)CC2)c2c1CS(=O)(=O)c1ccccc1-2)N1CCOCC1] |
| 171 | 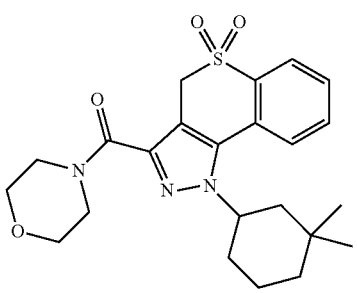 [SMILES: CC1(C)CCCC(n2nc(C(=O)N3CCOCC3)c3c2-c2ccccc2S(=O)(=O)C3)C1] |
| 172 | 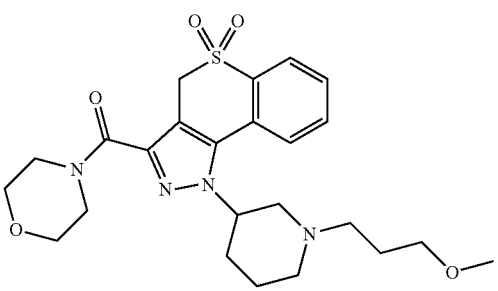 [SMILES: COCCCN1CCCC(n2nc(C(=O)N3CCOCC3)c3c2-c2ccccc2S(=O)(=O)C3)C1] |
| 173 | 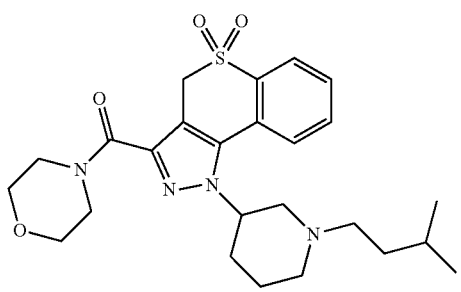 [SMILES: CC(C)CCN1CCCC(n2nc(C(=O)N3CCOCC3)c3c2-c2ccccc2S(=O)(=O)C3)C1] |
| 174 | 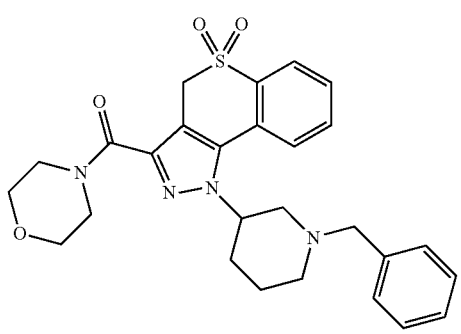 [SMILES: O=C(c1nn(C2CCCN(Cc3ccccc3)C2)c2c1CS(=O)(=O)c1ccccc1-2)N1CCOCC1] |

| Example No | structures |
|---|---|
| 175 | 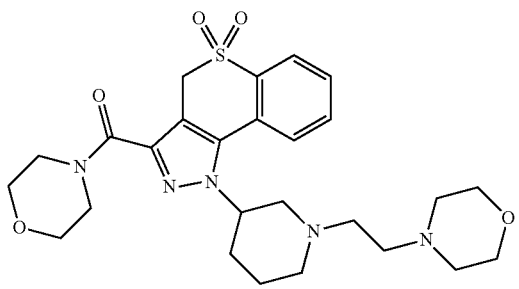 |
| 176 | 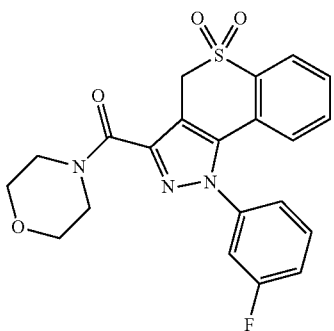 [SMILES: O=C(c1nn(-c2cccc(F)c2)c2c1CS(=O)(=O)c1ccccc1-2)N1CCOCC1] |
| 177 | 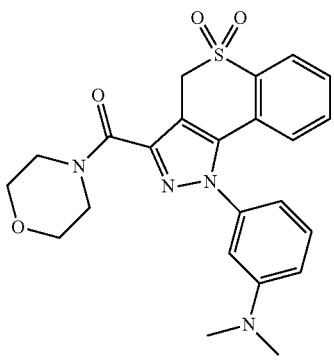 [SMILES: CN(C)c1cccc(-n2nc(C(=O)N3CCOCC3)c3c2-c2ccccc2S(=O)(=O)C3)c1] |
| 178 | 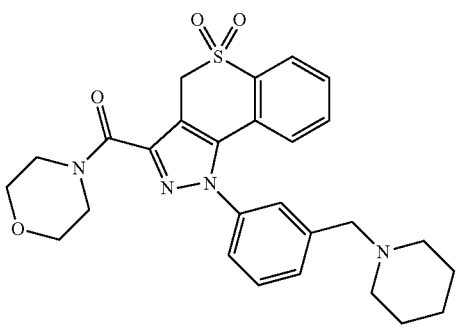 |

| Example No | structures |
|---|---|
| 179 | 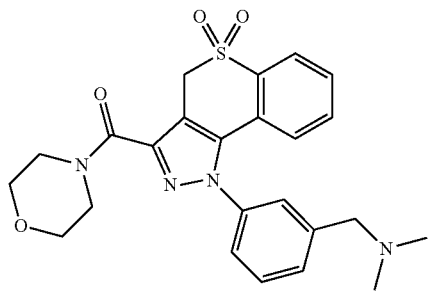 [SMILES: CN(C)Cc1cccc(-n2nc(C(=O)N3CCOCC3)c3c2-c2ccccc2S(=O)(=O)C3)c1] |
| 180 | 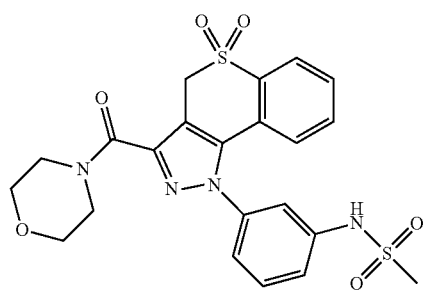 [SMILES: CS(=O)(=O)Nc1cccc(-n2nc(C(=O)N3CCOCC3)c3c2-c2ccccc2S(=O)(=O)C3)c1] |
| 181 | 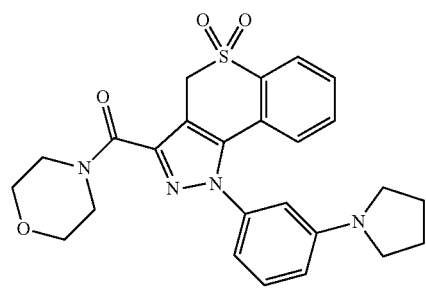 [SMILES: O=C(c1nn(-c2cccc(N3CCCC3)c2)c2c1CS(=O)(=O)c1ccccc1-2)N1CCOCC1] |
| 182 | 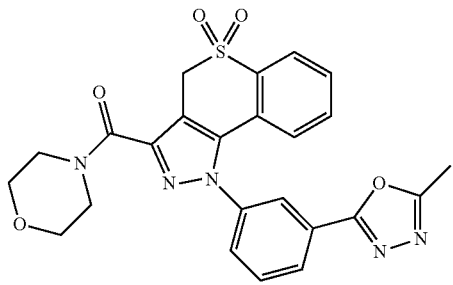 [SMILES: Cc1nnc(-c2cccc(-n3nc(C(=O)N4CCOCC4)c4c3-c3ccccc3S(=O)(=O)C4)c2)o1] |
| 183 | 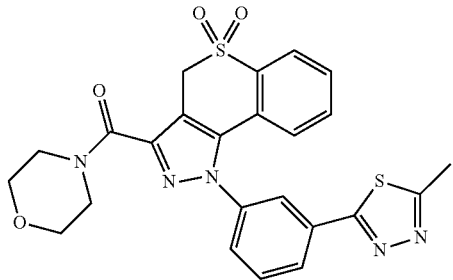 |

| Example No | structures |
|---|---|
| 184 | 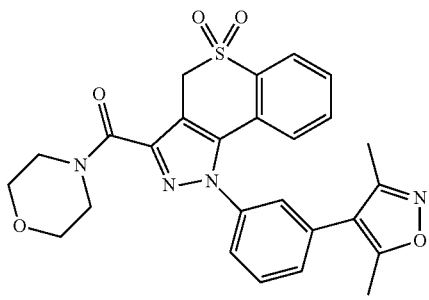 [SMILES: Cc1noc(C)c1-c1cccc(-n2nc(C(=O)N3CCOCC3)c3c2-c2ccccc2S(=O)(=O)C3)c1] |
| 185 | 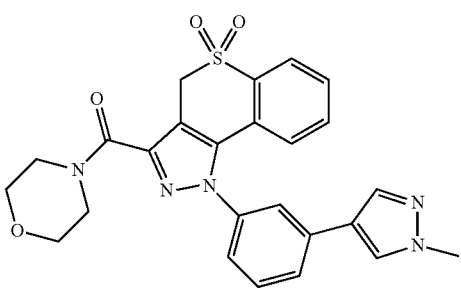 [SMILES: Cn1cc(-c2cccc(-n3nc(C(=O)N4CCOCC4)c4c3-c3ccccc3S(=O)(=O)C4)c2)cn1] |
| 186 | 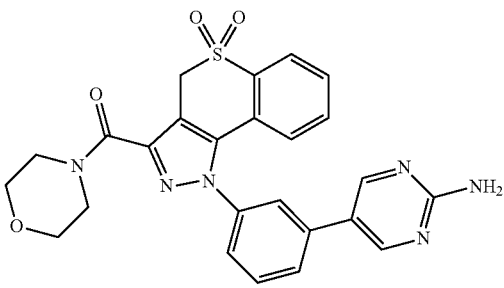 [SMILES: Nc1ncc(-c2cccc(-n3nc(C(=O)N4CCOCC4)c4c3-c3ccccc3S(=O)(=O)C4)c2)cn1] |
| 187 | 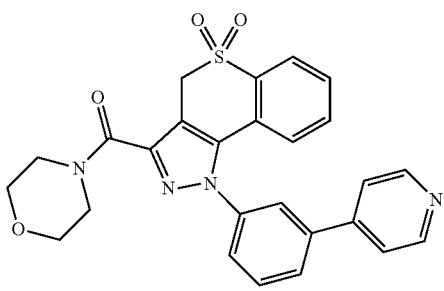 [SMILES: O=C(c1nn(-c2cccc(-c3ccncc3)c2)c2c1CS(=O)(=O)c1ccccc1-2)N1CCOCC1] |
| 188 | 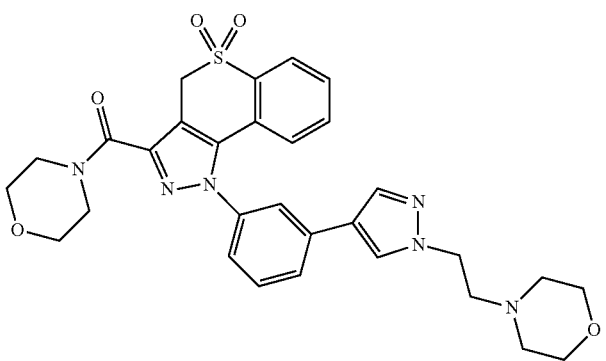 [SMILES: O=C(c1nn(-c2cccc(-c3cnn(CCN4CCOCC4)c3)c2)c2c1CS(=O)(=O)c1ccccc1-2)N1CCOCC1] |

| Example No | structures |
|---|---|
| 189 | 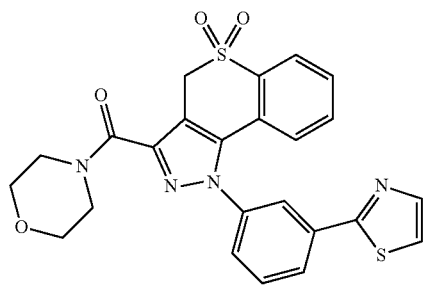 [SMILES: O=C(c1nn(-c2cccc(-c3nccs3)c2)c2c1CS(=O)(=O)c1ccccc1-2)N1CCOCC1] |
| 190 | 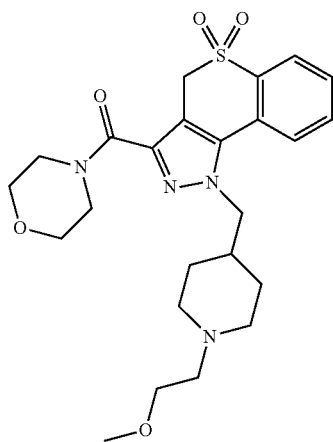 [SMILES: COCCN1CCC(Cn2nc(C(=O)N3CCOCC3)c3c2-c2ccccc2S(=O)(=O)C3)CC1] |
| 191 | 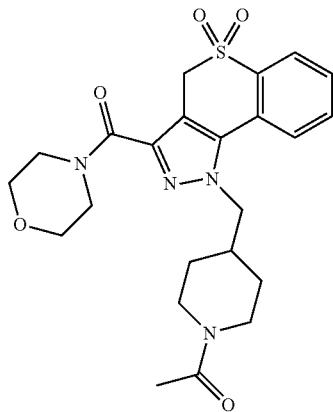 [SMILES: CC(=O)N1CCC(Cn2nc(C(=O)N3CCOCC3)c3c2-c2ccccc2S(=O)(=O)C3)CC1] |
| 192 | 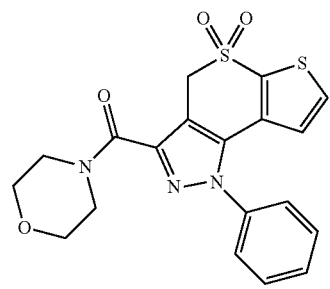 [SMILES: O=C(c1nn(-c2ccccc2)c2c1CS(=O)(=O)c1sccc1-2)N1CCOCC1] |

-continued
| Example No | structures |
|---|---|
| 193 | 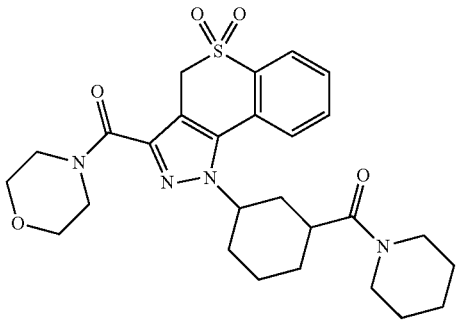 [SMILES: O=C(c1nn(C2CCCC(C(=O)N3CCCCC3)C2)c2c1CS(=O)(=O)c1ccccc1-2)N1CCOCC1] |
| 194 | 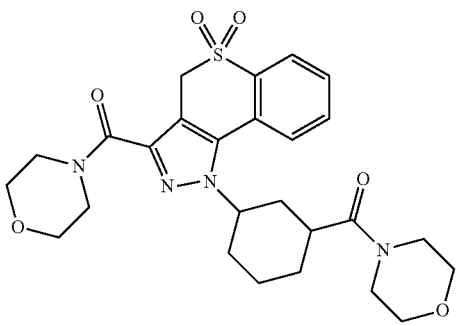 [SMILES: O=C(c1nn(C2CCCC(C(=O)N3CCOCC3)C2)c2c1CS(=O)(=O)c1ccccc1-2)N1CCOCC1] |
| 195 | 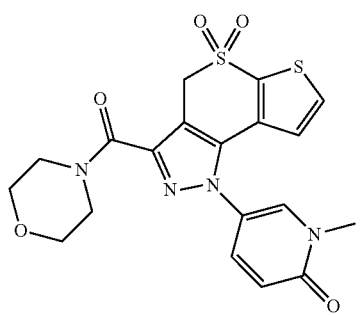 [SMILES: Cn1cc(-n2nc(C(=O)N3CCOCC3)c3c2-c2ccsc2S(=O)(=O)C3)ccc1=O] |
| 196 | 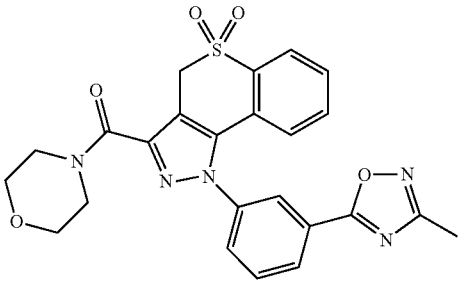 [SMILES: Cc1noc(-c2cccc(-n3nc(C(=O)N4CCOCC4)c4c3-c3ccccc3S(=O)(=O)C4)c2)n1] |
| 197 | 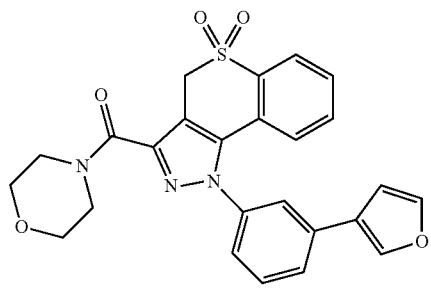 [SMILES: O=C(c1nn(-c2cccc(-c3ccoc3)c2)c2c1CS(=O)(=O)c1ccccc1-2)N1CCOCC1] |

-continued
| Example No | structures |
|---|---|
| 198 | 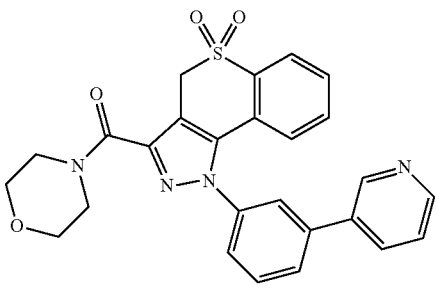 [SMILES: O=C(c1nn(-c2cccc(-c3cccnc3)c2)c2c1CS(=O)(=O)c1ccccc1-2)N1CCOCC1] |
| 199 | 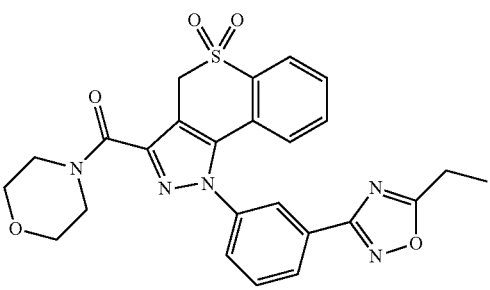 [SMILES: CCc1nc(-c2cccc(-n3nc(C(=O)N4CCOCC4)c4c3-c3ccccc3S(=O)(=O)C4)c2)no1] |
| 200 | 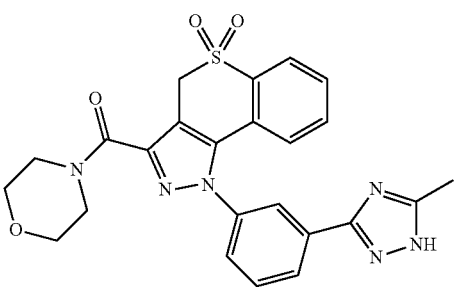 [SMILES: Cc1nc(-c2cccc(-n3nc(C(=O)N4CCOCC4)c4c3-c3ccccc3S(=O)(=O)C4)c2)n[nH]1] |
| 201 | 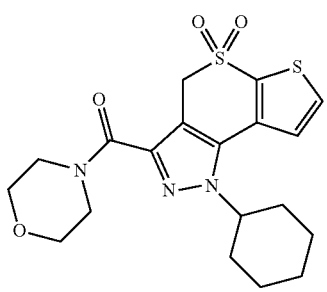 [SMILES: O=C(c1nn(C2CCCCC2)c2c1CS(=O)(=O)c1sccc1-2)N1CCOCC1] |
| 202 | 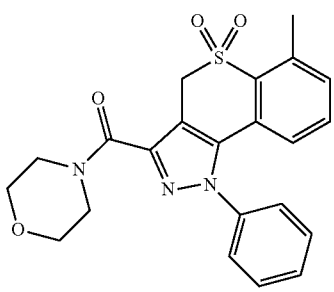 [SMILES: Cc1cccc2c1S(=O)(=O)Cc1c(C(=O)N3CCOCC3)nn(-c3ccccc3)c1-2] |

| Example No | structures |
|---|---|
| 203 | 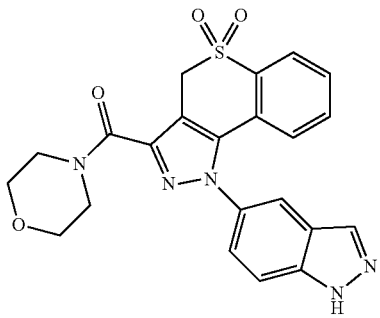 [SMILES: O=C(c1nn(-c2ccc3[nH]ncc3c2)c2c1CS(=O)(=O)c1ccccc1-2)N1CCOCC1] |
| 204 | 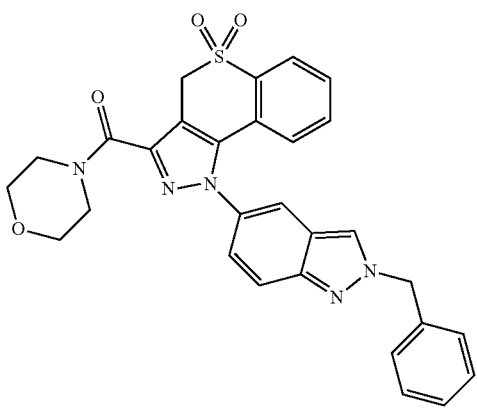 [SMILES: O=C(c1nn(-c2ccc3nn(Cc4ccccc4)cc3c2)c2c1CS(=O)(=O)c1ccccc1-2)N1CCOCC1] |
| 205 | 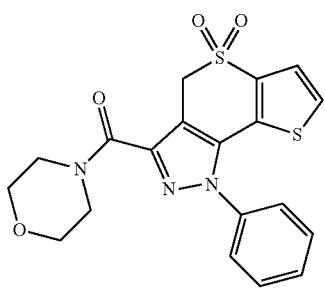 [SMILES: O=C(c1nn(-c2ccccc2)c2c1CS(=O)(=O)c1ccsc1-2)N1CCOCC1] |
| 206 | 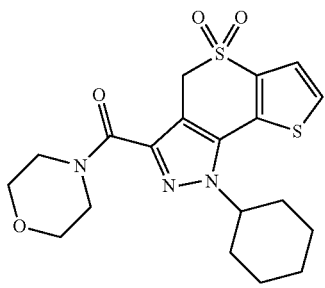 [SMILES: O=C(c1nn(C2CCCCC2)c2c1CS(=O)(=O)c1ccsc1-2)N1CCOCC1] |
| 207 | 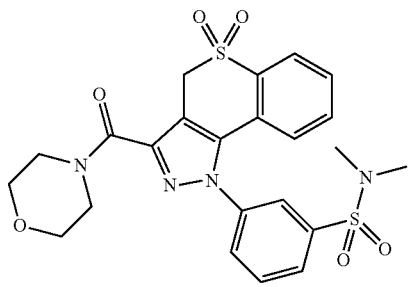 [SMILES: CN(C)S(=O)(=O)c1cccc(-n2nc(C(=O)N3CCOCC3)c3c2-c2ccccc2S(=O)(=O)C3)c1] |

-continued
| Example No | structures |
|---|---|
| 208 | 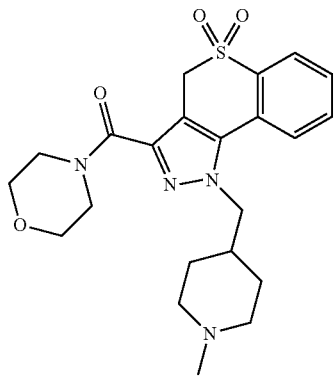 [SMILES: CN1CCC(Cn2nc(C(=O)N3CCOCC3)c3c2-c2ccccc2S(=O)(=O)C3)CC1] |
| 209 | 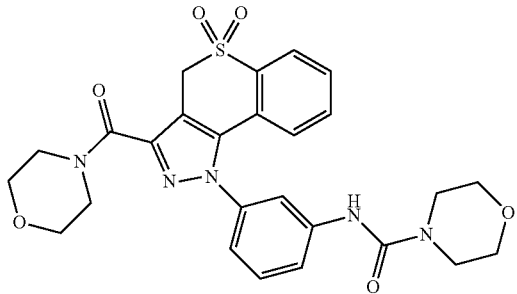 [SMILES: O=C(Nc1cccc(-n2nc(C(=O)N3CCOCC3)c3c2-c2ccccc2S(=O)(=O)C3)c1)N1CCOCC1] |
| 210 | 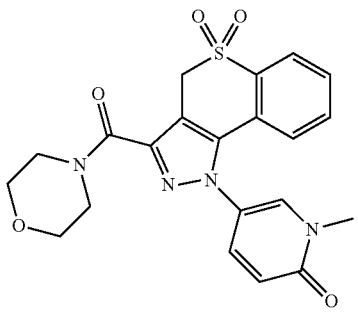 [SMILES: Cn1cc(-n2nc(C(=O)N3CCOCC3)c3c2-c2ccccc2S(=O)(=O)C3)ccc1=O] |
| 211 | 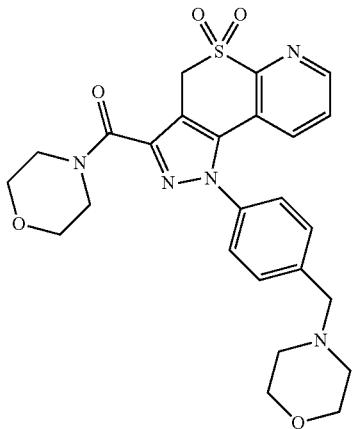 [SMILES: O=C(c1nn(-c2ccc(CN3CCOCC3)cc2)c2c1CS(=O)(=O)c1ncccc1-2)N1CCOCC1] |

| Example No | structures |
|---|---|
| 212 | 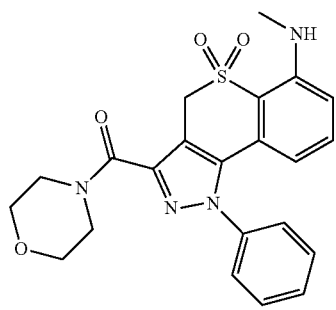 [SMILES: CNc1cccc2c1S(=O)(=O)Cc1c(C(=O)N3CCOCC3)nn(-c3ccccc3)c1-2] |
| 213 | 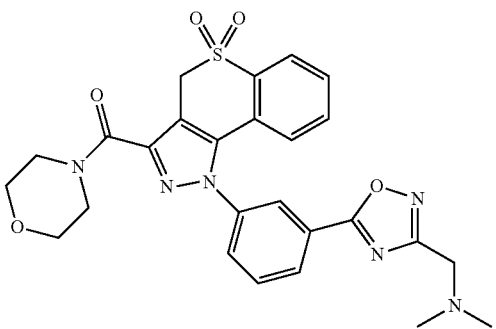 [SMILES: CN(C)Cc1noc(-c2cccc(-n3nc(C(=O)N4CCOCC4)c4c3-c3ccccc3S(=O)(=O)C4)c2)n1] |
| 214 | 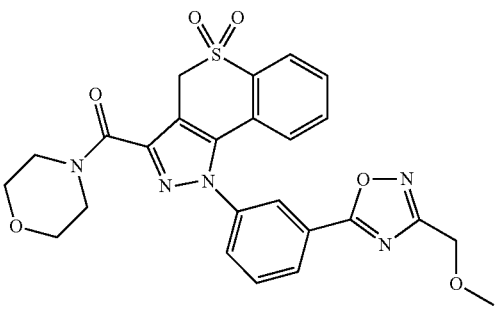 [SMILES: COCc1noc(-c2cccc(-n3nc(C(=O)N4CCOCC4)c4c3-c3ccccc3S(=O)(=O)C4)c2)n1] |
| 215 | 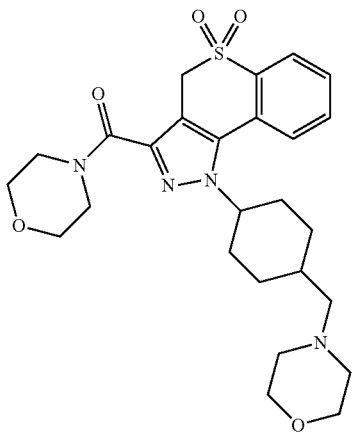 [SMILES: O=C(c1nn(C2CCC(CN3CCOCC3)CC2)c2c1CS(=O)(=O)c1ccccc1-2)N1CCOCC1] |

-continued
| Example No | structures |
|---|---|
| 216 | 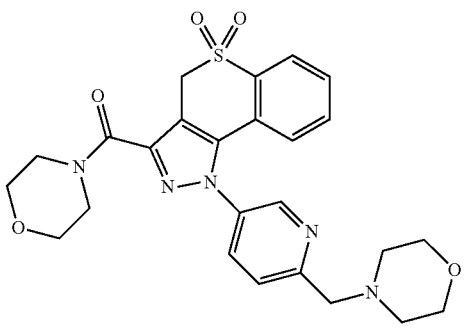 [SMILES: O=C(c1nn(-c2ccc(CN3CCOCC3)nc2)c2c1CS(=O)(=O)c1ccccc1-2)N1CCOCC1] |
| 217 | 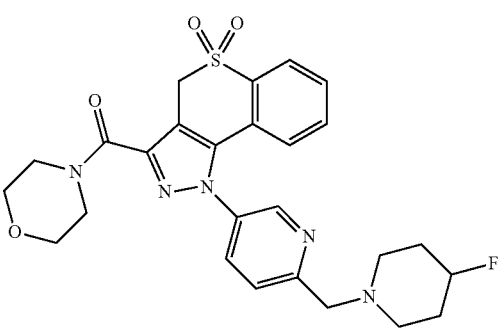 |
| 218 | 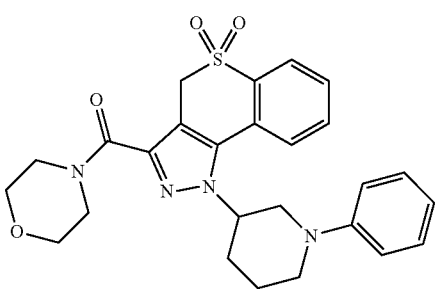 [SMILES: O=C(c1nn(C2CCCN(c3ccccc3)C2)c2c1CS(=O)(=O)c1ccccc1-2)N1CCOCC1] |
| 219 | 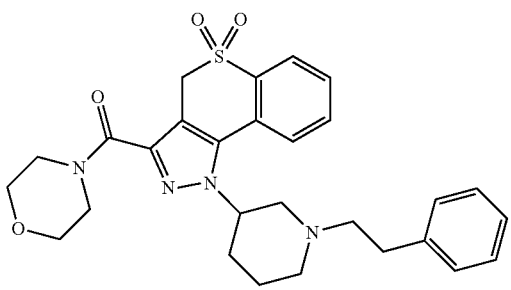 [SMILES: O=C(c1nn(C2CCCN(CCc3ccccc3)C2)c2c1CS(=O)(=O)c1ccccc1-2)N1CCOCC1] |
| 220 | 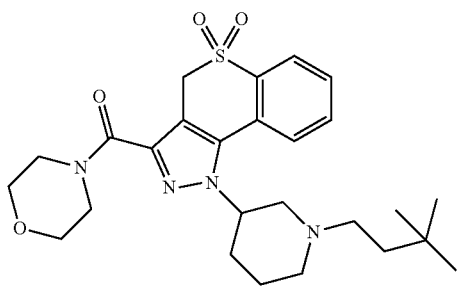 [SMILES: CC(C)(C)CCN1CCCC(n2nc(C(=O)N3CCOCC3)c3c2-c2ccccc2S(=O)(=O)C3)C1] |

| Example No | structures |
|---|---|
| 221 | 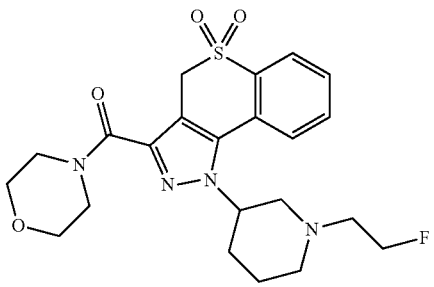 [SMILES: O=C(c1nn(C2CCCN(CCF)C2)c2c1CS(=O)(=O)c1ccccc1-2)N1CCOCC1] |
| 222 | 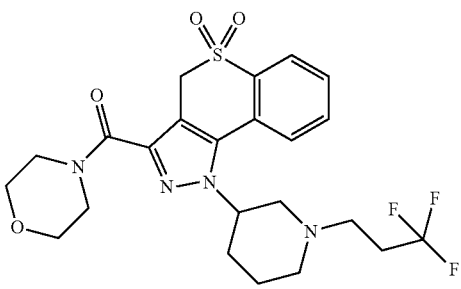 [SMILES: O=C(c1nn(C2CCCN(CCC(F)(F)F)C2)c2c1CS(=O)(=O)c1ccccc1-2)N1CCOCC1] |
| 223 | 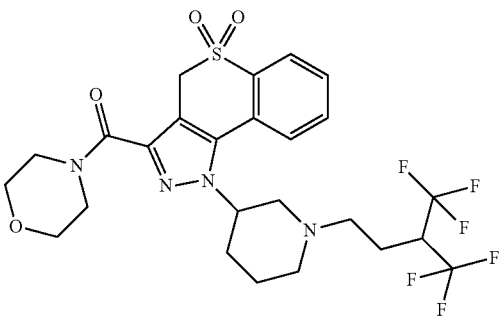 [SMILES: O=C(c1nn(C2CCCN(CCC(C(F)(F)F)C(F)(F)F)C2)c2c1CS(=O)(=O)c1ccccc1-2)N1CCOCC1] |
| 224 | 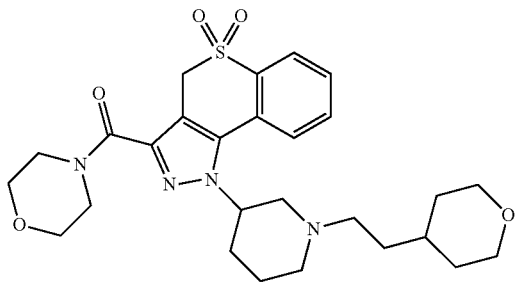 [SMILES: O=C(c1nn(C2CCCN(CCC3CCOCC3)C2)c2c1CS(=O)(=O)c1ccccc1-2)N1CCOCC1] |
| 225 | 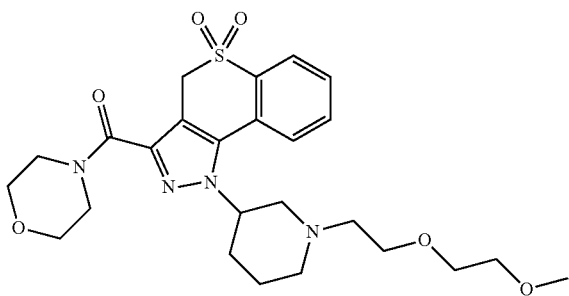 [SMILES: COCCOCCN1CCCC(n2nc(C(=O)N3CCOCC3)c3c2-c2ccccc2S(=O)(=O)C3)C1] |

| Example No | structures |
|---|---|
| 226 | 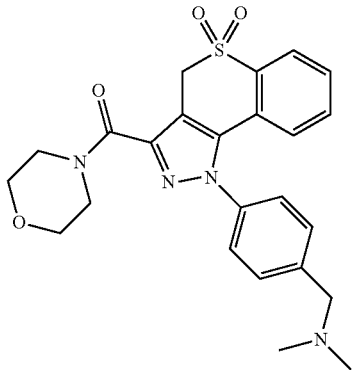 [SMILES: CN(C)Cc1ccc(-n2nc(C(=O)N3CCOCC3)c3c2-c2ccccc2S(=O)(=O)C3)cc1] |
| 227 | 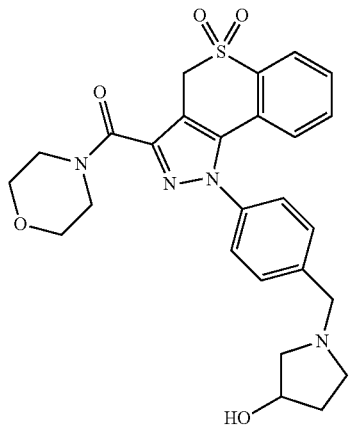 [SMILES: O=C(c1nn(-c2ccc(CN3CCC(O)C3)cc2)c2c1CS(=O)(=O)c1ccccc1-2)N1CCOCC1] |
| 228 | 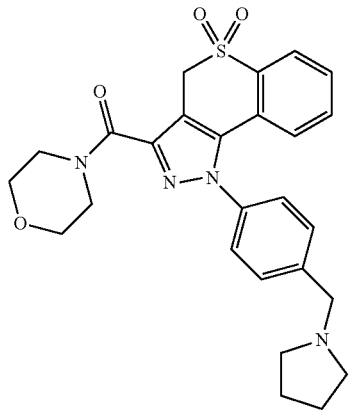 [SMILES: O=C(c1nn(-c2ccc(CN3CCCC3)cc2)c2c1CS(=O)(=O)c1ccccc1-2)N1CCOCC1] |

| Example No | structures |
|---|---|
| 229 | 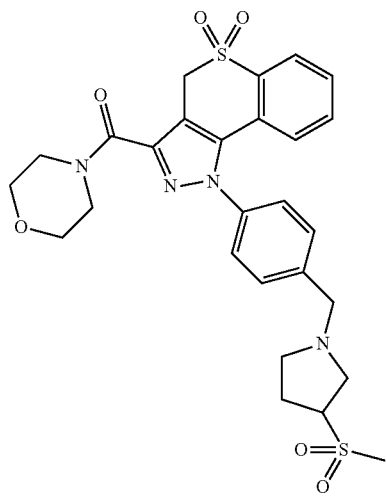 [SMILES: CS(=O)(=O)C1CCN(Cc2ccc(-n3nc(C(=O)N4CCOCC4)c4c3-c3ccccc3S(=O)(=O)C4)cc2)C1] |
| 230 | 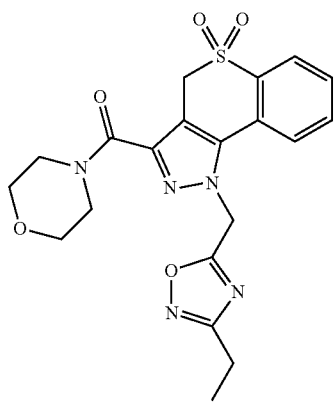 [SMILES: CCc1noc(Cn2nc(C(=O)N3CCOCC3)c3c2-c2ccccc2S(=O)(=O)C3)n1] |
| 231 | 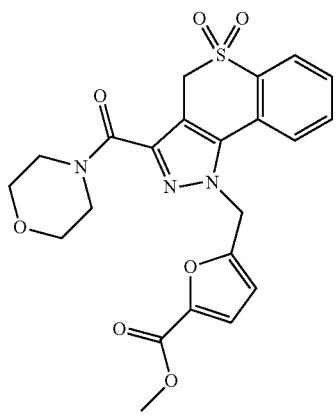 [SMILES: COC(=O)c1ccc(Cn2nc(C(=O)N3CCOCC3)c3c2-c2ccccc2S(=O)(=O)C3)o1] |

| Example No | structures |
|---|---|
| 232 | 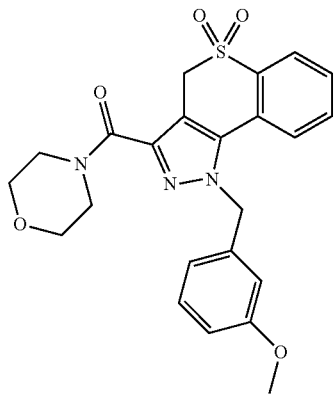 [SMILES: COc1cccc(Cn2nc(C(=O)N3CCOCC3)c3c2-c2ccccc2S(=O)(=O)C3)c1] |
| 233 | 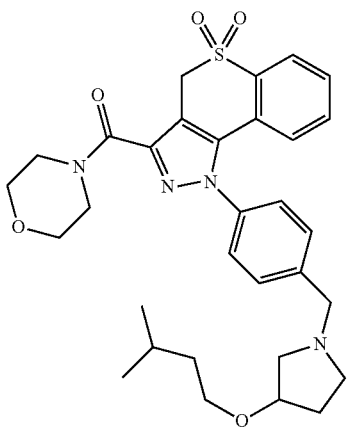 [SMILES: CC(C)CCOC1CCN(Cc2ccc(-n3nc(C(=O)N4CCOCC4)c4c3-c3ccccc3S(=O)(=O)C4)cc2)C1] |
| 234 | 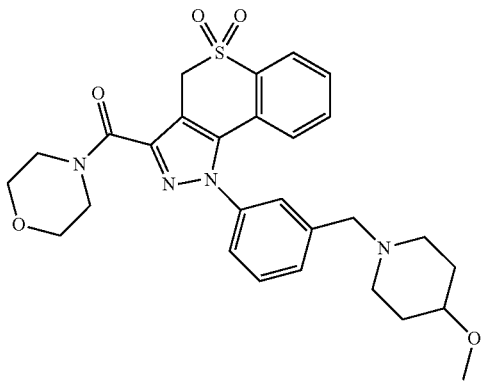 [SMILES: COC1CCN(Cc2cccc(-n3nc(C(=O)N4CCOCC4)c4c3-c3ccccc3S(=O)(=O)C4)c2)CC1] |

| Example No | structures |
|---|---|
| 235 | 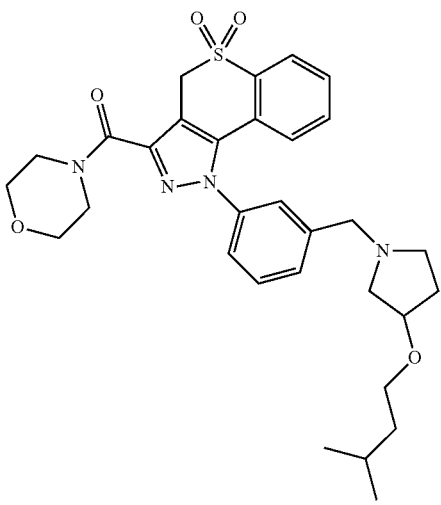 [SMILES: CC(C)CCOC1CCN(Cc2cccc(-n3nc(C(=O)N4CCOCC4)c4c3-c3ccccc3S(=O)(=O)C4)c2)C1] |
| 236 | 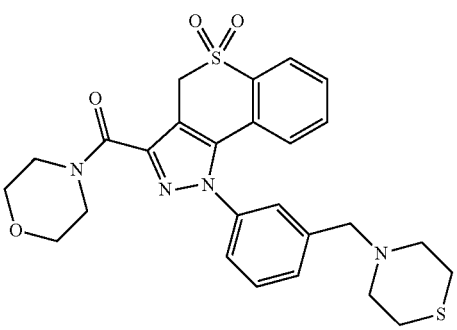 [SMILES: O=C(c1nn(-c2cccc(CN3CCSCC3)c2)c2c1CS(=O)(=O)c1ccccc1-2)N1CCOCC1] |
| 237 | 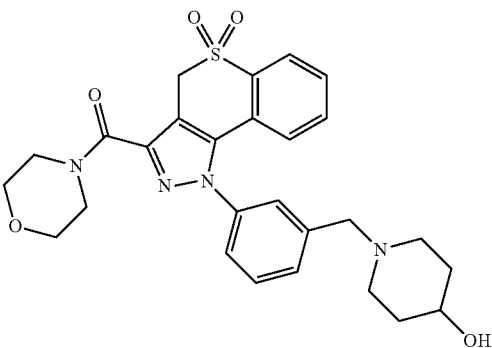 |

| Example No | structures |
|---|---|
| 238 | 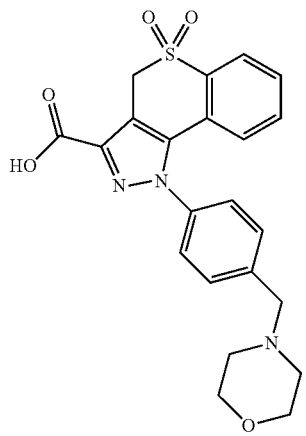 [SMILES: O=C(O)c1nn(-c2ccc(CN3CCOCC3)cc2)c2c1CS(=O)(=O)c1ccccc1-2] |
| 239 | 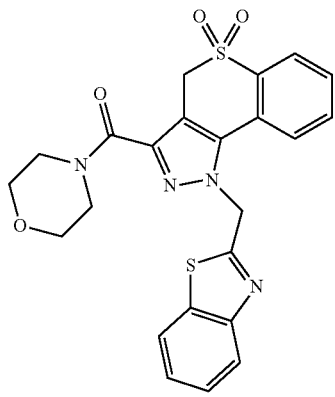 [SMILES: O=C(c1nn(Cc2nc3ccccc3s2)c2c1CS(=O)(=O)c1ccccc1-2)N1CCOCC1] |
| 240 | 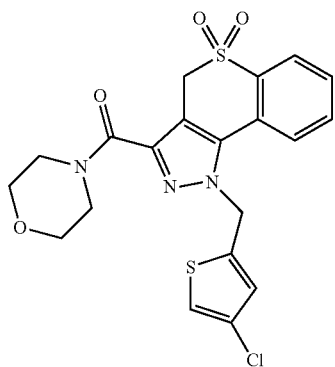 [SMILES: O=C(c1nn(Cc2cc(Cl)cs2)c2c1CS(=O)(=O)c1ccccc1-2)N1CCOCC1] |
| 242 | 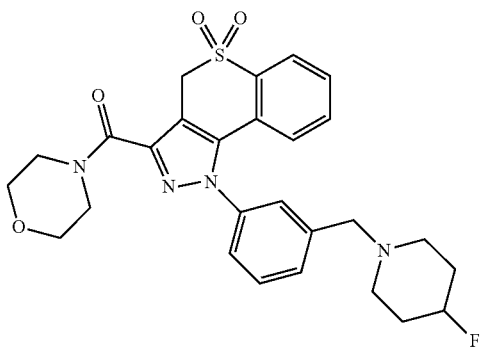 [SMILES: O=C(c1nn(-c2cccc(CN3CCC(F)CC3)c2)c2c1CS(=O)(=O)c1ccccc1-2)N1CCOCC1] |

-continued
| Example No | structures |
|---|---|
| 243 | 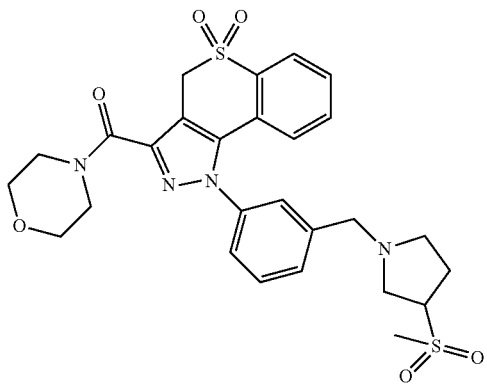 [SMILES: CS(=O)(=O)C1CCN(Cc2cccc(-n3nc(C(=O)N4CCOCC4)c4c3-c3ccccc3S(=O)(=O)C4)c2)C1] |
| 244 | 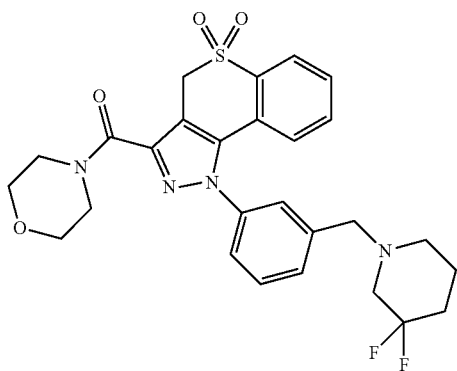 [SMILES: O=C(c1nn(-c2cccc(CN3CCCC(F)(F)C3)c2)c2c1CS(=O)(=O)c1ccccc1-2)N1CCOCC1] |
| 245 | 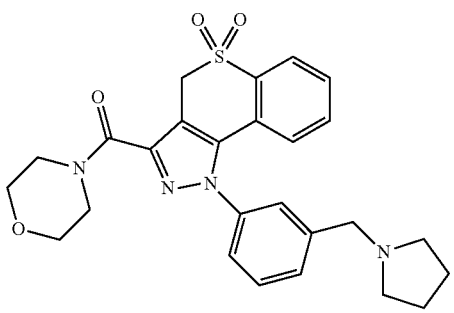 [SMILES: O=C(c1nn(-c2cccc(CN3CCCC3)c2)c2c1CS(=O)(=O)c1ccccc1-2)N1CCOCC1] |
| 246 | 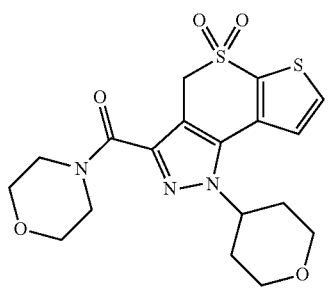 [SMILES: O=C(c1nn(C2CCOCC2)c2c1CS(=O)(=O)c1sccc1-2)N1CCOCC1] |

| Example No | structures |
|---|---|
| 247 | 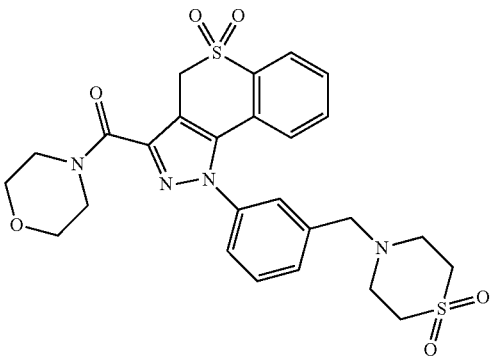 [SMILES: O=C(c1nn(-c2cccc(CN3CCS(=O)(=O)CC3)c2)c2c1CS(=O)(=O)c1ccccc1-2)N1CCOCC1] |
| 248 | 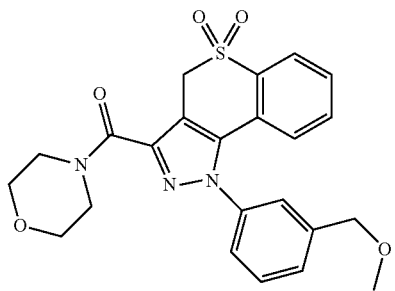 [SMILES: COCc1cccc(-n2nc(C(=O)N3CCOCC3)c3c2-c2ccccc2S(=O)(=O)C3)c1] |
| 249 | 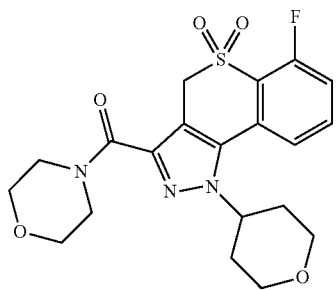 [SMILES: O=C(c1nn(C2CCOCC2)c2c1CS(=O)(=O)c1c(F)cccc1-2)N1CCOCC1] |
| 250 | 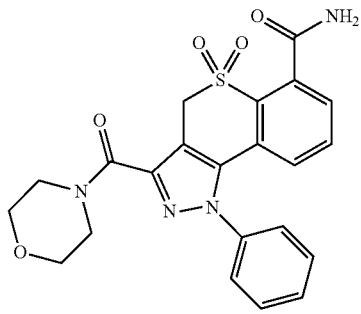 [SMILES: NC(=O)c1cccc2c1S(=O)(=O)Cc1c(C(=O)N3CCOCC3)nn(-c3ccccc3)c1-2] |

| Example No | structures |
|---|---|
| 251 | 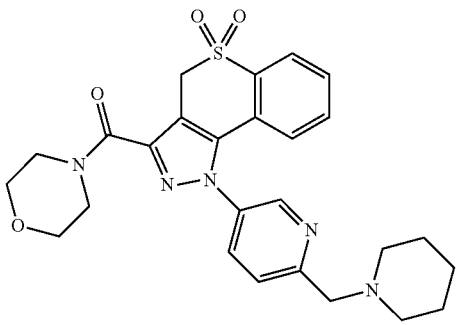 [SMILES: O=C(c1nn(-c2ccc(CN3CCCCC3)nc2)c2c1CS(=O)(=O)c1ccccc1-2)N1CCOCC1] |
| 252 | 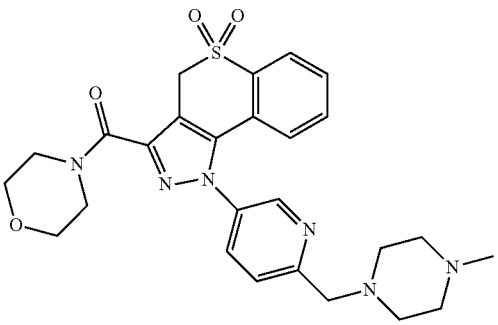 [SMILES: CN1CCN(Cc2ccc(-n3nc(C(=O)N4CCOCC4)c4c3-c3ccccc3S(=O)(=O)C4)cn2)CC1] |
| 253 | 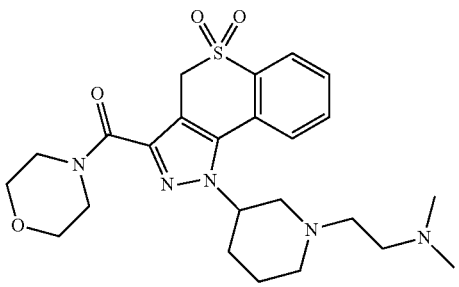 |
| 254 | 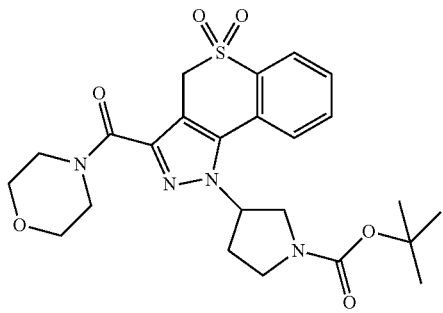 [SMILES: CC(C)(C)OC(=O)N1CCC(n2nc(C(=O)N3CCOCC3)c3c2-c2ccccc2S(=O)(=O)C3)C1] |

-continued
| Example No | structures |
|---|---|
| 255 | 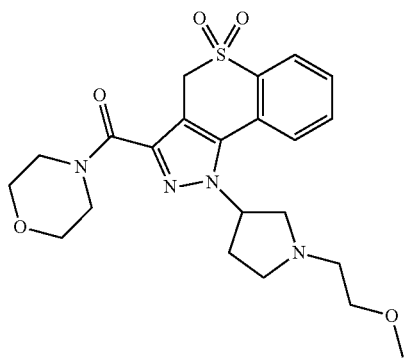 [SMILES: COCCN1CCC(n2nc(C(=O)N3CCOCC3)c3c2-c2ccccc2S(=O)(=O)C3)C1] |
| 256 | 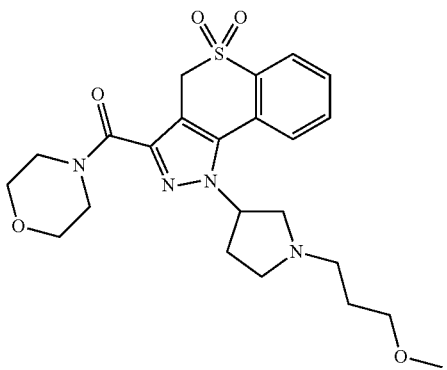 [SMILES: COCCCN1CCC(n2nc(C(=O)N3CCOCC3)c3c2-c2ccccc2S(=O)(=O)C3)C1] |
| 257 | 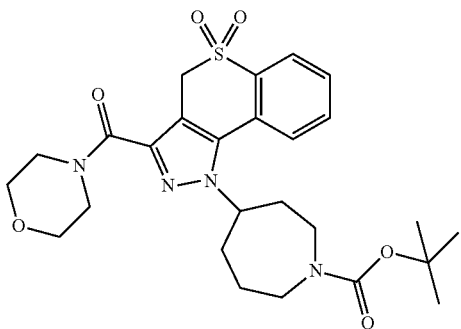 [SMILES: CC(C)(C)OC(=O)N1CCCC(n2nc(C(=O)N3CCOCC3)c3c2-c2ccccc2S(=O)(=O)C3)CC1] |
| 258 | 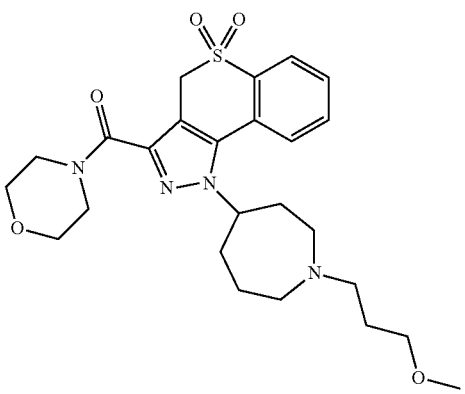 [SMILES: COCCCN1CCCC(n2nc(C(=O)N3CCOCC3)c3c2-c2ccccc2S(=O)(=O)C3)CC1] |

| Example No | structures |
|---|---|
| 259 | 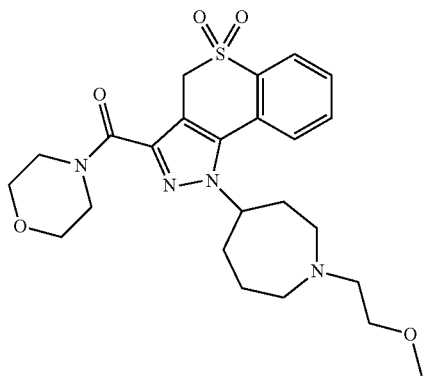 [SMILES: COCCN1CCCC(n2nc(C(=O)N3CCOCC3)c3c2-c2ccccc2S(=O)(=O)C3)CC1] |
| 260 | 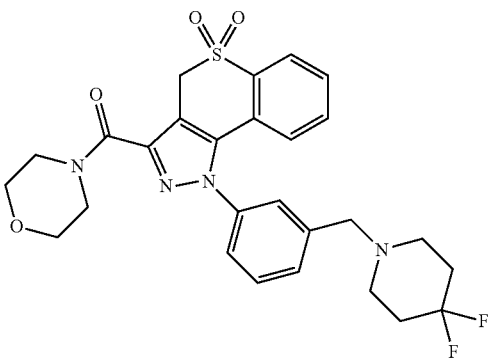 [SMILES: O=C(c1nn(-c2cccc(CN3CCC(F)(F)CC3)c2)c2c1CS(=O)(=O)c1ccccc1-2)N1CCOCC1] |
| 261 | 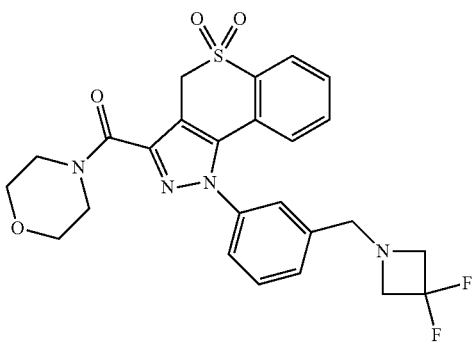 [SMILES: O=C(c1nn(-c2cccc(CN3CC(F)(F)C3)c2)c2c1CS(=O)(=O)c1ccccc1-2)N1CCOCC1] |
| 262 | 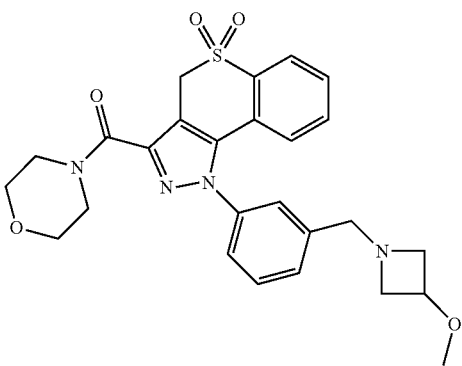 [SMILES: COC1CN(Cc2cccc(-n3nc(C(=O)N4CCOCC4)c4c3-c3ccccc3S(=O)(=O)C4)c2)C1] |

| Example No | structures |
|---|---|
| 263 | 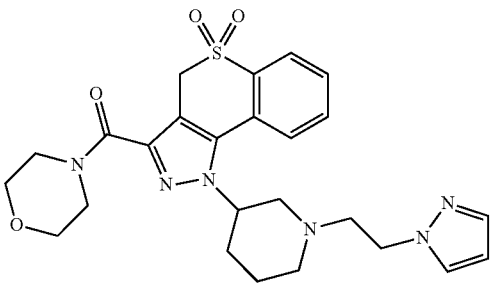 [SMILES: O=C(c1nn(C2CCCN(CCn3cccn3)C2)c2c1CS(=O)(=O)c1ccccc1-2)N1CCOCC1] |
| 264 | 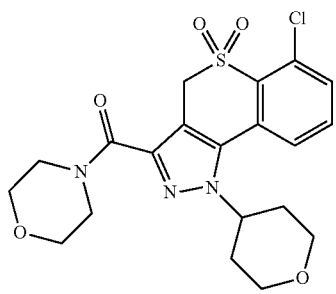 [SMILES: O=C(c1nn(C2CCOCC2)c2c1CS(=O)(=O)c1c(Cl)cccc1-2)N1CCOCC1] |
| 265 | 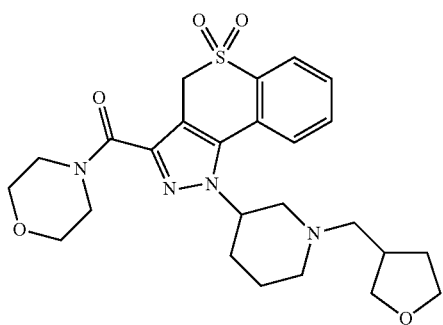 [SMILES: O=C(c1nn(C2CCCN(CC3CCOC3)C2)c2c1CS(=O)(=O)c1ccccc1-2)N1CCOCC1] |
| 266 | 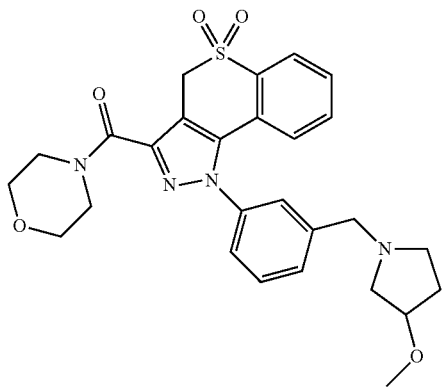 [SMILES: COC1CCN(Cc2cccc(-n3nc(C(=O)N4CCOCC4)c4c3-c3ccccc3S(=O)(=O)C4)c2)C1] |

-continued
| Example No | structures |
|---|---|
| 267 | 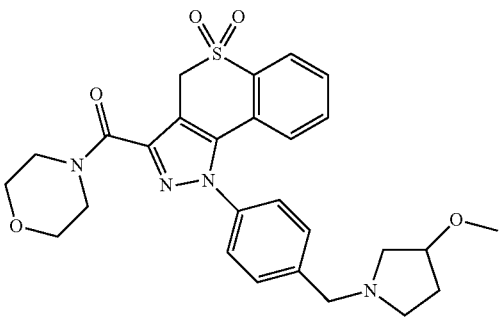 [SMILES: COC1CCN(Cc2ccc(-n3nc(C(=O)N4CCOCC4)c4c3-c3ccccc3S(=O)(=O)C4)cc2)C1] |
| 268 | 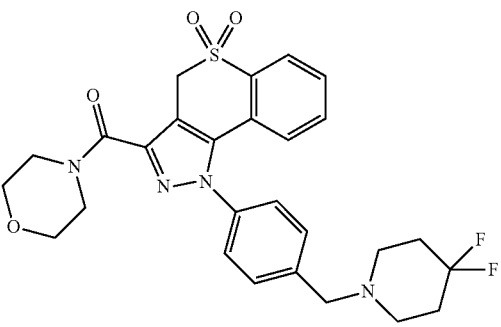 [SMILES: O=C(c1nn(-c2ccc(CN3CCC(F)(F)CC3)cc2)c2c1CS(=O)(=O)c1ccccc1-2)N1CCOCC1] |
| 269 | 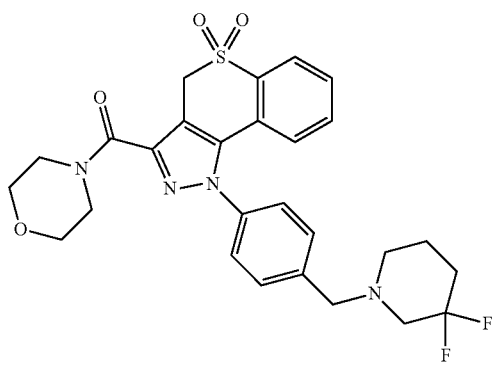 [SMILES: O=C(c1nn(-c2ccc(CN3CCCC(F)(F)C3)cc2)c2c1CS(=O)(=O)c1ccccc1-2)N1CCOCC1] |
| 270 | 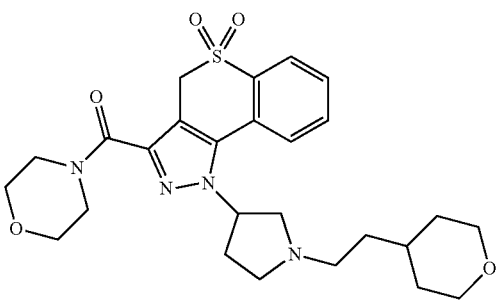 [SMILES: O=C(c1nn(C2CCN(CCC3CCOCC3)C2)c2c1CS(=O)(=O)c1ccccc1-2)N1CCOCC1] |

| Example No | structures |
|---|---|
| 271 | 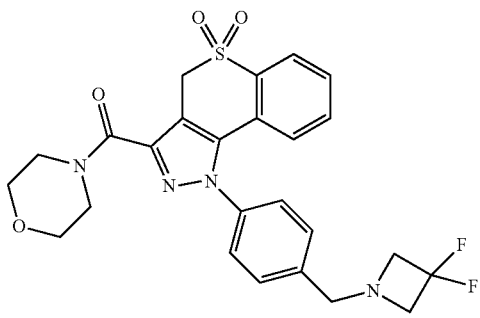 [SMILES: O=C(c1nn(-c2ccc(CN3CC(F)(F)C3)cc2)c2c1CS(=O)(=O)c1ccccc1-2)N1CCOCC1] |
| 272 | 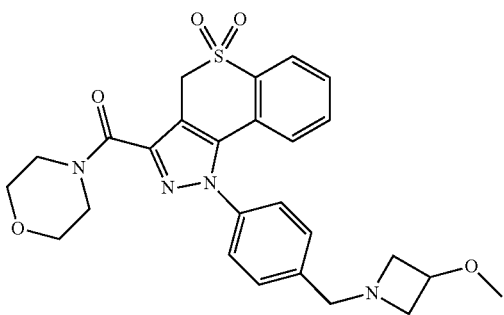 [SMILES: COC1CN(Cc2ccc(-n3nc(C(=O)N4CCOCC4)c4c3-c3ccccc3S(=O)(=O)C4)cc2)C1] |
| 273 | 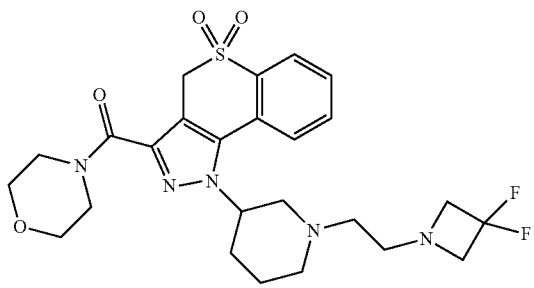 [SMILES: O=C(c1nn(C2CCCN(CCN3CC(F)(F)C3)C2)c2c1CS(=O)(=O)c1ccccc1-2)N1CCOCC1] |
| 274 | 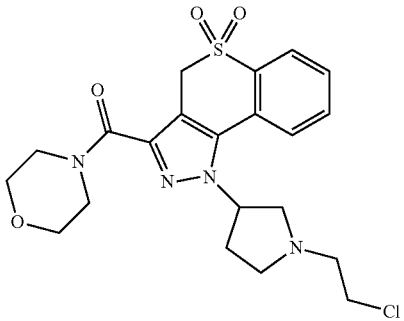 [SMILES: O=C(c1nn(C2CCN(CCCl)C2)c2c1CS(=O)(=O)c1ccccc1-2)N1CCOCC1] |

-continued
| Example No | structures |
|---|---|
| 275 | 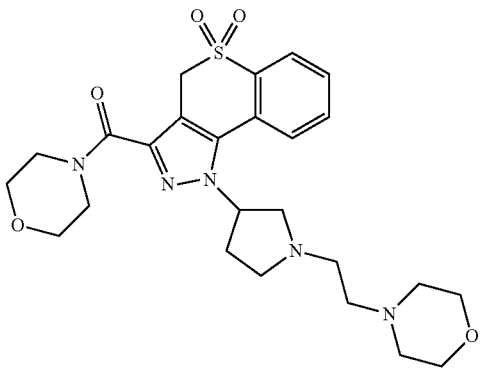 [SMILES: O=C(c1nn(C2CCN(CCN3CCOCC3)C2)c2c1CS(=O)(=O)c1ccccc1-2)N1CCOCC1] |
| 276 | 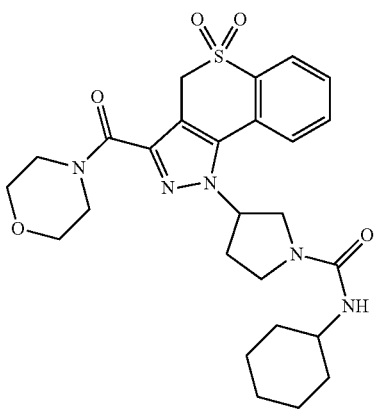 [SMILES: O=C(NC1CCCCC1)N1CCC(n2nc(C(=O)N3CCOCC3)c3c2-c2ccccc2S(=O)(=O)C3)C1] |
| 277 | 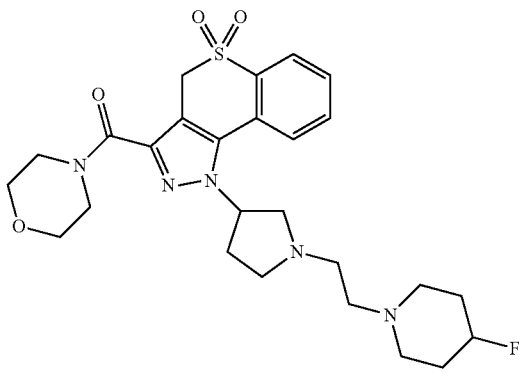 [SMILES: O=C(c1nn(C2CCN(CCN3CCC(F)CC3)C2)c2c1CS(=O)(=O)c1ccccc1-2)N1CCOCC1] |
| 278 | 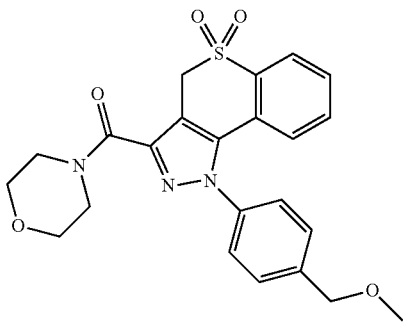 [SMILES: COCc1ccc(-n2nc(C(=O)N3CCOCC3)c3c2-c2ccccc2S(=O)(=O)C3)cc1] |

-continued
| Example No | structures |
|---|---|
| 279 | 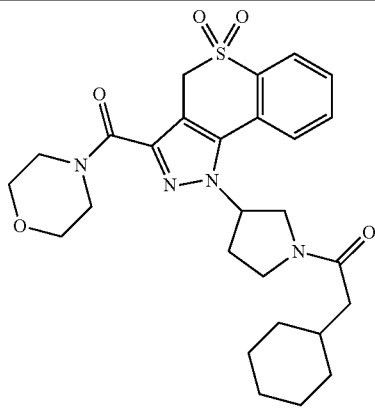 |
| 280 | 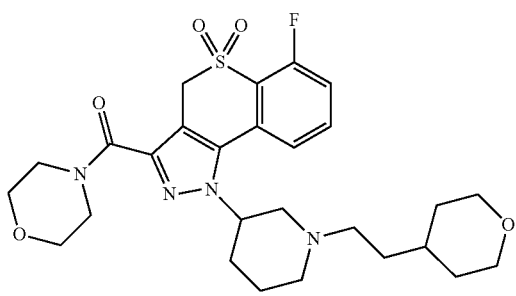 [SMILES: O=C(c1nn(C2CCCN(CCC3CCOCC3)C2)c2c1CS(=O)(=O)c1c(F)cccc1-2)N1CCOCC1] |
| 281 | 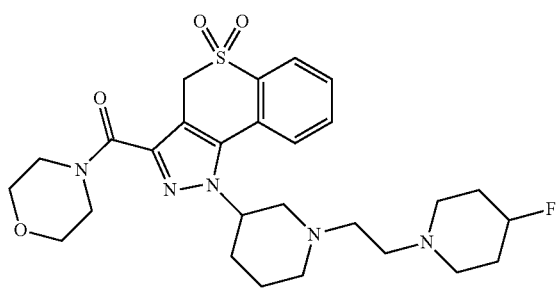 [SMILES: O=C(c1nn(C2CCCN(CCN3CCC(F)CC3)C2)c2c1CS(=O)(=O)c1ccccc1-2)N1CCOCC1] |
| 282 | 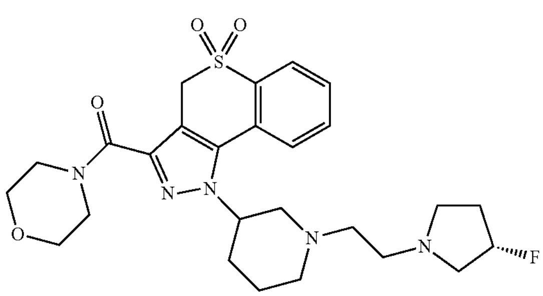 [SMILES: O=C(c1nn(C2CCCN(CCN3CC[C@H](F)C3)C2)c2c1CS(=O)(=O)c1ccccc1-2)N1CCOCC1] |
| 283 | 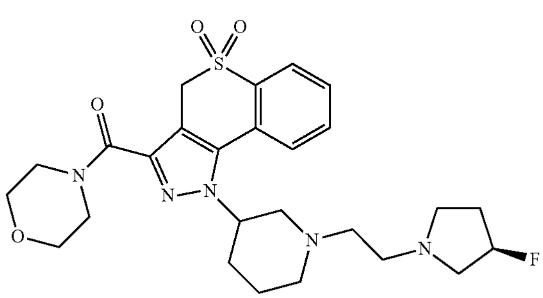 [SMILES: O=C(c1nn(C2CCCN(CCN3CC[C@@H](F)C3)C2)c2c1CS(=O)(=O)c1ccccc1-2)N1CCOCC1] |

-continued
| Example No | structures |
|---|---|
| 284 | 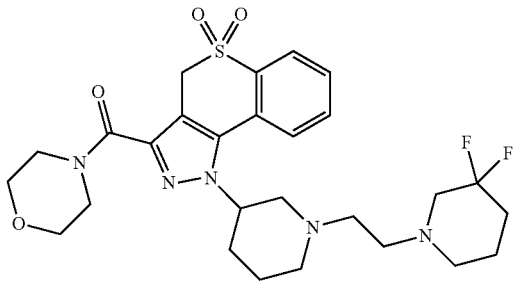 [SMILES: O=C(c1nn(C2CCCN(CCN3CCCC(F)(F)C3)C2)c2c1CS(=O)(=O)c1ccccc1-2)N1CCOCC1] |
| 285 | 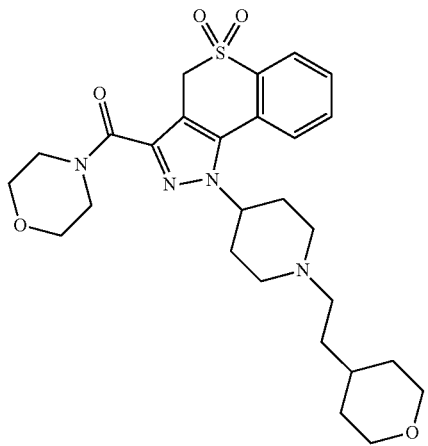 [SMILES: O=C(c1nn(C2CCN(CCC3CCOCC3)CC2)c2c1CS(=O)(=O)c1ccccc1-2)N1CCOCC1] |
| 286 | 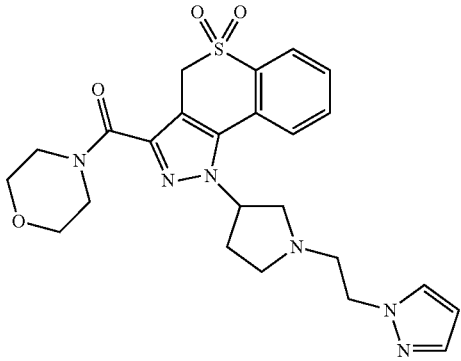 [SMILES: O=C(c1nn(C2CCN(CCn3cccn3)C2)c2c1CS(=O)(=O)c1ccccc1-2)N1CCOCC1] |
| 287 | 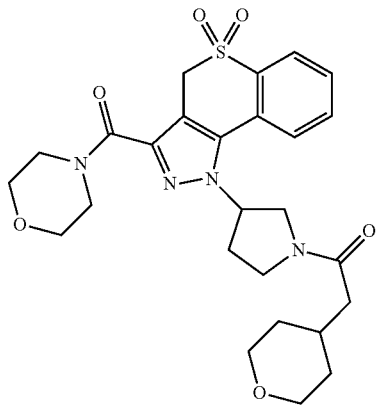 [SMILES: O=C(CC1CCOCC1)N1CCC(n2nc(C(=O)N3CCOCC3)c3c2-c2ccccc2S(=O)(=O)C3)C1] |

-continued
| Example No | structures |
|---|---|
| 288 | 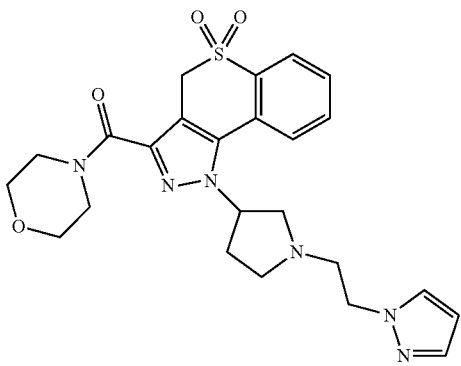 [SMILES: O=C(c1nn(C2CCN(CCn3cccn3)C2)c2c1CS(=O)(=O)c1ccccc1-2)N1CCOCC1] |
| 289 | 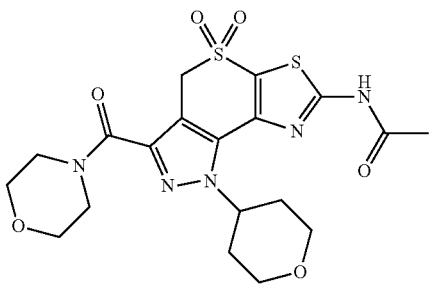 [SMILES: CC(=O)Nc1nc2c(s1)S(=O)(=O)Cc1c(C(=O)N3CCOCC3)nn(C3CCOCC3)c1-2] |
| 290 | 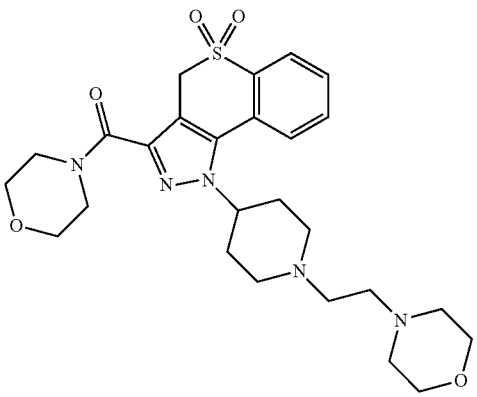 [SMILES: O=C(c1nn(C2CCN(CCN3CCOCC3)CC2)c2c1CS(=O)(=O)c1ccccc1-2)N1CCOCC1] |
| 291 | 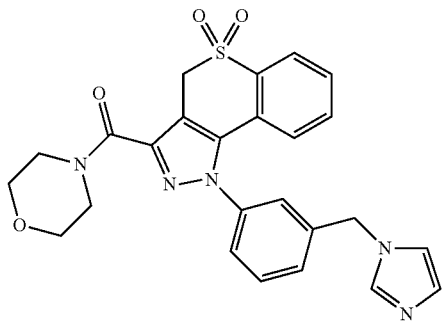 [SMILES: O=C(c1nn(-c2cccc(Cn3ccnc3)c2)c2c1CS(=O)(=O)c1ccccc1-2)N1CCOCC1] |

-continued

| Example No | structures |
|---|---|
| 292 | 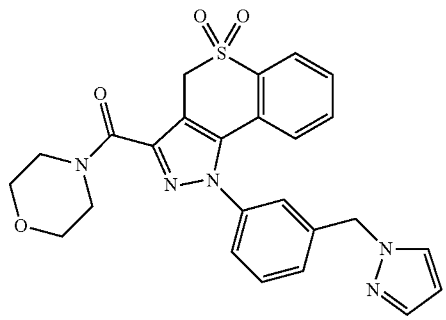 [SMILES: O=C(c1nn(-c2cccc(Cn3cccn3)c2)c2c1CS(=O)(=O)c1ccccc1-2)N1CCOCC1] |
| 293 | 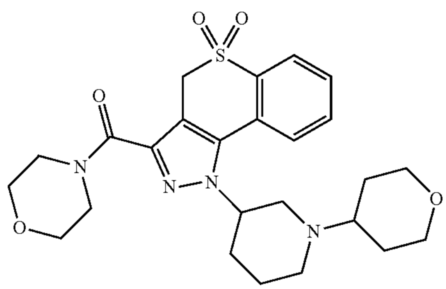 |
| 294 | 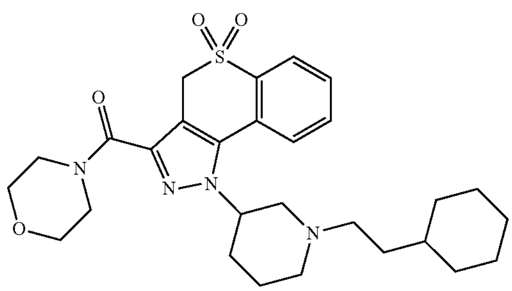 [SMILES: O=C(c1nn(C2CCCN(CCC3CCCCC3)C2)c2c1CS(=O)(=O)c1ccccc1-2)N1CCOCC1] |
| 295 | 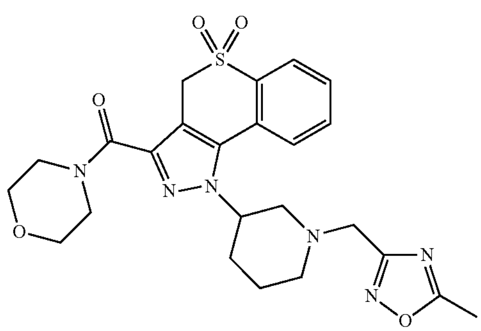 [SMILES: Cc1nc(CN2CCCC(n3nc(C(=O)N4CCOCC4)c4c3-c3ccccc3S(=O)(=O)C4)C2)no1] |
| 296 | 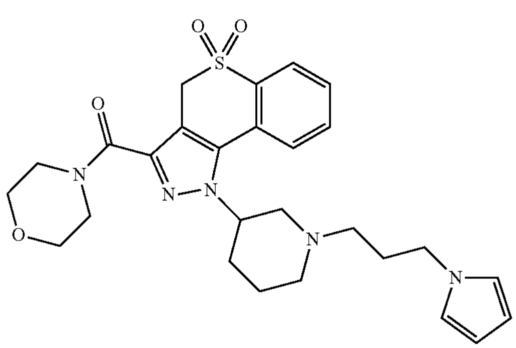 [SMILES: O=C(c1nn(C2CCCN(CCCn3cccc3)C2)c2c1CS(=O)(=O)c1ccccc1-2)N1CCOCC1] |

-continued
| Example No | structures |
|---|---|
| 297 | 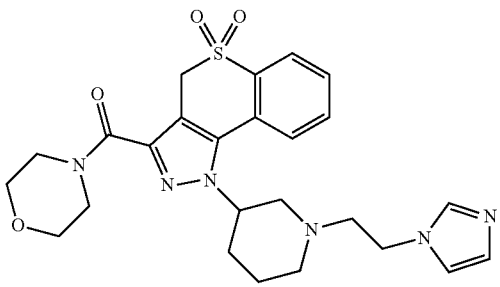 [SMILES: O=C(c1nn(C2CCCN(CCn3ccnc3)C2)c2c1CS(=O)(=O)c1ccccc1-2)N1CCOCC1] |
| 298 | 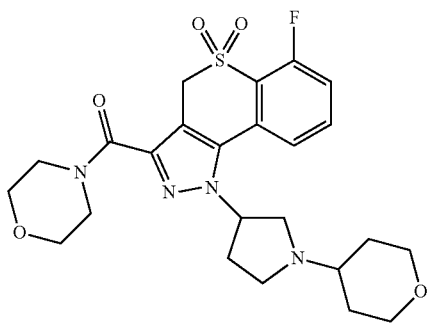 |
| 299 | 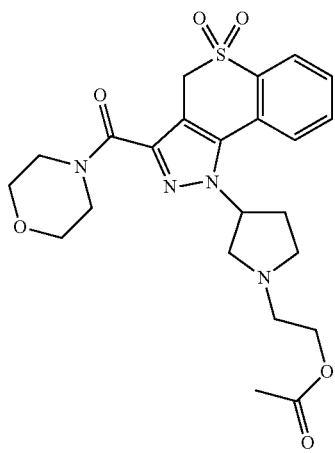 [SMILES: CC(=O)OCCN1CCC(n2nc(C(=O)N3CCOCC3)c3c2-c2ccccc2S(=O)(=O)C3)C1] |
| 300 | 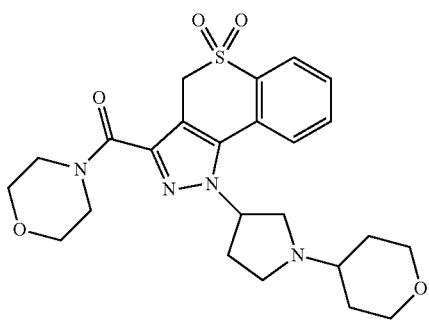 [SMILES: O=C(c1nn(C2CCN(C3CCOCC3)C2)c2c1CS(=O)(=O)c1ccccc1-2)N1CCOCC1] |

-continued
| Example No | structures |
|---|---|
| 301 | 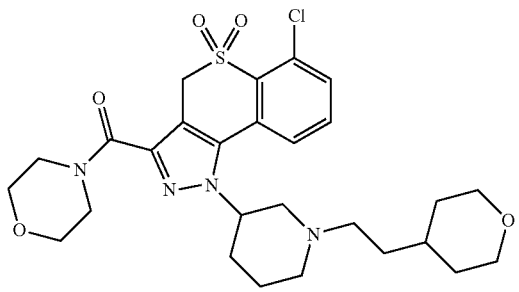 |
| 302 | 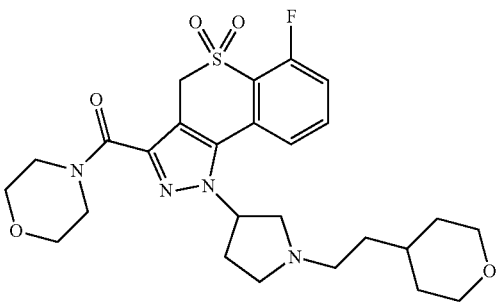 |
| 303 | 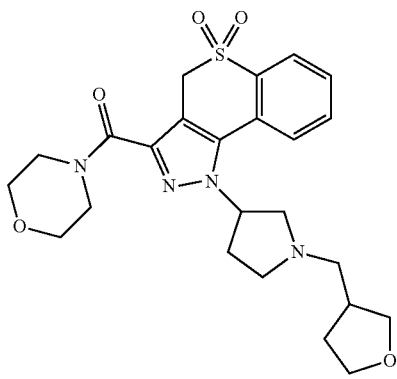 [SMILES: O=C(c1nn(C2CCN(CC3CCOC3)C2)c2c1CS(=O)(=O)c1ccccc1-2)N1CCOCC1] |
| 304 | 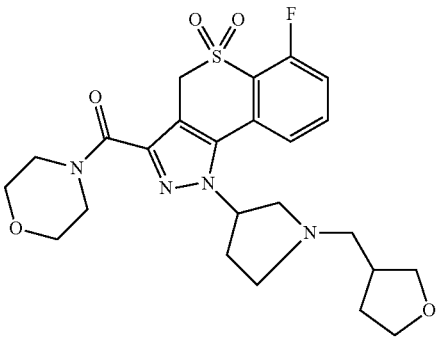 [SMILES: O=C(c1nn(C2CCN(CC3CCOC3)C2)c2c1CS(=O)(=O)c1c(F)cccc1-2)N1CCOCC1] |

| Example No | structures |
|---|---|
| 305 | 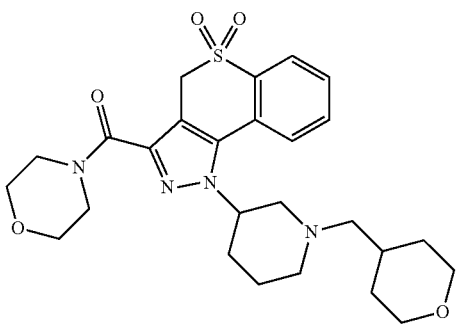 |
| 306 | 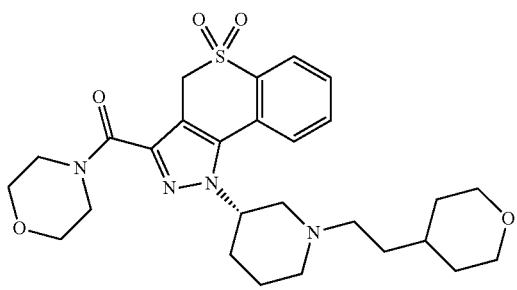 [SMILES: O=C(c1nn([C@H]2CCCN(CCC3CCOCC3)C2)c2c1CS(=O)(=O)c1ccccc1-2)N1CCOCC1] |
| 307 | 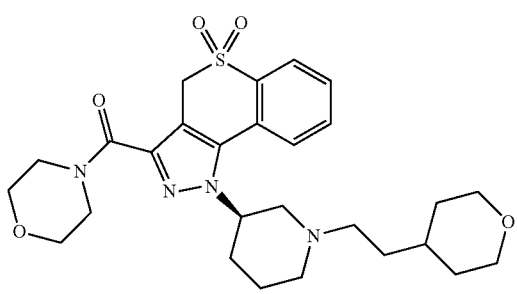 [SMILES: O=C(c1nn([C@@H]2CCCN(CCC3CCOCC3)C2)c2c1CS(=O)(=O)c1ccccc1-2)N1CCOCC1] |
| 308 | 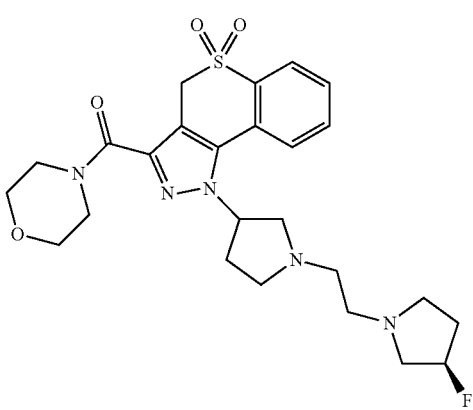 [SMILES: O=C(c1nn(C2CCN(CCN3CC[C@@H](F)C3)C2)c2c1CS(=O)(=O)c1ccccc1-2)N1CCOCC1] |

| Example No | structures |
|---|---|
| 309 | 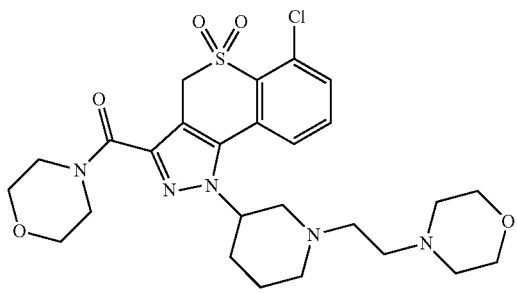 |
| 310 | 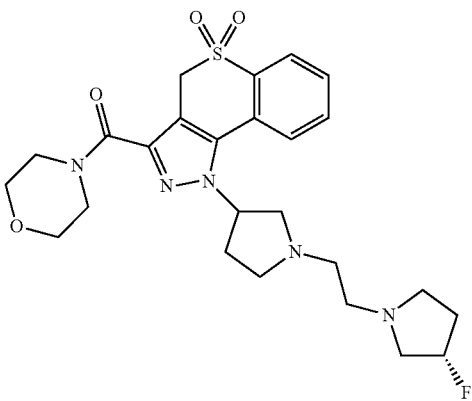 [SMILES: O=C(c1nn(C2CCN(CCN3CC[C@H](F)C3)C2)c2c1CS(=O)(=O)c1ccccc1-2)N1CCOCC1] |
| 311 | 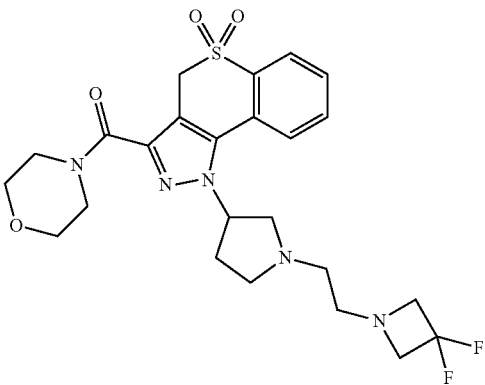 [SMILES: O=C(c1nn(C2CCN(CCN3CC(F)(F)C3)C2)c2c1CS(=O)(=O)c1ccccc1-2)N1CCOCC1] |
| 312 | 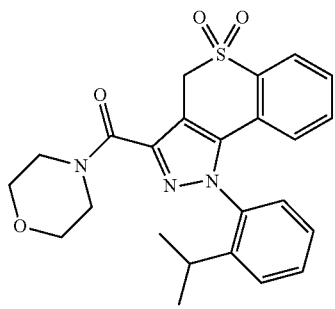 [SMILES: CC(C)c1ccccc1-n1nc(C(=O)N2CCOCC2)c2c1-c1ccccc1S(=O)(=O)C2] |

-continued
| Example No | structures |
|---|---|
| 313 | 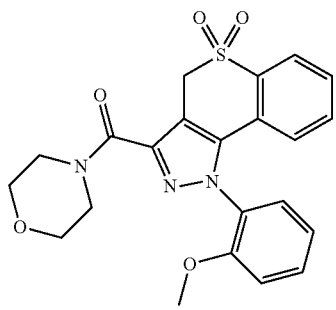 [SMILES: COc1ccccc1-n1nc(C(=O)N2CCOCC2)c2c1-c1ccccc1S(=O)(=O)C2] |
| 314 | 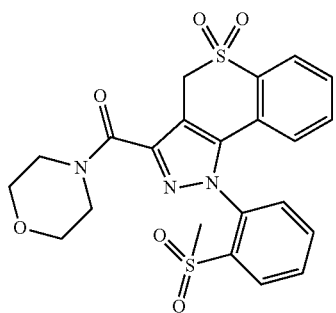 [SMILES: CS(=O)(=O)c1ccccc1-n1nc(C(=O)N2CCOCC2)c2c1-c1ccccc1S(=O)(=O)C2] |
| 315 | 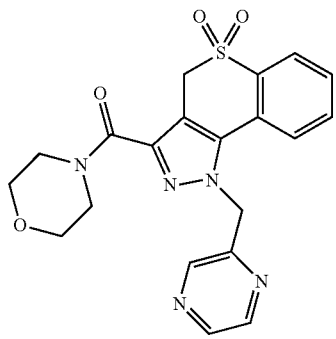 [SMILES: O=C(c1nn(Cc2cnccn2)c2c1CS(=O)(=O)c1ccccc1-2)N1CCOCC1] |
| 316 | 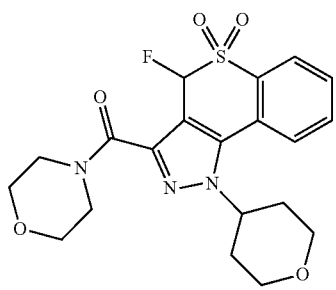 [SMILES: O=C(c1nn(C2CCOCC2)c2c1C(F)S(=O)(=O)c1ccccc1-2)N1CCOCC1] |

-continued
| Example No | structures |
|---|---|
| 317 | 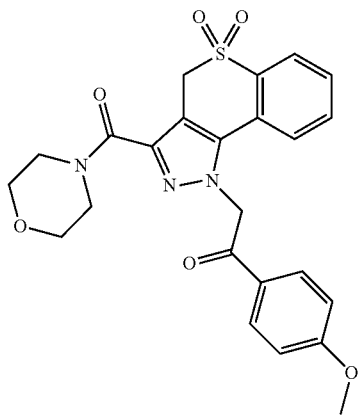 [SMILES: COc1ccc(C(=O)Cn2nc(C(=O)N3CCOCC3)c3c2-c2ccccc2S(=O)(=O)C3)cc1] |
| 318 | 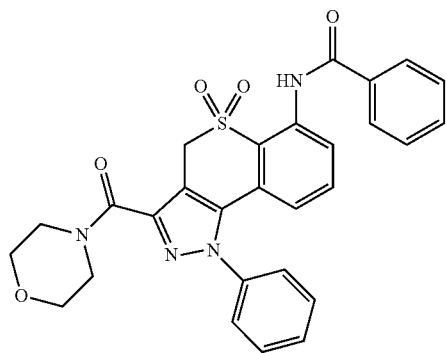 [SMILES: O=C(Nc1cccc2c1S(=O)(=O)Cc1c(C(=O)N3CCOCC3)nn(-c3ccccc3)c1-2)c1ccccc1] |
| 319 | 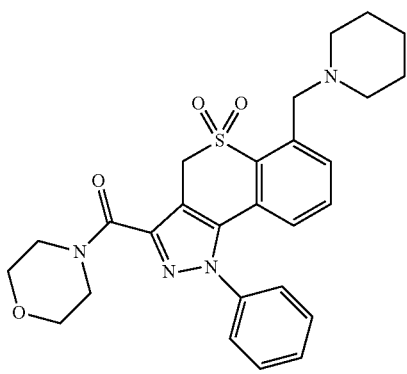 [SMILES: O=C(c1nn(-c2ccccc2)c2c1CS(=O)(=O)c1c(CN3CCCCC3)cccc1-2)N1CCOCC1] |
| 320 | 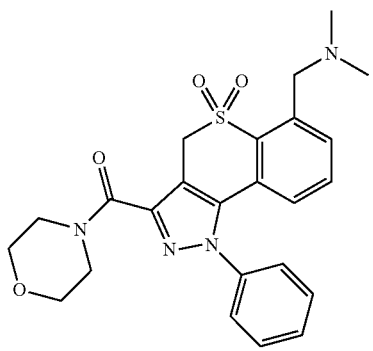 [SMILES: CN(C)Cc1cccc2c1S(=O)(=O)Cc1c(C(=O)N3CCOCC3)nn(-c3ccccc3)c1-2] |

| Example No | structures |
|---|---|
| 321 | 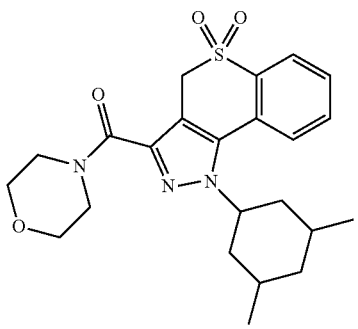 [SMILES: CC1CC(C)CC(n2nc(C(=O)N3CCOCC3)c3c2-c2ccccc2S(=O)(=O)C3)C1] |
| 322 | 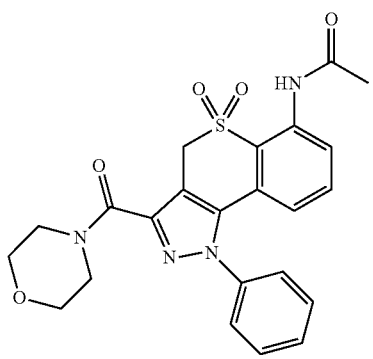 [SMILES: CC(=O)Nc1cccc2c1S(=O)(=O)Cc1c(C(=O)N3CCOCC3)nn(-c3ccccc3)c1-2] |
| 323 | 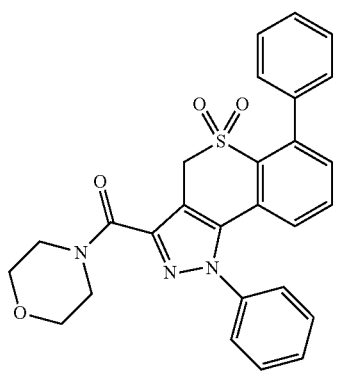 [SMILES: O=C(c1nn(-c2ccccc2)c2c1CS(=O)(=O)c1c(-c3ccccc3)cccc1-2)N1CCOCC1] |
| 324 | 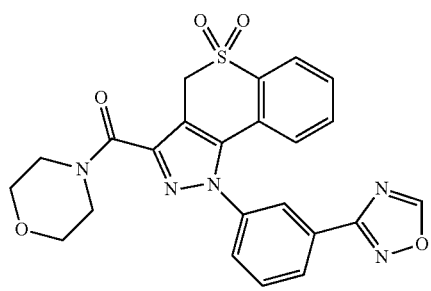 [SMILES: O=C(c1nn(-c2cccc(-c3ncon3)c2)c2c1CS(=O)(=O)c1ccccc1-2)N1CCOCC1] |

-continued
| Example No | structures |
|---|---|
| 325 | 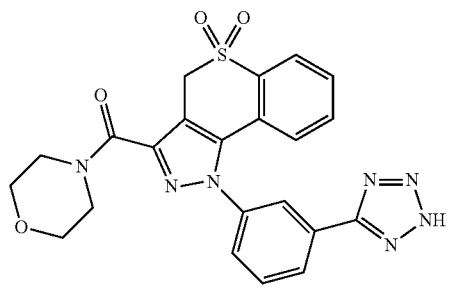 [SMILES: O=C(c1nn(-c2cccc(-c3nn[nH]n3)c2)c2c1CS(=O)(=O)c1ccccc1-2)N1CCOCC1] |
| 326 | 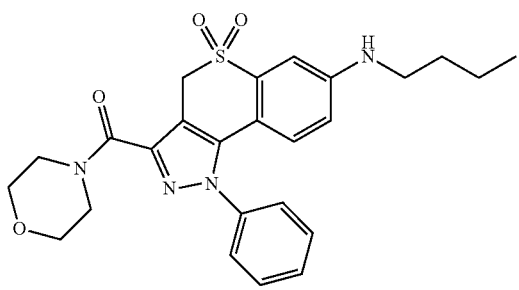 [SMILES: CCCCNc1ccc2c(c1)S(=O)(=O)Cc1c(C(=O)N3CCOCC3)nn(-c3ccccc3)c1-2] |
| 327 | 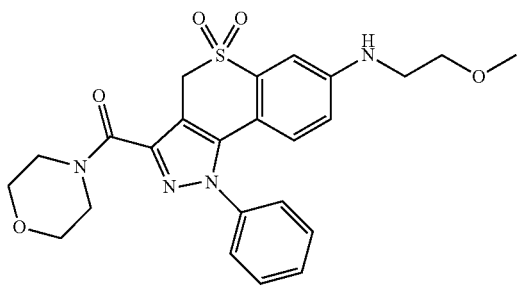 [SMILES: COCCNc1ccc2c(c1)S(=O)(=O)Cc1c(C(=O)N3CCOCC3)nn(-c3ccccc3)c1-2] |
| 328 | 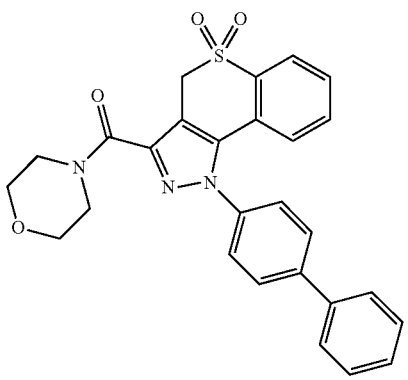 [SMILES: O=C(c1nn(-c2ccc(-c3ccccc3)cc2)c2c1CS(=O)(=O)c1ccccc1-2)N1CCOCC1] |
| 329 | 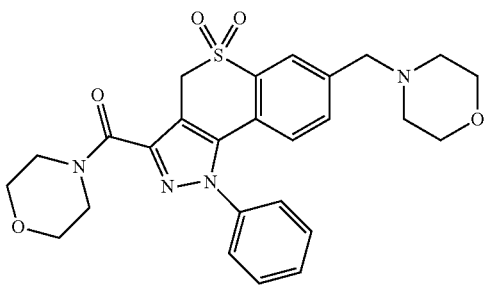 [SMILES: O=C(c1nn(-c2ccccc2)c2c1CS(=O)(=O)c1cc(CN3CCOCC3)ccc1-2)N1CCOCC1] |

| Example No | structures |
|---|---|
| 330 | 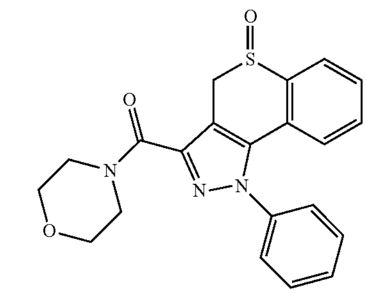 [SMILES: O=C(c1nn(-c2ccccc2)c2c1CS(=O)c1ccccc1-2)N1CCOCC1] |
| 331 | 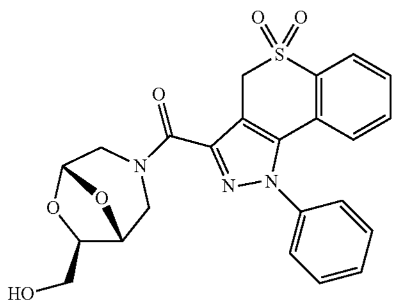 [SMILES: O=C(c1nn(-c2ccccc2)c2c1CS(=O)(=O)c1ccccc1-2)N1C[C@H]2O[C@H](CO)[C@@H](C1)O2] |
| 332 | 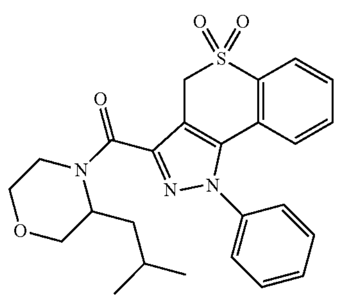 [SMILES: CC(C)CC1COCCN1C(=O)c1nn(-c2ccccc2)c2c1CS(=O)(=O)c1ccccc1-2] |
| 333 | 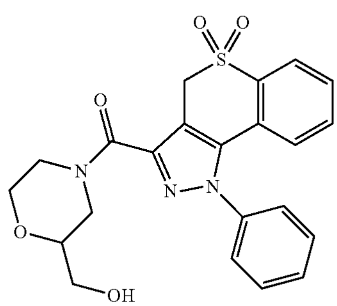 [SMILES: O=C(c1nn(-c2ccccc2)c2c1CS(=O)(=O)c1ccccc1-2)N1CCOC(CO)C1] |
| 334 | 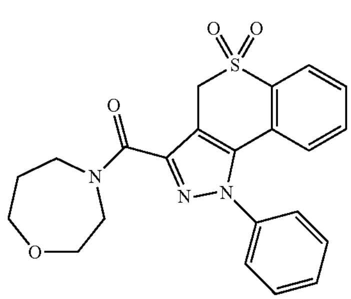 [SMILES: O=C(c1nn(-c2ccccc2)c2c1CS(=O)(=O)c1ccccc1-2)N1CCCOCC1] |

-continued
| Example No | structures |
|---|---|
| 335 | 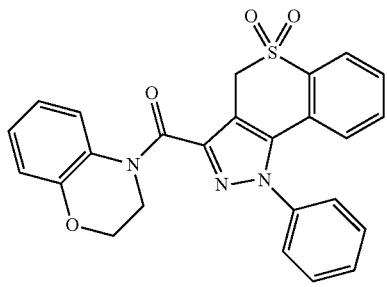 [SMILES: O=C(c1nn(-c2ccccc2)c2c1CS(=O)(=O)c1ccccc1-2)N1CCOc2ccccc21] |
| 336 | 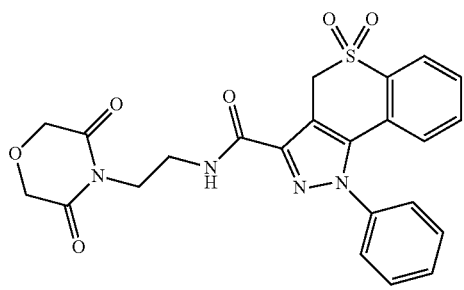 [SMILES: O=C(NCCN1C(=O)COCC1=O)c1nn(-c2ccccc2)c2c1CS(=O)(=O)c1ccccc1-2] |
| 337 | 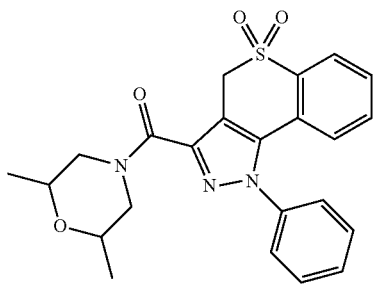 [SMILES: CC1CN(C(=O)c2nn(-c3ccccc3)c3c2CS(=O)(=O)c2ccccc2-3)CC(C)O1] |
| 338 | 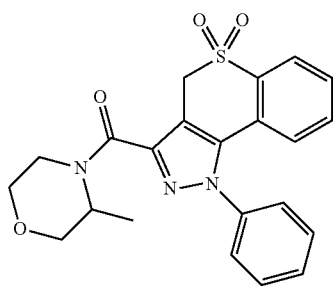 [SMILES: CC1COCCN1C(=O)c1nn(-c2ccccc2)c2c1CS(=O)(=O)c1ccccc1-2] |

-continued
| Example No | structures |
|---|---|
| 339 | 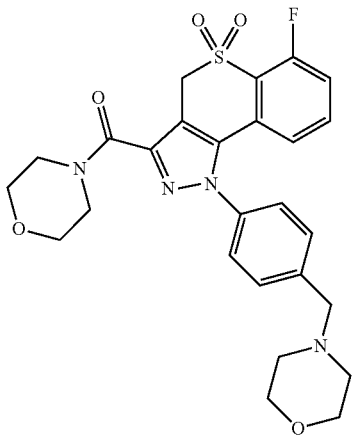 [SMILES: O=C(c1nn(-c2ccc(CN3CCOCC3)cc2)c2c1CS(=O)(=O)c1c(F)cccc1-2)N1CCOCC1] |
| 340 | 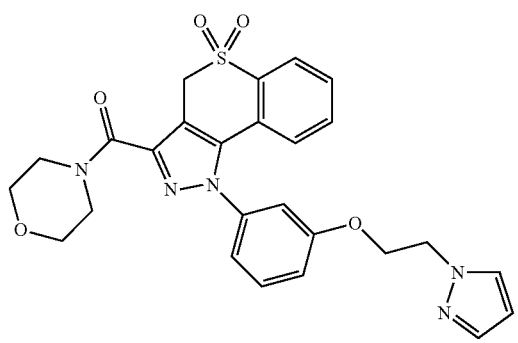 [SMILES: O=C(c1nn(-c2cccc(OCCn3cccn3)c2)c2c1CS(=O)(=O)c1ccccc1-2)N1CCOCC1] |
| 341 | 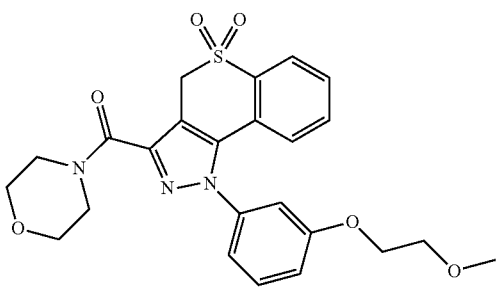 [SMILES: COCCOc1cccc(-n2nc(C(=O)N3CCOCC3)c3c2-c2ccccc2S(=O)(=O)C3)c1] |
| 342 | 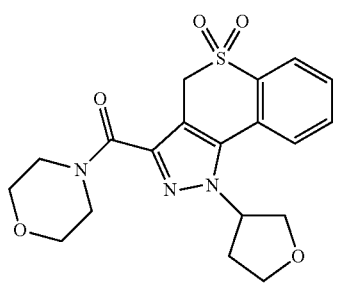 [SMILES: O=C(c1nn(C2CCOC2)c2c1CS(=O)(=O)c1ccccc1-2)N1CCOCC1] |

-continued
| Example No | structures |
|---|---|
| 343 | 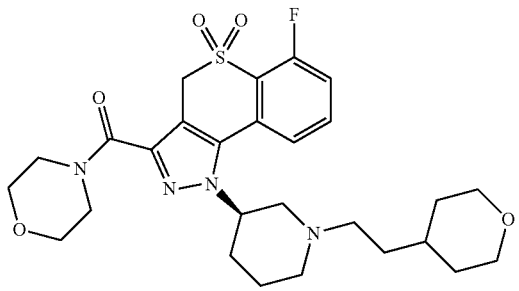 [SMILES: O=C(c1nn([C@@H]2CCCN(CCC3CCOCC3)C2)c2c1CS(=O)(=O)c1c(F)cccc1-2)N1CCOCC1] |
| 344 | 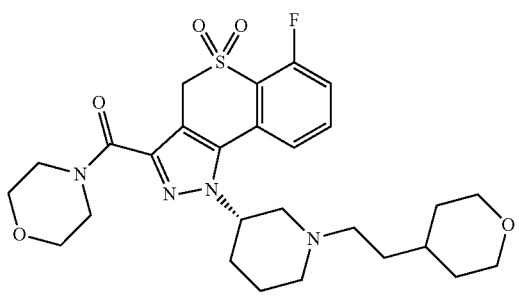 [SMILES: O=C(c1nn([C@H]2CCCN(CCC3CCOCC3)C2)c2c1CS(=O)(=O)c1c(F)cccc1-2)N1CCOCC1] |
| 345 | 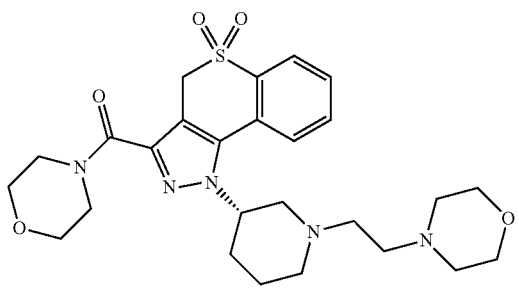 [SMILES: O=C(c1nn([C@H]2CCCN(CCN3CCOCC3)C2)c2c1CS(=O)(=O)c1ccccc1-2)N1CCOCC1] |
| 346 | 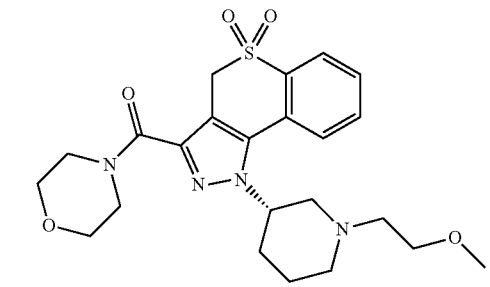 [SMILES: COCCN1CCC[C@H](n2nc(C(=O)N3CCOCC3)c3c2-c2ccccc2S(=O)(=O)C3)C1] |
| 347 | 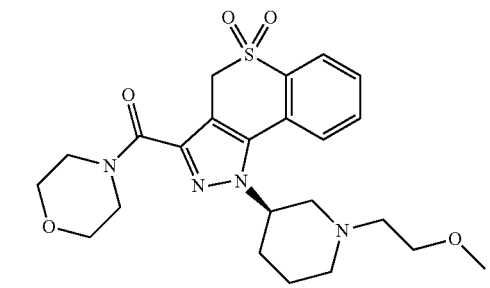 [SMILES: COCCN1CCC[C@@H](n2nc(C(=O)N3CCOCC3)c3c2-c2ccccc2S(=O)(=O)C3)C1] |

| Example No | structures |
|---|---|
| 348 | 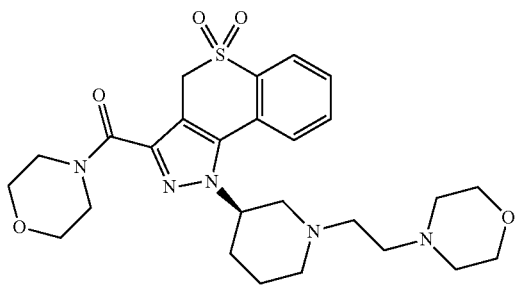 [SMILES: O=C(c1nn([C@@H]2CCCN(CCN3CCOCC3)C2)c2c1CS(=O)(=O)c1ccccc1-2)N1CCOCC1] |
| 349 | 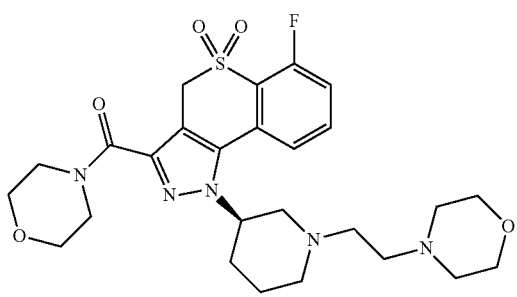 [SMILES: O=C(c1nn([C@@H]2CCCN(CCN3CCOCC3)C2)c2c1CS(=O)(=O)c1c(F)cccc1-2)N1CCOCC1] |
| 350 | 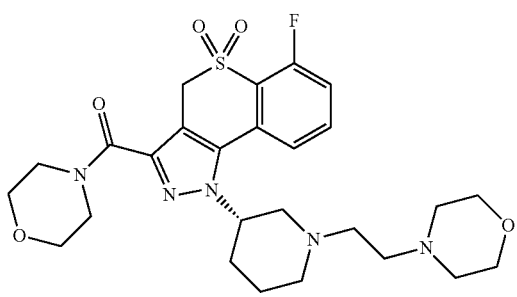 |
| 353 | 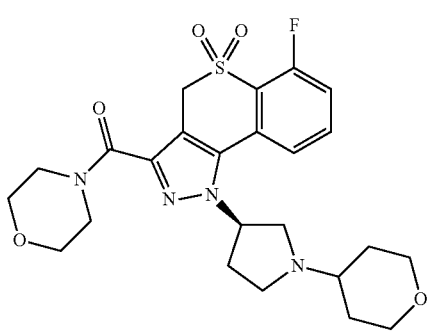 [SMILES: O=C(c1nn([C@@H]2CCN(C3CCOCC3)C2)c2c1CS(=O)(=O)c1c(F)cccc1-2)N1CCOCC1] |
| 354 | 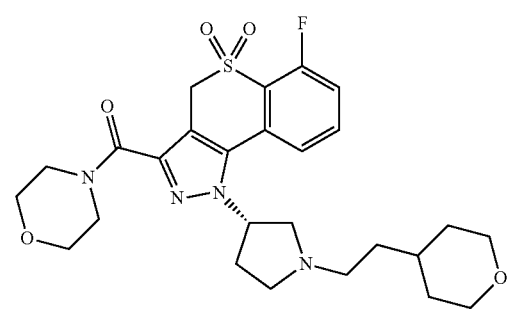 [SMILES: O=C(c1nn([C@H]2CCN(CCC3CCOCC3)C2)c2c1CS(=O)(=O)c1c(F)cccc1-2)N1CCOCC1] |

| Example No | structures |
|---|---|
| 355 | 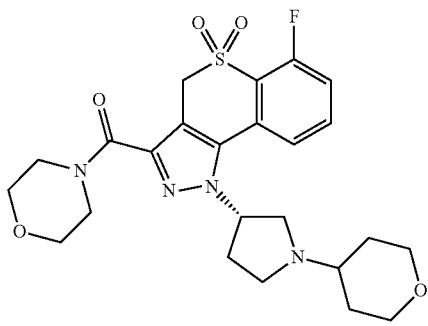 [SMILES: O=C(c1nn([C@H]2CCN(C3CCOCC3)C2)c2c1CS(=O)(=O)c1c(F)cccc1-2)N1CCOCC1] |
| 356 | 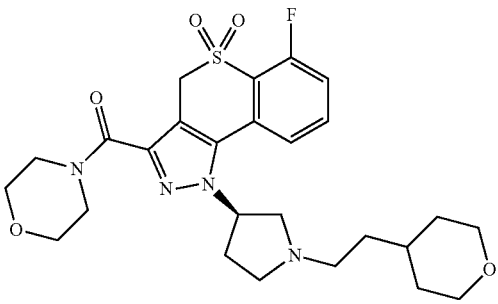 [SMILES: O=C(c1nn([C@@H]2CCN(CCC3CCOCC3)C2)c2c1CS(=O)(=O)c1c(F)cccc1-2)N1CCOCC1] |
| 357 | 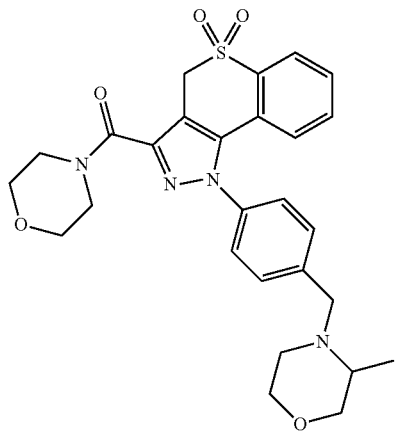 [SMILES: CC1COCCN1Cc1ccc(-n2nc(C(=O)N3CCOCC3)c3c2-c2ccccc2S(=O)(=O)C3)cc1] |
| 358 | 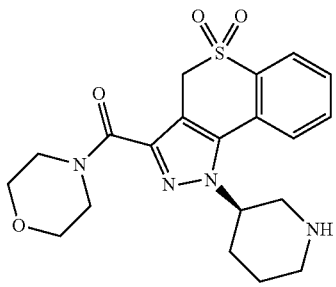 [SMILES: O=C(c1nn([C@@H]2CCCNC2)c2c1CS(=O)(=O)c1ccccc1-2)N1CCOCC1] |

-continued

| Example No | structures |
|---|---|
| 359 | 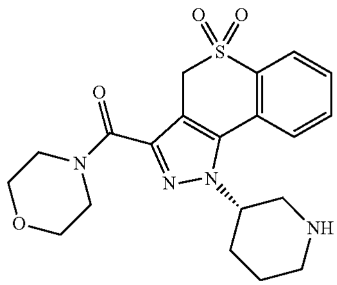 [SMILES: O=C(c1nn([C@H]2CCCNC2)c2c1CS(=O)(=O)c1ccccc1-2)N1CCOCC1] |
| 360 | 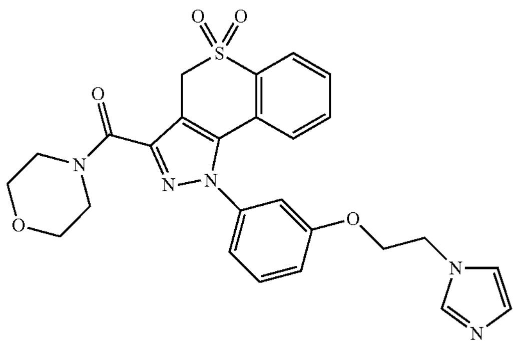 [SMILES: O=C(c1nn(-c2cccc(OCCn3ccnc3)c2)c2c1CS(=O)(=O)c1ccccc1-2)N1CCOCC1] |
| 361 | 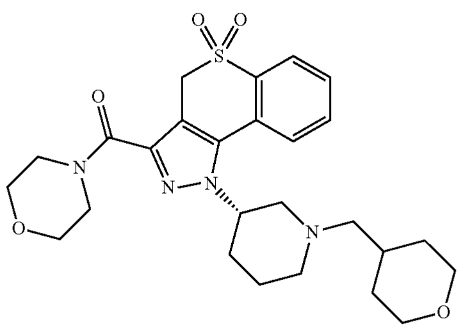 [SMILES: O=C(c1nn([C@H]2CCCN(CC3CCOCC3)C2)c2c1CS(=O)(=O)c1ccccc1-2)N1CCOCC1] |
| 362 | 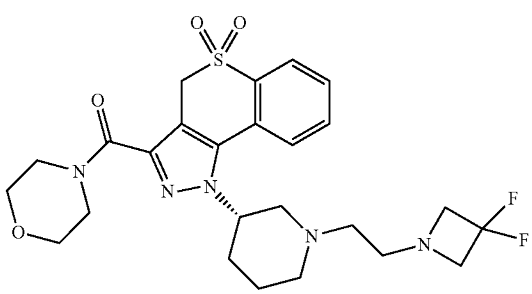 [SMILES: O=C(c1nn([C@H]2CCCN(CCN3CC(F)(F)C3)C2)c2c1CS(=O)(=O)c1ccccc1-2)N1CCOCC1] |
| 363 | 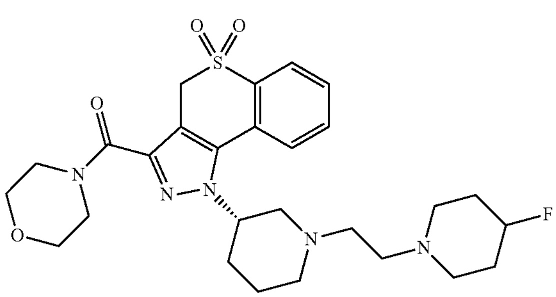 [SMILES: O=C(c1nn([C@H]2CCCN(CCN3CCC(F)CC3)C2)c2c1CS(=O)(=O)c1ccccc1-2)N1CCOCC1] |

-continued
| Example No | structures |
|---|---|
| 364 | 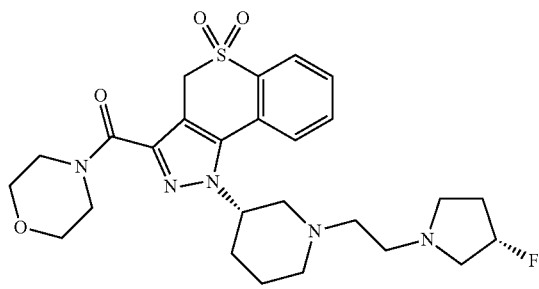 [SMILES: O=C(c1nn([C@H]2CCCN(CCN3CC[C@H](F)C3)C2)c2c1CS(=O)(=O)c1ccccc1-2)N1CCOCC1] |
| 365 | 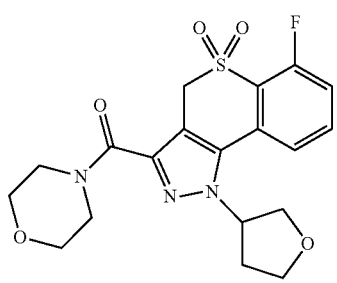 [SMILES: O=C(c1nn(C2CCOC2)c2c1CS(=O)(=O)c1c(F)cccc1-2)N1CCOCC1] |
| 366 | 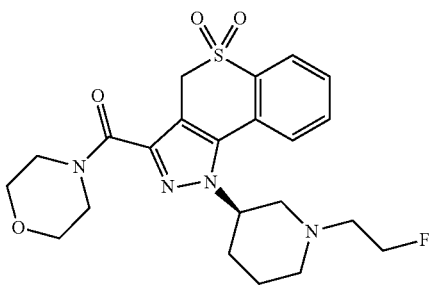 [SMILES: O=C(c1nn([C@@H]2CCCN(CCF)C2)c2c1CS(=O)(=O)c1ccccc1-2)N1CCOCC1] |
| 367 | 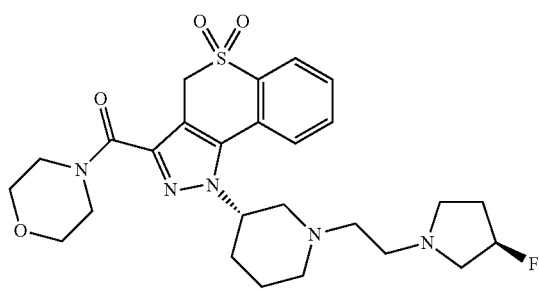 [SMILES: O=C(c1nn([C@H]2CCCN(CCN3CC[C@@H](F)C3)C2)c2c1CS(=O)(=O)c1ccccc1-2)N1CCOCC1] |
| 368 | 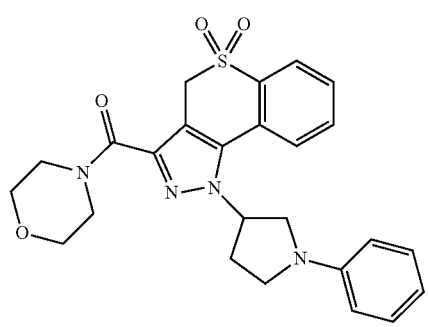 [SMILES: O=C(c1nn(C2CCN(c3ccccc3)C2)c2c1CS(=O)(=O)c1ccccc1-2)N1CCOCC1] |

| Example No | structures |
|---|---|
| 369 | 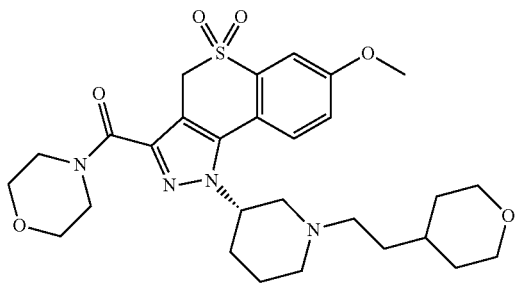 [SMILES: COc1ccc2c(c1)S(=O)(=O)Cc1c(C(=O)N3CCOCC3)nn([C@H]3CCCN(CCC4CCOCC4)C3)c1-2] |
| 370 | 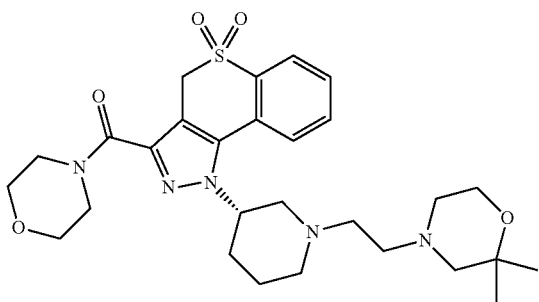 [SMILES: CC1(C)CN(CCN2CCC[C@H](n3nc(C(=O)N4CCOCC4)c4c3-c3ccccc3S(=O)(=O)C4)C2)CCO1] |
| 371 | 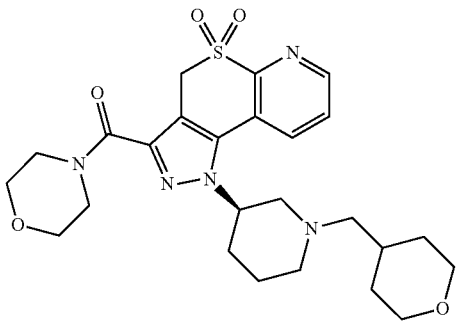 [SMILES: O=C(c1nn([C@@H]2CCCN(CC3CCOCC3)C2)c2c1CS(=O)(=O)c1ncccc1-2)N1CCOCC1] |
| 372 | 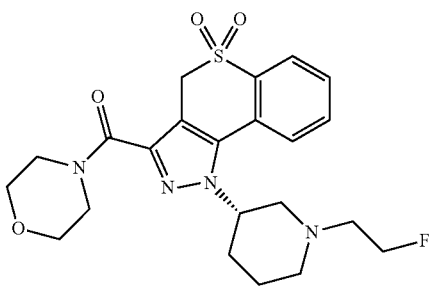 [SMILES: O=C(c1nn([C@H]2CCCN(CCF)C2)c2c1CS(=O)(=O)c1ccccc1-2)N1CCOCC1] |
| 373 | 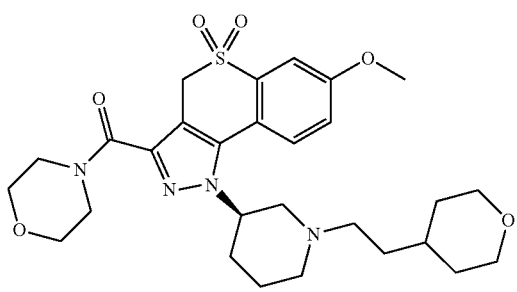 [SMILES: COc1ccc2c(c1)S(=O)(=O)Cc1c(C(=O)N3CCOCC3)nn([C@@H]3CCCN(CCC4CCOCC4)C3)c1-2] |

| Example No | structures |
|---|---|
| 374 | 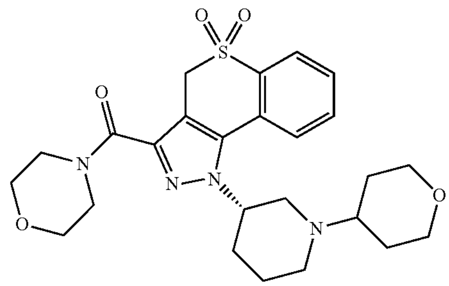 |
| 375 | 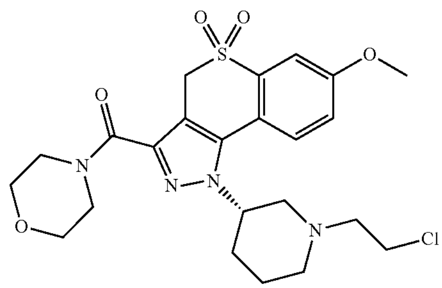 [SMILES: COc1ccc2c(c1)S(=O)(=O)Cc1c(C(=O)N3CCOCC3)nn([C@H]3CCCN(CCCl)C3)c1-2] |
| 376 | 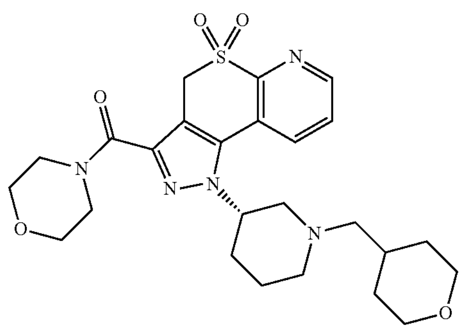 [SMILES: O=C(c1nn([C@H]2CCCN(CC3CCOCC3)C2)c2c1CS(=O)(=O)c1ncccc1-2)N1CCOCC1] |
| 377 | 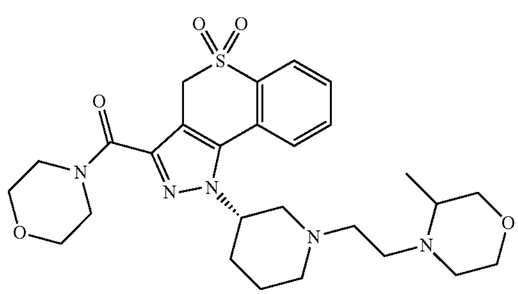 [SMILES: CC1COCCN1CCN1CCC[C@H](n2nc(C(=O)N3CCOCC3)c3c2-c2ccccc2S(=O)(=O)C3)C1] |
| 378 | 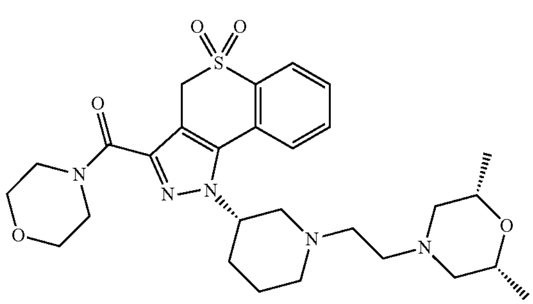 [SMILES: C[C@@H]1CN(CCN2CCC[C@H](n3nc(C(=O)N4CCOCC4)c4c3-c3ccccc3S(=O)(=O)C4)C2)C[C@H](C)O1] |

-continued
| Example No | structures |
|---|---|
| 379 | 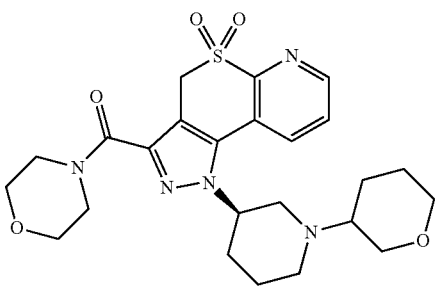 [SMILES: O=C(c1nn([C@@H]2CCCN(C3CCCOC3)C2)c2c1CS(=O)(=O)c1ncccc1-2)N1CCOCC1] |
| 380 | 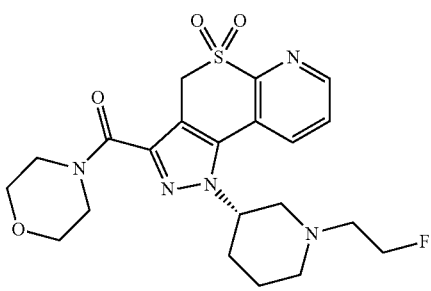 [SMILES: O=C(c1nn([C@H]2CCCN(CCF)C2)c2c1CS(=O)(=O)c1ncccc1-2)N1CCOCC1] |
| 381 | 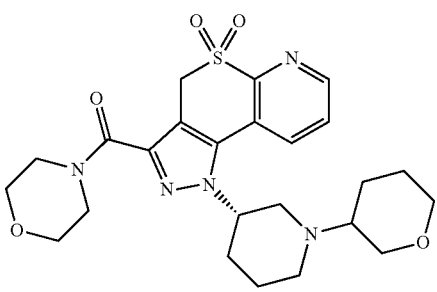 [SMILES: O=C(c1nn([C@H]2CCCN(C3CCCOC3)C2)c2c1CS(=O)(=O)c1ncccc1-2)N1CCOCC1] |
| 382 | 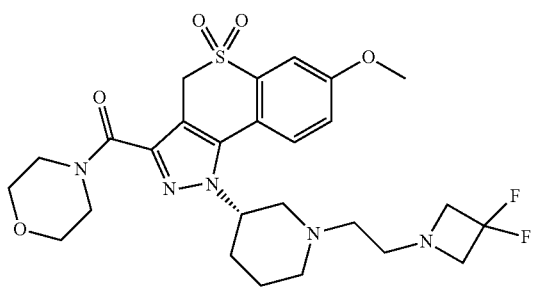 [SMILES: COc1ccc2c(c1)S(=O)(=O)Cc1c(C(=O)N3CCOCC3)nn([C@H]3CCCN(CCN4CC(F)(F)C4)C3)c1-2] |
| 383 | 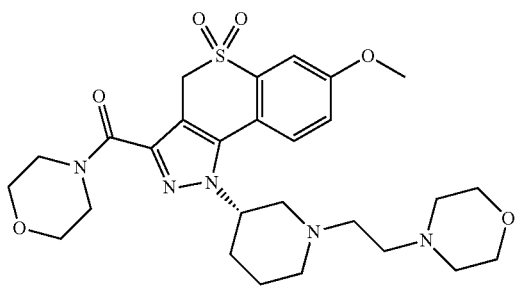 |

| Example No | structures |
|---|---|
| 384 | 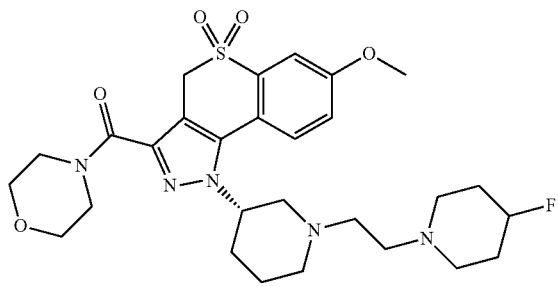 [SMILES: COc1ccc2c(c1)S(=O)(=O)Cc1c(C(=O)N3CCOCC3)nn([C@H]3CCCN(CCN4CCC(F)CC4)C3)c1-2] |
| 385 | 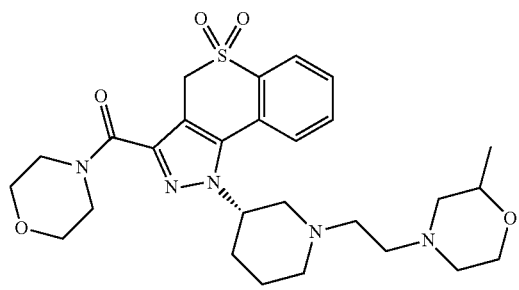 [SMILES: CC1CN(CCN2CCC[C@H](n3nc(C(=O)N4CCOCC4)c4c3-c3ccccc3S(=O)(=O)C4)C2)CCO1] |
| 386 | 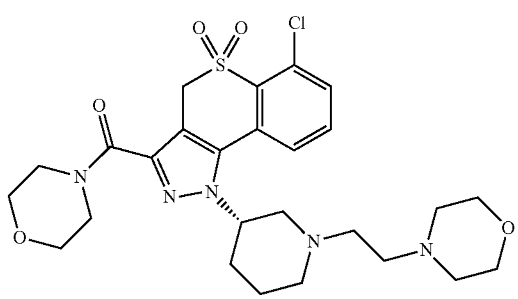 |
| 387 | 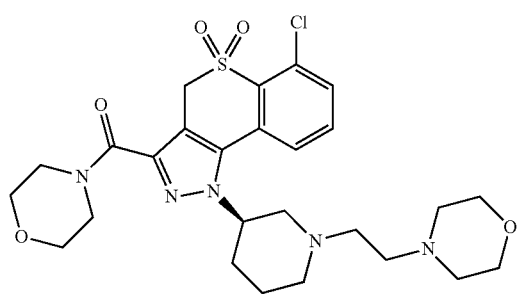 |

-continued
| Example No | structures |
|---|---|
| 388 | 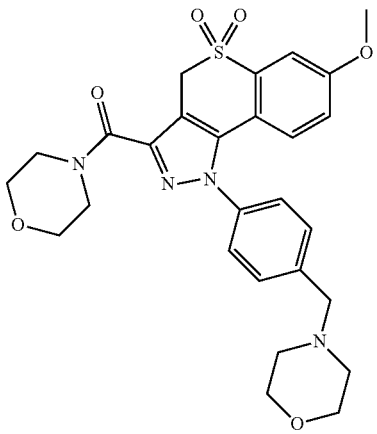 [SMILES: COc1ccc2c(c1)S(=O)(=O)Cc1c(C(=O)N3CCOCC3)nn(-c3ccc(CN4CCOCC4)cc3)c1-2] |
| 389 | 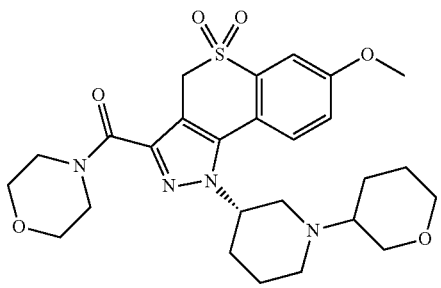 [SMILES: COc1ccc2c(c1)S(=O)(=O)Cc1c(C(=O)N3CCOCC3)nn([C@H]3CCCN(C4CCCOC4)C3)c1-2] |
| 390 | 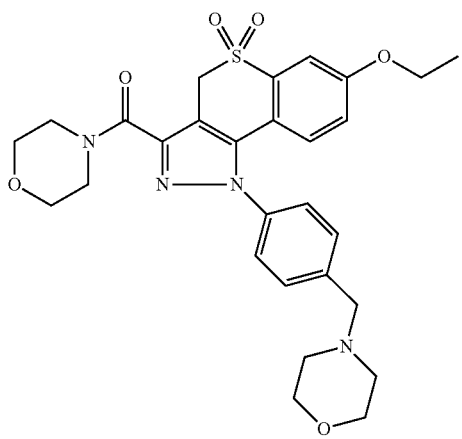 [SMILES: CCOc1ccc2c(c1)S(=O)(=O)Cc1c(C(=O)N3CCOCC3)nn(-c3ccc(CN4CCOCC4)cc3)c1-2] |
| 391 | 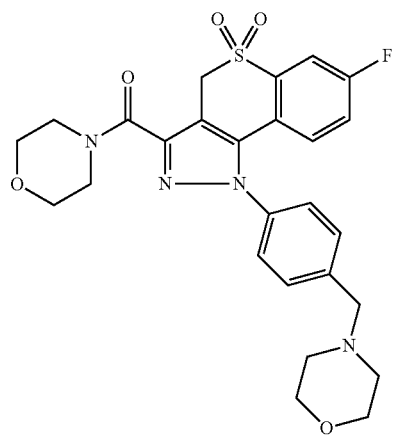 [SMILES: O=C(c1nn(-c2ccc(CN3CCOCC3)cc2)c2c1CS(=O)(=O)c1cc(F)ccc1-2)N1CCOCC1] |

| Example No | structures |
|---|---|
| 392 | 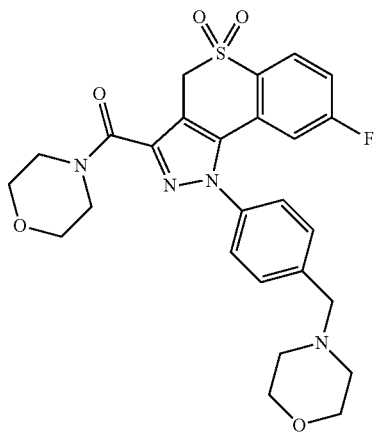 [SMILES: O=C(c1nn(-c2ccc(CN3CCOCC3)cc2)c2c1CS(=O)(=O)c1ccc(F)cc1-2)N1CCOCC1] |
| 393 | 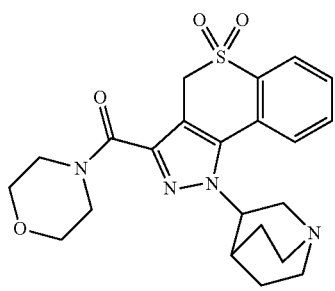 [SMILES: O=C(c1nn(C2CN3CCC2CC3)c2c1CS(=O)(=O)c1ccccc1-2)N1CCOCC1] |
| 394 | 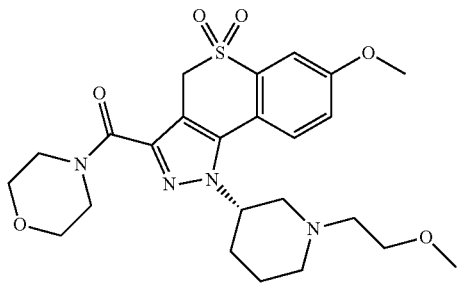 [SMILES: COCCN1CCC[C@H](n2nc(C(=O)N3CCOCC3)c3c2-c2ccc(OC)cc2S(=O)(=O)C3)C1] |
| 395 | 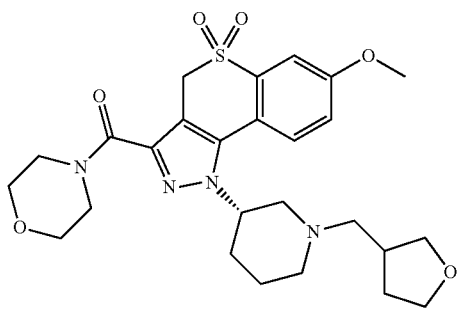 [SMILES: COc1ccc2c(c1)S(=O)(=O)Cc1c(C(=O)N3CCOCC3)nn([C@H]3CCCN(CC4CCOC4)C3)c1-2] |

| Example No | structures |
|---|---|
| 396 | 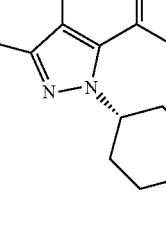 |
| 397 | 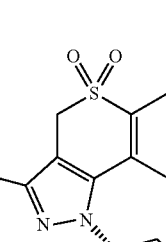 |
| 398 | 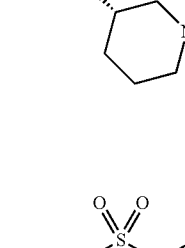 |
| 399 | 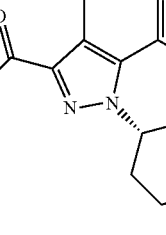 |

-continued
| Example No | structures |
|---|---|
| 400 | 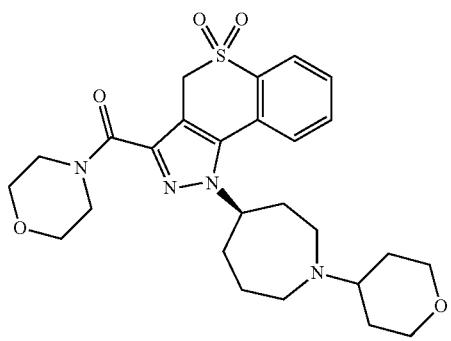 [SMILES: O=C(c1nn([C@@H]2CCCN(C3CCOCC3)CC2)c2c1CS(=O)(=O)c1ccccc1-2)N1CCOCC1] |
| 401 | 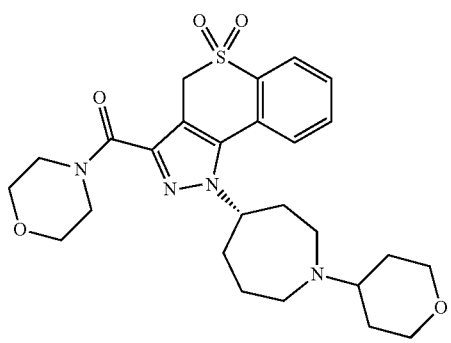 [SMILES: O=C(c1nn([C@H]2CCCN(C3CCOCC3)CC2)c2c1CS(=O)(=O)c1ccccc1-2)N1CCOCC1] |
| 402 | 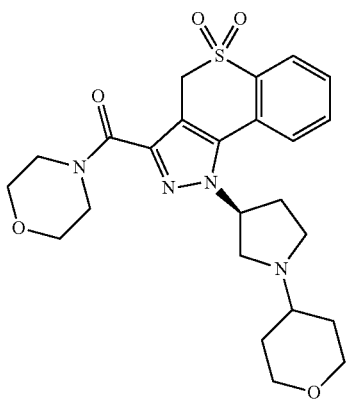 [SMILES: O=C(c1nn([C@H]2CCN(C3CCOCC3)C2)c2c1CS(=O)(=O)c1ccccc1-2)N1CCOCC1] |
| 403 | 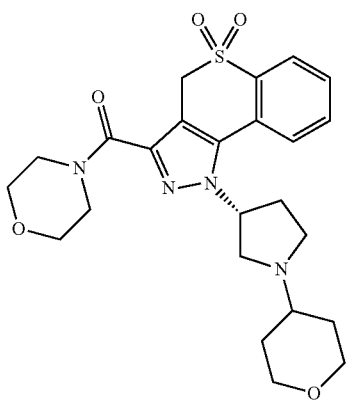 [SMILES: O=C(c1nn([C@@H]2CCN(C3CCOCC3)C2)c2c1CS(=O)(=O)c1ccccc1-2)N1CCOCC1] |

| Example No | structures |
|---|---|
| 404 | 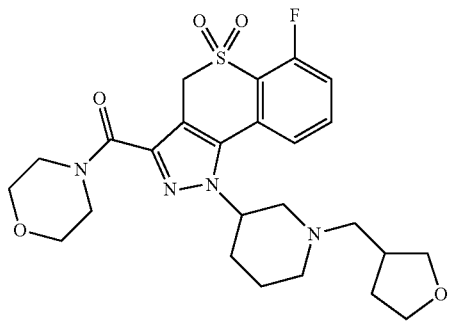 [SMILES: O=C(c1nn(C2CCCN(CC3CCOC3)C2)c2c1CS(=O)(=O)c1c(F)cccc1-2)N1CCOCC1] |
| 405 | 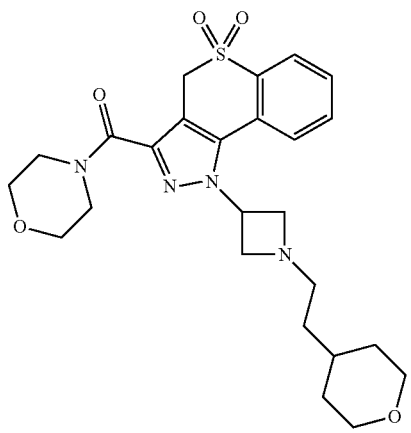 [SMILES: O=C(c1nn(C2CN(CCC3CCOCC3)C2)c2c1CS(=O)(=O)c1ccccc1-2)N1CCOCC1] |
| 406 | 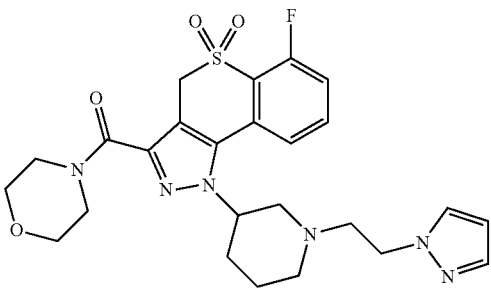 [SMILES: O=C(c1nn(C2CCCN(CCn3cccn3)C2)c2c1CS(=O)(=O)c1c(F)cccc1-2)N1CCOCC1] |
| 407 | 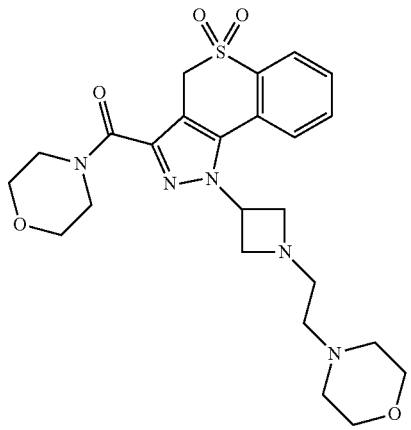 |

-continued

| Example No | structures |
|---|---|
| 408 | 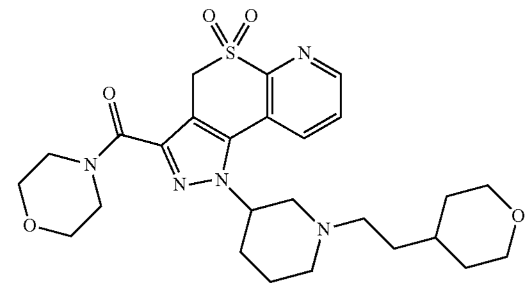 [SMILES: O=C(c1nn(C2CCCN(CCC3CCOCC3)C2)c2c1CS(=O)(=O)c1ncccc1-2)N1CCOCC1] |
| 409 | 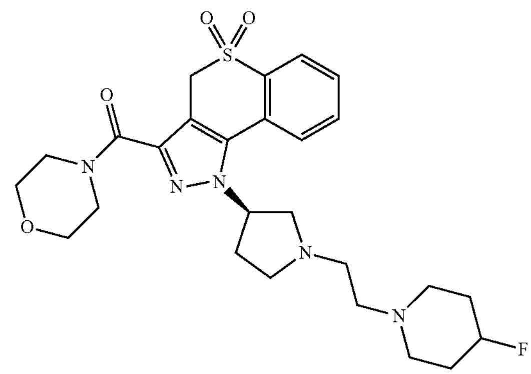 [SMILES: O=C(c1nn([C@@H]2CCN(CCN3CCC(F)CC3)C2)c2c1CS(=O)(=O)c1ccccc1-2)N1CCOCC1] |
| 410 | 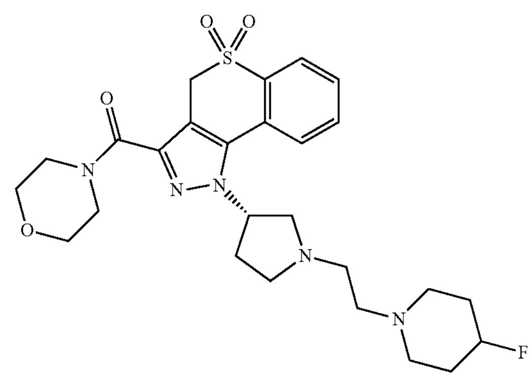 [SMILES: O=C(c1nn([C@H]2CCN(CCN3CCC(F)CC3)C2)c2c1CS(=O)(=O)c1ccccc1-2)N1CCOCC1] |
| 411 | 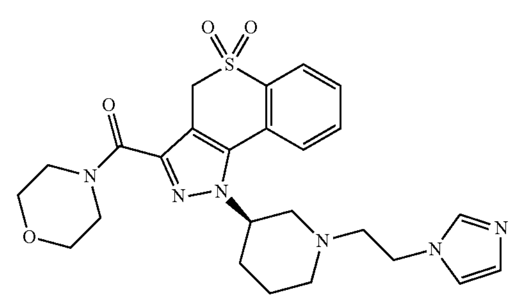 [SMILES: O=C(c1nn([C@@H]2CCCN(CCn3ccnc3)C2)c2c1CS(=O)(=O)c1ccccc1-2)N1CCOCC1] |

| Example No | structures |
|---|---|
| 412 | 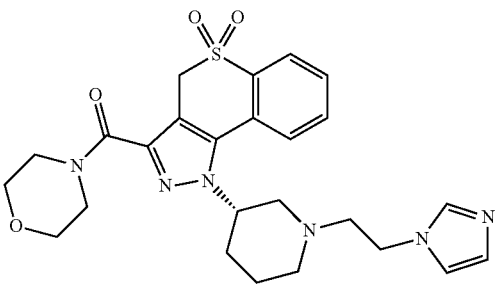 [SMILES: O=C(c1nn([C@H]2CCCN(CCn3ccnc3)C2)c2c1CS(=O)(=O)c1ccccc1-2)N1CCOCC1] |
| 413 | 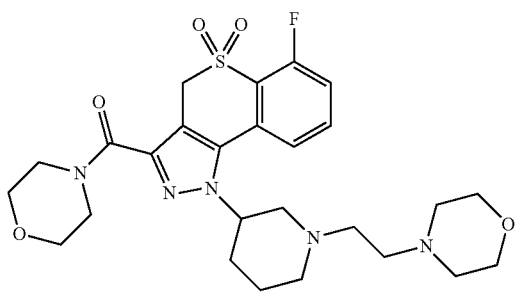 [SMILES: O=C(c1nn(C2CCCN(CCN3CCOCC3)C2)c2c1CS(=O)(=O)c1c(F)cccc1-2)N1CCOCC1] |
| 414 | 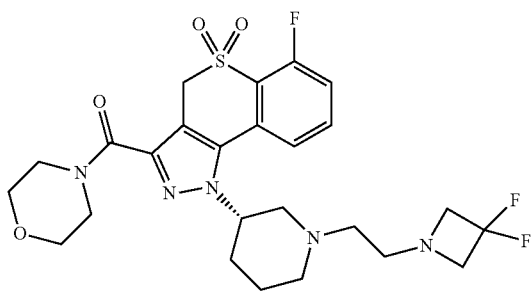 |
| 415 | 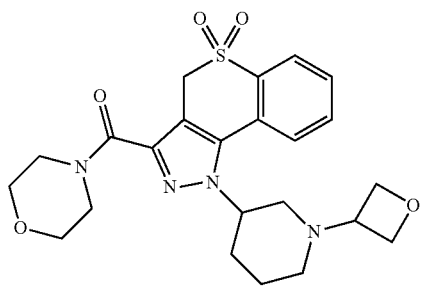 [SMILES: O=C(c1nn(C2CCCN(C3COC3)C2)c2c1CS(=O)(=O)c1ccccc1-2)N1CCOCC1] |
| 422 | 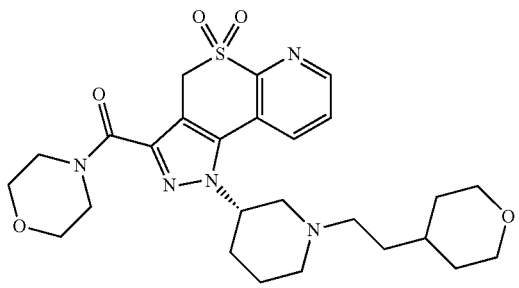 |

| Example No | structures |
|---|---|
| 423 | 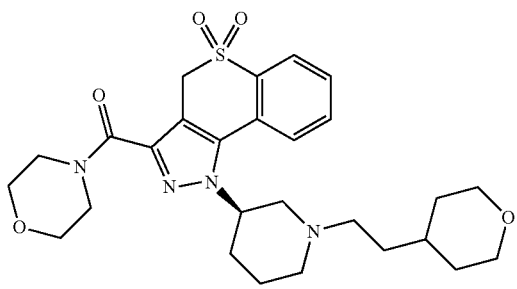 [SMILES: O=C(c1nn([C@@H]2CCCN(CCC3CCOCC3)C2)c2c1CS(=O)(=O)c1ccccc1-2)N1CCOCC1] |
| 424 | 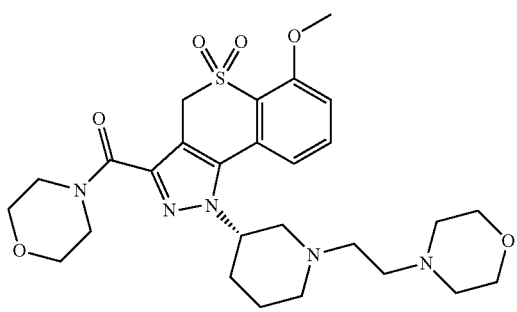 [SMILES: COc1cccc2c1S(=O)(=O)Cc1c(C(=O)N3CCOCC3)nn([C@H]3CCCN(CCN4CCOCC4)C3)c1-2] |
| 425 | 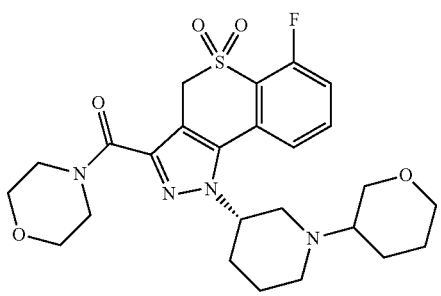 [SMILES: O=C(c1nn([C@H]2CCCN(C3CCCOC3)C2)c2c1CS(=O)(=O)c1c(F)cccc1-2)N1CCOCC1] |
| 426 | 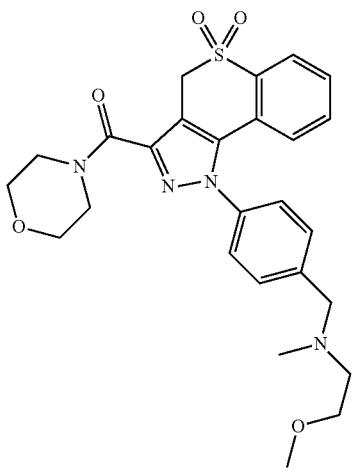 [SMILES: COCCN(C)Cc1ccc(-n2nc(C(=O)N3CCOCC3)c3c2-c2ccccc2S(=O)(=O)C3)cc1] |

-continued
| Example No | structures |
|---|---|
| 427 | 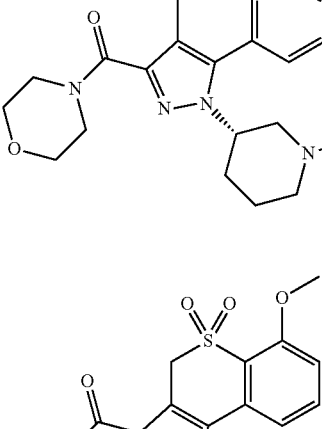 |
| 428 | 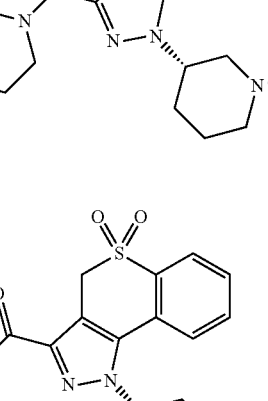 |
| 429 | 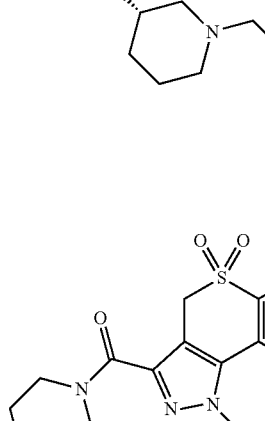 |
| 430 | 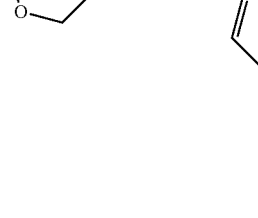 |

US 9,073,940 B2
243
-continued
| Example No | structures |
|---|---|
| 431 | 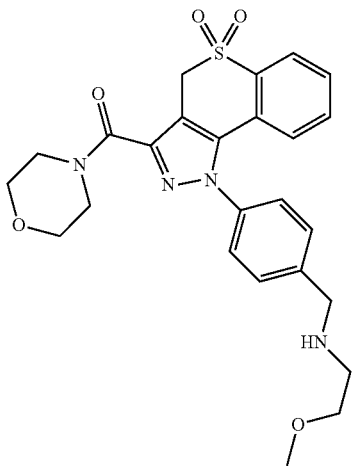 [SMILES: COCCNCc1ccc(-n2nc(C(=O)N3CCOCC3)c3c2-c2ccccc2S(=O)(=O)C3)cc1] |
| 432 | 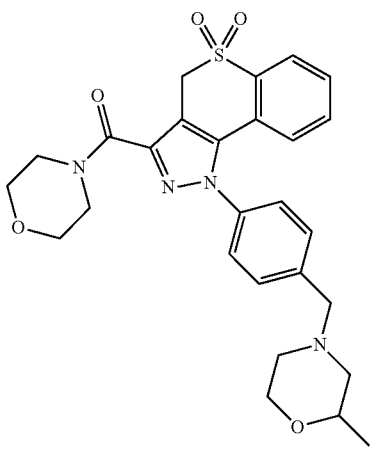 [SMILES: CC1CN(Cc2ccc(-n3nc(C(=O)N4CCOCC4)c4c3-c3ccccc3S(=O)(=O)C4)cc2)CCO1] |
| 433 | 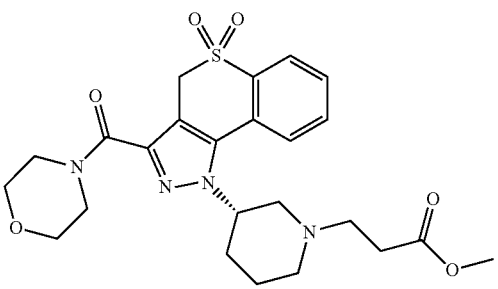 [SMILES: COC(=O)CCN1CCC[C@H](n2nc(C(=O)N3CCOCC3)c3c2-c2ccccc2S(=O)(=O)C3)C1] |
| 434 | 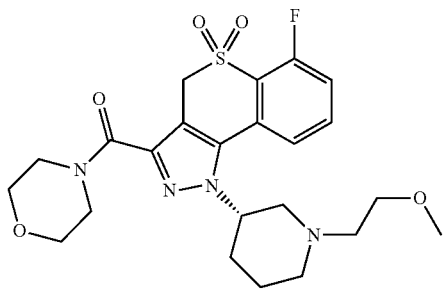 [SMILES: COCCN1CCC[C@H](n2nc(C(=O)N3CCOCC3)c3c2-c2cccc(F)c2S(=O)(=O)C3)C1] |

| Example No | structures |
|---|---|
| 435 | 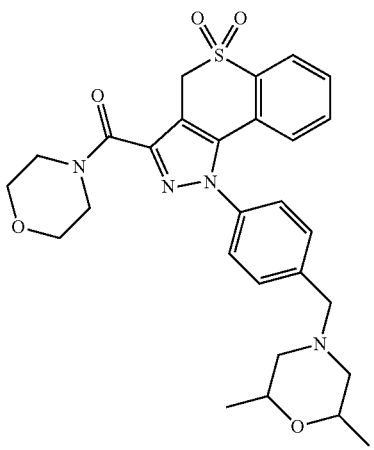 [SMILES: CC1CN(Cc2ccc(-n3nc(C(=O)N4CCOCC4)c4c3-c3ccccc3S(=O)(=O)C4)cc2)CC(C)O1] |
| 436 | 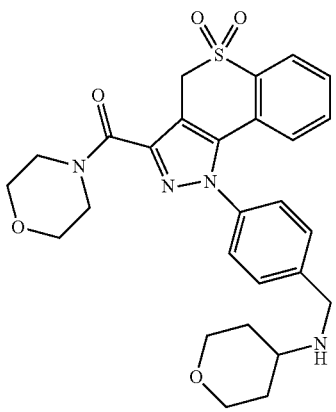 [SMILES: O=C(c1nn(-c2ccc(CNC3CCOCC3)cc2)c2c1CS(=O)(=O)c1ccccc1-2)N1CCOCC1] |
| 437 | 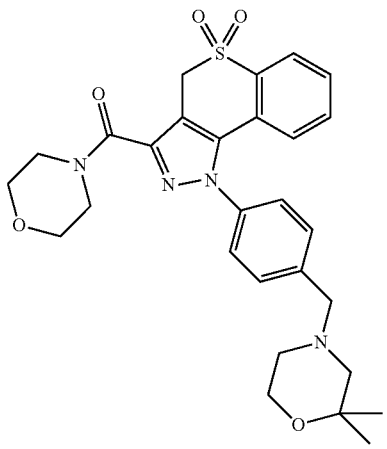 [SMILES: CC1(C)CN(Cc2ccc(-n3nc(C(=O)N4CCOCC4)c4c3-c3ccccc3S(=O)(=O)C4)cc2)CCO1] |

-continued
| Example No | structures |
|---|---|
| 438 | 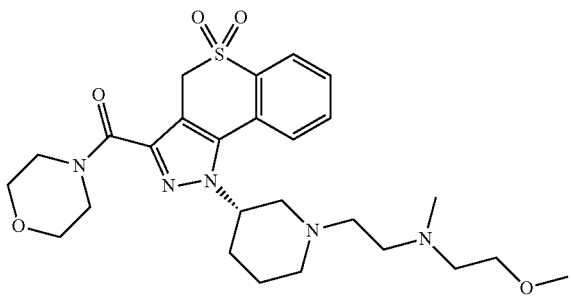 [SMILES: COCCN(C)CCN1CCC[C@H](n2nc(C(=O)N3CCOCC3)c3c2-c2ccccc2S(=O)(=O)C3)C1] |
| 439 | 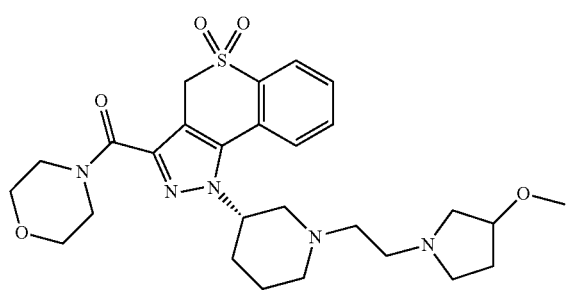 [SMILES: COC1CCN(CCN2CCC[C@H](n3nc(C(=O)N4CCOCC4)c4c3-c3ccccc3S(=O)(=O)C4)C2)C1] |
| 440 | 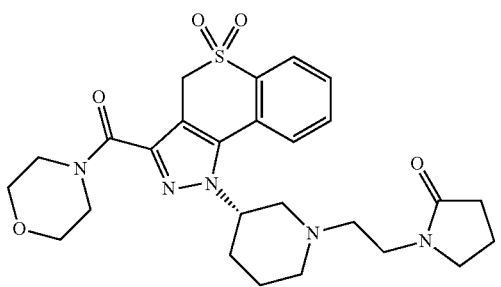 [SMILES: O=C1CCCN1CCN1CCC[C@H](n2nc(C(=O)N3CCOCC3)c3c2-c2ccccc2S(=O)(=O)C3)C1] |
| 441 | 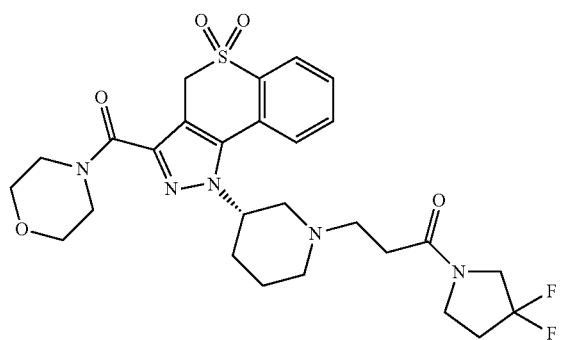 [SMILES: O=C(CCN1CCC[C@H](n2nc(C(=O)N3CCOCC3)c3c2-c2ccccc2S(=O)(=O)C3)C1)N1CCC(F)(F)C1] |
| 442 | 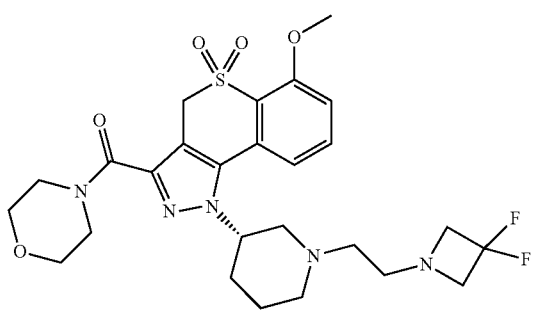 [SMILES: COc1cccc2c1S(=O)(=O)Cc1c(C(=O)N3CCOCC3)nn([C@H]3CCCN(CCN4CC(F)(F)C4)C3)c1-2] |

| Example No | structures |
|---|---|
| 443 | 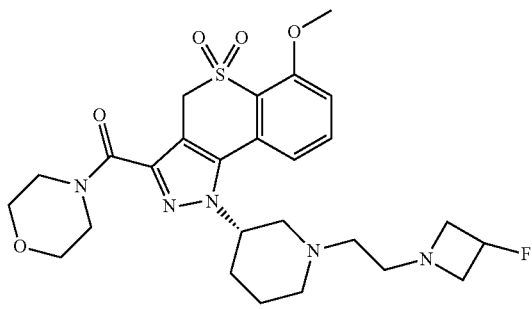 [SMILES: COc1cccc2c1S(=O)(=O)Cc1c(C(=O)N3CCOCC3)nn([C@H]3CCCN(CCN4CC(F)C4)C3)c1-2] |
| 444 | 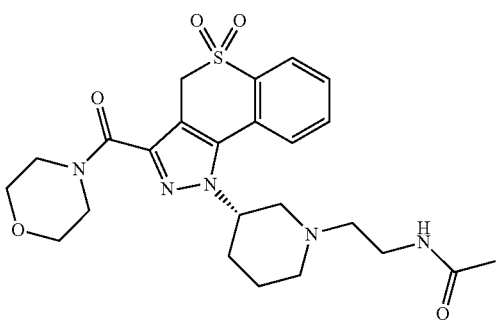 [SMILES: CC(=O)NCCN1CCC[C@H](n2nc(C(=O)N3CCOCC3)c3c2-c2ccccc2S(=O)(=O)C3)C1] |
| 445 | 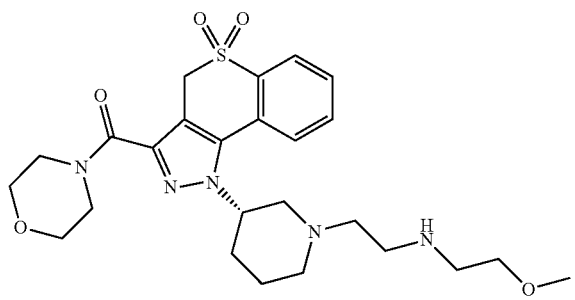 [SMILES: COCCNCCN1CCC[C@H](n2nc(C(=O)N3CCOCC3)c3c2-c2ccccc2S(=O)(=O)C3)C1] |
| 446 | 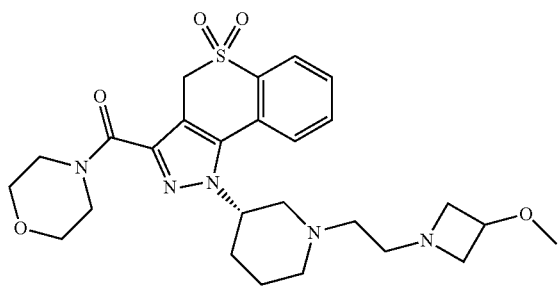 [SMILES: COC1CN(CCN2CCC[C@H](n3nc(C(=O)N4CCOCC4)c4c3-c3ccccc3S(=O)(=O)C4)C2)C1] |
| 447 | 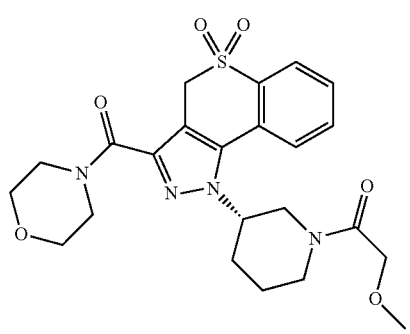 [SMILES: COCC(=O)N1CCC[C@H](n2nc(C(=O)N3CCOCC3)c3c2-c2ccccc2S(=O)(=O)C3)C1] |

-continued
| Example No | structures |
|---|---|
| 448 | 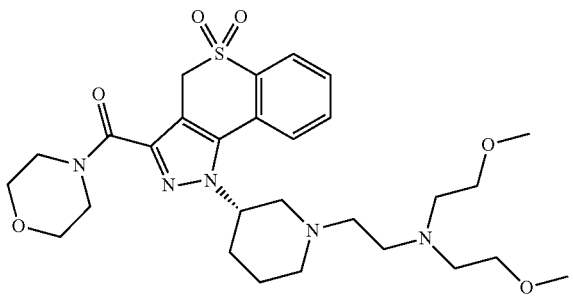 [SMILES: COCCN(CCOC)CCN1CCC[C@H](n2nc(C(=O)N3CCOCC3)c3c2-c2ccccc2S(=O)(=O)C3)C1] |
| 449 | 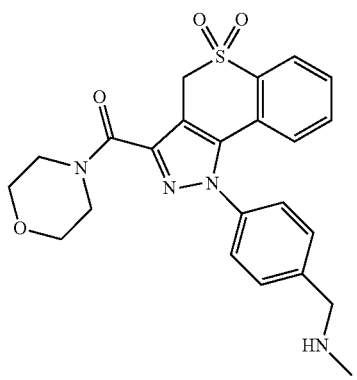 [SMILES: CNCc1ccc(-n2nc(C(=O)N3CCOCC3)c3c2-c2ccccc2S(=O)(=O)C3)cc1] |
| 450 | 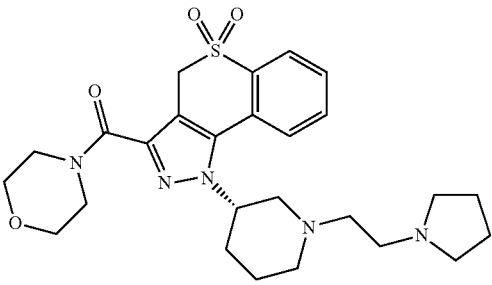 [SMILES: O=C(c1nn([C@H]2CCCN(CCN3CCCC3)C2)c2c1CS(=O)(=O)c1ccccc1-2)N1CCOCC1] |
| 451 | 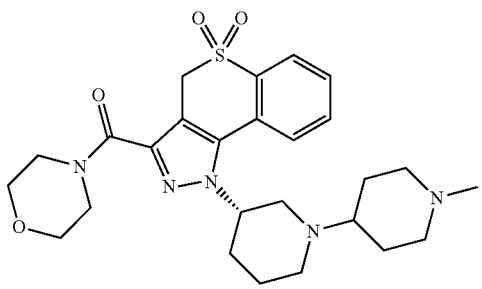 [SMILES: CN1CCC(N2CCC[C@H](n3nc(C(=O)N4CCOCC4)c4c3-c3ccccc3S(=O)(=O)C4)C2)CC1] |
| 452 | 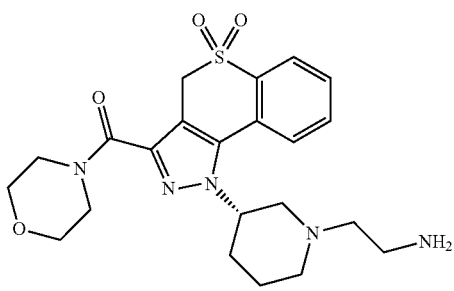 [SMILES: NCCN1CCC[C@H](n2nc(C(=O)N3CCOCC3)c3c2-c2ccccc2S(=O)(=O)C3)C1] |

| Example No | structures |
|---|---|
| 453 | 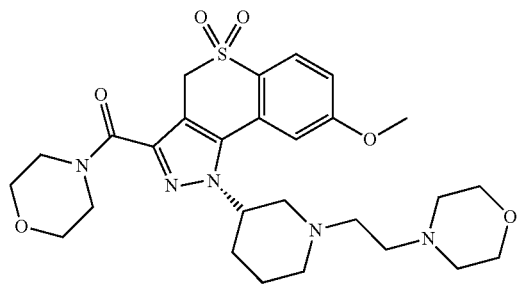 |
| 454 | 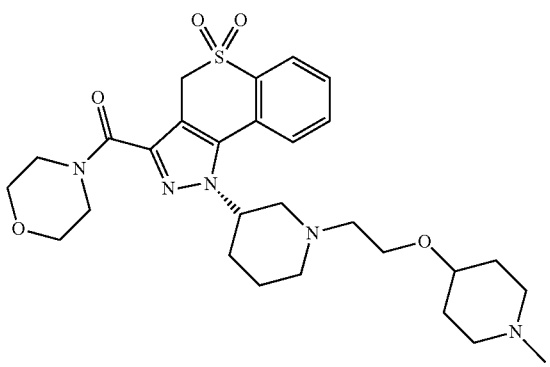 |
| 455 | 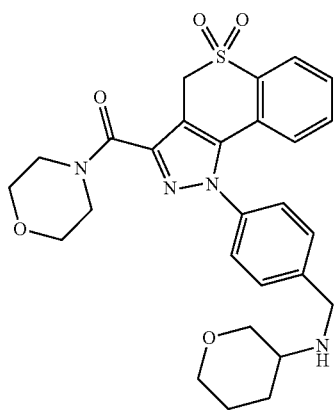 [SMILES: O=C(c1nn(-c2ccc(CNC3CCCOC3)cc2)c2c1CS(=O)(=O)c1ccccc1-2)N1CCOCC1] |
| 456 | 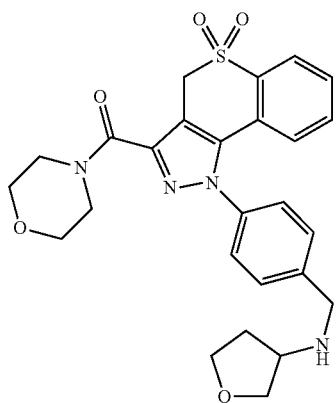 [SMILES: O=C(c1nn(-c2ccc(CNC3CCOC3)cc2)c2c1CS(=O)(=O)c1ccccc1-2)N1CCOCC1] |

| Example No | structures |
|---|---|
| 457 | 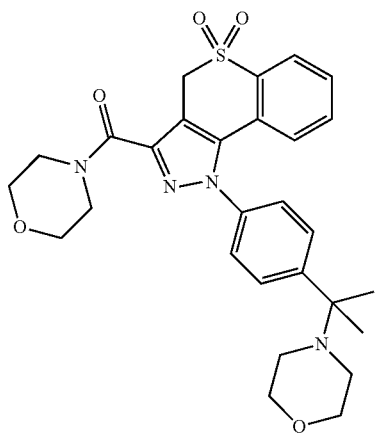 [SMILES: CC(C)(c1ccc(-n2nc(C(=O)N3CCOCC3)c3c2-c2ccccc2S(=O)(=O)C3)cc1)N1CCOCC1] |
| 458 | 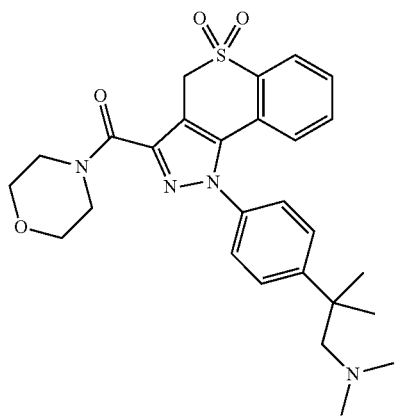 [SMILES: CN(C)CC(C)(C)c1ccc(-n2nc(C(=O)N3CCOCC3)c3c2-c2ccccc2S(=O)(=O)C3)cc1] |
| 459 | 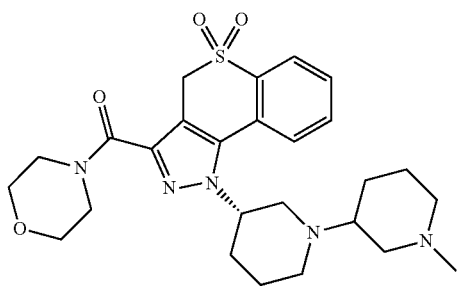 [SMILES: CN1CCCC(N2CCC[C@H](n3nc(C(=O)N4CCOCC4)c4c3-c3ccccc3S(=O)(=O)C4)C2)C1] |
| 460 | 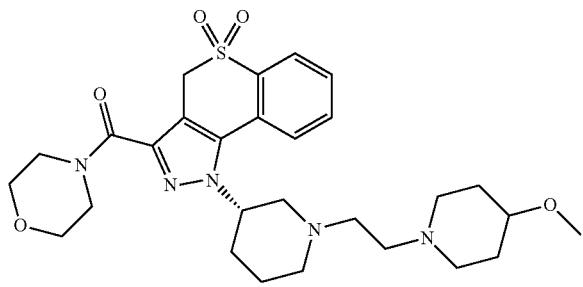 [SMILES: COC1CCN(CCN2CCC[C@H](n3nc(C(=O)N4CCOCC4)c4c3-c3ccccc3S(=O)(=O)C4)C2)CC1] |

| Example No | structures |
|---|---|
| 461 | 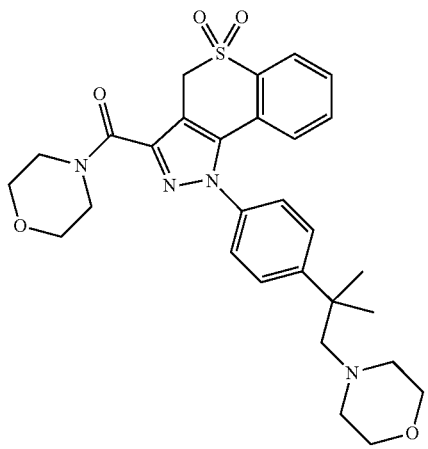 [SMILES: CC(C)(CN1CCOCC1)c1ccc(-n2nc(C(=O)N3CCOCC3)c3c2-c2ccccc2S(=O)(=O)C3)cc1] |
| 462 | 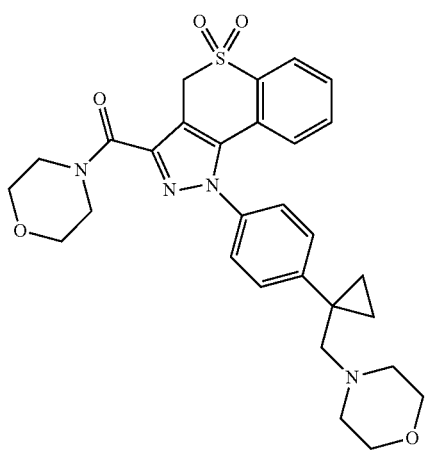 [SMILES: O=C(c1nn(-c2ccc(C3(CN4CCOCC4)CC3)cc2)c2c1CS(=O)(=O)c1ccccc1-2)N1CCOCC1] |
| 463 | 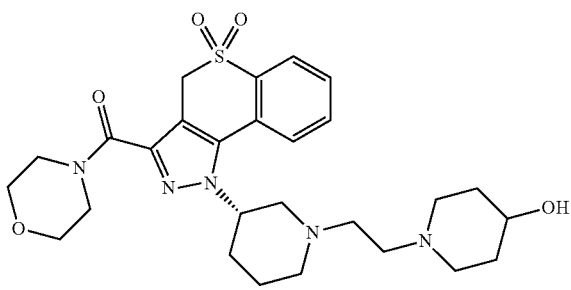 [SMILES: O=C(c1nn([C@H]2CCCN(CCN3CCC(O)CC3)C2)c2c1CS(=O)(=O)c1ccccc1-2)N1CCOCC1] |
| 464 | 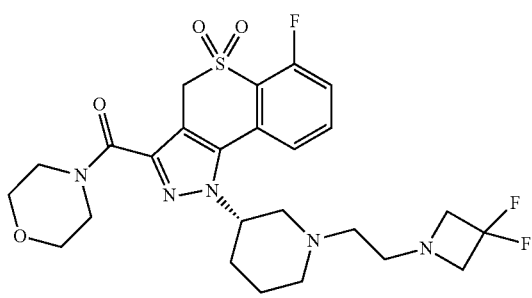 [SMILES: O=C(c1nn([C@H]2CCCN(CCN3CC(F)(F)C3)C2)c2c1CS(=O)(=O)c1c(F)cccc1-2)N1CCOCC1] |

-continued
| Example No | structures |
|---|---|
| 465 | 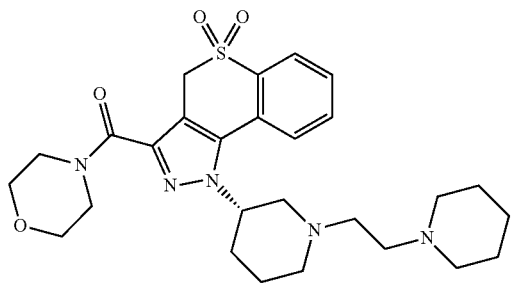 [SMILES: O=C(c1nn([C@H]2CCCN(CCN3CCCCC3)C2)c2c1CS(=O)(=O)c1ccccc1-2)N1CCOCC1] |
| 466 | 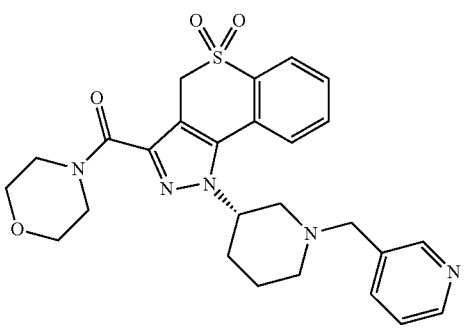 [SMILES: O=C(c1nn([C@H]2CCCN(Cc3cccnc3)C2)c2c1CS(=O)(=O)c1ccccc1-2)N1CCOCC1] |
| 467 | 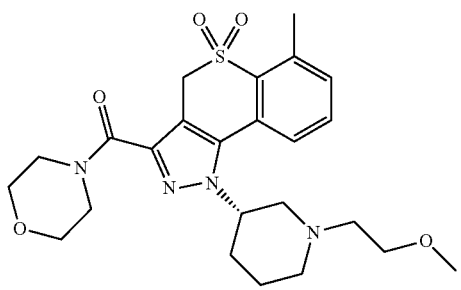 [SMILES: COCCN1CCC[C@H](n2nc(C(=O)N3CCOCC3)c3c2-c2cccc(C)c2S(=O)(=O)C3)C1] |
| 468 | 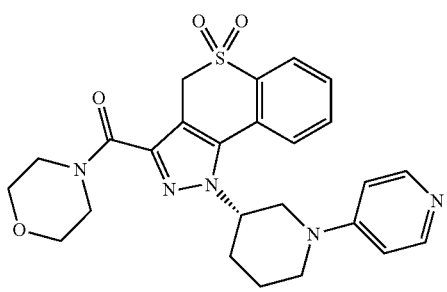 [SMILES: O=C(c1nn([C@H]2CCCN(c3ccncc3)C2)c2c1CS(=O)(=O)c1ccccc1-2)N1CCOCC1] |
| 469 | 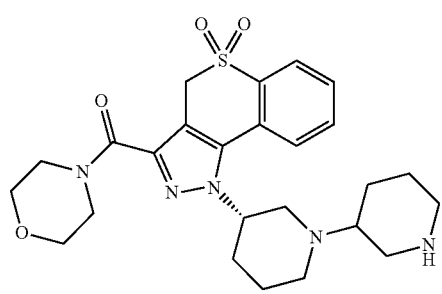 [SMILES: O=C(c1nn([C@H]2CCCN(C3CCCNC3)C2)c2c1CS(=O)(=O)c1ccccc1-2)N1CCOCC1] |

| Example No | structures |
|---|---|
| 470 | 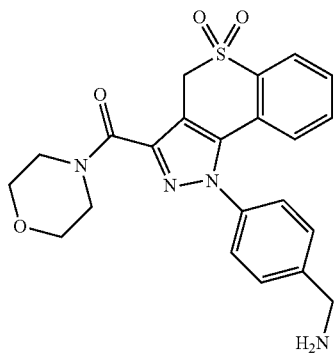 [SMILES: NCc1ccc(-n2nc(C(=O)N3CCOCC3)c3c2-c2ccccc2S(=O)(=O)C3)cc1] |
| 471 | 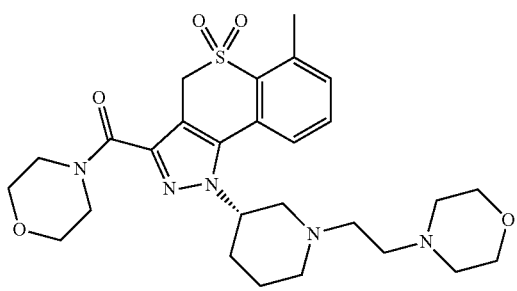 [SMILES: Cc1cccc2c1S(=O)(=O)Cc1c(C(=O)N3CCOCC3)nn([C@H]3CCCN(CCN4CCOCC4)C3)c1-2] |
| 472 | 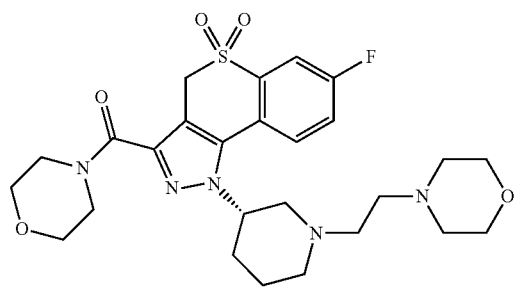 |
| 473 | 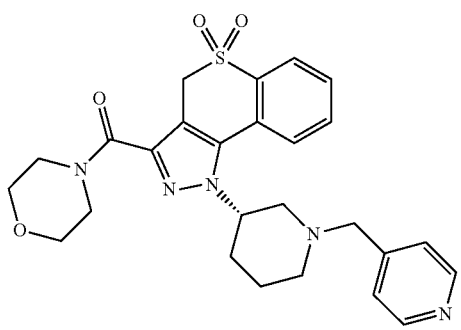 [SMILES: O=C(c1nn([C@H]2CCCN(Cc3ccncc3)C2)c2c1CS(=O)(=O)c1ccccc1-2)N1CCOCC1] |
| 474 | 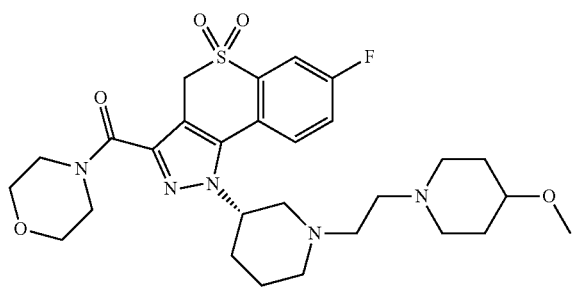 |

-continued

| Example No | structures |
|---|---|
| 481 | 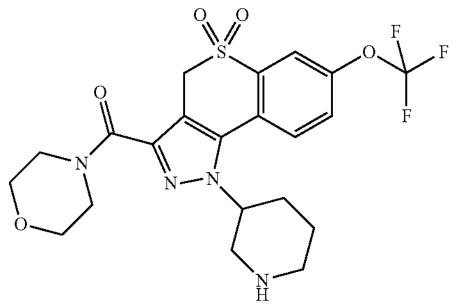 [SMILES: O=C(c1nn(C2CCCNC2)c2c1CS(=O)(=O)c1cc(OC(F)(F)F)ccc1-2)N1CCOCC1] |
| 485 | 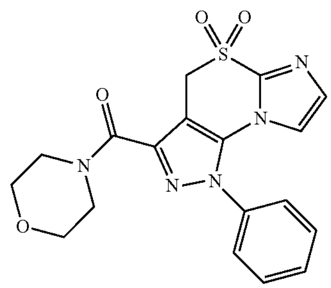 [SMILES: O=C(c1nn(-c2ccccc2)c2c1CS(=O)(=O)c1nccn1-2)N1CCOCC1] |
| 486 | 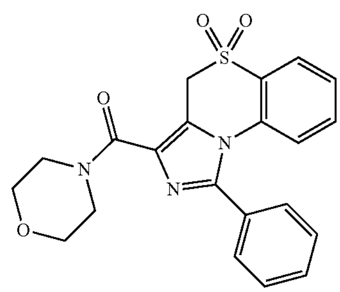 [SMILES: O=C(c1nc(-c2ccccc2)n2c1CS(=O)(=O)c1ccccc1-2)N1CCOCC1] |
| 487 | 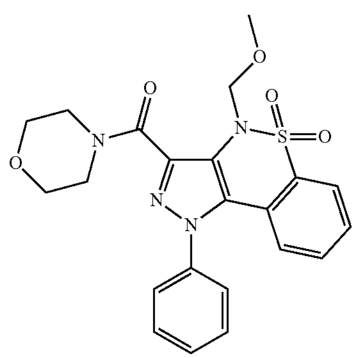 [SMILES: COCN1c2c(C(=O)N3CCOCC3)nn(-c3ccccc3)c2-c2ccccc2S1(=O)=O] |
| 488 | 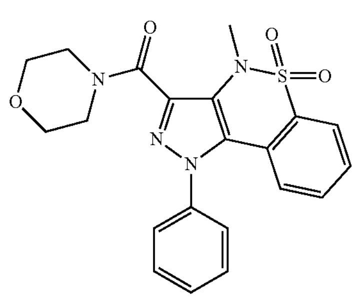 [SMILES: CN1c2c(C(=O)N3CCOCC3)nn(-c3ccccc3)c2-c2ccccc2S1(=O)=O] |

| Example No | structures |
|---|---|
| 489 | 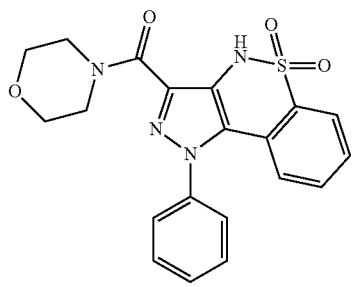 [SMILES: O=C(c1nn(-c2ccccc2)c2c1NS(=O)(=O)c1ccccc1-2)N1CCOCC1] |
| 490 | 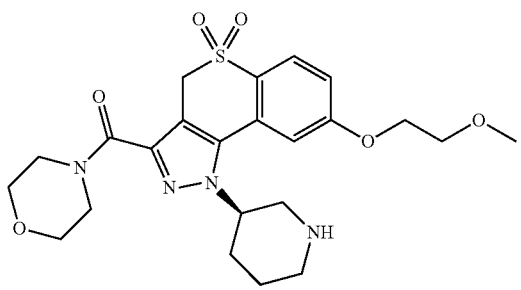 [SMILES: COCCOc1ccc2c(c1)-c1c(c(C(=O)N3CCOCC3)nn1[C@@H]1CCCNC1)CS2(=O)=O] |
| 491 | 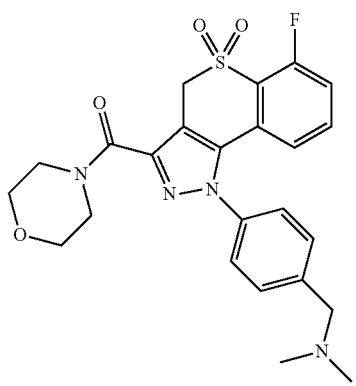 [SMILES: CN(C)Cc1ccc(-n2nc(C(=O)N3CCOCC3)c3c2-c2cccc(F)c2S(=O)(=O)C3)cc1] |
| 492 | 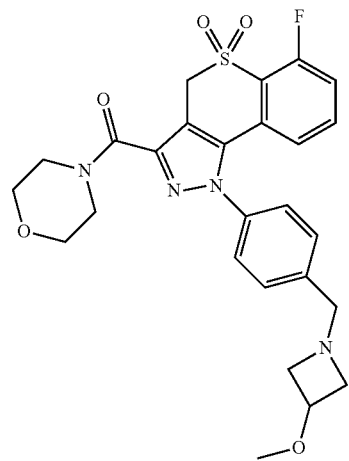 [SMILES: COC1CN(Cc2ccc(-n3nc(C(=O)N4CCOCC4)c4c3-c3cccc(F)c3S(=O)(=O)C4)cc2)C1] |

-continued

| Example No | structures |
|---|---|
| 493 | 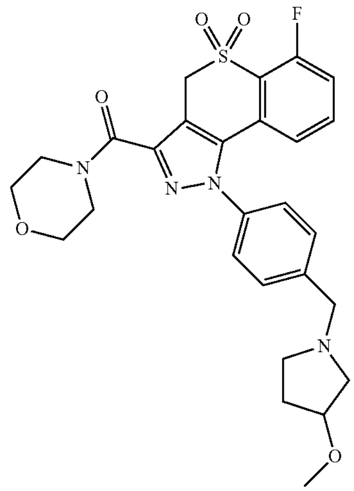 [SMILES: COC1CCN(Cc2ccc(-n3nc(C(=O)N4CCOCC4)c4c3-c3cccc(F)c3S(=O)(=O)C4)cc2)C1] |
| 494 | 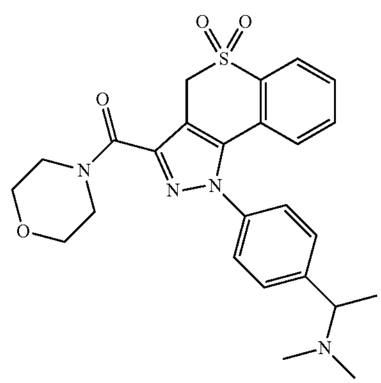 [SMILES: CC(c1ccc(-n2nc(C(=O)N3CCOCC3)c3c2-c2ccccc2S(=O)(=O)C3)cc1)N(C)C] |
| 495 | 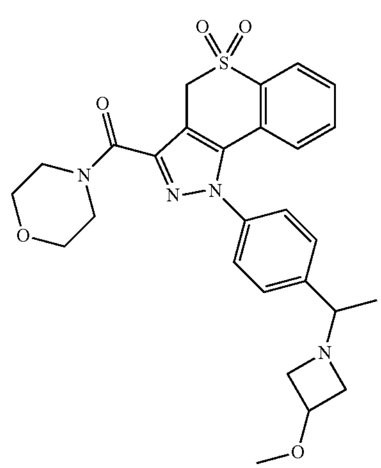 [SMILES: COC1CN(C(C)c2ccc(-n3nc(C(=O)N4CCOCC4)c4c3-c3ccccc3S(=O)(=O)C4)cc2)C1] |

| Example No | structures |
|---|---|
| 496 | 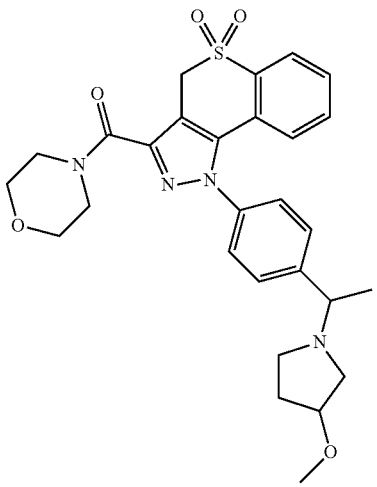 [SMILES: COC1CCN(C(C)c2ccc(-n3nc(C(=O)N4CCOCC4)c4c3-c3ccccc3S(=O)(=O)C4)cc2)C1] |
| 497 | 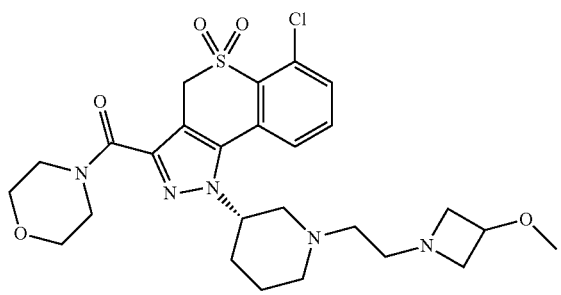 [SMILES: COC1CN(CCN2CCC[C@H](n3nc(C(=O)N4CCOCC4)c4c3-c3cccc(Cl)c3S(=O)(=O)C4)C2)C1] |
| 498 | 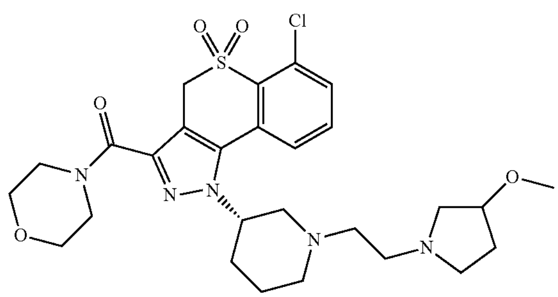 [SMILES: COC1CCN(CCN2CCC[C@H](n3nc(C(=O)N4CCOCC4)c4c3-c3cccc(Cl)c3S(=O)(=O)C4)C2)C1] |
| 499 | 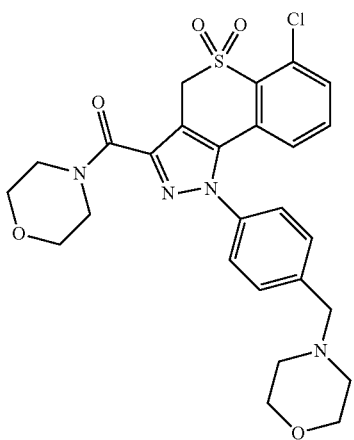 |

-continued
| Example No | structures |
|---|---|
| 500 | 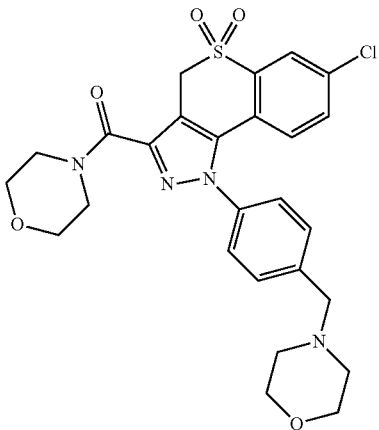 [SMILES: O=C(c1nn(-c2ccc(CN3CCOCC3)cc2)c2c1CS(=O)(=O)c1cc(Cl)ccc1-2)N1CCOCC1] |
| 501 | 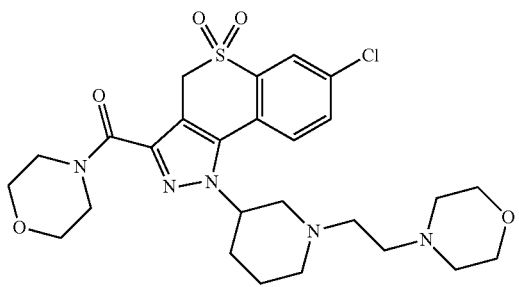 [SMILES: O=C(c1nn(C2CCCN(CCN3CCOCC3)C2)c2c1CS(=O)(=O)c1cc(Cl)ccc1-2)N1CCOCC1] |
| 502 | 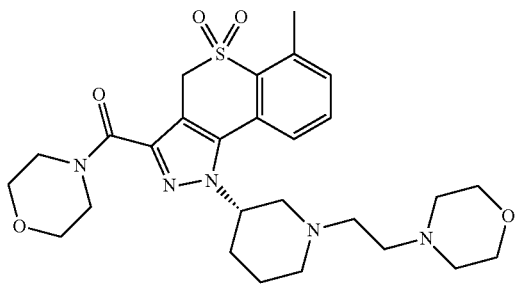 [SMILES: Cc1cccc2c1S(=O)(=O)Cc1c(C(=O)N3CCOCC3)nn([C@H]3CCCN(CCN4CCOCC4)C3)c1-2] |
| 503 | 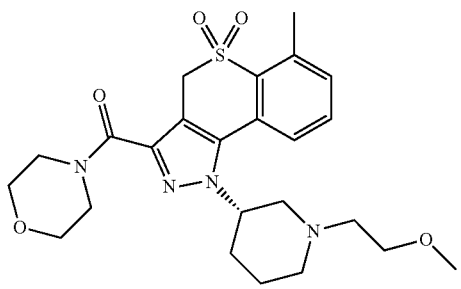 [SMILES: COCCN1CCC[C@H](n2nc(C(=O)N3CCOCC3)c3c2-c2cccc(C)c2S(=O)(=O)C3)C1] |

-continued
| Example No | structures |
|---|---|
| 504 | 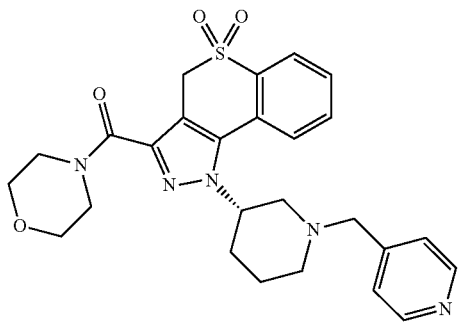 [SMILES: O=C(c1nn([C@H]2CCCN(Cc3ccncc3)C2)c2c1CS(=O)(=O)c1ccccc1-2)N1CCOCC1] |
| 505 | 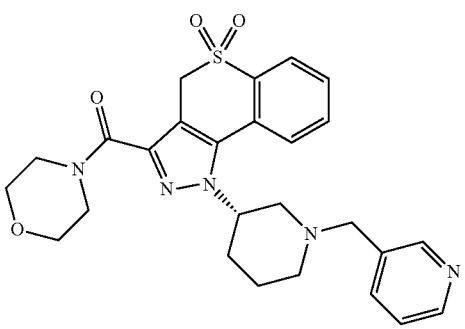 [SMILES: O=C(c1nn([C@H]2CCCN(Cc3cccnc3)C2)c2c1CS(=O)(=O)c1ccccc1-2)N1CCOCC1] |
| 506 | 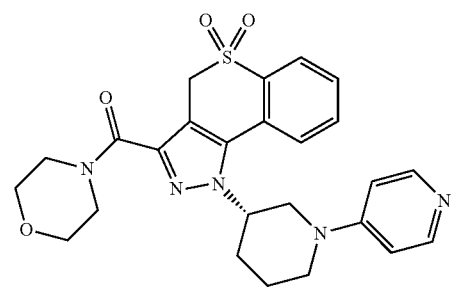 [SMILES: O=C(c1nn([C@H]2CCCN(c3ccncc3)C2)c2c1CS(=O)(=O)c1ccccc1-2)N1CCOCC1] |
| 507 | 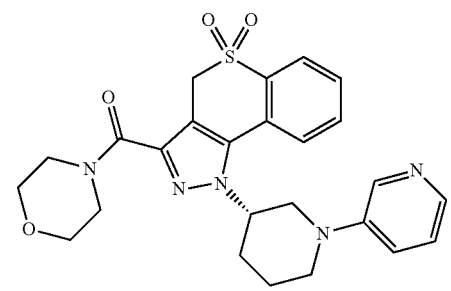 [SMILES: O=C(c1nn([C@H]2CCCN(c3cccnc3)C2)c2c1CS(=O)(=O)c1ccccc1-2)N1CCOCC1] |
| 508 | 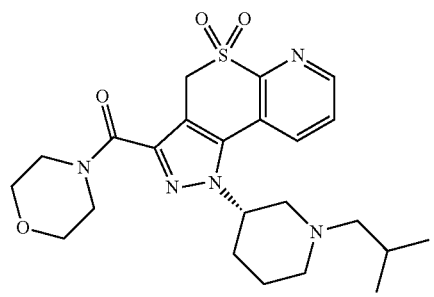 [SMILES: CC(C)CN1CCC[C@H](n2nc(C(=O)N3CCOCC3)c3c2-c2cccnc2S(=O)(=O)C3)C1] |

| Example No | structures |
|---|---|
| 509 | 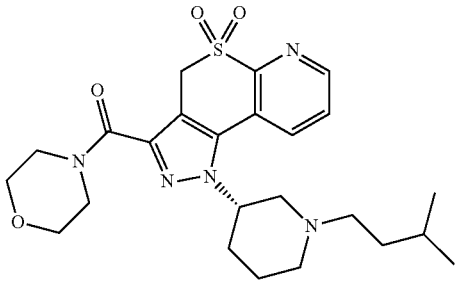 [SMILES: CC(C)CCN1CCC[C@H](n2nc(C(=O)N3CCOCC3)c3c2-c2cccnc2S(=O)(=O)C3)C1] |
| 510 | 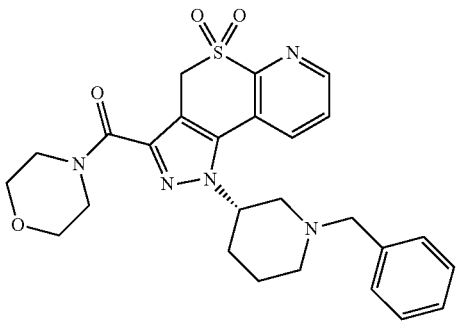 [SMILES: O=C(c1nn([C@H]2CCCN(Cc3ccccc3)C2)c2c1CS(=O)(=O)c1ncccc1-2)N1CCOCC1] |

Synthesis of Compounds of the Invention

The following abbreviations refer respectively to the definitions below:

aq (aqueous), h (hour), g (gram), L (liter), mg (milligram), MHz (Megahertz), µM (micromolar), min. (minute), mm (millimeter), mmol (millimole), mM (millimolar), m.p. (melting point), eq (equivalent), mL (milliliter), µL (microliter), ACN (acetonitrile), BOC (tert-butoxy-carbonyl), CBZ (carbobenzoxy), CDCl$_3$(deuterated chloroform), CD$_3$OD (deuterated methanol), CH$_3$CN (acetonitrile), c-hex (cyclohexane), DCC (dicyclohexyl carbodiimide), DCM (dichloromethane), DIC (diisopropyl carbodiimide), DIEA (diisopropylethyl-amine), DMA (dimethylacetamide), DMF (dimethylformamide), DMSO (dimethylsulfoxide), DMSO-d$_6$ (deuterated dimethylsulfoxide), EDC (1-(3-dimethyl—amino—propyl)—3-ethylcarbodiimide), ESI (Electro-spray ionization), EtOAc (ethyl acetate), Et$_2$O (diethyl ether), EtOH (ethanol), FMOC (fluorenylmethyloxycarbonyl), HATU (dimethylamino-([1,2,3 ]triazolo [4, 5-b]pyridin-3-yloxy)-methylene-dimethyl-ammonium hexafluorophosphate), HPLC (High Performance Liquid Chromatography), i-PrOH (2-propanol), K$_2$CO$_3$ (potassium carbonate), LC (Liquid Chromatography), MeCN (Acetonitrile), MeOH (methanol), MgSO$_4$ (magnesium sulfate), MS (mass spectrometry), MTBE (Methyl tert-butyl ether), Mtr. (4-Methoxy-2, 3, 6-trimethylbenzensulfonyl), MW(microwave), NaHCO$_3$ (sodium bicarbonate), NaBH$_4$ (sodium borohydride), NMM (N-methyl morpholine), NMR (Nuclear Magnetic Resonance), POA (phenoxyacetate), PyBOP (benzotriazole-1-yl-oxy-tris-pyrrolidino-phosphonium hexafluorophosphate), RT (room temperature), Rt (retention time), SPE (solid phase extraction), T3P (propane phosphonic acid anhydride), tBu (tert-butyl), TEA (triethylamine), TFA (trifluoroacetic acid), THF (tetrahydrofuran), TLC (Thin Layer Chromatography), UV (Ultraviolet).

The following general methods and procedures described hereinafter in the examples may be used to prepare compounds of formula (I) and related formulae.

The compounds according to Formula (I) may be prepared from readily available starting materials using the following general methods and procedures. If such starting materials are not commercially available they may be prepared by standard synthetic techniques. It will be appreciated that where typical or preferred experimental conditions (i.e. reaction temperatures, time, stoechiometry of reagents, solvents, etc.) are given, other experimental conditions can also be used unless otherwise stated. Generally, the compounds according to the general Formula (I) may be obtained by several processes using both solution-phase and/or solid-phase chemistry protocols. Examples of synthetic pathways for the preparation of compounds according to the general Formula (I) are described herebelow. Optimum reaction conditions may vary with particular reactants or solvents used, but such conditions can be determined by the person skilled in the art, using routine optimization procedures.

Below, all substituents, such as Q, $R^1$, $R^2$, $R^3$, $R^4$, $R^5$, $R^6$, T, $U_1$, $U_2$, $U_3$, $U_4$, A, Het, Ar, m, n, r and p have the meaning indicated under the formulae (I) and (I*), unless expressly stated otherwise.

Depending on the nature of $R^1$, $R^2$, $R^3$, $R^4$, $R^5$, $U_1$, $U_2$, $U_3$, and $U_4$, different synthetic strategies may be selected for the synthesis of compounds of Formula (I). In general, the synthesis pathways for any individual compound of Formula (I) or (I*) will depend on the specific substitutents of each molecule and upon the availability of intermediates; again such factors being appreciated by those skilled in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

The compounds according to Formula (I*) may be prepared following the synthetic pathway described in the general scheme A:

Scheme A:

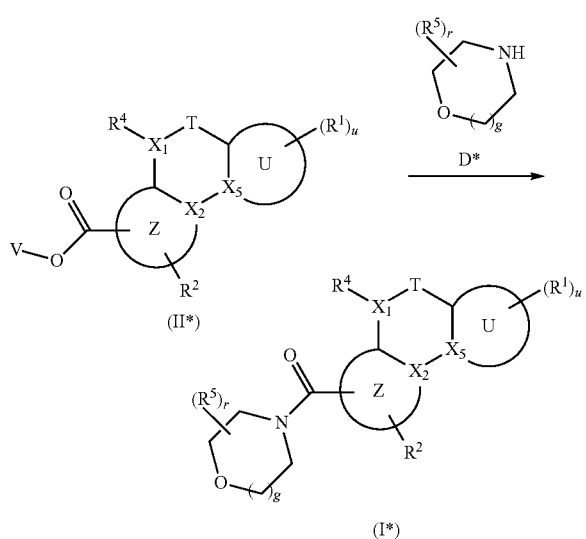

Wherein $R^5$, g, $R^4$, $R^2$, $R^1$, T, U, Z, $X_1$, $X_2$, $X_5$, u and r are as above defined and wherein V denotes H or Y.

As a representative example, the compounds according to Formula (I) may be prepared following the synthetic pathways described in the general scheme 1. According to a preferred synthetic pathway, compounds of Formula (I), may be prepared from the corresponding derivatives of Formula (Ib), by one or two alkylation reaction with $R^3$—X (and possibly $R^4$—X) where X is a leaving group such as a halogen or a sulfonate group and wherein $R^3$ and $R^4$ are as defined above. Preferred conditions consist in the treatment of compounds of Formula (Ib) with a base such as NaH followed by addition of alkyl or benzyl halide in a suitable solvent such as THF at room temperature.

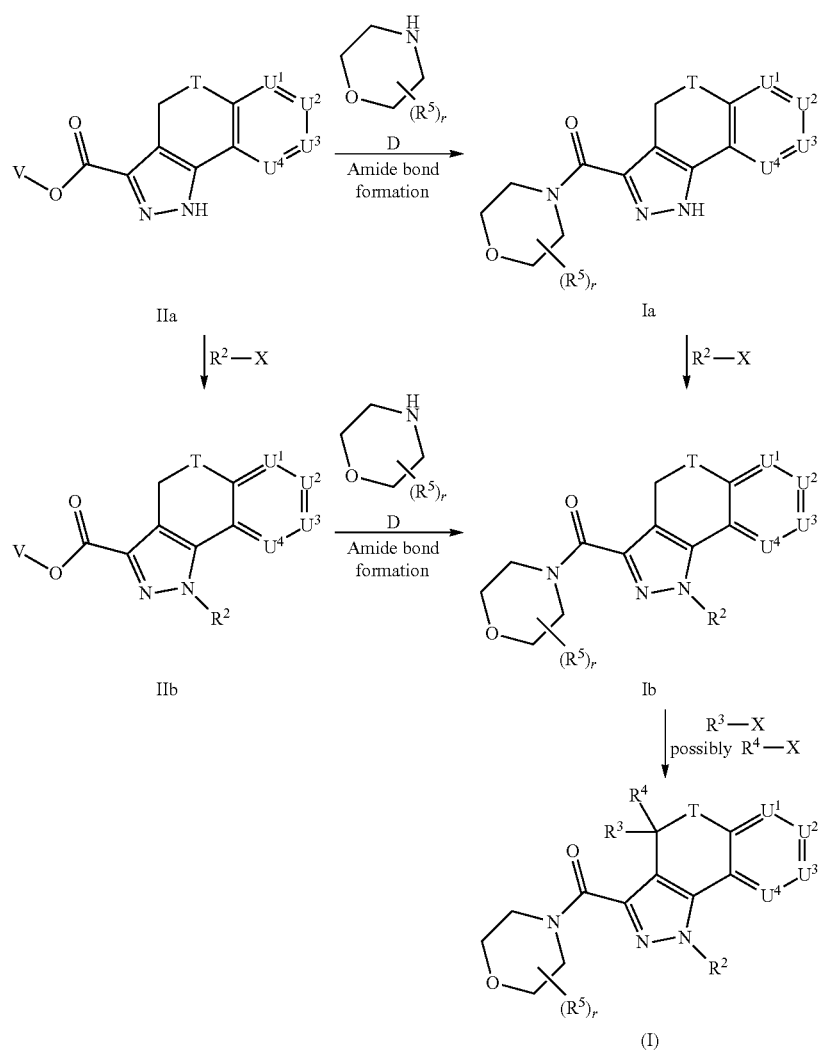

Compounds of Formula (Ib) may be prepared from the corresponding derivatives of Formula (IIb), wherein $R^2$ is as above defined and V denotes H or Y which is as defined above, either directly by reaction of compounds of Formula (IIb) where V is Y with an amine, or via the hydrolysis of the ester (IIb) into an acid wherein V is H and subsequent coupling with an amine. Starting from the acid (IIb) wherein V is H, compounds of formula (Ib) can be obtained using usual conditions for the formation of an amide starting from a carboxylic acid and an amine by using coupling agents such as DCC, DIC, EDC, HATU or via the formation of an acid chloride or an activated ester. Preferred conditions consist in the treatment of compounds of Formula (IIb) with a solution of propane phosphonic acid anhydride 50% in EtOAc followed with the addition of morpholine derivatives (D), wherein $R^5$ and r are as defined above, in the presence of a base such as triethylamine in a suitable solvent such as THF at room temperature. Another preferred condition is the pre-treatment of amine derivative D with $AlCl_3$ or $AlMe_3$ followed by the addition of compounds of formulae (IIb) where V is an alkyl group in a suitable solvent such as DCM or THF at a temperature between 0° C. to 50° C.

The corresponding carboxylic acid can be obtained by hydrolysis of the corresponding esters using reagents such as, but not limited to, LiOH, NaOH or KOH in solvents such water, alcohol, THF, dioxane, or mixture thereof.

Compounds (IIb) may be prepared from compounds of Formula (IIa) by alkylation reaction with $R^2$—X wherein X is a halogen or a sulfonate group. Preferred conditions consist in the treatment of compounds of formula (IIa) with an alkyl halide in the presence of a base such as potassium carbonate, in a suitable solvent such as acetonitrile at a temperature between room temperature and 60° C.

An alternative pathway for the synthesis of compounds of Formula (Ib) consists in alkylating compounds of Formula (Ia) with $R^2$—X wherein X is a halogen or a sulfonate group. Preferred conditions consist in the treatment of compounds of formula (Ia) with an alkyl halide in the presence of a base such as potassium carbonate in a suitable solvent such as acetonitrile at a temperature between room temperature and 60° C.

Compounds of Formula (Ia) may be prepared from the corresponding derivatives of Formula (IIa), wherein $R^2$ and V are as defined above, either directly by reaction with a morpholine derivative D, or via the hydrolysis of the ester (IIb) into an acid wherein V is H and subsequent coupling with a morpholine derivative D. Starting from the acid (IIb) wherein V is H, compounds of formula (Ia) can be obtained using usual conditions for the formation of an amide starting from a carboxylic acid and an amine by using coupling agent such as DCC, DIC, EDC, HATU or via the formation of an acid chloride or an activated ester. Preferred conditions consist in the treatment of compounds of Formula (IIb) with 50% propane phosphonic acid anhydride in EtOAc followed with the addition of morpholine derivative D, wherein $R^5$ and r are as defined above, in a suitable solvent such as THF, at room temperature. Another preferred condition is the pre-treatment of amine derivative D with $AlCl_3$ or $AlMe_3$ followed by the addition of compounds of formulae (IIb) where V is an alkyl group in a suitable solvent such as DCM or THF at a temperature between 0° C. to 50° C.

The corresponding carboxylic acid can be obtained by hydrolysis of esters using reagents such as, but not limited to, LiOH, NaOH or KOH in solvents such water, alcohol, THF, dioxane, or mixture thereof.

Compounds of Formula (IIa) and Formula (IIb) may be prepared from compounds of Formula (III) by cyclization with hydrazine, substituted hydrazines, and protected hydrazines, e.g. hydrazine having a PG group, wherein $R^2$ is as defined above, respectively (scheme 2). Hydrazine derivatives VII may or may not be protected by a protecting group such as a Boc group. Preferred conditions consist in the treatment of compounds (III) with hydrazine derivatives in a presence of an acid such as acetic acid in a suitable solvent such as methanol or ethanol at reflux. Another preferred condition is the treatment of compounds (III) with Boc-hydrazine derivatives in a presence of an acid such as HCl in a suitable solvent such as ethanol at reflux.

Compounds of Formula (III) may be prepared from compounds of Formula (IV) by reaction with V—OCOCO—X, wherein V and X are as defined above, in the presence of a base. Preferably, the base is a metal alkoxide. Preferred conditions consist in the treatment of compounds (IV) with butyl lithium and then V—OCOCO—X in a suitable solvent such as THF, MTBE or Toluene at a temperature between −78° C. and room temperature. Preferably, V—OCOCO—X is the diethyl oxalate. Other preferred conditions consists in the treatment of compounds (IV) with sodium ethoxide and then diethyloxalate in a suitable solvent such as toluene or MTBE at a temperature between 0° C. and room temperature.

Compounds of Formulae (I), (Ia), (Ib), (IIa) and (IIb) may be converted to alternative compounds of Formulae (I), (Ia), (Ib), (IIa) and (IIb) respectively, using suitable interconversion procedures such as those described hereinafter in the examples, or conventional interconversion procedures, well known by one skilled in the art.

Compounds of Formulae (I), (Ia), (Ib), (IIa) and (IIb), wherein T is S may be converted to the corresponding compounds of Formulae (I), (Ia), (Ib), (IIa) and (IIb), wherein T is SO or $SO_2$, by oxidation. Preferred conditions consist in the treatment of compounds of Formulae (I), (Ia), (Ib), (IIa) and (IIb) by hydrogen peroxide 30% in water in a suitable solvent such as acetic acid at a temperature of 100° C.

Scheme 2

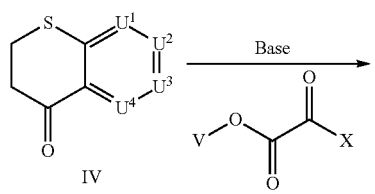

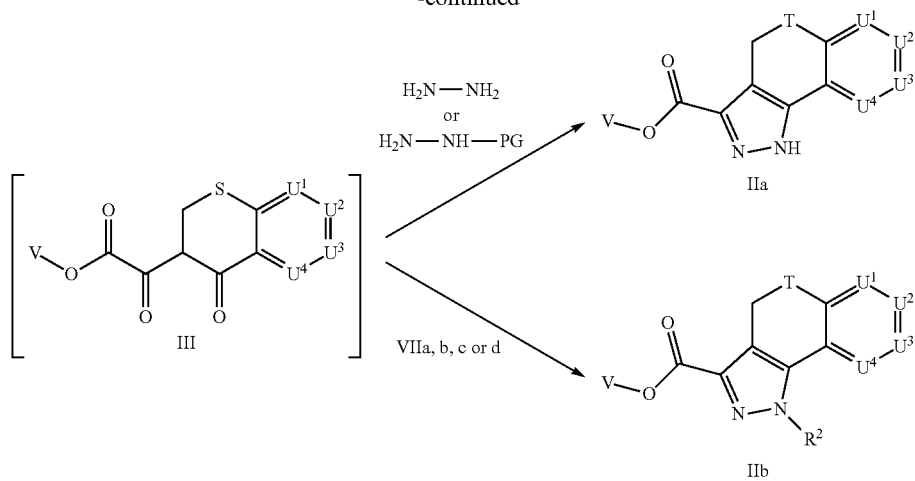

X: Leaving group such as OY, Halogen

Compounds of Formula (IV) wherein $U_1$, $U_2$, $U_3$ and $U_4$ are as defined above, (e.g. $U_1$, $U_2$, $U_3$ and $U_4$ denote $CR^1$) may be obtained either from commercial sources or they may be prepared from compounds of Formula (V) by Friedel-Craft type reaction (scheme 3). Preferred conditions consist in the treatment of compounds (V) by oxalyl chloride and by tin (IV) chloride in a suitable solvent such as dichloromethane at a temperature between 0° C. and room temperature. Other preferred conditions consist in the treatment of compounds (V) with polyphosphoric acid at a temperature ranging from 80° C. to 120° C.

Compounds of formulae (IV) wherein $U_1$, denote N and $U_2$, $U_3$ and $U_4$ denote $CR^1$ may be obtained either from commercial sources or following procedure described in Journal of Heterocyclic Chemistry, 37(2), 379-382; 2000.

Compounds of formulae (IV) wherein $U_3$, denotes N and $U_1$, $U_2$ and $U_4$ denote $CR^1$ may be obtained following procedure described in Journal of Heterocyclic Chemistry, 37(2), 379-382; 2000 starting from 4-chloronicotinic acid.

Compounds of formulae (IV) wherein $U_1$ denotes S and $U_2$-$U_3$ and $U_4$ denote $CR^1$ to form a 5 member ring may be obtained either from commercial sources or following procedure described in Tetrahedron, 54(21), 5599-5606; 1998.

Compounds of formulae (IV) wherein $U_4$ denotes S and $U_2$-$U_3$ and $U_1$ denote $CR^1$ to form a 5 member ring may be obtained either from commercial sources or following procedure described in Tetrahedron, 54(21), 5599-5606; 1998 starting from 3-bromothiophene.

Compounds of formulae (IV) wherein $U_4$ denotes N, $U_1$ denotes S and $U_2$-$U_3$ denotes $CR^1$ to form a 5 member ring may be obtained either from commercial sources or following procedure described in Tetrahedron, 54(21), 5599-5606; 1998 starting from tert-butyl (5-bromo-1,3-thiazol-2-yl)carbamate.

Scheme 3

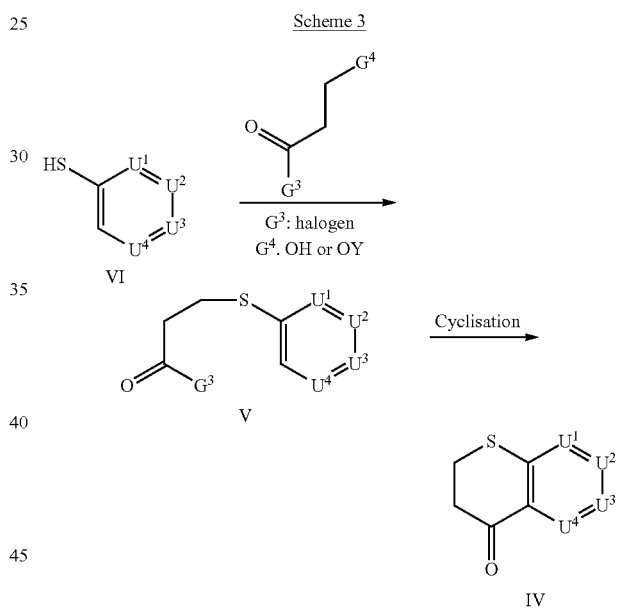

Compounds of Formula (V), wherein $U_1$, $U_2$, $U_3$ and $U_4$ are as defined as above, may be prepared from compounds of Formula (VI) by alkylation. Preferred conditions consist in the treatment of compounds of formula (VI) by $G^4$-$CH_2CH_2CO$-$G^{3'}$ wherein $G^4$ is halogen and $G^3$ is OH or OY, whereby Y is as above defined, in the presence of a base such as potassium carbonate in a suitable solvent such as dimethylformamide at a temperature of 60° C.

Preparation of compounds of general formulae (VII) is described in general scheme 4. Compounds of formulae (VIIa) or (VIIb), wherein $R^2$ is Ar or Het and PG represents a protecting group, including by way of non limiting examples, carabamate groups or alkyl groups, may be prepared from compounds of formulae (IX) and $R^2$—X when $R^2$ is an aryl or heteroaryl group. X is then either an halogen or a sulfonate group and coupling is catalysed by a metal as described in Journal of Organic Chemistry, 74(12), 4542-4546; 2009. Preferred conditions consist in the treatment of compounds of formulae (IX) with aryl halide, preferably iodine derivatives, in the presence of copper iodide and $Cs_2CO_3$ in a suitable solvent such as DMSO at a temperature between 50° C. and 100° C.

Compounds of formulae (VIIa), wherein $G^1CHG^2$ represents $R^2$ may be prepared from compounds of formulae (VIII) by a reduction reaction (scheme 4B). Preferred conditions consist in the treatment of compounds of formulae (VIII) with sodium cyanoborohydride in a suitable solvent such as a mixture of acetic acid and water at a temperature between 0° C. and RT.

Compounds of formulae (VIIc) and (VIId), wherein $G^1CHG^2$ represents $R^2$ may be prepared from compounds of formulae (VIII) by reduction with hydrogen in the presence of suitable catalysts or ligands/catalysts. Appropriate choice of ligand and/or catalyst and/or protecting group can either favour the formation of (VIIc) or the formation of (VIId). The use of achiral conditions gives compounds of formulae (VIIa). For chiral reduction, preferred conditions consist in the treatment of compounds of formulae (VIII) with bis(cyclooct-1,5-dien) rhodium(I)tetrafluoroborate and one enantiomer of Josiphos ligand under a pressure of 30 bar of hydrogen in a suitable solvent such as MeOH at RT.

Compounds of formulae (VIII), wherein $G^1$ and $G^2$ are independently from one another H or A or G1 and G2 together represent Cyc, may be prepared from compounds of formulae $G^1COG^2$ by reaction with hydrazine derivatives (IX) (scheme 4B). Preferred conditions consist in the treatment of derivatives $G^1COG^2$ with Boc-hydrazine, in a suitable solvent such as toluene at a temperature of 60° C. Enantiomers VIIc and VIId result from an asymmetric reduction of compound VIII. This reaction can be perform using a known asymmetric reduction or one of the procedures detailed below in the experimental part.

Scheme 4

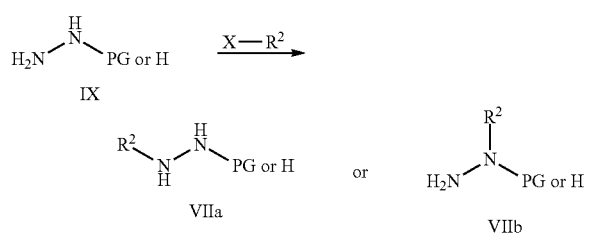

Scheme 4B

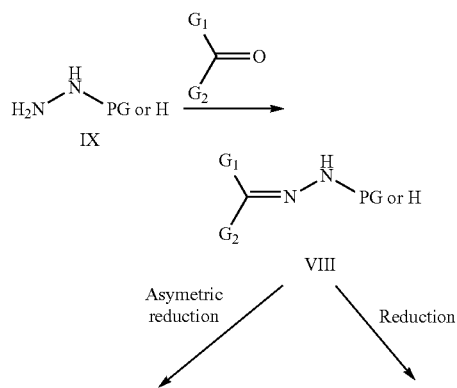

-continued

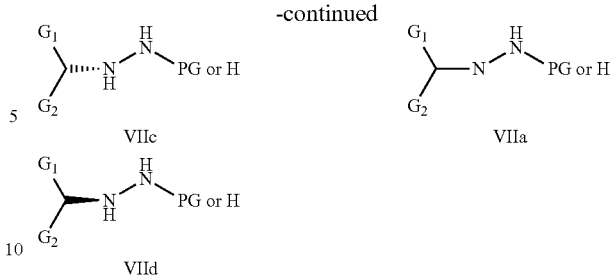

Preparation of compounds of general formulae (A) wherein $R^5$, $R^2$, $R^4$, T and $U^1$, $U^2$, $U^3$ $U^4$ are as above defined is described in general scheme 5. Compounds of formulae (A) wherein $R^4$ is as above defined may be prepared either by reaction of derivatives of formulae (Ic) with compounds of formulae $R^4$—X wherein X is a halogen or a sulfonate group or by intramolecular cyclisation of compounds of formulae (Xb). Preferred conditions for the alkylation are the treatment of compounds of formulae (Ic) with sodium hydride in a suitable solvent such as THF followed by the addition of an alkyl halide at a temperature ranging from 0° C. to 50° C. Preferred conditions for the intramolecular cyclisation are the treatment of compounds of formulae (Xb) with a palladium source such as palladium acetate, a ligand such as triphenylphosphine and a base such as $Cs_2CO_3$ in a suitable solvent such as toluene at a temperature ranging from 80° C. to 110° C.

Compounds of formulae (Ic) may either be prepared from derivatives of formulae (Xa) following palladium catalysed cyclisation reaction described above or by dealkylation of compounds of formulae (A) when $R^4$ is an alkyl ether protecting group such as a MOM group. Preferred conditions for the cleavage of a MOM protecting group are the treatment of compounds of formulae (A) with a suitable acid such as HCl in a suitable solvent such as dioxane at a temperature of 100° C.

Compounds of formulae (Xb) may be prepared from derivatives of formulae (Xa) by treatment of compounds of formulae (Xa) with alkyl derivatives $R^4$—X wherein X is a halogen or a sulfonate group and where $R^4$ is as above defined. Preferred conditions for the alkylation are the treatment of compounds of formulae (Ic) with sodium hydride in a suitable solvent such as THF followed by the addition of an alkyl halide at a temperature ranging from 0° C. to 50° C.

Compounds of formulae (Xa), where T is $SO_2$, may be prepared by reaction of compounds of formulae (XI) with sulfonylchloride derivatives. Preferred conditions are the treatment of compounds of formulae (XI) with sulfonyl chloride derivatives in a suitable solvent such as DCM in the presence of a base such as pyridine or TEA at RT.

Compounds of formulae (XI) may be prepared from compounds of formulae (XII) by a reduction reaction. Preferred conditions are the treatment of nitro derivatives (XII) with Pd/C 10% in a suitable solvent such as AcOEt under one atmosphere of hydrogen at RT.

Compounds (XII) may be prepared from compounds of formulae (XIII) by a coupling reaction with compounds of formulae $R^2$—Y* wherein Y* is a boronic acid or boronic ester group. Preferred conditions consist in the treatment of compounds of formulae (XIII) with an aromatic boronic acid in the presence of a base such as TEA and copper acetate, in a suitable solvent such as DCM at a temperature between RT and 60° C.

Compounds of formulae (XIII) may be prepared from the corresponding derivatives of formulae (XIV), wherein V is as defined above, following conditions described for general scheme 1.

compounds of formulae E wherein T is a thiol group and $U_2$, $U_3$ represents $CR^1$. Preferred conditions are the treatment of compounds of formulae (XVIc) wherein X are bromine atoms, $R^2$ represents an aryl or an heteroaryl and V represents

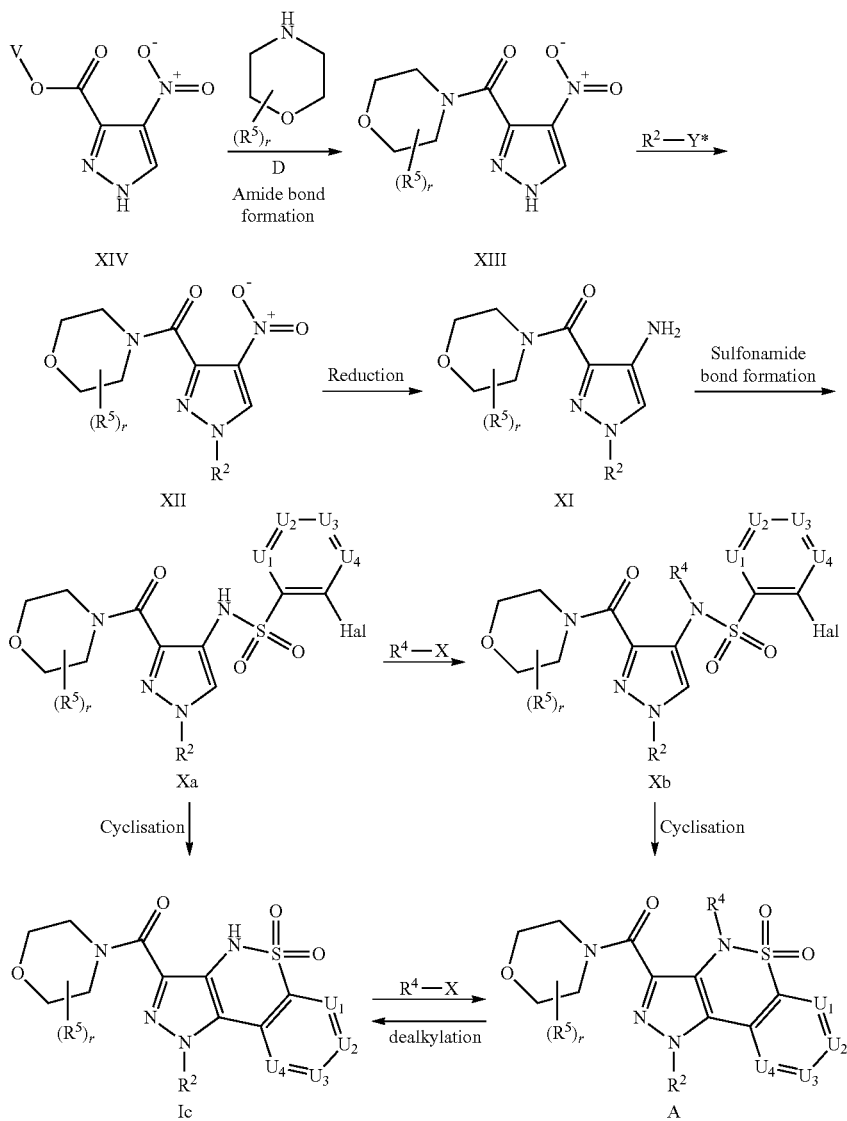

Scheme 5

Preparation of compounds of general formulae (B) wherein $R^5$, $R^2$, T and $U^2$, $U^3$ are as above defined is described in general scheme 6. Compounds of formulae (B) may be prepared from the corresponding derivatives of formulae (IIc), wherein V is as defined above, following conditions described for general scheme 1.

Compounds of formulae (IIc) may be prepared from derivatives of formulae (XV) by a intramolecular cyclisation reaction. Preferred conditions for the intramolecular cyclisation are the treatment of compounds of formulae (XV) with CuI in the presence or not of a ligand such as N,N-dimethylglycine in a suitable solvent such as DMSO at a temperature ranging from 100° C. to 180° C.

Compounds of formulae (XV) may be prepared by nucleophilic substitution on derivatives of formulae (XVIc) with an ethyl group with a thiol derivative E in the presence of a base such as $K_2CO_3$ in a suitable solvent such as ACN at a temperature ranging from RT to 90° C.

Compounds of formulae (XVIc) may be prepared from derivatives of formulae (XVIb) by an halogenation reaction. Preferred conditions are the treatment of compounds of formulae (XVIb) with a brominating agent such as phosphorus tribromide in a suitable solvent such as $Et_2O$ at a temperature ranging from 0° C. to RT.

Compounds of formulae (XVIb) may be prepared from derivatives of formulae (XVIa) by a reduction reaction. Preferred conditions are the treatment of compounds of formulae (XVIa) with a reductive agent such as sodium borohydride in a suitable solvent such as a mixture of THF and EtOH at a temperature between 0° C. to RT.

Compounds of formulae (XVIa) may be prepared from derivatives of formulae (XVII) by a Vilsmeier-Haack reaction. Preferred conditions are the treatment of compounds of formulae (XVII) with phosphorus oxy bromide and DMF in a suitable solvent such as DCM at a temperature ranging from 50° C. to 100° C.

Compounds of formulae (XVII) may be obtained either from commercial sources or following the procedure described in Synthesis (2003), (15), 2353-2357.

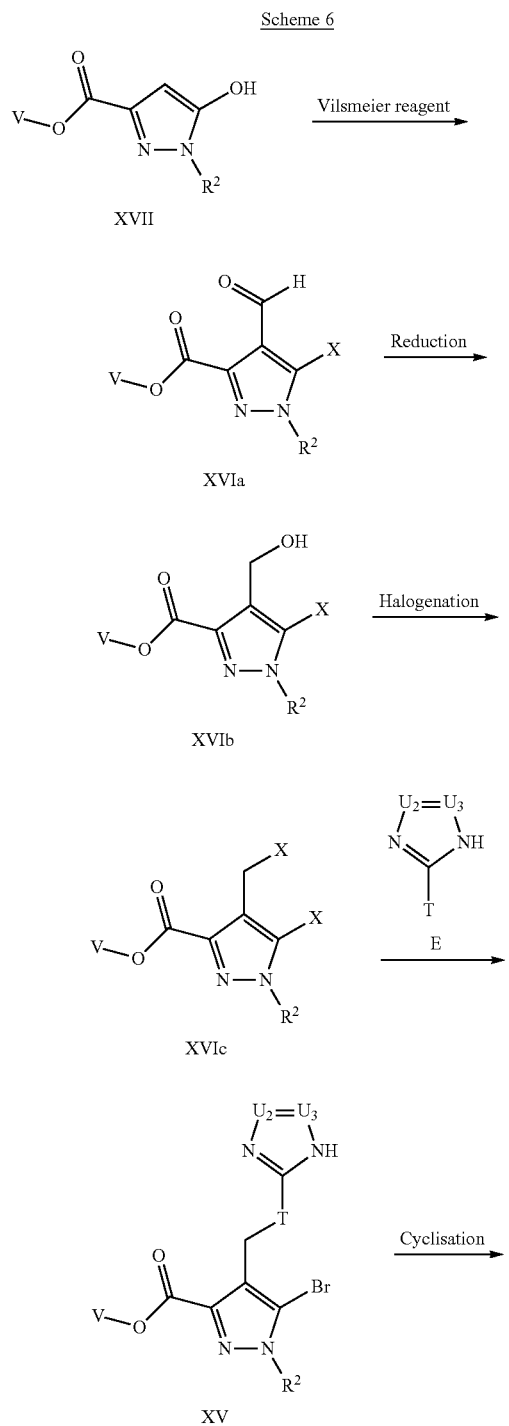

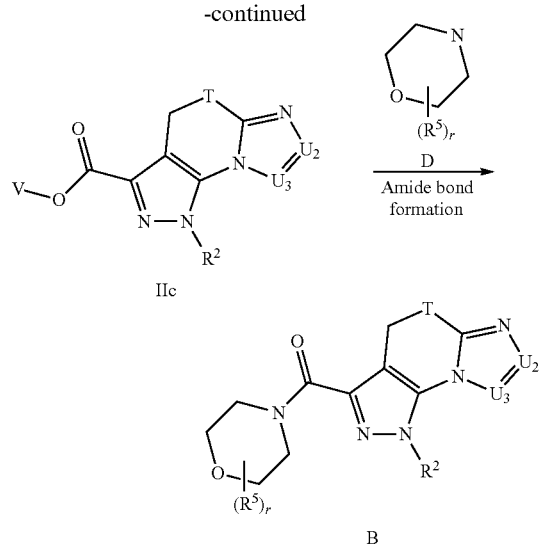

Preparation of compounds of general formulae (C) wherein $R^5$, $R^2$, T and $U^1$, $U^2$, $U^3$ $U^4$ are as above defined is described in general scheme 7. Compounds of formulae (C) may be prepared from the corresponding derivatives of formulae (IId), wherein V is as defined above, following conditions described for general scheme 1.

Compounds (IId) may be prepared from compounds of formulae (IIe) by reaction with $R^2$—X wherein X is a halogen or a sulfonate group. Preferred conditions consist in the treatment of compounds of formulae (IIe) with an alkyl halide in the presence of CuI and PdOAc in a suitable solvent such as DMF at a temperature ranging from 100° C. to 150° C.

Compounds of formulae (IIe) may be obtained from compounds of formulae (XVIII) by cyclisation reaction with compounds F where V is as above defined. Preferred conditions are the treatment of compounds of formulae (XVIII) with a base such as potassium tert-butoxide and diethyl chloro phosphonate followed by the addition of ethyl isocyano acetate in a suitable solvent such as DMF at a temperature ranging from 0° C. to RT.

Compounds of formulae (XVIII) wherein T, U1 U2, U3 and U4 are as above defined may be obtained either from commercial sources or following procedure described in Journal of Medicinal Chemistry (2010), 53(17), 6386-6397

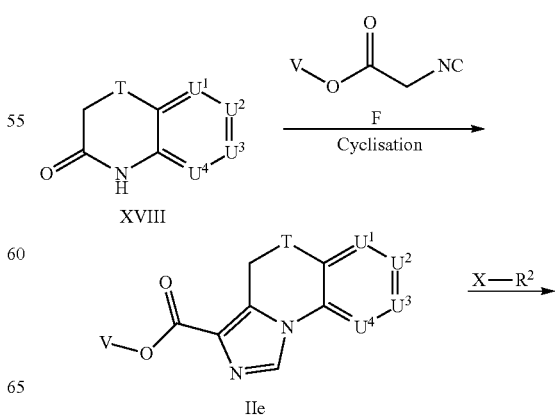

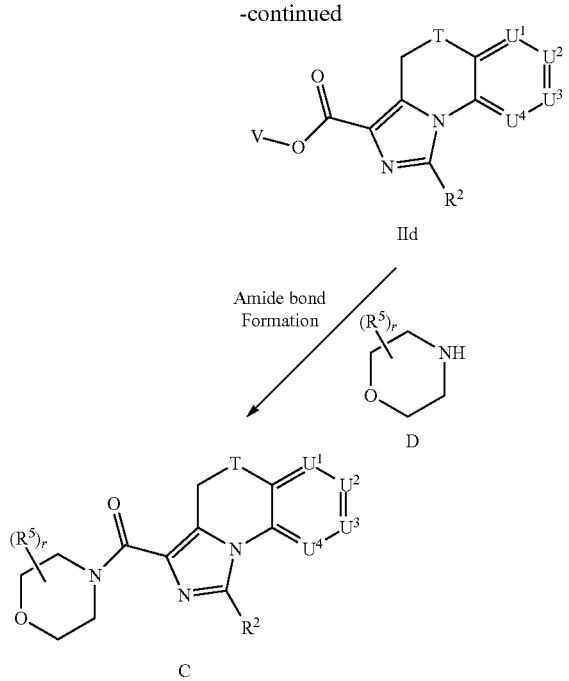

Compounds of Formula (I*) can be obtained following the procedures outlined in schemes 1 to 8 wherein compound D

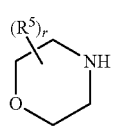

is replaced by compounds D*:

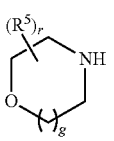

Wherein g is as above defined.

In a specific embodiment, the present invention provides a process wherein compounds of Formula (I) or (I*) wherein T is S are oxydised to compounds of Formula (I) or (I*) wherein T is $SO_2$. This oxidation step is performed using usual oxydizing agents, including mCPBA, $H_2O_2$, or $KMnO_4$.

Compounds of formulae (I), (I*), (Ia), (Ib), (Ic), (IIa), (IIb), (IIc), (IId), (IIe), (A), (B) and (C) may be converted to alternative compounds of formulae (I), (Ia), (Ib), (Ic), (IIa), (IIb), (IIc), (IId), (IIe), (A), (B) and (C) respectively, using suitable interconversion procedures such as those described hereinafter in the examples, or conventional interconversion procedures, well known by one skilled in the art.

Compounds of formulae (I), (I*), (Ia), (Ib), (IIa), (IIb), (IIc), (IId), (IIe), (B) and (C) wherein T is S may be converted to the corresponding compounds of formulae (I), (Ia), (Ib), (Ic), (IIa), (IIb), (IId), (IIe), (B) and (C), wherein T is SO or $SO_2$, by oxidation. Preferred conditions consist in the treatment of compounds of formulae (I), (Ia), (Ib), (Ic), (IIa), (IIb), (IIc), (IId), (IIe), (A), (B) and (C) by hydrogen peroxide 30% in water in a suitable solvent such as acetic acid at a temperature of 100° C. or treatment of compounds of formulae (I), (Ia), (Ib), (Ic), (IIa), (IIb), (IIc), (IId), (IIe), (A), (B) and (C) by meta-chloroperbenzoic acid in a suitable solvent such as DCM at a temperature between RT and 50° C.

Compounds of Formula (VI), E, F, (IX), XIV), (XVII), (XVIII) and reagents of Formulae $G^3$-$CH_2CH_2CO$-$G^4$, V—OCOCO—X, $H_2N$—NH—$R^2$, $R^2$—X, morpholine derivatives D, D*, $R^3$—X and $R^4$—X may be obtained either from commercial sources or they may be prepared from known compounds using procedures such as those described hereinafter in the examples, or conventional procedures, well known by one skilled in the art.

If the above set of general synthetic methods is not applicable to obtain compounds according to Formula (I) and/or necessary intermediates for the synthesis of compounds of Formula (I), suitable methods of preparation known by a person skilled in the art should be used.

Compounds of this invention can be isolated in association with solvent molecules by crystallization from an appropriate solvent or by evaporation of an appropriate solvent.

The pharmaceutically acceptable anionic salts of the compounds of Formula (I), (I*) and related Formulae, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

Compounds of the formula (I), (I*) and related formulae can furthermore be obtained by liberating compounds of the formula (I), (I*) and related Formulae from one of their functional derivatives by treatment with a solvolysing or hydrogenolysing agent.

Preferred starting materials for the solvolysis or hydrogenolysis are those which conform to the formula (I), (I*) and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the formula (I), (I*) and related Formulae, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms.

The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula (I), (I*) and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

The formula (I) and related formulae also encompasses the optically active forms (stereoisomers), the enantiomers, the racemates, the diastereomers and the hydrates and solvates of these compounds.

The term "solvates of the compounds" is taken to mean adductions of inert solvent molecules onto the compounds which form owing to their mutual attractive force. Solvates are, for example, mono- or dihydrates or alcoholates.

The term "hydrates of the compounds" refers to compounds of formula (I) associated with 1, 2, 3 or 4 molecules of water. Preferably, hydrates are mono- or dihydrates.

Use can also be made here of variants which are known per se, but are not mentioned here in greater detail.

If desired, the starting materials can also be formed in situ so that they are not isolated from the reaction mixture, but instead are immediately converted further into the compounds of the formula (I).

The starting compounds for the preparation of compounds of formula (I) and related formulae are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethyl-formamide (DMF); nitriles, such as acetonitrile; sulfoxides, such as dimethyl sulfoxide (DMSO); carbon disulfide; carboxylic acids, such as formic acid or acetic acid; esters, such as ethyl acetate, or mixtures of the said solvents.

In another aspect, the invention relates to a mixture of several compounds of formula (I), (I*) and related Formulae preferably a mixture of 2 to 10 compounds, more preferably, a mixture of 2 or 3 compounds of Formula (I). In another aspect, the invention may also encompass isomers, stereoisomers, diasteroisomers, enentiomers, as well as geometric isomers of compounds of Formula (I) or (I*). The invention also encompasses mixtures of isomers, e.g. stereoisomers, diasteroisomers, enentiomers and geometric isomers, of compounds of Formula (I), (I*) and related Formulae.

In a further aspect, the invention provides pharmaceutically acceptable derivatives, solvates, hydrates, tautomers, salts and stereoisomers of Formula (I), (I*) and related Formulae.

Accordingly, the invention relates, in particular, to the use of compounds of formula (I), (I*) and related formulae as defined above, as a medicament.

Accordingly, the invention relates, in particular, to the use of compounds of the formula(I) (I*) and related formulae as defined above, for the preparation of pharmaceutical formulations for the prevention and/or the treatment of inflammatory or autoimmune diseases, multiple sclerosis, cancers and related disorders.

The present invention also encompasses the metabolites of compounds of formula (I).

The said compounds of the formula (I), (I*) and related formulae can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula (I), (I*) and related Formulae are for the most part prepared by conventional methods. If the compound of the formula (I), (I*) and related formulae contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassium methoxide and sodium or potassium propoxide, alkalihydrides, such as sodium- or potassium hydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula (I), (I*) and related formulae are likewise included. In the case of certain compounds of the formula I and related formulae, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula (I), (I*) and related formulae include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclo-pentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydro-chloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula (I), (I*) and related formulae include aluminium, ammonium, calcium, copper, iron(III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-aminoethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula (I), (I*) and related formulae of the present invention which contain basic nitrogen-containing groups can be quaternised using agents such as ($C_1$-$C_4$)-alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$) alkyl halides, for example decyl, do-decyl, lauryl, myristyl and stearyl chloride, bromide and iodide; and aryl-($C_1$-$C_4$) alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stea-rate, sulfate, sulfosalicylate, tartrate, thiomalate, tosylate and tro-meth-amine, but this is not intended to represent a restriction.

As mentioned, the pharmaceutically acceptable base-addition salts of the compounds of the formula (I), (I*) and related Formulae are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

If a compound of the formula (I), (I*) and related formulae contains more than one group which is capable of forming pharmaceutically acceptable salts of this type, the formula (I), (I*) and related Formulae also encompass multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula (I), (I*) and related formulae in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The term "leaving group" or "leaving groups" denotes an atom or a group of atoms easily cleaved, hydrolysed or substituted with a reagent. Preferred leaving groups are halogens, alkylsulfonates, arylsulfonates, alcoholates or activated esters.

The term "reducing agent" denotes a reagent able to donate electrons. Preferred reducing agents are Boranes, Catecholborane, Copper hydride, Copper (low valent), Chromium (low valent), Decaborane, DIBAL-H, Diborane, Diethyl 1,4-dihydro-2,6-dimethyl-3,5-pyridinedicarboxylate, Diisobutylaluminium hydride, Dimethylsulfide borane, DMSB, Fe, Formaldehyde, Formic acid, Hantzsch Ester, Hydrazine, Hydrogen, Indium (low valent), Iron, Isopropanol, LAH, Lithium, Lithium aluminum hydride, Lithium tetrahydridoaluminate, LiBH4, Magnesium, Manganese, 3-Mercaptopropionic acid, 3-MPA, Neodymium (low valent), Nickel, Nickel borohydride, Niobium (low valent), Phenylsilane, PMHS, Polymethylhydrosiloxane, Potassium, 2-Propanol, Red-Al, Rongalite, Samarium (low valent), Silanes, Sodium, Sodium bis(2-methoxyethoxy)aluminumhydride, Sodium borohydride, Sodium cyanoborohydride, Sodium dithionite, Sodium hydrosulfite, Sodium hydroxymethanesulfinate, Sodium tetrahydroborate, Sodium triacetoxyborohydride, Strontium, Tetramethyldisiloxane, Tin hydrides, Titanium (low valent), TMDSO, Tributylstannane, Tributyltin hydride, Trichlorosilane, Triphenylphosphine, Triphenylphosphite, Triethylsilane, Tris(trimethylsilyl)silane, TTMSS, Zinc.

The term "prodrug derivatives" or "prodrug" is taken to mean compounds of the formula (I) or (I*) which have been modified with, for example, alkyl or acyl groups, sugars or oligopeptides and which are rapidly cleaved in the organism to form the active compounds.

These also include biodegradable polymer derivatives of the compounds according to the invention, as described, for example, in Int. J. Pharm. 115, 61-67 (1995).

The term "metabolite" designates compounds of formula (I) or (I*) which have been modified within the organism, through the reactions naturally occurring in the body.

Owing to their molecular structure, the compounds of the formula (I), (I*) and related formulae can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/ acetonitrile, for example in the ratio 82:15:3.

The invention furthermore relates to the use of compounds of Formula (I) or (I*) for the manufacture of a medicament for the prevention and/or the treatment of the diseases associated to Phosphoinositide 3-kinases disorders.

The invention also relates to the use of compounds of Formula (I) or (I*) for the manufacture of a medicament for the prevention and/or the treatment of inflammatory diseases, autoimmune disorder, multiple sclerosis, cancers, and related disorders.

In particular, the present invention relates to the use of compounds of Formula (I) or (I*) for the manufacture of a medicament for the prevention and/or treatment of Rheumatoid arthritis, Asthma and other autoimmune diseases selected from Acute disseminated encephalomyelitis (ADEM), Addison's disease, Alopecia areata, Ankylosing spondylitis, Antiphospholipid antibody syndrome (APS), Autoimmune hemolytic anemia, Autoimmune hepatitis, Autoimmune inner ear disease, Bullous pemphigoid, Behcet's disease, Coeliac disease, Anti-transglutaminase, Chagas disease, Chronic obstructive pulmonary disease, Crohn's Disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Multiple sclerosis (MS), Myasthenia gravis, Narcolepsy, Neuromyotonia, Pemphigus vulgaris, Pernicious anaemia, Psoriasis, Psoriatic Arthritis, Polymyositis, Primary biliary cirrhosis, Schizophrenia, Scleroderma, Sjogren's syndrome, Stiff person syndrome, Temporal arteritis, Ulcerative Colitis, Vasculitis, Vitiligo, Wegener's granulomatosis.

The invention also relates to the use of compounds of Formula (I) or (I*) for the manufacture of a medicament for the prevention and/or the treatment of the disease selected from the group consisting of amyotrophic lateral sclerosis (ALS), systemic lupus erythematosus, chronic rheumatoid arthritis, lupus, dermatomyositis, autoimmune neuropathies, immune thrombocytopenic purpura, haemolytic anaemia, inflammatory bowel disease, psoriasis, autoimmune myositis, Wegener's granulomatosis, ichthyosis, bone marrow or organ transplant rejection or graft-versus-host disease, Hashimoto's thyroiditis, myasthenia gravis, uveitis, posterior uveitis, rheumatic fever inflammatory and hyperproliferative skin diseases, atopic dermatitis, contact dermatitis, areata, keratoconjunctivitis, autoimmune hemolytic anemia, agranulocytosis, cutaneous T cell lymphoma, chronic lymphocytic leukemia, arteriosclerosis, atherosclerosis, aortitis syndrome, polyarteritis nodosa, lung cancer, carcinogenesis, metastasis of carcinoma and hypobaropathy, disease caused by histamine or leukotriene-C4 release, autoimmune hepatitis, primary biliary cirrhosis, Parkinson's disease.

The invention furthermore relates to the use of compounds of formula (I), (I*) and related formulae in combination with at least one further medicament active ingredient, preferably medicaments used in the treatment of inflammatory diseases or immune disorders such as methotrexate, leflunomide, rituxan, or anti-TNF like enbrel (etanercept), remicade (infliximab), humira (adalimumab), or with immunomodulating agents such as Fingolimod, cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate;dexamethasone tebutate;dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes. The invention furthermore relates to the use of compounds of formula (I) and related formulae in combination with at least one further medicament active ingredient, preferably medicaments used in the treatment of cancer wherein said antitumoral compounds are selected from those well known by the one skilled in the related art.

These compositions can be used as medicaments in human and veterinary medicine.

Other Embodiments

Embodiments 1: A compound of Formula (I):

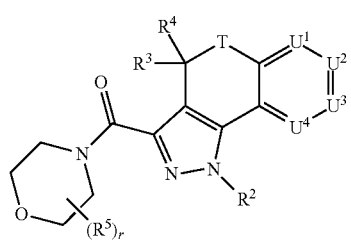

(I)

wherein
$R^2$ denotes H, Ar, Het, A, Cyc,
$R^3$, $R^4$ denote independently from one another H, Y, $(CH_2)_n$Ar, $(CH_2)_n$Cyc, $(CH_2)_n$Het
$R^5$ denotes H, Y or Ar,
$U^1$, $U^2$, $U^3$, and $U^4$ denote $CR^1$ or one or two of $U^1$, $U^2$, $U^3$ and $U^4$ are independently N, and the remaining are $CR^1$
$R^1$ denotes H, A, Hal, CN, $NO_2$, $N(R^6)_2$, $OR^6$, Ar, Het, Y, $—NR^6COR^6$, $CON(R^6)_2$
T denotes S, SO or $SO_2$.
r denotes 0, 1 or 2,
Ar denotes a monocyclic or fused bicyclic, unsaturated or aromatic carbocyclic ring having 6 to 14 carbon atoms, which is unsubstituted or monosubstituted, disubstituted or trisubstituted by Hal, $OCF_3$, $NO_2$, CN, perfluoroalkyl, A, $OR^6$, $N(R^6)_2$, $COR^6$, $—O_2R^6$, $CON(R^6)_2$, COHet, $—NHCOR^6$, $—NHSO_2A$, $—NHSO_2Ar$, $—NHSO_2—N(R^6)_2$, $N(H)_{1-q}A_qCOR^6$, $N(H)_{1-q}A_qSO_2—N(H)_{2-m}(A)_m$, $—N(H)_{1-q}A_qCON(H)_{2-m}(A)_m$, $—SO_2A$, $—SO_2Ar$, $—SO_2N(H)_{2-m}(A)_m$, $—SO_2Het$, $—(CH_2)_n—N(R^6)_2$, $—(CH_2)_n—OR^6$, $—(CH_2)_n—N(R^6)SO_2A$, $—(CH_2)_n—N(R^6)SO_2R^6$;
Het denotes a monocyclic or bicyclic saturated, unsaturated or aromatic heterocyclic ring having 1, 2, 3 or 4 N, 0 and/or S atoms which is unsubstituted or monosubstituted, disubstituted or trisubstituted by Hal, $OCF_3$, $NO_2$, CN, perfluoroalkyl, A, $OR^6$, $N(R^6)_2$, $COR^E$, $—CO_2R^6$, $CON(R^6)_2$, $-NHCOR^6$, $—NHSO_2A$, $—NHSO_2R^6$, $—NHSO_2—N(H)_{2-m}(A)_m$, $N(H)_{1-q}A_qCOR^6$, $N(H)_{1-q}A_qSO_2—N(H)_{2-m}(A)_m$, $—N(H)_{1-q}A_qCON(H)_{2-m}(A)_m$, $—SO_2A$, $—SO_2Ar$, $—SO_2N(H)_{2-m}(A)_m$, COHet, $—SO_2Het$, $—(CH_2)_n—N(H)_{2-m}(A)_m$, $—(CH_2)_n—OR^6$, $—(CH_2)_n—N(R^6)SO_2A$, $—(CH_2)_n—N(R^6)SO_2R^6$;
Cyc denotes a saturated carbocyclic ring having 1 to 8 carbon atoms, which is unsubstituted, mono-substituted, di-substituted or tri-substituted by Hal, $OCF_3$, $NO_2$, CN, perfluoroalkyl, A, $OR^6$, $N(R^6)_2$, $COR^6$, $CON(R^6)_2$, $—NHCOR^6$, $—NHSO_2A$, $—NHSO_2R^6$, $—NHSO_2—N(H)_{2-m}(A)_m$, $N(H)_{1-q}A_qCOR^6$, $N(H)_{1-q}A_qSO_2—N(H)_{2-m}(A)_m$, $—N(H)_{1-q}A_qCON(H)_{2-m}(A)_m$, $—COOR^6$, $—SO_2A$, $—SO_2Ar$, $—SO_2N(H)_{2-m}(A)_m$, $—SO_2Het$, $—(CH_2)_p—N(H)_{2-m}(A)_m$, $—(CH_2)_n—OR^6$, $—(CH_2)_n—N(R^6)SO_2A$, $—(CH_2)_n—N(R^6)SO_2R^6$;
A is a branched or linear alkyl having 1 to 12 C-atoms, wherein one or more, preferably 1 to 7 H-atoms may be replaced by Hal, Ar, Het, Cyc, $OR^6$, $—CN$, $—CO_2Y$ or $N(R^6)_2$ and wherein one or more, preferably 1 to 7 non-adjacent $CH_2—$ groups may be replaced by O, $NR^6$, $CONR^6—$ and/or by $—CH=CH—$ or $—C≡C—$ groups, or denotes cycloalkyl or cycloalkylalkylen having 3-7 ring C atoms;
Y denotes a branched or linear alkyl having 1 to 8 carbon atoms.
$R^6$ is H, A or Ar.
Hal denotes F, Cl, Br or I,
q is 0 or 1,
m is 0, 1 or 2,
n is 1, 2, 3, or 4
and pharmaceutically acceptable derivatives, solvates, tautomers, salts, hydrates and stereoisomers thereof, including mixtures thereof in all ratios, for use as a medicament.
Embodiment 2: A compound of Formula (I) according to embodiment 1 for the prevention and/or treatment of the diseases associated to Phosphoinositide 3-kinases disorders.

Embodiment 3: A compound according to embodiment 2 wherein the disease is inflammatory disease, autoimmune disorder, cancer or multiple sclerosis and related disorders.

Embodiment 4: A compound according to embodiment 3 wherein the autoimmune disease is selected from the group consisting of Asthma, Rheumatoid arthritis, Acute disseminated encephalomyelitis (ADEM), Addison's disease, Alopecia areata, Ankylosing spondylitis, Antiphospholipid antibody syndrome (APS), Autoimmune hemolytic anemia, Autoimmune hepatitis, Autoimmune inner ear disease, Bullous pemphigoid, Behcet's disease, Coeliac disease, Anti-transglutaminase, Chagas disease, Chronic obstructive pulmonary disease, Crohn's Disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Multiple sclerosis (MS), Myasthenia gravis, Narcolepsy, Neuromyotonia, Pemphigus vulgaris, Pernicious anaemia, Psoriasis, Psoriatic Arthritis, Polymyositis, Primary biliary cirrhosis, Rheumatoid arthritis, Schizophrenia, Scleroderma, Sjögren's syndrome, Stiff person syndrome, Temporal arteritis, Ulcerative Colitis, Vasculitis, Vitiligo, Wegener's granulomatosis Embodiment 5: A kit consisting of separate packs of:
(a) an effective amount of a compound of the formula (I) and/or pharmaceutically usable derivatives, solvates, salts, hydrates and stereoisomers thereof, including mixtures thereof in all ratios, and
(b) an effective amount of a further medicament active ingredient.

Embodiment 6: A Pharmaceutical compositions containing at least one of the compounds of Formula (I) according to any one of embodiment 1 to 5.

Embodiment 7: A pharmaceutical composition according to embodiment 6 wherein compounds of formula (I) are combined with at least one further medicament used in the treatment of inflammatory diseases or immune disorders.

Embodiment 8: A pharmaceutical composition according to embodiment 7 wherein compounds of Formula (I) are combined with at least one further immunomodulating agents.

Embodiment 9: A process for producing compounds of Formula (I) according to embodiment 1 to 5, wherein $R^3$ and $R^4$ are both H, comprising the step of reacting compounds of Formula (IIb)

wherein V is H or Y, and wherein $R^2$, T, Y and $U_1$, $U_2$, $U_3$ and $U_4$ are as defined in embodiment 1, with a morpholine derivative D:

wherein $R^5$ and r are as defined in embodiment 1,
or reacting compounds of Formula (Ia)

wherein $R^5$, r, T and $U_1$, $U_2$, $U_3$ and $U_4$ are as defined in embodiment 1 with compounds of formula $R^2$—X, wherein $R^2$ is as defined in embodiment 1 and X is a leaving group.

Embodiment 10: A process according to embodiment 9 further comprising the step of reaction a compound of Formula (Ib)

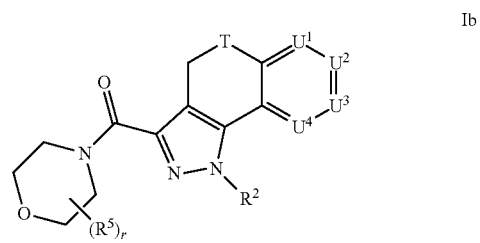

wherein $R^5$, $R^2$, r, T and $U_1$, $U_2$, $U_3$ and $U_4$ are as defined in embodiment 1, with $R^3$—X and $R^4$—X,
wherein X is a leaving group and $R^3$ and $R^4$ are as defined in embodiment 1.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I), (I*) and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I), (I*) and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I), (I*) and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a PI3K related disorder, comprising administering to said subject an effective amount of a compound of formula I and related formulae. The present invention preferably relates to a method, wherein the PI3K associated disorder is an autoimmune disorder or condition associated with an overactive immune response or cancer. The present invention furthermore relates to a method of treating a subject suffering from an immunoregulatory abnormality, comprising administering to said subject a compound of formula (I), (I*) and related formulae in an amount that is effective for treating said immunoregulatory abnormality The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, and chronic bacterial infection.

Preferred compounds of formula (I), (I*) and related formulae exhibit a $IC_{50}$ for the binding to PI3K of less than about 5 μM, preferably less than about 1 μM and even more preferably less than about 0.100 μM.

Compounds according to formula (I), (I*) and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In general, the synthesis pathways for any individual compound of formula (I), (I*) and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula (I), (I*) and related formulae which contain a basic center may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I), (I*) and related formulae, which contain an acid center, with a suitable base. Both types of salts may be formed or interconverted using ion-exchange resin techniques.

In the following the present invention shall be illustrated by means of some examples, which are not construed to be viewed as limiting the scope of the invention.

Experimental Part $^1$H NMR was recorded on 400 MHz spectrometers. Chemical shifts (δ) are reported in ppm relative to the residual solvent signal (δ=2.49 ppm for $^1$H NMR in DMSO-d6). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

NMR, HPLC and MS data provided in the examples described below are registered on:

NMR: Bruker DPX-300, using residual signal of deuterated solvent as internal reference.

HPLC: Waters Alliance 2695, column Waters XBridge C8 3.5 μm 4.6×50 mm, conditions: solvent A ($H_2O$ with 0.1% TFA), solvent B (ACN with 0.05% TFA), gradient 5% B to 100% B over 8 min, UV detection with PDA Water 996 (230-400 nm).

LCMS method: 0.1% TFA in $H_2O$, B: 0.1% TFA in ACN Flow Rate: 2.0 mL/min Column: Xbridge C8 (50*4.6 mm, 3.5μ).

UPLC/MS: Waters Acquity, column Waters Acquity UPLC BEH C18 1.7 μm 2.1×50 mm, conditions: solvent A (10 mM ammonium acetate in water+5% ACN), solvent B (ACN), gradient 5% B to 100% B over 3 min, UV detection (PDA, 230-400 nm) and MS detection (SQ detector, positive and negative ESI modes, cone voltage 30V).

Autoprep purification: preparative HPLC purifications are performed with a mass directed autopurification Fractionlynx from Waters equipped with a Sunfire Prep C18 OBD column 19×100 mm 5 μm, unless otherwise reported. All HPLC purifications were performed with a gradient of ACN/$H_2$O or ACN/$H_2$O/HCOOH (0.1%).

Chiral analytical HPLC: Waters Alliance 2695, column Waters chiralcel OJ-H, OB-H, OD-H, OZ-H or a Chirapak AD-H, AS, IA-3, IB, IC-3, AY-H or (SS) Whelk 01, (RR) Whelk 01 Chiralcel OJ-H, OB-H, OD-H, OZ-H or a Chiralpak AD-H, AS, IA-3, IB, IC-3, AY-H from Chiral Technologies or (SS) Whelk -01 from Regis Technologies on Alliance system (Waters) with a flow rate of 1 ml min UV detection with PDA Water 996 (230-400 nm).

Chiral chromatography separations have been performed with stationary phase chosen from either chiralcel OJ-H, OD-H or a Chirapak AD-H, IC-3, AY-H or Welk 01 on either a 2777C Sample Manager PAL, Prep LC 4000 using a Waters 2487 Dual Detector and Waters Fraction collector III that operates with Fraction lynx software or on a Hipersep 80 (supplier: NOVASEP), Detection wavelength between 305 and 320 nm.

Alpha D were determined on a Polarimeter Jasco P-2000 at 25° C. using Spectra Manager as software.

Chiral centers of enantiomerically enriched material have been drawn arbitrarily. Isolated enantiomers have been named "enantiomer (A)" and "enantiomer (B)" arbitrarily.

INTERMEDIATES

Intermediate A.0

4-Chloronicotinic Acid

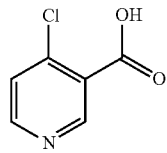

4-Chloropyridine hydrochloride (25 g) is neutralized with aq. $Na_2CO_3$ (10%) and extracted with DCM. The organic layer is separated, dried over $Na_2SO_4$ and concentrated under reduced pressure to afford 4-chloropyridine (19 g). To a solution of diisopropylamine (31 mL, 217.6 mmol) in dry THF is added n-butyllithium (115 mL, 184.1 mmol) dropwise at −78° C. under nitrogen. After 30 min, a solution of 4-chloropyridine (19 g, 167.4 mmol) in dry THF is slowly added under nitrogen. The reaction mixture is further stirred for 1 h at −78° C. before addition of solid $CO_2$, let warmed to RT and stirred at RT for 12 h under nitrogen. After this time, reaction mixture is concentrated under reduced pressure and acidified with aq. HCl solution (1.5 N) under ice-cooled condition. Precipitate is filtered under reduced pressure and dried overnight under vacuum to afford 15 g (57%) of the title compound. $^1$H NMR (DMSO-$d_6$, 400 MHz): δ 6 13.83 (bs, 1H), 8.92 (s, 1H), 8.64-8.63 (d, J=5.4 Hz, 1H), 7.66-7.65 (d, J=5.4 Hz, 1H).

Procedure A

Intermediate A.1

3-[(2-methoxyphenyl)thio]propanoic acid

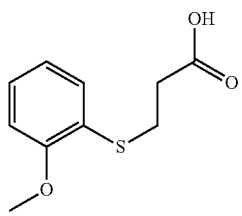

To a solution of 2-methoxythiophenol (5.0 g, 3.56 mmol) in DMF (125 mL) is added potassium carbonate (14.76 g, 10.69 mmol, 3 Eq) at 60° C. under nitrogen. The reaction mixture is stirred for 30 minutes then bromopropionic acid (6.0 g, 3.92 mmol, 1.1 Eq) is added and the resulting mixture is stirred for 90 minutes at 60° C. under nitrogen. The solvent is removed under reduced pressure and the residue is taken up in water then washed with EtOAc. The aqueous layer is acidified with aq. solution of HCl and the product is extracted with EtOAc. The organic layer is dried over $MgSO_4$ and concentrated in under reduced pressure to afford 5.7 g (75%) of the title compound as a yellow oil.

$^1$H NMR (DMSO-d6, 400 MHz): δ 7.23-7.16 (m, 2H), 6.98-6.91 (m, 2H), 3.79 (s, 3H), 3.03 (t, J=7.0 Hz, 2H), 2.51-2.48 (m, 2H).MS (ESI+): 213.0. HPLC (max plot) 99.5%; Rt 3.59 min.

Intermediates described below are obtained following procedure A

---

Intermediate A.2: 3-[(3-Bromophenyl)thio]propanoic acid

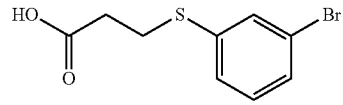 [SMILES: O=C(O)CCSc1cccc(Br)c1]

12 g (87%) of the title compound. $^1$H NMR (DMSO-$d_6$, 400 MHz): δ 12.41 (bs, 1H), 7.51-7.49 (m, 1H), 7.39-7.35 (m, 1H), 7.33-7.31 (m, 1H), 7.27-7.23 (m, 1H), 3.20-3.14 (m, 2H), 2.61-2.53 (m, 2H).

Intermediate A.3: 3-{[3-(Trifluoromethyl)phenyl]thio}propanoic acid

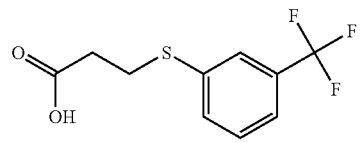 [SMILES: O=C(O)CCSc1cccc(C(F)(F)F)c1]

12 g (87%) of the title compound. $^1$H NMR (DMSO-$d_6$, 400 MHz): δ 12.39 (bs, 1H), 7.63-7.61 (m, 2H), 7.56-7.52 (m, 2H), 3.24-3.20 (t, J = 7.0 Hz, 2H), 2.56-2.53 (t, J = 7.0 Hz, 2H).

Intermediate A.4: 3-[(4-Methoxyphenyl)thio]propanoic acid

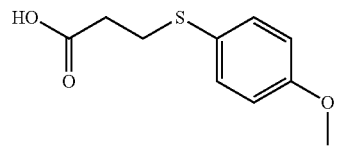

12 g (79%) of the title compound. $^1$H NMR (DMSO-$d_6$, 400 MHz): δ 12.32 (bs, 1H), 7.34-7.31 (dd, J = 2.1, 8.8 Hz, 2H), 6.93-6.89 (dd, J = 1.9, 8.8 Hz, 2H), 4.16 (s, 3H), 3.00 (t, J = 7.1 Hz, 2H), 2.44-2.41 (t, J = 7.0 Hz, 2H)

Intermediate A.5: 4-[(2-Carboxyethyl)thio]nicotinic acid

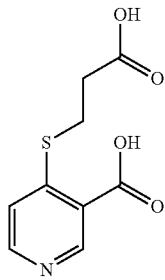 [SMILES: O=C(O)CCSc1ccncc1C(=O)O]

15 g (82%) of the title compound. $^1$H NMR (DMSO-$d_6$, 400 MHz): d 13.30 (bs, 1H), 12.50 (bs, 1H), 8.89 (s, 1H), 8.51-8.49 (d, J = 5.6 Hz, 1H), 7.43-7.41 (d, J = 5.6 Hz, 1H), 3.33-3.13 (m, 2H), 2.64-2.61 (m, 2H).

Intermediate A.6: 3-[(2-Chlorophenyl)thio]propanoic acid

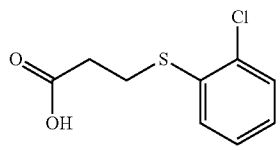 [SMILES: O=C(O)CCSc1ccccc1Cl]

17.5 g (97%) of the title compound. HPLC (max plot) 53.3%; Rt 1.42 min. MS (ESI–): 214.8.

Procedure B

Intermediate B.1

8-methoxy-2,3-dihydro-4H-thiochromen-4-one

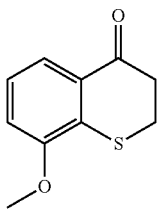

To a solution of 3-[(2-methoxyphenyl)thio]propanoic acid (5.0 g, 23.6 mmol) in dry DCM (50 mL) at 0° C. is added oxalyl chloride (6.01 g, 4.09 mL, 47.2 mmol, 2 Eq) followed by few drops of DMF. The reaction mixture is stirred at 0° C. for 30 minutes. After 30 minutes, the solvent is removed under reduced pressure. To a solution of the acid chloride in DCM (150 mL) at 0° C. is added a solution of tin (IV) chloride in DCM (26 mL, 1 M, 26.0 mmol, 1.1 Eq) and the reaction mixture is stirred for 2 h. The reaction is quenched by addition of water and the product is extracted with DCM. The organic layer is dried over MgSO$_4$, concentrated under reduced pressure. The crude residue is purified by flash chromatography (eluent: ethyl acetate/hexane 4/6) to afford 3.2 g of the title compound as a white solid.$^1$H NMR (DMSO-$d_6$, 400 MHz): δ 7.59-7.57 (m, 1H), 7.18 (m, 2H), 3.84 (s, 3H), 3.24-3.21 (m, 2H), 2.84-2.81 (m, 2H). MS (ESI+): 196.0. HPLC (max plot) 89.4%; Rt 3.36 min.

Intermediates described below are obtained following procedure B

Intermediate B.2: 7-Bromo-2,3-dihydro-4H-thiochromen-4-one

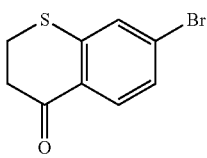 [SMILES: O=C1CCSc2cc(Br)ccc21]

6 g of the title compound as a brown solid. $^1$H NMR (DMSO-$d_6$, 400 MHz): δ 7.84-7.82 (d, J = 8.5 Hz, 1H), 7.65 (s, 1H), 7.41-7.39 (dd, J$_1$ = 1.8, 8.5 Hz, 1H), 3.34-3.31 (m, 2H), 2.90-2.86 (m, 2H).

Intermediate B.3: 7-(Trifluoromethyl)-2,3-dihydro-4H-thiochromen-4-one

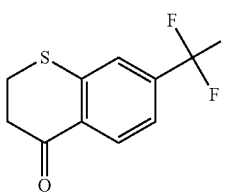

4 g of the title compound as a pale brown solid. $^1$H NMR (DMSO-$d_6$, 400 MHz): δ 8.12-8.10 (d, J = 8.2 Hz, 1H), 7.78 (s, 1H), 7.54-7.52 (dd, J = 1.2, 8.2 Hz, 1H), 3.40-3.39 (t, J = 6.3 Hz, 2H), 2.97-2.95 (t, J = 6.5 Hz, 2H).

Intermediate B.4: 6-Methoxy-2,3-dihydro-4H-thiochromen-4-one

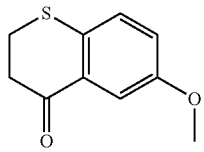

4.5 g (82%) yield of the title compound as a brown liquid. $^1$H NMR (DMSO-$d_6$, 400 MHz): δ 7.45 (d, J = 3.0 Hz, 1H), 7.29-7.26 (d, J = 8.7 Hz, 1H), 7.12-7.09 (dd, J = 3.0, 8.6 Hz, 1H), 3.75 (s, 3H), 3.27-3.24 (m, 2H), 2.88-2.85 (m, 2H).

Intermediate B.5: 8-Chloro-2,3-dihydro-4H-thiochromen-4-one

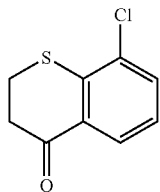 [SMILES: O=C1CCSc2c(Cl)cccc21]

8 g of the title compound as a pale orange solid. 1H NMR (DMSO-d6) δ 7.92-7.96 (m, 1H), 7.67-7.70 (m, 1H), 7.21-7.29 (t, J = 6 Hz, 1H), 3.32-3.37 (m, 2H), 2.87-2.91 (m, 2H). HPLC (max plot) 94.8%; Rt 3.02 min.

Procedure C

Intermediate C.1

2,3-Dihydro-4H-thiopyrano[3,2-c]pyridin-4-one

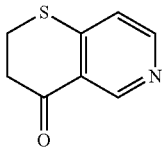 [SMILES: O=C1CCSc2ccncc21]

Following the Procedure C (thiochromanone, 2,3-dihydro-4H-thiopyrano[3,2-c]pyridin-4-one is obtained from 4-[(2-Carboxyethyl)thio]nicotinic acid to afford 1.4 g of the title compound as a brown solid. $^1$H NMR (DMSO-$d_6$, 400 MHz): δ 8.89 (s, 1H), 8.41-8.40 (d, J=5.4 Hz, 1H), 7.41-7.39 (d, J=5.5 Hz, 1H), 3.42-3.39 (m, 2H), 2.93-2.90 (m, 2H).

Procedure D

Intermediate D.1

6-nitro-2,3-dihydro-4H-thiochromen-4-one

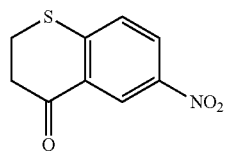 [SMILES: O=C1CCSc2ccc([N+](=O)[O-])cc21]

To 4-nitrothiophenol (5.0 g, 3.22 mmol) in 40 mL DMF was added potassium carbonate (13.4 g, 9.69 mmol, 3 Eq) at 60° C. under nitrogen and stirred for 30 minutes. To this was added bromopropionic acid (5.43 g, 3.54 mmol, 1.1 Eq) and stirring continued for further 90 minutes at 60° C. under nitrogen, At the end, the solvent was removed under vacuo. The residue was extracted with ethyl acetate to remove non-polar impurities. Then the aqueous layer was acidified with concentrated HCl and again extracted with ethyl acetate. The organic layer dried with MgSO$_4$ and concentrated in vacuo to yield yellowish oil (7.3 g). To this yellowish oil (1.0 g, 4.44 mmol) was added polyphosphonic acid (15.0 g). The reaction mixture was stirred at 100° C. for 30 minutes. After 30 minutes the solvent was removed under high vacuum the compound was purified by column chromatography (1:7 ethyl acetate/hexane) to afford the title compound as a white solid. $^1$H NMR (DMSO-$d_6$, 400 MHz) δ 8.94 (d, J=2.6 Hz, 1H), 8.20 (dd, J=8.7 Hz, J=2.6 Hz, 1H), 7.45 (d, J=8.7 Hz, 1H), 3.36-3.33 (m, 2H), 3.07-3.04 (m, 2H). MS (ESI+): 210.0. HPLC (max plot) 99.7%; Rt 5.44 min.

Intermediate D.2 tert-Butyl 1,3-thiazol-2-ylcarbamate

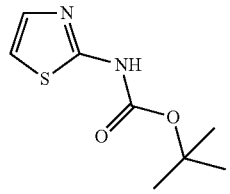

To a suspension of 2-aminothiazole (50 g, 499 mmol, 1 eq.) and 4-dimethylaminopyridine (0.1 g) in acetonitrile (125 mL) is added boc anhydride (130.6 g, 599 mmol, 1.2 eq.) over a period of 30 min at RT. The reaction mixture is then stirred at RT overnight. The reaction mass is then concentrated and partitioned between EtOAc and water by which time solid precipitated and is filtered to get 40 g of the product. The organic layer is washed with brine, separated and dried over sodium sulfate and concentrated to get the product (50 g) which is mixed with the initially obtained product to give 90 g (90%) of the title compound. $^1$H NMR (DMSO-d6, 400 MHz): δ 11.41 (bs, 1H), 7.34-7.33 (d, J=3.56 Hz, 1H), 7.13-7.12 (d, J=3.56 Hz, 1H), 1.46 (s, 9H).

Intermediate D.3 tert-Butyl (5-bromo-1,3-thiazol-2-yl)carbamate

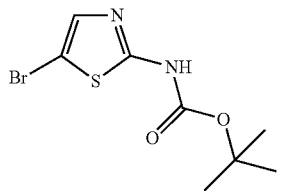

Tert-butyl 1,3-thiazol-2-ylcarbamate (90 g, 449.8 mmol, 1 eq.) is taken in THF (1.4 L) to which is added N-bromosuccinimide (88.06 g, 494.8 mmol, 1.1 eq.) portion wise. The reaction mixture is then stirred at RT overnight. The reaction mass is concentrated to remove THF. The crude is purified by column chromatography to get the titled produce. $^1$H NMR (DMSO-d6, 400 MHz): δ 11.73 (bs, 1H), 7.42 (s, 1H), 1.46 (s, 9H).

Intermediate D.4

Methyl -3-({2-[tert-butoxycarbonyl)amino]-1,3-thiazol-5-yl}thio)propanoate

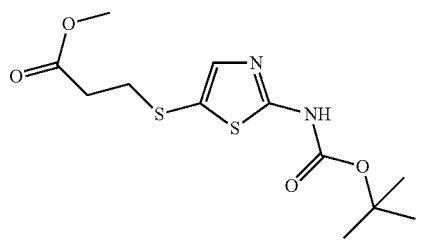 [SMILES: COC(=O)CCSc1cnc(NC(=O)OC(C)(C)C)s1]

tert-Butyl-(5-bromo-1,3-thiazol-2-yl)carbamate (12 g, 43.17 mmol, 1 eq.), 3-mercapto propionic acid methylester (5.7 g, 47.4 mmol, 1.1 eq.), tris(dibenzylidene acetone)di Pd(0) (1 g, 1.07 mmol, 0.025 eq.), 9,9'-dimethyl-4,5-bis(diphenyl phosphino) xanthene (1.24 g, 2.15 mmol, 0.05 eq.) and N,N-diisopropyl ethyl amine (11.15 g, 86.34 mmol, 2 eq.) are taken in degassed 1,4-dioxane (200 mL) in a pressure tube and heated under sealed condition at 125° C. overnight. Reaction mixture is filtered through celite, concentrated under vacuum and purified by flash chromatography to afford 9.5 g (69%) of the product. $^1$H NMR (DMSO-d6, 400 MHz): δ 11.64 (bs, 1H), 7.38 (s, 1H), 3.58 (s, 3H), 2.90-2.87 (t, J=6.8 Hz, 2H), 2.59-2.55 (t, J=6.9 Hz, 2H), 1.46 (s, 9H).

Intermediate D.5

3-({2-[tert-Butoxycarbonyl)amino]-1,3-thizol-5-yl}thio)propanoic acid

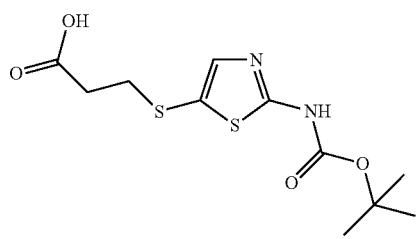 [SMILES: CC(C)(C)OC(=O)Nc1ncc(SCCC(=O)O)s1]

Methyl -3-({2-[tert-butoxycarbonyl)amino]-1,3-thiazol-5-yl}thio)propanoate (9.5 g, 29.8 mmol, 1 eq.) is taken in THF/H$_2$O (3:1) and LiOH (1.87 g, 44.75 mmol, 1.5 eq.) and the reaction mixture is stirred at RT overnight after which it is evaporated under vacuum then diluted with water and acidified with citric acid to pH (5-6) and the formed solid is filtered, washed with water and dried to give 8 g (92%) of the title compound. $^1$H NMR (DMSO-d6, 400 MHz): δ 11.82 (bs, 2H), 7.38 (s, 1H), 2.86-2.83 (t, J=6.8 Hz, 2H), 2.48-2.45 (t, J=7.0 Hz, 2H), 1.46 (s, 9H).

Intermediate D.6

2-Amino-5,6-dihydro-7H-thiopyrano[3,2-d][1,3]thiazol-7-one

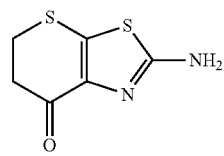 [SMILES: Nc1nc2c(s1)SCCC2=O]

3-({2-[tert-butoxycarbonyl)amino]-1,3-thizol-5-yl}thio)propanoic acid (8 g, 26.31 mmol, 1 eq) is taken in polyphosphoric acid (80 g) and heated at 60° C. for 1h. The reaction mixture is diluted with ice-cold water and neutralized with NaHCO$_3$ and the solid formed is filtered. The solid is dissolved in EtOAc and washed with water, dried over Na$_2$SO$_4$ and concentrated to afford the title compound. $^1$H NMR (DMSO-d6, 400 MHz): δ 7.21 (bs, 2H), 3.39-3.35 (m, 3H), 2.72-2.69 (m, 3H).

Intermediate D.7 tert-Butyl-(7-oxo-6,7-dihydro-5H-thiopyrano[3,2-d][1,3]thiazol-2-yl)carbamate

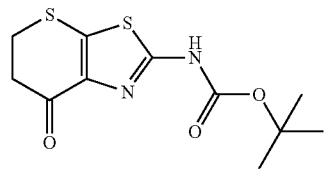 [SMILES: CC(C)(C)OC(=O)Nc1nc2c(s1)SCCC2=O]

To a solution of 2-amino-5,6-dihydro-7H-thiopyrano[3,2-d][1,3]thiazol-7-one (3 g, 16.1 mmol, 1 eq) in DMF (60 mL) is added dimethylamino pyridine (0.075 g). The reaction mixture is cooled with ice and boc anhydride (7.02 g, 32.2 mmol, 2 eq) is added and stirred at RT for 48 hours. The solvent is removed under reduced pressure and the residue taken in EtOAc, washed with water, dried over Na$_2$SO$_4$ and concentrated. The crude is purified by column chromatography to afford the title compound. $^1$H NMR (DMSO-d6, 400 MHz): δ 11.80 (bs, 1H), 3.46-3.42 (m, 2H), 2.81-2.77 (t, J=6.3 Hz, 2H), 1.45 (s, 9H). MS (ESI+): 287.0. HPLC (max plot): 96.63%; Rt 3.95 min.

Procedure E

Intermediate E.1

Ethyl oxo(4-oxo-3,4-dihydro-2H-thiochromen-3-yl)acetate

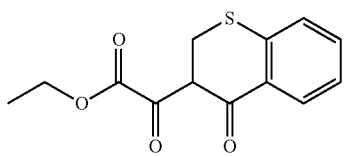 [SMILES: CCOC(=O)C(=O)C1CSc2ccccc2C1=O]

A solution of diethyloxalate (30.9 mL; 228.34 mmol; 1.5 eq.) in toluene (250 mL) is added dropwise at 0° C. to a solution of sodium ethoxide 21% w/w in EtOH (9.87 g; 182.67 mmol; 2 eq.). A solution of thiochroman-4-one (25 g; 152.23 mmol; 1 eq.) in toluene (250 mL) is added dropwise at 0° C. and the reaction mixture is allowed to warm up to rt. After overnight stirring, the solvent is removed and DCM (200 mL) and water (200 ml) are added. The aqueous phase is washed with DCM then acidified to pH=1-2 with 5N HCl (~50 mL). The product is extracted with EtOAc (2×200 mL). The organic phases are combined, dried over MgSO4 and the solvent evaporated to afford 39.4 g (98%) of the title compound as an orange oil. MS (ESI+): 265.9.

Intermediates described below are obtained following Procedure E

Intermediate E.2: Ethyl (8-fluoro-4-oxo-3,4-dihydro-2H-thiochromen-3-yl)(oxo)acetate

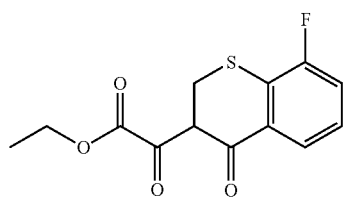 [SMILES: CCOC(=O)C(=O)C1CSc2c(F)cccc2C1=O]

15 g (97%) of the title compound as an orange oil. MS (ESI+): 283.06.

Intermediate E.3: Ethyl (8-methoxy-4-oxo-3,4-dihydro-2H-thiochromen-3-yl)(oxo)acetate

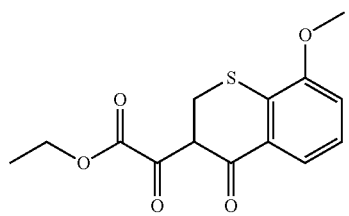 [SMILES: CCOC(=O)C(=O)C1CSc2c(OC)cccc2C1=O]

23.5 g (100%) of the title compound. HPLC (max plot) 51.4%; Rt 4.55 min. MS (ESI+): 295.0

Intermediate E.4: Ethyl (8-chloro-4-oxo-3,4-dihydro-2H-thiochromen-3-yl)(oxo)acetate

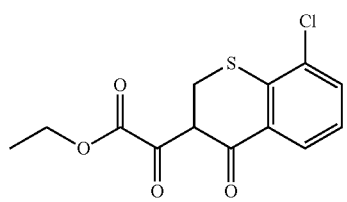 [SMILES: CCOC(=O)C(=O)C1CSc2c(Cl)cccc2C1=O]

12 g (100%) of the title compound. MS (ESI+): 298.95.

Intermediate E.5: Ethyl (8-methyl-4-oxo-3,4-dihydro-2H-thiochromen-3-yl)(oxo)acetate

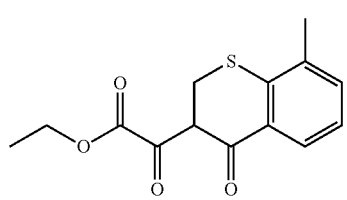 [SMILES: CCOC(=O)C(=O)C1CSc2c(C)cccc2C1=O]

37 g (94%) of the title compound. MS (ESI+): 278.9.

Intermediate E.6: Ethyl (7-methoxy-4-oxo-3,4-dihydro-2H-thiochromen-3-yl)(oxo)acetate

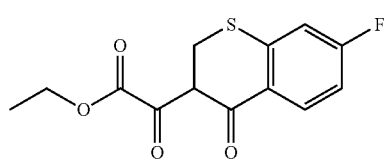 [SMILES: CCOC(=O)C(=O)C1CSc2cc(F)ccc2C1=O]

17.2 g (quant) of the title compound as a slowly crystallising oil. HPLC (max plot) 74.5%; Rt 4.73 min. MS (ESI+): 294.96

Intermediate E.7: Ethyl oxo[4-oxo-7-(trifluoromethoxy)-3,4-dihydro-2H-thiochromen-3-yl]acetate

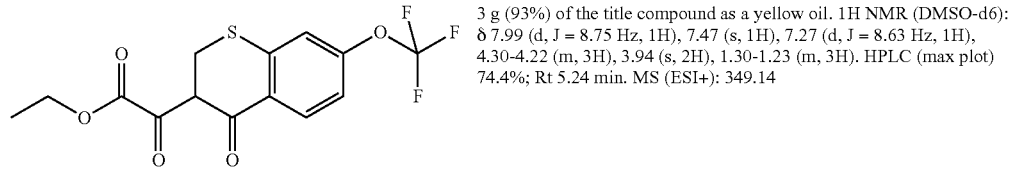

3 g (93%) of the title compound as a yellow oil. 1H NMR (DMSO-d6): δ 7.99 (d, J = 8.75 Hz, 1H), 7.47 (s, 1H), 7.27 (d, J = 8.63 Hz, 1H), 4.30-4.22 (m, 3H), 3.94 (s, 2H), 1.30-1.23 (m, 3H). HPLC (max plot) 74.4%; Rt 5.24 min. MS (ESI+): 349.14

Intermediate E.8: (6-Fluoro-4-oxo-thiochroman-3-yl)-oxo-acetic acid ethyl ester

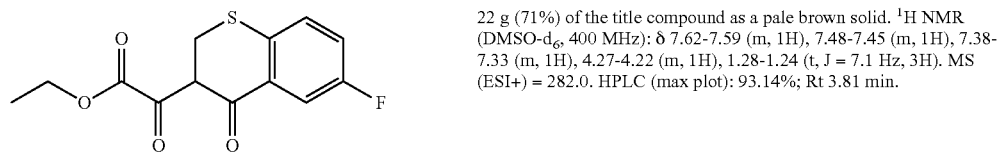

22 g (71%) of the title compound as a pale brown solid. $^1$H NMR (DMSO-$d_6$, 400 MHz): δ 7.62-7.59 (m, 1H), 7.48-7.45 (m, 1H), 7.38-7.33 (m, 1H), 4.27-4.22 (m, 1H), 1.28-1.24 (t, J = 7.1 Hz, 3H). MS (ESI+) = 282.0. HPLC (max plot): 93.14%; Rt 3.81 min.

Intermediate E.9: Ethyl (6-methoxy-4-oxo-3,4-dihydro-2H-thiochromen-3-yl)(oxo)acetate

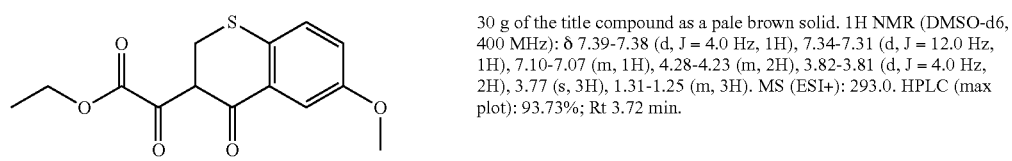

30 g of the title compound as a pale brown solid. 1H NMR (DMSO-d6, 400 MHz): δ 7.39-7.38 (d, J = 4.0 Hz, 1H), 7.34-7.31 (d, J = 12.0 Hz, 1H), 7.10-7.07 (m, 1H), 4.28-4.23 (m, 2H), 3.82-3.81 (d, J = 4.0 Hz, 2H), 3.77 (s, 3H), 1.31-1.25 (m, 3H). MS (ESI+): 293.0. HPLC (max plot): 93.73%; Rt 3.72 min.

Intermediate E.10: Ethyl-4-oxo-3,4-dihydro-2H-thiopyrano[2,3-b]pyridine-3-carboxylate

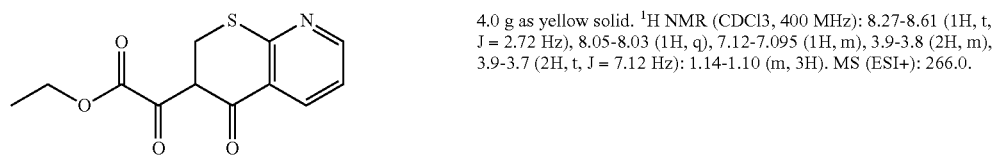

4.0 g as yellow solid. $^1$H NMR (CDCl3, 400 MHz): 8.27-8.61 (1H, t, J = 2.72 Hz), 8.05-8.03 (1H, q), 7.12-7.095 (1H, m), 3.9-3.8 (2H, m), 3.9-3.7 (2H, t, J = 7.12 Hz): 1.14-1.10 (m, 3H). MS (ESI+): 266.0.

Intermediate E.11: Ethyl oxo(4-oxo-5,6-dihydro-4H-thieno[2,3-b]thiopyran-5-yl)acetate

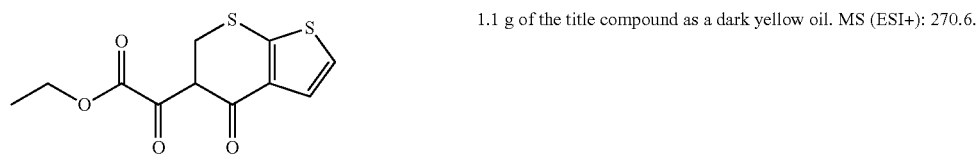

1.1 g of the title compound as a dark yellow oil. MS (ESI+): 270.6.

Procedure F

Intermediate F.1 tert-Butyl (3E)-3-[(tert-butoxycarbonyl)hydrazono]piperidine-1-carboxlate

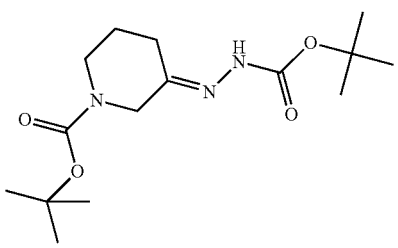 [SMILES: CC(C)(C)OC(=O)N/N=C1\CCCN(C(=O)OC(C)(C)C)C1]

1-Boc-3-piperidone (25 g; 125.47 mmol; 1.00 eq.) is dissolved in toluene (250 mL) to which tert-butyl-carbazate (16.58 g; 125.47 mmol; 1.00 eq.) is added and reaction mixture is heated to 60° C. for 4 hours. After this time reaction mixture is evaporated to dryness, taken up in ethyl acetate (100 mL) and heptane (100 mL), and the suspension is heated, then cooled down to rt and the suspension is filtered and dried to give 15 g (95%) of the title compound as a beige solid. MS (ESI−): 311.9.

Intermediates described below are obtained following procedure F

Intermediate F.2: tert-Butyl 3-[(tert-butoxycarbonyl)hydrazono]azetidine-1-carboxylate

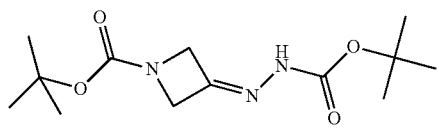 [SMILES: CC(C)(C)OC(=O)NN=C1CN(C(=O)OC(C)(C)C)C1]

25 g (84%) of the title compound as a white solid. $^1$H NMR (DMSO-d6 400 MHz): δ 10.19 (bs, 1H), 4.49-4.48 (m, 4H), 1.42 (s, 9H), 1.38 (s, 9H).

Intermediate F.3: tert-Butyl (3E)-3-[(tert-butoxycarbonyl)hydrazono]pyrrolidine-1-carboxylate

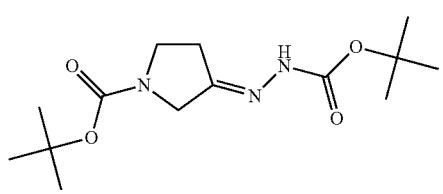 [SMILES: CC(C)(C)OC(=O)N/N=C1\CCN(C(=O)OC(C)(C)C)C1]

1.12 g (92%) of the title compound. $^1$H NMR (DMSO-$d_6$, 400 MHz): 9.66 (bs, 1H), 3.85 (m, 2H), 3.48-3.45 (m, 2H), 2.58 (m, 2H), 1.42 (s, 9H), 1.39 (s, 9H).

Intermediate F.4: tert-Butyl (4Z)-[(tert-butoxycarbonyl)hydrazono[azepane-1-carboxylate

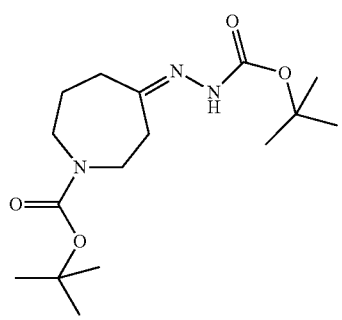 [SMILES: CC(C)(C)OC(=O)N/N=C1/CCCN(C(=O)OC(C)(C)C)CC1]

1 g of the title compound. $^1$H NMR (DMSO-$d_6$, 400 MHz): δ 9.66 (bs, 1H), 3.85 (m, 2H), 3.48-3.45 (m, 2H), 2.58 (m, 2H), 1.42 (s, 9H), 1.39 (s, 9H).

Procedure G

Intermediate G.1 tert-Butyl 4-[2-(tert-butoxycarbonyl)hydrazino]piperidine-1-carboxylate

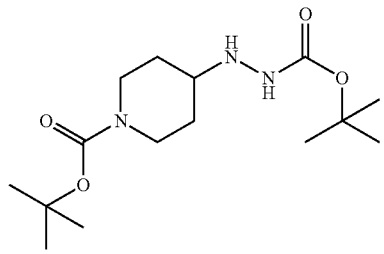 [SMILES: CC(C)(C)OC(=O)NNC1CCN(C(=O)OC(C)(C)C)CC1]

To tert-butyl 4-[(tert-butoxycarbonyl)hydrazono]piperidine-1-carboxylate (15.7 g; 50.1 mmol; 1 eq.) in water (78.5 mL) and glacial acetic acid (78.5 mL) is added sodium cyanoborohydride (3.15 g; 50.1 mmol; 1 eq.) and the reaction mixture is stirred at rt overnight. The solvents are removed to near dryness and the product is extracted with AcOEt. The combined organic phase is washed with NaOH (1 M), dried over MgSO$_4$, filtered and concentrated to afford: 14.1 g (89%) of the title compound. $^1$H NMR (300 MHz, DMSO): δ 8.22 (s, 1H), 4.61-4.14 (m, 1H), 3.81-3.55 (m, 2H), 3.08-2.67 (m, 2H), 1.73-1.50 (m, 2H), 1.38 (s, 18H), 1.22-0.98 (m, 2H).

Intermediates described below are obtained following procedure G

Intermediate G.2: tert-Butyl 3-[2-(tert-butoxycarbonyl)hydrazino]azetidine-1-carboxylate

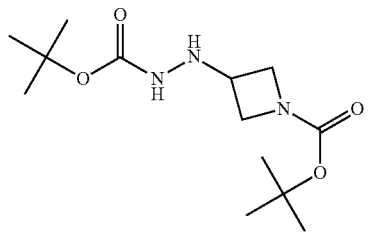 [SMILES: CC(C)(C)OC(=O)NNC1CN(C(=O)OC(C)(C)C)C1]

18 g (90%) of the title compound as a colorless liquid. $^1$H NMR (DMSO-d6, 400 MHz): δ 8.35 (bs, 1H), 4.94-4.92 (m, 1H), 3.79-3.69 (m, 2H), 3.67-3.64 (m, 1H), 3.63-3.58 (m, 2H), 1.37 (s, 9H), 1.35 (s, 9H). HPLC (max plot): 99.88%; Rt 3.93 min.

Intermediate G.3: tert-Butyl 3-[2-(tert-butoxycarbonyl)hydrazino]pyrrolidine-1-carboxylate

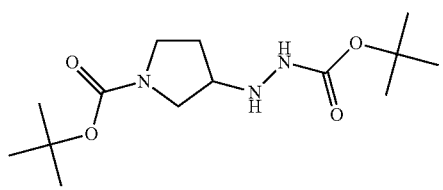 [SMILES: CC(C)(C)OC(=O)NNC1CCN(C(=O)OC(C)(C)C)C1]

14 mg of the title compound as a brown solid. $^1$H NMR (CDCl$_3$, 400 MHz): δ 8.17-8.15 (m, 1H), 7.80-7.78 (m, 1H), 7.65-7.61 (m, 2 H), 5.07 (m, 1H), 4.65 (s, 2H), 4.14 (bs, 2H), 3.75 (m, 6H), 3.48-3.46 (m, 2H), 3.34 (s, 3H), 3.03-2.82 (m, 6H), 2.42 (m, 2H), 2.30 (m, 2H), 2.02 (m, 2H), 1.92 (m, 2H). MS (ESI+): 503.3. HPLC (max plot) 99.02%; Rt 2.57 min.

Intermediate G.4: tert-Butyl 3-[2-(tert-butoxycarbonyl)hydrazino]piperidine-1-carboxylate

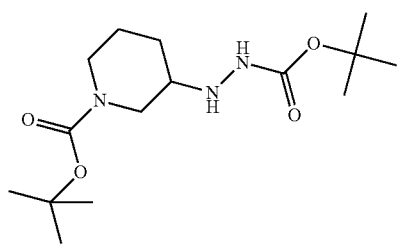 [SMILES: CC(C)(C)OC(=O)NNC1CCCN(C(=O)OC(C)(C)C)C1]

15 g (99%) of the title compound as a yellow oil. 1H NMR (DMSO-d6, 400 MHz): δ 8.17 (bs, 1H), 4.38 (bs, 1H), 3.88-3.85 (m, 1H), 3.70-3.67 (m, 2H), 2.66-2.5 (m, 2H), 2.50-2.48 (m, 1H), 1.74-1.71 (d, J = 12.3 Hz, 1H), 1.62-1.59 (m, 1H), 1.37 (s, 9H), 1.36 (s, 9H). MS (ESI+): 216.2. HPLC (max plot): 90.75%; Rt 5.33 min.

Intermediate G.5: tert-Butyl 4-[2-(tert-butoxycarbonyl)hydrazino]azepane-1-carboxylate

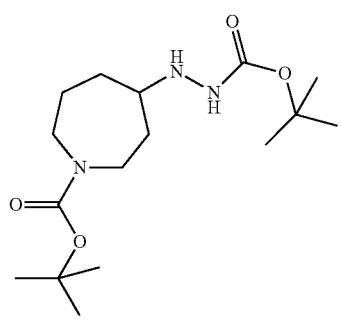 [SMILES: CC(C)(C)OC(=O)NNC1CCCN(C(=O)OC(C)(C)C)CC1]

1g (99%) of the title compound. $^1$H NMR (DMSO-d$_6$, 400 MHz): δ 8.32 (bs, 1H), 4.53 (m, 1H), 3.52 (m, 1H), 3.32-3.20 (m, 2H), 3.15-3.13 (m, 2H), 1.74-1.69 (m, 2H), 1.37 (s, 18H).

Intermediate G.6

2-(4-Iodophenyl)-2-methylpropanal

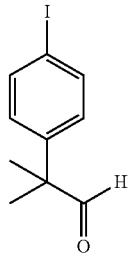

To a solution of 2-(4-Iodophenyl)-2-methylpropanenitrile (19 g, 0.066 mol) in toluene (150 mL) is added Diisobutyl aluminum hydride (1.0 M in THF, 200 mL, 0.199 mol) in a dropwise fashion at −78° C. The reaction mixture is stirred at same temperature for 30 min and then at Rt for 12 h. After completion of the reaction, the reaction mixture is quenched with saturated sodium sulphate (100 mL) and extracted with EtOAc (200 mL). The organic layer is washed with water (100 mL), brine (50 mL), dried over sodium sulphate and concentrated under reduced pressure to afford the title compound as pale brown liquid. $^1$H NMR (DMSO-$d_6$, 400 MHz): δ 9.48 (s, 1H), 7.74-7.72 (t, J=4 Hz, 2H), 7.11-7.09 (t, J=1.4 Hz, 2H), 1.35 (s, 6H). MS (ESI+): 276.0.

Intermediate G.7

2-(4-Iodophenyl)propan-2-ol

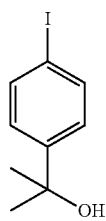

To a solution of methyl magnesium bromide (59 mL, 3 M in THF, 17 mmol) in THF (100 mL) is added methyl-4-iodobenzoate (20 g, 76.2 mmol) in THF (100 mL) in drops at −78° C. The reaction mixture was stirred at the same temperature for 30 min and then added a second portion of methyl magnesium bromide (59 mL, 3 M in THF, 17 mmol) in drops at −78° C. The resulting mixture is stirred for another 2 h and quenched with saturated ammonium chloride solution (100 mL) and extracted with EtOAc (200 mL). The combined organic layer is washed with water (100 mL), brine (50 mL), dried over sodium sulphate and concentrated under reduced pressure to afford 18 g (90%) the title compound as pale yellow liquid. $^1$H NMR (DMSO-$d_6$, 400 MHz): δ 7.63-7.617 (dd, J=2.0, 6.8 Hz, 2H), 7.27-7.24 (d, J=6.8 Hz, 2H), 5.071 (s, 1H), 1.37 (s, 6H).

Intermediate G.8

1-(1-Chloro-1-methylethyl)-4-iodobenzene

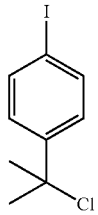

To a stirred solution of 2-(4-Iodophenyl)propan-2-ol (15 g, 0.057 mol) in dry DCM (150 mL) is added thionyl chloride (8.4 mL, 7 mmol) in drops at 0° C. under nitrogen atmosphere. The mixture is heated to 40° C. for 12 h. After the completion the reaction, the reaction mixture is diluted with DCM (100 mL), washed with 10% sodium bicarbonate, brine, dried over sodium sulphate and concentrated under vacuum. The crude product is further purified by column chromatography (10% EtOAc in pet ether) to afford 15 g (95%) of title compound as light brown solid. $^1$H NMR (DMSO-$d_6$, 400 MHz) δ 7.73-7.71 (d, J=8.8 Hz, 2H), 7.41-7.38 (d, J=8.8 Hz, 2H), 1.92 (s, 6H).

Intermediate G.9

4-[2-(4-Iodophenyl)-2-methylpropy]morpholine

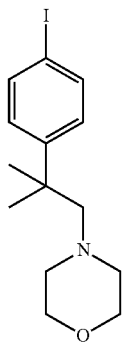 [SMILES: CC(C)(CN1CCOCC1)c1ccc(I)cc1]

To a solution of 2-(4-Iodophenyl)-2-methylpropanal (7 g, 0.025 mol) in 1,2-Dichloro ethane (100 mL) is added morpholine (4.4 mL, 0.051 mol) in drops at 0° C. After 10 min, NaBH$_3$CN (2 g, 30 mmol) is added in a portion wise fashion at 0° C. followed by acetic acid (500 μL). The reaction mixture is stirred for another 1 h at same temperature and then at Rt for 10 h. After this time, the reaction mixture is quenched with 10% sodium bicarbonate (50 mL) and extracted with EtOAc. The combined organic layer is washed with water, brine, dried over sodium sulphate and evaporated. The crude product is purified by column chromatography (pet ether and EtOAc) to afford the title compound as a pale yellow liquid. $^1$H NMR (DMSO-$d_6$, 400 MHz): δ 7.61-7.59 (q, J=1.8, 6.6 Hz, 2H), 7.19-7.17 (q, J=1.9, 6.6 Hz, 2H), 3.42-3.40 (m, 4H), 2.38-2.36 (d, 2H), 2.17-2.15 (m, 4H), 1.21 (s, 6H). MS (ESI+): 346.0.

Intermediate G.10

4-[1-(4-Iodophenyl)-1-methylethyl]morpholine

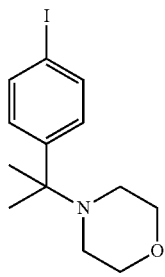 [SMILES: CC(C)(c1ccc(I)cc1)N1CCOCC1]

To a solution of 1-(1-Chloro-1-methylethyl)-4-iodobenzene (2 g, 7 mmol) in morpholine (10 mL) is added KI (0.5 g). The mixture is irradiated under microwave irradiation for 20 min at 160° C. (×10). The combined reaction mixtures are dissolved in EtOAc, washed with water, brine and dried over sodium sulphate. The solvent is concentrated under vacuum and purified by column chromatography (50% EtOAc in pet ether) to afford title compound as a light brown liquid. $^1$H NMR (DMSO-$d_6$, 400 MHz): δ 7.65-7.63 (dd, J=2, 6.8 Hz, 2H), 7.30-7.28 (dd, J=2, 6.8 Hz, 2H), 3.53-3.65 (t, 4H), 2.33-2.31 (t, 4H), 1.22 (s, 6H).

Intermediate G.11 tert-Butyl 1-[4-(1-methyl-1-morpholin-4-ylethyl)phenyl]hydrazinecarboxylate

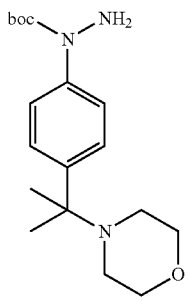

A solution of 4-[1-(4-Iodophenyl)-1-methylethyl]morpholine (3.4 g, 10 mmol) in DMSO (35 mL) is added cesium carbonate (5.1 g, 15 mmol) and tert-butyl carbazate (1.5 g, 11 mmol) at RT under argon. The reaction mixture is stirred for 10 min at RT after which copper (I) iodide (0.1 g, 0.5 mol) is added. The reaction mixture is stirred at 50° C. for 6 h under nitrogen. After this time, reaction mixture is cooled to RT, diluted with water and extracted with MTBE. The combined organic layer is concentrated under vacuum and purified by acid-base work up using 10% citric acid, sodium bicarbonate and MTBE to afford the title compound as pale a brown liquid. $^1$H NMR (DMSO-$d_6$, 400 MHz): δ 737 (s, 4H), 5.00 (bs, 2H), 3.54-3.521 (m, 4H), 2.35-2.33 (m, 4H), 1.43 (s, 9H), 1.26 (s, 6H). MS (ESI+): 249.0. HPLC (max plot): 96.0%; Rt 2.57 min.

Intermediate G.12 tert-Butyl 1-[4-(1,1-dimethyl-2-morpholin-4-ylethyl)phenyl]hydrazinecarboxylate

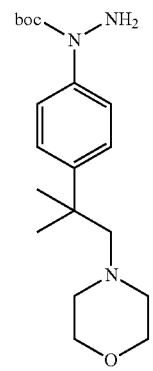

To a solution of 4-[2-(4-Iodophenyl)-2-methylpropyl]morpholine (3.2 g, 0.092 mol) in DMSO (30 mL) is added cesium carbonate (4.6 g, 0.013 mol) and tert-Butyl carbazate (1.35 g, 0.010 mol) at RT under argon. The reaction mixture is stirred for 10 min at RT after which is added copper (I) iodide (0.09 g, 0.4 mmol). The reaction mixture is stirred at 50° C. for 2 h under nitrogen then cooled to RT, diluted with water and extracted with EtOAc. The combined organic layer is washed with water, brine, dried over sodium sulphate and purified by column chromatography (Neutral alumina, pet ether and EtOAc) to afford the titled compound as pale brown liquid. $^1$H NMR (DMSO-$d_6$, 400 MHz): δ 7.34-7.32 (d, J=8 Hz, 2H), 7.28-7.25 (t, J=4 Hz, 2H), 4.98 (bs, 2H), 3.42-3.40 (m, 4H), 2.36 (s, 2H), 2.17-2.15 (m, 4H), 1.41 (s, 9H), 1.24 (s, 6H). MS (ESI+): 350.0. HPLC (max plot): 91%, Rt 6.38 min

Intermediate G.13

[2-(4-Iodophenyl)-2-methylpropyl]dimethylamine

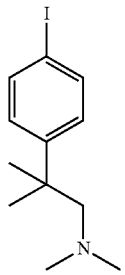

To a solution of 2-(4-Iodophenyl)-2-methylpropanal (7 g, 0.025 mol) in 1,2-Dichloro ethane (100 mL) is added dimethylamine (2 M in THF, 46 mL, 92 mmol) in drops at 0° C. After 10 min, NaBH$_3$CN (1.8 g, 27 mmol) is added in a portion wise fashion at 0° C. followed by acetic acid (500 μL). The reaction mixture is stirred for another 1 h at same temperature and then at Rt for 10 h. After this time, the reaction mixture is quenched with 10% sodium bicarbonate and extracted with EtOAc. The combined organic layer is washed with water, brine, dried over sodium sulphate and evaporated. The crude product is purified by column chromatography (pet ether and EtOAc) to afford the title compound as brown liquid. $^1$H NMR (DMSO-$d_6$, 400 MHz) δ 7.62-7.60 (q, J$_1$=4 Hz, J$_2$=8 Hz, 2H), 7.17-7.15 (d, J=8 Hz, 2H), 2.35 (s, 2H), 1.96 (s, 6H), 1.20 (s, 6H).

Intermediate G.14 tert-Butyl 1-{4-[2-(dimethylamino)-1,1-dimethyl-ethyl]phenyl}hydrazinecarboxylate

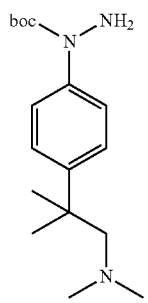

To a solution of [2-(4-Iodophenyl)-2-methylpropyl]dimethylamine (5 g, 0.01 mol) in DMSO (50 mL) is added cesium carbonate (3.6 g, 0.01 mol) and tert-butyl carbazate (2.4 g, 0.018 mol) at RT under argon. The reaction mixture is stirred for 10 min at RT after which is added copper (I) iodide (0.16 g, 0.8 mmol). The reaction mixture is stirred at 50° C. for 2 h under nitrogen then cooled to RT, diluted with water and extracted with EtOAc. The combined organic layer is washed with water, brine, dried over sodium sulphate and purified by column chromatography (Neutral alumina, pet ether and EtOAc) to afford the title compound as pale brown liquid. $^1$H NMR (DMSO-$d_6$, 400 MHz): δ 7.34-7.32 (d, J=8 Hz, 2H), 7.25-7.23 (d, J=8 Hz, 2H), 4.99 (bs, 2H), 2.37 (s, 2H), 1.97 (s, 6H), 1.41 (s, 9H), 1.23 (s, 6H). MS (ESI+): 350.0. HPLC (max plot): 89%; 2.66 min.

Intermediate G.15

1-(4-iodophenyl)cyclopropanecarbaldehyde

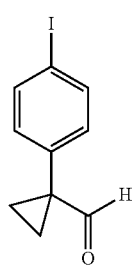 [SMILES: O=CC1(c2ccc(I)cc2)CC1]

To a solution of 2-(4-Iodophenyl)-2-methylpropanenitrile (9 g, 0.033 mol) in toluene (250 mL) is added diisobutyl aluminum hydride (1.0 M in THF, 66 mL, 66 mmol) in a dropwise fashion at −78° C. The reaction mixture is stirred at same temperature for 2 h after which it is quenched with saturated sodium sulphate (100 mL) and extracted with EtOAc (200 mL). The organic layer is washed with water (100 mL), brine (50 mL), dried over sodium sulphate and concentrated under reduced pressure to afford. Purification by column chromatography (7% EtOAc in pet ether) gives the title compound as pale yellow solid. $^1$H NMR (DMSO-$d_6$, 400 MHz): δ 8.85 (s,1H) 7.69-7.67 (m, 2), 7.09-7.07 (m, 2H), 1.57-1.54 (m, 2H), 1.40-1.37 (m, 2H).

Intermediate G.16

4-{[1-(4-Iodophenyl)cyclopropyl]methyl}morpholine

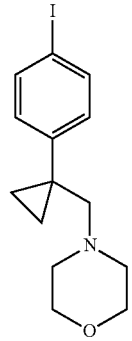 [SMILES: Ic1ccc(C2(CN3CCOCC3)CC2)cc1]

To a solution of 1-(4-iodophenyl)cyclopropanecarbaldehyde (7 g, 0.025 mol) in 1,2-Dichloroethane (100 mL) is added morpholine (4.5 mL, 0.051 mol) in drops at 0° C. After 10 min, NaBH$_3$CN (3.2 g, 30 mmol) is added in a portion wise fashion at 0° C. followed by acetic acid (500 μL). The reaction mixture is stirred for another 1 h at same temperature and then at Rt for 10 h. After this time, the reaction mixture is quenched with 10% sodium bicarbonate and extracted with EtOAc. The combined organic layer is washed with water, brine, dried over sodium sulphate and evaporated. The crude product is purified by column chromatography (pet ether and EtOAc) to afford the title compound as colourless liquid. $^1$H NMR (DMSO-$d_6$, 400 MHz) δ 7.60-7.56 (m, 2H), 7.13-7.08 (m, 2H), 3.47-3.43 (m, 4H), 2.50-2.46 (m, 2H), 2.34 (bs, 4H) 0.0.80-0.77 (m, 2H),0.72-00.69 (m, 2H).

Intermediate G.17 tert-Butyl 1-{4-[1-(morpholin-4-ylmethyl)cyclopropyl]phenyl}hydrazinecarboxylate

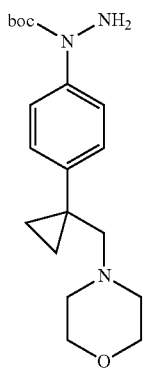

To a solution of 4-{[1-(4-Iodophenyl)cyclopropyl]methyl}morpholine (4 g, 11 mmol) in DMSO (40 mL) is added cesium carbonate (5.3 g, 16 mmol) and tert-Butyl carbazate (1.59 g, 0.012 mol) at RT under argon. The reaction mixture is stirred for 10 min at RT after which is added copper (I) iodide (0.1 g, 0.5 mmol). The reaction mixture is stirred at 50° C. for 2 h under nitrogen then cooled to RT, diluted with water and extracted with EtOAc. The combined organic layer is washed with water, brine, dried over sodium sulphate and purified by column chromatography (Neutral alumina, 30% pet ether and EtOAc) to afford the title compound as a colourless liquid. $^1$H NMR (DMSO-$d_6$, 400 MHz): δ 7.30-7.28 (d, J=8.7 Hz, 2H), 7.21-7.18 (d, J=8.7 Hz, 2H), 5.00 (bs, 2H), 3.47-3.44 (m, 4H), 2.46 (s, 2H), 2.36 (m, 4H), 1.42 (s, 9H), 0.76-0.75 (t, J=5.2 Hz, 2H), 0.68-0.67 (t, J=5.2 Hz, 2H). MS (ESI+): 348.0. HPLC (max plot): 90.3%; Rt 5.72 min.

Procedure H

Intermediate H.1 ethyl 6-methoxy-1-phenyl-1,4-dihydrothiochromeno [4,3-c]pyrazole-3-carboxlate

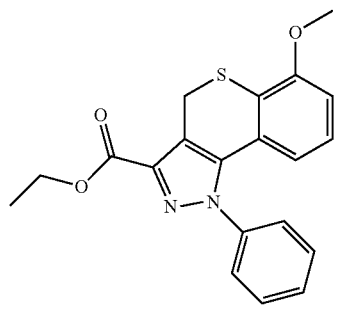 [SMILES: CCOC(=O)c1nn(-c2ccccc2)c2c1CSc1c(OC)cccc1-2]

To a solution of diisopropylamine (0.67 g, 0.9 mL, 6.7 mmol, 1.3 Eq) in THF (8 mL) at −78° C. under nitrogen is added a solution of n-butyl lithium (3.8 mL, 1.6M in hexane) and the reaction mixture is stirred at −20° C. for 30 minutes. The reaction mixture is again cooled to −78° C. and a solution of 8-methoxy-2,3-dihydro-4H-thiochromen-4-one (1.0 g, 5.1 mmol) in THF (15 mL) is added slowly over 40 minutes followed by the addition of a solution of diethyl oxalate (1.05 g, 7.21 mmol, 1.4 Eq) in THF (10 mL). The resulting mixture is stirred at −78° C. for 2 h then allowed to reach 0° C. The solvent is removed under reduced pressure at 25° C. The yellow solid (1.3 g, 4.4 mmol) obtained is dissolved in a 1:1 mixture of acetic acid/methanol (40 mL) and phenyl hydrazine (0.7 mL, 6.6 mmol, 1.5 Eq) is added. The resulting mixture is stirred under nitrogen at 90° C. for 5 h. The solvent is removed under reduced pressure. An aq. solution of NaHCO$_3$ 10% is added to the residue and after 15 minutes stirring, the solid obtained is filtered off then recrystallized from diethyl ether to afford 1.2 g (74%) of the title compound as a pale yellow solid. $^1$H NMR (DMSO-$d_6$, 400 MHz): δ 7.58-7.53 (m, 3H), 7.43-7.41 (m, 2H), 6.93 (t, J=4.6 Hz, 2H), 6.30 (t, J=9.00 Hz, 1H), 4.32 (q, J=7.0 Hz, 2H), 4.15 (s, 2H), 3.85 (s, 3H), 1.31 (t, J=7.12 Hz, 3H). MS (ESI+): 367.0. HPLC (max plot) 96.7%; Rt 5.29 min.

Intermediate H.2 ethyl 6-methoxy-1-methyl-1,4-dihydrothiochromeno [4,3-c]pyrazole-3-carbox late

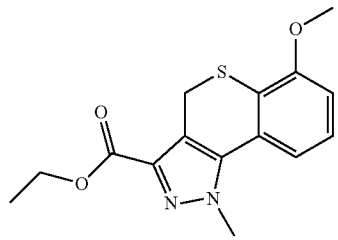 [SMILES: CCOC(=O)c1nn(C)c2c1CSc1c(OC)cccc1-2]

Following the protocol outlined in Procedure H, ethyl 6-methoxy-1-methyl-1,4-dihydrothiochromeno[4,3-c]pyrazole-3-carboxylate is obtained from 8-methoxy-2,3-dihydro-4H-thiochromen-4-one, diethyl oxalate and methyl hydrazine to afford the title compound. $^1$H NMR (DMSO-d6, 400 MHz): δ 7.48-7.46 (m, 1H), 7.30 (t, J=8.1 Hz, 1H), 7.06 (d, J=7.6 Hz, 1H), 4.28 (q, J=7.12 Hz, 2H), 4.12 (s, 3H), 4.06 (s, 2H), 3.85 (s, 3H), 1.30 (t, J=7.12 Hz, 3H). MS (ESI+): 305.0. HPLC (max plot) 97.0%; Rt 4.28 min.

Intermediate H.3 ethyl 7-methoxy-1-methyl-1,4-dihydrothiochromeno [4,3-c]pyrazole-3-carboxlate

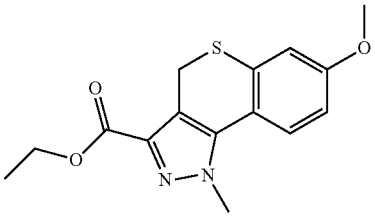 [SMILES: CCOC(=O)c1nn(C)c2c1CSc1cc(OC)ccc1-2]

Following the protocol outlined in Procedure H, ethyl 7-methoxy-1-methyl-1,4-dihydrothiochromeno [4,3-c]pyrazole-3-carboxylate is obtained from 7-methoxy-2,3-dihydro-4H-thiochromen-4-one, diethyl oxalate and methyl hydrazine to afford the title compound. $^1$H NMR (DMSO-$d_6$, 400 MHz,) δ =7.78 (d, J=8.7 Hz, 1H), 7.09 (d, J=2.6 Hz, 1H), 6.90 (dd, J=8.6 Hz, J=2.5 Hz, 1H), 4.28 (q, J=7.1 Hz, 2H), 4.12 (s, 2H), 4.11 (s, 3H), 3.79 (s, 3H), 1.29 (t, J=7.0 Hz, 3H). MS (ESI+): 305.0. HPLC (max plot) 99.4%; Rt 4.51 min.

Intermediate H.4 ethyl 1-phenyl-1,4-dihydrothiochromeno[4,3-c]pyrazole-3-carboxlate

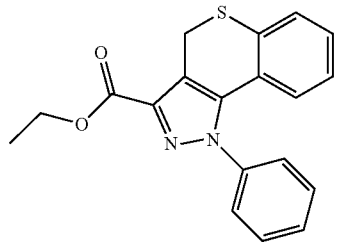 [SMILES: CCOC(=O)c1nn(-c2ccccc2)c2c1CSc1ccccc1-2]

Following the protocol outlined in Procedure AA, ethyl 1-phenyl-1,4-dihydrothiochromeno[4,3-c]pyrazole-3-carboxylate is obtained from 2,3-dihydro-4H-thiochroman-4-one, diethyl oxalate and phenyl hydrazine to afford the title compound. $^1$H NMR (DMSO-$d_6$, 400 MHz): δ 7.59-7.57 (m, 3H), 7.49-7.45 (m, 3H), 7.20 (t, J=7.6 Hz, 1H), 6.96 (d, J=6.36 Hz, 1H), 6.66 (d, J=7.92 Hz, 1H), 4.33 (q, J=7.04 Hz, 2H) 4.24 (s, 2H), 1.31 (d, J=7.08 Hz, 3H). MS (ESI+): 337.0. HPLC (max plot) 98.7%; Rt 6.64 min.

Intermediate H.5 ethyl 1-methyl-1,4-dihydrothiochromeno[4,3-c]pyrazole-3-carboxlate

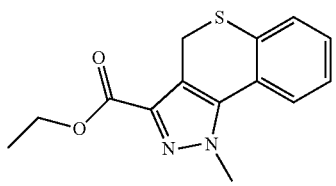 [SMILES: CCOC(=O)c1nn(C)c2c1CSc1ccccc1-2]

Following the protocol outlined in Procedure AA, ethyl 1-methyl-1,4-dihydrothiochromeno[4,3-c]pyrazole-3-carboxylate is obtained from 2,3-dihydro-4H-thiochroman-4-one, diethyl oxalate and methyl hydrazine to afford the title compound. $^1$H NMR (DMSO-$d_6$, 400 MHz): δ 7.85 (dd, J=7.1 Hz, J=1.6 Hz, 1H), 7.52 (dd, J=7.2 Hz, J=1.3 Hz, 1H), 7.37-7.29 (m, 2H), 4.30 (q, J=7.1 Hz, 2H), 4.15 (d, J=4.8 Hz, 2H), 1.31 (t, J=7.1 Hz, 3H). MS (ESI+): 275.0. HPLC (max plot) 98.9%; Rt 4.50 min.

Intermediate H.6 ethyl 1,4-dihydrothiochromeno[4,3-c]pyrazole-3-carboxylate

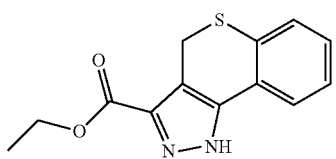 [SMILES: CCOC(=O)c1n[nH]c2c1CSc1ccccc1-2]

Following the protocol outlined in Procedure AA, ethyl 1,4-dihydrothiochromeno[4,3-c]pyrazole-3-carboxylate is obtained from 2,3-dihydro-4H-thiochroman-4-one, diethyl oxalate and methyl hydrazine to afford 0.87 g (80%) of the title compound as a white solid. $^1$H NMR (DMSO-$d_6$, 400 MHz): δ 14.0 (s, 1H), 7.83-7.72 (m, 1H), 7.36-7.33 (m, 1H), 7.23 (brs, 2H), 4.35-4.21 (m, 4H), 1.34-1.29 (m, 3H). MS (ESI+): 261.0. HPLC (max plot) 98.2%; Rt 4.34 min.

Intermediate H.7 ethyl 7-methoxy-1-phenyl-1,4-dihydrothiochromeno[4,3-c]pyrazole-3-carboxlate

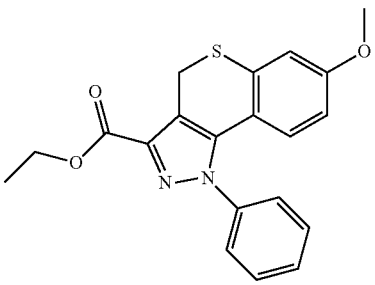 [SMILES: CCOC(=O)c1nn(-c2ccccc2)c2c1CSc1cc(OC)ccc1-2]

Following the protocol outlined in Procedure AA, ethyl 7-methoxy-1-methyl-1,4-dihydrothiochromeno[4,3-c]pyrazole-3-carboxylate is obtained from 7-methoxy-2,3-dihydro-4H-thiochromen-4-one, diethyl oxalate and phenyl hydrazine to afford 1.32 g (81%) of the title compound. $^1$H NMR (400 MHz, DMSO-$d_6$) δ 7.59-7.56 (m, 3H), 7.46-7.43 (m, 2H), 7.05 (s, 1H), 6.58 (m, 2H), 4.31 (q, J=8.8 Hz, 2H), 4.21 (s, 2H), 3.71 (s, 3H), 1.31 (t, J=7.0 Hz, 3H). MS (ESI+): 367.0. HPLC (max plot) 98.9%; Rt 5.46 min.

Intermediate H.8 ethyl 1-(3-methylphenyl)-1,4-dihydrothiochromeno[4,3-c]pyrazole-3-carboxylate

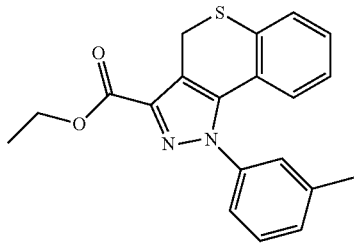 [SMILES: CCOC(=O)c1nn(-c2cccc(C)c2)c2c1CSc1ccccc1-2]

Following the protocol outlined in Procedure AA, ethyl 1-(3-methylphenyl)-1,4-dihydrothiochromeno[4,3-c]pyrazole-3-carboxylate is obtained from 2,3-dihydro-4H-thiochroman-4-one, diethyl oxalate and 3-methyl phenyl hydrazine to afford the title compound. $^1$H NMR (DMSO-$d_6$, 400 MHz) δ 7.49-7.39 (m, 3H), 7.31 (s, 1H), 7.21-7.18 (m, 2H), 7.01-6.97 (m, 1H), 6.70 (dd, J=7.9 Hz, J=1.0 Hz, 1H), 4.32 (q, J=7.1 Hz, 2H), 4.23 (s, 2H), 2.37 (m, 3H), 1.31 (t, J=7.1 Hz, 3H). MS (ESI+): 351.0. HPLC (max plot) 99.2%; Rt 5.84 min.

Intermediate H.9 ethyl 1-(4-methylphenyl)-1,4-dihydrothiochromeno[4,3-c]pyrazole-3-carboxlate

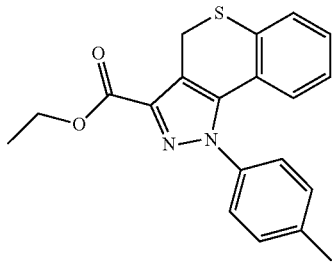 [SMILES: CCOC(=O)c1nn(-c2ccc(C)cc2)c2c1CSc1ccccc1-2]

Following the protocol outlined in Procedure AA, ethyl 1-(4-methylphenyl)-1,4-dihydrothiochromeno[4,3-c]pyrazole-3-carboxylate is obtained from 2,3-dihydro-4H-thiochroman-4-one, diethyl oxalate and 4-methyl phenyl hydrazine to afford the title compound. $^1$H NMR (DMSO-d$_6$, 400 MHz) δ 7.47 (d, J=7.8 Hz, 1H), 7.38-7.31 (m, 4H), 7.19 (t, J=7.6 Hz, 1H), 6.99 (t, J=7.8 Hz, 1H), 6.70 (d, J=7.8 Hz, 1H), 4.32 (q, J=7.1 Hz, 2H), 4.22 (s, 2H), 2.41 (m, 3H), 1.31 (t, J=7.1 Hz, 3H). MS (ESI+): 351.0. HPLC (max plot) 99.7%; Rt 5.79 min.

Intermediate H.10 ethyl 1-(5-fluoro-2-methylphenyl)-1,4-dihydrothiochromeno[4,3-c]pyrazole-3-carboxylate

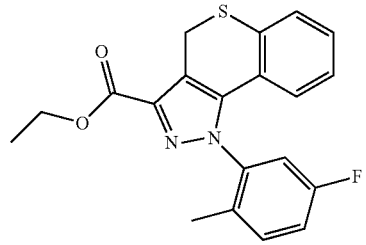 [SMILES: CCOC(=O)c1nn(-c2cc(F)ccc2C)c2c1CSc1ccccc1-2]

Following the protocol outlined in Procedure AA, ethyl 1-(5-fluoro-2-methylphenyl)-1,4-dihydrothio chromeno[4,3-c]pyrazole-3-carboxylate is obtained from 2,3-d ihydro-4H-thiochroman-4-one, diethyl oxalate and (5-fluoro-2-methylphenyl)-hydrazine to afford the title compound. $^1$H NMR (DMSO-d$_6$, 400 MHz) δ 7.52-7.42 (m, 4H), 7.22-7.18 (m, 1H), 7.00-6.96 (m, 1H), 6.58 (d, J=7.0 Hz, 1H), 4.35-4.22 (m, 4H), 1.78 (s, 3H), 1.31 (t, J=7.1 Hz, 3H). MS (ESI+): 369.0. HPLC (max plot) 99.2%; Rt 5.76 min.

Intermediate H.11 ethyl 1-(3-methoxyphenyl)-1,4-dihydrothiochromeno[4,3-c]pyrazole-3-carboxlate

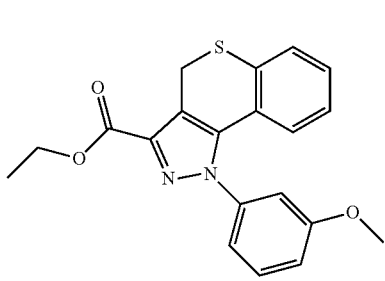 [SMILES: CCOC(=O)c1nn(-c2cccc(OC)c2)c2c1CSc1ccccc1-2]

Following the protocol outlined in Procedure AA, ethyl 1-(3-methoxyphenyl)-1,4-dihydrothio chromeno[4,3-c] pyrazole-3-carboxylate is obtained from 2,3-dihydro-4H-thiochroman-4-one, diethyl oxalate and 3-methoxy phenyl hydrazine hydrochloride to afford the title compound.

$^1$H NMR (DMSO-d$_6$, 400 MHz) δ 7.48-7.44 (m, 2H), 7.22-7.15 (m, 2H), 7.06-6.95 (m, 2H), 6.73 (d, J=7.9 Hz, 2H), 4.32 (q, J=7.0 Hz, 2H), 4.23 (s, 2H), 3.78 (s, 3H), 1.31 (t, J=7.1 Hz, 3H). MS (ESI+): 367.0. HPLC (max plot) 97.5%; Rt 5.55 min.

Intermediate H.12 ethyl 1-(4-methoxyphenyl)-1,4-dihydrothiochromeno[4,3-c]pyrazole-3-carboxlate

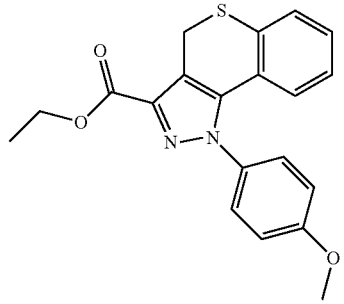 [SMILES: CCOC(=O)c1nn(-c2ccc(OC)cc2)c2c1CSc1ccccc1-2]

Following the protocol outlined in Procedure AA, ethyl 1-(4-methoxyphenyl)-1,4-dihydrothiochromeno[4,3-c]pyrazole-3-carboxylate is obtained from 2,3-dihydro-4H-thiochroman-4-one, diethyl oxalate and 4-methoxy phenyl hydrazine to afford 1.38 g (71%) of the title compound. $^1$H NMR (DMSO-d$_6$, 400 MHz) δ 7.47 (d, J=7.8 Hz, 1H), 7.38 (d, J=8.6 Hz, 1H), 7.19 (t, J=7.4 Hz, 1H), 7.10 (d, J=8.7 Hz, 2H), 7.00 (t, J=7.7 Hz, 1H), 6.71 (d, J=7.9 Hz, 2H), 4.32 (q, J=7.1 Hz, 2H), 4.22 (s, 2H), 3.84 (s, 3H), 1.31 (t, J=7.1 Hz, 3H). MS (ESI+): 367.0. HPLC (max plot) 98.6%; Rt 5.51 min.

Intermediate H.13 ethyl 1-pyridin-2-yl-1,4-dihydrothiochromeno[4,3-c]pyrazole-3-carboxlate

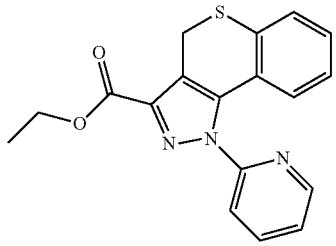 [SMILES: CCOC(=O)c1nn(-c2ccccn2)c2c1CSc1ccccc1-2]

Following the protocol outlined in Procedure AA, ethyl 1-pyridin-2-yl-1,4-dihydrothiochromeno[4,3-c]pyrazole-3-carboxylate is obtained from 2,3-dihydro-4H-thiochroman-4-one, diethyl oxalate and 4-methoxy phenyl hydrazine to afford the title compound. $^1$H NMR (DMSO-d$_6$, 400 MHz) δ 8.51 (dd, J=4.8 Hz, J=0.8 Hz, 1H), 8.18-8.13 (m, 1H), 7.79 (d, J=7.9 Hz, 1H), 7.65-7.62 (m, 1H), 7.48 (d, J=7.8 Hz, 1H), 7.23-7.19 (m, 1H), 7.02-6.98 (m, 1H), 6.64-6.62 (m, 1H), .4.34 (q, J=7.1 Hz, 2H), 4.22 (s, 2H), 1.32 (t, J=7.1 Hz, 3H). MS (ESI+): 338.0. HPLC (max plot) 98.5%; Rt 4.81 min.

Intermediate H.14 ethyl 1-cyclohexyl-1,4-dihydrothiochromeno[4,3-c]pyrazole-3-carboxlate

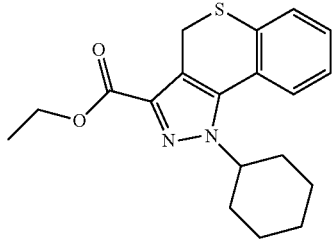 [SMILES: CCOC(=O)c1nn(C2CCCCC2)c2c1CSc1ccccc1-2]

Following the protocol outlined in Procedure AA, ethyl 1-cyclohexyl-1,4-dihydrothiochromeno[4,3-c]pyrazole-3-carboxylate is obtained from 2,3-dihydro-4H-thiochroman-4-one, diethyl oxalate and cyclohexyl hydrazine to afford the title compound. $^1$H NMR (DMSO-$d_6$, 400 MHz) δ 7.61 (d, J=7.8 Hz, 1H), 7.55 (d, J=7.6 Hz, 1H), 7.39 (t, J=7.5 Hz, 1H), 7.32 (t, J=7.5 Hz, 1H), 4.57-4.52 (m, 1H), 4.30 (q, J=7.1 Hz, 2H), 4.09 (s, 2H), 2.00-1.81 (m, 4H), 1.69-1.66 (m, 2H), 1.49-1.42 (m, 3H), 1.38 (t, J=7.1 Hz, 3H). MS (ESI+): 343.0. HPLC (max plot) 99.5%; Rt 5.98 min.

Intermediate H.15 ethyl 6-bromo-1-methyl-1,4-dihydrothiochromeno[4,3-c]pyrazole-3-carboxylate

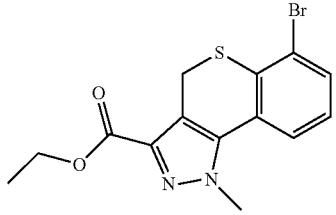 [SMILES: CCOC(=O)c1nn(C)c2c1CSc1c(Br)cccc1-2]

Following the protocol outlined in Procedure AA, ethyl 6-bromo-1-methyl-1,4-dihydrothiochromeno[4,3-c]pyrazole-3-carboxylate is obtained from 8-bromo-2,3-dihydro-4H-thiochromen-4-one, diethyl oxalate and methyl hydrazine to afford the title compound. $^1$H NMR (DMSO-$d_6$, 400 MHz) δ 7.86 (dd, J=7.8 Hz, J=1.0 Hz, 1H), 7.62 (dd, J=8.0 Hz, J=1.0 Hz, 1H), 7.27 (t, J=8.0 Hz, 1H), 4.29 (q, J=7.1 Hz, 2H), 4.21 (s, 2H), 4.13 (s, 3H), 1.30 (t, J=7.0 Hz, 3H). MS (ESI+): 354.0. HPLC: RT 5.03 min (HPLC purity 98.6%, 97.6%).

Intermediate H.16 ethyl 1-methyl-8-nitro-1,4-dihydrothiochromeno[4,3-c]pyrazole-3-carboxylate

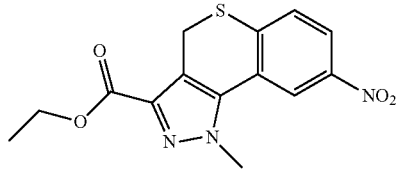 [SMILES: CCOC(=O)c1nn(C)c2c1CSc1ccc([N+](=O)[O-])cc1-2]

Following the protocol outlined in Procedure AA, ethyl 1-methyl-8-nitro-1,4-dihydrothiochromeno[4,3-c]pyrazole-3-carboxylate is obtained from 6-nitro-2,3-dihydro-4H-thiochromen-4-one, diethyl oxalate and methyl hydrazine to afford of the title compound. $^1$H NMR (DMSO-$d_6$, 400 MHz) δ 8.56 (d, J=2.3 Hz, 1H), 8.11 (dd, J=8.7 Hz, J=2.4 Hz, 1H), 7.77 (d, J=8.7 Hz, 1H), 4.31-4.21 (m, 4H), 4.24 (s, 3H), 1.31 (t, J=7.12 Hz, 3H). MS (ESI+) 320.0. HPLC (max plot) 98.3%; Rt 4.53 min.

Intermediate H.17 ethyl 6-fluoro-1-methyl-1,4-dihydrothiochromeno[4,3-c]pyrazole-3-carboxlate

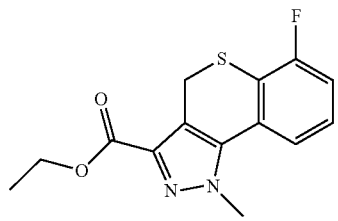 [SMILES: CCOC(=O)c1nn(C)c2c1CSc1c(F)cccc1-2]

Following the protocol outlined in Procedure AA, ethyl 6-fluoro-1-methyl-1,4-dihydrothiochromeno[4,3-c]pyrazole-3-carboxylate is obtained from 8-fluoro-2,3-dihydro-4H-thiochromen-4-one, diethyl oxalate and methyl hydrazine to afford the title compound. $^1$H NMR (DMSO-$d_6$, 400 MHz) δ 7.72 (d, J=7.8 Hz, 1H), 7.41-7.35 (m, 1H), 7.29-7.26 (m, 1H), 4.29 (q, J=7.1 Hz, 2H), 4.19 (s, 2H), 4.16 (s, 3H), 1.30 (t, J=7.1 Hz, 3H). MS (ESI+): 293.0. HPLC (max plot) 98.2%; Rt 4.61 min.

Intermediate H.18 ethyl 6-fluoro-1-phenyl-1,4-dihydrothiochromeno[4,3-c]pyrazole-3-carboxlate

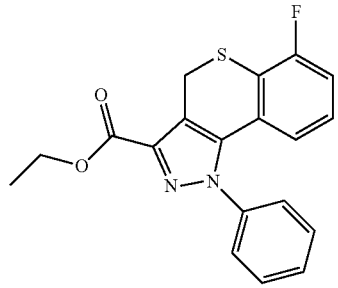 [SMILES: CCOC(=O)c1nn(-c2ccccc2)c2c1CSc1c(F)cccc1-2]

Following the protocol outlined in Procedure AA, ethyl 6-fluoro-1-phenyl-1,4-dihydrothiochromeno[4,3-c]pyrazole-3-carboxylate is obtained from 8-fluoro-2,3-dihydro-4H-thiochromen-4-one, diethyl oxalate and phenyl hydrazine to afford the title compound. $^1$H NMR (DMSO-$d_6$, 400 MHz) δ 7.60-7.55 (m, 3H), 7.48-7.46 (m, 2H), 7.18 (t, J=8.6 Hz, 1H), 7.06-7.01 (m, 1H), 6.51 (d, J=7.8 Hz, 1H), 4.33 (q, J=7.1 Hz, 2H), 4.28 (s, 2H), 1.31 (t, J=7.1 Hz, 3H). MS (ESI+): 355.0.

Intermediate H.19 ethyl 8-fluoro-1-methyl-1,4-dihydrothiochromeno[4,3-c]pyrazole-3-carboxlate

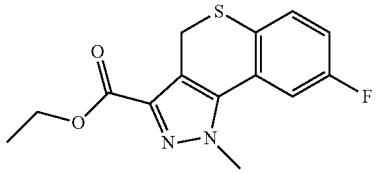 [SMILES: CCOC(=O)c1nn(C)c2c1CSc1ccc(F)cc1-2]

Following the protocol outlined in Procedure AA, ethyl 8-fluoro-1-methyl-1,4-dihydrothiochromeno[4,3-c]pyrazole-3-carboxylate is obtained from 6-fluoro-2,3-dihydro-4H-thiochromen-4-one, diethyl oxalate and methyl hydrazine to afford the title compound. $^1$H NMR (DMSO-$d_6$, 400 MHz) δ 7.72 (dd, J=10.1 Hz, J=2.4 Hz, 1H), 7.57-7.53 (m, 1H), 7.22-7.17 (m, 1H), 4.29 (q, J=7.1 Hz, 2H), 4.17 (s, 2H), 4.13 (s, 3H), 1.30 (t, J=7.1 Hz, 3H). MS (ESI+): 293.0. HPLC (max plot) 98.8%; Rt 3.79 min.

Intermediate H.20 ethyl 8-fluoro-1-phenyl-1,4-dihydrothiochromeno[4,3-c]pyrazole-3-carboxlate

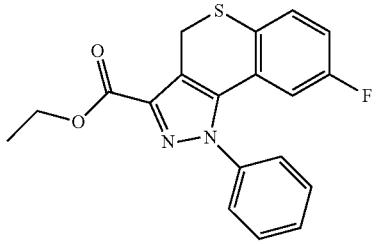 [SMILES: CCOC(=O)c1nn(-c2ccccc2)c2c1CSc1ccc(F)cc1-2]

Following the protocol outlined in Procedure AA, ethyl 8-fluoro-1-phenyl-1,4-dihydrothiochromeno[4,3-c]pyrazole-3-carboxylate is obtained from 6-fluoro-2,3-dihydro-4H-thiochromen-4-one, diethyl oxalate and phenyl hydrazine to afford the title compound. $^1$H NMR (DMSO-$d_6$, 400 MHz) δ 7.63-7.59 (m, 2H), 7.55-7.48 (m, 3H), 7.13-7.08 (m, 2H), 6.33 (dd, J=10.3 Hz, J=2.7 Hz, 1H), 4.33 (q, J=7.1 Hz, 2H), 4.24 (s, 2H), 1.30 (t, J=7.1 Hz, 3H). MS (ESI+): 355.0. HPLC (max plot) 98.7%; Rt 5.67 min.

Intermediate H.21 ethyl 6-bromo-1-phenyl-1,4-dihydrothiochromeno[4,3-c]pyrazole-3-carboxlate

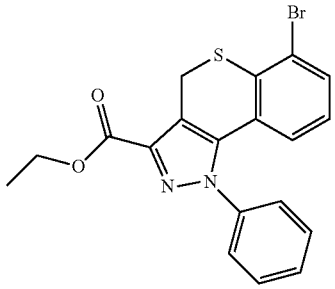 [SMILES: CCOC(=O)c1nn(-c2ccccc2)c2c1CSc1c(Br)cccc1-2]

Following the protocol outlined in Procedure AA, ethyl 6-bromo-1-phenyl-1,4-dihydrothiochromeno[4,3-c]pyrazole-3-carboxylate is obtained from 8-bromo-2,3-dihydro-4H-thiochromen-4-one, diethyl oxalate and phenyl hydrazine to afford the title compound. $^1$H NMR (DMSO-$d_6$, 400 MHz) δ 7.58-7.51 (m, 3H), 7.45 (d, J=8.0 Hz, 2H), 6.92 (t, J=8.0 Hz, 2H), 6.68 (d, J=7.9 Hz, 1H), 4.36-4.30 (m, 4H), 1.31 (t, J=7.0 Hz, 3H). MS (ESI+): 416.0. HPLC (max plot) 98.4%; Rt 5.96 min.

Intermediate H.22 ethyl 8-nitro-1-phenyl-1,4-dihydrothiochromeno[4,3-c]pyrazole-3-carboxlate

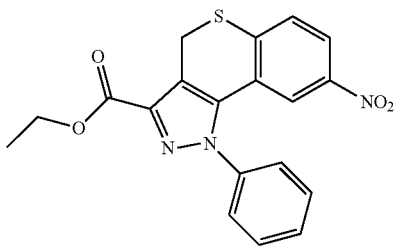 [SMILES: CCOC(=O)c1nn(-c2ccccc2)c2c1CSc1ccc([N+](=O)[O-])cc1-2]

Following the protocol outlined in Procedure AA, ethyl 8-nitro-1-phenyl-1,4-dihydrothiochromeno[4,3-c]pyrazole-3-carboxylate is obtained from 6-nitro-2,3-dihydro-4H-thiochromen-4-one, diethyl oxalate and phenyl hydrazine to afford the title compound. $^1$H NMR (DMSO-$d_6$, 400 MHz) δ 8.01 (dd, J=8.8 Hz, J=2.4 Hz, 1H), 7.50 (d, J=8.8 Hz, 1H), 7.66-7.60 (m, 3H), 7.53 (dd, J=8.0 Hz, J=1.2 Hz, 1H), 7.42 (s, 1H), 4.41 (s, 2H), 4.34 (q, J=7.1 Hz, 2H), 1.32 (t, J=7.1 Hz, 3H). MS (ESI+): 382.0. HPLC (max plot) 90.6%; Rt 7.10 min.

Intermediate H.23 ethyl 1-(2-methylphenyl)-1,4-dihydrothiochromeno[4,3-c]pyrazole-3-carboxlate

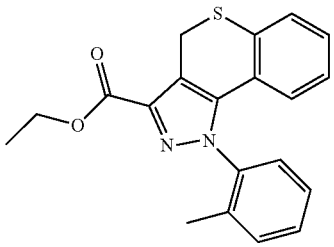 [SMILES: CCOC(=O)c1nn(-c2ccccc2C)c2c1CSc1ccccc1-2]

Following the protocol outlined in Procedure AA, ethyl 1-(2-methylphenyl)-1,4-dihydrothiochromeno[4,3-c]pyrazole-3-carboxylate is obtained from 2,3-dihydro-4H-thiochroman-4-one, diethyl oxalate and 2-methyl phenyl hydrazine to afford the title compound. $^1$H NMR (DMSO-$d_6$, 400 MHz) δ 7.56-7.42 (m, 5H), 7.20-7.16 (m, 1H), 6.95-6.90 (m, 1H), 6.53-6.51 (m, 1H), 4.32 (q, J=7.0 Hz, 2H), 4.28 (d, J=3.5 Hz, 2H), 1.85 (s, 3H), 1.31 (t, J=7.0 Hz, 3H). MS (ESI+): 351.0. HPLC (max plot) 98.0%; Rt 7.27 min

Intermediate H.24 ethyl 1-(2-bromophenyl)-1,4-dihydrothiochromeno[4,3-c]pyrazole-3-carboxlate

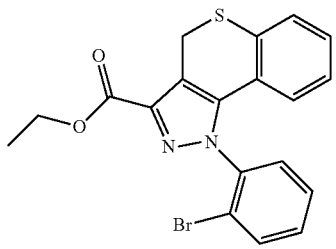 [SMILES: CCOC(=O)c1nn(-c2ccccc2Br)c2c1CSc1ccccc1-2]

Following the protocol outlined in Procedure AA, ethyl 1-(2-bromophenyl)-1,4-dihydrothiochromeno[4,3-c]pyrazole-3-carboxylate is obtained from 2,3-dihydro-4H-thiochroman-4-one, diethyl oxalate and 2-bromophenyl hydrazine to afford the title compound. $^1$H NMR (DMSO-d$_6$, 400 MHz) δ 7.90 (dd, J=7.6 Hz, J=1.2 Hz, 1H), 7.73-7.58 (m, 1H), 7.46 (d, J=8.0 Hz, 1H), 7.19 (t, J=7.6 Hz, 1H), 6.96 (t, J=7.8 Hz, 1H), 6.52 (d, J=8.0 Hz, 1H), 4.35-4.24 (m, 4H), 1.32 (t, J=7.0 Hz, 3H). MS (ESI+): 416.0.

Intermediate H.25 ethyl 1-(2-fluorophenyl)-1,4-dihydrothiochromeno[4,3-c]pyrazole-3-carboxlate

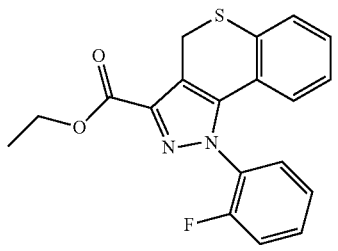 [SMILES: CCOC(=O)c1nn(-c2ccccc2F)c2c1CSc1ccccc1-2]

Following the protocol outlined in Procedure AA, ethyl 1-(2-fluorophenyl)-1,4-dihydrothiochromeno[4,3-c]pyrazole-3-carboxylate is obtained from 2,3-dihydro-4H-thiochroman-4-one, diethyl oxalate and 2-fluorophenyl hydrazine to afford 0.77 g (73%) of the title compound. $^1$H NMR (DMSO-d$_6$, 400 MHz) δ 7.74-7.67 (m, 2H), 7.53-7.45 (m, 3H), 7.23-7.19 (m, 1H), 7.02-6.98 (m, 1H), 6.68 (d, J=7.8 Hz, 1H), 4.36-4.25 (m, 4H), 1.31 (d, J=7.1 Hz, 3H). MS (ESI+): 355.0. HPLC (max plot) 97.7%, Rt 6.99 min.

Intermediate H.26 ethyl 1-(2-chlorophenyl)-1,4-dihydrothiochromeno[4,3-c]pyrazole-3-carboxlate

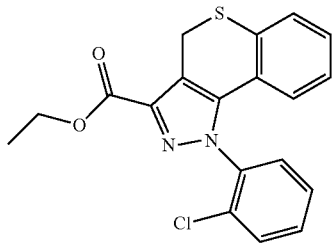 [SMILES: CCOC(=O)c1nn(-c2ccccc2Cl)c2c1CSc1ccccc1-2]

Following the protocol outlined in Procedure AA, ethyl 1-(2-chlorophenyl)-1,4-dihydrothiochromeno[4,3-c]pyrazole-3-carboxylate is obtained from 2,3-dihydro-4H-thiochroman-4-one, diethyl oxalate and 2-chlorophenyl hydrazine to afford 0.8 g (73%) of the title compound. $^1$H NMR (DMSO-d$_6$, 400 MHz) δ 7.76-7.67 (m, 2H), 7.64-7.60 (m, 1H), 7.47 (d, J=7.8 Hz, 1H), 7.21-7.17 (m, 2H), 6.98-6.94 (m, 1H), 6.54 (d, J=7.8 Hz, 1H) 4.35-4.30 (m, 2H), 4.28-4.23 (s, 2H), 1.31 (t, J=7.1 Hz, 3H). MS (ESI+): 370.0. HPLC (max plot) 99.2%; Rt 7.12 min.

Intermediate H.27 ethyl 1-[2-(methylthio)phenyl]-1,4-dihydrothiochromeno[4,3-c]pyrazole-3-carboxylate

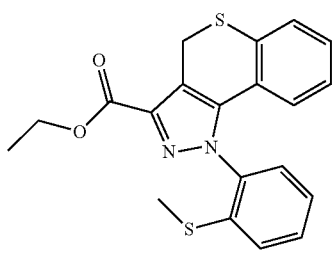 [SMILES: CCOC(=O)c1nn(-c2ccccc2SC)c2c1CSc1ccccc1-2]

Following the protocol outlined in Procedure AA, ethyl 1-[2-(methylthio)phenyl]-1,4-dihydrothiochromeno[4,3-c]pyrazole-3-carboxylate is obtained from 2,3-dihydro-4H-thiochroman-4-one, diethyl oxalate and [2-(methylthio)phenyl]hydrazine to afford the title compound. $^1$H NMR (DMSO-d$_6$, 400 MHz) δ 7.63-7.61 (m, 1H), 7.51 (d, J=7.2 Hz, 1H), 7.45 (d, J=2.4 Hz, 1H), 7.38-7.36 (m, 1H), 7.17-7.16 (m, 1H), 6.94-6.93 (m, 1H), 6.58 (dd, J=8.0 Hz, J=1.2 Hz, 1H), 4.30 (q, J=7.0 Hz, 2H), 4.26 (s, 2H), 2.34 (s, 3H), 1.31 (t, J=7.1 Hz, 3H). MS (ESI+): 415.0. HPLC (max plot) 97.6%; Rt 5.55 min.

Intermediate H.28 ethyl 1-(2,3-dihydro-1,4-benzodioxin-6-yl)-1,4-dihydrothiochromeno[4,3-c]pyrazole-3-carboxylate

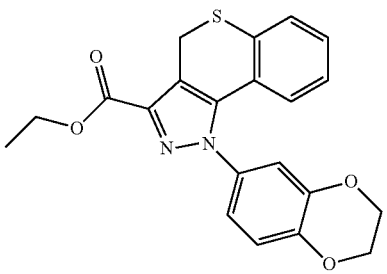 [SMILES: CCOC(=O)c1nn(-c2ccc3c(c2)OCCO3)c2c1CSc1ccccc1-2]

Following the protocol outlined in Procedure AA, ethyl 1-(2,3-dihydro-1,4-benzodioxin-6-yl)-1,4-dihydrothiochromeno[4,3-c]pyrazole-3-carboxylate is obtained from 2,3-dihydro-4H-thiochroman-4-one, diethyl oxalate and 2,3-dihydro-1,4-benzodioxin-6-ylhydrazine to afford the title compound. $^1$H NMR (DMSO-d$_6$, 400 MHz) δ 7.47 (d, J=7.8 Hz, 1H), 7.22-7.18 (m, 1H), 7.05-7.00 (m, 3H), 6.87-6.84 (m, 1H), 6.79-6.77 (m, 1H), 4.34-4.30 (m, 6H), 4.21 (s, 2H), 1.30 (t, J=7.1 Hz, 3H). MS (ESI+): 427.0. HPLC (max plot) 99.2%; Rt 5.39 min.

Intermediate H.29 ethyl 1-(2-methyl-1,3-benzothiazol-6-yl)-1,4-dihydrothiochromeno[4,3-c]pyrazole-3-carboxylate

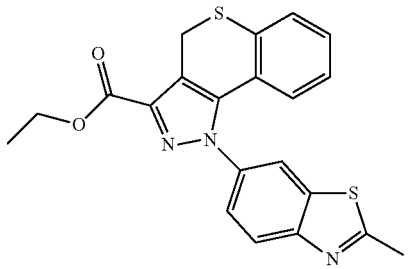 [SMILES: CCOC(=O)c1nn(-c2ccc3nc(C)sc3c2)c2c1CSc1ccccc1-2]

Following the protocol outlined in Procedure AA, ethyl 1-(2-methyl-1,3-benzothiazol-6-yl)-1,4-dihydrothiochromeno[4,3-c]pyrazole-3-carboxylate is obtained from 2,3-dihydro-4H-thiochroman-4-one, diethyl oxalate and 6-hydrazino-2-methyl-1,3-benzothiazole to afford the title compound. $^1$H NMR (DMSO-$d_6$, 400 MHz) δ 8.28 (d, J=2.0 Hz, 1H), 8.05 (d, J=8.2 Hz, 1H), 7.53-7.48 (m, 2H), 7.19 (t, J=7.5 Hz, 1H), 6.95 (t, J=7.8 Hz, 1H), 6.64 (d, J=8.0 Hz, 1H), 4.33 (q, J=7.0 Hz, 2H), 4.26 (s, 2H), 2.85 (s, 3H), 1.31 (t, J=7.1 Hz, 3H). MS (ESI+): 408.0. HPLC (max plot) 97.1%; Rt 7.30 min.

Intermediate H.30 ethyl 1-(3-bromophenyl)-1,4-dihydrothiochromeno[4,3-c]pyrazole-3-carboxylate

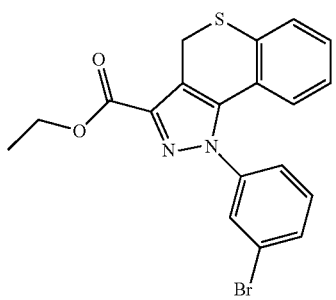 [SMILES: CCOC(=O)c1nn(-c2cccc(Br)c2)c2c1CSc1ccccc1-2]

Following the protocol outlined in Procedure AA, ethyl 1-(3-bromophenyl)-1,4-dihydrothiochromeno[4,3-c]pyrazole-3-carboxylate is obtained from 2,3-dihydro-4H-thiochroman-4-one, diethyl oxalate and (3-bromophenyl)hydrazine to afford 0.55 g (70%) of the title compound. $^1$H NMR (DMSO-$d_6$, 400 MHz) δ 7.81-7.78 (m, 2H), 7.54-7.45 (m, 3H), 7.25-7.20 (m, 1H), 7.06-7.02 (m, 1H), 6.74-6.72 (m, 1H), 4.33 (q, J=7.0 Hz, 2H), 4.23 (s, 2H), 1.31 (t, J=7.0 Hz, 3H). MS (ESI+): 416.0. HPLC (max plot) 98.4%; Rt 7.56 min.

Intermediate H.31 ethyl 1-(3-chlorophenyl)-1,4-dihydrothiochromeno[4,3-c]pyrazole-3-carboxylate

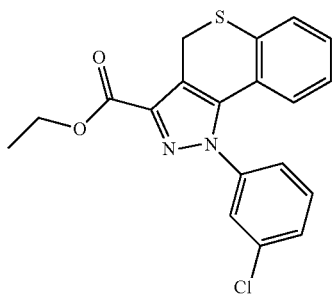 [SMILES: CCOC(=O)c1nn(-c2cccc(Cl)c2)c2c1CSc1ccccc1-2]

Following the protocol outlined in Procedure AA, ethyl 1-(3-chlorophenyl)-1,4-dihydrothiochromeno[4,3-c]pyrazole-3-carboxylate is obtained from 2,3-dihydro-4H-thiochroman-4-one, diethyl oxalate and (3-chlorophenyl)hydrazine to afford 0.56 g (79%) of the title compound. $^1$H NMR (DMSO-$d_6$, 400 MHz) δ 7.68-7.66 (m, 1H), 7.59 (t, J=7.8 Hz, 1H), 7.50 (t, J=7.8 Hz, 1H), 7.44-7.41 (m, 1H), 7.24-7.20 (m, 1H), 7.06-7.02 (m, 1H), 6.74-6.72 (m, 1H), 4.33 (q, J=7.2 Hz, 2H), 4.23 (s, 2H), 1.31 (t, J=7.2 Hz, 3H). MS (ESI+): 370.0. HPLC (max plot) 98.7%; Rt 7.51 min.

Intermediate H.32 ethyl 1-(4-bromophenyl)-1,4-dihydrothiochromeno[4,3-c]pyrazole-3-carboxlate

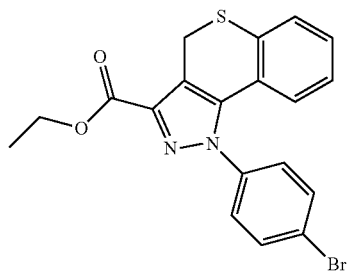 [SMILES: CCOC(=O)c1nn(-c2ccc(Br)cc2)c2c1CSc1ccccc1-2]

Following the protocol outlined in Procedure AA, ethyl 1-(4-bromophenyl)-1,4-dihydrothiochromeno[4,3-c]pyrazole-3-carboxylate is obtained from 2,3-dihydro-4H-thiochroman-4-one, diethyl oxalate and (4-bromophenyl)hydrazine to afford 1.1 g (70%) of the title compound. $^1$H NMR (DMSO-$d_6$, 400 MHz) δ 7.77 (dd, J=6.7 Hz, J=2.0 Hz, 1H), 7.50 (d, J=7.8 Hz, 2H), 7.45-7.43 (m, 2H), 7.24-7.20 (m, 1H), 7.07-7.03 (m, 1H), 6.75-6.73 (m, 1H), 4.32 (q, J=7.1 Hz, 2H), 1.31 (t, J=7.1 Hz, 3H). MS (ESI+): 416.0. HPLC (max plot) 99.6%; Rt 5.94 min.

Intermediate H.33 ethyl 1-(4-fluorophenyl)-1,4-dihydrothiochromeno[4,3-c]pyrazole-3-carboxlate

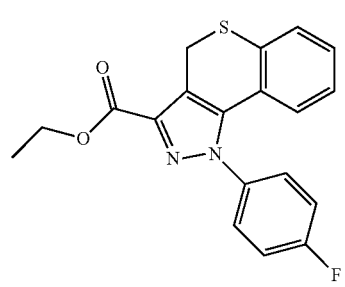 [SMILES: CCOC(=O)c1nn(-c2ccc(F)cc2)c2c1CSc1ccccc1-2]

Following the protocol outlined in Procedure AA, ethyl 1-(4-fluorophenyl)-1,4-dihydrothiochromeno[4,3-c]pyrazole-3-carboxylate is obtained from 2,3-dihydro-4H-thiochroman-4-one, diethyl oxalate and (4-fluorophenyl)hydrazine to afford 0.35 g (82%) of the title compound. $^1$H NMR (DMSO-$d_6$, 400 MHz) δ 7.53-7.40 (m, 5H), 7.23-7.18 (m, 1H), 7.04-7.00 (m, 1H), 6.70-6.68 (m, 1H), 4.32 (q, J=7.1 Hz, 2H), 4.23 (s, 2H), 1.31 (t, J=7.1 Hz, 3H). MS (ESI+): 355.0. HPLC (max plot) 99.5%; Rt 7.26 min.

Intermediate H.34 ethyl 1-(4-chlorophenyl)-1,4-dihydrothiochromeno[4,3-c]pyrazole-3-carboxlate

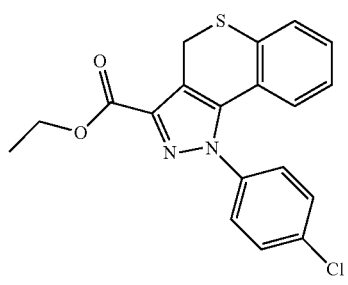 [SMILES: CCOC(=O)c1nn(-c2ccc(Cl)cc2)c2c1CSc1ccccc1-2]

Following the protocol outlined in Procedure AA, ethyl 1-(4-chlorophenyl)-1,4-dihydrothiochromeno[4,3-c]pyrazole-3-carboxylate is obtained from 2,3-dihyd ro-4H-thiochroman-4-one, diethyl oxalate and (4-chlorophenyl)hydrazine to afford the title compound. $^1$H NMR (DMSO-$d_6$, 400 MHz) δ 7.64 (dd, J=6.6 Hz, J=1.6 Hz, 1H), 7.52-7.48 (m, 3H), 7.24-7.20 (m, 1H), 7.07-7.03 (m, 1H), 6.74-6.72 (m, 1H), 4.33 (q, J=7.1 Hz, 2H), 4.22 (s, 2H), 1.31 (t, J=7.1 Hz, 3H). MS (ESI+): 371.0. HPLC (max plot) 99.4%; Rt 7.48 min.

Intermediate H.35 ethyl 1-(4-isopropylphenyl)-1,4-dihydrothiochromeno[4,3-c]pyrazole-3-carboxylate

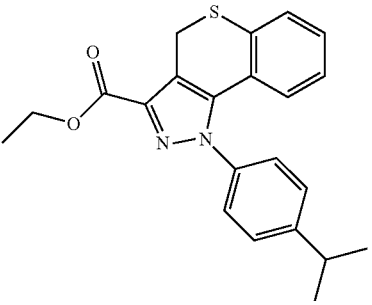 [SMILES: CCOC(=O)c1nn(-c2ccc(C(C)C)cc2)c2c1CSc1ccccc1-2]

Following the protocol outlined in Procedure AA, ethyl 1-(4-isopropylphenyl)-1,4-dihydrothiochromeno[4,3-c]pyrazole-3-carboxylate is obtained from 2,3-dihydro-4H-thiochroman-4-one, diethyl oxalate and (4-isopropylphenyl)hydrazine to afford the title compound. $^1$H NMR (DMSO-$d_6$, 400 MHz) δ 7.49-7.42 (m, 3H), 7.37-7.34 (m, 2H), 7.19 (t, J=7.5 Hz, 1H), 6.98 (t, J=7.7 Hz, 1H), 6.70 (d, J=8.1 Hz, 1H), 4.32 (q, J=7.1 Hz, 2H), 3.05-2.98 (m, 1H), 1.30 (t, J=7.1 Hz, 3H), 1.25 (d, J=6.8 Hz, 6H). MS (ESI+): 379.0. HPLC (max plot) 98.5%; Rt 7.80 min.

Intermediate H.36 ethyl 1-(4-methylpyridin-3-yl)-1,4-dihydrothiochromeno[4,3-c]pyrazole-3-carboxylate

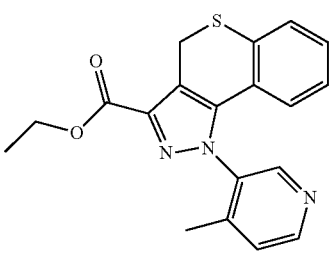 [SMILES: CCOC(=O)c1nn(-c2cnccc2C)c2c1CSc1ccccc1-2]

Following the protocol outlined in Procedure AA, ethyl 1-(4-methylpyridin-3-yl)-1,4-dihydrothiochromeno[4,3-c]pyrazole-3-carboxylate is obtained from 2,3-dihydro-4H-thiochroman-4-one, diethyl oxalate and 3-hydrazino-4-methylpyridine to afford the title compound. $^1$H NMR (DMSO-$d_6$, 400 MHz) δ 8.35 (d, J=2.1 Hz, 1H), 7.96 (dd, J=8.1 Hz, J=1.8 Hz, 1H), 7.67 (d, J=8.1 Hz, 1H), 7.48-7.46 (m, 1H), 7.22-7.18 (m, 1H), 7.02-6.98 (m, 1H), 6.63 (dd, J=7.9 Hz, J=1.0 Hz, 1H), 4.33 (q, J=7.0 Hz, 2H), 4.22 (s, 2H), 2.41 (s, 3H), 1.32 (t, J=7.0 Hz, 3H). MS (ESI+): 352.0. HPLC (max plot) 98.6%; Rt 5.11 min.

Intermediate H.37 ethyl 1-(tetrahydro-2H-pyran-4-yl)-1,4-dihydrothiochromeno[4,3-c]pyrazole-3-carboxylate

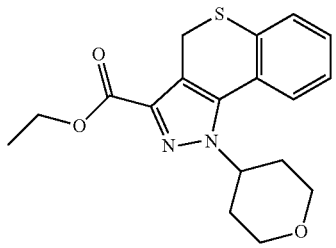 [SMILES: CCOC(=O)c1nn(C2CCOCC2)c2c1CSc1ccccc1-2]

Following the protocol outlined in Procedure AA, ethyl 1-(tetrahydro-2H-pyran-4-yl)-1,4-dihydrothiochromeno[4,3-c]pyrazole-3-carboxylate is obtained from 2,3-dihydro-4H-thiochroman-4-one, diethyl oxalate and tetrahydro-2H-pyran-4-ylhydrazine to afford of the title compound. $^1$H NMR (DMSO-d$_6$, 400 MHz) δ 7.70 (d, J=7.3 Hz, 1H), 7.55 (dd, J=7.6 Hz, J=1.2 Hz, 1H), 7.40-7.30 (m, 2H), 4.88-4.84 (m, 1H), 4.30 (q, J=7.0 Hz, 1H), 4.10 (s, 2H), 3.98-3.94 (m, 2H), 3.51 (t, J=11.1 Hz, 3H), 2.16-2.10 (m, 2H), 1.97-1.94 (m, 2H), 1.31 (t, J=7.0 Hz, 3H). MS (ESI+): 345.0. HPLC (max plot) 98.0%; Rt 4.79 min.

Intermediates described below are obtained following procedure AA described below

---

Intermediate H.38: Ethyl 1-[4-(methylthio)phenyl]-1,4-dihydrothiochromeno[4,3-c]pyrazole-3-carboxylate

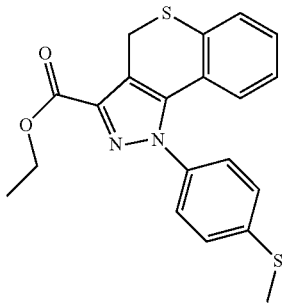 [SMILES: CCOC(=O)c1nn(-c2ccc(SC)cc2)c2c1CSc1ccccc1-2]

300 mg of the title compound. $^1$H NMR (DMSO-d$_6$, 400 MHz): δ 7.49-7.48 (d, J = 7.8 Hz, 1H), 7.43-7.37 (m, 4H), 7.23-7.19 (t, J = 7.6 Hz, 1H), 7.05-7.01 (t, J = 7.7 Hz, 1H), 6.77-6.75 (d, J = 7.9 Hz, 1H), 4.35-4.30 (m, 2H), 4.22 (s, 2H), 2.54 (s, 3H), 1.33-1.29 (t, J = 5.6 Hz, 3H). MS (ESI+): 383.0. HPLC (max plot): 93.72%; Rt 5.85 min.

Intermediate H.39: Ethyl 1-(3-fluorophenyl)-1,4-dihydrothiochromeno[4,3-c]pyrazole-3-carboxylate

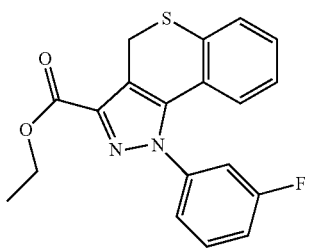 [SMILES: CCOC(=O)c1nn(-c2cccc(F)c2)c2c1CSc1ccccc1-2]

150 mg of the title compound. $^1$H NMR (DMSO-d$_6$, 400 MHz): δ 7.64-7.58 (m, 1H), 7.50-7.45 (m, 3H), 7.30 (d, J = 7.5 Hz, 1H), 7.24-7.20 (m, 1H), 7.05-7.01 (m, 1H), 6.75-6.71 (m, 1H), 4.35-4.30 (m, 2H), 4.23 (s, 2H), 1.33-1.29 (t, J = 7.1 Hz, 3H). MS (ESI+): 355.0.

Intermediate H.40: Ethyl 1-(3-cyanophenyl)-1,4-dihydrothiochromeno[4,3-c]pyrazole-3-carboxylate

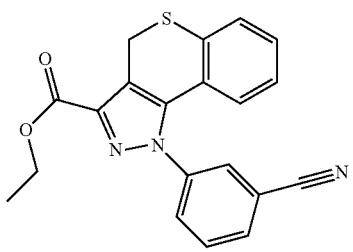 [SMILES: CCOC(=O)c1nn(-c2cccc(C#N)c2)c2c1CSc1ccccc1-2]

0.50 g (81%) of the title compound. 1H NMR (DMSO-d6, 400 MHz) δ 8.12 (s, 1H), 8.07 (d, J = 6.0 Hz, 1H), 7.80-7.77 (m, 2H), 7.51 (d, J = 7.8 Hz, 1H), 7.23 (t, J = 7.5 Hz, 1H), 7.03 (t, J = 7.8 Hz, 1H), 6.69 (d, J = 7.8 Hz, 1H), 4.34 (d, J = 7.8 Hz, 2H), 4.24 (s, 2H), 1.31 (t, J = 7.0 Hz, 3H). MS (ESI+): 362.0. HPLC (max plot) 98.0%; Rt 5.22 min Intermediate H.41: Ethyl 1-(pyridin-3-yl)-1,4-dihydrothiochromeno[4,3-c]pyrazole-3-carboxylate

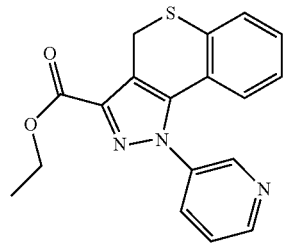 [SMILES: CCOC(=O)c1nn(-c2cccnc2)c2c1CSc1ccccc1-2]

320 mg of the title compound. ¹H NMR (DMSO-d₆, 400 MHz): δ = 8.78-8.77 (dd, J = 1.4, 4.7 Hz, 1H), 8.70-8.69 (m, 1H), 8.00-7.97 (m, 1H), 7.65-7.62 (m, 1H), 7.52-7.50 (m, 1H), 7.23-7.20 (m, 1H), 7.04-7.00 (m, 1H), 6.69-6.67 (m, 1H), 4.36-4.31 (q, 2H), 4.24 (s, 2H), 1.33-1.29 (t, J = 7.12 Hz, 3H). MS (ESI+): 338.0; HPLC (max plot) 97.09%; Rt 4.33 min Intermediate H.42: Ethyl 1-(6-methylpyridin-3-yl)-1,4-dihydrothiochromeno[4,3-c]pyrazole-3-carboxylate

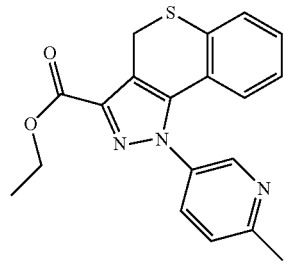 [SMILES: CCOC(=O)c1nn(-c2ccc(C)nc2)c2c1CSc1ccccc1-2]

¹H NMR (DMSO-d₆, 400 MHz): δ 8.54-8.53 (m, 1H), 7.86-7.83 (dd, J = 2.6, 8.2 Hz, 1H), 7.51-7.47 (m, 2H), 7.24-7.20 (m, 1H), 7.05-7.01 (m, 1H), 6.73-6.71 (d, J = 7.8 Hz, 1H), 4.36-4.30 (q, 2H), 4.23 (s, 2H), 2.59 (s, 3H), 1.33-1.29 (t, J = 11.1 Hz, 3H). MS (ESI+): 352.2

Intermediate H.43: Ethyl 1-(6-methoxypyridin-3-yl)-1,4-dihydrothiochromeno[4,3-c]pyrazole-3-carboxylate

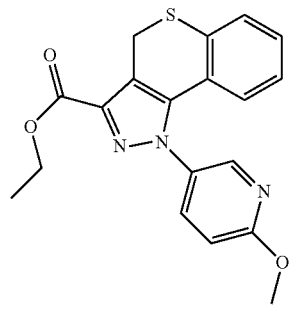 [SMILES: CCOC(=O)c1nn(-c2ccc(OC)nc2)c2c1CSc1ccccc1-2]

¹H NMR (DMSO-d₆, 400 MHz): δ 8.32-8.31 (s, 1H), 7.87-7.84 (dd, J = 2.7, 8.8 Hz, 1H), 7.50-7.48 (m, 1H), 7.24-7.19 (m, 1H), 7.07-7.00 (m, 2H), 6.78-6.76 (d, J = 7.8 Hz, 1H), 4.35-4.30 (m, 2H), 4.23 (s, 2H), 3.94 (s, 3H), 1.33-1.29 (t, J = 7.1 Hz, 3H). MS (ESI+): 368.0 HPLC (max plot) 98.87%; Rt 5.32 min.

Intermediate H.44: Ethyl 1-[3-(methylthio)phenyl]-1,4-dihydrothiochromeno[4,3-c]pyrazole-3-carboxylate

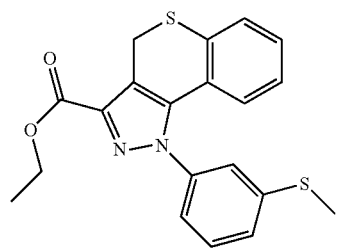 [SMILES: CCOC(=O)c1nn(-c2cccc(SC)c2)c2c1CSc1ccccc1-2]

220 mg of the title compound. ¹H NMR (DMSO-d₆, 400 MHz): δ 7.50-7.46 (m, 3H), 7.36 (s, 1H), 7.23-7.15 (m, 2H), 7.04-7.00 (m, 1H), 6.74-6.73 (d, J = 7.2 Hz, 1H), 4.35-4.30 (m, 2H), 4.23 (s, 2H), 1.33-1.30 (t, J = 7.1 Hz, 3H). MS (ESI+): 383.0. HPLC (max plot) 98.45%; Rt 5.83 min Intermediate H.45: Ethyl 1-(1H-indazol-4-yl)-1,4-dihydrothiochromeno[4,3-c]pyrazole-3-carboxylate

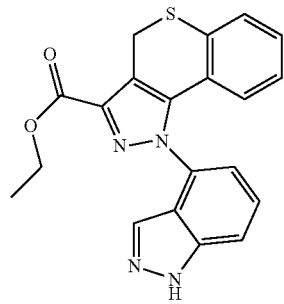 [SMILES: CCOC(=O)c1nn(-c2cccc3[nH]ncc23)c2c1CSc1ccccc1-2]

500 mg of the title compound. $^1$H NMR (DMSO-d$_6$, 400 MHz): δ 13.35 (s, 1H), 8.23 (s, 1H), 7.95-7.93 (d, J = 8.5 Hz, 1H), 7.66 (s, 1H), 7.49-7.47 (d, J = 7.7 Hz, 1H), 7.20-7.16 (m, 1H), 7.13-7.10 (m, 1H), 6.95-6.91 (m, 1H), 6.67-6.65 (d, J = 7.9 Hz, 1H), 4.32 (q, J = 7.1 Hz, 2H), 4.25 (s, 2H), 1.31 (t, J = 7.0 Hz, 3H). MS (ESI+): 377.1.

Intermediate H.46: Ethyl 1-(2-benzyl-2H-indazol-4-yl)-1,4-dihydrothiochromeno[4,3-c]pyrazole-3-carboxylate

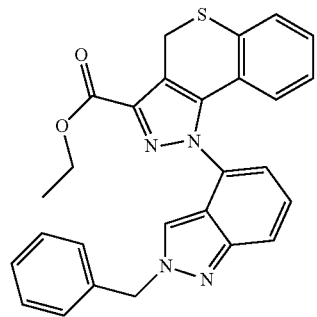 [SMILES: CCOC(=O)c1nn(-c2cccc3nn(Cc4ccccc4)cc23)c2c1CSc1ccccc1-2]

500 mg (35%) of the title compound. MS (ESI+): 467.2.

Intermediate H.47: Ethyl 1-{3-[(dimethylamino)sulfonyl]phenyl}-1,4-dihydrothiochromeno[4,3-c]pyrazole-3-carboxylate

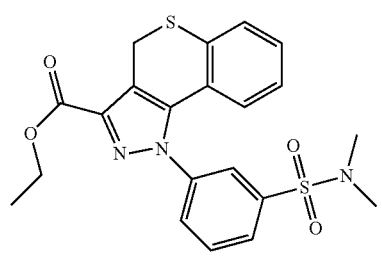 [SMILES: CCOC(=O)c1nn(-c2cccc(S(=O)(=O)N(C)C)c2)c2c1CSc1ccccc1-2]

300 mg (18%) of the title compound. MS (ESI+): 444.2.

Intermediate H.48: Ethyl 1-(2-isopropylphenyl)-1,4-dihydrothiochromeno[4,3-c]pyrazole-3-carboxylate

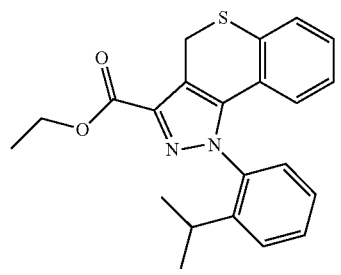 [SMILES: CCOC(=O)c1nn(-c2ccccc2C(C)C)c2c1CSc1ccccc1-2]

700 mg of the title compound. $^1$H NMR (400 MHz, DMSO-d$_6$) δ: 7.62-7.58 (m, 2H), 7.46-7.37 (m, 3H), 7.16 (t, J = 7.1 Hz, 1H), 6.91 (t, J = 7.1 Hz, 1H), 6.51 (dd, J = 1.0, 7.9 Hz, 1H), 4.34-4.23 (m, 4H), 2.31-2.29 (m, 1H), 1.31 (t, J = 7.1 Hz, 3H), 1.04 (t, J = 6.8 Hz, 3H), 0.81 (t, J = 6.8 Hz, 3H). MS (ESI+): 379.0. HPLC (max plot): 95.2%; Rt 6.23 min -continued Intermediate H.49: Ethyl 1-(2-methoxyphenyl)-1,4-dihydrothiochromeno[4,3-c]pyrazole-3-carboxylate

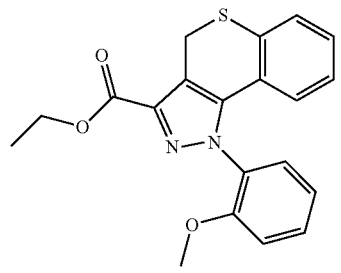 [SMILES: CCOC(=O)c1nn(-c2ccccc2OC)c2c1CSc1ccccc1-2]

385 mg of the title compound. $^1$H NMR (400 MHz, DMSO-d$_6$) δ: 7.63-7.58 (m, 1H), 7.46-7.43 (m, 2H), 7.27 (d, J = 8.4 Hz, 1H), 7.18-7.12 (m, 2H), 6.96-6.92 (m, 1H), 6.67 (dd, J = 1.1, 7.9 Hz, 1H), 4.34-4.30 (m, 2H), 4.29-4.24 (m, 2H), 3.58 (s, 3H), 1.32 (t, J = 7.1 Hz, 3H). MS (ESI+): 367.0. HPLC (max plot): 99.4%; Rt 5.40 min.

Intermediate H.50: Ethyl 1-(4-{[(methylsulfonyl)amino]methyl}phenyl)-1,4-dihydrothiochromeno[4,3-c]pyrazole-3-carboxylate

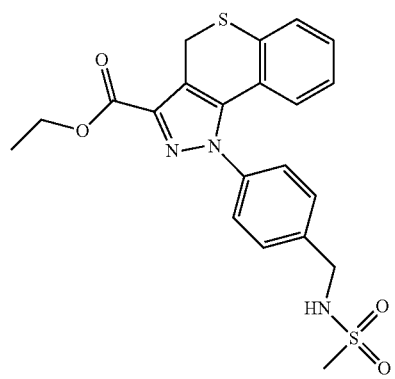 [SMILES: CCOC(=O)c1nn(-c2ccc(CNS(C)(=O)=O)cc2)c2c1CSc1ccccc1-2]

270 mg of the title compound. 1H NMR (400 MHz, DMSO-d6) δ = 7.58-7.47 (m, 5H), 7.22-7.18 (t, J = 7.6 Hz, 1H), 7.06-7.03 (m, 1H), 6.98-6.94 (m, 1H), 6.72-6.70 (m, 1H), 4.48 (s, 2H), 4.35-4.29 (m, 2H), 4.23 (s, 2H), 2.57-2.56 (d, 3H), 1.32-1.29 (m, 3H). MS (ESI+): 444, HPLC: HPLC (max plot): 96.88%; Rt 4.84 min.

Intermediate H.51: Ethyl 1-phenyl-7-(trifluoromethyl)-1,4-dihydrothiochromeno[4,3-c]pyrazole-3-carboxylate

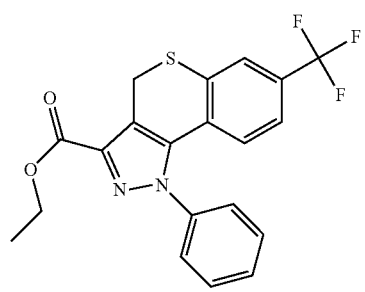 [SMILES: CCOC(=O)c1nn(-c2ccccc2)c2c1CSc1cc(C(F)(F)F)ccc1-2]

320 mg of the title compound. $^1$H NMR (DMSO-d$_6$, 400 MHz): δ 7.86 (s, 1H), 7.60-7.56 (m, 3H), 7.50-7.47 (m, 2H), 7.38-7.36 (m, 1H), 6.84-6.82 (d, J = 8.2 Hz, 1H), 4.36-4.31 (m, 2H), 1.33-1.30 (t, J = 7.1 Hz, 3H). MS (ESI+): 405.2. HPLC (max plot) 97.10%; Rt 6.18 min.

Intermediate H.52: Ethyl 8-methoxy-1-phenyl-1,4-dihydrothiochromeno[4,3-c]pyrazole-3-carboxylate

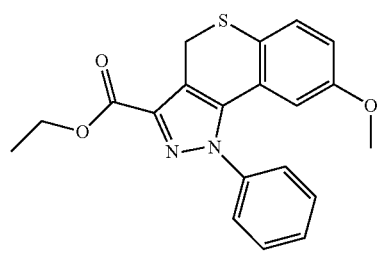 [SMILES: CCOC(=O)c1nn(-c2ccccc2)c2c1CSc1ccc(OC)cc1-2]

1.6 g of the title compound. $^1$H NMR (DMSO-d$_6$, 400 MHz): δ 7.61-7.60 (m, 3H), 7.51-7.47 (m, 2H), 7.39 (d, J = 8.6 Hz, 1H), 6.82 (dd, J = 2.7, 8.6 Hz, 1H), 6.21-6.20 (d, J = 2.7 Hz, 1H), 4.35-4.30 (m, 2H), 4.18 (s, 2H), 3.13 (s, 3H), 1.33-1.29 (t, J = 7.1 Hz, 3H). MS (ESI+): 367.0. HPLC (max plot) 98.48%; Rt 5.11 min.

Intermediate H.53: Ethyl 8-bromo-1-phenyl-1,4-dihydrothiochromeno[4,3-c]pyrazole-3-carboxylate

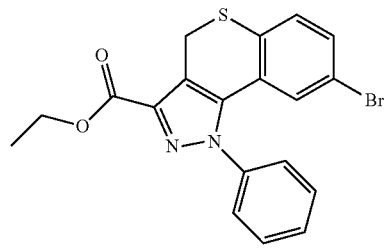 [SMILES: CCOC(=O)c1nn(-c2ccccc2)c2c1CSc1ccc(Br)cc1-2]

0.50 g of the title compound. 1H NMR (400 mHz, DMSO-d6) δ = 7.64-7.59 (m, 3H), 7.52-7.39 (m, 3H), 7.39-7.36 (m, 1H), 6.68 (d, J = 2.0 Hz, 1H), 4.35-4.30 (m, 2H), 4.26 (s, 2H), 1.33-1.29 (t, J = 7.1 Hz, 3H). MS (ESI+): 416.0. HPLC (max plot) 89.65%; Rt 5.96 min Intermediate H.54: Ethyl 1-cyclopentyl-1,4-dihydrothiochromeno[4,3-c]pyrazole-3-carboxylate

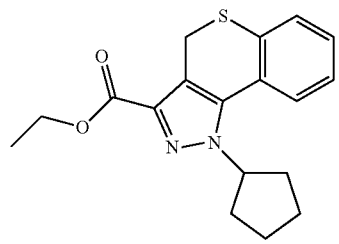 [SMILES: CCOC(=O)c1nn(C2CCCC2)c2c1CSc1ccccc1-2]

600 mg (96%) of the title compound. $^1$H NMR (400 MHz, DMSO-d$_6$): δ = 7.75-7.72 (d, J = 8.2 Hz, 1H), 7.55-7.53 (d, J = 7.5 Hz, 1H), 7.39-7.30 (m, 1H), 5.14-5.11 (t, J = 7.16 Hz 1H), 4.32-4.27 (q, J = 7.1 14.2 Hz, 2H), 4.09 (s, 2H), 2.31 (m, 2H), 2.16-2.15 (m, 2H), 2.06-2.03 (t, J = 6.6 Hz, 2H), 1.88 (m, 2H), 1.32 (m, 3H). MS (ESI+): 329. HPLC (max plot) 98.12%; Rt 5.76 min.

Intermediate H.55: Ethyl 1-(4-methylcyclohexyl)-1,4-dihydrothiochromeno[4,3-c]pyrazole-3-carboxylate

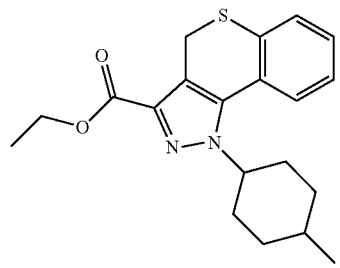 [SMILES: CCOC(=O)c1nn(C2CCC(C)CC2)c2c1CSc1ccccc1-2]

400 mg (59%) of the title compound. MS (ESI+): 357.0.

Intermediate H.56: Ethyl 1-(4-tert-butylcyclohexyl)-1,4-dihydrothiochromeno[4,3-c]pyrazole-3-carboxylate

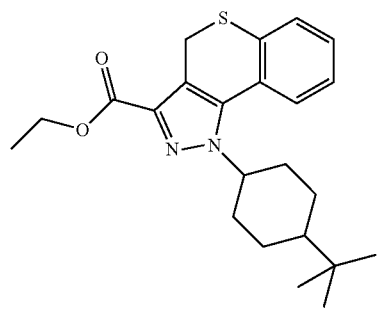 [SMILES: CCOC(=O)c1nn(C2CCC(C(C)(C)C)CC2)c2c1CSc1ccccc1-2]

220 mg of the title compound. MS (ESI+): 399.3.

Intermediate H.57: Ethyl 1-(4,4-difluorocyclohexyl)-1,4-dihydrothiochromeno[4,3-c]pyrazole-3-carboxylate

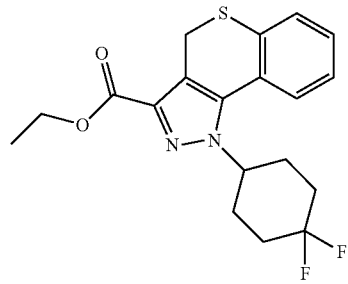 [SMILES: CCOC(=O)c1nn(C2CCC(F)(F)CC2)c2c1CSc1ccccc1-2]

230 mg of the title compound. $^1$H NMR (DMSO-d$_6$, 400 MHz) δ 7.70-7.68 (d, J = 7.6 Hz, 1H), 7.56-7.54 (d, J = 7.5 Hz, 1H), 7.40-7.31 (m, 2H), 4.87 (m, 1H), 4.33-4.28 (m, 2H), 4.09 (s, 2H), 2.18-2.08 (m, 8H), 1.32-1.29 (t, J = 7.6 Hz, 3H). MS (ESI+): 379.2. HPLC (max plot) 98.69%; Rt 5.74 min Intermediate H.58: Ethyl 1-(3,3-dimethylcyclohexyl)-1,4-dihydrothiochromeno[4,3-c]pyrazole-3-carboxylate

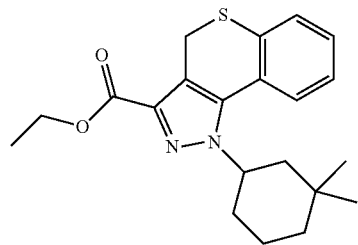 [SMILES: CCOC(=O)c1nn(C2CCCC(C)(C)C2)c2c1CSc1ccccc1-2]

300 mg (81%) of the compound. $^1$H NMR (DMSO-d$_6$, 400 MHz): δ 7.62-7.60 (d, J = 7.7 Hz, 1H), 7.56-7.54 (d, J = 7.7 Hz, 1H), 7.54-7.30 (m, 2H), 4.74 (m, 1H), 4.32-4.24 (m, 2H), 4.09 (s, 2H), 1.97-1.95 (m, 2H), 1.79-1.61 (m, 4H), 1.39-1.22 (m, 4H), 1.01 (s, 3H), 0.96 (s, 3H). MS (ESI+): 371.2. HPLC (max plot) 93.91%; Rt 6.54 min Intermediate H.59: 3-[3-(Ethoxycarbonyl)thiochromeno[4,3-c]pyrazol-1(4H)-yl]cyclohexanecarboxylic acid

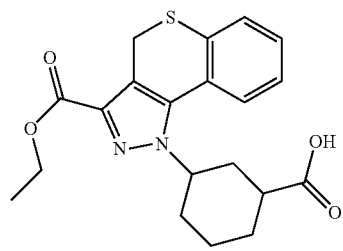 [SMILES: CCOC(=O)c1nn(C2CCCC(C(=O)O)C2)c2c1CSc1ccccc1-2]

200 mg of the title compound. $^1$H NMR (DMSO-d$_6$, 400 MHz): δ 12.23 (bs, 1H), 7.65-7.63 (d, J = 7.7 Hz, 1H), 7.55-7.54 (d, J = 7.6 Hz, 1H), 7.38-7.32 (m, 2H), 4.71 (m, 1H), 4.33-4.28 (m, 2H), 4.10 (s, 2H), 2.49-2.48 (m, 2H), 2.04 (m, 1H), 2.00-1.84 (m, 5H), 1.33-1.29 (m, 4H). MS (ESI+): 387.0.

Intermediate H.60: 4-[3-(Ethoxycarbonyl)thiochromeno[4,3-c]pyrazol-1(4H)-yl]cyclohexanecarboxylic acid

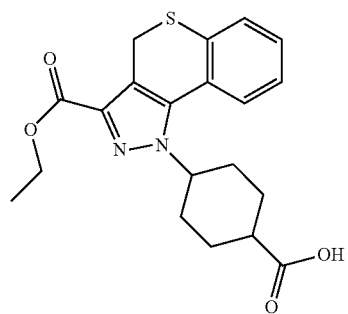 [SMILES: CCOC(=O)c1nn(C2CCC(C(=O)O)CC2)c2c1CSc1ccccc1-2]

500 mg of the title compound. MS (ESI+): 387.0.

-continued

Intermediate H.61: Ethyl 1-(4-hydroxycyclohexyl)-1,4-dihydrothiochromeno[4,3-c]pyrazole-3-carboxylate

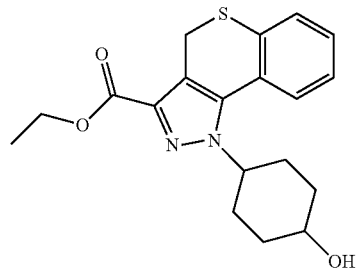 [SMILES: CCOC(=O)c1nn(C2CCC(O)CC2)c2c1CSc1ccccc1-2]

160 mg yield of the title compound. MS (ESI+): 359.0.

Intermediate H.62: Ethyl 1-(tetrahydro-2H-pyran-3-yl)-1,4-dihydrothiochromeno[4,3-c]pyrazole-3-carboxylate

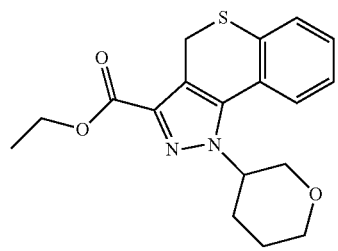

250 mg of the title compound. MS (ESI+): 345.2

Intermediate H.63: Ethyl 1-cycloheptyl-1,4-dihydrothiochromeno[4,3-c]pyrazole-3-carboxylate

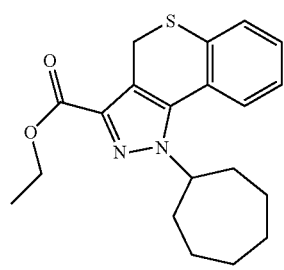 [SMILES: CCOC(=O)c1nn(C2CCCCCC2)c2c1CSc1ccccc1-2]

400 mg of the title compound. $^1$H NMR (400 MHz, DMSO-d$_6$) δ = 7.61-7.59 (m, 1H), 7.56-7.54 (m, 1H), 7.54-7.33 (m, 1H), 7.33-7.31 (m, 1H), 4.75 (m, 1H), 4.32-4.27 (q, 2H), 4.08 (s, 2H), 2.1-2.04 (m, 4H), 1.80-1.77 (m, 2H), 1.61-1.50 (m, 6H), 1.32-1.29 (t, J = 5.64 Hz, 3H).

Intermediate H.64: Ethyl 7-bromo-1-cyclohexyl-1,4-dihydrothiochromeno[4,3-c]pyrazole-3-carboxylate

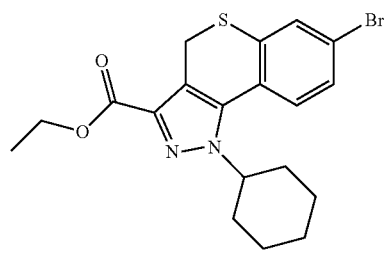 [SMILES: CCOC(=O)c1nn(C2CCCCC2)c2c1CSc1cc(Br)ccc1-2]

420 mg of the title compound. $^1$H NMR (DMSO-d$_6$, 400 MHz): δ 7.78 (s, 1H), 7.58-7.53 (m, 2H), 4.53-4.48 (m 1H), 4.32-4.27 (m, 2H), 4.12 (s, 2H), 2.03-1.80 (m, 7H), 1.68-1.65 (m, 1H), 1.48-1.38 (m, 2H), 1.32-1.26 (m, 4H). MS (ESI+): 423.0. HPLC (max plot) 88.86%; Rt 6.54 min.

Intermediate H.65: Ethyl 8-bromo-1-methyl-1,4-dihydrothiochromeno[4,3-c]pyrazole-3-carboxylate

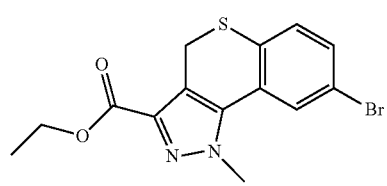 [SMILES: CCOC(=O)c1nn(C)c2c1CSc1ccc(Br)cc1-2]

360 mg (90%) of the title compound. $^1$H NMR (400 MHz, DMSO-d$_6$) δ = 7.98-7.97 (d, 1H), 7.51-7.46 (m, 2H), 4.29 (q, J = 7.1 Hz, 2H), 4.17-4.15 (m, 5H), 1.31-1.28 (t, J = 7.0 Hz, 3H). MS (ESI+): 354.0. (HPLC (max plot) 98.48%; Rt 5.11 min.

Intermediate H.66: Ethyl 1-phenyl-1,4-dihydropyrazolo[3',4':4,5]thiopyrano[2,3-b]pyridine-3-carboxylate

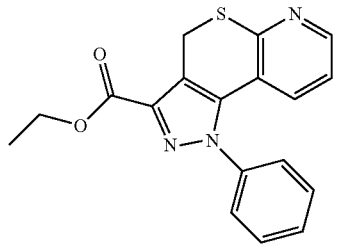 [SMILES: CCOC(=O)c1nn(-c2ccccc2)c2c1CSc1ncccc1-2]

400 mg of the title compound. $^1$H NMR (DMSO-$d_6$, 400 MHz): δ 8.27-8.26 (dd, J = 1.6, 4.5 Hz, 1H), 7.61-7.56 (m, 3H), 7.49-7.47 (m, 2H), 6.99-6.96 (dd, J = 4.7, 7.9 Hz, 1H), 6.88-6.86 (dd, J = 1.1, 6.8 Hz, 1H), 4.41 (s, 2H), 4.36-4.30 (m, 2H), 1.33-1.30 (t, J = 7.2 Hz, 3H). MS (ESI+): 338.0. HPLC (max plot) 97.34%; Rt 4.18 min.

Intermediate H.67: Ethyl 1-cyclohexyl-1,4-dihydropyrazolo[3',4':4,5]thiopyrano[2,3-b]pyridine-3-carboxylate

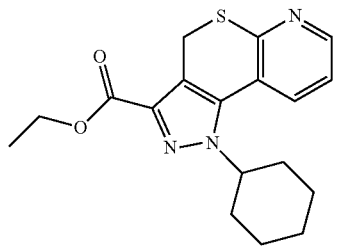

230 mg yield of the title compound. $^1$H NMR (400 MHz, DMSO-$d_6$) δ = 8.37-8.36 (dd, J1 = 1.32 Hz, J2 = 4.72 Hz, 1H), 7.95-7.93 (m, 1H), 7.36-7.33 (dd, J1 = 4.76 Hz, J2 = 7.96 Hz, 1H), 4.49-4.44 (m, 1H), 4.33-4.28 (q, 2H), 4.26 (s, 2H), 1.99-1.96 (m, 2H), 1.92-1.86 (m, 4H), 1.83-1.79 (m, 1H), 1.68-1.64 (m, 2H), 1.46-1.40 (t, J = 13 Hz, 3H), 1.32 (m, 1H). MS (ESI+): 344.0. HPLC (max plot) 95.77%; Rt 4.67 min.

Intermediate H.68: 4-[3-(Ethoxycarbonyl)pyrazolo[3',4':4,5]thiopyrano[2,3-b]pyridin-1(4H)-yl]benzoic acid

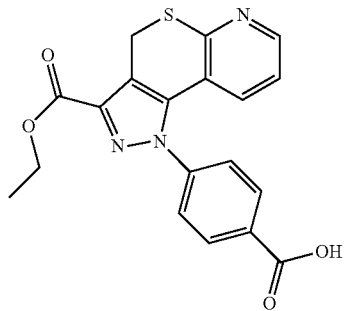 [SMILES: CCOC(=O)c1nn(-c2ccc(C(=O)O)cc2)c2c1CSc1ncccc1-2]

960 mg of the title compound. $^1$H NMR (DMSO-$d_6$, 400 MHz): δ 8.28-8.26 (m, 1H), 8.05-8.03 (m, 2H), 7.49-7.47 (d, J = 8.0 Hz, 2H), 7.02-76.99 (m, 1H), 6.95-6.93 (d, J = 7.9 Hz, 1H), 4.40 (s, 2H), 4.35-4.30 (m, 2H), 1.33-1.29 (t, J = 7.1 Hz, 3H). MS (ESI+): 382.0.

Intermediate H.69: Ethyl 1-phenyl-1,4-dihydropyrazolo[3',4':4,5]thiopyrano[3,2-c]pyridine-3-carboxylate

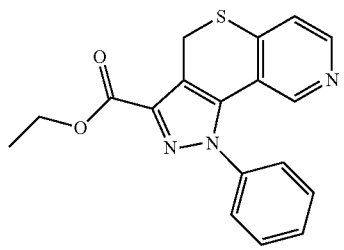 [SMILES: CCOC(=O)c1nn(-c2ccccc2)c2c1CSc1ccncc1-2]

450 mg of the title compound. $^1$H NMR (DMSO-$d_6$, 400 MHz): δ 8.22-8.21 (d, J = 5.2 Hz, 1H), 7.69 (s, 1H), 7.62-7.61 (d, J = 7.0 Hz, 3H), 7.52-7.49 (m, 3H), 4.37 (s, 2H), 4.35-4.30 (m, 2H), 1.33-1.30 (t, J = 7.1 Hz, 3H). MS (ESI+): 338.2. HPLC (max plot) 94.29%; Rt 3.02 min.

Intermediate H.70: Ethyl 1-phenyl-1,4-dihydrothieno[3',2':5,6]thiopyrano[4,3-c]pyrazole-3-carboxylate

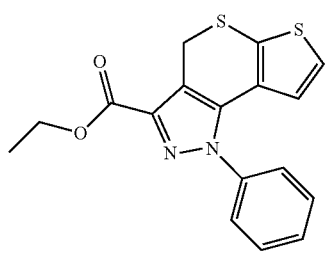 [SMILES: CCOC(=O)c1nn(-c2ccccc2)c2c1CSc1sccc1-2]

357 mg of the title compound. $^1$H NMR (DMSO-$d_6$, 400 MHz): δ 7.61 (m, 3H), 7.52-7.50 (m, 2H), 7.35-7.34 (d, J = 5.4 Hz, 1H), 6.23-6.21 (d, J = 5.4 Hz, 1H), 4.40 (s, 2H), 4.34-4.29 (q, 2H), 1.34-1.30 (t, J = 7.1 Hz, 3H). MS (ESI+): 343.0. HPLC (max plot) 95.37%; Rt 5.51 min.

Intermediate H.71: Ethyl 1-(6-methoxypyridin-3-yl)-1,4-dihydrothieno[3',2':5,6]thiopyrano[4,3-c]pyrazole-3-carboxylate

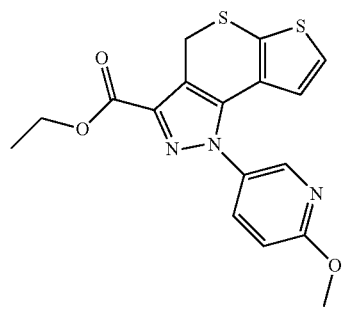 [SMILES: CCOC(=O)c1nn(-c2ccc(OC)nc2)c2c1CSc1sccc1-2]

300 mg of the title compound. MS (ESI+): 374.0.

Intermediate H.72: Ethyl 1-cyclohexyl-1,4-dihydrothieno[3',2':5,6]thiopyrano[4,3-c]pyrazole-3-carboxylate

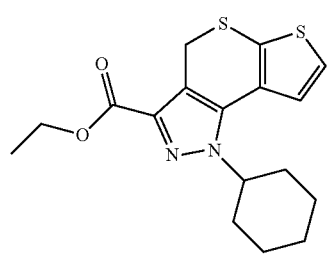 [SMILES: CCOC(=O)c1nn(C2CCCCC2)c2c1CSc1sccc1-2]

200 mg of the title compound. MS (ESI+): 349.2.

Intermediate H.73: Ethyl 1-phenyl-1,4-dihydrothieno[2',3': 5,6]thiopyrano[4,3-c]pyrazole-3-carboxylate

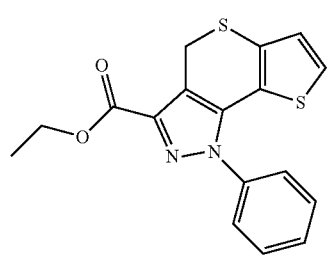 [SMILES: CCOC(=O)c1nn(-c2ccccc2)c2c1CSc1ccsc1-2]

450 mg of the title compound. MS (ESI+): 343.0.

Intermediate H.74: Ethyl 1-cyclohexyl-1,4-dihydrothieno[2',3':5,6]thiopyrano[4,3-c]pyrazole-3-carboxylate

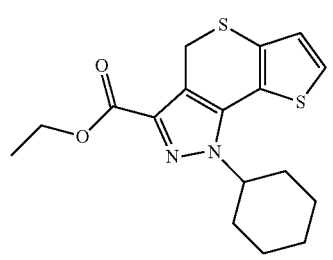 [SMILES: CCOC(=O)c1nn(C2CCCCC2)c2c1CSc1ccsc1-2]

350 mg of the title compound. MS (ESI+): 349.2.

-continued

Intermediate H.75: Ethyl 7-[(tert-butoxycarbonyl)amino]-1-(tetrahydro-2H-pyran-4-yl)-1,4-dihydropyrazolo[3',4':4,5]thiopyrano[3,2-d][1,3]thiazole-3-carboxylate

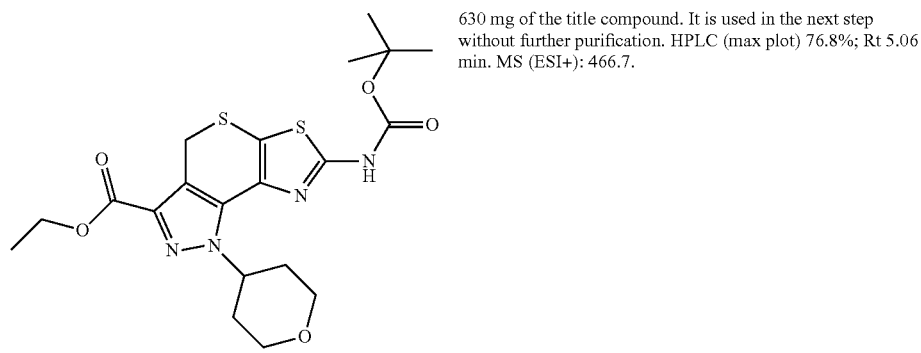

630 mg of the title compound. It is used in the next step without further purification. HPLC (max plot) 76.8%; Rt 5.06 min. MS (ESI+): 466.7.

Procedure I

Intermediate I.1

4-[3-(Ethoxycarbonl)thiochromeno[4,3-c]pyrazol-1(4H)-yl]benzoic acid

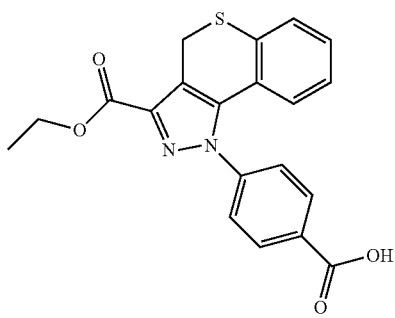 [SMILES: CCOC(=O)c1nn(-c2ccc(C(=O)O)cc2)c2c1CSc1ccccc1-2]

To a solution of ethyl oxo(4-oxo-3,4-dihydro-2H-thiochromen-3-yl)acetate (10.1 g; 38.21 mmol; 1 eq.) in EtOH (100 mL) and acetic acid (6.56 mL) is added 4-hydrazinobenzoic acid 97% (8.39 g; 53.5 mmol; 1.4 eq.). The reaction mixture is heated up to reflux for 2 h. The precipitate is filtrated off and washed with water. The filtrate is evaporated to dryness. Water is added and the mixture is sonicated then filtered off, washed with water (×3) and dried under reduced pressure to afford an orange solid. The 2 solid residues are combined and taken up in MTBE (250 ml) then heated to reflux for 30 min. The precipitate is filtered off, washed with MTBE (×2) and dried under reduced pressure to afford 19.05 g of the title compound. $^1$H NMR (DMSO-$d_6$) δ 13.30 (br s, 1H), 8.11 (d, J=8.6 Hz, 2H), 7.60 (d, J=8.6 Hz, 2H), 7.53-7.51 (m, 1H), 7.27-7.19 (m, 1H), 7.07-7.01 (m, 1H), 6.77-6.73 (m, 1H), 4.35 (q, J=7.1 Hz, 2H), 4.24 (s, 2H), 1.33 (t, J=7.1 Hz, 3H). HPLC (max plot) 61.0%; Rt 4.15 min. MS (ESI+): 380.9

Intermediates described below are obtained following procedure I

Intermediate I.2: 3-[3-(Ethoxycarbonyl)thiochromeno[4,3-c]pyrazol-1(4H)-yl]benzoic acid

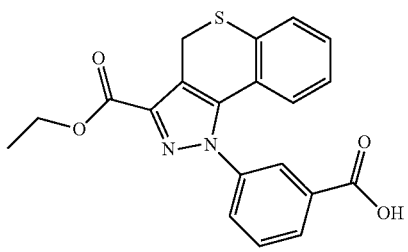 [SMILES: CCOC(=O)c1nn(-c2cccc(C(=O)O)c2)c2c1CSc1ccccc1-2]

14 g of the title compound as an orange powder. HPLC (max plot) 56.4%; Rt 4.11 min. MS (ESI+): 380.8.

Intermediate I.3: Ethyl 1-(3-(benzyloxy)phenyl)-1,4-dihydrothiochromeno[4,3-c]pyrazole-3-carboxylate

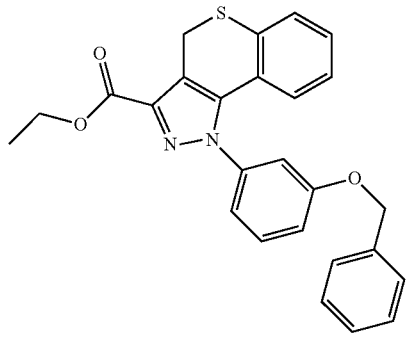 [SMILES: CCOC(=O)c1nn(-c2cccc(OCc3ccccc3)c2)c2c1CSc1ccccc1-2]

6.5 g (77%) of the title compund as a light brown liquid. $^1$H NMR (DMSO-d$_6$, 400 MHz): δ 7.467-7.315 (m, 7H), 7.250-7.003 (m, 3H), 6.987-6.965 (m, 2H), 6.721-6.699 (m, 1H), 5.149 (s, 2H), 4.354-4.301 (m, 2H), 4.231 (s, 2H), 1.332-1.297 (m, 3H). MS (ESI+): 443.0. HPLC (max plot): 92%; Rt 6.13 min.

Intermediate I.4: Ethyl 6-fluoro-1-[4-(morpholin-4-ylmethyl)phenyl]-1,4-dihydrothiochromeno[4,3-c]pyrazole-3-carboxylate 5,5-dioxide

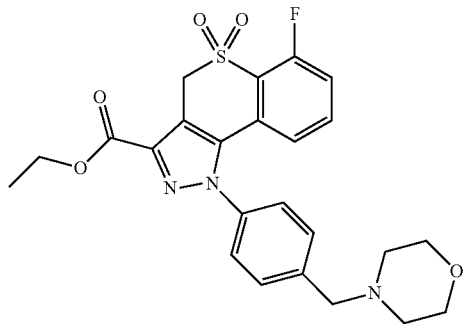 [SMILES: CCOC(=O)c1nn(-c2ccc(CN3CCOCC3)cc2)c2c1CS(=O)(=O)c1c(F)cccc1-2]

160 mg of the title compound. $^1$H NMR (DMSO-d$_6$) δ. HPLC (max plot) 82.2%; Rt 2.45 min. MS (ESI+): 486.3.

Intermediate I.5: Ethyl 7-fluoro-1-[4-(morpholin-4-ylmethyl)phenyl]-1,4-dihydrothiochromeno[4,3-c]pyrazole-3-carboxylate 5,5-dioxide

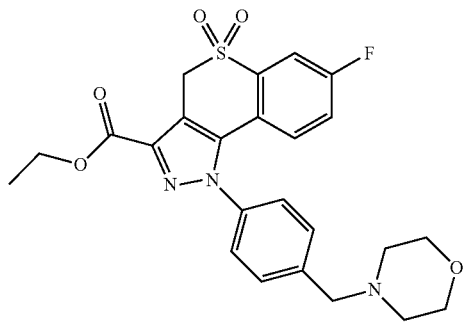 [SMILES: CCOC(=O)c1nn(-c2ccc(CN3CCOCC3)cc2)c2c1CS(=O)(=O)c1cc(F)ccc1-2]

250 mg of the title compound as a yellow solid. $^1$H NMR (DMSO-d$_6$) δ (, H), 7.83-7.80 (m, 1H), 7.54 (d, J = 7.5 Hz, 2H), 7.46 (d, J = 7.5 Hz, 2H), 7.13-7.09 (m, 1H), 6.93-6.90 (m, 1H), 4.84 (s, 2H), 4.49 (q, J = 9 Hz, 2H), 3.78-3.74 (m, 4H), 3.62 (s, 2H), 2.50-2.48 (m, 4H), 1.45 (t, J = 9 Hz, 3H). HPLC (max plot) 92.7%; Rt 3.20 min. MS (ESI−): 484.4.

Intermediate I.6: Ethyl 7-methoxy-1-[4-(morpholin-4-ylmethyl)phenyl]-1,4-dihydrothiochromeno[4,3-c]pyrazole-3-carboxylate 5,5-dioxide

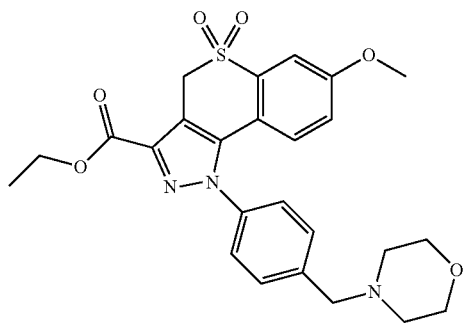 [SMILES: CCOC(=O)c1nn(-c2ccc(CN3CCOCC3)cc2)c2c1CS(=O)(=O)c1cc(OC)ccc1-2]

350 mg (83%) of the title compound as a orange oil. HPLC (max plot) 59.8%; Rt 4.12 min. MS (ESI+): 498.3.

Intermediate I.7: Ethyl 8-fluoro-1-[4-(morpholin-4-ylmethyl)phenyl]-1,4-dihydrothiochromeno[4,3-c]pyrazole-3-carboxylate 5,5-dioxide

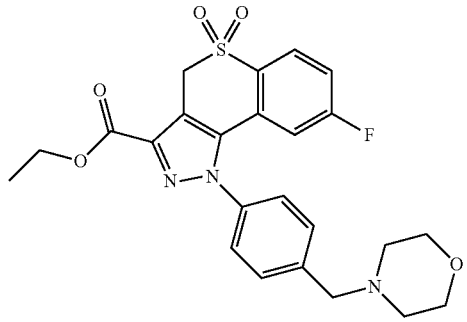 [SMILES: CCOC(=O)c1nn(-c2ccc(CN3CCOCC3)cc2)c2c1CS(=O)(=O)c1ccc(F)cc1-2]

200 mg (86%) of the title compound as a yellow solid. 1H NMR (DMSO-d6) δ 8.11 (dd, J = 5.6, 8.7 Hz, 1H), 7.66-7.44 (m, 5H), 6.40 (dd, J = 2.47, 10.1 Hz, 1H), 5.03 (s, 2H), 4.38 (q, J = 7.09 Hz, 2H), 3.69-3.54 (m, 6H), 2.46-2.36 (m, 4H), 1.35 (tr, 3H). HPLC (max plot) 99.3%; Rt 2.59 min. MS (ESI+): 486.3.

Intermediate I.8: Ethyl 1-azetidin-3-yl-1,4-dihydrothiochromeno[4,3-c]pyrazole-3-carboxylate

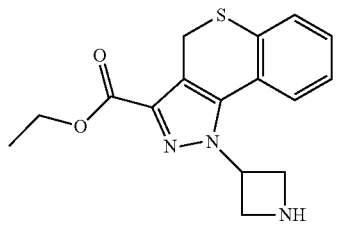 [SMILES: CCOC(=O)c1nn(C2CNC2)c2c1CSc1ccccc1-2]

5.75 g (86%) of the title compound as a beige powder. HPLC (max plot) 61.3%; Rt 2.91 min. MS (ESI+): 315.8.

Intermediate I.9: Ethyl 1-pyrrolidin-3-yl-1,4-dihydrothiochromeno[4,3-c]pyrazole-3-carboxylate

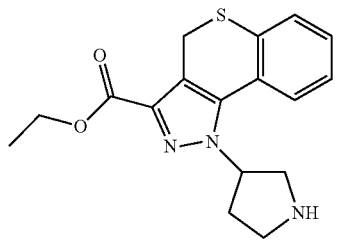 [SMILES: CCOC(=O)c1nn(C2CCNC2)c2c1CSc1ccccc1-2]

7 g (93.2%) of the title compound as a brown solid. It is used in the next step without further purification. MS (ESI+): 330.0.

Intermediate I.10: Ethyl 1-(tetrahydrofuran-3-yl)-1,4-dihydrothiochromeno[4,3-c]pyrazole-3-carboxylate

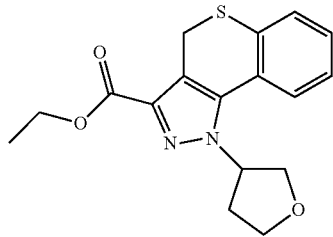 [SMILES: CCOC(=O)c1nn(C2CCOC2)c2c1CSc1ccccc1-2]

945 mg of the title compound as a brown oil. $^1$H NMR (DMSO-d$_6$) δ 7.75-7.72 (m, 1H), 7.58-7.55 (m, 1H), 7.41-7.31 (m, 2H), 5.52-5.45 (m, 1H), 4.35-4.28 (quad, J = 7.10 Hz, 2H), 4.18-3.98 (m, 5H), 3.90-3.83 (m, 1H), 2.47-2.31 (m, 2H), 1.34-1.30 (t, J = 7.10 Hz, 3H). HPLC (max plot) 95.7%; Rt 4.47 min. MS (ESI+): 331.1.

Intermediate I.11: Ethyl 1-piperidin-4-yl-1,4-dihydrothiochromeno[4,3-c]pyrazole-3-carboxylate

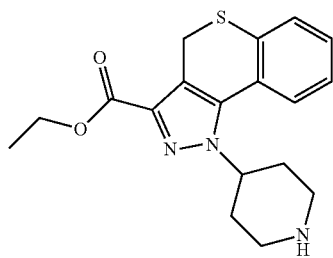 [SMILES: CCOC(=O)c1nn(C2CCNCC2)c2c1CSc1ccccc1-2]

2.95 g (97%) of the title compound as a yellow foam. HPLC (max plot) 77.3%; Rt 3.09 min.

Intermediate I.12: Ethyl 1-piperidin-3-yl-1,4-dihydrothiochromeno[4,3-c]pyrazole-3-carboxylate

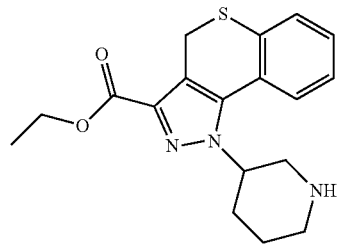 [SMILES: CCOC(=O)c1nn(C2CCCNC2)c2c1CSc1ccccc1-2]

13.9 g of the title compound as a brown sticky solid. $^1$H NMR (DMSO-$d_6$) δ 1H NMR (300 MHz, DMSO) δ 7.66 (dd, J = 7.7, 1.1, 1H), 7.56 (dd, J = 7.6, 1.5, 1H), 7.37 (dtd, J = 19.4, 7.5, 1.4, 2H), 4.67-4.49 (m, 1H), 4.31 (q, J = 7.1, 2H), 4.10 (s, 2H), 3.15 (dd, J = 12.2, 3.6, 1H), 3.00-2.85 (m, 2H), 2.63-2.40 (m, 2H), 2.22-2.02 (m, 2H), 1.83-1.67 (m, 1H), 1.66-1.45 (m, 1H), 1.32 (t, J = 7.1, 3H). HPLC (max plot) 87.8%; Rt 3.58 min. MS (ESI+): 344.1.

Intermediate I.13: Ethyl 1-azepan-4-yl-1,4-dihydrothiochromeno[4,3-c]pyrazole-3-carboxylate

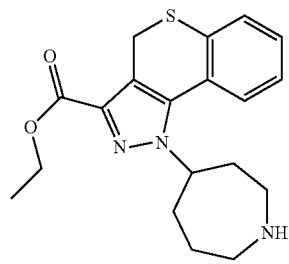 [SMILES: CCOC(=O)c1nn(C2CCCNCC2)c2c1CSc1ccccc1-2]

700 mg (quant.) of the title compound. The crude is taken as such for next step. MS (ESI+): 358.2.

Intermediate I.14: Ethyl 6-fluoro-1-pyrrolidin-3-yl-1,4-dihydrothiochromeno[4,3-c]pyrazole-3-carboxylate

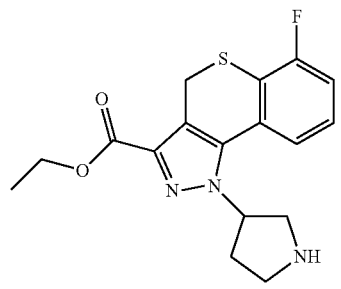 [SMILES: CCOC(=O)c1nn(C2CCNC2)c2c1CSc1c(F)cccc1-2]

5.8 g (94%) of the title compound as a solid. It is use in the next step without further purification. MS (ESI+): 347.8.

Intermediate I.15: Ethyl 6-fluoro-1-(tetrahydrofuran-3-yl)-1,4-dihydrothiochromeno[4,3-c]pyrazole-3-carboxylate

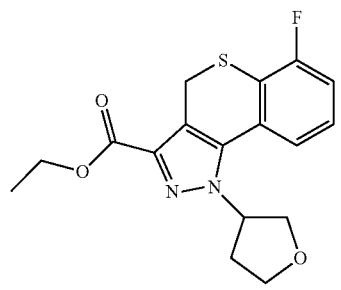 [SMILES: CCOC(=O)c1nn(C2CCOC2)c2c1CSc1c(F)cccc1-2]

752 mg of the title compound as a brown glue. $^1$H NMR (DMSO-$d_6$) δ 7.63-7.60 (m, 1H), 7.46-7.38 (m, 1H), 7.36-7.30 (m, 1H), 5.52-5.45 (m, 1H), 4.36-4.29 (quad, J = 7.10 Hz, 2H), 4.18-3.98 (m, 5H), 3.90-3.83 (m, 1H), 2.49-2.31 (m, 2H), 1.35-1.30 (t, J = 7.10 Hz, 3H). HPLC (max plot) 73.5%; Rt 4.47 min. MS (ESI+): 349.1.

Intermediate I.16: Ethyl 6-fluoro-1-piperidin-3-yl-1,4-dihydrothiochromeno[4,3-c]pyrazole-3-carboxylate

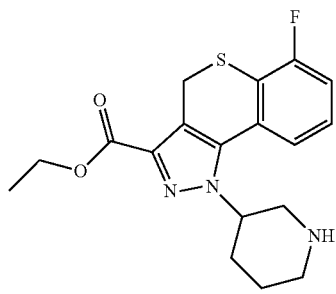 [SMILES: CCOC(=O)c1nn(C2CCCNC2)c2c1CSc1c(F)cccc1-2]

3.3 g of the title compound. It is use in the next step without further purification. MS (ESI+): 461.8.

Intermediate I.17: Ethyl 6-fluoro-1-(tetrahydro-2H-pyran-4-yl)-1,4-dihydrothiochromeno[4,3-c]pyrazole-3-carboxylate

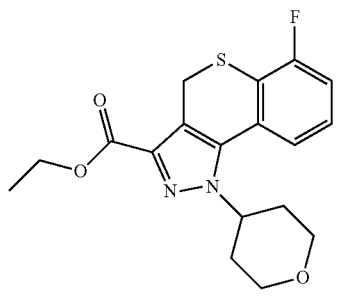 [SMILES: CCOC(=O)c1nn(C2CCOCC2)c2c1CSc1c(F)cccc1-2]

480 mg (75%) of the title compound. HPLC (max plot) 61.2%; Rt 4.31 min. MS (ESI+): 462.8

Intermediate I.18: Ethyl 6-chloro-1-piperidin-3-yl-1,4-dihydrothiochromeno[4,3-c]pyrazole-3-carboxylate

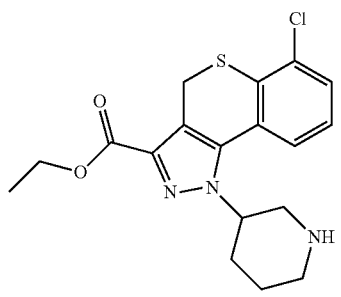 [SMILES: CCOC(=O)c1nn(C2CCCNC2)c2c1CSc1c(Cl)cccc1-2]

3.9 g of the title compund as a solid. MS (ESI+): 378.1.

Intermediate I.19: Ethyl 6-chloro-1-(tetrahydro-2H-pyran-4-yl)-1,4-dihydrothiochromeno[4,3-c]pyrazole-3-carboxylate

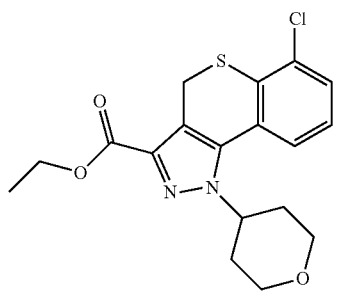 [SMILES: CCOC(=O)c1nn(C2CCOCC2)c2c1CSc1c(Cl)cccc1-2]

425 mg of the title compound as beige needles. MS (ESI+): 378.7

-continued

Intermediate I.20: Ethyl 1-(tetrahydro-2H-pyran-4-yl)-1,4-dihydrothieno[3',2':5,6]thiopyrano[4,3-c]pyrazole-3-carboxylate

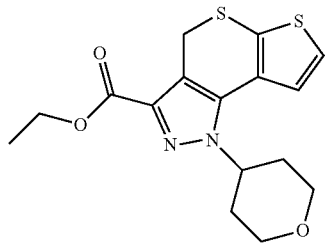 [SMILES: CCOC(=O)c1nn(C2CCOCC2)c2c1CSc1sccc1-2]

400 mg of the title compound as a white powder.. HPLC (max plot) 80.2%; Rt 4.23 min. MS (ESI+): 350.7.

Procedure J

Intermediate J.1

Ethyl 1-piperidin-3-yl-7-(trifluoromethoxy)-1,4-dihydrothiochromeno[4,3-c]pyrazole-3-carboxylate

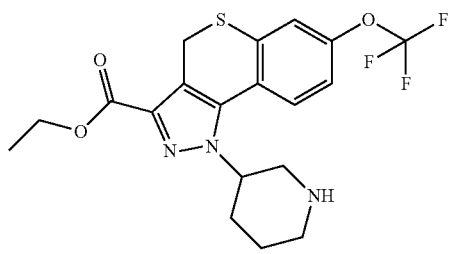 [SMILES: CCOC(=O)c1nn(C2CCCNC2)c2c1CSc1cc(OC(F)(F)F)ccc1-2]

To a solution of ethyl oxo[4-oxo-7-(trifluoromethoxy)-3,4-dihydro-2H-thiochromen-3-yl]acetate (3.00 g; 8.61 mmol; 1 eq.) and tert-butyl 3-[2-(tert-butoxycarbonyl)hydrazino]piperidine-1-caroxylate (4.08 g; 12.92 mmol; 1.50 eq.) in EtOH (80 ml) is added HCl (4M in dioxane, 42.38 mL) were added in a dropwise fashion. Reaction mixture is heated at 75° C. for 5 h after which it is concentrated under vacuum, partitioned between NaHCO₃ sat (pH 7-8) and EtOAc. Organic layer is washed NaHCO₃ sat and brine, dried over MgSO4 to give 3.1 g (88%) of the title compound as a brown solid. $^1$H NMR (DMSO, 300 MHz): δ 7.77 (d, J=9.43 Hz, 1H), 7.62 (s, 1H), 7.39 (d, J=7.7 Hz, 1H), 4.61-4.46 (m, 1H), 4.40-4.26 (m, 2H), 4.17 (s, 1H), 4.09-3.98 (m, 1H), 3.19-3.06 (m, 1H), 2.97-2.82 (m, 2H), 2.17-2.05 (m, 2H), 1.99 (s, 1H), 1.80-1.67 (m, 1H), 1.67-1.45 (m, 1H), 1.32 (t, J=7.0 Hz, 3H), 1.18 (t, J=6.9 Hz, 1H).

Intermediates described below are obtained following protocol outlined in procedure J Intermediate J.2: Ethyl 1-[4-(1-methyl-1-morpholin-4-ylethyl)phenyl]-1,4-dihydrothiochromeno[4,3-c]pyrazole-3-carboxylate 5,5-dioxide

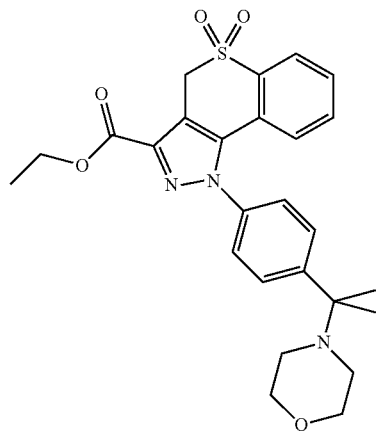 [SMILES: CCOC(=O)c1nn(-c2ccc(C(C)(C)N3CCOCC3)cc2)c2c1CS(=O)(=O)c1ccccc1-2]

96 mg of the title compound as an orange solid. $^1$H NMR (DMSO-d₆, 300 MHz): δ 8.09-7.97 (m, 1H), 7.72-7.61 (m, 1H), 7.61-7.48 (m, 3H), 7.48-7.34 (m, 2H), 6.87-6.74 (m, 1H), 4.99 (s, 2H), 4.37 (q, J = 7.1 Hz, 2H), 3.58-3.39 (m, 4H), 2.61 (s, 2H), 2.48-2.29 (m, 4H), 1.34 (t, J = 7.1 Hz, 3H), 1.01-0.92 (m, 2H), 0.88-0.76 (m, 2H). MS (ESI+): 508.4.

Intermediate J.3: Ethyl 1-[4-(1,1-dimethyl-2-morpholin-4-ylethyl)phenyl]-1,4-dihydrothiochromeno[4,3-c]pyrazole-3-carboxylate 5,5-dioxide

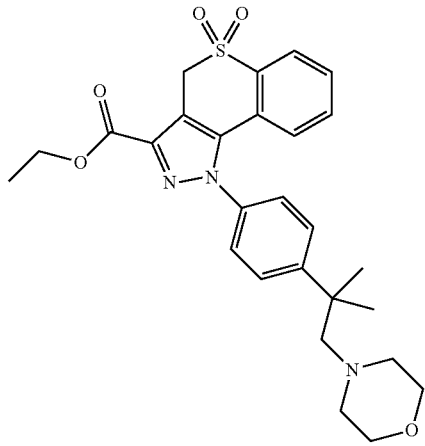 [SMILES: CCOC(=O)c1nn(-c2ccc(C(C)(C)CN3CCOCC3)cc2)c2c1CS(=O)(=O)c1ccccc1-2]

630 mg of the title compound as a orange solid. $^1$H NMR (DMSO-$d_6$, 300 MHz): δ 8.11-7.97 (m, 1H), 7.72-7.59 (m, 3H), 7.55-7.36 (m, 3H), 6.83-6.70 (m, 1H), 4.99 (s, 2H), 4.44-4.31 (m, 2H), 2.54-3.39 (m, 4H), 2.56-2.43 (m, 4H), 2.31-2.18 (m, 2H), 1.47-1.24 (m, 9H). MS (ESI+): 510.36.

Intermediate J.4: Ethyl 1-{4-[2-(dimethylamino)-1,1-dimethylethyl)phenyl}-1,4-dihydrothiochromeno[4,3-c]pyrazole-3-carboxylate 5,5-dioxide

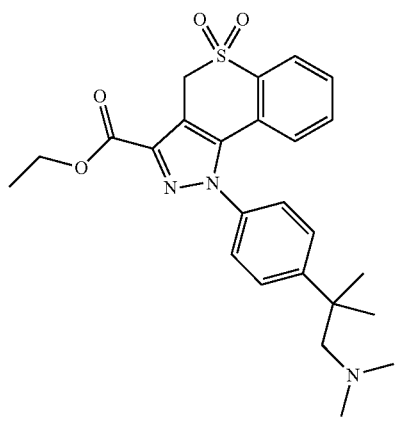 [SMILES: CCOC(=O)c1nn(-c2ccc(C(C)(C)CN(C)C)cc2)c2c1CS(=O)(=O)c1ccccc1-2]

700 mg (88%) of the title compound as a orange solid. $^1$H NMR (DMSO-$d_6$, 300 MHz): δ 8.10-7.96 (m, 1H), 7.72-7.56 (m, 3H), 7.56-7.36 (m, 3H), 6.82-6.71 (m, 1H), 4.99 (s, 2H), 4.37 (q, J = 7.09 Hz, 2H), 2.53-2.45 (m, 2H), 2.03 (s, 6H), 1.40-1.28 (m, 9H). MS (ESI+): 468.3.

Intermediate J.5: Ethyl 1-{4-[1-(morpholin-4-ylmethyl)cyclopropyl]phenyl}-1,4-dihydrothiochromeno[4,3-c]pyrazole-3-carboxylate 5,5-dioxide

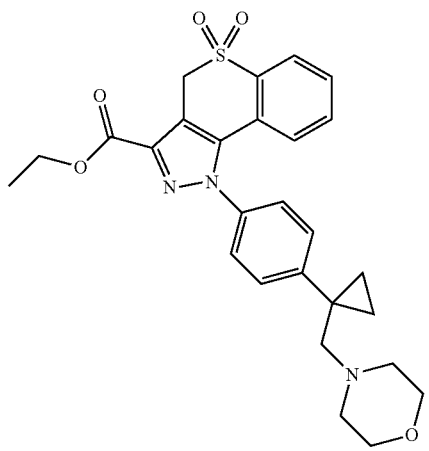 [SMILES: CCOC(=O)c1nn(-c2ccc(C3(CN4CCOCC4)CC3)cc2)c2c1CS(=O)(=O)c1ccccc1-2]

189 mg of the title compound as an orange solid. $^1$H NMR (DMSO-$d_6$, 300 MHz): δ 8.09-7.97 (m, 1H), 7.72-7.61 (m, 1H), 7.61-7.48 (m, 3H), 7.48-7.34 (m, 2H), 6.87-6.74 (m, 1H), 4.99 (s, 2H), 4.37 (q, J = 7.1 Hz, 2H), 3.58-3.39 (m, 4H), 2.61 (s, 2H), 2.48-2.29 (m, 4H), 1.34 (t, J = 7.1 Hz, 3H), 1.01-0.92 (m, 2H), 0.88-0.76 (m, 2H). MS (ESI+): 508.44..

Intermediate J.6: Ethyl 6-methoxy-1-piperidin-3-yl-1,4-dihydrothiochromeno[4,3-c]pyrazole-3-carboxylate

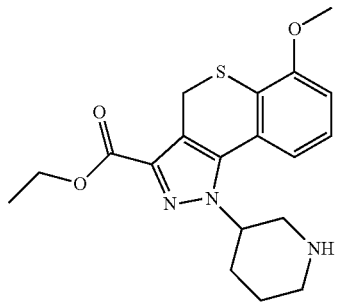 [SMILES: CCOC(=O)c1nn(C2CCCNC2)c2c1CSc1c(OC)cccc1-2]

13.8 g (90%) of the title compound as an orange solid. MS (ESI+): 374.24..

Intermediate J.7: Ethyl 6-methyl-1-piperidin-3-yl-1,4-dihydrothiochromeno[4,3-c]pyrazole-3-carboxylate

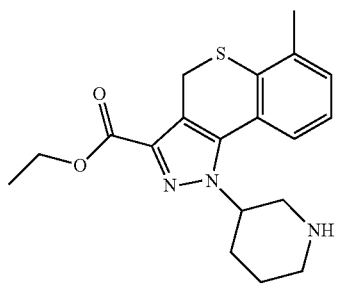 [SMILES: CCOC(=O)c1nn(C2CCCNC2)c2c1CSc1c(C)cccc1-2]

12 g (80%) of the title compound. HPLC (max plot) 61.4%; Rt 3.18 min. MS (ESI+): 358.21

Intermediate J.8: Ethyl 7-fluoro-1-piperidin-3-yl-1,4-dihydrothiochromeno[4,3-c]pyrazole-3-carboxylate

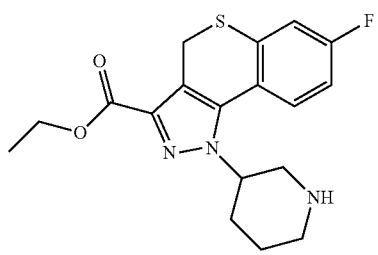 [SMILES: CCOC(=O)c1nn(C2CCCNC2)c2c1CSc1cc(F)ccc1-2]

5.4 g of the title compound a white powder. MS (ESI+): 362.19. HPLC (max plot) 79.6%; Rt 3.70 min Intermediate J.9: Ethyl 7-methoxy-1-piperidin-3-yl-1,4-dihydrothiochromeno[4,3-c]pyrazole-3-carboxylate

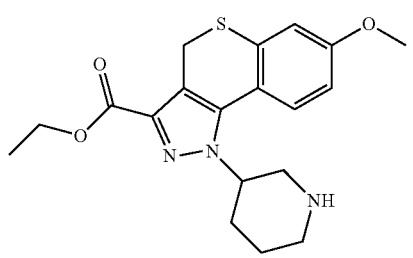 [SMILES: CCOC(=O)c1nn(C2CCCNC2)c2c1CSc1cc(OC)ccc1-2]

6 mg of the title compound as a brown solid. $^1$H NMR (DMSO-$d_6$, 300 MHz): δ 7.59 (d, J = 8.8, 1H), 7.14 (d, J = 2.7, 1H), 6.96 (dd, J = 8.7, 2.7, 1H), 4.61-4.44 (m, 1H), 4.30 (q, J = 7.1, 2H), 4.09 (s, 2H), 3.81 (s, 3H), 3.12 (dd, J = 12.3, 3.5, 1H), 3.00-2.82 (m, 3H), 2.63-2.40 (m, 1H), 2.19-2.01 (m, 2H), 1.81-1.66 (m, 1H), 1.64-1.47 (m, 1H), 1.31 (t, J = 7.1, 3H). MS (ESI+): 372.22. HPLC (max plot) 92.1%; Rt 3.67 min.

Intermediate J.10: Ethyl 8-methoxy-1-piperidin-3-yl-1,4-dihydrothiochromeno[4,3-c]pyrazole-3-carboxylate

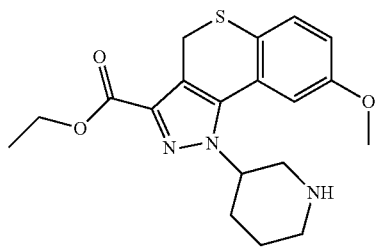 [SMILES: CCOC(=O)c1nn(C2CCCNC2)c2c1CSc1ccc(OC)cc1-2]

3.5 g of the title compound a brown oil. $^1$H NMR (300 MHz, DMSO) δ 7.49 (d, J = 8.6, 1H), 7.14 (d, J = 2.6, 1H), 6.97 (dd, J = 8.6, 2.6, 1H), 4.68-4.51 (m, 1H), 4.31 (q, J = 7.1, 2H), 3.84 (s, 3H), 3.33 (s, 7H), 3.13 (d, J = 9.9, 1H), 3.01-2.83 (m, 2H), 2.12 (s, 2H), 1.82-1.46 (m, 2H), 1.17 (dd, J = 8.6, 5.6, 3H).

Procedure K

Intermediate K.1

Ethyl 1-[1-(tert-butoxycarbonyl)piperidin-4-yl]-1,4-dihydrothio chromeno[4,3-c]pyrazole-3-carboxylate

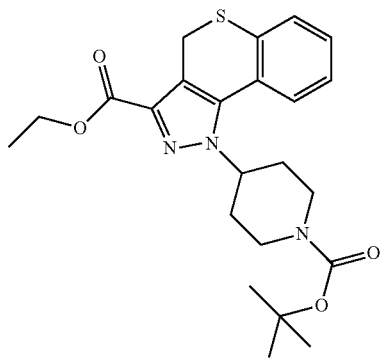 [SMILES: CCOC(=O)c1nn(C2CCN(C(=O)OC(C)(C)C)CC2)c2c1CSc1ccccc1-2]

Ethyl 1-piperidin-4-yl-1,4-dihydrothiochromeno[4,3-c]pyrazole-3-carboxylate (2.95 g; 8.59 mmol; 1 eq.), di-tert-butyl dicarbonate (2.25 g; 10.31 mmol; 1.2 eq.) and trietylamine (1.2 ml; 8.59 mmol; 1 eq.) are dissolved in DCM (29.5 ml) and the reaction mixture is stirred for 3 days at room temperature. DCM is added and the organic phase is washed with water, dried over $MgSO_4$, filtered and concentrated. The residue is purified on silica eluting from 5 to 15% EtOAc in cyclohexane to afford, after concentration of the desired fractions, 3.05 g (80%) of the title compound as a beige foam. $^1$H NMR (DMSO-$d_6$) δ 7.69 (d, 1 H, J=7.6 Hz): 7.56 (dd, 1H, J=7.5 Hz): 7.43-7.30 (m, 2H), 4.84 (m, 1H), 4.1 (q, 2H, J=7.7 Hz): 4.10 (s, 2H), 3.10-2.85 (m, 2H), 2.06-1.86 (m, 4H), 1.49 (s, 9H), 1.31 (t, 3H, J=7.7 Hz). HPLC (max plot) 85.2%; Rt 5.79 min.

Intermediates described below are obtained following Procedure K.

Intermediate K.2: Ethyl 1-[1-(tert-butoxycarbonyl)azetidin-3-yl]-1,4-dihydrothio chromeno[4,3-c]pyrazole-3-carboxylate

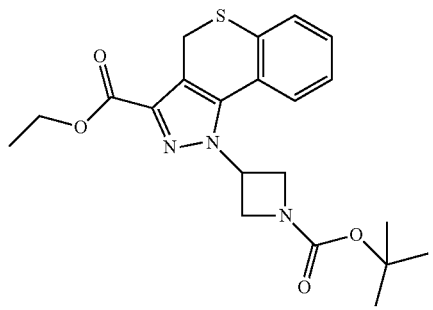 [SMILES: CCOC(=O)c1nn(C2CN(C(=O)OC(C)(C)C)C2)c2c1CSc1ccccc1-2]

5.57 g (82%) of the title compound as a brown solid. $^1$H NMR (DMSO-$d_6$) δ 7.56-7.53 (m, 2H), 7.36-7.33 (m, 2H), 5.65-5.58 (m, 1H), 4.45-4.40 (m, 2H), 4.38-4.31 (m, 2H), 4.29-4.24 (m, 2H), 4.13 (m, 2H), 1.42 (s, 9H), 1.37-1.36 (m, 3H). HPLC (max plot) 56.7%; Rt 5.22 min.

Intermediate K.3: Ethyl 1-[1-(tert-butoxycarbonyl)pyrrolidin-3-yl]-1,4-dihydrothio chromeno[4,3-c]pyrazole-3-carboxylate

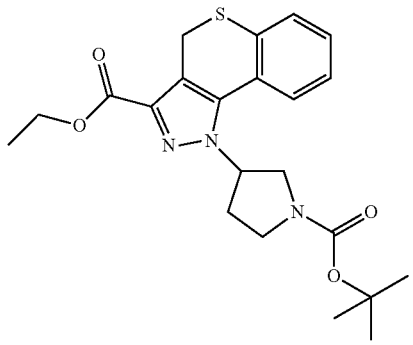 [SMILES: CCOC(=O)c1nn(C2CCN(C(=O)OC(C)(C)C)C2)c2c1CSc1ccccc1-2]

5.2 g of the title compound as a white foam. $^1$H NMR (DMSO-$d_6$, 400 MHz): δ 7.73-7.71 (d, J = 7.4 Hz, 1H), 7.56-7.54 (m, 1H), 7.39-7.30 (m, 2H), 5.45-5.44 (m, 1H), 4.32-4.27 (q, 2H), 4.11 (s, 2H), 3.82-3.80 (m, 1H), 3.62-3.53 (m, 2H), 3.42 (m, 1H), 2.32 (m, 2H), 1.41-1.35 (m, 9H), 1.32-1.28 (t, J = 7.1 Hz, 3H). MS (ESI+): 330.2 (M-Boc).

Intermediate K.4: Ethyl 1-[1-(tert-butoxycarbonyl)piperidin-3-yl]-1,4-dihydrothio chromeno[4,3-c]pyrazole-3-carboxylate

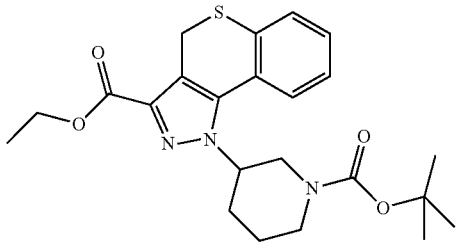 [SMILES: CCOC(=O)c1nn(C2CCCN(C(=O)OC(C)(C)C)C2)c2c1CSc1ccccc1-2]

17.7 g (99%) of the title compound as a orange sticky solid. $^1$H NMR (300 MHz, DMSO) δ 7.75 (bs, 1H), 7.65-7.52 (m, 1H), 7.47-7.27 (m, 2H), 4.58 (bs, 1H), 4.32 (q, J = 7.1, 2H), 4.26-4.01 (m, 3H), 4.02-3.84 (m, 1H), 3.17 (t, J = 11.0, 1H), 2.84 (bs, 1H), 2.36-2.02 (m, 2H), 1.92-1.51 (m, 2H), 1.50-1.21 (m, 12H). HPLC (max plot) 85.1%; Rt 5.95 min. MS (ESI+): 444.26.

Intermediate K.5: Ethyl 1-[1-(tert-butoxycarbonyl)azepan-4-yl]-1,4-dihydrothiochromeno[4,3-c]pyrazole-3-carboxylate

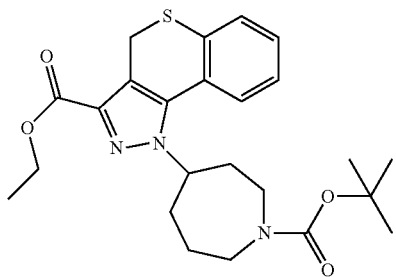 [SMILES: CCOC(=O)c1nn(C2CCCN(C(=O)OC(C)(C)C)CC2)c2c1CSc1ccccc1-2]

350 mg of the title compound as a white solid. $^1$H NMR (DMSO-$d_6$, 400 MHz): δ 7.60-7.54 (m, 2H), 7.34-7.32 (m, 2H), 4.67 (m, 1H), 4.32-4.27 (q, 2H), 4.09 (s, 2H), 3.55-3.51 (m, 2H), 3.38 (m, 2H), 2.20 (m, 2H), 2.02 (m, 2H), 1.84 (m, 1H), 1.70 (m, 1H), 1.40 (m, 9H), 1.36-1.32 (m, 3H). MS (ESI+): 358.2 (M-Boc).

Intermediate K.6: Ethyl 1-[1-(tert-butoxycarbonyl)pyrrolidin-3-yl]-6-fluoro-1,4-dihydrothiochromeno[4,3-c]pyrazole-3-carboxylate

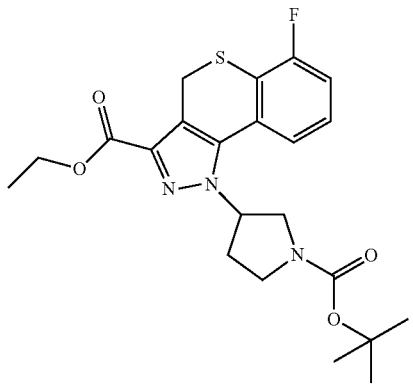 [SMILES: CCOC(=O)c1nn(C2CCN(C(=O)OC(C)(C)C)C2)c2c1CSc1c(F)cccc1-2]

12 g (93%) of the title compound. HPLC (max plot) 57.4%; Rt 5.73 min.

Intermediate K.7: tert-Butyl 3-[6-fluoro-3-(morpholin-4-ylcarbonyl)thiochromeno[4,3-c]pyrazol-1 (4H)-yl]piperidine-1-carboxylate

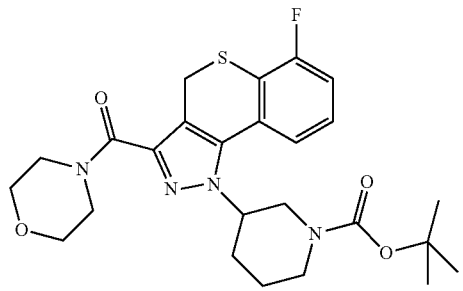 [SMILES: CC(C)(C)OC(=O)N1CCCC(n2nc(C(=O)N3CCOCC3)c3c2-c2cccc(F)c2SC3)C1]

2.8 g (75%) of the title compound as a pale brown oil. HPLC (max plot) 88.7%; Rt 4.73 min. MS (ESI-Boc): 402.8.

Intermediate K.8: Ethyl 1-[1-(tert-butoxycarbonyl)piperidin-3-yl]-6-methoxy-1,4-dihydrothiochromeno[4,3-c]pyrazole-3-carboxylate

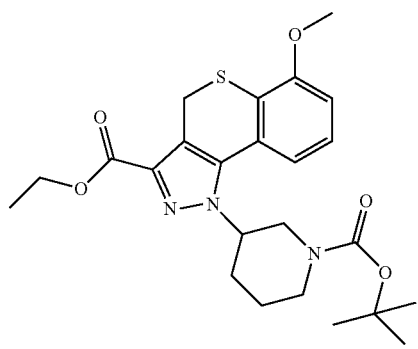 [SMILES: CCOC(=O)c1nn(C2CCCN(C(=O)OC(C)(C)C)C2)c2c1CSc1c(OC)cccc1-2]

5.6 g of the title compound as an orange solid. $^1$H NMR (DMSO-$d_6$, 300 MHz): δ 7.78-7.76 (m, 1H), 7.53-7.36 (m, 2H), 4.80 (s, 2H), 4.65 (bs, 1H), 4.35 (q, J = 7 Hz, 2H), 4.18 (bs, 1H), 4.00-3.94 (m, 4H), 3.23-3.15 (m, 1H), 2.9 (bs, 1H), 2.27-2.15 (m, 2H), 1.83-1.79 (m, 1H), 1.60-1.56 (m, 1H), 1.38-1.30 (m, 12H). HPLC (max plot) 71.5%; Rt 4.74 min.

Intermediate K.9: Ethyl 1-[1-(tert-butoxycarbonyl)piperidin-3-yl]-6-chloro-1,4-dihydrothiochromeno[4,3-c]pyrazole-3-carboxylate

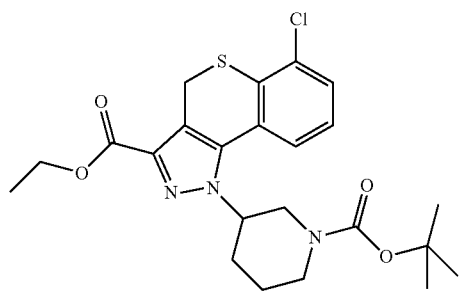 [SMILES: CCOC(=O)c1nn(C2CCCN(C(=O)OC(C)(C)C)C2)c2c1CSc1c(Cl)cccc1-2]

5.3 g (quant) of the title compound. HPLC (max plot) 88.6%; Rt 5.41 min.

Intermediate K.10: Ethyl 1-[1-(tert-butoxycarbonyl)piperidin-3-yl]-6-methyl-1,4-dihydrothiochromeno[4,3-c]pyrazole-3-carboxylate

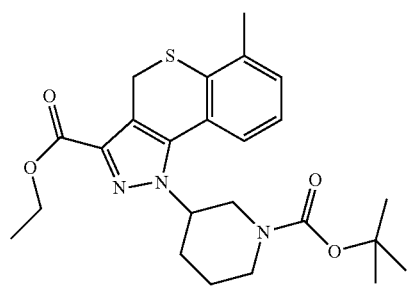 [SMILES: CCOC(=O)c1nn(C2CCCN(C(=O)OC(C)(C)C)C2)c2c1CSc1c(C)cccc1-2]

9.0 g of the title compound. MS (ESI+): 458.4.

Intermediate K.11: Ethyl 1-[1-(tert-butoxycarbonyl)piperidin-3-yl]-7-fluoro-1,4-dihydrothiochromeno[4,3-c]pyrazole-3-carboxylate

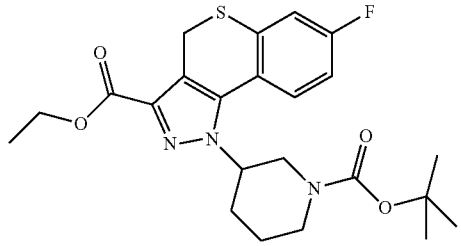 [SMILES: CCOC(=O)c1nn(C2CCCN(C(=O)OC(C)(C)C)C2)c2c1CSc1cc(F)ccc1-2]

12 g (quant) of the title compound. HPLC (max plot) 77.7%; Rt 6.05 min

Intermediate K.12: Ethyl 1-[1-(tert-butoxycarbonyl)piperidin-3-yl]-7-methoxy-1,4-dihydrothiochromeno[4,3-c]pyrazole-3-carboxylate

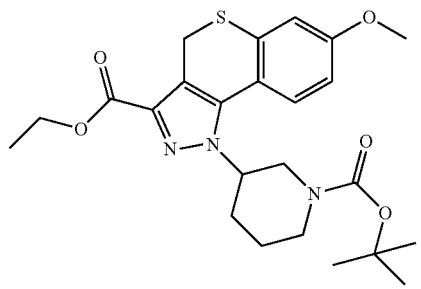 [SMILES: CCOC(=O)c1nn(C2CCCN(C(=O)OC(C)(C)C)C2)c2c1CSc1cc(OC)ccc1-2]

7.82 g (100%) of the title compound as a beige foam. $^1$H NMR (DMSO-$d_6$, 300 MHz): δ 7.68 (bs, 1H), 7.16 (d, J = 2.6, 1H), 6.90 (dd, J = 8.5, 1.4, 1H), 4.55 (bs, 1H), 4.31 (q, J = 7.1, 2H), 4.23-4.04 (m, 3H), 3.94 (m, 1H), 3.86-3.73 (s, 3H), 3.16 (t, J = 11.7, 1H), 2.85 (bs, 1H), 2.34-2.10 (m, 2H), 1.82 (m, 1H), 1.66-1.01 (m, 13H). MS (ESI+): 474.37. HPLC (max plot) 94.0%; Rt 5.59 min.

Intermediate K.13: Ethyl 1-[1-(tert-butoxycarbonyl)piperidin-3-yl]-7-(trifluoromethoxy)-1,4-dihydrothiochromeno[4,3-c]pyrazole-3-carboxylate

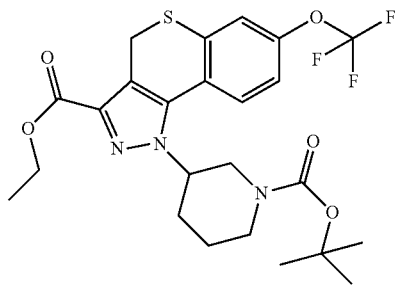 [SMILES: CCOC(=O)c1nn(C2CCCN(C(=O)OC(C)(C)C)C2)c2c1CSc1cc(OC(F)(F)F)ccc1-2]

1.2 g of the title compound as a white foam. 1H NMR (DMSO) δ 7.95-7.82 (m, 1H), 7.65 (s, 1H), 7.40-7.23 (m, 1H), 4.76-4.48 (m, 2H), 4.33 (q, J = 7.10, 7.14 Hz, 2H), 4.2 (s, 2H), 3.99-3.86 (m, 2H), 3.19-3.12 (m, 1H), 3.01-2.71 (m, 1H), 2.34-2.09 (m, 2H), 1.89-1.74 (m, 2H), 1.73-1.51 (m, 1H), 1.48-1.21 (m, 10H). HPLC (max plot) 79.8%; Rt 5.94 min.

Intermediate K.14: Ethyl 1-[1-(tert-butoxycarbonyl)piperidin-3-yl]-8-methoxy-1,4-dihydrothiochromeno[4,3-c]pyrazole-3-carboxylate

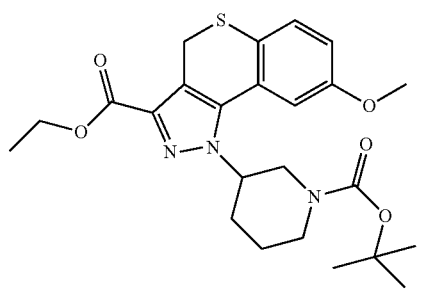 [SMILES: CCOC(=O)c1nn(C2CCCN(C(=O)OC(C)(C)C)C2)c2c1CSc1ccc(OC)cc1-2]

1.78 g of the title compound as a foam. 1H NMR (300 MHz, DMSO) δ 7.50 (d, J = 8.5, 1H), 7.22 (s, 1H), 7.00 (s, 1H), 4.65 (s, 1H), 4.32 (q, J = 7.1, 2H), 4.15-3.88 (m, 3H), 3.81 (s, 2H), 3.12 (t, J = 11.7, 1H), 2.84 (s, 1H), 2.19 (d, J = 27.5, 2H), 1.80 (s, 1H), 1.56 (s, 1H), 1.47-1.18 (m, 12H). HPLC (max plot) 98.0%; Rt 5.55 min

General protocole L.

Intermediate L.1

Ethyl 1-[3-(3-methyl-1,2,4-oxadiazol-5-yl)phenyl]-1,4-dihydrothiochromeno[4,3-c]pyrazole-3-carboxylate 5,5-dioxide

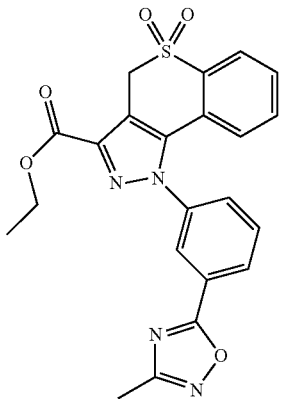 [SMILES: CCOC(=O)c1nn(-c2cccc(-c3nc(C)no3)c2)c2c1CS(=O)(=O)c1ccccc1-2]

To a solution of 3-[3-(ethoxycarbonyl)-5,5-dioxidothiochromeno[4,3-c]pyrazol-1(4H)-yl]benzoic acid (100 mg, 0.24 mmol) in EtOAc is added methylamidoxime (17 mg, 0.24 mmol) under nitrogen followed by TEA (0.1 mL, 0.73 mmol) and propane phosphonic acid cyclic anhydride (0.4 mL, 0.60 mmol) at 0° C. under nitrogen. The reaction mixture is refluxed at 80° C. for 12 h under nitrogen after which time, EtOAc is added. Organic layer is washed with 10% aq. solution $Na_2CO_3$ solution dried over $Na_2SO_4$ and concentrated under reduced pressure. The crude material obtained is purified by silica gel column chromatography (1.5% MeOH in DCM) to afford the title compound.

Intermediate L.2

Ethyl 1-(3-{3-[(dimethylamino)methyl]-1,2,4-oxadiazol-5-yl}phenyl)-1,4-dihydrothiochromeno[4,3-c]pyrazole-3-carboxylate 5,5-dioxide

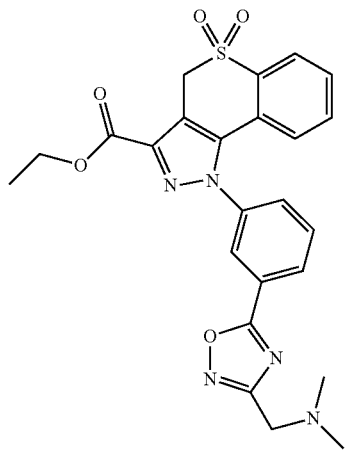 [SMILES: CCOC(=O)c1nn(-c2cccc(-c3nc(CN(C)C)no3)c2)c2c1CS(=O)(=O)c1ccccc1-2]

Following the protocol outlined in procedure L, ethyl 1-(3-{3-[(dimethylamino)methyl]-1,2,4-oxadiazol-5-yl}phenyl)-1,4-dihydrothiochromeno[4,3-c]pyrazole-3-carboxylate 5,5-dioxide is obtained from 3-[3-(ethoxycarbonyl)-5,5-dioxidothiochromeno[4,3-c]pyrazol-1(4H)-yl]benzoic acid and (1Z)-2-(dimethylamino)-N'-hydroxyethanimidamide to afford the title compound. MS (ESI+): 494.0.

Intermediate L.3

Ethyl 1-{3-[3-(methoxymethyl)-1,2,4-oxadiazol-5-yl]phenyl}-1,4-dihydrothiochromeno[4,3-c]pyrazole-3-carboxylate 5,5-dioxide

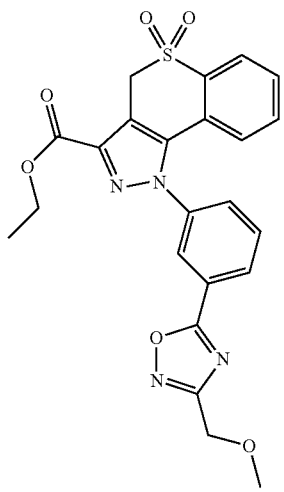 [SMILES: CCOC(=O)c1nn(-c2cccc(-c3nc(COC)no3)c2)c2c1CS(=O)(=O)c1ccccc1-2]

Following the protocol outlined in procedure L, ethyl 1-{3-[3-(methoxymethyl)-1,2,4-oxadiazol-5-yl]phenyl}-1,4-dihydrothiochromeno[4,3-c]pyrazole-3-carboxylate 5,5-dioxide is obtained from 3-[3-(ethoxycarbonyl)-5,5-dioxidothiochromeno[4,3-c]pyrazol-1(4H)-yl]benzoic acid and (1Z)-N'-hydroxy-2-methoxyethanimidamide to afford the title compound. $^1$H NMR (DMSO-$d_6$, 400 MHz): δ 8.38-8.36 (d, J=6.8 Hz,1H), 8.24 (s, 1H), 8.06-8.04 (d, J=7.7 Hz, 1H), 7.90-7.86 (m, 2H), 7.68-7.56 (m, 2H), 6.98-6.96 (d, J=7.8 Hz, 1H), 5.01-4.97 (s, 2H), 4.62 (s, 2H), 4.40-4.35 (m, 2H), 3.35 (s, 3H), 1.36-1.32 (t, J=7.1 Hz, 3H). MS (ESI+): 481.2.

Intermediate L.4

N'-hydroxy-3-[3-(morpholin-4-ylcarbonyl)-5,5-dioxidothiochromeno[4,3-c]pyrazol-1(4H)-yl]benzenecarboximidamide

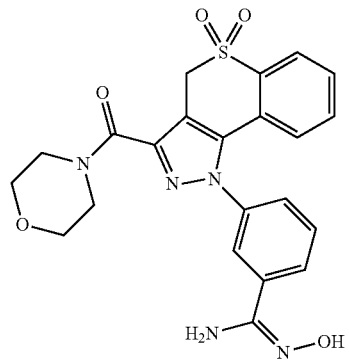 [SMILES: N/C(=N/O)c1cccc(-n2nc(C(=O)N3CCOCC3)c3c2-c2ccccc2S(=O)(=O)C3)c1]

To a solution of 3-[3-(morpholin-4-ylcarbonyl)-5,5-dioxidothiochromeno[4,3-c]pyrazol-1(4H)-yl]benzonitrile (0.3 g, 0.69 mmol) in EtOH (20 mL) is added 50% aq. hydroxylamine solution (0.14 mL, 2.07 mmol). The reaction mass is heated to 85° C. for 12 h. The solvent is removed completely under reduced pressure to afford 150 mg (89%) of the title compound as a white solid. MS (ESI+): 468.0.

Intermediate L.5

Ethyl 1-[3-(5-methyl-1,3,4-oxadiazol-2-yl)phenyl]-1,4-dihydrothiochromeno[4,3-c]pyrazole-3-carboxylate 5,5-dioxide

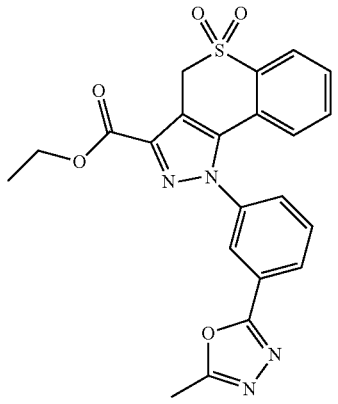 [SMILES: CCOC(=O)c1nn(-c2cccc(-c3nnc(C)o3)c2)c2c1CS(=O)(=O)c1ccccc1-2]

To a solution of 3-[3-(ethoxycarbonyl)-5,5-dioxidothiochromeno[4,3-c]pyrazol-1(4H)-yl]benzoic acid (200 mg, 0.485 mmol) in EtOAc is added acetic hydrazide (35 mg, 0.485 mmol) under nitrogen. Then TEA (0.2 mL, 1.45 mmol) and propane phosphonic acid cyclic anhydride (0.7 mL, 1.2 mmol) is added to the reaction mixture at 0° C. under nitrogen. The reaction mixture is refluxed at 80° C. for 12 h after which it is diluted with EtOAC and washed with 10% aq. Na₂CO₃ solution. The organic layer is separated, dried over Na₂SO₄ and concentrated under reduced pressure. The solid residue is purified by silica gel column chromatography over (1.5% MeOH in DCM to afford the title compound. MS (ESI+): 451.2.

Intermediate L.6

Ethyl 1-[3-(5-methyl-1,3,4-thiadiazol-2-yl)phenyl]-1,4-dihydrothiochromeno[4,3-c]pyrazole-3-carboxylate 5,5-dioxide

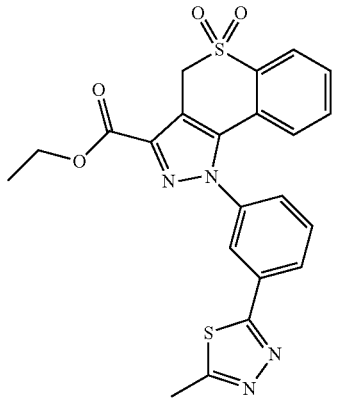 [SMILES: CCOC(=O)c1nn(-c2cccc(-c3nnc(C)s3)c2)c2c1CS(=O)(=O)c1ccccc1-2]

To a solution of 3-[3-(ethoxycarbonyl)-5,5-dioxidothiochromeno[4,3-c]pyrazol-1(4H)-yl]benzoic acid (0.4 g, 0.97 mmol) in EtOAc is added acetic hydrazide (72 mg, 0.97 mmol) under nitrogen. Then TEA (0.4 mL, 2.93 mmol), Lawssen's reagent (0.6 g, 1.46 mmol) and propane phosphonic acid cyclic anhydride (2 mL, 2.93 mmol) is added to the reaction mass at 0° C. under nitrogen. The reaction mixture is refluxed at 80° C. for 12 h under nitrogen after which time, EtOAc is added. Organic layer is washed with 10% aq. solution Na₂CO₃ solution dried over Na₂SO₄ and concentrated under reduced pressure. The crude material obtained is purified by silica gel column chromatography (1.5% MeOH in DCM) to afford the title compound. MS (ESI+):467.0.

Procedure M.

Intermediate M.1

Ethyl 1-(6-oxo-1,6-dihydropyridin-3-yl)-1,4-dihydrothieno[3',2':5,6]thiopyrano[4,3-c]pyrazole-3-carboxylate

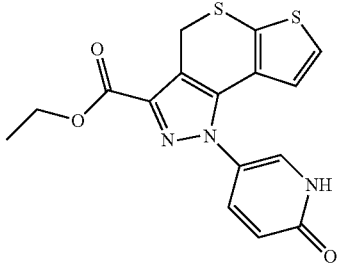 [SMILES: CCOC(=O)c1nn(-c2ccc(=O)[nH]c2)c2c1CSc1sccc1-2]

To a suspension of ethyl 1-(6-methoxypyridin-3-yl)-1,4-dihydrothieno3',2': 5,6]thiopyrano[4,3-c]pyrazole-3-carboxylate (200 mg, 0.535 mmol) and sodium iodide (80 mg, 0.535 mmol) in dry ACN is added trimethylsilylchloride (350 mg, 3.22 mmol) at RT under nitrogen. The reaction mass is heated to 80° C. for 48 h under nitrogen after which it is cooled to 0° C. Reaction mixture is diluted with sat. aq. solution of Na₂CO₃ and sat. sodiumthiosulphate solution and stirred for 0.5 h. The solid precipitated is filtered through vacuum, washed with water and dried overnight to afford 190 mg (98%) of the title compound. MS (ESI+): 360.0.

Intermediate M.2

Ethyl 1-(6-oxo-1,6-dihydropyridin-3-yl)-1,4-dihydrothiochromeno[4,3-c]pyrazole-3-carboxylate

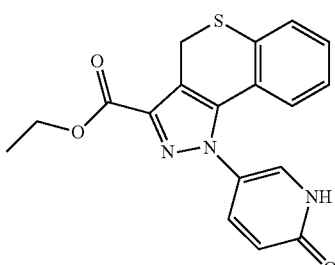

Following the protocol outlined in procedure AN, ethyl 1-(6-oxo-1,6-dihydropyridin-3-yl)-1,4-dihydrothiochromeno[4,3-c]pyrazole-3-carboxylate is obtained from ethyl 1-(6-methoxypyridin-3-yl)-1,4-dihydrothiochromeno[4,3-c]pyrazole-3-carboxylate to afford 230 mg (69%) of the title compound. MS (ESI+): 354.2.

Procedure N.

Intermediate N.1

Ethyl 1-(1-methyl-6-oxo-1,6-dihydropyridin-3-yl)-1,4-dihydrothieno[3',2':5,6]thiopyrano[4,3-c]pyrazole-3-carboxylate

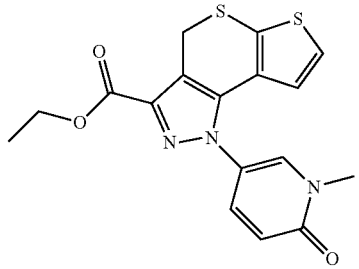 [SMILES: CCOC(=O)c1nn(-c2ccc(=O)n(C)c2)c2c1CSc1sccc1-2]

To a solution of ethyl 1-(6-oxo-1,6-dihydropyridin-3-yl)-1,4-dihydrothieno[3',2':5,6]thiopyrano[4,3-c]pyrazole-3-carboxylate (75 mg, 0.208 mmol) in water/DCM (1:2) is added tetrabutylammonium bromide (0.135 g, 0.417 mmol), sodium hydroxide (17 mg, 0.417 mmol) and methyl iodide (0.13 mL, 2.08 mmol). The reaction mass is stirred at RT for 12 h after which reaction mixture is diluted with DCM and washed with water. The organic layer is separated, dried over Na$_2$SO$_4$, concentrated under reduced pressure and purified by silica gel column chromatography over (5% MeOH in DCM) to afford the title compound. MS (ESI+): 374.0.

Intermediate N.2

Ethyl 1-(1-methyl-6-oxo-1,6-dihydropyridin-3-yl)-1,4-dihydrothiochromeno[4,3-c]pyrazole-3-carboxylate

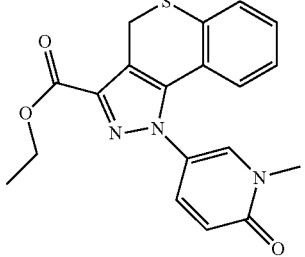

Following the protocol outlined in Procedure N, ethyl 1-(1-methyl-6-oxo-1,6-dihydropyridin-3-yl)-1,4-dihydrothiochromeno[4,3-c]pyrazole-3-carboxylate is obtained from 1-(6-oxo-1,6-dihydropyridin-3-yl)-1,4-dihydrothiochromeno[4,3-c]pyrazole-3-carboxylate to afford the title compound. $^1$H NMR (DMSO-d$_6$, 400 MHz): δ 8.25 (m, 1H), 7.49-7.46 (m, 2H), 7.26-7.22 (m, 1H), 7.18-7.15 (m, 2H), 6.50-6.47 (d, J=9.6 Hz, 1H), 4.35-4.29 (m, 2H), 4.22 (s, 2H), 3.46 (s, 3H), 1.32-1.29 (t, J=7.1 Hz, 3H). MS (ESI+): 368.2.

Intermediate O.1

Ethyl 1-{3-[(tert-butoxycarbonyl)amino]phenyl}-1,4-dihydrothiochromeno[4,3-c]pyrazole-3-carboxylate 5,5-dioxide

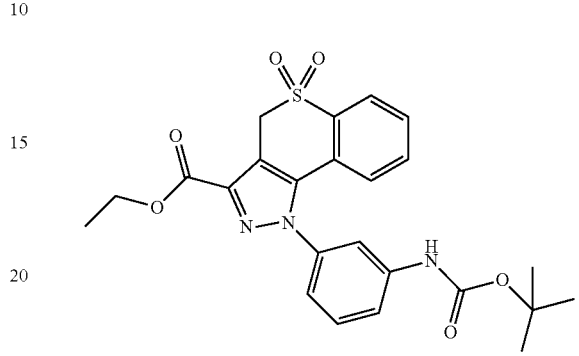

To a solution of 3-[3-(ethoxycarbonyl)-5,5-dioxidothiochromeno[4,3-c]pyrazol-1 (4H)-yl]benzoic acid (500 mg, 1.21 mmol) in tert-butanol:DMF (8: 2) is added TEA (0.68 mL, 4.85 mmol) under nitrogen followed by diphenylphosphonylazide (0.4 mL, 1.82 mmol). It is then heated to 60° C. for 20 min and slowly increased to 100° C. at which it is heated for 2 h. After this time, solvents are evaporated under reduced pressure, diluted with water and extracted with ethylacetate. The organic layer is separated, washed with brine, dried over Na$_2$SO$_4$, concentrated under reduced pressure and purified by silica gel column chromatography (20% EtOAc, pet. ether) to afford the title compound as white solid. MS (ESI+): 484.0.

Intermediate O.2

Ethyl 1-{3-[(phenoxycarbonyl)amino]phenyl}-1,4-dihydrothiochromeno[4,3-c]pyrazole-3-carboxylate 5,5-dioxide

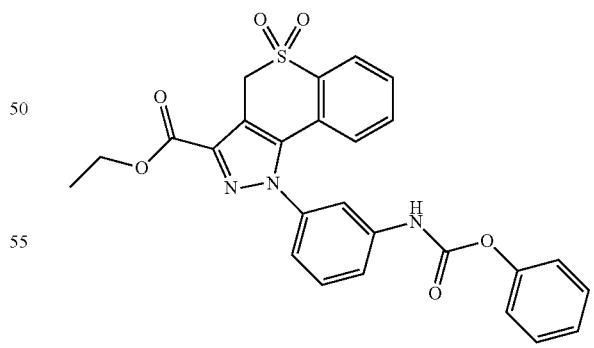

To a solution of ethyl 1-(3-aminophenyl)-1,4-dihydrothiochromeno[4,3-c]pyrazole-3-carboxylate 5,5-dioxide hydrochloride (100 mg, 0.243 mmol) in THF (10 mL) are added 2,4,6 collidine (0.06 mL, 0.487 mmol), phenylchloroformate (0.04 mL, 0.365 mmol) then stirred at RT for 18 h. After this time, reaction mixture is concentrated under reduced pressure, diluted with water, and extracted with EtOAc. The organic layer is separated, washed with brine, dried over Na₂SO₄ and concentrated under reduced pressure to afford 100 mg of the title compound.
MS (ESI+):504.0.

Intermediate O.3

Ethyl 1-{3-[(morpholin-4-ylcarbonyl)amino]phenyl}-1,4-dihydrothiochromeno[4,3-c]pyrazole-3-carboxylate 5,5-dioxide

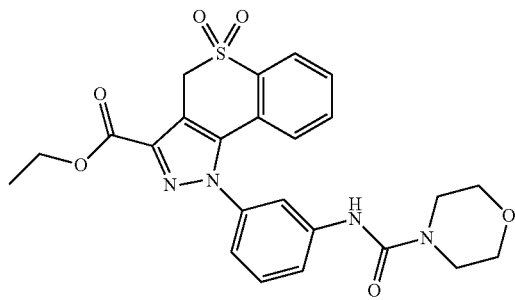 [SMILES: CCOC(=O)c1nn(-c2cccc(NC(=O)N3CCOCC3)c2)c2c1CS(=O)(=O)c1ccccc1-2]

A mixture of ethyl 1-{3-[(phenoxycarbonyl)amino]phenyl}-1,4-dihydrothiochromeno[4,3-c]pyrazole-3-carboxylate 5,5-dioxide (100 mg, 0.198 mmol), morpholine (0.03 mL, 0.3 mmol), triethylamine (0.03 mL, 0.3 mmol) in N-methyl-2-pyrrolidone is heated under microwave irradiation for 15 min at 55° C. The reaction mixture is diluted with water and is stirred for another hour. The precipitate is filtered and dried under vacuum to afford 80 mg (81%) of the title compound. MS (ESI+): 497.2.

Intermediate O.4

Ethyl 6-cyano-1-phenyl-1,4-dihydrothiochromeno[4,3-c]pyrazole-3-carboxlate

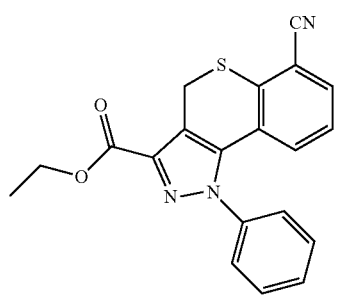 [SMILES: CCOC(=O)c1nn(-c2ccccc2)c2c1CSc1c(C#N)cccc1-2]

Ethyl 6-bromo-1-phenyl-1,4-dihydrothiochromeno[4,3-c]pyrazole-3-carboxylate (200 mg, 0.483 mmol) in DMF/water (10:1, 4.4 mL) is taken in a sealed tube and purged with nitrogen for 10 min. Zinc cyanide (64 mg, 0.545 mmol), Pd₂(dba)₃ (18 mg, 0.019 mmol) and s-phos (20 mg, 0.483 mmol) are then added and heated to 120° C. for 2 h. After this time, the reaction mixture is diluted with DCM, filtered through acelite pad, washed with water, dried over Na₂SO₄ and concentrated under reduced pressure to afford 200 mg of the title compound. ¹H NMR (DMSO-d₆, 400 MHz): δ 7.74-7.72 (m, 1H), 7.60-7.55 (m, 3H), 7.48-7.46 (m, 2H), 7.18-7.14 (m, 1H), 6.91-6.89 (dd, J=1.1, 8.0 Hz, 1H), 4.40 (s, 2H), 4.36-4.31 (m, 2H), 1.33-1.29 (t, J=7.1 Hz, 3H). MS (ESI+): 362.2.

Procedure P

Intermediate P.1 ethyl 6-methoxy-1-phenyl-1,4-dihydrothiochromeno[4,3-c]pyrazole-3-carboxylate 5,5-dioxide

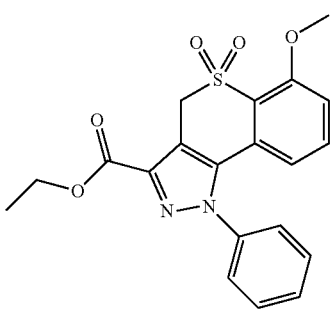 [SMILES: CCOC(=O)c1nn(-c2ccccc2)c2c1CS(=O)(=O)c1c(OC)cccc1-2]

A solution of ethyl 6-methoxy-1-phenyl-1,4-dihydrothiochromeno[4,3-c]pyrazole-3-carboxylate (0.30 g, 0.81 mmol) in acetic acid (5 mL) is heated at 100° C. under nitrogen. Hydrogen peroxide 30% in water (0.5 mL, 3.6 mmol, 4.5 Eq) is added and the reaction mixture is heated for 30 minutes. After 30 minutes, the solvent is removed under reduced pressure. An aq. solution of NaHCO₃ 10% is added to the residue. After 15 minutes stirring, the solid obtained is filtered off then dried to afford 0.26 g (79%) of the title compound. ¹H NMR (DMSO-d₆, 400 MHz): δ 7.63-7.58 (m, 3H), 7.46-7.42 (m, 3H), 7.26 (d, J=8.6 Hz, 1H), 6.34 (d, J=7.92 Hz, 1H), 4.90 (s, 2H), 4.36 (q, J=7.0 Hz, 2H), 3.33 (s, 3H), 1.32 (t, J=7.08 Hz, 3H). MS (ESI+): 399.0. HPLC (max plot) 94.0%; Rt 4.17 min.

Intermediate P.2 ethyl 6-methoxy-1-methyl-1,4-dihydrothiochromeno[4,3-c]pyrazole-3-carboxylate 5,5-dioxide

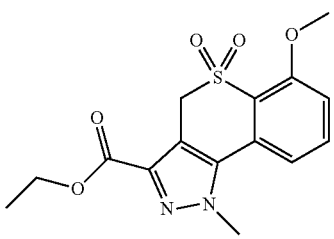 [SMILES: CCOC(=O)c1nn(C)c2c1CS(=O)(=O)c1c(OC)cccc1-2]

Following the protocol outlined in Procedure P, ethyl 6-methoxy-1-methyl-1,4-dihydrothiochromeno[4,3-c]pyrazole-3-carboxylate 5,5-dioxide is obtained from ethyl 6-methoxy-1-methyl-1,4-dihydrothio chromeno[4,3-c]pyrazole-3-carboxylate and hydrogen peroxide to afford the title compound. ¹H NMR (DMSO-d₆, 400 MHz): δ 7.78 (t, J=8.16 Hz, 1H), 7.53 (d, J=7.44 Hz, 1H), 7.38 (d, J=8.4 Hz, 1H), 4.79

(s, 2H), 4.32 (q, J=7.08 Hz, 2H), 4.20 (s, 3H), 3.92 (s, 3H), 1.31 (t, J=7.12 Hz, 3H). MS (ESI+): 337.0. HPLC (max plot) 96.5%; Rt 4.01 min.

Intermediate P.3 ethyl 1-phenyl-1,4-dihydrothiochromeno[4,3-c]pyrazole-3-carboxylate 5,5-dioxide

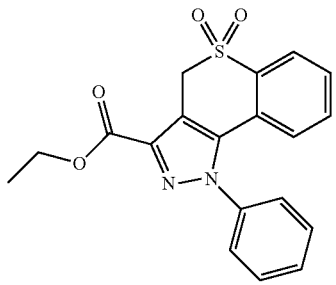 [SMILES: CCOC(=O)c1nn(-c2ccccc2)c2c1CS(=O)(=O)c1ccccc1-2]

Following the protocol outlined in Procedure P, ethyl 1-phenyl-1,4-dihydrothiochromeno[4,3-c]pyrazole-3-carboxylate 5,5-dioxide is obtained from ethyl 1-phenyl-1,4-dihydrothiochromeno[4,3-c]pyrazole-3-carboxylate and hydrogen peroxide to afford title compound. $^1$H NMR (DMSO-d$_6$, 400 MHz): δ 8.03-8.01 (m, 1H), 7.68-7.62 (m, 4H), 7.59-7.52 (m, 3H), 6.80 (d, J=7.7 Hz, 1H), 4.99 (s, 2H), 4.36 (q, J=7.0 Hz, 2H), 1.33 (t, J=7.1 Hz, 3H). MS (ESI+): 369.0. HPLC (max plot) 96.9%; Rt 4.42 min.

Intermediate P.4 ethyl 1-methyl-1,4-dihydrothiochromeno[4,3-c]pyrazole-3-carboxylate 5,5-dioxide

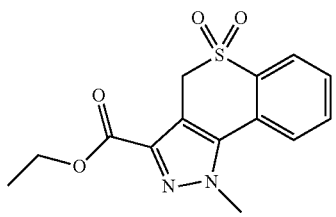 [SMILES: CCOC(=O)c1nn(C)c2c1CS(=O)(=O)c1ccccc1-2]

Following the protocol outlined in Procedure P, ethyl 1-methyl-1,4-dihydrothiochromeno[4,3-c]pyrazole-3-carboxylate 5,5-dioxide is obtained from ethyl 1-methyl-1,4-dihydrothiochromeno[4,3-c]pyrazole-3-carboxylate and hydrogen peroxide to afford the title compound. $^1$H NMR (DMSO-d$_6$, 400 MHz): δ 8.07-8.02 (m, 2H), 7.91-7.87 (m, 1H), 7.75-7.71 (m, 1H), 4.88 (s, 2H), 4.32 (q, J=7.0 Hz, 2H), 4.29 (s, 3H), 1.32 (t, J=7.1 Hz, 3H). MS (ESI+): 307.0. HPLC (max plot) 96.6%; Rt 3.25 min.

Intermediate P.5 ethyl 1,4-dihydrothiochromeno[4,3-c]pyrazole-3-carboxylate 5,5-dioxide

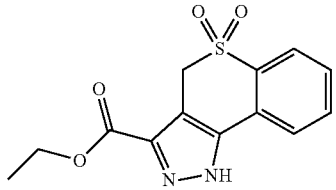 [SMILES: CCOC(=O)c1n[nH]c2c1CS(=O)(=O)c1ccccc1-2]

Following the protocol outlined in Procedure P, ethyl 1,4-dihydrothiochromeno[4,3-c]pyrazole-3-carboxylate 5,5-dioxide is obtained from ethyl 1,4-dihydrothiochromeno[4,3-c]pyrazole-3-carboxylate and hydrogen peroxide to afford 1.0 g (90%) of the title compound as a white solid. $^1$H NMR (DMSO-d$_6$, 400 MHz): δ 14.6 (s, 1H), 8.06-7.93 (m, 2H), 7.88-7.78 (m, 1H), 7.70-7.63 (m, 1H), 4.88 (s, 2H), 4.40-4.32 (m, 2H), 1.37-1.31 (m, 3H). MS (ESI+): 293.0 HPLC (max plot) 93.1%; Rt 3.19 min.

Intermediate P.6 ethyl 7-methoxy-1-methyl-1,4-dihydrothiochromeno[4,3-c]pyrazole-3-carboxylate 5,5-dioxide

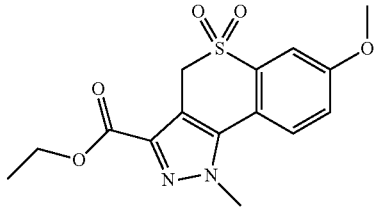 [SMILES: CCOC(=O)c1nn(C)c2c1CS(=O)(=O)c1cc(OC)ccc1-2]

Following the protocol outlined in Procedure P, ethyl 7-methoxy-1-methyl-1,4-dihydrothiochromeno[4,3-c]pyrazole-3-carboxylate 5,5-dioxide is obtained from ethyl 7-methoxy-1-methyl-1,4-dihydrothio chromeno[4,3-c]pyrazole-3-carboxylate and hydrogen peroxide to afford 0.49 g (87%) of the title compound. $^1$H NMR (DMSO-d$_5$, 400 MHz) δ 10.20 (s, 1H), 8.00 (d, J=8.8 Hz, 1H), 7.48 (s, 1H), 7.43-7.40 (m, 1H), 4.85 (s, 2H), 4.32 (q, J=7.1 Hz, 2H), 4.25 (s, 3H), 3.92 (s, 3H), 1.31 (t, J=7.1 Hz, 3H). MS (ESI+): 337.0. HPLC (max plot) 98.7%; Rt 3.55 min.

Intermediate P.7 ethyl 7-methoxy-1-phenyl-1,4-dihydrothiochromeno[4,3-c]pyrazole-3-carboxylate 5,5-dioxide

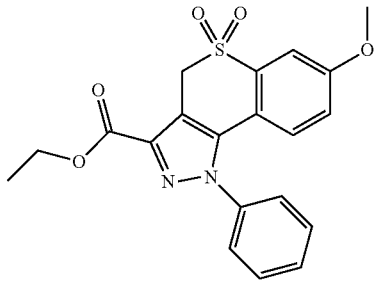 [SMILES: CCOC(=O)c1nn(-c2ccccc2)c2c1CS(=O)(=O)c1cc(OC)ccc1-2]

Following the protocol outlined in Procedure P, ethyl 7-methoxy-1-phenyl-1,4-dihydrothiochromeno[4,3-c]pyrazole-3-carboxylate 5,5-dioxide is obtained from ethyl 7-methoxy-1-phenyl-1,4-dihydrothio chromeno[4,3-c]pyrazole-3-carboxylate and hydrogen peroxide to afford 1.01 g (85%) of the title compound. $^1$H NMR (DMSO-$d_6$, 400 MHz) δ 7.65-7.62 (m, 3H), 7.53-7.45 (m, 3H), 7.17 (dd, J=8.8 Hz, J=3.1 Hz, 1H), 6.73 (d, J=8.8 Hz, 1H), 4.95 (s, 2H), 4.36 (q, J=7.1 Hz, 2H), 3.84 (s, 3H), 1.33 (t, J=7.1 Hz, 3H). MS (ESI+): 399.0. HPLC (max plot) 98.0%; Rt 4.63 min.

Intermediate P.8 ethyl 1-(3-methylphenyl)-1,4-dihydrothiochromeno[4,3-c]pyrazole-3-carboxylate 5,5-dioxide

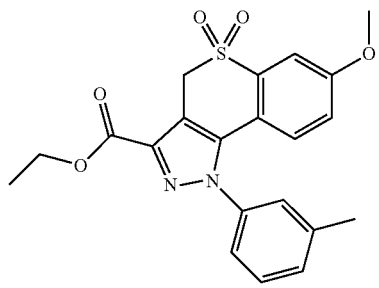 [SMILES: CCOC(=O)c1nn(-c2cccc(C)c2)c2c1CS(=O)(=O)c1cc(OC)ccc1-2]

Following the protocol outlined in Procedure P, ethyl 1-(3-methylphenyl)-1,4-dihydrothiochromeno[4,3-c]pyrazole-3-carboxylate 5,5-dioxide is obtained from ethyl 1-(3-methylphenyl)-1,4-dihydrothio chromeno[4,3-c]pyrazole-3-carboxylate and hydrogen peroxide to afford 1.08 g (97%) of the title compound. $^1$H NMR (DMSO-$d_6$, 400 MHz) δ 8.02 (dd, J=7.7 Hz, J=1.3 Hz, 1H), 7.66-7.56 (m, 3H), 7.53-7.46 (m, 2H), 7.38 (s, 1H), 7.28 (d, J=7.4 Hz, 1H), 4.98 (s, 2H), 4.36 (q, J=7.1 Hz, 2H), 2.40 (s, 3H), 1.33 (t, J=7.1 Hz, 3H). MS (ESI+): 383.0. HPLC (max plot) 97.3%; Rt 4.85 min.

Intermediate P.9 ethyl 1-(4-methylphenyl)-1,4-dihydrothiochromeno[4,3-c]pyrazole-3-carboxylate 5,5-dioxide

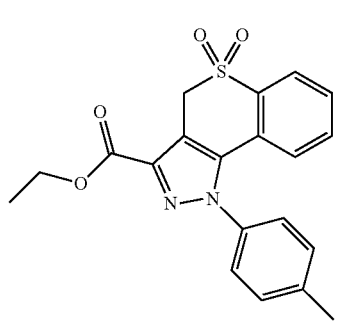 [SMILES: CCOC(=O)c1nn(-c2ccc(C)cc2)c2c1CS(=O)(=O)c1ccccc1-2]

Following the protocol outlined in Procedure P, ethyl 1-(4-methylphenyl)-1,4-dihydrothiochromeno[4,3-c]pyrazole-3-carboxylate 5,5-dioxide is obtained from ethyl 1-(4-methylphenyl)-1,4-dihydrothio chromeno[4,3-c]pyrazole-3-carboxylate and hydrogen peroxide to afford 1.1 g (92%) of the title compound. $^1$H NMR (DMSO-$d_6$, 400 MHz) δ 8.01 (d, J=7.4 Hz, 1H), 7.63-7.57 (m, 2H), 7.45-7.39 (m, 4H), 6.84 (s, 1H), 4.97 (s, 2H), 4.36 (q, J=7.1 Hz, 2H), 2.44 (s, 3H), 1.33 (t, J=7.1 Hz, 3H). MS (ESI+): 383.0. HPLC (max plot) 97.5%; Rt 4.77 min.

Intermediate P.10 ethyl 1-(5-fluoro-2-methylphenyl)-1,4-dihydrothiochromeno[4,3-c]pyrazole-3-carboxylate 5,5-dioxide

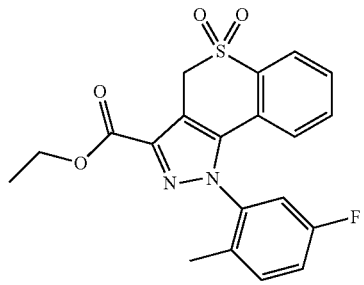 [SMILES: CCOC(=O)c1nn(-c2cc(F)ccc2C)c2c1CS(=O)(=O)c1ccccc1-2]

Following the protocol outlined in Procedure P, ethyl 1-(5-fluoro-2-methylphenyl)-1,4-dihydrothio chromeno[4,3-c]pyrazole-3-carboxylate 5,5-dioxide is obtained from ethyl 1-(5-fluoro-2-methyl phenyl)-1,4-dihydrothiochromeno[4,3-c]pyrazole-3-carboxylate and hydrogen peroxide to afford 0.7 g (92%) of the title compound. $^1$H NMR (DMSO-$d_6$, 400 MHz) δ 8.03 (dd, J=7.6 Hz, J=1.1 Hz, 1H), 7.65-7.60 (m, 3H), 7.54-7.50 (m, 2H), 6.74 (d, J=7.9 Hz, 1H), 5.01 (s, 2H), 4.39-4.34 (m, 2H), 1.76 (s, 3H), 1.33 (t, J=7.1 Hz, 3H). MS (ESI+): 401.0. HPLC (max plot) 98.4%; Rt 4.71 min.

Intermediate P.11 ethyl 1-(3-methoxyphenyl)-1,4-dihydrothiochromeno[4,3-c]pyrazole-3-carboxylate 5,5-dioxide

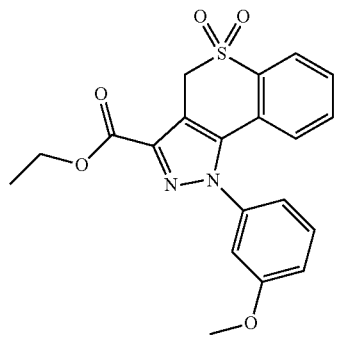 [SMILES: CCOC(=O)c1nn(-c2cccc(OC)c2)c2c1CS(=O)(=O)c1ccccc1-2]

Following the protocol outlined in Procedure P, ethyl 1-(3-methoxyphenyl)-1,4-dihydrothiochromeno [4,3-c]pyrazole-3-carboxylate 5,5-dioxide is obtained from ethyl 1-(3-methoxyphenyl)-1,4-dihydrothio chromeno[4,3-c]pyrazole-3-carboxylate and hydrogen peroxide to afford 0.625 g (88%) of the title compound. $^1$H NMR (DMSO-$d_6$, 400 MHz) δ 8.03-8.01 (m, 1H), 7.66-7.58 (m, 1H), 7.52 (t, J=8.0 Hz, 1H), 7.23 (dd, J=8.1 Hz, J=1.3 Hz, 1H), 7.15-7.13 (m, 1H), 7.13 (s, 1H), 7.02 (d, J=7.8 Hz, 1H), 6.87 (d, J=7.5 Hz, 1H), 4.98 (s, 2H), 4.36 (q, J=7.1 Hz, 2H), 3.81 (s, 3H), 1.33 (t, J=7.1 Hz, 3H). MS (ESI+): 399.0. HPLC (max plot) 92.3%; Rt 4.55 min.

Intermediate P.12 ethyl 1-(4-methoxyphenyl)-1,4-dihydrothio-chromeno[4,3-c]pyrazole-3-carboxylate 5,5-dioxide

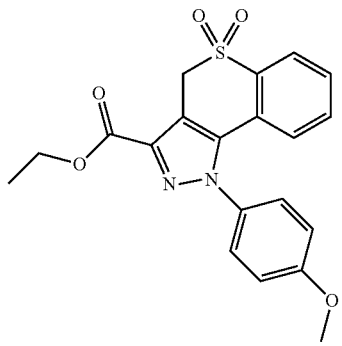 [SMILES: CCOC(=O)c1nn(-c2ccc(OC)cc2)c2c1CS(=O)(=O)c1ccccc1-2]

Following the protocol outlined in Procedure P, ethyl 1-(4-methoxyphenyl)-1,4-dihydrothiochromeno[4,3-c]pyrazole-3-carboxylate 5,5-dioxide is obtained from ethyl 1-(4-methoxyphenyl)-1,4-dihydrothio chromeno[4,3-c]pyrazole-3-carboxylate and hydrogen peroxide to afford 1.0 g (82%) of the title compound. $^1$H NMR (DMSO-d$_6$, 400 MHz) δ 8.02-8.00 (m, 1H), 7.65-7.58 (m, 2H), 7.47-7.43 (m, 2H), 7.17-7.13 (m, 2H), 6.86-6.84 (m, 1H), 4.97 (s, 2H), 4.36 (q, J=7.1 Hz, 2H), 1.33 (t, J=7.1 Hz, 3H). MS (ESI+): 399.0. HPLC (max plot) 95.4%; Rt 4.49 min.

Intermediate P.13 ethyl 1-pyridin-2-yl-1,4-dihydrothiochromeno[4,3-c]pyrazole-3-carboxylate 5,5-dioxide

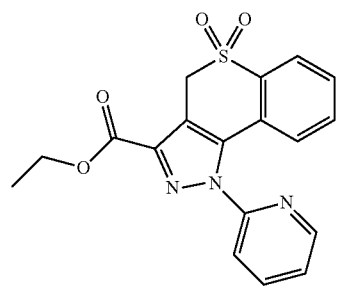 [SMILES: CCOC(=O)c1nn(-c2ccccn2)c2c1CS(=O)(=O)c1ccccc1-2]

Following the protocol outlined in Procedure P, ethyl 1-pyridin-2-yl-1,4-dihydrothiochromeno[4,3-c]pyrazole-3-carboxylate 5,5-dioxide is obtained from ethyl 1-pyridin-2-yl-1,4-dihydrothiochromeno [4,3-c]pyrazole-3-carboxylate and hydrogen peroxide to afford the title compound. $^1$H NMR (DMSO-d$_6$, 400 MHz) δ 8.55-8.54 (m, 1H), 8.24-8.20 (m, 2H), 8.01 (dd, J=7.7 Hz, J=1.0 Hz, 1H), 7.90 (d, J=8.0 Hz, 2H), 7.70-7.57 (m, 1H), 6.87 (d, J=7.9 Hz, 1H), 4.98 (s, 2H), 4.36 (q, J=7.1 Hz, 2H), 1.34 (t, J=7.1 Hz, 3H). MS (ESI+): 370.0. HPLC (max plot) 97.9%; Rt 3.76 min.

Intermediate P.14 ethyl 1-cyclohexyl-1,4-dihydrothiochromeno[4,3-c]pyrazole-3-carboxylate 5,5-dioxide

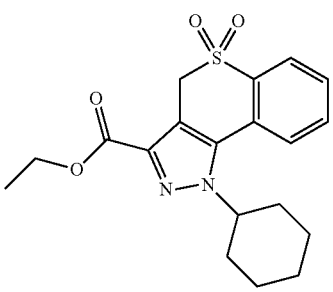 [SMILES: CCOC(=O)c1nn(C2CCCCC2)c2c1CS(=O)(=O)c1ccccc1-2]

Following the protocol outlined in Procedure P, ethyl 1-cyclohexyl-1,4-dihydrothiochromeno[4,3-c]pyrazole-3-carboxylate 5,5-dioxide is obtained from ethyl 1-cyclohexyl-1,4-dihydrothiochromeno[4,3-c]pyrazole-3-carboxylate and hydrogen peroxide to afford 1.1 g (92%) of the title compound. $^1$H NMR (DMSO-d$_6$, 400 MHz) δ 8.04 (d, J=7.6 Hz, 1H), 7.93 (t, J=7.2 Hz, 1H), 7.85 (d, J=7.7 Hz, 1H), 7.74 (t, J=7.6 Hz, 1H), 4.85 (s, 2H), 4.76-4.71 (m, 1H), 4.34 (q, J=7.1 Hz, 2H), 2.02-1.82 (m, 6H), 1.70-1.67 (m, 1H), 1.56-1.49 (m, 2H), 1.38 (t, J=7.1 Hz, 3H). MS (ESI+): 375.0. HPLC (max plot) 98.5%; Rt 4.91 min.

Intermediate P.15 ethyl 6-bromo-1-methyl-1,4-dihydrothiochromeno[4,3-c]pyrazole-3-carboxylate 5,5-dioxide

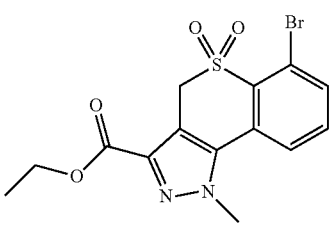

Following the protocol outlined in Procedure P, ethyl 6-bromo-1-methyl-1,4-dihydrothiochromeno[4,3-c]pyrazole-3-carboxylate 5,5-dioxide is obtained from ethyl 6-bromo-1-methyl-1,4-dihydrothiochromeno[4,3-c]pyrazole-3-carboxylate and hydrogen peroxide to afford the title compound. $^1$H NMR (400 MHz, DMSO-d$_6$, 400 MHz) δ 8.02 (d, J=7.8 Hz, 1H), 7.93 (dd, J=8.0 Hz, J=1.0 Hz, 1H), 7.71 (t, J=8.0 Hz, 1H), 4.98 (s, 2H), 4.33 (q, J=7.1 Hz, 2H), 4.22 (s, 3H), 1.32 (t, J=7.1 Hz, 3H). MS (ESI+): 386.0. HPLC (max plot) 98.7%; Rt 3.80 min.

Intermediate P.16 ethyl 6-fluoro-1-methyl-1,4-dihydrothiochromeno[4,3-c]pyrazole-3-carboxylate 5,5-dioxide

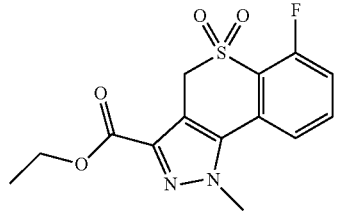 [SMILES: CCOC(=O)c1nn(C)c2c1CS(=O)(=O)c1c(F)cccc1-2]

Following the protocol outlined in Procedure P, ethyl 6-fluoro-1-methyl-1,4-dihydrothiochromeno[4,3-c]pyrazole-3-carboxylate 5,5-dioxide is obtained from ethyl 6-fluoro-1-methyl-1,4-dihydrothiochromeno[4,3-c]pyrazole-3-carboxylate and hydrogen peroxide to afford the title compound. $^1$H NMR (DMSO-d$_6$, 400 MHz) δ 7.94-7.85 (m, 1H), 7.59-7.54 (m, 1H), 4.97 (s, 2H), 4.32 (q, J=7.1 Hz, 2H), 4.26 (s, 3H), 1.32 (t, J=7.1 Hz, 3H). MS (ESI+): 325.0. HPLC (max plot) 98.7%; Rt 3.45 min.

Intermediate P.17 ethyl 6-fluoro-1-phenyl-1,4-dihydrothiochromeno[4,3-c]pyrazole-3-carboxylate 5,5-dioxide

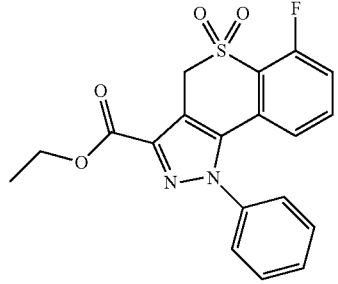 [SMILES: CCOC(=O)c1nn(-c2ccccc2)c2c1CS(=O)(=O)c1c(F)cccc1-2]

Following the protocol outlined in Procedure P, ethyl 6-fluoro-1-phenyl-1,4-dihydrothiochromeno[4,3-c]pyrazole-3-carboxylate 5,5-dioxide is obtained from ethyl 6-fluoro-1-phenyl-1,4-dihydrothiochromeno[4,3-c]pyrazole-3-carboxylate and hydrogen peroxide to afford the title compound. $^1$H NMR (DMSO-d$_6$, 400 MHz) δ 7.65-7.57 (m, 4H), 7.52-7.45 (m, 3H), 6.63 (d, J=7.9 Hz, 1H), 5.08 (s, 2H), 4.36 (q, J=7.1 Hz, 2H), 1.33 (t, J=7.1 Hz, 3H). MS (ESI+): 387.0. HPLC (max plot) 97.9%; Rt 4.55 min.

Intermediate P.18 ethyl 8-fluoro-1-methyl-1,4-dihydrothiochromeno[4,3-c]pyrazole-3-carboxylate 5,5-dioxide

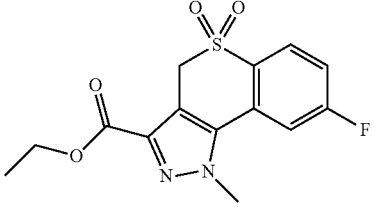 [SMILES: CCOC(=O)c1nn(C)c2c1CS(=O)(=O)c1ccc(F)cc1-2]

Following the protocol outlined in Procedure P, ethyl 8-fluoro-1-methyl-1,4-dihydrothiochromeno[4,3-c]pyrazole-3-carboxylate 5,5-dioxide is obtained from ethyl 8-fluoro-1-methyl-1,4-dihydrothiochromeno[4,3-c]pyrazole-3-carboxylate and hydrogen peroxide to afford the title compound. $^1$H NMR (DMSO-d$_6$, 400 MHz) δ 10.2 (brs, 1H), 8.11-8.08 (m, 1H), 7.91 (dd, J=9.9 Hz, J=2.4 Hz, 1H), 7.60-7.55 (m, 1H), 4.90 (m, 2H), 4.32 (q, J=7.1 Hz, 2H), 1.32 (t, J=7.1 Hz, 3H). MS (ESI+): 325.0.

Intermediate P.19 ethyl 8-fluoro-1-phenyl-1,4-dihydrothiochromeno[4,3-c]pyrazole-3-carboxylate 5,5-dioxide

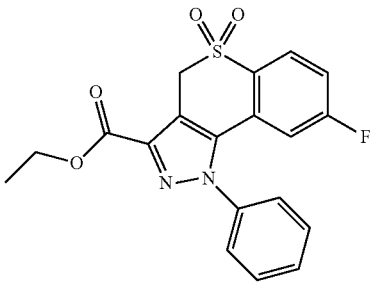 [SMILES: CCOC(=O)c1nn(-c2ccccc2)c2c1CS(=O)(=O)c1ccc(F)cc1-2]

Following the protocol outlined in Procedure P, ethyl 8-fluoro-1-phenyl-1,4-dihydrothiochromeno[4,3-c]pyrazole-3-carboxylate 5,5-dioxide is obtained from ethyl 8-fluoro-1-phenyl-1,4-dihydrothiochromeno[4,3-c]pyrazole-3-carboxylate and hydrogen peroxide to afford 0.71 g (73%) of the title compound. $^1$H NMR (DMSO-d$_6$, 400 MHz) δ 8.12-8.09 (m, 1H), 7.70-7.49 (m, 1H), 6.42 (d, J=10.1 Hz, 2H), 5.02 (m, 2H), 4.37 (q, J=7.1 Hz, 2H), 1.33 (t, J=7.1 Hz, 3H). MS (ESI+): 387.0. HPLC (max plot) 98.6%; Rt 4.71 min.

Intermediate P.20 ethyl 6-bromo-1-phenyl-1,4-dihydrothiochromeno[4,3-c]pyrazole-3-carboxylate 5,5-dioxide

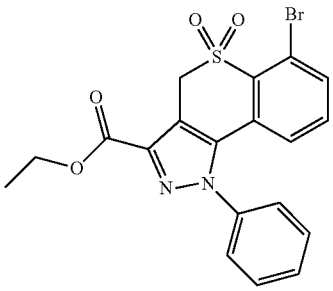 [SMILES: CCOC(=O)c1nn(-c2ccccc2)c2c1CS(=O)(=O)c1c(Br)cccc1-2]

Following the protocol outlined in Procedure P, ethyl 6-bromo-1-phenyl-1,4-dihydrothiochromeno[4,3-c]pyrazole-3-carboxylate 5,5-dioxide is obtained from ethyl 6-bromo-1-phenyl-1,4-dihydrothiochromeno[4,3-c]pyrazole-3-carboxylate and hydrogen peroxide to afford 0.4 g (79%) of the title compound. $^1$H NMR (DMSO-d$_6$, 400 MHz) δ 7.84 (d, J=8.0 Hz, 1H), 7.61 (d, J=6.8 Hz, 2H), 7.48-7.46 (m, 2H), 7.38 (t, J=8.0 Hz, 2H), 6.83 (d, J=8.0 Hz, 1H), 5.08 (s, 2H), 4.37 (q, J=7.1 Hz, 2H), 1.33 (t, J=7.0 Hz, 3H). MS (ESI+): 448.0. HPLC (max plot) 99.2%; Rt 4.84 min.

Intermediate P.21 ethyl 1-(2-methylphenyl)-1,4-dihydrothiochromeno[4,3-c]pyrazole-3-carboxylate 5,5-dioxide

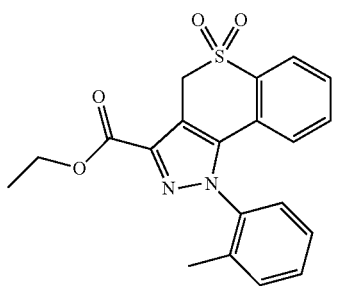 [SMILES: CCOC(=O)c1nn(-c2ccccc2C)c2c1CS(=O)(=O)c1ccccc1-2]

Following the protocol outlined in Procedure P, ethyl 1-(2-methylphenyl)-1,4-dihydrothiochromeno[4,3-c]pyrazole-3-carboxylate 5,5-dioxide is obtained from ethyl 1-(2-methylphenyl)-1,4-dihydrothiochromeno[4,3-c]pyrazole-3-carboxylate and hydrogen peroxide to afford 0.62 g (88%) of the title compound. $^1$H NMR (DMSO-$d_6$, 400 MHz) δ 8.01 (dd, J=7.8 Hz, J=1.0 Hz, 1H), 7.65-7.50 (m, 6H), 6.65 (d, J=7.4 Hz, 1H), 5.01 (s, 2H), 4.37-4.34 (m, 2H), 1.85 (s, 3H), 1.33 (t, J=7.1 Hz, 3H). MS (ESI+): 383.0. HPLC (max plot) 96.7%; Rt 5.85 min.

Intermediate P.22 ethyl 1-(2-bromophenyl)-1,4-dihydrothiochromeno[4,3-c]pyrazole-3-carboxylate 5,5-dioxide

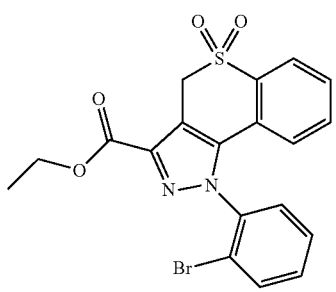 [SMILES: CCOC(=O)c1nn(-c2ccccc2Br)c2c1CS(=O)(=O)c1ccccc1-2]

Following the protocol outlined in Procedure P, ethyl 1-(2-bromophenyl)-1,4-dihydrothiochromeno[4,3-c]pyrazole-3-carboxylate 5,5-dioxide is obtained from ethyl 1-(2-bromophenyl)-1,4-dihydrothiochromeno[4,3-c]pyrazole-3-carboxylate and hydrogen peroxide to afford 0.55 g (82%) of the title compound. $^1$H NMR (DMSO-$d_6$, 400 MHz) δ 8.03 (dd, J=7.8 Hz, J=1.2 Hz, 1H), 7.95 (dd, J=7.8 Hz, J=1.6 Hz, 1H), 7.80 (dd, J=7.8 Hz, J=1.6 Hz, 1H), 7.73-7.58 (m, 4H), 6.76 (d, J=6.7 Hz, 1H), 5.08-4.97 (m, 2H), 4.37 (q, J=7.0 Hz, 2H), 1.34 (t, J=7.0 Hz, 3H). MS (ESI+): 448.0. HPLC (max plot) 97.6%; Rt 4.61 min.

Intermediate P.23 ethyl 1-(2-fluorophenyl)-1,4-dihydrothiochromeno[4,3-c]pyrazole-3-carboxylate 5,5-dioxide

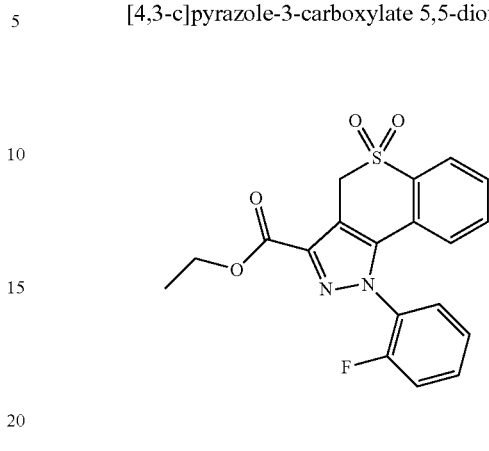

Following the protocol outlined in Procedure P, ethyl 1-(2-fluorophenyl)-1,4-dihydrothiochromeno[4,3-c]pyrazole-3-carboxylate 5,5-dioxide is obtained from ethyl 1-(2-fluorophenyl)-1,4-dihydrothiochromeno[4,3-c]pyrazole-3-carboxylate and hydrogen peroxide to afford 0.65 g (78%) of the title compound. $^1$H NMR (DMSO-$d_6$, 400 MHz) δ 8.04 (dd, J=7.7 Hz, J=1.2 Hz, 1H), 7.81-7.53 (m, 6H), 6.84 (d, J=7.6 Hz, 1H), 5.01 (d, J=7.0 Hz, 2H), 4.37 (q, J=7.1 Hz, 2H), 1.33 (t, J=7.1 Hz, 3H). MS (ESI+): 387.0. HPLC (max plot) 97.4%; Rt 4.43 min.

Intemediate P.24 ethyl 1-(2-chlorophenyl)-1,4-dihydrothiochromeno[4,3-c]pyrazole-3-carboxylate 5,5-dioxide

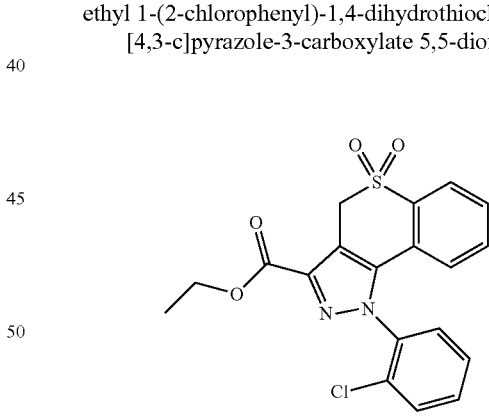

Following the protocol outlined in Procedure P, ethyl 1-(2-chlorophenyl)-1,4-dihydrothiochromeno[4,3-c]pyrazole-3-carboxylate 5,5-dioxide is obtained from ethyl 1-(2-chlorophenyl)-1,4-dihydrothiochromeno[4,3-c]pyrazole-3-carboxylate and hydrogen peroxide to afford 0.74 g (90%) of the title compound. $^1$H NMR (DMSO-$d_6$, 400 MHz) δ 8.04-8.02 (m, 1H), 7.85-7.73 (m, 3H), 7.70-7.56 (m, 3H), 6.69 (d, J=7.7 Hz, 1H), 5.03-4.97 (m, 2H), 4.37 (q, J=7.0 Hz, 1H), 1.34 (t, J=7.1 Hz, 3H). MS (ESI+): 403.0. HPLC (max plot) 99.1%; Rt 5.94 min.

Intermediate P.25 ethyl 1-[2-(methylsulfonyl)phenyl]-1,4-dihydrothiochromeno[4,3-c]pyrazole-3-carboxylate 5,5-dioxide

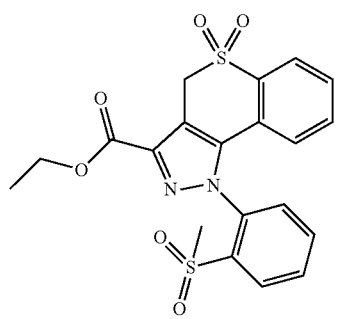 [SMILES: CCOC(=O)c1nn(-c2ccccc2S(C)(=O)=O)c2c1CS(=O)(=O)c1ccccc1-2]

Following the protocol outlined in Procedure P, ethyl 1-[2-(methylsulfonyl)phenyl]-1,4-dihydrothiochromeno[4,3-c]pyrazole-3-carboxylate 5,5-dioxide is obtained from ethyl 1-(2-chlorophenyl)-1,4-dihydrothiochromeno[4,3-c]pyrazole-3-carboxylate and hydrogen peroxide to afford 0.5 g (71%) of the title compound. $^1$H NMR (DMSO-d$_6$, 400 MHz) δ 8.30-8.28 (m, 1H), 8.03-7.94 (m, 3H), 7.64-7.56 (m, 3H), 6.60 (dd, J=7.8 Hz, J=1.0 Hz, 1H), 5.04 (s, 2H), 4.38 (q, J=7.0 Hz, 2H), 3.40 (s, 3H), 1.33 (t, J=7.1 Hz, 3H). MS (ESI+): 447.0. HPLC (max plot) 97.7%; Rt 3.98 min.

Intermediate P.26 ethyl 1-(2,3-dihydro-1,4-benzodioxin-6-yl)-1,4-dihydrothiochromeno[4,3-c]pyrazole-3-carboxylate 5,5-dioxide

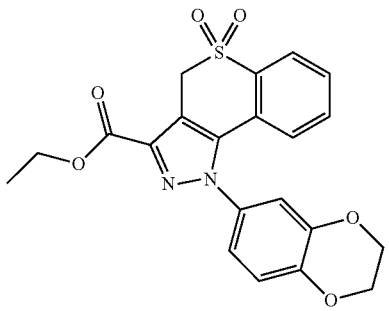 [SMILES: CCOC(=O)c1nn(-c2ccc3c(c2)OCCO3)c2c1CS(=O)(=O)c1ccccc1-2]

Following the protocol outlined in Procedure P, ethyl 1-(2,3-dihydro-1,4-benzodioxin-6-yl)-1,4-dihydrothiochromeno[4,3-c]pyrazole-3-carboxylate 5,5-dioxide is obtained from ethyl 1-(2,3-dihydro-1,4-benzodioxin-6-yl)-1,4-dihydrothiochromeno[4,3-c]pyrazole-3-carboxylate and hydrogen peroxide to afford 0.2 g (93%) of the title compound. $^1$H NMR (DMSO-d$_6$, 400 MHz) δ 8.01 (dd, J=7.0 Hz, 1H), 7.64-7.61 (m, 2H), 7.09-7.05 (m, 2H), 6.94-6.90 (m, 2H), 4.96 (m, 2H), 4.38-4.33 (m, 6H), 1.33 (t, J=7.1 Hz, 3H). MS (ESI+): 427.0. HPLC (max plot) 96.3%; Rt 4.45 min.

Intermediate P.27 ethyl 1-(2-methyl-1,3-benzothiazol-6-yl)-1,4-dihydrothiochromeno[4,3-c]pyrazole-3-carboxylate 5,5-dioxide

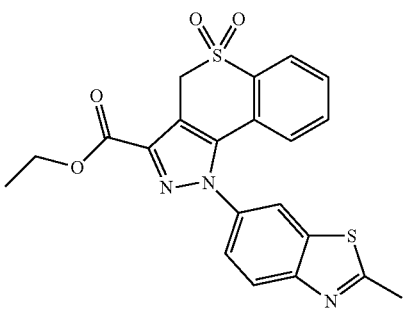 [SMILES: CCOC(=O)c1nn(-c2ccc3nc(C)sc3c2)c2c1CS(=O)(=O)c1ccccc1-2]

Following the protocol outlined in Procedure P, ethyl 1-(2-methyl-1,3-benzothiazol-6-yl)-1,4-dihydrothiochromeno[4,3-c]pyrazole-3-carboxylate 5,5-dioxide is obtained from ethyl 1-(2-methyl-1,3-benzothiazol-6-yl)-1,4-dihydrothiochromeno[4,3-c]pyrazole-3-carboxylate and hydrogen peroxide to afford the title compound. $^1$H NMR (DMSO-d$_6$, 400 MHz) δ 8.38 (d, J=1.3 Hz, 1H), 8.11 (d, J=8.2 Hz, 1H), 8.03 (d, J=6.6 Hz, 1H), 7.64-7.52 (m, 3H), 6.79 (d, J=7.8 Hz, 1H), 5.01 (s, 2H), 4.37 (q, J=7.2 Hz, 2H), 2.86 (s, 3H), 1.33 (t, J=7.1 Hz, 3H). MS (ESI+): 440.0. HPLC (max plot) 95.5%; Rt 4.31 min.

Intermediate P.28 ethyl 1-(3-bromophenyl)-1,4-dihydrothiochromeno[4,3-c]pyrazole-3-carboxylate 5,5-dioxide

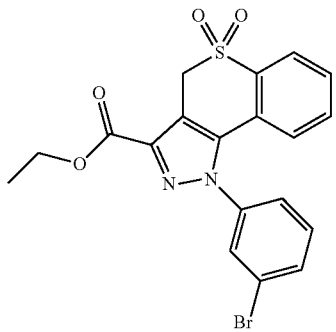 [SMILES: CCOC(=O)c1nn(-c2cccc(Br)c2)c2c1CS(=O)(=O)c1ccccc1-2]

Following the protocol outlined in Procedure P, ethyl 1-(3-bromophenyl)-1,4-dihydrothiochromeno[4,3-c]pyrazole-3-carboxylate 5,5-dioxide is obtained from ethyl 1-(3-bromophenyl)-1,4-dihydrothiochromeno[4,3-c]pyrazole-3-carboxylate and hydrogen peroxide to afford 0.417 g (86%) of the title compound. $^1$H NMR (DMSO-d$_6$, 400 MHz) δ 8.04 (d, J=7.0 Hz, 1H), 7.88-7.87 (m, 2H), 7.67-7.63 (m, 2H), 7.57-7.53 (m, 2H), 6.90 (d, J=7.0 Hz, 1H), 4.99 (s, 2H), 4.39-4.36 (m, 2H), 1.33 (t, J=7.0 Hz, 3H). MS (ESI+): 448.0. HPLC (max plot) 96.9%; Rt 4.91 min.

Intermediate P.29 ethyl 1-(3-chlorophenyl)-1,4-dihydrothiochromeno[4,3-c]pyrazole-3-carboxylate 5,5-dioxide

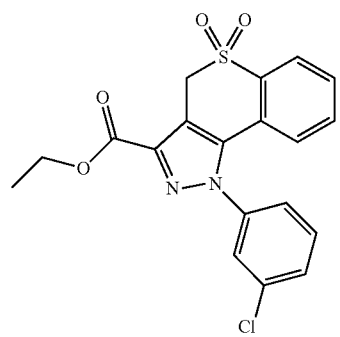 [SMILES: CCOC(=O)c1nn(-c2cccc(Cl)c2)c2c1CS(=O)(=O)c1ccccc1-2]

Following the protocol outlined in Procedure P, ethyl 1-(3-chlorophenyl)-1,4-dihydrothiochromeno[4,3-c]pyrazole-3-carboxylate 5,5-dioxide is obtained from ethyl 1-(3-chlorophenyl)-1,4-dihydrothiochromeno[4,3-c]pyrazole-3-carboxylate and hydrogen peroxide to afford 0.39 g (79%) of the title compound. $^1$H NMR (DMSO-$d_6$, 400 MHz) δ 8.05-8.03 (m, 1H), 7.77-7.74 (m, 2H), 7.67-7.62 (m, 3H), 7.50-7.47 (m, 1H), 6.91-6.88 (m, 1H), 4.99 (s, 2H), 4.35 (q, J=7.2 Hz, 2H), 1.33 (t, J=7.2 Hz, 3H). MS (ESI+): 403.0. HPLC (max plot) 97.7%; Rt 4.84 min.

Intermediate P.30 ethyl 1-(4-bromophenyl)-1,4-dihydrothiochromeno[4,3-c]pyrazole-3-carboxylate 5,5-dioxide

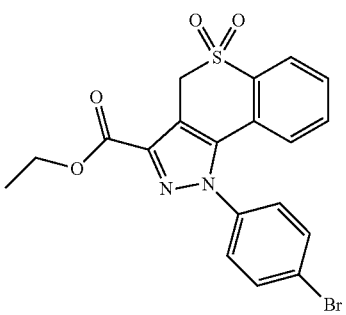 [SMILES: CCOC(=O)c1nn(-c2ccc(Br)cc2)c2c1CS(=O)(=O)c1ccccc1-2]

Following the protocol outlined in Procedure P, ethyl 1-(4-bromophenyl)-1,4-dihydrothiochromeno[4,3-c]pyrazole-3-carboxylate 5,5-dioxide is obtained from ethyl 1-(4-bromophenyl)-1,4-dihydrothiochromeno[4,3-c]pyrazole-3-carboxylate and hydrogen peroxide to afford 0.3 g (85%) of the title compound. $^1$H NMR (DMSO-$d_6$, 400 MHz) δ 8.04-8.02 (m, 1H), 7.84-7.82 (m, 2H), 7.66-7.62 (m, 2H), 7.52-7.50 (m, 2H), 6.92-6.90 (m, 1H), 4.98 (s, 2H), 4.36 (q, J=7.1 Hz, 2H), 1.33 (t, J=7.1 Hz, 3H). MS (ESI+): 448.0. HPLC (max plot) 99.7%; Rt 4.90 min

Intermediate P.31 ethyl 1-(4-fluorophenyl)-1,4-dihydrothiochromeno[4,3-c]pyrazole-3-carboxylate 5,5-dioxide

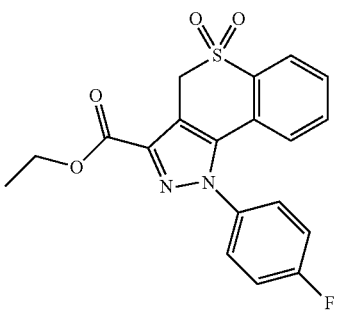 [SMILES: CCOC(=O)c1nn(-c2ccc(F)cc2)c2c1CS(=O)(=O)c1ccccc1-2]

Following the protocol outlined in Procedure P, ethyl 1-(4-fluorophenyl)-1,4-dihydrothiochromeno[4,3-c]pyrazole-3-carboxylate 5,5-dioxide is obtained from ethyl 1-(4-fluorophenyl)-1,4-dihydrothiochromeno[4,3-c]pyrazole-3-carboxylate and hydrogen peroxide to afford 0.38 g (94%) of the title compound. $^1$H NMR (DMSO-$d_6$, 400 MHz) δ 8.03 (dd, J=7.7 Hz, J=1.6 Hz, 1H), 7.67-7.59 (m, 4H), 7.50-7.46 (m, 2H), 6.85-6.83 (m, 1H), 4.98 (m, 2H), 4.36 (q, J=7.1 Hz, 2H), 1.33 (t, J=7.1 Hz, 3H). MS (ESI+): 387.0. HPLC (max plot) 98.6%; Rt 4.54 min.

Intermediate P.32 ethyl 1-(4-chlorophenyl)-1,4-dihydrothiochromeno[4,3-c]pyrazole-3-carboxylate 5,5-dioxide

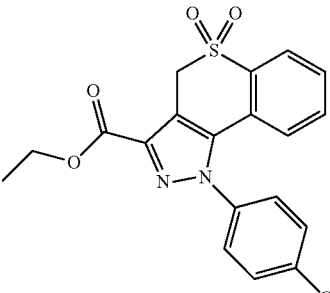

Following the protocol outlined in Procedure P, ethyl 1-(4-chlorophenyl)-1,4-dihydrothiochromeno[4,3-c]pyrazole-3-carboxylate 5,5-dioxide is obtained from ethyl 1-(4-chlorophenyl)-1,4-dihydrothiochromeno[4,3-c]pyrazole-3-carboxylate and hydrogen peroxide to afford 0.32 g (84%) of the title compound. $^1$H NMR (DMSO-$d_6$, 400 MHz) δ 8.04-8.02 (m, 2H), 7.71-7.57 (m, 5H), 6.91-6.89 (m, 1H), 4.98 (s, 2H), 4.37 (q, J=7.1 Hz, 2H), 4.22 (s, 2H), 1.33 (t, J=7.1 Hz, 3H). MS (ESI+): 403.0. HPLC (max plot) 97.3%; Rt 4.82 min.

Intermediate P.33 ethyl 1-(4-isopropylphenyl)-1,4-dihydrothio-chromeno[4,3-c]pyrazole-3-carboxylate 5,5-dioxide

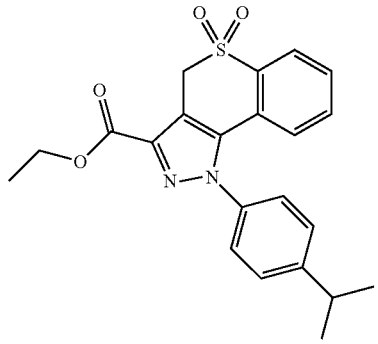 [SMILES: CCOC(=O)c1nn(-c2ccc(C(C)C)cc2)c2c1CS(=O)(=O)c1ccccc1-2]

Following the protocol outlined in Procedure P, ethyl 1-(4-isopropylphenyl)-1,4-dihydrothiochromeno[4,3-c]pyrazole-3-carboxylate 5,5-dioxide is obtained from ethyl 1-(4-isopropylphenyl)-1,4-dihydrothiochromeno[4,3-c]pyrazole-3-carboxylate and hydrogen peroxide to afford 0.6 g (79%) of the title compound. $^1$H NMR (DMSO-d$_6$, 400 MHz) δ 8.02 (q, J=7.6 Hz, 1H), 7.65-7.56 (m, 2H), 7.51-7.43 (m, 4H), 6.83 (d, J=7.8 Hz, 1H), 4.98 (s, 2H), 4.36 (q, J=7.0 Hz, 2H), 3.06-3.03 (m, 1H), 1.33 (t, J=7.1 Hz, 3H), 1.25 (d, J=6.8 Hz, 6H). MS (ESI+): 411.0. HPLC (max plot) 98.2%; Rt 6.79 min.

Intermediate P.34 ethyl 1-(4-methylpyridin-3-yl)-1,4-dihydrothio-chromeno[4,3-c]pyrazole-3-carboxylate 5,5-dioxide

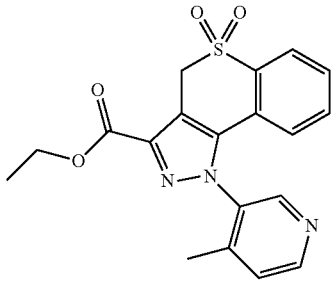 [SMILES: CCOC(=O)c1nn(-c2cnccc2C)c2c1CS(=O)(=O)c1ccccc1-2]

Following the protocol outlined in Procedure P, ethyl 1-(4-methylpyridin-3-yl)-1,4-dihydrothiochromeno[4,3-c]pyrazole-3-carboxylate 5,5-dioxide is obtained from ethyl 1-(4-methylpyridin-3-yl)-1,4-dihydrothiochromeno[4,3-c]pyrazole-3-carboxylate and hydrogen peroxide to afford 0.3 g (83%) of the title compound. $^1$H NMR (DMSO-d$_6$, 400 MHz) δ 8.38 (d, J=1.4 Hz, 1H), 8.04-7.99 (m, 2H), 7.78 (d, J=8.1 Hz, 1H), 7.66-7.57 (m, 2H), 6.86 (d, J=7.6 Hz, 1H), 4.97 (s, 2H), 4.37 (q, J=7.1 Hz, 2H), 2.43 (s, 3H), 1.34 (t, J=7.1 Hz, 3H). MS (ESI+): 384.0. HPLC (max plot) 96.1%;Rt 4.13 min.

Intermediate P.35 ethyl 1-(tetrahydro-2H-pyran-4-yl)-1,4-dihydrothio-chromeno[4,3-c]pyrazole-3-carboxylate 5,5-dioxide

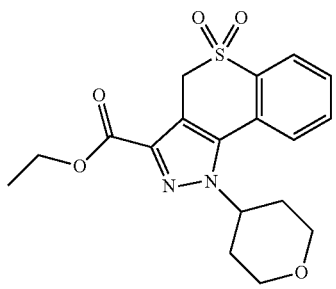 [SMILES: CCOC(=O)c1nn(C2CCOCC2)c2c1CS(=O)(=O)c1ccccc1-2]

Following the protocol outlined in Procedure P, ethyl 1-(tetrahydro-2H-pyran-4-yl)-1,4-dihydrothiochromeno[4,3-c]pyrazole-3-carboxylate 5,5-dioxide is obtained from ethyl 1-(tetrahydro-2H-pyran-4-yl)-1,4-dihydrothiochromeno[4,3-c]pyrazole-3-carboxylate and hydrogen peroxide to afford 0.6 g (91%) of the title compound. $^1$H NMR (DMSO-d$_6$, 400 MHz) δ 8.06-8.04 (m, 1H), 7.96-7.89 (m, 2H), 7.77-7.73 (m, 1H), 5.09-5.04 (m, 1H), 4.86 (s, 2H), 4.34 (q, J=7.0 Hz, 1H), 4.00-3.96 (m, 2H), 3.60-3.54 (m, 3H), 2.21-2.11 (m, 2H), 2.02-1.99 (m, 2H), 1.33 (t, J=7.1 Hz, 3H). MS (ESI+): 377.0. HPLC (max plot) 94.4%; Rt 3.61 min.

Intermediates described below are obtained following procedure P

---

Intermediate P.36: 1-(3-(Benzyloxy)phenyl)-1,4-dihydrothiochromeno[4,3-c]pyrazole-3-carboxylate 5,5-dioxide

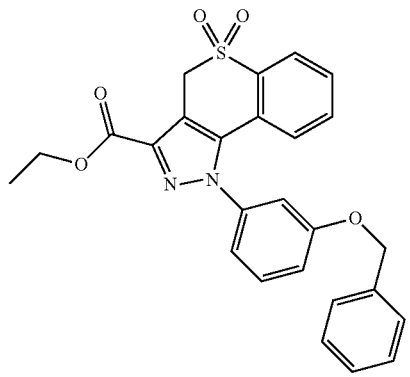 [SMILES: CCOC(=O)c1nn(-c2cccc(OCc3ccccc3)c2)c2c1CS(=O)(=O)c1ccccc1-2]

11 g of the title compound as an off white solid. $^1$H NMR (DMSO-d$_6$, 400 MHz): δ 8.03-8.01 (t, J = 6.8 Hz, 1H), 7.64-7.64 (d, J = 7.0 Hz, 1H), 7.62-7.51 (m, 2H), 7.44-7.42 (m, 2H), 7.38-7.38 (d, J = 1.2 Hz, 2H), 7.36-7.29 (m, 2H), 7.23-7.22 (m, 1H), 7.05 (m, 1H), 6.84-6.82 (m, 1H), 5.18 (s, 2H), 4.98 (s, 2H), 4.38-4.36 (m, 2H), 1.35-1.32 (m, 3H). MS (ESI+): 475.0. HPLC (max plot): 96%; Rt 5.30 min.

Intermediate P.37: Ethyl 1-(pyridin-3-yl)-1,4-dihydrothiochromeno[4,3-c]pyrazole-3-carboxylate 5,5-dioxide

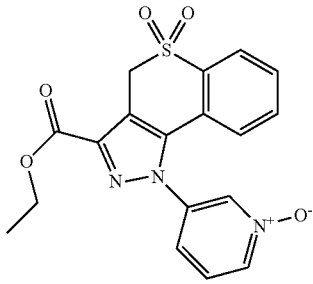 [SMILES: CCOC(=O)c1nn(-c2ccc[n+]([O-])c2)c2c1CS(=O)(=O)c1ccccc1-2]

300 mg of the title compound. MS (ESI+): 386.2

Intermediate P.38: Ethyl 1-(6-methyl-1-oxidopyridin-3-yl)-1,4-dihydrothiochromeno[4,3-c]pyrazole-3-carboxylate 5,5-dioxide

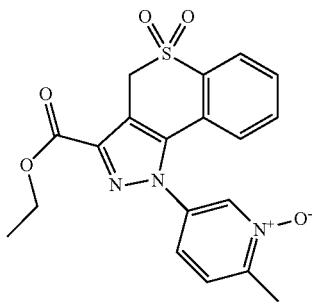 [SMILES: CCOC(=O)c1nn(-c2ccc(C)[n+]([O-])c2)c2c1CS(=O)(=O)c1ccccc1-2]

$^1$H NMR (DMSO-d$_6$, 400 MHz): δ 8.69 (m, 1H), 8.05-8.03 (d, J = 8.1 Hz, 1H), 7.69-7.65 (m, 3H), 7.44-7.42 (d, J = 8.4 Hz, 1H), 7.19-7.18 (d, J = 6.6 Hz, 1H), 4.98 (m, 2H), 4.40-4.34 (q, 2H), 2.49 (s, 3H), 1.35-1.31 (t, J = 7.1 Hz, 3H). MS (ESI+): 400.0

Intermediate P.39: Ethyl 1-(3-fluorophenyl)-1,4-dihydrothiochromeno[4,3-c]pyrazole-3-carboxylate 5,5-dioxide

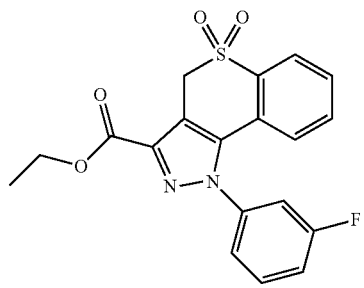 [SMILES: CCOC(=O)c1nn(-c2cccc(F)c2)c2c1CS(=O)(=O)c1ccccc1-2]

110 mg of the title compound. $^1$H NMR (DMSO-d$_6$, 400 MHz): δ 8.04-8.02 (d, J = 7.4 Hz, 1H), 7.69-7.52 (m, 5H), 7.36-7.34 (d, J = 8.8 Hz, 1H), 6.89-6.87 (d, J = 6.9 Hz, 1H), 4.99 (s, 2H), 4.39-4.34 (m, 2H), 1.35-1.31 (t, J = 7.1 Hz, 3H). MS (ESI+): 387.0. HPLC (max plot) 95.14%; Rt 4.58 min.

Intermediate P.40: Ethyl 1-(3-cyanophenyl)-1,4-dihydrothiochromeno[4,3-c]pyrazole-3-carboxylate 5,5-dioxide

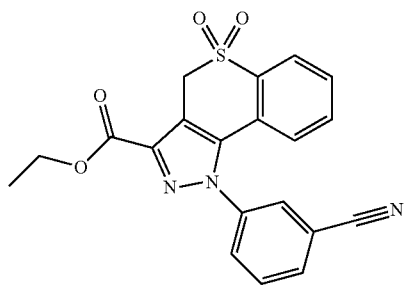 [SMILES: CCOC(=O)c1nn(-c2cccc(C#N)c2)c2c1CS(=O)(=O)c1ccccc1-2]

0.22 g of the title compound. $^1$H NMR (DMSO-d$_6$, 400 MHz) δ 8.24 (s, 1H), 8.15-8.13 (d, J = 7.5 Hz, 1H), 8.04 (d, J = 7.6 Hz, 1H), 7.88-7.79 (m, 2H), 7.69-7.59 (m, 2H), 6.87 (d, J = 7.8 Hz, 1H), 5.00 (s, 2H), 4.37 (q, J = 7.8 Hz, 2H), 1.33 (t, J = 7.2 Hz, 3H). MS (ESI+): 394.0. HPLC (max plot) 96.7%; Rt 4.26 min.

Intermediate P.41: Ethyl 1-[4-(methylsulfonyl)phenyl]-1,4-dihydrothiochromeno[4,3-c]pyrazole-3-carboxylate 5,5-dioxide

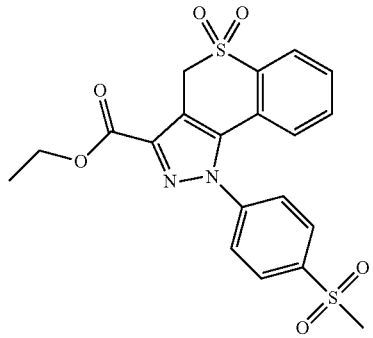 [SMILES: CCOC(=O)c1nn(-c2ccc(S(C)(=O)=O)cc2)c2c1CS(=O)(=O)c1ccccc1-2]

260 mg (80%) of the title compound. $^1$H NMR (DMSO-d$_6$, 400 MHz): δ 7.49-7.48 (d, J = 7.8 Hz,1H), 7.43-7.37 (m, 4H), 7.23-7.19 (t, J = 7.6 Hz, 1H), 7.05-7.01 (t, J = 7.7 Hz, 1H), 6.77-6.75 (d, J = 7.9 Hz, 1H), 4.35-4.30 (m, 2H), 4.22 (s, 2H), 2.54 (s, 3H), 1.33-1.29 (t, J = 5.6 Hz, 3H). MS (ESI-): 444.8. HPLC (max plot) 95.32%; Rt 3.88 min.

Intermediate P.42: Ethyl 1-[3-(methylsulfonyl)phenyl]-1,4-dihydrothiochromeno[4,3-c]pyrazole-3-carboxylate 5,5-dioxide

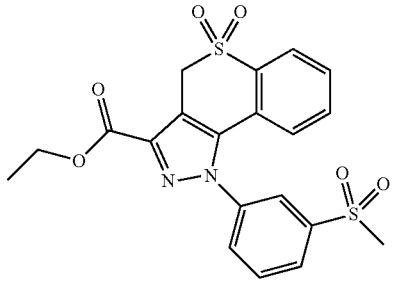 [SMILES: CCOC(=O)c1nn(-c2cccc(S(C)(=O)=O)c2)c2c1CS(=O)(=O)c1ccccc1-2]

220 mg (94%) of the title compound. $^1$H NMR (DMSO-d$_6$, 400 MHz): δ 7.49-7.48 (dd, J = 2.4, 3.9 Hz, 1H), 8.12 (s, 1H), 8.06-8.04 (dd, J = 1.2, 7.8 Hz, 1H), 7.93-7.08 (m, 2H), 7.69-7.59 (m, 2H), 6.92-6.90 (d, J = 7.4 Hz, 1H), 5.01 (s, 2H), 4.41-4.36 (m, 2H), 1.36-1.32 (t, J = 7.1 Hz, 3H). MS (ESI+): 446.7. HPLC (max plot) 97.52%; Rt 3.87 min.

Intermediate P.43: Ethyl 1-(6-methoxypyridin-3-yl)-1,4-dihydrothiochromeno[4,3-c]pyrazole-3-carboxylate 5,5-dioxide

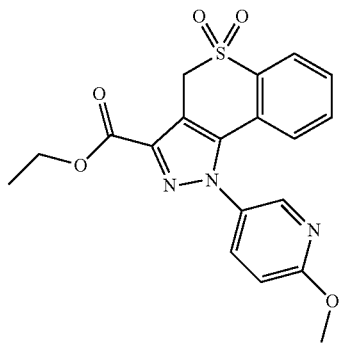

250 mg (71%) of the title compound. $^1$H NMR (DMSO-d$_6$, 400 MHz): δ 8.41 (s, 1H),7.05-8.02 (m, 1H), 7.94-7.91 (dd, J$_1$ = 2.8, 8.9 Hz, 1H), 7.68-7.64 (m, 2H), 7.08-7.05 (d, J = 8.8 Hz, 1H), 6.97-6.94 (m, 1H), 4.99 (s, 2H), 4.39-4.34 (m, 2H), 3.96 (s, 3H), 1.35-1.31 (t, J = 7.1 Hz, 3H). MS (ESI+): 400.0. HPLC (max plot) 89.85%; Rt 4.19 min.

Intermediate P.44: Ethyl 1-(1-methyl-6-oxo-1,6-dihydropyrtidin-3-yl)-1,4-dihydrothiochromeno[4,3-c]pyrazole-3-carboxylate 5,5-dioxide

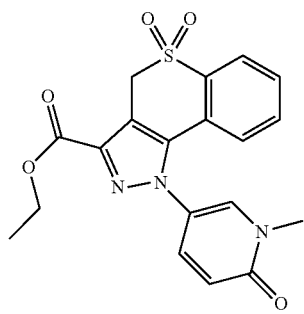 [SMILES: CCOC(=O)c1nn(-c2ccc(=O)n(C)c2)c2c1CS(=O)(=O)c1ccccc1-2]

75 mg of the title compound. $^1$H NMR (DMSO-d$_6$, 400 MHz): δ 8.40 (m, 1H), 8.04-8.02 (m, 1H), 7.93-7.90 (m, 1H), 7.66-7.64 (m, 2H), 7.07-7.05 (d, J = 8.9 Hz, 1H), 6.96-6.94 (m, 1H), 4.99 (s, 2H), 4.39-4.34 (m, 2H), 3.96 (s, 2H), 1.35-1.31 (t, J = 7.1 Hz, 3H). MS (ESI+): 400.2.

Intermediate P.45: Ethyl 1-(1H-indazol-4-yl)-1,4-dihydrothiochromeno[4,3-c]pyrazole-3-carboxylate 5,5-dioxide

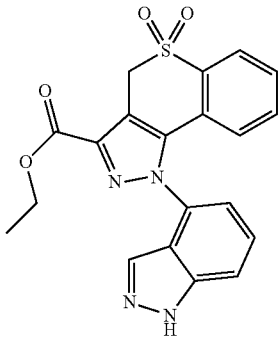 [SMILES: CCOC(=O)c1nn(-c2cccc3[nH]ncc23)c2c1CS(=O)(=O)c1ccccc1-2]

420 mg (78%) of the title compound. $^1$H NMR (DMSO-$d_6$, 400 MHz): δ 13.40 (s, 1H), 8.28 (s, 1H), 8.03-8.01 (m, 2H), 7.74 (s, 1H), 7.68-7.60 (m, 1H), 7.20-7.16 (m, 1H), 7.54-7.50 (m, 1H), 7.18-7.16 (m, 1H), 6.81-6.79 (d, J = 7.9 Hz, 1H), 5.0 (s, 2H), 4.36 (q, J = 7.1 Hz, 2H), 1.34 (t, J = 7.1 Hz, 3H). MS (ESI+): 409.1.

Intermediate P.46: Ethyl 1-(2-benzyl-2H-indazol-4-yl)-1,4-dihydrothiochromeno[4,3-c]pyrazole-3-carboxylate 5,5-dioxide

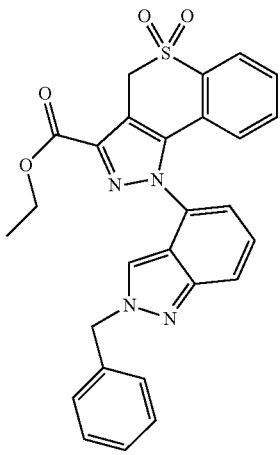 [SMILES: CCOC(=O)c1nn(-c2cccc3nn(Cc4ccccc4)cc23)c2c1CS(=O)(=O)c1ccccc1-2]

100 mg of the title compound. MS (ESI+): 499.2.

Intermediate P.47: Ethyl 1-{3-[(dimethylamino)sulfonyl]phenyl}-1,4-dihydrothiochromeno[4,3-c]pyrazole-3-carboxylate 5,5-dioxide

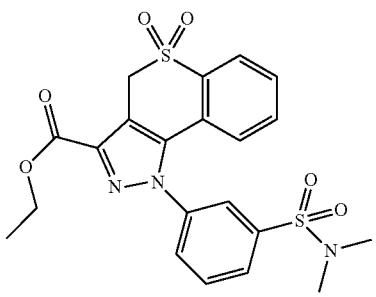 [SMILES: CCOC(=O)c1nn(-c2cccc(S(=O)(=O)N(C)C)c2)c2c1CS(=O)(=O)c1ccccc1-2]

100 mg of the title compound. MS (ESI+): 476.0.

Intermediate P.48: Ethyl 1-(2-isopropylphenyl)-1,4-dihydrothiochromeno[4,3-c]pyrazole-3-carboxylate 5,5-dioxide

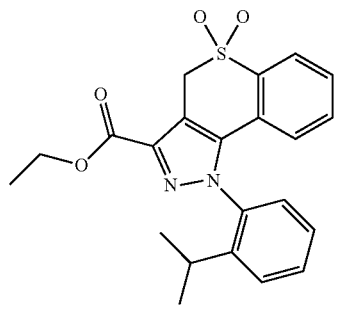 [SMILES: CCOC(=O)c1nn(-c2ccccc2C(C)C)c2c1CS(O)(O)c1ccccc1-2]

67 mg (95%) of the title compound. $^1$H NMR (400 MHz, DMSO-$d_6$) δ: 8.01 (d, J = 7.7 Hz, 1H), 7.70-7.45 (m, 6H), 6.63 (d, J = 7.8 Hz, 1H), 5.01 (s, 2H), 4.40-4.32 (m, 2H), 2.32-2.29 (m, 1H), 1.34 (t, J = 7.1 Hz, 3H), 1.05 (t, J = 6.8 Hz, 3H), 0.81 (t, J = 6.8 Hz, 3H). MS (ESI+): 411.0. HPLC (max plot): 97.6%; Rt 5.21 min.

Intermediate P.49: Ethyl 1-(2-methoxyphenyl)-1,4-dihydrothiochromeno[4,3-c]pyrazole-3-carboxylate 5,5-dioxide

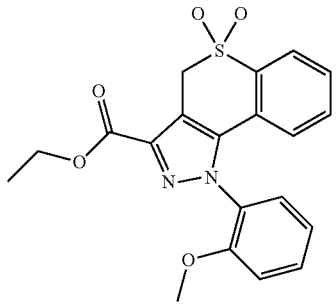 [SMILES: CCOC(=O)c1nn(-c2ccccc2OC)c2c1CS(O)(O)c1ccccc1-2]

240 mg of the title compound. $^1$H NMR (400 MHz, DMSO-d$_6$) δ: 8.00 (dd, J = 1.2, 7.7 Hz, 1H), 7.68-7.53 (m, 2H), 7.32 (d, J = 8.4 Hz, 1H), 7.22-7.18 (m, 2H), 6.82-6.80 (m, 2H), 5.03-4.93 (m, 2H), 4.35 (q, J = 7.1 Hz, 2H), 3.57 (s, 3H), 1.34 (t, J = 7.1 Hz, 3H). MS (ESI+): 399.0. HPLC (max plot): 95.2%; Rt 4.41 min.

Intermediate P.50: 4-[3-(Ethoxycarbonyl)-5,5-dihydrothiochromeno[4,3-c]pyrazol-1(4H)-yl]benzoic acid

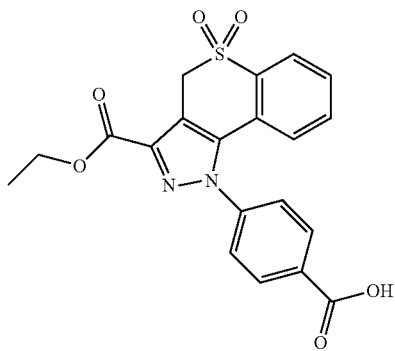 [SMILES: CCOC(=O)c1nn(-c2ccc(C(=O)O)cc2)c2c1CS(=O)(=O)c1ccccc1-2]

18.4 g (89%) of the title compound. 1H NMR (DMSO-d6) δ 13.28 (br s, 1H), 8.17 (d, J = 8.6 Hz, 2H), 8.07-8.04 (m, 1H), 7.70-7.59 (m, 4H), 6.94-6.90 (m, 1H), 5.01 (s, 2H), 4.39 (q, J = 7.1 Hz, 2H), 1.35 (t, J = 7.1 Hz, 3H). HPLC (max plot) 63.4%; Rt 3.26 min. MS (ESI+): 412.7.

Intermediate P.51: 3-[3-(Ethoxycarbonyl)-5,5-dihydrothiochromeno[4,3-c]pyrazol-1(4H)-yl]benzoic acid

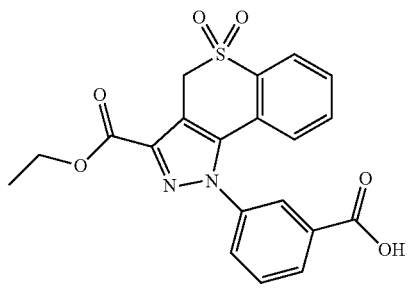 [SMILES: CCOC(=O)c1nn(-c2cccc(C(=O)O)c2)c2c1CS(=O)(=O)c1ccccc1-2]

1.6 g (78%) of the title compound. 1H NMR (DMSO-d6) δ 13.44 (br s, 1H), 8.22-8.18 (m, 1H), 8.07-7.99 (m, 2H), 7.83-7.75 (m, 2H), 7.70-7.58 (m, 2H), 6.92-6.88 (m, 1H), 5.02-5.01 (m, 2H), 4.39 (q, J = 7.1 Hz, 2H), 1.35 (t, J = 7.1 Hz, (3H). HPLC (max plot) 50.1%; Rt 3.37 min. MS (ESI+): 413.0.

Intermediate P.52: Ethyl 1-(4-{[(methylsulfonyl)amino]methyl}phenyl)-1,4-dihydrothiochromeno[4,3-c]pyrazole-3-carboxylate 5,5-dioxide

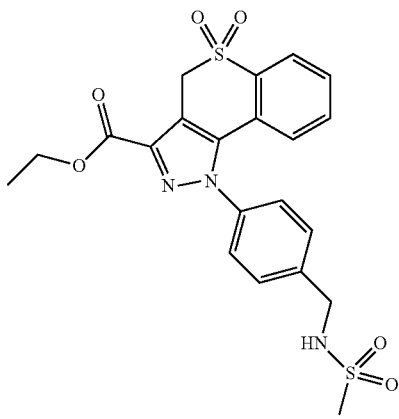 [SMILES: CCOC(=O)c1nn(-c2ccc(CNS(C)(=O)=O)cc2)c2c1CS(=O)(=O)c1ccccc1-2]

220 mg (89%) of the title compound. 1H NMR (400 MHz, DMSO-d6) δ = 8.04-8.02 (d, 1H), 7.64-7.62 (m, 3H), 7.57-7.55 (m, 3H), 7.06-7.05 (m, 1H), 6.87-6.85 (m, 1H), 4.99 (s, 2H), 4.52 (s, 2H), 4.37-4.35 (m, 2H), 2.59-2.58 (m, 2H), 1.35-1.31 (m, 3H). MS (ESI+): 476.

Intermediate P.53: Ethyl 6-cyano-1-phenyl-1,4-dihydrothiochromeno[4,3-c]pyrazole-3-carboxylate 5,5-dioxide

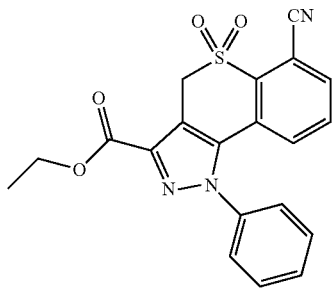

170 mg (78%) of the title compound. MS (ESI+): 394.0

Intermediate P.54: Ethyl 1-phenyl-7-(trifluoromethyl)-1,4-dihydrothiochromeno[4,3-c]pyrazole-3-carboxylate 5,5-dioxide

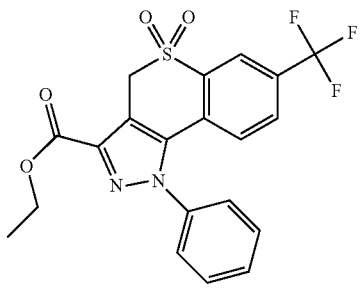 [SMILES: CCOC(=O)c1nn(-c2ccccc2)c2c1CS(=O)(=O)c1cc(C(F)(F)F)ccc1-2]

220 mg of the title compound. $^1$H NMR (DMSO-d$_6$, 400 MHz): δ 8.22 (m, 1H), 8.06-8.03 (dd, J = 1.4, 8.4 Hz, 1H), 7.68-7.63 (m, 3H), 7.59-7.56 (m, 2H), 7.03-7.01 (d, J = 8.3 Hz, 1H), 5.12 (s, 2H), 4.40-4.35 (m, 2H), 1.36-1.32 (t, J = 7.1 Hz, 3H). MS (ESI+): 437.0. HPLC (max plot) 96.42%; Rt 5.28 min.

Intermediate P.55: Ethyl 8-methoxy-1-phenyl-1,4-dihydrothiochromeno[4,3-c]pyrazole-3-carboxylate 5,5-dioxide

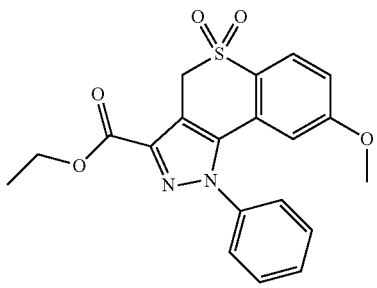 [SMILES: CCOC(=O)c1nn(-c2ccccc2)c2c1CS(=O)(=O)c1ccc(OC)cc1-2]

300 mg (80%) of the title compound. $^1$H NMR (DMSO-d$_6$, 400 MHz): δ 7.95-7.93 (d, J = 8.7 Hz, 1H), 7.67-7.65 (m, 3H), 7.57-7.54 (m, 2H), 7.17 (dd, J = 2.4, 8.8 Hz, 1H), 6.21 (d, J = 2.3 Hz, 1H), 4.92 (s, 2H), 4.39-4.34 (m, 2H), 3.53 (s, 3H), 1.35-1.31 (t, J = 7.1 Hz, 3H). MS (ESI+): 399.0. HPLC (max plot) 95.46%; Rt 4.59 min.

Intermediate P.56: Ethyl 1-cyclopentyl-1,4-dihydrothiochromeno[4,3-c]pyrazole-3-carboxylate 5,5-dioxide

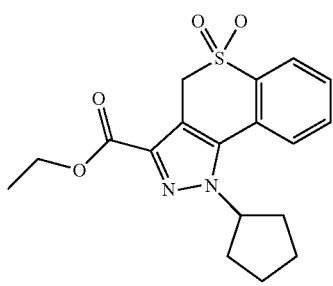

500 mg (76%) of the title compound. 1H NMR (400 MHz, DMSO-d6) δ = 8.05-8.03 (m, 1H), 7.8.03-7.97 (m, 1H), 7.92-7.88 (m, 1H), 7.76-7.72 (m, 1H), 5.31 (m, 1H), 4.36-4.31 (q, J = 7.1 Hz, 2H), 2.27-2.22 (m, 2H), 2.09-2.05 (m, 2H), 1.91-1.87 (m, 2H), 1.72-1.68 (m, 2H), 1.34-1.30 (t, J = 7.1 Hz, 3H). MS (ESI+): 361. HPLC (max plot) 97.62%; Rt 4.68 min Intermediate P.57: Ethyl 1-(4-methylcyclohexyl)-1,4-dihydrothiochromeno[4,3-c]pyrazole-3-carboxylate 5,5-dioxide

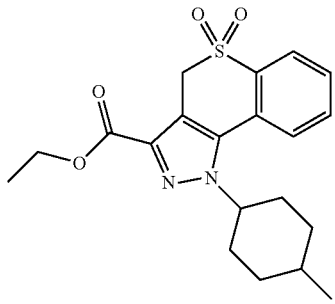 [SMILES: CCOC(=O)c1nn(C2CCC(C)CC2)c2c1CS(=O)(=O)c1ccccc1-2]

400 mg (92%) of the title compound. MS (ESI+): 389.0.

Intermediate P.58: Ethyl 1-(4-tert-butylcyclohexyl)-1,4-dihydrothiochromeno[4,3-c]pyrazole-3-carboxylate 5,5-dioxide

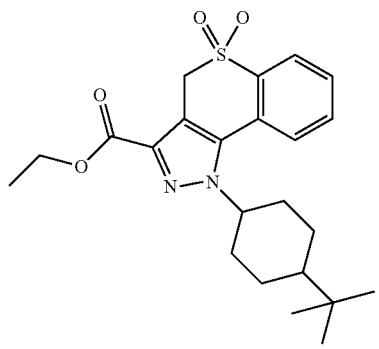

170 mg, 79% yield of the title compound. MS (ESI+): 431.3.

Intermediate P.59: Ethyl 1-(4,4-difluorocyclohexyl)-1,4-dihydrothiochromeno[4,3-c]pyrazole-3-carboxylate 5,5-dioxide

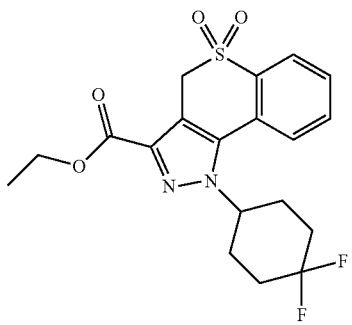 [SMILES: CCOC(=O)c1nn(C2CCC(F)(F)CC2)c2c1CS(=O)(=O)c1ccccc1-2]

180 mg (72%) of the title compound. $^1$H NMR (DMSO-$d_6$, 400 MHz): δ 8.06-8.04 (d, J = 7.6 Hz, 1H), 7.94-7.89 (m, 2H), 7.77-7.73 (m, 1H), 5.06 (m, 1H), 4.86 (s, 2H), 4.37-4.31 (m, 2H), 2.28-2.12 (m, 8H), 1.34-1.31 (t, J = 7.2 Hz, 3H). MS (ESI+): 411.2. HPLC (max plot) 97.57%; Rt 4.78 min.

Intermediate P.60: Ethyl 1-(3,3-dimethylcyclohexyl)-1,4-dihydrothiochromeno[4,3-c]pyrazole-3-carboxylate 5,5-dioxide

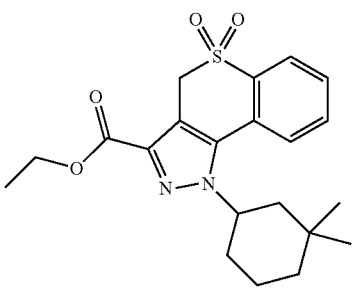 [SMILES: CCOC(=O)c1nn(C2CCCC(C)(C)C2)c2c1CS(=O)(=O)c1ccccc1-2]

200 mg of the title compound. $^1$H NMR (DMSO-$d_6$, 400 MHz): δ 8.06-8.04 (d, J = 7.6 Hz, 1H), 7.95-7.91 (m, 1H), 7.85-7.83 (d, J = 7.8 Hz, 1H), 7.76-7.72 (m, 1H), 4.93 (m, 1H), 4.92 (s, 2H), 4.36-4.31 (m, 2H), 2.04-2.01 (m, 1H), 1.94-1.89 (m, 1H), 1.80-1.70 (m, 5H), 1.41-1.37 (m, 4H), 1.34 (s, 3H), 1.32 (s, 3H). MS (ESI+): 403.2. HPLC (max plot) 97.09%; Rt 5.52 min.

-continued

Intermediate P.61: 3-[3-(Ethoxycarbonyl)thiochromeno[4,3-c]pyrazol-1(4H)-yl]cyclohexanecarboxylic acid 5,5-dioxide

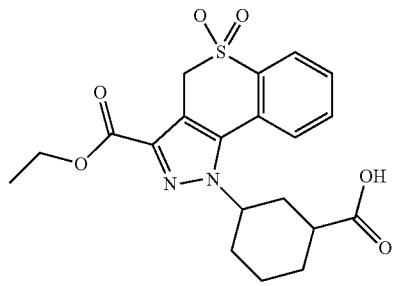

200 mg (92%) of the title compound. MS (ESI+): 419.2.

Intermediate P.62: 4-[3-(Ethoxycarbonyl)thiochromeno[4,3-c]pyrazol-1(4H)-yl]cyclohexanecarboxylic acid

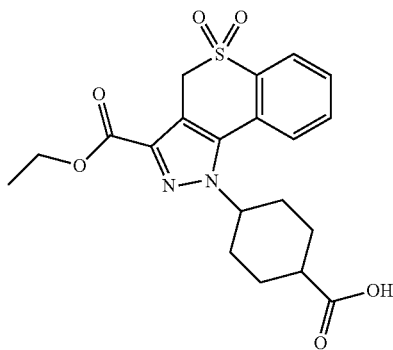 [SMILES: CCOC(=O)c1nn(C2CCC(C(=O)O)CC2)c2c1CS(=O)(=O)c1ccccc1-2]

450 mg (83%) of the title compound. MS (ESI+): 419.2.

Intermediate P.63: Ethyl 1-(4-hydroxycyclohexyl)-1,4-dihydrothiochromeno[4,3-c]pyrazole-3-carboxylate 5,5-dioxide

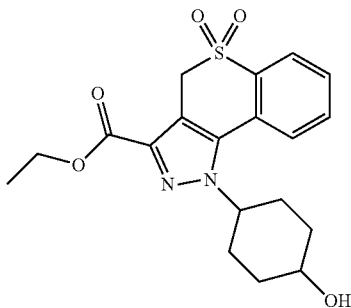 [SMILES: CCOC(=O)c1nn(C2CCC(O)CC2)c2c1CS(=O)(=O)c1ccccc1-2]

90 mg of the title compound. MS (ESI+): 391.0.

Intermediate P.64: Ethyl 1-(tetrahydro-2H-pyran-3-yl)-1,4-dihydrothiochromeno[4,3-c]pyrazole-3-carboxylate 5,5-dioxide

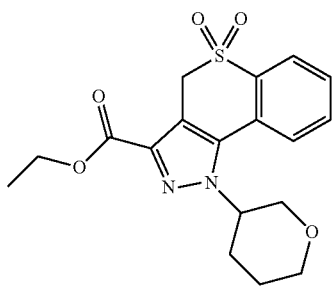

250 mg (91%) of the title compound. MS (ESI+): 377.2

Intermediate P.65: Ethyl 1-cycloheptyl-1,4-dihydrothiochromeno[4,3-c]pyrazole-3-carboxylate 5,5-dioxide

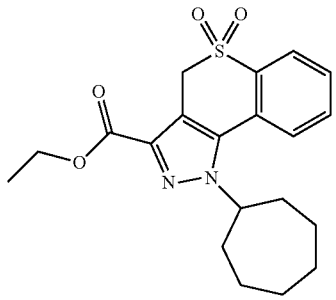 [SMILES: CCOC(=O)c1nn(C2CCCCCC2)c2c1CS(=O)(=O)c1ccccc1-2]

230 mg (84%) of the title compound. $^1$H NMR (400 MHz, DMSO-d$_6$) δ = 8.05-8.03 (m, 1H), 7.95-7.91 (m, 1H), 7.85-7.83 (d, J = 7.8 Hz,1H), 7.76-7.72 (m, 1H), 4.96-4.93 (m, 1H), 4.84 (s, 2H), 4.36-4.31 (m, 2H), 2.1-2.08 (m, 4H), 1.80-1.78 (m,2H), 1.64-1.62 (m, 6H), 1.34-1.30 (t, J = 7.1 Hz, 3H). HPLC (max plot) 90.98%; Rt 5.25 min.

Intermediate P.66: Ethyl 6-fluoro-1-(tetrahydro-2H-pyran-4-yl)-1,4-dihydrothiochromeno [4,3-c]pyrazole-3-carboxylate 5,5-dioxide

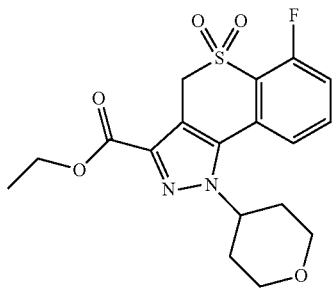

430 mg (82%) of the title compound. HPLC (max plot) 60.1%; Rt 3.13 min. (ESI+): 394.7

Intermediate P.67: Ethyl 6-chloro-1-(tetrahydro-2H-pyran-4-yl)-1,4-dihydrothiochromeno [4,3-c]pyrazole-3-carboxylate 5,5-dioxide

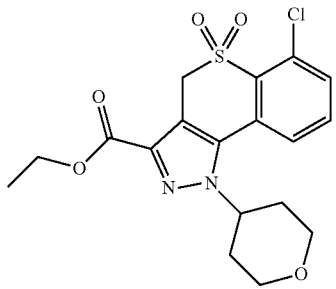 [SMILES: CCOC(=O)c1nn(C2CCOCC2)c2c1CS(=O)(=O)c1c(Cl)cccc1-2]

330 mg (72%) of the title compound as an off-white solid. 1H NMR (DMSO-d6) δ 7.73-7.82 (m, 3H), 4.88-4.97 (m, 3H), 4.30-4.37 (q, J = 9 Hz, 2H), 3.93-3.98 (m, 2H), 3.47-3.55 (m, 2H), 2.07-2.20 (m, 2H), 1.95-1.99 (m, 2H), 1.30-1.35 (t, 3H). MS (ESI+): 410.

Intermediate P.68: Ethyl 7-bromo-1-cyclohexyl-1,4-dihydrothiochromeno[4,3-c]pyrazole-3-carboxylate 5,5-dioxide

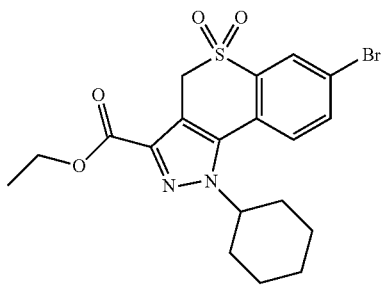 [SMILES: CCOC(=O)c1nn(C2CCCCC2)c2c1CS(=O)(=O)c1cc(Br)ccc1-2]

320 mg (74%) of the title compound. $^1$H NMR (DMSO-d$_6$, 400 MHz): δ 8.12-8.11 (m, 2H), 7.80-7.78 (d, J = 9.0 Hz, 1H), 4.90 (s, 2H), 4.70 (m, 1H), 4.34-4.31 (m, 2H), 2.03-1.80 (m, 6H), 1.70-1.67 (m, 1H), 1.51-1.47 (m, 2H), 1.34-1.32 (m, 4H). MS (ESI+): 453.0. HPLC (max plot) 87.26%; Rt 5.50 min.

Intermediate P.69: Ethyl 1-phenyl-1,4-dihydropyrazolo[3',4':4,5]thiopyrano[2,3-b]pyridine-3-carboxylate 5,5-dioxide

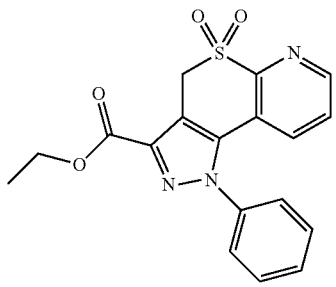 [SMILES: CCOC(=O)c1nn(-c2ccccc2)c2c1CS(=O)(=O)c1ncccc1-2]

200 mg (91%) of the title compound. $^1$H NMR (DMSO-d$_6$, 400 MHz): δ 8.72-8.71 (d, J = 4.4 Hz, 1H), 7.68-7.61 (m, 4H), 7.56-7.55 (d, J = 6.8 Hz, 2H), 7.17-7.15 (d, J = 8.0 Hz, 1H), 5.10 (s, 2H), 4.40-4.35 (m, 2H), 1.36-1.32 (t, J = 7.1 Hz, 3H). MS (ESI+): 370.0. HPLC (max plot) 94.77%; Rt 3.69 min.

Intermediate P.70: Ethyl 1-cyclohexyl-1,4-dihydropyrazolo[3',4':4,5]thiopyrano[2,3-b]pyridine-3-carboxylate 5,5-dioxide

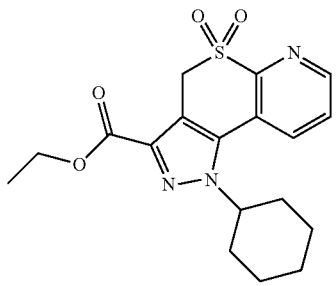

160 mg (73%) of the title compound. 1H NMR (400 MHz, DMSO-d6) δ = 8.80-8.79 (d, J = 4.64 Hz, 1H), 8.31-8.29 (d, J = 8.2 Hz, 1H), 7.94-7.91 (dd, J1 = 4.68 Hz, J2 = 8.16 Hz, 1H), 5.01 (s, 2H), 4.72-4.67 (m, 1H), 4.37-4.31 (q, 2H), 2.04-2.02 (m, 2H), 1.95-1.81 (m, 4H), 1.69-1.66 (m, 1H), 1.52-1.46 (m, 2H), 1.34-1.31 (t, J = 7.12 Hz, 3H), 1.28 (m, 1H). MS (ESI+): 376.2. HPLC (max plot) 92.62%; Rt 4.24 min.

Intermediate P.71: Ethyl 8-bromo-1-methyl-1,4-dihydrothiochromeno[4,3-c]pyrazole-3-carboxylate 5,5-dioxide

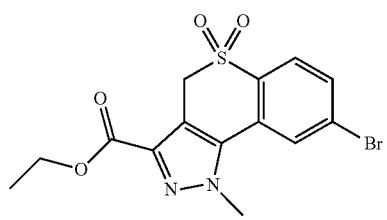 [SMILES: CCOC(=O)c1nn(C)c2c1CS(=O)(=O)c1ccc(Br)cc1-2]

300 mg (80%) of the title compound. 1H NMR (400 MHz, DMSO-d6) δ = 8.19 (s, 1H), 7.94 (s, 2H), 4.91 (s, 2H), 4.35-4.30 (m, 5H), 1.33-1.30 (t, J = 7.1 Hz, 3H). MS (ESI+): 386. (HPLC (max plot) 98.7%; Rt 3.97 min.

Intermediate P.72: Ethyl 1-phenyl-1,4-dihydropyrazolo[3',4':4,5]thiopyrano[3,2-c]pyridine-3-carboxylate 5,5,8-trioxide

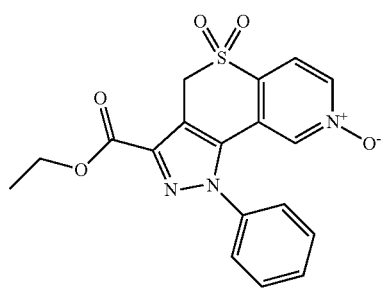 [SMILES: CCOC(=O)c1nn(-c2ccccc2)c2c1CS(=O)(=O)c1cc[n+]([O-])cc1-2]

100 mg of the title compound. MS (ESI+): 386.0.

Intermediate P.73: Ethyl 1-phenyl-1,4-dihydrothieno[3',2':5,6]thiopyrano[4,3-c]pyrazole-3-carboxylate 5,5-dioxide

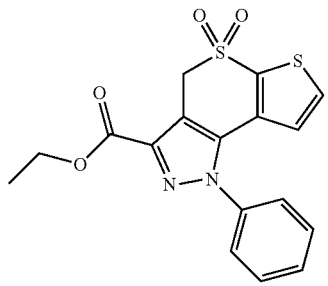 [SMILES: CCOC(=O)c1nn(-c2ccccc2)c2c1CS(=O)(=O)c1sccc1-2]

290 mg (76%) of the title compound. $^1$H NMR (DMSO-$d_6$, 400 MHz): δ 8.02-8.00 (d, J = 5.2 Hz, 1H), 7.67-7.58 (m, 5H), 6.32-6.31 (d, J = 5.0 Hz, 1H), 5.07 (s, 2H), 4.38-4.33 (m, 2H), 1.34-1.31 (t, J = 6.8 Hz, 3H). MS (ESI+): 375.0. HPLC (max plot) 94.33%; Rt 4.42 min.

Intermediate P.74: Ethyl 1-(1-methyl-6-oxo-1,6-dihydropyridin-3-yl)-1,4-dihydrothieno[3',2':5,6]thiopyrano[4,3-c]pyrazole-3-carboxylate 5,5-dioxide

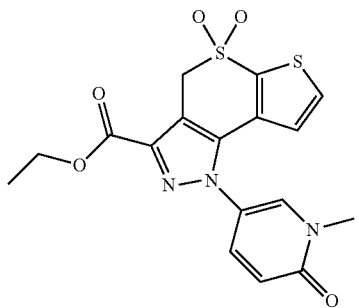 [SMILES: CCOC(=O)c1nn(-c2ccc(=O)n(C)c2)c2c1CS(O)(O)c1sccc1-2]

30 mg (92%) of the title compound. MS (ESI+): 405.9.

Intermediate P.75: Ethyl 1-cyclohexyl-1,4-dihydrothieno[3',2':5,6]thiopyrano[4,3-c]pyrazole-3-carboxylate 5,5-dioxide

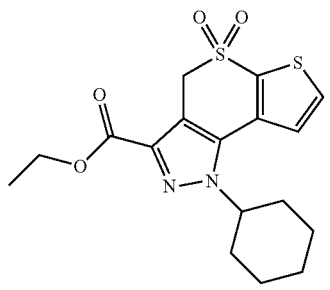 [SMILES: CCOC(=O)c1nn(C2CCCCC2)c2c1CS(=O)(=O)c1sccc1-2]

200 mg (92%) of the title compound. MS (ESI+): 381.2.

Intermediate P.76: Ethyl 1-(tetrahydro-2H-pyran-4-yl)-1,4-dihydrothieno[3',2':5,6]thiopyrano[4,3-c]pyrazole-3-carboxylate 5,5-dioxide

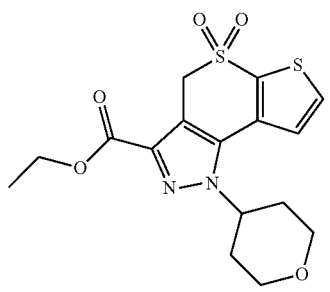 [SMILES: CCOC(=O)c1nn(C2CCOCC2)c2c1CS(=O)(=O)c1sccc1-2]

70 mg (64%) of the title compound as a yellow powder. HPLC (max plot) 80.4%; Rt 3.18 min. MS (ESI+): 382.7.

Intermediate P.77: Ethyl 1-phenyl-1,4-dihydrothieno[3',2':5,6]thiopyrano[4,3-c]pyrazole-3-carboxylate 5,5-dioxide

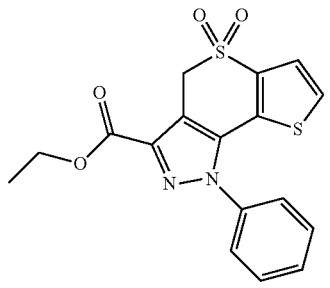 [SMILES: CCOC(=O)c1nn(-c2ccccc2)c2c1CS(=O)(=O)c1ccsc1-2]

250 mg of the title compound. MS (ESI+): 375.0.

Intermediate P.78: Ethyl 1-cyclohexyl-1,4-dihydrothieno[3',2':5,6]thiopyrano[4,3-c]pyrazole-3-carboxylate 5,5-dioxide

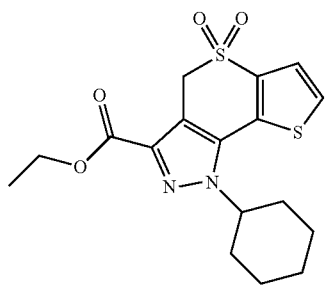 [SMILES: CCOC(=O)c1nn(C2CCCCC2)c2c1CS(=O)(=O)c1ccsc1-2]

150 mg of the title compound. MS (ESI+): 381.2.

Intermediate P.79: Ethyl 1-phenyl-1,4-dihydrothiochromeno[4,3-c]pyrazole-3-carboxylate 5-oxide

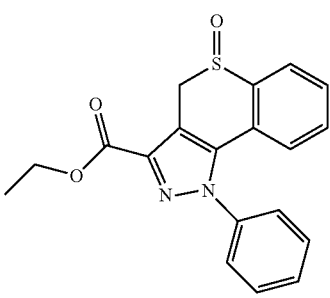 [SMILES: CCOC(=O)c1nn(-c2ccccc2)c2c1CS(=O)c1ccccc1-2]

140 mg of the title compound as a white solid. 1H NMR (DMSO-d6) δ 7.94 (dd, J = 1.2, 7.7 Hz, 1H), 7.67-7.62 (m, 3H), 7.60-7.53 (m, 3H), 7.47 (td, J = 1.4, 7.7 Hz, 1H), 6.84-6.81 (m, 1H), 4.72 (d, J = 15.5 Hz, 1H), 4.46 (d, J = 15.5 Hz, 1H), 4.38 (q, J = 7.1 Hz, 2H), 1.35 (t, J = 7.1 Hz, 3H). HPLC (max plot) 97.3%; Rt 3.25 min.

Intermediate P.80

Ethyl 1-pyridin-3-yl-1,4-dihydrothiochromeno[4,3-c]pyrazole-3-carboxylate 5,5-dioxide

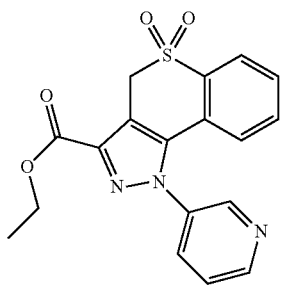 [SMILES: CCOC(=O)c1nn(-c2cccnc2)c2c1CS(=O)(=O)c1ccccc1-2]

To a solution of ethyl 1-(1-oxidopyridin-3-yl)-1,4-dihydrothiochromeno[4,3-c]pyrazole-3-carboxylate 5,5-dioxide (300 mg, 0.78 mmol) in glacial acetic acid (15 mL) is added iron powder (175 mg, 3.12 mmol). The reaction mass is heated to 85° C. for 1 h under nitrogen. The reaction progress is monitored by TLC. The solvent is removed completely under reduced pressure. The crude material obtained is diluted with water and is extracted with ethylacetate. The organic layer is separated and is dried using sodium sulphate and concentrated under reduced pressure to afford the title compound. $^1$H NMR (400 MHz, DMSO-d$_6$) δ=8.85-8.84 (d, J=4.7 Hz, 1H), 8.79-8.78 (m, 1H), 8.07-8.03 (m, 2H), 7.70-7.59 (m, 3H), 6.87-6.85 (d, J=7.84 Hz, 1H), 5.00 (s, 2H), 4.40-4.35 (q, 2H), 1.35-1.32 (t, J=7.12 Hz, 3H). MS (ESI+): 370.2. HPLC (max plot): 97.29%; Rt 3.24 min.

433
Intermediate P.81

Ethyl 1-phenyl-1,4-dihydropyrazolo[3',4':4,5]thiopyrano[3,2-c]pyridine-3-carboxylate 5,5-dioxide

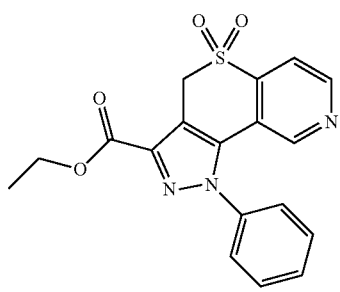 [SMILES: CCOC(=O)c1nn(-c2ccccc2)c2c1CS(=O)(=O)c1ccncc1-2]

To a solution of ethyl 1-phenyl-1,4-dihydropyrazolo[3',4':4,5]thiopyrano[3,2-c]pyridine-3-carboxylate 5,5,8-trioxide (0.1 g, 0.259 mmol) in glacial acetic acid is added iron powder (58 mg, 1.038 mmol) under nitrogen and the reaction mass is heated to 85° C. for 1 h. The reaction mass is concentrated completely under reduced pressure and is partitioned between water and ethylacetate. The organic layer is separated, dried using sodium sulphate and is concentrated under reduced pressure to afford 80 mg, 83% yield of the title compound. $^{1}$H NMR (400 MHz, DMSO-d$_{6}$) δ=8.85-8.84 (d, J=5.2 Hz, 1H), 8.00-7.98 (m, 2H), 7.68-7.66 (m, 3H), 7.61 (m,1H), 5.12 (s, 2H), 4.38-4.36 (q, 2H), 1.35-1.32 (t, J=7.12 Hz, 3H). MS (ESI+): 370.0.

434
Procedure Q

Intermediate Q.1

Ethyl 1-[1-(tert-butoxycarbonyl)piperidin-4-yl]-1,4-dihydrothio chromeno[4,3-c]pyrazole-3-carboxylate 5,5-dioxide

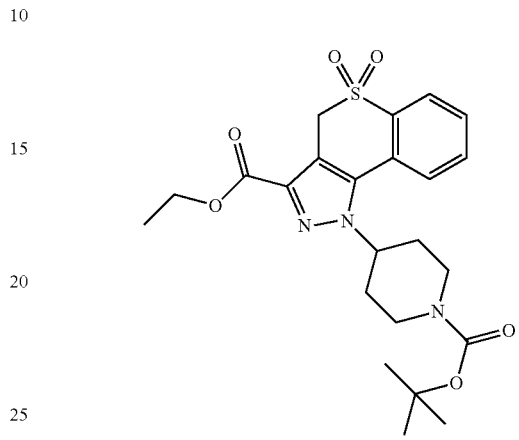

To a solution of ethyl 1-[1-(tert-butoxycarbonyl)piperidin-4-yl]-1,4-dihydrothiochromeno [4,3-c]pyrazole-3-carboxylate (3.05 g; 6.88 mmol; 1 eq.) in DCM (36.6 ml) at 0° C. is added 3-chloroperoxybenzoic acid (2.97 g; 17.19 mmol; 2.5 eq.) and the reaction mixture is stirred at rt for 30 min. DCM is added and the organic phase is washed 3 times with a saturated aqueous solution of NaHCO$_{3}$, dried over MgSO$_{4}$ then concentrated to afford 2.8 g (86%) of the title compound. HPLC (max plot) 64.9%; Rt 4.90 min. MS (ESI−): 474.3
Intermediates described below are obtained following protocol outlined in procedure Q

---

Intermediate Q.2: Ethyl (1,1-dioxido-4-oxo-3,4-dihydro-2H-thiochromen-3-yl)(oxo)acetate

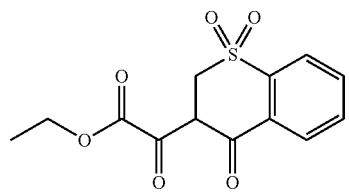 [SMILES: CCOC(=O)C(=O)C1CS(=O)(=O)c2ccccc2C1=O]

7.18 g (78%) of the title compound as a yellow powder. $^{1}$H NMR (DMSO-d$_{6}$, 300 MHz): δ 8.08-7.98 (m, 1H), 7.98-7.90 (m, 1H), 7.90-7.79 (m, 2H), 4.46 (s, 2H), 4.27 (q, J = 7.2 Hz, 2H), 1.29 (t, J = 7.2 Hz, 3H). 1H $^{1}$H NMR (DMSO-d$_{6}$, 300 MHz): δ (DMSO) δ 8.08-7.98 (m, 1H), 7.98-7.90 (m, 1H), 7.90-7.79 (m, 2H), 5.00-4.33cf cf (bs, 1H), 4.46 (s, 2H), 4.27 (q, J = 7.2 Hz, 2H), 1.29 (t, J = 7.2 Hz, 3H). MS (ESI+): 297.06. HPLC (max plot) 89.7%; Rt 2.59 min.

Intermediate Q.3: Ethyl (6-fluoro-1,1-dioxido-4-oxo-3,4-dihydro-2H-thiochromen-3-yl)(oxo)acetate

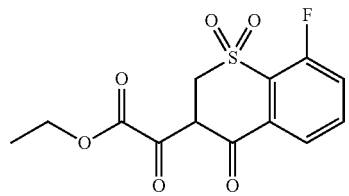 [SMILES: CCOC(=O)C(=O)C1CS(=O)(=O)c2c(F)cccc2C1=O]

1.44 g (quant) of the title compound. It is used in the next step without further purification. MS (ESI+): 339.09. HPLC (max plot) 73.7%; Rt 3.37 min Intermediate Q.4: Ethyl (7-fluoro-1,1-dioxido-4-oxo-3,4-dihydro-2H-thiochromen-3-yl)(oxo)acetate

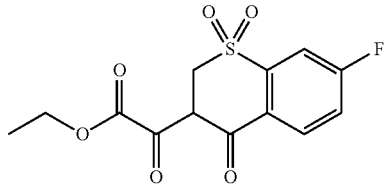 [SMILES: CCOC(=O)C(=O)C1CS(=O)(=O)c2cc(F)ccc2C1=O]

1 g (89%) of the title compound. It is used in the next step without further purification. MS (ESI−): 313.15.

Intermediate Q.5: Ethyl (7-methoxy-1,1-dioxido-4-oxo-3,4-dihydro-2H-thiochromen-3-yl)(oxo)acetate

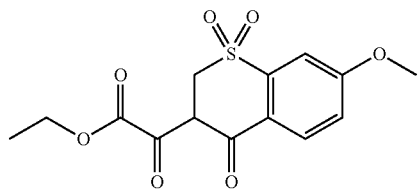 [SMILES: CCOC(=O)C(=O)C1CS(=O)(=O)c2cc(OC)ccc2C1=O]

550 mg (99%) of the title compound as a yellow powder. MS (ESI+): 327.1..

Intermediate Q.6: Ethyl (8-fluoro-1,1-dioxido-4-oxo-3,4-dihydro-2H-thiochromen-3-yl)(oxo)acetate

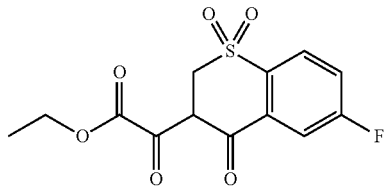 [SMILES: CCOC(=O)C(=O)C1CS(=O)(=O)c2ccc(F)cc2C1=O]

150 mg of the title compound as a white solid. MS (ESI−): 313.9.

Intermediate Q.7: 8-Bromo-3-(morpholin-4-ylcarbonyl)-1-phenyl-1,4-dihydrothiochromeno[4,3-c]pyrazole 5,5-dioxide

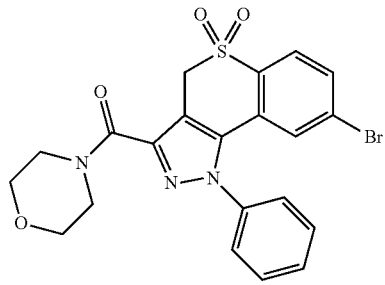 [SMILES: O=C(c1nn(-c2ccccc2)c2c1CS(=O)(=O)c1ccc(Br)cc1-2)N1CCOCC1]

27 mg of the title compound. 1H NMR (400 mHz, DMSO-d6) δ = 7.93 (d, J = 8.4 Hz, 1H), 7.85-7.82 (m, 2H), 7.68-7.65 (m, 3H), 7.57-7.55 (m, 2H), 4.93 (s, 2H), 3.93 (brs, 2H), 3.66-3.60 (m, 6H). MS (ESI+): 488.0. HPLC (max plot) 93.05%; Rt 4.5 min.

Intermediate Q.8: Ethyl 1-[1-(tert-butoxycarbonyl)azetidin-3-yl]-1,4-dihydrothiochromeno[4,3-c]pyrazole-3-carboxylate 5,5-dioxide

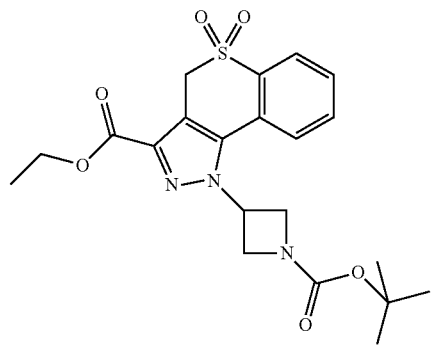 [SMILES: CCOC(=O)c1nn(C2CN(C(=O)OC(C)(C)C)C2)c2c1CS(=O)(=O)c1ccccc1-2]

5.45 g (91%) of the title compound. 1H NMR (DMSO-d6) δ 8.07-8.04 (m, 1H), 7.80-7.74 (m, 2H), 5.82-5.77 (m, 1H), 4.93-4.90 (m, 2H), 4.53-4.47 (m, 2H), 4.42-4.34 (m, 4H), 1.43 (s, 9H), 1.38-1.35 (m, 3H), 7.90-7.87 (m, 1H). HPLC (max plot) 56.8%; Rt 4.23 min. MS (ESI−): 345.8

Intermediate Q.9: Ethyl 1-[1-(tert-butoxycarbonyl)pyrrolidin-3-yl]-1,4-dihydrothiochromeno[4,3-c]pyrazole-3-carboxylate 5,5-dioxide

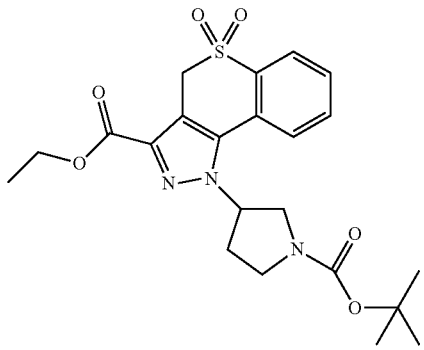 [SMILES: CCOC(=O)c1nn(C2CCN(C(=O)OC(C)(C)C)C2)c2c1CS(=O)(=O)c1ccccc1-2]

4.84 g (87%) of the title compound as a white foam. HPLC (max plot) 83.8%; Rt 4.30 min. MS (ESI−): 460.90.

Intermediate Q.10: Ethyl 1-(tetrahydrofuran-3-yl)-1,4-dihydrothiochromeno[4,3-c]pyrazole-3-carboxylate 5,5-dioxide

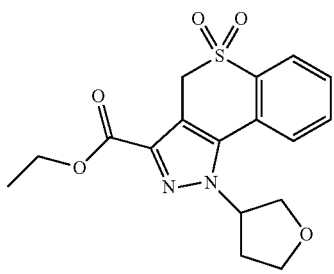 [SMILES: CCOC(=O)c1nn(C2CCOC2)c2c1CS(=O)(=O)c1ccccc1-2]

1.13 g (quant) of the title compound as a beige solid. HPLC (max plot) 77.5%; Rt 3.19 min. MS (ESI+): 363.15.

Intermediate Q.11: Ethyl 1-[1-(tert-butoxycarbonyl)piperidin-3-yl]-1,4-dihydrothiochromeno[4,3-c]pyrazole-3-carboxylate 5,5-dioxide

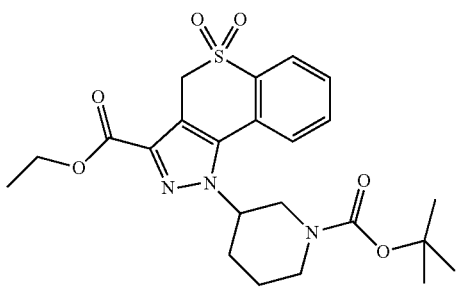 [SMILES: CCOC(=O)c1nn(C2CCCN(C(=O)OC(C)(C)C)C2)c2c1CS(=O)(=O)c1ccccc1-2]

13.25 g (82%) of the title compound as a white solid. 1H NMR (300 MHz, DMSO) δ 8.14-7.72 (m, 4H), 4.89 (d, J = 0.9, 2H), 4.83 (s, 1H), 4.43-4.30 (m, 2H), 4.21 (s, 1H), 4.04-3.83 (m, 1H), 3.20 (t, J = 11.6, 1H), 2.89 (s, 1H), 2.39-2.06 (m, 2H), 1.95-1.74 (m, 1H), 1.75-1.55 (m, 1H), 1.53-1.20 (m, 11H). MS (ESI−): 474.4.

Intermediate Q.12: Ethyl 1-[1-(tert-butoxycarbonyl)azepan-4-yl]-1,4-dihydrothiochromeno[4,3-c]pyrazole-3-carboxylate 5,5-dioxide

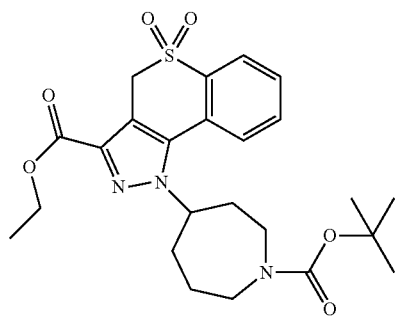 [SMILES: CCOC(=O)c1nn(C2CCCN(C(=O)OC(C)(C)C)CC2)c2c1CS(=O)(=O)c1ccccc1-2]

4 g (83%) of the title compound. MS (ESI−): 488.

Intermediate Q.13: Ethyl 6-fluoro-1-(tetrahydrofuran-3-yl)-1,4-dihydrothiochromeno[4,3-c]pyrazole-3-carboxylate 5,5-dioxide

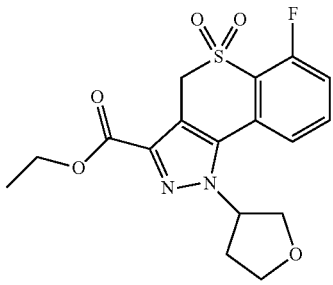 [SMILES: CCOC(=O)c1nn(C2CCOC2)c2c1CS(=O)(=O)c1c(F)cccc1-2]

900 mg (quant) of the title compound as a white solid. HPLC (max plot) 73.4%; Rt 3.24 min. MS (ESI+): 381.16.

Intermediate Q.14: Ethyl 1-[1-(tert-butoxycarbonyl)pyrrolidin-3-yl]-6-fluoro-1,4-dihydrothiochromeno[4,3-c]pyrazole-3-carboxylate 5,5-dioxide

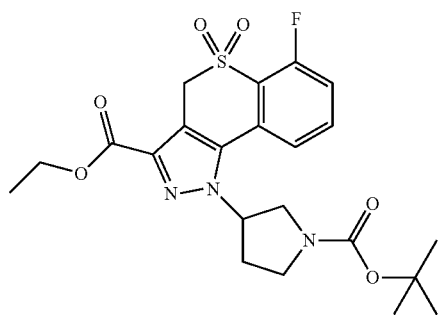 [SMILES: CCOC(=O)c1nn(C2CCN(C(=O)OC(C)(C)C)C2)c2c1CS(=O)(=O)c1c(F)cccc1-2]

10.5 g (98%) of the title compound. It is used in the next step without further purification. HPLC (max plot) 53.3%; Rt 4.80 min. MS (ESI−): 477.8.

Intermediate Q.15: Ethyl 1-[1-(tert-butoxycarbonyl)piperidin-3-yl]-6-fluoro-1,4-dihydrothiochromeno[4,3-c]pyrazole-3-carboxylate 5,5-dioxide

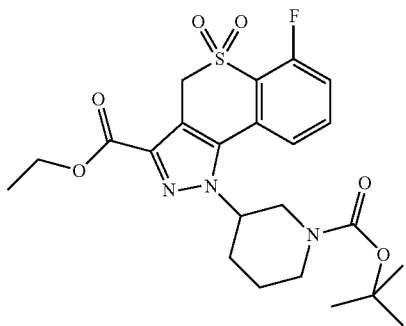 [SMILES: CCOC(=O)c1nn(C2CCCN(C(=O)OC(C)(C)C)C2)c2c1CS(=O)(=O)c1c(F)cccc1-2]

1.13 g (91%) of the title compound as a white solid. MS (ESI−): 491.7

Intermediate Q.16: Ethyl 1-[1-(tert-Butoxycarbonyl)piperidin-3-yl]-6-methoxy-1,4-dihydrothiochromeno[4,3-c]pyrazole-3-carboxylate 5,5-dioxide

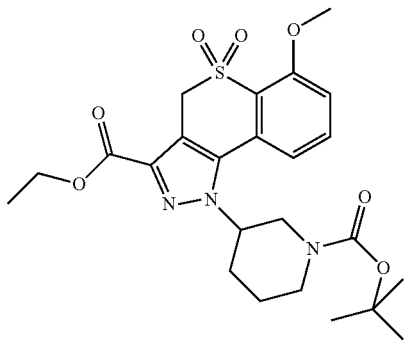 [SMILES: CCOC(=O)c1nn(C2CCCN(C(=O)OC(C)(C)C)C2)c2c1CS(=O)(=O)c1c(OC)cccc1-2]

5.6 g of the title compound as a white powder. $^1$H NMR (DMSO-d$_6$, 300 MHz): δ 7.78-7.76 (m, 1H), 7.53-7.36 (m, 2H), 4.80 (s, 2H), 4.65 (bs, 1H), 4.35 (q, J = 7 Hz, 2H), 4.18 (bs, 1H), 4.00-3.94 (m, 4H), 3.23-3.15 (m, 1H), 2.9 (bs, 1H), 2.27-2.15 (m, 2H), 1.83-1.79 (m, 1H), 1.60-1.56 (m, 1H), 1.38-1.30 (m, 12H). MS (ESI+): 504.44. HPLC (max plot) 71.5%; Rt 4.74 min.

Intermediate Q.17: Ethyl 1-[1-(tert-butoxycarbonyl)piperidin-3-yl]-6-chloro-1,4-dihydrothiochromeno[4,3-c]pyrazole-3-carboxylate 5,5-dioxide

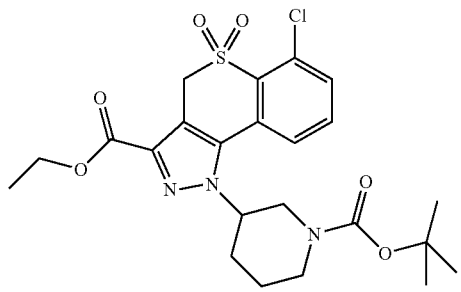 [SMILES: CCOC(=O)c1nn(C2CCCN(C(=O)OC(C)(C)C)C2)c2c1CS(=O)(=O)c1c(Cl)cccc1-2]

5.8 g (97%) of the title compound. HPLC (max plot) 62.7%; Rt 4.52 min. MS (ESI–): 508.29.

Intermediate Q.18: Ethyl 1-[1-(tert-butoxycarbonyl)piperidin-3-yl]-6-methyl-1,4-dihydrothiochromeno[4,3-c]pyrazole-3-carboxylate 5,5-dioxide

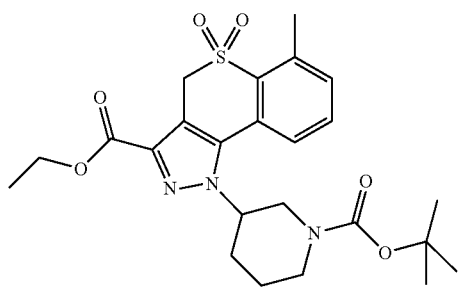

9.4 g (91%) of the title compound. MS (ESI–): 488.5.

Intermediate Q.19: Ethyl 1-[1-(tert-butoxycarbonyl)piperidin-3-yl]-7-fluoro-1,4-dihydrothiochromeno[4,3-c]pyrazole-3-carboxylate 5,5-dioxide

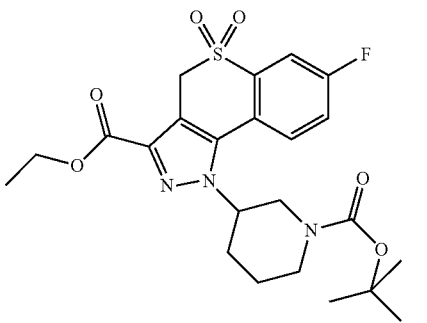 [SMILES: CCOC(=O)c1nn(C2CCCN(C(=O)OC(C)(C)C)C2)c2c1CS(=O)(=O)c1cc(F)ccc1-2]

9 g (88%) of the title compound as a white powder. HPLC (max plot) 75.7%; Rt 5.22 min. MS (ESI–): 492.4

Intermediate Q.20: Ethyl 1-[1-(tert-butoxycarbonyl)piperidin-3-yl]-7-methoxy-1,4-dihydrothiochromeno[4,3-c]pyrazole-3-carboxylate 5,5-dioxide

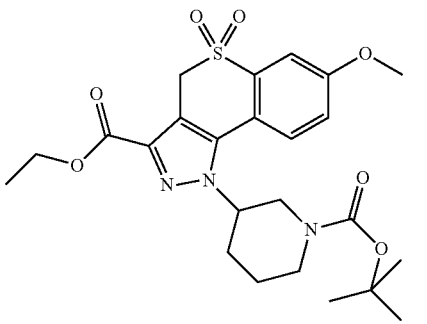 [SMILES: CCOC(=O)c1nn(C2CCCN(C(=O)OC(C)(C)C)C2)c2c1CS(=O)(=O)c1cc(OC)ccc1-2]

5.56 mg of the title compound as a white powder. $^1$H NMR (DMSO-$d_6$, 300 MHz): δ 7.94 (bs, 1H), 7.53 (d, J = 2.7, 1H), 7.47-7.29 (m, 1H), 4.86 (s, 2H), 4.72 (bs, 1H), 4.35 (q, J = 7.1, 2H), 4.18 (bs, 1H), 3.94 (s, 3H), 3.19 (t, J = 11.6, 1H), 2.88 (bs, 1H), 2.20 (s, 2H), 1.93-1.76 (m. 1H), 1.72-1.57 (m, 1H), 1.48-1.22 (m, 12H). MS (ESI–): 504.44.

Intermediate Q.21: Ethyl 1-[1-(tert-butoxycarbonyl)piperidin-3-yl]-7-(trifluoromethoxy)-1,4-dihydrothiochromeno[4,3-c]pyrazole-3-carboxylate 5,5-dioxide

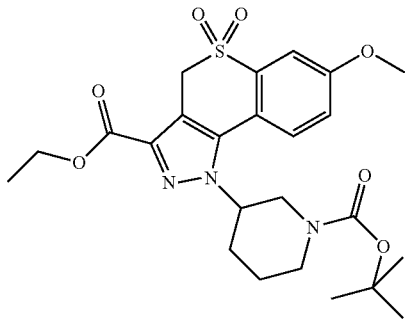 [SMILES: CCOC(=O)c1nn(C2CCCN(C(=O)OC(C)(C)C)C2)c2c1CS(=O)(=O)c1cc(OC)ccc1-2]

800 mg of the title compound as a yellow foam. $^1$H NMR (DMSO) δ 8.22-8.09 (m, 1H), 7.99 (brs, 1H), 7.96-7.84 (m, 1H), 5.00 (s, 2H), 4.93-4.70 (m, 1H), 4.36 (q, J = 7.06, 7.08 Hz, 2H), 4.28-4.00 (m, 1H), 3.99-3.85 (m, 1H), 3.27-3.12 (m, 1H), 3.07-2.73 (m, 1H), 2.33-2.14 (m, 2H), 1.91-1.77 (m, 1H), 1.76-1.54 (m, 1H), 1.53-1.20 (m, 12H). HPLC (max plot) 92.0%; Rt 5.33 min. UPLC/MS: (MS+) 504.1.

Intermediate Q.22: Ethyl 1-[1-(tert-butoxycarbonyl)piperidin-3-yl]-8-methoxy-1,4-dihydrothiochromeno[4,3-c]pyrazole-3-carboxylate 5,5-dioxide

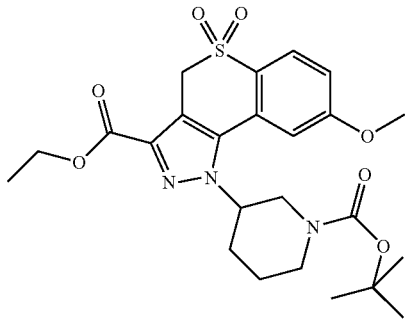 [SMILES: CCOC(=O)c1nn(C2CCCN(C(=O)OC(C)(C)C)C2)c2c1CS(=O)(=O)c1ccc(OC)cc1-2]

1.9 g (93%) of the title compound as a white foam. HPLC (max plot) 89.1%; Rt 4.74 min. MS (ESI−): 504.5

Intermediate Q.23: Ethyl 7-[(tert-butoxycarbonyl)amino]-1-(tetrahydro-2H-pyran-4-yl)-1,4-dihydropyrazolo[3',4':4,5]thiopyrano[3,2-d][1,3]thiazole-3-carboxylate 5,5-dioxide

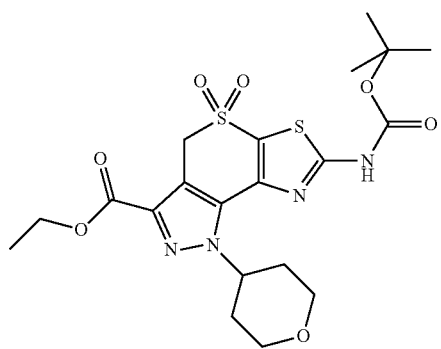 [SMILES: CCOC(=O)c1nn(C2CCOCC2)c2c1CS(=O)(=O)c1sc(NC(=O)OC(C)(C)C)nc1-2]

190 mg of the title compound as a pale yellow solid. HPLC (max plot) 90.6%; Rt 4.39 min. MS (ESI+): 498.7.

Intermediate Q.24: Ethyl 1-phenyl-1,4-dihydroimidazo[2,1-b]pyrazolo[3,4-d][1,3]thiazine-3-carboxylate 5,5-dioxide

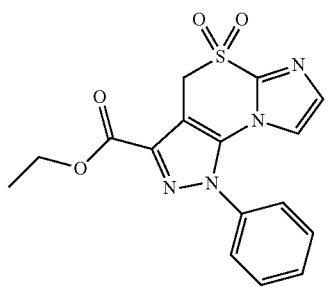 [SMILES: CCOC(=O)c1nn(-c2ccccc2)c2c1CS(=O)(=O)c1nccn1-2]

37 mg of the title compound. $^1$H NMR (DMSO-d$_6$, 400 MHz): δ 7.72-7.64 (m, 5H), 7.28 (d, J = 1.4 Hz, 1H), 6.71 (d, J = 1.4 Hz, 1H), 5.15 (s, 2H), 4.37 (q, J = 7.7 Hz, 2H), 1.33 (t, J = 7.7 Hz, 3H). MS (ESI+): 359.2: HPLC (max plot) 98.94%; Rt 3.70 min.

445

Intermediate Q.25

Ethyl 7-amino-1-(tetrahydro-2H-pyran-4-yl)-1,4-dihydropyrazolo[3',4':4,5]thiopyrano[3,2-d][1,3]thiazole-3-carboxylate 5,5-dioxide

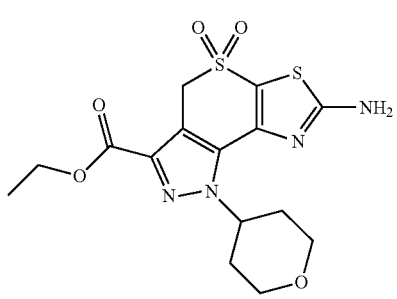 [SMILES: CCOC(=O)c1nn(C2CCOCC2)c2c1CS(=O)(=O)c1sc(N)nc1-2]

To a fine suspension of ethyl 7-[(tert-butoxycarbonyl)amino]-1-(tetrahydro-2H-pyran-4-yl)-1,4-dihydropyrazolo[3',4':4,5]thiopyrano[3,2-d][1,3]thiazole-3-carboxylate 5,5-dioxide (182 mg; 0.37 mmol; 1.00 eq.) in DCM (540 µl) is added TFA (180 µl; 2.34 mmol; 6.40 eq.). The mixture is stirred at rt overnight after which water is added to the reaction mixture. The precipitate is washed with water then dried under vacuum to afford the title compound as an off-white powder. 1H NMR (DMSO) δ 8.34 (bs, 2H), 5.61-5.43 (m, 1H), 4.91 (s, 2H), 4.33 (q, J=7.1 Hz, 2H), 4.12-3.93 (m, 2H), 3.52-3.35 (m, 2H), 3.20-1.87 (m, 4H), 1.33 (t, J=7.1 Hz, 3H). HPLC (max plot) 95.1%; Rt 2.28 min. MS (ESI+): 398.7.

446

Procedure R

Intermediate R.1

Ethyl 1-[4-(hydroxymethyl)phenyl]-1,4-dihydrothiochromeno[4,3-c]pyrazole-3-carboxylate 5,5-dioxide

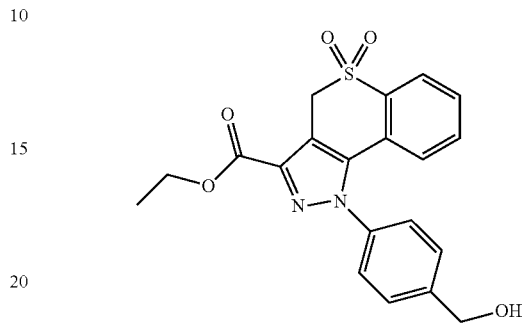

To a solution of 4-[3-(ethoxycarbonyl)-5,5-dioxidothiochromeno[4,3-c]pyrazol-1 (4H)-yl]benzoic acid (21.88 g; 53.05 mmol; 1 eq.) in THF (350 ml) is added triethylamine (14.71 ml; 106.11 mmol; 2 eq.) followed by isobutyl chloroformate (13.83 ml; 106.11 mmol; 2 eq.) at 0° C. under nitrogen. The reaction mixture is stirred at rt for 30 min then cooled at 0° C. Sodium borohydride (10 g; 265.27 mmol; 5 eq.) is added portionwise. After 5 h, THF (100 mL) is added and the reaction mixture is heated at 35° C. for 1 day then at rt for 2 days. Sodium borohydride is added (1 eq) and after 6 h stirring the reaction is quenched by dropwise addition of water at 0° C. over 2 h. The product is extracted with EtOAc, the organic layers washed with HCl 1 m (2×) and brine then dried over MgSO$_4$. After evaporation of the solvent, the residue is taken up in DCM and HCl 1 m. The precipitate formed is filtered off and recrystallized in DCE to afford the title compound as a white solid. $^1$H NMR (DMSO-d$_6$) δ 8.05-8.02 (m, 1H), 7.68-7.48 (m, 6H), 6.88-6.84 (m, 1H), 5.76 (s, 2H), 4.99 (s, 2H), 4.37 (q, J=7.1 Hz, 2H), 3.90 (s, 1H), 1.35 (t, J=7.1 Hz, 3H). HPLC (max plot) 68.2%; Rt 3.02 min. MS (ESI+): 398.9

Compounds described below are obtained following protocol outlined in procedure R.

---

Intermediate R.2: Ethyl 1-[3-(hydroxymethyl)phenyl]-1,4-dihydrothiochromeno[4,3-c]pyrazole-3-carboxylate 5,5-dioxide

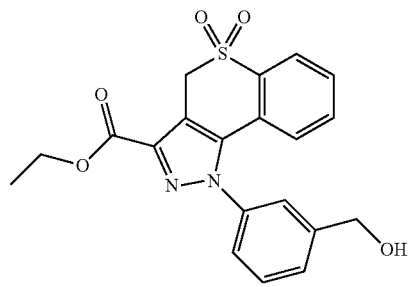 [SMILES: CCOC(=O)c1nn(-c2cccc(CO)c2)c2c1CS(=O)(=O)c1ccccc1-2]

title compound as an orange paste. HPLC (max plot) 63.4%; Rt 3.64 min. MS (ESI+): 399.0.

-continued

Intermediate R.3: Ethyl 1-[4-(hydroxymethyl)cyclohexyl]-1,4-dihydrothiochromeno[4,3-c]pyrazole-3-carboxylate 5,5-dioxide

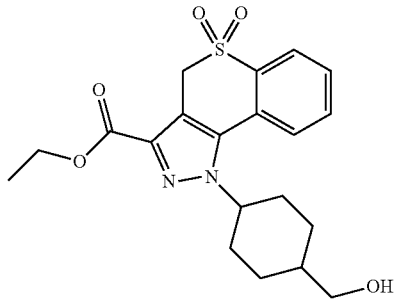 [SMILES: CCOC(=O)c1nn(C2CCC(CO)CC2)c2c1CS(=O)(=O)c1ccccc1-2]

350 mg (80%) of the title compound. MS (ESI+): 406.0.

Intermediate R.4: Ethyl 1-[4-(hydroxymethyl)phenyl]-1,4-dihydropyrazolo[3',4':4,5]thiopyrano[2,3-b]pyridine-3-carboxylate 5,5-dioxide

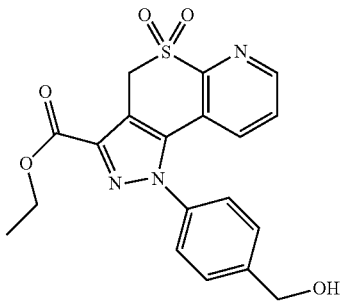 [SMILES: CCOC(=O)c1nn(-c2ccc(CO)cc2)c2c1CS(=O)(=O)c1ncccc1-2]

160 mg of the title compound. $^1$H NMR (DMSO-d$_6$, 400 MHz): δ 8.72-8.71 (d, J = 4.6 Hz, 1H), 7.63-7.60 (m, 1H), 7.56-7.54 (m, 2H), 7.50-7.48 (m, 2H), 7.20-7.18 (d, J = 8.1 Hz, 1H), 5.46-5.43 (m, 1H), 5.09 (s, 2H), 4.64-4.63 (d, J = 5.7 Hz, 2H), 4.39-4.34 (m, 2H), 1.35-1.31 (t, J = 7.2 Hz, 3H). MS (ESI+): 400.0.

Procedure S

Intermediate S.1

6-methoxy-1-phenyl-1,4-dihydrothiochromeno[4,3-c]pyrazole-3-carboxylic acid 5,5-dioxide

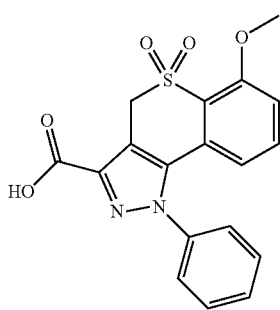 [SMILES: COc1cccc2c1S(=O)(=O)Cc1c(C(=O)O)nn(-c3ccccc3)c1-2]

To a solution of ethyl 6-methoxy-1-phenyl-1,4-dihydrothiochromeno[4,3-c]pyrazole-3-carboxylate 5,5-dioxide (0.23 g, 0.57 mmol) in THF (10 mL) is added aq. solution of NaOH (2.8 mL, 1 M, 2.85 mmol, 5 Eq) at 0° C. and the reaction mixture is stirred for 4 h. The solvent is removed under reduced pressure and aq. solution of HCl 1 M is added. The product is extracted with EtOAc (2×). The organic layer is washed with brine, dried over MgSO$_4$ and concentrated under reduced pressure to afford 0.2 g (70%) of the title compound as a white solid. $^1$H NMR (DMSO-d$_6$, 400 MHz) δ 13.5 (brs, 1H), 7.61-7.57 (m, 3H), 7.46-7.42 (m, 3H), 7.26 (d, J=8.6 Hz, 1H), 6.35 (d, J=8.0 Hz, 1H), 4.88 (s, 2H), 3.90 (s, 3H). MS (ESI+): 371.0. HPLC (max plot) 98.9%; Rt 3.30 min.

Intermediate S.2

6-methoxy-1-methyl-1,4-dihydrothiochromeno[4,3-c]pyrazole-3-carboxylic acid 5,5-dioxide

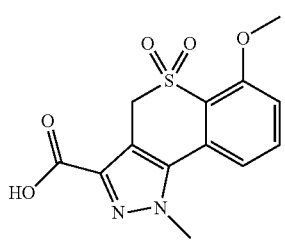 [SMILES: COc1cccc2c1S(=O)(=O)Cc1c(C(=O)O)nn(C)c1-2]

Following the protocol outlined in Procedure S, 6-methoxy-1-methyl-1,4-dihydrothiochromeno[4,3-c]pyrazole-3-carboxylic acid 5,5-dioxide is obtained from ethyl 6-methoxy-1-methyl-1,4-dihydrothio chromeno[4,3-c]pyrazole-3-carboxylate 5,5-dioxide to afford the title compound as a white solid. $^1$H NMR (DMSO-d6, 400 MHz): δ 13.3 (bs, 1H), 7.78 (t, J=8.12 Hz, 1H), 7.52 (t, J=7.76 Hz, 1H), 7.37 (d, J=8.5 Hz, 1H), 4.77 (s, 2H), 4.15 (s, 3H), 3.92 (s, 3H). MS (ESI+): 309.0. HPLC (max plot) 96.3%; Rt 2.12 min.

Intermediate S.3

1-phenyl-1,4-dihydrothiochromeno[4,3-c]pyrazole-3-carboxylic acid 5,5-dioxide

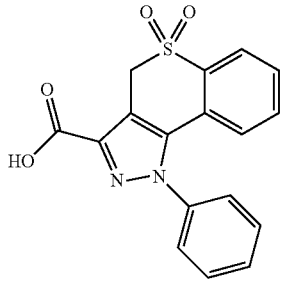 [SMILES: O=C(O)c1nn(-c2ccccc2)c2c1CS(=O)(=O)c1ccccc1-2]

Following the protocol outlined in Procedure S, 1-phenyl-1,4-dihydrothiochromeno[4,3-c]pyrazole-3-carboxylic acid 5,5-dioxide is obtained from ethyl 1-phenyl-1,4-dihydrothiochromeno[4,3-c]pyrazole-3-carboxylate 5,5-dioxide to afford 0.47 g (quant.) of the title compound as a white solid. $^1$H NMR (DMSO-d$_6$, 400 MHz): δ 13.5 (brs, 1H), 8.01 (d, J=7.72 Hz, 1H), 7.65-7.57 (m, 5H), 7.55-7.51 (m, 2H), 6.80 (d, J=7.64 Hz, 1H), 4.97 (s, 2H). MS (ESI+): 341.0. HPLC (max plot) 97.0%; Rt 3.48 min.

Intermediate S.4

1-methyl-1,4-dihydrothiochromeno[4,3-c]pyrazole-3-carboxylic acid 5,5-dioxide

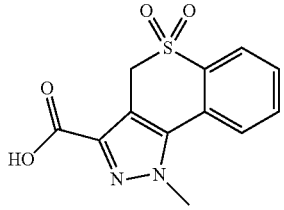 [SMILES: Cn1nc(C(=O)O)c2c1-c1ccccc1S(=O)(=O)C2]

Following the protocol outlined in Procedure S, 1-methyl-1,4-dihydrothiochromeno[4,3-c]pyrazole-3-carboxylic acid 5,5-dioxide is obtained from ethyl 1-methyl-1,4-dihydrothiochromeno[4,3-c]pyrazole-3-carboxylate 5,5-dioxide to afford 0.69 g (94%) of the title compound as a white solid. $^1$H NMR (DMSO-d$_6$, 400 MHz): δ 13.32 (s, 1H), 8.06-8.01 (m, 2H), 7.90-7.86 (m, 1H), 7.72 (t, J=7.6 Hz, 1H), 4.86 (s, 2H), 4.27 (s, 3H). MS (ESI+): 279.0. HPLC (max plot) 95.4%; Rt 2.3 min.

Intermediate S.5

1,4-dihydrothiochromeno[4,3-c]pyrazole-3-carboxylic acid 5,5-dioxide

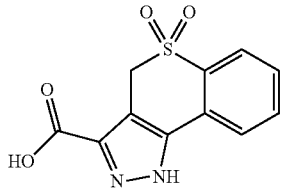 [SMILES: O=C(O)c1n[nH]c2c1CS(=O)(=O)c1ccccc1-2]

Following the protocol outlined in Procedure S, 1,4-dihydrothiochromeno[4,3-c]pyrazole-3-carboxylic acid 5,5-dioxide is obtained from ethyl 1,4-dihydrothiochromeno[4,3-c]pyrazole-3-carboxylate 5,5-dioxide to afford 0.32 g (71%) of the title compound as an off-white solid. $^1$H NMR (DMSO-d$_6$, 400 MHz): δ 8.01 (d, J=7.6 Hz, 1H), 7.94 (d, J=7.7 Hz, 1H), 7.81 (t, J=7.52 Hz, 1H), 7.64 (t, J=7.7 Hz, 1H), 4.85 (s, 2H). MS (ESI+): 265.0. HPLC (max plot) 93.5%; Rt 2.32 min.

Intermediate S.6

7-methoxy-1-methyl-1,4-dihydrothiochromeno[4,3-c]pyrazole-3-carboxylic acid 5,5-dioxide

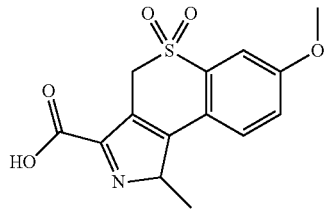 [SMILES: COc1ccc2c(c1)S(=O)(=O)CC1=C2C(C)N=C1C(=O)O]

Following the protocol outlined in Procedure S, 7-methoxy-1-methyl-1,4-dihydrothiochromeno[4,3-c]pyrazole-3-carboxylic acid 5,5-dioxide is obtained from ethyl 7-methoxy-1-methyl-1,4-dihydrothio chromeno[4,3-c]pyrazole-3-carboxylate 5,5-dioxide to afford 0.34 g (89%) of the title compound. $^1$H NMR (DMSO-d$_6$, 400 MHz) δ 13.26 (brs, 1H), 7.99 (d, J=8.7 Hz, 1H), 7.47 (s, 1H), 7.43-7.40 (m, 1H), 4.83 (s, 2H), 4.23 (s, 3H), 3.91 (s, 3H). MS (ESI+): 309.0. HPLC (max plot) 99.4%; Rt 2.63 min.

Intermediate S.7

7-methoxy-1-phenyl-1,4-dihydrothiochromeno[4,3-c]pyrazole-3-carboxylic acid 5,5-dioxide

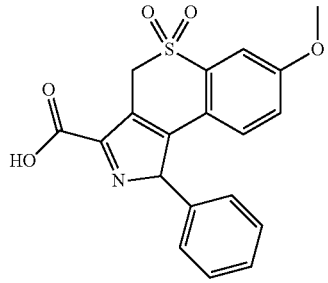 [SMILES: COc1ccc2c(c1)S(=O)(=O)CC1=C2C(c2ccccc2)N=C1C(=O)O]

Following the protocol outlined in Procedure S, 7-methoxy-1-phenyl-1,4-dihydrothiochromeno[4,3-c]pyrazole-3-carboxylic acid 5,5-dioxide is obtained from ethyl 7-methoxy-1-phenyl-1,4-dihydrothio chromeno[4,3-c]pyrazole-3-carboxylate 5,5-dioxide to afford 0.49 g (87%) of the title compound. $^1$H NMR (DMSO-d$_6$, 400 MHz) δ 7.64-7.61 (m, 3H), 7.52-7.45 (m, 2H), 7.17-7.14 (m, 2H), 6.73 (d, J=8.8 Hz, 1H), 4.93 (s, 2H), 3.84 (s, 3H). MS (ESI+): 371.0. HPLC (max plot) 97.9%; Rt 3.72 min.

Intermediate S.8

1-(3-methylphenyl)-1,4-dihydrothiochromeno[4,3-c]pyrazole-3-carboxylic acid 5,5-dioxide

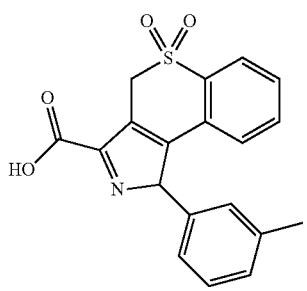 [SMILES: Cc1cccc(C2N=C(C(=O)O)C3=C2c2ccccc2S(=O)(=O)C3)c1]

Following the protocol outlined in Procedure S, 1-(3-methylphenyl)-1,4-dihydrothiochromeno[4,3-c]pyrazole-3-carboxylic acid 5,5-dioxide is obtained from ethyl 1-(3-methylphenyl)-1,4-dihydrothiochromeno[4,3-c]pyrazole-3-carboxylate 5,5-dioxide to afford 0.70 g (83%) of the title compound as an off-white solid. $^1$H NMR (DMSO-$d_6$, 400 MHz) δ 8.01 (dd, J=7.7 Hz, J=1.3 Hz, 1H), 7.65-7.56 (m, 2H), 7.52-7.45 (m, 2H), 7.37 (s, 1H), 7.28 (d, J=7.4 Hz, 1H), 6.85-6.83 (m, 1H), 4.96 (s, 2H), 2.39 (s, 3H). MS (ESI+): 355.0. HPLC (max plot) 97.9%; Rt 3.85 min.

Intermediate S.9

1-(4-methylphenyl)-1,4-dihydrothiochromeno[4,3-c]pyrazole-3-carboxylic acid 5,5-dioxide

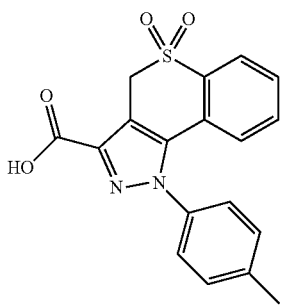 [SMILES: Cc1ccc(-n2nc(C(=O)O)c3c2-c2ccccc2S(=O)(=O)C3)cc1]

Following the protocol outlined in Procedure S, 1-(4-methylphenyl)-1,4-dihydrothiochromeno[4,3-c]pyrazole-3-carboxylic acid 5,5-dioxide is obtained from ethyl 1-(4-methylphenyl)-1,4-dihydrothio chromeno[4,3-c]pyrazole-3-carboxylate 5,5-dioxide to afford 0.88 g (95%) of the title compound as an off-white solid. $^1$H NMR (DMSO-$d_6$, 400 MHz) δ 13.55 (brs, 1H), 8.01 (dd, J=7.6 Hz, J=1.4 Hz, 1H), 7.64-7.56 (m, 2H), 7.44-7.38 (m, 4H), 6.84 (d, J=7.8 Hz, 1H), 4.95 (s, 2H), 2.43 (s, 3H). MS (ESI+): 355.0. HPLC (max plot) 98.0%; Rt 3.84 min.

Intermediate S.10

1-(5-fluoro-2-methylphenyl)-1,4-dihydrothiochromeno[4,3-c]pyrazole-3-carboxylic acid 5,5-dioxide

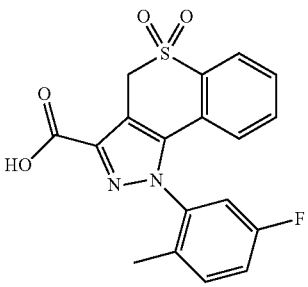 [SMILES: Cc1ccc(F)cc1-n1nc(C(=O)O)c2c1-c1ccccc1S(=O)(=O)C2]

Following the protocol outlined in Procedure S, 1-(5-fluoro-2-methylphenyl)-1,4-dihydrothiochromeno[4,3-c]pyrazole-3-carboxylic acid 5,5-dioxide is obtained from ethyl 1-(5-fluoro-2-methylphenyl)-1,4-dihydrothiochromeno[4,3-c]pyrazole-3-carboxylate 5,5-dioxide to afford 0.54 g (96%) of the title compound. $^1$H NMR (DMSO-$d_6$, 400 MHz) δ 13.62 (brs, 1H), 8.02 (dd, J=7.7 Hz, J=1.3 Hz, 1H), 7.66-7.47 (m, 5H), 6.74-6.72 (m, 1H), 4.99 (s, 2H), 1.77 (s, 3H). MS (ESI+): 373.0. HPLC (max plot) 97.6%; Rt 3.84 min.

Intermediate S.11

1-(3-methoxyphenyl)-1,4-dihydrothiochromeno[4,3-c]pyrazole-3-carboxylic acid 5,5-dioxide

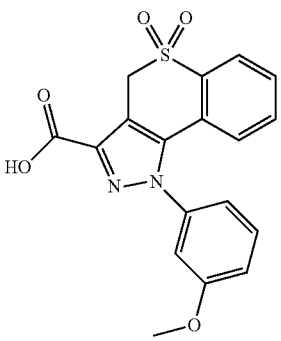 [SMILES: COc1cccc(-n2nc(C(=O)O)c3c2-c2ccccc2S(=O)(=O)C3)c1]

Following the protocol outlined in Procedure S, 1-(3-methoxyphenyl)-1,4-dihydrothiochromeno[4,3-c]pyrazole-3-carboxylic acid 5,5-dioxide is obtained from ethyl 1-(3-methoxyphenyl)-1,4-dihydrothio chromeno[4,3-c]pyrazole-3-carboxylate 5,5-dioxide to afford 0.35 g (75%) of the title compound as an off-white solid. $^1$H NMR (DMSO-$d_6$, 400 MHz) δ 8.01 (dd, J=7.7 Hz, J=1.3 Hz, 1H), 7.65-7.57 (m, 2H), 7.51 (t, J=8.1 Hz, 1H), 7.21 (dd, J=8.2 Hz, J=2.2 Hz, 1H), 7.12 (s, 1H), 7.02-7.00 (m, 1H), 6.88-6.86 (m, 1H), 4.96 (s, 2H), 3.80 (s, 3H). MS (ESI+): 371.0. HPLC (max plot) 93.5%; Rt 3.62 min.

Intermediate S.12

1-(4-methoxyphenyl)-1,4-dihydrothiochromeno[4,3-c]pyrazole-3-carboxylic acid 5,5-dioxide

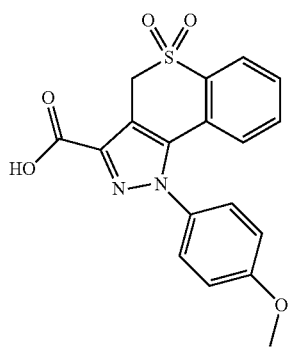 [SMILES: COc1ccc(-n2nc(C(=O)O)c3c2-c2ccccc2S(=O)(=O)C3)cc1]

Following the protocol outlined in Procedure S, 1-(4-methoxyphenyl)-1,4-dihydrothiochromeno[4,3-c]pyrazole-3-carboxylic acid 5,5-dioxide is obtained from ethyl 1-(4-methoxyphenyl)-1,4-dihydrothio chromeno[4,3-c]pyrazole-3-carboxylate 5,5-dioxide to afford 0.83 g (99%) of the title compound as an off-white solid. $^1$H NMR (DMSO-$d_6$, 400 MHz) δ 13.54 (brs, 1H), 8.00 (dd, J=7.6 Hz, J=1.4 Hz, 2H), 7.64-7.58 (m, 2H), 7.44 (d, J=8.8 Hz, 1H), 7.15 (d, J=8.8 Hz, 1H), 6.86-6.83 (m, 2H), 4.95 (s, 2H), 2.43 (s, 3H). MS (ESI+): 371.0. HPLC (max plot) 92.3%; Rt 3.57 min.

Intermediate S.13

1-pyridin-2-yl-1,4-dihydrothiochromeno[4,3-c]pyrazole-3-carboxylic acid 5,5-dioxide

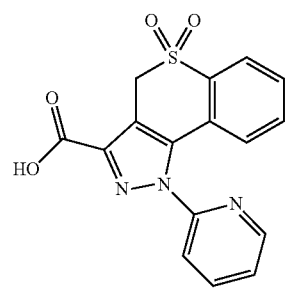 [SMILES: O=C(O)c1nn(-c2ccccn2)c2c1CS(=O)(=O)c1ccccc1-2]

Following the protocol outlined in Procedure S, 1-pyridin-2-yl-1,4-dihydrothiochromeno[4,3-c]pyrazole-3-carboxylic acid 5,5-dioxide is obtained ethyl 1-pyridin-2-yl-1,4-dihydrothiochromeno[4,3-c]pyrazole-3-carboxylate 5,5-dioxide to afford 0.22 g (95%) of the title compound as an off-white solid. $^1$H NMR (DMSO-$d_6$, 400 MHz) δ 13.68 (brs, 1H), 8.54 (dd, J=4.7 Hz, J=0.8 Hz, 1H), 8.23-8.19 (m, 1H), 8.00 (dd, J=7.5 Hz, J=1.0 Hz, 1H), 7.89 (d, J=7.9 Hz, 1H), 7.69-7.56 (m, 3H), 6.89 (d, J=7.6 Hz, 1H), 4.95 (s, 2H). MS (ESI+): 342.0. HPLC (max plot) 98.0%; Rt 2.79 min.

Intermediate S.14

1-cyclohexyl-1,4-dihydrothiochromeno[4,3-c]pyrazole-3-carboxylic acid 5,5-dioxide

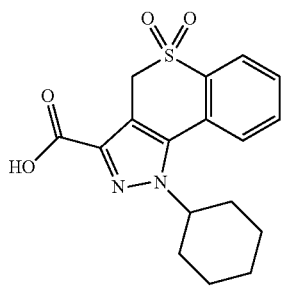 [SMILES: O=C(O)c1nn(C2CCCCC2)c2c1CS(=O)(=O)c1ccccc1-2]

Following the protocol outlined in Procedure S, 1-cyclohexyl-1,4-dihydrothiochromeno[4,3-c]pyrazole-3-carboxylic acid 5,5-dioxide is obtained from ethyl 1-cyclohexyl-1,4-dihydrothiochromeno[4,3-c]pyrazole-3-carboxylate 5,5-dioxide to afford 0.88 g (95%) of the title compound as an off-white solid. $^1$H NMR (DMSO-$d_6$, 400 MHz) δ 13.34 (brs, 1H), 8.03 (d, J=7.8 Hz, 1H), 7.92 (t, J=7.8 Hz, 1H), 7.85 (d, J=8.0 Hz, 1H), 7.31 (d, J=7.6 Hz, 1H), 4.83 (s, 2H), 4.72 (t, J=11.0 Hz, 1H), 2.04-1.82 (m, 8H), 1.70-1.67 (m, 1H), 1.56-1.49 (m, 1H). MS (ESI+): 347.0. HPLC (max plot) 98.8%; Rt 3.89 min.

Intermediate S.15

6-bromo-1-methyl-1,4-dihydrothiochromeno[4,3-c]pyrazole-3-carboxylic acid 5,5-dioxide

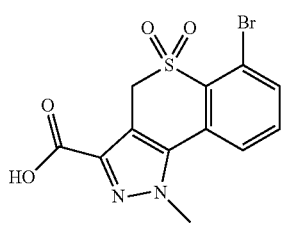 [SMILES: Cn1nc(C(=O)O)c2c1-c1cccc(Br)c1S(=O)(=O)C2]

Following the protocol outlined in Procedure S, 6-bromo-1-methyl-1,4-dihydrothiochromeno[4,3-c]pyrazole-3-carboxylic acid 5,5-dioxide is obtained from ethyl 6-bromo-1-methyl-1,4-dihydrothiochromeno[4,3-c]pyrazole-3-carboxylate 5,5-dioxide to afford the title compound. $^1$H NMR (DMSO-$d_6$, 400 MHz) δ 13.3 (brs, 1H), 8.01 (d, J=8.0 Hz, 1H), 7.92 (d, J=8.0 Hz, 1H), 7.70 (t, J=8.0 Hz, 1H), 4.96 (s, 2H), 4.20 (s, 3H). MS (ESI+): 357.0. HPLC (max plot) 99.2%; Rt 2.89 min.

Intermediate S.16

1-methyl-8-nitro-1,4-dihydrothiochromeno[4,3-c]pyrazole-3-carboxylic acid

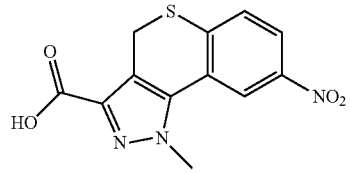 [SMILES: Cn1nc(C(=O)O)c2c1-c1cc([N+](=O)[O-])ccc1SC2]

Following the protocol outlined in Procedure S, 1-methyl-8-nitro-1,4-dihydrothiochromeno[4,3-c]pyrazole-3-carboxylic acid is obtained from ethyl 1-methyl-8-nitro-1,4-dihydrothiochromeno[4,3-c]pyrazole-3-carboxylate to afford 0.088 g (72%) of the title compound as a white solid. $^1$H NMR (DMSO-$d_6$, 400 MHz,) δ 13.1 (brs, 1H), 8.55 (d, J=2.3 Hz, 1H), 8.11 (dd, J=8.7 Hz, J=2.3 Hz, 1H), 7.76 (d, J=8.6 Hz, 1H), 4.29 (s, 2H), 4.22 (s, 2H). MS (ESI+): 292.0. HPLC (max plot) 96.8%; Rt 3.55 min.

Intermediate S.17

6-fluoro-1-methyl-1,4-dihydrothiochromeno[4,3-c]pyrazole-3-carboxylic acid 5,5-dioxide

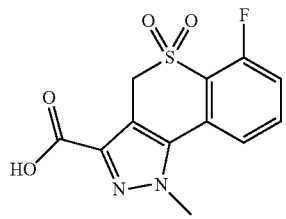 [SMILES: Cn1nc(C(=O)O)c2c1-c1cccc(F)c1S(=O)(=O)C2]

Following the protocol outlined in Procedure S, 6-fluoro-1-methyl-1,4-dihydrothiochromeno[4,3-c]pyrazole-3-carboxylic acid 5,5-dioxide is obtained from ethyl 6-fluoro-1-methyl-1,4-dihydrothiochromeno[4,3-c]pyrazole-3-carboxylate 5,5-dioxide to afford 0.24 g (77%) of the title compound. $^1$H NMR (DMSO-$d_6$, 400 MHz) δ 13.3 (brs, 1H), 7.93-7.84 (m, 2H), 7.56 (m, 1H), 4.96 (s, 2H), 4.24 (s, 3H). MS (ESI+): 297.0. HPLC (max plot) 96.3%; Rt 2.46 min.

Intermediate S.18

6-fluoro-1-phenyl-1,4-dihydrothiochromeno[4,3-c]pyrazole-3-carboxylic acid 5,5-dioxide

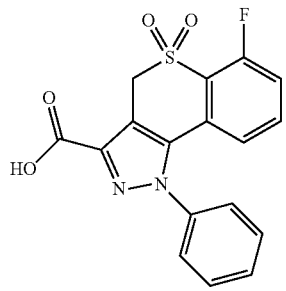 [SMILES: O=C(O)c1nn(-c2ccccc2)c2c1CS(=O)(=O)c1c(F)cccc1-2]

Following the protocol outlined in Procedure S, 6-fluoro-1-phenyl-1,4-dihydrothiochromeno[4,3-c]pyrazole-3-carboxylic acid 5,5-dioxide is obtained from ethyl 6-fluoro-1-phenyl-1,4-dihydrothiochromeno[4,3-c]pyrazole-3-carboxylate 5,5-dioxide to afford 0.29 g (78%) of the title compound. MS (ESI+): 359.0.

Intermediate S.19

8-fluoro-1-methyl-1,4-dihydrothiochromeno[4,3-c]pyrazole-3-carboxylic acid 5,5-dioxide

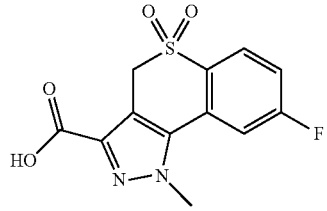 [SMILES: Cn1nc(C(=O)O)c2c1-c1cc(F)ccc1S(=O)(=O)C2]

Following the protocol outlined in Procedure S, 8-fluoro-1-methyl-1,4-dihydrothiochromeno[4,3-c]pyrazole-3-carboxylic acid 5,5-dioxide is obtained from ethyl 8-fluoro-1-methyl-1,4-dihydrothiochromeno[4,3-c]pyrazole-3-carboxylate 5,5-dioxide to afford the title compound. $^1$H NMR (DMSO-$d_6$, 400 MHz) δ 8.11-8.07 (m, 1H), 7.91-7.88 (m, 1H), 7.59-7.55 (m, 1H), 4.27 (s, 2H), 3.72 (s, 3H). MS (ESI+): 297.0.

Intermediate S.20

8-fluoro-1-phenyl-1,4-dihydrothiochromeno[4,3-c]pyrazole-3-carboxylic acid 5,5-dioxide

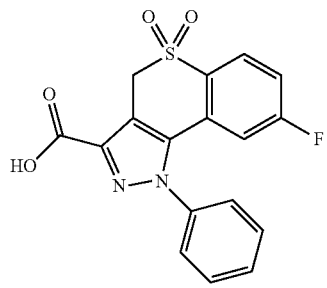

Following the protocol outlined in Procedure S, 8-fluoro-1-phenyl-1,4-dihydrothiochromeno[4,3-c]pyrazole-3-carboxylic acid 5,5-dioxide is obtained from ethyl 8-fluoro-1-phenyl-1,4-dihydrothiochromeno[4,3-c]pyrazole-3-carboxylate 5,5-dioxide to afford the title compound. $^1$H NMR (DMSO-$d_6$, 400 MHz) δ 8.12-8.08 (m, 1H), 7.69-7.63 (m, 2H), 7.57-7.48 (m, 2H), 7.25-7.11 (m, 2H), 6.43-6.40 (m, 1H), 4.97 (s, 2H). MS (ESI+): 359.0.

Intermediate S.21

6-bromo-1-phenyl-1,4-dihydrothiochromeno[4,3-c]pyrazole-3-carboxylic acid 5,5-dioxide

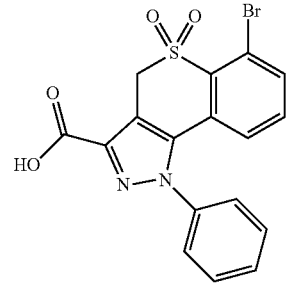 [SMILES: O=C(O)c1nn(-c2ccccc2)c2c1CS(=O)(=O)c1c(Br)cccc1-2]

Following the protocol outlined in Procedure S, 6-bromo-1-phenyl-1,4-dihydrothiochromeno[4,3-c]pyrazole-3-carboxylic acid 5,5-dioxide is obtained from ethyl 6-bromo-1- phenyl-1,4-dihydrothiochromeno[4,3-c]pyrazole-3-carboxylate 5,5-dioxide to afford the title compound. $^1$H NMR (DMSO-d$_6$, 400 MHz) δ 13.6 (brs, 1H), 7.83 (d, J=8.0 Hz, 1H), 7.61-7.57 (m, 3H), 7.46 (d, J=7.9 Hz, 1H), 7.38 (t, J=8.0 Hz, 1H), 7.25-7.13 (m, 1H), 6.83 (d, J=8.0 Hz, 1H), 5.08 (s, 2H), 4.37 (q, J=7.1 Hz, 2H), 1.33 (t, J=7.9 Hz, 3H). MS (ESI+): 420.0. HPLC (max plot) 97.8%; Rt 3.96 min.

Intermediate S.22

8-nitro-1-phenyl-1,4-dihydrothiochromeno[4,3-c]pyrazole-3-carboxylic acid

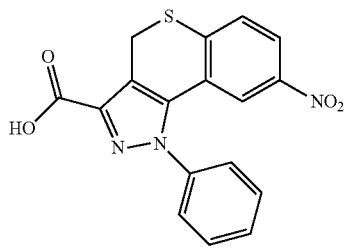 [SMILES: O=C(O)c1nn(-c2ccccc2)c2c1CSc1ccc([N+](=O)[O-])cc1-2]

Following the protocol outlined in Procedure S, 8-nitro-1-phenyl-1,4-dihydrothiochromeno[4,3-c]pyrazole-3-carboxylic acid is obtained from ethyl 8-nitro-1-phenyl-1,4-dihydrothiochromeno[4,3-c]pyrazole-3-carboxylate to afford 0.7 g (71%) of the title compound. $^1$H NMR (DMSO-d$_6$, 400 MHz) δ 13.3 (brs, 1H), 8.01-7.98 (m, 1H), 7.50 (d, J=8.8 Hz, 1H), 7.74 (d, J=8.2 Hz, 3H), 7.65-7.59 (m, 3H), 7.52 (dd, J=8.2 Hz, J=1.2 Hz, 1H), 7.42 (s, 1H), 4.40 (s, 2H). MS (ESI+): 354.0. HPLC (max plot) 93.2%; Rt 4.33 min.

Intermediate S.23

1-(2-methylphenyl)-1,4-dihydrothiochromeno[4,3-c]pyrazole-3-carboxylic acid 5,5-dioxide

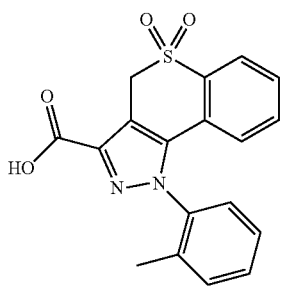 [SMILES: Cc1ccccc1-n1nc(C(=O)O)c2c1-c1ccccc1S(=O)(=O)C2]

Following the protocol outlined in Procedure S, 1-(2-methylphenyl)-1,4-dihydrothiochromeno[4,3-c]pyrazole-3-carboxylic acid 5,5-dioxide is obtained from ethyl 1-(2-methylphenyl)-1,4-dihydrothiochromeno[4,3-c]pyrazole-3-carboxylate 5,5-dioxide to afford 0.4 g (85%) of the title compound. $^1$H NMR (DMSO-d$_6$, 400 MHz) δ 13.6 (brs, 1H), 8.00 (dd, J=7.8 Hz, J=1.2 Hz, 1H), 7.63-7.48 (m, 6H), 6.65 (d, J=7.8 Hz, 1H), 5.00 (s, 2H), 1.85 (s, 3H). MS (ESI+): 355.0. HPLC (max plot) 96.9%; Rt 3.74 min.

Intermediate S.24

1-(2-bromophenyl)-1,4-dihydrothiochromeno[4,3-c]pyrazole-3-carboxylic acid 5,5-dioxide

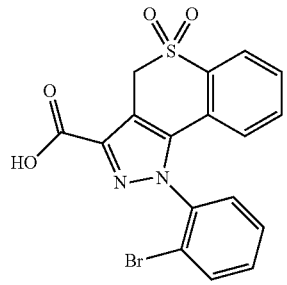 [SMILES: O=C(O)c1nn(-c2ccccc2Br)c2c1CS(=O)(=O)c1ccccc1-2]

Following the protocol outlined in Procedure S, 1-(2-bromophenyl)-1,4-dihydrothiochromeno[4,3-c]pyrazole-3-carboxylic acid 5,5-dioxide is obtained from ethyl 1-(2-bromophenyl)-1,4-dihydrothiochromeno[4,3-c]pyrazole-3-carboxylate 5,5-dioxide to afford 0.3 g (71%) of the title compound. $^1$H NMR (DMSO-d$_6$, 400 MHz) δ 13.6 (s, 1H), 8.02 (dd, J=7.8 Hz, J=1.2 Hz, 1H), 7.95 (dd, J=7.8 Hz, J=1.2 Hz, 1H), 7.79 (dd, J=7.8 Hz, J=1.2 Hz, 1H), 7.73-7.58 (m, 4H), 6.66-6.64 (m, 1H), 5.06-4.95 (m, 2H). MS (ESI+): 420.0. HPLC (max plot) 98.0%; Rt 3.70 min.

Intermediate S.25

1-(2-fluorophenyl)-1,4-dihydrothiochromeno[4,3-c]pyrazole-3-carboxylic acid 5,5-dioxide

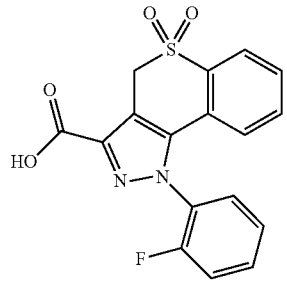 [SMILES: O=C(O)c1nn(-c2ccccc2F)c2c1CS(=O)(=O)c1ccccc1-2]

Following the protocol outlined in Procedure S, 1-(2-fluorophenyl)-1,4-dihydrothiochromeno[4,3-c]pyrazole-3-carboxylic acid 5,5-dioxide is obtained from ethyl 1-(2-fluorophenyl)-1,4-dihydrothiochromeno[4,3-c]pyrazole-3-carboxylate 5,5-dioxide to afford the title compound. $^1$H NMR (DMSO-d$_6$, 400 MHz) δ 13.6 (brs, 1H), 8.02 (dd, J=7.7 Hz, J=1.2 Hz, 1H), 7.81-7.74 (m, 2H), 7.67-7.50 (m, 4H), 6.84 (d, J=7.6 Hz, 1H), 4.99 (d, J=7.0 Hz, 2H). MS (ESI+): 359.0. HPLC (max plot) 99.0%; Rt 3.48 min.

Intermediate S.26

1-(2-chlorophenyl)-1,4-dihydrothiochromeno[4,3-c]pyrazole-3-carboxylic acid 5,5-dioxide

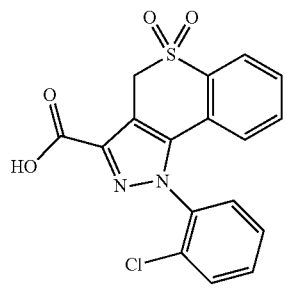 [SMILES: O=C(O)c1nn(-c2ccccc2Cl)c2c1CS(=O)(=O)c1ccccc1-2]

Following the protocol outlined in Procedure S, 1-(2-chlorophenyl)-1,4-dihydrothiochromeno[4,3-c]pyrazole-3-carboxylic acid 5,5-dioxide is obtained from ethyl 1-(2-chlorophenyl)-1,4-dihydrothiochromeno[4,3-c]pyrazole-3-carboxylate 5,5-dioxide to afford the title compound. $^1$H NMR (DMSO-d$_6$, 400 MHz) δ 13.6 (brs, 1H), 8.02 (d, J=7.6 Hz, 1H), 7.83-7.56 (m, 6H), 6.68 (d, J=7.7 Hz, 1H), 5.06-4.95 (m, 2H). MS (ESI+): 375.0. HPLC (max plot) 97.6%; Rt 3.65 min.

Intermediate S.27

1-[2-(methylsulfonyl)phenyl]-1,4-dihydrothiochromeno[4,3-c]pyrazole-3-carboxylic acid 5,5-dioxide

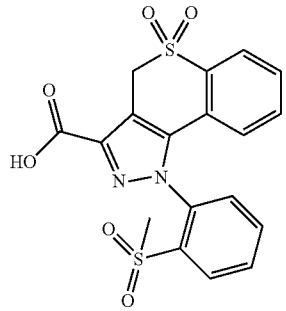 [SMILES: CS(=O)(=O)c1ccccc1-n1nc(C(=O)O)c2c1-c1ccccc1S(=O)(=O)C2]

Following the protocol outlined in Procedure S, 142-(methylsulfonyl)phenyl]-1,4-dihydrothiochromeno[4,3-c]pyrazole-3-carboxylic acid 5,5-dioxide is obtained from ethyl 1-[2-(methylsulfonyl)phenyl]-1,4-dihydrothiochromeno[4,3-c]pyrazole-3-carboxylate 5,5-dioxide to afford 0.35 g (74%) of the title compound. $^1$H NMR (DMSO-d$_6$, 400 MHz) δ 8.29 (dd, J=7.8 Hz, J=1.2 Hz, 1H), 8.02-7.92 (m, 3H), 7.65-7.54 (m, 3H), 6.60 (d, J=7.2 Hz, 1H), 5.02 (s, 2H), 3.42 (s, 3H). MS (ESI+): 419.0. HPLC (max plot) 96.6%; Rt 3.09 min.

Intermediate S.28

1-(2,3-dihydro-1,4-benzodioxin-6-yl)-1,4-dihydrothiochromeno[4,3-c]pyrazole-3-carboxylic acid 5,5-dioxide

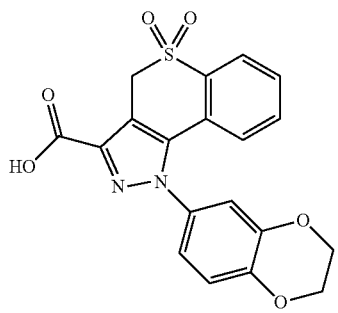 [SMILES: O=C(O)c1nn(-c2ccc3c(c2)OCCO3)c2c1CS(=O)(=O)c1ccccc1-2]

Following the protocol outlined in Procedure S, 1-(2,3-dihydro-1,4-benzodioxin-6-yl)-1,4-dihydrothiochromeno[4,3-c]pyrazole-3-carboxylic acid 5,5-dioxide is obtained from ethyl 1-(2,3-dihydro-1,4-benzodioxin-6-yl)-1,4-dihydrothiochromeno[4,3-c]pyrazole-3-carboxylate 5,5-dioxide to afford 0.15 g (97%) of the title compound. $^1$H NMR (DMSO-d$_6$, 400 MHz) δ 13.5 (brs, 1H), 8.00 (dd, J=7.2 Hz, J=4.2 Hz, 1H), 7.65-7.60 (m, 2H), 7.07-7.04 (m, 2H), 6.93-6.89 (m, 2H), 4.94 (s, 2H), 4.35-4.34 (m, 4H). MS (ESI+): 399.0. HPLC (max plot) 96.4%; Rt 3.35 min.

Intermediate S.29

1-(2-methyl-1,3-benzothiazol-6-yl)-1,4-dihydrothiochromeno[4,3-c]pyrazole-3-carboxylic acid 5,5-dioxide

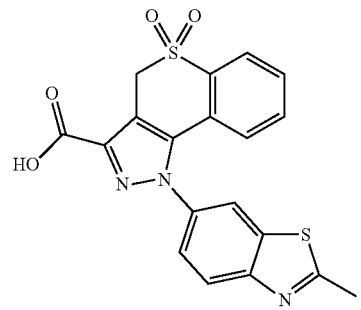 [SMILES: Cc1nc2ccc(-n3nc(C(=O)O)c4c3-c3ccccc3S(=O)(=O)C4)cc2s1]

Following the protocol outlined in Procedure S, 1-(2-methyl-1,3-benzothiazol-6-yl)-1,4-dihydrothiochromeno[4,3-c]pyrazole-3-carboxylic acid 5,5-dioxide is obtained from ethyl 1-(2-methyl-1,3-benzothiazol-6-yl)-1,4-dihydrothiochromeno[4,3-c]pyrazole-3-carboxylate 5,5-dioxide to afford 0.090 g (79%) of the title compound. $^1$H NMR (DMSO-d$_6$, 400 MHz) δ 13.6 (brs, 1H), 8.36 (d, J=2.0 Hz, 1H), 8.11 (d, J=8.3 Hz, 1H), 8.02 (dd, J=7.8 Hz, J=1.1 Hz, 1H), 7.64-7.53 (m, 3H), 6.79 (d, J=7.8 Hz, 1H), 4.99 (s, 2H), 2.86 (s, 3H). MS (ESI+): 412.0. HPLC (max plot) 95.9%; Rt 3.24 min.

Intermediate S.30

1-(3-bromophenyl)-1,4-dihydrothiochromeno[4,3-c]pyrazole-3-carboxylic acid 5,5-dioxide

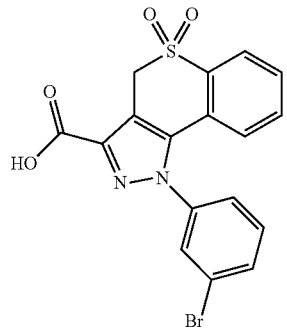 [SMILES: O=C(O)c1nn(-c2cccc(Br)c2)c2c1CS(=O)(=O)c1ccccc1-2]

Following the protocol outlined in Procedure S, 1-(3-bromophenyl)-1,4-dihydrothiochromeno[4,3-c]pyrazole-3-carboxylic acid 5,5-dioxide is obtained from ethyl 1-(3-bromophenyl)-1,4-dihydrothiochromeno[4,3-c]pyrazole-3-carboxylate 5,5-dioxide to afford 0.29 g (88%) of the title compound. $^1$H NMR (DMSO-d$_6$, 400 MHz) δ 13.6 (brs, 1H), 8.04-8.02 (m, 1H), 7.87-7.85 (m, 2H), 7.67-7.50 (m, 4H), 6.91-6.89 (m, 1H), 4.97 (s, 2H). MS (ESI+): 420.0. HPLC (max plot) 98.7%; Rt 3.95 min.

Intermediate S.31

1-(3-chlorophenyl)-1,4-dihydrothiochromeno[4,3-c]pyrazole-3-carboxylic acid 5,5-dioxide

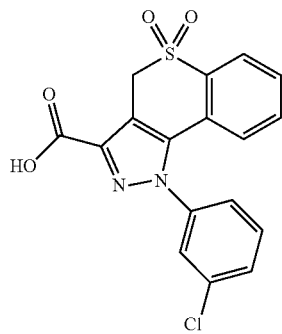 [SMILES: O=C(O)c1nn(-c2cccc(Cl)c2)c2c1CS(=O)(=O)c1ccccc1-2]

Following the protocol outlined in Procedure S, 1-(3-chlorophenyl)-1,4-dihydrothiochromeno[4,3-c]pyrazole-3-carboxylic acid 5,5-dioxide is obtained from ethyl 1-(3-chlorophenyl)-1,4-dihydrothiochromeno[4,3-c]pyrazole-3-carboxylate 5,5-dioxide to afford 0.28 g (97%) of the title compound. $^1$H NMR (DMSO-$d_6$, 400 MHz) δ 13.6 (brs, 1H), 8.04-8.02 (m, 1H), 7.75-7.73 (m, 2H), 7.67-7.60 (m, 1H), 7.48-7.46 (m, 1H), 6.91-6.89 (m, 1H), 4.97 (s, 2H). MS (ESI+): 375.0. HPLC (max plot) 98.0%; Rt 5.87 min.

Intermediate S.32

1-(4-bromophenyl)-1,4-dihydrothiochromeno[4,3-c]pyrazole-3-carboxylic acid 5,5-dioxide

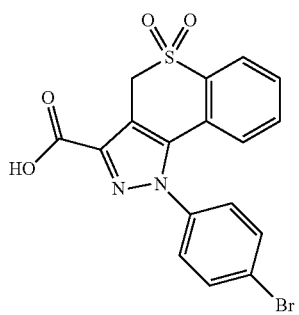 [SMILES: O=C(O)c1nn(-c2ccc(Br)cc2)c2c1CS(=O)(=O)c1ccccc1-2]

Following the protocol outlined in Procedure S, 1-(4-bromophenyl)-1,4-dihydrothiochromeno[4,3-c]pyrazole-3-carboxylic acid 5,5-dioxide is obtained from ethyl 1-(4-bromophenyl)-1,4-dihydrothiochromeno[4,3-c]pyrazole-3-carboxylate 5,5-dioxide to afford the title compound. $^1$H NMR (DMSO-$d_6$, 400 MHz) δ 13.6 (brs, 1H), 8.03-8.01 (m, 1H), 7.83 (d, J=8.6 Hz, 2H), 7.67-7.62 (m, 2H), 7.52-7.49 (m, 2H), 6.93-6.90 (m, 1H), 4.96 (s, 2H). MS (ESI+): 420.0. HPLC (max plot) 96.4%; Rt 4.03 min.

Intermediate S.33

1-(4-fluorophenyl)-1,4-dihydrothiochromeno[4,3-c]pyrazole-3-carboxylic acid 5,5-dioxide

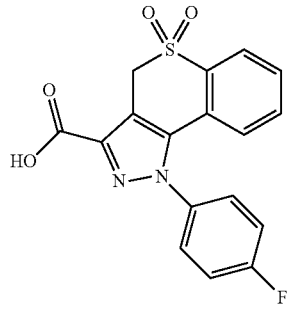 [SMILES: O=C(O)c1nn(-c2ccc(F)cc2)c2c1CS(=O)(=O)c1ccccc1-2]

Following the protocol outlined in Procedure S, 1-(4-fluorophenyl)-1,4-dihydrothiochromeno[4,3-c]pyrazole-3-carboxylic acid 5,5-dioxide is obtained from ethyl 1-(4-fluorophenyl)-1,4-dihydrothiochromeno[4,3-c]pyrazole-3-carboxylate 5,5-dioxide to afford the title compound. $^1$H NMR (DMSO-$d_6$, 400 MHz) δ 13.6 (brs, 1H), 8.02 (d, J=7.7 Hz, 1H), 7.66-7.59 (m, 4H), 7.50-7.45 (m, 2H), 6.85-6.83 (m, 1H), 4.96 (m, 2H). MS (ESI+): 359.0. HPLC (max plot) 99.0%; Rt 3.57 min.

Intermediate S.34

1-(4-chlorophenyl)-1,4-dihydrothiochromeno[4,3-c]pyrazole-3-carboxylic acid 5,5-dioxide

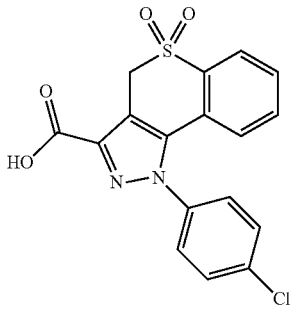 [SMILES: O=C(O)c1nn(-c2ccc(Cl)cc2)c2c1CS(=O)(=O)c1ccccc1-2]

Following the protocol outlined in Procedure S, 1-(4-chlorophenyl)-1,4-dihydrothiochromeno[4,3-c]pyrazole-3-carboxylic acid 5,5-dioxide is obtained from ethyl 1-(4-chlorophenyl)-1,4-dihydrothiochromeno[4,3-c]pyrazole-3-carboxylate 5,5-dioxide to afford the title compound. $^1$H NMR (DMSO-$d_6$, 400 MHz) δ 13.63 (m, 1H), 8.04-8.02 (m, 1H), 7.71-7.56 (m, 6H), 6.92-6.89 (m, 1H), 4.96 (s, 2H). MS (ESI+): 343.0. HPLC (max plot) 98.5%, Rt 3.93 min.

Intermediate S.35

1-(4-isopropylphenyl)-1,4-dihydrothiochromeno[4,3-c]pyrazole-3-carboxylic acid 5,5-dioxide

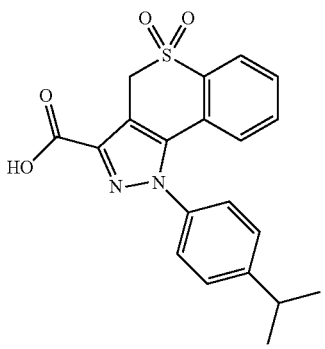 [SMILES: CC(C)c1ccc(-n2nc(C(=O)O)c3c2-c2ccccc2S(=O)(=O)C3)cc1]

Following the protocol outlined in Procedure S, 1-(4-isopropylphenyl)-1,4-dihydrothiochromeno[4,3-c]pyrazole-3-carboxylic acid 5,5-dioxide is obtained from ethyl 1-(4-isopropylphenyl)-1,4-dihydrothiochromeno[4,3-c]pyrazole-3-carboxylate 5,5-dioxide to afford 0.45 g (88%) of the title compound. $^1$H NMR (DMSO-$d_6$, 400 MHz) δ 13.5 (brs, 1H), 8.01 (d, J=7.6 Hz, 1H), 7.64-7.56 (m, 2H), 7.50-7.42 (m, 4H), 6.83 (d, J=7.7 Hz, 1H), 4.95 (s, 2H), 3.07-3.00 (m, 1H), 1.27 (d, J=6.9 Hz, 6H). MS (ESI+): 383.0. HPLC (max plot) 95.2%; Rt 4.56 min.

Intermediate S.36

1-(4-methylpyridin-3-yl)-1,4-dihydrothiochromeno[4,3-c]pyrazole-3-carboxylic acid 5,5-dioxide

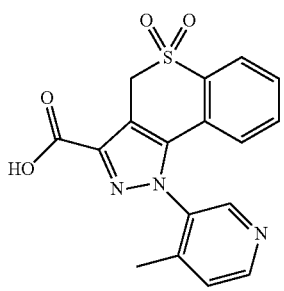 [SMILES: Cc1ccncc1-n1nc(C(=O)O)c2c1-c1ccccc1S(=O)(=O)C2]

Following the protocol outlined in Procedure S, 1-(4-methylpyridin-3-yl)-1,4-dihydrothiochromeno[4,3-c]pyrazole-3-carboxylic acid 5,5-dioxide is obtained from ethyl 1-(4-methylpyridin-3-yl)-1,4-dihydrothiochromeno[4,3-c]pyrazole-3-carboxylate 5,5-dioxide to afford the title compound. $^1$H NMR ((DMSO-$d_6$, 400 MHz) δ 13.65 (brs, 1H), 8.37 (d, J=1.6 Hz, 1H), 8.03-7.98 (m, 2H), 7.77 (d, J=8.0 Hz, 1H), 7.65-7.56 (m, 2H), 6.88-6.86 (m, 1H), 4.95 (s 2H), 2.43 (s, 3H). MS (ESI+): 356.0. HPLC (max plot) 97.4%; Rt 3.22 min.

Intermediate S.37

1-(tetrahydro-2H-pyran-4-yl)-1,4-dihydrothiochromeno[4,3-c]pyrazole-3-carboxylic acid 5,5-dioxide

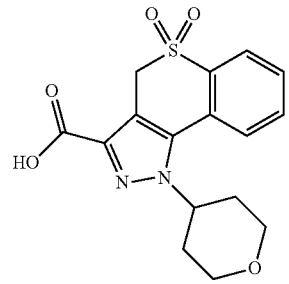 [SMILES: O=C(O)c1nn(C2CCOCC2)c2c1CS(=O)(=O)c1ccccc1-2]

Following the protocol outlined in Procedure S, 1-(tetrahydro-2H-pyran-4-yl)-1,4-dihydrothiochromeno[4,3-c]pyrazole-3-carboxylic acid 5,5-dioxide is obtained from ethyl 1-(tetrahydro-2H-pyran-4-yl)-1,4-dihydrothiochromeno[4,3-c]pyrazole-3-carboxylate 5,5-dioxide to afford 0.35 g (75%) of the title compound. $^1$H NMR (DMSO-$d_6$, 400 MHz) δ 13.3 (brs, 1H), 8.04 (q, J=7.9 Hz, 1H), 7.95-7.89 (m, 2H), 7.74 (t, J=6.7 Hz, 1H), 5.07-5.02 (m, 1H), 4.84 (s, 2H), 4.00-3.96 (m, 2H), 4.00-3.96 (m, 2H), 3.60-3.54 (m, 1H), 2.21-2.18 (m, 1H), 2.17-2.12 (m, 2H). MS (ESI+): 349.0. HPLC (max plot) 94.6%; Rt 2.69 min.

Compounds described below are obtained following procedure S.

---

Intermediate S.38: 3-(3-Thienylthio)propanic acid

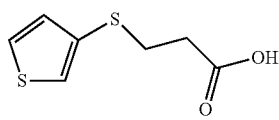 [SMILES: O=C(O)CCSc1ccsc1]

5.4 g (96%) of the title compound. $^1$H NMR (DMSO-$d_6$, 400 MHz): δ 12.35 (s, 1H), 7.63-7.61 (m, 1H), 7.43-7.42 (m, 1H), 7.09-7.08 (m, 1H), 3.06-3.03 (t, J = 7.1 Hz, 2H), 2.52-2.49 (m, 2H).

Intermediate S.39: 1-Phenyl-1,4-dihydrothiochromeno[4,3-c]pyrazole-3-carboxylic acid 5-oxide

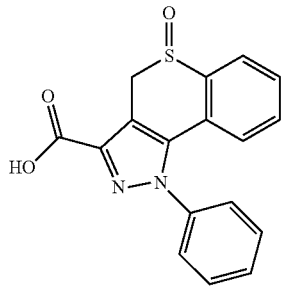 [SMILES: O=C(O)c1nn(-c2ccccc2)c2c1CS(=O)c1ccccc1-2]

30 mg of the title compound. 1H NMR (DMSO-d6) δ 13.25 (br s, 1H), 7.63-7.56 (m, 4H), 7.49-7.46 (m, 2H), 7.31-7.26 (m, 1H), 7.07-7.01 (m, 1H), 6.86-6.83 (m, 1H), 6.53 (s, 1H). HPLC (max plot) 89.4%; Rt 3.10 min.

Intermediate S.40: 1-[3-(Benzyloxy)phenyl]-1,4-dihydrothiochromeno[4,3-c]pyrazole-3-carboxylic acid 5,5-dioxide

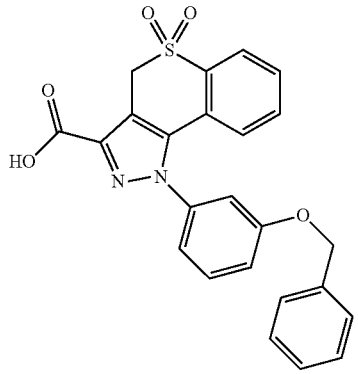 [SMILES: O=C(O)c1nn(-c2cccc(OCc3ccccc3)c2)c2c1CS(=O)(=O)c1ccccc1-2]

4.4 g (85%) of the title compound as an off white solid. $^1$H NMR (400 MHz, DMSO-d$_6$) δ: δ 13.30 (1H, bs), 8.020-8.001 (d, J = 7.6 Hz, 1H), 7.648-7.610 (m, 1H), 7.578-7.519 (m, 2H), 7.499-7.4217 (m, 2H), 7.384-7.327 (m, 2H), 7.309-7.279 (m, 2H), 7.223-7.219 (t, J = 1.6 Hz, 1H), 7.039-7.019 (t, J = 8.0 Hz, 1H), 6.852-6.832 (d, J = 8.0 Hz, 1H), 5.178 (s, 2H), 4.963 (s, 2H). MS (ESI+): 447.0. HPLC (max plot): 96%; Rt 4.56 min.

Intermediate S.41: 1-(2-Isopropylphenyl)-1,4-dihydrothiochromeno[4,3-c]pyrazole-3-carboxylic acid 5,5-dioxide

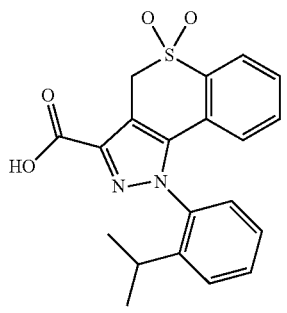 [SMILES: CC(C)c1ccccc1-n1nc(C(=O)O)c2c1-c1ccccc1S(O)(O)C2]

550 mg (96%) of the title compound. $^1$H NMR (400 MHz, DMSO-d$_6$): δ 8.00 (dd, J = 1.1, 7.7 Hz, 1H), 7.70-7.44 (m, 6H), 6.62 (d, J = 6.6 Hz, 1H), 4.99 (s, 2H), 2.32-2.29 (m, 1H), 1.06 (t, J = 6.8 Hz, 3H), 0.82 (t, J = 6.8 Hz, 3H). MS (ESI+): 383.0. HPLC (max plot): 98.9%; Rt 4.27 min.

Intermediate S.42: 1-(2-Methoxyphenyl)-1,4-dihydrothiochromeno[4,3-c]pyrazole-3-carboxylic acid 5,5-dioxide

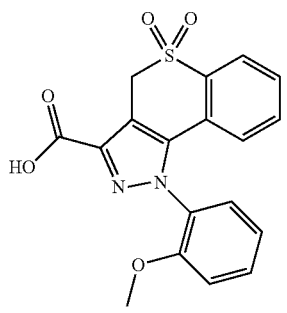 [SMILES: COc1ccccc1-n1nc(C(=O)O)c2c1-c1ccccc1S(=O)(=O)C2]

150 mg (81%) of the title compound as an off-white solid. $^1$H NMR (400 MHz, DMSO-d$_6$): δ 13.50 (bs, 1H), 7.99 (dd, J = 1.0, 7.7 Hz, 1H), 7.67-7.51 (m, 4H), 7.31 (d, J = 8.3 Hz, 1H), 7.20 (d, J = 7.6 Hz, 1H), 6.80 (d, J = 7.6 Hz, 1H), 5.02-4.91 (m, 2H), 3.57 (s, 3H). MS (ESI+): 371.0. HPLC (max plot): 98.1%; Rt 3.50 min.

Intermediate S.43: 1-(1-Methyl-6-oxo-1,6-dihydropyridin-3-yl)-1,4-dihydrothiochromeno[4,3-c]pyrazole-3-carboxylic acid 5,5-dioxide

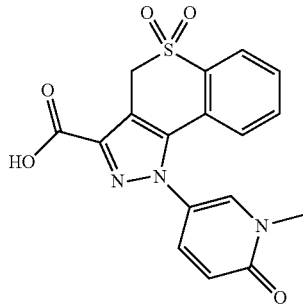 [SMILES: Cn1cc(-n2nc(C(=O)O)c3c2-c2ccccc2S(=O)(=O)C3)ccc1=O]

32 mg of the title compound. ¹H NMR (DMSO-d₆, 400 MHz): δ 8.29 (m, 1H), 8.01-8.00 (d, J = 7.5 Hz, 1H), 7.71-7.65 (m, 2H), 7.53-7.51 (m, 1H), 7.35-7.33 (d, J = 7.5 Hz, 1H), 6.54-6.51 (d, J = 9.6 Hz, 1H), 4.99 (s, 2H), 3.48 (s, 3H). MS (ESI+): 372.0.

Intermediate S.44: 1-(3-Fluorophenyl)-1,4-dihydrothiochromeno[4,3-c]pyrazole-3-carboxylic acid 5,5-dioxide

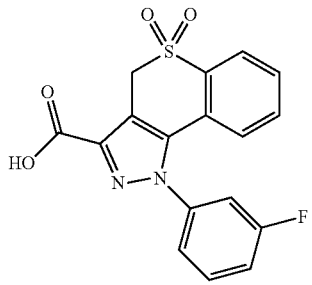 [SMILES: O=C(O)c1nn(-c2cccc(F)c2)c2c1CS(=O)(=O)c1ccccc1-2]

80 mg (82%) of the title compound. ¹H NMR (DMSO-d₆, 400 MHz): δ 13.64 (bs, 1H), 8.03-8.01 (dd, J = 1.6, 7.8 Hz, 1H), 7.69-7.51 (m, 5H), 7.36-7.34 (d, J = 7.8 Hz, 1H), 6.89-6.87 (d, J = 7.5 Hz, 1H), 4.96 (s, 2H). MS (ESI+): 359.0.

Intermediate S.45: 1-(3-Cyanophenyl)-1,4-dihydrothiochromeno[4,3-c]pyrazole-3-carboxylic acid 5,5-dioxide

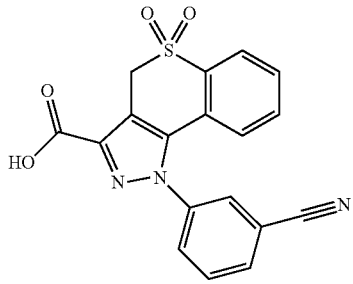 [SMILES: N#Cc1cccc(-n2nc(C(=O)O)c3c2-c2ccccc2S(=O)(=O)C3)c1]

365 mg (83%) of the title compound. 1H NMR (400 MHz, DMSO-d6) δ = 13.3 (s, 1H), 8.24 (s, 1H), 8.15-8.13 (m, 1H), 8.05-8.03 (m, 1H), 7.88-7.86 (m, 1H), 7.83-7.79 (m, 1H), 7.69-7.65 (t, J = 7.6 Hz, 1H), 7.63-7.61 (t, J = 7.6 Hz, 2H), 6.88-6.86 (d, J = 7.7 Hz, 1H), 5.00 (s, 2H). MS (ESI+): 366.0.

Intermediate S.46: 1-[4-(Methylsulfonyl)phenyl]-1,4-dihydrothiochromeno[4,3-c]pyrazole-3-carboxylic acid 5,5-dioxide

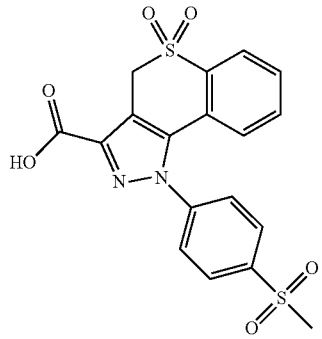 [SMILES: CS(=O)(=O)c1ccc(-n2nc(C(=O)O)c3c2-c2ccccc2S(=O)(=O)C3)cc1]

200 mg (85%) of the title compound. MS (ESI−): 416.8. HPLC (max plot) 95.78%; Rt 3.00 min.

Intermediate S.47: 1-[3-(Methylsulfonyl)phenyl]-1,4-dihydrothiochromeno[4,3-c]pyrazole-3-carboxylic acid 5,5-dioxide

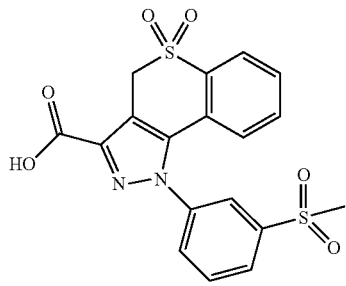 [SMILES: CS(=O)(=O)c1cccc(-n2nc(C(=O)O)c3c2-c2ccccc2S(=O)(=O)C3)c1]

150 mg (80%) of the title compound. $^1$H NMR (DMSO-d$_6$, 400 MHz): δ 13.70 (bs, 1H), 8.19-8.17 (m, 1H), 8.16 (s, 1H), 8.10-8.03 (m, 1H), 7.69-7.59 (m, 4H), 6.93-6.91 (d, J = 7.8 Hz, 1H), 4.99 (s, 2H), 3.32 (s, 3H). MS (ESI-): 416.8. HPLC (max plot) 96.98%; Rt 2.97 min.

Intermediate S.48: 1-{3-[(Dimethylamino)sulfonyl]phenyl}-1,4-dihydrothiochromeno[4,3-c]pyrazole-3-carboxylic acid 5,5-dioxide

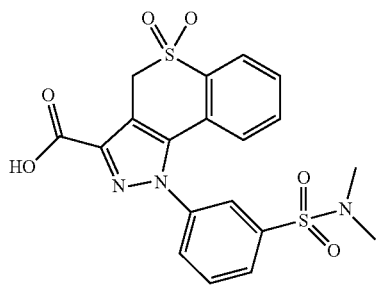

65 mg of the title compound. MD (ESI+): 448.0.

Intermediate S.49: 3-(Morpholin-4-ylcarbonyl)-1pyridin-3-yl-1,4-dihydrothiochromeno[4,3-c]pyrazole 5,5-dioxide

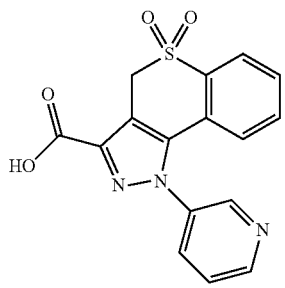 [SMILES: O=C(O)c1nn(-c2cccnc2)c2c1CS(=O)(=O)c1ccccc1-2]

50 mg, 77% yield of the title compound. 1H NMR (400 MHz, DMSO-d6) δ = 13.66 (bs, 1H), 8.84-8.83 (d, J = 5.12 Hz, 1H), 8.00-7.98 (m, 2H), 7.69-7.66 (m, 3H), 7.60-7.58 (m, 2H), 5.10 (s, 2H). MS (ESI+): 342.0.

Intermediate S.50: 1-(6-Methoxypyridin-3-yl)-1,4-dihydrothiochromeno[4,3-c]pyrazole-3-carboxylic acid 5,5-dioxide

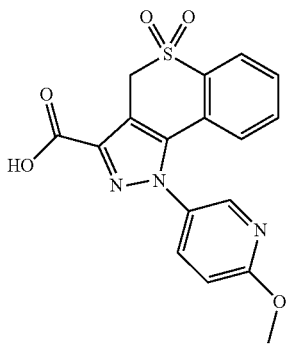

170 mg (83%) of the title compound. $^1$H NMR (DMSO-d$_6$, 400 MHz): δ 13.62 (bs, 1H), 8.40-8.39 (m, 1H), 8.04-8.02 (m, 1H), 7.93-7.90 (dd, J$_1$ = 2.7, 8.8 Hz, 1H), 7.67-7.63 (m, 2H), 7.07-7.05 (d, J = 8.8 Hz, 1H), 6.97-6.94 (m, 1H), 4.97 (s, 2H), 3.96 (s, 3H). MS (ESI−): 370.0. HPLC (max plot) 90.31%; Rt 3.26 min.

Intermediate S.51: 1-(4-Carboxyphenyl)-1,4-dihydrothiochromeno[4,3-c]pyrazole-3-carboxylic acid
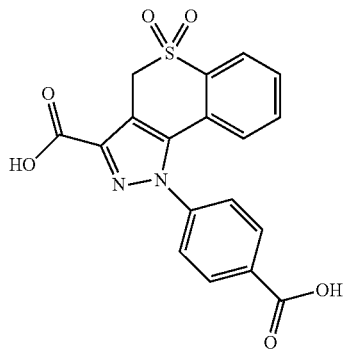 [SMILES: O=C(O)c1ccc(-n2nc(C(=O)O)c3c2-c2ccccc2S(=O)(=O)C3)cc1]
140 mg (75%) of the title compound. MS (ESI+): 385.0.
Intermediate S.52: 1-(3-carboxyphenyl)-1,4-dihydrothiochromeno[4,3-c]pyrazole-3-carboxylic acid 5,5-dioxide
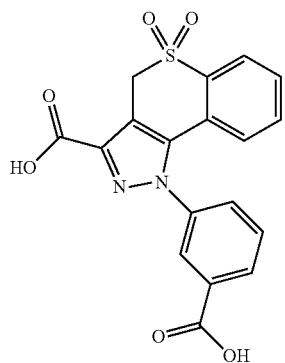 [SMILES: O=C(O)c1cccc(-n2nc(C(=O)O)c3c2-c2ccccc2S(=O)(=O)C3)c1]
MS (ESI+): 385.0. HPLC (max plot) 51.4%; Rt 2.58 min.
Intermediate S.53: 1-[3-(aminocarbonyl)phenyl]-1,4-dihydrothiochromeno[4,3-c]pyrazole-3-carboxylic acid 5,5-dioxide
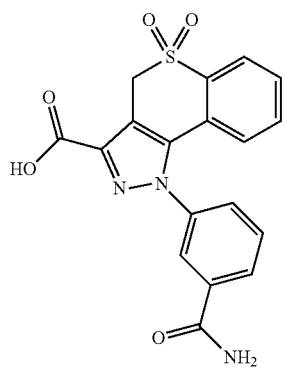 [SMILES: NC(=O)c1cccc(-n2nc(C(=O)O)c3c2-c2ccccc2S(=O)(=O)C3)c1]
MS (ESI+) 384.0. HPLC (max plot): 41.6%; Rt 2.98 min.

Intermediate S.54: 1-{3-[(4-Methylpiperazin-1-yl)carbonyl]phenyl}-1,4-dihydrothiochromeno[4,3-c]pyrazole-3-carboxylic acid 5,5-dioxide

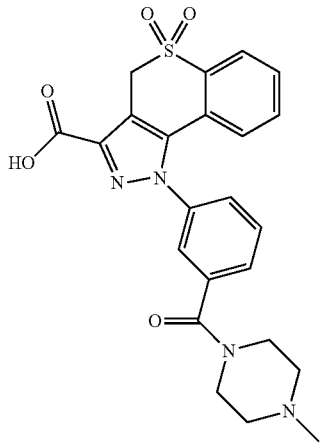 [SMILES: CN1CCN(C(=O)c2cccc(-n3nc(C(=O)O)c4c3-c3ccccc3S(=O)(=O)C4)c2)CC1]

80 mg of the title compound as a white solid.

Intermediate S.55: 1-[3-(Piperidin-1-ylcarbonyl)phenyl]-1,4-dihydrothiochromeno[4,3-c]pyrazole-3-carboxylic acid 5,5-dioxide

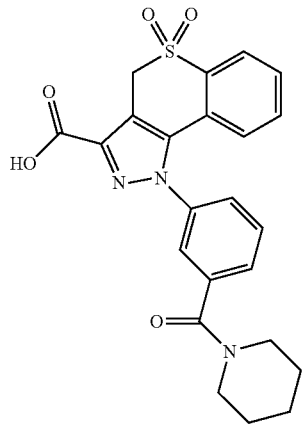 [SMILES: O=C(O)c1nn(-c2cccc(C(=O)N3CCCCC3)c2)c2c1CS(=O)(=O)c1ccccc1-2]

240 mg (85%) of the title compound. MS (ESI+): 452.0.

Intermediate S.56: 1-(3-{[(2-Methoxyethyl)amino]carbonyl}phenyl)-1,4-dihydrothiochromeno[4,3-c]pyrazole-3-carboxylic acid 5,5-dioxide

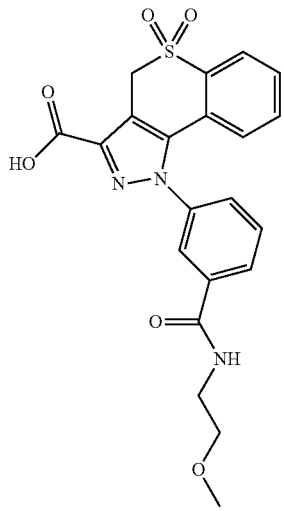 [SMILES: COCCNC(=O)c1cccc(-n2nc(C(=O)O)c3c2-c2ccccc2S(=O)(=O)C3)c1]

60 mg (91%) of the title compound as a white solid. MS (ESI+): 442.0.

Intermediate S.57: 1-{3-[(4-Methoxypiperidin-1-yl)carbonyl]phenyl}-1,4-dihydrothiochromeno[4,3-c]pyrazole-3-carboxylic acid 5,5-dioxide

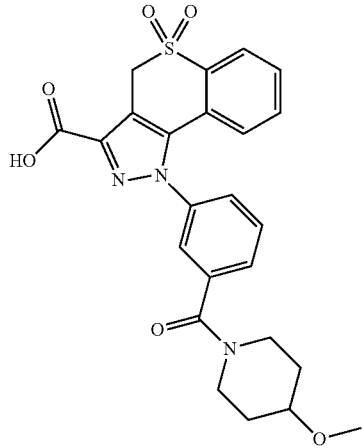 [SMILES: COC1CCN(C(=O)c2cccc(-n3nc(C(=O)O)c4c3-c3ccccc3S(=O)(=O)C4)c2)CC1]

80 mg (77%) of the title compound. MS (ESI+): 482.0.

Intermediate S.58: 1-{3-[(4-Hydroxypiperidin-1-yl)carbonyl]phenyl}-1,4-dihydrothiochromeno[4,3-c]pyrazole-3-carboxylic acid 5,5-dioxide

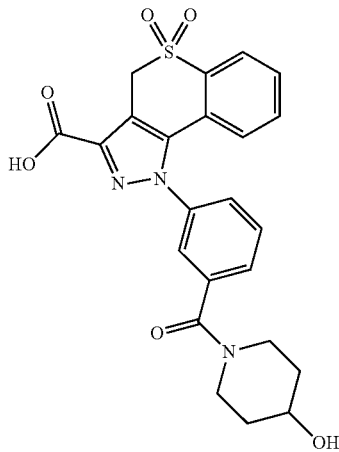 [SMILES: O=C(O)c1nn(-c2cccc(C(=O)N3CCC(O)CC3)c2)c2c1CS(=O)(=O)c1ccccc1-2]

75 mg of the title compound. MS (ESI+): 468.0.

Intermediate S.59: 1-{3-[(3-Hydroxypiperidin-1-yl)carbonyl]phenyl}-1,4-dihydrothiochromeno[4,3-c]pyrazole-3-carboxylic acid 5,5-dioxide

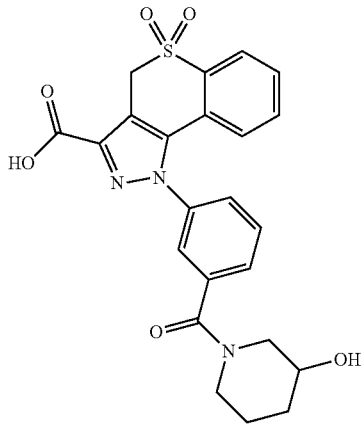

60 mg (80%) of the title compound. MS (ESI+): 468.0.

Intermediate S.60: 1-(3-{[3-(Hydroxymethyl)piperidin-1-yl]carbonyl}phenyl)-1,4-dihydrothiochromeno[4,3-c]pyrazole-3-carboxylic acid 5,5-dioxide

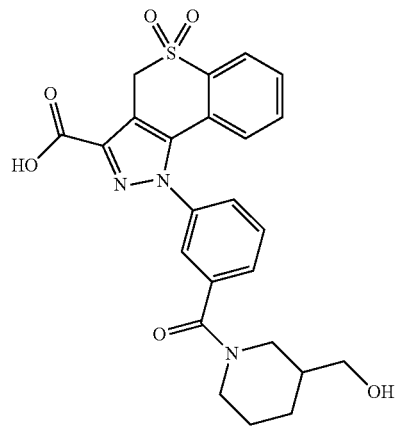 [SMILES: O=C(O)c1nn(-c2cccc(C(=O)N3CCCC(CO)C3)c2)c2c1CS(=O)(=O)c1ccccc1-2]

50 mg of the title compound. MS (ESI+): 482.0.

Intermediate S.61: 1-{3-[(1,1-Dioxidothiomorpholin-4-yl)carbonyl]phenyl}-1,4-dihydrothiochromeno[4,3-c]pyrazole-3-carboxylic acid 5,5-dioxide

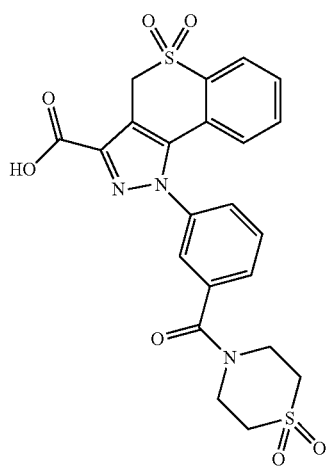 [SMILES: O=C(O)c1nn(-c2cccc(C(=O)N3CCS(=O)(=O)CC3)c2)c2c1CS(=O)(=O)c1ccccc1-2]

95 mg of the title compound. MS (ESI+): 502.0.

Intermediate S.62: 1-{3-[(Tetrahydro-2H-pyran-4-ylamino)carbonyl]phenyl}-1,4-dihydrothiochromeno[4,3-c]pyrazole-3-carboxylic acid 5,5-dioxide

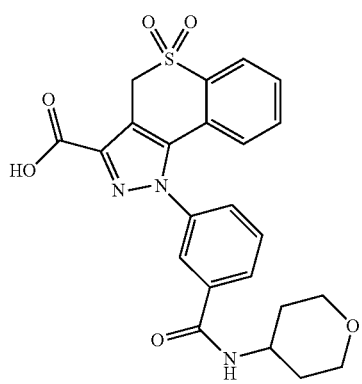 [SMILES: O=C(NC1CCOCC1)c1cccc(-n2nc(C(=O)O)c3c2-c2ccccc2S(=O)(=O)C3)c1]

90 mg (88%) of the title compound. MS (ESI+): 468.

Intermediate S.63: 1-{3-[(Pyridin-3-ylamino)carbonyl]phenyl}-1,4-dihydrothiochromeno[4,3-c]pyrazole-3-carboxylic acid 5,5-dioxide

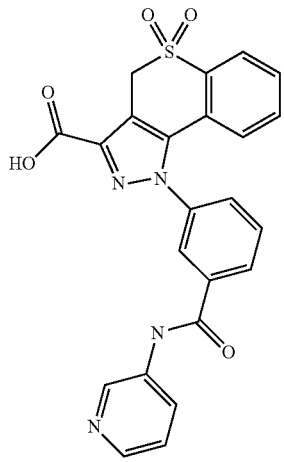 [SMILES: O=C(Nc1cccnc1)c1cccc(-n2nc(C(=O)O)c3c2-c2ccccc2S(=O)(=O)C3)c1]

70 mg (82%) of the title compound. MS (ESI+): 461.0.

Intermediate S.64: 1-[4-(Piperidin-1-ylcarbonyl)phenyl]-1,4-dihydrothiochromeno[4,3-c]pyrazole-3-carboxylic acid 5,5-dioxide

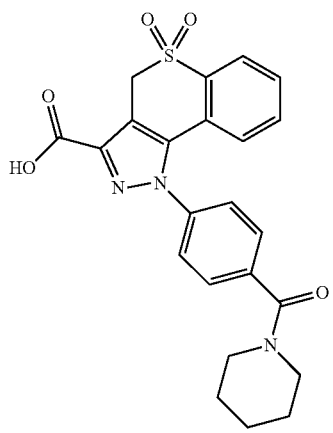 [SMILES: O=C(O)c1nn(-c2ccc(C(=O)N3CCCCC3)cc2)c2c1CS(=O)(=O)c1ccccc1-2]

120 mg (75%) of the title compound. MS (ESI+): 453.0.

Intermediate S.65: 1-{3-[(3-Methoxypiperidin-1-yl)carbonyl]phenyl}-1,4-dihydrothiochromeno[4,3-c]pyrazole-3-carboxylic acid 5,5-dioxide

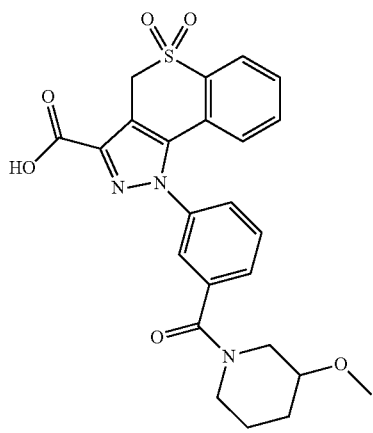 [SMILES: COC1CCCN(C(=O)c2cccc(-n3nc(C(=O)O)c4c3-c3ccccc3S(=O)(=O)C4)c2)C1]

60 mg (70%) of the title compound. MS (ESI+): 482.0.

Intermediate S.66: 1-(1H-indazol-4-yl)-1,4-dihydrothiochromeno[4,3-c]pyrazole-3-carboxylic acid 5,5-dioxide

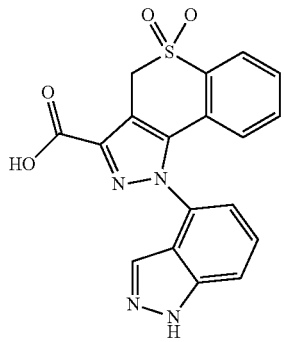

300 mg (77%) of the title compound. $^1$H NMR (DMSO-d$_6$, 400 MHz): δ 13.40 (s, 1H), 8.27 (s, 1H), 8.02-7.99 (m, 2H), 7.72 (s, 1H), 7.63-7.59 (m, 1H), 7.54-7.52 (m, 1H), 7.18-7.15 (m, 1H), 6.81-6.79 (d, J = 7.9 Hz, 1H), 4.98 (s, 2H). MS (ESI+): 381.2.

Intermediate S.67: 1-(2-Benzyl-indazol-4-yl)-1,4-dihydrothiochromeno[4,3-c]pyrazole-3-carboxylic acid 5,5-dioxide

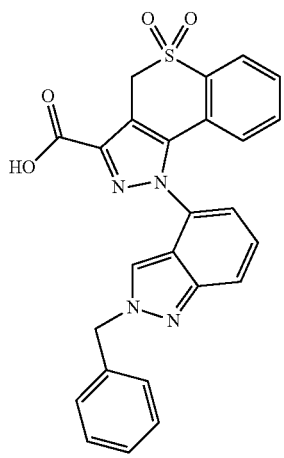 [SMILES: O=C(O)c1nn(-c2cccc3nn(Cc4ccccc4)cc23)c2c1CS(=O)(=O)c1ccccc1-2]

300 mg (77%) of the title compound. MS (ESI+): 471.2.

Intermediate S.68: 1-{3-[(Morpholin-4-ylcarbonyl)amino]phenyl}-1,4-dihydrothiochromeno[4,3-c]pyrazole-3-carboxylic acid 5,5-dioxide

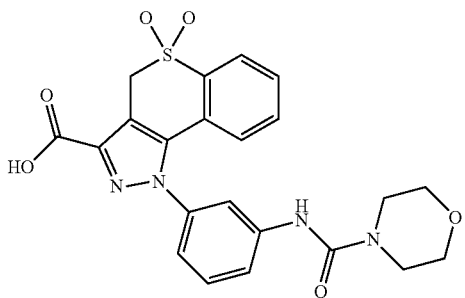 [SMILES: O=C(O)c1nn(-c2cccc(NC(=O)N3CCOCC3)c2)c2c1CS(O)(O)c1ccccc1-2]

60 mg (79%) of the title compound.

Intermediate S.69: 1-[3-(5-Methyl-1,3,4-oxadiazol-2-yl)phenyl]-1,4-dihydrothiochromeno[4,3-c]pyrazole-3-carboxylic acid 5,5-dioxide

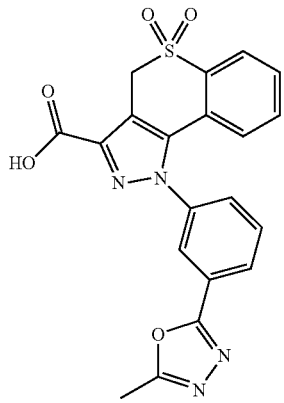 [SMILES: Cc1nnc(-c2cccc(-n3nc(C(=O)O)c4c3-c3ccccc3S(=O)(=O)C4)c2)o1]

20 mg of the title compound. MS (ESI+): 423.0.

Intermediate S.70: 1-[3-(5-Methyl-1,3,4-thiadazol-2-yl)phenyl]-1,4-dihydrothiochromeno[4,3-c]pyrazole-3-carboxylic acid 5,5-dioxide

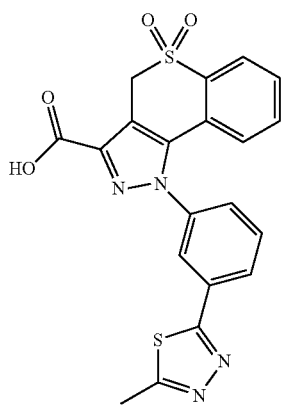 [SMILES: Cc1nnc(-c2cccc(-n3nc(C(=O)O)c4c3-c3ccccc3S(=O)(=O)C4)c2)s1]

100 mg of the title compound. MS (ESI+): 371.0.

Intermediate S.71: 1-[3-(3-Methyl-1,2,4-oxadiazol-5-yl)phenyl]-1,4-dihydrothiochromeno[4,3-c]pyrazole-3-carboxylic acid 5,5-dioxide

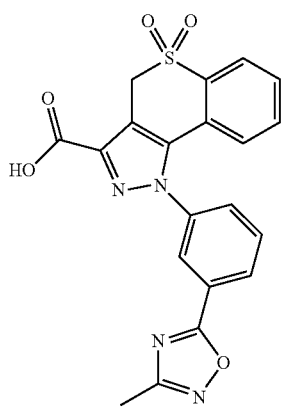 [SMILES: Cc1noc(-c2cccc(-n3nc(C(=O)O)c4c3-c3ccccc3S(=O)(=O)C4)c2)n1]

25 mg of the title compound. MS (ESI+): 423.0.

Intermediate S.72: 1-(3-{3-[(Dimethylamino)methyl]-1,2,4-oxadiazol-5-yl}phenyl)-1,4-dihydrothiochromeno[4,3-c]pyrazole-3-carboxylic acid 5,5-dioxide

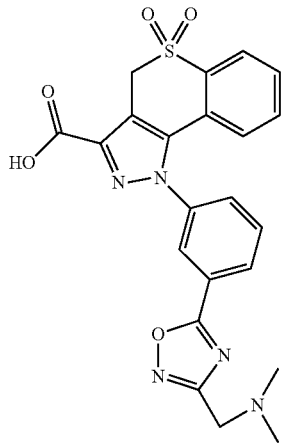 [SMILES: CN(C)Cc1noc(-c2cccc(-n3nc(C(=O)O)c4c3-c3ccccc3S(=O)(=O)C4)c2)n1]

100 mg (70%) of the title compound. MS (ESI+): 466.0.

Intermediate S.73: 1-{3-[3-(Methoxymethyl)-1,2,4-oxadiazol-5-yl]phenyl}-1,4-dihydrothiochromeno[4,3-c]pyrazole-3-carboxylic acid 5,5-dioxide

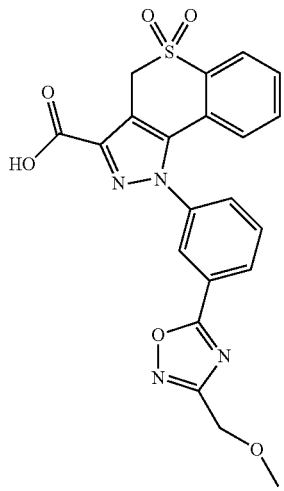 [SMILES: COCc1noc(-c2cccc(-n3nc(C(=O)O)c4c3-c3ccccc3S(=O)(=O)C4)c2)n1]

220 mg (78%) of the title compound. MS (ESI+): 453.0.

Intermediate S.74: 1-[4-(1-Methyl-1-morpholin-4-ylethyl)phenyl]-1,4-dihydrothiochromeno[4,3-c]pyrazole-3-carboxylic acid 5,5-dioxide hydrochloride

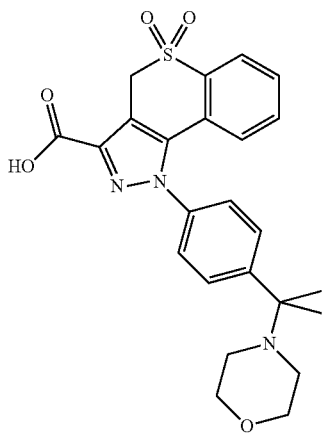 [SMILES: CC(C)(c1ccc(-n2nc(C(=O)O)c3c2-c2ccccc2S(=O)(=O)C3)cc1)N1CCOCC1]

81 mg (89%) of the title compound as a brown solid. MS (ESI+): 466.32. HPLC (max plot) 91.0%; Rt 2.08 min.

Intermediate S.75: 1-[4-(1,1-Dimethyl-2-morpholin-4-ylethyl)phenyl]-1,4-dihydrothiochromeno[4,3-c]pyrazole-3-carboxylic acid 5,5-dioxide

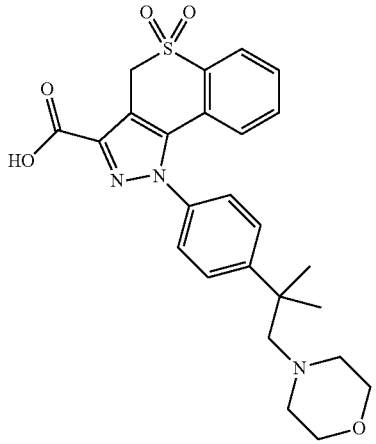 [SMILES: CC(C)(CN1CCOCC1)c1ccc(-n2nc(C(=O)O)c3c2-c2ccccc2S(=O)(=O)C3)cc1]

483 mg (79%) of the title compound as a white solid. $^1$H NMR (DMSO-d$_6$, 300 MHz): δ 13.62 (bs, 1H), 9.98 (s, 1H), 8.09-7.99 (m, 1H), 7.87-7.70 (m, 2H), 7.70-7.61 (m, 1H), 7.61-7.44 (m, 3H), 6.92-6.76 (m, 1H), 4.98 (s, 2H), 4.04-4.75 (m, 4H), 4.75-4.59 (s, 2H), 3.25-3.06 (m, 2H), 3.06-2.78 (m, 2H), 1.54 (s, 6H). MS (ESI+): 482.3. HPLC (max plot) 96.2%; Rt 2.26 min.

Intermediate S.76: 1-{4-[2-(Dimethylamino)-1,1-dimethyl]phenyl}-1,4-dihydrothiochromeno[4,3-c]pyrazole-3-carboxylic acid 5,5-dioxide

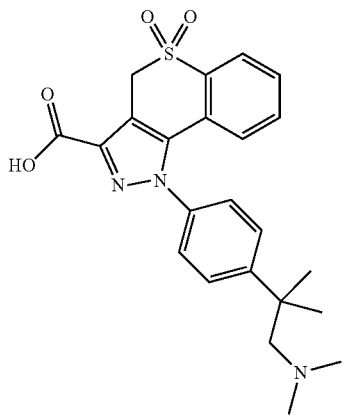 [SMILES: CN(C)CC(C)(C)c1ccc(-n2nc(C(=O)O)c3c2-c2ccccc2S(=O)(=O)C3)cc1]

679 mg (95%) of the title compound as a beige solid. $^1$H NMR (DMSO-d$_6$, 300 MHz): δ 13.20 (bs, 1H), 8.10-7.98 (m, 1H), 7.86-7.71 (m, 2H), 7.71-7.60 (m, 1H), 7.60-7.47 (m, 3H), 6.88-6.75 (m, 1H), 4.98 (s, 2H), 2.67-2.54 (m, 6H), 2.54-2.46 (m, 2H), 1.15 (s, 6H). MS (ESI+): 440.3. HPLC (max plot) 99.7%; Rt 2.24 min.

Intermediate S.77: 1-{4-[1-(Morpholin-4-ylmethyl)cyclopropyl]phenyl}-1,4-dihydrothiochromeno[4,3-c]pyrazole-3-carboxylic acid 5,5-dioxide

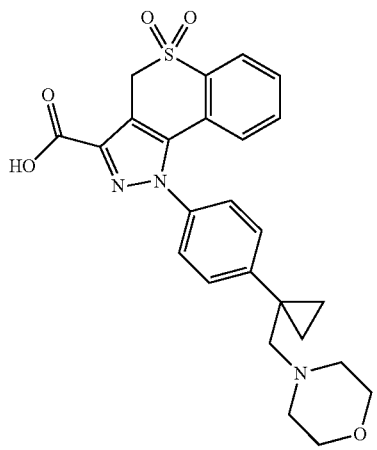 [SMILES: O=C(O)c1nn(-c2ccc(C3(CN4CCOCC4)CC3)cc2)c2c1CS(=O)(=O)c1ccccc1-2]

82 mg of the title compound. $^1$H NMR (DMSO-d$_6$, 300 MHz): δ 13.51 (bs, 1H), 10.05 (bs, 1H), 8.08-7.98 (m, 1H), 7.82-7.43 (m, 6H), 7.07-7.94 (m, 1H), 4.97 (s, 2H), 4.00-3.83 (m, 2H), 3.83-3.68 (m, 2H), 3.68-3.52 (m, 2H), 3.19-2.94 (m, 2H), 1.44-1.02 (m, 6H). MS (ESI+): 482.3. HPLC (max plot) 97.6%; Rt 2.34 min.

-continued

Intermediate S.78: 1-[4-(Hydroxymethyl)phenyl]-1,4-dihydrothiochromeno[4,3-c]pyrazole-3-carboxylic acid 5,5-dioxide

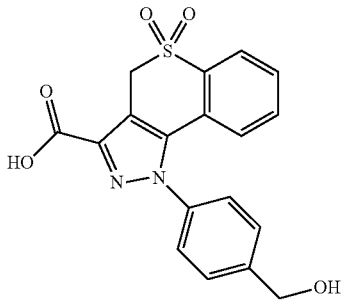 [SMILES: O=C(O)c1nn(-c2ccc(CO)cc2)c2c1CS(=O)(=O)c1ccccc1-2]

5.29 g (100%) of the title compound. 1H NMR (DMSO-d6) δ 13.57 (br s, 1H), 8.04-8.01 (m, 1H), 7.67-7.47 (m, 6H), 6.876.84 (m, 1H), 5.45 (br t, 2H), 4.97 (s, 2H), 4.65 (br d, 1H). HPLC (max plot) 96.2%; Rt 2.26 min. MS (ESI+): 371.0.

Intermediate S.79: 1-(4-{[(Methylsulfonyl)amino]methyl}phenyl)-1,4-dihydrothiochromeno[4,3-c]pyrazole-3-carboxylic acid 5,5-dioxide

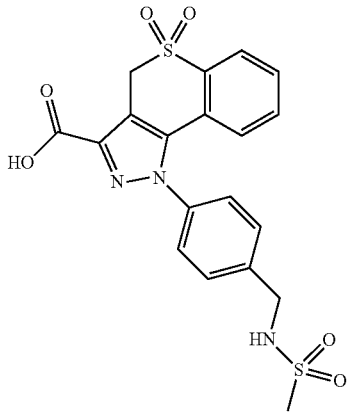 [SMILES: CS(=O)(=O)NCc1ccc(-n2nc(C(=O)O)c3c2-c2ccccc2S(=O)(=O)C3)cc1]

70 mg of the title compound. 1H NMR (400 MHz, DMSO-d6) δ = 13.5 (s, 1H), 8.03-8.01 (d, 1H), 7.65-7.61 (m, 3H), 7.56-7.51 (m, 3H), 7.08-7.05 (m, 1H), 6.87-6.85 (m, 1H), 4.97 (s, 2H), 4.51 (s, 2H), 2.59-2.58 (m, 3H). MS (ESI+): 448. HPLC (max plot) 83.6%; Rt 3.04 min.

Intermediate S.80: 1-[6-(Hydroxymethyl)pyridin-3-yl]-1,4-dihydrothiochromeno[4,3-c]pyrazole-3-carboxylic acid 5,5-dioxide

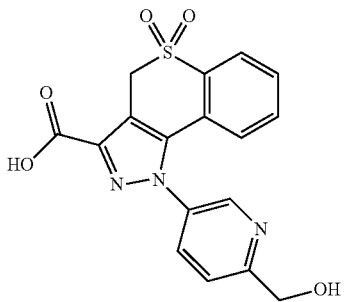 [SMILES: O=C(O)c1nn(-c2ccc(CO)nc2)c2c1CS(=O)(=O)c1ccccc1-2]

550 mg (94%) of the title compound MS (ESI+): 372.0

Intermediate S.81: 6-Fluoro-1-[4-(morpholin-4-ylmethyl)phenyl]-1,4-dihydrothiochromeno[4,3-c]pyrazole-3-carboxylic acid 5,5-dioxide

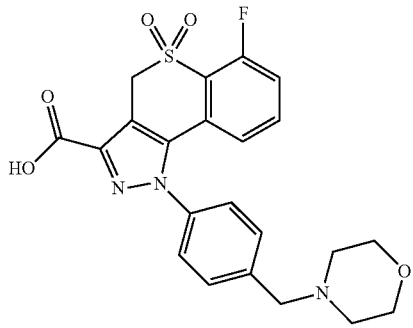 [SMILES: O=C(O)c1nn(-c2ccc(CN3CCOCC3)cc2)c2c1CS(=O)(=O)c1c(F)cccc1-2]

141 mg (100%) of the title compound. MS (ESI+): 458.3.

Intermediate S.82: 6-Bromo-1-phenyl-1,4-dihydrothiochromeno[4,3-c]pyrazole-3-carboxylic acid

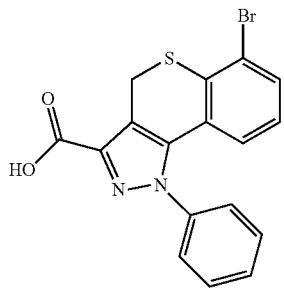 [SMILES: O=C(O)c1nn(-c2ccccc2)c2c1CSc1c(Br)cccc1-2]

1.5 g (80%) of the title compound. $^1$H NMR (DMSO-$d_6$, 400 MHz): δ 7.53-7.44 (m, 4H), 7.36-7.33 (m, 2H), 6.90-6.86 (m, 1H), 6.69-6.67 (m, 1H), 4.30 (s, 2H). MS (ESI+): (M + 2): 389.0.

Intermediate S.83: 7-Fluoro-1-[4-(morpholin-4-ylmethyl)phenyl]-1,4-dihydrothiochromeno[4,3-c]pyrazole-3-carboxylic acid 5,5-dioxide

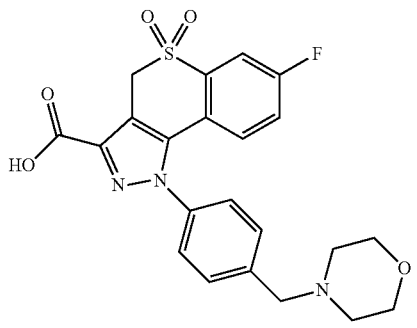

HPLC (max plot) 73.4%; Rt 2.62 min. MS (ESI+): 458.3.

Intermediate S.84: 7-Methoxy-1-[4-(morpholin-4-ylmethyl)phenyl]-1,4-dihydrothiochromeno[4,3-c]pyrazole-3-carboxylic acid 5,5-dioxide

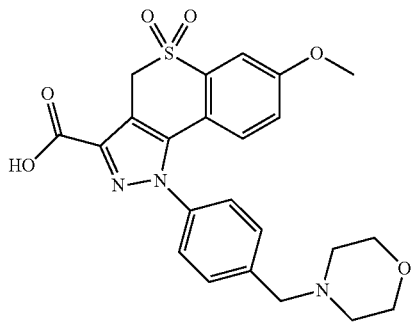 [SMILES: COc1ccc2c(c1)S(=O)(=O)Cc1c(C(=O)O)nn(-c3ccc(CN4CCOCC4)cc3)c1-2]

17 mg of the title compound as a yellow oil. HPLC (max plot) 75.7%; Rt 3.30 min. MS (ESI+): 470.29.

Intermediate S.85: 8-Fluoro-1-[4-(morpholin-4-ylmethyl)phenyl]-1,4-dihydrothiochromeno[4,3-c]pyrazole-3-carboxylic acid 5,5-dioxide

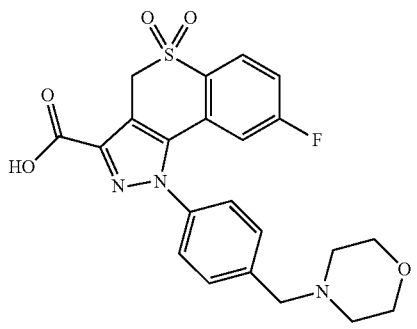 [SMILES: O=C(O)c1nn(-c2ccc(CN3CCOCC3)cc2)c2c1CS(=O)(=O)c1ccc(F)cc1-2]

300 mg (quant) of the title compound as a yellow solid. MS (ESI+): 458.2.

Intermediate S.86: 8-Bromo-1-phenyl-1,4-dihydrothiochromeno[4,3-c]pyrazole-3-carboxylic acid

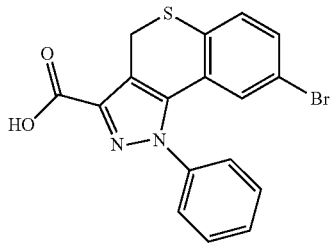 [SMILES: O=C(O)c1nn(-c2ccccc2)c2c1CSc1ccc(Br)cc1-2]

0.730 g (98%) of the title compound. 1H NMR (400 mHz, DMSO-d6): δ 13.30 (brs, 1H), 7.62-7.60 (m, 3H), 7.49-7.42 (m, 3H), 7.38-7.36 (m, 1H), 6.69-6.68 (d, 1H), 4.25 (s, 2H) MS (ESI+): 480.3. HPLC (max plot) 93.18%; Rt 4.94 min.

Intermediate S.87: 1-[1-(tert-Butoxycarbonyl)pyrrolidin-3-yl]-1,4-dihydrothiochromeno[4,3-c]pyrazole-3-carboxylic acid 5,5-dioxide

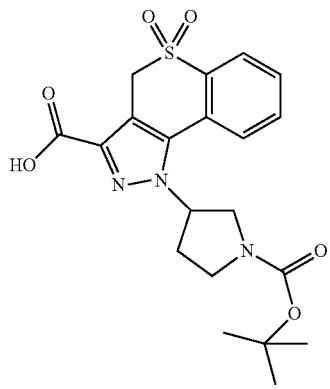 [SMILES: CC(C)(C)OC(=O)N1CCC(n2nc(C(=O)O)c3c2-c2ccccc2S(=O)(=O)C3)C1]

350 mg of the title compound. MS (ESI−): 432.0.

Intermediate S.88: 1-[1-(tert-Butoxycarbonyl)piperidin-4-yl]-1,4-dihydrothiochromeno[4,3-c]pyrazole-3-carboxylic acid 5,5-dioxide

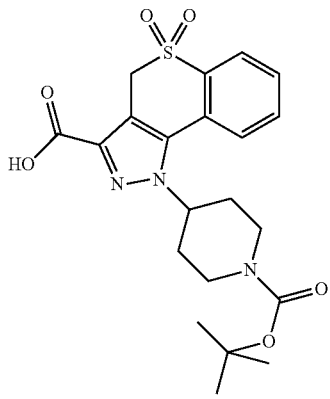 [SMILES: CC(C)(C)OC(=O)N1CCC(n2nc(C(=O)O)c3c2-c2ccccc2S(=O)(=O)C3)CC1]

2.48 g (95%) of the title compound as a yellow solid. MS (ESI−): 445.7.

Intermediate S.89: 1-Cyclopentyl-1,4-dihydrothiochromeno[4,3-c]pyrazole-3-carboxylic acid 5,5-dioxide

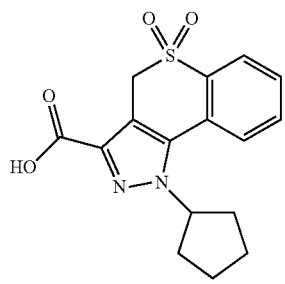 [SMILES: O=C(O)c1nn(C2CCCC2)c2c1CS(=O)(=O)c1ccccc1-2]

320 mg (77%) of the title compound. 1H NMR (400 MHz, DMSO-d6): δ 13.3 (s, 1H), 8.04-8.02 (m, 1H), 7.99-7.97 (m, 1H), 7.91-7.90 (m, 1H), 7.74-7.71 (m, 1H), 5.32-5.29 (t, J = 6.3 Hz,1H), 4.83 (s, 2H), 2.26-2.20 (m, 2H), 2.09-2.03 (m, 2H), 1.91-1.89 (m, 2H), 1.72-1.68 (m, 2H). MS (ESI+): 349. HPLC (max plot): 98.12%; Rt 3.65 min.

Intermediate S.90: 1-(4-Methylcyclohexyl)-1,4-dihydrothiochromeno[4,3-c]pyrazole-3-carboxylic acid 5,5-dioxide

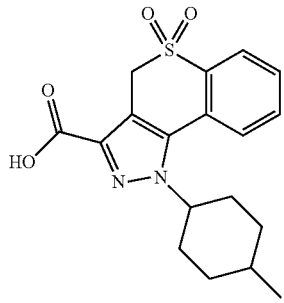 [SMILES: CC1CCC(n2nc(C(=O)O)c3c2-c2ccccc2S(=O)(=O)C3)CC1]

350 mg (97%) of the title compound. MS (ESI−): 359.0.

Intermediate S.91: 1-(4-tert-Butoxycyclohexyl)-1,4-dihydrothiochromeno[4,3-c]pyrazole-3-carboxylic acid 5,5-dioxide

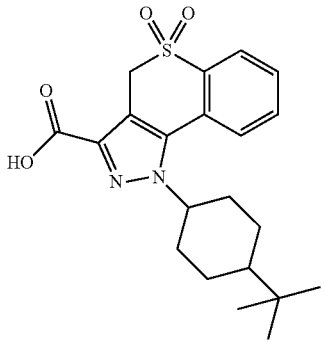 [SMILES: CC(C)(C)C1CCC(n2nc(C(=O)O)c3c2-c2ccccc2S(=O)(=O)C3)CC1]

100 mg of the title compound. MS (ESI−): 401.0.

Intermediate S.92: 1-(4,4-Difluorocyclohexyl)-1,4-dihydrothiochromeno[4,3-c]pyrazole-3-carboxylic acid 5,5-dioxide

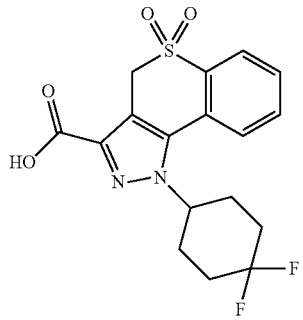 [SMILES: O=C(O)c1nn(C2CCC(F)(F)CC2)c2c1CS(=O)(=O)c1ccccc1-2]

143 mg (85%) of the title compound. $^1$H NMR (DMSO-$d_6$, 400 MHz): δ 13.49 (bs, 1H), 8.05-8.03 (d, J = 7.6 Hz, 1H), 7.93-7.89 (m, 2H), 7.76-7.72 (m, 1H), 5.04 (m, 1H), 4.86 (s, 2H), 2.31-2.18 (m, 8H). MS (ESI+): 383.2. HPLC (max plot) 92.83%; Rt 3.80 min.

Intermediate S.93: 1-(3,3-Dimethylcyclohexyl)-1,4-dihydrothiochromeno[4,3-c]pyrazole-3-carboxylic acid 5,5-dioxide

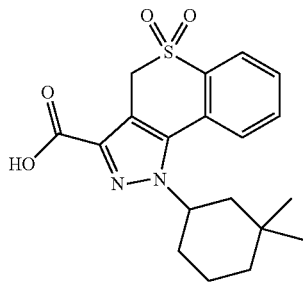 [SMILES: CC1(C)CCCC(n2nc(C(=O)O)c3c2-c2ccccc2S(=O)(=O)C3)C1]

123 mg of the title compound. $^1$H NMR (DMSO-$d_6$, 400 MHz) δ 8.06-8.01 (m, 1H), 7.92-7.88 (m, 1H), 7.85-7.79 (m, 1H), 7.76-7.68 (m, 1H), 4.85 (m, 3H), 2.00-1.89 (m, 2H), 1.82-1.69 (m, 4H), 1.41-1.32 (m, 2H), 1.30 (s, 3H), 1.28 (s, 3H). MS (ESI+): 375.2. HPLC (max plot) 88.06%; Rt 4.62 min.

Intermediate S.94: 1-(3-Carboxycyclohexyl)-1,4-dihydrothiochromeno[4,3-c]pyrazole-3-carboxylic acid 5,5-dioxide

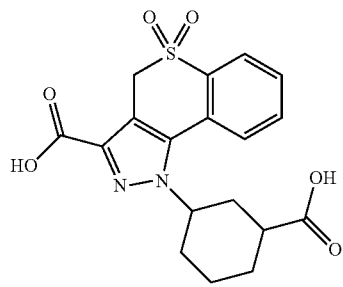 [SMILES: O=C(O)c1nn(C2CCCC(C(=O)O)C2)c2c1CS(=O)(=O)c1ccccc1-2]

90 mg of the title compound. The crude material is used as such for next step.

Intermediate S.95: 1-[3-(Piperidin-1-ylcarbonyl)cyclohexyl]-1,4-dihydrothiochromeno[4,3-c]pyrazole-3-carboxylic acid 5,5-dioxide

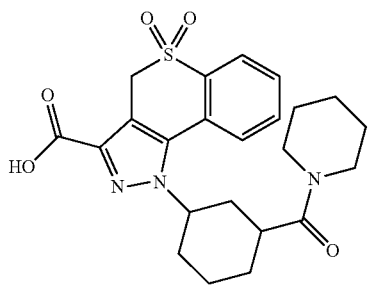

38 mg of the title compound. MS (ESI+): 458.2

Intermediate S.96: 1-[4-(Hydroxymethyl)cyclohexyl]-1,4-dihydrothiochromeno[4,3-c]pyrazole-3-carboxylic acid 5,5-dioxide

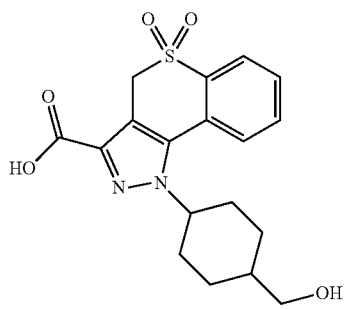 [SMILES: O=C(O)c1nn(C2CCC(CO)CC2)c2c1CS(=O)(=O)c1ccccc1-2]

250 mg (77%) of the title compound. MS (ESI+): 378.0.

Intermediate S.97: 1-(4-Hydroxycyclohexyl)-1,4-dihydrothiochromeno[4,3-c]pyrazole-3-carboxylic acid 5,5-dioxide

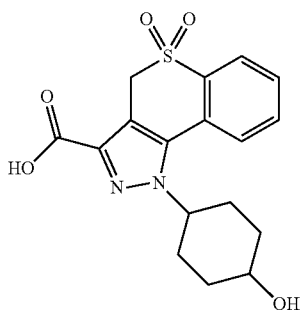 [SMILES: O=C(O)c1nn(C2CCC(O)CC2)c2c1CS(=O)(=O)c1ccccc1-2]

afford 60 mg, 72% yield of the title compound. MS (ESI+): 362.8.

Intermediate S.98: 1-(Tetrahydro-2H-pyran-3-yl)-1,4-dihydrothiochromeno[4,3-c]pyrazole-3-carboxylic acid 5,5-dioxide

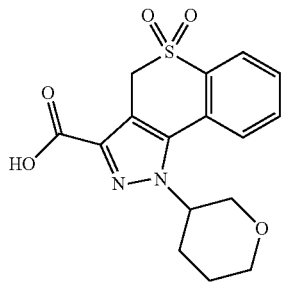

210 mg (91%) of the title compound. MS (ESI+): 349.2.

Intermediate S.99: 1-Cycloheptyl-1,4-dihydrothiochromeno[4,3-c]pyrazole-3-carboxylic acid 5,5-dioxide

150 mg, 77% yield of the title compound. $^1$H NMR (400 MHz, DMSO-$d_6$) δ = 13.31 (brs, 1H), 8.04-8.02 (m, 1H), 7.94-7.90 (m, 1H), 7.85-7.83 (d, J = 7.72 Hz, 1H), 7.75-7.71 (m, 1H), 4.97-4.90 (m, 1H), 4.82 (s, 2H), 2.09-2.08 (m, 4H), 1.84-1.81 (m, 2H), 1.63-1.58 (m, 6H). HPLC (max plot): 96.59%; Rt 4.28 min.

Intermediate S.100: 1-[1-(tert-Butoxycarbonyl)azepan-4-yl]-1,4-dihydrothiochromeno[4,3-c]pyrazole-3-carboxylic acid 5,5-dioxide

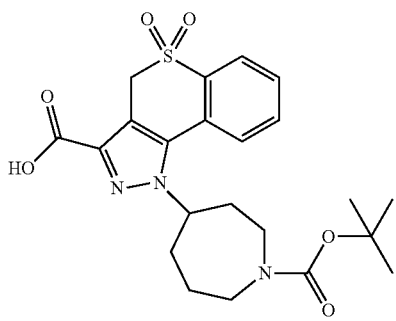 [SMILES: CC(C)(C)OC(=O)N1CCCC(n2nc(C(=O)O)c3c2-c2ccccc2S(=O)(=O)C3)CC1]

300 mg of the title compound. MS (ESI−): 460.0.

Intermediate S.101: 7-Bromo-1-cyclohexyl-1,4-dihydrothiochromeno[4,3-c]pyrazole-3-carboxylic acid 5,5-dioxide

3.9 g (92%) of the title compound. $^1$H NMR (DMSO-$d_6$, 400 MHz) δ = 8.17-8.12 (m, 2H), 7.80-7.77 (d, J = 9.2 Hz, 1H), 4.88 (s, 2H), 4.71-4.66 (m, 1H), 2.03-1.82 (m, 6H), 1.70-1.67 (m, 1H), 1.54-1.47 (m, 2H), 1.44 (m, 1H). MS (ESI−): 424.8. HPLC (max plot) 90.90%; Rt 4.60 min.

Intermediate S.102: 1-Phenyl-7-(trifluoromethyl)-1,4-dihydrothiochromeno[4,3-c]pyrazole-3-carboxylic acid 5,5-dioxide

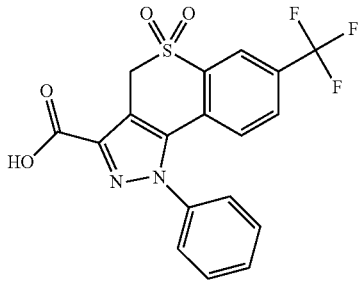

170 mg (91%) of the title compound. $^1$H NMR (DMSO-d$_6$, 400 MHz): δ 13.70 (bs, 1H), 8.21 (s, 1H), 8.05-8.03 (d, J = 8.4 Hz, 1H), 7.67-7.62 (m, 3H), 7.57-7.55 (m, 2H), 7.03-7.01 (d, J = 8.4 Hz, 1H), 5.09 (s, 2H). MS (ESI−): 406.8. HPLC (max plot) 98.57%; Rt 4.48 min.

Intermediate S.103: 1-Methyl-8-bromo-1,4-dihydrothiochromeno[4,3-c]pyrazole-3-carboxylic acid 5,5-dioxide

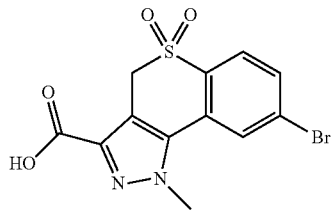 [SMILES: Cn1nc(C(=O)O)c2c1-c1cc(Br)ccc1S(=O)(=O)C2]

15 mg of the title compound. 1H NMR (400 MHz, DMSO-d6) δ = 13.3 (brs, 1H), 8.18 (s, 1H), 7.93 (s, 1H), 4.89 (s, 2H), 4.30 (s, 3H). MS (ESI+): 357.0. HPLC (max plot) 95.44%; Rt 3.08 min.

Intermediate S.104: 8-Methoxy-1-phenyl-1,4-dihydrothiochromeno[4,3-c]pyrazole-3-carboxylic acid 5,5-dioxide

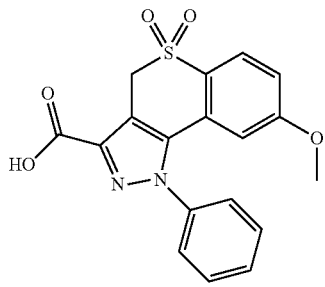 [SMILES: COc1ccc2c(c1)-c1c(c(C(=O)O)nn1-c1ccccc1)CS2(=O)=O]

440 mg of the title compound. $^1$H NMR (DMSO-d$_6$, 400 MHz): δ 13.5 (bs, 1H), 7.94-7.92 (d, J = 8.8 Hz, 1H), 7.68-7.64 (m, 3H), 7.56-7.54 (m, 2H), 7.17-7.14 (dd, J = 2.5, 8.8 Hz, 1H), 6.22-6.21 (d, J = 2.4 Hz, 1H), 4.90 (s, 2H), 3.53 (s, 3H). MS (ESI+): 371.0. HPLC (max plot) 85.84%; Rt 3.61 min.

Intermediate S.105: 1-Phenyl-1,4-dihydropyrazolo[3',4':4,5]thiopyrano[2,3-b]pyridine-3-carboxylate 5,5-dioxide

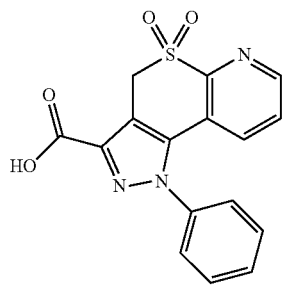 [SMILES: O=C(O)c1nn(-c2ccccc2)c2c1CS(=O)(=O)c1ncccc1-2]

170 mg (92%) of the title compound. $^1$H NMR (DMSO-d$_6$, 400 MHz): δ 13.65 (bs, 1H), 8.72-8.70 (m, 1H), 7.67-7.60 (m, 4H), 7.55-7.54 (d, J = 6.3 Hz, 2H), 7.17-7.16 (d, J = 7.1 Hz, 1H), 5.08 (s, 2H). MS (ESI+): 342.0. HPLC (max plot) 97.09%; Rt 2.63 min.

Intermediate S.106: 1-Cyclohexyl-1,4-dihydropyrazolo[3',4':4,5]thiopyrano[2,3-b]pyridine-3-carboxylate 5,5-dioxide

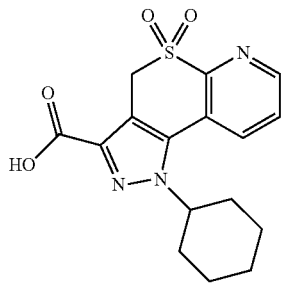

100 mg of the title compound. 1H NMR (400 MHz, DMSO-d6): δ 13.39 (bs, 1H), 8.79-8.78 (d, J = 4.5 Hz, 1H), 8.31-8.29 (d, J = 8.2 Hz, 1H), 7.93-7.92 (d, J = 4.7, 8.1 Hz, 1H), 4.95 (s, 2H), 4.68 (m, 1H), 2.04-2.01 (m, 2H), 1.95-1.81 (m, 4H), 1.70-1.67 (m, 1H), 1.52-1.49 (m, 2H), 1.3-1.20 (m, 1H). MS (ESI+): 348.2. HPLC (max plot) 97.30%; Rt 3.12 min.

Intermediate S.107: 1-[4-(Morpholin-4-ylmethyl)phenyl]-1,4-dihydropyrazolo[3',4':4,5]thiopyrano[2,3-b]pyridine-3-carboxylic acid 5,5-dioxide

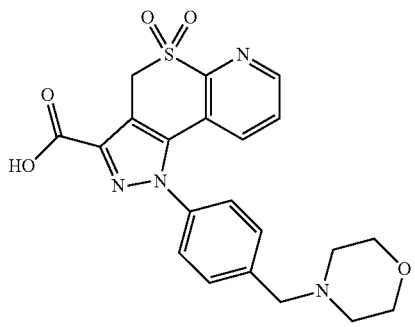 [SMILES: O=C(O)c1nn(-c2ccc(CN3CCOCC3)cc2)c2c1CS(=O)(=O)c1ncccc1-2]

90 mg (80%) of the title compound. MS (ESI+): 441.0.

Intermediate S.108: 1-Phenyl-1,4-dihydropyrazolo[3',4':4,5]thiopyrano[3,2-c]pyridine-3-carboxylic acid 5,5-dioxide

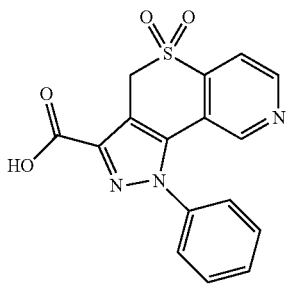 [SMILES: O=C(O)c1nn(-c2ccccc2)c2c1CS(=O)(=O)c1ccncc1-2]

50 mg (77%) of the title compound. 1H NMR (DMSO-d6, 400 MHz): δ 13.66 (bs, 1H), 8.84-8.83 (d, J = 5.1 Hz, 1H), 8.00-7.98 (m, 2H), 7.69-7.66 (m, 3H), 7.60-7.58 (m, 2H), 5.10 (s, 2H). MS (ESI+): 342.0.

Intermediate S.109: 1-Phenyl-1,4-dihydrothieno[3',2':5,6]thiopyrano[4,3-c]pyrazole-3-carboxylic acid 5,5-dioxide

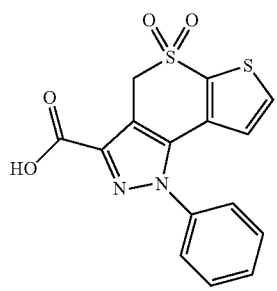 [SMILES: O=C(O)c1nn(-c2ccccc2)c2c1CS(=O)(=O)c1sccc1-2]

220 mg (82%) of the title compound. $^1$H NMR (DMSO-d$_6$, 400 MHz): δ 13.57 (bs, 1H), 8.01-8.00 (d, J = 5.1 Hz, 1H), 7.66-7.58 (m, 5H), 6.34-6.32 (d, J = 5.1 Hz, 1H), 5.05 (s, 2H). MS (ESI+): 347.0. HPLC (max plot) 97.07%; Rt 3.43 min.

Intermediate S.110: 1-(1-Methyl-6-oxo-1,6-dihydropyridin-3-yl)-1,4-dihydrothieno[3',2':5,6]thiopyrano[4,3-c]pyrazole-3-carboxylic acid 5,5-dioxide

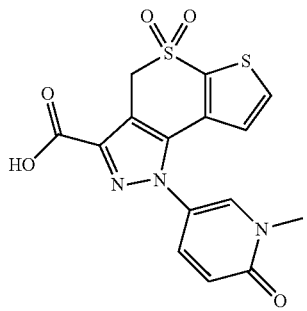 [SMILES: Cn1cc(-n2nc(C(=O)O)c3c2-c2ccsc2S(=O)(=O)C3)ccc1=O]

25 mg (89%) of the title compound. MS (ESI+): 378.0.

Intermediate S.111: 1-Cyclohexyl-1,4-dihydrothieno[3',2':5,6]thiopyrano[4,3-c]pyrazole-3-carboxylic acid 5,5-dioxide

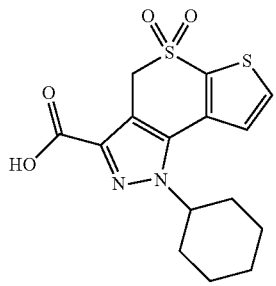 [SMILES: O=C(O)c1nn(C2CCCCC2)c2c1CS(=O)(=O)c1sccc1-2]

185 mg (99%) of the title compound. MS (ESI+): 353.0.

Intermediate S.112: 1-(Tetrahydro-2H-pyran-4-yl)-1,4-dihydrothieno[3',2':5,6]thiopyrano[4,3-c]pyrazole-3-carboxylic acid 5,5-dioxide

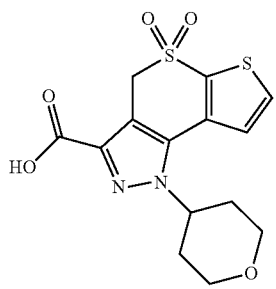 [SMILES: O=C(O)c1nn(C2CCOCC2)c2c1CS(=O)(=O)c1sccc1-2]

71 mg (85%) of the title compound as a pale yellow powder. HPLC (max plot) 98.2%; Rt 2.23 min. MS (ESI+): 354.7.

Intermediate S.113: 1-Phenyl-1,4-dihydrothieno[2',3':5,6]thiopyrano[4,3-c]pyrazole-3-carboxylic acid 5,5-dioxide

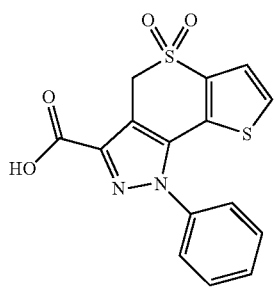 [SMILES: O=C(O)c1nn(-c2ccccc2)c2c1CS(=O)(=O)c1ccsc1-2]

150 mg of the title compound. MS (ESI−): 345.0.

Intermediate S.114: 1-Cyclohexyl-1,4-dihydrothieno[2',3':5,6]thiopyrano[4,3-c]pyrazole-3-carboxylic acid 5,5-dioxide

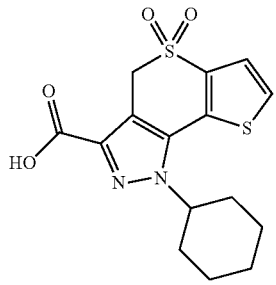 [SMILES: O=C(O)c1nn(C2CCCCC2)c2c1CS(=O)(=O)c1ccsc1-2]

80 mg of the title compound. MS (ESI−): 351.0.

Intermediate S.115: 7-(Acetylamino)-1-(tetrahydro-2H-pyran-4-yl)-1,4-dihydropyrazolo[3',4':4,5]thiopyrano[3,2-d][1,3]thiazole-3-carboxylic acid 5,5-dioxide

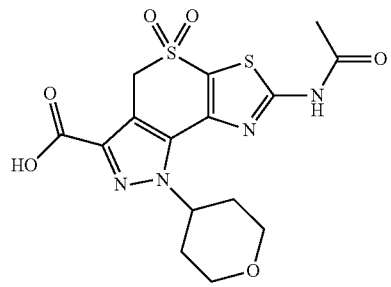 [SMILES: CC(=O)Nc1nc2c(s1)S(=O)(=O)Cc1c(C(=O)O)nn(C3CCOCC3)c1-2]

77 mg (quant) of the title compound as a pale yellow powder. HPLC (max plot) 98.2%; Rt 2.38 min. MS (ESI+): 413.1.

Intermediate S.116: 1-Phenyl-1, 4-dihydroimidazo [2, 1-b] pyrazolo [3, 4-d][1,3]thiazine-3-carboxylic acid 5,5-dioxide

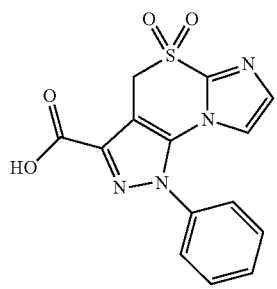 [SMILES: O=C(O)c1nn(-c2ccccc2)c2c1CS(=O)(=O)c1nccn1-2]

25 mg (77%) of the title compound. $^1$H NMR (DMSO-d6, 400 MHz): δ 13.79 (bs, 1H), 7.70-7.63 (m, 5H), 7.28 (d, J = 1.2 Hz, 1H), 6.71 (d, J = 1.2 Hz, 1H), 5.12 (s, 2H). MS (ESI+): 331.0, HPLC (max plot) 97.02%; Rt 2.61 min.

Intermediate S.117: 1-Phenyl-4H-imidazo [5, 1-c] [1, 4] benzothiazine-3-carboxylic acid

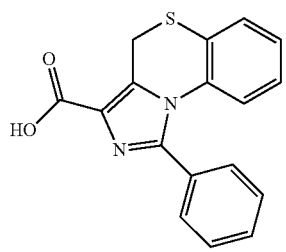 [SMILES: O=C(O)c1nc(-c2ccccc2)n2c1CSc1ccccc1-2]

30 mg of the title compound. MS (ESI+): 309.2.

Intermediate S.118

6-(Aminocarbonyl)-1-phenyl-1,4-dihydrothiochromeno[4,3-c]pyrazole-3-carboxylic acid 5,5-dioxide

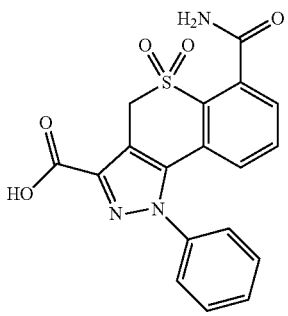 [SMILES: NC(=O)c1cccc2c1S(=O)(=O)Cc1c(C(=O)O)nn(-c3ccccc3)c1-2]

To a solution of Ethyl 6-cyano-1-phenyl-1,4-dihydrothiochromeno[4,3-c]pyrazole-3-carboxylate 5,5-dioxide (100 mg, 0.254 mmol) in EtOH (10 mL) is added an aq. solution of NaOH (10%, 1 mL) and 30% hydrogen peroxide (2 mL) at 100° C. and the heating is continued for another 2 h. The reaction mixture is evaporated under vacuum, acidified with HCl (1.5 N) and extracted with EtOAc. The organic layer is separated, dried over $Na_2SO_4$ and concentrated under reduced pressure to afford the title compound. MS (ESI+): 384.0.

Procedure T

Intermediate T.1

1-methyl-3-(morpholin-4-ylcarbonyl)-8-nitro-1,4-dihydrothiochromeno[4,3-c]pyrazole

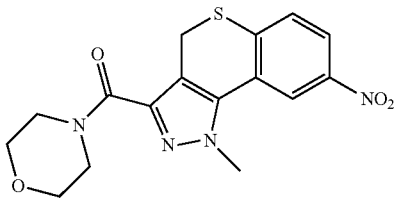 [SMILES: Cn1nc(C(=O)N2CCOCC2)c2c1-c1cc([N+](=O)[O-])ccc1SC2]

To 1-methyl-8-nitro-1,4-dihydrothiochromeno[4,3-c]pyrazole-3-carboxylic acid (0.088 g, 0.30 mmol) in THF is added triethylamine (0.13 mL, 0.9 mmol, 3 Eq) followed by 50% T3P (propane phosphonic acid anhydride) in EtOAc (0.50 mL, 0.81 mmol, 2.7 Eq). The reaction mixture is cooled to 0° C. and then morpholine (0.38 mL, 0.60 mmol, 2Eq) is added and the reaction is stirred overnight at rt. Then the solvent is removed under vacuo and the residue is diluted with EtOAc. The organic layer is washed with 10% $NaHCO_3$ followed by brine. The organic layer is dried over $MgS)_4$ and concentrated in vacuo to afford 0.084 g (77%) of the title compound as a white solid. $^1$H NMR (DMSO-$d_6$, 400 MHz) δ 8.55 (d, J=2.4 Hz, 1H), 8.10 (dd, J=8.5 Hz, J=2.4 Hz, 1H), 7.76 (d, J=8.7 Hz, 1H), 4.20 (s, 3H), 4.19 (s, 2H), 3.95 (brs, 2H), 3.63 (brs, 6H). MS (ESI+): 359.0. HPLC (max plot) 96.9%; Rt 3.78 min.

Intermediate T.2

3-(morpholin-4-ylcarbonyl)-8-nitro-1-phenyl-1,4-dihydrothiochromeno[4,3-c]pyrazole

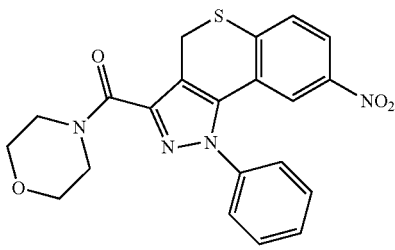 [SMILES: O=C(c1nn(-c2ccccc2)c2c1CSc1ccc([N+](=O)[O-])cc1-2)N1CCOCC1]

Following the protocol outlined in Procedure G, 3-(morpholin-4-ylcarbonyl)-8-nitro-1-phenyl-1,4-dihydrothiochromeno[4,3-c]pyrazole is obtained from 8-nitro-1-phenyl-1,4-dihydrothiochromeno[4,3-c]pyrazole-3-carboxylic acid and morpholine to afford 0.628 g (79%) of the title compound. MS (ESI+): 423.0.

Intermediates described below are obtained following procedure T.

---

Intermediate T.3: 1-[3-(Benzyloxy)phenyl]-3-(morpholin-4-ylcarbonyl)-1,4-dihydrothiochromeno[4,3-c]pyrazole 5,5-dioxide

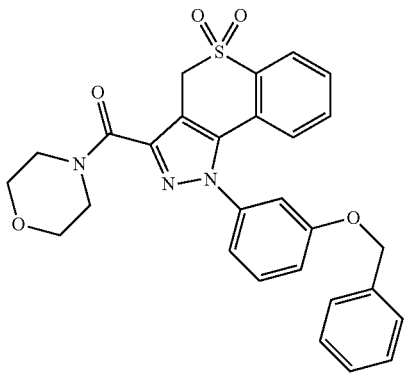 [SMILES: O=C(c1nn(-c2cccc(OCc3ccccc3)c2)c2c1CS(=O)(=O)c1ccccc1-2)N1CCOCC1]

9.2 g (88%) of the title compound as an off white solid. $^1$H NMR (DMSO-$d_6$, 400 MHz): δ 8.17-8.14 (d, J = 1.2 Hz, 1H), 7.98-7.95 (d, J = 1.2 Hz, 1H), 7.6307.601 (m, 1H), 7.56-7.56 (m, 1H), 7.53-7.51 (m, 2H), 7.49-7.42 (m, 2H), 7.39-7.32 (m, 2H), 7.29-7.22 (m, 1H), 7.04-7.02 (t, J = 8.8 Hz, 1H), 6.87-6.85 (d, J = 7.6 Hz, 1H), 5.17 (s, 2H), 4.89 (s, 2H), 3.95-3.93 (m, 2H), 3.66-3.60 (m, 4H), 3.59 (s, 2H). MS (ESI+): 516.0.

Intermediate T.4: Ethyl 1-{3-[(4-methylpiperazin-1-yl)carbonyl]phenyl}-1,4-dihydrothiochromeno[4,3-c]pyrazole-3-carboxylate 5,5-dioxide

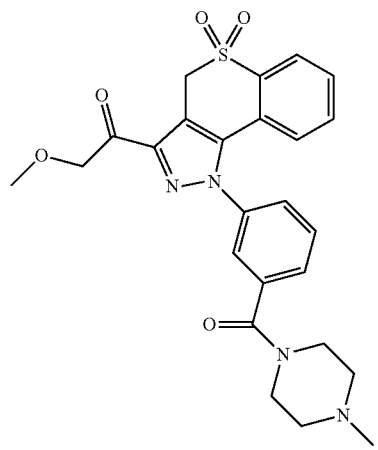

60 mg of the title compound. MS (ESI+): 495.0.

Intermediate T.5: Ethyl 1-[3-(piperidin-1-ylcarbonyl)phenyl]-1,4-dihydrothiochromeno[4,3-c]pyrazole-3-carboxylate 5,5-dioxide

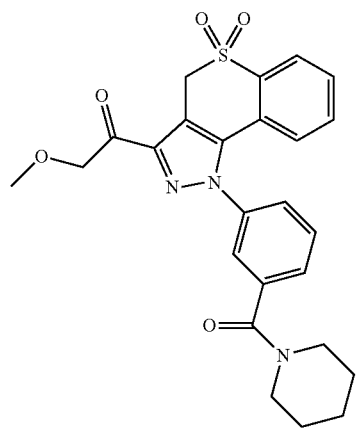 [SMILES: COCC(=O)c1nn(-c2cccc(C(=O)N3CCCCC3)c2)c2c1CS(=O)(=O)c1ccccc1-2]

310 mg (76%) of the title compound. MS (ESI+): 480.0.

Intermediate T.6: Ethyl 1-(3-{[(2-methoxyethyl)amino]carbonyl}phenyl)-1,4-dihydrothiochromeno[4,3-c]pyrazole-3-carboxylate 5,5-dioxide

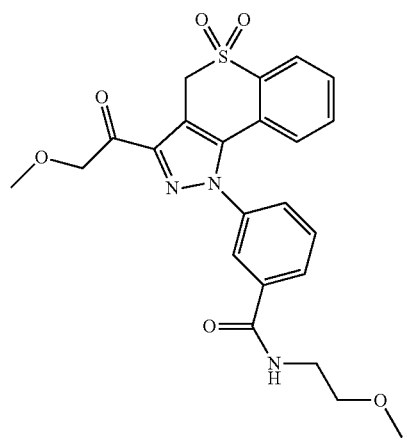

80 mg of the title compound. MS (ESI+): 470.0

Intermediate T.7: Ethyl 1-{3-[(4-methoxypiperidin-1-yl)carbonyl]phenyl}-1,4-dihydrothiochromeno[4,3-c]pyrazole-3-carboxylate 5,5-dioxide

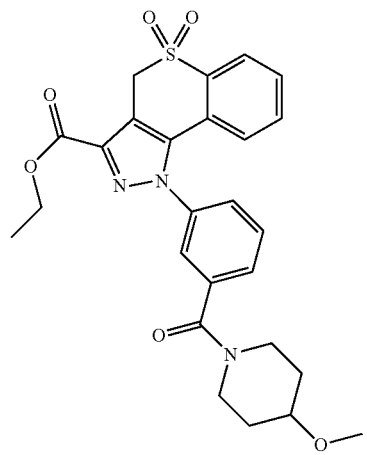 [SMILES: CCOC(=O)c1nn(-c2cccc(C(=O)N3CCC(OC)CC3)c2)c2c1CS(=O)(=O)c1ccccc1-2]

110 mg (74%) of the title compound. MS (ESI+): 510.0.

Intermediate T.8: Ethyl 1-{3-[(4-hydroxypiperidin-1-yl)carbonyl]phenyl}-1,4-dihydrothiochromeno[4,3-c]pyrazole-3-carboxylate 5,5-dioxide

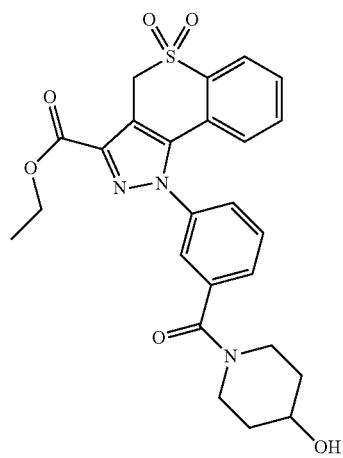 [SMILES: CCOC(=O)c1nn(-c2cccc(C(=O)N3CCC(O)CC3)c2)c2c1CS(=O)(=O)c1ccccc1-2]

115 mg (95%) of the title compound. MS (ESI+): 496.0.

Intermediate T.9: Ethyl 1-{3-[(3-hydroxypiperidin-1-yl)carbonyl]phenyl}-1,4-dihydrothiochromeno[4,3-c]pyrazole-3-carboxylate 5,5-dioxide

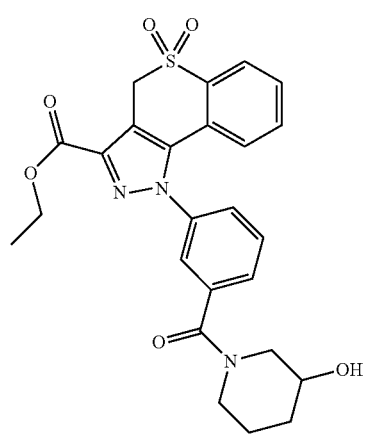 [SMILES: CCOC(=O)c1nn(-c2cccc(C(=O)N3CCCC(O)C3)c2)c2c1CS(=O)(=O)c1ccccc1-2]

80 mg of the title compound. MS (ESI+): 496.0.

Intermediate T.10: Ethyl 1-(3-{[3-(hydroxymethyl)piperidin-1-yl]carbonyl}phenyl)-1,4-dihydrothiochromeno[4,3-c]pyrazole-3-carboxylate 5,5-dioxide

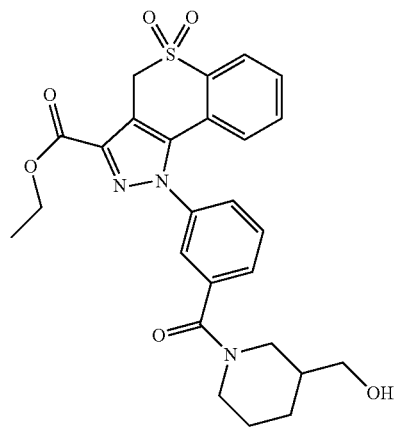 [SMILES: CCOC(=O)c1nn(-c2cccc(C(=O)N3CCCC(CO)C3)c2)c2c1CS(=O)(=O)c1ccccc1-2]

80 mg of the title compound. MS (ESI+): 510.0.

Intermediate T.11: Ethyl 1-{3-[(1,1-dioxidothiomorpholin-4-yl)carbonyl]phenyl}-1,4-dihydrothiochromeno[4,3-c]pyrazole-3-carboxylate 5,5-dioxide

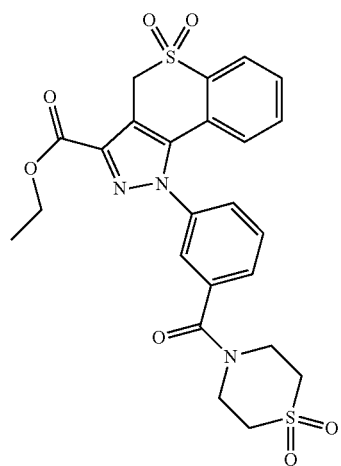 [SMILES: CCOC(=O)c1nn(-c2cccc(C(=O)N3CCS(=O)(=O)CC3)c2)c2c1CS(=O)(=O)c1ccccc1-2]

150 mg (94%) of the title compound. MS (ESI+): 530.0.

Intermediate T.12: Ethyl 1-{3-[(tetrahydro-2H-pyran-4-ylamino)carbonyl]phenyl}-1,4-dihydrothiochromeno[4,3-c]pyrazole-3-carboxylate 5,5-dioxide

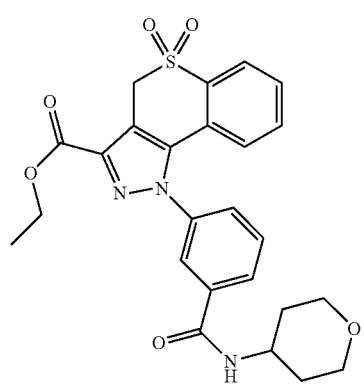 [SMILES: CCOC(=O)c1nn(-c2cccc(C(=O)NC3CCOCC3)c2)c2c1CS(=O)(=O)c1ccccc1-2]

108 mg (90%) of the title compound. MS (ESI+): 496.

Intermediate T.13: Ethyl 1-{3-[(pyridin-3-ylamino)carbonyl]phenyl}-1,4-dihydrothiochromeno[4,3-c]pyrazole-3-carboxylate 5,5-dioxide

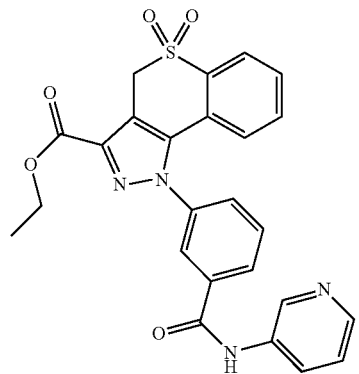 [SMILES: CCOC(=O)c1nn(-c2cccc(C(=O)Nc3cccnc3)c2)c2c1CS(=O)(=O)c1ccccc1-2]

90 mg (76%) of the title compound. MS (ESI+): 489.0.

Intermediate T.14: Ethyl 1-[4-(piperidin-1-ylcarbonyl)phenyl]-1,4-dihydrothiochromeno[4,3-c]pyrazole-3-carboxylate 5,5-dioxide

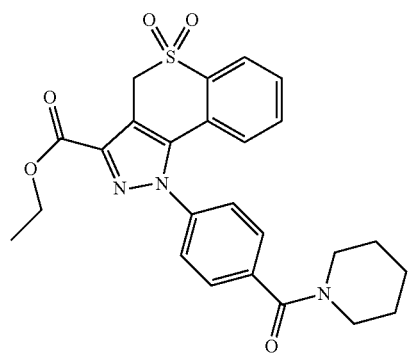 [SMILES: CCOC(=O)c1nn(-c2ccc(C(=O)N3CCCCC3)cc2)c2c1CS(=O)(=O)c1ccccc1-2]

170 mg (97%) of the title compound. MS (ESI+): 482.0.

Intermediate T.15: Ethyl 1-{3-[(3-methoxypiperidin-1-yl)carbonyl]phenyl}-1,4-dihydrothiochromeno[4,3-c]pyrazole-3-carboxylate 5,5-dioxide

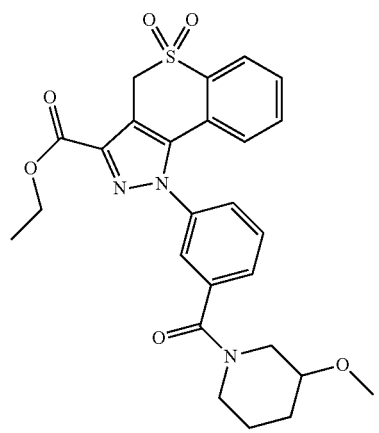 [SMILES: CCOC(=O)c1nn(-c2cccc(C(=O)N3CCCC(OC)C3)c2)c2c1CS(=O)(=O)c1ccccc1-2]

90 mg of the title compound. MS (ESI+): 510.0.

Intermediate T.16: {5-[3-(Morpholin-4-ylcarbonyl)-5,5-dioxidothiochromeno[4,3-c]pyrazol-1(4H)-yl]pyridin-2-yl}methanol

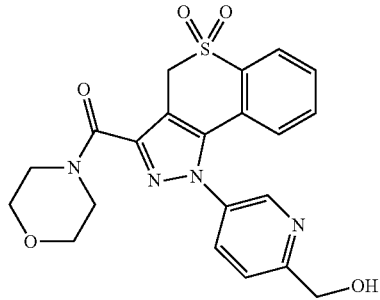 [SMILES: O=C(c1nn(-c2ccc(CO)nc2)c2c1CS(=O)(=O)c1ccccc1-2)N1CCOCC1]

230 mg of the title compound. MS (ESI+): 442.0

Intermediates described below are obtained following procedure AA, described below.

Intermediate U.1: 6-Bromo-3-(morpholin-4-ylcarbonyl)-1-phenyl-1,4-dihydrothiochromeno[4,3-c]pyrazole

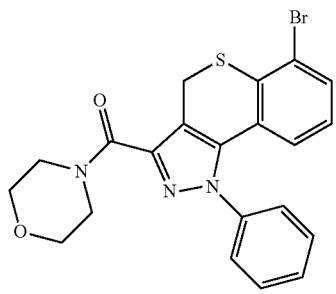 [SMILES: O=C(c1nn(-c2ccccc2)c2c1CSc1c(Br)cccc1-2)N1CCOCC1]

1.2 g yield of the title compound as an off white solid. $^1$H NMR (DMSO-d$_6$, 400 MHz): δ 7.55-7.50 (m, 4H), 7.45-7.43 (m, 2H), 6.93-6.98 (m, 1H), 6.70-6.68 (d, J = 7.9 Hz, 1H), 4.17 (s, 2H), 3.94 (m, 2H), 3.64-3.60 (m, 6H). MS (ESI+): 456.0.

Intermediate U.2: 8-Bromo-3-(morpholin-4-ylcarbonyl)-1-phenyl-1,4-dihydrothiochromeno[4,3-c]pyrazole

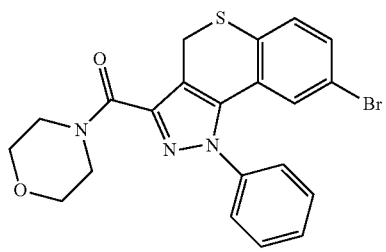 [SMILES: O=C(c1nn(-c2ccccc2)c2c1CSc1ccc(Br)cc1-2)N1CCOCC1]

0.450 g of the title compound. $^1$H NMR (400 mHz, DMSO-d6) δ = 7.61-7.59 (m, 3H), 7.49-7.43 (m, 3H), 7.38-7.36 (m, 1H), 6.70-6.70 (m, 1H), 4.13 (s, 2H), 3.93 (s, 2H), 3.64-3.59 (m, 6H). MS (ESI+): 488.0. HPLC (max plot) 97.88%; Rt 5.20 min

Intermediate U.3: tert-Butyl 3-[3-(morpholin-4-ylcarbonyl)-5,5-dioxidothiochromeno[4,3-c]pyrazol-1 (4H)-yl]pyrrolidine-1-carboxylate

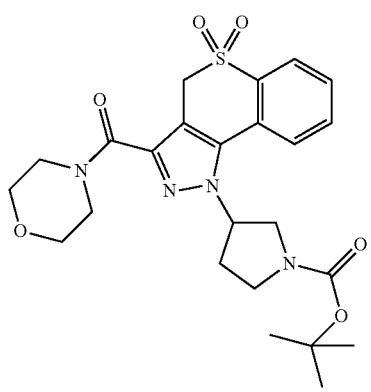 [SMILES: CC(C)(C)OC(=O)N1CCC(n2nc(C(=O)N3CCOCC3)c3c2-c2ccccc2S(=O)(=O)C3)C1]

150 mg of the title compound as a white solid. $^1$H NMR (DMSO-d$_6$, 400 MHz): δ 8.05-8.02 (m, 1H), 7.94-7.87 (m, 2H), 7.75-7.71 (m, 1H), 5.58 (m, 1H), 4.80 (s, 2H), 3.92 (m, 2H), 3.83-3.78 (m, 8H), 3.64 (m, 2H), 2.32-2.31 (m, 1H), 1.41-1.37 (m, 9H). MS (ESI + 18): 520.0. HPLC (max plot) 97.37%; Rt 4.18 min.

Intermediate U.4: Ethyl 1-[3-(piperidin-1-ylcarbonyl)cyclohexyl]-1,4-dihydrothiochromeno[4,3-c]pyrazole-3-carboxylate 5,5-dioxide

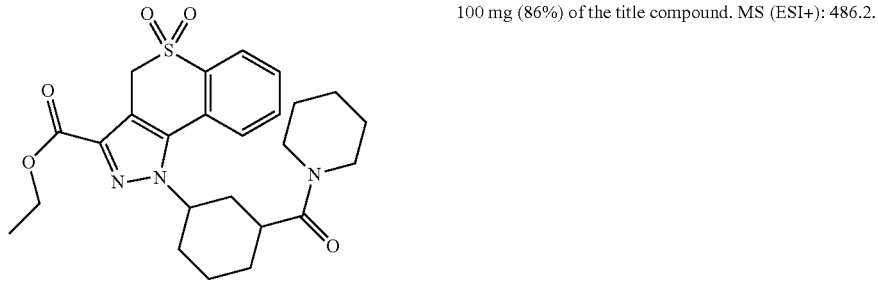

100 mg (86%) of the title compound. MS (ESI+): 486.2.

Intermediate U.5: {4-[3-(Morpholin-4-ylcarbonyl)-5,5-dioxidothiochromeno[4,3-c]pyrazol-1(4H)-yl]cyclohexyl}methanol

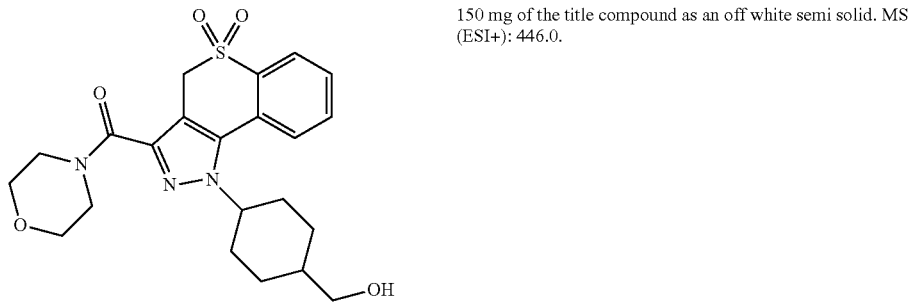

150 mg of the title compound as an off white semi solid. MS (ESI+): 446.0.

Intermediate U.6: tert-Butyl 4-[3-(morpholin-4-ylcarbonyl)-5,5-dioxidothiochromeno[4,3-c]pyrazol-1(4H)-yl]azepane-1-carboxylate

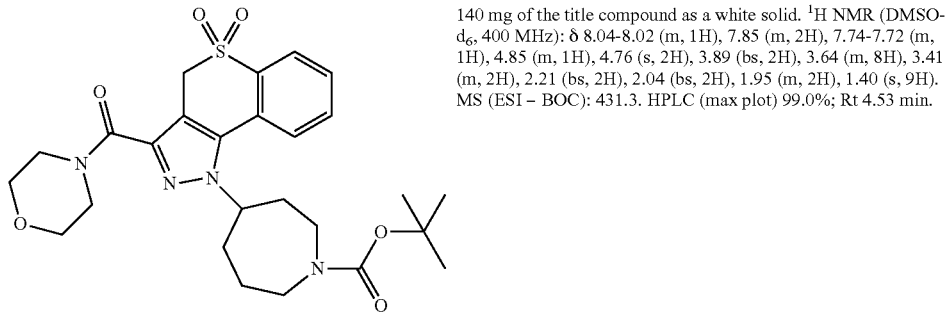

140 mg of the title compound as a white solid. $^1$H NMR (DMSO-$d_6$, 400 MHz): δ 8.04-8.02 (m, 1H), 7.85 (m, 2H), 7.74-7.72 (m, 1H), 4.85 (m, 1H), 4.76 (s, 2H), 3.89 (bs, 2H), 3.64 (m, 8H), 3.41 (m, 2H), 2.21 (bs, 2H), 2.04 (bs, 2H), 1.95 (m, 2H), 1.40 (s, 9H). MS (ESI − BOC): 431.3. HPLC (max plot) 99.0%; Rt 4.53 min.

Intermediate U.7: 8-Bromo-3-(morpholin-4-ylcarbonyl)-1-methyl-5,5-dioxidothiochromeno[4,3-c]pyrazole

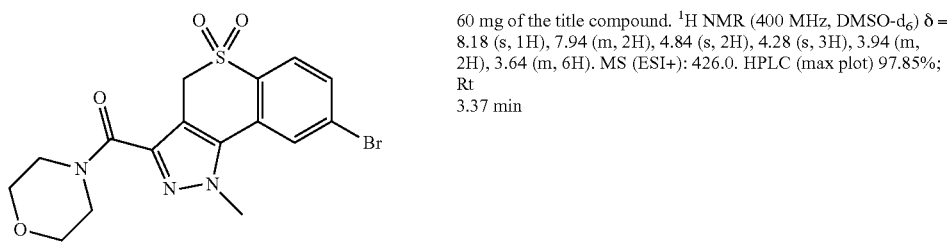

60 mg of the title compound. $^1$H NMR (400 MHz, DMSO-$d_6$) δ = 8.18 (s, 1H), 7.94 (m, 2H), 4.84 (s, 2H), 4.28 (s, 3H), 3.94 (m, 2H), 3.64 (m, 6H). MS (ESI+): 426.0. HPLC (max plot) 97.85%; Rt 3.37 min Intermediates described below are synthesised following procedure AC, described below,

---

Intermediate V.1: tert-Butyl 3-[3-(morpholin-4-ylcarbonyl)-5,5-dioxidothiochromeno[4,3-c]pyrazol-1(4H)-yl]azetidine-1-carboxylate

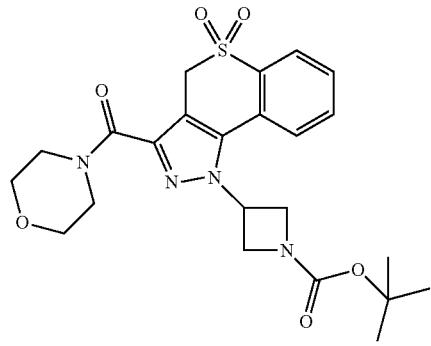 [SMILES: CC(C)(C)OC(=O)N1CC(n2nc(C(=O)N3CCOCC3)c3c2-c2ccccc2S(=O)(=O)C3)C1]

2.87 g of the title compound as a white foam. 1H NMR (DMSO-d6) δ 8.05-8.02 (m, 1H), 7.91-7.86 (m, 1H), 7.80-7.72 (m, 2H), 5.80-5.74 (m, 1H), 4.79 (s, 2H), 4.51-4.45 (m, 2H), 4.32-4.27 (m, 2H), 3.92-3.91 (m, 2H), 3.68-3.64 (m, 6H), 1.42 (s, 9H). HPLC (max plot) 98.3%; Rt 3.60 min. MS (ESI−): 486.8.

Intermediate V.2: tert-Butyl 3-[3-(morpholin-4-ylcarbonyl)-5,5-dioxidothiochromeno[4,3-c]pyrazol-1(4H)-yl]piperidine-1-carboxylate

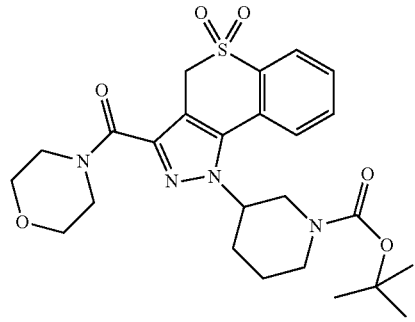 [SMILES: CC(C)(C)OC(=O)N1CCCC(n2nc(C(=O)N3CCOCC3)c3c2-c2ccccc2S(=O)(=O)C3)C1]

13.09 g (92%) of the title compound as an off white solid. MS (ESI+): 515.5. HPLC (max plot) 99.5%; Rt 4.39 min Intermediate V.3: tert-Butyl 3-[6-fluoro-3-(morpholin-4-ylcarbonyl)-5,5-dioxidothiochromeno[4,3-c]pyrazol-1(4H)-yl]pyrrolidine-1-carboxylate

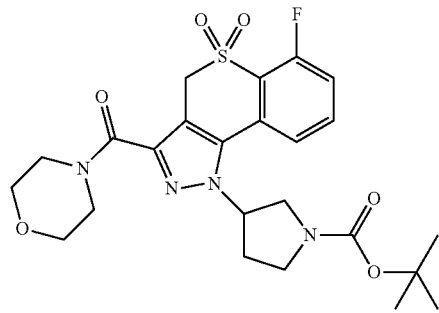 [SMILES: CC(C)(C)OC(=O)N1CCC(n2nc(C(=O)N3CCOCC3)c3c2-c2cccc(F)c2S(=O)(=O)C3)C1]

2.8 g of the title compound as a white solid. $^1$H NMR (DMSO-d$_6$) δ 7.96-7.94 (m, 1H), 7.75 (d, J = 7 Hz, 1H), 7.60 (t, J = 7 Hz, 1H), 5.55-5.45 (m, 1H), 4.94 (s, 2H), 4.05-3.40 (m, 12H), 2.50-2.40 (m, 2H), 1.45-1.40 (m, 9H). HPLC (max plot) 91.0%; Rt 4.10 min. MS (ESI+): 519.3.

Intermediate V.4: tert-Butyl 3-[6-fluoro-3-(morpholin-4-ylcarbonyl)-5,5-dioxidothiochromeno[4,3-c]pyrazol-1(4H)-yl]piperidine-1-carboxylate

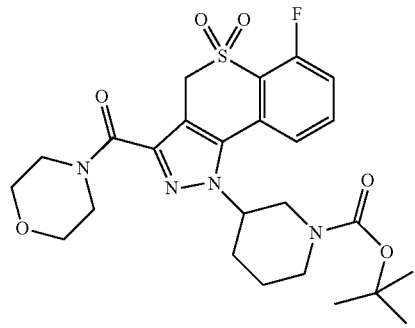 [SMILES: CC(C)(C)OC(=O)N1CCCC(n2nc(C(=O)N3CCOCC3)c3c2-c2cccc(F)c2S(=O)(=O)C3)C1]

3 g (87%) of the title compound as a beige solid. HPLC (max plot) 99.2%; Rt 4.21 min. MS (ESI−): 533.34.

Intermediate V.5: tert-Butyl 3-[6-methoxy-3-(morpholin-4-ylcarbonyl)-5,5-dioxidothiochromeno[4,3-c]pyrazol-1(4H)-yl]piperidine-1-carboxylate

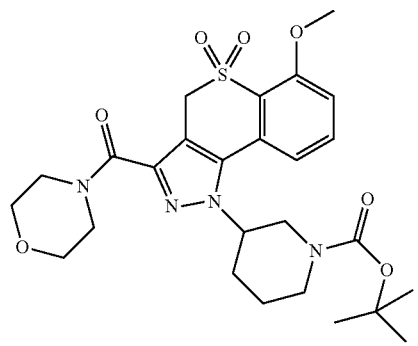 [SMILES: COc1cccc2c1S(=O)(=O)Cc1c(C(=O)N3CCOCC3)nn(C3CCCN(C(=O)OC(C)(C)C)C3)c1-2]

2.38 g of the title compound as a beige solid. HPLC (max plot) 93.7%; Rt 4.77 min.. MS (ESI−): 545.6

Intermediate V.6: tert-Butyl 3-[6-chloro-3-(morpholin-4-ylcarbonyl)-5,5-dioxidothiochromeno[4,3-c]pyrazol-1(4H)-yl]piperidine-1-carboxamide

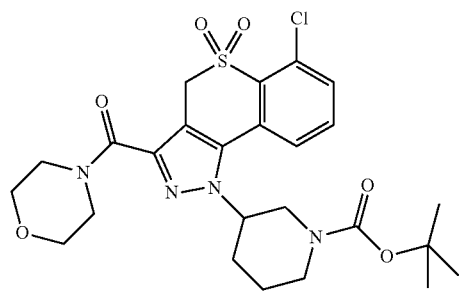 [SMILES: CC(C)(C)OC(=O)N1CCCC(n2nc(C(=O)N3CCOCC3)c3c2-c2cccc(Cl)c2S(=O)(=O)C3)C1]

5.5 g (85%) of the title compound. HPLC (max plot) 91.7%; Rt 4.01 min.

Intermediate V.7: tert-Butyl 3-[6-methyl-3-(morpholin-4-ylcarbonyl)-5,5-dioxidothiochromeno[4,3-c]pyrazol-1(4H)-yl]piperidine-1-carboxylate

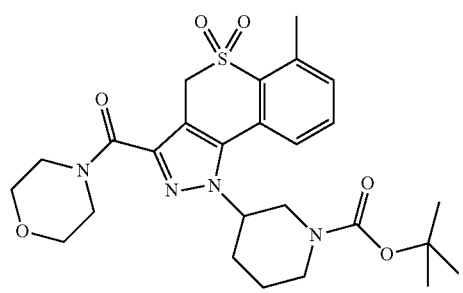 [SMILES: Cc1cccc2c1S(=O)(=O)Cc1c(C(=O)N3CCOCC3)nn(C3CCCN(C(=O)OC(C)(C)C)C3)c1-2]

MS (ESI−): 588.4.

Intermediate V.8: tert-Butyl 3-[7-fluoro-3-(morpholin-4-ylcarbonyl)-5,5-dioxidothiochromeno[4,3-c]pyrazol-1(4H)-yl]piperidine-1-carboxylate

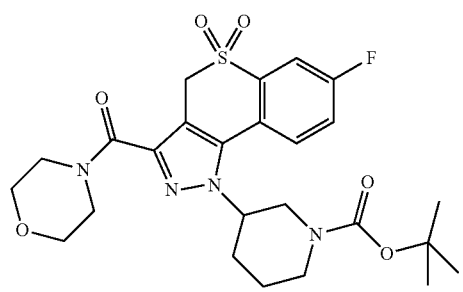 [SMILES: CC(C)(C)OC(=O)N1CCCC(n2nc(C(=O)N3CCOCC3)c3c2-c2ccc(F)cc2S(=O)(=O)C3)C1]

MS (ESI−): 533.5

Intermediate V.9: tert-Butyl 3-[7-methoxy-3-(morpholin-4-ylcarbonyl)-5,5-dioxidothiochromeno[4,3-c]pyrazol-1(4H)-yl]piperidine-1-carboxylate

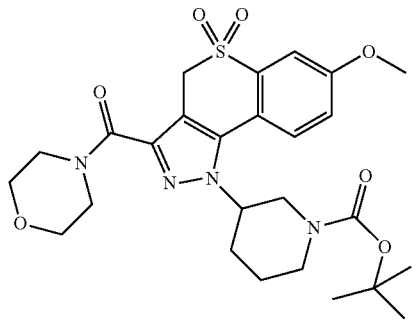 [SMILES: COc1ccc2c(c1)S(=O)(=O)Cc1c(C(=O)N3CCOCC3)nn(C3CCCN(C(=O)OC(C)(C)C)C3)c1-2]

5.56 mg (92%) of the title compound as a light yellow powder. MS (ESI−): 547.7. HPLC (max plot) 100.0%; Rt 4.59 min.

Intermediate V.10: tert-Butyl 3-[7-trifluoromethoxy-3-(morpholin-4-ylcarbonyl)-5,5-dioxidothiochromeno[4,3-c]pyrazol-1(4H)-yl]piperidine-1-carboxylate

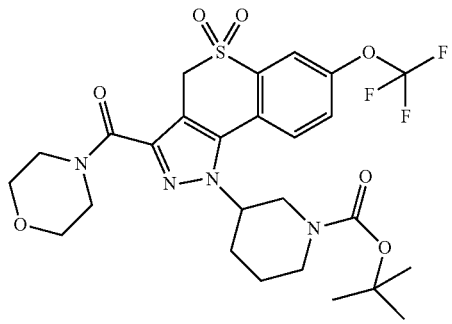 [SMILES: CC(C)(C)OC(=O)N1CCCC(n2nc(C(=O)N3CCOCC3)c3c2-c2ccc(OC(F)(F)F)cc2S(=O)(=O)C3)C1]

700 mg (82%) of the title compound as a white solid. $^1$H NMR (DMSO) δ 8.22-8.05 (m, 1H), 7.97 (brs, 1H), 7.95-7.81 (m, 1H), 4.91 (s, 2H), 4.89-4.67 (m, 1H), 4.31-4.07 (m, 1H), 3.97-3.80 (m, 3H), 3.80-3.56 (m, 5H), 3.29-3.12 (m, 1H), 3.04-2.76 (m, 1H), 2.33-2.08 (m, 2H), 1.95-1.76 (m, 1H), 1.76-1.54 (m, 1H), 1.53-1.20 (m, 10H). HPLC (max plot) 96.3%; Rt 4.74 min. MS (ESI−): 599.3

Intermediate V.11: tert-Butyl 3-[8-methoxy-3-(morpholin-4-ylcarbonyl)-5,5-dioxidothiochromeno[4,3-c]pyrazol-1(4H)-yl]piperidine-1-carboxylate

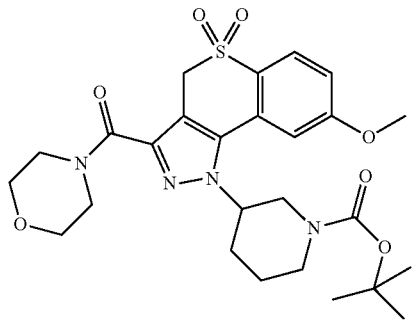 [SMILES: COc1ccc2c(c1)-c1c(c(C(=O)N3CCOCC3)nn1C1CCCN(C(=O)OC(C)(C)C)C1)CS2(=O)=O]

1.22 g of the title compound as an oil. MS (ESI + H$_2$O): 546.3.

Intermediate V.12: 3-(Morpholin-4-ylcarbonyl)-1-phenyl-4H-imidazo[5,1-c][1,4]benzothiazine

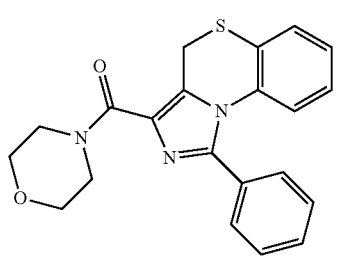 [SMILES: O=C(c1nc(-c2ccccc2)n2c1CSc1ccccc1-2)N1CCOCC1]

22 mg of the title compound. $^1$H NMR (DMSO-d6, 400 MHz): δ 7.64-7.62 (d, J = 7.8 Hz, 1H), 7.47-7.42 (m, 3H), 7.39-7.37 (m, 2H), 7.24 (t, J = 7.7 Hz, 1H), 7.08 (t, J = 7.6 Hz, 1H), 6.86-6.84 (d, J = 8.2 Hz, 1H), 4.30 (s, 2H), 4.16 (m, 2H), 3.60 (m, 6H). MS (ESI+): 378.2.

Procedure W

Intermediate W.1

4-[3-(Morpholin-4-ylcarbonyl)-5,5-dioxidothiochromeno[4,3-c]pyrazol-1(4H)-yl]benzyl methanesulfonate

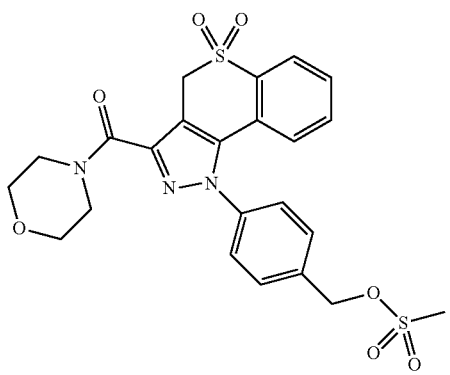 [SMILES: CS(=O)(=O)OCc1ccc(-n2nc(C(=O)N3CCOCC3)c3c2-c2ccccc2S(=O)(=O)C3)cc1]

To a solution of {4-[3-(morpholin-4-ylcarbonyl)-5,5-dioxidothiochromeno[4,3-c]pyrazol-1(4H)-yl]phenyl}methanol (300 mg; 0.68 mmol; 1 eq.) in DCM (15 mL) is added trietylamine (190.28 µl; 1.37 mmol; 2 eq.) and methanesulfonyl chloride (105.67 µl; 1.37 mmol; 2 eq.) at 0° C. under nitrogen. The reaction mixture is stirred at rt for 1 h. The reaction is stopped by addition of water and the product is extracted with DCM. The organic layers are dried over MgSO4 and the solvent evaporated to afford 400 mg (quant) of the title compound as a beige oil. It is used in the next steps without further purification. MS (ESI+): 518.0.

Intermediate W.2

3-[3-(Morpholin-4-ylcarbonyl)-5,5-dioxidothiochromeno[4,3-c]pyrazol-1(4H)-yl]benzyl methanesulfonate

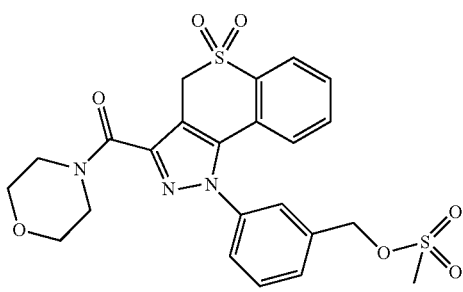 [SMILES: CS(=O)(=O)OCc1cccc(-n2nc(C(=O)N3CCOCC3)c3c2-c2ccccc2S(=O)(=O)C3)c1]

Following the protocol outlined in procedure W (New: mesylate formation), 3-[3-(morpholin-4-ylcarbonyl)-5,5-dioxidothiochromeno[4,3-c]pyrazol-1(4H)-yl]benzyl methanesulfonate is obtained from {4-[3-(morpholin-4-ylcarbonyl)-5,5-dioxidothiochromeno[4,3-c]pyrazol-1(4H)-yl]phenyl}methanol to afford 1.85 g (quant) of the title compound. HPLC (max plot) 62.6%; Rt 3.69 min. HPLC (max plot) 78.4%; Rt 3.66 min. MS (ESI+): 517.9.

Compounds described below are obtained following protocol outlined in procedure AM, described below.

---

Intermediate X.3: 1-Azetidin-3-yl-3-(morpholin-4-ylcarbonyl)-1,4-dihydrothiochromeno[4,3-c]pyrazole 5,5-dioxide (hydrochloride)

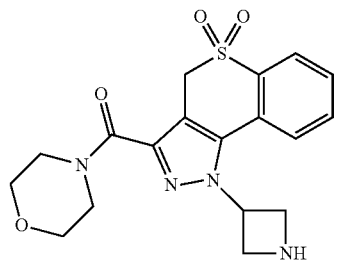 [SMILES: O=C(c1nn(C2CNC2)c2c1CS(=O)(=O)c1ccccc1-2)N1CCOCC1]

1.16 g of the title compound as a white powder. 1H NMR (DMSO-d6) δ 9.35 (s, 1H), 8.07-8.04 (m, 1H), 7.94-7.88 (m, 1H), 7.82-7.74 (m, 2H), 5.95-5.85 (quint, J = 7.25 Hz, 1H), 4.82 (s, 2H), 4.61-4.45 (m, 4H), 3.96-3.93 (m, 2H), 3.69 (s, 6H). HPLC (max plot) 100.0%; Rt 1.57 min. MS (ESI+): 388.8.

Intermediate X.4: 3-(Morpholin-4-ylcarbonyl)-1-pyrrolidin-3-yl-1,4-dihydrothiochromeno[4,3-c]pyrazole 5,5-dioxide (hyrochloride)

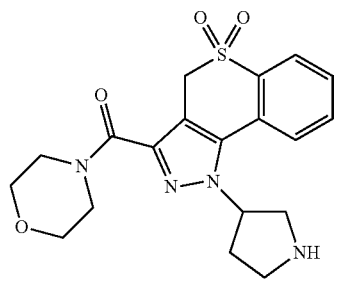

3.06 g (91%) of the title compound as a white powder. HPLC (max plot) 73.6%; Rt 1.66 min. MS (ESI+): 403.2.

Intermediate X.5: 3-(Morpholin-4-ylcarbonyl)-1-piperidin-4-yl-1,4-dihydrothiochromeno[4,3-c]pyrazole 5,5-dioxide (hydrochloride)

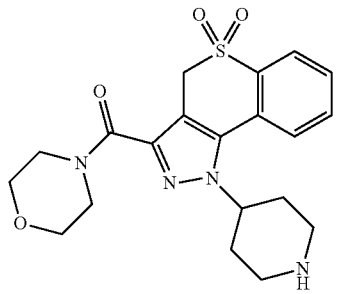 [SMILES: O=C(c1nn(C2CCNCC2)c2c1CS(=O)(=O)c1ccccc1-2)N1CCOCC1]

610 mg (99%) of the title compound as a white powder. HPLC (max plot) 70.9%; Rt 1.71 min. MS (ESI+): 417.15.

Intermediate X.6: 3-(Morpholin-4-ylcarbonyl)-1-piperidin-3-yl-1,4-dihydrothiochromeno[4,3-c]pyrazole 5,5-dioxide

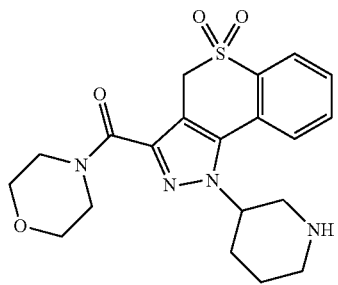

10.4 g (92%) of the title compound as a colourless foam.
$^1$H NMR (DMSO-d$_6$, 300 MHz): δ 8.10-7.98 (m, 1H), 7.97-7.85 (m, 2H), 7.80-7.70 (m, 1H), 4.88-4.55 (m, 3H), 3.99-3.84 (m, 2H), 3.66 (bs, 6H), 3.18 (d, J = 10.7, 1H), 3.00-2.77 (m, 2H), 2.66-2.35 (m, 2H), 2.27-1.99 (m, 2H), 1.84-1.48 (m, 2H). MS (ESI+): 417.3. HPLC (max plot) 100.0%; Rt 2.21 min Intermediate X.7: 6-Fluoro-3-(morpholin-4-ylcarbonyl)-1-pyrrolidin-3-yl-1,4-dihydrothiochromeno[4,3-c]pyrazole 5,5-dioxide

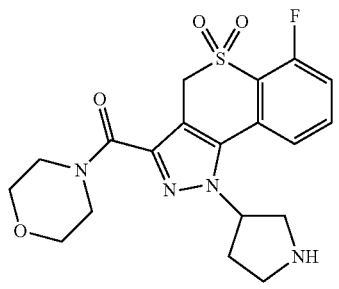 [SMILES: O=C(c1nn(C2CCNC2)c2c1CS(=O)(=O)c1c(F)cccc1-2)N1CCOCC1]

3 g (74%) of the title compound as a brown oil. It is used in the next step without further purification. MS (ESI+): 420.8

Intermediate X.8: 6-Fluoro-3-(morpholin-4-ylcarbonyl)-1-piperidin-3-yl-1,4-dihydrothiochromeno[4,3-c]pyrazole 5,5-dioxide (hydrochloride)

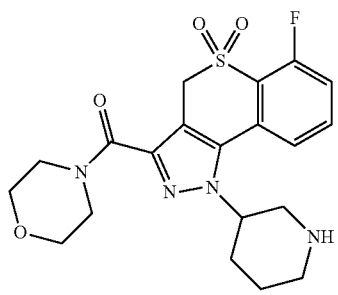 [SMILES: O=C(c1nn(C2CCCNC2)c2c1CS(=O)(=O)c1c(F)cccc1-2)N1CCOCC1]

2.1 g (79%) of the title compound. MS (ESI+): 434.8.

Intermediate X.9: 6-Chloro-3-(morpholin-4-ylcarbonyl)-1-piperidin-3-yl-1,4-dihydrothiochromeno[4,3-c]pyrazole 5,5-dioxide

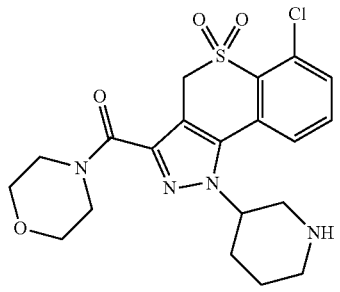

4.2 g (quant) of the title compound as a beige foam. HPLC (max plot) 93.8%; Rt 1.88 min. MS (ESI+): 450.9.

Intermediate X.10: 6-Methyl-3-(morpholin-4-ylcarbonyl)-1-piperidin-3-yl-1,4-dihydrothiochromeno[4,3-c]pyrazole 5,5-dioxide

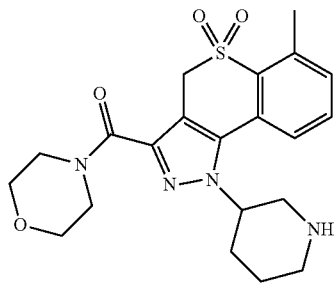 [SMILES: Cc1cccc2c1S(=O)(=O)Cc1c(C(=O)N3CCOCC3)nn(C3CCCNC3)c1-2]

900 mg (quant) of the title compound. HPLC (max plot) 93.8%; Rt 2.49 min. MS (ESI+): 431.5.

Intermediate X.11: Enantiomer B of 1-[(1,3'-bipiperidin-3-yl]-3-(morpholin-4-ylcarbonyl)-1,4-dihydrothiochromeno[4,3-c]pyrazole 5,5-dioxide

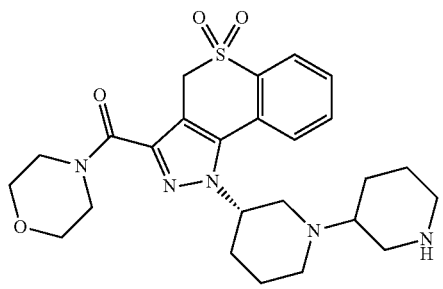 [SMILES: O=C(c1nn([C@H]2CCCN(C3CCCNC3)C2)c2c1CS(=O)(=O)c1ccccc1-2)N1CCOCC1]

Obtained from enantiomer B of tert-butyl (3-[3-(morpholin-4-ylcarbonyl)-5,5-dioxidothiochromeno[4,3-c]pyrazol-1(4H)-yl]-1,3'-bipiperidine-1'-carboxylate to give 85 mg of the title compound. $^1$H NMR (DMSO-$d_6$, 300 MHz): 8.79 (bs, 1H), 8.40 (bs, 1H), 8.09-8.06 (d, J = 9 Hz, 1H), 7.96-7.82 (m, 2H), 7.79-7.74 (t, J = 9 Hz, 1H), 4.86-4.74 (m, 3H), 3.86-2.73 (m, 18H), 2.20-1.58 (m, 8H). MS (ESI+): 500.2. HPLC (max plot) 100.0%; Rt 1.57 min Procedure Y Intermediate Y.1

4-Hydrazinopiperidine (hydrochloride)

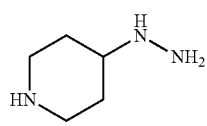

To tert-butyl 4[2-(tert-butoxycarbonl)hydrazine]piperidine-1-carboxylate (15 g; 47.56 mmol; 1 eq.) in DCM (100 ml) is added a solution of hydrogen chloride in 1,4-dioxane (30 ml; 4 M; 120 mmol; 2.52 eq.). The reaction mixture is stirred 2h at rt then concentrated under reduced pressure. The solid obtained is dried under vacuum to afford 9.1 g (100%) of the title compound as a white powder. 1H NMR (300 MHz, DMSO) δ 9.26-9.06 (m, 2H), 7.95 (bs, 5H), 3.39-3.05 (m, 3H), 3.02-2.69 (m, 2H), 2.21-1.95 (m, 2H ), 1.84-1.61 (m, 2H).

Compounds described below are obtained following protocol outlined in procedure Y Intermediate Y.2: 3-Hydrazinoazetidine bis hydrochloride

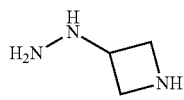

18.5 g (83%) of the title compound as an off white solid. $^{1}$H NMR (DMSO-d6 400 MHz): δ 9.48 (bs, 2H), 9.41 (bs, 2H), 9.23 (bs, 2H), 4.09-4.04 (m, 1H), 4.02-3.99 (m, 2H), 3.91-3.85 (m, 2H). HPLC (max plot): 99.61%; Rt 1.27 min.

Intermediate Y.3: 3-Hydrazinopiperidine bis-hydrochloride

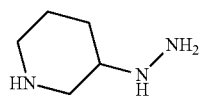

500 mg (96%) of the title compound. $^{1}$H NMR (DMSO-d$_{6}$, 300 MHz): 9.64-9.03 (m, 2H), 5.56 (m, 3H), 3.56-2.84 (m, 4H), 1.95-1.40 (m, 4H)

Intermediate Y.4: 3-Hydrazinopyrrolidine bis-hydrochloride

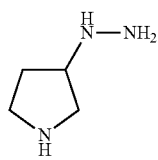

500 mg (96%) of the title compound. $^{1}$H NMR (DMSO-d$_{6}$, 400 MHz): δ 9.32 (bs, 3H), 3.81 (m, 1H), 3.32-3.14 (m, 5H), 2.03-2.01 (m, 2H).

Intermediate Y.5: 4-Hydrazinoazepane bis-hydrochloride

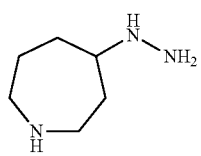

600 mg (97%) of the title compound. $^{1}$H NMR (DMSO-d$_{6}$, 400 MHz): δ 9.32 (bs, 3H), 3.81 (m, 1H), 3.32-3.14 (m, 5H), 2.03-2.01 (m, 2H).

Intermediate Y.6: Ethyl 1-(3-aminophenyl)-1,4-dihydrothiochromeno[4,3-c]pyrazole-3-carboxylate 5,5-dioxide hydrochloride

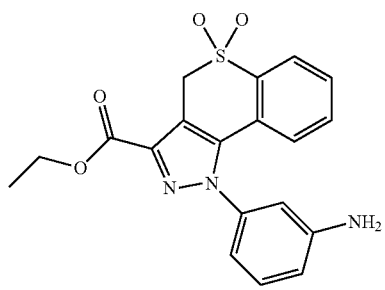 [SMILES: CCOC(=O)c1nn(-c2cccc(N)c2)c2c1CS(O)(O)c1ccccc1-2]

100 mg (99%) of the title compound. MS (ESI − HCl) 384.2.

Intermediate Y.7: Enantiomer A of 3-(morpholin-4-ylcarbonyl)-1-[pyrrolidin-3-yl]-1,4-dihydrothiochromeno[4,3-c]pyrazole 5,5-dioxide

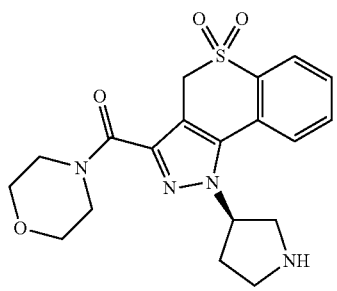 [SMILES: O=C(c1nn([C@@H]2CCNC2)c2c1CS(=O)(=O)c1ccccc1-2)N1CCOCC1]

Obtained from Enantiomer A of tert-butyl 3-[3-(morpholin-4-ylcarbonyl)-5,5-dioxidothiochromeno[4,3-c]pyrazol-1(4H)-yl]pyrrolidine-1-carboxylate to give 760 mg (100%) of the title compound as a white powder. $^{1}$H NMR (DMSO-d$_{6}$, 300 MHz): δ 9.62 (s, 4H), 8.14-8.02 (m, 2H), 8.00-7.85 (m, 4H), 7.83-7.70 (m, 2H), 5.78 (dd, J = 6.8, 3.5, 2H), 4.80 (s, 4H), 3.97-3.74 (m, 6H), 3.68 (d, J = 9.5, 13H), 3.53-3.38 (m, 4H), 2.57 (dd, J = 13.9, 7.2, 2H), 2.41 (m, 2H). HPLC (max plot) 73.7%; Rt 1.82 min.

Intermediate Y.8: Enantiomer B of 3-(morpholin-4-ylcarbonyl)-1-[pyrrolidin-3-yl]-1,4-dihydrothiochromeno[4,3-c]pyrazole 5,5-dioxide

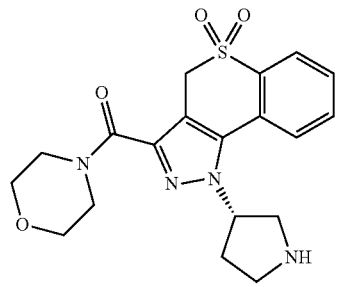

Obtained from Enantiomer B of tert-butyl 3-[3-(morpholin-4-ylcarbonyl)-5,5-dioxidothiochromeno[4,3-c]pyrazol-1(4H)-yl]pyrrolidine-1-carboxylate to give 500 mg (85%) of the title compound as a pink powder. $^1$H NMR (DMSO-d$_6$, 300 MHz): δ 9.56 (s, 4H), 8.12-8.02 (m, 2H), 7.93 (qd, J = 8.0, 4.0, 4H), 7.84-7.69 (m, 2H), 5.87-5.67 (m, 2H), 4.79 (s, 4H), 3.95-3.74 (m, 6H), 3.74-3.59 (m, 13H), 3.53-3.41 (m, 4H), 2.68-2.52 (m, 2H), 2.41 (m, 2H). HPLC (max plot) 50.3%; Rt 1.68 min.

Intermediate Y.9: Enantiomer A of 1-azepan-4-yl-3-(morpholin-4-ylcarbonyl)-1,4-dihydrothiochromeno[4,3-c]pyrazole 5,5-dioxide

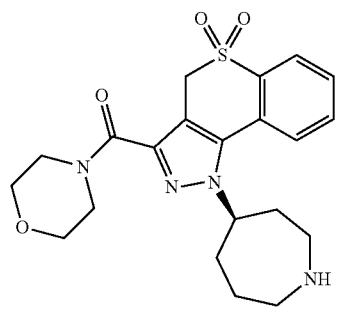 [SMILES: O=C(c1nn([C@@H]2CCCNCC2)c2c1CS(=O)(=O)c1ccccc1-2)N1CCOCC1]

Obtained from Enantiomer A of tert-butyl 4-[3-(morpholin-4-ylcarbonyl)-5,5-dioxidothiochromeno[4,3-c]pyrazol-1(4H)-yl]azepane-1-carboxylate to give 245 mg (92%) of the title compound as a white solid. MS (ESI+): 431.3. HPLC (max plot) 77.5%; Rt 2.23 min Intermediate Y.10: Enantiomer B of 1-azepan-4-yl-3-(morpholin-4-ylcarbonyl)-1,4-dihydrothiochromeno[4,3-c]pyrazole 5,5-dioxide

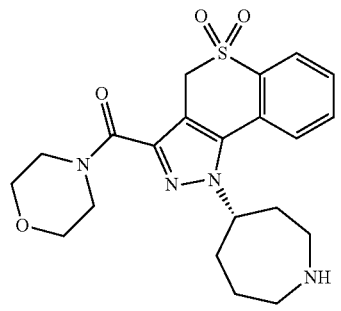 [SMILES: O=C(c1nn([C@H]2CCCNCC2)c2c1CS(=O)(=O)c1ccccc1-2)N1CCOCC1]

Obtained from Enantiomer B of tert-butyl 4-[3-(morpholin-4-ylcarbonyl)-5,5-dioxidothiochromeno[4,3-c]pyrazol-1(4H)-yl]azepane-1-carboxylate to give 498 mg (94%) of the title compound as a white solid. MS (ESI+): 431.3. HPLC (max plot) 96.3%; Rt 2.22 min Intermediate Y.11: Enantiomer A of 6-fluoro-3-(morpholin-4-ylcarbonyl)-1-[pyrrolidin-3-yl]-1,4-dihydrothiochromeno[4,3-c]pyrazole 5,5-dioxide hydrochloride

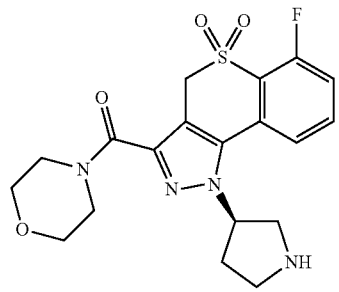 [SMILES: O=C(c1nn([C@@H]2CCNC2)c2c1CS(=O)(=O)c1c(F)cccc1-2)N1CCOCC1]

Obtained from Enantiomer A of tert-butyl 3-[6-fluoro-3-(morpholin-4-ylcarbonyl)-5,5-dioxidothiochromeno[4,3-c]pyrazol-1(4H)-yl]pyrrolidine-1-carboxylate to give 850 mg (100%) of the title compound. MS (ESI+): 421.23. HPLC (max plot) 100.0%; Rt 2.16 min.

Intermediate Y.12: Enantiomer B of 6-fluoro-3-(morpholin-4-ylcarbonyl)-1-[pyrrolidin-3-yl]-1,4-dihydrothiochromeno[4,3-c]pyrazole 5,5-dioxide hydrochloride

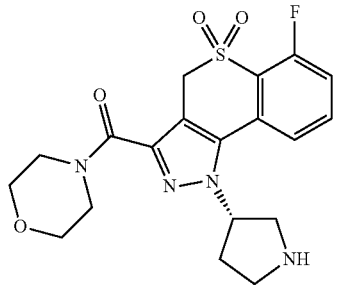

Obtained from Enantiomer B of tert-butyl 3-[6-fluoro-3-(morpholin-4-ylcarbonyl)-5,5-dioxidothiochromeno[4,3-c]pyrazol-1(4H)-yl]pyrrolidine-1-carboxylate to give 750 mg (84%) of the title compound. HPLC (max plot) 99.7%; Rt 2.16 min.

Intermediate Y.13: 6-Methoxy-3-(morpholin-4-ylcarbonyl)-1-[piperidin-3-yl]-1,4-dihydrothiochromeno[4,3-c]pyrazole 5,5-dioxide

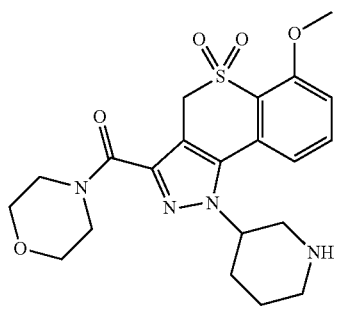 [SMILES: COc1cccc2c1S(=O)(=O)Cc1c(C(=O)N3CCOCC3)nn(C3CCCNC3)c1-2]

1700 mg of the title compound as a white solid. MS (ESI−): 455.5.

Intermediate Y.14: 7-Fluoro-3-(morpholin-4-ylcarbonyl)-1-piperidin-3-yl-1,4-dihydrothiochromeno[4,3-c]pyrazole 5,5-dioxide

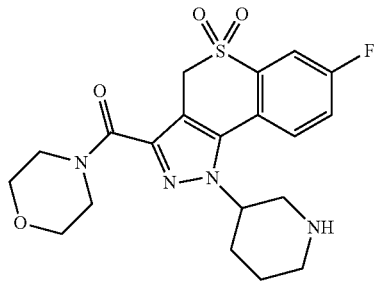 [SMILES: O=C(c1nn(C2CCCNC2)c2c1CS(=O)(=O)c1cc(F)ccc1-2)N1CCOCC1]

3.10 mg (82%) of the title compound as an oil.. MS (ESI+): 435.3. HPLC (max plot) 98.8%; Rt 2.40 min Intermediate Y.15: 7-Methoxy-3-(morpholin-4-ylcarbonyl)-1-piperidin-3-yl-1,4-dihydrothiochromeno[4,3-c]pyrazole 5,5-dioxide

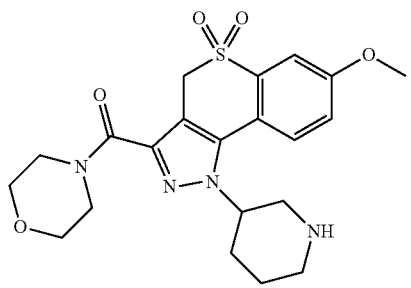 [SMILES: COc1ccc2c(c1)S(=O)(=O)Cc1c(C(=O)N3CCOCC3)nn(C3CCCNC3)c1-2]

3.88 mg (79%) of the title compound as a beige foam. $^1$H NMR (DMSO-$d_6$, 300 MHz): δ. MS (ESI+): 447.27. HPLC (max plot) 99.4%; Rt 2.44 min Intermediate Y.16: 7-(Trifluoromethoxy)-3-(morpholin-4-ylcarbonyl)-1-piperidin-3-yl-1,4-dihydrothiochromeno[4,3-c]pyrazole 5,5-dioxide (example 481)

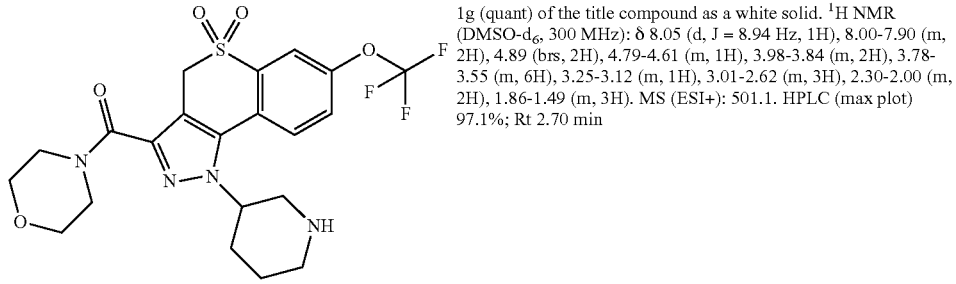

1g (quant) of the title compound as a white solid. $^1$H NMR (DMSO-$d_6$, 300 MHz): δ 8.05 (d, J = 8.94 Hz, 1H), 8.00-7.90 (m, 2H), 4.89 (brs, 2H), 4.79-4.61 (m, 1H), 3.98-3.84 (m, 2H), 3.78-3.55 (m, 6H), 3.25-3.12 (m, 1H), 3.01-2.62 (m, 3H), 2.30-2.00 (m, 2H), 1.86-1.49 (m, 3H). MS (ESI+): 501.1. HPLC (max plot) 97.1%; Rt 2.70 min Intermediate Y.17: Enantiomer B of 6-chloro-3-(morpholin-4-ylcarbonyl)-1-[piperidin-3-yl]-1,4-dihydrothiochromeno[4,3-c]pyrazole 5,5-dioxide

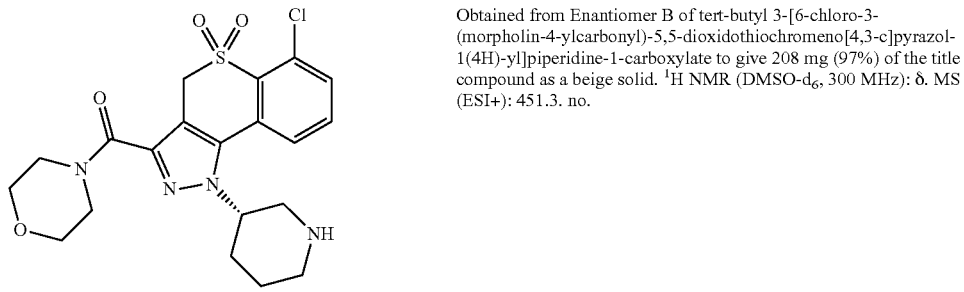

Obtained from Enantiomer B of tert-butyl 3-[6-chloro-3-(morpholin-4-ylcarbonyl)-5,5-dioxidothiochromeno[4,3-c]pyrazol-1(4H)-yl]piperidine-1-carboxylate to give 208 mg (97%) of the title compound as a beige solid. $^1$H NMR (DMSO-$d_6$, 300 MHz): δ. MS (ESI+): 451.3. no.

Procedure Z

Intermediate Z.1

1-[1-(2-Chloroethyl)piperidin-4-yl]-3-(morpholin-4-ylcarbonyl)-1,4-dihydrothiochromeno[4,3-c]pyrazole 5,5-dioxide

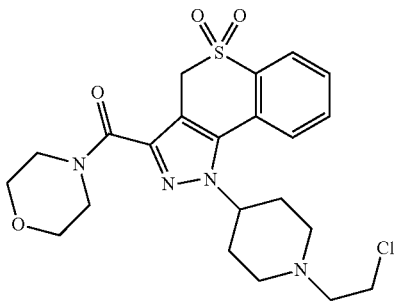 [SMILES: O=C(c1nn(C2CCN(CCCl)CC2)c2c1CS(=O)(=O)c1ccccc1-2)N1CCOCC1]

A suspension of 3-(morpholin-4-ylcarbonyl)-1-piperidin-4-yl-1,4-dihydrothiochromeno[4,3-c]pyrazole 5,5-dioxide hydrochloride (100 mg; 0.23 mmol; 1 eq.), chloroacetaldehyde (31.13 mg; 0.24 mmol; 1.1 eq.) in DCE (4.2 ml) is added sodium triacetoxyborohydride (229.27 mg; 1.08 mmol; 1.4 eq) and the reaction mixture is stirred at 65° C. overnight. The reaction mixture is diluted with DCM and the organic phase is washed with a saturated aqueous solution of NaHCO3 then dried on MgSO4 and concentrated. The residue is purified by flash chromatography eluting from 100% to 30% AcOEt and MeOH to afford after concentration of the desired fractions of the title compound as a brown oil. HPLC (max plot) 89.6%; Rt 2.33 min.

Intermediates described below are obtained following protocol outlined in procedure Z Intermediate Z.2: 1-[1-(2-Chloroethyl)azetidin-3-yl]-3-(morpholin-4-ylcarbonyl)-1,4-dihydrothiochromeno[4,3-c]pyrazole 5,5-dioxide

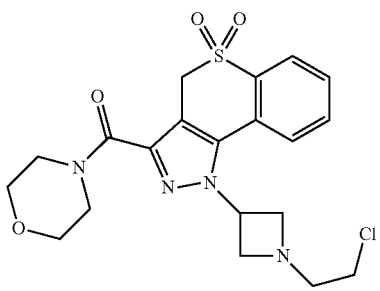 [SMILES: O=C(c1nn(C2CN(CCCl)C2)c2c1CS(=O)(=O)c1ccccc1-2)N1CCOCC1]

240 mg of the title compound as a white foam. 1H NMR (DMSO-d6) δ 8.04-8.01 (m, 1H), 7.93-7.83 (m, 2H), 7.76-7.71 (m, 1H), 5.60-5.51 (q, 1H), 4.80 (s, 2H), 3.97-3.92 (m, 4H), 3.68-3.57 (m, 10H), 2.88-2.84 (m, 2H). HPLC (max plot) 96.7%; Rt 1.83 min. MS (ESI+): 450.8.

Intermediate Z.3: 1-[1-(2-Chloroethyl)pyrrolidin-3-yl]-3-(morpholin-4-ylcarbonyl)-1,4-dihydrothiochromeno[4,3-c]pyrazole 5,5-dioxide

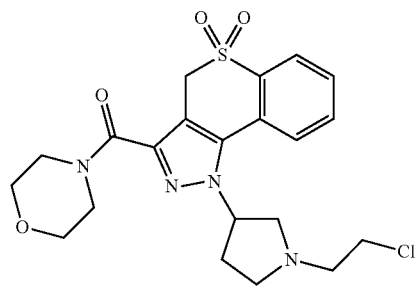 [SMILES: O=C(c1nn(C2CCN(CCCl)C2)c2c1CS(=O)(=O)c1ccccc1-2)N1CCOCC1]

500 mg of the title compound as a beige foam. HPLC (max plot) 100.0%; Rt 2.25 min. (ESI+): 464.7.

Intermediate Z.4: 1-[1-(2-Chloroethyl)piperidin-3-yl]-3-(morpholin-4ylcarbonyl)-1,4-dihydrothiochromeno[4,3-c]pyrazole 5,5-dioxide

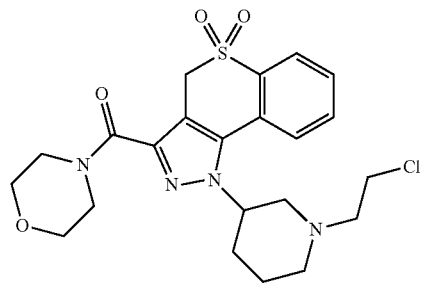 [SMILES: O=C(c1nn(C2CCCN(CCCl)C2)c2c1CS(=O)(=O)c1ccccc1-2)N1CCOCC1]

911 mg (86%) of the title compound. $^1$H NMR (DMSO-$d_6$) δ 8.06 (dd, J = 7.8, 1.2 Hz, 1H), 7.96-7.90 (m, 1H), 7.85-7.83 (m, 1H), 7.78-7.73 (m, 1H), 4.79-4.73 (m, 3H), 3.93-3.91 (m, 3H), 3.74-3.62 (m, 9H), 3.26-3.23 (m, 1H), 2.78-2.73 (m, 2H), 2.16-2.12 (m, 2H), 2.01-1.89 (m, 1H), 1.79-1.66 (m, 2H). HPLC (max plot) 89.0%; Rt 1.82 min. (ESI+): 478.7.

Intermediate Z.5: Enantiomer A of 1-[1-(2-chloroethyl)piperidin-3-yl]-3-(morpholin-4-ylcarbonyl)-1,4-dihydrothiochromeno[4,3-c]pyrazole 5,5-dioxide

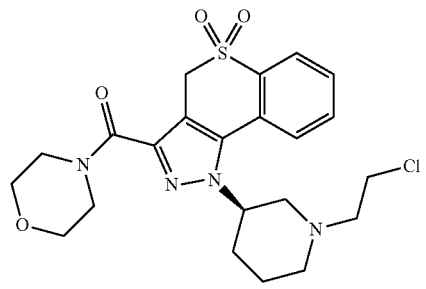 [SMILES: O=C(c1nn([C@@H]2CCCN(CCCl)C2)c2c1CS(=O)(=O)c1ccccc1-2)N1CCOCC1]

Obtained from enantiomer A of 3-(morpholin-4-ylcarbonyl)-1-[piperidin-3-yl]-1,4-dihydrothiochromeno[4,3-c]pyrazole 5,5-dioxide to give 274 mg of the title compound. HPLC (max plot) 96.5%; Rt 1.77 min.

Intermediate Z.6: Enantiomer B of 1-[1-(2-chloroethyl)piperidin-3-yl]-3-(morpholin-4-ylcarbonyl)-1,4-dihydrothiochromeno[4,3-c]pyrazole 5,5-dioxide

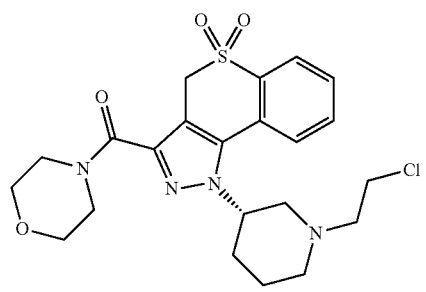 [SMILES: O=C(c1nn([C@H]2CCCN(CCCl)C2)c2c1CS(=O)(=O)c1ccccc1-2)N1CCOCC1]

Obtained from enantiomer B of 3-(morpholin-4-ylcarbonyl)-1-[piperidin-3-yl]-1,4-dihydrothiochromeno[4,3-c]pyrazole 5,5-dioxide to give 1.78 g (77%) of the title compound as a white foam. HPLC (max plot) 73.8%; Rt 1.88 min. MS (ESI+): 479.2.

Intermediate Z.7: 1-[1-(2-Chloroethyl)piperidin-3-yl]-6-fluoro-3-(morpholin-4-ylcarbonyl)-1,4-dihydrothiochromeno[4,3-c]pyrazole 5,5-dioxide

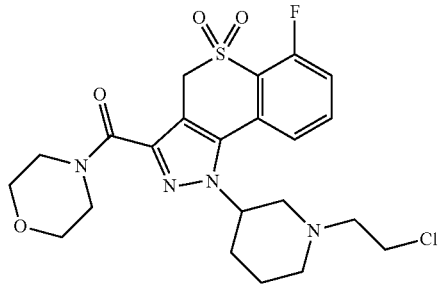 [SMILES: O=C(c1nn(C2CCCN(CCCl)C2)c2c1CS(=O)(=O)c1c(F)cccc1-2)N1CCOCC1]

680 mg (82%) of the title compound. MS (ESI+): 496.8. (max plot) 69.6%; Rt 1.81 min.

Intermediate Z.8: Enantiomer A of 1-[1-(2-chloroethyl)piperidin-3-yl]-6-fluoro-3-(morpholin-4-ylcarbonyl)-1,4-dihydrothiochromeno[4,3-c]pyrazole 5,5-dioxide

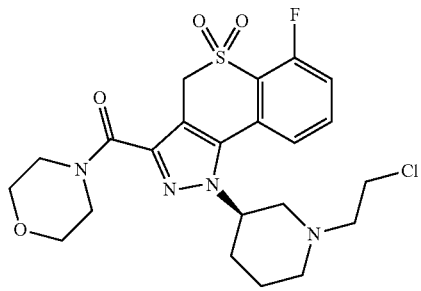 [SMILES: O=C(c1nn([C@@H]2CCCN(CCCl)C2)c2c1CS(=O)(=O)c1c(F)cccc1-2)N1CCOCC1]

Obtained from enantiomer A of 6-fluoro-3-(morpholin-4-ylcarbonyl)-1-[piperidin-3-yl]-1,4-dihydrothiochromeno[4,3-c]pyrazole 5,5-dioxide to give 800 mg (quant) of the title compound as a white foam. MS (ESI+): 497.3.

Intermediate Z.9: Enantiomer B of 1-[1-(2-chloroethyl)piperidin-3-yl]-6-fluoro-3-(morpholin-4-ylcarbonyl)-1,4-dihydrothiochromeno[4,3-c]pyrazole 5,5-dioxide

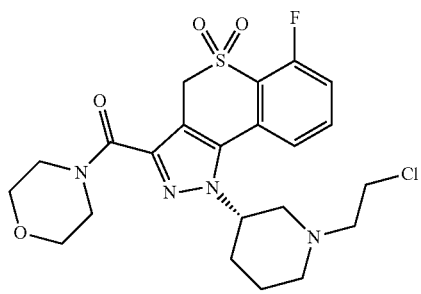 [SMILES: O=C(c1nn([C@H]2CCCN(CCCl)C2)c2c1CS(=O)(=O)c1c(F)cccc1-2)N1CCOCC1]

Obtained from enantiomer B of 6-fluoro-3-(morpholin-4-ylcarbonyl)-1-[piperidin-3-yl]-1,4-dihydrothiochromeno[4,3-c]pyrazole 5,5-dioxide to give 720 mg (quant) of the title compound. MS (ESI+): 497.3

Intermediate Z.10: Enantiomer B of 1-[1-(2-chloroethyl)piperidin-3-yl]-6-methoxy-3-(morpholin-4-ylcarbonyl)-1,4-dihydrothiochromeno[4,3-c]pyrazole 5,5-dioxide

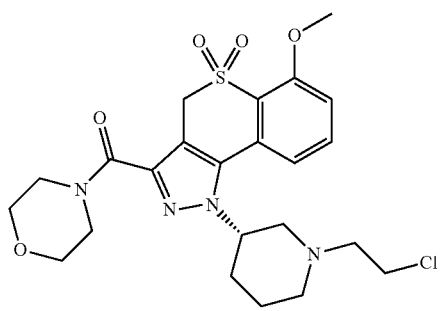 [SMILES: COc1cccc2c1S(=O)(=O)Cc1c(C(=O)N3CCOCC3)nn([C@H]3CCCN(CCCl)C3)c1-2]

Obtained from enantiomer B of 6-methoxy-3-(morpholin-4-ylcarbonyl)-1-[piperidin-3-yl]-1,4-dihydrothiochromeno[4,3-c]pyrazole 5,5-dioxide to give 800 mg (88%) of the title compound as a white solid.

Intermediate Z.11: 6-Chloro-1-[1-(2-chloroethyl)piperidin-3-yl]-3-(morpholin-4-yl carbonyl)-1,4-dihydrothiochromeno[4,3-c]pyrazole 5,5-dioxide

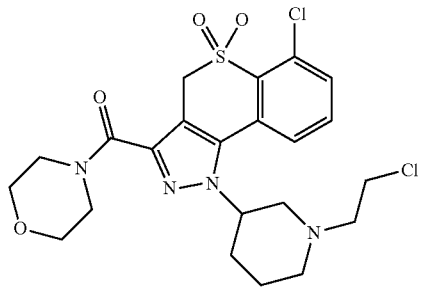

200 mg (95%) of the title compound. MS (ESI+): 512.8.

Intermediate Z.12: Enantiomer B of 6-chloro-1-[1-(2-chloroethyl)piperidin-3-yl]-3-(morpholin-4-ylcarbonyl)-1,4-dihydrothiochromeno[4,3-c]pyrazole 5,5-dioxide

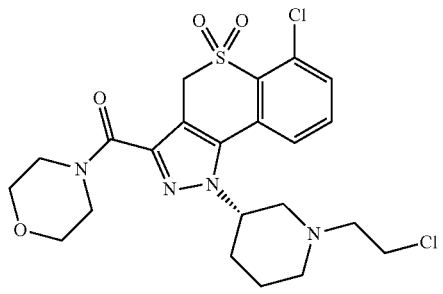 [SMILES: O=C(c1nn([C@H]2CCCN(CCCl)C2)c2c1CS(=O)(=O)c1c(Cl)cccc1-2)N1CCOCC1]

Obtained from enantiomer B of 3-[6-chloro-3-(morpholin-4-ylcarbonyl)-5,5-dioxidothiochromeno[4,3-c]pyrazol-1(4H)-yl]piperidine-1-carboxylate to give 78 mg (75%) of the title compound as a white foam. $^1$H NMR (DMSO-$d_6$, 300 MHz): δ 7.92-7.81 (m, 1H), 7.81-7.69 (m, 2H), 4.91 (s, 2H), 4.74-4.54 (m, 1H), 3.99-3.84 (m, 2H), 3.79-3.55 (m, 8H), 3.24-3.13 (m, 1H), 2.98-2.84 (m, 1H), 2.82-2.65 (m, 2H), 2.59-2.45 (m, 1H), 2.23-2.02 (m, 2H), 2.02-2.1.83 (m, 1H), 1.83-1.57 (m, 2H). MS (ESI+): 513.37. HPLC (max plot) 95.9%; Rt 7.88 min Intermediate Z.13: Enantiomer B of 1-[1-(2-chloroethyl)piperidin-3-yl]-6-methyl-3-(morpholin-4-ylcarbonyl)-1,4-dihydrothiochromeno[4,3-c]pyrazole 5,5-dioxide

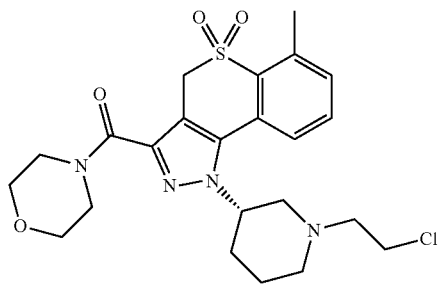 [SMILES: Cc1cccc2c1S(=O)(=O)Cc1c(C(=O)N3CCOCC3)nn([C@H]3CCCN(CCCl)C3)c1-2]

Obtained from enantiomer B of 6-methyl-3-(morpholin-4-ylcarbonyl)-1-[piperidin-3-yl]-1,4-dihydrothiochromeno[4,3-c]pyrazole 5,5-dioxide to give 780 mg (97%) of the title compound as a colourless foam. $^1$H NMR (DMSO-$d_6$, 300 MHz): δ. HPLC (max plot) 94.5%; Rt 2.06 min Intermediate Z.14: Enantiomer B 1-[1-(2-chloroethyl)piperidin-3-yl]-7-fluoro-3-(morpholin-4-ylcarbonyl)-1,4-dihydrothiochromeno[4,3-c]pyrazole 5,5-dioxide

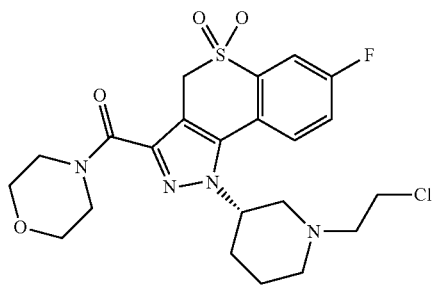

Obtained from enantiomer B of 7-fluoro-3-(morpholin-4-ylcarbonyl)-1-[piperidin-3-yl]-1,4-dihydrothiochromeno[4,3-c]pryazole 5,5-dioxide to give 25 mg (72%) of the title compound as an oil. δ. MS (ESI+): 497.21.

Intermediate Z.15: Enantiomer B of 1-[1-(2-chloroethyl)piperidin-3-yl]-7-methoxy-3-(morpholin-4-ylcarbonyl)-1,4-dihydrothiochromeno[4,3-c]pyrazole 5,5-dioxide

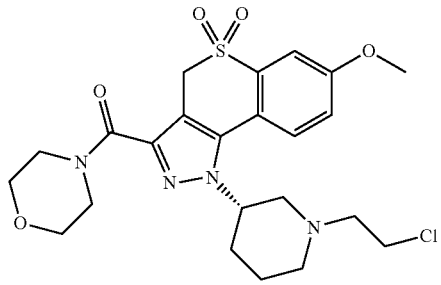 [SMILES: COc1ccc2c(c1)S(=O)(=O)Cc1c(C(=O)N3CCOCC3)nn([C@H]3CCCN(CCCl)C3)c1-2]

Obtained from enantiomer B of 7-methoxy-3-(morpholin-4-ylcarbonyl)-1-[piperidin-3-yl]-1,4-dihydrothiochromeno[4,3-c]pyrazole 5,5-dioxide to give 600 mg (70%) of the title compound as a white foam. $^1$H NMR (DMSO-$d_6$, 300 MHz): δ 7.78 (d, J = 8.7 Hz, 1H), 7.51-7.44 (m, 2H), 4.78-4.64 (m, 4H), 3.96-3.88 (m, 4H), 3.75-3.60 (m, 7H), 3.22 (d, J = 10.0 Hz, 1H), 2.93 (d, J = 10.6 Hz, 1H), 2.75 (td, J = 6.7, 2.4 Hz, 2H), 2.56-2.46 (m, 2H), 2.20-2.06 (m, 2H), 1.96-1.85 (m, 1H), 1.84-1.62 (m, 2H).. MS (ESI+): 509.4. HPLC (max plot) 100.0%; Rt 2.27 min Intermediate Z.16: Enantiomer B of 1-[1-(2-chloroethyl)piperidin-3-yl]-3-(morpholin-4-ylcarbonyl)-7-(trifluoromethoxy)-1,4-dihydrothiochromeno[4,3-c]pyrazole 5,5-dioxide

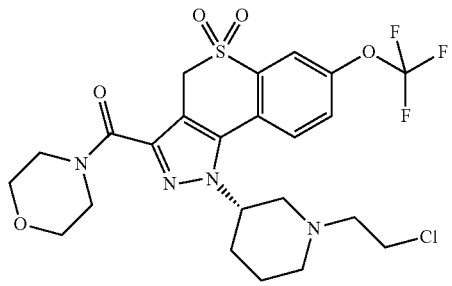 [SMILES: O=C(c1nn([C@H]2CCCN(CCCl)C2)c2c1CS(=O)(=O)c1cc(OC(F)(F)F)ccc1-2)N1CCOCC1]

Obtained from enantiomer B of 3-(morpholin-4-ylcarbonyl)-1-[piperidin-3-yl]-7-(trifluoromethoxy)-1,4-dihydrothiochromeno[4,3-c]pyrazole 5,5-dioxide to give 390 mg (quant %) of the title compound as the white foam. $^1$H NMR (DMSO-$d_6$, 300 MHz): δ 8.01-7.94 (m, 3H), 4.90 (s, 2H), 4.84-4.69 (m, 1H), 3.94-3.86 (m, 2H), 3.77-3.59 (m, 8H), 3.29-3.19 (m, 1H), 2.99-2.88 (m, 1H), 2.81-2.70 (m, 2H), 2.58-2.52 (m, 1H), 2.21-2.06 (m, 2H), 2.04-1.86 (m, 1H), 1.85-1.63 (m, 2H). MS (ESI+): 563.2. HPLC (max plot) 91.7%; Rt 2.87 min Intermediate Z.17: Enantiomer B of 1-[1-(2-chloroethyl)piperidin-3-yl]-8-methoxy-3-(morpholin-4-ylcarbonyl)-1,4-dihydrothiochromeno[4,3-c]pyrazole 5,5-dioxide

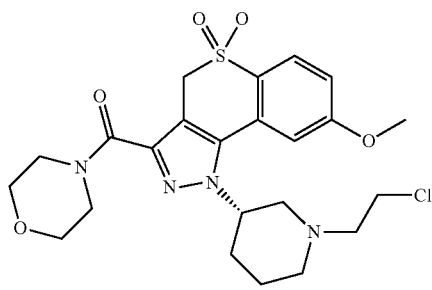

Obtained from enantiomer B of 3-(morpholin-4-ylcarbonyl)-1-[piperidin-3-yl]-8-(methoxy)-1,4-dihydrothiochromeno[4,3-c]pyrazole 5,5-dioxide to give 50 mg of the title compound as an oil. MS (ESI+): 509.2.

Intermediate Z.18: Enantiomer B of tert-butyl (3-[3-(morpholin-4-ylcarbonyl)-5,5-dioxidothiochromeno[4,3-c]pyrazol-1(4H)-yl]-1,3'-bipiperidine-1'-carboxylate

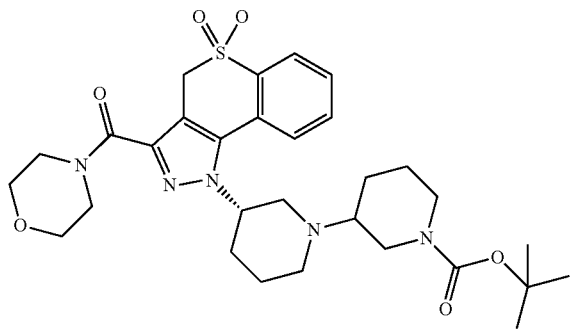

Obtained from enantiomer B of 3-(morpholin-4-ylcarbonyl)-1-[piperidin-3-yl]-1,4-dihydrothiochromeno[4,3-c]pyrazole 5,5-dioxide to give 410 mg (94%) of the title compound. MS (ESI+): 604.

Intermediate Z.19

3-[3-(Morpholin-4-ylcarbonyl)-5,5-dioxidothio-chromeno[4,3-c]pyrazol-1(4H)-yl]phenol

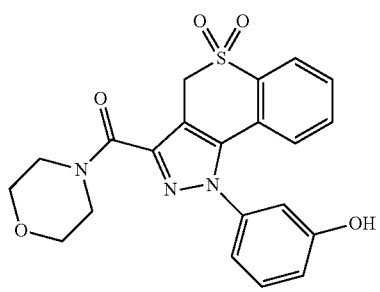 [SMILES: O=C(c1nn(-c2cccc(O)c2)c2c1CS(=O)(=O)c1ccccc1-2)N1CCOCC1]

To a solution 1-[3-(benzyloxy)phenyl]-3-(morpholin-4-yl-carbonyl)-1,4-dihydrothiochromeno[4,3-c]pyrazole 5,5-dioxide (8 g, 155 mmol) in MeOH (500 mL) is added 10% Pd/C (0.5 g) and the reaction mixture is hydrogenated at 12 Kg/cm$^2$ pressure of hydrogen at RT for 20 h in Autoclave. The catalyst is filtered through celite and filtrate is concentrated to afford 4.9 g (89%) of the title compound as a brown solid. $^1$H NMR (DMSO-d$_6$, 400 MHz): δ 10.08 (s, 1H), 8.02-8.00 (dd, J=2.4, 3.2 Hz, 1H), 7.65-7.59 (m, 2H), 7.42-7.38 (t, J=8.0 Hz, 1H), 7.01-6.99 (t, J=8.4 Hz, 1H), 6.93-6.88 (m, 3H), 4.88 (s, 2H), 3.95 (m, 2H), 3.66-3.61 (m, 4H), 3.56 (s, 2H). MS (ESI+): 426.0. HPLC (max plot): 96%; Rt 3.25 min.

Intermediate Z.20

Ethyl 1-{6-[(acetyloxy)methyl]pyridin-3-yl}-1,4-dihydrothiochromeno[4,3-c]pyrazole-3-carboxylate 5,5-dioxide.

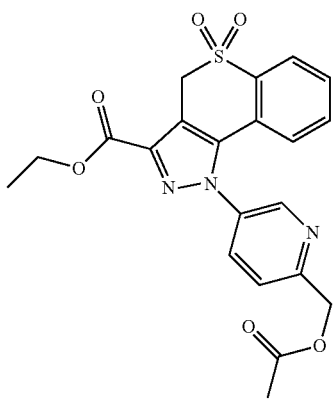 [SMILES: CCOC(=O)c1nn(-c2ccc(COC(C)=O)nc2)c2c1CS(=O)(=O)c1ccccc1-2]

A solution of ethyl 1-(1-oxidopyridin-3-yl)-1,4-dihydrothiochromeno[4,3-c]pyrazole-3-carboxylate 5,5-dioxide (637 mg) in acetic anhydride (30 mL) is heated to 130° C. for 2 h under nitrogen. After completion of the reaction, the reaction mass is concentrated under reduced pressure and triturated in water, filtered and dried to afford 700 mg (99%) of the title compound. MS (ESI+): 442.0.

Intermediate Z.21

3-[3-(Morpholin-4-ylcarbonyl)-5,5-dioxidothio-chromeno[4,3-c]pyrazol-1(4H)-yl]aniline:

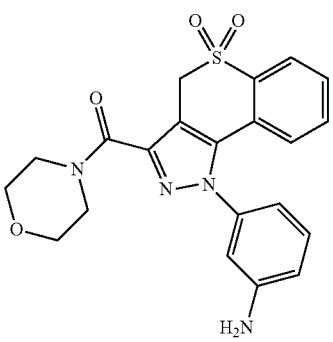 [SMILES: Nc1cccc(-n2nc(C(=O)N3CCOCC3)c3c2-c2ccccc2S(=O)(=O)C3)c1]

1-(3-Bromophenyl)-3-(morpholin-4-ylcarbonyl)-1,4-dihydrothiochromeno[4,3-c]pyrazole 5,5-dioxide (0.15 g, 0.308 mmol), copper acetate (6 mg, 0.03 mmol), cesium carbonate (200 mg, 0.616 mmol) and acetyl acetone (13 μL, 0.123 mmol) are taken DMF purged with NH$_3$ gas. The reaction mixture is heated to 90° C. for 24 h. After this time, reaction mixture is concentrated under reduced pressure and purified by column chromatography (100% EtOAc) to afford the title compound as a pale brown solid. $^1$H NMR (400 MHz, DMSO-d$_6$) δ=7.99-7.97 (m, 1H), 7.62-7.60 (m, 1H), 7.24-7.20 (t, J=7.84 Hz, 1H), 6.98-6.95 (m, 1H), 6.75-6.73 (d, J=9.32 Hz, 1H), 6.58-6.56 (m, 2H), 5.57 (s, 2H), 4.87 (s, 2H), 3.95 (m, 2H), 3.66 (m, 6H), MS (ESI+): 425.0. HPLC (max plot): 94.69%; Rt 2.65 min.

Intermediate Z.22

Ethyl 7-(acetylamino)-1-(tetrahydro-2H-pyran-4-yl)-1,4-dihydropyrazolo[3',4':4,5]thiopyrano[3,2-d][1,3]thiazole-3-carboxylate 5,5-dioxide

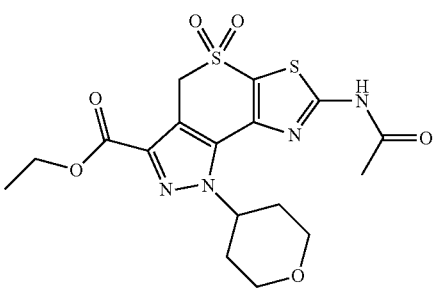 [SMILES: CCOC(=O)c1nn(C2CCOCC2)c2c1CS(=O)(=O)c1sc(NC(C)=O)nc1-2]

To suspension of ethyl 7-amino-1-(tetrahydro-2H-pyran-4-yl)-1,4-dihydropyrazolo[3',4':4,5]thiopyrano[3,2-d][1,3]thiazole-3-carboxylate 5,5-dioxide (71 mg; 0.18 mmol; 1 eq.) and triethylamine (98.8 μL; 0.71 mmol; 4 eq.) in DCM (710 μL) at 0° C. is added acetylchloride (30 μL; 0.46 mmol; 2.5 eq.). The suspension is stirred at rt overnight then heated up to 100° C. for 1 day. Water is added to reacture mixture and the product is extracted with DCM (×2). The combined organic

Intermediate Z.23

4-[(4-Nitro-1H-pyrazol-3-yl)carbonyl]morpholine

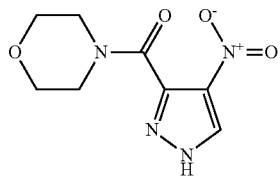 [SMILES: O=C(c1n[nH]cc1[N+](=O)[O-])N1CCOCC1]

Following protocol outlined in procedure AD (described below), 4-[(4-nitro-1H -pyrazol-3-yl)carbonyl]morpholine is obtained from 4-nitro-1H-pyrazole-3-carboxylic acid and morpholine to give 3.0g (41%) of the title compound as a white solid. 1H NMR 14.22(brs, 1H),8.92(brs,1H), 3.66(s, 4H), 3.52-3.45(m, 2H), MS (ESI+):226.9.

Intermediate Z.24

4-[(4-Nitro-1-phenyl-1H-pyrazol-3-yl)carbonyl]morpholine

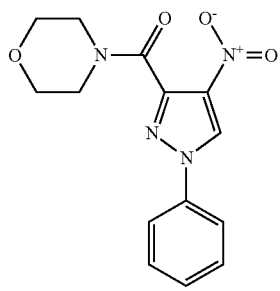 [SMILES: O=C(c1nn(-c2ccccc2)cc1[N+](=O)[O-])N1CCOCC1]

A solution of 4-[(4-nitro-1H-pyrazol-3-yl)carbonyl]morpholine (1.50 g; 6.63 mmol; 1.00 eq.) and copper acetate (1 204.49 mg; 6.63 mmol; 1.00 eq.) in DCM (5 mL) is stirred at rt for 18 h after which phenylboronic acid (808.58 mg; 6.63 mmol; 1.00 eq.) and TEA (1.83 mL) are added and the mixture is stirred at room temperature for 18 h. After this time, reaction mixture is diluted with DCM, ished with sat. aq. NaHCO3 then brine, dried over MgSO4, filtered through a short plug of silica and concentrated in vacuo to give as a pale yellow oil. Purification by column chromatography (DCM to 15% ethyl acetate in DCM) followed by crystallization from MTBE afford 60 mg of the title compound as a white solid. $^1$H NMR (DMSO) 9.76 (s, 1H), 8.00-7.91 (m, 2H), 7.65-7.54 (m, 2H), 7.53-7.43 (m, 1H), 3.70 (s, 4H), 3.60-3.48 (m, 2H), 3.41-3.32 (m, 2H). MS (ESI+): 303.0.

Intermediate Z.25

3-(Morpholin-4-ylcarbonyl)-1-phenyl-1H-pyrazol-4-amine

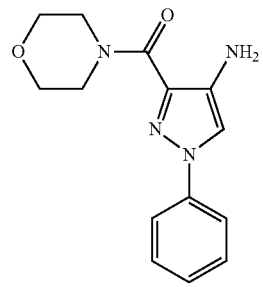 [SMILES: Nc1cn(-c2ccccc2)nc1C(=O)N1CCOCC1]

To a solution of 4-[(4-nitro-1-phenyl-1H-pyrazol-3-yl)carbonyl]morpholine (376 mg; 1.24 mmol; 1.00 eq.) in AcOEt (10 mL) is added Pd/C 10% (-50% H$_2$O) (13.24 mg; 0.12 mmol; 0.10 eq.) and under H$_2$ Atm. (1 atm.). After 18 h, reaction mixture is filtered over a celite bed, ished with AcOEt to give 310 mg (92%) of the title compound as a purple solid. 1H NMR (DMSO): δ 7.85 (s, 1H), 7.77-7.72 (m, 2H), 7.53-7.44 (m, 2H), 7.30 (t, J=7.4 Hz, 1H), 5.14-4.90 (m, 2H), 4.31-4.14 (m, 2H), 3.73-3.58 (m, 4H), 3.43-3.23 (m, 2H). HPLC (max plot) 95.6%; Rt 2.01 min. MS (ESI+): 272.9.

Intermediate Z.26

2-Bromo-N-[3-(morpholin-4-ylcarbonyl)-1-phenyl-1H-pyrazol-4-yl]benzenesulfonamide

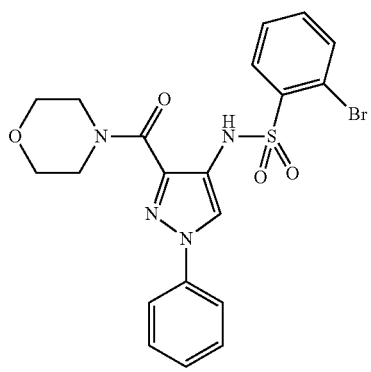 [SMILES: O=C(c1nn(-c2ccccc2)cc1NS(=O)(=O)c1ccccc1Br)N1CCOCC1]

To a solution of 3-(morpholin-4-ylcarbonyl)-1-phenyl-1H-pyrazol-4-amine (260 mg; 0.95 mmol; 1 eq.) in DCM (10 mL) is added pyridine (151 μL; 1.91 mmol; 2.00 eq.) and 2-bromobenzene-1-sulfonyl chloride (317 mg; 1.24 mmol; 1.30 eq.). The reaction is stirred for 48 h at room temperature. After this time, DCM is added to the reaction mixture which is ished with NH$_4$Cl sat, dried over MgSO$_4$ and purified by flash chromatography (AcOEt/heptane 4:1) to give 440 mg (94%) of the title compound as a white solid. $^1$H NMR (DMSO) δ 9.93 (s, 1H), 8.43 (s, 1H), 8.11-8.02 (m, 1H), 7.91-7.84 (m, 1H), 7.84-7.76 (m, 2H), 7.59-7.45 (m, 4H), 7.40-7.31 (m,

--- layers are washed with brine, dried over Na$_2$SO$_4$ then concentrated under vacuum affording a beige solid residue. The residue is triturated then sonicated in Et$_2$O and the solid is filtered-off to afford the title compound. HPLC (max plot) 98.8%; Rt 3.28 min. MS (ESI+): 441.1.

1H), 3.81-3.69 (m, 2H), 3.67-3.49 (m, 6H) HPLC (max plot) 94.6%; Rt 4.83 min. MS (ESI+): 493.2.

Intermediate Z.27

2-Bromo-N-(methoxymethyl)-N-[3-(morpholin-4-ylcarbonyl)-1-phenyl-1H-pyrazol-4-yl]benzenesulfonamide

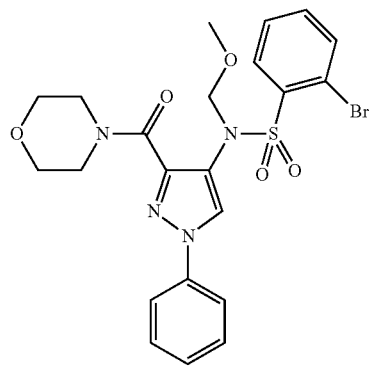 [SMILES: COCN(c1cn(-c2ccccc2)nc1C(=O)N1CCOCC1)S(=O)(=O)c1ccccc1Br]

To a solution of 2-bromo-N-[3-(morpholin-4-ylcarbonyl)-1-phenyl-1H-pyrazol-4-yl]benzenesulfonamide (200 mg; 0.41 mmol; 1.00 eq.) in THF (30 mL) is added NaH (24 mg; 0.61 mmol; 1.50 eq.) in a portionwise manner and the resulting mixture is stirred at room temperature for 15 minutes whereupon Chloromethyl methyl ether (82 µl; 0.81 mmol; 2.00 eq.) is added dropwise. The reaction mixture is stirred at room temperature for 2 hours then quenched with sat. aq. NaHCO$_3$. Extraction with ethyl acetate (2×), ishing with brine, drying over magnesium sulfate and concentration in vacuo gives 240 mg (quant) of the title compound as a colourless oil. $^1$H NMR (DMSO) δ 8.82 (s, 1H), 7.93-7.8 (m, 4H), 7.64-7.46 (m, 4H), 7.39 (t, J=7.4 Hz, 1H), 5.32 (s, 2H), 3.59-3.51 (m, 2H), 3.42 (s, 3H), 3.46-3.37 (m, 4H), 3.15-3.06 (m, 2H). MS (ESI+): 505.2.

Intermediate Z.28

2-Bromo-N-methyl-N-[3-(morpholin-4-ylcarbonyl)-1-phenyl-1H-pyrazol-4-yl]benzenesulfonamide

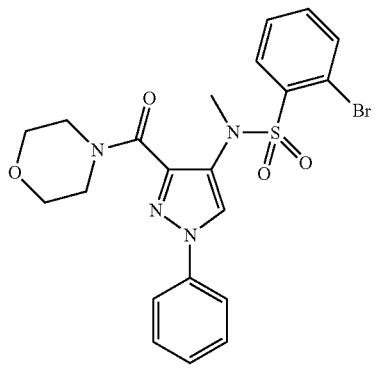 [SMILES: CN(c1cn(-c2ccccc2)nc1C(=O)N1CCOCC1)S(=O)(=O)c1ccccc1Br]

To a solution of 2-bromo-N-[3-(morpholin-4-ylcarbonyl)-1-phenyl-1H-pyrazol-4-yl]benzenesulfonamide (30 mg; 0.06 mmol; 1.00 eq.) in THF (6 mL) is added sodium hydride (3 mg; 0.07 mmol; 1.20 eq.) and the reaction is stirred for 10 min before the addition of iodomethane (4 µL; 0.07 mmol; 1.10 eq.). After 12 h, DCM is added to the reaction mixture, ished with water (×2) and dried the organic phase over MgSO4 give 30 mg (97%) of the title compound as a white solid. 1H NMR (DMSO) δ 8.64 (s, 1H), 7.93-7.86 (m, 2H), 7.80-7.73 (m, 2H), 7.62-7.47 (m, 4H), 7.41-7.32 (m, 1H), 3.65-3.51 (m, 6H), 3.48-3.42 (m, 2H), 3.35 (s, 3H). HPLC (max plot) 89.7%; Rt 3.98 min. MS (ESI+): 507.2.

Intermediate Z.29

Ethyl 5-hydroxy-1-phenyl-1H-pyrazole-3-carboxylate

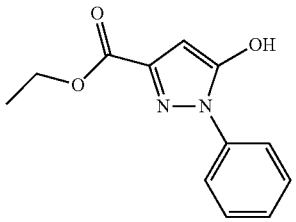 [SMILES: CCOC(=O)c1cc(O)n(-c2ccccc2)n1]

To a solution of phenyl hydrazine (10 g, 92.6 mmol) in absolute ethanol (100 mL) is added dry K$_2$CO$_3$ (15.3 g, 111 mmol) and followed by slow addition of diethylacetylene dicarboxylate (10.6 g, 62.03 mmol) and the reaction mixture is heated at 85° C. for 12 h. The reaction mixture is then cooled to rt and 38 mL of 6N HCl is added dropwise. The reaction mixture is diluted with 150 mL water, extracted with ethylacetate. The organic layer is washed with water twice, dried over Na$_2$SO$_4$ and concentrated under vacuum. The residue is triturated with MTBE and the solid formed is filtered, washed with MTBE and dried to afford the title compound. $^1$H NMR (DMSO-d6, 400 MHz): δ 12.12 (bs, 1H), 7.72-7.70 (m, 2H), 7.51-7.47 (m, 2H), 7.37-7.34 (m, 1H), 5.93 (s, 1H), 4.26 (q, J=4.1 Hz, 2H), 1.27 (t, J=7.1 Hz, 3H). MS (ESI+): 233.2.

Intermediate Z.30

Ethyl 5-bromo-4-formyl-1-phenyl-1H-pyrazole-3-carboxylate:

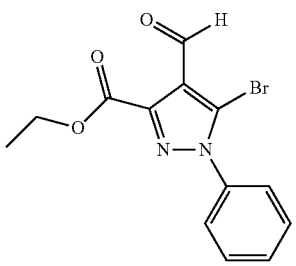 [SMILES: CCOC(=O)c1nn(-c2ccccc2)c(Br)c1C=O]

To a solution of ethyl 5-hydroxy-1-phenyl-1H-pyrazole-3-carboxylate (6.47 g, 27.52 mmol) in DCE (70 mL) is added phosphorus oxy bromide (13.86 g, 48.16 mmol) and DMF (4 mL, 51.46 mmol). The reaction mixture is refluxed at 90° C. for 3 h. Phosphorus oxy bromide (34.8 g, 121.38 mmol) is added again and the reaction mixture is refluxed at 90° C. for 20 h. The reaction mixture is poured over ice and extracted with DCM twice. The organic layer is dried over Na$_2$SO$_4$ and concentrated. The crude is purified by column chromatography to afford the title compound. $^1$H NMR (DMSO-d6, 400 MHz): δ 10.30 (s, 1H), 7.63-7.61 (m, 5H), 4.38 (q, J=3.6 Hz, 2H), 1.32 (t, J=7.1 Hz, 3H). MS (ESI+): 325.0, HPLC (max plot) 97.37%, Rt 4.42 min.

Intermediate Z.31

Ethyl 5-bromo-4-(hydroxymethyl)-1-phenyl-1H-pyrazole-3-carboxlate

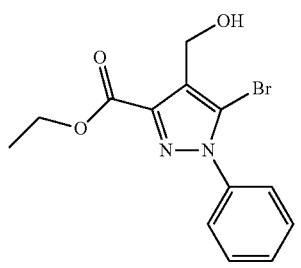 [SMILES: CCOC(=O)c1nn(-c2ccccc2)c(Br)c1CO]

To an ice cooled solution of ethyl 5-bromo-4-formyl-1-phenyl-1H-pyrazole-3-carboxylate (3.82 g, 11.86 mmol, 1 eq) in a 1:1 mixture of THF: EtOH is added sodium borohydride (0.5 g, 13.04 mmol, 1.1 eq) portion wise. The reaction mixture is stirred at RT for 2 h. The reaction mixture is quenched with sat. NH$_4$Cl solution and extracted with EtOAc. The organic layer is dried over Na$_2$SO$_4$ and concentrated. The crude is purified by column chromatography to afford 2.91 g (75%) of the title compound. $^1$H NMR (DMSO-d6, 400 MHz): δ 7.60-7.56 (m, 5H), 4.95 (t, J=5.4 Hz, 1H), 4.60-4.58 (d, J=5.4 Hz, 2H), 4.32 (q, J=7.01 Hz, 2H), 1.30 (t, J=7.7 Hz, 3H). HPLC (max plot) 96.75%; Rt 3.69 min Intermediate Z.32

Ethyl 5-bromo-4-(bromomethyl)-1-phenyl-1H-pyrazole-3-carboxylate

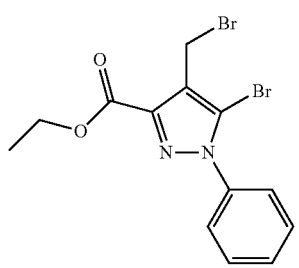 [SMILES: CCOC(=O)c1nn(-c2ccccc2)c(Br)c1CBr]

To a solution of ethyl-5-bromo-4-(hydroxymethyl)-1-phenyl-1H-pyrazole-3-carboxylate (2.91 g, 8.98 mmol, 1 eq) in Et$_2$O cooled at −10° C. is added phosphorus tribromide (1.02 mL, 10.77 mmol, 1.2 eq) and the reaction mixture is stirred at Rt for 1 h. The reaction mixture is poured over ice and extracted with MTBE. The organic layer is washed with brine, dried over Na$_2$SO$_4$ and concentrated to afford 2.1 g (60%) of the title compound. $^1$H NMR (DMSO-d6, 400 MHz): δ 7.65-7.57 (m, 5H), 4.77 (s, 2H), 4.35 (q, J=6.0 Hz, 2H), 1.32 (t, J=6.6 Hz, 3H). HPLC (max plot) 83.30%; Rt 5.33 min.

Intermediate Z.33

Ethyl-5-bromo-4-[(1H-imidazol-2ylthio)methyl]-1-phenyl-1H-pyrazole-3-carboxylate

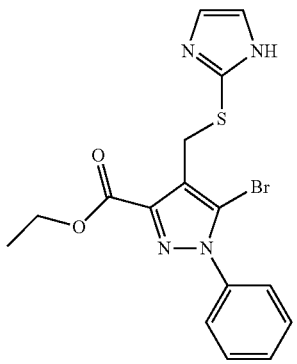 [SMILES: CCOC(=O)c1nn(-c2ccccc2)c(Br)c1CSc1ncc[nH]1]

To a solution of ethyl-5-bromo-4-(bromomethyl)-1-phenyl-1H-pyrazole-3-carboxylate (2.1 g, 5.44 mmol, 1 eq) and 2-mercaptoimidazole (0.6 g, 5.98 mmol, 1.1 eq) in ACN (30 mL) is added dry K$_2$CO$_3$ (2.25 g, 16.32 mmol, 3 eq) and the reaction mixture is heated at 85° C. for 1 h. The reaction mixture is diluted with DCM and filtered. The filtrate is concentrated and the residue is partitioned between DCM/water. The organic layer is dried over Na$_2$SO$_4$ and concentrated to afford the title compound. $^1$H NMR (DMSO-d6, 400 MHz): δ 12.29 (bs, 1H), 7.59-7.53 (m, 5H), 7.16 (d, J=1.4 Hz, 1H), 6.94 (d, J=1.4 Hz, 1H), 4.28-4.26 (m, 2H), 4.19 (s, 2H), 1.29 (t, J=7.7 Hz, 3H).

Intermediate Z.34

Ethyl 1-phenyl-1,4-dihydroimidazo[2,1-b]pyrazolo[3,4-d][1,3]thiazine-3-carboxylate

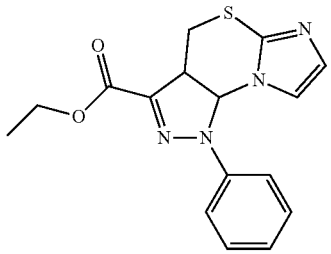 [SMILES: CCOC(=O)C1=NN(c2ccccc2)C2C1CSc1nccn12]

Ethyl-5-bromo-4-[(1H-imidazol-2ylthio) methyl]-1-phenyl-1H-pyrazole-3-carboxylate (0.3 g, 0.74 mmol, 1 eq), CuI (14 mg, 0.074 mmol, 0.1 eq), N,N-dimethylglycine (15 mg, 0.147 mmol, 0.2 eq), K$_2$CO$_3$ (0.2 g, 1.47 mmol, 2 eq) are taken in DMSO (6 mL) heated at 180° C. for 0.5 h under microwave irradiation. The reaction mixture is diluted with DCM and filtered through a pad of celite. The filtrate is partitioned between DCM and water. The organic layer is washed with brine, dried over Na$_2$SO$_4$ and concentrated. The crude is purified by flash chromatography to afford the title compound. ¹H NMR (DMSO-d6, 400 MHz): δ 7.67-7.59 (m, 5H), 6.93 (d, J=1.5 Hz, 1H), 6.48 (d, J=1.4 Hz, 1H), 4.40 (s, 2H), 4.34 (q, J=7.7 Hz, 2H), 1.31 (t, J=7.7 Hz, 3H). MS (ESI+): 313.2. HPLC (max plot) 97.73%; Rt 2.73 min.

Intermediate Z.35

2H-1,4-Benzothiazin-3(4H)-one:

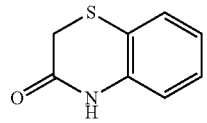 [SMILES: O=C1CSc2ccccc2N1]

Sodium methoxide is prepared by dissolving 920 mg of sodium metal in 40 mL of ethanol and 5 g of ortho-aminothiophenol is added to it and the reaction mixture is stirred at RT for 10 min. Then the reaction mixture is cooled with ice and 4.8 mL of ethylbromoacetate is added dropwise and the reaction mixture is stirred at RT for 3 h. The precipitated solid is filtered off and the filtrate is concentrated and triturated with ether and the solid formed is filtered, washed with water, hexane and dried. The solid is then azeotroped with toluene and taken for next step. ¹H NMR (DMSO-d6, 400 MHz): δ 10.55 (bs, 1H), 7.31-7.29 (d, J=8.2 Hz, 1H), 7.17-7.13 (m, 1H), 6.97-6.93 (m, 2H), 3.49 (s, 2H). MS (ESI+): 166.0.

Intermediate Z.36

Ethyl 4H-imidazo[5,1-c][1,4]benzothiazine-3-carboxylate

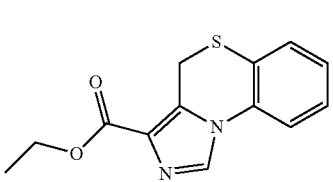 [SMILES: CCOC(=O)c1ncn2c1CSc1ccccc1-2]

To a solution of 2H-1,4-benzothiazin-3(4H)-one (0.7 g, 4.24 mmol, 1 eq) in DMF (20 mL) is added potassium tert-butoxide (0.50 g, 4.49 mmol, 1.06 eq) and the reaction mixture is stirred at RT for 10 min. The reaction mixture is cooled with ice and diethyl chloro phosphonate (1.1 mL, 7.63 mmol, 1.8 eq) is added and the reaction mixture is stirred at RT for 5 minutes. The reaction mixture is then cooled with ice and a solution of ethyl isocyano acetate (0.65 mL, 5.94 mmol, 1.4 eq) in DMF and potassium tert-butoxide (0.66 g, 5.93 mmol, 1.4 eq) are sequentially added and the reaction mixture is stirred at RT overnight. The reaction mixture is acidified with 10 mL of acetic acid, diluted with water and poured into ice and extracted with ethylacetate. The organic layer is dried over Na₂SO₄ and concentrated. The crude is purified by column chromatography to afford the title compound. ¹H NMR (DMSO-d6, 400 MHz): δ 8.50 (s, 1H), 7.90-7.88 (d, J=7.3 Hz, 1H), 7.56-7.54 (m, 1H), 7.39-7.36 (m, 1H), 7.32-7.30 (m, 1H), 4.42 (s, 2H), 4.27 (q, J=7.7 Hz, 2H), 1.29 (t, J=6.6 Hz, 3H). MS (ESI+): 261.2. HPLC (max plot) 95.13%; Rt 3.62 min.

Intermediate Z.37

Ethyl 1-phenyl-4H-imidazo[5,1-c][1,4]benzothiazine-3-carboxlate

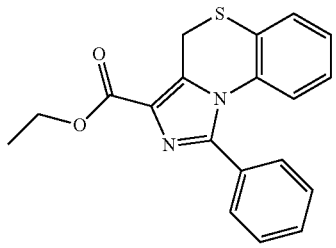 [SMILES: CCOC(=O)c1nc(-c2ccccc2)n2c1CSc1ccccc1-2]

Iodo benzene (0.15 mL, 1.15 mmol, 2 eq), palladium (II) acetate (6.4 mg, 0.03 mmol, 0.05 eq), and CuI (0.22 g, 1.15 mmol, 2 eq) are taken in pressure tube to which is added ethyl 4H-imidazo[5,1-c][1,4]benzothiazine-3-carboxylate (0.15 g, 0.576 mmol, 1 eq) taken in degassed DMF (6 mL) and the contents are heated at 140° C. for 12 h. The reaction mixture is diluted with DCM and filtered through celite. The filtrate is concentrated, passed through a plug of silica gel and concentrated to get the crude product 60 mg which is taken as such to next step. MS (ESI+): 337.2.

EXAMPLES

Procedure AA

Example 1

6-methoxy-3-(morpholin-4-ylcarbonyl)-1-phenyl-1,4-dihydrothiochromeno[4,3-c]pyrazole 5,5-dioxide

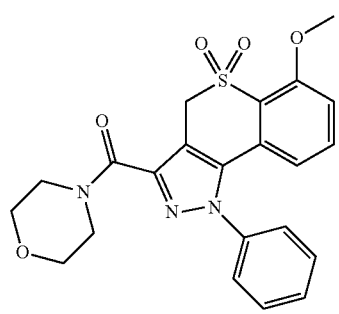 [SMILES: COc1cccc2c1S(=O)(=O)Cc1c(C(=O)N3CCOCC3)nn(-c3ccccc3)c1-2]

To a solution of 6-methoxy-1-phenyl-1,4-dihydrothiochromeno[4,3-c]pyrazole-3-carboxylic acid 5,5-dioxide (0.20 g, 0.54 mmol) in THF (20 mL) is added triethylamine (0.20 mL, 1.63 mmol) followed by 50% propane phosphonic acid anhydride in EtOAc (0.70 mL, 0.347 g, 1.09 mmol). The reaction mixture is cooled to 0° C. and then morpholine (0.049 g, 0.59 mmol) is added and the reaction mixture is stirred overnight at room temperature. The solvent is removed under reduced pressure and the residue is diluted with EtOAc. The organic layer is washed with 10% NaHCO₃ then brine, dried over MgSO₄ and concentrated under reduced pressure. The residue is purified by column chromatography (eluent 1 to 2% MeOH in DCM) to afford the title compound as an off-white solid. ¹H NMR (DMSO-d₆, 400 MHz): δ 7.59-7.58

(m, 3H) 7.46-7.42 (m, 3H) 7.25 (d, J=8.60 Hz, 1H), 6.35 (d, J=7.92 Hz, 1H), 4.82 (s, 2H), 3.95 (br, 2H), 3.90 (s, 3H), 3.65 (br, 4H), 3.59 (br, 2H). MS (ESI+): 440.0. HPLC (max plot) 96.0%; Rt 4.81 min.

Example 2

6-methoxy-1-methyl-3-(morpholin-4-ylcarbonyl)-1,4-dihydrothiochromeno[4,3-c]pyrazole 5,5-dioxide

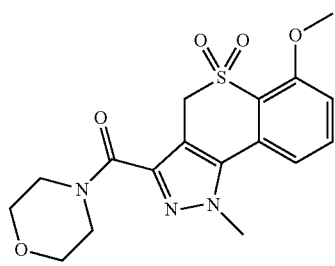 [SMILES: COc1cccc2c1S(=O)(=O)Cc1c(C(=O)N3CCOCC3)nn(C)c1-2]

Following the protocol outlined in Procedure AA, 6-methoxy-1-methyl-3-(morpholin-4-ylcarbonyl)-1,4-dihydrothiochromeno[4,3-c]pyrazole 5,5-dioxide is obtained from 6-methoxy-1-methyl-1,4-dihydro thiochromeno[4,3-c]pyrazole-3-carboxylic acid 5,5-dioxide and morpholine to afford 0.15 g (98%) of the title compound as a white solid. $^1$H NMR (DMSO-$d_6$, 400 MHz): δ 7.77 (t, J=8.08 Hz, 1H), 7.51 (d, J=7.84 Hz, 1H), 7.36 (d, J=8.44 Hz, 1H), 4.72 (m, 2H), 4.15 (s, 3H), 3.95 (br, 2H), 3.91 (s, 3H), 3.64-3.62 (m, 6H). MS (ESI+): 378.0. HPLC (max plot) 97.0%; Rt 2.51 min.

Example 3

3-(morpholin-4-ylcarbonyl)-2,4-dihydrothiochromeno[4,3-c]pyrazole 5,5-dioxide

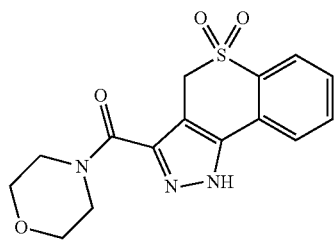 [SMILES: O=C(c1n[nH]c2c1CS(=O)(=O)c1ccccc1-2)N1CCOCC1]

Following the protocol outlined in Procedure AA, 3-(morpholin-4-ylcarbonyl)-2,4-dihydrothiochromeno[4,3-c]pyrazole 5,5-dioxide is obtained from 2,4-dihydrothiochromeno[4,3-c]pyrazole-3-carboxylic acid 5,5-dioxide and morpholine to afford the title compound as a white solid. $^1$H NMR (DMSO-$d_6$, 400 MHz): δ 7.99-7.94 (m, 2H), 7.83 (t, J=7.28 Hz, 1H), 7.65 (t, J=7.6 Hz, 1H), 4.81 (s, 2H), 4.57 (q, J=7.12 Hz, 2H), 3.82-3.54 (m, 8H). MS (ESI+): 334.0. HPLC (max plot) 97.5%; Rt 2.32 min.

Example 4

7-methoxy-1-methyl-3-(morpholin-4-ylcarbonyl)-1,4-dihydrothiochromeno[4,3-c]pyrazole 5,5-dioxide

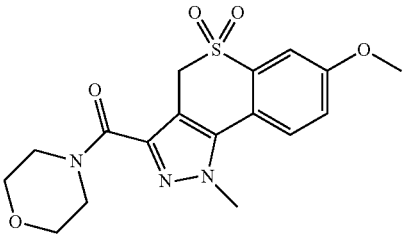 [SMILES: COc1ccc2c(c1)S(=O)(=O)Cc1c(C(=O)N3CCOCC3)nn(C)c1-2]

Following the protocol outlined in Procedure AA, 7-methoxy-1-methyl-3-(morpholin-4-ylcarbonyl)-1,4-dihydrothiochromeno[4,3-c]pyrazole 5,5-dioxide is obtained from 7-methoxy-1-methyl-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 7.98 (d, J=8.7 Hz, 1H), 7.47 (d, J=2.6 Hz, 1H), 7.42-7.40 (m, 1H), 4.77 (s, 2H), 4.20 (s, 3H), 3.95 (brs, 2H), 3.91 (s, 3H), 3.65-3.62 (m, 6H). MS (ESI+): 378.0. HPLC (max plot) 99.0%; Rt 2.94 min.

Example 5

7-methoxy-3-(morpholin-4-ylcarbonyl)-1-phenyl-1,4-dihydrothiochromeno[4,3-c]pyrazole 5,5-dioxide

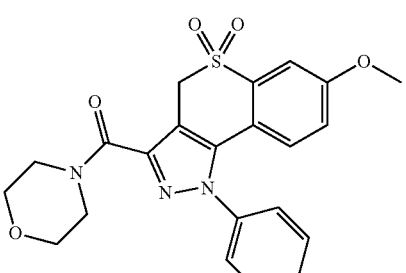

Following the protocol outlined in Procedure AA, 7-methoxy-3-(morpholin-4-ylcarbonyl)-1-phenyl-1,4-dihydrothiochromeno[4,3-c]pyrazole 5,5-dioxide is obtained from 7-methoxy-1-phenyl-1,4-dihydro thiochromeno[4,3-c]pyrazole-3-carboxylic acid 5,5-dioxide and morpholine to afford 0.13 g (74%) of the title compound as a white solid. $^1$H NMR (DMSO-$d_6$, 400 MHz) δ 7.63-7.61 (m, 3H), 7.54-7.44 (m, 3H), 7.17-7.14 (m, 1H), 6.75 (d, J=8.8 Hz, 1H), 4.86 (s, 2H), 3.96-3.94 (m, 2H), 3.84 (s, 3H), 3.66-3.59 (m, 6H). MS (ESI+): 440.0. HPLC (max plot) 98.8%; Rt 4.04 min.

Example 6

1-(3-methylphenyl)-3-(morpholin-4-ylcarbonyl)-1,4-dihydrothiochromeno[4,3-c]pyrazole 5,5-dioxide

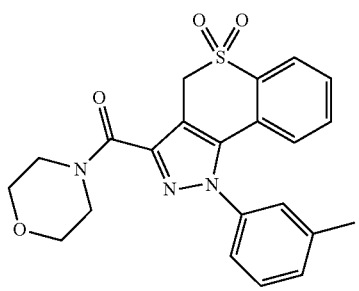 [SMILES: Cc1cccc(-n2nc(C(=O)N3CCOCC3)c3c2-c2ccccc2S(=O)(=O)C3)c1]

Following the protocol outlined in Procedure AA, 1-(3-methylphenyl)-3-(morpholin-4-ylcarbonyl)-1,4-dihydrothiochromeno[4,3-c]pyrazole 5,5-dioxide is obtained from 1-(3-methylphenyl)-1,4-dihydrothio chromeno[4,3-c]pyrazole-3-carboxylic acid 5,5-dioxide and morpholine to afford 0.14 g (78%) of the title compound as a white solid. $^1$H NMR (DMSO-$d_6$, 400 MHz) δ 8.00 (dd, J=7.7 Hz, J=1.3 Hz, 1H), 7.64-7.55 (m, 3H), 7.52-7.43 (m, 2H), 7.37 (s, 1H), 6.84 (dd, J=7.9 Hz, J=1.2 Hz, 1H), 4.89 (s, 2H), 3.94-3.92 (m, 2H), 3.66-3.32 (m, 6H), 2.38 (s, 3H). MS (ESI+): 424.0. HPLC (max plot) 98.8%; Rt 4.18 min.

Example 7

1-(4-methylphenyl)-3-(morpholin-4-ylcarbonyl)-1,4-dihydrothiochromeno[4,3-c]pyrazole 5,5-dioxide

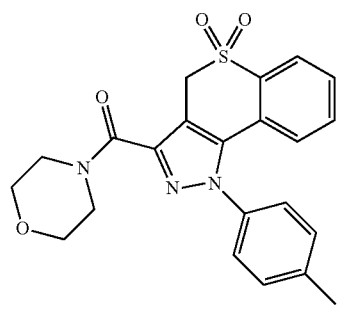 [SMILES: Cc1ccc(-n2nc(C(=O)N3CCOCC3)c3c2-c2ccccc2S(=O)(=O)C3)cc1]

Following the protocol outlined in Procedure AA, 1-(4-methylphenyl)-3-(morpholin-4-ylcarbonyl)-1,4-dihydrothiochromeno[4,3-c]pyrazole 5,5-dioxide is obtained from 1-(4-methylphenyl)-1,4-dihydrothio chromeno[4,3-c]pyrazole-3-carboxylic acid 5,5-dioxide and morpholine to afford the title compound as a white solid. $^1$H NMR (DMSO-$d_6$, 400 MHz) δ 8.00 (dd, J=8.0 Hz, J=1.5 Hz, 1H), 7.62-7.58 (m, 2H), 7.41 (m, 4H), 6.85 (dd, J=6.5 Hz, J=1.4 Hz, 1H), 4.88 (s, 2H), 3.94 (m, 2H), 3.66-3.60 (m, 6H), 2.43 (s, 3H). MS (ESI+): 424.0. HPLC (max plot) 98.3%; Rt 4.18 min.

Example 8

1-(5-fluoro-2-methylphenyl)-3-(morpholin-4-ylcarbonyl)-1,4-dihydrothiochromeno[4,3-c]pyrazole 5,5-dioxide

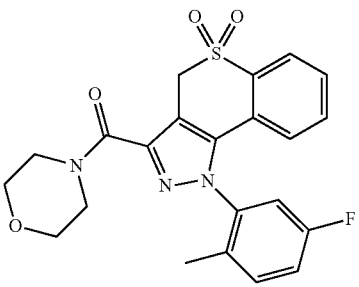 [SMILES: Cc1ccc(F)cc1-n1nc(C(=O)N2CCOCC2)c2c1-c1ccccc1S(=O)(=O)C2]

Following the protocol outlined in Procedure AA, 1-(5-fluoro-2-methylphenyl)-3-(morpholin-4-ylcarbonyl)-1,4-dihydrothiochromeno[4,3-c]pyrazole 5,5-dioxide is obtained from 1-(5-fluoro-2-methylphenyl)-1,4-dihydrothiochromeno[4,3-c]pyrazole-3-carboxylic acid 5,5-dioxide and morpholine to afford 0.15 g (89%) of the title compound as a white solid. $^1$H NMR (DMSO-$d_6$, 400 MHz) δ 8.01 (d, J=7.6 Hz, 1H), 7.65-7.45 (m, 5H), 6.73 (d, J=7.6 Hz, 1H), 4.97-4.86 (m, 2H), 3.92-3.90(m, 2H), 3.70-3.60 (m, 6H), 1.79 (s, 3H). MS (ESI+): 442.0. HPLC (max plot) 99.3%; Rt 4.13 min.

Example 9

1-(3-methoxyphenyl)-3-(morpholin-4-ylcarbonyl)-1,4-dihydrothiochromeno[4,3-c]pyrazole 5,5-dioxide

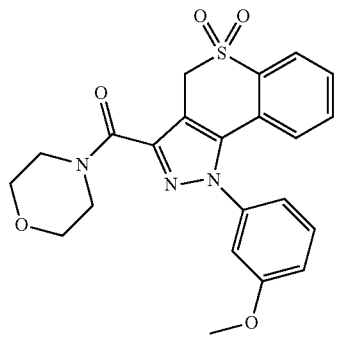 [SMILES: COc1cccc(-n2nc(C(=O)N3CCOCC3)c3c2-c2ccccc2S(=O)(=O)C3)c1]

Following the protocol outlined in Procedure AA, 1-(3-methoxyphenyl)-3-(morpholin-4-ylcarbonyl)-1,4-dihydrothiochromeno[4,3-c]pyrazole 5,5-dioxide is obtained from 1-(3-methoxyphenyl)-1,4-dihydro thiochromeno[4,3-c]pyrazole-3-carboxylic acid 5,5-dioxide and morpholine to afford 0.13 g (73%) of the title compound as a white solid. $^1$H NMR (DMSO-$d_6$, 400 MHz) δ 8.00 (dd, J=7.8 Hz, J=1.5 Hz, 1H), 7.65-7.57 (m, 2H), 7.53-7.48 (m, 2H), 7.20 (dd, J=8.1 Hz, J=2.2 Hz, 1H), 7.13 (s, 1H), 7.02 (d, J=8.1 Hz, J=1.3 Hz, 1H), 4.89 (s, 2H), 3.93-3.92 (m, 2H), 3.80 (s, 3H), 3.66-3.59 (m, 6H). MS (ESI+): 440.0. HPLC (max plot) 98.7%; Rt 3.94 min.

Example 10

1-(4-methoxyphenyl)-3-(morpholin-4-ylcarbonyl)-1,4-dihydrothiochromeno[4,3-c]pyrazole 5,5-dioxide

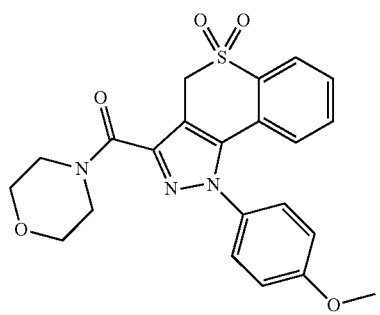 [SMILES: COc1ccc(-n2nc(C(=O)N3CCOCC3)c3c2-c2ccccc2S(=O)(=O)C3)cc1]

Following the protocol outlined in Procedure AA, 1-(4-methoxyphenyl)-3-(morpholin-4-ylcarbonyl)-1,4-dihydrothiochromeno[4,3-c]pyrazole 5,5-dioxide is obtained from 1-(4-methoxyphenyl)-1,4-dihydro thiochromeno[4,3-c]pyrazole-3-carboxylic acid 5,5-dioxide and morpholine to afford the title compound as a white solid. $^1$H NMR (DMSO-$d_6$, 400 MHz) δ 8.01-7.99 (m, 1H), 7.64-7.57 (m, 2H), 7.47-7.43 (m, 2H), 7.16-7.12 (m, 2H), 6.87-6.85 (m, 1H), 4.88 (s, 2H), 3.95-3.93 (m, 2H), 3.85 (s, 3H), 3.66-3.59 (m, 6H). MS (ESI+): 440.0. HPLC (max plot) 97.1%; Rt 3.90 min.

Example 11

3-(morpholin-4-ylcarbonyl)-1-pyridin-2-yl-1,4-dihydrothiochromeno[4,3-c]pyrazole 5,5-dioxide

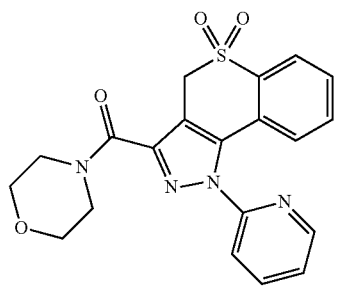

Following the protocol outlined in Procedure AA, 3-(morpholin-4-ylcarbonyl)-1-pyridin-2-yl-1,4-dihydro thiochromeno[4,3-c]pyrazole 5,5-dioxide is obtained from 1-pyridin-2-yl-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.53 (dd, J=7.6 Hz, J=1.6 Hz, 1H), 8.19 (dd, J=7.8 Hz, J=1.8 Hz, 1H), 7.99 (dd, J=8.0 Hz, J=1.6 Hz, 1H), 7.89 (d, J=8.0 Hz, 1H), 7.66-7.56 (m, 3H), 6.92 (d, J=7.6 Hz, 1H), 4.88 (s, 2H), 3.92-3.91 (m, 2H), 3.67-3.60 (m, 6H). MS (ESI+): 411.0. HPLC (max plot) 98.4%; Rt 3.11 min.

Example 12

1-cyclohexyl-3-(morpholin-4-ylcarbonyl)-1,4-dihydrothiochromeno[4,3-c]pyrazole 5,5-dioxide

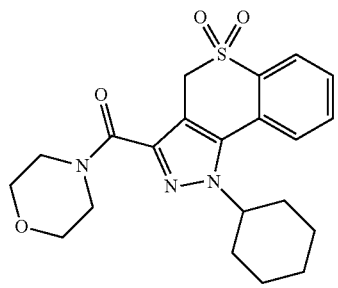 [SMILES: O=C(c1nn(C2CCCCC2)c2c1CS(=O)(=O)c1ccccc1-2)N1CCOCC1]

Following the protocol outlined in Procedure AA, 1-cyclohexyl-3-(morpholin-4-ylcarbonyl)-1,4-dihydro thiochromeno[4,3-c]pyrazole 5,5-dioxide is obtained from 1-cyclohexyl-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.03 (d, J=7.6 Hz, 1H), 7.91 (t, J=7.2 Hz, 1H), 7.84 (d, J=7.7 Hz, 1H), 7.72 (t, J=7.5 Hz, 1H), 4.76 (s, 2H), 4.73-4.68 (m, 1H), 3.93 (m, 2H), 3.64 (m, 6H), 2.03-1.81 (m, 6H), 1.70-1.67 (m, 1H), 1.56-1.53 (m, 2H), 1.49-1.47 (m, 1H). MS (ESI+): 416.0. HPLC (max plot) 99.0%; Rt 4.31 min.

Example 13

6-bromo-1-methyl-3-(morpholin-4-ylcarbonyl)-1,4-dihydrothiochromeno[4,3-c]pyrazole 5,5-dioxide

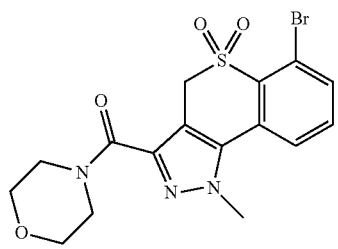

Following the protocol outlined in Procedure AA, 6-bromo-1-methyl-3-(morpholin-4-ylcarbonyl)-1,4-dihydrothiochromeno[4,3-c]pyrazole 5,5-dioxide is obtained from 6-bromo-1-methyl-1,4-dihydrothiochromeno[4,3-c]pyrazole-3-carboxylic acid 5,5-dioxide and morpholine to afford 0.13 g (73%) of the title compound as an off-white solid. $^1$H NMR (DMSO-$d_6$, 400 MHz) δ 7.99 (d, J=7.8 Hz, 1H), 7.92 (d, J=7.9 Hz, 1H), 7.70 (t, J=8.0 Hz, 1H), 4.91 (s, 2H), 4.17 (s, 3H), 3.96 (brs, 2H), 3.65-3.62 (m, 6H). MS (ESI+): 427.0. HPLC (max plot) 97.6%; Rt 3.05 min.

Example 14

6-fluoro-1-methyl-3-(morpholin-4-ylcarbonyl)-1,4-dihydrothiochromeno[4,3-c]pyrazole 5,5-dioxide

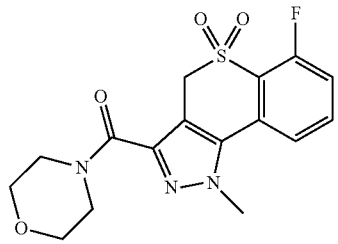 [SMILES: Cn1nc(C(=O)N2CCOCC2)c2c1-c1cccc(F)c1S(=O)(=O)C2]

Following the protocol outlined in Procedure AA, 6-fluoro-1-methyl-3-(morpholin-4-ylcarbonyl)-1,4-dihydrothiochromeno[4,3-c]pyrazole 5,5-dioxide is obtained from 6-fluoro-1-methyl-1,4-dihydrothiochromeno[4,3-c]pyrazole-3-carboxylic acid 5,5-dioxide and morpholine to afford the title compound as an off-white solid. $^1$H NMR (DMSO-$d_6$, 400 MHz) δ 7.92-7.83 (m, 2H), 7.57-7.53 (m, 1H), 4.90 (s, 2H), 4.21 (s, 3H), 3.94 (brs, 2H), 3.65-3.62 (m, 6H). MS (ESI+): 366.0. HPLC (max plot) 97.2%; Rt 2.67 min.

Example 15

6-fluoro-3-(morpholin-4-ylcarbonyl)-1-phenyl-1,4-dihydrothiochromeno[4,3-c]pyrazole 5,5-dioxide

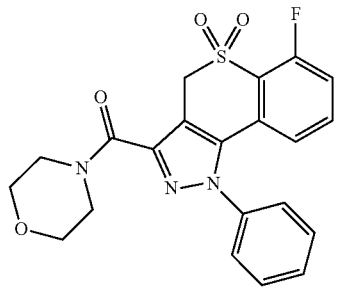 [SMILES: O=C(c1nn(-c2ccccc2)c2c1CS(=O)(=O)c1c(F)cccc1-2)N1CCOCC1]

Following the protocol outlined in Procedure AA, 6-fluoro-3-(morpholin-4-ylcarbonyl)-1-phenyl-1,4-dihydrothiochromeno[4,3-c]pyrazole 5,5-dioxide is obtained from 6-fluoro-1-phenyl-1,4-dihydrothiochromeno[4,3-c]pyrazole-3-carboxylic acid 5,5-dioxide and morpholine to afford the title compound as an off-white solid. $^1$H NMR (DMSO-$d_6$, 400 MHz) δ 7.63-7.56 (m, 4H), 7.52-7.43 (m, 3H), 6.64-6.62 (m, 1H), 5.00 (s, 2H), 3.95-3.93 (m, 2H), 3.66-3.59 (m, 6H). MS (ESI+): 428.0. HPLC (max plot) 97.95%; Rt 3.83 min.

Example 16

8-fluoro-1-methyl-3-(morpholin-4-ylcarbonyl)-1,4-dihydrothiochromeno[4,3-c]pyrazole 5,5-dioxide

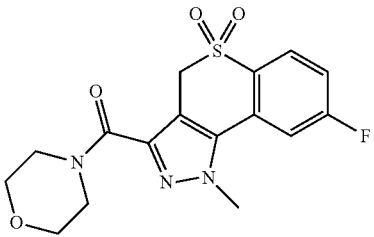 [SMILES: Cn1nc(C(=O)N2CCOCC2)c2c1-c1cc(F)ccc1S(=O)(=O)C2]

Following the protocol outlined in Procedure AA, 8-fluoro-1-methyl-3-(morpholin-4-ylcarbonyl)-1,4-dihydrothiochromeno[4,3-c]pyrazole 5,5-dioxide is obtained from 8-fluoro-1-methyl-1,4-dihydrothiochromeno[4,3-c]pyrazole-3-carboxylic acid 5,5-dioxide and morpholine to afford the title compound as an off-white solid. $^1$H NMR (DMSO-$d_6$, 400 MHz) δ 8.08 (dd, J=8.7 Hz, J=5.6 Hz, 1H), 7.88 (dd, J=10.0 Hz, J=2.3 Hz, 1H), 7.58-7.54 (m, 1H), 4.82 (s, 2H), 4.26 (s, 3H), 3.92 (brs, 2H), 3.65-3.62 (m, 6H). MS (ESI+): 366.0. HPLC (max plot) 98.0%; Rt 2.85 min.

Example 17

8-fluoro-3-(morpholin-4-ylcarbonyl)-1-phenyl-1,4-dihydrothiochromeno[4,3-c]pyrazole 5,5-dioxide

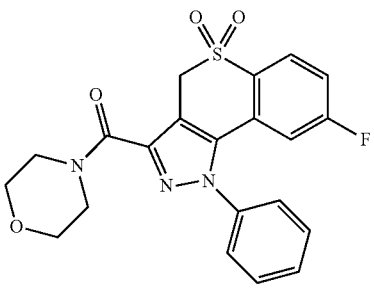

Following the protocol outlined in Procedure AA, 8-fluoro-3-(morpholin-4-ylcarbonyl)-1-phenyl-1,4-dihydrothiochromeno[4,3-c]pyrazole 5,5-dioxide is obtained from 8-fluoro-1-phenyl-1,4-dihydrothiochromeno[4,3-c]pyrazole-3-carboxylic acid 5,5-dioxide and morpholine to afford the title compound as an off-white solid. $^1$H NMR (DMSO-$d_6$, 400 MHz) δ 8.09 (dd, J=8.7 Hz, J=5.5 Hz, 1H), 7.66-7.63 (m, 3H), 7.57-7.55 (m, 2H), 7.52-7.47 (m, 1H), 6.43 (dd, J=10.0 Hz, J=2.4 Hz, 1H), 4.93 (s, 2H), 3.93 (brs, 2H), 3.66-3.60 (m, 6H). MS (ESI+): 428.0. HPLC (max plot) 96.1%; Rt 4.11 min.

Example 18

6-bromo-1-phenyl-1,4-dihydrothiochromeno[4,3-c]pyrazole-3-carboxylic acid 5,5-dioxide

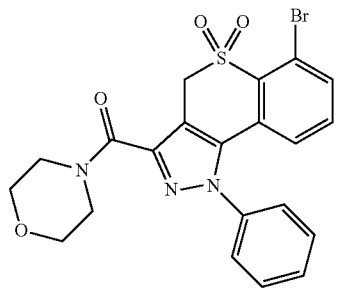

Following the protocol outlined in Procedure AA, 6-bromo-1-phenyl-1,4-dihydrothiochromeno[4,3-c]pyrazole-3-carboxylic acid 5,5-dioxide is obtained from 6-bromo-1-phenyl-1,4-dihydrothiochromeno[4,3-c]pyrazole-3-carboxylic acid 5,5-dioxide and morpholine to afford the title compound as an off-white solid. $^1$H NMR (DMSO-$d_6$, 400 MHz) δ 7.82 (dd, J=8.0 Hz, J=0.7 Hz, 1H), 7.61-7.57 (m, 3H), 7.48-7.45 (m, 2H), 7.38 (t, J=8.0 Hz, 1H), 5.01 (s, 2H), 3.96-3.94 (m, 2H), 3.66-3.59 (m, 6H). MS (ESI+): 488.0. HPLC (max plot) 98.2%; Rt 4.24 min.

Example 19

1-(2-methylphenyl)-3-(morpholin-4-ylcarbonyl)-1,4-dihydrothiochromeno[4,3-c]pyrazole 5,5-dioxide

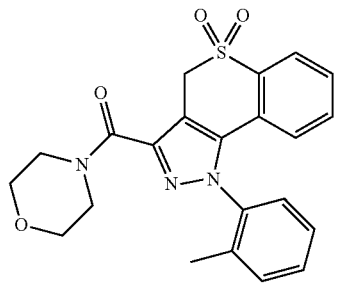

Following the protocol outlined in Procedure AA, 1-(2-methylphenyl)-3-(morpholin-4-ylcarbonyl)-1,4-dihydrothiochromeno[4,3-c]pyrazole 5,5-dioxide is obtained from 1-(2-methylphenyl)-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.00 (dd, J=7.7 Hz, J=1.0 Hz, 1H), 7.63-7.45 (m, 5H), 6.65 (d, J=7.5 Hz, 1H), 4.92 (s, 2H), 3.95-3.90 (m, 2H), 3.69-3.60 (m, 6H), 1.88 (s, 3H). MS (ESI+): 424.0. HPLC (max plot) 97.2%; Rt 4.11 min.

Example 20

1-(2-bromophenyl)-3-(morpholin-4-ylcarbonyl)-1,4-dihydrothiochromeno[4,3-c]pyrazole 5,5-dioxide

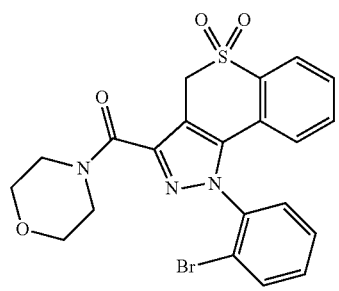

Following the protocol outlined in Procedure AA, 1-(2-bromophenyl)-3-(morpholin-4-ylcarbonyl)-1,4-dihydrothiochromeno[4,3-c]pyrazole 5,5-dioxide is obtained from 1-(2-bromophenyl)-1,4-dihydrothiochromeno[4,3-c]pyrazole-3-carboxylic acid 5,5-dioxide and morpholine to afford the title compound as an off-white solid. $^1$H NMR (DMSO-$d_6$, 400 MHz) δ 8.01 (dd, J=7.8 Hz, J=1.1 Hz, 1H), 7.94 (dd, J=7.7 Hz, J=1.4 Hz, 1H), 7.79 (dd, J=7.6 Hz, J=1.8 Hz, 1H), 7.69-7.56 (m, 4H), 6.65 (d, J=7.2 Hz, 1H), 4.98-4.87 (m, 2H), 3.95-3.92 (m, 2H), 3.70-3.59 (m, 6H). MS (ESI+): 488.0. HPLC 8max plot) 98.7%; Rt 4.01 min.

Example 21

1-(2-fluorophenyl)-3-(morpholin-4-ylcarbonyl)-1,4-dihydrothiochromeno[4,3-c]pyrazole 5,5-dioxide

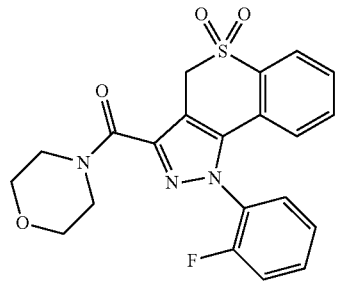 [SMILES: O=C(c1nn(-c2ccccc2F)c2c1CS(=O)(=O)c1ccccc1-2)N1CCOCC1]

Following the protocol outlined in Procedure AA, 1-(2-fluorophenyl)-3-(morpholin-4-ylcarbonyl)-1,4-dihydrothiochromeno[4,3-c]pyrazole 5,5-dioxide is obtained from 1-(2-fluorophenyl)-1,4-dihydrothiochromeno[4,3-c]pyrazole-3-carboxylic acid 5,5-dioxide and morpholine to afford 0.104 g (73%) of the title compound as an off-white solid. $^1$H NMR (DMSO-$d_6$, 400 MHz) δ 8.02 (dd, J=7.7 Hz, J=1.4 Hz, 1H), 7.82-7.70 (m, 2H), 7.67-7.49 (m, 4H), 6.84 (d, J=7.5 Hz, J=1.4 Hz, 1H), 4.94-4.89 (m, 2H), 3.90 (brs, 2H), 3.66-3.60 (m, 6H). MS (ESI+): 428.0. HPLC (max plot) 99.0%; Rt 3.75 min.

Example 22

1-(2-chlorophenyl)-3-(morpholin-4-ylcarbonyl)-1,4-dihydrothiochromeno[4,3-c]pyrazole 5,5-dioxide

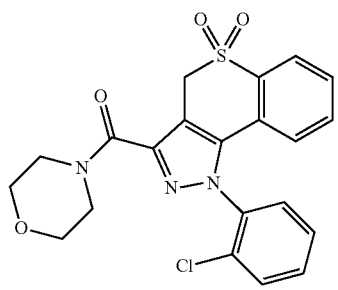 [SMILES: O=C(c1nn(-c2ccccc2Cl)c2c1CS(=O)(=O)c1ccccc1-2)N1CCOCC1]

Following the protocol outlined in Procedure AA, 1-(2-chlorophenyl)-3-(morpholin-4-ylcarbonyl)-1,4-dihydrothiochromeno[4,3-c]pyrazole 5,5-dioxide is obtained from 1-(2-chlorophenyl)-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.01 (d, J=7.4 Hz, 1H), 7.83-7.78 (m, 2H), 7.74-7.55 (m, 4H), 6.68 (d, J=7.7 Hz, 1H), 4.98-4.86 (m, 2H), 3.93-3.84 (m, 2H), 3.70-3.61 (m, 6H). MS (ESI+): 444.0. HPLC (max plot) 99.3%; Rt 3.89 min.

Example 23

1-(2,3-dihydro-1,4-benzodioxin-6-yl)-3-(morpholin-4-ylcarbonyl)-1,4-dihydrothiochromeno[4,3-c]pyrazole 5,5-dioxide

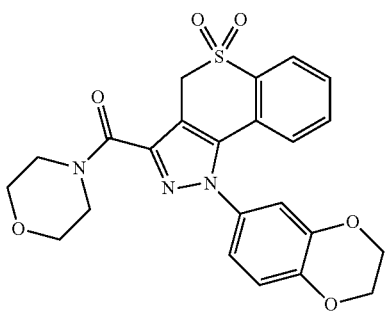 [SMILES: O=C(c1nn(-c2ccc3c(c2)OCCO3)c2c1CS(=O)(=O)c1ccccc1-2)N1CCOCC1]

Following the protocol outlined in Procedure AA, 1-(2,3-dihydro-1,4-benzodioxin-6-yl)-3-(morpholin-4-ylcarbonyl)-1,4-dihydrothiochromeno[4,3-c]pyrazole 5,5-dioxide is obtained from 1-(2,3-dihydro-1,4-benzodioxin-6-yl)-1,4-dihydrothiochromeno[4,3-c]pyrazole-3-carboxylic acid 5,5-dioxide and morpholine to afford 0.103 g (77%) of the title compound as a yellow solid. $^1$H NMR (DMSO-$d_6$, 400 MHz) δ 8.05-8.02 (m, 1H), 7.63-7.61 (m, 2H), 7.10 (d, J=2.4 Hz, 1H), 7.04 (d, J=8.5 Hz, 1H), 6.91-6.90 (m, 2H), 4.87 (s, 2H), 4.34-4.33 (m, 4H), 3.95 (brs, 2H), 3.65-3.59 (m, 6H). MS (ESI+): 468.0. HPLC (max plot) 98.3%; Rt 3.85 min.

Example 24

1-(2-methyl-1,3-benzothiazol-6-yl)-3-(morpholin-4-ylcarbonyl)-1,4-dihydrothiochromeno[4,3-c]pyrazole 5,5-dioxide

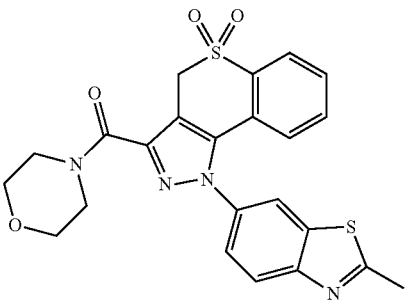 [SMILES: Cc1nc2ccc(-n3nc(C(=O)N4CCOCC4)c4c3-c3ccccc3S(=O)(=O)C4)cc2s1]

Following the protocol outlined in Procedure AA, 1-(2-methyl-1,3-benzothiazol-6-yl)-3-(morpholin-4-ylcarbonyl)-1,4-dihydrothiochromeno[4,3-c]pyrazole 5,5-dioxide is obtained from 1-(2-methyl-1,3-benzothiazol-6-yl)-1,4-dihydrothiochromeno[4,3-c]pyrazole-3-carboxylic acid 5,5-dioxide and morpholine to afford 0.03 g (76%) of the title compound as an off-white solid. $^1$H NMR (DMSO-$d_6$, 400 MHz) δ 8.36 (d, J=2.0 Hz, 1H), 8.09 (d, J=8.6 Hz, 1H), 8.01 (dd, J=7.8 Hz, J=1.0 Hz, 1H), 7.63-7.51 (m, 3H), 6.79 (d, J=7.8 Hz, 1H), 4.91 (s, 2H), 3.96-3.94 (m, 2H), 3.67-3.60 (m, 6H), 2.86 (s, 3H). MS (ESI+): 481.0. HPLC (max plot) 97.2%; Rt 3.70 min.

Example 25

1-(3-bromophenyl)-3-(morpholin-4-ylcarbonyl)-1,4-dihydrothiochromeno[4,3-c]pyrazole 5,5-dioxide

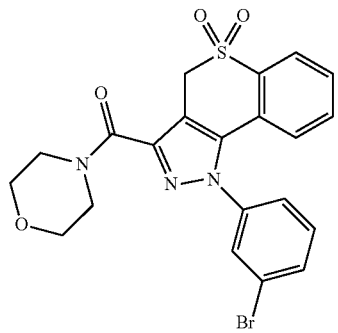 [SMILES: O=C(c1nn(-c2cccc(Br)c2)c2c1CS(=O)(=O)c1ccccc1-2)N1CCOCC1]

Following the protocol outlined in Procedure AA, 1-(3-bromophenyl)-3-(morpholin-4-ylcarbonyl)-1,4-dihydrothiochromeno[4,3-c]pyrazole 5,5-dioxide is obtained from 1-(3-bromophenyl)-1,4-dihydrothiochromeno[4,3-c]pyrazole-3-carboxylic acid 5,5-dioxide and morpholine to afford the title compound as a pale brown solid. $^1$H NMR (DMSO-$d_6$, 400 MHz) δ 8.03-8.01 (m, 1H), 7.88-7.83 (m, 1H), 7.67-7.60 (m, 2H), 7.57-7.50 (m, 2H), 6.91-6.89 (m, 1H), 4.89 (s, 2H), 3.93-3.91 (m, 2H), 3.66-3.59 (m, 6H). MS (ESI+): 488.0. HPLC (max plot) 96.7%; Rt 4.29 min.

Example 26

1-(3-chlorophenyl)-3-(morpholin-4-ylcarbonyl)-1,4-dihydrothiochromeno[4,3-c]pyrazole 5,5-dioxide

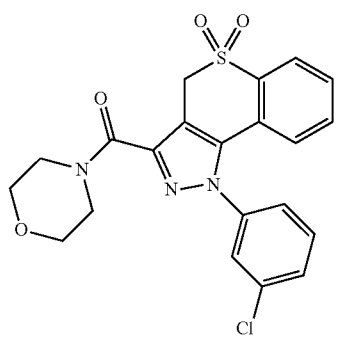 [SMILES: O=C(c1nn(-c2cccc(Cl)c2)c2c1CS(=O)(=O)c1ccccc1-2)N1CCOCC1]

Following the protocol outlined in Procedure AA, 1-(3-chlorophenyl)-3-(morpholin-4-ylcarbonyl)-1,4-dihydrothiochromeno[4,3-c]pyrazole 5,5-dioxide is obtained from 1-(3-chlorophenyl)-1,4-dihydrothiochromeno[4,3-c]pyrazole-3-carboxylic acid 5,5-dioxide and morpholine to afford 0.12 g (78%) of the title compound as an off-white solid. $^1$H NMR (DMSO-$d_6$, 400 MHz) δ 8.02 (dd, J=7.7 Hz, J=1.9 Hz, 1H), 7.77-7.60 (m, 4H), 7.48-7.46 (m, 1H), 6.91-6.89 (m, 1H), 4.89 (s, 2H), 3.93-3.91 (m, 2H), 3.66-3.59 (m, 6H). MS (ESI+): 444.0. HPLC (max plot) 97.8%; Rt 4.22 min.

Example 27

1-(4-bromophenyl)-3-(morpholin-4-ylcarbonyl)-1,4-dihydrothiochromeno[4,3-c]pyrazole 5,5-dioxide

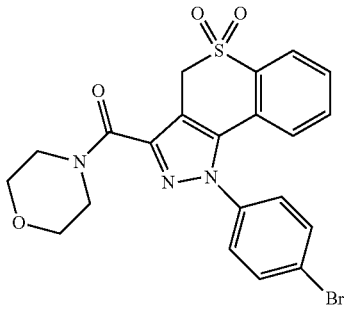 [SMILES: O=C(c1nn(-c2ccc(Br)cc2)c2c1CS(=O)(=O)c1ccccc1-2)N1CCOCC1]

Following the protocol outlined in Procedure AA, 1-(4-bromophenyl)-3-(morpholin-4-ylcarbonyl)-1,4-dihydrothiochromeno[4,3-c]pyrazole 5,5-dioxide is obtained from 1-(4-bromophenyl)-1,4-dihydrothiochromeno[4,3-c]pyrazole-3-carboxylic acid 5,5-dioxide and morpholine to afford the title compound as an off-white solid.

$^1$H NMR (DMSO-$d_6$, 400 MHz) δ 7.78-7.76 (m, 1H), 7.81 (dd, J=6.7 Hz, J=1.7 Hz, 2H), 7.67-7.63 (m, 2H), 7.51 (dd, J=8.6 Hz, J=1.8 Hz, 1H), 6.94-6.92 (m, 2H), 4.89 (s, 2H), 3.93-3.90 (m, 2H), 3.66-3.58 (m, 6H). MS (ESI+): 488.0. HPLC (max plot) 98.3%; Rt 3.85 min.

Example 28

1-(4-fluorophenyl)-3-(morpholin-4-ylcarbonyl)-1,4-dihydrothiochromeno[4,3-c]pyrazole 5,5-dioxide

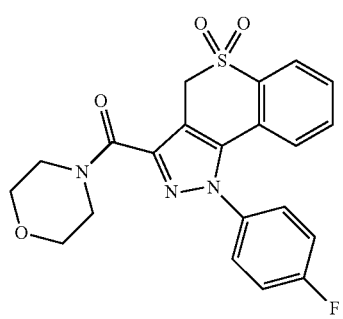 [SMILES: O=C(c1nn(-c2ccc(F)cc2)c2c1CS(=O)(=O)c1ccccc1-2)N1CCOCC1]

Following the protocol outlined in Procedure AA, 1-(4-fluorophenyl)-3-(morpholin-4-ylcarbonyl)-1,4-dihydrothiochromeno[4,3-c]pyrazole 5,5-dioxide is obtained from 1-(4-fluorophenyl)-1,4-dihydrothiochromeno[4,3-c]pyrazole-3-carboxylic acid 5,5-dioxide and morpholine to afford 0.1 g (70%) of the title compound as a white solid. $^1$H NMR (DMSO-$d_6$, 400 MHz) δ 8.01 (d, J=7.7 Hz, 2H), 7.63-7.60 (m, 3H), 7.48-7.44 (m, 2H), 6.85 (d, J=7.4 Hz, 1H), 4.89 (s, 2H), 3.94-3.92 (m, 2H), 3.66-3.60 (m, 6H). MS (ESI+): 428.0. HPLC (max plot) 99.0%; Rt 3.89 min.

Example 29

1-(4-chlorophenyl)-3-(morpholin-4-ylcarbonyl)-1,4-dihydrothiochromeno[4,3-c]pyrazole 5,5-dioxide

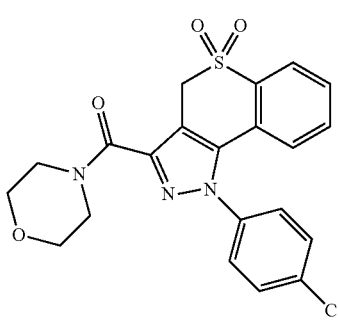

Following the protocol outlined in Procedure AA, 1-(4-chlorophenyl)-3-(morpholin-4-ylcarbonyl)-1,4-dihydrothiochromeno[4,3-c]pyrazole 5,5-dioxide is obtained from 1-(4-chlorophenyl)-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.03-8.01 (m, 1H), 7.69-7.67 (m, 2H), 7.65-7.63 (m, 2H), 7.58 (d, J=8.2 Hz, 1H), 6.95-6.93 (m, 2H), 4.89 (s, 2H), 3.93-3.91 (m, 2H), 3.66-3.60 (m, 6H). MS (ESI+): 444.0. HPLC (max plot) 98.9%; Rt 4.25 min.

Example 30

1-(4-isopropylphenyl)-3-(morpholin-4-ylcarbonyl)-1,4-dihydrothiochromeno[4,3-c]pyrazole 5,5-dioxide

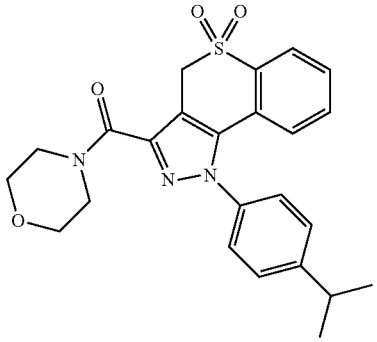 [SMILES: CC(C)c1ccc(-n2nc(C(=O)N3CCOCC3)c3c2-c2ccccc2S(=O)(=O)C3)cc1]

Following the protocol outlined in Procedure AA, 1-(4-isopropylphenyl)-3-(morpholin-4-ylcarbonyl)-1,4-dihydrothiochromeno[4,3-c]pyrazole 5,5-dioxide is obtained from 1-(4-isopropylphenyl)-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.00 (dd, J=7.6 Hz, J=1.7 Hz, 1H), 7.64-7.55 (m, 2H), 7.49-7.42 (m, 4H), 6.84 (dd, J=7.6 Hz, J=1.2 Hz, 1H), 4.89 (s, 2H), 3.95-3.94 (m, 2H), 3.66-3.60 (m, 6H), 3.06-2.99 (m, 1H). 1.26 (d, J=6.9 Hz, 6H). MS (ESI+): 452.0. HPLC (max plot) 96.0%; Rt 4.91 min.

Example 31

1-(4-methylpyridin-3-yl)-3-(morpholin-4-ylcarbonyl)-1,4-dihydrothiochromeno[4,3-c]pyrazole 5,5-dioxide

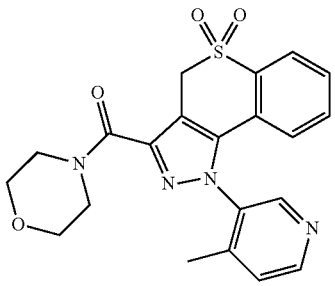 [SMILES: Cc1ccncc1-n1nc(C(=O)N2CCOCC2)c2c1-c1ccccc1S(=O)(=O)C2]

Following the protocol outlined in Procedure AA, 1-(4-methylpyridin-3-yl)-3-(morpholin-4-ylcarbonyl)-1,4-dihydrothiochromeno[4,3-c]pyrazole 5,5-dioxide is obtained from 1-(4-methylpyridin-3-yl)-1,4-dihydrothiochromeno[4,3-c]pyrazole-3-carboxylic acid 5,5-dioxide and morpholine to afford the title compound as a white solid. $^1$H NMR (DMSO-$d_6$, 400 MHz) δ 8.36 (s, 1H), 8.01-7.98 (m, 2H), 7.77 (d, J=8.1 Hz, 1H), 7.65-7.58 (m, 2H), 6.91 (d, J=7.2 Hz, 1H), 4.88 (s, 2H), 3.92-3.91 (m, 2H), 3.67-3.61 (m, 6H), 2.49 (s, 3H). MS (ESI+): 425.0. HPLC (max plot) 98.4%; Rt 3.50 min.

Example 32

3-(morpholin-4-ylcarbonyl)-1-(tetrahydro-2H-pyran-4-yl)-1,4-dihydrothiochromeno[4,3-c]pyrazole 5,5-dioxide

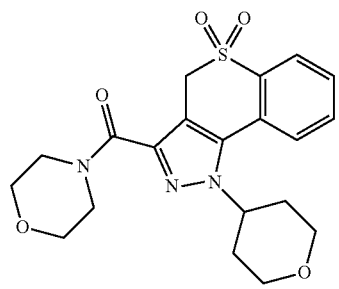 [SMILES: O=C(c1nn(C2CCOCC2)c2c1CS(=O)(=O)c1ccccc1-2)N1CCOCC1]

Following the protocol outlined in Procedure AA, 3-(morpholin-4-ylcarbonyl)-1-(tetrahydro-2H-pyran-4-yl)-1,4-dihydrothiochromeno[4,3-c]pyrazole 5,5-dioxide is obtained from 1-(tetrahydro-2H-pyran-4-yl)-1,4-dihydrothiochromeno[4,3-c]pyrazole-3-carboxylic acid 5,5-dioxide and morpholine to afford 0.05 g (86%) of the title compound as a white solid. $^1$H NMR (DMSO-$d_6$, 400 MHz) δ 8.03 (d, J=7.5 Hz, 1H), 7.94-7.88 (m, 2H), 7.75-7.71 (m, 1H), 5.05-5.00 (m, 1H), 4.78 (s, 2H), 3.98-3.95 (m, 4H), 3.66-3.65 (m, 6H), 3.60-3.55 (m, 2H), 2.18-2.11 (m 2H), 2.09-1.99 (m, 2H). MS (ESI+): 418.0. HPLC (max plot) 97.7%; Rt 3.03 min.

Compounds described below are obtained following procedure AA

---

Example 203: 1-(1H-Indazol-5-yl)-3-(morpholin-4-ylcarbonyl)-1,4-dihydrothiochromeno[4,3-c]pyrazole 5,5-dioxide

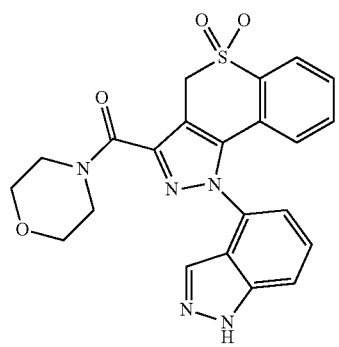

28 mg of the title compound as a white solid. $^1$H NMR (DMSO-$d_6$, 400 MHz): δ 13.36 (s, 1H), 8.26 (s, 1H), 8.02-7.97 (m, 2H), 7.73 (s, 1H), 7.63-7.58 (m, 1H), 7.54-7.50 (m, 1H), 7.19-7.17 (dd, J = 1.8, 8.5 Hz, 1H), 6.82-6.81 (d, J = 7.4 Hz, 1H), 4.91 (s, 2H), 3.97-3.96 (m, 2H), 3.67 (m, 4H), 3.61-3.59 (m, 2H). MS (ESI+): 450.0. HPLC (max plot) 97.68%; Rt 3.27 min.

Example 207: N,N-Dimethyl-3-[3-(morpholin-4-ylcarbonyl)-5,5-dioxidothiochromeno[4,3-c]pyrazol-1 (4H)-yl]benzenesulfonamide

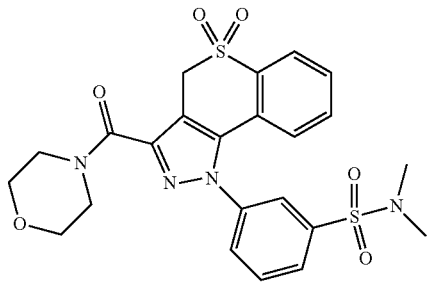 [SMILES: CN(C)S(=O)(=O)c1cccc(-n2nc(C(=O)N3CCOCC3)c3c2-c2ccccc2S(=O)(=O)C3)c1]

57 mg (80%) of the title compound as a pale brown solid. $^1$H NMR (DMSO-d$_6$, 400 MHz): δ 8.04-8.02 (d, J = 7.6 Hz, 1H), 7.97-7.90 (m, 3H), 7.78 (s, 1H), 7.66-7.60 (m, 2H), 6.93-6.91 (d, J = 7.7 Hz, 1H), 4.90 (s, 2H), 3.90 (m, 2H), 3.67 (m, 4H), 3.60 (m, 2H), 2.63 (s, 6H). MS (ESI+): 517.0. HPLC (max plot) 90.61%; Rt 3.75 min.

Example 182: 1-[3-(5-Methyl-1,3,4-oxadiazol-2-yl)phenyl]-3-(morpholin-4-ylcarbonyl)-1,4-dihydrothiochromeno[4,3-c]pyrazole 5,5-dioxide

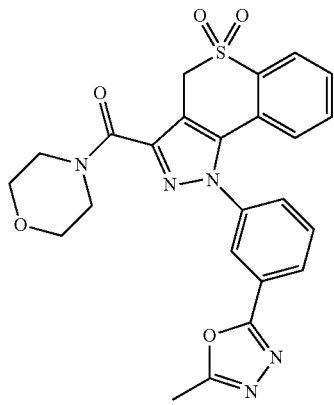 [SMILES: Cc1nnc(-c2cccc(-n3nc(C(=O)N4CCOCC4)c4c3-c3ccccc3S(=O)(=O)C4)c2)o1]

16 mg of the title compound as a white solid. $^1$H NMR (DMSO-d$_6$, 400 MHz): δ 8.21-8.19 (d, J = 7.6 Hz, 1H), 8.06 (s, 1H), 8.06-8.04 (d, J = 9.5 Hz, 1H), 7.85-7.81 (t, J = 8.0 Hz, 1H), 7.78-7.76 (d, J = 8.8 Hz, 1H), 7.66-7.62 (t, J = 7.5 Hz, 1H), 7.59-7.55 (t, J = 7.8 Hz, 1H), 6.94-6.92 (d, J = 7.9 Hz, 1H), 4.91 (s, 2H), 3.92 (m, 2H), 3.67 (m, 4H), 3.60 (m, 2H), 2.57 (s, 3H). MS (ESI+): 492.0. HPLC (max plot) 89.44%; Rt 3.33 min.

Example 183: 1-[3-(5-Methyl-1,3,4-thiadiazol-2-yl)phenyl]-3-(morpholin-4-ylcarbonyl)-1,4-dihydrothiochromeno[4,3-c]pyrazole 5,5-dioxide

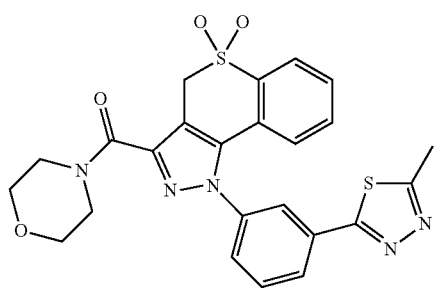 [SMILES: Cc1nnc(-c2cccc(-n3nc(C(=O)N4CCOCC4)c4c3-c3ccccc3S(O)(O)C4)c2)s1]

60 mg of the title compound as a white solid. $^1$H NMR (DMSO-d$_6$, 400 MHz): δ 8.16-8.14 (d, J= 8.0 Hz, 1H ), 8.10 (s, 1H), 8.09-8.02 (m, 1H), 7.79-7.76 (t, J =7.9 Hz, 1H), 7.71-7.68 (m, 1H), 7.66-7.60 (m, 1H), 7.60-7.56 (m, 1H), 6.98-6.96 (d, J = 7.8 Hz, 1H), 4.91 (s, 2H), 3.93 (m, 2H), 3.67 (m, 4H), 3.62-3.61 (m, 2H), 2.77 (s, 3H). MS (ESI+): 508.0. HPLC (max plot) 93.88%; Rt 3.54 min.

Example 196: 1-[3-(3-Methyl-1,2,4-oxadiazol-5-yl)phenyl]-3-(morpholin-4-ylcarbonyl)-1,4-dihydrothiochromeno[4,3-c]pyrazole 5,5-dioxide

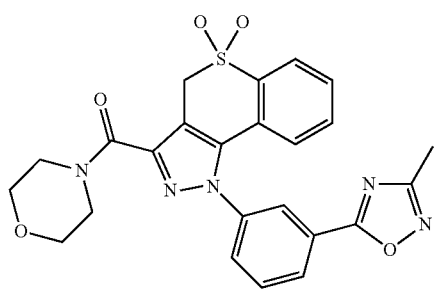 [SMILES: Cc1noc(-c2cccc(-n3nc(C(=O)N4CCOCC4)c4c3-c3ccccc3S(O)(O)C4)c2)n1]

4 mg of the title compound as an off white solid. $^1$H NMR (DMSO-d$_6$, 400 MHz): δ 8.32-8.30 (m, 1H), 8.18 (s, 1H), 8.04-8.02 (d, J = 8.0 Hz, 1H), 7.86-7.85 (m, 2H), 7.66-7.62 (m, 1H), 7.59-7.55 (m, 1H), 6.95-6.94 (d, J = 7.6 Hz, 1H), 4.91 (s, 2H), 3.92-3.91 (m, 2H), 367 (m, 4H), 3.61-3.60 (m, 2H), 2.41 (s, 3H). MS (ESI+): 492.0. HPLC (max plot) 95.31%; Rt 3.87 min.

Example 213: N,N-Dimethyl-1-(5-{3-[3-(morpholin-4-ylcarbonyl)-5,5-dioxidothiochromeno[4,3-c]pyrazol-1 (4H)-yl]phenyl}-1,2,4-oxadiazol-3-yl)-methanamine

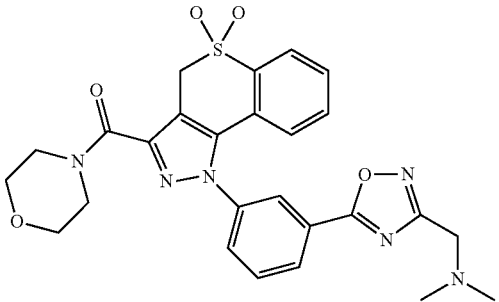 [SMILES: CN(C)Cc1noc(-c2cccc(-n3nc(C(=O)N4CCOCC4)c4c3-c3ccccc3S(O)(O)C4)c2)n1]

4.5 mg of the title compound as an off white solid. $^1$H NMR (DMSO-d$_6$, 400 MHz): δ 8.40-8.35 (m, 2H), 8.15-8.13 (dd, J = 1.4, 7.8 Hz, 1H), 7.73-7.66 (m, 2H), 7.68-7.56 (m, 1H),7.60-7.55 (m, 1H), 7.50-7.45 (m, 1H), 6.91-6.89 (d, J = 7.5 Hz, 1H), 4.77 (s, 2H), 4.19-4.21 (m, 2H), 3.90-3.85 (m, 4H), 3.80-3.75 (m, 2H), 3.70 (m, 2H), 2.39 (s, 6H). MS (ESI+): 535.0. HPLC (max plot) 97.78%; Rt 2.80 min.

Example 214: 1-{3-[3-(Methoxymethyl)-1,2,4-oxadiazol-5-yl]phenyl)-3-(morpholin-4-ylcarbonyl)-1,4-dihydrothiochromeno[4,3-c]pyrazole 5,5-dioxide

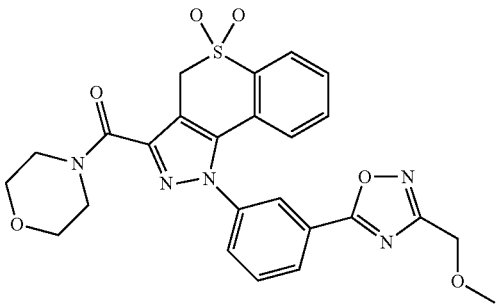 [SMILES: COCc1noc(-c2cccc(-n3nc(C(=O)N4CCOCC4)c4c3-c3ccccc3S(O)(O)C4)c2)n1]

62 mg of the title compound as an off white solid. $^1$H NMR (DMSO-d$_6$, 400 MHz): δ 8.35-8.34 (m, 1H), 8.23 (s, 1H), 8.04-8.02 (d, J = 7.8 Hz, 2H), 7.86 (m, 2H),7.66-7.62 (m, 1H), 7.59-7.55 (m, 1H), 6.96-6.94 (d, J = 8.0 Hz, 1H), 4.91 (s, 2H), 4.62 (s, 2H), 3.92 (m, 2H), 3.67 (m, 4H), 3.60 (m, 2H), 3.36 (s, 3H). MS (ESI+): 522.0. HPLC (max plot) 95.16%; Rt 10.32 min.

Example 210: 1-Methyl-5-[3-(morpholin-4-ylcarbonyl)-5,5-dioxidothiochromeno[4,3-c]pyrazol-1 (4H)-pyridin-2 (1H)-one

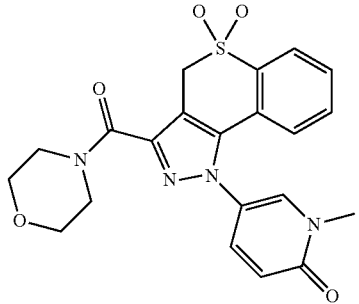 [SMILES: Cn1cc(-n2nc(C(=O)N3CCOCC3)c3c2-c2ccccc2S(O)(O)C3)ccc1=O]

21 mg of the title compound as a white solid. $^1$H NMR (DMS0-d$_6$, 400 MHz): δ 8.41-8.42 (d, J = 2.7 Hz, 1H), 8.03-8.00 (dd, J = 1.8, 4.8 Hz, 1H), 7.92-7.89 (dd, J = 2.7, 8.8, 1H), 7.65-7.63 (t, J = 3.6 Hz, 1H), 7.05-7.03 (d, J = 8.8 Hz, 2H), 6.98-6.96 (d, J = 4.5 Hz, 1H), 4.89 (s, 2H), 3.95-3.92 (m, 5H), 3.66 (m, 4H), 3.61-3.60 (m, 2H). MS (ESI+): 441.0. HPLC (max plot) 95.93%; Rt 10.32 min.

Example 204: 1-(2-Benzyl-2H-indazol-5-yl)-3-(morpholin-4-ylcarbonyl)-1,4-dihydrothiochromeno[4,3-c]pyrazole 5,5-dioxide

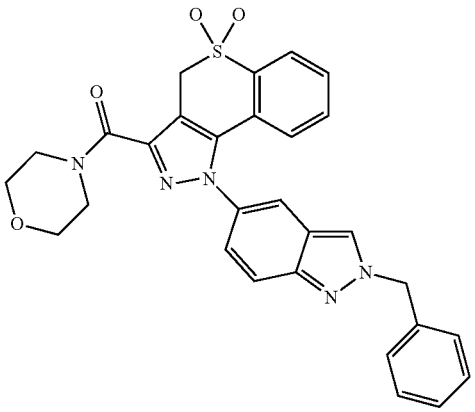 [SMILES: O=C(c1nn(-c2ccc3nn(Cc4ccccc4)cc3c2)c2c1CS(O)(O)c1ccccc1-2)N1CCOCC1]

8.5 mg of the title compound as a yellow solid. $^1$H NMR (DMSO-d$_6$, 400 MHz): δ 8.71 (s, 1H), 8.01-7.99 (dd, J = 1.2, 7.9 Hz, 1H), 7.94-7.87 (m, 1H), 7.87 (s, 1H), 7.61-7.58 (m, 1H), 7.54-7.49 (m, 1H), 7.4-7.32 (m, 4H), 7.02-7.0 (m, 1H), 6.99-6.90 (m, 1H), 5.75 (s, 1H), 4.9 (s, 1H), 3.97 (m, 1H), 3.66 (m, 4H), 3.60 (m, 2H). MS (ESI+): 540.0. HPLC (max plot) 96.2%; Rt 4.35 min.

Example 209: N-{3-[3-(Morpholin-4-ylcarbonyl)-5,5-dioxidothiochromeno[4,3-c]pyrazol-1(4H)-yl]phenyl}morpholine-4-carboxamide

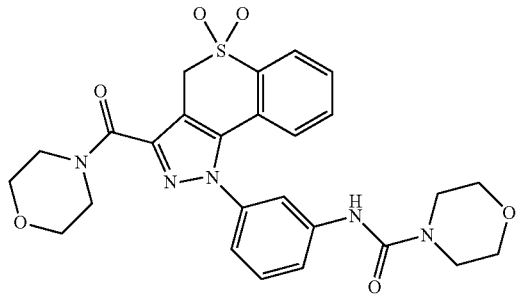 [SMILES: O=C(Nc1cccc(-n2nc(C(=O)N3CCOCC3)c3c2-c2ccccc2S(O)(O)C3)c1)N1CCOCC1]

16 mg of the title compound as an off white solid. ¹H NMR (DMSO-d$_6$, 400 MHz): δ 8.88 (s, 1H), 8.01 (dd, J = 1.9, 7.6 Hz, 1H), 7.74 (d, J = 8.4 Hz, 1H), 7.64-7.58 (m, 3H), 7.50-7.46 (t, J = 8.0 Hz, 1H), 7.13-7.08 (dd, J = 1.2, 7.3 Hz, 1H), 6.91-6.89 (t, J = 7.2 Hz, 1H), 4.89 (s, 2H), 3.92 (m, 2H), 3.66 (m, 4H), 3.61-3.56 (m, 6H), 3.40-3.38 (m, 4H). MS (ESI+): 538.0. HPLC (max plot) 92.90%; Rt 3.25 min.

Example 312: 1-(2-Isopropylphenyl)-3-(morpholin-4-ylcarbonyl)-1,4-dihydrothiochromeno[4,3-c]pyrazole 5,5-dioxide

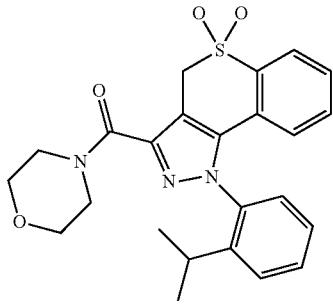 [SMILES: CC(C)c1ccccc1-n1nc(C(=O)N2CCOCC2)c2c1-c1ccccc1S(O)(O)C2]

69 mg of the title compound as a white solid. ¹H NMR (400 MHz, DMSO-d$_6$) δ: 7.98 (d, J = 1.2 Hz, 1H), 7.65-7.60 (m, 4H), 7.44-7.43 (m, 2H), 6.63 (d, J = 7.2 Hz, 1H), 4.92 (m, 2H), 3.68-3.60 (m, 8H), 2.32-2.29 (m, 1H), 1.06 (t, J = 6.8 Hz, 3H), 0.87 (t, J = 6.8 Hz, 3H). MS (ESI+): 452.0. HPLC (max plot): 99.3%; Rt 4.63 min.

Example 313: 1-(2-Methoxyphenyl)-3-(morpholin-4-ylcarbonyl)-1,4-dihydrothiochromeno[4,3-c]pyrazole 5,5-dioxide

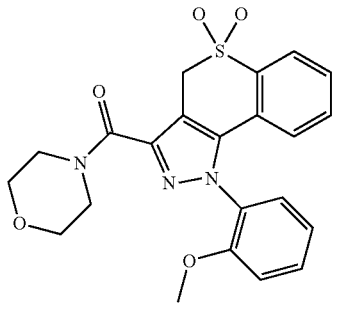 [SMILES: COc1ccccc1-n1nc(C(=O)N2CCOCC2)c2c1-c1ccccc1S(O)(O)C2]

90 mg (76%) of the title compound as a white solid. ¹H NMR (400 MHz, DMSO-d$_6$) δ: 7.98 (dd, J = 1.3, 7.6 Hz, 1H), 7.65-7.52 (m, 4H), 7.30 (d, J = 8.4 Hz, 1H), 7.21-7.17 (m, 1H), 6.80 (d, J = 7.8 Hz, 1H), 4.96-4.81 (m, 2H), 3.94 (m, 2H) 3.66-3.60 (m, 6H), 3.57 (s, 3H). MS (ESI+): 440.0. HPLC (max plot): 99.5%; Rt 3.80 min.

Example 176: 1-(3-Fluorophenyl)-3-(morpholin-4-ylcarbonyl)-1,4-dihydrothiochromeno[4,3-c]pyrazole 5,5-dioxide

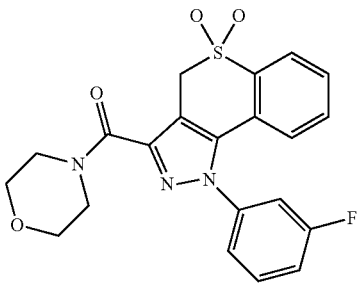 [SMILES: O=C(c1nn(-c2cccc(F)c2)c2c1CS(O)(O)c1ccccc1-2)N1CCOCC1]

42 mg of the title compound as a white solid. ¹H NMR (DMSO-d$_6$, 400 MHz): δ 8.03-8.02 (m, 1H), 7.66-7.58 (m, 4H), 7.50 (m, 1H), 7.35-7.33 (d, J = 7.7 Hz, 1H), 6.91-6.89 (d, J = 7.3 Hz, 1H), 4.89 (s, 2H), 3.93 (m, 2H), 3.66 (m, 4H), 3.60 (m, 2H). MS (ESI+): 428.0. HPLC (max plot) 96.79%; Rt 3.97 min.

Example 176: 1-(3-Cyanophenyl)-3-(morpholin-4-ylcarbonyl)-1,4-dihydrothiochromeno[4,3-c]pyrazole 5,5-dioxide

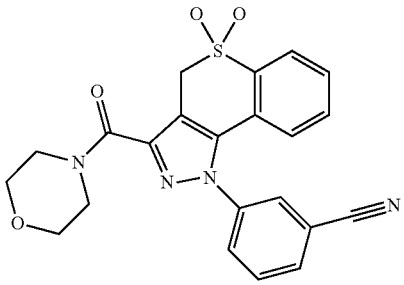 [SMILES: N#Cc1cccc(-n2nc(C(=O)N3CCOCC3)c3c2-c2ccccc2S(O)(O)C3)c1]

23 mg of the title compound. 1H NMR (400 MHz, DMSO-d6) δ = 8.25 (s, 1H), 8.10 (d, J = 7.7 Hz, 1H), 8.03 (d, J = 7.5 Hz, 1H), 7.86-7.77 (m, 2H), 7.68-7.58 (m, 2H), 6.89 (d, J = 7.7 Hz, 1H), 4.90 (s, 1H), 3.92 (bs, 2H), 3.67-3.61 (m, 6H). MS (ESI+): 435.0. HPLC: HPLC (max plot) 99.22%; Rt 3.66 min.

Example 130: 1-[4-(Methylsulfonyl)phenyl]-3-(morpholin-4-ylcarbonyl)-1,4-dihydrothiochromeno[4,3-c]pyrazole 5,5-dioxide

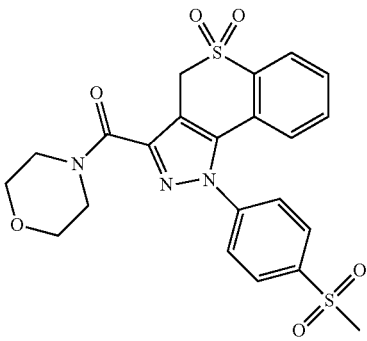 [SMILES: CS(=O)(=O)c1ccc(-n2nc(C(=O)N3CCOCC3)c3c2-c2ccccc2S(=O)(=O)C3)cc1]

36 mg of the title compound as a pale brown solid. $^1$H NMR (DMSO-d$_6$, 400 MHz): δ 8.15-8.13 (d, J = 8.6 Hz, 2H), 8.05-8.02 (dd, J = 1.6, 7.7 Hz, 1H), 7.84-7.82 (d, J = 8.6 Hz, 2H), 7.65-7.61 (m, 2H), 6.96-6.95 (d, J = 7.4 Hz, 1H), 4.90 (s, 2H), 3.92 (m, 2H), 3.67 (m, 4H), 3.61-3.60 (m, 2H), 3.33 (s, 3H). MS (ESI+): 487.8. HPLC (max plot) 98.79%; Rt 3.21 min.

Example 66: N-{4-[3-(Morpholin-4-ylcarbonyl)-5,5-dioxidothiochromeno[4,3-c]pyrazol-1(4H)-yl]benzyl}methanesulfonamide

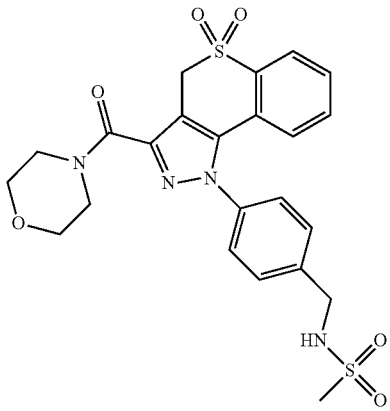 [SMILES: CS(=O)(=O)NCc1ccc(-n2nc(C(=O)N3CCOCC3)c3c2-c2ccccc2S(=O)(=O)C3)cc1]

26 mg of the title compound. $^1$H NMR (400 MHz, DMSO-d$_6$) δ = 8.02 (d, J = 7.3 Hz, 1H), 7.65-7.53 (m, 6H), 7.09 (d, J = 3.5 Hz, 1H), 6.86 (d, J = 8.0 Hz, 1H), 4.90 (s, 1H), 5.00 (s, 1H), 3.95 (brs, 2H), 3.66-3.61 (m, 6H), 2.61 (s, 3H). MS (ESI+): 517. HPLC (max plot) 96.19%; Rt 3.19 min.

Example 88: 3-(Morpholin-4-ylcarbonyl)-1-pyridin-3-yl-1,4-dihydrothiochromeno[4,3-c]pyrazole 5,5-dioxide

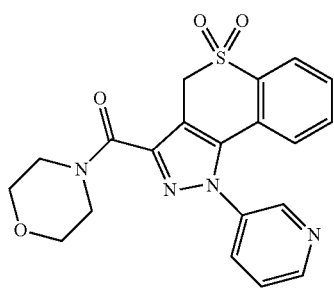 [SMILES: O=C(c1nn(-c2cccnc2)c2c1CS(=O)(=O)c1ccccc1-2)N1CCOCC1]

50 mg of the title compound as a pale brown solid. 1H NMR (400 MHz, DMSO-d6): δ 8.82-8.80 (m, 2H), 8.06-8.02 (m, 2H), 7.68-7.59 (m, 3H), 6.90-6.88 (m, 1H), 4.91 (s, 2H), 3.93-3.91 (m, 2H), 3.67 (m, 4H), 3.61-3.60 (m, 2H). MS (ESI+): 411.0. HPLC (max plot) 96.65%; Rt 2.60 min.

Example 131: 1-(6-Methoxypyridin-3-yl)-3-(morpholin-4-ylcarbonyl)-1,4-dihydrothiochromeno[4,3-c]pyrazole 5,5-dioxide

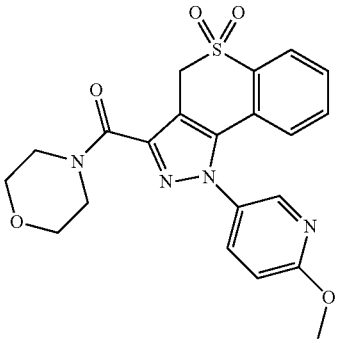

26 mg of the title compound as an off white solid. $^1$H NMR (DMSO-$d_6$, 400 MHz): δ 8.42-8.41 (m, 1H), 8.03-8.00 (m, 1H), 7.92-7.89 (dd, J = 2.9, 8.8 Hz, 1H), 7.65-7.62 (m, 2H), 7.05-7.03 (d, J = 8.8 Hz, 1H), 6.98-6.96 (m, 1H), 4.89 (s, 2H), 3.95-3.92 (m, 5H), 3.66 (m, 4H), 3.61-3.60 (m, 2H). MS (ESI+): 441. HPLC (max plot) 98.38%; Rt 3.52 min Example 138: 1-[3-(Methylsulfonyl)phenyl]-3-(morpholin-4-ylcarbonyl)-1,4-dihydrothiochromeno[4,3-c]pyrazole 5,5-dioxide

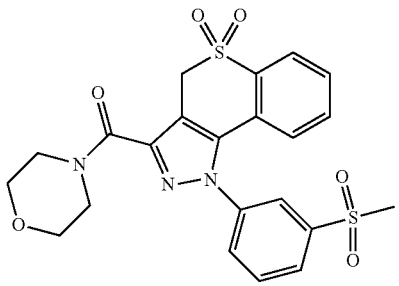 [SMILES: CS(=O)(=O)c1cccc(-n2nc(C(=O)N3CCOCC3)c3c2-c2ccccc2S(=O)(=O)C3)c1]

26 mg of the title compound as an off white solid. $^1$H NMR (DMSO-$d_6$, 400 MHz): δ 8.16-8.14 (d, J = 7.5 Hz, 1H), 8.06-8.02 (m, 2H), 7.95-7.87 (m, 2H), 7.68-7.58 (m, 2H), 6.92-6.90 (d, J = 7.8 Hz, 1H), 4.91 (s, 2H), 3.89-3.88 (m, 2H), 3.67 (s, 4H), 3.61-3.60 (m, 2H, 3.32 (s, 3H). MS (ESI+): 488.0. HPLC (max plot) 99.47%; Rt 3.22 min.

Example 73: 1-Cyclopentyl-3-(morpholin-4-ylcarbonyl)-1,4-dihydrothiochromeno[4,3-c]pyrazole 5,5-dioxide

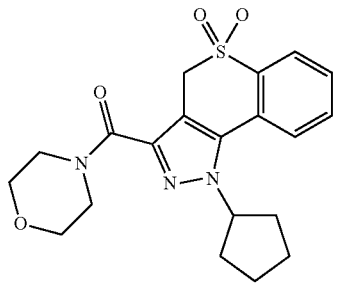

65 mg of the title compound as a white solid. 1H NMR (400 MHz, DMSO-d6) δ = 8.02 (d, J = 6.9 Hz, 1H), 7.97 (d, J = 7.7 Hz, 1H), 7.89 (t, J = 7.6 Hz, 1H), 7.72 (t, J = 7.7 Hz, 1H), 5.30 (t, J = 5.5 Hz, 1H), 4.77 (s, 2H), 4.65 (t, J = 5.8 Hz, 1H), 3.94 (brs, 2H), 3.65-3.63 (m, 6H), 2.25-2.19 (m, 2H), 2.06-2.03 (m, 2H), 1.87-1.86 (m, 2H), 1.71-1.70 (m, 2H).
MS (ESI+): 402.0. HPLC (max plot) 98.51%; Rt 3.65 min.

Example 194: 3-(Morpholin-4-ylcarbonyl)-1-[3-(morpholin-4-ylcarbonyl)cyclohexyl]-1,4-dihydrothiochomeno[4,3-c]pyrazole 5,5-dioxide

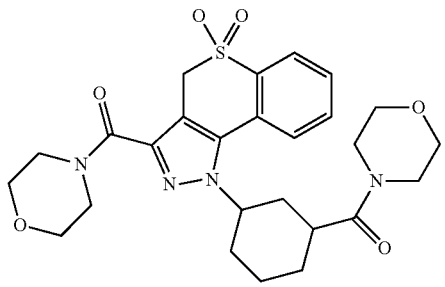

6.9 mg of the title compound as an off white solid. $^1$H NMR (DMSO-$d_6$, 400 MHz): δ 8.19-8.17 (d, J = 7.8 Hz, 1H), 7.75-7.73 (d, J = 7.8 Hz, 1H), 7.65-7.61 (t, J = 7.6 Hz, 1H), 7.51-7.49 (d, J = 7.9 Hz, 1H), 4.81-4.77 (m, 2H), 4.65-4.61 (m, 1H), 4.59 (m, 1H), 4.22-4.20 (m, 2H), 3.80 (m, 6H), 3.68-3.62 (m, 4H), 3.52 (m, 2H), 2.7 (m, 1H), 2.49-2.46 (m, 1H), 2.17-2.10 (m, 4H), 1.9 (m, 1H), 1.8-1.6 (m, 3H). MS (ESI+): 529.0. HPLC (max plot) 96.46%; Rt 3.24 min.

-continued

Example 193: 3-(Morpholin-4-ylcarbonyl)-1-[3-(piperidin-1-ylcarbonyl)cyclohexyl]-1,4-dihydrothiochromeno[4,3-c]pyrazole 5,5-dioxide

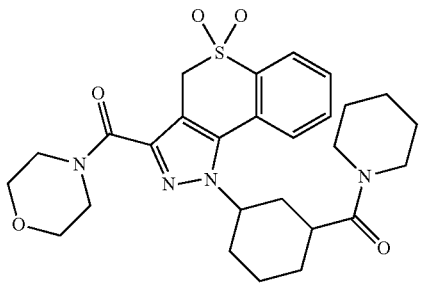 [SMILES: O=C(c1nn(C2CCCC(C(=O)N3CCCCC3)C2)c2c1CS(O)(O)c1ccccc1-2)N1CCOCC1]

12 mg of the title compound as an off white semi solid. $^1$H NMR (DMSO-d$_6$, 400 MHz): δ 8.18-8.17 (d, J = 6.8 Hz, 1H), 7.77-7.73 (m, 1H), 7.64-7.61 (t, J = 7.7 Hz, 1H), 7.53-7.51 (d, J = 7.8 Hz, 1H), 4.79-4.75 (d, J = 16.5 Hz, 1H), 4.69-4.65 (d, J = 16.5 Hz, 1H), 4.59-4.57 (m, 1H), 3.59-3.43 (m, 4H), 2.77-2.71 (m, 1H), 2.49-2.40 (m, 1H), 2.18-2.07 (m, 4H), 1.88-1.85 (m, 1H), 1.70-1.64 (m, 3H). MS (ESI+): 527.0. HPLC (max plot) 97.6%; Rt 3.96 min Example 170: 1-(4,4-Difluorocyclohexyl)-3-(morpholin-4-ylcarbonyl)-1,4-dihydrothiochromeno[4,3-c]pyrazole 5,5-dioxide

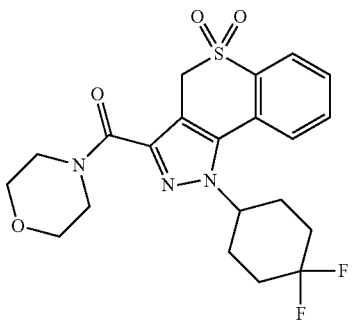 [SMILES: O=C(c1nn(C2CCC(F)(F)CC2)c2c1CS(=O)(=O)c1ccccc1-2)N1CCOCC1]

61 mg of the title compound as a white solid. $^1$H NMR (DMSO-d$_6$, 400 MHz): δ 8.04-8.03 (d, J = 7.4 Hz, 1H), 7.94-7.88 (m, 2H), 7.76-7.72 (m, 1H), 5.03 (m, 1H), 4.77 (s, 2H), 3.89-3.88 (m, 2H), 3.65-3.63 (m, 6H), 2.16-2.14 (m, 8H). MS (ESI+): 452.0. HPLC (max plot) 98.29%; Rt 4.15 min.

Example 171: 1-(3,3-Dimethylcyclohexyl)-3-(morpholin-4-ylcarbonyl)-1,4-dihydrothiochromeno[4,3-c]pyrazole 5,5-dioxide

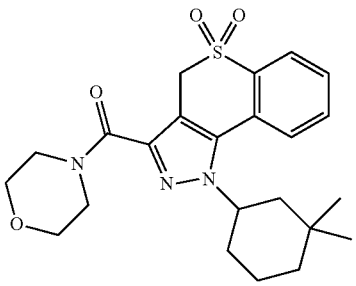 [SMILES: CC1(C)CCCC(n2nc(C(=O)N3CCOCC3)c3c2-c2ccccc2S(=O)(=O)C3)C1]

61 mg of the title compound as a pale pink solid. NMR (DMSO-d$_6$, 400 MHz): δ 8.04-8.02 (d, J = 7.8 Hz, 1H), 7.93-7.90 (m, 1H), 7.85-7.83 (d, J = 7.8 Hz, 1H), 7.72-7.70 (m, 1H), 4.92-4.85 (m, 1H), 4.76 (s, 2H), 3.90 (m, 2H), 3.64 (m, 6H), 2.05-2.02 (m, 1H), 1.88-1.86 (m, 1H), 1.71-1.65 (m, 4H), 1.41-1.37 (m, 1H), 1.34-1.30 (m, 1H), 1.26 (s, 3H), 1.22 (s, 3H). MS (ESI+): 444.0. HPLC (max plot) 92.55%; Rt 4.99 min.

Example 127: 1-(4-Methylcyclohexyl)-3-(morpholin-4-ylcarbonyl)-1,4-dihydrothiochromeno[4,3-c]pyrazole 5,5-dioxide

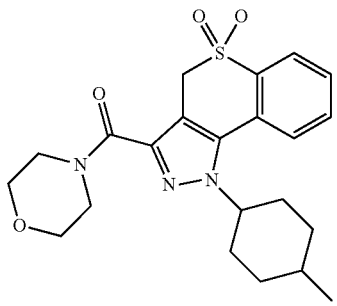

17 mg of the title compound as a white solid. $^1$H NMR (DMSO-d$_6$, 400 MHz): δ 8.03-8.01 (d, J = 7.5 Hz, 1H), 7.93-7.88 (m, 1H), 7.85-7.83 (d, J = 7.7 Hz, 1H), 7.74-7.70 (t, J = 7.8 Hz, 1H), 4.77 (s, 2H), 4.68 (m, 1H), 3.96-3.92 (m, 2H), 3.65-3.64 (m, 6H), 2.04-2.01 (m, 2H), 1.95 (m, 1H), 1.90-1.89 (m, 2H), 1.70-1.57 (m, 2H), 1.48 (m, 2H), 1.28-1.25 (m, 3H). MS (ESI+): 430.3. HPLC (max plot) 97.73%; Rt 5.99 min.

Example 94: 1-(4-tert-Butylcyclohexyl)-3-(morpholin-4-ylcarbonyl)-1,4-dihydrothiochromeno[4,3-c]pyrazole 5,5-dioxide

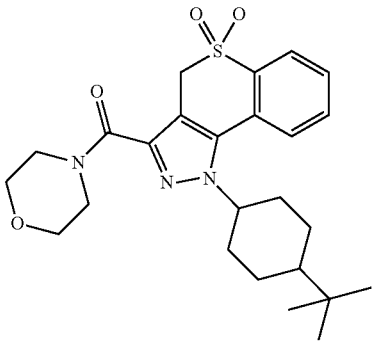

54 mg of the title compound as a white solid. $^1$H NMR (400 MHz, DMSO-d$_6$) δ = 8.03-8.01 (d, J = 7.8 Hz, 1H), 7.94-7.90 (m, 1H), 7.86-7.84 (d, J = 7.8 Hz, 1H), 7.74-7.70 (t, J = 7.5 Hz, 1H), 4.77 (s, 2H), 4.68 (m, 1H), 3.95 (m, 2H), 3.64 (m, 6H), 2.12-2.09 (d, J = 11.2 Hz, 2H), 1.95-1.85 (m, 4H), 1.32-1.26 (m, 2H), 1.16-1.13 (m, 1H), 0.88 (s, 9H). MS (ESI+): 472.3. HPLC (max plot) 97.00%; Rt 5.63 min.

Example 98: 4-[3-(Morpholin-4-ylcarbonyl)-5,5-dioxidothiochromeno[4,3-c]pyrazol-1(4H)-yl]cyclohexanol

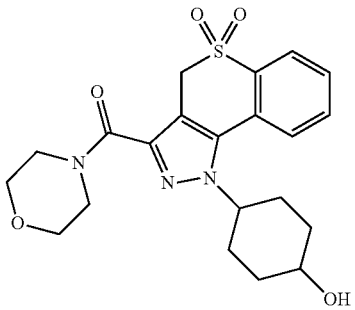 [SMILES: O=C(c1nn(C2CCC(O)CC2)c2c1CS(=O)(=O)c1ccccc1-2)N1CCOCC1]

0.009 g of the title compound as a pale brown solid. $^1$H NMR (DMSO-d$_6$, 400 MHz) δ 8.03-8.001 (d, J = 7.8 Hz, 1H), 7.93-7.74 (m, 2H), 7.74-7.70 (m, 1H), 4.75 (s, 2H), 4.71-4.70 (d, J = 4.2 Hz, 1H), 3.90 (m, 2H), 3.65-3.63 (m, 6H), 3.55 (m, 2H), 2.00-1.91 (m, 6H), 1.51-1.42 (m, 2H). MS (ESI+): 432.0. HPLC (max plot): 92.66%; Rt 2.67 min Example 99: 3-(Morpholin-4-ylcarbonyl)-1-tetrahydro-2H-pyran-3-yl)-1,4-dihydrothiochromeno[4,3-c]pyrazole 5,5-dioxide

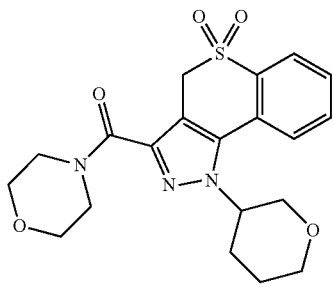

MSC2324368A, MC006_300
176 mg (74%) of the title compound as a white solid.
1H NMR (DMSO-d6, 400 MHz) δ 8.04-8.02 (d, J = 7.4 Hz, 1H), 7.92 (m, 2H), 7.75-7.71 (m, 1H), 4.88 (m, 1H), 4.78 (s, 2H), 4.03-4.02 (m, 1H), 3.90 (m, 3H), 3.75-3.60 (m, 7H), 3.40 (m, 1H), 2.21-2.15 (m, 2H), 1.84-1.79 (m, 2H). MS (ESI+): 418.0: HPLC (max plot): 98.53%; Rt 3.27 min Example 78: 1-Cycloheptyl-3-(morpholin-4-ylcarbonyl)-1,4-dihydrothiochromeno[4,3-c]pyrazole 5,5-dioxide

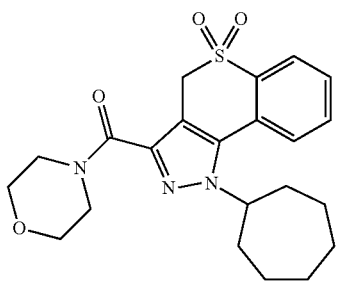 [SMILES: O=C(c1nn(C2CCCCCC2)c2c1CS(=O)(=O)c1ccccc1-2)N1CCOCC1]

38 mg of the title compound as a white solid. $^1$H NMR (400 MHz, DMSO-d$_6$): δ 8.03-8.01 (dd, J = 1.1, 7.8 Hz, 1H), 7.93-7.89 (m, 1H), 7.85-7.83 (d, J = 7.5 Hz, 1H), 7.73-7.70 (m, 1H), 4.96-4.92 (m, 1H), 4.76 (s, 2H), 3.93 (m, 2H), 3.64 (bs, 6H), 2.08-2.04 (m, 4H), 1.81-1.77 (m, 2H), 1.60-1.57 (m, 6H). MS (ESI+): 430.3. HPLC (max plot) 95.39%; Rt 4.69 min.

Example 128: 7-Bromo-1-cyclohexyl-3-(morpholin-4-ylcarbonyl)-1,4-dihydrothiochromeno[4,3-c]pyrazole 5,5-dioxide

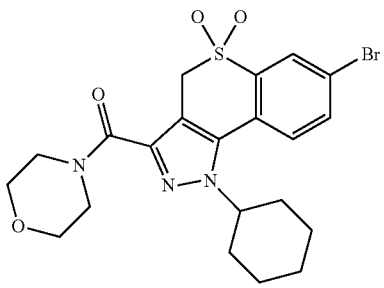 [SMILES: O=C(c1nn(C2CCCCC2)c2c1CS(O)(O)c1cc(Br)ccc1-2)N1CCOCC1]

27 mg of the title compound as an off white solid. $^1$H NMR (DMSO-d$_6$, 400 MHz): δ 8.11-8.09 (m, 2H), 7.80-7.78 (d, J = 9.0 Hz, 1H), 4.82 (s, 2H), 4.70-4.64 (m, 1H), 3.92 (s, 2H), 3.65-3.64 (m, 6H), 2.04-2.01 (m, 2H), 1.90-1.81 (m, 4H), 1.69-1.66 (m, 1H), 1.54-1.51 (m, 2H), 1.48 (m, 1H). MS (ESI+): 494.0. HPLC (max plot) 97.50%; Rt 4.95 min.

Example 158: 3-(Morpholin-4-ylcarbonyl)-1-phenyl-7-(trifluoromethyl)-1,4-dihydrothiochromeno[4,3-c]pyrazole 5,5-dioxide

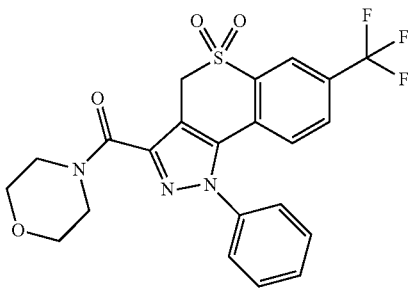 [SMILES: O=C(c1nn(-c2ccccc2)c2c1CS(=O)(=O)c1cc(C(F)(F)F)ccc1-2)N1CCOCC1]

82 mg of the title compound as a white solid. $^1$H NMR (DMSO-d$_6$, 400 MHz): δ 8.20 (s, 1H), 8.04-8.02 (d, J = 8.3 Hz, 1H), 7.64-7.63 (m, 3H), 7.58-7.56 (m, 2H), 7.04-7.02 (d, J = 8.5 Hz, 1H), 5.03 (s, 2H), 3.93 (m, 2H), 3.67 (m, 4H), 3.61 (m, 2H). MS (ESI+): 477.8. HPLC (max plot) 99.17%; Rt 4.77 min.

Example 113: 8-Methoxy-3-(morpholin-4-ylcarbonyl)-1-phenyl-1,4-dihydrothiochromeno[4,3-c]pyrazole 5,5-dioxide

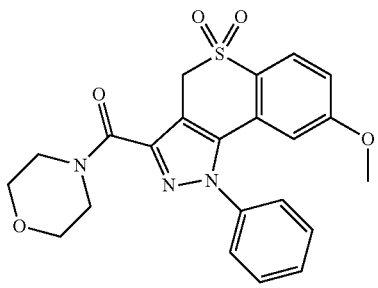 [SMILES: COc1ccc2c(c1)-c1c(c(C(=O)N3CCOCC3)nn1-c1ccccc1)CS2(=O)=O]

23 mg of the title compound as a pale yellow solid. $^1$H NMR (DMSO-d$_6$, 400 MHz): δ 7.94-7.92 (d, J = 8.8 Hz, 1H), 7.65-7.64 (m, 3H), 7.57-7.54 (m, 2H), 7.16-7.14 (m, 1H), 6.23-6.22 (d, J = 2.4 Hz, 1H), 4.83 (s, 2H), 3.94 (s, 2H), 3.66 (m, 4H), 3.53 (m, 2H), 3.32 (s, 3H). MS (ESI+): 440. HPLC (max plot) 94.21%; Rt 4.02 min.

Example 132: 3-(Morpholin-4-ylcarbonyl)-1-phenyl-1,4-dihydropyrazolo[3',4':4,5]thiopyrano[2,3-b]pyridine 5,5-dioxide

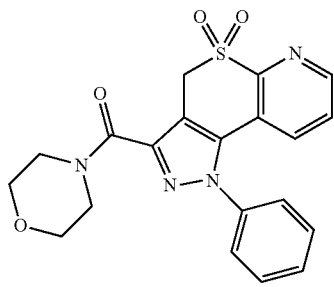 [SMILES: O=C(c1nn(-c2ccccc2)c2c1CS(=O)(=O)c1ncccc1-2)N1CCOCC1]

130 mg of the title compound as an off white solid. $^1$H NMR (DMSO-d$_6$, 400 MHz): δ 8.71-8.69 (dd, J = 1.4, 4.7 Hz,1H), 7.64-7.59 (m, 4H), 7.56-7.53 (m, 2H), 7.19-7.16 (dd, J = 1.4, 6.8 Hz, 1H), 5.00 (s, 2H), 3.93-3.92 (m, 2H), 3.66 (m, 4H), 3.60 (m, 2H). MS (ESI+): 411.0. HPLC (max plot) 99.52%; Rt 3.13 min.

Example 211: 3-(Morpholin-4-ylcarbonyl)-1-[4-(morpholin-4-ylmethyl)phenyl-1,4-dihydropyrazolo[3',4':4,5]thiopyrano[2,3-b]pyridine 5,5-dioxide

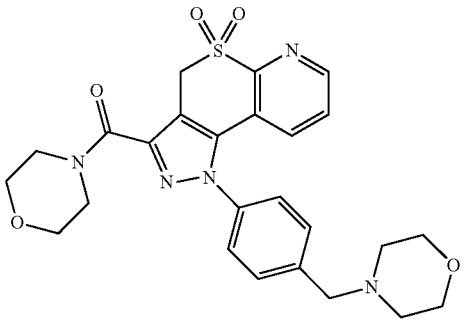 [SMILES: O=C(c1nn(-c2ccc(CN3CCOCC3)cc2)c2c1CS(=O)(=O)c1ncccc1-2)N1CCOCC1]

45 mg of the title compound as a pale brown solid. $^1$H NMR (DMSO-d$_6$, 400 MHz): δ 8.70-8.69 (dd, J = 1.4, 4.7 Hz, 1H), 7.62-7.58 (dd, J = 1.4, 4.7 Hz, 1H), 7.55-7.53 (d, J = 8.4 Hz, 2H), 7.50-7.48 (d, J = 8.4 Hz, 2H), 7.20-7.17 (dd, J = 1.3, 8.2 Hz, 1H), 5.00 (s, 2H), 3.93 (m, 2H), 3.66-3.61 (m, 4H), 3.61-3.42 (m, 8H), 2.40 (m, 4H). MS (ESI+): 510.3. HPLC (max plot) 95.80%; Rt 4.19 min.

Example 79: 3-(Morpholin-4-ylcarbonyl)-1-cyclohexyl-1,4-dihydropyrazolo[3',4':4,5]thio pyrano[2,3-b]pyridine 5,5-dioxide

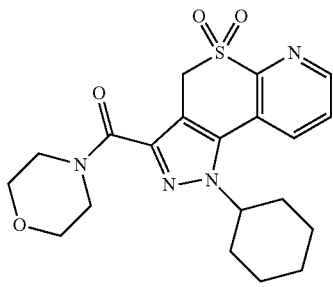 [SMILES: O=C(c1nn(C2CCCCC2)c2c1CS(=O)(=O)c1ncccc1-2)N1CCOCC1]

17 mg (75%) of the title compound as an off white solid. 1H NMR (400 MHz, DMSO-d6): δ 8.78-8.77 (d, J = 4.6 Hz, 1H), 8.31-8.29 (d, J = 8.1 Hz, 1H), 7.92-7.89 (dd, J = 4.7, 8.1 Hz, 1H), 4.88 (s, 2H), 4.69-4.63 (m, 1H), 3.92 (s, 2H), 3.65 (s, 6H), 2.06-2.02 (m, 2H), 1.90-1.81 (m, 4H), 1.70-1.66 (m, 1H), 1.56-1.46 (m, 2H), 1.25-1.22 (m, 1H). MS (ESI+): 417.0. HPLC (max plot) 98.54%; Rt 3.65 min.

Example 150: 3-(Morpholin-4-ylcarbonyl)-1-phenyl-1,4-dihydropyrazolo[3',4':4,5]thiopyrano[3,2-c]pyridine 5,5-dioxide

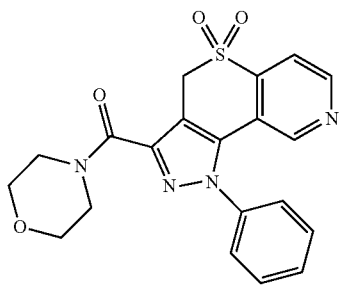 [SMILES: O=C(c1nn(-c2ccccc2)c2c1CS(=O)(=O)c1ccncc1-2)N1CCOCC1]

16 mg of the title compound as a pale brown solid. $^1$H NMR (DMSO-d$_6$, 400 MHz): δ 8.83-8.82 (d, J = 5.0 Hz, 1H), 8.0-7.97 (m, 2H), 7.66-7.62 (m, 3H), 7.61-7.60 (m, 2H), 5.03 (s, 2H), 3.93 (m, 2H), 3.67 (m, 4H), 3.62-3.61 (m, 2H). MS (ESI+): 411.0. HPLC (max plot) 96.9%; Rt 3.28 min.

Example 192: 3-(Morpholin-4-ylcarbonyl)-1-phenyl-1,4-dihydrothieno[3',2':5,6]thiopyrano[4,3-c]pyrazole 5,5-dioxide

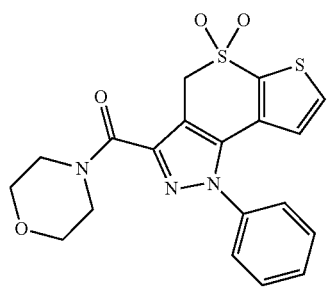

101 mg (83%) of the title compound as a brown solid. $^1$H NMR (DMSO-d$_6$, 400 MHz): δ 8.01-8 (d, J = 5.0 Hz, 1H), 7.64-7.60 (m, 5H), 6.36-6.35 (d, J = 5.0 Hz, 1H), 4.98 (s, 2H), 3.95 (m, 2H), 3.66-3.60 (m, 4H), 3.32 (m, 2H). MS (ESI+): 416.0. HPLC (max plot) 97.91%; Rt 3.82 min.

Example 195: 1-Methyl-5-[3-(morpholin-4-ylcarbonyl)-5,5-dioxidothieno[3',2':5,6]thiopyrano[4,3-c]pyrazole-1 (4H)-yl]pyridin-2 (1H)-one

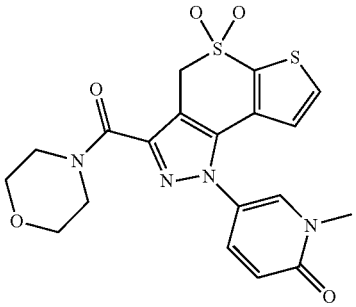 [SMILES: Cn1cc(-n2nc(C(=O)N3CCOCC3)c3c2-c2ccsc2S(O)(O)C3)ccc1=O]

2 mg of the title compound as an off white solid. ¹H NMR (DMSO-d$_6$, 400 MHz): δ 8.35-8.34 (d, J = 2.6 Hz, 1H), 8.09-8.07 (d, J = 5.1 Hz, 1H), 7.65-7.62 (dd, J = 2.8, 9.6 Hz, 1H), 6.92-6.91 (d, J = 5.1 Hz, 1H), 6.55-6.52 (d, J = 9.4 Hz, 1H), 4.96 (s, 2H), 3.93 (m, 2H), 3.65 (m, 4H), 3.6 (m, 2H), 3.47 (s, 3H). MS (ESI+): 447.0. HPLC (max plot) 93.44%; Rt 2.49 min.

Example 201: 1-Cyclohexyl-3-(morpholin-4-ylcarbonyl)-1,4-dihydrothieno[3',2':5,6]thiopyrano[4,3-c]pyrazole 5,5-dioxide

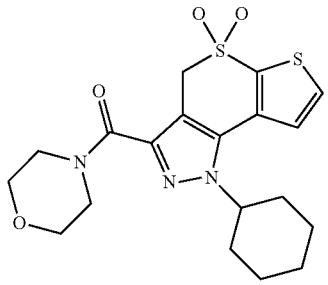 [SMILES: O=C(c1nn(C2CCCCC2)c2c1CS(O)(O)c1sccc1-2)N1CCOCC1]

74 mg of the title compound as an off white solid. ¹H NMR (DMSO-d$_6$, 400 MHz): δ 8.26-8.25 (d, J = 5.0 Hz, 1H), 7.68-7.66 (d, J = 5.0 Hz, 1H), 4.86 (m, 2H), 4.68-4.63 (m, 1H), 3.94 (m, 2H), 3.63 (m, 6H), 2.01-1.99 (m, 2H), 1.83-1.8 (m, 4H), 1.69-1.66 (m, 1H), 1.58-1.48 (m, 2H), 1.24-1.21 (m, 2H), 1.07 (m, 1H). MS (ESI+): 422.0. HPLC (max plot) 98.29%; Rt 4.29 min.

Example 205: 3-(Morpholin-4-ylcarbonyl)-1-phenyl-1,4-dihydrothieno[3',2':5,6]thiopyrano[4,3-c]pyrazole 5,5-dioxide

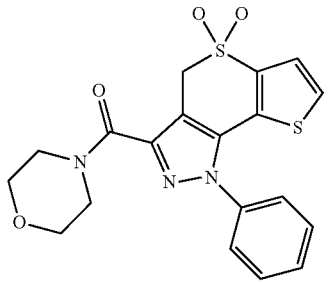 [SMILES: O=C(c1nn(-c2ccccc2)c2c1CS(O)(O)c1ccsc1-2)N1CCOCC1]

62 mg of the title compound as a pale yellow solid. ¹H NMR (DMSO-d$_6$, 400 MHz): δ 7.75-7.74 (d, J = 5.3 Hz, 1H), 7.69-7.66 (m, 5H), 7.53-7.52 (d, J= 5.3 Hz, 1H), 4.90 (s, 2H), 3.95 (m, 2H), 3.66 (m, 4H), 3.61-3.60 (m, 2H). MS (ESI+): 416.0. HPLC (max plot) 97.57%; Rt 3.73 min.

Example 206: 1-Cyclohexyl-3-(morpholin-4-ylcarbonyl)-1,4-dihydrothieno[3',2':5,6]thiopyrano[4,3-c]pyrazole 5,5-dioxide

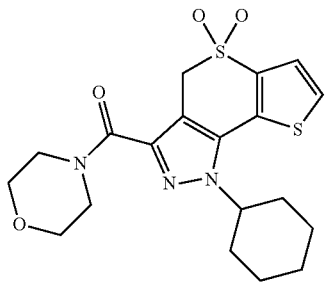 [SMILES: O=C(c1nn(C2CCCCC2)c2c1CS(O)(O)c1ccsc1-2)N1CCOCC1]

20 mg of the title compound as an off white solid. ¹H NMR (DMSO-d$_6$, 400 MHz): δ 8.0-7.99 (d, J = 5.3 Hz, 1H), 7.62-7.61 (d, J = 5.3 Hz, 1H), 4.80 (s, 2H), 4.55-4.49 (m, 1H), 3.93 (m, 2H), 3.65-3.63 (m, 6H), 2.06-2.03 (m, 2H), 1.90-1.79 (m, 4H), 1.72-1.68 (m, 1H), 1.52 (m, 2H), 1.48 (m, 1H). MS (ESI+): 422.0. HPLC (max plot) 96.89%; Rt 4.31 min.

-continued

Example 485: 3-(Morpholin-4-ylcarbonyl)-1-phenyl-1,4-dihydroimidazo [2,1-b]
pyrazolo [3,4-d]1,3] thiazine-3-carboxylic acid 5,5-dioxide

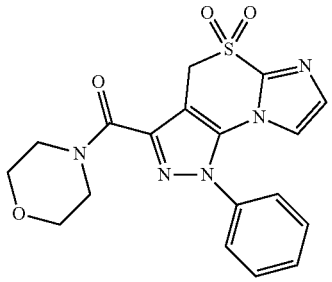 [SMILES: O=C(c1nn(-c2ccccc2)c2c1CS(=O)(=O)c1nccn1-2)N1CCOCC1]

10 mg of the title compound. $^1$H NMR (DMSO-$d_6$, 400 MHz): δ 7.67-7.64 (m, 5H), 7.28 (d, J = 1.4 Hz, 1H), 6.73 (d, J = 1.4 Hz, 1H), 5.06 (s, 2H), 3.93-3.91 (m, 2H), 3.66-3.58 (m, 6H). MS (ESI+): 400.0. HPLC (max plot) 96.59%; Rt 3.14 min.

Examples described below are obtained following procedure T, described above:

Example 330: 3-(Morpholin-4-ylcarbonyl)-1-phenyl-1,4-dihydrothiochromeno[4,3-c]pyrazole 5-oxide

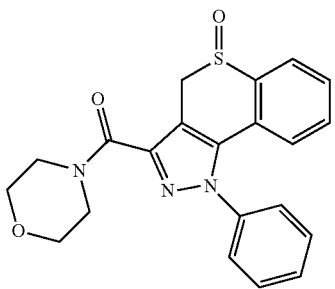 [SMILES: O=C(c1nn(-c2ccccc2)c2c1CS(=O)c1ccccc1-2)N1CCOCC1]

8 mg of the title compound as a white solid. $^1$H NMR (DMSO-$d_6$) δ 7.61-7.49 (m, 6H), 7.31-7.26 (m, 1H), 7.11-7.02 (m, 1H), 6.88-6.86 (m, 1H), 6.57 (d, J = 5.9 Hz, 1H), 6.40 (d, J = 5.9 Hz, 1H), 4.00-3.54 (m, 8H). HPLC (max plot) 95.0%; Rt 3.33 min.

Example 153: {4-[3-(Morpholin-4-ylcarbonyl)-5,5-dioxidothiochromeno[4,3-c]pyrazol-1(4H)-yl]phenyl}methanol

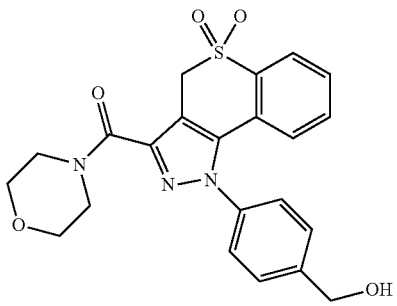

3.5 g of the title compound as an off white foam. HPLC (max plot) 88.3%; Rt 2.48 min; MS (ESI+): 439.98.

Example 163: 3-[(2-Methylmorpholin-4-yl)carbonyl]-1-phenyl-1,4-dihydrothiochromeno [4,3-c]pyrazole 5,5-dioxide

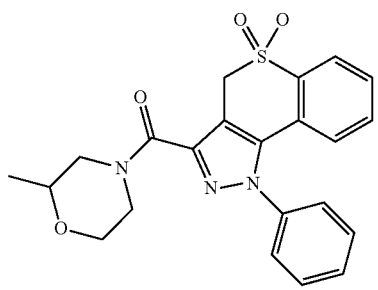

49 mg of the title compound as a white solid. 1H NMR (DMSO-d6) δ 8.04-8.01 (m, 1H), 7.67-7.53 (m, 7H), 6.85-6.82 (m, 1H), 4.91 (s, 2H), 4.57-4.31 (m, 2H), 3.93-3.81 (m, 1H), 3.57-3.44 (m, 2H), 3.31-3.26 (m, 0.5H), 3.04-2.91 (m, 1H), 2.66-2.58 (m, 0.5H), 1.11 (dd, J = 6.3, 28.8 Hz, 3H). HPLC (max plot) 99.6%; Rt 3.50 min.

Example 338: 3-[(3-Methylmorpholin-4-yl)carbonyl]-1-phenyl-1,4-dihydrothiochromeno[4,3-c]pyrazole 5,5-dioxide

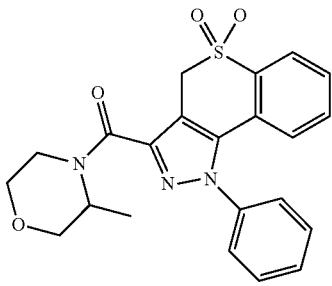

36 mg of the title compound as a white solid. 1H NMR (DMSO-d6) δ 8.04-8.01 (m, 1H), 7.67-7.53 (m, 7H), 6.84 (d, J = 7.5 Hz, 1H), 4.90 (s, 2H), 4.71-4.20 (m, 2H), 3.96-3.38 (m, 4.5H), 3.24-3.10 (m, 0.5H), 1.32-1.30 (m, 3H). HPLC (max plot) 99.5%; Rt 3.48 min. MS(ESI+): 424.1.

Example 333: {4-[(5,5-Dioxido-1-phenyl-1,4-dihydrothiochromeno[4,3-c]pyrazol-3-yl)carbonyl]morpholin-2-yl}methanol

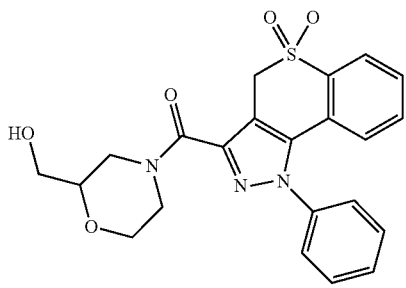

73 mg of the title compound as a off-white powder. $^1$H NMR (DMSO-d$_6$) δ 8.04-8.01 (m, 1H), 7.66-7.54 (m, 7H), 6.85-6.82 (m, 1H), 4.92-4.91 (m, 2H), 4.91-4.74 (m, 1H), 4.64-4.32 (m, 2H), 3.96-3.83 (m, 1H), 3.56-3.27 (m, 4.5H), 3.13-2.92 (m, 1H), 2.78-2.67 (m, 0.5H). HPLC (max plot) 91.9%; Rt 2.98 min. MS (ESI+): 440.1.

Example 334: 3-(1,4-Oxazepan-4-ylcarbonyl)-1-phenyl-1,4-dihydrothiochromeno[4,3-c]pyrazole 5,5-dioxide

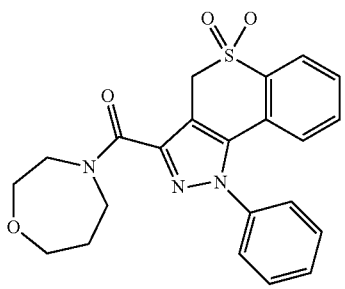

58 mg of the title compound as a off-white powder. 1H NMR (DMSO-d6) δ 8.04-8.01 (m, 1H), 7.67-7.52 (m, 7H), 6.87-6.83 (m, 1H), 4.90 (s, 2H), 3.98-3.93 (m, 2H), 3.77-3.66 (m, 6H), 1.93-1.85 (m, 2H). HPLC (max plot) 99.3%; Rt 3.51 min. MS (ESI+): 423.9. m.p. = 190-195° C.

Example 124: 1-{3-[(4-Methylpiperazin-1-yl)carbonyl]phenyl}-3-(morpholin-4-ylcarbonyl)-1,4-dihydrothiochromeno[4,3-c]pyrazole 5,5-dioxide

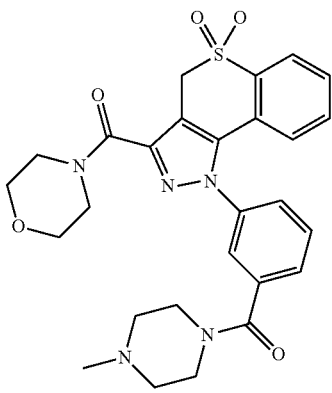

85 mg of the title compound as an off white solid. $^1$H NMR (DMSO-d$_6$, 400 MHz): δ 8.03 (dd, J = 1.3, 7.8 Hz, 1H), 7.72-7.57 (m, 5H), 7.46 (s, 1H), 6.91-6.89 (d, J = 7.9 Hz, 1H), 4.89 (s, 2H), 3.93-3.91 (m, 2H), 3.66 (m, 4H), 3.60-3.59 (m, 4H), 3.27 (m, 2H), 2.49-2.48 (m, 2H), 2.31 (m, 5H). MS (ESI+): 536.3.0. HPLC (max plot) 98.02%; Rt 2.42 min.

Example 125: 3-(Morpholin-4-ylcarbonyl)-1-[3-(piperidin-1-ylcarbonyl)phenyl]-1,4-dihydrothiochromeno[4,3-c]pyrazole 5,5-dioxide

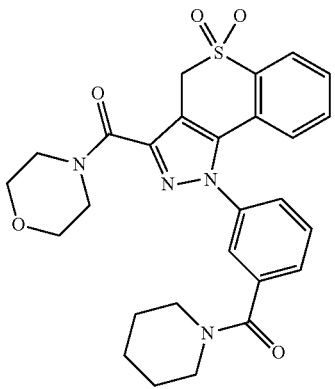

0.135 g of the title compound as an off white solid. $^1$H NMR (DMSO-d$_6$, 400 MHz); δ 8.03-8.01 (d, J = 7.8 Hz, 1H), 7.72-7.56 (m, 5H), 7.44 (s, 1H), 6.90-6.88 (d, J = 7.7 Hz, 1H), 4.89 (s, 2H), 3.93 (m, 2H), 3.66 (m, 4H), 3.61-3.60 (m, 2H), 3.53 (m, 2H), 3.32 (m, 2H), 1.55 (m, 4H), 1.33 (m, 2H). MS (ESI+): 521.3.0. HPLC (max plot) 96.49%; Rt 3.67 min.

Example 126: N-(2-Methoxyethyl)-3-[3-(morpholin-4-ylcarbonyl)-5,5-dioxidothiochromeno[4,3-c]pyrazol-1 (4H)-yl]benzamide

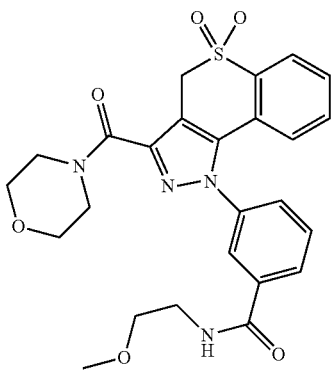

40 mg of the title compound as an off white solid. $^1$H NMR (DMSO-d$_6$, 400 MHz): δ 8.77-8.76 (m, 1H), 8.11-8.10 (d, J = 5.3 Hz, 1H), 8.03-8.00 (d, J = 11.2 Hz, 2H), 7.72-7.70 (d, J = 6.6 Hz, 2H), 7.65-7.61 (t, J = 7.6 Hz, 1H), 7.58-7.55 (t, J = 7.7 Hz, 1H), 6.83-6.81 (d, J = 7.8 Hz, 1H), 4.91 (s, 2H), 3.92 (m, 2H), 3.67 (m, 4H), 3.60 (m, 2H), 3.43-3.40 (m, 4H), 3.23 (s, 3H). MS (ESI+): 511.0. HPLC (max plot) 98.31%; Rt 3.07 min.

Example 142: 1-{3-[(4-Methoxypiperidin-1-yl)carbonyl]phenyl}-3-(morpholin-4-ylcarbonyl)-1,4-dihydrothiochromeno[4,3-c]pyrazole 5,5-dioxide

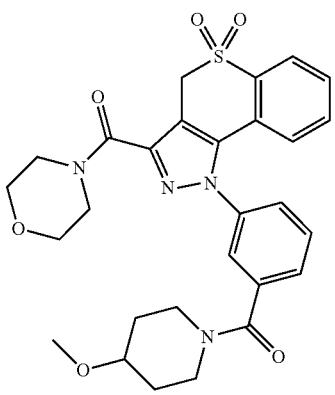 [SMILES: COC1CCN(C(=O)c2cccc(-n3nc(C(=O)N4CCOCC4)c4c3-c3ccccc3S(=O)(=O)C4)c2)CC1]

37 mg of the title compound as an off white solid. $^1$H NMR (DMSO-d6, 400 MHz): δ 8.03-8.01 (d, J = 7.7 Hz, 1H), 7.72-7.57 (m, 5H), 7.48 (s, 1H), 6.90-6.88 (d, J = 7.7 Hz, 1H), 4.89 (s, 2H), 3.93 (m, 2H), 3.86 (m, 1H), 3.66 (m, 3H), 3.61-3.60 (m, 2H), 3.59 (m, 2H), 3.39-3.37 (m, 2H), 3.22 (s, 3H), 3.11 (m, 1H), 1.83 (m, 1H), 1.67 (m, 1H), 1.44 (m, 1H), 1.34 (m, 1H). MS (ESI+): 550.8. HPLC (max plot) 90.67%; Rt 3.31 min.

Example 143: 1-{3-[3-(Morpholin-4-ylcarbonyl)-5,5-dioxidothiochromeno[4,3-c]pyrazol-1(4H)-yl]benzoyl}piperidin-4-ol

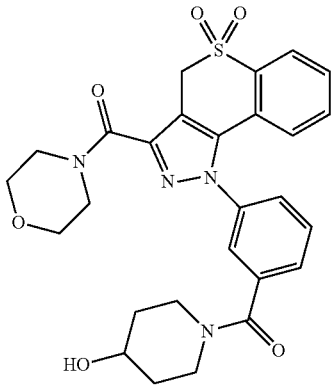

25 mg of the title compound as a white solid. $^1$H NMR (DMSO-d6, 400 MHz): δ 8.03-8.01 (d, J = 7.2 Hz, 1H), 7.70-7.58 (m, 5H), 7.46 (s, 1H), 6.90-6.88 (d, J = 7.8 Hz, 1H), 4.89 (s, 2H), 4.77-4.76 (d, J = 3.9 Hz, 1H), 3.93 (m, 3H), 3.66-3.61 (m, 5H), 3.60 (m, 2H), 3.42 (m, 1H), 3.21 (m, 1H), 3.08 (m, 1H), 1.75 (m, 1H), 1.58 (m, 1H), 1.38 (m, 1H). MS (ESI+): 537.0. HPLC (max plot) 97.84%; Rt 2.74 min.

Example 144: 1-{3-[3-(Morpholin-4-ylcarbonyl)-5,5-dioxidothiochromeno[4,3-c]pyrazol-1(4H)-yl]benzoyl}piperidin-3-ol

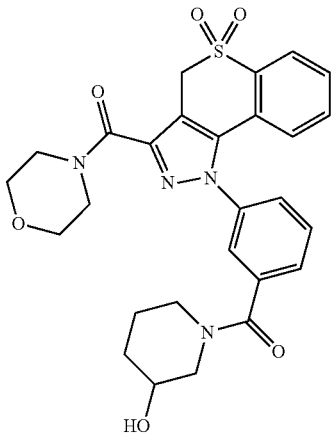 [SMILES: O=C(c1cccc(-n2nc(C(=O)N3CCOCC3)c3c2-c2ccccc2S(=O)(=O)C3)c1)N1CCCC(O)C1]

4.5 mg of the title compound as a white solid. $^1$H NMR (DMSO-d6, 400 MHz): δ 8.03-8.01 (d, J = 7.7 Hz, 1H), 7.69-7.57 (m, 5H), 7.51-7.44 (m, 1H), 6.90 (s, 1H), 4.89 (s, 2H), 3.93 (m, 2H), 3.66 (m, 4H), 3.60 (m, 2H), 3.48 (m, 2H), 3.39-3.36 (m, 1H), 3.08 (m, 1H), 1.75 (m, 2H), 1.43 (m, 2H). MS (ESI+): 536.8. HPLC (max plot) 97.31%; Rt 2.89 min.

Example 145: (1-{3-[3-(Morpholin-4-ylcarbonyl)-5,5-dioxidothiochromeno[4,3-c]pyrazol-1(4H)-yl]benzoyl}piperidin-3-yl)methanol

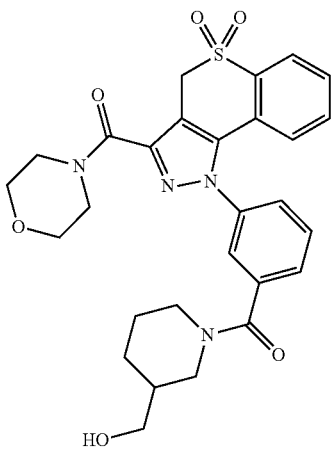 [SMILES: O=C(c1cccc(-n2nc(C(=O)N3CCOCC3)c3c2-c2ccccc2S(=O)(=O)C3)c1)N1CCCC(CO)C1]

5 mg of the title compound as a white solid. $^1$H NMR (DMSO-d6, 400 MHz): δ 8.03-8.01 (d, J = 7.6 Hz, 1H), 7.66-7.56 (m, 5H), 7.51-7.45 (m, 1H), 6.88 (s, 1H), 4.89 (s, 2H), 4.57 (m, 1H), 4.48-4.43 (m, 1H), 4.40-4.25 (m, 1H), 3.93 (m, 2H), 3.66 (m, 4H), 3.60 (m, 2H), 3.48-3.45 (m, 1H), 3.25 (m, 1H), 3.08 (m, 1H), 2.93 (m, 1H), 2.81 (m, 1H), 1.69-1.66 (m, 2H), 1.55 (m, 1H), 1.45 (m, 1H), 1.22-1.14 (m, 3H). MS (ESI+): 550.8. HPLC (max plot) 96.77%; Rt 3.05 min.

Example 146: 1-{3-[(1,1-Dioxidothiomorpholin-4-yl)carbonyl]phenyl}-3-(morpholin-4-ylcarbonyl)-1,4-dihydrothiochromeno[4,3-c]pyrazole 5,5-dioxide

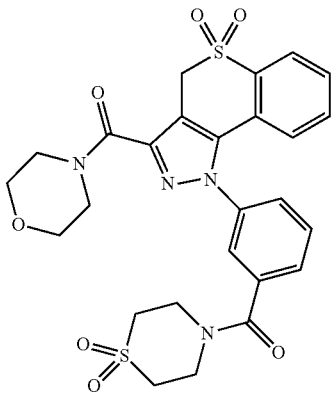 [SMILES: O=C(c1cccc(-n2nc(C(=O)N3CCOCC3)c3c2-c2ccccc2S(=O)(=O)C3)c1)N1CCS(=O)(=O)CC1]

89.6 mg (70%) of the title compound as a white solid. $^1$H NMR (DMSO-d6, 400 MHz): δ 8.03-8.02 (d, J = 6.4 Hz, 1H), 7.74-7.61 (m, 6H), 6.90-6.88 (d, J = 7.3 Hz, 1H), 4.90 (s, 2H), 3.93 (m, 4H), 3.66-3.60 (m, 8H), 3.27-3.24 (m, 2H), 3.08 (m, 2H), MS (ESI+): 571.0. HPLC (max plot) 93.47%; Rt 3.00 min.

Example 147: 3-(Morpholin-4-ylcarbonyl)-1-[4-(morpholin-4-ylcarbonyl)phenyl]-1,4-dihydrothiochromeno[4,3-c]pyrazole 5,5-dioxide

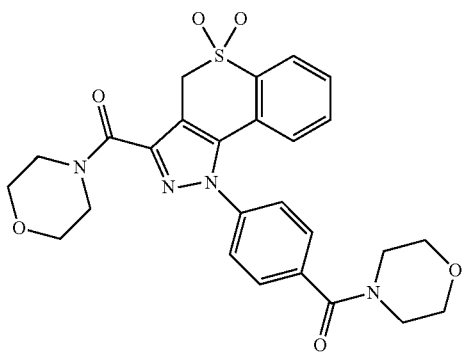

56 mg of the title compound as an off white solid. $^1$H NMR (DMSO-d$_6$, 400 MHz): δ 8.03-8.01 (t, J = 1.7 Hz, 1H), 7.66-7.59 (m, 6H), 6.94-6.91 (t, J = 7.4 Hz, 1H), 4.90 (s, 2H), 3.93 (m, 2H), 3.66-3.60 (m, 14H). MS (ESI+): 522.8. HPLC(max plot) 91.11%; RT 3.00 min.

Example 148: 3-[3-(Morpholin-4-ylcarbonyl)-5,5-dioxidothiochromeno[4,3-c]pyrazol-1(4H)-yl]-N-(tetrahydro-2H-pyran-4-yl)benzamide

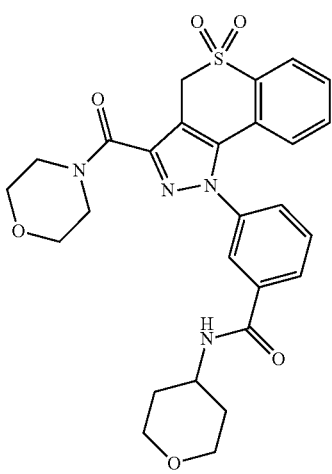 [SMILES: O=C(NC1CCOCC1)c1cccc(-n2nc(C(=O)N3CCOCC3)c3c2-c2ccccc2S(=O)(=O)C3)c1]

52 mg of the title compound as a white solid. $^1$H NMR (DMSO-d6, 400 MHz): δ 8.55-8.53 (d, J = 7.6 Hz, 1H), 8.12-8.11 (d, J = 7.1 Hz, 1H), 8.03-8.01 (m, 2H), 7.73-7.71 (m, 2H), 7.69-7.61 (m, 1H), 7.65-7.55 (m, 1H), 6.83-6.81 (d, J = 7.8 Hz, 1H), 4.91 (s, 2H), 4.00 (m, 1H), 3.99-3.84 (m, 4H), 3.67 (m, 4H), 3.61-3.60 (m, 2H), 3.32 (m, 2H), 1.75 (m, 2H), 1.59-1.52 (m, 2H). MS (ESI+): 537.0. HPLC (max plot) 96.23%; Rt 3.16 min.

-continued

Example 149: 3-[3-(Morpholin-4-ylcarbonyl)-5,5-dioxidothiochromeno[4,3-c]pyrazol-1(4H)-yl]-N-pyridin-3-ylbenzamide

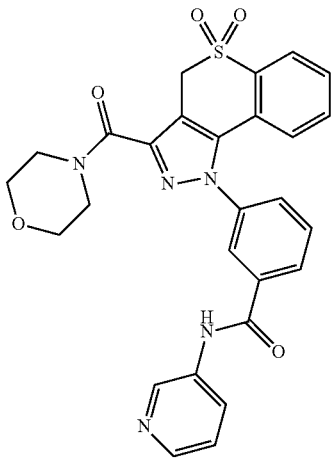 [SMILES: O=C(Nc1cccnc1)c1cccc(-n2nc(C(=O)N3CCOCC3)c3c2-c2ccccc2S(=O)(=O)C3)c1]

24.5 mg of the title compound as a white solid. $^1$H NMR (DMSO-$d_6$, 400 MHz): δ 10.62 (s, 1H), 8.90 (s, 1H), 8.32-8.31 (d, J= 4.6 Hz, 1H), 8.25-8.23 (d, J = 6.8 Hz, 1H), 8.17-8.15 (m, 2H), 8.04-8.02 (d, J = 7.8 Hz, 1H), 7.80-7.79 (m, 1H), 7.64-7.58 (m, 2H), 7.41-7.38 (m, 2H), 6.89-6.87 (d, J = 7.7 Hz, 1H), 4.92 (s, 2H), 3.93 (m, 2H), 3.67 (m, 4H), 3.61 (m, 2H). MS (ESI+): 530.0. HPLC (max plot) 93.53%; Rt 2.73 min.

Example 151: 3-(Morpholin-4-ylcarbonyl)-1-[4-(piperidin-1-ylcarbonyl)phenyl]-1,4-dihydrothiochromeno[4,3-c]pyrazole 5,5-dioxide

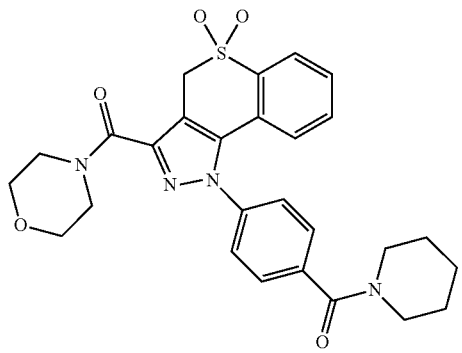 [SMILES: O=C(c1ccc(-n2nc(C(=O)N3CCOCC3)c3c2-c2ccccc2S(O)(O)C3)cc1)N1CCCCC1]

77 mg of the title compound as a white solid. $^1$H NMR (DMSO-$d_6$, 400 MHz): δ 8.02-8.0 (d, J = 7.7 Hz, 1H), 7.66-7.58 (m, 6H), 6.91-6.89 (d, J = 7.6 Hz, 1H), 4.87 (s, 2H), 3.92 (m, 2H), 3.65 (m, 4H), 3.60 (m, 4H), 3.31 (m, 2H), 1.61-1.48 (m, 6H). MS (ESI+): 520.8. HPLC (max plot) 95.89%; Rt 3.72 min.

Example 159: 1-{3-[(3-Methoxypiperidin-1-yl)carbonyl]phenyl}-3-(morpholin-4-ylcarbonyl)-1,4-dihydrothiochromeno[4,3-c]pyrazole 5,5-dioxide

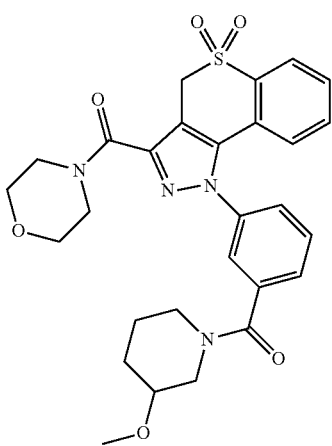 [SMILES: COC1CCCN(C(=O)c2cccc(-n3nc(C(=O)N4CCOCC4)c4c3-c3ccccc3S(=O)(=O)C4)c2)C1]

8 mg of the title compound as a grey solid. $^1$H NMR (DMSO-$d_6$, 400 MHz): δ 8.03-8.01 (d, J = 7.8 Hz, 1H), 7.73-7.58 (m, 5H), 7.51-7.40 (m, 1H), 6.90-6.88 (d, J = 7.8 Hz, 1H), 4.90 (s, 2H), 3.92 (m, 2H), 3.84-3.82 (m, 1H), 3.66-3.60 (m, 6H), 3.42 (m, 3H), 3.16 (s, 3H), 2.94 (m, 1H), 1.85-1.49 (m, 2H), 1.40 (m, 2H). MS (ESI+): 550.8. HPLC (max plot) 93.53%; Rt 3.40 min.

Procedure AC

Example 141

{3-[3-(Morpholin-4-ylcarbonyl)-5,5-dioxidothiochromeno[4,3-c]pyrazol-1(4H)-yl]phenyl}methanol

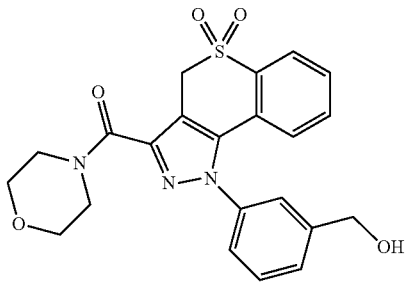 [SMILES: O=C(c1nn(-c2cccc(CO)c2)c2c1CS(=O)(=O)c1ccccc1-2)N1CCOCC1]

To a solution of aluminium chloride (5.13 g; 38.49 mmol; 4.93 eq.) in THF (30 mL) stirred for 25 min at 4° C. is added morpholine (5.40 ml; 61.36 mmol; 7.86 eq.) and the reaction mixture is stirred at 4° C. for 1 h. Ethyl 1-[3-(hydroxymethyl)phenyl]-1,4-dihydrothiochromeno[4,3-c]pyrazole-3-carboxylate 5,5-dioxide (3.11 g; 7.81 mmol; 1 eq.) is added and the reaction mixture is allowed to warm up to rt. After 22 h, the reaction mixture is cooled down to 0° C. then water is added slowly (total volume 25 mL). After 30 min stirring, the product is extracted with DCM. The organic phase is washed with an aqueous solution of Rochelle salts (~0.7 m; pH=5), brine then dried over MgSO4. The solvent is removed under reduced pressure to afford 3.39 g (99%) of the title compound as a pale yellow solid. HPLC (max plot) 95.6%; Rt 3.08 min. MS (ESI+): 440.0.

Compounds Described Below are Obtained Following Procedure AC

---

Example 264: 6-Chloro-3-(morpholin-4-ylcarbonyl)-1-(tetrahydro-2H-pyran-4-yl)-1,4-dihydrothiochromeno[4,3-c]pyrazole 5,5-dioxide

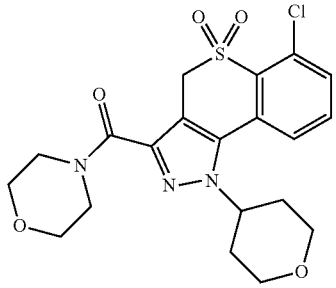

150 mg of the title compound as a white solid. $^1$H NMR (DMSO-d$_6$) δ 7.81-7.84 (m, 2H), 7.73-7.77 (m, 1H), 4.85-4.92 (m, 3H), 3.93-3.97 (m, 4H), 3.65 (m, 6H), 3.48-3.55 (m, 2H), 2.04-2.18 (m, 2H), 1.95-1.98 (m, 2H). HPLC (max plot) 98.8%; Rt 2.82 min. MS (ESI+): 451.7

Example 249: 6-Fluoro-3-(morpholin-4-ylcarbonyl)-1-(tetrahydro-2H-pyran-4-yl)-1,4-dihydrothiochromeno[4,3-c]pyrazole 5,5-dioxide

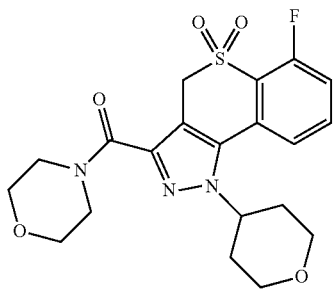 [SMILES: O=C(c1nn(C2CCOCC2)c2c1CS(=O)(=O)c1c(F)cccc1-2)N1CCOCC1]

120 mg of the title compound as a white solid. $^1$H NMR (DMSO-d6) δ 7.88-7.95 (m, 1H), 7.71-7.73 (m, 1H), 7.53-7.59 (m, 1H), 4.91-4.98 (m, 1H), 4.88 (s, 2H), 3.93-4.00 (m, 4H), 3.50-3.64 (m, 8H), 1.96-2.18 (m, 4H). HPLC (max plot) 97.4%; Rt 2.58 min. MS (ESI+): 435.7.

Example 342: 3-(Morpholin-4-ylcarbonyl)-1-(tetrahydrofuran-3-yl)-1,4-dihydrothiochromeno[4,3-c]pyrazole 5,5-dioxide

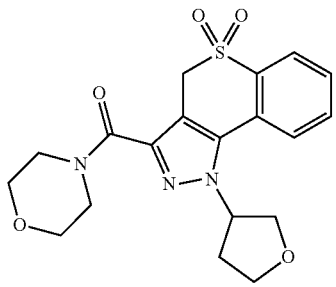 [SMILES: O=C(c1nn(C2CCOC2)c2c1CS(=O)(=O)c1ccccc1-2)N1CCOCC1]

599 mg of the title compound as a white foam. $^1$H NMR (DMSO-d6) δ 8.06-8.03 (m, 1H), 7.97-7.87 (m, 2H), 7.77-7.71 (m, 1H), 5.67-5.61 (m, 1H), 4.85-4.74 (m, 2H), 4.25-4.20 (m, 1H), 4.04-3.89 (m, 5H), 3.66-3.62 (m, 6H), 2.48-2.34 (m, 2H). HPLC (max plot) 99.5%; Rt 2.59 min. MS (ESI+): 404.2.

Example 365: 6-Fluoro-3-(morpholin-4-ylcarbonyl)-1-(tetrahydrofuran-3-yl)-1,4-dihydrothiochromeno[4,3-c]pyrazole 5,5-dioxide

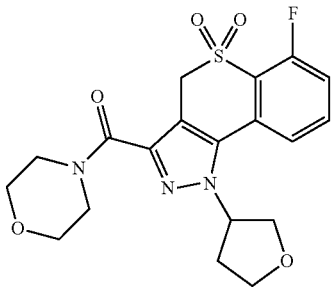 [SMILES: O=C(c1nn(C2CCOC2)c2c1CS(=O)(=O)c1c(F)cccc1-2)N1CCOCC1]

402 mg of the title compound as an off-white powder. $^1$H NMR (DMSO-d6) δ 7.95-7.87 (m, 1H), 7.75-7.73 (m, 1H), 7.61-7.54 (m, 1H), 5.60-5.53 (m, 1H), 4.90 (s, 2H), 4.22-4.17 (m, 1H), 4.06-3.88 (m, 5H), 3.66-3.64 (m, 6H), 2.53-2.32 (m, 2H). HPLC (max plot) 98.6%; Rt 2.48 min. MS (ESI+): 422.3.

Example 390: 7-ethoxy-3-(morpholin-3-ylcarbonyl)-1-[4-(morpholin-4-ylmethyl)phenyl]-1,4-dihydrothiochromeno[4,3-c]pyrazole 5,5-dioxide formic acid

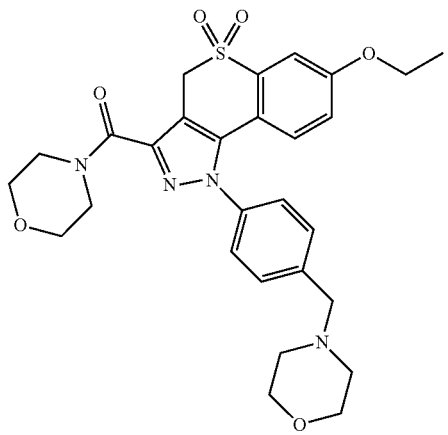 [SMILES: CCOc1ccc2c(c1)S(=O)(=O)Cc1c(C(=O)N3CCOCC3)nn(-c3ccc(CN4CCOCC4)cc3)c1-2]

10 mg of the title compound as a yellow powder. $^1$H NMR (DMSO-d6): δ 8.47 (s, 1H), 7.57-7.41 (m, 5H), 7.14 (d, J = 7 Hz, 1H), 6.77 (d, J = 7 Hz, 1H), 4.88 (s, 2H), 4.13 (q, J = 7.5 Hz, 2H), 4.01-3.93 (m, 2H), 3.67-3.59 (m, 12H), 2.41-2.37 (m, 4H), 1.30 (t, J = 7.5 Hz, 3H). UPLC (max plot): 99.1%; Rt 2.97 min. MS (ESI+): 553.5.

Procedure AD

Example 33

3-(morpholin-4-ylcarbonyl)-1-phenyl-1,4-dihydrothiochromeno[4,3-c]pyrazole 5,5-dioxide

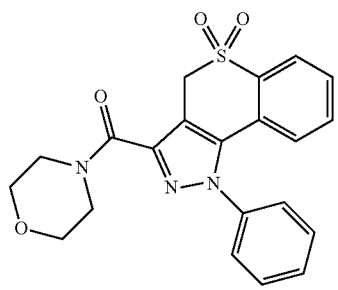

1-phenyl-1,4-dihydrothiochromeno[4,3-c]pyrazole-3-carboxylic acid 5,5-dioxide (150.00 mg; 0.44 mmol; 1.00 Eq) is suspended in DCM (4.00 ml) and 2 drops of DMF and then Oxalyl chloride (3 mL) is added dropwise. The reaction mixture is stirred at room temperature for 30 min. The solution is evaporated to dryness. The residue is suspended in DCM (4.00 ml) and morpholine (350.00 µL; 4.02 mmol; 9.12 Eq) is added dropwise. The reaction mixture is stirred at rt for 30 min then diluted with aq. solution of HCl 0.05 M. The two layers are separated. The aqueous layer is extracted with DCM (2×). The organic layers are washed with a saturated solution of NaHCO$_3$ and brine, dried over MgSO$_4$ and evaporated to give foam. The foam is recrystallised in EtOH to the title compound as a white solid. $^1$H NMR (DMSO-d$_6$, 300 MHz) δ 8.04-8.01 (m, 1H), 7.67-7.53 (m, 7H), 6.85-6.82 (m, 1H), 4.91 (s, 2H), 3.98-3.94 (m, 2H), 3.68-3.61 (m, 6H). UPLC/MS: (ES+): 410.1, (ES−): 408.1. HPLC (max plot) 100.0%; Rt 3.36 min.

Example 34

1-methyl-3-(morpholin-4-ylcarbonyl)-1,4-dihydrothiochromeno[4,3-c]pyrazole 5,5-dioxide

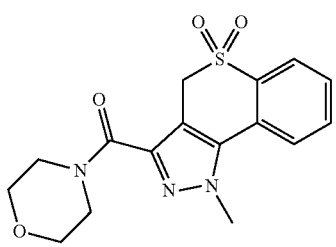 [SMILES: Cn1nc(C(=O)N2CCOCC2)c2c1-c1ccccc1S(=O)(=O)C2]

Following the protocol outlined in Procedure AD, 1-methyl-3-(morpholin-4-ylcarbonyl)-1,4-dihydrothiochromeno

[4,3-c]pyrazole 5,5-dioxide is obtained from 1-methyl-1,4-dihydrothiochromeno[4,3-c]pyrazole-3-carboxylic acid 5,5-dioxide, oxalyl chloride and morpholine to afford 0.62 g (83%) of the title compound as a white solid. $^1$H NMR (DMSO-d$_6$, 300 MHz) δ 8.07-8.02 (m, 2H), 7.92-7.87 (m, 1H), 7.76-7.71 (m, 1H), 4.81 (s, 2H), 4.26 (s, 3H), 3.99-3.93 (m, 2H), 3.70-3.60 (m, 6H). UPLC/MS: (ES+): 347.9, (ES−): 346.1. HPLC (max plot) 99.9%; Rt 2.15 min.

Compounds described below are obtained following protocol outlined in procedure AQ Example 457: 1-[4-(1-Methyl-1-morpholin-4-ylethyl)phenyl]-3-(morpholin-4-ylcarbonyl)-1,4-dihydrothiochromeno[4,3-c]pyrazole 5,5-dioxide

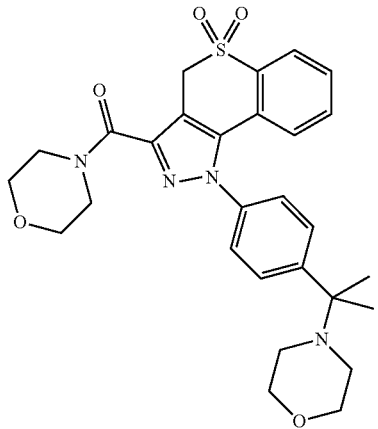 [SMILES: CC(C)(c1ccc(-n2nc(C(=O)N3CCOCC3)c3c2-c2ccccc2S(=O)(=O)C3)cc1)N1CCOCC1]

189 mg of the title compound as an orange solid. $^1$H NMR (DMSO-d$_6$, 300 MHz): δ 8.06-7.97 (m, 1H), 7.80-7.68 (m, 2H), 7.68-7.58 (m, 1H), 7.58-7.42 (m, 3H), 6.82-6.72 (m, 1H), 4.90 (s, 2H), 4.00-3.88 (m, 2H), 3.80-3.53 (m, 10H), 2.47-2.34 (m, 4H), 1.37 (s, 6H). MS (ESI+): 537.2. (max plot) 98.0%; Rt 2.23 min.

Example 458: N,N,2-Trimethyl-2-{4-[3-(morpholin-4-ylcarbonyl)-5,5-dioxidothiochromeno[4,3-c]pyrazol-1(4H)-yl]phenyl}propan-1-amine hydrochloride

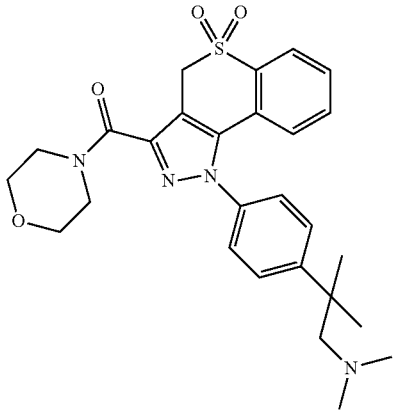 [SMILES: CN(C)CC(C)(C)c1ccc(-n2nc(C(=O)N3CCOCC3)c3c2-c2ccccc2S(=O)(=O)C3)cc1]

544 mg (88%) of the title compound as an off-white solid. $^1$H NMR (DMSO-d$_6$, 300 MHz): δ 8.09-7.95 (m, 1H), 7.78-7.54 (m, 3H), 7.54-7.31 (m, 3H), 6.83-6.69 (m, 1H), 4.91 (s, 2H), 4.015-3.89 (m, 2H), 3.74-3.54 (m, 6H), 2.57-2.38 (m, 2H), 2.05 (bs, 6H), 1.35 (bs, 6H). MS (ESI+): 509.4. HPLC (max plot) 93.5%; Rt 4.07 min Example 461: 1-[4-(1,1-Dimethyl-2-morpholin-4-ylethyl)phenyl]-3-(morpholin-4-ylcarbonyl)-1,4-dihydrothiochromeno[4,3-c]pyrazole 5,5-dioxide

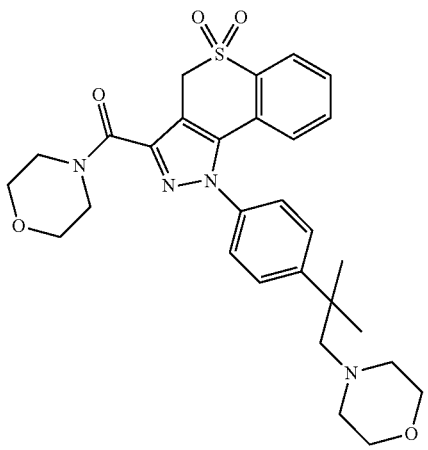 [SMILES: CC(C)(CN1CCOCC1)c1ccc(-n2nc(C(=O)N3CCOCC3)c3c2-c2ccccc2S(=O)(=O)C3)cc1]

376 mg (71%) of the title compound as a white solid. $^1$H NMR (DMSO-d$_6$, 300 MHz): δ 8.06-7.98 (m, 1H), 7.70-7.58 (m, 3H), 7.54-7.36 (m, 3H), 6.82-6.71 (m, 1H), 4.90 (s, 2H), 4.03-3.86 (m, 2H), 3.78-3.54 (m, 6H), 3.54-3.43 (m, 4H), 2.51-2.43 (m, 2H), 2.37-2.12 (m, 4H), 1.35 (s, 6H). MS (ESI+): 551.3. HPLC (max plot) 99.2%; Rt 2.47 min Example 462: 3-(Morpholin-4-ylcarbonyl)-1-{4-[1-(morpholin-4-ylmethyl)cyclopropyl]phenyl}-1,4-dihydrothiochromeno[4,3-c]pyrazole 5,5-dioxide

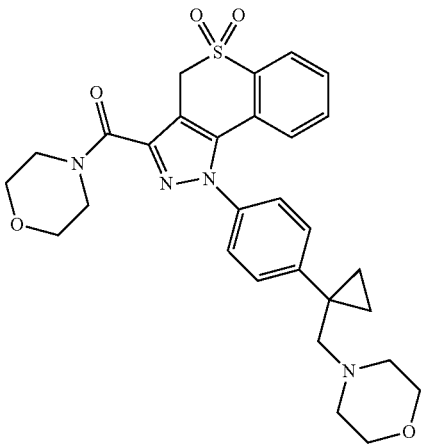 [SMILES: O=C(c1nn(-c2ccc(C3(CN4CCOCC4)CC3)cc2)c2c1CS(=O)(=O)c1ccccc1-2)N1CCOCC1]

58 mg (74%) of the title compound as a white powder. $^1$H NMR (DMSO-$d_6$, 300 MHz): δ 8.06-7.97 (m, 1H), 7.71-7.60 (m, 1H), 7.60-7.46 (m, 3H), 7.46-7.35 (m, 2H), 6.86-6.76 (m, 1H), 4.90 (s, 2H), 4.12-3.84 (m, 2H), 3.81-3.56 (m, 6H), 3.56-3.41 (m, 4H), 2.60 (s, 2H), 2.48-2.32 (m, 4H), 1.01-0.91 (m, 2H), 0.87-0.76 (m, 2H). MS (ESI+): 549.2. HPLC (max plot): 99.0%; Rt 2.44 min Example 339: 6-Fluoro-3-(morpholin-4-ylcarbonyl)-1-[4-(morpholin-4-ylmethyl)phenyl]-1,4-dihydrothiochromeno[4,3-c]pyrazole 5,5-dioxide

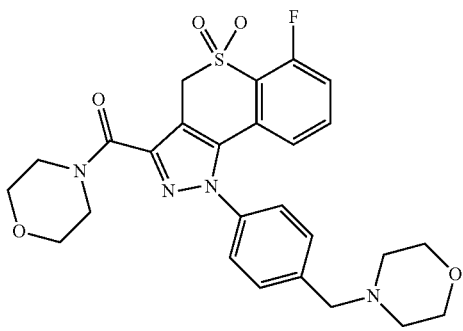

27.5 mg of the title compound as a beige solid. 1H NMR (DMSO-d6) δ 7.43-7.63 (m, 6H), 6.64-6.67 (d, J = 9 Hz, 1H), 5.01 (s, 2H), 3.95 (m, 2H), 3.59-3.68 (m, 12H), 2.41 (m, 4H). HPLC (max plot) 98.9%; Rt 1.96 min. MS (ESI+): 527.4.

Example 391: 7-Ethoxy-3-(morpholin-4-ylcarbonyl)-1-[4-(morpholin-4-ylmethyl)phenyl]-1,4-dihydrothiochromeno[4,3-c]pyrazole 5,5-dioxide

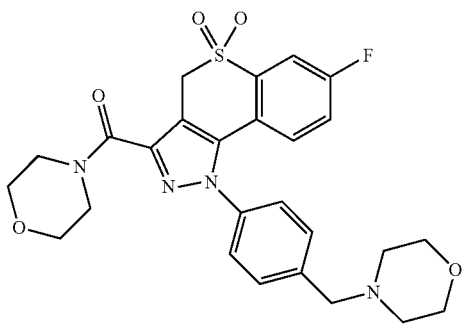

105 mg of the title compound as a yellow powder. $^1$H NMR (DMSO-d6) δ 8.47 (s, 1H), 7.57-7.41 (m, 5H), 7.14 (d, J = 7 Hz, 1H), 6.77 (d, J = 7 Hz, 1H), 4.88 (s, 2H), 4.13 (q, J = 7.5 Hz, 2H), 4.01-3.93 (m, 2H), 3.67-3.59 (m, 12H), 2.41-2.37 (m, 4H), 1.30 (t, J = 7.5 Hz, 3H). HPLC (max plot) 99.1%; Rt 2.97 min. m.p. = 196° C. MS (ESI+): 527.4.

Example 388: 7-Methoxy-3-(morpholin-4-ylcarbonyl)-1-[4-(morpholin-4-ylmethyl)
phenyl]-1,4-dihydrothiochromeno[4,3-c]pyrazole 5,5-dioxide

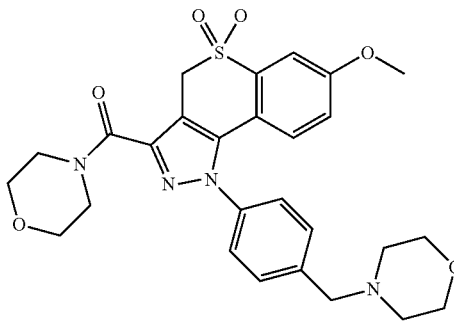

Give of the title compound as a yellow oil. HPLC (max plot) 95.6%; Rt 2.23 min. MS (ESI+): 498.23.

Example 392: 8-Fluoro-3-(morpholin-4-ylcarbonyl)-1-[4-(morpholin-4-ylmethyl)
phenyl]-1,4-dihydrothiochromeno[4,3-c]pyrazole 5,5-dioxide

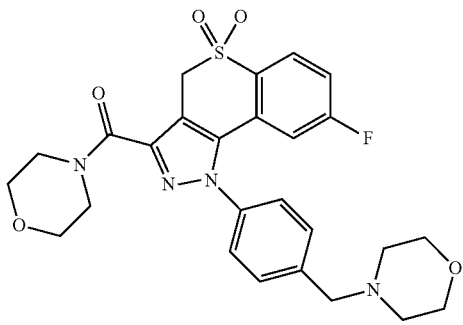

130 mg of the title compound as a white foam. $^1$H NMR (DMSO-d6) δ 8.10 (dd, J = 5.5, 8.8 Hz, 1H), 7.63-7.44 (m, 5H), 6.41 (dd, J = 2.5, 10.1 Hz, 1H), 4.94 (s, 2H), 4.0-3.89 (m, 2H), 3.68 (bs, 4H), 3.65-3.53 (m, 8H), 2.47-2.35 (m, 4H). HPLC (max plot) 99.8%; Rt 2.27 min. MS (ESI+): 527.2.

Example 119: tert-Butyl 4-[3-(morpholin-4-ylcarbonyl)-5,5-dioxidothiochromeno[4,3-
c]pyrazol-1(4H)-yl]piperidine-1-carboxylate

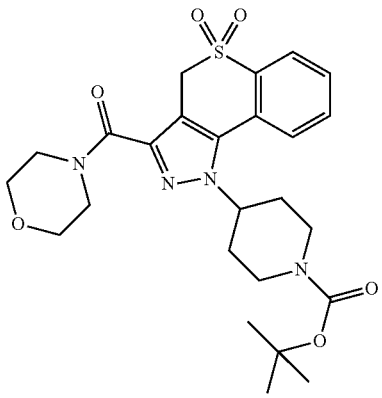 [SMILES: CC(C)(C)OC(=O)N1CCC(n2nc(C(=O)N3CCOCC3)c3c2-c2ccccc2S(=O)(=O)C3)CC1]

700 mg of the title compound as a beige solid. HPLC (max plot) 87.9%; Rt 3.72 min. MS (ESI−): 515.3.

Example 289: N-[3-(Morpholin-4-ylcarbonyl)-5,5-dioxido-1-(tetrahydro-2H-pyran-4-yl)-
1,4-dihydropyrazolo[3',4':4,5]thiopyrano[3,2-d][1,3]thiazol-7-yl]acetamide

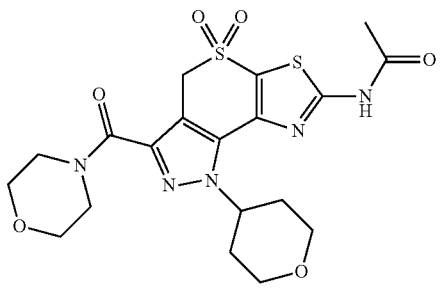 [SMILES: CC(=O)Nc1nc2c(s1)S(=O)(=O)Cc1c(C(=O)N3CCOCC3)nn(C3CCOCC3)c1-2]

6.7 mg of the title compound as a white solid. $^1$H NMR (DMSO-d6): δ 12.90 (s, 1H), 5.56-5.38 (m, 1H), 4.93 (s, 2H), 4.16-3.89 (m, 4H), 3.79-3.59 (m, 6H), 3.59-3.44 (m, 2H), 2.30 (s, 3H), 2.20-1.92 (m, 4H). HPLC (max plot) 97.0%; Rt 2.70 min. MS (ESI+): 482.2.

Example 246: 3-(Morpholin-4-ylcarbonyl)-1-(tetrahydro-2H-pyran-4-yl)-1,4-dihydrothieno[3',2':5,6]thiopyrano[4,3-c]pyrazole 5,5-dioxide

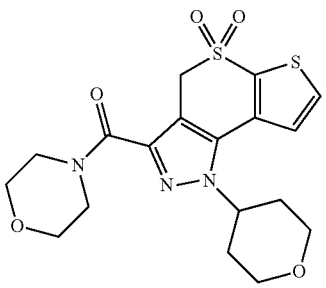

40 mg of the title compound as a pale yellow powder. 1H NMR (DMSO-d6) δ 8.28 (d, J = 5.2 Hz, 1H), 7.80 (d, J = 5.2 Hz, 1H), 5.05-4.92 (m, 1H), 4.89 (s, 2H), 3.97 (m, 4H), 3.72-3.55 (m, 8H), 2.18-1.89 (m, 4H). HPLC (max plot) 96.0%; Rt 2.47 min. MS (ESI+): 423.7.

Procedure AE

Example 250

3-(Morpholin-4-ylcarbonyl)-1-phenyl-1,4-dihydrothiochromeno[4,3-c]pyrazole-6-carboxamide 5,5-dioxide

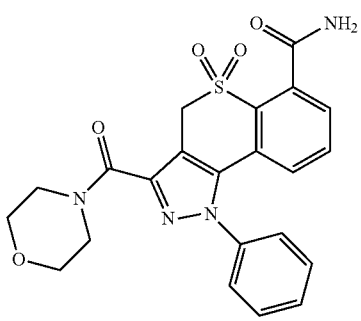 [SMILES: NC(=O)c1cccc2c1S(=O)(=O)Cc1c(C(=O)N3CCOCC3)nn(-c3ccccc3)c1-2]

To a solution of 6-cyano-1-phenyl-1,4-dihydrothiochromeno[4,3-c]pyrazole-3-carboxylate 5,5-dioxide (50 mg, 0.135 mmol) in dry DCM (10 mL) are added morpholine (0.02 mL, 0.156 mmol) and TEA (0.03 mL, 0.196 mmol) after which reaction mixture is cooled to 0° C. EDC.HCl (38 mg, 0.196 mmol) and HOBt (2 mg, 0.013 mmol) are then added to the reaction mixture which is stirred at RT for 12 h under nitrogen. After this time, DCM is added and organic phase is washed with Na$_2$CO$_3$ sat, dried over Na$_2$SO$_4$ concentrated under reduced pressure and purified by silica gel column chromatography (3% MeOH in DCM) to afford the title compound as a pale yellow solid. $^1$H NMR (DMSO-d$_6$, 400 MHz): δ 7.89 (s, 1H), 7.63-7.60 (m, 3H), 7.55-7.44 (m, 4H), 6.84-6.82 (d, J=7.8 Hz, 1H), 5.74 (s, 2H), 4.78 (s, 2H), 3.97 (m, 2H), 3.66-3.61 (m, 6H). MS (ESI+): 453.0. HPLC (max plot) 96.54%; Rt 3.98 min.

Procedure AF

Example 35

1-methyl-3-(morpholin-4-ylcarbonyl)-8-nitro-1,4-dihydrothiochromeno[4,3-c]pyrazole 5,5-dioxide

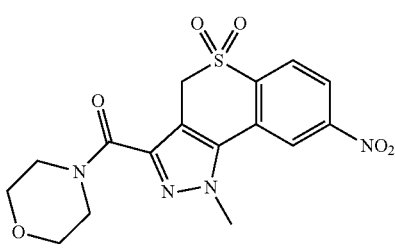 [SMILES: Cn1nc(C(=O)N2CCOCC2)c2c1-c1cc([N+](=O)[O-])ccc1S(=O)(=O)C2]

A solution of 1-methyl-3-(morpholin-4-ylcarbonyl)-8-nitro-1,4-dihydrothiochromeno[4,3-c]pyrazole (0.084 g, 0.23 mmol) in acetic acid is heated at 100° C. under nitrogen. Hydrogen peroxide 30% in water (0.5 mL, 3.6 mmol, 15 Eq) is added and the reaction mixture is heated for 30 minutes. After 30 minutes, the solvent is removed under reduced pressure. 10% aqueous NaHCO$_3$ is added to the residue. The mixture is stirred for few minutes and then extracted with DCM. The organic layer is concentrated and purified by column chromatography to afford the title compound as a yellow solid. $^1$H NMR (DMSO-d$_6$, 400 MHz) δ 8.66 (s, 1H), 8.48 (dd, J=8.5 Hz, J=2.3 Hz, 1H), 8.28 (J=11.8 Hz, 1H), 4.96 (s, 2H), 4.33 (s, 3H), 3.94 (brs, 2H), 3.66-3.63 (m, 6H). MS (ESI+): 393.0. HPLC (max plot) 90.8%; Rt 3.08 min.

Example 36

3-(morpholin-4-ylcarbonyl)-8-nitro-1-phenyl-1,4-dihydrothiochromeno[4,3-c]pyrazole 5,5-dioxide

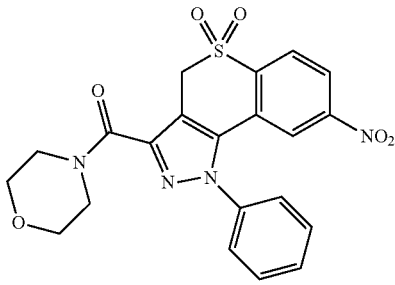 [SMILES: O=C(c1nn(-c2ccccc2)c2c1CS(=O)(=O)c1ccc([N+](=O)[O-])cc1-2)N1CCOCC1]

Following the protocol outlined in Procedure AF, 3-(morpholin-4-ylcarbonyl)-8-nitro-1-phenyl-1,4-dihydrothiochromeno[4,3-c]pyrazole 5,5-dioxide is obtained from 3-(morpholin-4-ylcarbonyl)-8-nitro-1-phenyl-1,4-dihydrothiochromeno[4,3-c]pyrazole and hydrogen peroxide to afford of the title compound as a yellow solid. $^1$H NMR (DMSO-d$_6$, 400 MHz) δ 8.38 (dd, J=8.5 Hz, J=2.2 Hz, 1H), 8.27 (d, J=8.6 Hz, 1H), 7.70-7.59 (m, 5H), 7.51 (d, J=2.1 Hz, 1H), 5.06 (s, 2H), 3.95-3.93 (m, 2H), 3.67-3.60 (m, 6H). MS (ESI+): 455.0. HPLC (max plot) 95.5%; Rt 4.18 min.

Procedure AG

Example 37

1-ethyl-3-(morpholin-4-ylcarbonyl)-1,4-dihydrothiochromeno[4,3-c]pyrazole 5,5-dioxide

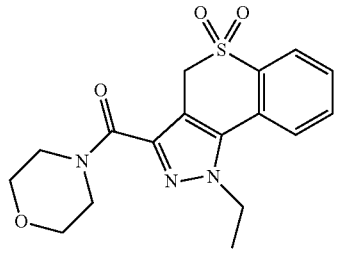 [SMILES: CCn1nc(C(=O)N2CCOCC2)c2c1-c1ccccc1S(=O)(=O)C2]

To a solution of 3-(morpholin-4-ylcarbonyl)-2,4-dihydrothiochromeno[4,3-c]pyrazole 5,5-dioxide (0.400 g, 1.2 mmol) in acetonitrile (10 mL) is added potassium carbonate (0.49 g, 3.6 mmol) followed by ethyl iodide (0.56 g, 3.6 mmol). The reaction mixture is heated at 60° C. overnight. The crude reaction mixture is filtered through a celite pad and the filtrate concentrated under reduced pressure. The residue is purified by preparative HPLC to afford the title compound as an off-white solid. $^1$H NMR (DMSO-d$_6$, 400 MHz): δ 8.02 (d, J=7.72 Hz, 1H), 7.94 (d, J=7.84 Hz, 1H), 7.89 (t, J=7.52 Hz, 1H), 7.72 (t, J=7.64 Hz, 1H), 4.79 (s, 2H), 4.57 (q, J=7.12 Hz, 2H), 3.94 (brs, 2H), 3.66-3.63 (m, 6H), 1.46 (t, J=7.16 Hz, 3H). MS (ESI+): 362.0. HPLC (max plot) 95.0%; Rt 2.99 min.

Example 38

1-(4-methoxybenzyl)-3-(morpholin-4-ylcarbonyl)-1,4-dihydrothiochromeno[4,3-c]pyrazole 5,5-dioxide

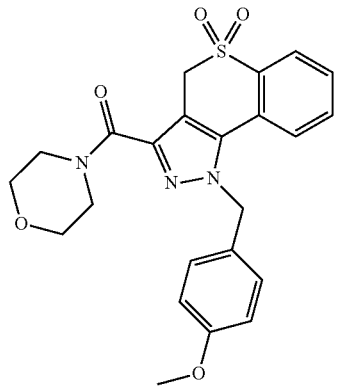 [SMILES: COc1ccc(Cn2nc(C(=O)N3CCOCC3)c3c2-c2ccccc2S(=O)(=O)C3)cc1]

Following the protocol outlined in Procedure AG, 1-(4-methoxybenzyl)-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 4-methoxybenzyl bromide to afford the title compound as a white solid. $^1$H NMR (DMSO-d$_6$, 300 MHz) δ 8.01-7.98 (m, 1H), 7.84-7.76 (m, 2H), 7.70-7.65 (m, 1H), 7.08 (d, J=8.8 Hz, 2H), 6.91 (d, J=8.8 Hz, 2H), 5.79 (s, 2H), 4.84 (s, 2H), 3.96-3.93 (m, 2H), 3.71 (s, 3H), 3.70-3.60 (m, 6H) UPLC/MS: (ES+): 454.0, (ES−): 452.1. HPLC (max plot) 100.0%; Rt 3.40 min.

Example 39

3-(morpholin-4-ylcarbonyl)-1-propyl-1,4-dihydrothiochromeno[4,3-c]pyrazole 5,5-dioxide

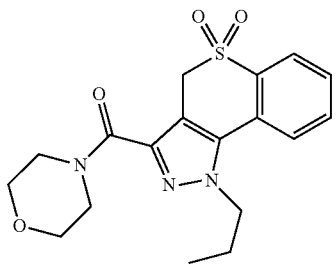 [SMILES: CCCn1nc(C(=O)N2CCOCC2)c2c1-c1ccccc1S(=O)(=O)C2]

Following the protocol outlined in Procedure AG, 3-(morpholin-4-ylcarbonyl)-1-propyl-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and propyl bromide to afford the title compound as an off-white solid. $^1$H NMR (DMSO-d$_6$, 400 MHz) δ 8.02 (d, J=7.8 Hz, 1H), 7.95 (d, J=7.7 Hz, 1H), 7.88 (t, J=7.7 Hz, 1H), 7.89 (t, J=7.8 Hz, 1H), 4.79 (s, 2H), 4.51 (t, J=7.1 Hz, 2H), 3.93 (brs, 2H), 3.65-3.62 (m, 6H), 1.97-1.81 (m, 2H), 0.86 (t, J=7.2 Hz, 3H). MS (ESI+): 376.0. HPLC (max plot) 99.0%; Rt 3.39 min.

Example 40

1-benzyl-3-(morpholin-4-ylcarbonyl)-1,4-dihydrothiochromeno[4,3-c]pyrazole 5,5-dioxide

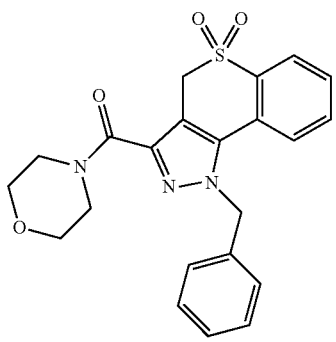 [SMILES: O=C(c1nn(Cc2ccccc2)c2c1CS(=O)(=O)c1ccccc1-2)N1CCOCC1]

Following the protocol outlined in Procedure AG, 1-benzyl-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and benzyl bromide to afford the title compound as a white solid. $^1$H NMR (DMSO-d$_6$, 400 MHz) δ 7.98 (d, J=7.7 Hz, 1H), 7.75-7.74 (m, 2H), 7.67-7.63 (m, 1H), 7.36-7.26 (m, 3H), 7.10 (d, J=7.4 Hz, 1H), 5.87 (s, 2H), 4.84 (s, 2H), 4.02-3.92 (m, 2H), 3.65-3.62 (m, 6H). MS (ESI+): 424.0. HPLC (max plot) 99.0%; Rt 3.92 min.

Example 41

3-(morpholin-4-ylcarbonyl)-1-(2-phenylethyl)-1,4-dihydrothiochromeno[4,3-c]pyrazole 5,5-dioxide

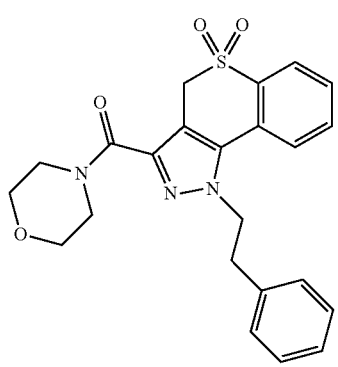

Following the protocol outlined in Procedure AG, 3-(morpholin-4-ylcarbonyl)-1-(2-phenylethyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and (2-bromoethyl)benzene to afford the title compound as a white solid. $^1$H NMR (DMSO-$d_6$, 400 MHz) δ 8.03-7.98 (m, 2H), 7.87 (t, J=7.5 Hz, 1H), 7.71 (t, J=7.6 Hz, 1H), 7.20-7.13 (m, 3H), 7.06 (d, J=7.6 Hz, 1H), 4.85 (t, J=6.5 Hz, 2H), 4.74 (s, 2H), 3.61-3.29 (m, 8H), 3.08 (t, J=6.5 Hz, 2H). MS (ESI+): 438.0. HPLC (max plot) 98.4%; Rt 4.02 min.

Example 42

N,N-dimethyl-2-[3-(morpholin-4-ylcarbonyl)-5,5-dioxidothiochromeno[4,3-c]pyrazol-1(4H)-yl]ethanamine

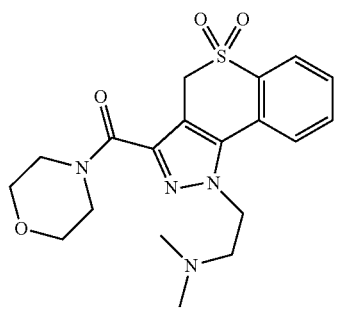 [SMILES: CN(C)CCn1nc(C(=O)N2CCOCC2)c2c1-c1ccccc1S(=O)(=O)C2]

Following the protocol outlined in Procedure AG, N,N-dimethyl-2-[3-(morpholin-4-ylcarbonyl)-5,5-dioxidothiochromeno[4,3-c]pyrazol-1(4H)-yl]ethanamine is obtained from 3-(morpholin-4-ylcarbonyl)-2,4-dihydrothiochromeno[4,3-c]pyrazole 5,5-dioxide and 2-bromo-N,N-dimethylethanamine to afford the title compound as a white solid. $^1$H NMR (DMSO-$d_6$, 400 MHz) δ 8.05-8.01 (m, 2H), 7.89 (t, J=7.6 Hz, 1H), 7.71 (t, J=7.6 Hz, 1H), 4.77 (s, 2H), 4.61 (t, J=6.4 Hz, 1H), 3.93 (br, 2H), 3.65-3.63 (m, 6H), 2.73 (t, J=6.5 Hz, 1H), 2.13 (s, 6H). MS (ESI+): 405.0. HPLC (max plot) 97.9%; Rt 2.00 min.

Example 43 tert-butyl 4-{[3-(morpholin-4-ylcarbonyl)-5,5-dioxidothiochromeno[4,3-c]pyrazol-1(4H)-yl]methyl}piperidine-1-carboxylate

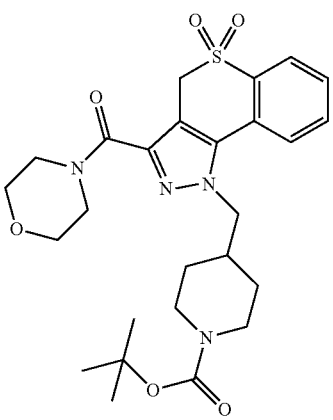 [SMILES: CC(C)(C)OC(=O)N1CCC(Cn2nc(C(=O)N3CCOCC3)c3c2-c2ccccc2S(=O)(=O)C3)CC1]

Following the protocol outlined in Procedure AG, tert-butyl 4-{[3-(morpholin-4-ylcarbonyl)-5,5-dioxidothiochromeno[4,3-c]pyrazol-1(4H)-yl]methyl}piperidine-1-carboxylate is obtained from 3-(morpholin-4-ylcarbonyl)-2,4-dihydrothiochromeno[4,3-c]pyrazole 5,5-dioxide and tert-butyl 4-(bromomethyl)piperidine-1-carboxylate to afford the title compound as a white solid. $^1$H NMR (DMSO-$d_6$, 400 MHz) δ 8.03-7.98 (m, 2H), 7.89-7.86 (m, 1H), 7.71 (t, J=8.0 Hz, 1H), 4.78 (s, 2H), 4.48 (d, J=7.2 Hz, 2H), 3.91-3.85 (m, 3H), 3.65-3.63 (m, 6H), 2.66-2.62 (m, 2H), 2.04 (t, J=3.6 Hz, 2H), 1.47-1.44 (m, 2H), 1.35 (s, 9H), 1.14-1.08 (m, 2H). MS (ESI+): 431.0. HPLC (max plot) 96.8%; Rt 4.41 min.

Example 44

1-(3-methoxypropyl)-3-(morpholin-4-ylcarbonyl)-1,4-dihydrothiochromeno[4,3-c]pyrazole 5,5-dioxide

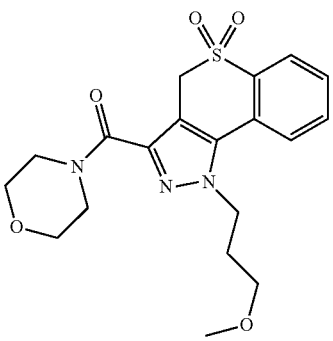 [SMILES: COCCCn1nc(C(=O)N2CCOCC2)c2c1-c1ccccc1S(=O)(=O)C2]

Following the protocol outlined in Procedure AG, 1-(3-methoxypropyl)-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno

[4,3-c]pyrazole 5,5-dioxide and 1-bromo-3-methoxypropane to afford the title compound as an off-white solid. $^1$H NMR (DMSO-d$_6$, 400 MHz) δ 8.03-7.98 (m, 2H), 7.90-7.86 (m, 1H), 7.73-7.70 (m, 1H), 4.78 (s, 2H), 4.59 (t, J=7.0 Hz, 2H), 3.93 (m, 2H), 3.65-3.63 (m, 6H), 3.27-3.21 (m, 2H), 3.13 (s, 3H), 2.09 (t, J=6.28 Hz, 2H). MS (ESI+): 406.0 HPLC (max plot) 97.2%; Rt 3.07 min.

Example 45

3-(morpholin-4-ylcarbonyl)-1-(tetrahydrofuran-2-ylmethyl)-1,4-dihydrothiochromeno[4,3-c]pyrazole 5,5-dioxide

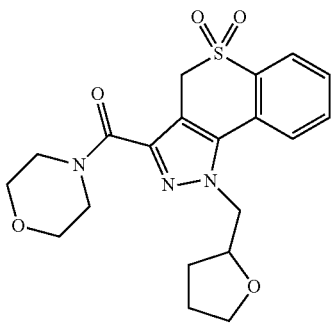 [SMILES: O=C(c1nn(CC2CCCO2)c2c1CS(=O)(=O)c1ccccc1-2)N1CCOCC1]

Following the protocol outlined in Procedure AG, 3-(morpholin-4-ylcarbonyl)-1-(tetrahydrofuran-2-ylmethyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 2-(bromomethyl)tetrahydrofuran to afford the title compound as an off-white solid. $^1$H NMR (DMSO-d$_6$, 400 MHz) δ 8.17 (d, J=7.9 Hz, 1H), 8.00 (d, J=7.1 Hz, 1H), 7.87 (t, J=6.9 Hz, 1H), 7.70 (t, J=7.6 Hz, 2H), 4.84-4.80 (m, 2H), 4.77-4.73 (m, 2H), 4.34-4.31 (m, 1H), 3.92 (brs, 2H), 3.69-3.56 (m, 8H), 2.49 (m, 2H), 2.03 (t, J=6.6 Hz, 2H). MS (ESI+): 418.0. HPLC (max plot) 95.0%; Rt 3.14 min.

Example 46

2-[3-(morpholin-4-ylcarbonyl)-5,5-dioxidothiochromeno[4,3-c]pyrazol-1(4H)-yl]ethanol

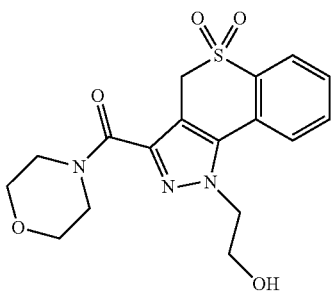 [SMILES: O=C(c1nn(CCO)c2c1CS(=O)(=O)c1ccccc1-2)N1CCOCC1]

Following the protocol outlined in Procedure AG, 2-[3-(morpholin-4-ylcarbonyl)-5,5-dioxidothiochromeno[4,3-c]pyrazol-1(4H)-yl]ethanol is obtained from 3-(morpholin-4-ylcarbonyl)-2,4-dihydrothiochromeno[4,3-c]pyrazole 5,5-dioxide and 2-bromoethanol to afford the title compound as a pale brown solid. $^1$H NMR (DMSO-d$_6$, 400 MHz) δ 8.26 (d, J=7.9 Hz, 1H), 8.01 (d, J=7.7 Hz, 1H), 7.87 (t, J=7.7 Hz, 1H), 7.71 (t, J=7.6 Hz, 1H), 5.22 (t, J=5.2 Hz, 1H), 4.78 (s, 2H), 4.54 (t, J=5.2 Hz, 2H), 3.95-3.93 (m, 4H), 3.66-3.62 (m, 6H). MS (ESI+): 378.0. HPLC (max plot) 93.9%; Rt 2.32 min.

Example 47

3-(morpholin-4-ylcarbonyl)-1-(pyridin-2-ylmethyl)-1,4-dihydrothiochromeno[4,3-c]pyrazole 5,5-dioxide

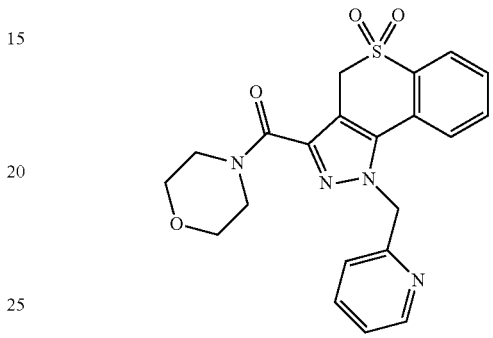

Following the protocol outlined in Procedure AG, 3-(morpholin-4-ylcarbonyl)-1-(pyridin-2-ylmethyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 2-(bromomethyl)pyridine to afford the title compound as a pale brown solid. $^1$H NMR (DMSO-d$_6$, 400 MHz) δ 8.53 (d, J=4.7 Hz, 1H), 8.00-7.97 (m, 2H), 7.82-7.67 (m, 3H), 7.36-7.33 (m, 1H), 7.24 (d, J=7.8 Hz, 1H), 5.89 (s, 2H), 4.83 (s, 2H), 3.88 (m, 2H), 3.65-3.58 (m, 6H). MS (ESI+): 425.0. HPLC (max plot) 97.5%; Rt 2.55 min.

Example 48

1-butyl-3-(morpholin-4-ylcarbonyl)-1,4-dihydrothiochromeno[4,3-c]pyrazole 5,5-dioxide

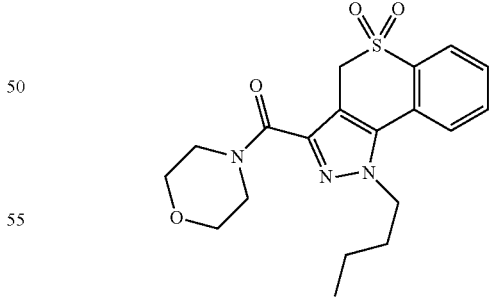

Following the protocol outlined in Procedure AG, 1-butyl-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 1-bromobutane to afford the title compound as an off-white solid. $^1$H NMR (DMSO-d$_6$, 400 MHz) δ 8.02 (d, J=7.8 Hz, 1H), 7.95 (d, J=7.7 Hz, 1H), 7.88 (t, J=7.7 Hz, 1H), 7.89 (t, J=7.8 Hz, 1H), 4.79 (s, 2H), 4.51 (t, J=7.1 Hz, 2H), 3.93 (brs, 2H), 3.65-3.62 (m, 6H), 1.97-1.81 (m, 2H), 0.86 (t, J=7.2 Hz, 3H). MS (ESI+): 376.0. HPLC (max plot) 99.0%; Rt 3.39 min.

Example 49

1-(cyclopentylmethyl)-3-(morpholin-4-ylcarbonyl)-1,4-dihydrothiochromeno[4,3-c]pyrazole 5,5-dioxide

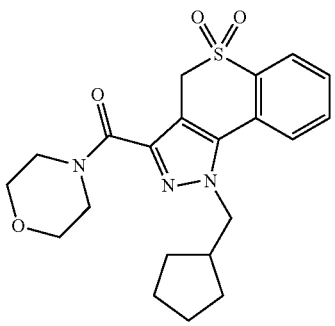 [SMILES: O=C(c1nn(CC2CCCC2)c2c1CS(=O)(=O)c1ccccc1-2)N1CCOCC1]

Following the protocol outlined in Procedure AG, 1-(cyclopentylmethyl)-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and (bromomethyl)cyclopentane to afford the title compound as an off-white solid. $^1$H NMR (DMSO-$d_6$, 400 MHz) δ 8.01 (dd, J=7.7 Hz, J=2.1 Hz, 1H), 7.88 (t, J=7.4 Hz, 1H), 7.70 (t, J=7.7 Hz, 1H), 4.78 (m, 2H), 4.50 (d, J=7.5 Hz, 2H), 3.93 (brs, 2H), 3.65-3.62 (m, 6H), 2.42-2.35 (m, 1H), 1.60-1.57 (m, 4H), 1.54-1.50 (m, 2H), 1.47-1.44 (m, 2H). MS (ESI+): 376.0. HPLC (max plot) 982%; Rt 4.29 min.

Example 50

1-isobutyl-3-(morpholin-4-ylcarbonyl)-1,4-dihydrothiochromeno[4,3-c]pyrazole 5,5-dioxide

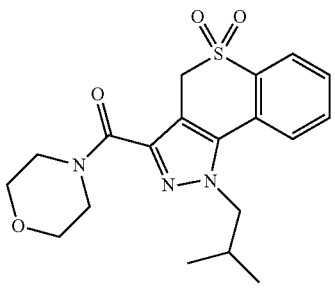 [SMILES: CC(C)Cn1nc(C(=O)N2CCOCC2)c2c1-c1ccccc1S(=O)(=O)C2]

Following the protocol outlined in Procedure AG, 1-isobutyl-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 1-bromo-2-methylpropane to afford the title compound as a white solid. $^1$H NMR (DMSO-$d_6$, 400 MHz) δ 8.00 (d, J=7.9 Hz, 2H), 7.88 (t, J=7.6 Hz, 1H), 7.70 (t, J=7.7 Hz, 1H), 4.78 (s, 2H), 4.40 (d, J=7.4 Hz, 2H), 3.92 (brs, 2H), 3.65-3.62 (m, 6H), 2.15-2.08 (m, 1H), 0.82 (d, J=7.4 Hz, 6H). MS (ESI+): 390.0. HPLC (max plot) 98.3%; Rt 3.74 min.

Example 51

1-(cyclohexylmethyl)-3-(morpholin-4-ylcarbonyl)-1,4-dihydrothiochromeno[4,3-c]pyrazole 5,5-dioxide

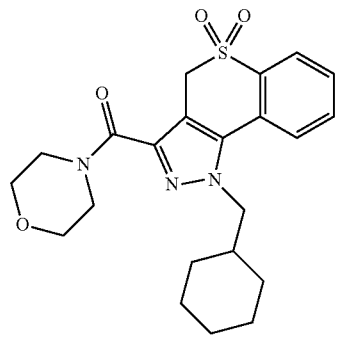 [SMILES: O=C(c1nn(CC2CCCCC2)c2c1CS(=O)(=O)c1ccccc1-2)N1CCOCC1]

Following the protocol outlined in Procedure AG, 1-(cyclohexylmethyl)-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and (bromomethyl)cyclohexane to afford the title compound as a white solid. $^1$H NMR (DMSO-$d_6$, 400 MHz) δ 8.02-7.98 (m, 2H), 7.88 (t, J=7.6 Hz, 1H), 7.70 (t, J=7.6 Hz, 1H), 4.77 (s, 2H), 4.42 (d, J=7.3 Hz, 2H), 3.92-3.89 (m, 2H), 3.65-3.62 (m, 6H), 1.86-1.80 (m, 1H), 1.60-1.54 (m, 6H), 1.50-1.47 (m, 3H), 1.09-0.99 (m, 2H). MS (ESI+): 430.0. HPLC (max plot) 97.4%; Rt 4.56 min.

Example 52

3-(morpholin-4-ylcarbonyl)-1-(tetrahydro-2H-pyran-4-ylmethyl)-1,4-dihydrothiochromeno[4,3-c]pyrazole 5,5-dioxide

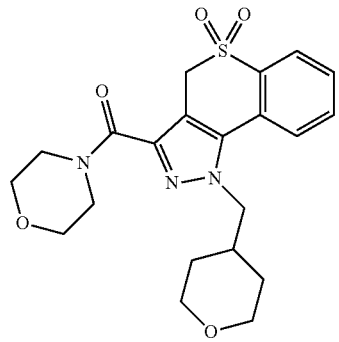 [SMILES: O=C(c1nn(CC2CCOCC2)c2c1CS(=O)(=O)c1ccccc1-2)N1CCOCC1]

Following the protocol outlined in Procedure AG, 3-(morpholin-4-ylcarbonyl)-1-(tetrahydro-2H-pyran-4-ylmethyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 4-(bromomethyl)tetrahydro-2H-pyran to afford the title compound as an off-white solid. $^1$H NMR (DMSO-$d_6$, 400 MHz) δ 8.02-8.00 (m, 2H), 7.90-7.86 (m, 1H), 7.71 (t, J=7.7 Hz, 1H), 4.78 (s, 2H), 4.48 (d, J=7.3 Hz, 2H), 3.90-3.89 (m, 2H), 3.79-3.76 (m, 2H), 3.65-3.63 (m, 6H), 3.18 (d, J=11.8 Hz, 2H), 2.12-2.07 (m, 1H), 1.47-1.40 (m, 2H), 1.35-1.30 (m, 3H). MS (ESI+): 432.0. HPLC (max plot) 97.1%; Rt 3.04 min.

Example 53

1-(2-methoxyethyl)-3-(morpholin-4-ylcarbonyl)-1,4-dihydrothiochromeno[4,3-c]pyrazole 5,5-dioxide

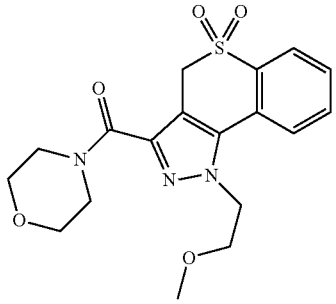

Following the protocol outlined in Procedure AG, 1-(2-methoxyethyl)-3-(morpholin-4-ylcarbonyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 1-bromo-2-methoxyethane to afford the title compound as a white solid. $^1$H NMR (DMSO-d$_6$, 400 MHz) δ 8.14 (d, J=7.9 Hz, 1H), 8.01 (d, J=7.8 Hz, 1H), 7.87 (t, J=7.6 Hz, 1H), 7.71 (t, J=7.6 Hz, 1H), 4.78 (s, 2H), 4.67 (t, J=5.12 Hz, 2H), 3.93-3.85 (m, 4H), 3.66-3.64 (m, 2H), 3.21 (s, 3H). MS (ESI+): 392.0. HPLC (max plot) 94.2%; Rt 2.97 min.

Example 54

3-[3-(morpholin-4-ylcarbonyl)-5,5-dioxidothiochromeno[4,3-c]pyrazol-1(4H)-yl]propan-1-ol

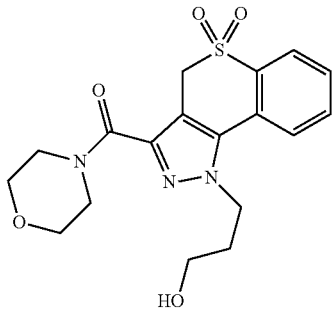 [SMILES: O=C(c1nn(CCCO)c2c1CS(=O)(=O)c1ccccc1-2)N1CCOCC1]

Following the protocol outlined in Procedure AG, 343-(morpholin-4-ylcarbonyl)-5,5-dioxidothiochromeno[4,3-c]pyrazol-1(4H)-yl]propan-1-ol is obtained from 3-(morpholin-4-ylcarbonyl)-2,4-dihydrothiochromeno[4,3-c]pyrazole 5,5-dioxide and 3-bromopropan-1-ol to afford the title compound as a white solid. $^1$H NMR (DMSO-d$_6$, 400 MHz) δ 8.03-8.01 (m, 2H), 7.88 (t, J=7.9 Hz, 1H), 7.71 (t, J=7.8 Hz, 1H), 4.78 (s, 2H), 4.74 (t, J=4.8 Hz, 1H), 4.59 (t, J=7.1 Hz, 1H), 3.92 (brs, 2H), 3.65-3.63 (m, 6H), 3.49-3.48 (m, 2H), 2.05-1.99 (m, 2H). MS (ESI+): 392.0. HPLC (max plot) 99.0%; Rt 2.45 min.

Example 55

3-(morpholin-4-ylcarbonyl)-1-(2-pyridin-2-ylethyl)-1,4-dihydrothiochromeno[4,3-c]pyrazole 5,5-dioxide

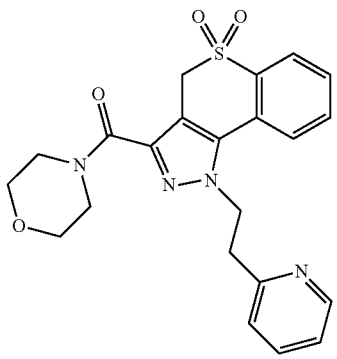

Following the protocol outlined in Procedure AG, 13-(morpholin-4-ylcarbonyl)-1-(2-pyridin-2-ylethyl)-1,4-dihydrothiochromeno[4,3-c]pyrazole 5,5-dioxide is obtained from 3-(morpholin-4-ylcarbonyl)-2,4-dihydrothiochromeno[4,3-c]pyrazole 5,5-dioxide and 2-(2-bromoethyl)pyridine to afford the title compound as a white solid. $^1$H NMR (DMSO-d$_6$, 400 MHz) δ 8.50 (d, J=4.6 Hz, 1H), 8.07 (d, J=7.8 Hz, 1H), 8.02 (d, J=7.7 Hz, 1H), 7.89 (t, J=7.1 Hz, 1H), 7.75-7.70 (m, 2H), 7.30-7.22 (m, 2H), 4.98 (t, J=6.7 Hz, 2H), 4.75 (s, 2H), 3.61-3.58 (m, 6H), 3.50-3.48 (m, 2H), 3.40-3.37 (m, 2H). MS (ESI+): 439.0. HPLC (max plot) 98.7%; Rt 2.12 min.

Compounds described below are obtained following protocol outlined in procedure AG

---

Example 69: N,N-Dimethyl-3-[3-(morpholin-4-ylcarbonyl)-5,5-dioxidothiochromeno[4,3-c]pyrazol-1(4H)-yl]propan-1-amine

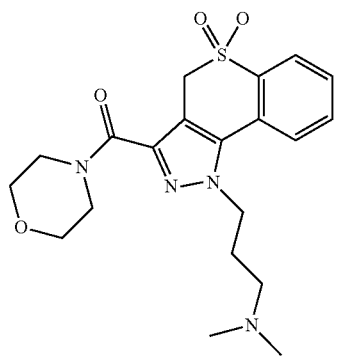

11 mg of the title compound as a pale brown solid 1H NMR (400 MHz, DMSO-d6): δ 8.05-8.00 (m, 2H), 7.88 (d, J = 6.5 Hz, 1H), 7.71 (t, J = 7.7 Hz, 1H), 4.78 (s, 1H), 4.56 (t, J = 6.7 Hz, 1H), 3.93 (bs, 2H), 3.65-3.63 (m, 6H), 2.19 (d, J = 7.7 Hz, 1H), 2.07-1.96 (m, 8H). MS (ESI+): 419.3. HPLC (max plot) 98.68%; Rt 2.11 min.

Example 70: 1-[(1-Methylpiperidin-3-yl)methyl]-3-(morpholin-4-ylcarbonyl)-1,4-dihydrothiochromeno[4,3-c]pyrazole 5,5-dioxide

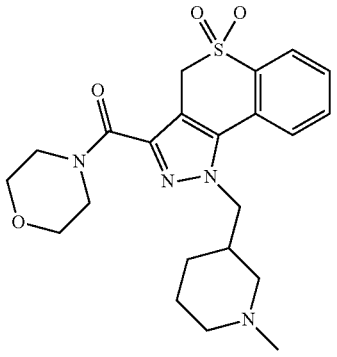

71 mg of the title compound as an off white solid. 1H NMR (400 MHz, DMSO-d6) δ = 8.05-8.03 (m, 2H), 7.88 (t, J = 7.6 Hz, 1H), 7.71 (t, J = 7.7 Hz, 1H), 4.78 (s, 2H), 4.56-4.45 (m, 1H), 3.92 (bs, 2H), 3.66-3.62 (m, 6H), 2.49-2.48 (m, 2H), 1.57-1.55 (m, 5H), 1.50-1.48 (m, 1H), 1.38-1.35 (m, 4H). MS (ESI+): 445.3. HPLC (max plot) 98.64%; Rt 2.20 min Example 71: 1-[2-(1-Methylpyrrolidin-2-yl)ethyl]-3-(morpholin-4-ylcarbonyl)-1,4-dihydrothiochromeno[4,3-c]pyrazole 5,5-dioxide

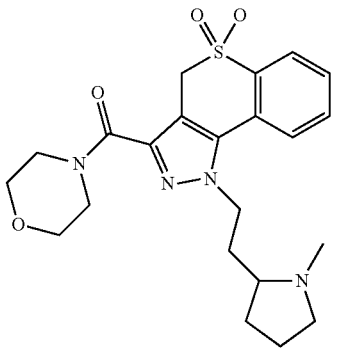

30 mg of the title compound as an off white solid. 1H NMR (400 MHz, DMSO-d6) δ = 8.10 (d, J = 7.9 Hz, 1H), 8.01 (d, J = 7.7 Hz, 1H), 7.87 (t, J = 7.7 Hz, 1H), 7.71 (t, J = 7.6 Hz, 1H), 4.76 (s, 2H), 4.65 (t, J = 5.8 Hz, 1H), 3.93 (bs, 2H), 3.65-3.62 (m, 6H), 2.90-2.88 (m, 1H), 2.11 (s, 3H), 2.01 (t, J = 8.5 Hz, 1H), 1.99-1.97 (m, 2H), 1.81-1.76 (m, 3H). MS (ESI+): 445.3. HPLC (max plot) 98.2%; Rt 2.26 min Example 72: 3-(Morpholin-4-ylcarbonyl)-1-(2-morpholin-4-ylethyl)-1,4-dihydrothiochromeno[4,3-c]pyrazole 5,5-dioxide

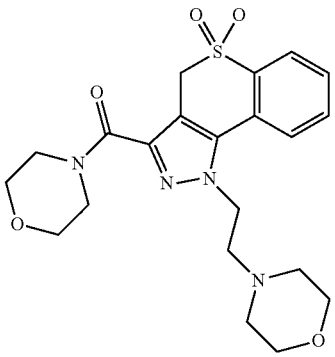

57 mg of the title compound as a white solid. 1H NMR (400 MHz, DMSO-d6) δ = 8.10 (d, J = 7.9 Hz, 1H), 8.01 (d, J = 7.7 Hz, 1H), 7.87 (t, J = 7.7 Hz, 1H), 7.71 (t, J = 7.6 Hz, 1H), 4.76 (s, 2H), 4.65 (t, J = 5.8 Hz, 1H), 3.93 (bs, 2H), 3.65-3.62 (m, 6H), 3.32 (m, 4H), 2.76-2.73 (m, 2H), 2.31-2.29 (m, 4H). MS (ESI+): 447.0. HPLC (max plot) 97.97%; Rt 2.05 min Example 232: 1-(3-Methoxybenzyl)-3-(morpholin-4-ylcarbonyl)-1,4-dihydrothiochromeno[4,3-c]pyrazole 5,5-dioxide

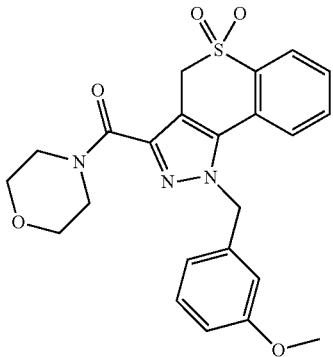

23 mg of the title compound as a white solid. $^1$H NMR (DMSO-$d_6$): δ 8.11-8.14 (m, 1H), 7.54-7.61 (m, 2H), 7.41-7.44 (m, 1H), 7.28-7.35 (m, 1H), 6.86-6.89 (m, 1H), 6.69-6.71 (m, 1H), 6.65-6.66 (m, 1H), 5.67 (s, 2H), 4.76 (s, 2H), 4.19-4.22 (m, 2H), 3.74-3.81 (m, 9H). HPLC (max plot) 98.2%; Rt 3.41 min. MS (ESI+): 453.7.

Example 230: 1-[(3-Ethyl-1,2,4-oxadiazol-5-yl)methyl]-3-(morpholin-4-ylcarbonyl)-1,4-dihydrothiochromeno[4,3-c]pyrazole 5,5-dioxide

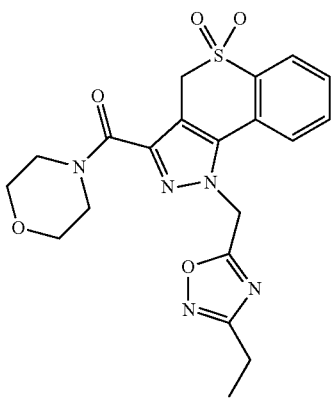

50 mg of the title compound as an white solid. 1H NMR (DMSO-d6): δ 8.01-8.04 (m, 1H), 7.89-7.92 (m, 1H), 7.80-7.86 (m, 1H), 7.69-7.74 (m, 1H), 6.24 (s, 2H), 4.83 (s, 2H), 3.80-3.82 (m, 2H), 3.55-3.64 (m, 6H), 2.65-2.72 (m, 2H), 1.12-1.17 (m, 3H). HPLC (max plot) 97.8%; Rt 2.82 min. MS (ESI+): 443.7.

Example 231: Methyl 5-{[3-(morpholin-4-ylcarbonyl)-5,5-dioxidothiochromeno[4,3-c]pyrazol-1(4H)-yl]methyl}-2-furoate

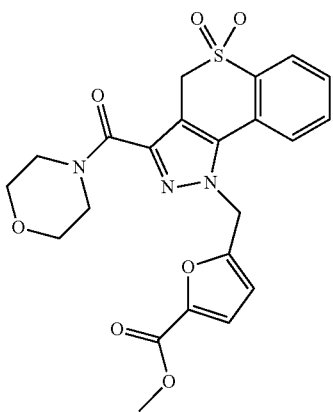

15 mg of the title compound as a white solid. 1H NMR (DMSO-d6) δ 8.01-8.03 (m, 2H), 7.84-7.89 (m, 1H), 7.69-7.75 (m, 1H), 7.27-7.28 (m, 1H), 6.60-6.61 (d, 1H), 5.95 (s, 2H), 4.81 (s, 2H), 3.84-3.86 (m, 2H), 3.76 (s, 3H), 3.49-3.72 (m, 6H). 1H NMR (DMSO-d6) δ. HPLC (max plot) 98.3%; Rt 2.59 min. MS (ESI−): 470.0.

-continued

Example 239: 1-(1,3-Benzothiazol-2-ylmethyl)-3-(morpholin-4-ylcarbonyl)-1,4-dihydrothiochromeno[4,3-c]pyrazole 5,5-dioxide

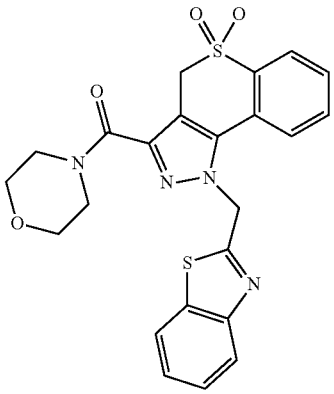

42 mg of the title compound as a pale beige solid. 1H NMR (DMSO-d6) δ 8.08-8.11 (m, 1H), 8.00-8.04 (m, 3H), 7.80-7.85 (m, 1H), 7.67-7.72 (m, 1H), 7.42-7.55 (m, 2H), 6.32 (s, 2H), 4.85 (s, 2H), 3.90-3.91 (m, 2H), 3.60-3.66 (m, 6H). 1H NMR (DMSO-d6) δ. HPLC (max plot) 99.9%; Rt 2.97 min. MS (ESI+): 480.7.

Example 240: 1-[(4-Chloro-2-thienyl)methyl]-3-(morpholin-4-ylcarbonyl)-1,4-dihydrothiochromeno[4,3-c]pyrazole 5,5-dioxide

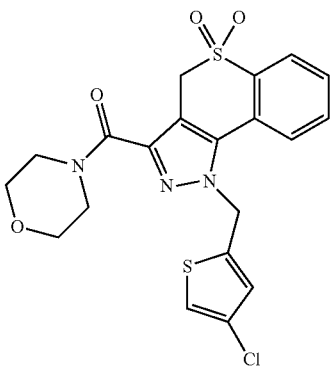

34 mg of the title compound as a white solid. HPLC (max plot) 99.2%; Rt 3.57 min. MS (ESI+): 463.6.

Example 315: N-[3-(Morpholin-4-ylcarbonyl)-5,5-dioxido-1-phenyl-1,4-dihydrothiochromeno[4,3-c]pyrazol-6-yl]benzamide

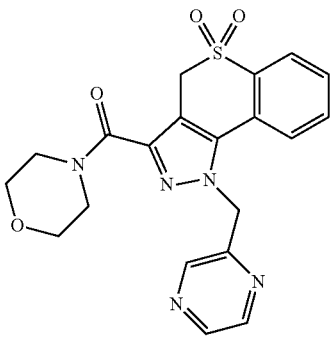 [SMILES: O=C(c1nn(Cc2cnccn2)c2c1CS(=O)(=O)c1ccccc1-2)N1CCOCC1]

13 mg as off-white solid. $^1$H NMR (DMSO-$d_6$, 400 MHz): δ 8.68 (s, 1H), 8.61-8.60 (d, J = 4.6 Hz, 2H), 8.02-8.00 (d, J = 8.0 Hz, 2H), 7.79 (m, 1H), 7.71-7.69 (m, 1H), 4.76 (s, 2H), 6.01 (s, 2H), 4.82 (s, 2H), 3.83 (m, 2H), 3.63-3.55 (m, 6H). MS (ESI+): 426.0. HPLC (max plot) 96.72%; Rt 2.75 min -continued Example 190: 1-{[1-(2-Methoxyethyl)piperidin-4-yl]methyl}-3-(morpholin-4-ylcarbonyl)-1,4-dihydrothiochromeno[4,3-c]pyrazole 5,5-dioxide

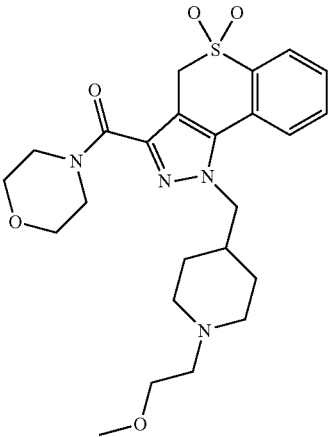 [SMILES: COCCN1CCC(Cn2nc(C(=O)N3CCOCC3)c3c2-c2ccccc2S(O)(O)C3)CC1]

3 mg of the title compound as a pale brown solid. $^1$H NMR (CDCl$_3$, 400 MHz): δ 8.16-8.14 (d, J = 7.6 Hz, 1H), 7.74-7.62 (m, 3H), 4.68 (s, 2H), 4.39-4.37 (m, 2H), 4.17 (brs, 3H), 3.79 (bs, 7H), 3.79 (m, 3H), 3.34 (bs, 3H), 3.04 (m, 2H), 2.61 (m, 2H), 2.03 (m, 3H), 1.61 (m, 1H). MS (ESI+): 489.0. HPLC (max plot) 94.22%; Rt 2.34 min Example 407: 3-(Morpholin-4-ylcarbonyl)-1-[1-(2-morpholin-4-ylethyl)azetidin-3-yl]-1,4-dihydrothiochromeno[4,3-c]pyrazole 5,5-dioxide

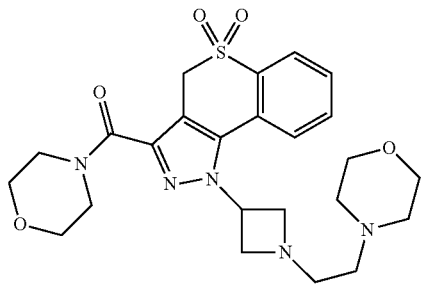 [SMILES: O=C(c1nn(C2CN(CCN3CCOCC3)C2)c2c1CS(=O)(=O)c1ccccc1-2)N1CCOCC1]

73 mg of the title compound as a white foam. $^1$H NMR (DMSO-d$_6$): δ 8.04-8.01 (m, 1H), 7.92-7.82 (m, 2H), 7.75-7.70 (m, 1H), 5.54-5.46 (quint, J = 6.65 Hz, 1H), 4.79 (s, 2H), 3.95-3.86 (m, 4H), 3.67 (s, 6H), 3.56-3.46 (m, 6H), 2.64-2.60 (m, 2H), 2.38-2.27 (m, 6H). HPLC (max plot) 99.0%; Rt 5.30 min. MS (ESI+): 562.3.

Example 275: 3-(Morpholin-4-ylcarbonyl)-1-[1-(2-morpholin-4-ylethyl)pyrrolidin-3-yl]-1,4-dihydrothiochromeno[4,3-c]pyrazole 5,5-dioxide

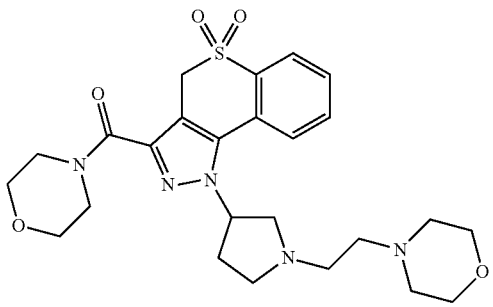 [SMILES: O=C(c1nn(C2CCN(CCN3CCOCC3)C2)c2c1CS(=O)(=O)c1ccccc1-2)N1CCOCC1]

80 mg (72%) of the title compound as a white foam. 1H NMR (DMSO-d6): δ 8.03 (dd, J = 7.8 Hz, 1H,): 7.97 (m, 1H), 7.89 (m, 1H), 7.73 (m, 1H), 5.47 (m, 1H), 4.77 (m, 2H), 3.95 (m, 2H), 3.72-3.61 (m, 6H), 3.54 (m, 4H), 3.28 (m, 2H), 2.86 (m, 1H), 2.77 (m, 2H), 2.67-2.55 (m, 2H), 2.46-2.34 (m, 6H), 2.30-2.18 (m, 1H). HPLC (max plot) 74.2%; Rt 1.60 min. MS (ESI+): 516.3.

Example 277: 1-{1-[2-(4-Fluoropiperidin-1-yl)ethyl]pyrrolidin-3-yl}-3-(morpholin-4-ylcarbonyl)-1,4-dihydrothiochromeno[4,3-c]pyrazole 5,5-dioxide

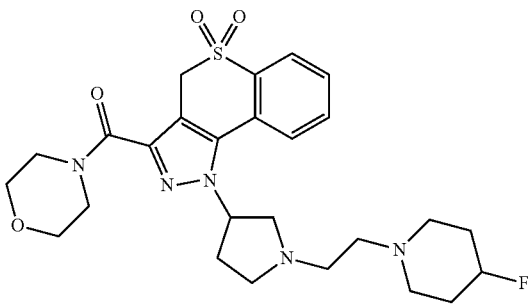 [SMILES: O=C(c1nn(C2CCN(CCN3CCC(F)CC3)C2)c2c1CS(=O)(=O)c1ccccc1-2)N1CCOCC1]

80 mg of the title compound as a white foam. 1H NMR (DMSO-d6) δ 8.32-8.30 (m, 1H): 7.97 (m, 1H), 7.89 (m, 1H), 7.73 (m, 1H), 5.46 (m, 1H), 4.78 (s, 2H), 4.72 (m, 0.5H), 4.56 (m, 0.5H), 3.96 (m, 2H), 3.72-3.60 (m, 6H), 3.27 (m, 1H), 2.86 (m, 1H), 2.76 (m, 2H), 2.67-2.52 (m, 3H), 2.47-2.36 (m, 2H), 2.35-2.16 (m, 3H), 190-1.50 (m, 3H). HPLC (max plot) 99.7%; Rt 1.50 min. MS (ESI+): 532.3.

Example 286: 3-(Morpholin-4-ylcarbonyl)-1-{1-[2-(1H-pyrazol-1-yl)ethyl]pyrrolidin-3-yl}-1,4-dihydrothiochromeno[4,3-c]pyrazole 5,5-dioxide

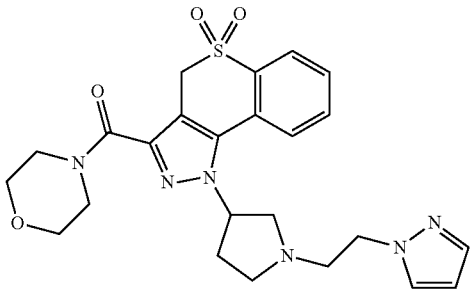 [SMILES: O=C(c1nn(C2CCN(CCn3cccn3)C2)c2c1CS(=O)(=O)c1ccccc1-2)N1CCOCC1]

20 mg (27%) of the title compound as a pale yellow foam. 1H NMR (DMSO-d6): δ 8.04 (d, J = 8.2, 1H), 8.00-7.84 (m, 2H), 7.75 (d, J = 6.5 Hz, 2H), 7.41 (s, 1H), 6.20 (s, 1H), 5.49 (s, 1H), 4.78 (s, 2H), 4.23 (s, 2H), 3.93 (s, 2H), 3.66 (s, 5H), 3.30-3.21 (m, 1H), 2.84 (d, J = 3.1 Hz, 4H), 2.45-2.33 (m, 1H), 2.27 (s, 2H). HPLC (max plot) 98.5%; Rt 2.00 min. MS (ESI+): 497.2.

Example 288: 1-{1-[2-(1H-Imidazol-1-yl)ethyl]pyrrolidin-3-yl}-3-(morpholin-4-ylcarbonyl)-1,4-dihydrothiochromeno[4,3-c]pyrazole 5,5-dioxide

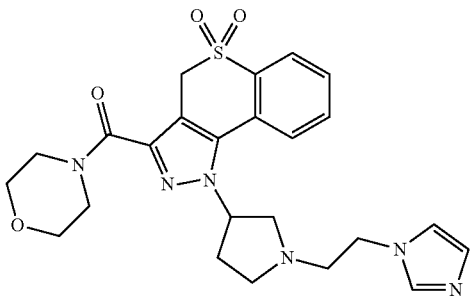 [SMILES: O=C(c1nn(C2CCN(CCn3ccnc3)C2)c2c1CS(=O)(=O)c1ccccc1-2)N1CCOCC1]

40 mg of the title compound as a white foam. 1H NMR (DMSO-d6) δ 8.04 (d, J = 7.5 Hz, 1H), 8.00-7.83 (m, 2H), 7.74 (t, J = 7.4 Hz, 1H), 7.65 (s, 1H), 7.20 (s, 1H), 6.85 (s, 1H), 5.48 (s, 1H), 4.78 (s, 2H), 4.08 (t, J = 6.1 Hz, 2H), 3.94 (s, 2H), 3.66 (s, 5H), 3.28 (d, J = 9.4 Hz, 1H), 2.93 (dd, J = 9.7, 4.7 Hz, 1H), 2.87-2.73 (m, 4H), 2.43 (d, J = 8.2 Hz, 1H), 2.25 (d, J = 7.6 Hz, 1H). HPLC (max plot) 86.7%; Rt 1.55 min. MS (ESI+): 497.2.

Example 310: 1-(1-{2-[(3S)-3-Fluoropyrrolidin-1-yl]ethyl}pyrrolidin-3-yl)-3-(morpholin-4-ylcarbonyl)-1,4-dihydrothiochromeno[4,3-c]pyrazole 5,5-dioxide

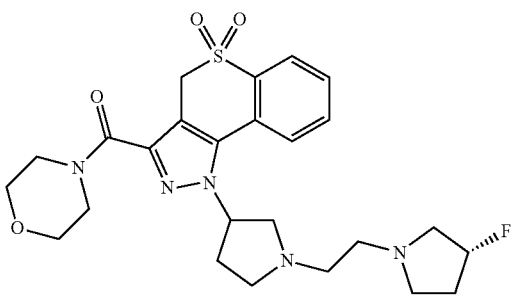 [SMILES: O=C(c1nn(C2CCN(CCN3CC[C@@H](F)C3)C2)c2c1CS(=O)(=O)c1ccccc1-2)N1CCOCC1]

50 mg of the title compound as a pale yellow foam. $^1$H NMR (DMSO-d$_6$): δ 8.03 (dd, J = 7.8 Hz, 1.1, 1H), 7.97 (d, J = 7.5 Hz, 1H), 7.89 (t, J = 7.6 Hz, 1H), 7.73 (t, J = 7.6 Hz, 1H), 5.47 (s, 1H), 5.25 (s, 1H), 5.06 (s, 1H), 4.86-4.71 (m, 2H), 3.96 (s, 2H), 3.66 (s, 6H), 3.27 (d, J = 8.2 Hz, 1H), 2.92-2.71 (m, 5H), 2.59 (dt, J = 15.7, 8.4 Hz, 5H), 2.47-2.36 (m, 1H), 2.28 (dd, J = 15.3, 7.2 Hz, 2H), 2.10-2.08 (m, 1H), 1.94-1.69 (m, 1H).. HPLC (max plot) 100.0%; Rt 1.77 min. MS (ESI+): 517.9.

Example 308: 1-(1-{2-[(3R)-3-Fluoropyrrolidin-1-yl]ethyl}pyrrolidin-3-yl)-3-(morpholin-4-ylcarbonyl)-1,4-dihydrothiochromeno[4,3-c]pyrazole 5,5-dioxide

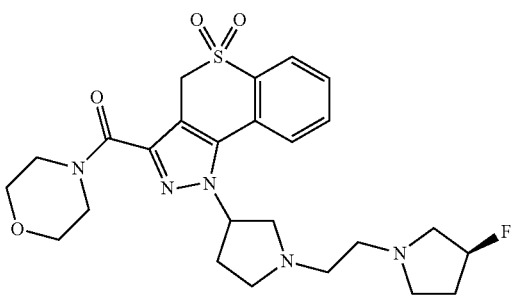 [SMILES: O=C(c1nn(C2CCN(CCN3CC[C@H](F)C3)C2)c2c1CS(=O)(=O)c1ccccc1-2)N1CCOCC1]

36 mg of the title compound as a pale yellow foam. 1H NMR (DMSO-d6): δ 8.03 (d, J = 7.6 Hz, 1H), 8.00-7.83 (m, 2H), 7.73 (t, J = 7.7 Hz, 1H), 5.47 (s, 1H), 5.25 (s, 1H), 5.07 (s, 1H), 4.78 (s, 2H), 3.96 (s, 2H), 3.66 (s, 5H), 3.27 (d, J = 8.7 Hz, 1H), 2.93-2.70 (m, 5H), 2.69-2.53 (m, 4H), 2.42 (d, J = 8.9 Hz, 1H), 2.35-2.16 (m, 2H), 2.16-1.97 (m, 1H), 1.94-1.70 (m, 2H). HPLC (max plot) 100.0%; Rt 1.69 min. MS (ESI+): 517.8.

Example 311: 1-{1-[2-(3,3-Difluoroazetidin-1-yl)ethyl]pyrrolidin-3-yl}-3-(morpholin-4-ylcarbonyl)-1,4-dihydrothiochromeno[4,3-c]pyrazole 5,5-dioxide

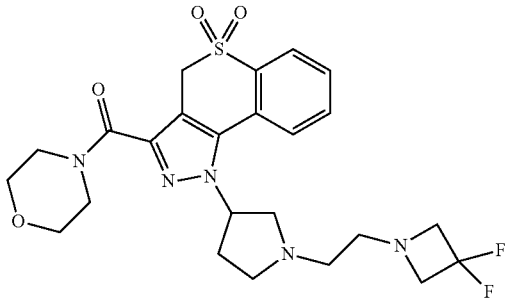 [SMILES: O=C(c1nn(C2CCN(CCN3CC(F)(F)C3)C2)c2c1CS(=O)(=O)c1ccccc1-2)N1CCOCC1]

50 mg of the title compound as a pale yellow foam. $^1$H NMR (DMSO-$d_6$): δ 8.04 (dd, J = 7.8 Hz, 1.2, 1H), 7.99-7.85 (m, 2H), 7.74 (dd, J = 11.4, 4.9 Hz, 1H), 5.47 (s, 2H), 4.78 (s, 2H), 3.95 (s, 2H), 3.66 (s, 5H), 3.57 (t, J = 12.5 Hz, 4H), 3.25 (s, 1H), 2.83 (d, J = 37.8 Hz, 3H), 2.65 (s, 2H), 2.47-2.37 (m, 1H), 2.24 (d, J = 5.6 Hz, 1H). HPLC (max plot) 98.2%; Rt 2.45 min. HPLC (max plot) 66.3%; Rt 2.19 min. MS (ESI+): 521.8.

Example 255: 1-[1-(2-Methoxyethyl)pyrrolidin-3-yl]-3-(morpholin-4-ylcarbonyl)-1,4-dihydrothiochromeno[4,3-c]pyrazole 5,5-dioxide

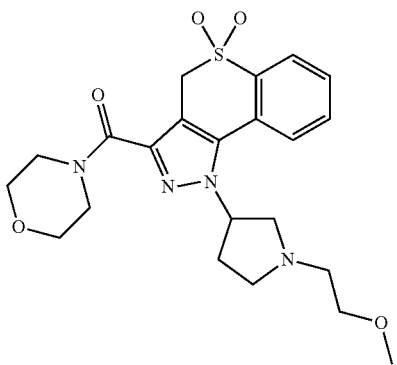 [SMILES: COCCN1CCC(n2nc(C(=O)N3CCOCC3)c3c2-c2ccccc2S(O)(O)C3)C1]

MS (ESI+): 461.2. HPLC (max plot) 97.52%; Rt 2.31 min

Example 256: 1-[1-(3-Methoxypropyl)pyrrolidin-3-yl]-3-(morpholin-4-ylcarbonyl)-1,4-dihydrothiochromeno[4,3-c]pyrazole 5,5-dioxide

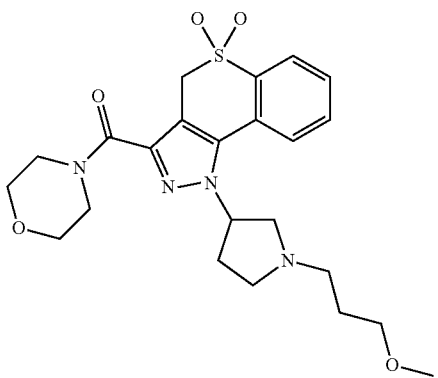 [SMILES: COCCCN1CCC(n2nc(C(=O)N3CCOCC3)c3c2-c2ccccc2S(O)(O)C3)C1]

7 mg of the title compound as a pale yellow solid. $^1$H NMR (DMSO-$d_6$, 400 MHz): δ 8.03-8.01 (m, 1H), 7.96-7.94 (m, 1H), 7.90-7.86 (m, 1H), 7.74-7.70 (m, 1H), 5.46 (m, 1H), 4.81-4.76 (s, 2H), 3.95 (m, 2H), 3.65 (m, 6H), 3.36-3.35 (m, 2H), 3.26 (s, 3H), 3.26 (m, 1H), 3.20 (m, 2H), 2.20 (m, 1H), 1.69-1.65 (m, 2H). MS (ESI+): 475.0. HPLC (max plot) 94.52%; Rt 2.41 min Example 121: 2-{4-[3-(Morpholin-4-ylcarbonyl)-5,5-dioxidothiochromeno[4,3-c]pyrazol-1 (4H)-yl]piperidin-1-yl}ethanol

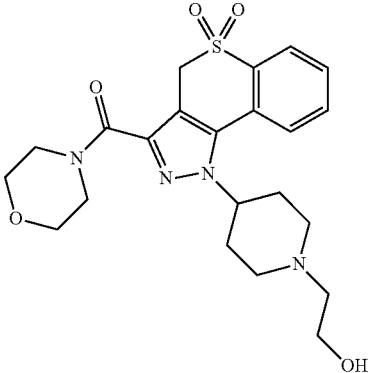 [SMILES: O=C(c1nn(C2CCN(CCO)CC2)c2c1CS(=O)(=O)c1ccccc1-2)N1CCOCC1]

21 mg of the title compound as an off white solid. $^1$H NMR (DMSO-$d_6$, 400 MHz): δ 8.04-8.03 (d, J = 1.1 Hz, 1H), 8.03-7.85 (m, 2H), 7.74-7.70 (t, J = 7.7 Hz, 1H), 4.78 (s, 2H), 4.73-4.71 (m, 1H), 4.44-4.41 (t, J = 5.4 Hz, 1H), 3.98 (m, 2H), 3.65 (s, 6H), 3.53-3.50 (t, J = 11.7 Hz, 2H), 2.49-2.48 (m, 2H), 2.26-2.20 (m, 2H), 2.16-2.11 (m, 2H), 2.01-1.98 (d, J = 10.8 Hz, 2H). MS (ESI+): 461.0. HPLC (max plot) 98.47%; Rt 2.16 min Example 101: 1-[1-(2-Methoxyethyl)piperidin-4-yl]-3-(morpholin-4-ylcarbonyl)-1,4-dihydrothiochromeno[4,3-c]pyrazole 5,5-dioxide

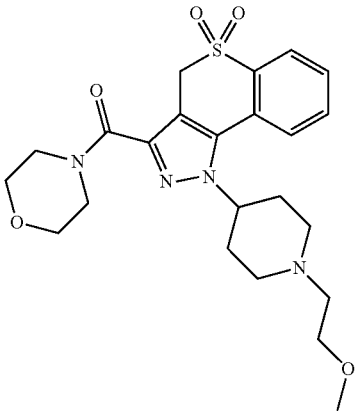 [SMILES: COCCN1CCC(n2nc(C(=O)N3CCOCC3)c3c2-c2ccccc2S(=O)(=O)C3)CC1]

10 mg of the title compound as an off white solid. $^1$H NMR (400 MHz, DMSO-$d_6$): δ 8.03-8.02 (d, J = 6.8 Hz, 1H), 7.91-7.85 (m, 2H), 7.74-7.70 (t, J = 7.8 Hz, 1H), 4.78 (s, 2H), 4.71 (m, 1H), 3.98 (m, 2H), 3.65 (s, 6H), 3.46-3.42 (t, J = 6.8 Hz, 2H), 3.23 (s, 3H), 3.00-2.97 (d, J = 11.7 Hz, 2H), 2.53-2.52 (m, 2H), 2.27-2.21 (m, 2H), 2.15-2.10 (m, 2H), 2.01-1.99 (d, J = 9.8 Hz, 2H). MS (ESI+): 475.3. HPLC (max plot): 90.61%; Rt 2.37 min.

Example 175: 3-(Morpholin-4-ylcarbonyl)-1-[1-(2-morpholin-4-ylethyl)piperidin-3-yl]-1,4-dihydrothiochromeno[4,3-c]pyrazole 5,5-dioxide

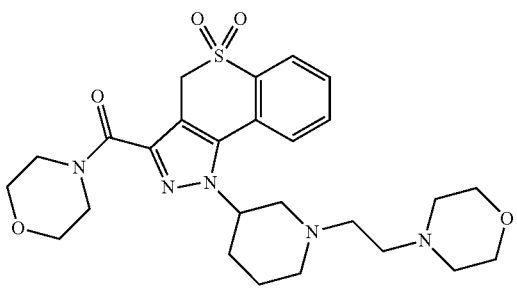

50 mg of the title compound as a off-white solid. 1H NMR (300 MHz, DMSO): δ 8.05 (dd, J = 7.8, 1.2 Hz, 1H), 7.98-7.89 (m, 1H), 7.85 (d, J = 7.6 Hz, 1H), 7.79-7.68 (m, 1H), 5.06-4.55 (m, 3H), 4.00-3.84 (m, 2H), 3.77-3.56 (m, 6H), 3.55-3.46 (m, 4H), 3.32-3.30 (m, 2H), 3.28-3.15 (m, 1H), 2.90 (d, J = 10.7 Hz, 1H), 2.46-2.24 (m, 7H), 2.21-1.85 (m, 3H), 1.84-1.61 (m, 2H). HPLC (max plot) 98.6%; Rt 1.63 min. MS(ESI+): 529.4.

Example 263: 3-(Morpholin-4-ylcarbonyl)-1-{1-[2-(1H-pyrazol-1-yl)ethyl]piperidin-3-yl}-1,4-dihydrothiochromeno[4,3-c]pyrazole 5,5-dioxide

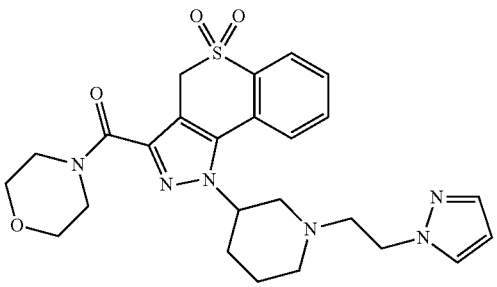 [SMILES: O=C(c1nn(C2CCCN(CCn3cccn3)C2)c2c1CS(=O)(=O)c1ccccc1-2)N1CCOCC1]

73 mg of the title compound as a white foam. 1H NMR (DMSO-d6) δ 8.07-8.04 (m, 1H), 7.96-7.90 (m, 1H), 7.79-7.73 (m, 3H), 7.41-7.40 (m, 1H), 6.20 (m, 1H), 4.78 (s, 2H), 4.75-4.67 (m, 1H), 4.26-4.21 (m, 2H), 3.91-3.89 (m, 2H), 3.66 (s, 6H), 3.18-3.15 (m, 1H), 2.89-2.74 (m, 3H), 2.45-2.42 (m, 1H), 2.14-1.65 (m, 5H). HPLC (max plot) 98.3%; Rt 2.07 min. MS (ESI+): 510.8.

Example 273: 1-{1-[2-(3,3-Difluoroazetidin-1-yl)ethyl]piperidin-3-yl}-3-(morpholin-4-ylcarbonyl)-1,4-dihydrothiochromeno[4,3-c]pyrazole 5,5-dioxide

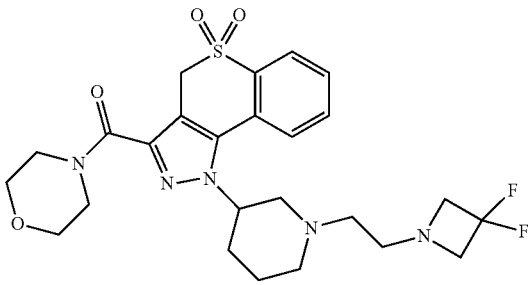 [SMILES: O=C(c1nn(C2CCCN(CCN3CC(F)(F)C3)C2)c2c1CS(=O)(=O)c1ccccc1-2)N1CCOCC1]

37 mg of the title compound as a white solid. $^1$H NMR (DMSO-$d_6$) δ 8.07-8.04 (m, 1H), 7.95-7.84 (m, 2H), 7.78-7.73 (m, 1H), 4.79 (s, 3H), 3.93-3.90 (m, 2H), 3.70-3.63 (m, 6H), 3.55 (t, J = 12.5 Hz, 4H), 3.20-3.16 (m, 1H), 2.92-2.89 (m, 1H), 2.67-2.62 (m, 2H), 2.46-2.37 (m, 3H), 2.14-1.69 (m, 5H). HPLC (max plot) 97.7%; Rt 2.00 min. MS (ESI+): 535.8.

Example 265: 3-(Morpholin-4-ylcarbonyl)-1-[1-(tetrahydrofuran-3-ylmethyl)piperidin-3-yl]-1,4-dihydrothiochromeno[4,3-c]pyrazole 5,5-dioxide

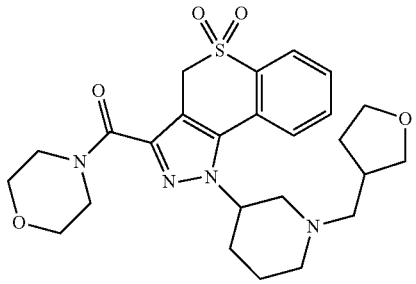 [SMILES: O=C(c1nn(C2CCCN(CC3CCOC3)C2)c2c1CS(=O)(=O)c1ccccc1-2)N1CCOCC1]

36 mg of the title compound as a white solid. $^1$H NMR (DMSO-$d_6$) δ 8.07-8.04 (m, 1H), 7.96-7.91 (m, 1H), 7.84-7.72 (m, 2H), 4.84-4.73 (m, 3H), 3.95-3.87 (m, 2H), 3.74-3.54 (m, 8H), 3.40-3.33 (m, 2H), 3.21-3.13 (m, 1H), 2.95-2.86 (m, 1H), 2.43-2.28 (m, 4H), 2.16-1.71 (m, 6H), 1.58-1.43 (m, 1H). HPLC (max plot) 97.1%; Rt 1.80 min. MS (ESI+): 500.8.

Example 281: 1-{1-[2-(4-Fluoropiperidin-1-yl)ethyl]piperidin-3-yl}-3-(morpholin-4-ylcarbonyl)-1,4-dihydrothiochromeno[4,3-c]pyrazole 5,5-dioxide

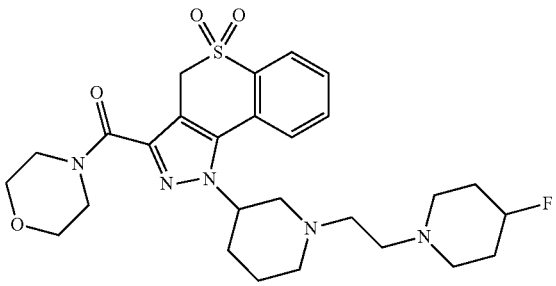 [SMILES: O=C(c1nn(C2CCCN(CCN3CCC(F)CC3)C2)c2c1CS(=O)(=O)c1ccccc1-2)N1CCOCC1]

38 mg of the title compound as a beige solid. $^1$H NMR (DMSO-$d_6$): δ 8.06 (dd, J = 7.8, 1.2 Hz, 1H), 7.96-7.91 (m, 1H), 7.86-7.81 (m, 1H), 7.78-7.73 (m, 1H), 4.79 (s, 3H), 4.74-4.52 (m, 1H), 3.93-3.90 (m, 2H), 3.70-3.62 (m, 6H), 3.23-3.20 (m, 1H), 2.91-2.88 (m, 1H), 2.55-2.46 (m, 4H), 2.45-2.36 (m, 3H), 2.29-2.21 (m, 2H), 2.14-1.89 (m, 3H), 1.85-1.55 (m, 6H). HPLC (max plot) 100%; Rt 1.86 min. MS (ESI+): 545.9.

Example 282: 1-(1-{2-[(3S)-3-Fluoropyrrolidin-1-yl]ethyl}piperidin-3-yl)-3-(morpholin-4-ylcarbonyl)-1,4-dihydrothiochromeno[4,3-c]pyrazole 5,5-dioxide (mixture 2 diasteriomers

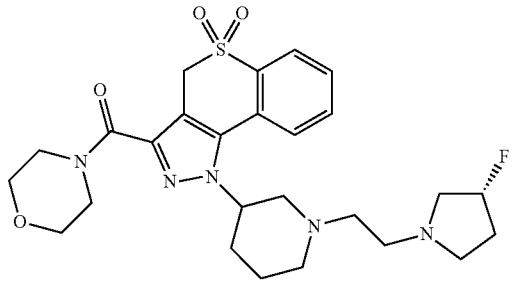 [SMILES: O=C(c1nn(C2CCCN(CCN3CC[C@@H](F)C3)C2)c2c1CS(=O)(=O)c1ccccc1-2)N1CCOCC1]

19 mg of the title compound as a white solid. $^1$H NMR (DMSO-$d_6$): δ 8.06 (dd, J = 7.8, 1.2 Hz, 1H), 7.96-7.90 (m, 1H), 7.85-7.83 (m, 1H), 7.78-7.72 (m, 1H), 5.26-5.02 (m, 1H), 4.79 (s, 3H), 3.93-3.90 (m, 2H), 3.69-3.62 (m, 6H), 3.23-3.19 (m, 1H), 2.94-2.73 (m, 3H), 2.63-2.38 (m, 6H), 2.29-1.70 (m, 8H). HPLC (max plot) 100%; Rt 1.58 min. MS (ESI+): 532.3.

-continued

Example 283: 1-(1-{2-[(3R)-3-Fluoropyrrolidin-1-yl]ethyl}piperidin-3-yl)-3-(morpholin-4-ylcarbonyl)-1,4-dihydrothiochromeno[4,3-c]pyrazole 5,5-dioxide

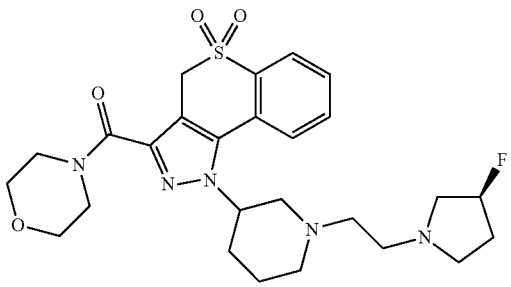 [SMILES: O=C(c1nn(C2CCCN(CCN3CC[C@H](F)C3)C2)c2c1CS(=O)(=O)c1ccccc1-2)N1CCOCC1]

20 mg of the title compound as a white solid. $^1$H NMR (DMSO-$d_6$): δ 8.06 (dd, J = 7.8, 1.2 Hz, 1H), 7.96-7.90 (m, 1H), 7.85-7.83 (m, 1H), 7.78-7.72 (m, 1H), 5.27-5.02 (m, 1H), 4.79-4.74 (m, 3H), 3.93-3.90 (m, 2H), 3.70-3.63 (m, 6H), 3.23-3.20 (m, 1H), 2.93-2.90 (m, 1H), 2.86-2.73 (m, 2H), 2.63-2.38 (m, 6H), 2.29-2.21 (m, 1H), 2.17-1.70 (m, 7H). HPLC (max plot) 100%; Rt 1.58 min. MS (ESI+): 532.3.

Example 284: 1-{1-[2-(3,3-Difluoropiperidin-1-yl)ethyl]piperidin-3-yl}-3-(morpholin-4-ylcarbonyl)-1,4-dihydrothiochromeno[4,3-c]pyrazole 5,5-dioxide

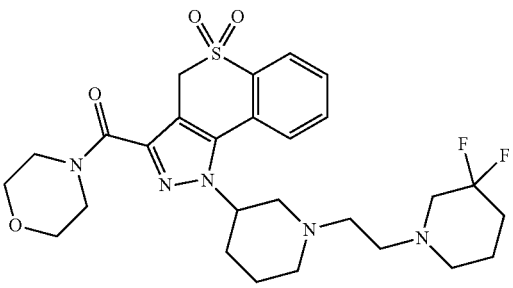 [SMILES: O=C(c1nn(C2CCCN(CCN3CCCC(F)(F)C3)C2)c2c1CS(=O)(=O)c1ccccc1-2)N1CCOCC1]

44 mg of the title compound as a white solid. $^1$H NMR (DMSO-$d_6$): δ 8.06 (dd, J = 7.8, 1.3 Hz, 1H), 7.95-7.90 (m, 1H), 7.84-7.81 (m, 1H), 7.78-7.73 (m, 1H), 4.79-4.73 (m, 3H), 3.93-3.91 (m, 2H), 3.70-3.62 (m, 6H), 3.24-3.21 (m, 1H), 2.93-2.89 (m, 1H), 2.69-2.61 (m, 2H), 2.58-2.46 (m, 4H), 2.43-2.38 (m, 3H), 2.12-1.55 (m, 9H) HPLC (max plot) 98.8%; Rt 2.14 min. MS (ESI+): 564.3.

Example 294: 1-[1-(2-Cyclohexylethyl)piperidin-3-yl]-3-(morpholin-4-ylcarbonyl)-1,3-dihydrothiochromeno[4,3-c]pyrazole 5,5-dioxide

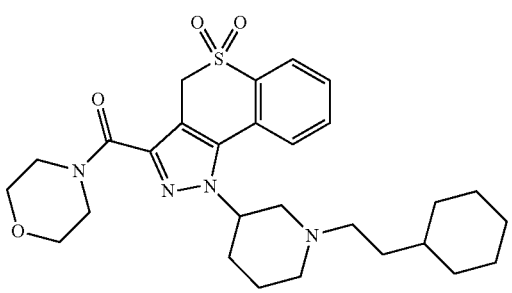 [SMILES: O=C(c1nn(C2CCCN(CCC3CCCCC3)C2)c2c1CS(=O)(=O)c1ccccc1-2)N1CCOCC1]

32 mg of the title compound as an off-white solid. $^1$H NMR (DMSO-$d_6$) δ 8.06 (dd, J = 1.2, 7.8 Hz, 1H), 7.95-7.89 (m, 1H), 7.84-7.81 (m, 1H), 7.78-7.73 (m, 1H), 4.82-4.75 (m, 3H), 3.93-3.90 (m, 2H), 3.69-3.62 (m, 6H), 3.14-3.11 (m, 1H), 2.90-2.86 (m, 1H), 2.41-2.27 (m, 3H), 2.15-2.11 (m, 1H), 2.00-1.57 (m, 9H), 1.34-1.07 (m, 6H), 0.91-0.80 (m, 2H). HPLC (max plot) 99.3%; Rt 3.01 min.). MS (ESI+): 527.4.

Example 295: 1-{1-[(5-Methyl-1,2,4-oxadiazol-3-yl)methyl]piperidin-3-yl}-3-(morpholin-4-ylcarbonyl)-1,4-dihydrothiochromeno[4,3-c]pyrazole 5,5-dioxide

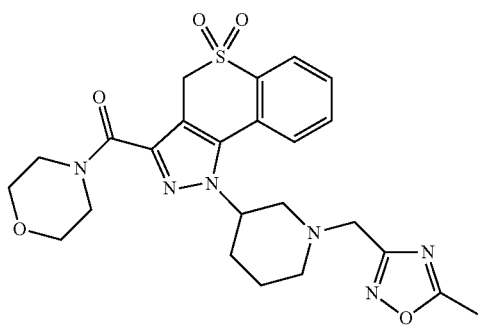 [SMILES: Cc1nc(CN2CCCC(n3nc(C(=O)N4CCOCC4)c4c3-c3ccccc3S(=O)(=O)C4)C2)no1]

20 mg of the title compound as a white solid. $^1$H NMR (DMSO-$d_6$) δ 8.05 (dd, J = 1.2, 7.8 Hz, 1H), 7.95-7.89 (m, 1H), 7.86-7.83 (m, 1H), 7.78-7.73 (m, 1H), 4.85-4.78 (m, 3H), 3.91-3.88 (m, 2H), 3.78-3.75 (m, 2H), 3.70-3.62 (m, 6H), 3.24-3.21 (m, 1H), 2.94-2.91 (m, 1H), 2.61-2.57 (m, 4H), 2.26-1.73 (m, 5H). HPLC (max plot) 92.7%; Rt 6.56 min. HPLC (max plot) 95.2%; Rt 6.56 min. MS (ESI+): 513.2.

Example 296: 3-(Morpholin-4-ylcarbonyl)-1-{1-[3-(1H-pyrrol-1-yl)propyl]piperidin-3-yl}-1,4-dihydrothiochromeno[4,3-c]pyrazole 5,5-dioxide

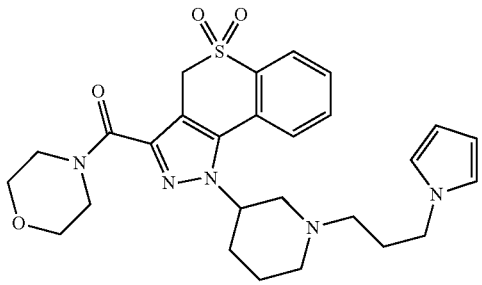 [SMILES: O=C(c1nn(C2CCCN(CCCn3cccc3)C2)c2c1CS(=O)(=O)c1ccccc1-2)N1CCOCC1]

11 mg of the title compound as a white solid. $^1$H NMR (DMSO-$d_6$) δ 8.10-8.05 (m, 1H), 7.97-7.92 (m, 1H), 7.87-7.84 (m, 1H), 7.78-7.73 (m, 1H), 6.71 (t, J = 2.1 Hz, 2H), 5.93 (t, J = 2.1 Hz, 2H), 4.87-4.79 (m, 3H), 3.91-3.87 (m, 4H), 3.69-3.62 (m, 6H), 3.10-3.07 (m, 1H), 2.88-2.84 (m, 1H), 2.37-2.08 (m, 4H), 2.00-1.75 (m, 6H). HPLC (max plot) 98.6%; Rt 8.02 min. MS (ESI+): 524.3.

Example 297: 1-{1-[2-(1H-Imidazol-1-yl)ethyl]piperidin-3-yl}-3-(morpholin-4-ylcarbonyl)-1,4-dihydrothiochromeno[4,3-c]pyrazole 5,5-dioxide

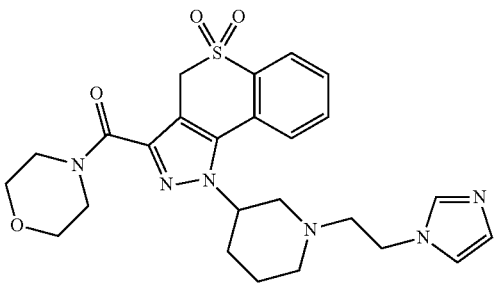 [SMILES: O=C(c1nn(C2CCCN(CCn3ccnc3)C2)c2c1CS(=O)(=O)c1ccccc1-2)N1CCOCC1]

41 mg of the title compound as a white solid. $^1$H NMR (DMSO-$d_6$) δ 8.06 (dd, J = 1.2, 7.8 Hz, 1H), 7.97-7.91 (m, 1H), 7.78-7.71 (m, 2H), 7.65 (t, J = 1.0 Hz, 1H), 7.19 (t, J = 1.2 Hz, 1H), 6.88 (t, J = 1.0 Hz, 1H), 4.79-4.69 (m, 3H), 4.11-4.06 (m, 2H), 3.92-3.89 (m, 2H), 3.69-3.62 (m, 6H), 3.20-3.17 (m, 1H), 2.94-2.90 (m, 1H), 2.83-2.66 (m, 2H), 2.55-2.45 (m, 1H), 2.14-1.60 (m, 5H). HPLC (max plot) 99.7%; Rt 6.04 min. MS (ESI+): 511.3.

Example 133: 1-[1-(2-Methoxyethyl)piperidin-3-yl]-3-(morpholin-4-ylcarbonyl)-1,4-dihydrothiochromeno[4,3-c]pyrazole 5,5-dioxide

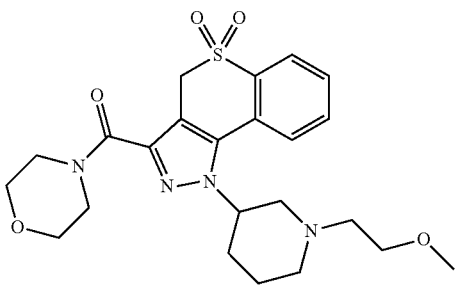

13.2 mg of the title compound as an off white solid. $^1$H NMR (DMSO-$d_6$, 400 MHz): δ 8.05-8.03 (m, 1H), 7.92 (m, 1H), 7.82 (m, 1H), 7.73 (m, 1H), 4.77 (s, 3H), 3.89 (m, 2H), 3.65-3.64 (m, 6H), 3.42 (m, 2H), 3.18 (m, 4H), 2.95 (m, 1H), 2.66 (m, 2H), 2.49 (m, 2H), 2.22 (m, 2H), 1.98 (m, 1H), 1.85 (m, 2H). MS (ESI+): 475.3. HPLC (max plot) 91.17%; Rt 2.34 min.

Example 134: 2-{3-[3-(Morpholin-4-ylcarbonyl)-5,5-dioxidothiochromeno[4,3-c]pyrazol-1 (4H)-yl]piperidin-1-yl}ethanol

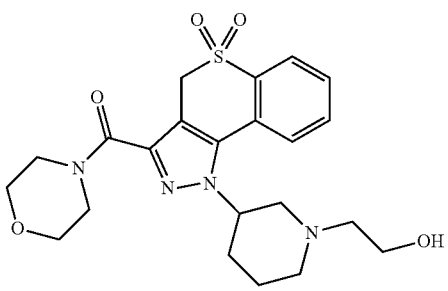 [SMILES: O=C(c1nn(C2CCCN(CCO)C2)c2c1CS(=O)(=O)c1ccccc1-2)N1CCOCC1]

14 mg of the title compound as an off white solid. $^1$H NMR (DMSO-$d_6$, 400 MHz): δ 8.04-8.02 (d, J = 7.9 Hz, 1H), 7.92-7.90 (m, 1H), 7.83-7.81 (d, J = 7.9 Hz, 1H), 7.75-7.73 (m, 1H), 4.77 (m, 3H), 4.42-4.40 (t, J = 5.3 Hz, 1H), 3.89 (m, 2H), 3.64 (m, 6H), 3.51-3.45 (m, 2H), 3.20 (m, 1H), 2.90-2.87 (m, 1H), 2.44 (m, 3H), 2.09-2.05 (m, 2H), 1.95 (m, 1H), 1.75-1.72 (m, 2H). MS (ESI+): 461.2. HPLC (max plot) 97.14%; Rt 2.15 min.

Example 172: 1-[1-(3-Methoxypropyl)piperidin-3-yl]-3-(morpholin-4-ylcarbonyl)-1,4-dihydrothiochromeno[4,3-c]pyrazole 5,5-dioxide

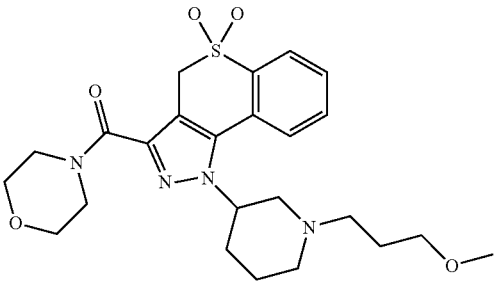 [SMILES: COCCCN1CCCC(n2nc(C(=O)N3CCOCC3)c3c2-c2ccccc2S(O)(O)C3)C1]

14 mg of the title compound as a pale brown solid. $^1$H NMR (DMSO-$d_6$, 400 MHz): δ 8.05-8.03 (m, 1H), 7.94-7.90 (m, 1H), 7.82-7.80 (d, J = 7.9 Hz, 1H), 7.75-7.71 (t, J = 7.7 Hz, 1H), 4.77 (s, 2H), 3.89 (m, 2H), 3.65-3.64 (m, 6H), 3.18 (m, 1H), 3.18 (s, 3H), 3.13-3.10 (m, 1H), 2.88-2.85 (m, 1H), 2.49 (m, 1H), 2.41-2.30 (m, 3H), 2.12 (m, 1H), 1.86-1.98 (m, 2H), 1.84-1.76 (m, 2H), 1.7-1.6 (m, 2H). MS (ESI+): 489.0. HPLC (max plot) 94.24%; RT 2.44 min Example 173: 1-[1-(3-Methylbutyl)piperidin-3-yl]-3-(morpholin-4-ylcarbonyl)-1,4-dihydrothiochromeno[4,3-c]pyrazole 5,5-dioxide

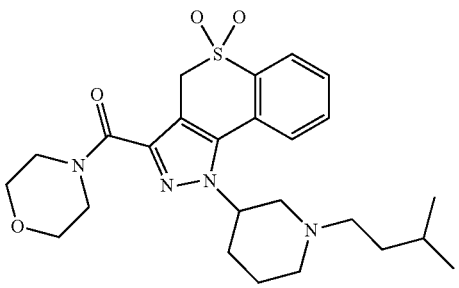 [SMILES: CC(C)CCN1CCCC(n2nc(C(=O)N3CCOCC3)c3c2-c2ccccc2S(O)(O)C3)C1]

23 mg of the title compound as a pale brown solid. $^1$H NMR (DMSO-$d_6$, 400 MHz): δ 8.05-8.03 (d, J = 7.8 Hz, 1H), 7.91-7.89 (m, 1H), 7.82-7.80 (d, J = 7.8 Hz, 1H), 7.75-7.71 (t, J = 7.8 Hz, 1H), 4.77 (bs, 3H), 3.89 (m, 2H), 3.64 (m, 6H), 3.12-3.10 (m, 1H), 2.88-2.85 (m, 1H), 2.48-2.27 (m, 3H), 2.10 (m, 1H), 1.94-1.91 (m, 2H), 1.85-1.66 (m, 2H), 1.54-1.57 (m, 1H), 1.31-1.22 (m, 2H), 0.84-0.82 (d, J = 6.7 Hz, 6H). MS (ESI+): 487.0. HPLC (max plot) 95.39%; Rt 3.03 min Example 174: 1-(1-Benzylpiperidin-3-yl)-3-(morpholin-4-ylcarbonyl)-1,4-dihydrothiochromeno[4,3-c]pyrazole 5,5-dioxide

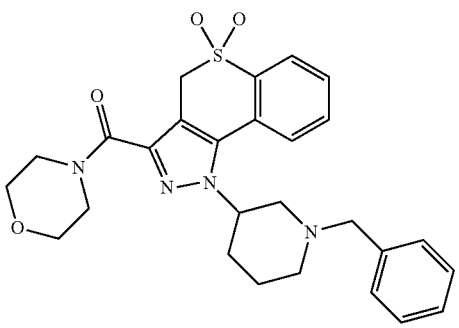

9 mg of the title compound as an off white solid. $^1$H NMR (DMSO-$d_6$, 400 MHz): δ 8.02-8.0 (dd, J = 1.2, 7.8 Hz, 1H), 7.88-7.85 (t, J = 7.8 Hz, 1H), 7.73-7.69 (t, J = 7.6 Hz, 1H), 7.60-7.58 (d, J = 7.8 Hz, 1H), 7.33-7.29 (m, 4H), 7.23-7.20 (m, 1H), 4.79-4.69 (m, 3H), 3.88 (m, 2H), 3.68-3.62 (m, 6H), 3.42 (m, 1H), 3.32 (m, 1H), 3.05-3.02 (m, 1H), 2.91-2.88 (m, 1H), 2.34-2.28 (m, 1H), 2.10-1.96 (m, 3H), 1.82-1.72 (m, 2H). MS (ESI+): 507.0. HPLC (max plot) 92.29%; Rt 2.94 min Example 219: 3-(Morpholin-4-ylcarbonyl)-1-[1-(2-phenylethyl)piperidin-3-yl]-1,4-dihydrothiochromeno[4,3-c]pyrazole 5,5-dioxide

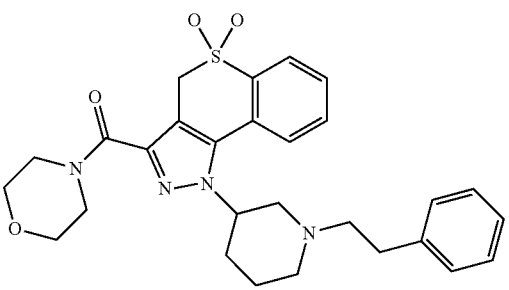

21 mg of the title compound as a white solid. $^1$H NMR (DMSO-$d_6$, 400 m Hz): δ 8.05-8.03 (dd, J = 1.2, 7.8 Hz, 1H), 7.93-7.90 (t, J = 7.4 Hz, 1H), 7.83-7.81 (d, J = 8.0 Hz, 1H), 7.75-7.71 (t, J = 7.6 Hz, 1H), 4.77 (s, 2H), 3.89 (m, 2H), 3.64 (m, 6H), 3.12-3.10 (m, 1H), 2.89-2.86 (m, 1H), 2.36-2.34 (m, 3H), 2.11 (m, 1H), 1.95 (m, 2H), 1.77-1.71 (m, 2H), 1.33-1.30 (m, 2H), 0.91 (s, 9H). MS (ESI+): 501.3. HPLC (max plot) 96.24%; Rt 3.40 min.

Example 220: 1-[1-(3,3-Dimethylbutyl)piperidin-3-yl]-3-(morpholin-4-ylcarbonyl)-1,4-dihydrothiochromeno[4,3-c]pyrazole 5,5-dioxide

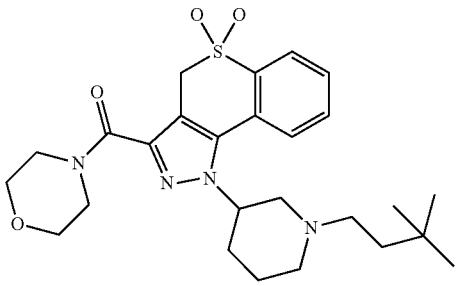 [SMILES: CC(C)(C)CCN1CCCC(n2nc(C(=O)N3CCOCC3)c3c2-c2ccccc2S(O)(O)C3)C1]

21 mg of the title compound as a white solid. $^1$H NMR (DMSO-$d_6$, 400 m Hz): δ8.05-8.03 (dd, J = 1.2, 7.8 Hz, 1H), 7.93-7.90 (t, J = 7.4 Hz, 1H), 7.83-7.81 (d, J = 8.0 Hz, 1H), 7.75-7.71 (t, J = 7.6 Hz, 1H), 4.77 (s, 2H), 3.89 (m, 2H), 3.64 (m, 6H), 3.12-3.10 (m, 1H), 2.89-2.86 (m, 1H), 2.36-2.34 (m, 3H), 2.11 (m, 1H), 1.95 (m, 2H), 1.77-1.71 (m, 2H), 1.33-1.30 (m, 2H), 0.91 (s, 9H). MS (ESI+): 501.3. HPLC (max plot) 96.24%; Rt 3.40 min Example 222: 3-(Morpholin-4-ylcarbonyl)-1-[1-(3,3,3-trifluoropropyl)piperidin-3-yl]-1,4-dihydrothiochromeno[4,3-c]pyrazole 5,5-dioxide

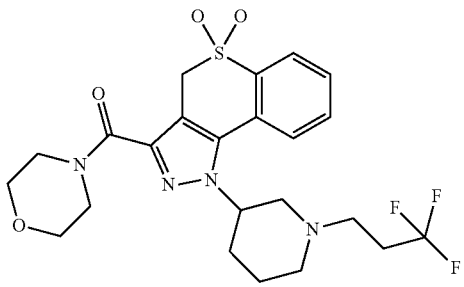

13 mg of the title compound as an off white solid. $^1$H NMR (CDCl$_3$, 400 MHz): δ 8.18-8.16 (d, J = 7.7 Hz, 1H), 7.79-7.76 (t, J = 7.6 Hz, 1H), 7.64-7.59 (m, 2H), 4.77-4.61 (m, 3H), 4.15 (s, 2H), 3.80 (m, 6H), 3.19-2.98 (m, 1H), 2.95-2.74 (m, 1H), 2.73-2.68 (m, 2H), 2.61-2.55 (m, 1H), 2.36-2.29 (m, 2H), 2.18-2.09 (m, 3H), 1.96-1.93 (m, 1H), 1.78-1.75 (m, 1H). MS (ESI+): 513.0. HPLC (max plot) 97.57%; Rt 2.76 min Example 223: 3-(Morpholin-4-ylcarbonyl)-1-[4,4,4-trifluoro-3-(trifluoromethyl)butyl]piperidin-3-yl}-1,4-dihydrothiochromeno[4,3-c]pyrazole 5,5-dioxide

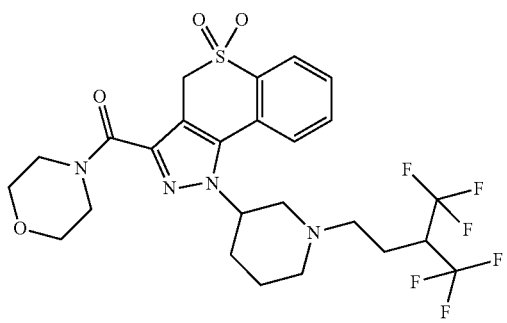

10 mg of the title compound as a white solid. $^1$H NMR (DMSO-$d_6$, 400 MHz): δ 8.05-8.03 (m, 1H), 7.90-7.86 (m, 1H), 7.83-7.81 (d, J = 7.4 Hz, 1H), 7.75-7.71 (m, 1H), 4.85-4.77 (m, 3H), 3.98-3.96 (m, 1H), 3.89 (m, 2H), 3.65-3.64 (m, 6H), 3.14-3.11 (m, 1H), 2.87-2.85 (m, 1H), 2.48 (m, 1H), 2.14-2.11 (m, 2H), 2.07-2.02 (m, 1H), 1.94-1.89 (m, 3H), 1.78 (m, 2H), MS (ESI+): 595.0. HPLC (max plot) 95.52%; Rt 3.59 min.

Example 225: 1-{1-[2-(2-Methoxyethoxy)ethyl]piperidin-3-yl}-3-(morpholin-4-ylcarbonyl)-1,4-dihydrothiochromeno[4,3-c]pyrazole 5,5-dioxide

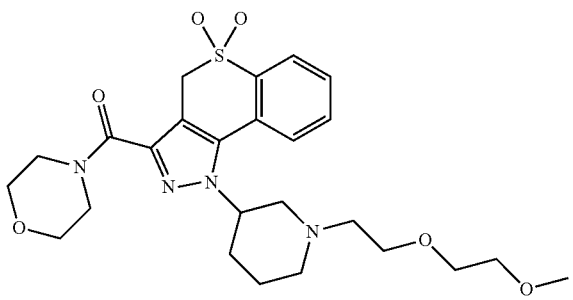 [SMILES: COCCOCCN1CCCC(n2nc(C(=O)N3CCOCC3)c3c2-c2ccccc2S(O)(O)C3)C1]

74 mg (74%) of the title compound as colorless semi solid. $^1$H NMR (CDCl$_3$, 400 MHz): δ 8.17-8.15 (d, J = 6.8 Hz, 1H), 7.77-7.75 (m, 1H), 7.69-7.67 (d, J = 7.8 Hz, 1H), 7.64-7.60 (m, 1H), 4.79-4.60 (m, 3H), 4.16 (m, 2H), 3.80 (m, 6H), 3.65-3.59 (m, 4H), 3.53-3.50 (m, 2H), 3.34 (s, 3H), 3.29 (m, 1H), 3.04 (m, 1H), 2.76-2.73 (m, 2H), 2.71-2.68 (m, 1H), 2.58-2.53 (m, 1H), 2.17-2.08 (m, 2H), 2.07-1.89 (m, 2H). MS (ESI+): 519.3. HPLC (max plot) 98.77%; Rt 2.59 min Example 253: N,N-Dimethyl-2-{3-[3-(morpholin-4-ylcarbonyl)-5,5-dioxidothiochromeno[4,3-c]pyrazol-1 (4H)-yl]piperidin-1-yl}ethanamine

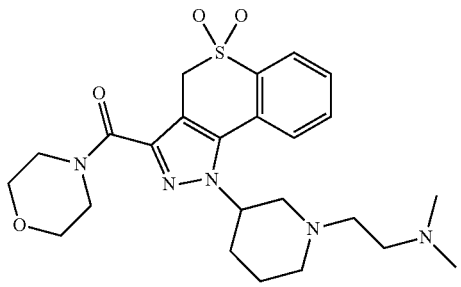

13 mg of the title compound as a pale yellow gummy solid. $^1$H NMR (CDCl$_3$, 400 MHz): δ 8.15-8.13 (d, J = 7.6 Hz, 1H), 7.85 (m, 2H), 6.64-7.62 (m, 1H), 4.94 (m, 1H), 4.72-4.62 (m, 2H), 4.14 (m, 2H), 3.80 (m, 7H), 3.27-3.25 (m, 1H), 3.02-2.99 (m, 1H), 2.78 (m, 4H), 2.63 (m, 6H), 2.20-2.17 (m, 2H), 2.05-1.92 (m, 3H). MS (ESI+): 488.3. HPLC (max plot) 95.34; Rt 3.79 min.

Example 258: 1-[1-(3-Methoxypropyl)azepan-4-yl]-3-(morpholin-4-ylcarbonyl)-1,4-dihydrothiochromeno[4,3-c]pyrazole 5,5-dioxide

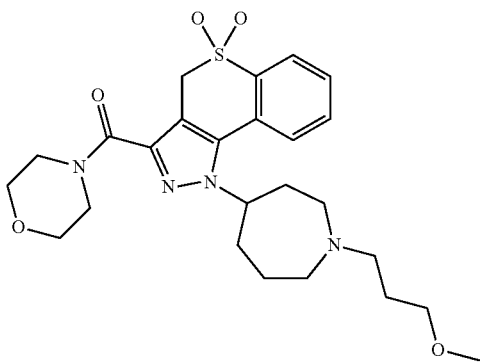 [SMILES: COCCCN1CCCC(n2nc(C(=O)N3CCOCC3)c3c2-c2ccccc2S(O)(O)C3)CC1]

14 mg of the title compound as a brown solid. $^1$H NMR (CDCl$_3$, 400 MHz): δ 8.17-8.15 (m, 1H), 7.80-7.78 (m, 1H), 7.65-7.61 (m, 2H), 5.07 (m, 1H), 4.65 (s, 2H), 4.14 (bs, 2H), 3.75 (m, 6H), 3.48-3.46 (m, 2H), 3.34 (s, 3H), 3.03-2.82 (m, 6H), 2.42 (m, 2H), 2.30 (m, 2H), 2.02 (m, 2H), 1.92 (m, 2H). MS (ESI+): 503.3. HPLC (max plot) 99.02%; Rt 2.57 min Example 259: 1-(2-Isopropylphenyl)-3-(morpholin-4-ylcarbonyl)-1,4-dihydrothiochromeno[4,3-c]pyrazole 5,5-dioxide

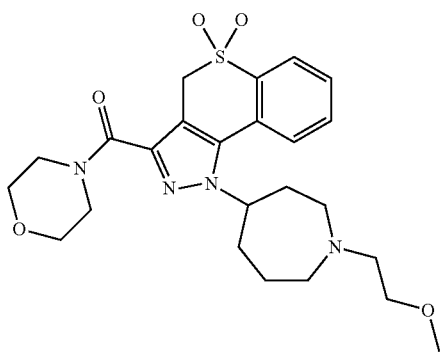 [SMILES: COCCN1CCCC(n2nc(C(=O)N3CCOCC3)c3c2-c2ccccc2S(O)(O)C3)CC1]

13.9 mg of the title compound as a brown solid. 1H NMR (400 MHz, CDCl$_3$): δ 8.17-8.15 (m, 1H), 7.80-7.78 (m, 1H), 7.65-7.61 (m, 2H), 5.07 (m, 1H), 4.65 (s, 2H), 4.14 (brs, 2H), 3.75 (m, 6H), 3.47 (t, 2H), 3.34 (s, 3H), 3.03-2.82 (m, 6H), 2.42 (m, 2H), 2.30 (m, 2H), 2.02 (m, 2H), 1.92 (m, 2H). MS (ESI+): 503.3. HPLC (max plot: 99.0%; Rt 2.57 min.

Example 309: 6-Chloro-3-(morpholin-4-ylcarbonyl)-1-[1-(2-morpholin-4-ylethyl)piperidin-3-yl]-1,4-dihydrothiochromeno[4,3-c]pyrazole 5,5-dioxide

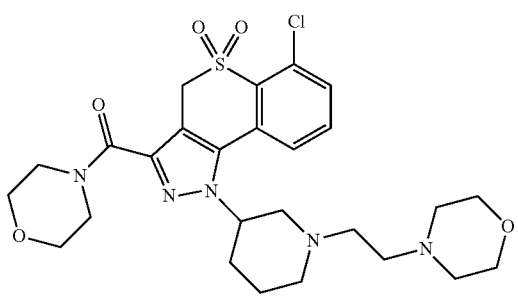

35 mg of the title compound as a beige solid. 1H NMR (300 MHz, DMSO-d$_6$): δ 7.84-7.90 (m, 1H), 7.76-7.78 (m, 2H), 4.91 (s, 2H), 4.66 (bs, 1H), 3.94 (bs, 2H), 3.66 (bs, 6H), 3.49-3.52 (m, 4H), 3.14-3.18 (m, 1H), 2.86-2.90 (m, 1H), 1.69-2.47 (m, 14H). MS (ESI+): 563.8.

Example 386: Enantiomer B of 6-chloro-3-(morpholin-4-ylcarbonyl)-1-[1-(2-morpholin-4-ylethyl) piperidin-3-yl]-1,4-dihydrothiochromeno[4,3-c]pyrazole 5,5-dioxide

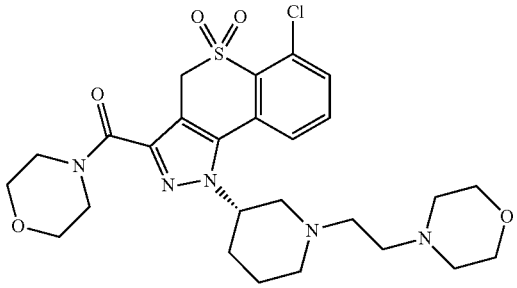

Obtained from enantiomer B of 6-chloro-1-[1-(2-chloroethyl)piperidin-3-yl]-3-(morpholin-4-ylcarbonyl)-1,4-dihydrothiochromeno[4,3-c]pyrazole 5,5-dioxide to give 853 mg (75%) of the title compound as a beige solid. 1H NMR (300 MHz, DMSO-$d_6$): δ 7.91-7.82 (m, 1H), 7.82-7.72 (m, 3H), 4.91 (s, 2H), 4.74-4.58 (m, 1H), 4.03-3.83 (m, 2H), 3.79-3.57 (m, 6H), 3.57-3.41 (m, 4H), 3.22-3.08 (m, 1H), 2.97-2.78 (m, 1H), 2.50-2.44 (m, 1H), 2.44-2.22 (m, 7H), 2.19-1.83 (m, 3H), 1.83-1.54 (m, 2H). MS (ESI): 564.5. HPLC (max plot) 99.4%; Rt 6.21 min. $[α]^{25}$ D +1.17 (1.1, EtOH).

Example 441: Enantiomer B of 1-{1-[3-(3,3-difluoropyrrolidin-1-yl)-3-oxopropyl]piperidin-3-yl}-3-(morpholin-4-ylcarbonyl)-1,4-dihydrothiochromeno[4,3-c]pyrazole 5,5-dioxide

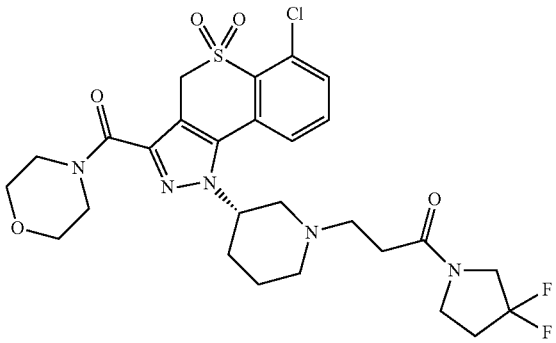 [SMILES: O=C(CCN1CCC[C@H](n2nc(C(=O)N3CCOCC3)c3c2-c2cccc(Cl)c2S(=O)(=O)C3)C1)N1CCC(F)(F)C1]

Obtained from enantiomer B of 3-(morpholin-4-ylcarbonyl)-1-[piperidin-3-yl]-1,4-dihydrothiochromeno[4,3-c]pyrazole 5,5-dioxide to give 70 mg of the title compound as a white powder. $^1$H NMR (DMSO-$d_6$, 300 MHz): δ 8.06 (dd, J = 1.1, 7.8 Hz, 1H), 7.94 (t, J = 7.3 Hz, 1H), 7.83 (d, J = 8.0 Hz, 1H), 7.75 (t, J = 7.5 Hz, 1H), 4.84-4.67 (m, 3H), 3.98-3.85 (m, 3H), 3.74-3.60 (m, 8H), 3.48 (t, J = 7.4 Hz, 1H), 3.24-3.15 (m, 1H), 2.96-2.85 (m, 1H), 2.74-2.57 (m, 2H), 2.49-2.26 (m, 5H), 2.18-1.59 (m, 5H). MS (ESI+): 578.6 HPLC (max plot) 99.6%; Rt 2.32 min Example 450: Enantiomer B of 3-(morpholin-4-ylcarbonyl)-1-[1-(2-pyrrolidin-1-ylethyl)piperidin-3-yl]-1,4-dihydrothiochromeno[4,3-c]pyrazole 5,5-dioxide

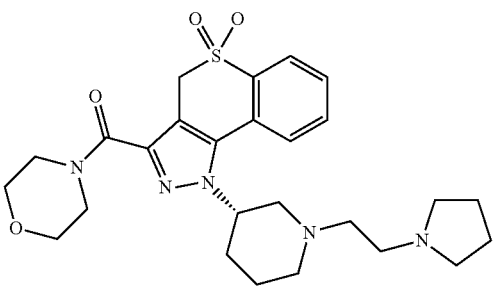

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 40 mg of the title compound as a yellow foam. $^1$H NMR (DMSO-$d_6$, 300 MHz): δ 8.06 (d, J = 7.6 Hz, 1H), 7.91 (d, J = 7.3 Hz, 1H), 7.85 (d, J = 7.8 Hz, 1H), 7.75 (t, J = 7.5 Hz, 1H), 4.79 (s, 3H), 3.96-3.86 (m, 2H), 3.73-3.59 (m, 4H), 3.34 (s, 8H), 3.27-3.16 (m, 1H), 2.96-2.86 (m, 1H), 2.45-2.33 (m, 4H), 2.22-1.86 (m, 3H), 1.85-1.68 (m, 2H), 1.67-1.56 (m, 3H). MS (ESI+): 514.4. HPLC (max plot) 92.8%; Rt 5.91 min Example 362: Enantiomer B of 1-{1-[2-(3,3-difluoroazetidin-1-yl)ethyl]piperidin-3-yl}-3-(morpholin-4-ylcarbonyl)-1,4-dihydrothiochromeno[4,3-c]pyrazole 5,5-dioxide

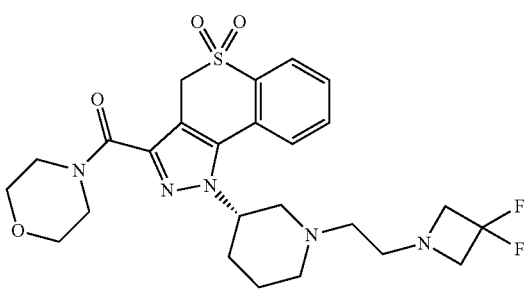 [SMILES: O=C(c1nn([C@H]2CCCN(CCN3CC(F)(F)C3)C2)c2c1CS(=O)(=O)c1ccccc1-2)N1CCOCC1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 160 mg of the title compound as a pale yellow foam. 1H NMR (300 MHz, DMSO-d6): δ 8.05 (dd, J = 7.8, 1.2 Hz, 1H), 7.98-7.81 (m, 2H), 7.75 (dd, J = 11.7, 4.4 Hz, 1H), 4.79 (s, 3H), 3.91 (d, J = 2.3 Hz, 2H), 3.66 (s, 6H), 3.54 (t, J = 12.5 Hz, 4H), 3.17 (d, J = 10.1 Hz, 1H), 2.89 (d, J = 11.0 Hz, 1H), 2.64 (t, J = 6.5 Hz, 2H), 2.47-2.33 (m, 3H), 2.21-1.85 (m, 3H), 1.77 (s, 2H). HPLC (max plot) 100.0%; Rt 2.59 min. MS (ESI+): 536.3.

Example 363: Enantiomer B of 1-{1-[2-(4-fluoropiperidin-1-yl)ethyl]piperidin-3-yl}-3-(morpholin-4-ylcarbonyl)-1,4-dihydrothiochromeno[4,3-c]pyrazole 5,5-dioxide

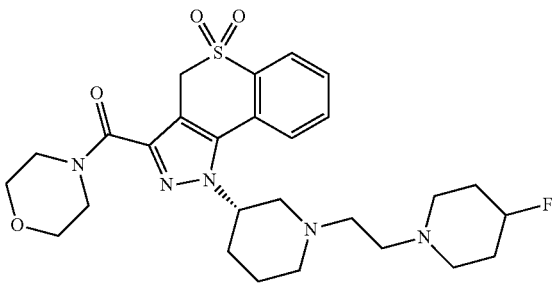 [SMILES: O=C(c1nn([C@H]2CCCN(CCN3CCC(F)CC3)C2)c2c1CS(=O)(=O)c1ccccc1-2)N1CCOCC1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 210 mg (74%) of the title compound as a pale yellow foam. 1H NMR (300 MHz, DMSO-$d_6$): δ 8.05 (dd, J = 7.8, 1.1 Hz, 1H), 7.92 (dd, J = 11.4, 3.9 Hz, 1H), 7.84 (d, J = 7.7 Hz, 1H), 7.75 (t, J = 7.5 Hz, 1H), 4.79 (s, 3H), 4.73 (d, J = 10.5 Hz, 1H), 4.54 (d, J = 3.2 Hz, 1H), 3.91 (d, J = 3.6 Hz, 2H), 3.66 (s, 6H), 3.22 (d, J = 9.6 Hz, 1H), 2.90 (d, J = 10.8 Hz, 1H), 2.61-2.35 (m, 8H), 2.27 (s, 2H), 2.17-1.87 (m, 4H), 1.87-1.53 (m, 6H). HPLC (max plot) 79.1%; Rt 2.30 min. MS (ESI+): 546.4.

Example 364: Enantiomer B of 1-(1-{2-[3-fluoropyrrolidin-1-yl]ethyl}piperidin-3-yl)-3-(morpholin-4-ylcarbonyl)-1,4-dihydrothiochromeno[4,3-c]pyrazole 5,5-dioxide

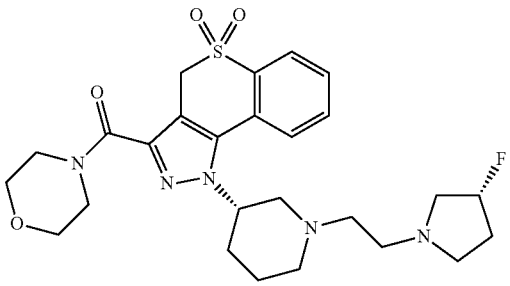 [SMILES: O=C(c1nn([C@H]2CCCN(CCN3CC[C@@H](F)C3)C2)c2c1CS(=O)(=O)c1ccccc1-2)N1CCOCC1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 190 mg of the title compound as a yellow solid. $^1$H NMR (300 MHz, DMSO-$d_6$) δ 8.05 (dd, J = 7.8, 1.2 Hz, 1H), 7.99-7.88 (m, 1H), 7.83 (d, J = 7.5 Hz, 1H), 7.75 (t, J = 7.6 Hz, 1H), 5.24 (s, 1H), 5.05 (s, 1H), 4.79 (s, 3H), 3.91 (s, 2H), 3.66 (s, 6H), 3.33 (s, 4H), 3.21 (d, J = 10.8 Hz, 1H), 3.00-2.67 (m, 3H), 2.67-2.35 (m, 9H), 2.26 (d, J = 7.1 Hz, 1H), 2.19-1.57 (m, 8H). HPLC (max plot) 67.6%; Rt 1.82 min. MS (ESI+): 532.4.

Example 221: 1-[1-(2-fluoroethyl)piperidin-3-yl]-3-(morpholin-4-ylcarbonyl)-1,4-dihydrothiochromeno[4,3-c]pyrazole 5,5-dioxide

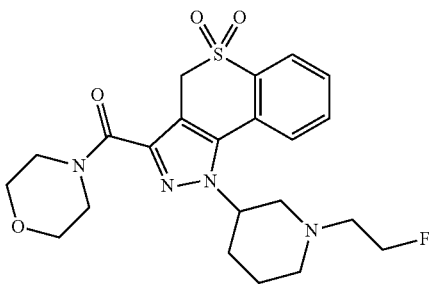 [SMILES: O=C(c1nn(C2CCCN(CCF)C2)c2c1CS(=O)(=O)c1ccccc1-2)N1CCOCC1]

Obtained from enantiomer B of 3-(morpholin-4-ylcarbonyl)-1-[piperidin-3-yl]-1,4-dihydrothiochromeno[4,3-c]pyrazole 5,5-dioxide to give 30 mg of the title compound as a pale brown solid. $^1$H NMR (400 MHz, CDCl$_3$) δ = 8.18-8.17 (dd, J = 7.7, 0.9 Hz 1H), 7.79-7.75 (m, 1H), 7.65-7.61 (t, J = 6.7 Hz, 1H), 4.79-4.61 (m, 4H), 4.55-4.53 (t, J = 4.7 Hz, 1H), 4.16 (m, 2H), 3.80 (m, 6H), 3.30-3.27 (m, 1H), 3.03-3.06 (m, 1H), 2.87-2.84 (m, 2H), 2.77-2.80 (m, 1H), 2.68-2.63 (m, 1H), 2.24-2.09 (m, 2H), 2.17 (m, 1H), 1.92 (m, 1H), 1.57 (m, 1H). HPLC (max plot): 97.23%; Rt 2.32 min. MS (ESI+): 463.0.

Example 367: Enantiomer B of 1-(1-{2-[(3R)-3-fluoropyrrolidin-1-yl]ethyl}piperidin-3-yl)-3-(morpholin-4-ylcarbonyl)-1,4-dihydrothiochromeno[4,3-c]pyrazole 5,5-dioxide

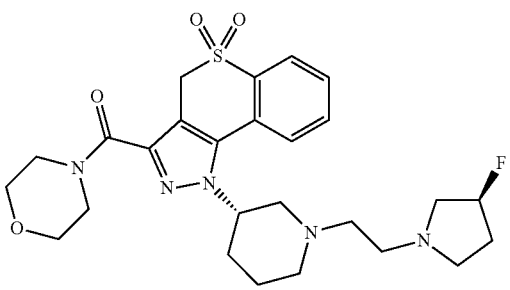 [SMILES: O=C(c1nn([C@H]2CCCN(CCN3CC[C@H](F)C3)C2)c2c1CS(=O)(=O)c1ccccc1-2)N1CCOCC1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 135 mg (48%) of the title compound as a yellow foam solid. 1H NMR (300 MHz, DMSO) δ 8.06 (dd, J = 7.8, 1.2 Hz, 1H), 7.92 (dd, J = 10.8, 4.4 Hz, 1H), 7.84 (d, J = 7.5 Hz, 1H), 7.75 (t, J = 7.6 Hz, 1H), 5.30 (s, 1H), 5.11 (s, 1H), 4.79 (s, 3H), 3.90 (s, 2H), 3.61 (m, 6H), 3.24 (m, 2H), 3.04-2.54 (m, 7H), 2.09 (m, 4H), 1.97-1.63 (m, 4H). MS (ESI+): 532.3

Example 370: Enantiomer B of 1-{1-[2-(2,2-dimethylmorpholin-4-yl)ethyl]piperidin-3-yl}-3-(morpholin-4-ylcarbonyl)-1,4-dihydrothiochromeno[4,3-c]pyrazole 5,5-dioxide

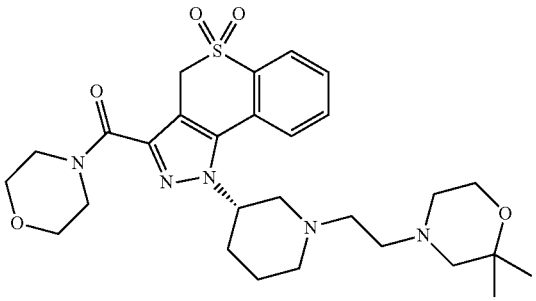 [SMILES: CC1(C)CN(CCN2CCC[C@H](n3nc(C(=O)N4CCOCC4)c4c3-c3ccccc3S(=O)(=O)C4)C2)CCO1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 130 mg (74%) of the title compound as a white foam. 1H NMR (DMSO-d6) δ 8.06 (dd, J = 1.2, 7.8 Hz, 1H), 7.97-7.89 (m, 1H), 7.87-7.81 (m, 1H), 7.75 (t, J = 7.56 Hz, 1H), 4.79 (s, 3H), 4.00-3.86 (m, 2H), 3.72-3.60 (m, 6H), 3.53-3.45 (m, 2H), 3.30-3.21 (m, 1H), 2.96-2.85 (m, 1H), 2.48-2.31 (m, 4H), 2.30-2.21 (m, 2H), 2.19-1.65 (m, 8H), 1.06 (d, J = 3.3 Hz, 6H). HPLC (max plot) 100.0%; Rt 2.37 min. MS (ESI+): 558.5.

Example 377: Enantiomer B of 1-{1-[2-(3-methylmorpholin-4-yl)ethyl]piperidin-3-yl}-3-(morpholin-4-ylcarbonyl)-1,4-dihydrothiochromeno[4,3-c]pyrazole 5,5-dioxide

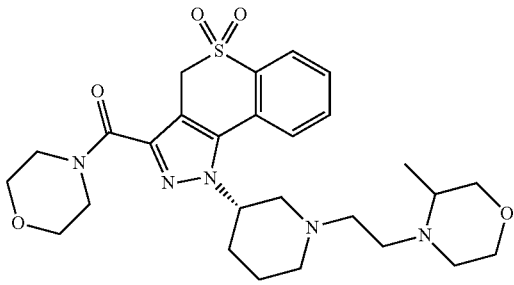 [SMILES: CC1COCCN1CCN1CCC[C@H](n2nc(C(=O)N3CCOCC3)c3c2-c2ccccc2S(=O)(=O)C3)C1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 190 mg (84%) of the title compound as a white solid. 1H NMR (DMSO-d6) δ 8.06 (dd, J = 1.2, 7.8 Hz, 1H), 8.00-7.82 (m, 2H), 7.80-7.71 (m, 1H), 4.79 (s, 3H), 3.96-3.87 (m, 2H), 3.73-3.61 (m, 4H), 3.61-3.57 (m, 1H), 3.52 (dd, J = 3.3, 10.6 Hz, 1H), 3.44-3.38 (m, 1H), 3.28-3.18 (m, 2H), 302-2.55 (m, 5H), 2.48-1.90 (m, 8H), 1.85-1.61 (m, 3H), 1.83 (d, J = 6.3 Hz, 3H). HPLC (max plot) 99.7%; Rt 1.92 min. MS (ESI+): 544.4.

Example 378: Enantyiomer B of 1-(1-{2-[(2R,6S)-2,6-dimethylmorpholin-4-yl]ethyl}piperidin-3-yl)-3-(morpholin-4-ylcarbonyl)-1,4-dihydrothiochromeno[4,3-c]pyrazole 5,5-dioxide

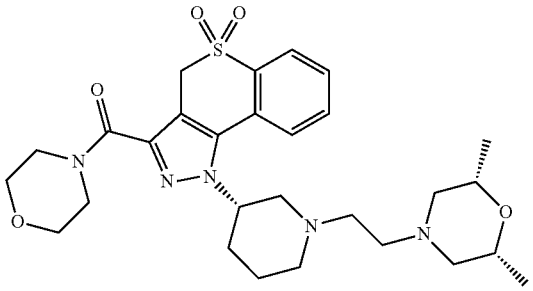 [SMILES: C[C@@H]1CN(CCN2CCC[C@H](n3nc(C(=O)N4CCOCC4)c4c3-c3ccccc3S(=O)(=O)C4)C2)C[C@H](C)O1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 75 mg of the title compound as a white foam. 1H NMR (DMSO-d6): δ 8.06 (dd, J = 1.2, 7.8 Hz, 1H), 7.97-7.91 (m, 1H), 7.85 (d, J = 7.4 Hz, 1H), 7.76 (t, J = 7.6 Hz, 1H), 4.79 (s, 2H), 3.96-3.88 (m, 2H), 3.83-3.76 (m, 1H), 3.72-3.61 (m, 4H), 3.51-3.38 (m, 3H), 3.28-3.20 (m, 1H), 2.94-2.85 (m, 1H), 2.81-2.65 (m, 3H), 2.43-2.34 (m, 3H), 2.29-1.91 (m, 4H), 1.86. 1.66 (m, 2H), 1.60-1.50 (m, 2H), 1.09 (d, J = 6.5 Hz, 1H), 1 (dd, J = 2.1, 6.2 Hz, 6H). HPLC (max plot) 99.0%; Rt 1.94 min. MS (ESI+): 558.4.

Example 385: Enantiomer B of 1-{1-[2-(2-methylmorpholin-4-yl)ethyl]piperidin-3-yl}-3-(morpholin-4-ylcarbonyl)-1,4-dihydrothiochromeno[4,3-c]pyrazole 5,5-dioxide

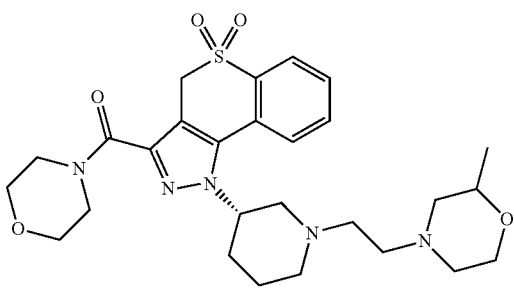 [SMILES: CC1CN(CCN2CCC[C@H](n3nc(C(=O)N4CCOCC4)c4c3-c3ccccc3S(=O)(=O)C4)C2)CCO1]

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 190 mg (84%) of the title compound as a white solid. 1H NMR (DMSO-d6): δ 8.09-8.02 (m, 1H), 7.98-7.81 (m, 2H), 7.75 (t, J = 7.5 Hz, 1H), 4.79 (s, 3H), 3.96-3.86 (m, 2H), 3.73-3.59 (m, 7H), 3.44-3.34 (m, 2H), 3.30-3.17 (m, 1H), 2.95-2.84 (m, 1H), 2.76-2.54 (m, 3H), 2.46-2.32 (m, 3H), 2.19-1.55 (m, 8H), 0.99 (dd, J = 2.7, 6.3 Hz, 3H). HPLC (max plot) 100.0%; Rt 2.55 min. MS (ESI+): 544.4.

Example 345: Enantiomer B of 3-(morpholin-4-ylcarbonyl)-1-[1-(2-morpholin-4-ylethyl)piperidin-3-yl]-1,4-dihydrothiochromeno[4,3-c]pyrazole 5,5-dioxide

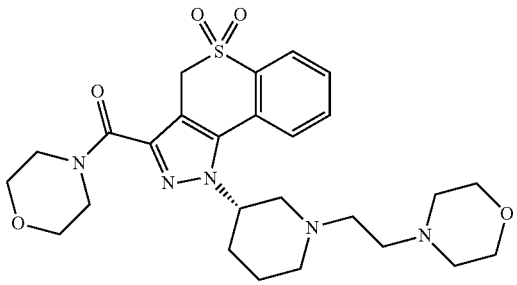

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 195 mg of the title compound as a white solid. $^1$H NMR (DMSO-$d_6$) δ 8.05 (dd, J = 7.8, 1.2 Hz, 1H), 7.98-7.89 (m, 1H), 7.85 (d, J = 7.6 Hz, 1H), 7.79-7.68 (m, 1H), 5.06-4.55 (m, 3H), 4.00-3.84 (m, 2H), 3.77-3.56 (m, 6H), 3.55-3.46 (m, 4H), 3.32-3.30 (m, 2H), 3.28-3.15 (m, 1H), 2.90 (d, J = 10.7 Hz, 1H), 2.46-2.24 (m, 7H), 2.21-1.85 (m, 3H), 1.84-1.61 (m, 2H). HPLC (max plot) 99.5%; Rt 1.54 min. [α]$^{25}$D −3.79 (c 1.06, DCM).

Example 468: Enantiomer B of 3-(morpholin-4-ylcarbonyl)-1-[1-pyridin-4-ylpiperidin-3-yl]-1,4-dihydrothiochromeno[4,3-c]pyrazole 5,5-dioxide

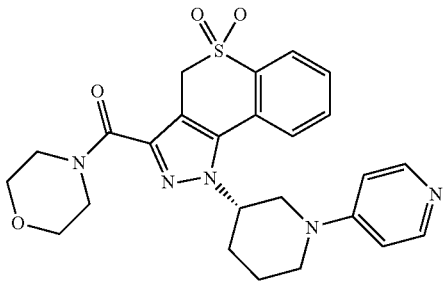

Obtained from enantiomer B of 3-(morpholin-4-ylcarbonyl)-1-[piperidin-3-yl]-1,4-dihydrothiochromeno[4,3-c]pyrazole 5,5-dioxide to give 85 mg of the title compound as a white solid. $^1$H NMR (DMSO-$d_6$, 300 MHz): δ 8.14-8.12 (d, J = 6.0 Hz, 2H), 8.07-8.05 (d, J = 6.0 Hz, 1H), 7.88-7.83 (m, 2H), 7.76-7.71 (m, 1H), 6.85-6.84 (d, J = 3.0 Hz, 2H), 4.91 (bs, 1H), 4.81 (s, 2H), 4.28-4.24 (d, J = 12.0 Hz, 1H), 3.95-3.88 (m, 3H), 3.66-3.60 (m, 5H), 3.52-3.47 (m, 1H), 3.11-3.04 (m, 1H), 2.23-1.80 (m, 5H). MS (ESI+): 494.2. HPLC (max plot) 98.0%; Rt 2.12 min Example 406: 6-Fluoro-3-(morpholin-4-ylcarbonyl)-1-{1-[2-(1H-pyrazol-1-yl)ethyl]piperidin-3-yl}-1,4-dihydrothiochromeno[4,3-c]pyrazole 5,5-dioxide

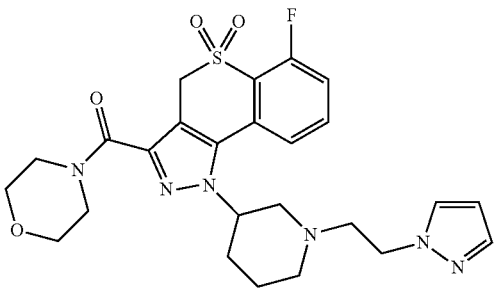 [SMILES: O=C(c1nn(C2CCCN(CCn3cccn3)C2)c2c1CS(=O)(=O)c1c(F)cccc1-2)N1CCOCC1]

62 mg of the title compound as a white powder. $^1$H NMR (DMSO-$d_6$, 300 MHz): δ 7.98-7.91 (m, 1H), 7.73-7.72 (m, 1H), 7.62-7.56 (m, 1H), 7.41 (m, 1H), 6.21-6.20 (m, 1H), 4.90 (s, 2H), 4.64 (bs, 1H), 4.24 (bs, 2H), 3.90 (bs, 2H), 3.66 (bs, 6H), 3.15-3.12 (m, 1H), 2.88-2.74 (m, 3H), 2.49-2.41 (m, 1H), 2.09-1.66 (m, 6H). MS (ESI+): 529.3. HPLC (max plot) 96.5%; Rt 2.00 min.

Example 413: 6-fluoro-3-(morpholin-4-ylcarbonyl)-1-[1-(2-morpholin-4-ylethyl)piperidin-3-yl]-1,4-dihydrothiochromeno[4,3-c]pyrazole 5,5-dioxide

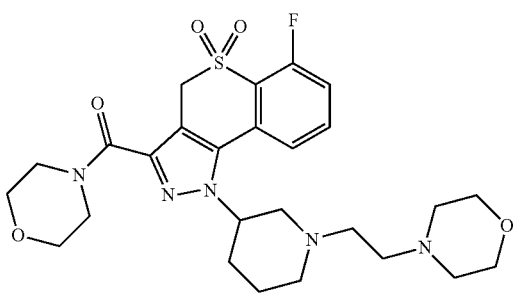

27 mg of the title compound as a white powder. $^1$H NMR (DMSO-$d_6$, 300 MHz): δ 8.27 (m, 2H), 7.92-7.99 (m, 1H), 7.56-7.66 (m, 2H), 4.90 (s, 2H), 4.71 (br s, 1H), 3.92 (br s, 2H), 3.66 (b s, 6H), 3.21 (br s, 1H), 2.89 (m, 2H), 2.73 (s, 1H), 1.70-2.43 (m, 14H). MS (ESI+): 548.4.

Example 414: 1-{1-[2-(3,3-Difluoroazetidin-1-yl)ethyl]piperidin-3-yl}-6-fluoro-3-(morpholin-4-ylcarbonyl)-1,4-dihydrothiochromeno[4,3-c]pyrazole 5,5-dioxide

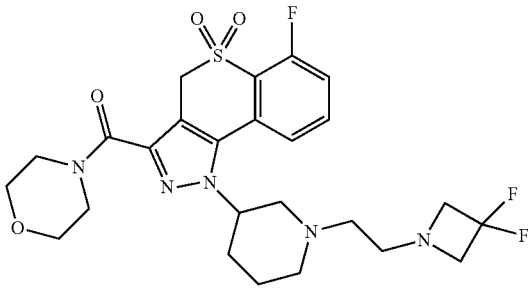 [SMILES: O=C(c1nn(C2CCCN(CCN3CC(F)(F)C3)C2)c2c1CS(=O)(=O)c1c(F)cccc1-2)N1CCOCC1]

37 mg of the title compound as a white powder. $^1$H NMR (DMSO-d$_6$, 300 MHz): δ 7.92-7.90 (m, 1H), 7.66-7.56 (m, 2H), 4.90 (s, 2H), 4.74 (bs, 1H), 3.91 (bs, 2H), 3.66 (bs, 6H), 3.58-3.49 (t, J = 12 Hz, 4H), 3.15-3.12 (m, 1H), 2.90-2.87 (m, 1H), 2.65-2.61 (m, 2H), 2.44-2.37 (m, 2H), 2.12-1.66 (m, 6H). MS (ESI+): 519.3. HPLC (max plot) 97.7%; Rt 2.05 min Example 349: Enantiomer A of 6-fluoro-3-(morpholin-4-ylcarbonyl)-1-[1-(2-morpholin-4-ylethyl)piperidin-3-yl]-1,4-dihydrothiochromeno[4,3-c]pyrazole 5,5-dioxide hydrochloride salt

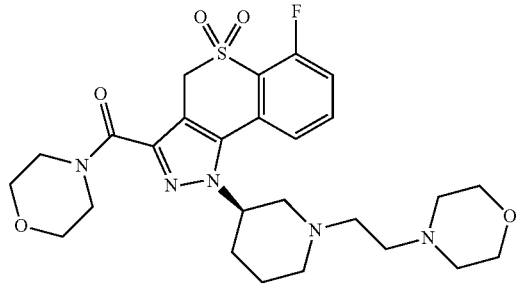

Obtained from enantiomer A of 6-fluoro-1-[1-(2-chloroethyl)piperidin-3-yl]-3-(morpholin-4-ylcarbonyl)-1,4-dihydrothiochromeno[4,3-c]pyrazole 5,5-dioxide to give 93 mg of the title compound as a white powder. $^1$H NMR (DMSO-d$_6$, 300 MHz): δ 7.87-7.93 (m, 2H), 7.58-7.64 (m, 1H), 5.28 (br s, 1H), 4.92 (br s, 2H), 3.09-3.84 (m, 24H), 1.91-2.28 (m, 4H) MS (ESI+): 548.4. HPLC (max plot) 98.1%; Rt 2.27 min. HPLC (chiralpack OZ-3, MeOH/0.1% DEA, max plot): Rt 22.54 min.

Example 350: Enantiomer B of 6-fluoro-3-(morpholin-4-ylcarbonyl)-1-[1-(2-morpholin-4-ylethyl)piperidin-3-yl]-1,4-dihydrothiochromeno[4,3-c]pyrazole 5,5-dioxide hydrochloride salt

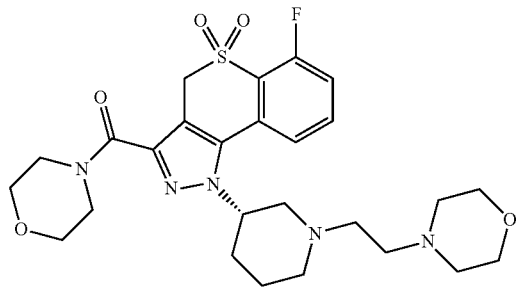

Obtained from enantiomer B of 6-fluoro-1-[1-(2-chloroethyl)piperidin-3-yl]-3-(morpholin-4-ylcarbonyl)-1,4-dihydrothiochromeno[4,3-c]pyrazole 5,5-dioxide to give 20 mg of the title compound as a white powder. MS (ESI+): 548.4. HPLC (max plot) 99.7%; Rt 2.23 min. HPLC (chiralpack OZ-3, MeOH/0.1% DEA, max plot): 100.0%, Rt 18.14 min. [α]$^{25}$ D −0.34 (1.2, EtOH).

Example 428: Enantiomer B of 6-methoxy-1-[1-(2-methoxyethyl)piperidin-3-yl]-3-(morpholin-4-ylcarbonyl)-1,4-dihydrothiochromeno[4,3-c]pyrazole 5,5-dioxide

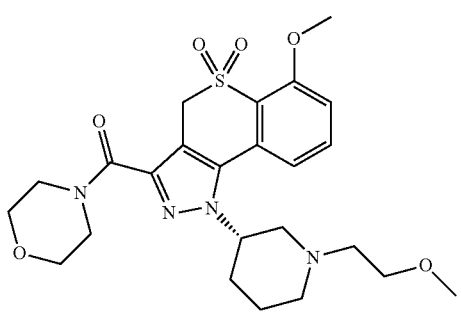 [SMILES: COCCN1CCC[C@H](n2nc(C(=O)N3CCOCC3)c3c2-c2cccc(OC)c2S(=O)(=O)C3)C1]

Obtained from enantiomer B of 6-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 37 mg of the title compound as a white solid. $^1$H NMR (DMSO-d$_6$, 300 MHz): δ 7.86-7.80 (t, J = 9.0 Hz, 1H), 7.41-7.30 (m, 2H), 4.71 (s, 2H), 4.66-4.62 (m, 1H), 3.94 (s, 5H), 3.65 (s, 6H), 3.44-3.41 (t, J = 6.0 Hz, 2H), 3.20 (s, 3H), 3.16-3.13 (m, 1H), 2.90-2.87 (m, 1H), 2.58-2.53 (m, 2H), 2.46-2.39 (m, 1H), 2.10-1.69 (m, 5H). MS (ESI+): 505.4. HPLC (max plot) 99.1%; Rt 1.68 min.

-continued

Example 467: Enantiomer B of 1-[1-(2-methoxyethyl)piperidin-3-yl]-6-methyl-3-(morpholin-4-ylcarbonyl)-1,4-dihydrothiochromeno[4,3-c]pyrazole 5,5-dioxide

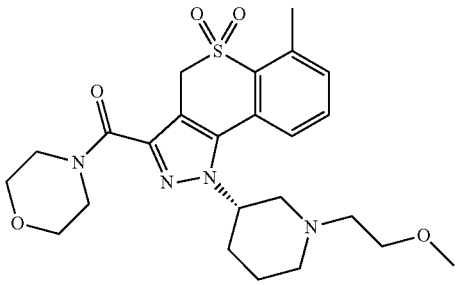 [SMILES: COCCN1CCC[C@H](n2nc(C(=O)N3CCOCC3)c3c2-c2cccc(C)c2S(=O)(=O)C3)C1]

Obtained from enantiomer B of 6-methyl-1-[1-(2-chloroethyl)piperidin-3-yl]-3-(morpholin-4-ylcarbonyl)-1,4-dihydrothiochromeno[4,3-c]pyrazole 5,5-dioxide to give 33 mg (34%) of the title compound as a white solid. $^1$H NMR (DMSO-d$_6$, 300 MHz): δ 7.80-7.75 (m, 1H), 7.63-7.61 (m, 1H), 7.54-7.51 (m, 1H), 4.79 (s, 2H), 4.66 (m, 1H), 3.95 (m, 2H), 3.66 (s, 6H), 3.44-3.41 (m, 2H), 3.19 (s, 3H), 3.13 (m, 1H), 2.90-2.87 (m, 1H), 2.68 (s, 3H), 2.55 (m, 2H), 2.47-2.40 (m, 1H), 2.06-1.65 (m, 5H). MS (ESI+): 489.3. HPLC (max plot) 97.7%; Rt 2.05 min Example 394: Enantiomer B of 7-methoxy-1-[1-(2-methoxyethyl)piperidin-3-yl]-3-(morpholin-4-ylcarbonyl)-1,4-dihydrothiochromeno[4,3-c]pyrazole 5,5-dioxide

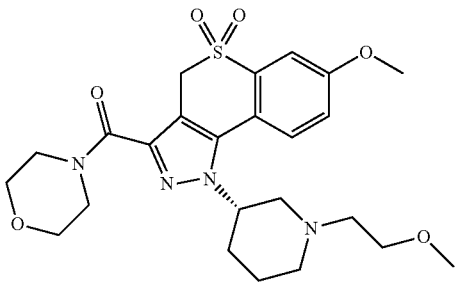 [SMILES: COCCN1CCC[C@H](n2nc(C(=O)N3CCOCC3)c3c2-c2ccc(OC)cc2S(=O)(=O)C3)C1]

Obtained from enantiomer B of 7-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 30 mg (94%) of the title compound as a white foam. $^1$H NMR (DMSO-d$_6$, 300 MHz): δ 10.70 (s, 1H), 7.97 (d, J = 9.1 Hz, 1H), 7.52 (d, J = 2.6 Hz, 1H), 7.42 (d, J = 8.3 Hz, 1H), 5.34 (s, 1H), 4.77 (s, 2H), 3.94 (s, 3H), 3.89-3.53 (m, 13H), 3.53-3.37 (m, 3H), 3.15-3.00 (m, 2H), 2.08 (t, J = 34.5 Hz, 4H).. MS (ESI+): 505.3. HPLC (max plot) 98.7%; Rt 2.39 min Procedure AH Example 348

Enantiomer A of 3-(morpholin-4-ylcarbonyl)-1-[1-(2-morpholin-4-ylethyl)piperidin-3-yl]-1,4-dihydrothiochromeno[4,3-c]pyrazole 5,5-dioxide

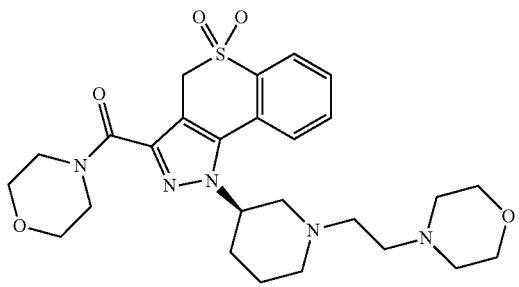

Enantiomer A of 1- [1-(2-chloroethyl)piperidin-3-yl]-3-(morpholin-4-ylcarbonyl)-1,4-dihydrothiochromeno[4,3-c]pyrazole 5,5-dioxide (274 mg; 0.57 mmol; 1.00 eq.), morpholine (199 µl; 2.29 mmol; 4.00 eq.), sodium iodide (85 mg; 0.57 mmol; 1.00 eq.) and K$_2$CO$_3$ (237 mg; 1.72 mmol; 3.00 eq.) are taken up in ACN (6 mL). The reaction mixture is stirred at 60° C. overnight. The reaction mixture is diluted in DCM and washed with water, brine, then dried over MgSO$_4$ and evaporated. Purification by flash chromatography (DCM/MeOH 0 to 5%) followed by dissolution in ACN : water and freeze drying gives the title compound as a white solid. $^1$H NMR (DMSO-d$_6$, 300 MHz): δ 8.05 (dd, J =1.2, 7.8 Hz, 1H), 7.94 (td, J =1.3, 7.8 Hz, 1H), 7.88-7.81 (m, 11-1), 7.80-7.70 (m, 1H), 5.05-4.62 (m, 3H), 4.05-3.79 (m, 2H), 3.79-3.58 (m, 6H), 3.56-3.42 (m, 4H), 3.32-3.08 (m, 3I-1), 2.91 (d, J =10.8 Hz, 1H), 2.46-2.22 (m, 8H), 2.20-1.60 (m, 6H). MS (ESI+): 530.46. HPLC (max plot) 99.4%; Rt 1.56 min. [α]$^{25}$D+4.20 (c 1.09, DCM).

Compounds described below are obtained following protocol outlined in procedure AH Example 290: 3-(Morpholin-4-ylcarbonyl)-1-[1-(2-morpholin-4-ylethyl)piperidin-4-yl]-1,4-dihydrothiochromeno[4,3-c]pyrazole 5,5-dioxide

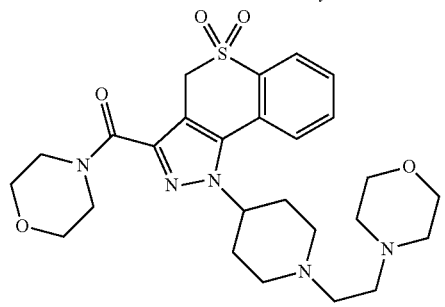

42 mg of the title compound as a white powder. 1H NMR (DMSO-d6) δ δ 8.04 (d, J = 7.6 Hz, 1H), 7.90 (q, J = 7.8 Hz, 2H), 7.74 (t, J = 7.3 Hz, 1H), 4.79 (s, 2H), 4.73 (s, 1H), 3.98 (s, 2H), 3.66 (s, 5H), 3.60-3.48 (m, 4H), 3.00 (d, J = 11.0 Hz, 2H), 2.47-2.33 (m, 6H), 2.31-2.00 (m, 5H). HPLC (max plot) 74.2%; Rt 1.65 min. MS (ESI+): 529.9.

Example 429: Enantiomer B of 1-{1-[3-(3,3-difluoroazetidin-1-yl)-3-oxopropyl]piperidin-3-yl}-3-(morpholin-4-ylcarbonyl)-1,4-dihydrothiochromeno[4,3-c]pyrazole 5,5-dioxide

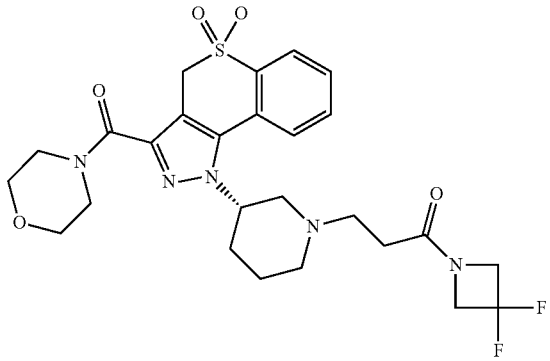

Obtained from enantiomer B of 3-(morpholin-4-ylcarbonyl)-1-[piperidin-3-yl]-1,4-dihydrothiochromeno[4,3-c]pyrazole 5,5-dioxide to give 25 mg of the title compound as a white solid. $^1$H NMR (DMSO-d$_6$, 300 MHz): δ 8.06 (d, J = 7.8 Hz, 1H), 7.98-7.89 (m, 1H), 7.86-7.71 (m, 2H), 4.82-4.67 (m, 3H), 4.57 (t, J = 12.7 Hz, 2H), 4.24 (t, J = 12.8 Hz, 2H), 3.94-3.87 (m, 2H), 3.73-3.58 (m, 5H), 3.21-3.10 (m, 1H), 2.94-2.82 (m, 1H), 2.74-2.54 (m, 2H), 2.48-2.25 (m, 3H), 2.19-1.65 (m, 6H). MS (ESI+): 564.3. HPLC (max plot) 98.4%; Rt 2.65 min Example 433: Enantiomer B of methyl 3-{3-[3-(morpholin-4-ylcarbonyl)-5,5-dioxidothiochromeno[4,3-c]pyrazol-1(4H)-yl]piperidin-1-yl}propanoate

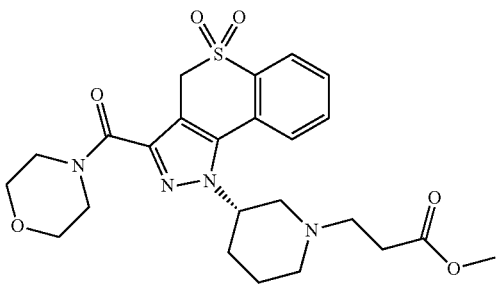 [SMILES: COC(=O)CCN1CCC[C@H](n2nc(C(=O)N3CCOCC3)c3c2-c2ccccc2S(=O)(=O)C3)C1]

Obtained from enantiomer B of 3-(morpholin-4-ylcarbonyl)-1-[piperidin-3-yl]-1,4-dihydrothiochromeno[4,3-c]pyrazole 5,5-dioxide to give 90 mg (75%) of the title compound as a yellow foam. $^1$H NMR (DMSO-d$_6$, 300 MHz): δ 8.06 (d, J = 7.5 Hz, 1H), 7.94 (t, J = 7.2 Hz, 1H), 7.89-7.71 (m, 2H), 4.89-4.65 (m, 3H), 4.02-3.76 (m, 3H), 3.75-3.50 (m, 9H), 3.27-3.10 (m, 1H), 3.08-2.79 (m, 2H), 2.78-2.55 (m, 2H), 2.47-2.31 (m, 1H), 2.26-1.53 (m, 5H). MS (ESI+): 503.4. HPLC (max plot) 93.9%; Rt 1.93 min Example 434: Enantiomer B of 6-Fluoro-1-[1-(2-methoxyethyl)piperidin-3-yl]-3-(morpholin-4-ylcarbonyl)-1,4-dihydrothiochromeno[4,3-c]pyrazole 5,5-dioxide

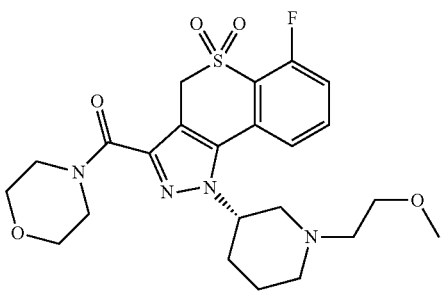 [SMILES: COCCN1CCC[C@H](n2nc(C(=O)N3CCOCC3)c3c2-c2cccc(F)c2S(=O)(=O)C3)C1]

Obtained from enantiomer B of 6-fluoro-1-[1-(2-chloroethyl)piperidin-3-yl]-3-(morpholin-4-ylcarbonyl)-1,4-dihydrothiochromeno[4,3-c]pyrazole 5,5-dioxide to give73 mg of the title compound as a white powder. $^1$H NMR (DMSO-d$_6$, 300 MHz): δ 8.02-7.89 (m, 1H), 7.71-7.51 (m, 2H), 4.89 (s, 2H), 4.79-4.61 (m, 1H), 3.99-3.82 (m, 2H), 3.79-3.55 (m, 6H), 3.50-3.37 (m, 2H), 3.19 (s, 3H), 3.18-3.10 (m, 1H), 2.96-2.81 (m, 1H), 2.66-2.52 (m, 2H), 2.48-2.35 (m, 1H), 2.19-2.00 (m, 2H), 2.00-1.58 (m, 1H), 1.83-1.58 (m, 2H). MS (ESI+): 493.4. HPLC (max plot) 100.0%; Rt 1.92 min Example 438: Enantiomer B of 2-methoxy-N-methyl-N-(2-{3-[3-(morpholin-4-ylcarbonyl)-5,5-dioxidothiochromeno[4,3-c]pyrazol-1(4H)-yl]piperidin-1-yl}ethyl)ethanamine

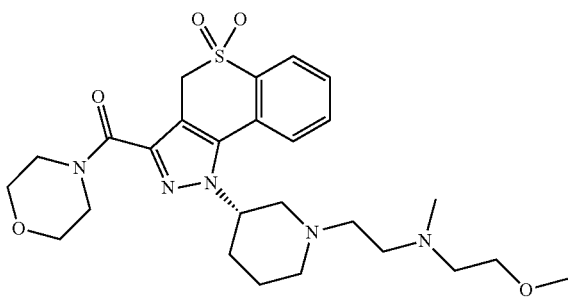

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give14 mg of the title compound as a beige solid. $^1$H NMR (DMSO-d$_6$, 300 MHz): δ 8.05 (d, J = 7.4 Hz, 1H), 7.94 (t, J = 7.3 Hz, 1H), 7.85 (d, J = 7.8 Hz, 1H), 7.75 (t, J = 7.5 Hz, 1H), 4.85-4.67 (m, 3H), 3.98-3.85 (m, 2H), 3.75-3.58 (m, 7H), 3.29-3.18 (m, 2H), 3.16 (s, 3H), 2.96-2.83 (m, 1H), 2.57-2.48 (m, 4H), 2.43-2.32 (m, 2H), 2.16 (s, 3H), 2.14-1.61 (m, 6H). MS (ESI+): 532.6. HPLC (max plot) 100.0%; Rt 1.75 min.

Example 439: Enantiomer B of 1-{1-[2-(3-methoxypyrrolidin-1-yl)ethyl]piperidin-3-yl}-3-(morpholin-4-ylcarbonyl)-1,4-dihydrothiochromeno[4,3-c]pyrazole 5,5-dioxide

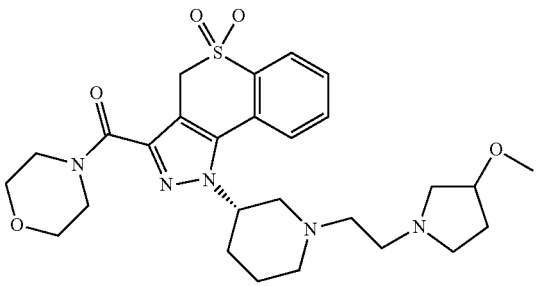

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give15 mg of the title compound as a yellow solid. $^1$H NMR (DMSO-$d_6$, 300 MHz): δ 8.05 (dd, J = 1.1, 7.8 Hz, 1H), 7.94 (tr, J = 7.7 Hz, 1H), 7.84 (d, J = 7.7 Hz, 1H), 7.75 (t, J = 7.5 Hz, 1H), 4.84-4.70 (m, 3H), 3.96-3.86 (m, 2H), 3.85-3.75 (m, 1H), 3.73-3.57 (m, 7H), 3.26-3.16 (m, 2H), 3.12 (d, J = 2.7 Hz, 3H), 2.96-2.84 (m, 1H), 2.70-2.53 (m, 2H), 2.47-2.31 (m, 4H), 2.20-1.47 (m, 8H). MS (ESI+): 544.6. HPLC (max plot) 100.0%; Rt 1.75 min Example 444: Enantiomer B of N-(2-{3-[3-(morpholin-4-ylcarbonyl)-5,5-dioxidothiochromeno[4,3-c]pyrazol-1(4H)-yl]piperidin-1-yl}ethyl)acetamide

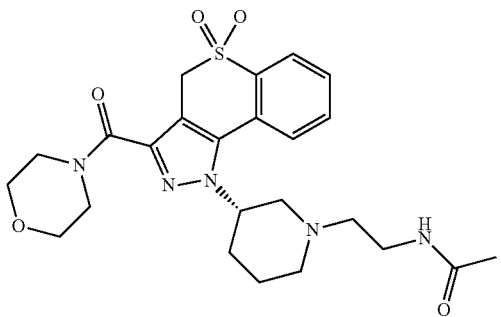

Obtained from enantiomer B of 3-(morpholin-4-ylcarbonyl)-1-[piperidin-3-yl]-1,4-dihydrothiochromeno[4,3-c]pyrazole 5,5-dioxide to give61 mg of the title compound as a white solid. $^1$H NMR (DMSO-$d_6$, 300 MHz): δ 8.05 (d, J = 7.7 Hz, 1H), 7.95 (t, J = 7.3 Hz, 1H), 7.85 (d, J = 7.6 Hz, 1H), 7.82-7.71 (m, 2H), 4.83-4.71 (m, 3H), 3.94-3.86 (m, 2H), 3.72-3.60 (m, 5H), 3.27-3.02 (m, 4H), 2.93-2.83 (m, 1H), 2.48-2.33 (m, 3H), 2.19-1.84 (m, 4H), 1.79 (s, 3H), 1.76-1.64 (m, 1H). MS (ESI+): 502.4. HPLC (max plot) 100.0%; Rt 1.84 min Example 445: Enantiomer B of 2-methoxy-N-(2-{3-[3-(morpholin-4-ylcarbonyl)-5,5-dioxidothiochromeno[4,3-c]pyrazol-1(4H)-yl]piperidin-1-yl}ethyl)ethanamine

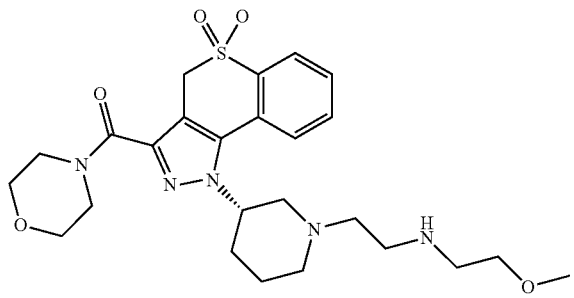

Obtained from enantiomer B of 3-(morpholin-4-ylcarbonyl)-1-[piperidin-3-yl]-1,4-dihydrothiochromeno[4,3-c]pyrazole 5,5-dioxide to give 32 mg of the title compound as a yellow solid. $^1$H NMR (DMSO-$d_6$, 300 MHz): δ 8.09-8.02 (m, 1H), 7.98-7.89 (t, J = 7.1 Hz, 1H), 7.87-7.71 (m, 2H), 4.85-4.71 (m, 3H), 3.97-3.86 (m, 2H), 3.73-3.58 (m, 6H), 3.45-3.38 (m, 3H), 3.19 (s, 3H), 3.17-3.10 (m, 1H), 2.93-2.82 (m, 2H), 2.71-2.59 (m, 4H), 2.48-2.32 (m, 2H), 2.22-1.61 (m, 5H). MS (ESI+): 518.5. HPLC (max plot) 100.0%; Rt 1.80 min Example 446: Enantiomer B of 1-{1-[2-(3-methoxyazetidin-1-yl)ethyl]piperidin-3-yl}-3-(morpholin-4-ylcarbonyl)-1,4-dihydrothiochromeno[4,3-c]pyrazole 5,5-dioxide

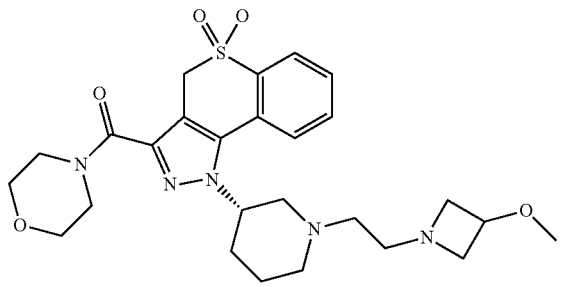

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give35 mg of the title compound as a yellow foam. $^1$H NMR (DMSO-$d_6$, 300 MHz): δ 8.06 (dd, J = 1.2, 7.8 Hz, 1H), 7.98-7.90 (m, 1H), 7.89-7.81 (m, 1H), 7.80-7.7 (m, 1H), 4.84-4.69 (m, 3H), 3.96-3.86 (m, 2H), 3.73-3.59 (m, 4H), 3.56-3.45 (m, 2H), 3.41-3.27 (m, 6H), 3.23-3.14 (m, 1H), 2.94-2.71 (m, 3H), 2.6-2.53 (m, 1H), 2.46-2.29 (m, 3H), 2.19-1.61 (m, 6H). MS (ESI+): 530.5. HPLC (max plot) 80.5%; Rt 1.85 min Example 448: Enantiomer B of 2-methoxy-N-(2-methoxyethyl)-N-(2-{3-[3-(morpholin-4-ylcarbonyl)-5,5-dioxidothiochromeno[4,3-c]pyrazol-1(4H)-yl]piperidin-1-yl}ethyl)ethanamine

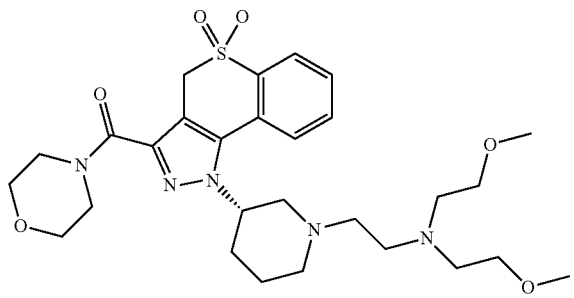

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 75 mg of the title compound as a yellow foam. $^1$H NMR (DMSO-$d_6$, 300 MHz): δ 8.05 (d, J = 6.9 Hz, 1H), 7.94 (t, J = 7.7 Hz, 1H), 7.84 (d, J = 7.9 Hz, 1H), 7.75 (t, J = 7.6 Hz, 1H), 4.83-4.69 (m, 3H), 3.96-3.88 (m, 2H), 3.72-3.60 (m, 5H), 3.38-3.31 (m, 8H), 3.24-3.18 (m, 1H), 3.16 (s, 4H), 2.94-2.84 (m, 1H), 2.66-2.55 (m, 5H), 2.47-2.36 (m, 2H), 2.19-1.62 (m, 6H). MS (ESI+): 576.6. HPLC (max plot) 99.7%; Rt 6.17 min.

Example 460: Enantiomer B of 1-{1-[2-(4-methoxypiperidin-1-yl)ethyl]piperidin-3-yl}-3-(morpholin-4-ylcarbonyl)-1,4-dihydrothiochromeno[4,3-c]pyrazole 5,5-dioxide

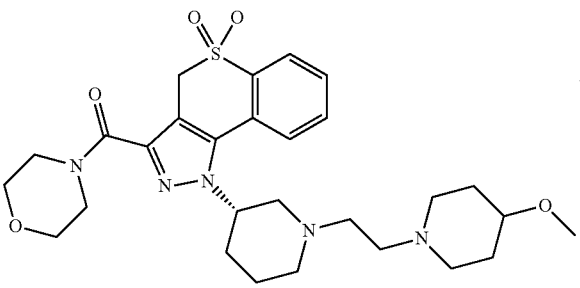

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 115 mg of the title compound as a white solid. $^1$H NMR (DMSO-$d_6$, 300 MHz): δ 8.05 (d, J = 7.8 Hz, 1H), 7.97-7.89 (m, 1H), 7.84 (d, J = 7.9 Hz, 1H), 7.8 (t, J = 7.8 Hz, 1H), 4.83-4.70 (m, 3H), 3.96-3.87 (m, 2H), 3.73-3.61 (m, 5H), 3.28-3.22 (m, 1H), 3.20 (s, 3H), 3.16-3.04 (m, 2H), 2.94-2.84 (m, 1H), 2.71-2.60 (m, 2H), 2.46-2.33 (m, 4H), 2.16-1.85 (m, 6H), 1.85-1.63 (m, 4H), 1.40-1.25 (m, 2H). MS (ESI+): 558.6. HPLC (max plot) 100.0%; Rt 1.77 min Example 463: Enantiomer B of 1-(2-{3-[3-(morpholin-4-ylcarbonyl)-5,5-dioxidothiochromeno[4,3-c]pyrazol-1(4H)-yl]piperidin-1-yl}ethyl)piperidin-4-ol

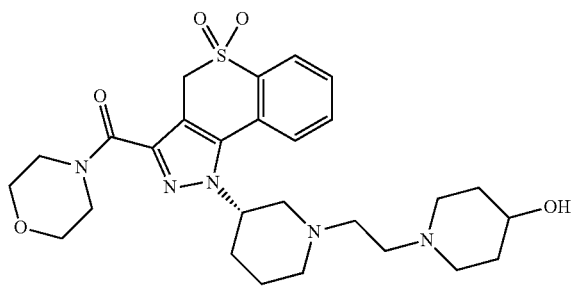

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 60 mg of the title compound as a white solid. $^1$H NMR (DMSO-$d_6$, 300 MHz): δ 5 8.05 (d, J = 7.9 Hz, 1H), 7.98-7.89 (m, 1H), 7.84 (d, J = 7.4 Hz, 1H), 7.75 (t, J = 7.4 Hz, 1H), 4.83-4.69 (m, 3H), 4.55-4.46 (m, 1H), 3.96-3.87 (m, 2H), 3.72-3.60 (m, 5H), 3.28-3.18 (m, 2H), 2.94-2.85 (m, 1H), 2.75-2.62 (m, 2H), 2.46-2.3 (m, 4H), 2.17-1.85 (m, 5H), 1.84-1.54 (m, 5H), 1.39-1.20 (m, 3H). MS (ESI+): 544.5. HPLC (max plot) 100.0%; Rt 1.63 min Example 465: Enantiomer B of 3-(morpholin-4-ylcarbonyl)-1-[1-(2-piperidin-1-ylethyl)piperidin-3-yl]-1,4-dihydrothiochromeno[4,3-c]pyrazole 5,5-dioxide

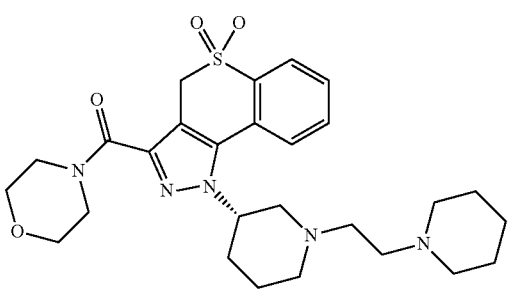

Obtained from enantiomer B of 1-[1-(2-chloroethyl)piperidin-3-yl]-3-(morpholin-4-ylcarbonyl)-1,4-dihydrothiochromeno[4,3-c]pyrazole 5,5-dioxide to give 90 mg (82%) of the title compound as a yellow solid. $^1$H NMR (DMSO-$d_6$, 300 MHz): δ 8.06 (d, J = 7.8 Hz, 1H), 7.97-7.88 (m, 1H), 7.84 (d, J = 7.8 Hz, 1H), 7.80-7.71 (m, 1H), 4.79 (bs, 3H), 3.97-3.87 (m, 2H), 3.76-3.59 (m, 6H), 3.27-3.17 (m, 1H), 3.05-2.96 (m, 1H), 2.96-2.85 (m, 1H), 2.48-2.35 (m, 5H), 2.19-1.86 (m, 4H), 1.85-1.52 (m, 5H), 1.52-1.29 (m, 5H). MS (ESI+): 528.3. HPLC (max plot) 68.1%; Rt 1.96 min.

Example 424: Enantiomer B of 6-methoxy-3-(morpholin-4-ylcarbonyl)-1-[1-(2-morpholin-4-ylethyl)piperidin-3-yl]-1,4-dihydrothiochromeno[4,3-c]pyrazole 5,5-dioxide

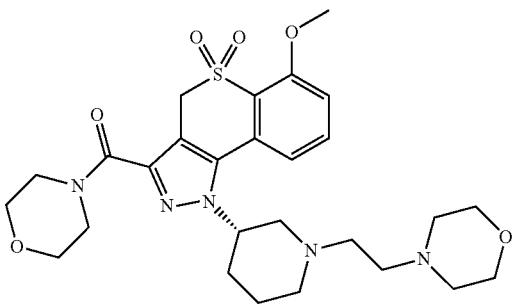 [SMILES: COc1cccc2c1S(=O)(=O)Cc1c(C(=O)N3CCOCC3)nn([C@H]3CCCN(CCN4CCOCC4)C3)c1-2]

Obtained from enantiomer B of 6-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 164 mg of the title compound as a white solid. $^1$H NMR (DMSO-$d_6$, 300 MHz): δ 7.85-7.80 (t, J = 9.0 Hz, 1H), 7.42-7.31 (m, 2H), 4.72 (s, 2H), 4.66 (m, 1H), 3.94 (s, 5H), 3.65 (s, 6H), 3.56-3.49 (m, 4H), 3.18-3.15 (m, 1H), 2.90-2.87 (m, 1H), 2.76-2.73 (m, 1H), 2.50-2.33 (m, 7H), 2.06-1.67 (m, 6H). MS (ESI+): 560.5. HPLC (max plot) 98.0%; Rt 1.52 min Example 442: Enantiomer B of 1-{1-[2-(3,3-difluoroazetidin-1-yl)ethyl]piperidin-3-yl}-6-methoxy-3-(morpholin-4-ylcarbonyl)-1,4-dihydrothiochromeno[4,3-c]pyrazole 5,5-dioxide

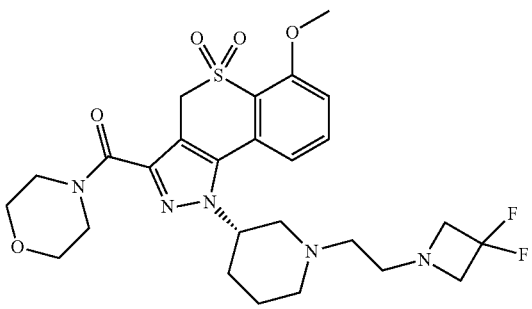 [SMILES: COc1cccc2c1S(=O)(=O)Cc1c(C(=O)N3CCOCC3)nn([C@H]3CCCN(CCN4CC(F)(F)C4)C3)c1-2]

Obtained from enantiomer B of 6-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 57 mg of the title compound as a white powder. $^1$H NMR (DMSO-$d_6$, 300 MHz): δ 7.84-7.78 (t, J = 9.0 Hz, 1H), 7.42-7.32 (m, 2H), 4.71 (s, 2H), 4.65-4.62 (m, 1H), 3.94 (s, 5H), 3.65 (s, 5H), 3.58-3.50 (t, J = 9.0 Hz, 4H), 3.12-3.09 (m, 1H), 2.90-2.86 (m, 1H), 2.65-2.61 (m, 2H), 2.43-2.36 (m, 4H), 2.10-1.63 (m, 5H). MS (ESI+): 566.6. HPLC (max plot) 98.1%; Rt 1.86 min.

Example 443: Enantiomer B of 1-{1-[2-(3-fluoroazetidin-1-yl)ethyl]piperidin-3-yl}-6-methoxy-3-(morpholin-4-ylcarbonyl)-1,4-dihydrothiochromeno[4,3-c]pyrazole 5,5-dioxide

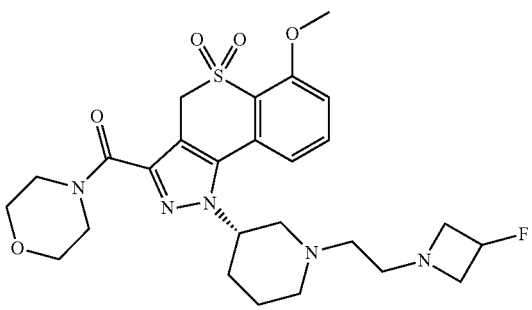 [SMILES: COc1cccc2c1S(=O)(=O)Cc1c(C(=O)N3CCOCC3)nn([C@H]3CCCN(CCN4CC(F)C4)C3)c1-2]

Obtained from enantiomer B of 6-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 10 mg of the title compound as a beige solid. $^1$H NMR (DMSO-$d_6$, 300 MHz): δ 8.15 (s, 1H), 7.85-7.80 (t, J = 9.0 Hz, 1H), 7.42-7.31 (m, 2H), 5.22-4.99 (m, 2H), 4.71 (s, 2H), 4.65 (m, 1H), 3.94 (s, 5H), 3.65 (s, 6H), 3.50 (m, 2H), 3.06-2.73 (m, 4H), 2.51 (m, 1H), 2.34-1.63 (m, 9H). MS (ESI+): 548.5. HPLC (max plot) 95.3%; Rt 1.53 min Example 471: Enantiomer B of 6-methyl-3-(morpholin-4-ylcarbonyl)-1-[1-(2-morpholin-4-ylethyl)piperidin-3-yl]-1,4-dihydrothiochromeno[4,3-c]pyrazole 5,5-dioxide

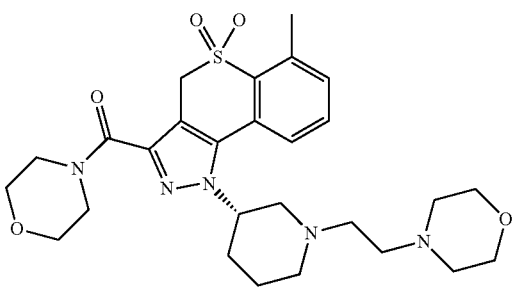

Obtained from enantiomer B of 6-methyl-1-[1-(2-chloroethyl)piperidin-3-yl]-3-(morpholin-4-ylcarbonyl)-1,4-dihydrothiochromeno[4,3-c]pyrazole 5,5-dioxide to give 83 mg (75%) of the title compound as a white powder. $^1$H NMR (DMSO-$d_6$, 300 MHz): δ 7.79-7.74 (m, 1H), 7.65-7.62 (m, 1H), 7.54-7.51 (m, 1H), 4.79 (s, 2H), 4.70-4.63 (m, 1H), 3.95 (m, 2H), 3.66 (s, 7H), 3.52-3.49 (m, 4H), 3.18-3.16 (m, 2H), 2.90-2.87 (m, 1H), 2.68 (s, 3H), 2.43-1.64 (m, 12H). MS (ESI+): 544.4. HPLC (max plot) 94.9%; Rt 1.88 min Example 472: Enantiomer B of 7-fluoro-3-(morpholin-4-ylcarbonyl)-1-[1-(2-morpholin-4-ylethyl)piperidin-3-yl]-1,4-dihydrothiochromeno[4,3-c]pyrazole 5,5-dioxide

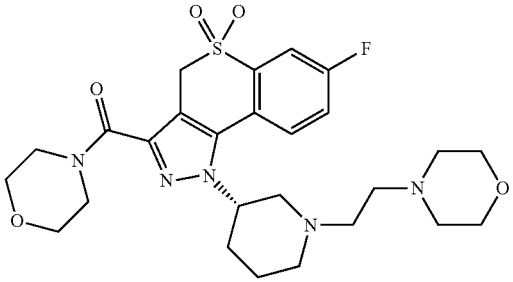

Obtained from enantiomer B of 7-fluoro-1-[1-(2-chloroethyl)piperidin-3-yl]-3-(morpholin-4-ylcarbonyl)-1,4-dihydrothiochromeno[4,3-c]pyrazole 5,5-dioxide to give 10 mg of the title compound as a yellow foam. $^1$H NMR (DMSO-$d_6$, 300 MHz): δ 7.99-7.86 (m, 2H), 7.82 (t, J = 8.6 Hz, 1H), 4.90-4.67 (m, 3H), 4.77 (d, J = 10.4 Hz, 1H), 3.95-3.85 (m, 2H), 3.72-3.62 (m, 6H), 3.55-3.42 (m, 4H), 3.21 (d, J = 10.1 Hz, 1H), 2.90 (d, J = 9.9 Hz, 1H), 2.45-2.27 (m, 7H), 2.16-1.86 (m, 4H), 1.85-1.60 (m, 2H). MS (ESI+): 548.5. HPLC (max plot) 66.6%; Rt 1.97 min. HPLC (Chiralpack IA, EtOH/0.1%DEA, max plot): 99.57%, Rt 8.87 min (enantiomer A: Rt 7.81 min). [α]$^{25}$ D −1.87 (1.1, MeOH)

Example 474: Enantiomer B of 7-fluoro-1-{1-[2-(4-methoxypiperidin-1-yl)ethyl]piperidin-3-yl}-3-(morpholin-4-ylcarbonyl)-1,4-dihydrothiochromeno[4,3-c]pyrazole 5,5-dioxide

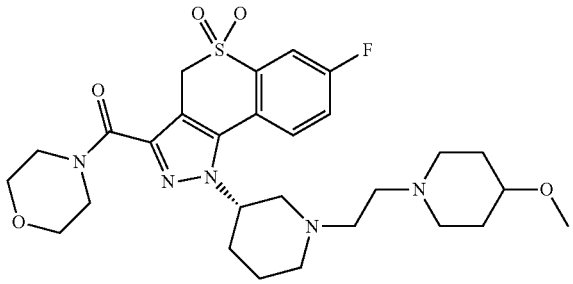

Obtained from enantiomer B of 7-fluoro-1-[1-(2-chloroethyl)piperidin-3-yl]-3-(morpholin-4-ylcarbonyl)-1,4-dihydrothiochromeno[4,3-c]pyrazole 5,5-dioxide to give 60 mg (61%) of the title compound as a white foam. $^1$H NMR (DMSO-$d_6$, 300 MHz): δ 7.95-7.86 (m, 2H), 7.85-7.76 (m, 1H), 4.84 (s, 2H), 4.80-4.67 (m, 1H), 3.95-3.87 (m, 2H), 3.71-3.61 (m, 6H), 3.19 (s, 4H), 3.15-3.05 (m, 1H), 2.88 (d, J = 10.0 Hz, 1H), 2.68-2.57 (m, 2H), 2.45-2.30 (m, 2H), 2.20-1.84 (m, 6H), 1.82-1.62 (m, 4H), 1.38-1.22 (m, 4H).. MS (ESI+): 576.4. HPLC (max plot) 57.0%; Rt 2.07 min Example 382: Enantiomer B of 1-{1-[2-(3,3-difluoroazetidin-1-yl)ethyl]piperidin-3-yl}-7-methoxy-3-(morpholin-4-ylcarbonyl)-1,4-dihydrothiochromeno[4,3-c]pyrazole 5,5-dioxide

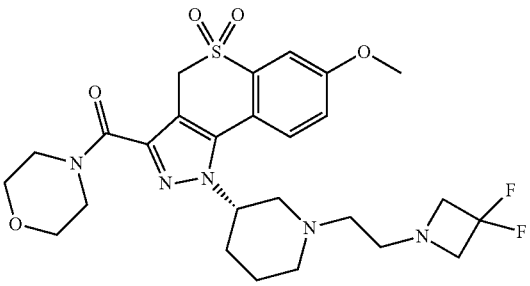 [SMILES: COc1ccc2c(c1)S(=O)(=O)Cc1c(C(=O)N3CCOCC3)nn([C@H]3CCCN(CCN4CC(F)(F)C4)C3)c1-2]

Obtained from enantiomer B of 7-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 75 mg of the title compound as a white foam. $^1$H NMR (DMSO-$d_6$, 300 MHz): δ 7.80 (d, J = 8.8 Hz, 1H), 7.50 (d, J = 2.7 Hz, 1H), 7.45 (dd, J = 8.7, 2.8 Hz, 1H), 4.73 (d, J = 16.4 Hz, 3H), 3.93 (s, 5H), 3.65 (s, 6H), 3.54 (t, J = 12.5 Hz, 4H), 3.15 (d, J = 8.8 Hz, 1H), 2.89 (d, J = 9.5 Hz, 1H), 2.64 (t, J = 6.2 Hz, 2H), 2.39 (t, J = 8.2 Hz, 3H), 2.15-1.63 (m, 5H).. MS (ESI+): 566.4. HPLC (max plot) 98.9%; Rt 2.48 min.

Example 383: Enantiomer B of 7-methoxy-3-(morpholin-4-ylcarbonyl)-1-[1-(2-morpholin-4-ylethyl)piperidin-3-yl]-1,4-dihydrothiochromeno[4,3-c]pyrazole 5,5-dioxide

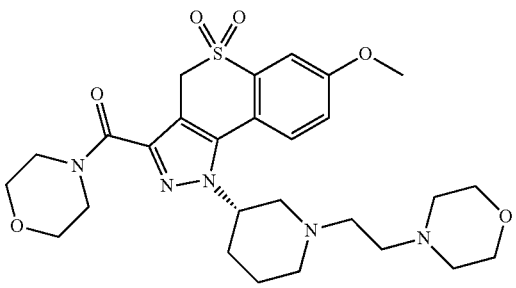

Obtained from enantiomer B of 7-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 90 mg (82%) of the title compound as a white foam. $^1$H NMR (DMSO-$d_6$, 300 MHz): δ 7.79 (d, J = 8.6 Hz, 1H), 7.48 (dd, J = 13.1, 2.6 Hz, 2H), 4.74 (d, J = 13.4 Hz, 3H), 3.93 (s, 5H), 3.62 (d, J = 19.2 Hz, 6H), 3.56-3.43 (m, 4H), 3.21 (d, J = 10.1 Hz, 1H), 2.87 (dd, J = 17.1, 7.8 Hz, 1H), 2.55-2.45 (m, 2H), 2.46-2.23 (m, 7H), 2.15-1.60 (m, 5H). MS (ESI+): 560.4. HPLC (max plot) 64.8%; Rt 2.04 min.

Example 384: Enantiomer B of 1-{1-[2-(4-fluoropiperidin-1-yl)ethyl]piperidin-3-yl}-7-methoxy-3-(morpholin-4-ylcarbonyl)-1,4-dihydrothiochromeno[4,3-c]pyrazole 5,5-dioxide

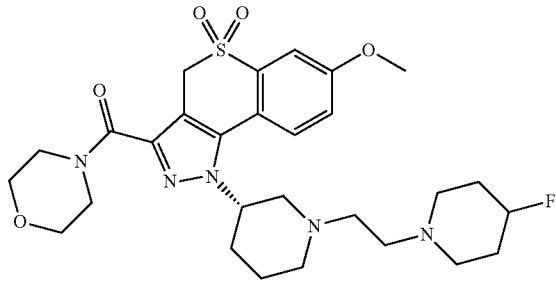 [SMILES: COc1ccc2c(c1)S(=O)(=O)Cc1c(C(=O)N3CCOCC3)nn([C@H]3CCCN(CCN4CCC(F)CC4)C3)c1-2]

Obtained from enantiomer B of 7-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 75 mg of the title compound as a white foam. $^1$H NMR (DMSO-$d_6$, 300 MHz): δ 7.79 (d, J = 8.7 Hz, 1H), 7.47 (dt, J = 8.6, 2.7 Hz, 2H), 5.05-4.80 (m, 1H), 4.74 (d, J = 12.0 Hz, 3H), 4.56 (s, 1H), 3.93 (s, 5H), 3.65 (s, 6H), 3.25-2.98 (m, 3H), 2.90 (d, J = 10.7 Hz, 1H), 2.38 (m, 4H), 2.17-1.51 (m, 11H). MS (ESI+): 576.5. HPLC (max plot) 68.7%; Rt 2.03 min Example 453: Enantiomer B of 8-methoxy-3-(morpholin-4-ylcarbonyl)-1-[1-(2-morpholin-4-ylethyl)piperidin-3-yl]-1,4-dihydrothiochromeno[4,3-c]pyrazole 5,5-dioxide

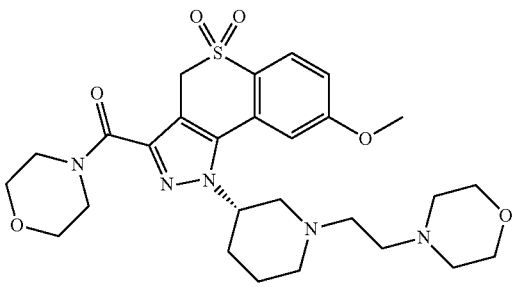

Obtained from enantiomer B of 8-methoxy-1-[1-(2-chloroethyl)piperidin-3-yl]-3-(morpholin-4-ylcarbonyl)-1,4-dihydrothiochromeno[4,3-c]pyrazole 5,5-dioxide to give 23 mg of the title compound as an orange foam. $^1$H NMR (DMSO-$d_6$, 300 MHz): δ 7.98 (d, J = 8.7 Hz, 1H), 7.35-7.16 (m, 2H), 4.74 (m, 3H), 3.95 (s, 3H), 3.91 (m, 2H), 3.65 (m, 5H), 3.57-3.42 (m, 4H), 3.30-3.23 (m, 2H), 2.92 (m, 2H), 2.44-2.24 (m, 6H), 2.20-1.87 (m, 4H), 1.73 (m, 3H). MS (ESI+): 560.3. HPLC (max plot) 66.6%; Rt 1.81 min Example 490: Enantiomer B of 3-(morpholin-4-ylcarbonyl)-1-[1-(2-morpholin-4-ylethyl)piperidin-3-yl]-7-(trifluoromethoxy)-1,4-dihydrothiochromeno[4,3-c]pyrazole 5,5-dioxide

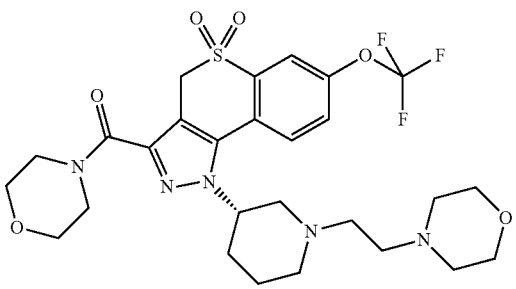 [SMILES: O=C(c1nn([C@H]2CCCN(CCN3CCOCC3)C2)c2c1CS(=O)(=O)c1cc(OC(F)(F)F)ccc1-2)N1CCOCC1]

Obtained from enantiomer B of 7-(trifluoromethoxy)-1-[1-(2-chloroethyl)piperidin-3-yl]-3-(morpholin-4-ylcarbonyl)-1,4-dihydrothiochromeno[4,3-c]pyrazole 5,5-dioxide to give 121 mg of the title compound as a white foam. $^1$H NMR (DMSO-$d_6$, 300 MHz): δ 8.04-7.92 (m, 3H), 4.90 (s, 2H), 4.86-4.70 (m, 1H), 3.98-3.84 (m, 2H), 3.75-3.58 (m, 6H), 3.58-3.42 (m, 4H), 3.29-3.16 (m, 1H), 2.95-2.84 (m, 1H), 2.46-2.23 (m, 7H), 2.20-1.57 (m, 6H). MS (ESI+): 614.3. HPLC (max plot) 99.9%; Rt 5.01 min Example 353: Enantiomer A of 6-fluoro-3-(morpholin-4-ylcarbonyl)-1-[1-(tetrahydro-2H-pyran-4-yl)pyrrolidin-3-yl]-1,4-dihydrothiochromeno[4,3-c]pyrazole 5,5-dioxide hydrochloride salt

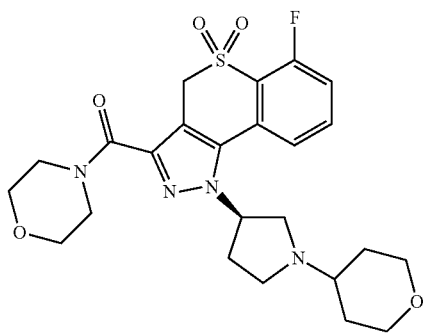 [SMILES: O=C(c1nn([C@@H]2CCN(C3CCOCC3)C2)c2c1CS(=O)(=O)c1c(F)cccc1-2)N1CCOCC1]

Obtained from enantiomer A of 6-fluoro-3-(morpholin-4-ylcarbonyl)-1-pyrrolidin-3-yl-1,4-dihydrothio chromeno[4,3-c]pyrazole 5,5-dioxide to give 217 mg (81%) of the title compound as a pink solid. $^1$H NMR (DMSO-$d_6$, 300 MHz): δ 11.86-11.76 (m, 1H), 7.99-7.90 (m, 1H), 7.78-7.72 (m, 1H), 7.66-7.57 (m, 1H), 5.79-5.66 (m, 1H), 4.96-4.89 (m, 2H), 4.24-4.12 (m, 1H), 4.04-3.87 (m, 4H), 3.68-3.56 (m, 8H), 3.37-3.23 (m, 4H), 2.82-2.70 (m, 2H), 2.13-1.71 (m, 4H). MS (ESI+): 505.33. HPLC (max plot) 98.2%; Rt 2.27 min. HPLC (Chiralcel OJ-H, MeOH/01%DEA, max plot): Rt 5.49 min. [α]$^{25}$ D +12.53 (c 1.1, EtOH)

Example 354: Enantiomer B of 6-fluoro-3-(morpholin-4-ylcarbonyl)-1-{1-[2-(tetrahydro-2H-pyran-4-yl)ethyl]pyrrolidin-3-yl}-1,4-dihydrothiochromeno[4,3-c]pyrazole 5,5-dioxide hydrochloride salt

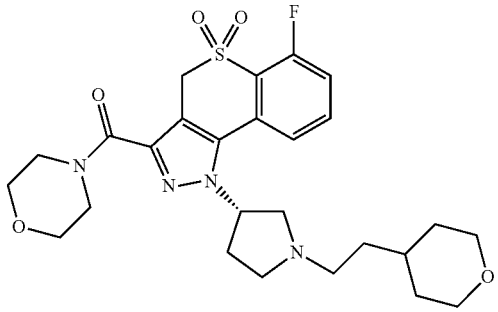 [SMILES: O=C(c1nn([C@H]2CCN(CCC3CCOCC3)C2)c2c1CS(=O)(=O)c1c(F)cccc1-2)N1CCOCC1]

Obtained from enantiomer B of 6-fluoro-3-(morpholin-4-ylcarbonyl)-1-pyrrolidin-3-yl-1,4-dihydrothio chromeno[4,3-c]pyrazole 5,5-dioxide to give 210 mg (85%) of the title compound as a pink powder. $^1$H NMR (DMSO-$d_6$, 300 MHz): δ 11.48-11.36 (m, 1H), 7.99-7.89 (m, 1H), 7.77-7.71 (m, 1H), 7.65-7.58 (t, J = 7.5 Hz, 1H), 5.82-5.68 (m, 1H), 4.94-4.89 (m, 2H), 4.03-3.80 (m, 4H), 3.67-3.59 (m, 8H), 3.39-3.21 (m, 4H), 2.86-2.56 (m, 3H), 1.79-1.51 (m, 6H), 1.27-1.12 (m, 2H). MS (ESI+): 533.4. HPLC (max plot) 97.5%; Rt 2.55 min. [α]$^{25}$ D– 13.18 (c 1.56, EtOH). HPLC (Chiralcel OJ-H, MeOH/0.1% DEA, max plot): 98.94%; Rt 9.01 min.

Example 355: Enantiomer B of 6-fluoro-3-(morpholin-4-ylcarbonyl)-1-[1-(tetrahydro-2H-pyran-4-yl)pyrrolidin-3-yl]-1,4-dihydrothiochromeno[4,3-c]pyrazole 5,5-dioxide hydrochloride salt

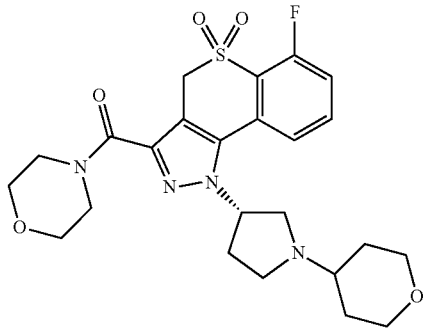 [SMILES: O=C(c1nn([C@H]2CCN(C3CCOCC3)C2)c2c1CS(=O)(=O)c1c(F)cccc1-2)N1CCOCC1]

Obtained from enantiomer B of 6-fluoro-3-(morpholin-4-ylcarbonyl)-1-pyrrolidin-3-yl-1,4-dihydrothio chromeno[4,3-c]pyrazole 5,5-dioxide to give 178 mg (72%) of the title compound as a white powder. $^1$H NMR (DMSO-$d_6$, 300 MHz): δ 11.86-11.76 (m, 1H), 7.99-7.90 (m, 1H), 7.78-7.72 (m, 1H), 7.66-7.57 (m, 1H), 5.79-5.66 (m, 1H), 4.96-4.89 (m, 2H), 4.24-4.12 (m, 1H), 4.04-3.87 (m, 4H), 3.68-3.56 (m, 8H), 3.37-3.23 (m, 4H), 2.82-2.70 (m, 2H), 2.13-1.71 (m, 4H). MS (ESI+): 505.4. HPLC (max plot) 97.9%; Rt 2.31 min. HPLC (Chiralcel OJ-H, MeOH/0.1% DEA, max plot): 98.21%; Rt 5.96 min. [α]$^{25}$ D– 13.78 (c 1.09, EtOH).

Example 356: Enantiomer A of 6-fluoro-3-(morpholin-4-ylcarbonyl)-1-{1-[2-(tetrahydro-2H-pyran-4-yl)ethyl]pyrrolidin-3-yl}-1,4-dihydrothiochromeno[4,3-c]pyrazole 5,5-dioxide hydrochloride salt

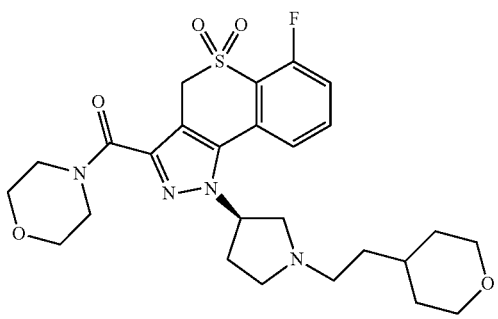 [SMILES: O=C(c1nn([C@@H]2CCN(CCC3CCOCC3)C2)c2c1CS(=O)(=O)c1c(F)cccc1-2)N1CCOCC1]

Obtained from enantiomer A of 6-fluoro-3-(morpholin-4-ylcarbonyl)-1-pyrrolidin-3-yl-1,4-dihydrothio chromeno[4,3-c]pyrazole 5,5-dioxide to give 230 mg (86%) of the title compound as a pink solid. $^1$H NMR (DMSO-$d_6$, 300 MHz): δ 11.48-11.36 (m, 1H), 7.99-7.89 (m, 1H), 7.77-7.71 (m, 1H), 7.65-7.58 (t, J = 7.5 Hz, 1H), 5.82-5.68 (m, 1H), 4.94-4.89 (m, 1H), 4.03-3.80 (m, 4H), 3.67-3.59 (m, 8H), 3.39-3.21 (m, 4H), 2.86-2.56 (m, 3H), 1.79-1.51 (m, 6H), 1.27-1.12 (m, 2H). MS (ESI+): 533.43. HPLC (max plot) 96.4%; Rt 2.51 min. HPLC (Chiralcel OJ-H, MeOH/01%DEA, max plot): Rt 11.20 min. [α]$^{25}$ D +12.77 (c 1.38, EtOH).

Example 343: Enantiomer A of 6-fluoro-3-(morpholin-4-ylcarbonyl)-1-{1-[2-(tetrahydro-2H-pyran-4-yl)ethyl]piperidin-3-yl}-1,4-dihydrothiochromeno[4,3-c]pyrazole 5,5-dioxide hydrochloride salt

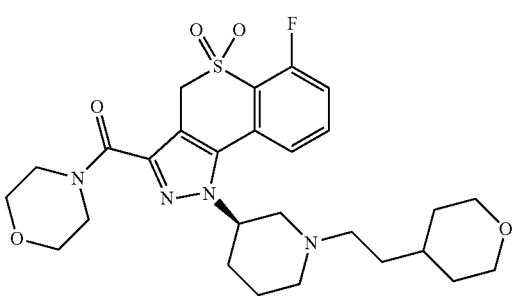

Obtained from enantiomer A of 6-fluoro-3-(morpholin-4-ylcarbonyl)-1-[piperidin-3-yl]-1,4-dihydrothiochromeno[4,3-c]pyrazole 5,5-dioxide to give 167 mg of the title compound as an off white solid. $^1$H NMR (DMSO-$d_6$, 300 MHz): δ 10.78 (bs, 1H), 7.96-7.84 (m, 2H), 7.64-7.58 (m, 1H), 5.32 (bs, 1H), 4.91 (s, 2H), 3.84-3.79 (m, 5H), 3.68-3.57 (m, 7H), 3.30-3.16 (m, 5H), 3.01-2.99 (m, 1H), 2.23-2.03 (m, 4H), 1.69-1.35 (m, 5H), 1.23-1.15 (m, 2H). MS (ESI+): 547.4. HPLC (max plot) 97.7%; Rt 2.61 min.

Example 344: Enantiomer B of 6-fluoro-3-(morpholin-4-ylcarbonyl)-1-{1-[2-(tetrahydro-2H-pyran-4-yl)ethyl]piperidin-3-yl}-1,4-dihydrothiochromeno[4,3-c]pyrazole 5,5-dioxide

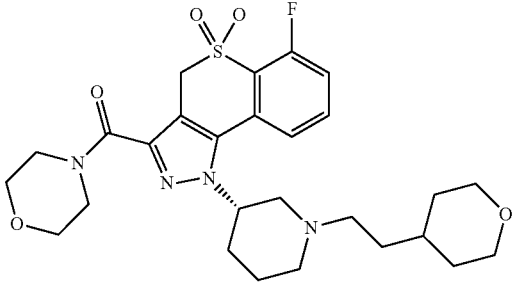

Obtained from enantiomer B of 6-fluoro-3-(morpholin-4-ylcarbonyl)-1-[piperidin-3-yl]-1,4-dihydrothiochromeno[4,3-c]pyrazole 5,5-dioxide to give 152 mg of the title compound as a white solid. $^1$H NMR (DMSO-$d_6$, 300 MHz): δ 10.75 (bs, 1H), 7.96-7.84 (m, 2H), 7.64-7.58 (m, 1H), 5.32 (bs, 1H), 4.91 (s, 2H), 3.83-3.79 (m, 5H), 3.68-3.57 (m, 7H), 3.30-3.13 (m, 5H), 3.01-2.99 (m, 1H), 2.23-2.03 (m, 4H), 1.69-1.54 (m, 5H), 1.23-1.12 (m, 2H). MS (ESI+): 547.4. HPLC (max plot) 100.0%; Rt 2.63 min Procedure AJ Example 360

1-{3-[2-(1H-Imidazol-1-yl)ethoxy]phenyl}-3-(morpholin-4-ylcarbonyl)-1,4-dihydrothiochromeno[4,3-c]pyrazole 5,5-dioxide

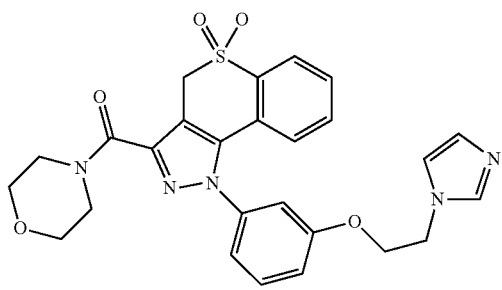

To a suspension of 3-[3-(morpholin-4-ylcarbonyl)-5,5-dioxidothiochromeno[4,3-c]pyrazol-1(4H)-yl]phenol (206.5 mg; 0.49 mmol; 1 eq.), potassium carbonate (401.6 mg; 2.91 mmol; 5.99 eq.) and sodium iodide (11.7 mg; 0.08 mmol; 0.16 eq.) in DMF (4 ml) is added N-(2-chloroethyl)-imidazole hydrochloride (158.4 mg; 0.95 mmol; 1.95 eq.). The suspension is stirred at 80° C. 2 days then in the microwave at 120° C. for 30 min. The reaction mixture is diluted with water and the product is extracted with EtOAc. The combined organic layer is washed with water then with brine, dried over MgSO4 and the solvent removed under vacuum to afford a brown residue. After purification by flask chromatography (silica; DCM/MeOH 98/2 to 0/100), it affords the title compound as a fluffy yellow powder. 1H NMR (DMSO-d6): δ 8.07-7.98 (m, 1H), 7.73-7.55 (m, 3H), 7.55-7.44 (m, 1H), 7.28-7.13 (m, 3H), 7.09-7.00 (m, 1H), 6.93-6.83 (m, 2H), 4.10 (s, 2H), 4.44-4.22 (m, 4H), 4.00-3.87 (m, 2H), 3.75-3.55 (m, 6H). HPLC (max plot) 93.5%; Rt 2.48 min. MS (ESI+): 520.4.

Example 340

3-(Morpholin-4-ylcarbonyl)-1-{3-[2-(1H-pyrazol-1-yl)ethoxy]phenyl}-1,4-dihydrothiochromeno[4,3-c]pyrazole 5,5-dioxide

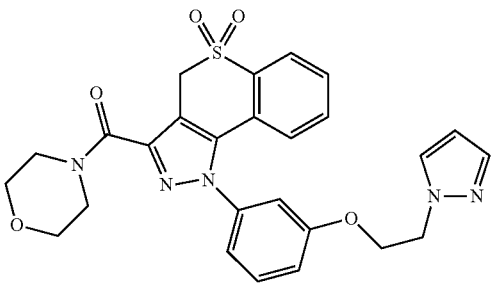 [SMILES: O=C(c1nn(-c2cccc(OCCn3cccn3)c2)c2c1CS(=O)(=O)c1ccccc1-2)N1CCOCC1]

Following the protocol outlined in procedure AJ, 3-(morpholin-4-ylcarbonyl)-1-{3-[2-(1H-pyrazol-1-yl)ethoxy]phenyl}-1,4-dihydrothiochromeno[4,3-c]pyrazole 5,5-dioxide is obtained from 3-[3-(morpholin-4-ylcarbonyl)-5,5-dioxidothiochromeno[4,3-c]pyrazol-1(4H)-yl]phenol and 1-(2-bromo ethyl)-1H-pyrazole to afford the title compound as a white powder. 1H NMR (DMSO-d6) δ 8.07-7.97 (m, 1H), 7.82-7.75 (m, 1H), 7.70-7.54 (m, 2H), 7.54-7.46 (m, 1H), 7.46-7.41 (m, 1H), 7.22-7.14 (m, 1H), 7.14-7.08 (m, 1H), 7.08-7.00 (m, 1H), 6.92-6.84 (m, 1H), 6.26-6.18 (m, 1H), 4.90 (s, 2H), 4.55-4.45 (m, 2H), 4.45-4.34 (m, 2H), 4.01-3.88 (m, 2H), 3.76-3.56 (m, 6H). HPLC (max plot) 96.2%; Rt 4.14 min. MS (ESI+): 520.3.

Example 341

1-[3-(2-Methoxyethoxy)phenyl]-3-(morpholin-4-ylcarbonyl)-1,4-dihydrothiochromeno[4,3-c]pyrazole 5,5-dioxide

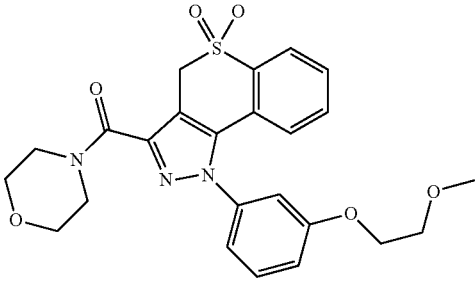

Following the protocol outlined in procedure AJ, 1-[3-(2-methoxyethoxy)phenyl]-3-(morpholin-4-ylcarbonyl)-1,4-dihydrothiochromeno[4,3-c]pyrazole 5,5-dioxide is obtained from 3-[3-(morpholin-4-ylcarbonyl)-5,5-dioxidothiochromeno[4,3-c]pyrazol-1(4H)-yl]phenol and 2-bromoethyl methylether to afford the title compound as a white solid. 1H NMR (DMSO-d6) δ 8.09-7.96 (m, 1H), 7.71-7.56 (m, 2H), 7.56-7.44 (m, 1H), 7.29-7.11 (m, 2H), 7.11-6.97 (m, 1H), 6.97-6.82 (m, 1H), 4.90 (s, 2H), 4.25-4.08 (m, 2H), 4.05-3.87 (m, 2H), 3.79-3.53 (m, 8H), 3.29 (s, 3H). HPLC (max plot) 99.5%; Rt 3.53 min. MS (ESI+): 484.3. m.p.=[142-144]° C. on Optimelt.

Procedure AK

Example 168

1-{4-[4-Methoxypiperidin-1-yl)methyl]phenyl}-3-(morpholin-4-ylcarbonyl)-1,4-dihydrothiochromeno[4,3-c]pyrazole 5,5-dioxide

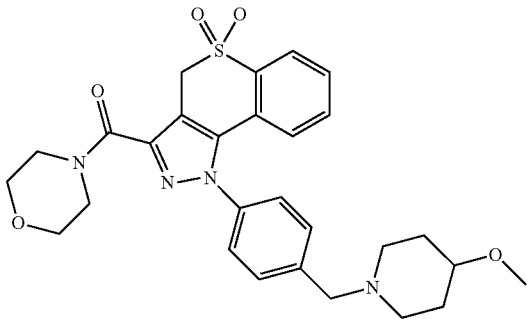

To a solution of 4-[3-(morpholin-4-ylcarbonyl)-5,5-dioxidothiochromeno[4,3-c]pyrazol-1 (4H)-yl]benzyl methanesulfonate (230 mg; 0.44 mmol; 1 eq.) in DMF (10 mL) are added K$_2$CO$_3$ (184 mg; 1.33 mmol; 3 eq.) and 4-methoxypiperidine (102 mg; 0.89 mmol; 2 eq.). The reaction mixture is stirred at 85° C. for 30 min then diluted with water, extracted with EtOAc, washed dEtOAc, washed with brine and dried over MgSO$_4$. The solvent is removed and the residue is purified by MD-Autoprep to afford the title compound as a white solid. 1H NMR (DMSO-d6) δ 8.07-8.04 (m, 1H), 7.70-7.50 (m, 6H), 6.88-6.85 (m, 1H), 4.94 (s, 2H), 4.01-3.98 (m, 2H), 3.71-3.62 (m, 8H), 3.27 (s, 3H), 3.27-3.22 (m, 1H), 2.76-2.70 (m, 2H), 2.23-2.14 (m, 2H), 1.92-1.84 (m, 2H), 1.55-1.44 (m, 2H). HPLC (max plot) 100%; Rt 2.23 min. MS (ESI+): 537.0.

Compounds described below are obtained following protocol outlined in procedure AK Example 167: 1-{4-[(4-Fluoropiperidin-1-yl)methyl]phenyl}-3-(morpholin-4-ylcarbonyl)-1,4-dihydrothiochromeno[4,3-c]pyrazole 5,5-dioxide

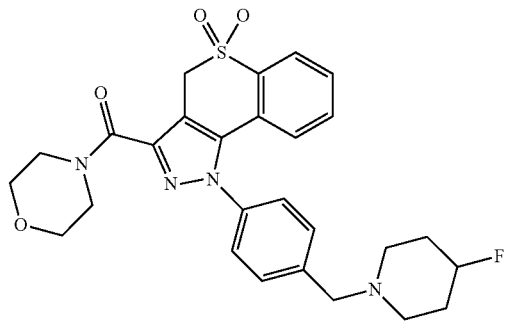

110 mg of the title compound as a white powder. HPLC (max plot) 99.3%; Rt 2.27 min. MD (ESI+): 524.8.

Example 169: 3-(Morpholin-4-ylcarbonyl)-1-[4-(piperidin-1-ylmethyl)phenyl]-1,4-dihydrothiochromeno[4,3-c]pyrazole 5,5-dioxide

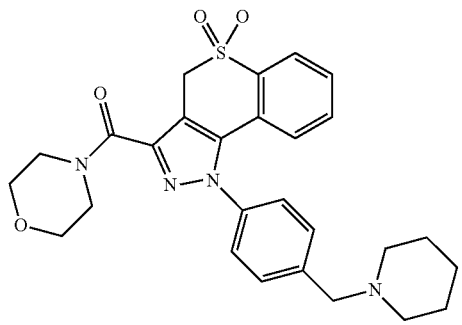

42 mg title compound as a white solid. ¹H NMR (DMSO-d$_6$) δ 8.04-8.01 (m, 1H), 7.66-7.46 (m, 6H), 6.85-6.82 (m, 1H), 4.91 (s, 2H), 3.98-3.95 (m, 2H), 3.68-3.60 (m, 6H), 3.55 (s, 2H), 2.41-2.35 (m, 4H), 1.57-1.38 (m, 6H). HPLC (max plot) 100.0%; Rt 2.25 min; MS (ESI+): 507.1.

Example 226: N,N-Dimethyl-1-{4-[3-(morpholin-4-ylcarbonyl)-5,5-dioxidothiochromeno[4,3-c]pyrazol-1(4H)-yl]phenyl}methanamine

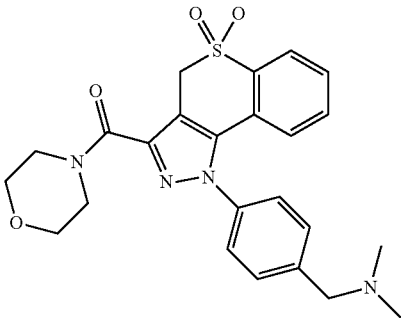

18 mg of the title compound as a white solid. 1H NMR (DMSO-d6) δ 8.04-8.01 (m, 1H), 7.66-7.47 (m, 6H), 6.85-6.82 (m, 1H), 4.91 (s, 2H), 3.96-3.94 (m, 2H), 3.68-3.62 (m, 6H), 3.51 (s, 2H), 2.20 (s, 6H). HPLC (max plot) 99.1%; Rt 1.90 min. MS (ESI+): 466.8.

Example 227: 1-{4-[(3-(Morpholin-4-ylcarbonyl)-5,5-dioxidothiochromeno[4,3-c]pyrazol-1(4H)-yl]benzyl}pyrrolidin-3-ol

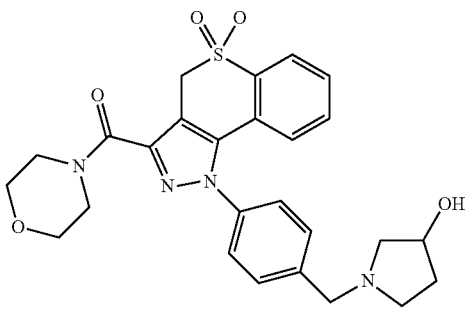

20 mg of the title compound as a white solid. 1H NMR (DMSO-d6) δ 8.04-8.01 (m, 1H), 7.66-7.46 (m, 6H), 6.85-6.82 (m, 1H), 4.91 (s, 2H), 4.74-4.72 (m, 1H), 4.25-4.19 (m, 1H), 3.97-3.94 (m, 2H), 3.69-3.62 (m, 8H), 2.75-2.70 (m, 1H), 2.64-2.59 (m, 1H), 2.47-2.43 (m, 1H), 2.38-2.34 (m, 1H), 2.08-1.99 (m, 1H), 1.59-1.54 (m, 1H). HPLC (max plot) 99.2%; Rt 1.85 min; MS (ESI+): 508.8.

Example 228: 3-(Morpholin-4-ylcarbonyl)-1-[4-(pyrrolidin-1-ylmethyl)phenyl]-1,4-dihydrothiochromeno[4,3-c]pyrazole 5,5-dioxide

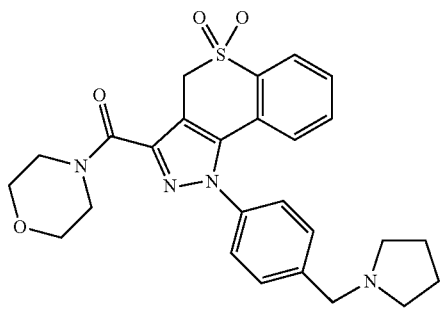

$^1$H NMR (DMSO-$d_6$) δ 8.04-8.01 (m, 1H), 7.66-7.46 (m, 6H), 6.86-6.83 (m, 1H), 4.91 (s, 2H), 3.96-3.94 (m, 2H), 3.70-3.60 (m, 8H), 1.75-1.71 (m, 4H), 2.50-2.47 (m, 4H). HPLC (max plot) 99.5%; Rt 2.01 min. MS (ESI+): 492.8.

Example 229: 1-(4-{[3-(Methylsulfonyl)pyrrolidin-1-yl]methyl}phenyl)-3-(morpholin-4-ylcarbonyl)-1,4-dihydrothiochromeno[4,3-c]pyrazole 5,5-dioxide

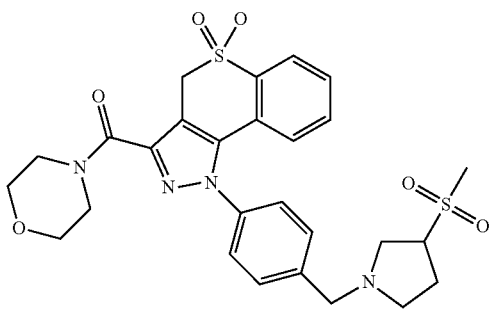

32 mg of the title compound as a white solid. $^1$H NMR (DMSO-$d_6$) δ 8.08-7.97 (m, 1H), 7.71-7.44 (m, 6H), 6.88-6.78 (m, 1H), 4.91 (s, 2H), 4.05-3.90 (m, 2H), 3.90-3.56 (m, 9H), 2.95 (s, 3H), 2.91-2.78 (m, 2H), 2.74-2.55 (m, 2H), 2.23-2.04 (m, 2H). HPLC (max plot) 95.5%; Rt 2.55 min; MS (ESI+): 571.0.

Example 233: 1-(4-{[3-(3-Methylbutoxy)pyrrolidin-1-yl]methyl}phenyl)-3-(morpholin-4-ylcarbonyl)-1,4-dihydrothiochromeno[4,3-c]pyrazole 5,5-dioxide

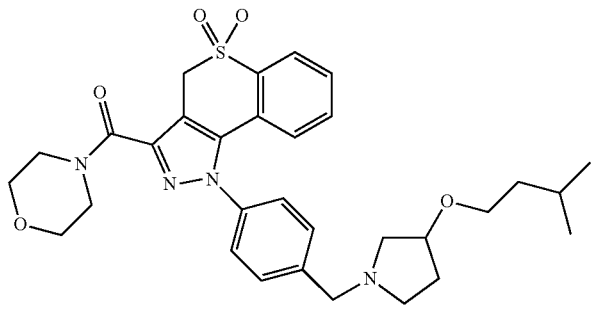

82 mg of the title compound as an orange powder. $^1$H NMR (DMSO-d$_6$) δ 8.11-7.96 (m, 1H), 7.72-7.39 (m, 6H), 6.92-6.77 (m, 1H), 4.91 (s, 2H), 4.12-3.85 (m, 3H), 3.85-3.53 (m, 8H), 3.47-3.21 (m, 2H), 2.87-2.33 (m, 4H), 2.15-1.92 (m, 1H), 1.80-1.52 (m, 2H), 1.36 (q, J = 6.6 Hz, 2H), 0.86 (dd, J = 6.6; 1.8 Hz, 6H). HPLC (max plot) 99%; Rt 3.78 min; MS (ESI+): 578.9; m.p. = [120-123]° C. on Optimelt;

Example 267: 1-{4-[(3-Methoxypyrrolidin-1-yl)methyl]phenyl}-3-(morpholin-4-ylcarbonyl)-1,4-dihydrothiochromeno[4,3-c]pyrazole 5,5-dioxide

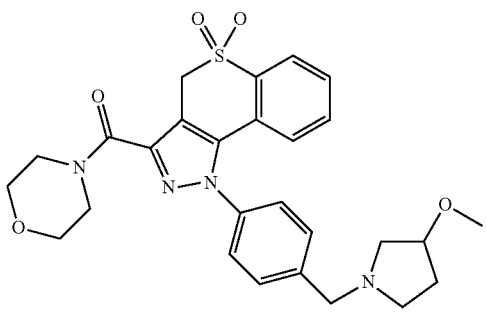

264 mg of the title compound as a white powder. $^1$H NMR (DMSO-d$_6$) δ 8.08-7.97 (m, 1H), 7.70-7.43 (m, 6H), 6.90-6.79 (m, 1H), 4.90 (s, 2H), 4.05-3.84 (m, 3H), 3.80-3.54 (m, 8H), 3.17 (s, 3H), 2.79-2.67 (m, 1H), 2.67-2.54 (m, 1H), 2.54-2.39 (m, 2H), 2.10-1.93 (m, 1H), 1.78-1.61 (m, 1H). HPLC (max plot) 99.9%; Rt 2.61 min. MS (ESI+): 522.8.

Example 268: 1-{4-[(4,4-Difluoropiperidin-1-yl)methyl]phenyl}-3-(morpholin-4-ylcarbonyl)-1,4-dihydrothiochromeno[4,3-c]pyrazole 5,5-dioxide

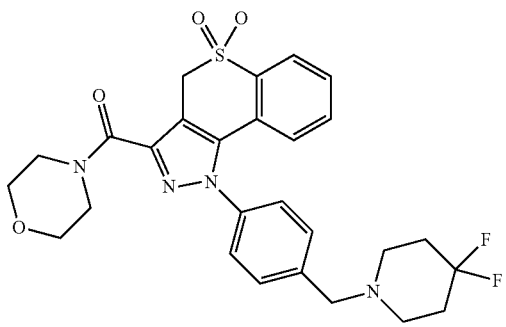

426 mg (83%) of the title compound as a white powder. $^1$H NMR (DMSO-d$_6$) δ 8.08-7.97 (m, 1H), 7.70-7.44 (m, 6H), 6.87-6.78 (m, 1H), 4.91 (s, 2H), 4.03-3.89 (m, 2H), 3.76-3.56 (m, 8H), 2.62-2.51 (m, 4H), 2.10-1.84 (m, 4H). HPLC (max plot) 100%; Rt 2.82 min. MS (ESI+): 542.8.

Example 269: 1-(4-{[(3,3-Difluoroazetidin-1-yl)methyl]phenyl}-3-(morpholin-4-ylcarbonyl)-1,4-dihydrothiochromeno[4,3-c]pyrazole 5,5-dioxide

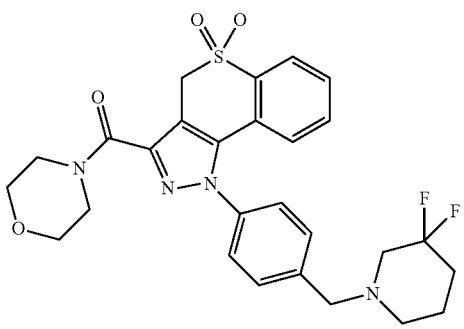

455 mg of the title compound as a white powder. HPLC (max plot) 99.3%; Rt 2.74 min; MS (ESI+): 542.8. CHN analysis: [C27H28N4O4SF2] Corrected: C58.79%, H5.30%, N10.16%; Found: C58.93%, H5.35%, N10.11%.

Example 271: 1-{4-[(3,3-Difluoroazetidin-1-yl)methyl]phenyl}-3-(morpholin-4-ylcarbonyl)-1,4-dihydrothiochromeno[4,3-c]pyrazole 5,5-dioxide

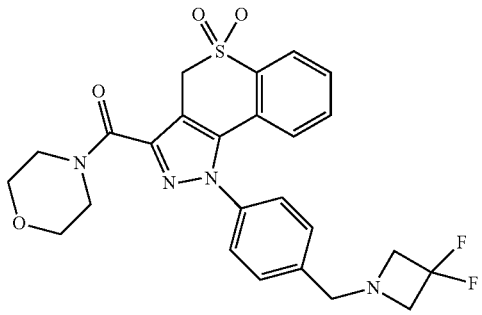

276 mg of the title compound as a white powder. $^1$H NMR (DMSO-d$_6$) δ 8.08-7.97 (m, 1H), 7.69-7.44 (m, 6H), 6.88-6.78 (m, 1H), 4.91 (s, 2H), 4.05-3.91 (m, 2H), 3.87 (bs, 2H), 3.78-3.55 (m, 10H). HPLC (max plot) 97.8%; Rt 2.15 min. MS (ESI+): 514.8. m.p. = [218-220]° C. on Optimelt.

Example 272: 1-{4-[(3-Methoxyazetidin-1-yl)methyl]phenyl}-3-(morpholin-4-ylcarbonyl)-1,4-dihydrothiochromeno[4,3-c]pyrazole 5,5-dioxide

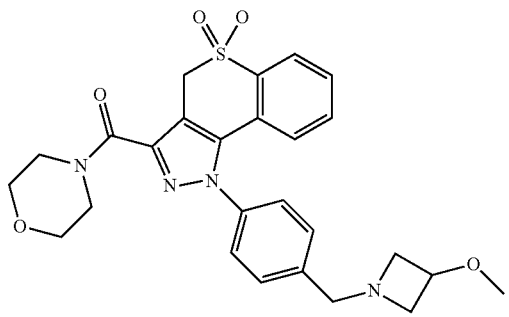

317 mg (81%) of the title compound as an off-white powder. 1H NMR (DMSO-d6) δ 8.06-8.00 (m, 1H), 7.68-7.43 (m, 6H), 6.86-6.79 (m, 1H), 4.90 (s, 2H), 4.07-3.90 (m, 3H), 3.75-3.58 (m, 8H), 3.58-3.49 (m, 2H), 3.17 (s, 3H), 2.98-2.87 (m, 2H). HPLC (max plot) 97.6%; Rt 2.13 min. MS (ESI+): 508.8.

Example 278: 1-[4-(Methoxymethyl)phenyl]-3-(morpholin-4-ylcarbonyl)-1,4-dihydrothiochromeno[4,3-c]pyrazole 5,5-dioxide

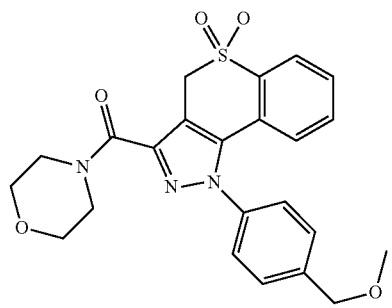

93.9 mg of the title compound as a white powder. $^1$H NMR (DMSO-d$_6$) δ 8.06-7.98 (m, 1H), 7.69-7.48 (m, 6H), 6.92-6.82 (m, 1H), 4.91 (s, 2H), 4.55 (s, 2H), 4.04-4.89 (m, 2H), 3.76-3.56 (m, 6H), 3.38 (s, 3H). HPLC (max plot) 99.7%; Rt 3.36 min. MS (ESI+): 454.1. CHN analysis: [C23H23N3O5S] Corrected: C60.91%, H5.11%, N9.27%; Found: C60.30%, H5.06%, N9.22%.

Example 234: 1-{3-[(4-Methoxypiperidin-1-yl)methyl]phenyl}-3-(morpholin-4-ylcarbonyl)-1,4-dihydrothiochromeno[4,3-c]pyrazole 5,5-dioxide

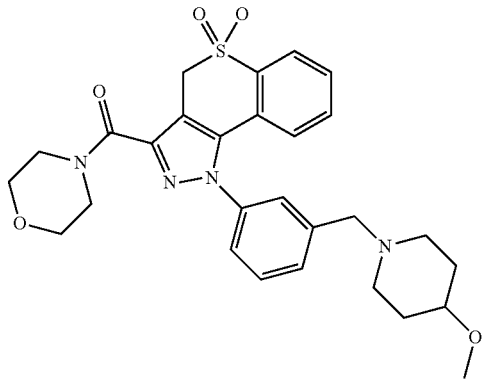

116 mg of the title compound as a white powder. $^1$H NMR (DMSO-d$_6$) δ 8.07-7.98 (m, 1H), 7.70-7.45 (m, 5H), 7.38-7.31 (m, 1H), 6.86-6.78 (m, 1H), 4.91 (s, 2H), 4.03-3.86 (m, 2H), 3.77-3.56 (m, 6H), 3.51 (bs, 2H), 3.19 (s, 3H), 3.18-3.04 (m, 1H), 2.70-2.53 (m, 2H), 2.14-1.96 (m, 2H), 1.81-1.65 (m, 2H), 1.19-1.39 (m, 2H). HPLC (max plot) 98.6%; Rt 2.23 min. MS (ESI+): 537.0.

Example 236: 3-(Morpholin-4-ylcarbonyl)-1-[3-(thiomorpholin-4-ylmethyl)phenyl]-1,4-dihydrothiochromeno[4,3-c]pyrazole 5,5-dioxide

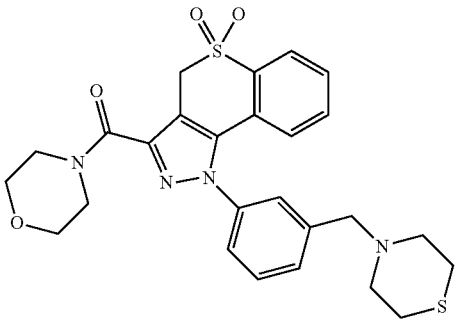

96 mg of the title compound as a white solid. $^1$H NMR (DMSO-d$_6$) δ 8.08-7.98 (m, 1H), 7.71-7.45 (m, 5H), 7.40-7.30 (m, 1H), 6.88-6.75 (m, 1H), 4.91 (s, 2H), 4.04-3.85 (m, 2H), 3.80-3.48 (m, 8H), 2.67-2.41 (m, 8H). HPLC (max plot) 98.3%; Rt 2.24 min. MS (ESI+): 524.7.

Example 243: 1-(3-{[3-(Methylsulfonyl)pyrrolidin-1-yl]methyl}phenyl)-3-(morpholin-4-ylcarbonyl)-1,4-dihydrothiochromeno[4,3-c]pyrazole 5,5-dioxide

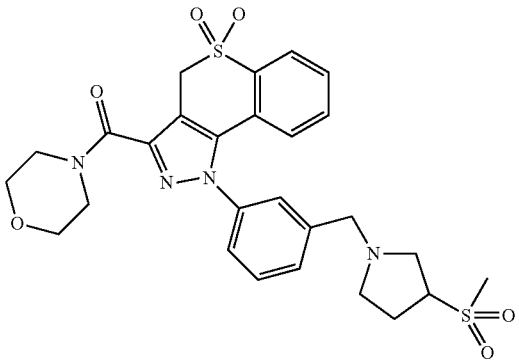

51 mg of the title compound as a white powder. $^1$H NMR (DMSO-d$_6$) δ 8.08-7.97 (m, 1H), 7.71-7.53 (m, 4H), 7.53-7.45 (m, 1H), 7.45-7.37 (m, 1H), 6.91-6.78 (m, 1H), 4.91 (s, 2H), 4.05-3.86 (m, 2H), 3.82-3.55 (m, 9H), 2.86 (s, 3H), 2.84-2.70 (m, 2H), 2.62-2.47 (m, 2H), 2.16-1.94 (m, 2H). HPLC (max plot) 96.8%; Rt 2.16 min. MS (ESI+): 571.0.

Example 244: 1-{3-[(3,3-Difluoropiperidin-1-yl)methyl]phenyl}-3-(morpholin-4-ylcarbonyl)-1,4-dihydrothiochromeno[4,3-c]pyrazole 5,5-dioxide

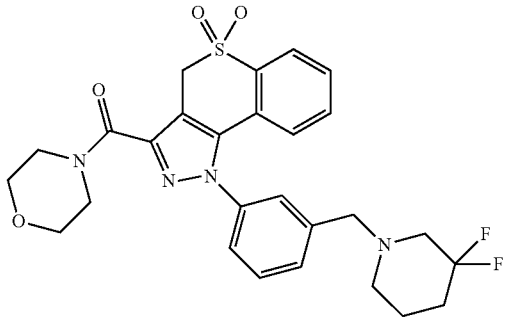

11 mg of the title compound as an off-white powder. $^1$H NMR (DMSO-d$_6$) δ 8.10-7.95 (m, 1H), 7.72-7.45 (m, 5H), 7.45-7.33 (m, 1H), 6.90-6.78 (m, 1H), 4.91 (s, 2H), 4.09-3.83 (m, 2H), 3.83-3.52 (m, 8H), 2.71-2.54 (m, 2H), 2.44-2.29 (m, 2H), 1.99-1.72 (m, 2H), 1.67-1.47 (m, 2H). HPLC (max plot) 96.8%; Rt 2.35 min. MS (ESI+): 543.1.

Example 245: 3-(Morpholin-4-ylcarbonyl)-1-[3-(pyrrolidin-1-ylmethyl)phenyl]-1,4-dihydrothiochromeno[4,3-c]pyrazole 5,5-dioxide

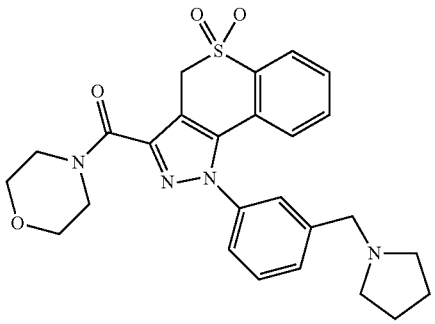

23 mg of the title compound as a white powder. $^1$H NMR (DMSO-d$_6$) δ 8.08-7.97 (m, 1H), 7.71-7.51 (m, 4H), 7.51-7.42 (m, 1H), 7.42-7.33 (m, 1H), 6.90-6.78 (m, 1H), 4.90 (s, 2H), 4.04-3.84 (m, 2H), 3.80-3.51 (m, 8H), 2.46-2.29 (m, 4H), 1.75-1.54 (m, 4H). HPLC (max plot) 96.6%; Rt 2.06 min. MS (ESI+): 493.0

Example 247: 1-{3-[(1,1-Dioxidothiomorpholin-4-yl)methyl]phenyl}-3-(morpholin-4-ylcarbonyl)-1,4-dihydrothiochromeno[4,3-c]pyrazole 5,5-dioxide

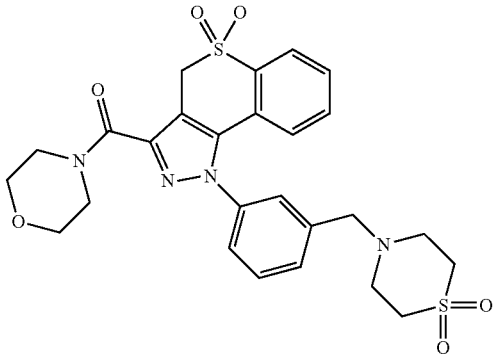

88 mg of the title compound as a white solid. ¹H NMR (DMSO-d₆) δ 8.10-7.96 (m, 1H), 7.75-7.48 (m, 5H), 7.48-7.38 (m, 1H), 6.90-6.76 (m, 1H), 4.91 (s, 2H), 4.06-3.85 (m, 2H), 3.85-3.51 (m, 8H), 3.12-3.16 (m, 4H), 3.16-2.72 (m, 4H). HPLC (max plot) 69.0%; Rt 2.81 min. MS (ESI–): 555.1.

Example 248: 1-[3-(Methoxylmethyl)phenyl]-3-(morpholin-4-ylcarbonyl)-1,4-dihydrothiochromeno[4,3-c]pyrazole 5,5-dioxide

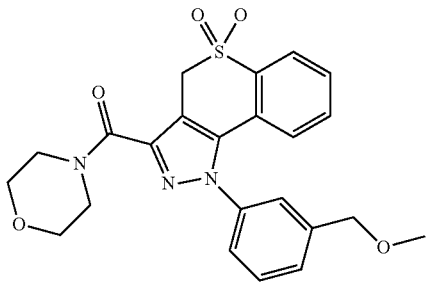

70 mg of the title compound as a white solid. 1H NMR (DMSO-d6) δ 8.09-7.95 (m, 1H), 7.74-7.52 (m, 4H), 7.52-7.40 (m, 2H), 6.89-6.79 (m, 1H), 4.91 (s, 2H), 4.51 (s, 2H), 4.03-3.86 (m, 2H), 3.77-3.53 (m, 6H), 3.29 (s, 3H). HPLC (max plot) 99.6%; Rt 3.36 min. MS (ESI+): 453.7. m.p. = [161-164]° C. on Optimelt. CHN analysis: [C23H23N3O5S] Corrected: C60.91%, H5.11%, N9.27%; Found: C60.28%, H5.08%, N8.95%.

Example 260: 1-{3-[(4,4-Difluoropiperidin-1-yl)methyl]phenyl}-3-(morpholin-4-ylcarbonyl)-1,4-dihydrothiochromeno[4,3-c]pyrazole 5,5-dioxide (hydrochloride salt)

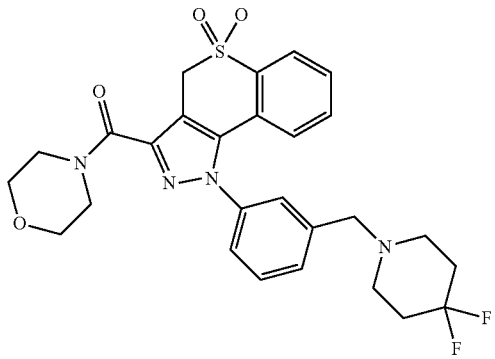

43 mg of the title compound as a yellow solid. ¹H NMR (DMSO-d₆) δ 11.27-10.92 (bs, 1H), 8.10-7.98 (m, 1H), 7.94-7.48 (m, 6H), 7.00-6.88 (m, 1H), 4.92 (s, 2H), 4.56-4.33 (m, 2H), 4.03-3.86 (m, 2H), 3.86-3.32 (m, 8H), 3.25-2.93 (m, 2H), 2.50-2.20 (m, 4H). HPLC (max plot) 94.3%; Rt 2.41 min. MS (ESI+): 542.7.

Example 261: 1-{3-[(3,3-Difluoroazetidin-1-yl)methyl]phenyl}-3-(morpholin-4-ylcarbonyl)-1,4-dihydrothiochromeno[4,3-c]pyrazole 5,5-dioxide

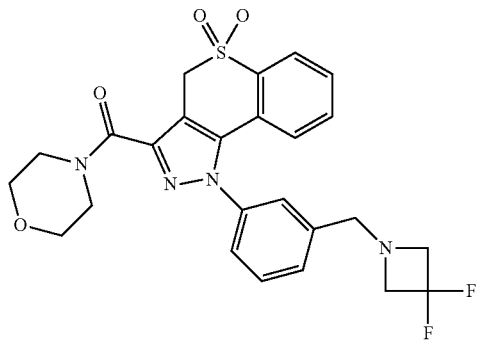

21 mg of the title compound as a white powder. ¹H NMR (DMSO-d₆) δ 8.08-7.98 (m, 1H), 7.72-7.53 (m, 4H), 7.53-7.45 (m, 1H), 7.45-7.38 (m, 1H), 6.86-6.77 (m, 1H), 4.91 (s, 2H), 4.03-3.87 (m, 2H), 3.86-3.75 (m, 2H), 3.75-3.48 (m, 10H). HPLC (max plot) 96.0%; Rt 2.20 min. MS (ESI+): 514.7.

Example 262: 1-{3-[(3-Methoxyazetidin-1-yl)methyl]phenyl}-3-(morpholin-4-ylcarbonyl)-1,4-dihydrothiochromeno[4,3-c]pyrazole 5,5-dioxide

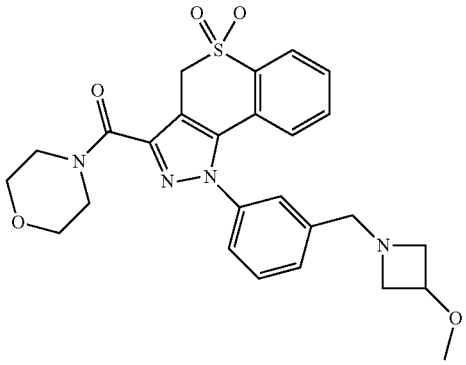

25 mg of the title compound as a yellow solid. $^1$H NMR (DMSO-d$_6$) δ 11.08-10.68 (m, 1H), 8.13-7.98 (, 1H), 7.88-7.51 (m, 6H), 6.94-6.78 (m, 1H), 4.92 (bs, 2H), 4.57-4.36 (m, 2H), 4.36-4.08 (m, 2H), 4.08-3.80 (m, 2H), 3.80-3. (m, 8H), 3.55-3.40 (m, 1H), 3.22 (s, 3H). HPLC (max plot) 96.4%; Rt 2.15 min. MS (ESI+): 508.7.

Example 266: 1-{3-[(3-Methoxypyrrolidin-1-yl)methyl]phenyl}-3-(morpholin-4-ylcarbonyl)-1,4-dihydrothiochromeno[4,3-c]pyrazole 5,5-dioxide

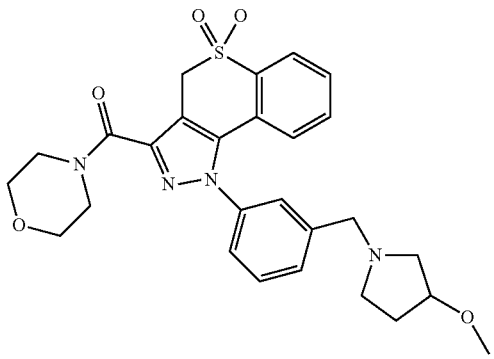

303 mg of the title compound as a yellow solid. $^1$H NMR (DMSO-d$_6$) δ 8.07-7.98 (m, 1H), 7.70-7.51 (m, 4H), 7.51-7.44 (m, 1H), 7.41-7.34 (m, 1H), 6.87-6.79 (m, 1H), 4.91 (s, 2H), 4.01-3.88 (m, 2H), 3.88-3.76 (m, 1H), 3.76-3.55 (m, 8H), 3.11 (s,3H), 2.71-2.58 (m, 1H), 2.58-2.45 (m, 1H), 2.45-2.30 (m, 2H), 2.01-1.84 (m, 1H), 1.69-1.52 (m, 1H). HPLC (max plot) 99.9%; Rt 2.13 min. MS (ESI+): 522.8.

Example 235: 1-(3-{[3-(3-Methylbutoxy)pyrrolidin-1-yl]methyl}phenyl)-3-(morpholin-4-ylcarbonyl)-1,4-dihydrothiochromeno[4,3-c]pyrazole 5,5-dioxide

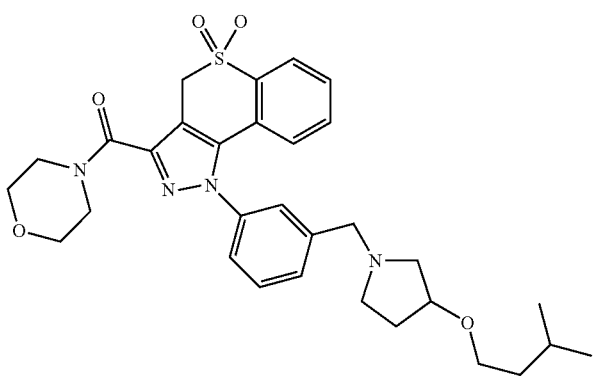

97 mg of the title compound as a yellow powder. $^1$H NMR (DMSO-d$_6$) δ 8.08-7.97 (m, 1H), 7.70-7.42 (m, 6H), 7.42-7.34 (m, 1H), 6.89-6.79 (m, 1H), 4.91 (s, 2H), 4.07-3.82 (m, 3H), 3.82-3.53 (m, 8H), 3.33-3.18 (m, 2H), 2.77-2.61 (m, 1H), 2.45-2.29 (m, 2H), 2.04-2.82 (m, 1H), 2.71-1.42 (m, 2H), 1.43-1.25 (m, 2H), 0.91-0.76 (m, 6H). HPLC (max plot) 96.2%; Rt 3.26 min. MS (ESI+): 579.1.

Example 237: 1-{3-[3-(Morpholin-4-ylcarbonyl)-5,5-dioxidothiochromeno[4,3-c]pyrazol-1(4H)-yl]benzyl}piperidin-4-ol

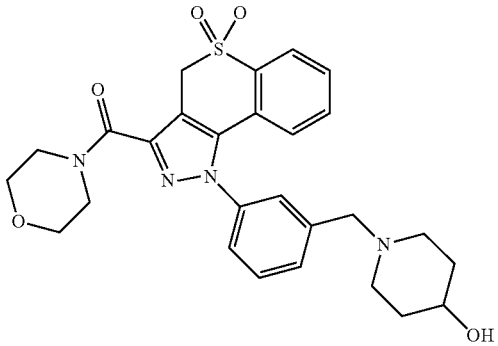

101 mg (100%) of the title compound as a yellow solid. ¹H NMR (DMSO-d₆) δ 8.08-7.97 (m, 1H), 7.74-7.43 (m, 5H), 7.41-7.29 (m, 1H), 6.90-6.76 (m, 1H), 4.91 (bs, 2H), 4.61-4.47 (m, 1H), 4.03-3.87 (m, 2H), 3.78-3.56 (m, 6H), 3.50 (bs, 2H), 3.47-3.36 (m, 1H), 2.70-2.56 (m, 2H), 2.13-1.90 (m, 2H), 1.74-1.51 (m, 2H), 1.39-1.15 (m, 2H). HPLC (max plot) 97.5%; Rt 2.46 min. m.p. = [121-130]° C. on Optimelt. MS (ESI+): 523.1.

Example 242: 1-{3-[(4-Fluoropiperidin-1-yl)methyl]phenyl}-3-(morpholin-4-ylcarbonyl)-1,4-dihydrothiochromeno[4,3-c]pyrazole 5,5-dioxide

53 mg of the title compound as a yellow solid. ¹H NMR (DMSO-d₆) δ 8.09-7.97 (m, 1H), 7.73-7.45 (m, 5H), 7.41-7.30 (m, 1H), 6.89-6.77 (m, 1H), 4.91 (s, 2H), 4.81-4.48 (m, 1H), 4.03-3.86 (m, 2H), 3.79-3.58 (m, 6H), 3.54 (s, 2H), 2.52-2.38 (m, 2H), 2.35-2.17 (m, 2H), 1.88-1.50 (m, 4H). HPLC (max plot) 97.1%; Rt 2.28 min. MS (ESI+): 525.1.

Example 291: 1-[3-(1H-imidazol-1-ylmethyl)phenyl]-3-(morpholin-4-ylcarbonyl)-1,4-dihydrothiochromeno[4,3-c]pyrazole 5,5-dioxide

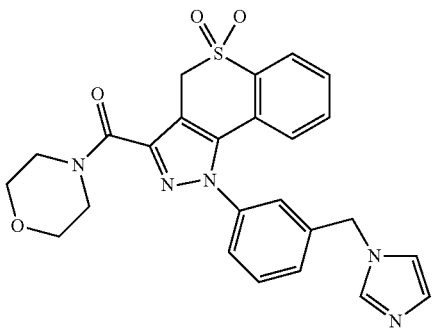

37 mg of the title compound as a white powder. ¹H NMR (DMSO-d₆) δ 8.07-7.99 (m, 1H), 7.80-7.74 (m, 1H), 7.70-7.59 (m, 2H), 7.59-7.48 (m, 3H), 7.48-7.43 (m, 1H), 7.23-7.16 (m, 1H), 6.91-6.87 (m, 1H), 6.83-6.78 (m, 1H), 5.29 (s, 2H), 4.90 (s, 2H), 3.97-3.86 (m, 2H), 3.76-3.55 (m, 6H). HPLC (max plot) 99.6%; Rt 2.13 min. MS (ESI+): 490.2.

Example 292: 3-(Morpholin-4-ylcarbonyl)-1-[3-(1H-pyrazol-1-ylmethyl)phenyl]-1,4-dihydrothiochromeno[4,3-c]pyrazole 5,5-dioxide

27 mg (11%) of the title compound as a white solid. ¹H NMR (DMSO-d₆) δ 8.06-7.98 (m, 1H), 7.87-7.81 (m, 1H), 7.69-7.41 (m, 6H), 7.39-7.33 (m, 1H), 6.86-6.77 (m, 1H), 6.28-6.22 (m, 1H), 5.44 (s, 2H), 4.89 (s, 2H), 3.98-3.83 (m, 2H), 3.76-3.54 (m, 6H). HPLC (max plot) 99.4%; Rt 3.22 min. MS (ESI+): 490.2.

Example 432: 1-{4-[(2-Methylmorpholin-4-yl)methyl]phenyl}-3-(morpholin-4-ylcarbonyl)-1,4-dihydrothiochromeno[4,3-c]pyrazole 5,5-dioxide

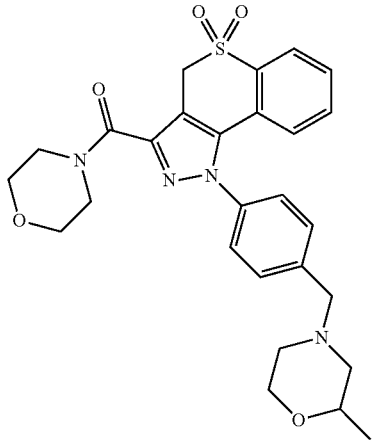 [SMILES: CC1CN(Cc2ccc(-n3nc(C(=O)N4CCOCC4)c4c3-c3ccccc3S(=O)(=O)C4)cc2)CCO1]

123 mg (95%) of the title compound as a white powder. $^1$H NMR (DMSO-$d_6$, 300 MHz): δ 8.06-7.98 (m, 1H), 7.69-7.44 (m, 6H), 7.88-7.78 (m, 1H), 4.91 (s, 2H), 4.04-3.87 (m, 2H), 3.83-3.38 (m, 11H), 2.79-2.59 (m, 2H), 2.15-2.02 (m, 1H), 1.85-1.73 (m, 1H), 1.09-1.00 (m, 3H). MS (ESI+): 523.4. HPLC (max plot) 98.4%; Rt 2.21 min Example 435: 1-{4-[(2,6-Dimethylmorpholin-4-yl)methyl]phenyl}-3-(morpholin-4-ylcarbonyl)-1,4-dihydrothiochromeno[4,3-c]pyrazole 5,5-dioxide

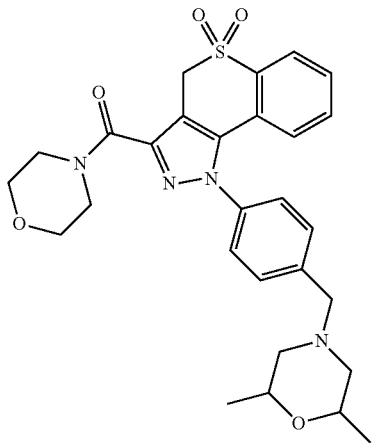 [SMILES: CC1CN(Cc2ccc(-n3nc(C(=O)N4CCOCC4)c4c3-c3ccccc3S(=O)(=O)C4)cc2)CC(C)O1]

62 mg of the title compound as a white powder. $^1$H NMR (DMSO-$d_6$, 300 MHz): δ 8.06-7.97 (m, 1H), 7.70-7.42 (m, 6H), 6.88-6.78 (m, 1H), 4.90 (s, 2H), 4.03-3.86 (m, 2H), 3.76-3.50 (m, 10H), 2.82-2.62 (m, 2H), 1.81-1.61 (m, 2H), 1.14-0.93 (m, 6H). MS (ESI+): 537.4. HPLC (max plot) 98.4%; Rt 2.29 min Example 436: N-{4-[3-(Morpholin-4-ylcarbonyl)-5,5-dioxidothiochromeno[4,3-c]pyrazol-1(4H)-yl]benzyl}tetrahydro-2H-pyran-4-amine

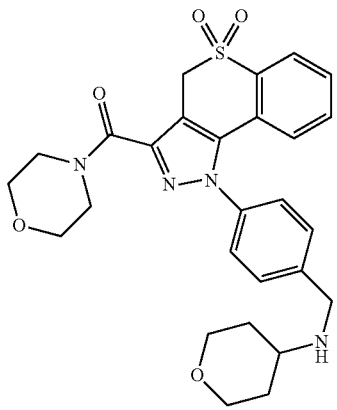

95 mg (73%) of the title compound as a white powder. $^1$H NMR (DMSO-$d_6$, 300 MHz): δ 8.08-7.97 (m, 1H), 7.70-7.51 (m, 4H), 7.51-7.39 (m, 2H), 6.90-6.79 (m, 1H), 4.90 (s, 2H), 4.07-3.91 (m, 2H), 3.91-3.77 (m, 4H), 3.77-3.53 (m, 6H), 3.33-3.18 (m, 2H), 2.70-2.55 (m, 1H), 2.39-2.10 (bs, 1H), 1.90-1.73 (m, 2H), 1.40-1.19 (m, 2H). MS (ESI+): 523.4. HPLC (max plot) 98.8%; Rt 5.76 min -continued Example 437: 1-{4-[(2,2-Dimethylmorpholin-4-yl)methyl]phenyl}-3-(morpholin-4-ylcarbonyl)-1,4-dihydrothiochromeno[4,3-c]pyrazole 5,5-dioxide

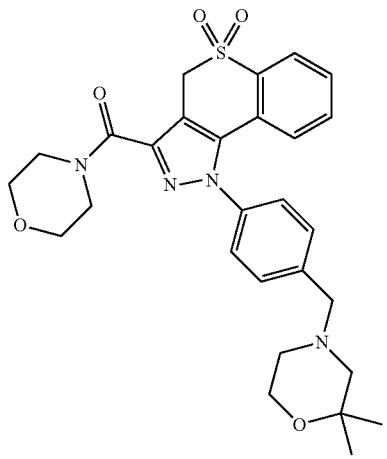 [SMILES: CC1(C)CN(Cc2ccc(-n3nc(C(=O)N4CCOCC4)c4c3-c3ccccc3S(=O)(=O)C4)cc2)CCO1]

93 mg of the title compound as a white powder. $^1$H NMR (DMSO-$d_6$, 300 MHz): δ 8.07-7.96 (m, 1H), 7.70-7.43 (m, 6H), 6.87-6.77 (m, 1H), 4.90 (s, 2H), 4.05-3.86 (m, 2H), 3.79-3.58 (m, 8H), 3.57 (s, 2H), 2.45-2.30 (m, 2H), 2.20 (bs, 2H), 1.18 (s, 6H). MS (ESI+): 537.4. HPLC (max plot) 100.0%; Rt 2.26 min.

Example 449: N-Methyl-1-{4-[3-(morpholin-4-ylcarbonyl)-5,5-dioxidothiochromeno[4,3-c]pyrazol-1 (4H)-yl]phenyl}methanamine

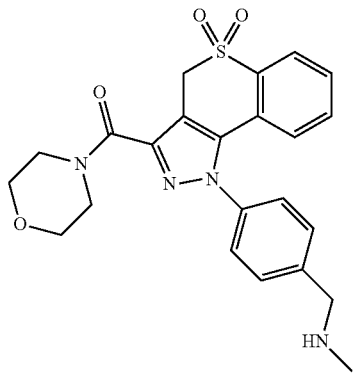 [SMILES: CNCc1ccc(-n2nc(C(=O)N3CCOCC3)c3c2-c2ccccc2S(=O)(=O)C3)cc1]

21 mg of the title compound as an off-white solid. $^1$H NMR (DMSO-$d_6$, 300 MHz): δ 8.07-7.96 (m, 1H), 7.71-7.52 (m, 4H), 7.52-7.41 (m, 2H), 6.90-6.80 (m, 1H), 4.90 (s, 2H), 4.06-3.88 (m, 2H), 3.79 (s, 2H), 3.75-3.55 (m, 6H), 2.32 (s, 3H). MS (ESI+): 453.4. HPLC (max plot) 98.6%; Rt 1.90 min Example 470: N-{4-[3-(Morpholin-4-ylcarbonyl)-5,5-dioxidothiochromeno[4,3-c]pyrazol-1 (4H)-yl]benzyl}tetrahydrofuran-3-amine

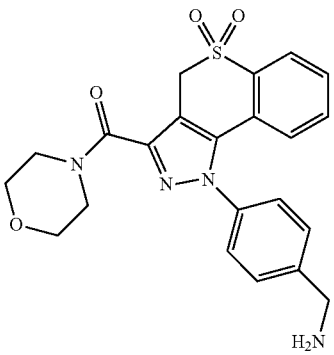 [SMILES: NCc1ccc(-n2nc(C(=O)N3CCOCC3)c3c2-c2ccccc2S(=O)(=O)C3)cc1]

289 mg of the title compound as a white powder. $^1$H NMR (DMSO-$d_6$, 300 MHz): δ 8.07-7.98 (m, 1H), 7.70-7.54 (m, 4H), 7.54-7.43 (m, 2H), 6.92-6.83 (m, 1H), 4.91 (s, 2H), 4.19-3.79 (m, 6H), 3.79-3.51 (m, 6H). MS (ESI+): 439.3. HPLC (max plot) 98.0%; Rt 1.83 min

Procedure AL

Example 357

1-{4-[(3-Methylmorpholin-4-yl)methyl]phenyl}-3-(morpholin-4-ylcarbonyl)-1,4-dihydrothiochromeno[4,3-c]pyrazole 5,5-dioxide

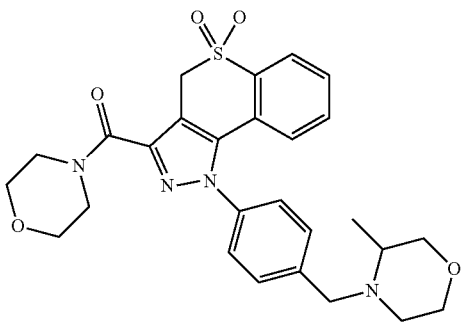

To a solution of {4-[3-(morpholin-4-ylcarbonyl)-5,5-dioxidothiochromeno[4,3-c]pyrazol-1(4H)-yl]phenyl}methanol (123 mg; 0.28 mmol; 1 eq.) and DIEA (330 µl; 1.93 mmol; 2.56 eq.) in DCM (13 mL) is added at 0° C. methanesulfonlyl chloride (75 µl; 0.97 mmol; 1.3 eq.). The solution is stirred for 30 min and allowed to warm up to rt. After this time, a suspension of sodium iodide (32 mg; 0.21 mmol; 0.28 eq.), K₂CO₃ (336 mg; 2.43 mmol; 3.22 eq.) and 3-methylmorpholine (166 µl; 1.51 mmol; 2 eq.) in DMF (50 mL) is added on the sulfonylchloride mixture. The resulting suspension is stirred at 80° C. for 2h after which time water is added after return to RT. The product is extracted with DCM and the combined organic layer is washed with brine, dried over MgSO₄ and purified by MD-Autoprep then triturated in a mixture of DCM and pentane to afford the title compound as an orange powder. 1H NMR (DMSO-d6): δ 8.02-7.98 (m, 1H), 7.69-7.43 (m, 6H), 6.87-6.79 (m, 1H), 4.91 (s, 2H), 4.18-4.03 (m, 1H), 4.03-3.88 (m, 2H), 3.79-3.56 (m, 8H), 3.56-3.41 (m, 1H), 3.33-3.24 (m, 2H), 3.24-3.10 (m, 1H), 2.52-2.66 (m, 1H), 2.50-2.36 (m, 1H), 2.29-2.09 (m, 1H), 1.03 (d, J=6.3 Hz, 3H). HPLC (max plot) 98.1%; Rt 2.09 min. HPLC (max plot) 76.8%; Rt 2.15 min. MS (ESI+): 523.4. Compounds described below are obtained following protocol outlined in procedure AL Example 215: 3-(Morpholin-4-ylcarbonyl)-1-[4-(morpholin-4-ylmethyl)cyclohexyl]-1,4-dihydrothiochromeno[4,3-c]pyrazole 5,5-dioxide

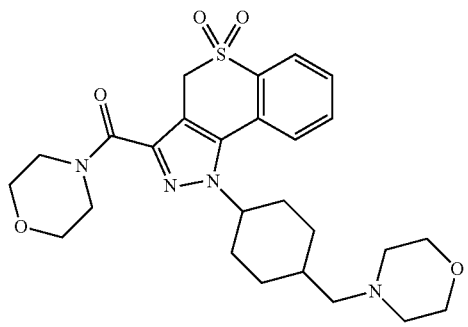 [SMILES: O=C(c1nn(C2CCC(CN3CCOCC3)CC2)c2c1CS(=O)(=O)c1ccccc1-2)N1CCOCC1]

3.4 mg of the title compound as an off white solid. ¹H NMR (400 MHz, DMSO-d₆) δ: 8.03-8.01 (d, J = 7.8 Hz, 1H), 7.90-7.73 (m, 1H), 7.73-7.70 (t, J = 7.6 Hz, 1H), 4.76 (s, 2H), 4.66 (m, 1H), 3.94 (bs, 6H), 3.57-3.56 (m, 4H), 2.32-2.26 (m, 4H), 2.13-2.11 (m, 1H), 2.05-1.89 (m, 5H), 1.70 (m, 2H), 1.22 (m, 2H). MS (ESI+): 515.5.

Example 216: 3-(Morpholin-4-ylcarbonyl)-1-[6-(morpholin-4-ylmethyl)pyridin-3-yl]-1,4-dihydrothiochromeno[4,3-c]pyrazole 5,5-dioxide

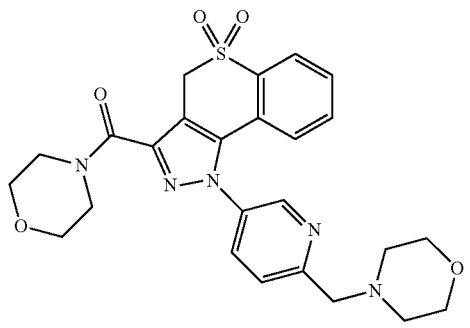

4.5 mg of the title compound as a pale yellow solid. ¹H NMR (DMSO-d₆, 400 MHz) δ 8.70 (d, J = 2.5 Hz, 1H), 8.04-7.98 (m, 2H), 7.70-7.59 (m, 3H), 6.91-6.90 (d, J = 7.6 Hz, 1H), 4.90 (s, 2H), 3.92 (m, 2H), 3.72 (m, 2H), 3.66 (m, 4H), 3.63-3.60 (m, 6H), 2.48-2.49 (m, 4H). MS (ESI+): 510.0. HPLC (max plot) 94.76%; Rt 2.36 min Example 217: 1-{6-[(4-Fluoropiperidin-1-yl)methyl]pyridin-3-yl}-3-(morpholin-4-ylcarbonyl)-1,4-dihydrothiochromeno[4,3-c]pyrazole 5,5-dioxide

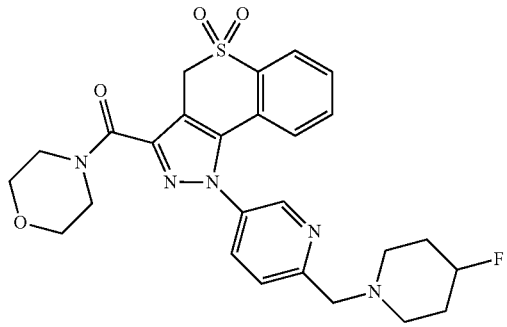 [SMILES: O=C(c1nn(-c2ccc(CN3CCC(F)CC3)nc2)c2c1CS(=O)(=O)c1ccccc1-2)N1CCOCC1]

8 mg of the title compound as a pale yellow solid. ¹H NMR (DMSO-d$_6$, 400 MHz): δ 8.70 (d, J = 2.5 Hz, 1H), 8.03-7.97 (m, 2H), 7.69-7.57 (m, 3H), 6.91-6.89 (d, J = 7.8 Hz, 1H), 4.90 (s, 2H), 3.92 (m, 2H), 3.73 (m, 2H), 3.66 (m, 4H), 3.60 (m, 2H), 2.62 (m, 3H), 2.43-2.40 (m, 2H), 1.70 (m, 2H), 1.76 (m, 2H). MS (ESI+): 526.0. HPLC (max plot) 95.95%; Rt 2.59 min Example 251: 1-{6-[(4-Methylpiperazin-1-yl)methyl]pyridin-3-yl}-3-(morpholin-4-ylcarbonyl)-1,4-dihydrothiochromeno[4,3-c]pyrazole 5,5-dioxide

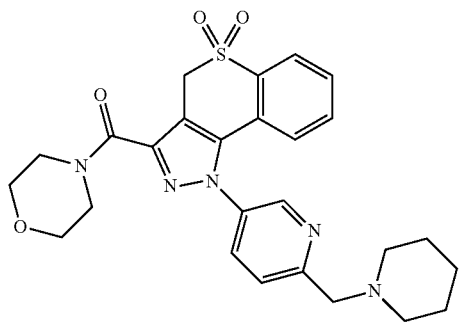 [SMILES: O=C(c1nn(-c2ccc(CN3CCCCC3)nc2)c2c1CS(=O)(=O)c1ccccc1-2)N1CCOCC1]

2 mg (of the title compound as an off white solid. ¹H NMR (DMSO-d$_6$, 400 MHz): δ 8.69 (s, 1H), 8.04-7.97 (m, 2H), 7.67-7.59 (m, 3H), 6.91-6.89 (d, J = 7.5 Hz, 1H), 4.90 (m, 2H), 3.92 (m, 2H), 3.67-3.60 (m, 8H), 2.53 (m, 6H), 2.43 (m, 2H), 1.54 (m, 4H), 1.41 (m, 2H). MS (ESI+): 508.0. HPLC (max plot) 95.22%; Rt 2.49 min.

Example 252: 1-{6-[(4-Methylpiperazin-1-yl)methyl]pyridin-3-yl}-3-(morpholin-4-ylcarbonyl)-1,4-dihydrothiochromeno[4,3-c]pyrazole 5,5-dioxide

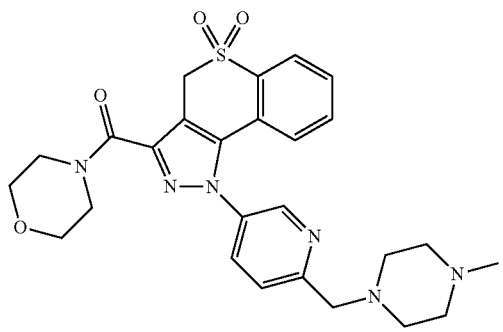 [SMILES: CN1CCN(Cc2ccc(-n3nc(C(=O)N4CCOCC4)c4c3-c3ccccc3S(=O)(=O)C4)cn2)CC1]

12 mg of the title compound as a pale brown solid. ¹H NMR (DMSO-d$_6$, 400 MHz): δ 8.70-8.70 (m, 1H), 8.04-7.98 (m, 2H), 7.67-7.58 (m, 3H), 6.91-6.89 (d, J = 7.7 Hz, 1H), 4.90 (s, 2H), 3.92 (m, 2H), 3.73 (m, 2H), 3.67-3.60 (m, 7H), 3.31 (m, 1H), 2.49 (m, 4H). MS (ESI+): 523.0. HPLC (max plot) 96.64%; Rt 2.16 min.

Example 178: 3-(Morpholin-4-ylcarbonyl)-1-[3-(piperidin-1-ylmethyl)phenyl]-1,4-dihydrothiochromeno[4,3-c]pyrazole 5,5-dioxide

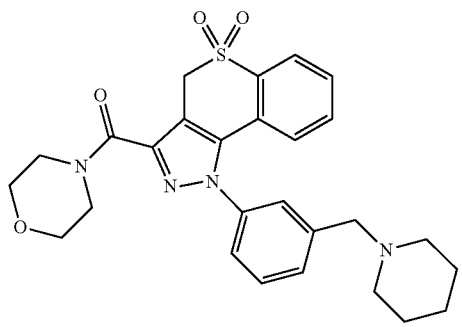

off white solid. ¹H NMR (DMSO-d$_6$, 400 MHz): δ 8.02-8.0 (d, J = 7.2 Hz, 1H), 7.64-7.47 (m, 5H), 7.33 (s, 1H), 6.82-6.80 (d, J = 7.8 Hz, 1H), 4.89 (s, 2H), 3.93 (m, 2H), 3.67 (m, 4H), 3.60 (m, 2H), 3.47 (m, 2H), 2.27 (m, 4H), 1.36 (m, 6H). MS (ESI+): 507.0. HPLC (max plot) 95.51%; Rt 2.73 min Example 179: N,N-Dimethyl-1-{3-[3-(morpholin-4-ylcarbonyl)-5,5-dioxidothiochromeno[4,3-c]pyrazol-1 (4H)-yl]phenyl}methanamine

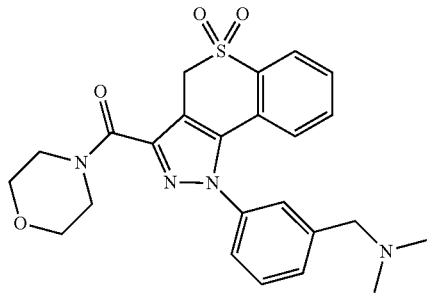 [SMILES: CN(C)Cc1cccc(-n2nc(C(=O)N3CCOCC3)c3c2-c2ccccc2S(=O)(=O)C3)c1]

white solid. ¹H NMR (DMSO-d₆, 400 MHz): δ 8.02-8.00 (d, J = 7.6 Hz, 1H), 7.64-7.48 (m, 5H), 7.36 (s, 1H), 6.82-6.81 (d, J = 7.5 Hz, 1H), 4.89 (s, 2H), 3.92 (m, 2H), 3.66 (m, 4H), 3.60 (m, 2H), 3.44 (m, 2H), 2.11 (m, 6H). MS (ESI+): 467.0. HPLC (max plot) 98.03%; Rt 2.49 min.

Example 168: 1-{4-[(4-Methoxypiperidin-1-yl)methyl]phenyl}-3-(morpholin-4-ylcarbonyl)-1,4-dihydrothiochromeno[4,3-c]pyrazole 5,5-dioxide

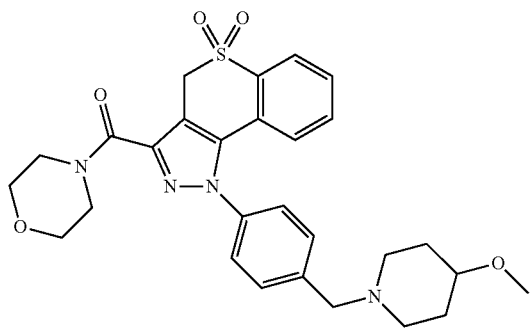 [SMILES: COC1CCN(Cc2ccc(-n3nc(C(=O)N4CCOCC4)c4c3-c3ccccc3S(=O)(=O)C4)cc2)CC1]

24 mg of the title compound as an off white solid. ¹H NMR (DMSO-d₆, 400 MHz): δ 8.01-7.99 (d, J = 7.5 Hz, 1H), 7.64-7.60 (m, 1H), 7.57-7.51 (m, 3H), 7.47-7.45 (d, J = 8.2 Hz, 1H), 6.82-6.80 (d, J = 7.8 Hz, 1H), 4.89 (s, 2H), 3.94 (m, 2H), 3.66 (m, 4H), 3.66 (m, 2H), 3.60 (m, 2H), 3.21 (s, 3H), 3.21-3.19 (m, 2H), 2.66 (m, 3H), 2.15-2.11 (m, 2H), 1.82 (m, 2H), 1.45-1.42 (m, 2H). MS (ESI+): 537.0. HPLC (max plot) 94.67%; Rt 2.70 min Example 169: 3-(Morpholin-4-ylcarbonyl)-1-[4-(piperidin-1-ylmethyl)phenyl]-1,4-dihydrothiochromeno[4,3-c]pyrazole 5,5-dioxide

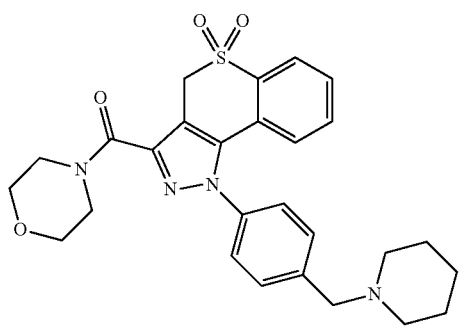 [SMILES: O=C(c1nn(-c2ccc(CN3CCCCC3)cc2)c2c1CS(=O)(=O)c1ccccc1-2)N1CCOCC1]

24 mg of the title compound as an off white solid. ¹H NMR (DMSO-d₆, 400 MHz): δ 8.01-7.99 (d, J = 7.5 Hz, 1H), 7.64-7.60 (m, 1H), 7.57-7.50 (m, 3H), 7.47-7.45 (m, 2H), 6.83-6.81 (d, J = 7.7 Hz, 1H), 4.89 (s, 2H), 3.94 (m, 2H), 3.66 (m, 4H), 3.6 (m, 2H), 3.54 (m, 2H), 2.36 (m, 4H), 1.51 (m, 4H), 1.40 (m, 2H). MS (ESI+): 507.0. HPLC (max plot) 96.42%; Rt 2.69 min Example 426: 2-Methoxy-N-methyl-N-{4-[3-(morpholin-4-ylcarbonyl)-5,5-dioxidothiochromeno[4,3-c]pyrazol-1(4H)-yl]benzyl}ethanamine

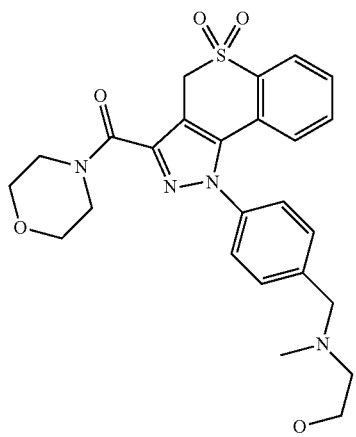 [SMILES: CN(CCO)Cc1ccc(-n2nc(C(=O)N3CCOCC3)c3c2-c2ccccc2S(=O)(=O)C3)cc1]

80 mg of the title compound as a yellow solid. ¹H NMR (DMSO-d₆, 300 MHz): δ 8.06-7.97 (m, 1H), 7.69-7.43 (m, 6H), 6.87-6.78 (m, 1H), 4.90 (s, 2H), 4.04-4.88 (m, 2H), 3.77-3.56 (m, 8H), 3.48 (t, J = 5.9 Hz, 2H), 3.25 (s, 3H), 2.58 (t, J = 5.9 Hz, 2H), 2.22 (s, 3H). MS (ESI+): 511.3. HPLC (max plot) 97.5%; Rt 6.88 min Example 430: 1-{4-[(3-Fluoroazetidin-1-yl)methyl]phenyl}-3-(morpholin-4-ylcarbonyl)-1,4-dihydrothiochromeno[4,3-c]pyrazole 5,5-dioxide

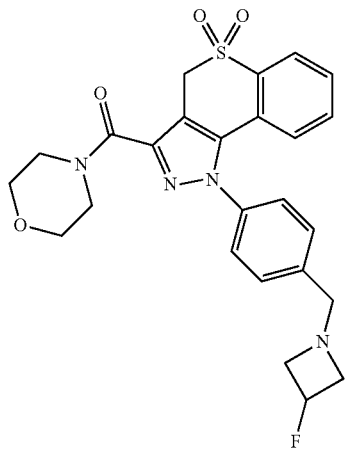 [SMILES: O=C(c1nn(-c2ccc(CN3CC(F)C3)cc2)c2c1CS(=O)(=O)c1ccccc1-2)N1CCOCC1]

68 mg of the title compound as a white powder. $^1$H NMR (DMSO-$d_6$, 300 MHz): δ 8.07-7.96 (m, 1H), 7.70-7.56 (m, 2H), 7.56-7.41 (m, 4H), 6.87-6.76 (m, 1H), 5.37-5.05 (m, 1H), 4.90 (s, 2H), 4.06-3.85 (m, 2H), 3.76 (s, 2H), 3.73-3.51 (m, 8H), 3.29-3.20 (m, 1H), 3.20-3.10 (m, 1H). MS (ESI+): 497.33. HPLC (max plot) 98.5%; Rt 7.03 min Example 431: 2-Methoxy-N-{4-[3-(morpholin-4-ylcarbonyl)-5,5-dioxidothiochromeno[4,3-c]pyrazol-1(4H)-yl]benzyl}ethanamine

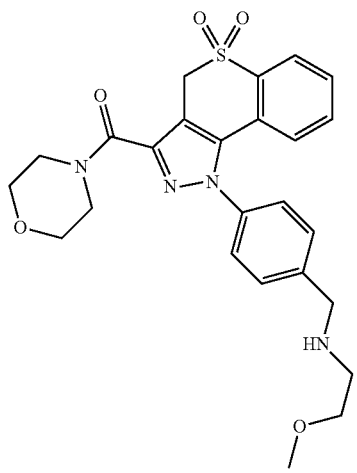 [SMILES: COCCNCc1ccc(-n2nc(C(=O)N3CCOCC3)c3c2-c2ccccc2S(=O)(=O)C3)cc1]

89 mg (76%) of the title compound as a white powder.
$^1$H NMR (DMSO-$d_6$, 300 MHz): δ 8.07-7.97 (m, 1H), 7.69-7.51 (m, 4H), 7.51-7.42 (m, 2H), 6.89-6.82 (m, 1H), 4.90 (s, 2H), 4.01-3.90 (m, 2H), 3.83 (s, 2H), 3.74-3.56 (m, 6H), 3.43 (t, J = 5.7 Hz, 2H), 3.25 (s, 3H), 3.24-3.17 (m, 1H), 2.69 (t, J = 5.7 Hz, 2H). MS (ESI+): 497.4. HPLC (max plot) 97.3%; Rt 2.03 min Example 455: N-{4-[3-(Morpholin-4-ylcarbonyl)-5,5-dioxidothiochromeno[4,3-c]pyrazol-1(4H)-yl]benzyl}tetrahydro-2H-pyran-3-amine

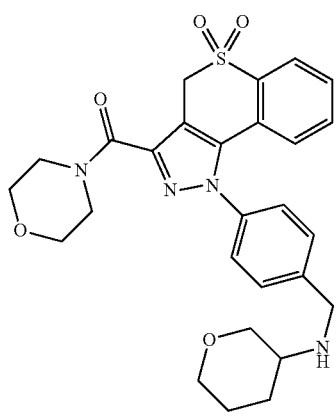 [SMILES: O=C(c1nn(-c2ccc(CNC3CCCOC3)cc2)c2c1CS(=O)(=O)c1ccccc1-2)N1CCOCC1]

83 mg of the title compound as a brown powder. $^1$H NMR (DMSO-$d_6$) 300 MHz): δ 8.09-7.96 (m, 1H), 7.71-7.51 (m, 4H), 7.51-7.41 (m, 2H), 6.89-6.77 (m, 1H), 4.90 (s, 2H), 4.08-3.89 (m, 2H), 3.89-3.77 (m, 3H), 3.77-3.54 (m, 7H), 3.31-3.17 (m, 1H), 3.10-2.96 (m, 1H), 2.62-2.43 (m, 2H), 2.04-1.87 (m, 1H), 1.72-1.55 (m, 1H), 1.55-1.36 (m, 1H), 1.36-1.18 (m, 1H). MS (ESI+): 523.23. HPLC (max plot) 99.6%; Rt 2.15 min Intermediate X: Ethyl 1-[4-(morpholin-4-ylmethyl)phenyl]-1,4-dihydropyrazolo[3',4':4,5]thiopyrano[2,3-b]pyridine-3-carboxylate 5,5-dioxide

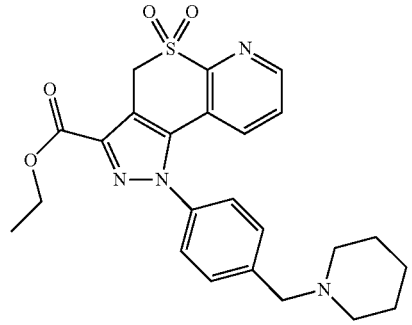 [SMILES: CCOC(=O)c1nn(-c2ccc(CN3CCCCC3)cc2)c2c1CS(=O)(=O)c1ncccc1-2]

120 mg of the title compound. $^1$H NMR (DMSO-$d_6$, 400 MHz): δ 8.70-8.70 (d, J = 3.3 Hz, 1H), 7.63-7.59 (m, 1H), 7.56-7.54 (m, 2H), 7.50-7.48 (m, 2H), 7.20-7.18 (d, J = 7.0 Hz, 1H), 5.09 (s, 2H), 4.39-4.34 (m, 2H), 3.59 (m, 6H), 2.40 (m, 4H), 1.34-1.31 (t, J = 7.1 Hz, 3H). MS (ESI+): 469.0

Example 137

3-(Morpholin-4-ylcarbonyl)-1-[4-(morpholin-4-ylmethyl)phenyl-1,4-dihydrothiochromeno[4,3-c]pyrazole 5,5-dioxide

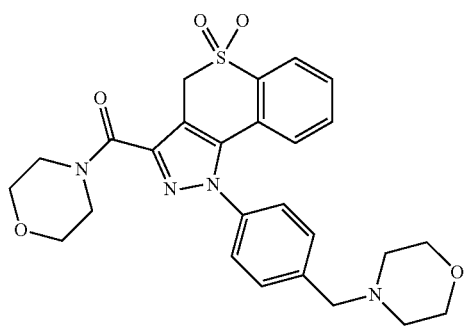

To a suspension of 1-[4-(hydroxymethyl)phenyl]-1,4-dihydrothiochromeno[4,3-c]pyrazole-3-carboxylic acid 5,5-dioxide (5.29 g; 14.29 mmol; 1 eq.) in DCE (212 mL) at 0° C. are added dropwise thionyl chloride (3.17 mL; 42.88 mmol; 3 eq.) over 15 min then DMF (2 mL). The reaction mixture is stirred at 40° C. for 6 h and then at rt overnight. The solvent is removed under reduced pressure and the residue is taken up in DCE (106 mL). The resulting solution is added dropwise to a solution of morpholine (26 mL) in DCE (106 mL) at 0° C. over 30 min after which reaction mixture is let to warm to rt and then heated to 50° C. for 4 h 30. The solvent is removed under reduced pressure. The residue is taken up in DCM and washed with water, brine, dried over MgSO$_4$ and evaporated under vacuum. The residue is triturated in ether and then filtered off to afford 5.77 g (79%) of the title compound as an off-white solid. $^1$H NMR (DMSO-$d_6$) δ 8.04-8.01 (m, 1H), 7.66-7.48 (m, 6H), 6.85-6.82 (m, 1H), 4.91 (s, 2H), 3.97-3.94 (m, 2H), 3.68-3.60 (m, 12H), 2.43-2.40 (m, 4H). HPLC (max plot) 99.4%; Rt 1.94 min; MS (ESI+): 509.0. CHN analysis: [C26H28N4O5S] Corrected: C61.40%, H5.55%, N11.02%; Found: C61.27%, H5.62%, N10.95%.

Procedure AM

Example 56

3-(morpholin-4-ylcarbonyl)-1-(piperidin-4-ylmethyl)-1,4-dihydrothiochromeno[4,3-c]pyrazole 5,5-dioxide

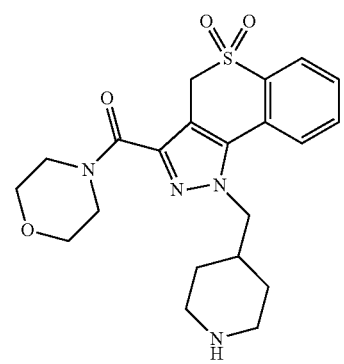 [SMILES: O=C(c1nn(CC2CCNCC2)c2c1CS(=O)(=O)c1ccccc1-2)N1CCOCC1]

To a solution of tert-butyl 4-{[3-(morpholin-4-ylcarbonyl)-5,5-dioxidothiochromeno[4,3-c]pyrazol-1(4H)-yl]methyl}piperidine-1-carboxylate (0.1 g, 0.21 mmol) in DCM (2.0 mL) is added TFA (0.119 g, 1.05 mmol, 5 Eq) and the reaction mixture is stirred at room temperature overnight. The crude reaction mixture is washed with sodium bicarbonate then brine and dried over MgSO$_4$. The crude residue is purified by flash chromatography to afford the title compound as a pale brown solid. $^1$H NMR (DMSO-$d_6$, 400 MHz) δ 8.03-7.98 (m, 2H), 7.88 (t, J=7.5 Hz, 1H), 7.73-7.70 (m, 1H), 4.78 (s, 2H), 4.47 (t, J=7.1 Hz, 2H), 3.91 (s, 2H), 3.66-3.63 (m, 6H), 2.98-2.95 (m, 2H), 2.00 (brs, 1H), 1.75-1.69 (m, 1H), 1.48-1.40 (m, 2H), 1.24-1.17 (m, 3H). MS (ESI+): 431.0. HPLC (max plot) 97.2%; Rt 2.16 min.

Example Described Below is Obtained Following Procedure AM

Example 140: 3-[3-(Morpholin-4-ylcarbonyl)-5,5-dioxido-1-phenyl-1,4-dihydro thiochromeno[4,3-c]pyrazol-4-yl]propan-1-amine

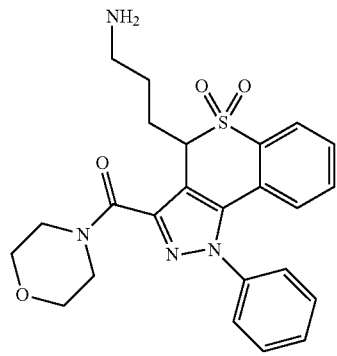 [SMILES: NCCCC1c2c(C(=O)N3CCOCC3)nn(-c3ccccc3)c2-c2ccccc2S1(=O)=O]

12 mg of the title compound as a off-white solid. 1H NMR (DMSO-d6) δ 8.05-8.02 (m, 1H), 7.69-7.51 (m, 7H), 6.85-6.82(m, 1H), 4.96-4.91 (m, 1H), 4.00-3.97 (m, 2H), 3.76-3.57 (m, 6H), 2.68-2.63 (m, 2H), 2.07-1.98 (m, 1H), 1.63-1.39 (m, 3H). HPLC (max plot) 99.3%; Rt 2.53 min. MS (ESI+): 467.4.

Procedure AN

Example 57

4-benzyl-3-(morpholin-4-ylcarbonyl)-1-phenyl-1,4-dihydrothiochromeno[4,3-c]pyrazole 5,5-dioxide

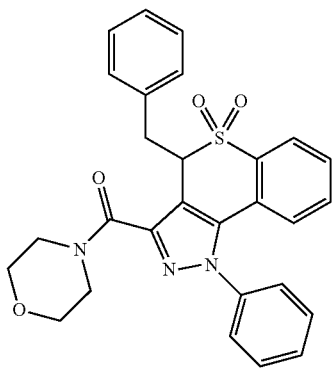 [SMILES: O=C(c1nn(-c2ccccc2)c2c1C(Cc1ccccc1)S(=O)(=O)c1ccccc1-2)N1CCOCC1]

To a solution of 3-(morpholin-4-ylcarbonyl)-1-phenyl-1,4-dihydrothiochromeno[4,3-c]pyrazole 5,5-dioxide (100 mg; 0.24 mmol; 1.0 eq.) in THF (4.0 mL) is added NaH (55% w/w in mineral oil) (12.79 mg; 0.29 mmol; 1.2 Eq.). After 15 min stirring, benzyl bromide (34.81 μL; 0.29 mmol; 1.2 eq.) is added and the reaction mixture is stirred at room temperature for 3h. The reaction is quenched with water and the product extracted with EtOAc. The combined organic phases are washed with brine, dried over MgSO4 and concentrated under reduced pressure. The crude residue is recrystallized from EtOH and dried under vacuum to afford the title compound as an off-white solid. $^1$H NMR (DMSO-d6, 300MHz) δ 8.01-7.98 (m, 1H), 7.63-7.58 (m, 4H), 7.53-7.46 (m, 3H), 7.12-7.07 (m, 3H), 6.89-6.86 (m, 2H), 6.66-6.64 (m, 1H), 5.29-5.25 (m, 1H), 3.93-3.88 (m, 1H), 3.63-3.53 (m, 5H), 3.45-3.36 (m, 2H), 3.26-3.20 (m, 1H), 2.76-2.69 (m, 1H). UPLC/MS: (ES+): 500.2, (ES−): 498.3. HPLC (max plot) 97.6%; Rt 4.32 min.

Example 58

4-(cyclopropylmethyl)-3-(morpholin-4-ylcarbonyl)-1-phenyl-1,4-dihydrothiochromeno[4,3-c]pyrazole 5,5-dioxide

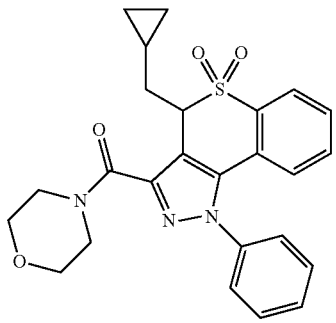 [SMILES: O=C(c1nn(-c2ccccc2)c2c1C(CC1CC1)S(=O)(=O)c1ccccc1-2)N1CCOCC1]

Following the protocol outlined in Procedure AN, 4-(cyclopropylmethyl)-3-(morpholin-4-ylcarbonyl)-1-phenyl-1,4-dihydrothiochromeno[4,3-c]pyrazole 5,5-dioxide is obtained from 3-(morpholin-4-yl carbonyl)-1-phenyl-1,4-dihydrothiochromeno[4,3-c]pyrazole 5,5-dioxide and cyclopropylmethyl bromide to afford the title compound as a white solid. UPLC/MS: (ES+): 464.1. HPLC (max plot) 98.1%; Rt 4.01 min.

Example 59

4-ethyl-3-(morpholin-4-ylcarbonyl)-1-phenyl-1,4-dihydrothiochromeno[4,3-c]pyrazole 5,5-dioxide

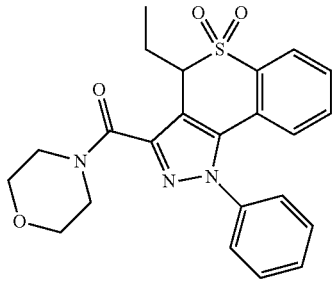 [SMILES: CCC1c2c(C(=O)N3CCOCC3)nn(-c3ccccc3)c2-c2ccccc2S1(=O)=O]

Following the protocol outlined in Procedure AN, 4-ethyl-3-(morpholin-4-ylcarbonyl)-1-phenyl-1,4-dihydrothiochromeno[4,3-c]pyrazole 5,5-dioxide is obtained from 3-(morpholin-4-ylcarbonyl)-1-phenyl-1,4-dihydrothiochromeno[4,3-c]pyrazole 5,5-dioxide and iodoethane to afford the title compound as a white solid. ¹H NMR (DMSO-d₆, 300 MHz) δ 8.03-8.00 (m, 1H), 7.67-7.53 (m, 7H), 6.84-6.81 (m, 1H), 4.85-4.80 (m, 1H), 3.99-3.95 (m, 2H), 3.80-3.50 (m, 6H), 2.08-1.95 (m, 1H), 1.53-1.38 (m, 1H), 0.82 (t, J=7.4 Hz, 3H). HPLC (max plot) 99.8%; Rt 3.67 min.

Example 60

4,4-dimethyl-3-(morpholin-4-ylcarbonyl)-1-phenyl-1,4-dihydrothiochromeno[4,3-c]pyrazole 5,5-dioxide

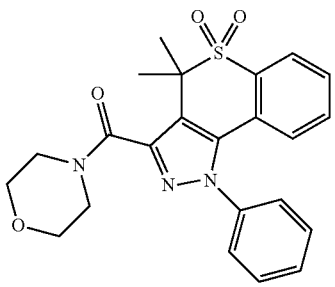 [SMILES: CC1(C)c2c(C(=O)N3CCOCC3)nn(-c3ccccc3)c2-c2ccccc2S1(=O)=O]

Following the protocol outlined in Procedure AN, 4,4-dimethyl-3-(morpholin-4-ylcarbonyl)-1-phenyl-1,4-dihydrothiochromeno[4,3-c]pyrazole 5,5-dioxide is obtained from 3-(morpholin-4-ylcarbonyl)-1-phenyl-1,4-dihydrothiochromeno[4,3-c]pyrazole 5,5-dioxide and iodomethane to afford the title compound as a white solid. ¹H NMR (DMSO-d₆, 300 MHz) δ 8.06-8.03 (m, 1H), 7.67-7.56 (m, 5H), 7.51-7.48 (m, 2H), 6.83-6.80 (m, 1H), 3.72-3.65 (m, 4H), 3.59-3.50 (m, 4H), 1.60 (s, 6H). HPLC (max plot) 100%; Rt 3.40 min.

Example 112

4-(3-Methoxypropyl)-3-(morpholin-4-ylcarbonyl)-1-phenyl-1,4-dihydrothiochromeno[4,3-c]pyrazole 5,5-dioxide

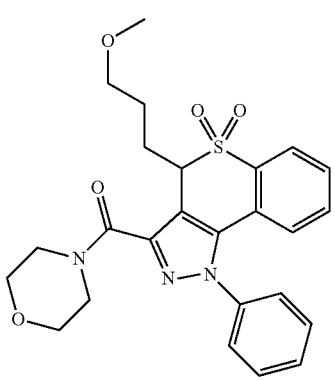 [SMILES: COCCCC1c2c(C(=O)N3CCOCC3)nn(-c3ccccc3)c2-c2ccccc2S1(=O)=O]

Following the protocol outlined in procedure AN, 4-(3-methoxypropyl)-3-(morpholin-4-ylcarbonyl)-1-phenyl-1,4-dihydrothiochromeno[4,3-c]pyrazole 5,5-dioxide is obtained from 3-(morpholin-4-ylcarbonyl)-1-phenyl-1,4-dihydrothiochromeno[4,3-c]pyrazole 5,5-dioxide and 1-bromo-3-methoxypropane to afford the title compound as a white solid. HPLC (max plot) 98.4%; Rt 3.64 min. MS (ESI+): 482.0.

Example 111

4-Benzyl-1-methyl-3-(morpholin-4-ylcarbonyl)-1,4-dihydrothiochromeno[4,3-c]pyrazole 5,5-dioxide

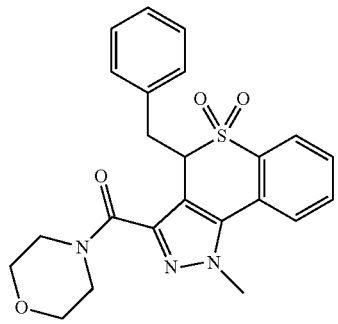 [SMILES: Cn1nc(C(=O)N2CCOCC2)c2c1-c1ccccc1S(=O)(=O)C2Cc1ccccc1]

Following the protocol outlined in procedure AN, 4-benzyl-1-methyl-3-(morpholin-4-ylcarbonyl)-1,4-dihydrothiochromeno[4,3-c]pyrazole 5,5-dioxide is obtained from 1-methyl-3-(morpholin-4-ylcarbonyl)-1,4-dihydrothiochromeno[4,3-c]pyrazole 5,5-dioxide and benzyl bromide to afford the title compound as a white solid. ¹H NMR (DMSO-d₆) δ 8.05-8.02 (m, 1H), 7.96-7.93 (m, 1H), 7.89-7.84 (m, 1H), 7.76-7.70 (m, 1H), 7.17-7.07 (m, 3H), 6.88-6.85 (m, 2H), 5.20 (q, J=5.0 Hz, 1H), 4.19 (s, 3H), 3.84-3.79 (m, 1H), 3.65-3.50 (m, 5H), 3.39-3.18 (m, 3H), 2.62-2.55 (m, 1H). HPLC (max plot) 100.0%; Rt 3.35 min. MS (ESI+): 438.2.

Example 316

4-Fluoro-3-(morpholin-4-ylcarbonyl)-1-(tetrahydro-2H-pyran-4-yl)-1,4-dihydrothiochromeno[4,3-c]pyrazole 5,5-dioxide

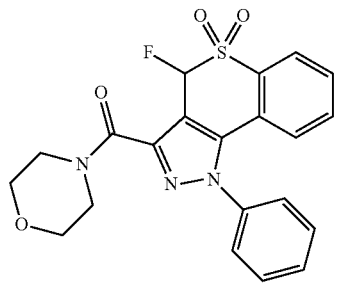 [SMILES: O=C(c1nn(-c2ccccc2)c2c1C(F)S(=O)(=O)c1ccccc1-2)N1CCOCC1]

Following the protocol outlined in procedure AN, 4-fluoro-3-(morpholin-4-ylcarbonyl)-1-(tetrahydro-2H-pyran-4-yl)-1,4-dihydrothiochromeno[4,3-c]pyrazole 5,5-dioxide is obtained from 3-(morpholin-4-ylcarbonyl)-1-(tetrahydro-2H-pyran-4-yl)-1,4-dihydrothiochromeno[4,3-c]pyrazole 5,5-dioxide and N-fluoro-N'-chloromethyl-triethylenediamine-bis(tetrafluoroborate) to afford the title compound as a white solid. HPLC (max plot) 90.0%; Rt 3.12 min. MS (ESI+): 435.8.

Procedure AO

Intermediate AO tert-Butyl {3-[3-(morpholin-4-ylcarbonyl)-5,5-di-oxido-1-phenyl-1,4-dihydrothiochromeno[4,3-c]pyrazol-4-yl]propyl}carbamate

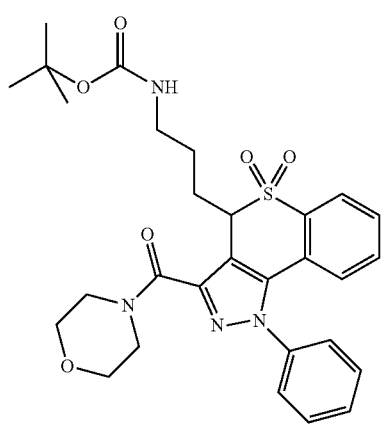 [SMILES: CC(C)(C)OC(=O)NCCCC1c2c(C(=O)N3CCOCC3)nn(-c3ccccc3)c2-c2ccccc2S1(=O)=O]

To a solution of 3-(morpholin-4-ylcarbonyl)-1-phenyl-1,4-dihydrothiochromeno[4,3-c]pyrazole 5,5-dioxide (150 mg; 0.37 mmol; 1 eq.) in THF (3 mL) is added potassium bis(trimethylsilyl)amide (879.19 µl; 0.5 M; 0.44 mmol; 1.2 eq.) and then 3-(boc-amino)propyl bromide (104.68 mg; 0.44 mmol; 1.20 eq.) The reaction mixture is stirred at rt for 2 days. The reaction is not complete even after addition of 2 eq. of 3-(boc-amino)propyl bromide. It is stopped by addition of water. The product is extracted with EtOAc and the combined organic phases are washed with brine, dried over MgSO4 and concentrated under reduced pressure, to afford 217 mg (quant) of the title compound. HPLC (max plot) 83.1%; Rt 4.08 min. MS (ESI−): 565.5.

Procedure AP

Example 123

1-[1-(Methylsulfonyl)piperidin-4-yl]-3-(morpholin-4-ylcarbonyl)-1,4-dihydrothiochromeno[4,3-c]pyrazole 5,5-dioxide

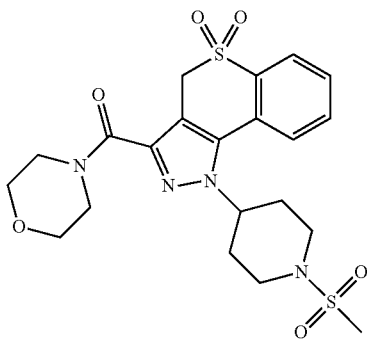 [SMILES: CS(=O)(=O)N1CCC(n2nc(C(=O)N3CCOCC3)c3c2-c2ccccc2S(=O)(=O)C3)CC1]

To a solution of 3-(morpholin-4-ylcarbonyl)-1-piperidin-4-yl-1,4-dihydrothiochromeno[4,3-c]pyrazole 5,5-dioxide (30 mg, 0.066 mmol) in THF (10 mL) is added triethylamine (40 µl, 0.26 mmol) and the reaction mass is cooled to 0° C. after which methane sulfonyl chloride (0.01 mL, 0.099 mmol) is slowly added. The reaction mixture is slowly warmed to RT then stirred for 12 h. After this time, water is added to the reaction mixture that is then extracted with EtOAc. The organic layer is separated, dried under sodium sulphate and concentrated under reduced pressure. Compound is then purified by neutral alumina column chromatography (0.2% MeOH in chloroform) to afford the title compound as an off white solid. $^1$H NMR (DMSO-d$_6$, 400 MHz): δ 8.20-8.18 (d, J=7.0 Hz, 1H), 7.78-7.75 (m, 1H), 7.67-7.64 (m, 1H), 7.52-7.49 (m, 1H), 4.70 (m, 3H), 4.18 (m, 2H), 4.05 (m, 2H), 3.81 (s, 6H), 2.99-2.94 (t, J=11.4 Hz, 2H), 2.80 (s, 3H), 2.47-2.42 (m, 2H), 2.24-2.18 (m, 2H). MS (ESI+): 495.0. HPLC (max plot) 93.19%; Rt 3.18 min.

Compounds described below are obtained following protocol outlined in Procedure AP

---

Example 118: N-[3-(Morpholin-4-ylcarbonyl)-5,5-dioxido-1-phenyl-1,4-dihydrothiochromeno[4,3-c]pyrazol-8-yl]methanesulfonamide

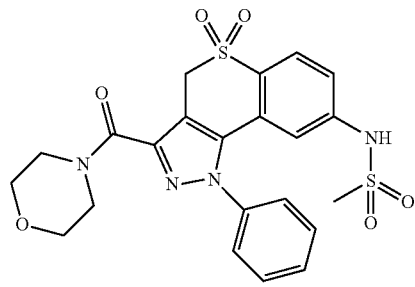 [SMILES: CS(=O)(=O)Nc1ccc2c(c1)-c1c(c(C(=O)N3CCOCC3)nn1-c1ccccc1)CS2(=O)=O]

5 mg of the title compound as an off white solid. $^1$H NMR (DMSO-d$_6$, 400 MHz): δ 10.47 (bs, 1H), 7.96-7.94 (d, J = 8.5 Hz, 1H), 7.60-7.59 (m, 3H), 7.53-7.52 (m, 2H), 7.28-7.26 (d, J = 8.6 Hz, 1H), 6.85 (S, 1H), 4.83 (s, 2H), 3.93 (m, 2H), 3.66 (m, 4H), 3.60 (m, 2H), 2.81 (s, 3H). MS (ESI+): 503.0. HPLC (max plot) 95.26%; Rt 3.26 min.

-continued

Example 180: N-{3-[3-(Morpholin-4-ylcarbonyl)-5,5-dioxidothiochromeno[4,3-c]pyrazol-1 (4H)-yl]phenyl}methanesulfonamide

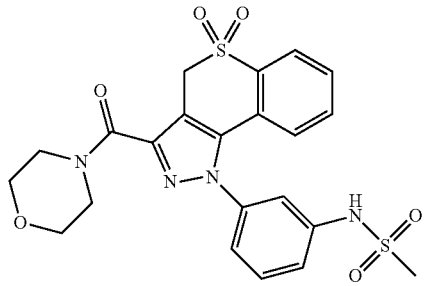 [SMILES: CS(=O)(=O)Nc1cccc(-n2nc(C(=O)N3CCOCC3)c3c2-c2ccccc2S(=O)(=O)C3)c1]

5 mg of the title product as an off white solid. $^1$H NMR (DMSO-d$_6$, 400 MHz): δ 10.10 (bs, 1H), 8.02-8 (d, J = 7.0 Hz, 1H), 7.65-7.60 (m, 2H), 7.58-7.53 (m, 1H), 7.40-7.38 (d J = 8.2 Hz, 1H), 7.25-7.21 (m, 2H), 6.95-6.93 (d, J = 7.2 Hz, 1H), 4.88 (s, 2H), 3.92 (m, 2H), 3.66 (m, 4H), 3.61 (m, 2H), 2.99 (s, 3H). MS (ESI+): 503.0. HPLC (max plot) 94.69%; Rt 3.35 min Example 135: 1[1-(Methylsulfonyl)piperidin-3-yl]-3-(morpholin-4-ylcarbonyl)-1,4-dihydrothiochromeno[4,3-c]pyrazole 5,5-dioxide

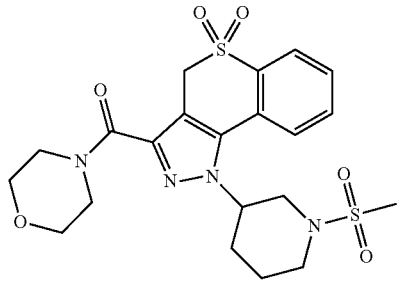 [SMILES: CS(=O)(=O)N1CCCC(n2nc(C(=O)N3CCOCC3)c3c2-c2ccccc2S(=O)(=O)C3)C1]

8 mg of the title compound as an off white solid. $^1$H NMR (DMSO-d$_6$, 400 MHz): δ 8.05-8.03 (d, J = 7.7 Hz, 1H), 7.90-7.89 (d, J = 3.7 Hz, 1H), 7.76-7.73 (m, 1H), 4.94-4.91 (m, 1H), 4.78 (s, 2H), 3.88 (bs, 1H), 3.82-3.80 (m, 2H), 3.65-3.64 (m, 7H), 3.17-3.11 (t, J = 10.6 Hz, 1H), 2.93 (s, 3H), 2.87-2.84 (t, J = 11.4 Hz, 1H), 2.22 (m, 1H), 2.10-2.07 (m, 1H), 1.94-1.91 (m, 1H), 1.82-1.79 (m, 1H). MS (ESI+ H$_2$0): 512.0. HPLC (max plot) 95.92%; Rt 3.26 min General Procedure AQ Example 152

N,N-Dimethyl-3-(morpholin-4-ylcarbonyl)-1-phenyl-1,4-dihydrothiochromeno[4,3-c]pyrazol-7-amine 5,5-dioxide

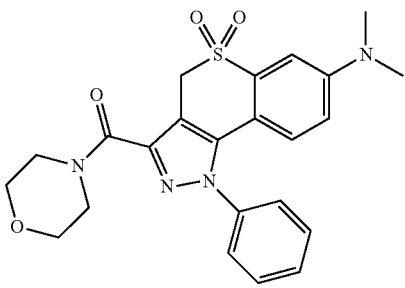 [SMILES: CN(C)c1ccc2c(c1)S(=O)(=O)Cc1c(C(=O)N3CCOCC3)nn(-c3ccccc3)c1-2]

7-bromo-3-(morpholin-4-ylcarbonyl)-1-phenyl-1,4-dihydrothiochromeno[4,3-c]pyrazole 5,5-dioxide (100 mg, 0.20 mmol, 1 eq.), NaOtBu (280 mg, 0.29 mmol, 1.4 eq.) are taken in degassed toluene in a sealed tube. Tris(dibenylidene acetone)dipalladium(0) (5 mg, 0.005 mmol, 0.025 eq.), 2-di-tertiary butyl phosphino-2',4',6'-triisopropyl biphenyl (3.5 mg, 0.008 mmol, 0.04 eq.) are then added followed by dimethylamine in THF (3 mL, 2 M) and the reaction mixture is heated at 90° C. for 16 h. After this time, reaction mixture is filtered through a celite pad, evaporated and purified by silica gel flash chromatography to afford the title compound as a pale brown solid. $^1$H NMR (DMSO-d$_6$, 400 MHz): δ 7.61-7.59 (m, 3H), 7.51-7.49 (m, 2H), 7.10 (s, 1H), 6.81-6.79 (dd, J=2.6, 9.0 Hz, 1H), 6.61-6.59 (d, J=9.0 Hz, 1H), 4.76 (s, 2H), 3.96 (m, 2H), 3.65 (m, 4H), 3.59 (m, 2H), 2.97 (s, 6H). MS (ESI+): 453.0. HPLC (max plot) 91.39%; Rt 4.20 min.

Compounds described below are obtained following protocol outlined in procedure AQ Example 177: N,N-Dimethyl-3-[3-(morpholin-4-ylcarbonyl)-5,5-dioxidothiochromeno[4,3-c]pyrazol-1 (4H)-yl]aniline

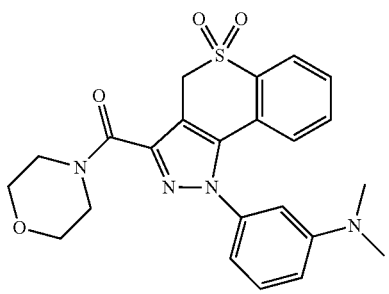 [SMILES: CN(C)c1cccc(-n2nc(C(=O)N3CCOCC3)c3c2-c2ccccc2S(=O)(=O)C3)c1]

12 mg of the title compound as a white solid. $^1$H NMR (DMSO-d$_6$, 400 MHz): δ 8.00-7.98 (m, 1H), 7.61-7.59 (m, 2H), 7.38-7.34 (m, 1H), 6.94-6.91 (m, 2H), 6.76 (s, 1H), 6.65-6.63 (d, J = 7.6 Hz, 1H), 4.88 (s, 2H), 3.94 (m, 2H), 3.66 (m, 4H), 3.60 (m, 2H), 2.92 (s, 6H). MS (ESI+): 453.0. HPLC (max plot) 99.67%: Rt 3.43 min Example 154: 3-(Morpholin-4-ylcarbonyl)-1-(3-morpholin-4-ylphenyl)-1,4-dihydrothiochromeno[4,3-c]pyrazole 5,5-dioxide

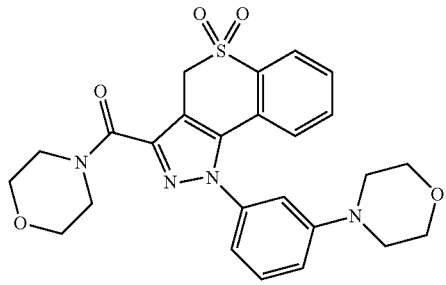 [SMILES: O=C(c1nn(-c2cccc(N3CCOCC3)c2)c2c1CS(=O)(=O)c1ccccc1-2)N1CCOCC1]

19 mg of the title compound as a pale brown solid. $^1$H NMR (DMSO-$d_6$, 400 MHz): δ 8.01-8.0 (d, J = 2.1 Hz, 1H), 7.62-7.59 (m, 2H), 7.44-7.40 (t, J= 8.2 Hz, 1H), 7.19-7.17 (m, 1H), 7.06 (s, 1H), 6.91-6.89 (m, 1H), 6.84-6.82 (d, J = 8.8 Hz, 1H), 4.88 (s, 2H), 3.93 (m, 2H), 3.72-3.69 (m, 4H), 3.66 (m, 4H), 3.61-3.60 (m, 2H), 3.17-3.15 (m, 4H), MS (ESI+): 495.0. HPLC (max plot) 98.46%; Rt 3.72 min Example 155: 3-(Morpholin-4-ylcarbonyl)-1-(4-morpholin-4-ylphenyl)-1,4-dihydrothiochromeno[4,3-c]pyrazole 5,5-dioxide

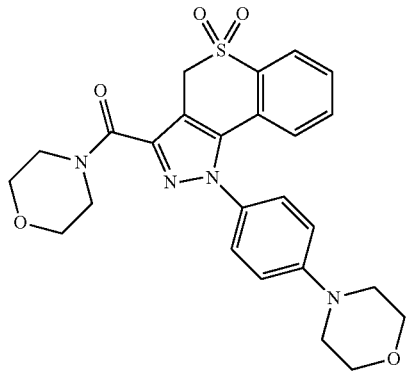 [SMILES: O=C(c1nn(-c2ccc(N3CCOCC3)cc2)c2c1CS(=O)(=O)c1ccccc1-2)N1CCOCC1]

3 mg of the title compound as an off white solid. $^1$H NMR (DMSO-$d_6$, 400 MHz): δ 8.00-7.98 (t, J = 3.2 Hz, 1H), 7.61-7.59 (m, 2H), 7.35-7.33 (m, 2H), 7.11-7.09 (m, 2H), 6.93-6.91 (t, J = 4.6 Hz, 1H), 4.87 (s, 2H), 3.95 (m, 2H), 3.76-3.75 (m, 4H), 3.65 (m, 4H), 3.60 (m, 2H), 3.24-3.23 (m, 4H). MS (ESI+): 495.0. HPLC (max plot) 94.20%; Rt 3.61 min.

Example 166: {3-[3-(Morpholin-4-ylcarbonyl)-5,5-dioxidothiochromeno[4,3-c]pyrazol-1(4H)-yl]phenyl}phenylamine

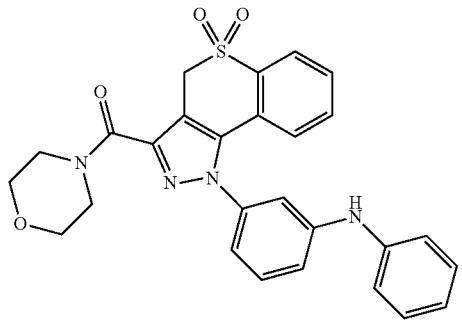 [SMILES: O=C(c1nn(-c2cccc(Nc3ccccc3)c2)c2c1CS(=O)(=O)c1ccccc1-2)N1CCOCC1]

4 mg of the title compound as a pale brown solid. $^1$H NMR (DMSO-$d_6$, 400 MHz): δ 8.54 (s, 1H), 8.02-8.0 (m, 1H), 7.68-7.65 (m, 2H), 7.45-7.41 (m, 1H), 7.25-7.17 (m, 3H), 7.06-7.01 (m, 4H), 6.91-6.85 (m, 2H), 4.87 (s, 2H), 3.94 (s, 2H), 3.66 (m, 2H), 3.66 (m, 4H), 3.61-3.60 (m, 2H). MS (ESI+): 501.0. HPLC (max plot) 99.16%; Rt 4.71 min Example 181: 3-(Morpholin-4-ylcarbonyl)-1-(3-pyrrolidin-1-ylphenyl)-1,4-dihydrothiochromeno[4,3-c]pyrazole 5,5-dioxide

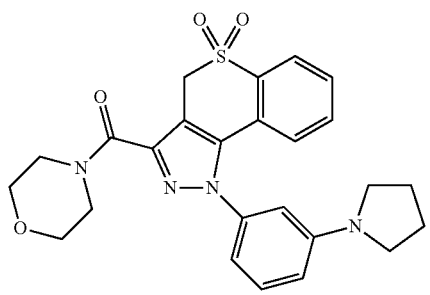 [SMILES: O=C(c1nn(-c2cccc(N3CCCC3)c2)c2c1CS(=O)(=O)c1ccccc1-2)N1CCOCC1]

12 mg of the title product as a pale brown solid. $^1$H NMR (DMSO-$d_6$, 400 MHz): δ 8.0-7.98 (dd, J = 2.6, 5.3 Hz, 1H), 7.63-7.59 (m, 2H), 7.35-7.31 (t, J = 7.8 Hz, 1H), 6.98-6.95 (dd, J = 3.9, 6.2 Hz, 1H), 6.75-6.73 (t, J = 7.4 Hz, 1H), 6.58-6.56 (m, 2H), 4.88 (s, 2H), 3.95 (m, 2H), 3.66 (m, 4H), 3.61 (m, 2H), 3.24-3.21 (m, 4H), 1.96-1.92 (m, 4H). MS (ESI+): 479.0. HPLC (max plot) 99.33%; Rt 4.71 min Example 368: 3-(Morpholin-4-ylcarbonyl)-1-(1-phenylpyrrolidin-3-yl)-1,4-dihydrothiochromeno[4,3-c]pyrazole 5,5-dioxide

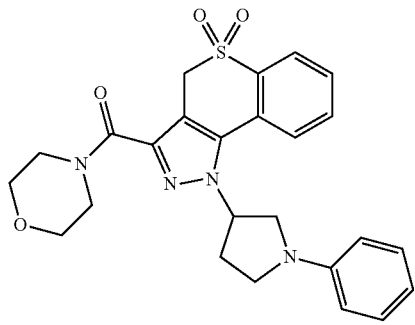 [SMILES: O=C(c1nn(C2CCN(c3ccccc3)C2)c2c1CS(=O)(=O)c1ccccc1-2)N1CCOCC1]

5 mg of the title compound as a white powder. MS (ESI+): 479.2. HPLC (max plot) 96.2%; Rt 4.58 min Example 218: 3-(Morpholin-4-ylcarbonyl)-1-(1-phenylpiperidin-3-yl)-1,4-dihydrothiochromeno[4,3-c]pyrazole 5,5-dioxide

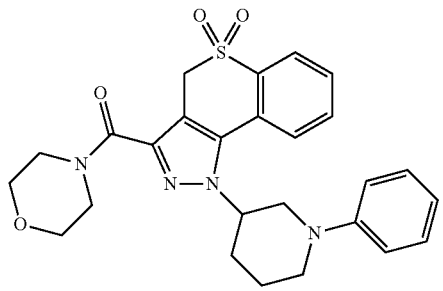 [SMILES: O=C(c1nn(C2CCCN(c3ccccc3)C2)c2c1CS(=O)(=O)c1ccccc1-2)N1CCOCC1]

7 mg of the title compound as an off white solid. $^1$H NMR (CDCl$_3$, 400 MHz) δ 8.19-8.16 (dd, J = 7.7, 0.9 Hz, 1H), 8.88-8.70 (m, 1H), 8.68-8.65 (m, 2H), 7.37-7.27 (m, 2H), 6.98-6.92 (m, 2H), 6.90 (m, 1H), 4.88 (m, 1H), 4.76-4.63 (m, 2H), 4.18-4.16 (m, 2H), 3.98-3.96 (m, 1H), 3.80-3.74 (m, 7H), 3.32-3.26 (t, J = 10.5 Hz, 1H), 2.89-2.86-(m, 1H), 2.29-2.25 (m, 2H), 2.06-2.03 (m, 1H), 1.95-2.0 (m, 1H). MS (ESI+): 493.0; HPLC (max plot) 99.09%; Rt 3.78 min.

Example 484: Enantiomer B of 3-(morpholin-4-ylcarbonyl)-1-[1-pyridin-3-ylpiperidin-3-yl]-1,4-dihydrothiochromeno[4,3-c]pyrazole 5,5-dioxide

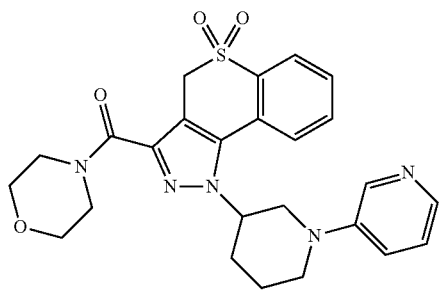 [SMILES: O=C(c1nn(C2CCCN(c3cccnc3)C2)c2c1CS(=O)(=O)c1ccccc1-2)N1CCOCC1]

7 mg of the title compound as a beige solid. $^1$H NMR (DMSO-d$_6$, 300 mHz) δ 8.35-8.36 (d, J = 3 Hz, 1H), 8.05-8.07 (d, J = 3 Hz, 1H), 7.99-8.00 (m, 1H), 7.88-7.89 (d, J = 3 Hz, 2H), 7.71-7.78 (m, 1H), 7.36-7.40 (m, 1H), 7.08-7.22 (m, 1H), 4.97 (bs, 1H), 4.81 (s, 2H), 4.10-4.12 (m, 1H), 3.92 (m, 2H), 3.77-3.81 (m, 1H), 3.62-3.66 (m, 5H), 3.27-3.31 (m, 1H), 2.83-2.92 (m, 1H), 1.90-2.22 (m, 5H). MS (ESI+): 494.2. HPLC (max plot) 95.05%; Rt 2.18 min.

Intermediate AQ-1: N-Methyl-3-(morpholin-4-ylcarbonyl)-1-phenyl-1,4-dihydrothiochromeno[4,3-c]pyrazol-6-amine

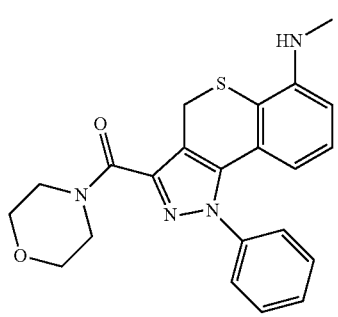 [SMILES: CNc1cccc2c1SCc1c(C(=O)N3CCOCC3)nn(-c3ccccc3)c1-2]

102 mg (76%) yield of the title compound. MS (ESI+): 407.0.

Example 156: N-(2-Methoxyethyl)-3-(morpholin-4-ylcarbonyl)-1-phenyl-1,4-dihydrothiochromeno[4,3-c]pyrazol-8-amine 5,5-dioxide

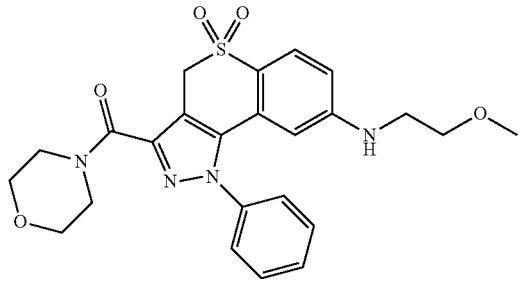 [SMILES: COCCNc1ccc2c(c1)-c1c(c(C(=O)N3CCOCC3)nn1-c1ccccc1)CS2(=O)=O]

9 mg of the title compound as a pale brown solid. $^1$H NMR (DMSO-$d_6$, 400 MHz): δ 7.63-7.54 (m, 4H), 7.53-7.52 (m, 2H), 6.77-6.74 (t, J = 5.6 Hz, 1H), 6.71-6.68 (dd, J = 2.0, 8.7 Hz, 1H), 5.88 (s, 1H), 4.68 (s, 2H), 3.94 (m, 2H), 3.65 (m, 4H), 3.59 (m, 2H), 3.19 (s, 3H), 3.17-3.12 (m, 2H), 2.49 (m, 2H). MS (ESI+): 483.0. HPLC (max plot) 95.75%; Rt 3.63 min Procedure AR Example 129

8-Methyl-3-(morpholin-4-ylcarbonyl)-1-phenyl-1,4-dihydrothiochromeno[4,3-c]pyrazole 5,5-dioxide

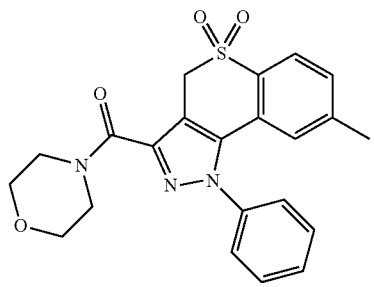 [SMILES: Cc1ccc2c(c1)-c1c(c(C(=O)N3CCOCC3)nn1-c1ccccc1)CS2(=O)=O]

8-bromo-3-(morpholin-4-ylcarbonyl)-1-phenyl-1,4-dihydrothiochromeno[4,3-c]pyrazole 5,5-dioxide (160 mg, 0.32 mmol) is dissolved in 1,4-Dioxane:water (4:2) to which is added methyltrifluoroborate potassium salt (80 mg, 0.65 mmol) and $K_2CO_3$ (90 mg, 0.65 mmol). The reaction mixture is degassed for 5 min and is added S-phos (6.5 mg, 0.016 mmol) followed by palladium acetate (3.6 mg, 0.016 mmol). The reaction mixture is heated under microwave for 2 h at 120° C. After this time, the reaction mass is concentrated and purified by silica gel flash chromatography to afford the title compound as an off white solid. $^1$H NMR (DMSO-$d_6$, 400 MHz): δ 7.90-7.88 (d, J=8.0 Hz, 1H), 7.64-7.62 (m, 3H), 7.54-7.52 (m, 2H), 7.43-6.55 (d, J=7.5 Hz, 1H), 6.55 (s, 1H), 4.85 (s, 2H), 3.94 (m, 2H), 3.66 (m, 4H), 3.62 (m, 2H), 2.11 (s, 3H). MS (ESI+): 424.0. HPLC (max plot) 91.94%; Rt 4.17 min.

Compounds described below are obtained following protocol outlined in procedure Ar Example 136: 1-[1-(Methylsulfonyl)piperidin-3-yl]-3-(morpholin-4-ylcarbonyl)-1,4-dihydrothiochromeno[4,3-c]pyrazole 5,5-dioxide

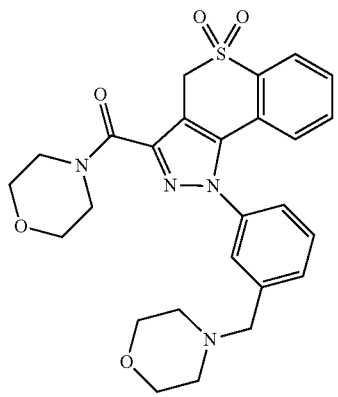 [SMILES: O=C(c1nn(-c2cccc(CN3CCOCC3)c2)c2c1CS(=O)(=O)c1ccccc1-2)N1CCOCC1]

21 mg of the title compound as a white solid. $^1$H NMR (DMSO-$d_6$, 400 MHz): δ 8.02-8.01 (d, J = 7.8 Hz, 1H), 7.65-7.59 (m, 2H), 7.55-7.36 (m, 3H), 7.36 (s, 1H), 6.82-6.80 (d, J =7.8 Hz, 1H), 4.90 (s, 2H), 3.93 (m, 2H), 3.67 (m, 4H), 3.60 (m, 2H), 3.52 (m, 2H), 3.47 (m, 4H), 2.31 (bs, 4H). MS (ESI+): 509.0. HPLC (max plot) 95.71%; Rt 2.49 min Intermediate AR-1: 6-Methyl-3-(morpholin-4-ylcarbonyl)-1-phenyl-1,4-dihydrothiochromeno[4,3-c]pyrazole

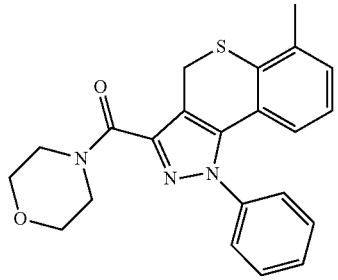 [SMILES: Cc1cccc2c1SCc1c(C(=O)N3CCOCC3)nn(-c3ccccc3)c1-2]

40 mg (93%) of the title compound. $^1$H NMR (DMSO-d$_6$, 400 MHz): δ 7.48-7.45 (m, 3H), 7.42-7.39 (m, 2H), 7.07-7.05 (d, J = 7.5 Hz, 1H), 6.81 (t, J = 7.7 Hz, 1H), 6.67-6.65 (d, J = 7.5 Hz, 1H), 4.18-4.16 (m, 4H), 3.81 (m, 4H), 3.75-3.74 (m, 2H), 2.42 (s, 3H).

Example 202: 6-Methyl-3-(morpholin-4-ylcarbonyl)-1-phenyl-1,4-dihydrothiochromeno[4,3-c]pyrazole 5,5-dioxide

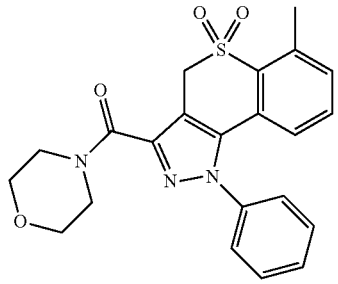 [SMILES: Cc1cccc2c1S(=O)(=O)Cc1c(C(=O)N3CCOCC3)nn(-c3ccccc3)c1-2]

13 mg of the title compound. $^1$H NMR (DMSO-d$_6$, 400 MHz): δ 7.59-7.58 (m, 3H), 7.46-7.43 (m, 2H), 7.38-7.37 (m, 2H), 6.69-6.67 (t, J = 5.1 Hz, 1H), 4.89 (s, 2H), 3.97 (m, 2H), 3.66 (m, 4H), 3.61 (m, 2H), 2.65 (s, 3H). MS (ESI+): 424.0. HPLC (max plot) 96.76%; Rt 4.22 min.

Example 139: 7-Methyl-3-(morpholin-4-ylcarbonyl)-1-phenyl-1,4-dihydrothiochromeno[4,3-c]pyrazole 5,5-dioxide

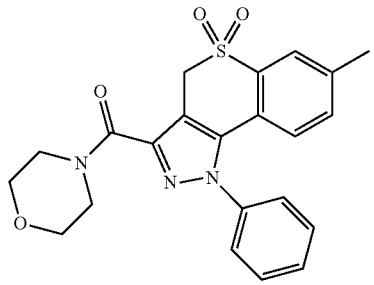 [SMILES: Cc1ccc2c(c1)S(=O)(=O)Cc1c(C(=O)N3CCOCC3)nn(-c3ccccc3)c1-2]

19 mg of the title compound as an off white solid. $^1$H NMR (DMSO-d$_6$, 400 MHz): δ 7.83 (s, 1H), 7.63-7.61 (m, 3H), 7.53-7.50 (m, 2H), 7.39-7.37 (d, J = 8.3 Hz, 1H), 6.71-6.69 (d, J = 8.0 Hz, 1H), 4.86 (s, 2H), 3.95 (m, 2H), 3.66 (m, 4H), 3.60 (m, 2H), 2.38 (s, 3H). MS (ESI+): 424.0. HPLC (max plot) 93.68%; Rt 4.18 min Example 162: 3-(Morpholin-4-ylcarbonyl)-8-(morpholin-4-ylmethyl)-1-phenyl-1,4-dihydrothiochromeno[4,3-c]pyrazole 5,5-dioxide

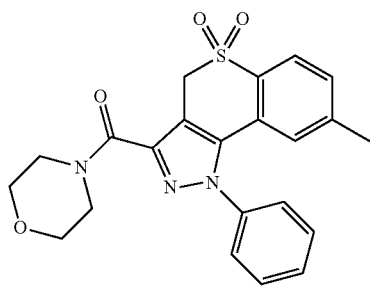

15.5 mg of the title compound as an off white solid. $^1$H NMR (DMSO-d$_6$, 400 MHz): δ 7.96-7.94 (d, J = 8.0 Hz, 1H), 7.64-7.62 (m, 3H), 7.54-7.52 (m, 3H), 6.86 (3, 1H), 4.87 (s, 2H), 3.94 (m, 2H), 3.66 (m, 4H), 3.60 (m, 2H), 3.42 (m, 4H), 3.30 (m, 2H), 2.13 (m, 4H), MS (ESI+): 508.8. HPLC (max plot) 96.17%; Rt 2.54 min Procedure AS Example 114

8-[(4-Methylpiperazin-1-yl)carbonyl]-3-(morpholin-4-ylcarbonyl)-1-phenyl-1,4-dihydrothiochromeno[4,3-c]pyrazole 5,5-dioxide

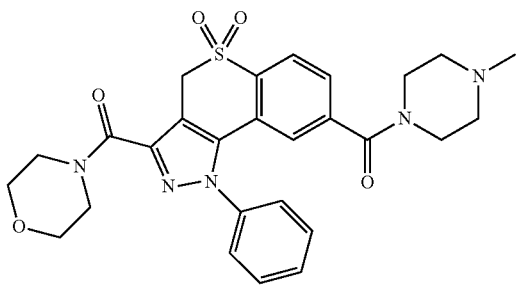 [SMILES: CN1CCN(C(=O)c2ccc3c(c2)-c2c(c(C(=O)N4CCOCC4)nn2-c2ccccc2)CS3(=O)=O)CC1]

To a solution 8-bromo-3-(morpholin-4-ylcarbonyl)-1-phenyl-1,4-dihydrothiochromeno[4,3-c]pyrazole 5,5-dioxide (200 mg, 0.4 mmol) in toluene (10 mL) is added Na$_2$CO$_3$ (65 mg, 0.6 mmol) and N-methyl piperidine (961 mg, 0.6 mmol). The reaction mixture is purged with nitrogen for 15 min after which it is purged with carbon monoxide followed by palladium acetate (4.4 mg, 0.02 mmol) and Xanthphos (11 mg, 0.02 mmol). The reaction mixture is heated at 110° C. and refluxed for 12 h under carbon monoxide atmosphere. After this time, solvents are removed under reduced pressure and compound purified by silica gel flash chromatography to afford the title compound as an off white solid. $^1$H NMR (DMSO-d$_6$, 400 MHz): δ 8.08-8.06 (d, J =7.6 Hz, 1H), 7.63-7.61 (m, 4H), 7.57-7.55 (m, 21-1), 6.71 (s, 1H), 4.93 (s, 211), 3.94 (m, 211), 3.66-3.60 (m, 6H), 3.45 (bs, 2H), 3.00 (bs, 2H), 2.21 (m, 2H), 2.16 (s, 3H), 2.05 (bs, 2H). MS (ESI+): 536.0. HPLC (max plot) 95.74%; Rt 2.45 min.

Example 115

N,N-Dimethyl-3-(morpholin-4-ylcarbonyl)-1-phenyl-1,4-dihydrothiochromeno[4,3-c]pyrazole-8-carboxamide 5,5-dioxide

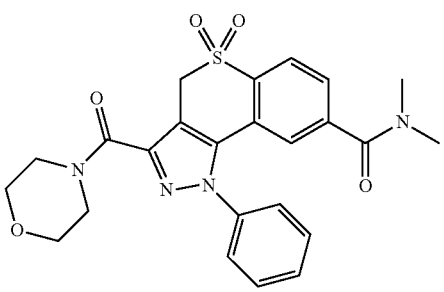 [SMILES: CN(C)C(=O)c1ccc2c(c1)-c1c(c(C(=O)N3CCOCC3)nn1-c1ccccc1)CS2(=O)=O]

Following new Procedure AS, N,N-dimethyl-3-(morpholin-4-ylcarbonyl)-1-phenyl-1,4-dihydrothiochromeno[4,3-c]pyrazole-8-carboxamide 5,5-dioxide is obtained from 8-bromo-3-(morpholin-4-ylcarbonyl)-1-phenyl-1,4-dihydrothiochromeno[4,3-c]pyrazole 5,5-dioxide and N,N-dimethylamine to afford the title compound as an off white solid. $^1$H NMR (DMSO-d$_6$, 400 MHz): δ 8.08-8.06 (d, J=8.0 Hz, 1H), 7.65-7.54 (m, 6H), 6.75 (s, 1H), 4.94 (s, 2H), 3.94 (m, 2H), 3.66 (m, 4H), 3.60 (m, 2H), 2.84 (s, 3H), 2.62 (s, 3H). MS (ESI+): 481. HPLC (max plot) 95.16%; Rt 3.19 min.

Example 116

3,8-Bis(morpholin-4-ylcarbonyl)-1-phenyl-1,4-dihydrothiochromeno[4,3-c]pyrazole 5,5-dioxide

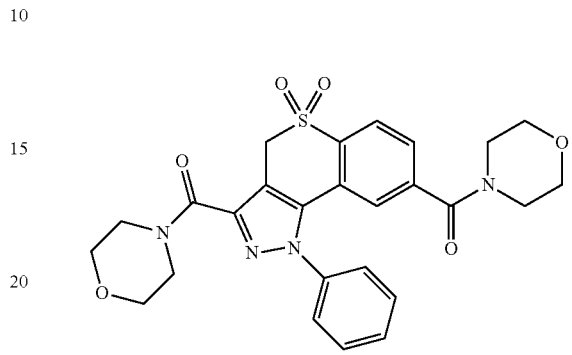

Following new Procedure AS, 3,8-bis(morpholin-4-ylcarbonyl)-1-phenyl-1,4-dihydrothiochromeno[4,3-c]pyrazole 5,5-dioxide is obtained from 8-bromo-3-(morpholin-4-ylcarbonyl)-1-phenyl-1,4-dihydrothiochromeno[4,3-c]pyrazole 5,5-dioxide and morpholine to afford the title compound as an off white solid. $^1$H NMR (DMSO-d$_6$, 400 MHz): δ 8.09-8.07 (d, J=8.0 Hz, 1H), 7.67-7.64 (m, 4H), 7.57-7.54 (m, 2H), 6.75 (s, 1H), 4.93 (s, 2H), 3.94 (m, 2H), 3.66 (m, 4H), 3.61 (m, 2H), 3.49 (m, 4H), 3.3 (m, 2H), 3.03 (m, 2H). MS (ESI+): 523.0. HPLC (max plot) 95.86%; Rt 3.17 min.

Example 117

3-(Morpholin-4-ylcarbonyl)-1-phenyl-8-(piperidin-1-ylcarbonyl)-1,4-dihydrothiochromeno[4,3-c]pyrazole 5,5-dioxide

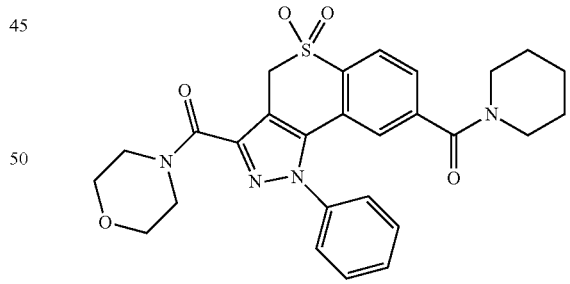

Following new Procedure AS, 3-(morpholin-4-ylcarbonyl)-1-phenyl-8-(piperidin-1-ylcarbonyl)-1,4-dihydrothiochromeno[4,3-c]pyrazole 5,5-dioxide is obtained from 8-bromo-3-(morpholin-4-ylcarbonyl)-1-phenyl-1,4-dihydrothiochromeno[4,3-c]pyrazole 5,5-dioxide and piperidine to afford the title compound as an off white solid. $^1$H NMR (DMSO-d$_6$, 400 MHz): δ 8.07-8.05 (d, J=8.0 Hz, 1H), 7.63-7.53 (m, 6H), 6.68 (s, 1H), 4.93 (s, 2H), 3.94 (m,2H), 3.66 (m, 4H), 3.61 (m, 2H), 3.42 (m, 2H), 2.98 (m, 2H), 1.54 (m, 2H), 1.40 (m, 2H), 1.22 (m, 2H). MS (ESI+): 521.0. HPLC (max plot) 93.95%; Rt 3.89 min.

Procedure AT

Example 157

1-Biphenyl-3-yl-3-(morpholin-4-ylcarbonyl)-1,4-dihydrothiochromeno[4,3-c]pyrazole 5,5-dioxide

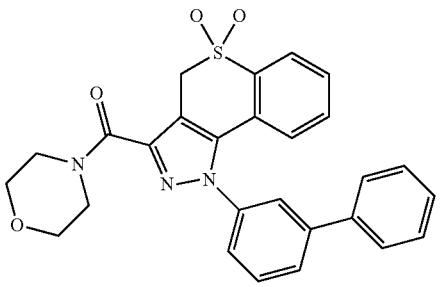 [SMILES: O=C(c1nn(-c2cccc(-c3ccccc3)c2)c2c1CS(O)(O)c1ccccc1-2)N1CCOCC1]

1-(3-Bromophenyl)-3-(morpholin-4-ylcarbonyl)-1,4-dihydrothiochromeno[4,3-c]pyrazole 5,5-dioxide (100 mg, 0.20 mmol), phenylboronic acid (37 mg, 0.31 mmol), cesium fluoride (124 mg, 0.82 mmol) are taken in dioxane-water (2:1) and bubbled with nitrogen for 5 min. Then bis(triphenyl phosphine)dichloro palladium(II) (21 g, 0.03 mmol) is added to reaction mass and heated under microwave irradiation for 1 h at 90° C. The reaction mixture is filtered through a celite pad, concentrated under reduced pressure and purified by flash chromatography to afford the title compound as a pale yellow solid. $^1$H NMR (DMSO-$d_6$, 400 MHz): δ 8.03-8.01 (m,1H), 7.95-7.93 (d, J=8.0 Hz, 1H),7.83 (s, 1H), 7.72-7.70 (m, 4H), 7.68-7.60 (m, 2H), 7.59-7.47 (m, 3H), 7.45-7.40 (m, 1H), 4.91 (s, 2H), 3.96 (m, 4H), 3.62-3.61 (m, 2H). MS (ESI+): 486.0. HPLC (max plot) 98.53%; Rt 4.84 min.

Compounds described below are obtained following protocol outlined in procedure AT

---

Example 160: 1-(2'-Methylbiphenyl-3-yl)-3-(morpholin-4-ylcarbonyl)-1,4-dihydrothiochromeno[4,3-c]pyrazole 5,5-dioxide

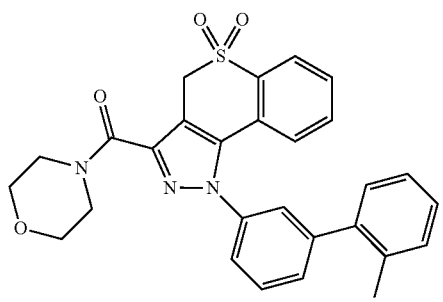 [SMILES: Cc1ccccc1-c1cccc(-n2nc(C(=O)N3CCOCC3)c3c2-c2ccccc2S(=O)(=O)C3)c1]

54 mg of the title compound as a pale yellow solid. $^1$H NMR (DMSO-$d_6$, 400 MHz): δ 8.01-8.00 (d, J = 3.6 Hz, 1H), 7.72-7.70 (m, 1H), 7.68-7.55 (m, 4H), 7.43 (s, 1H), 7.29-7.21 (m, 4H), 6.97-6.95 (dd, J = 3.7, 6.2 Hz, 1H), 4.90 (s, 2H), 3.95 (m, 2H), 3.66 (m, 4H), 3.61-3.60 (m, 2H), 2.21 (s, 3H). MS (ESI+): 500.0. HPLC (max plot) 97.85%; Rt 5.10 min.

Example 161: 1-(2'-Methylbiphenyl-4-yl)-3-(morpholin-4-ylcarbonyl)-1,4-dihydrothiochromeno[4,3-c]pyrazole 5,5-dioxide

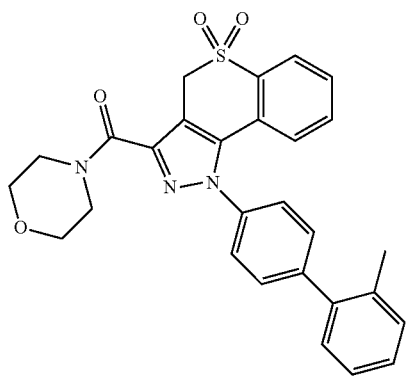 [SMILES: Cc1ccccc1-c1ccc(-n2nc(C(=O)N3CCOCC3)c3c2-c2ccccc2S(=O)(=O)C3)cc1]

35 mg of the title compound as a pale yellow solid. $^1$H NMR (DMSO-$d_6$, 400 MHz): δ 8.04-8.01 (d, J = 8.7 Hz, 1H), 7.66-7.58 (m, 6H), 7.34-7.31 (m, 4H), 6.94-6.92 (d, J = 7.3 Hz, 1H), 4.91 (s, 2H), 3.68-3.63 (m, 6H), 2.30 (s, 3H). MS (ESI+): 499.8. HPLC (max plot) 97.87%; Rt 5.15 min Example 197: 1-[3-(3-Furyl)phenyl]-3-(morpholin-4-ylcarbonyl)-1,4-dihydrothiochromeno[4,3-c]pyrazole 5,5-dioxide

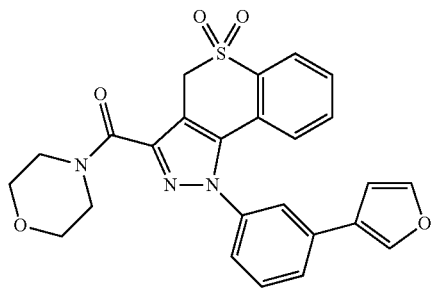 [SMILES: O=C(c1nn(-c2cccc(-c3ccoc3)c2)c2c1CS(=O)(=O)c1ccccc1-2)N1CCOCC1]

63 mg of the title compound. $^1$H NMR (DMSO-d$_6$, 400 MHz): δ 8.35 (s, 1H), 8.02-8 (m, 1H), 7.90-7.88 (d, J = 7.9 Hz, 1H), 7.86 (s, 1H), 7.76 (s, 1H), 7.63-7.59 (m, 1H), 7.57 (m, 3H), 7.36-7.34 (d, J = 7.6 Hz, 1H), 7.07 (s, 1H), 6.91-6.89 (d, J = 8.6 Hz, 1H), 4.91 (s, 2H), 3.95-3.94 (m, 2H), 3.67 (m, 4H), 3.62-3.61 (m, 2H). MS (ESI+): 476.0. HPLC (max plot) 98.26%; Rt 4.5 min.

Example 184: 1-[3-(3,5-Dimethylisoxazol-4-yl)phenyl]-3-(morpholin-4-ylcarbonyl)-1,4-dihydrothiochromeno[4,3-c]pyrazole 5,5-dioxide

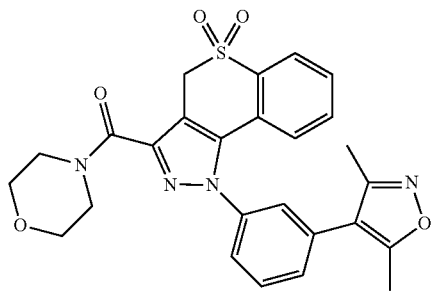 [SMILES: Cc1noc(C)c1-c1cccc(-n2nc(C(=O)N3CCOCC3)c3c2-c2ccccc2S(=O)(=O)C3)c1]

38 mg of the title compound as a white solid. $^1$H NMR (DMSO-d$_6$, 400 MHz): δ 8.03-8.01 (m, 1H), 7.65-7.60 (m, 3H), 7.57-7.53 (m, 2H), 6.95-6.94 (d, J = 7.0 Hz, 1H), 4.9 (s, 2H), 3.95 (m, 2H), 3.66 (m, 4H), 3.62-3.61 (m, 2H), 2.37 (s, 3H), 2.18 (s, 3H). MS (ESI+): 505.0. HPLC (max plot) 97.82%; Rt 4.14 min Example 185: 1-[3-(1-Methyl-1H-pyrazol-4-yl)phenyl]-3-(morpholin-4-ylcarbonyl)-1,4-dihydrothiochromeno[4,3-c]pyrazole 5,5-dioxide

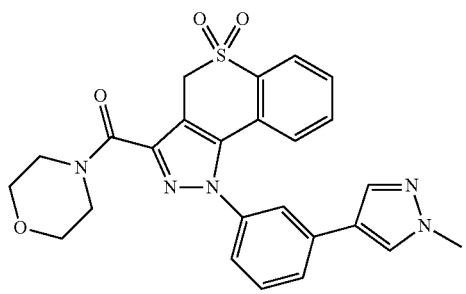 [SMILES: Cn1cc(-c2cccc(-n3nc(C(=O)N4CCOCC4)c4c3-c3ccccc3S(=O)(=O)C4)c2)cn1]

17 mg of the title compound as a pale brown solid. $^1$H NMR (DMSO-d$_6$, 400 MHz): δ 8.01-8.0 (m, 1H), 7.84-7.63 (m, 2H), 7.63-7.58 (m, 2H), 7.58-7.55 (m, 3H), 7.29-7.26 (m, 1H), 6.91-6.89 (m, 1H), 4.90 (s, 2 H), 3.95 (m, 2H), 3.83 (s, 3H), 3.67 (m, 4H), 3.62 (m, 2H). MS (ESI+): 490.0. HPLC (max plot) 97.49%; Rt 3.64 min Example 186: 5-{3-[3-(Morpholin-4-ylcarbonyl)-5,5-dioxidothiochromeno[4,3-c]pyrazol-1(4H)-yl]phenyl}pyrimidin-2-amine

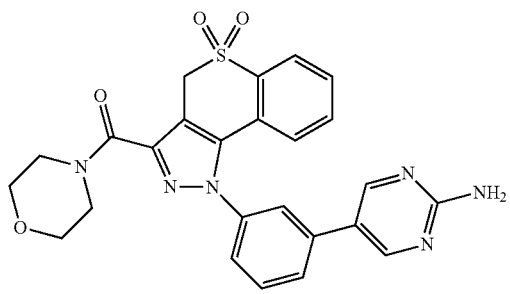 [SMILES: Nc1ncc(-c2cccc(-n3nc(C(=O)N4CCOCC4)c4c3-c3ccccc3S(=O)(=O)C4)c2)cn1]

51 mg of the title compound as a pale brown solid. $^1$H NMR (DMSO-d$_6$, 400 MHz): δ 8.63 (s, 2H), 8.02-8.0 (d, J = 7.4 Hz, 1H), 7.90-7.88 (m, 2H), 7.65-7.58 (m, 3H), 7.40-7.38 (d, J = 7.9 Hz, 1H), 6.95-6.93 (d, J = 7.7 Hz, 1H), 6.89 (s, 2H), 4.91 (s, 2H), 3.96 (m, 2H), 3.67 (m, 4H), 3.61 (m, 2H). MS (ESI+): 503.0. HPLC (max plot) 98.86%; Rt 2.88 min Example 187: 3-(Morpholin-4-ylcarbonyl)-1-(3-pyridin-4-ylphenyl)-1,4-dihydrothiochromeno[4,3-c]pyrazole 5,5-dioxide

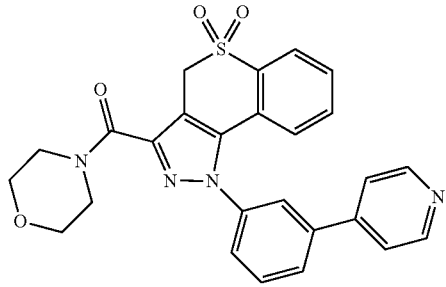 [SMILES: O=C(c1nn(-c2cccc(-c3ccncc3)c2)c2c1CS(=O)(=O)c1ccccc1-2)N1CCOCC1]

12 mg of the title compound as a pale brown solid. $^1$H NMR (DMSO-d$_6$, 400 MHz): δ 8.66-8.65 (d, J = 4.6 Hz, 2H), 8.09-8.07 (d, J = 8.2 Hz, 1H), 8.03-8.02 (d, J = 8.3 Hz, 2H), 7.78-7.76 (m, 3H), 7.63-7.58 (m, 3H), 6.94-6.92 (d, J = 7.8 Hz, 1H), 4.92 (s, 2H), 3.95 (bs, 2H), 3.67 (bs, 4H), 3.61 (bs, 2H). MS (ESI+): 487.0. HPLC (max plot) 97.27%; Rt 2.68 min Example 188: 3-(Morpholin-4-ylcarbonyl)-1-{3-[1-(2-morpholin-4-ylethyl)-1H-pyrazol-4-yl]phenyl}-1,4-dihydrothiochromeno[4,3-c]pyrazole 5,5-dioxide

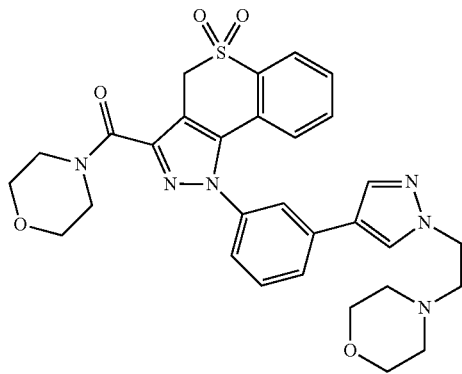 [SMILES: O=C(c1nn(-c2cccc(-c3cnn(CCN4CCOCC4)c3)c2)c2c1CS(=O)(=O)c1ccccc1-2)N1CCOCC1]

25 mg of the title compound as a white solid. $^1$H NMR (DMSO-d$_6$, 400 MHz): δ 8.30 (s, 1H), 8.02-8.0 (m, 1H), 7.98 (s, 1H), 7.84-7.83 (d, J = 7.9 Hz, 1H), 7.76 (s, 1H), 7.61-7.55 (m, 3H), 7.28-7.27 (d, J = 7.2 Hz, 1H), 6.92-6.90 (d, J = 8.0 Hz, 1H), 4.90 (s, 2H), 4.22-4.19 (t, J = 6.4 Hz, 2H), 3.95 (m, 2H), 3.67 (m, 4H), 3.62-3.61 (m, 2H), 3.52-3.50 (m, 4H), 2.72-2.68 (t, J = 6.5 Hz, 2H), 2.38 (m, 4H). MS (ESI+): 589.0. HPLC (max plot) 99.69%; Rt 3.04 min.

Example 198: 3-(Morpholin-4-ylcarbonyl)-1-(3-pyridin-3-ylphenyl)-1,4-dihydrothiochromeno[4,3-c]pyrazole 5,5-dioxide

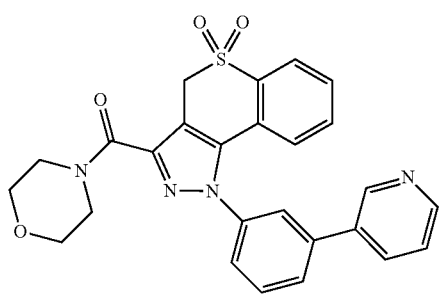 [SMILES: O=C(c1nn(-c2cccc(-c3cccnc3)c2)c2c1CS(=O)(=O)c1ccccc1-2)N1CCOCC1]

48 mg of the title compound. $^1$H NMR (DMSO-d$_6$, 400 MHz): δ 8.94 (s, 1H), 8.61-8.59 (d, J = 4.7 Hz, 1H), 8.15-8.13 (d, J = 8.0 Hz, 1H), 8.03-7.97 (m, 3H), 7.75-7.71 (t, J = 7.9 Hz, 1 H), 7.65-7.48 (m, 4H), 6.96-6.95 (d, J = 7.7 Hz, 1H), 4.91 (s, 2H), 3.96 (m 2H), 3.67 (m, 4H), 3.62-3.61 (m, 2H). MS (ESI+): 487.0. HPLC (max plot) 99.58%; Rt 2.68 min.

Procedure AU

Example 164

{3-[3-(Morpholin-4-ylcarbonyl)-5,5-dioxidothiochromeno[4,3-c]pyrazol-1(4H)-yl]phenyl}amine

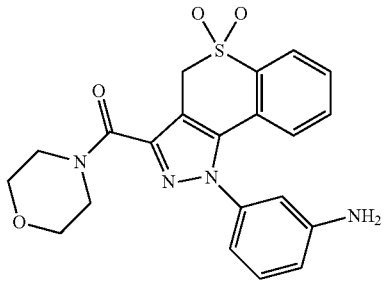 [SMILES: Nc1cccc(-n2nc(C(=O)N3CCOCC3)c3c2-c2ccccc2S(O)(O)C3)c1]

1-(3-bromophenyl)-3-(morpholin-4-ylcarbonyl)-1,4-dihydrothiochromeno[4,3-c]pyrazole 5,5-dioxide (150 mg, 0.31 mmol), cupric acetate (6.1 mg, 0.031 mmol), cesium carbonate (200 mg, 0.616 mmol) and acetyl acetone (13 □L, 0.123 mmol) are taken in a sealed tube to which is added a solution of DMF purged with NH₃ gas. The reaction mixture is heated to 90° C. for 24 h. After this time, reaction mixture is concentrated under reduced pressure and purified by silica gel column chromatography (100% EtOAc) to afford the title compound as a pale brown solid. ¹H NMR (DMSO-d₆, 400 MHz): δ 7.99-7.97 (m, 1H), 7.62-7.60 (m, 1H), 7.24-7.20 (t, J=7.8 Hz, 1H), 6.98-6.95 (m, 1H), 6.75-6.73 (d, J=9.3 Hz, 1H), 6.58-6.56 (m, 2H), 5.57 (s, 2H), 4.87 (s, 2H), 3.95 (m, 2H), 3.66 (m, 6H). MS (ESI+): 425.0.; HPLC (max plot) 94.69%; Rt 2.65 min.

Example 165

3-(Morpholin-4-ylcarbonyl)-1-phenyl-1,4-dihydrothiochromeno[4,3-c]pyrazol-7-amine 5,5-dioxide

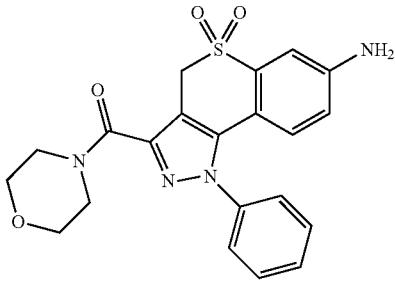 [SMILES: Nc1ccc2c(c1)S(=O)(=O)Cc1c(C(=O)N3CCOCC3)nn(-c3ccccc3)c1-2]

Following the protocol outlined in Procedure AU, 3-(morpholin-4-ylcarbonyl)-1-phenyl-1,4-dihydrothiochromeno[4,3-c]pyrazol-7-amine 5,5-dioxide is obtained from 7-bromo-3-(morpholin-4-ylcarbonyl)-1-phenyl-1,4-dihydrothiochromeno[4,3-c]pyrazole 5,5-dioxide and NH₃ gas to afford the title compound as a pale brown solid. ¹H NMR (DMSO-d₆, 400 MHz): δ 7.60-7.58 (m, 3H), 7.49-7.47 (m, 2H), 7.16 (s, 1H), 6.54 (m, 1H), 6.47 (m, 1H), 6.15 (s, 2H), 4.72 (s, 2H), 3.95 (m, 2H), 3.65 (m, 4H), 3.59 (m, 2H). MS (ESI+): 425.0. HPLC (max plot) 95.93%; Rt 3.36 min.

Example 65

3-(Morpholin-4-ylcarbonyl)-1-phenyl-1,4-dihydrothiochromeno[4,3-c]pyrazol-8-amine 5,5-dioxide

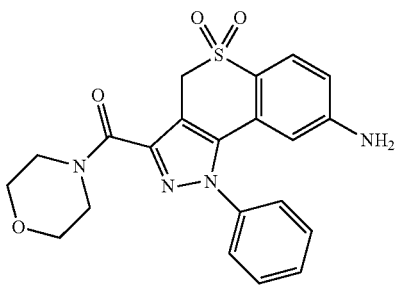

Following the protocol outlined in Procedure AU, 3-(morpholin-4-ylcarbonyl)-1-phenyl-1,4-dihydrothiochromeno[4,3-c]pyrazol-8-amine 5,5-dioxide is obtained from 8-bromo-3-(morpholin-4-ylcarbonyl)-1-phenyl-1,4-dihydrothiochromeno[4,3-c]pyrazole 5,5-dioxide and NH3 gas to afford the title compound as a pale brown solid. 1H NMR (400 MHz, DMSO-d6) δ =7.61-7.58 (m, 4H), 7.50-7.48 (m, 2H), 6.62 (dd, J=8.6, 2.1 Hz, 1H), 6.04 (s, 2H), 6.00 (d, J=1.9 Hz, 1H), 4.65 (s, 2H), 3.92 (bs, 2H), 3.65-3.59 (m, 6H). MS (ESI+): 425.0. HPLC (max plot) 94.64%; Rt 3.11 min.

Examples described below are obtained following protocol outlined in procedure Z, described above:

---

Example 456: N-{4-[3-(Morpholin-4-ylcarbonyl)-5,5-dioxidothiochromeno[4,3-c]pyrazol-1(4H)-yl]benzyl}tetrahydrofuran-3-amine

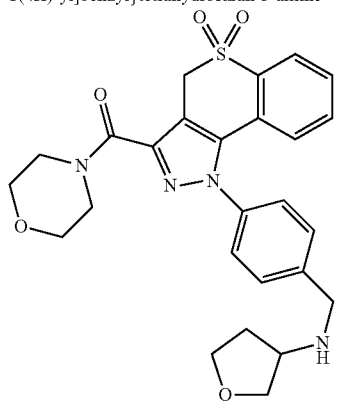

69 mg of the title compound as a beige powder. ¹H NMR (DMSO-d₆, 300 MHz): δ 8.07-8.-7.98 (m, 1H), 7.70-7.51 (m, 4H), 7.51-7.42 (m, 2H), 6.90-6.80 (m, 1H), 4.90 (s, 2H), 4.02-3.89 (m, 2H), 3.84-3.55 (m, 11H), 3.50-3.43 (m, 1H), 2.04-1.88 (m, 1H), 1.79-1.64 (m, 1H), 1.13-1.06 (m, 1H). MS (ESI+): 509.21. HPLC (max plot) 98.7%; Rt 2.12 min Example 208: 1-[(1-Methylpiperidin-4-yl)methyl]-3-(morpholin-4-ylcarbonyl)-1,4-dihydrothiochromeno[4,3-c]pyrazole 5,5-dioxide

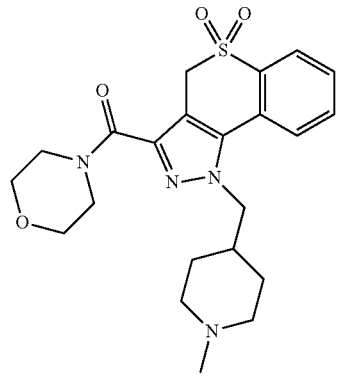 [SMILES: CN1CCC(Cn2nc(C(=O)N3CCOCC3)c3c2-c2ccccc2S(=O)(=O)C3)CC1]

30 mg of the title compound. $^1$H NMR (DMSO-$d_6$, 400 MHz): δ 8.02-7.98 (m, 2H), 7.88 (m, 1H), 7.71 (m, 1H), 4.77 (s, 2H), 4.47-4.46 (d, J = 7.4 Hz, 2H), 3.91 (m, 2H), 3.65-3.63 (m, 4H), 2.65 (m, 4H), 2.06 (s, 3H), 1.73-1.67 (m, 2H), 1.44-1.41 (m, 2H), 1.22 (m, 2H). MS (ESI+): 445.0. HPLC (max plot) 96.75%; Rt 2.19 min Example 77: 1-(1-Methylpiperidin-3-yl)-3-(morpholin-4-ylcarbonyl)-1,4-dihydrothiochromeno[4,3-c]pyrazole 5,5-dioxide

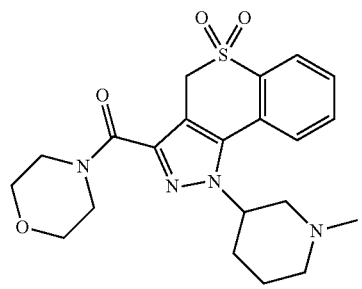 [SMILES: CN1CCCC(n2nc(C(=O)N3CCOCC3)c3c2-c2ccccc2S(=O)(=O)C3)C1]

10.3 mg of the title compound as an off white solid. $^1$H NMR (DMSO-$d_6$, 400 MHz) δ 8.17-8.15 (dd, J = 7.7, 1.1 Hz, 1H), 7.79-7.75 (t, J = 7.5 Hz, 1H), 7.67-7.61 (m, 1H), 4.82 (m, 1H), 4.75-58 (m, 2H), 4.16 (m, 2H), 3.80-(m, 6H), 3.19-3.17 (m, 1H), 2.97-2.94 (m, 1H), 2.54-2.48 (m, 1H), 2.4 (s, 3H), 2.18-2.17-(m, 3H), 2.14-2.10 (m, 2H). MS (ESI+): 431.0; HPLC (max plot) 94.65%; Rt 2.29 min Example 405: 3-(Morpholin-4-ylcarbonyl)-1-{1-[2-(tetrahydro-2H-pyran-4-yl)ethyl]azetidin-3-yl}-1,4-dihydrothiochromeno[4,3-c]pyrazole 5,5-dioxide

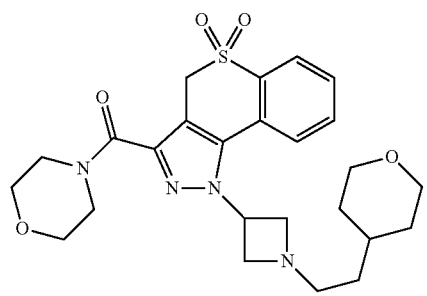 [SMILES: O=C(c1nn(C2CN(CCC3CCOCC3)C2)c2c1CS(=O)(=O)c1ccccc1-2)N1CCOCC1]

107 mg of the title compound as a white foam. $^1$H NMR (DMSO-$d_6$) δ 8.04-8.01 (m, 1H), 7.92-7.83 (m, 2H), 7.76-7.70 (m, 1H), 5.54-5.45 (quint, J = 6.75 Hz, 1H), 4.79 (s, 2H), 3.95-3.78 (m, 6H), 3.67 (s, 6H), 3.45-3.40 (m, 2H), 3.30-3.21 (m, 2H), 1.57-1.53 (m, 3H), 1.28-1.11 (m, 4H), 2.53 (m, 2H). HPLC (max plot) 98.0%; Rt 6.13 min. MS (ESI+): 501.2.

Example 299: 2{3-[3-(Morpholin-4-ylcarbonyl)-5,5-dioxidothiochromeno[4,3-c]pyrazol-1(4H)-yl]pyrrolidin-1-yl)ethyl acetate

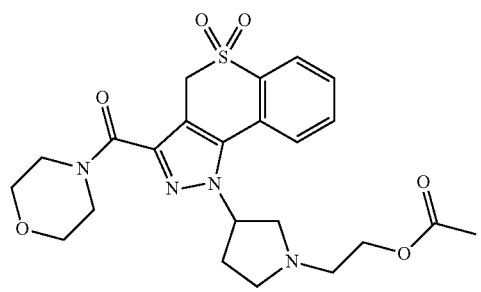 [SMILES: CC(=O)OCCN1CCC(n2nc(C(=O)N3CCOCC3)c3c2-c2ccccc2S(=O)(=O)C3)C1]

270 mg of the title compound as a brown foam.. HPLC (max plot) 99.0%; R12.28 min. (ESI+): 465.2:

Example 300: 3-(Morpholin-4-ylcarbonyl)-1-[1-(tetrahydro-2H-pyran-4-yl)pyrrolidin-3-yl]-1,4-dihydrothiochromeno[4,3-c]pyrazole 5,5-dioxide

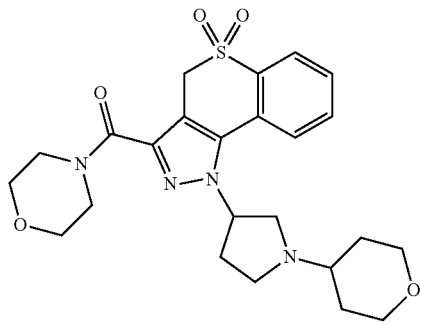 [SMILES: O=C(c1nn(C2CCN(C3CCOCC3)C2)c2c1CS(=O)(=O)c1ccccc1-2)N1CCOCC1]

47 mg of the title compound as a white foam. $^1$H NMR (DMSO-$d_6$) δ 8.03 (d, J = 7.7 Hz, 1H), 8.00-7.95 (m, 1H), 7.93-7.86 (m, 1H), 7.73 (t, J = 7.7 Hz, 1H), 5.54-5.42 (m, 1H), 4.85-4.72 (m, 2H), 4.01-3.94 (m, 2H), 3.88-3.80 (m, 2H), 3.71-3.62 (m, 6H), 3.36-3.25 (m, 4H), 2.92-2.88 (m, 1H), 2.79 (t, J = 6.7 Hz, 2H), 2.48-2.15 (m, 3H), 1.83-1.73 (m, 2H), 1.47-1.27 (m, 2H). HPLC (max plot) 100%; Rt 2.20 min. MS (ESI+): 487.2.

Example 303: 3-(Morpholin-4-ylcarbonyl)-1-[1-(tetrahydrofuran-3-ylmethyl)pyrrolidin-3-yl]-1,4-dihydrothiochromeno[4,3-c]pyrazole 5,5-dioxide

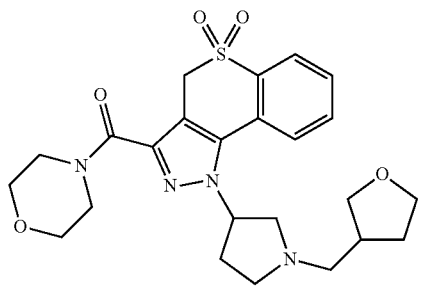 [SMILES: O=C(c1nn(C2CCN(CC3CCOC3)C2)c2c1CS(=O)(=O)c1ccccc1-2)N1CCOCC1]

50 mg of the title compound as a white foam. $^1$H NMR (DMSO-$d_6$) δ 8.03 (d, J = 7.7 Hz, 1H), 8.00-7.95 (m, 1H), 7.93-7.86 (m, 1H), 7.73 (t, J = 7.7 Hz, 1H), 5.54-5.42 (m, 1H), 4.85-4.72 (m, 2H), 4.01-3.94 (m, 2H), 3.80-3.56 (m, 9H), 3.41-3.34 (m, 1H), 3.31-3.21 (m, 1H), 2.92-2.82 (m, 1H), 2.81-2.69 (m, 2H), 2.48-2.30 (m, 4H), 2.28-2.14 (m, 1H), 2.01-1.87 (m, 1H), 1.59-1.45 (m, 1H). HPLC (max plot) 99.3%; Rt 2.22 min. MS (ESI+): 487.2.

Example 270: 3-(Morpholin-4-ylcarbonyl)-1-{1-[2-(tetrahydro-2H-pyran-4-yl)ethyl]pyrrolidin-3-yl}-1,4-dihydrothiochromeno[4,3-c]pyrazole 5,5-dioxide

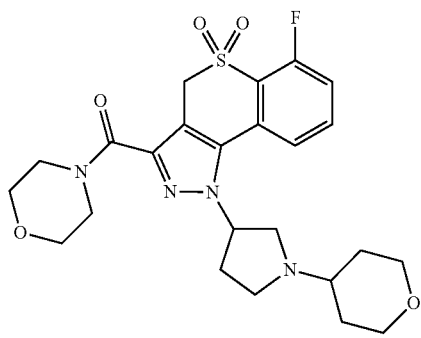 [SMILES: O=C(c1nn(C2CCN(C3CCOCC3)C2)c2c1CS(=O)(=O)c1c(F)cccc1-2)N1CCOCC1]

60 mg of the title compound as a white foam. HPLC (max plot) 100.0%; Rt 2.47 min. MS (ESI+): 514.8.

Example 298: 6-Fluoro-3-(morpholin-4-ylcarbonyl)-1-[1-(tetrahydro-2H-pyran-4-yl)pyrrolidin-3-yl]-1,4-dihydrothiochromeno[4,3-c]pyrazole 5,5-dioxide

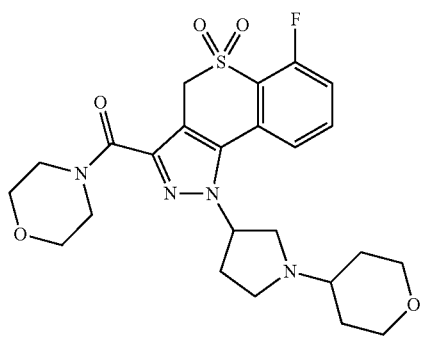 [SMILES: O=C(c1nn(C2CCN(C3CCOCC3)C2)c2c1CS(=O)(=O)c1c(F)cccc1-2)N1CCOCC1]

45 mg of the title compound as a yellow oil. $^1$H NMR (DMSO-$d_6$) δ 7.74-7.66 (m, 1H), 7.46 (d, J = 7.0 Hz, 1H), 7.31-7.23 (m, 1H), 5.31-5.25 (m, 1H), 4.73 (m, 2H), 4.20-4.14 (m, 2H), 4.02-3.88 (m, 2H), 3.81-3.79 (m, 8H), 3.10-2.85 (m, 4H), 2.50-2.28 (m, 4H), 1.87-1.75 (m, 2H), 1.68-1.62 (m, 2H). HPLC (max plot) 95.0%; Rt 2.30 min. MS (ESI+): 504.8.

Example 304: 6-Fluoro-3-(morpholin-4-ylcarbonyl)-1-[1-[(tetrahydrofuran-3-yl methyl)pyrrolidin-3-yl]-1,4-dihydrothiochromeno[4,3-c]pyrazole 5,5-dioxide

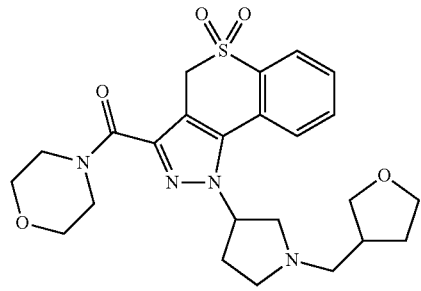 [SMILES: O=C(c1nn(C2CCN(CC3CCOC3)C2)c2c1CS(=O)(=O)c1ccccc1-2)N1CCOCC1]

50 mg of the title compound as a yellow oil. $^1$H NMR (DMSO-$d_6$) δ 7.69-7.62 (m, 1H), 7.37-7.33 (m, 1H), 7.25-7.21 (m, 1H), 5.24-5.14 (m, 1H), 4.70-4.67 (m, 2H), 4.16-4.09 (m, 2H), 3.90-3.65 (m, 6H), 3.50-3.43 (m, 1H), 3.31-3.19 (m, 2H), 2.95-2.78 (m, 4H), 2.56-2.22 (m, 6H), 2.05-1.92 (m, 1H), 1.63-1.49 (m, 1H). HPLC (max plot) 94.8%; Rt 2.34 min.. MS (ESI+): 505.2.

Example 302: 6-Fluoro-3-(morpholin-4-ylcarbonyl)-1-{1-[2-(tetrahydro-2H-pyran-4-yl)ethyl]pyrrolidin-3-yl}-1,4-dihydrothiochromeno[4,3-c]pyrazole 5,5-dioxide

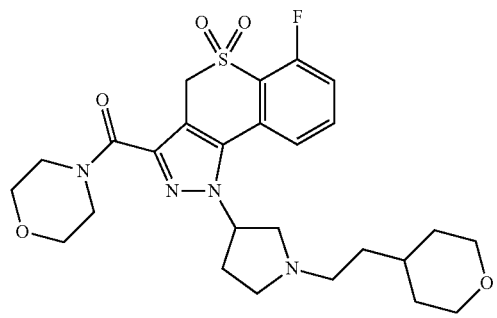 [SMILES: O=C(c1nn(C2CCN(CCC3CCOCC3)C2)c2c1CS(=O)(=O)c1c(F)cccc1-2)N1CCOCC1]

32 mg of the title compound as a yellow oil. $^1$H NMR (DMSO-$d_6$) δ 7.68-7.61 (m, 1H), 7.38 (6, J = 7 Hz, 1H), 7.25-7.21 (m, 1H), 5.27-5.18 (m, 1H), 4.68-4.66 (m, 2H), 4.14-4.06 (m, 2H), 3.92-3.84 (m, 4H), 3.74-3.68 (m, 8H), 3.38-3.20 (m, 2H), 3.00-2.93 (m, 1H), 2.84-2.48 (m, 6H), 1.58-1.39 (m, 4H). HPLC (max plot) 96.2%; Rt 2.51 min. MS (ESI+): 533.3.

Example 402: Enantiomer A of 3-(morpholin-4-ylcarbonyl)-1-[-1-(tetrahydro-2H-pyran-4-yl)pyrrolidin-3-yl-1,4-dihydrothiochromeno[4,3-c]pyrazole 5,5-dioxide

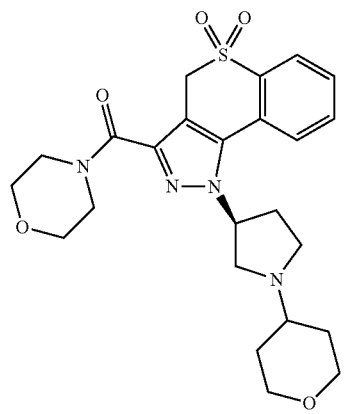 [SMILES: O=C(c1nn([C@H]2CCN(C3CCOCC3)C2)c2c1CS(=O)(=O)c1ccccc1-2)N1CCOCC1]

Obtained from enantiomer A of 3-(morpholin-4-ylcarbonyl)-1-pyrrolidin-3-yl-1,4-dihydrothio chromeno[4,3-c]pyrazole 5,5-dioxide to give 55 mg of the title compound as a white foam. $^1$H NMR (DMSO-$d_6$, 300 MHz): δ 8.03 (d, J = 6.7 Hz, 1H), 7.97 (d, J = 7.8 Hz, 1H), 7.90 (t, J = 7.7 Hz, 1H), 7.73 (t, J = 7.3 Hz, 1H), 5.47 (s, 1H), 4.78 (s, 2H), 3.97 (s, 2H), 3.84 (d, J = 11.6 Hz, 2H), 3.67 (s, 5H), 3.32-3.23 (m, 3H), 2.91 (dd, J = 9.6, 5.1 Hz, 1H), 2.79 (t, J = 6.9 Hz, 2H), 2.47-2.11 (m, 4H), 1.78 (d, J = 12.4 Hz, 2H), 1.49-1.27 (m, 2H). MS (ESI+): 487.4. HPLC (max plot) 70.1%; Rt 1.92 min.

Example 403: Enantiomer B of 3-(morpholin-4-ylcarbonyl)-1-[1-tetrahydro-2H-pyran-4-yl)pyrrolidin-3-yl]-1,4-dihydrothiochromeno[4,3-c]pyrazole 5,5-dioxide

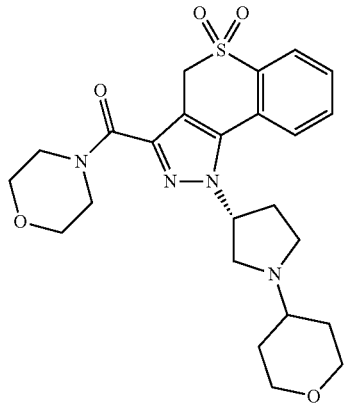 [SMILES: O=C(c1nn([C@@H]2CCN(C3CCOCC3)C2)c2c1CS(=O)(=O)c1ccccc1-2)N1CCOCC1]

Obtained from enantiomer B of 3-(morpholin-4-ylcarbonyl)-1-pyrrolidin-3-yl-1,4-dihydrothio chromeno[4,3-c]pyrazole 5,5-dioxide to give 58 mg of the title compound as a white foam. $^1$H NMR (DMSO-$d_6$, 300 MHz): δ 8.03 (dd, J = 7.8, 1.2 Hz, 1H), 7.97 (d, J = 7.6 Hz, 1H), 7.89 (t, J = 7.7 Hz, 1H), 7.74 (dd, J = 10.9, 4.2 Hz, 1H), 5.47 (s, 1H), 4.78 (d, J = 1.1 Hz, 2H), 4.00-3.93 (m, 2H), 3.84 (d, J = 11.3 Hz, 2H), 3.67 (s, 6H), 3.31-3.24 (m, 3H), 2.91 (dd, J = 9.5, 5.1, 1H), 2.79 (t, J = 6.8 Hz, 2H), 2.47-2.12 (m, 4H), 1.78 (d, J =12.3 Hz, 2H), 1.49-1.27 (m, 2H).. MS (ESI+): 487.4. HPLC (max plot) 66.1%; Rt 1.86 min.

Example 285: 3-(morpholin-4-ylcarbonyl)-1-{1-[2-(tetrahydro-2H-pyran-4-yl)ethyl]piperidin-4-yl}-1,4-dihydrothiochromeno[4,3-c]pyrazole 5,5-dioxide

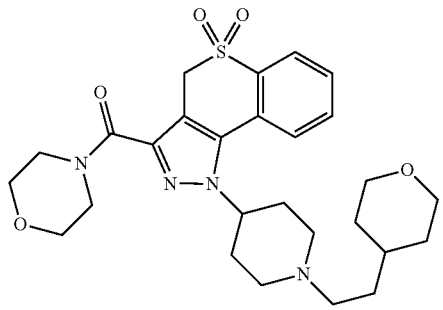 [SMILES: O=C(c1nn(C2CCN(CCC3CCOCC3)CC2)c2c1CS(=O)(=O)c1ccccc1-2)N1CCOCC1]

65 mg of the title compound as a white solid. $^1$H NMR (DMSO-$d_6$) δ δ 8.04 (d, J = 7.7 Hz, 1H), 7.96-7.83 (m, 2H), 7.73 (t, J = 7.3 Hz, 1H), 4.76 (d, J = 16.0 Hz, 3H), 3.97 (s, 2H), 3.82 (dd, J = 11.0, 3.5 Hz, 2H), 3.66 (s, 5H), 3.27 (t, J = 11.5 Hz, 2H), 2.97 (d, J = 6.0 Hz, 2H), 2.43-2.27 (m, 2H), 2.23-1.95 (m, 6H), 1.66-1.30 (m, 5H), 1.28-1.03 (m, 3H). HPLC (max plot) 98.8%; Rt 2.10 min. MS (ESI+): 529.3.

Example 305: 3-(morpholin-4-ylcarbonyl)-1-[1-(tetrahydro-2H-pyran-4-yl methyl)piperidin-3-yl]-1,4-dihydrothiochromeno[4,3-c]pyrazole 5,5-dioxide

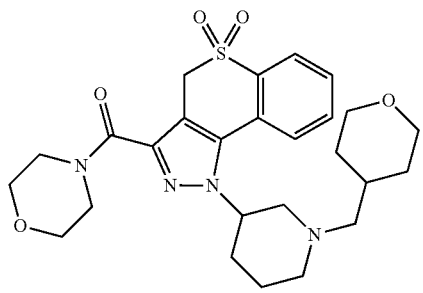 [SMILES: O=C(c1nn(C2CCCN(CC3CCOCC3)C2)c2c1CS(=O)(=O)c1ccccc1-2)N1CCOCC1]

56 mg of the title compound as a white solid. 1H NMR (DMSO-d6) δ 8.06 (dd, J = 1.2, 7.8 Hz, 1H), 7.93-7.88 (m, 1H), 7.84-7.81 (m, 1H), 7.78-7.72 (m, 1H), 4.82-4.75 (m, 3H), 3.93-3.90 (m, 2H), 3.85-3.77 (m, 2H), 3.69-3.62 (m, 6H), 3.27-3.19 (m, 2H), 3.13-3.10 (m, 1H), 2.87-2.84 (m, 1H), 2.37-2.30 (m, 1H), 2.25-2.15 (m, 3H), 2.04-1.53 (m, 7H), 1.16-1.03 (m, 2H). HPLC (max plot) 100%; Rt 1.81 min. MS (ESI+): 514.9.

Example 415: 3-(Morpholin-4-ylcarbonyl)-1-(1-oxetan-3-ylpiperidin-3-yl)-1,4-dihydrothiochromeno[4,3-c]pyrazole 5,5-dioxide

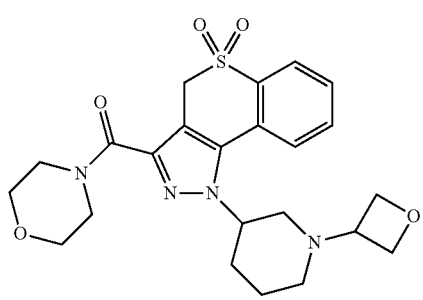 [SMILES: O=C(c1nn(C2CCCN(C3COC3)C2)c2c1CS(=O)(=O)c1ccccc1-2)N1CCOCC1]

21 mg of the title compound as a white solid. $^1$H NMR (DMSO-$d_6$) δ 1H NMR (300 MHz, DMSO) δ 8.17-7.91 (m, 2H), 7.91-7.66 (m, 2H), 5.02-4.67 (m, 3H), 4.62-4.29 (m, 4H), 3.88 (s, 2H), 3.65 (s, 7H), 3.56-3.44 (m, 2H), 3.00 (d, J = 9.7 Hz, 1H), 2.75 (d, J = 8.1 Hz, 2H), 2.29 (t, J = 10.4 Hz, 1H), 2.22-2.07 (m, 1H), 2.04-1.59 (m, 5H). HPLC (max plot) 98.4%; Rt 5.92 min. MS (ESI+): 473.3.

-continued

Example 224: 3-(Morpholin-4-ylcarbonyl)-1-{1-[2-(tetrahydro-2H-pyran-4-yl)ethyl]piperidin-3-yl)-1,4-dihydrothiochromeno[4,3-c]pyrazole 5,5-dioxide

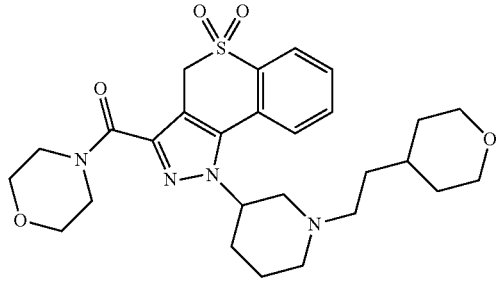 [SMILES: O=C(c1nn(C2CCCN(CCC3CCOCC3)C2)c2c1CS(=O)(=O)c1ccccc1-2)N1CCOCC1]

120 mg of the title compound as a white solid. $^1$H NMR (DMSO-d$_6$) δ 8.06 (dd, J = 7.8, 1.2 Hz, 1H), 7.95-7.90 (m, 1H), 7.84-7.82 (m, 1H), 7.78-7.73 (m, 1H), 4.79 (s, 3H), 3.93-3.90 (m, 2H), 3.82-3.77 (m, 2H), 3.70-3.62 (m, 6H), 3.29-3.21 (m, 2H), 3.16-3.09 (m, 1H), 2.92-2.85 (m, 1H), 2.42-2.28 (m, 3H), 2.18-2.09 (m, 1H), 2.01-1.88 (m, 2H), 1.83-1.66 (m, 2H), 1.57-1.44 (m, 3H), 1.39-1.31 (m, 2H), 1.19-1.05 (m, 2H). HPLC (max plot) 99.3%; Rt 2.00 min. MS (ESI+): 528.8. CHN analysis: [C27H36N4O5S] Corrected: C61.34%, H6.86%, N10.60%; Found: C61.13%, H6.67%, N10.44%.

Example 293: 3-(Morpholin-4-ylcarbonyl)-1-[1-(tetrahydro-2H-pyran-4-yl)piperidin-3-yl]-1,4-dihydrothiochromeno[4,3-c]pyrazole 5,5-dioxide

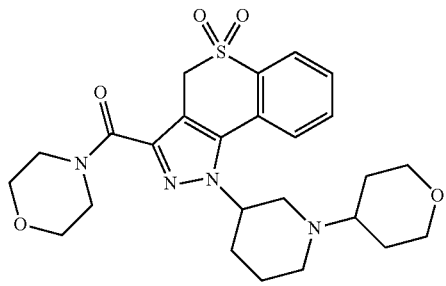

11 mg of the title compound as a white solid. 1H NMR (DMSO-d6) δ 8.06 (dd, J = 1.2, 7.8 Hz, 1H), 7.98-7.82 (m, 1H), 7.82-7.72 (m, 2H), 4.79-4.73 (m, 3H), 3.93-3.84 (m, 4H), 3.69-3.63 (m, 6H), 3.29-3.16 (m, 3H), 2.94-2.91 (m, 1H), 2.59-2.50 (m, 2H), 2.24-2.12 (m, 2H), 2.04-1.65 (m, 5H), 1.51-1.39 (m, 2H). HPLC (max plot) 97.8%; Rt 1.73 min. MS (ESI+): 501.3.

Example 374: Enantiomer B of 3-(morpholin-4-ylcarbonyl)-1-[1-(tetrahydro-2H-pyran-4-yl) piperidin-3-yl]-1,4-dihydrothiochromeno[4,3-c]pyrazole 5,5-dioxide

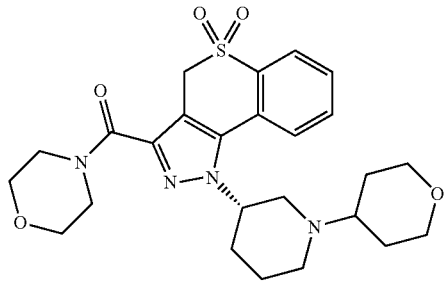 [SMILES: O=C(c1nn([C@H]2CCCN(C3CCOCC3)C2)c2c1CS(=O)(=O)c1ccccc1-2)N1CCOCC1]

Obtained from enantiomer B of 3-(morpholin-4-ylcarbonyl)-1-[piperidin-3-yl]-1,4-dihydrothiochromeno[4,3-c]pyrazole 5,5-dioxide to give 42 mg of the title compound as a white fluffy solid. $^1$H NMR (300 MHz, DMSO) δ 8.05 (dd, J = 7.8, 1.2 Hz, 1H), 7.94 (dd, J = 11.5, 4.0 Hz, 1H), 7.86-7.66 (m, 2H), 4.77 (m, 3H), 4.02-3.78 (m, 4H), 3.66 (m, 2H), 3.22 (m, 5H), 2.92 (d, J = 11.0 Hz, 1H), 2.69-2.53 (m, 4H), 2.18 (m, 2H), 2.06-1.76 (m, 2H), 1.67 (m, 3H), 1.56-1.29 (m, 2H). HPLC (max plot) 99%; Rt 2.19 min. MS (ESI+): 501.5.

Example 451: Enantiomer B of 1-[1'-methyl-1,4'-bipiperidin-3-yl]-3-(morpholin-4-ylcarbonyl)-1,4-dihydrothiochromeno[4,3-c]pyrazole 5,5-dioxide

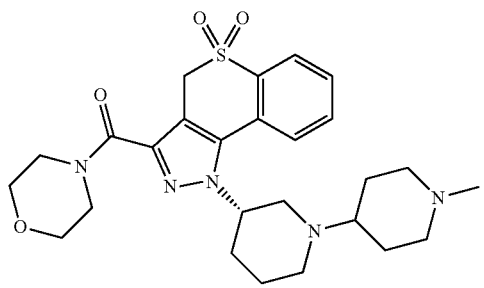 [SMILES: CN1CCC(N2CCC[C@H](n3nc(C(=O)N4CCOCC4)c4c3-c3ccccc3S(=O)(=O)C4)C2)CC1]

Obtained from enantiomer B of 3-(morpholin-4-ylcarbonyl)-1-[piperidin-3-yl]-1,4-dihydrothiochromeno[4,3-c]pyrazole 5,5-dioxide to give 43 mg of the title compound as a white solid. $^1$H NMR (DMSO-d$_6$, 300 MHz): δ 8.07-8.04 (m, 1H), 7.97-7.92 (m, 1H), 7.82-7.72 (m, 2H), 4.79-4.72 (m, 3H), 3.91 (m, 2H), 3.66 (s, 6H), 3.17-3.13 (m, 2H), 2.91-2.79 (m, 3H), 2.57-2.50 (m, 1H), 2.35-1.44 (m, 14H). MS (ESI+): 514.4. HPLC (max plot) 98.5%; Rt 1.52 min Example 459: Enantiomer B of 1-[1'-methyl-1,3'-bipiperidin-3-yl]-3-(morpholin-4-ylcarbonyl)-1,4-dihydrothiochromeno[4,3-c]pyrazole 5,5-dioxide

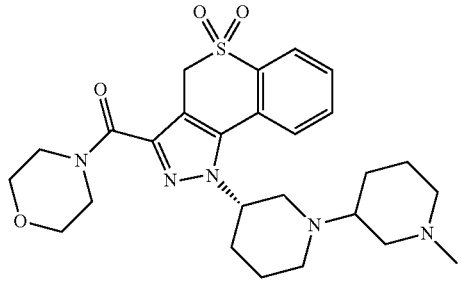 [SMILES: CN1CCCC(N2CCC[C@H](n3nc(C(=O)N4CCOCC4)c4c3-c3ccccc3S(=O)(=O)C4)C2)C1]

Obtained from enantiomer B of 3-(morpholin-4-ylcarbonyl)-1-[piperidin-3-yl]-1,4-dihydrothiochromeno[4,3-c]pyrazole 5,5-dioxide to give 21 mg of the title compound as an off-white. $^1$H NMR (DMSO-$d_6$, 300 MHz): δ 7.97-7.92 (m, 1H), 7.68-7.56 (m, 2H), 4.90 (s, 2H), 4.77 (bs, 1H), 3.91 (bs, 2H), 3.66-3.17 (m, 17H), 2.96 (bs, 1H), 2.73 (m, 3H), 2.12-1.74 (m, 6H). MS (ESI+): 514.3. HPLC (max plot) 98.9%; Rt 1.58 min Example 466: Enantiomer B of 3-(morpholin-4-ylcarbonyl)-1-[1-(pyridin-3-ylmethyl)piperidin-3-yl]-1,4-dihydrothiochromeno[4,3-c]pyrazole 5,5-dioxide

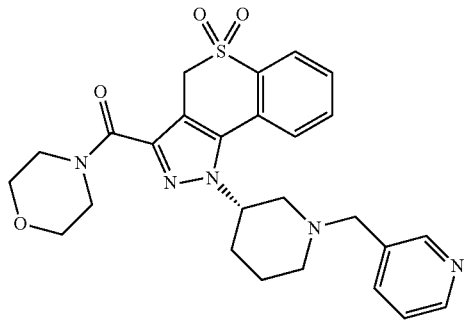 [SMILES: O=C(c1nn([C@H]2CCCN(Cc3cccnc3)C2)c2c1CS(=O)(=O)c1ccccc1-2)N1CCOCC1]

Obtained from enantiomer B of 3-(morpholin-4-ylcarbonyl)-1-[piperidin-3-yl]-1,4-dihydrothiochromeno[4,3-c]pyrazole 5,5-dioxide to give 162 mg of the title compound as a white solid. $^1$H NMR (DMSO-$d_6$, 300 MHz): δ 8.53 (m, 1H), 8.46-8.44 (m, 1H), 8.04-8.01 (m, 1H), 7.90-7.85 (m, 1H), 7.77-7.70 (m, 1H), 7.65-7.62 (m, 1H), 7.39-7.35 (m, 1H), 4.82-4.76 (m, 3H), 3.90 (m, 2H), 3.71-3.55 (m, 8H), 3.08-3.05 (m, 1H), 2.91-2.87 (m, 1H), 2.43-1.73 (m, 7H). MS (ESI+): 508.3. HPLC (max plot) 99.5%; Rt 1.60 min.

Example 473: Enantiomer B of 3-(morpholin-4-ylcarbonyl)-1-[1-(pyridin-4-ylmethyl)piperidin-3-yl]-1,4-dihydrothiochromeno[4,3-c]pyrazole 5,5-dioxide

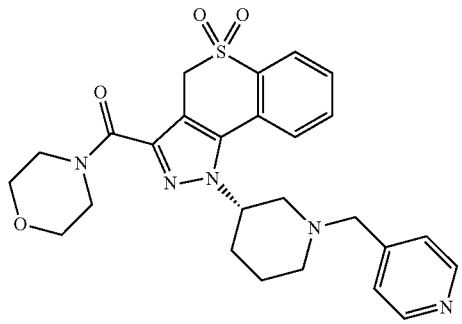 [SMILES: O=C(c1nn([C@H]2CCCN(Cc3ccncc3)C2)c2c1CS(=O)(=O)c1ccccc1-2)N1CCOCC1]

Obtained from enantiomer B of 3-(morpholin-4-ylcarbonyl)-1-[piperidin-3-yl]-1,4-dihydrothiochromeno[4,3-c]pyrazole 5,5-dioxide to give 187 mg (77%) of the title compound as a white solid. $^1$H NMR (DMSO-$d_6$, 300 MHz): δ 8.50-8.52 (m, 2H), 8.04-8.02 (m, 1H), 7.95-7.90 (m, 1H), 7.77-7.69 (m, 2H), 7.37-7.36 (m, 1H), 4.84-4.76 (m, 3H), 3.89 (m, 2H), 3.71-3.54 (m, 8H), 3.06-3.03 (m, 1H), 2.90-2.86 (m, 1H), 2.44-2.37 (m, 1H), 2.15-1.83 (m, 6H). MS (ESI+): 508.3. HPLC (max plot) 98.5%; Rt 1.57 min.

Example 361: Enantiomer B of 3-(morpholin-4-ylcarbonyl)-1-[1-(tetrahydro-2H-pyran-4-ylmethyl) piperidin-3-yl]-1,4-dihydrothiochromeno[4,3-c]pyrazole 5,5-dioxide

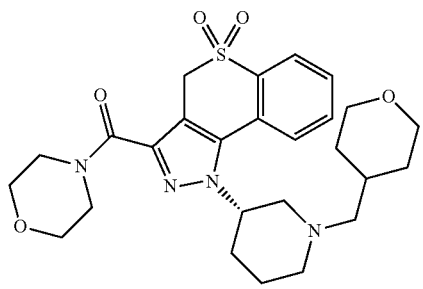 [SMILES: O=C(c1nn([C@H]2CCCN(CC3CCOCC3)C2)c2c1CS(=O)(=O)c1ccccc1-2)N1CCOCC1]

Obtained from enantiomer B of 3-(morpholin-4-ylcarbonyl)-1-[piperidin-3-yl]-1,4-dihydrothiochromeno[4,3-c]pyrazole 5,5-dioxide to give 120 mg of the title compound as a white foam. 1H NMR (DMSO-d6): δ 8.05 (d, J = 7.8 Hz, 1H), 7.89 (d, J = 7.2 Hz, 1H), 7.82 (d, J = 7.6 Hz, 1H), 7.75 (t, J = 7.6 Hz, 1H), 5.76 (S, 1H), 4.79 (s, 3H), 3.91 (s, 2H), 3.81 (s, 2H), 3.66 (s, 6H), 3.22 (t, J = 11.6 Hz, 2H), 3.11 (d, J = 9.3 Hz, 1H), 2.85 (d, J = 10.7 Hz, 1H), 2.33 (t, J = 10.6 Hz, 1H), 2.19 (dd, J = 14.2, 10.0 Hz, 3H), 2.07-1.86 (m, 2H), 1.85-1.48 (m, 5H), 1.10 (d, J = 10.6 Hz, 2H). HPLC (max plot) 72.7%; Rt 1.94 min. MS (ESI+): 515.3.

Example 416: Enantiomer A of 3-(morpholin-4-ylcarbonyl)-1-[1-(tetrahydro-2H-pyran-4-yl)azepan-4-yl]-1,4-dihydrothiochromeno[4,3-c]pyrazole 5,5-dioxide

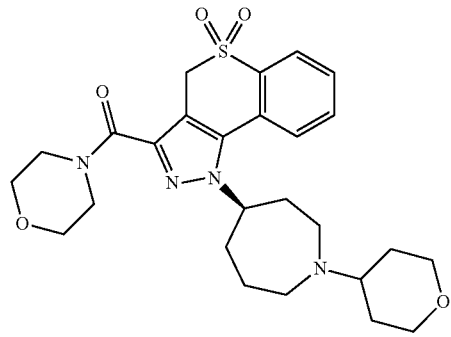 [SMILES: O=C(c1nn([C@@H]2CCCN(C3CCOCC3)CC2)c2c1CS(=O)(=O)c1ccccc1-2)N1CCOCC1]

Obtained from enantiomer A of 1-azepan-4-yl-3-(morpholin-4-ylcarbonyl)-1,4-dihydrothiochromeno[4,3-c]pyrazole 5,5-dioxide to give 31 mg of the title compound as a red oil. 1H NMR (DMSO-d6) δ 8.08 (d, J = 6.5 Hz, 1H), 7.75-7.70 (m, 1H), 7.57-7.52 (m, 2H), 4.96-4.86 (m, 1H), 4.59 (s, 2H), 4.14-3.93 (m, 4H), 3.72 (s, 6H), 3.36-3.27 (t, J = 7.5 Hz, 2H), 2.92-2.63 (m, 4H), 2.32-2.16 (m, 4H), 1.73-1.51 (m, 5H), 1.87-.85 (m, 2H). HPLC (max plot) 97.8%; Rt 2.39 min. MS (ESI+): 515.4.

Example 417: Enantiomer B of 3-(morpholin-4-ylcarbonyl)-1-[1-(tetrahydro-2H-pyran-4-yl)azepan-4-yl]-1,4-dihydrothiochromeno[4,3-c]pyrazole 5,5-dioxide

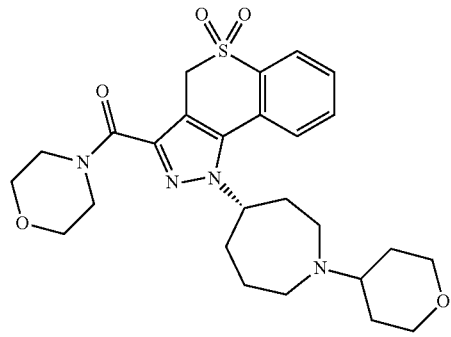 [SMILES: O=C(c1nn([C@H]2CCCN(C3CCOCC3)CC2)c2c1CS(=O)(=O)c1ccccc1-2)N1CCOCC1]

Obtained from enantiomer B of 1-azepan-4-yl-3-(morpholin-4-ylcarbonyl)-1,4-dihydrothiochromeno[4,3-c]pyrazole 5,5-dioxide to give 42.2 mg of the title compound as a red oil. $^1$H NMR (DMSO-d$_6$) δ 8.08 (d, J = 6.5 Hz, 1H), 7.75-7.70 (m, 1H), 7.57-7.52 (m, 2H), 4.96-4.86 (m, 1H), 4.59 (s, 2H), 4.14-3.93 (m, 4H), 3.72 (s, 6H), 3.36-3.27 (t, J = 7.5 Hz, 2H), 2.92-2.63 (m, 4H), 2.32-2.16 (m, 4H), 1.73-1.51 (m, 5H), 1.87-.85 (m, 2H). HPLC (max plot) 97.8%; Rt 2.35 min. MS (ESI+): 515.4. MS (ESI+): 515.4.

Example 404: 6-Fluoro-3-(morpholin-4-ylcarbonyl)-1-[1-(tetrahydrofuran-3-ylmethyl)piperidin-3-yl]-1,4-dihydrothiochromeno[4,3-c]pyrazole 5,5-dioxide

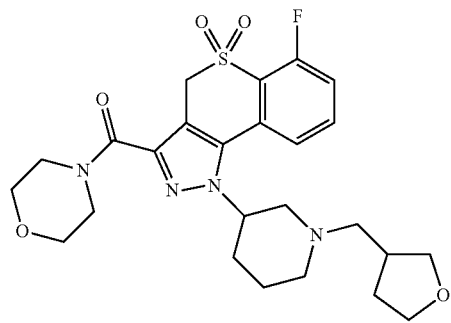 [SMILES: O=C(c1nn(C2CCCN(CC3CCOC3)C2)c2c1CS(=O)(=O)c1c(F)cccc1-2)N1CCOCC1]

33 mg of the title compound as a beige solid. $^1$H NMR (DMSO-d$_6$, 300 MHz): δ 8.00-7.92 (m, 1H), 7.65-7.55 (m, 2H), 4.90 (s, 2H), 4.71 (bs, 1H), 3.91 (bs, 2H), 3.73-3.54 (m, 8H), 3.38-3.35 (m, 1H), 3.18-3.09 (m, 1H), 2.94-2.85 (m, 1H), 2.42-1.45 (m, 12H). MS (ESI+): 519.3. HPLC (max plot) 93.8%; Rt 1.82 min Example 280: 6-Fluoro-3-(morpholin-4-ylcarbonyl)-1-{1-[2-(tetrahydro-2H-pyran-4-yl)ethyl]piperidin-3-yl)-1,4-dihydrothiochromeno[4,3-c]pyrazole 5,5-dioxide

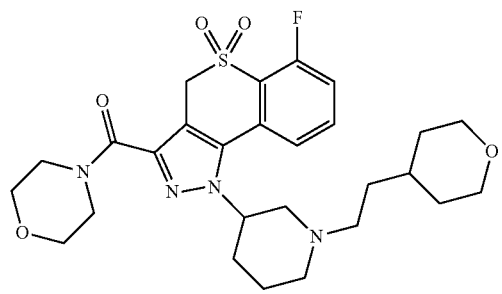 [SMILES: O=C(c1nn(C2CCCN(CCC3CCOCC3)C2)c2c1CS(=O)(=O)c1c(F)cccc1-2)N1CCOCC1]

29.1 mg of the title compound as a white fluffy solid. $^1$H NMR (DMSO-d$_6$) δ 7.89-7.97 (m, 1H), 7.54-7.63 (m, 2H), 4.88 (s, 2H), 4.71 (bs, 1H), 3.90 (bs, 1H), 3.76-3.80 (m, 3H), 3.64 (s, 5H), 3.19-3.27 (m, 2H), 3.06-3.09 (d, J = 9.0 Hz, 1H), 2.85-2.88 (d, J = 9.0 Hz, 1H), 1.09-2.37 (m, 16H). HPLC (max plot) 98.7%; Rt 2.05 min. MS (ESI+): 546.9.

Example 307: Enantiomer A of 3-(morpholin-4-ylcarbonyl)-1-{1-[2-(tetrahydro-2H-pyran-4-yl)ethyl]piperidin-3-yl}-1,4-dihydrothiochromeno[4,3-c]pyrazole 5,5-dioxide hydrochloride salt

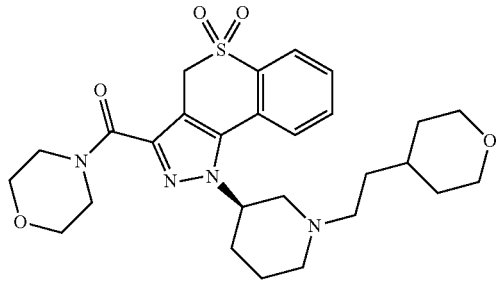 [SMILES: O=C(c1nn([C@@H]2CCCN(CCC3CCOCC3)C2)c2c1CS(=O)(=O)c1ccccc1-2)N1CCOCC1]

Obtained from enantiomer A of 3-(morpholin-4-ylcarbonyl)-1-[piperidin-3-yl]-1,4-dihydrothiochromeno[4,3-c]pyrazole 5,5-dioxide to give 165 mg of the title compound as a white solid. 1H NMR (DMSO-d6) δ 10.58 (s, 1H), 8.06 (dd, J = 11.0, 4.4 HZ, 2H), 7.91 (dd, J = 11.5, 3.8 Hz, 1H), 7.77 (t, J = 7.8 Hz, 1H), 5.35 (s, 1H), 4.80 (s, 2H), 3.94-3.51 (m, 10H), 3.51-3.37 (m, 1H), 3.25 (m, 3H), 3.03 (s, 1H), 2.10 (m, 4H), 1.60 (m, 4H), 1.17 (m, 2H). HPLC (max plot) 98.7%; Rt 2.31 min. MS (ESI+): 529.5. [α]$^{25}$D +15.53 (c 1.25, EtOH).

Example 306: Enantiomer B of 3-(morpholin-4-ylcarbonyl)-1-{1-[2-(tetrahydro-2H-pyran-4-yl)ethyl]piperidin-3-yl}-1,4-dihydrothiochromeno[4,3-c]pyrazole 5,5-dioxide hydrochloride salt

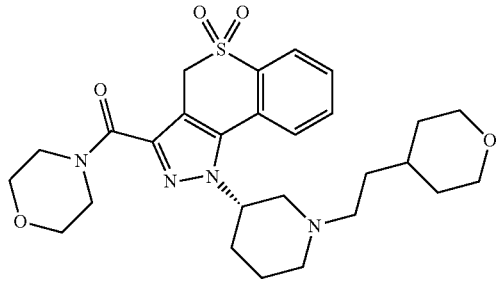

Obtained from enantiomer B of 3-(morpholin-4-ylcarbonyl)-1-[piperidin-3-yl]-1,4-dihydrothiochromeno[4,3-c]pyrazole 5,5-dioxide to give 142 mg of the title compound as a white solid. $^1$H NMR (DMSO-d$_6$) δ 10.58 (s, 1H), 8.06 (dd, J = 11.0, 4.4, 2H), 7.91 (dd, J = 11.5, 3.8, 1H), 7.77 (t, J = 7.8, 1H), 5.35 (s, 1H), 4.80 (s, 2H), 3.94-3.51 (m, 10H), 3.51-3.37 (m, 1H), 3.25 (m, 3H), 3.03 (s, 1H), 2.10 (m, 4H), 1.60 (m, 4H), 1.17 (m, 2H). HPLC (max plot) 99.1%; Rt 2.30 min. MS (ESI+): 529.5. [α]$^{25}$D −18.50 (c 1.23, EtOH).

Example 425: Enantiomer B of 6-Fluoro-3-(morpholin-4-ylcarbonyl)-1-[1-(tetrahydro-2H-pyran-3-yl)piperidin-3-yl]-1,4-dihydrothiochromeno[4,3-c]pyrazole 5,5-dioxide

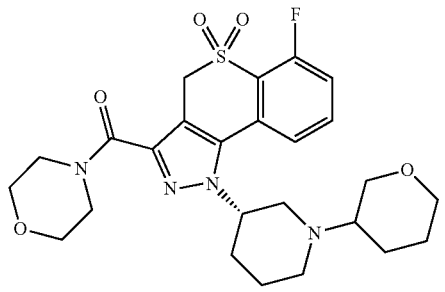 [SMILES: O=C(c1nn([C@H]2CCCN(C3CCCOC3)C2)c2c1CS(=O)(=O)c1c(F)cccc1-2)N1CCOCC1]

Obtained from enantiomer B of 6-fluoro-3-(morpholin-4-ylcarbonyl)-1-[piperidin-3-yl]-1,4-dihydrothiochromeno[4,3-c]pyrazole 5,5-dioxide to give 156 mg of the title compound as a white solid. $^1$H NMR (DMSO-d$_6$, 300 MHz): δ 8.00-7.93 (m, 1H), 7.62-7.55 (m, 2H), 4.89 (s, 2H), 4.64 (m, 1H), 3.91-3.82 (m, 3H), 3.66 (s, 6H), 3.23-3.16 (m, 3H), 2.90-2.87 (m, 1H), 2.66-2.56 (m, 1H), 2.30-1.42 (m, 11H). MS (ESI+): 519.4. HPLC (max plot) 95.9%; Rt 1.88 min Example 427: Enantiotner B of 6-fluoro-3-(morpholin-4-ylcarbonyl)-1-[1-(tetrahydro-2H-pyran-4-yl)piperidin-3-yl]-1,4-dihydrothiochromeno[4,3-c]pyrazole 5,5-dioxide

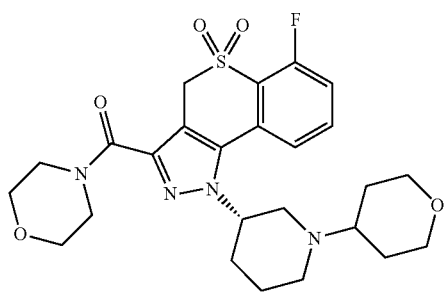 [SMILES: O=C(c1nn([C@H]2CCCN(C3CCOCC3)C2)c2c1CS(=O)(=O)c1c(F)cccc1-2)N1CCOCC1]

Obtained from enantiomer B of 6-fluoro-3-(morpholin-4-ylcarbonyl)-1-[piperidin-3-yl]-1,4-dihydrothiochromeno[4,3-c]pyrazole 5,5-dioxide to give 152 mg of the title compound as a white solid. $^1$H NMR (DMSO-d$_6$, 300 MHz): δ 8.01-7.93 (m, 1H), 7.62-7.55 (m, 2H), 4.90 (s, 2H), 4.69 (m, 1H), 3.91-3.84 (m, 4H), 3.66 (s, 5H), 3.28-3.13 (m, 3H), 2.93-2.89 (m, 1H), 2.56 (m, 2H), 2.22-1.40 (m, 10H). MS (ESI+): 519.4. HPLC (max plot) 96.8%; Rt 1.79 min Example 301: 6-Chloro-3-(morpholin-4-ylcarbonyl)-1-{1-[2-(tetrahydro-2H-pyran-4-yl)ethyl]piperidin-3-yl}-1,4-dihydrothiochromeno[4,3-c]pyrazole 5,5-dioxide

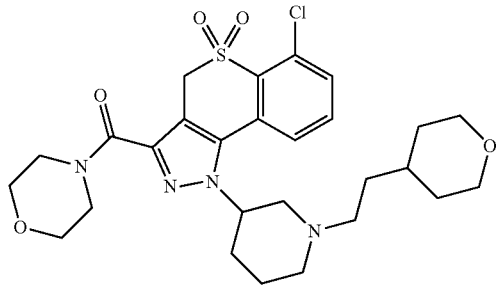

83 mg of the title compound as a beige foam. $^1$H NMR (DMSO-d6) δ 7.82-7.87 (m, 1H), 7.72-7.77 (m, 2H), 4.89 (s, 2H), 4.65 (bs, 1H), 3.91 (m, 2H), 3.75-3.80 (m, 2H), 3.64 (m, 5H), 3.18-3.29 (m, 2H), 3.04-3.06 (d, 1H), 2.83-2.87 (m, 1H), 1.05-2.37 (m, 16H). HPLC (max plot) 99.6%; Rt 2.80 min. MS (ESI+): 563.3.

Example 389: Enantiomer B of 7-methoxy-3-(morpholin-4-ylcarbonyl)-1-[1-(tetrahydro-2H-pyran-3-yl)piperidin-3-yl]-1,4-dihydrothiochromeno[4,3-c]pyrazole 5,5-dioxide

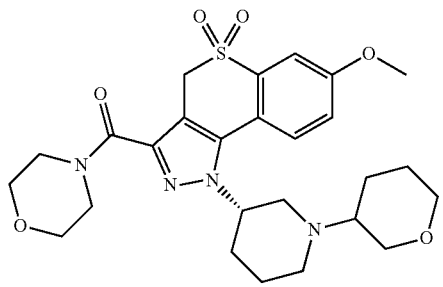 [SMILES: COc1ccc2c(c1)S(=O)(=O)Cc1c(C(=O)N3CCOCC3)nn([C@H]3CCCN(C4CCCOC4)C3)c1-2]

Obtained from enantiomer B of 7-methoxy-3-(morpholin-4-ylcarbonyl)-1-[piperidin-3-yl]-1,4-dihydrothiochromeno[4,3-c]pyrazole 5,5-dioxide to give $^1$H NMR (DMSO-d$_6$, 300 MHz): δ 7.74 (d, J = 9.7 Hz, 1H), 7.50 (t, J = 2.5 Hz, 2H), 4.76 (s, 2H), 4.70-4.58 (m, 1H), 3.96-3.82 (m, 6H), 3.72-3.58 (m, 6H), 3.27-3.08 (m, 3H), 2.88 (s, 1H), 2.65-2.55 (m, 1H), 2.55-2.45 (m, 2H), 2.27 (s, 1H), 2.07 (s, 1H), 2.02-1.74 (m, 3H), 1.71-1.36 (m, 4H).. MS (ESI+): 531.3. HPLC (max plot) 98.6%; Rt 2.18 min Example 395: Enantiomer B of 7-methoxy-3-(morpholin-4-ylcarbonyl)-1-[1-(tetrahydrofuran-3-ylmethyl)piperidin-3-yl]-1,4-dihydrothiochromeno[4,3-c]pyrazole 5,5-dioxide

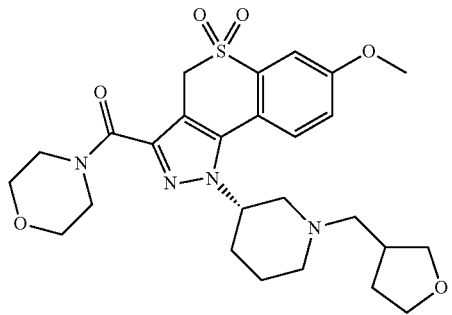 [SMILES: COc1ccc2c(c1)S(=O)(=O)Cc1c(C(=O)N3CCOCC3)nn([C@H]3CCCN(CC4CCOC4)C3)c1-2]

Obtained from enantiomer B of 7-methoxy-3-(morpholin-4-ylcarbonyl)-1-[piperidin-3-yl]-1,4-dihydrothiochromeno[4,3-c]pyrazole 5,5-dioxide to give the title compound. $^1$H NMR (DMSO-d$_6$, 300 MHz): δ 7.76 (dd, J = 8.8, 3.7 Hz, 1H), 7.58-7.42 (m, 2H), 4.78-4.65 (m, 3H), 3.95-3.88 (m, 4H), 3.79-3.48 (m, 7H), 3.44-3.33 (m, 2H), 3.24-3.05 (m, 1H), 3.02-2.80 (m, 1H), 2.46-2.24 (m, 3H), 2.17-2.05 (m, 1H), 2.03-1.37 (m, 6H). MS (ESI+): 531.4. HPLC (max plot) 64.2%; Rt 2.28 min.

Example 369: Enantiomer B of 7-methoxy-3-(morpholin-4-ylcarbonyl)-1-(1-[2-(tetrahydro-2H-pyran-4-yl)ethylpiperidin-3-yl}-1,4-dihydrothiochromeno[4,3-c]pyrazole 5,5-dioxide

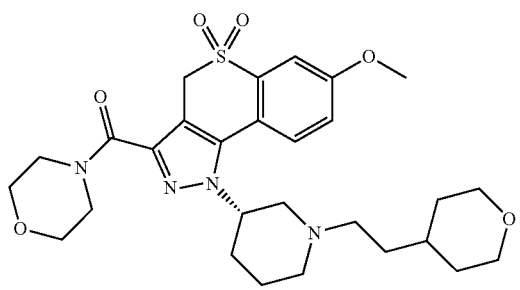 [SMILES: COc1ccc2c(c1)S(=O)(=O)Cc1c(C(=O)N3CCOCC3)nn([C@H]3CCCN(CCC4CCOCC4)C3)c1-2]

Obtained from enantiomer B of 7-methoxy-3-(morpholin-4-ylcarbonyl)-1-[piperidin-3-yl]-1,4-dihydrothiochromeno[4,3-c]pyrazole 5,5-dioxide to give 60 mg of the title compound as a white foam. $^1$H NMR (DMSO-d$_6$, 300 MHz): δ 7.77 (d, J = 8.8, 1H), 7.50 (d, J = 2.7, 1H), 7.45 (dd, J = 8.7, 2.8, 1H), 4.74 (d, J = 10.0, 3H), 3.93 (m, 4H), 3.79 (m, 2H), 3.65 (m, 5H), 3.23 (dd, J = 17.5, 6.1, 2H), 3.10 (d, J = 9.4, 1H), 2.88 (d, J = 10.7, 1H), 2.35 (m, 3H), 2.10 (s, 1H), 2.04-1.61 (m, 4H), 1.53 (m, 3H), 1.35 (m, 3H), 1.21-1.04 (m, 2H). MS (ESI+): 559.33. HPLC (max plot) 99.8%; Rt 2.76 min Example 408: 3-(Morpholin-4-ylcarbonyl)-1-{1-[2-(tetrahydro-2H-pyran-4-yl)ethyl]piperidin-3-yl}-1,4-dihydropyrazolo[3',4':4,5]thiopyrano[2,3-b]pyridine 5,5-dioxide

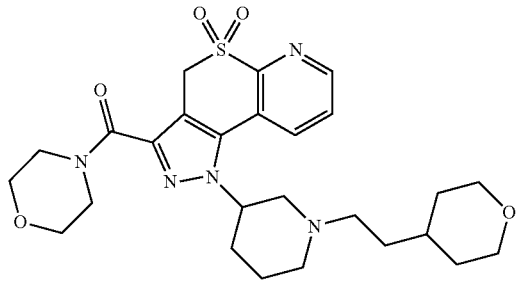

100 mg of the title compound as a white solid. $^1$H NMR (DMSO-$d_6$, 300 MHz): δ 9.00-8.65 (m, 1H), 8.28 (d, J = 8.3 Hz, 1H), 7.93 (dd, J = 8.2, 4.7 Hz, 1H), 4.90 (s, 2H), 4.74 (s, 1H), 3.97-3.86 (m, 2H), 3.84-3.73 (m, 2H), 3.72-3.57 (m, 6H), 3.31-3.19 (m, 2H), 3.16-3.05 (m, 1H), 2.96-2.81 (m, 1H), 2.45-2.21 (m, 3H), 2.19-2.04 (m, 1H), 2.03-1.63 (m, 4H), 1.60-1.42 (m, 3H), 1.39-1.24 (m, 2H), 1.21-1.00 (m, 2H). MS (ESI+): 530.39. HPLC (max plot) 94.8%; Rt 1.60 min Example 379: Enantiomer A of 3-(morpholin-4-ylcarbonyl)-1-[1-(tetrahydro-2H-pyran-3-yl)piperidin-3-yl]-1,4-dihydropyrazolo[3',4':4,5]thiopyrano[2,3-b]pyridine 5,5-dioxide

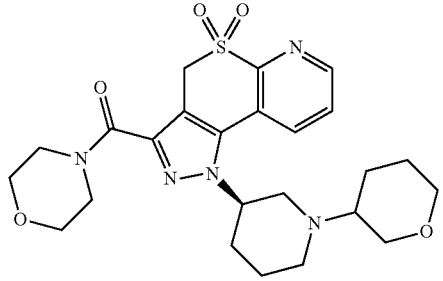 [SMILES: O=C(c1nn([C@@H]2CCCN(C3CCCOC3)C2)c2c1CS(=O)(=O)c1ncccc1-2)N1CCOCC1]

Obtained from enantiomer A of 3-(morpholin-4-ylcarbonyl)-1-[piperidin-3-yl]-1,4-dihydropyrazolo[3',4':4,5]thiopyrano[2,3-b]pyridine 5,5-dioxide to give 32 mg of the title compound as a white solid. $^1$H NMR (DMSO-$d_6$, 300 MHz): δ 8.84-8.73 (m, 1H), 8.28-8.16 (m, 1H), 8.00-7.91 (m, 1H), 4.90 (s, 2H), 4.74-4.57 (m, 1H), 3.98-3.77 (m, 3H), 3.77-3.54 (m, 7H), 3.26-3.04 (m, 3H), 2.96-2.81 (m, 1H), 2.68-2.52 (m, 1H), 2.37-2.18 (m, 1H), 2.18-2.03 (m, 1H), 2.00-1.73 (m, 3H), 1.73-1.55 (m, 2H), 1.55-1.32 (m, 3H). MS (ESI+): 502.4. HPLC (max plot) 94.1%; Rt 5.98 min Example 381: Enantiomer B of 3-(morpholin-4-ylcarbonyl)-1-[1-(tetrahydro-2H-pyran-3-yl)piperidin-3-yl]-1,4-dihydropyrazolo[3',4':4,5]thiopyrano[2,3-b]pyridine 5,5-dioxide

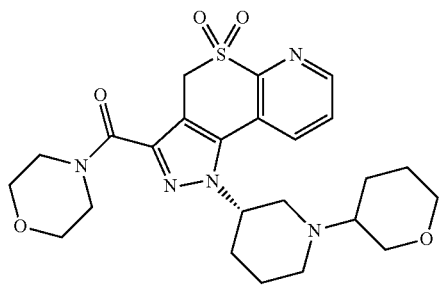 [SMILES: O=C(c1nn([C@H]2CCCN(C3CCCOC3)C2)c2c1CS(=O)(=O)c1ncccc1-2)N1CCOCC1]

Obtained from enantiomer B of 3-(morpholin-4-ylcarbonyl)-1-[piperidin-3-yl]-1,4-dihydropyrazolo[3',4':4,5]thiopyrano[2,3-b]pyridine 5,5-dioxide to give 32 mg of the title compound as a white solid. $^1$H NMR (DMSO-$d_6$, 300 MHz): δ 8.84-8.73 (m, 1H), 8.28-8.16 (m, 1H), 8.00-7.91 (m, 1H), 4.90 (s, 2H), 4.74-4.57 (m, 1H), 3.98-3.77 (m, 3H), 3.77-3.54 (m, 7H), 3.26-3.04 (m, 3H), 2.96-2.81 (m, 1H), 2.68-2.52 (m, 1H), 2.37-2.18 (m, 1H), 2.18-2.03 (m, 1H), 2.00-1.73 (m, 3H), 1.73-1.55 (m, 2H), 1.55-1.32 (m, 3H). MS (ESI+): 502.4. HPLC (max plot) 94.1%; Rt 5.98 min.

Example 371: Enantiomer A of 3-(morpholin-4-ylcarbonyl)-1-[1-(tetrahydro-2H-pyran-4-ylmethyl)piperidin-3-yl]-1,4-dihydropyrazolo[3',4':4,5]thiopyrano[2,3-b]pyridine 5,5-dioxide

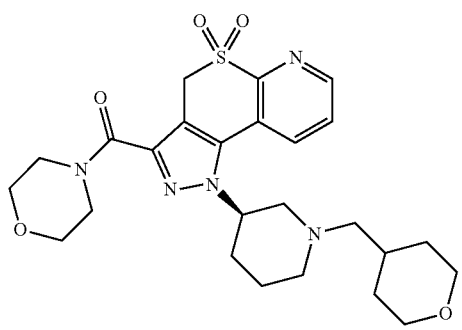 [SMILES: O=C(c1nn([C@@H]2CCCN(CC3CCOCC3)C2)c2c1CS(=O)(=O)c1ncccc1-2)N1CCOCC1]

Obtained from enantiomer A of 3-(morpholin-4-ylcarbonyl)-1-[piperidin-3-yl]-1,4-dihydropyrazolo[3',4':4,5]thiopyrano[2,3-b]pyridine 5,5-dioxide to give 52 mg (84%) of the title compound as a white fluffy solid. $^1$H NMR (DMSO-$d_6$, 300 MHz): δ 8.84-8.78 (m, 1H), 8.31-8.23 (m, 1H), 7.96-7.88 (m, 1H), 4.90 (s, 2H), 4.83-4.67 (m, 1H), 3.97-3.86 (m, 2H), 3.86-3.74 (m, 2H), 3.74-3.57 (m, 6H), 3.29-3.16 (m, 2H), 3.16-3.04 (m, 1H), 2.91-2.77 (m, 1H), 2.41-2.27 (m, 1H), 2.27-2.07 (m, 3H), 2.07-1.87 (m, 2H), 1.87-1.47 (m, 5H), 1.19-0.98 (m, 2H). MS (ESI+): 516.3. HPLC (max plot) 58.6%; Rt 1.58 min Example 376: Enantiomer B of 3-(morpholin-4-ylcarbonyl)-1-[1-[(tetrahydro-2H-pyran-4-ylmethyl)piperidin-3-yl]1,4-dihydropyrazolo[3',4':4,5]thiopyrano[2,3-b]pyridine 5,5-dioxide

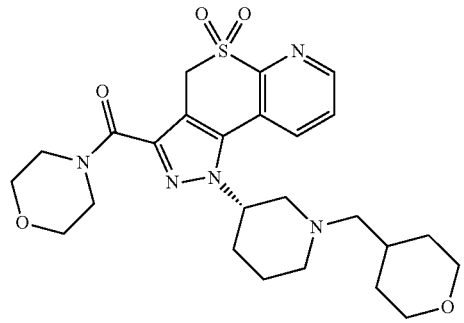

Obtained from enanliomer B of 3-(morpholin-4-ylcarbonyl)-1-[piperidin-3-yl]-1,4-dihydropyrazolo[3',4':4,5]thiopyrano[2,3-b]pyridine 5,5-dioxide to give 36 mg of the title compound as a white powder. $^1$H NMR (DMSO-d$_6$, 300 MHz): δ 8.84-8.78 (m, 1H), 8.31-8.23 (m, 1H), 7.96-7.88 (m, 1H), 4.90 (s, 2H), 4.83-4.67 (m, 1H), 3.97-3.86 (m, 2H), 3.86-3.74 (m, 2H), 3.74-3.57 (m, 6H), 3.29-3.16 (m, 2H), 3.16-3.04 (m, 1H), 2.91-2.77 (m, 1H), 2.41-2.27 (m, 1H), 2.27-2.07 (m, 3H), 2.07-1.87 (m, 2H), 1.87-1.47 (m, 5H), 1.19-0.98 (m, 2H). MS (ESI+): 516.5. HPLC (max plot) 90.8%; Rt 6.29 min.

20

Procedure AW: Compounds Below Obtained by Separation of Racemic Mixture by Chiral Chromatography Following Procedures Outlined Above. The Chiral Centers Have Been Drawn Arbitrarily Up or Down. Enantiomers Have Been Named "Enantiomer A" or "Enantiomer B" Arbitrarily.

Intermediate AW.1: Enantiomer A of tert-butyl 3-[3-(morpholin-4-ylcarbonyl)-5,5-dioxidothiochromeno[4,3-c]pyrazol-1(4H)-yl]pyrrolidine-1-carboxylate

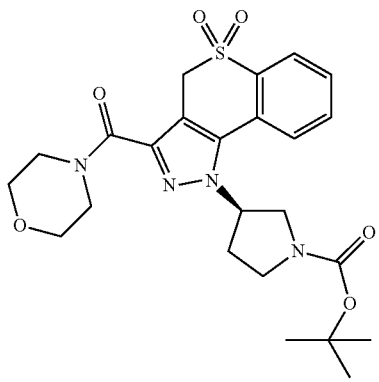 [SMILES: CC(C)(C)OC(=O)N1CC[C@@H](n2nc(C(=O)N3CCOCC3)c3c2-c2ccccc2S(=O)(=O)C3)C1]

Purified on a Chiralcel OD-H to give 803 mg of the title compound as a white solid. HPLC (max plot) 98.73%; Rt 3.45 min.. HPLC (chiralpack OJ-H, MeOH/0.1% TEA, max plot): 100.0%; Rt 5.99 min.

Intermediate AW.2: Enantiomer B of tert-butyl 3-[3-(morpholin-4-ylcarbonyl)-5,5-dioxidothiochromeno[4,3-c]pyrazol-1(4H)-yl]pyrrolidine-1-carboxylate

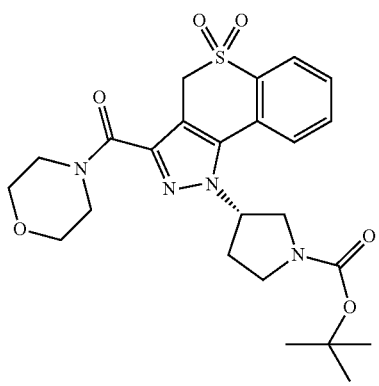 [SMILES: CC(C)(C)OC(=O)N1CC[C@H](n2nc(C(=O)N3CCOCC3)c3c2-c2ccccc2S(=O)(=O)C3)C1]

Purified on a Chiralcel OD-H to give 604 mg of the title compound as a white solid. HPLC (chiralpack OJ-H, MeOH/0.1% TEA, max plot): 99.76%; Rt 11.82 min Intermediate AW.3: Enantiomer A of tert-butyl 3-[6-fluoro-3-(morpholin-4-ylcarbonyl)-5,5-dioxidothiochromeno[4,3-c]pyrazol-1(4H)-yl] pyrrolidine-1-carboxylate

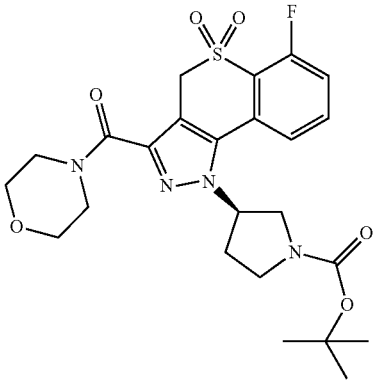 [SMILES: CC(C)(C)OC(=O)N1CC[C@@H](n2nc(C(=O)N3CCOCC3)c3c2-c2cccc(F)c2S(=O)(=O)C3)C1]

Purified on a Chiralcel OD-H to give 1.02 g (75%) of the title compound as a white solid. HPLC (chiralpack OJ-H, MeOH/0.1% TEA, max plot): 98.87%; Rt 5.85 min Intermediate AW.4: Enantiomer A of tert-butyl 3-[6-fluoro-3-(morpholin-4-ylcarbonyl)-5,5-dioxidothiochromeno[4,3-c]pyrazol-1(4H)-yl] pyrrolidine-1-carboxylate

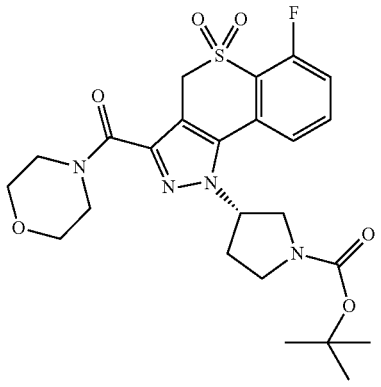 [SMILES: CC(C)(C)OC(=O)N1CC[C@H](n2nc(C(=O)N3CCOCC3)c3c2-c2cccc(F)c2S(=O)(=O)C3)C1]

Purified on a Chiralcel OD-H to give 1.17 g (87%) of the title compound as a white solid. HPLC (chiralpack OJ-H, MeOH/0.1% TEA, max plot): 95.01%; Rt 11.07 min Intermediate AW.5: Enantiomer B of 3-(morpholin-4-ylcarbonyl)-1-[piperidin-3-yl]-1,4-dihydrothiochromeno[4,3-c]pyrazole 5,5-dioxide

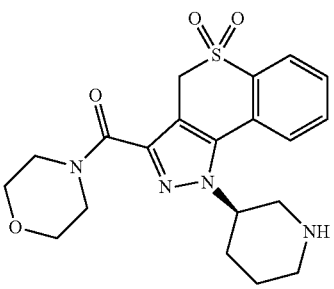 [SMILES: O=C(c1nn([C@@H]2CCCNC2)c2c1CS(=O)(=O)c1ccccc1-2)N1CCOCC1]

Purified on a Chiralcel OD-H to give 4.83 g (94%) of the title compound as a white solid. DPO00284N01. MS (ESI+): 417.2. HPLC (max plot) 97.6%; Rt 1.58 min. HPLC (chiralcel OD-H, EtOH/0.1% DEA, max plot): 99.48%; Rt 5.26 min. $[\alpha]^{25}$ D-0.99 (c 1.2, MeOH)

Intermediate AW.6: Enantiomer B of 3-(morpholin-4-ylcarbonyl)-1-[piperidin-3-yl]-1,4-dihydrothiochromeno[4,3-c]pyrazole 5,5-dioxide

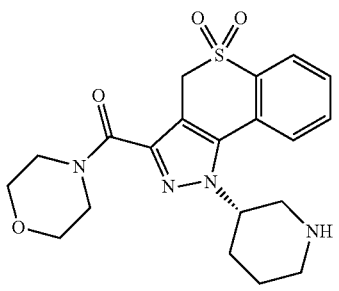

Purified on a Chiralcel OD-H to give 4.85 g (95%) of the title compound as a white solid. DPO00284N02. MS (ESI+): 417.2. HPLC (max plot) 97.6%; Rt 2.16 min. HPLC (chiralcel OD-H, EtOH/0.1% DEA, max plot): 99.40%; Rt 12.40 min Intermediate AW.7: Enantiomer A of 6-fluoro-3-(morpholin-4-ylcarbonyl)-1-[piperidin-3-yl]-1,4-dihydrothiochromeno[4,3-c]pyrazole 5,5-dioxide

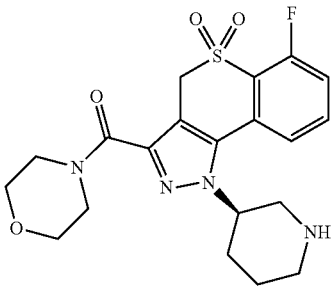 [SMILES: O=C(c1nn([C@@H]2CCCNC2)c2c1CS(=O)(=O)c1c(F)cccc1-2)N1CCOCC1]

Purified on a Chiralcel OD-H to give 1.04 g (91%) of the title compound as a white solid. DPO00283F01. HPLC (chiralcel OD-H, MeOH/0.1% DEA, max plot): 98.62%; Rt 1.38 min Intermediate AW.8: Enantiomer B of 6-fluoro-3-(morpholin-4-ylcarbonyl)-1-[piperidin-3-yl]-1,4-dihydrothiochromeno[4,3-c]pyrazole 5,5-dioxide

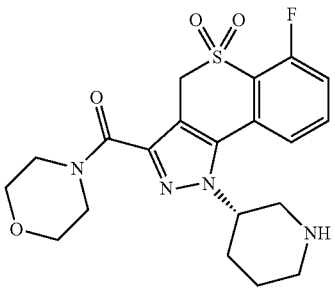

Purified on a Chiralcel OD-H to give 1.03 g (90%) of the title compound as a white solid. DPO00283F02. HPLC (chiralcel OD-H, MeOH/0.1% DEA, max plot): 100.0%; Rt 6.67 min Intermediate AW.9: Enantiomer B of 6-methoxy-3-(morpholin-4-ylcarbonyl)-1-[piperidin-3-yl]-1,4-dihydrothiochromeno[4,3-c]pyrazole 5,5-dioxide

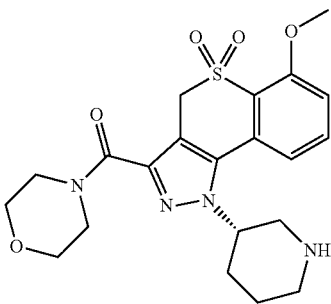

Purified on a Chiralcel OD-H to give 850 mg (80%) of the title compound as a white solid. HPLC (chiralcel OD-H, EtOH/0.1% DEA, max plot): 97.36%; Rt 18.02 min (enantiomer A: Rt 5.41 min).

Intermediate AW.10: Enantiomer B of 7-fluoro-3-(morpholin-4-ylcarbonyl)-1-[piperidin-3-yl]-1,4-dihydrothiochromeno[4,3-c]pyrazole 5,5-dioxide

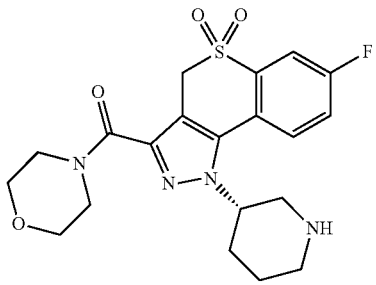 [SMILES: O=C(c1nn([C@H]2CCCNC2)c2c1CS(=O)(=O)c1cc(F)ccc1-2)N1CCOCC1]

Purified on a Chiralcel OD-H to give 1.20 g of the title compound as a white solid. HPLC (max plot) 96.5%; Rt 2.39 min. HPLC (chiralcel OD-H, EtOH/0.1% TEA, max plot): 100.0%; Rt 17.51 min (enantiomer A: Rt 5.12 min)

Intermediate AW.11: Enantiomer B of 7-methoxy-3-(morpholin-4-ylcarbonyl)-1-[piperidin-3-yl]-1,4-dihydrothiochromeno[4,3-c]pyrazole 5,5-dioxide

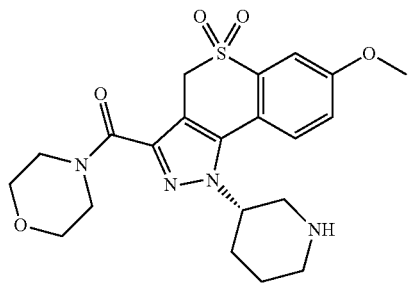 [SMILES: COc1ccc2c(c1)S(=O)(=O)Cc1c(C(=O)N3CCOCC3)nn([C@H]3CCCNC3)c1-2]

Purified on a Chiralcel OD-H to give 1.68 g (88%) of the title compound as a white solid.
HPLC (max plot): 99.9%; Rt 1.84 min. HPLC (chiralcel OD-H, MeOH/0.1% TEA, max plot): 99.86%; Rt 7.70 min (enantiomer (A: Rt 5.23 min)

Intermediate AW.12: Enantiomer B of 3-(morpholin-4-ylcarbonyl)-1-[piperidin-3-yl]-7-(trifluoromethoxy)-1,4-dihydrothiochromeno[4,3-c]pyrazole 5,5-dioxide

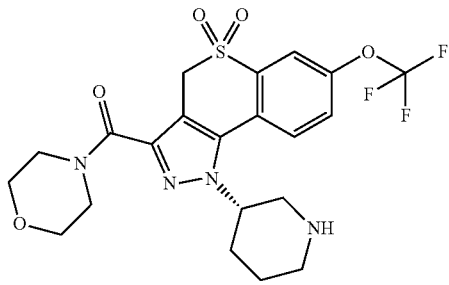 [SMILES: O=C(c1nn([C@H]2CCCNC2)c2c1CS(=O)(=O)c1cc(OC(F)(F)F)ccc1-2)N1CCOCC1]

Purified on a Chiralcel OD-H to give 335 mg of the title compound as a beige solid. HPLC (chiralcel OD-H, EtOH/0.1% TEA, max plot): 99.86%; Rt 11.78 min (enantiomer A: Rt 4.31 min)

Intermediate AW.13: Enantiomer B of 8-methoxy-3-(morpholin-4-ylcarbonyl)-1-[piperidin-3-yl]-1,4-dihydrothiochromeno[4,3-c]pyrazole 5,5-dioxide

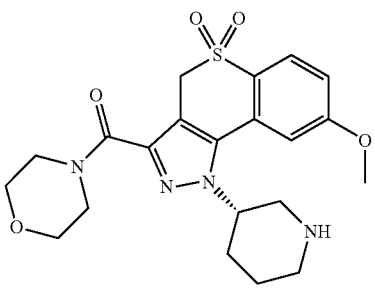 [SMILES: COc1ccc2c(c1)-c1c(c(C(=O)N3CCOCC3)nn1[C@H]1CCCNC1)CS2(=O)=O]

Purified on a Chiralcel OD-H. $^1$H NMR: 7.97-8.00 (d, 9 Hz, 1H), 7.20-7.30 (m, 2H), 7.71-7.75 (m, 3H), 3.97 (s, 3H), 3.92 (s, 1H), 3.66 (s, 6H), 3.33 (s, 1H), 3.20-3.24 (d, 12 Hz, 1H), 2.93-2.96 (m, 2H), 2.46-2.50 (m, 1H), 2.19-2.20 (m, 1H), 1.91-2.07 (m, 1H), 1.75-1.79 (m, 1H), 1.59-1.62 (m, 1H). MS (ESI+): 447.2. HPLC (chiralcel OD-H, EtOH/0.1% TEA, max plot): 100.0% Rt 10.69 min (enantiomer A: Rt 5.40 min).

Intermediate AW.14: Enantiomer A of tert-butyl 4-[3-(morpholin-4-ylcarbonyl)-5,5-dioxidothiochromeno[4,3-c]pyrazol-1(4H)-yl]azepane-1-carboxylate

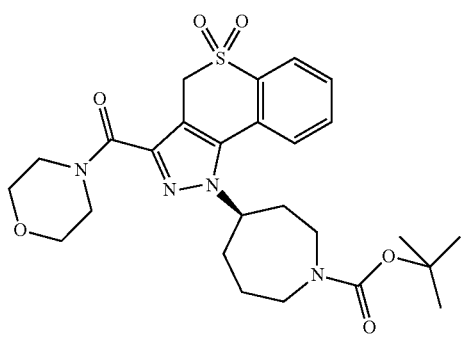 [SMILES: CC(C)(C)OC(=O)N1CCC[C@@H](n2nc(C(=O)N3CCOCC3)c3c2-c2ccccc2S(=O)(=O)C3)CC1]

Purified on a Chiralpak IC to give 300 mg of the title compound as a white powder. HPLC (chiralpak IC, 30% THF/70% Hexane, max plot): 98.23% Rt 11.59 min.

Intermediate AW.15: Enantiomer B of tert-butyl 4-[3-(morpholin-4-ylcarbonyl)-5,5-dioxidothiochromeno[4,3-c]pyrazol-1(4H)-yl]azepane-1-carboxylate

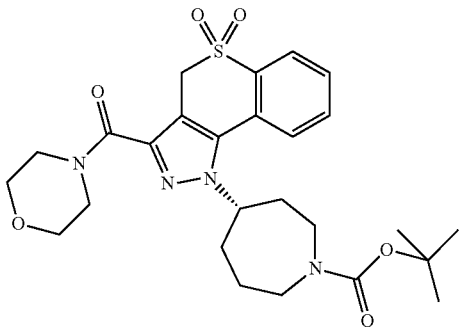 [SMILES: CC(C)(C)OC(=O)N1CCC[C@H](n2nc(C(=O)N3CCOCC3)c3c2-c2ccccc2S(=O)(=O)C3)CC1]

Purified on a Chiralpak IC to give 600 mg of the title compound as a white powder. MS (ESI+): 531.0. HPLC (chiralpak IC, 30% THF/70% Hexane, max plot): 98.23% Rt 14.06 min.

Intermediate AW.16: Enantiomer A of 3-(morpholin-4-ylcarbonyl)-1-[piperidin-3-yl]-1,4-dihydropyrazolo[3',4':4,5]thiopyrano[2,3-b]pyridine 5,5-dioxide

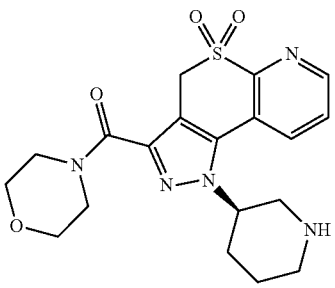

Purified on a Chiralcel OD-H to give 200 mg (36%) of the title compound. MS (ESI+): 418.29. HPLC (max plot) 98.6%; Rt 1.14 min.

Intermediate AW.17: Enantiomer B of 3-(morpholin-4-ylcarbonyl)-1-[piperidin-3-yl]-1,4-dihydropyrazolo[3',4':4,5]thiopyrano[2,3-b]pyridine 5,5-dioxide

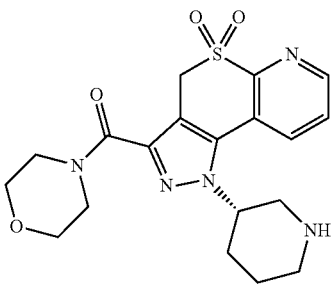

Purified on a Chiralcel OD-H to give 200 mg (36%) of the title compound. MS (ESI+): 418.28. (max plot) 98.9%; Rt 1.09 min.

Intermediate AW.18: Enantiomer B of tert-butyl 3-[6-chloro-3-(morpholin-4-ylcarbonyl)-5,5-dioxidothiochromeno[4,3-c]pyrazol-1(4H)-yl]piperidine-1-carboxylate

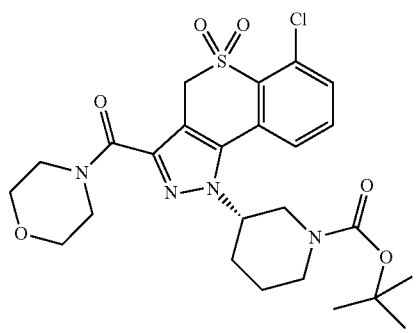 [SMILES: CC(C)(C)OC(=O)N1CCC[C@H](n2nc(C(=O)N3CCOCC3)c3c2-c2cccc(Cl)c2S(=O)(=O)C3)C1]

Purified on a Chiralpak AY-H to give 261 mg of the title compound. MS (ESI-): 549.46. HPLC (max plot) 99.70%; Rt 8.05 min. HPLC (chiralcel OD-H, 50% Hexane/50% is OH, max plot: 99.7%; Rt 8.05 min (enantiomer A: Rt 6.17 min).

Intermediate AW.19: Enantiomer B of 6-methyl-3-(morpholin-4-ylcarbonyl)-1-[piperidin-3-yl]-1,4-dihydrothiochromeno[4,3-c]pyrazole 5,5-dioxide

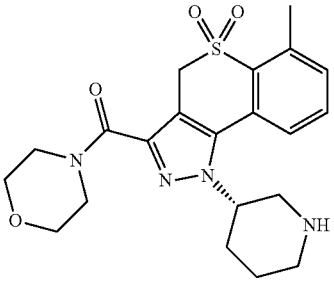 [SMILES: Cc1cccc2c1S(=O)(=O)Cc1c(C(=O)N3CCOCC3)nn([C@H]3CCCNC3)c1-2]

Purified on a Chiralcel OD-H to give 660 mg of the title compound as a white solid. MS (ESI+): 431.16. HPLC (max plot) 99.7%; Rt 2.49 min. HPLC (chiralcel OD-H, EtOH/0.1% TEA, max plot): 99.97%; Rt 17.10 min (enantiomer A: Rt 5.70 min).

Example 372: Enantiomer B of 1-[1-(2-fluoroethyl)piperidin-3-yl]-3-(morpholin-4-ylcarbonyl)-1,4-dihydrothiochromeno[4,3-c]pyrazole 5,5-dioxide

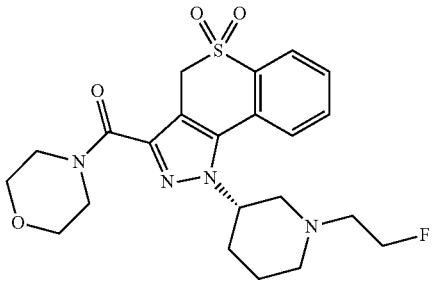

Purified on a Chiralpak AY-H to give 153 mg (quant) of the title compound as a. $^1$H NMR (300 MHz, DMSO): δ 8.16-8.00 (m, 1H), 7.99-7.89 (m, 1H), 7.88-7.80 (m, 1H), 7.80-7.63 (m, 1H), 4.94-4.68 (m, 3H), 4.62 (t, J = 4.8 Hz, 1H), 4.46 (t, J = 4.8 Hz, 1H), 4.00-3.83 (m, 2H), 3.75-3.55 (m, 5H), 3.20 (d, J = 10.2 Hz, 1H), 2.93 (d, J = 10.5 Hz, 1H), 2.77 (t, J = 4.7 Hz, 1H), 2.68 (t, J = 4.8 Hz, 1H), 2.62-2.49 (m, 2H), 2.14 (d, J = 10.3 Hz, 2H), 2.03-1.52 (m, 3H). HPLC (max plot) 96.7%; Rt 2.26 min.. HPLC (chiralpack AY, 50% hexane/50% EtOH/0.1% TEA, max plot): 96.28%; Rt 19.87 min (enantiomer A: Rt 14.79 min).

Example 409: Enantiomer A of 1-{1-[2-(4-fluoropiperidin-1-yl)ethyl]pyrrolidin-3-yl}-3-(morpholin-4-ylcarbonyl)-1,4-dihydrothiochromeno[4,3-c]pyrazole 5,5-dioxide

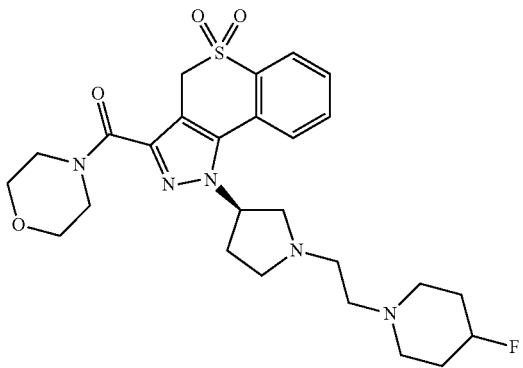

Purified on a Chiralpak AD-H to give 18 mg of the title compound as a white powder. $^1$H NMR (DMSO-$d_6$, 300 MHz): δ 8.03 (dd, J = 7.8, 1.2 Hz, 1H), 7.97 (d, J = 7.7 Hz, 1H), 7.93-7.85 (m, 1H), 7.74 (dd, J = 10.9, 4.3 Hz, 1H), 5.51-5.40 (m, 1H), 4.76 (s, 2H), 4.77-4.67 (m, 1H), 4.62-4.52- (m, 1H), 4.00-3.93 (m, 2H), 3.72-3.62 (m, 5H), 3.28 (dd, J = 9.6, 7.4 Hz, 1H), 2.86 (dd, J = 9.7, 5.2 Hz, 1H), 2.76 (t, J = 6.8 Hz, 2H), 2.60 (dd, J = 13.0, 6.4 Hz, 4H), 2.42 (t, J = 6.7 Hz, 3H), 2.34-2.17 (m, 3H), 1.92-1.57 (m, 4H).. MS (ESI+): 532.4. HPLC (max plot) 100.0%; Rt 1.80 min. HPLC (chiralpack AD-H, EtOH, max plot): 100.0%; Rt 8.01 min.

Example 410: Enantiomer B of 1-{1-[2-(4-fluoropiperidin-1-yl)ethyl]pyrrolidin-3-yl}-3-(morpholin-4-ylcarbonyl)-1,4-dihydrothiochromeno[4,3-c]pyrazole 5,5-dioxide

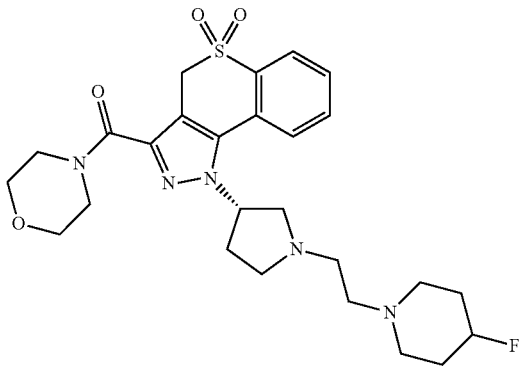

Purified on a Chiralpak AD-H to give 18 mg of the title compound as a white powder. $^1$H NMR (DMSO-$d_6$, 300 MHz): δ 8.03 (dd, J = 7.8, 1.2 Hz, 1H), 7.97 (d, J = 7.7 Hz, 1H), 7.93-7.85 (m, 1H), 7.74 (dd, J = 10.9, 4.3 Hz, 1H), 5.51-5.40 (m, 1H), 4.76 (s, 2H), 4.77-4.67 (m, 1H), 4.62-4.52 (m, 1H), 4.00-3.93 (m, 2H), 3.72-3.62 (m, 5H), 3.28 (dd, J = 9.6, 7.4 Hz, 1H), 2.86 (dd, J = 9.7, 5.2 Hz, 1H), 2.76 (t, J = 6.8 Hz, 2H), 2.60 (dd, J = 13.0, 6.4 Hz, 4H), 2.42 (t, J = 6.7 Hz, 3H), 2.34-2.17 (m, 3H), 1.92-1.57 (m, 4H).. MS (ESI+): 532.4. HPLC (max plot) 99.5%; Rt 2.11 min. HPLC (chiralpack AD-H, EtOH, max plot): 100.0%; Rt 13.27 min Example 411: Enantiomer A of 1-{1-[2-(1H-imidazol-1-yl)ethyl]piperidin-3-yl}-3-(morpholin-4-ylcarbonyl)-1,4-dihydrothiochromeno[4,3-c]pyrazole 5,5-dioxide

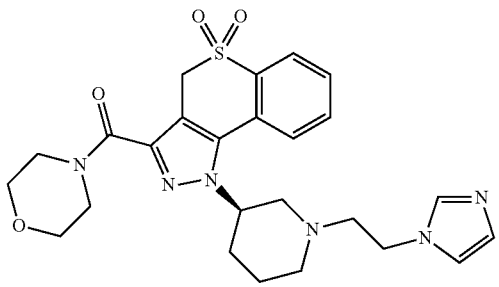 [SMILES: O=C(c1nn([C@@H]2CCCN(CCn3ccnc3)C2)c2c1CS(=O)(=O)c1ccccc1-2)N1CCOCC1]

Purified on a Chiralcel OD-H to give 8 mg of the title compound as a white powder. MS (ESI+): 511.31. HPLC (max plot) 95.3%; Rt 1.47 min. HPLC (chiralcel OD-H, EtOH, max plot): 100.0%; Rt 7.09 min Example 412: Enantiomer B of 1-{1-[2-(1H-imidazol-1-yl)ethyl]piperidin-3-yl}-3-(morpholin-4-ylcarbonyl)-1,4-dihydrothiochromeno[4,3-c]pyrazole 5,5-dioxide

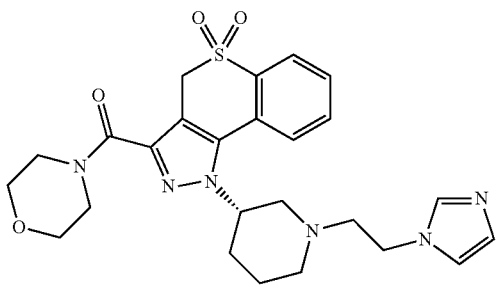 [SMILES: O=C(c1nn([C@H]2CCCN(CCn3ccnc3)C2)c2c1CS(=O)(=O)c1ccccc1-2)N1CCOCC1]

Purified on a Chiralcel OD-H to give 8 mg of the title compound as a white powder. MS (ESI+): 511.31. HPLC (max plot) 94.4%; Rt 1.46 min. HPLC (chiralcel OD-H, EtOH, max plot): 100.0%; Rt 10.21 min Example 423: Enantiomer A of 3-(morpholin-4-ylcarbonyl)-1-{1-[2-(tetrahydro-2H-pyran-4-yl)ethyl]piperidin-3-yl}-1,4-dihydropyrazolo[3',4':4,5]thiopyrano[2,3-b]pyridine 5,5-dioxide

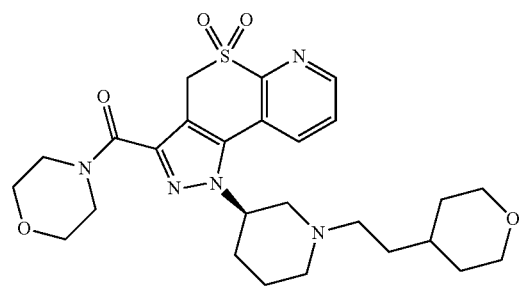 [SMILES: O=C(c1nn([C@@H]2CCCN(CCC3CCOCC3)C2)c2c1CS(=O)(=O)c1ncccc1-2)N1CCOCC1]

Purified on a Chiralpak AY-H to give 21 mg of the title compound as a white solid. $^1$H NMR (DMSO-$d_6$, 300 MHz): δ 8.85-8.76 (m, 1H), 8.34-8.22 (m, 1H), 7.99-7.87 (m, 1H), 4.90 (s, 2H), 4.82-4.67 (m, 1H), 3.97-3.85 (m, 2H), 3.85-3.74 (m, 2H), 3.74-3.57 (m, 6H), 3.30-3.17 (m, 2H), 3.17-3.03 (m, 1H), 2.95-2.77 (m, 1H), 2.45-2.22 (m, 3H), 2.22-2.03 (m, 1H), 2.03-1.83 (m, 2H), 1.83-1.61 (m, 2H), 1.61-1.40 (m, 3H), 1.40-1.26 (m, 2H), 1.21-1.00 (m, 2H). MS (ESI+): 530.5. HPLC (max plot) 91.9%; Rt 6.16 min. HPLC (chiralpak AY-H, 60% EtOH/40% is OH, max plot): 100.0%; Rt 18.17 min Example 422: Enantiomer B of 3-(morpholin-4-ylcarbonyl)-1-{1-[2-(tetrahydro-2H-pyran-4-yl)ethyl]piperidin-3-yl}-1,4-dihydropyrazolo[3',4':4,5]thiopyrano[2,3-b]pyridine 5,5-dioxide

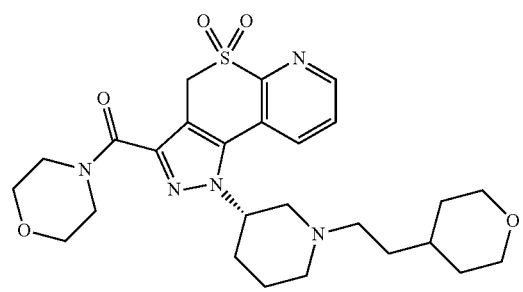 [SMILES: O=C(c1nn([C@H]2CCCN(CCC3CCOCC3)C2)c2c1CS(=O)(=O)c1ncccc1-2)N1CCOCC1]

Purified on a Chiralpak AY-H to give 30 mg of the title compound as a white solid. $^1$H NMR (DMSO-$d_6$, 300 MHz): δ 8.85-8.76 (m, 1H), 8.34-8.22 (m, 1H), 7.99-7.87 (m, 1H), 4.90 (s, 2H), 4.82-4.67 (m, 1H), 3.97-3.85 (m, 2H), 3.85-3.74 (m, 2H), 3.74-3.57 (m, 6H), 3.30-3.17 (m, 2H), 3.17-3.03 (m, 1H), 2.95-2.77 (m, 1H), 2.45-2.22 (m, 3H), 2.22-2.03 (m, 1H), 2.03-1.83 (m, 2H), 1.83-1.61 (m, 2H), 1.61-1.40 (m, 3H), 1.40-1.26 (m, 2H), 1.21-1.00 (m, 2H). MS (ESI+): 530.5. HPLC (max plot) 93.2%; Rt 6.15 min. HPLC (chiralpak AY-H, 60% EtOH/40% is OH, max plot): 100.0%; Rt 27.10 min Example 347: Enantiomer A of 1-[1-(2-methoxyethyl)piperidin-3-yl]-3-(morpholin-4-ylcarbonyl)-1,4-dihydrothiochromeno[4,3-c]pyrazole 5,5-dioxide

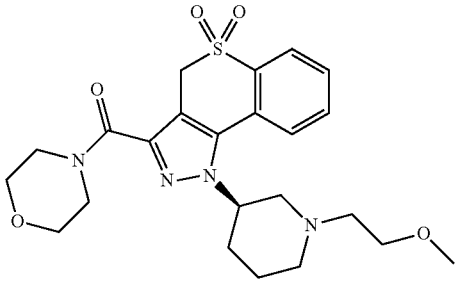 [SMILES: COCCN1CCC[C@@H](n2nc(C(=O)N3CCOCC3)c3c2-c2ccccc2S(=O)(=O)C3)C1]

Purified on a Chiralpak AY-H to give 240 mg of the title compound as a pale yellow solid. $^1$H NMR (DMSO-d$_6$, 300 MHz): δ 8.05 (dd, J = 1.2, 7.8 Hz, 1H), 7.99-7.89 (m, 1H), 7.87-7.80 (m, 1H), 7.79-7.71 (m, 1H), 4.95-4.67 (m, 3H), 4.04-3.85 (m, 2H), 3.75-3.58 (m, 6H), 3.44 (t, J = 5.6 Hz, 2H), 3.27-3.11 (m, 4H), 2.90 (d, J = 12.0 Hz, 1H), 2.64-2.53 (m, 2H), 2.47-2.36 (m, 1H), 2.20-1.61 (m, 6H). MS (ESI+): 475.37. HPLC (max plot) 96.7%; Rt 1.79 min. HPLC (Chiralpak AY-H, MeOH/01%DEA, max plot): 100.0%; Rt 8.19 min.

Example 346: Enantiomer B of 1-[1-(2-methoxyethyl)piperidin-3-yl]-3-(morpholin-4-ylcarbonyl)-1,4-dihydrothiochromeno[4,3-c]pyrazole 5,5-dioxide

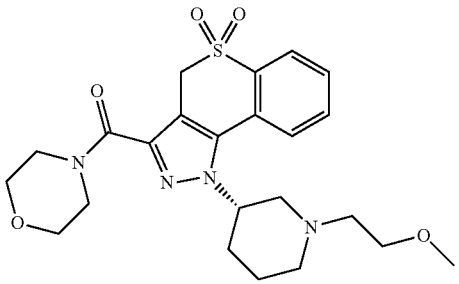 [SMILES: COCCN1CCC[C@H](n2nc(C(=O)N3CCOCC3)c3c2-c2ccccc2S(=O)(=O)C3)C1]

Purified on a Chiralpak AY-H to give 220 mg of the title compound as a pale yellow solid. $^1$H NMR (DMSO-d$_6$, 300 MHz): δ 8.05 (dd, J = 1.2, 7.8 Hz, 1H), 7.98-7.89 (m, 1H), 7.87-7.80 (m, 1H), 7.79-7.70 (m, 1H), 4.91-4.66 (m, 3H), 4.01-3.85 (m, 2H), 3.74-3.55 (m, 5H), 3.44 (t, J = 5.6 Hz, 2H), 3.25-3.15 (m, 4H), 2.90 (d, J = 10.7 Hz, 1H), 2.66-2.53 (m, 2H), 2.47-2.36 (m, 1H), 2.25-1.61 (m, 6H). MS (ESI+): 475.33. HPLC (max plot) 96.6%; Rt 1.76 min. HPLC (Chiralpak AY-H, MeOH/01%DEA, max plot): 100.0%; Rt 14.03 min Example 464: Enantiomer B of 1-{1-[2-(3,3-difluoroazetidin-1-yl)ethyl]piperidin-3-yl}-6-fluoro-3-(morpholin-4-ylcarbonyl)-1,4-dihydrothiochromeno[4,3-c]pyrazole 5,5-dioxide

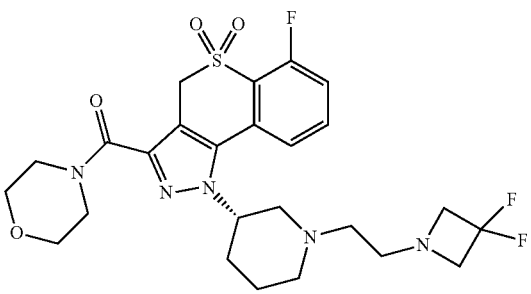 [SMILES: O=C(c1nn([C@H]2CCCN(CCN3CC(F)(F)C3)C2)c2c1CS(=O)(=O)c1c(F)cccc1-2)N1CCOCC1]

Purified on a Chiralpack IA to give 7 mg of the title compound as a beige solid. MS (ESI+): 554.43. HPLC (max plot) 97.5%; Rt 2.15 min. HPLC (Chiralpak IA-H, 60% hexane/40% EtOH/01%DEA, max plot): Rt 13.37 min (Enantiomer A: Rt 11.32 min)

Procedure AX

Example 418

Enantiomer B of 1-[1-(3-furoyl)piperidin-3-yl]-3-(morpholin-4-ylcarbonyl)-1,4-dihydrothiochromeno[4,3-c]pyrazole 5,5-dioxide

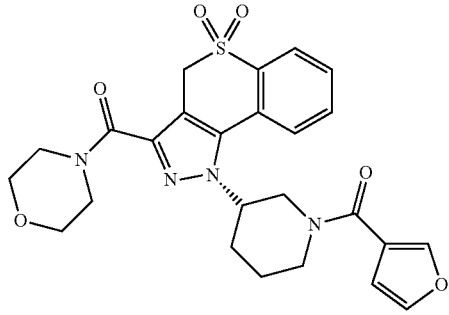

To a solution of Enantiomer B of 3-(morpholin-4-ylcarbonyl)-1-[piperidin-3-yl]-1,4-dihydrothiochromeno[4,3-c]pyrazole 5,5-dioxide (30 mg; 0.07 mmol; 1 eq.) in DCM (0.45 mL) is added N,N-diisopropylethylamine (25 µl; 0.14 mmol; 2 eq.) followed by 3-furoyl chloride (14 mg; 0.11 mmol; 1.5 eq.) and the reaction mixture is stirred at rt overnight. The solvent is concentrated and the residue is purified by flash chromatography (eluent MeOH/EtOAc 0 to 10%) to afford 20 mg (54%) of the title compound as a white foam. 1H NMR (DMSO-d6): δ 8.04 (d, J=7.7 Hz, 2H), 7.86 (s, 1H), 7.75 (d, J=7.8 Hz, 2H), 6.67 (s, 1H), 4.85 (s, 1H), 4.79 (s, 2H), 3.91 (s, 2H), 3.64 (d, J=9.7 Hz, 5H), 2.26 (s, 2H), 1.95-1.61 (m, 2H). HPLC (max plot) 99.4%; Rt 3.02 min. MS (ESI+): 511.30.

Compounds Described Below are Obtained Following Protocol Outlined in Procedure AX Example 61: 3-(Morpholin-4-ylcarbonyl)-1-[3-(morpholin-4-ylcarbonyl)phenyl]-1,4-dihydrothiochromeno[4,3-c]pyrazole 5,5-dioxide

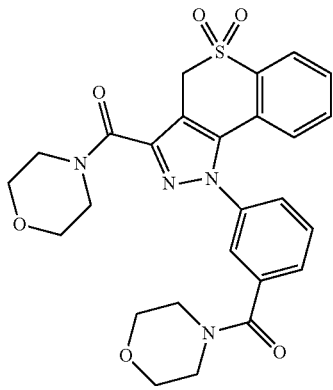 [SMILES: O=C(c1cccc(-n2nc(C(=O)N3CCOCC3)c3c2-c2ccccc2S(=O)(=O)C3)c1)N1CCOCC1]

18 mg of the title compound as an off-white solid. $^1$H NMR (DMSO-$d_6$, 400 MHz) δ 8.02 (d, J = 7.7 Hz, 1H), 7.73-7.57 (m, 5H), 7.51 (s, 1H), 6.91 (d, J = 7.7 Hz, 1H), 4.90 (s, 2H), 3.92-3.91 (m, 2H), 3.66-3.59 (m, 10H), 3.46 (bs, 2H), 3.37 (brs, 2H). MS (ESI+): 523.0. HPLC (max plot) 98.9%; Rt 3.04 min Example 62: 3-[3-(Morpholin-4-ylcarbonyl)-5,5-dioxidothiochromeno[4,3-c]pyrazol-1(4H)-yl]benzamide

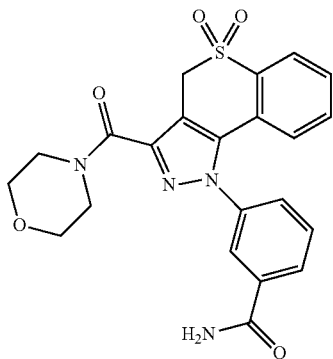 [SMILES: NC(=O)c1cccc(-n2nc(C(=O)N3CCOCC3)c3c2-c2ccccc2S(=O)(=O)C3)c1]

18 mg of the title compound as an off-white solid. $^1$H NMR (DMSO-$d_6$, 400 MHz) δ 8.19-8.17 (m, 1H), 8.13-8.11 (m, 5H), 8.02 (s, 1H), 6.91 (d, J = 7.7 Hz, 1H), 4.90 (s, 2H), 3.92-3.91 (m, 2H), 3.66-3.46 (m, 6H). MS (ESI+): 453.0. HPLC (max plot) 99.1%; Rt 2.81 min Example 100: N-[3-(Morpholin-4-ylcarbonyl)-5,5-dioxido-1-phenyl-1,4-dihydrothiochromeno[4,3-c]pyrazol-8-yl]acetamide

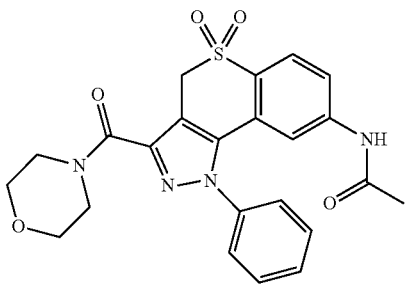 [SMILES: CC(=O)Nc1ccc2c(c1)-c1c(c(C(=O)N3CCOCC3)nn1-c1ccccc1)CS2(=O)=O]

12 mg of the title compound as a pale brown solid. $^1$H NMR (400 MHz, DMSO-$d_6$) δ = 10.25 (bs, 1H), 7.94-7.92 (d, J = 8.5 Hz, 1H), 7.63-7.58 (m, 4H), 7.50-7.48 (m, 3H), 4.81 (s, 2H), 3.93 (m, 2H), 3.66-3.60 (m, 6H), 1.94 (s, 3H). MS (ESI+): 467. HPLC (max plot): 96.32%; Rt 3.15 min.

Example 191: 1-[(1-Acetylpiperidin-4-yl)methyl]-3-(morpholin-4-ylcarbonyl)-1,4-dihydrothiochromeno[4,3-c]pyrazole 5,5-dioxide

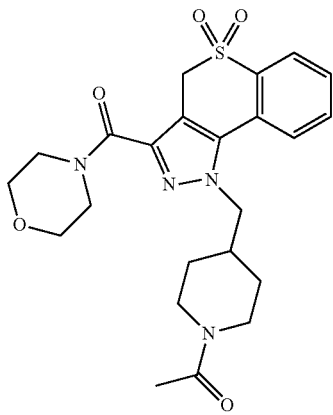 [SMILES: CC(=O)N1CCC(Cn2nc(C(=O)N3CCOCC3)c3c2-c2ccccc2S(=O)(=O)C3)CC1]

12 mg of the title compound as a white solid. $^1$H NMR (DMSO-$d_6$, 400 MHz): δ 8.02-7.99 (m, 2H), 7.89-7.86 (m, 1H), 7.73-7.69 (m, 1H), 4.78 (s, 2H), 4.49-4.47 (m, 2H), 4.30-4.27 (m, 2H), 3.90 (m, 1H), 3.76-3.72 (m, 1H), 3.65-3.64 (m, 6H), 2.94-2.88 (m, 1H), 2.43-2.40 (m, 1H), 2.11 (m, 1H), 1.93 (s, 3H), 1.49 (m, 2H), 1.19 (m, 1H), 1.16 (m, 1H). MS (ESI+): 473.0. HPLC (max plot) 96.64%; Rt 2.78 min.

Example 279: 1-[1-(Cyclohexylacetyl)pyrrolidin-3-yl]-3-(morpholin-4-ylcarbonyl)-1,4-dihydrothiochromeno[4,3-c]pyrazole 5,5-dioxide

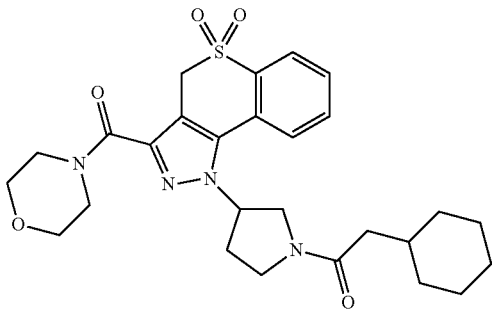 [SMILES: O=C(CC1CCCCC1)N1CCC(n2nc(C(=O)N3CCOCC3)c3c2-c2ccccc2S(=O)(=O)C3)C1]

40 mg of the title compound as a white foam. $^1$H NMR (DMSO-d$_6$) δ 8.05 (m, 1H), 7.99-7.86 (m, 2H), 7.75 (m, 1H), 5.68-5.55 (m, 1H), 4.80 (m, 2H), 3.96-3.82 (m, 3H), 3.73-3.50 (m, 8H), 2.64-2.40 (m, 2H), 2.19-2.08 (m, 2H), 1.77-1.55 (m, 6H), 1.28-1.05 (m, 2H), 1.03-0.82 (m, 2H). HPLC (max plot) 99.6%; Rt 3.49 min. MS (ESI+): 527.4.

Example 287: 3-(Morpholin-4-ylcarbonyl)-1-[1-(tetrahydro-2H-pyran-4-ylacetyl)pyrrolidin-3-yl]-1,4-dihydrothiochromeno[4,3-c]pyrazole 5,5-dioxide

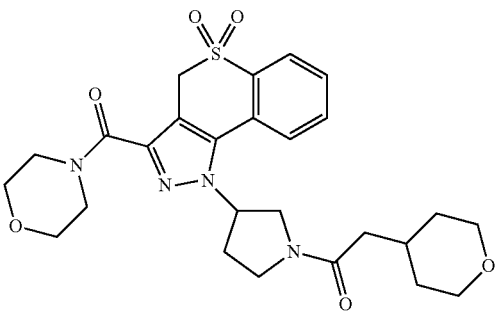 [SMILES: O=C(CC1CCOCC1)N1CCC(n2nc(C(=O)N3CCOCC3)c3c2-c2ccccc2S(=O)(=O)C3)C1]

35 mg (83%) of the title compound as a white foam. 1H NMR (DMSO-d6): δ 8.05 (d, J = 7.6 Hz, 1H), 7.93 (q, J = 8.1 Hz, 2H), 7.75 (t, J = 7.2 Hz, 1H), 5.61 (s, 1H), 4.88-4.71 (m, 2H), 4.10-3.97 (m, 1H), 3.85 (dd, J = 18.3, 14.1 Hz, 5H), 3.59 (d, J = 34.1 Hz, 7H), 3.30-3.19 (m, 2H), 2.36-2.14 (m, 2H), 1.89 (s, 1H), 1.58 (s, 2H), 1.19 (dd, J = 16.0, 8.9 Hz, 3H). HPLC (max plot) 100%; Rt 2.49 min. MS (ESI+): 528.8.

Example 419: Enantiomer B of 3-(morpholin-4-ylcarbonyl)-1-[1-(tetrahydro-2H-pyran-4-ylcarbonyl) piperidin-3-yl]-1,4-dihydrothiochromeno[4,3-c]pyrazole 5,5-dioxide

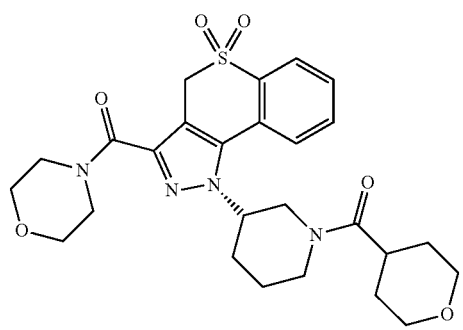

Obtained from enantiomer B of 3-(morpholin-4-ylcarbonyl)-1-[piperidin-3-yl]-1,4-dihydropyrazolo[3',4':4,5]thiopyrano[2,3-b]pyridine 5,5-dioxide to give 27 mg (71%) of the title compound as a white foam. 1H NMR (DMSO-d6) δ : 8.13-7.82 (m, 3H), 7.75 (d, J = 7.7 Hz, 1H), 4.72 (d, J = 4.3 Hz, 4H), 4.29-3.54 (m, 12H), 3.39 (s, 2H), 3.24-2.59 (m, 5H), 2.24 (s, 2H), 1.62 (t, J = 7.1 Hz, 7H). HPLC (max plot) 99.6%; Rt 2.73 min. MS (ESI+): 529.30.

Example 420: Enantiomer B of 3-(morpholin-4-ylcarbonyl)-1-[1-(tetrahydro-2H-pyran-4-ylacetyl) piperidin-3-yl]-1,4-dihydrothiochromeno[4,3-c]pyrazole 5,5-dioxide

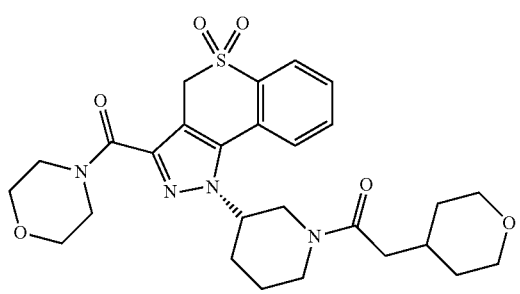

Obtained from enantiomer B of 3-(morpholin-4-ylcarbonyl)-1-[piperidin-3-yl]-1,4-dihydropyrazolo[3',4':4,5]thiopyrano[2,3-b]pyridine 5,5-dioxide to give 35 mg (90%) of the title compound as a white foam. 1H NMR (DMSO-d6) δ 8.13-7.81 (m, 3H), 7.74 (t, J = 7.6 Hz, 1H), 4.99-4.54 (m, 4H), 4.27-4.07 (m, 1H), 3.98-3.77 (m, 4H), 3.74-3.55 (m, 7H), 3.30-2.93 (m, 3H), 2.40-2.05 (m, 4H), 1.91-1.42 (m, 5H), 1.32-0.97 (m, 2H). HPLC (max plot) 98.4%; Rt 4.08 min. MS (ESI+): 543.30.

Example 421: Enantiomer B of 1-[1-(cyclohexylacetyl)piperidin-3-yl]-3-(morpholin-4-ylcarbonyl)-1,4-dihydrothiochromeno[4,3-c]pyrazole 5,5-dioxide

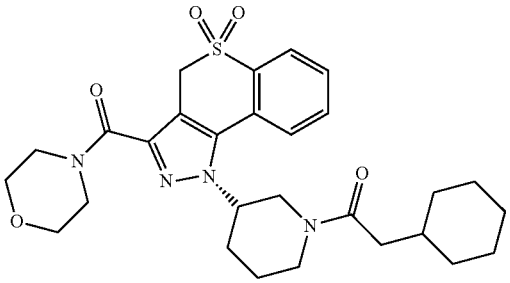

Obtained from enantiomer B of 3-(morpholin-4-ylcarbonyl)-1-[piperidin-3-yl]-1,4-dihydropyrazolo[3',4':4,5]thiopyrano[2,3-b]pyridine 5,5-dioxide to give 38 mg (98%) of the title compound as a white foam. 1H NMR (300 MHz, DMSO-d6) δ 8.05-7.80 (m, 3H), 7.74 (t, J = 7.7 Hz, 1H), 4.97-4.51 (m, 4H), 4.25-3.88 (m, 4H), 3.72-3.60 (m, 5H), 3.23-2.96 (m, 2H), 2.38-2.00 (m, 4H), 1.92-1.77 (m, 1H), 1.77-1.44 (m, 6H), 1.25-0.75 (m, 6H). HPLC (max plot) 98.4%; Rt 4.08 min. MS (ESI+): 441.

Example 447: Enantiomer B of 1-[1-(methoxyacetyl)piperidin-3-yl]-3-(morpholin-4-ylcarbonyl)-1,4-dihydrothiochromeno[4,3-c]pyrazole 5,5-dioxide

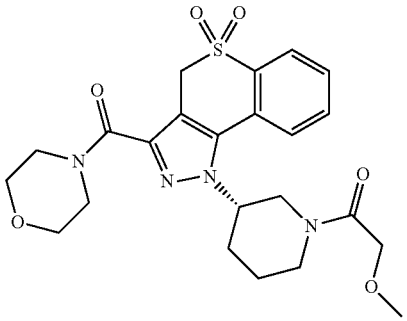 [SMILES: COCC(=O)N1CCC[C@H](n2nc(C(=O)N3CCOCC3)c3c2-c2ccccc2S(=O)(=O)C3)C1]

Obtained from enantiomer B of 3-(morpholin-4-ylcarbonyl)-1-[piperidin-3-yl]-1,4-dihydropyrazolo[3',4':4,5]thiopyrano[2,3-b]pyridine 5,5-dioxide to give 30 mg (82%) of the title compound as a white foam. MS (ESI+): 489.4. HPLC (max plot) 100.0%; Rt 2.90 min Example 276

N-Cyclohexyl-3-]3-(morpholin-4-ylcarbonyl)-5,5-dioxidothiochromeno[4,3-c]pyrazol-1(4H)-yl]pyrrolidine-1-carboxamide

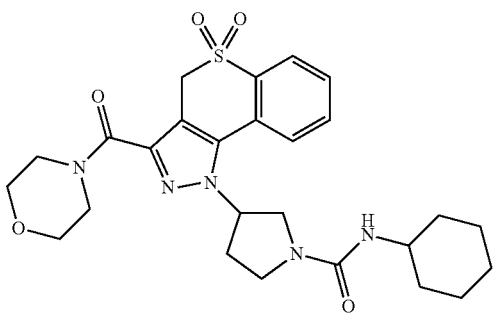

To a solution of 3-(morpholin-4-ylcarbonyl)-1-pyrrolidin-3-yl-1,4-dihydrothiochromeno[4,3-c]pyrazole5,5-dioxide hydrochloride (50 mg; 0.11 mmol; 1 eq.) and N,N-diisopropyl ethylamine (21.59 μl; 0.13 mmol; 1.10 eq.) in DCM (0.5 ml) is added cyclohexyl isocyanate (15.68 mg; 0.13 mmol; 1.1 eq.) and the reaction mixture is stirred at rt for 20 min. Aminomethyl resin is added and the reaction mixture is stirred at rt overnight. The resin is filtered off and the solvent removed under reduced pressure. The crude residue is purified by flash chromatography (eluting from 0 to 10% EtOAc in MeOH) to afford after concentration of the desired fractions 45 mg (75%) of the title compound as a white solid. HPLC (max plot) 99.7%; Rt 3.68 min. MS (ESI+): 528.3.

Example 189

3-(Morpholin-4-ylcarbonyl)-1-[3-(1,3-thiazol-2-yl)phenyl]-1,4-dihydrothiochromeno[4,3-c]pyrazole 5,5-dioxide

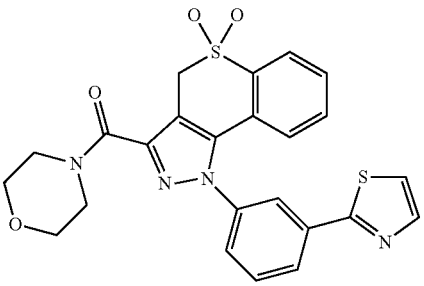 [SMILES: O=C(c1nn(-c2cccc(-c3nccs3)c2)c2c1CS(O)(O)c1ccccc1-2)N1CCOCC1]

1-(3-bromophenyl)-3-(morpholin-4-ylcarbonyl)-1,4-dihydrothiochromeno[4,3-c]pyrazole 5,5-dioxide (100 mg, 0.20 mmol, 1 eq.) is taken in THF in and bubbled with nitrogen for 5 minutes. To this are added thiazolyl zinc bromide (2 mL), tetrakis(triphenyl phosphine)palladium(0) (12 mg, 0.010 mmol, 0.05 eq.) and the reaction mixture is heated under sealed condition at 65° C. for 4 h. The reaction mixture is filtered through a celite pad, concentrated under reduced pressure and purified by flash chromatography to afford the title compound as a pink solid. $^1$H NMR (DMSO-d$_6$, 400 MHz): δ 8.18-8.16 (d, J=7.7 Hz, 1H), 8.07 (s, 1H), 8.04-8.02 (d, J=7.7 Hz, 1H), 7.96-7.95 (d, J=3.2 Hz, 1H), 7.87-7.86 (d, J=3.2 Hz, 1H), 7.76-7.72 (t, J=7.9 Hz, 1H), 7.65-7.56 (m, 3H), 6.98-6.96 (d, J=7.7 Hz, 1H), 4.91 (s, 2H), 3.93 (m, 2H), 3.67 (m, 4H), 3.62-3.61 (m, 2H). MS (ESI+): 493.0. HPLC (max plot) 98.44%; Rt 4.02 min.

Example 199

1-[3-(5-Ethyl-1,2,4-oxadiazol-3-yl)phenyl]-3-(morpholin-4-ylcarbonyl)-1,4-dihydrothiochromeno[4,3-c]pyrazole 5,5-dioxide

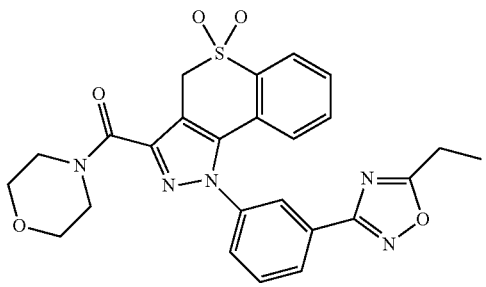 [SMILES: CCc1nc(-c2cccc(-n3nc(C(=O)N4CCOCC4)c4c3-c3ccccc3S(O)(O)C4)c2)no1]

To a solution of N'-hydroxy-3-[3-(morpholin-4-ylcarbonyl)-5,5-dioxidothiochromeno[4,3-c]pyrazol-1(4H)-yl]benzenecarboximidamide (150 mg, 0.32 mmol) in dry EtOAc is added propionic acid (13 µl, 0.32 mmol) under nitrogen followed by TEA (0.13 mL, 0.963 mmol) and propane phosphonic acid cyclic anhydride (0.51 mL, 0.80 mmol) at 0° C. under nitrogen. The reaction mixture is heated to 80° C. for 12 h under nitrogen and concentrated under vacuum. Solid residue is purified by silica gel column chromatography (1.2% MeOH in DCM) to afford the title compound as an off white solid. $^1$H NMR (DMSO-$d_6$, 400 MHz): δ 8.24-8.22 (d, J=7.4 Hz, 1H), 8.05-8.02 (m, 2H), 7.81-7.77 (m, 2H), 7.64 (m, 1H), 7.57 (m, 1H), 6.93-6.91 (d, J=7.9 Hz, 1H), 4.91 (s, 2H), 3.92-3.90 (m, 2H), 3.67 (m, 4H), 3.61-3.60 (m, 2H), 3.02-3.0 (m, 2H), 1.33-1.29 (t, J=7.6 Hz, 3H). MS (ESI+): 506.0. HPLC (max plot) 97.13%; Rt 4.34 min.

Example 200

1-[3-(5-Methyl-1H-1,2,4-triazol-3-yl)phenyl]-3-(morpholin-4-ylcarbonyl)-1,4-dihydrothiochromeno[4,3-c]pyrazole 5,5-dioxide

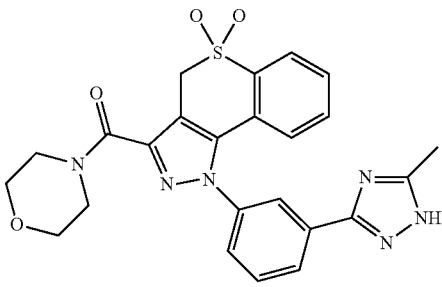 [SMILES: Cc1nc(-c2cccc(-n3nc(C(=O)N4CCOCC4)c4c3-c3ccccc3S(O)(O)C4)c2)n[nH]1]

To a solution of 3-[3-(morpholin-4-ylcarbonyl)-5,5-dioxidothiochromeno[4,3-c]pyrazol-1(4H)-yl]benzonitrile (100 mg, 0.23 mmol) in dry toluene is added acetic azide (34 mg, 0.46 mmol) and K$_2$CO$_3$ (158 mg, 0.115 mmol) under nitrogen. The reaction mixture is heated to 110° C. for 12 h under nitrogen after which it is concentrated under vacuum. The solid residue is purified by Preparative HPLC to afford the title compound as an off white solid. $^1$H NMR (DMSO-$d_6$, 400 MHz): δ 8.21-8.19 (d, J=7.7 Hz, 1H), 8.03-7.98 (m, 2H), 7.73-7.69 (m, 1H), 7.64-7.56 (m, 3H), 6.92-6.90 (d, J=7.8 Hz, 1H), 4.91 (s, 2H), 3.93 (m, 2H),3.75-3.67 (m, 4H), 3.62-3.61 (m, 2H), 2.37 (s, 3H). MS (ESI+): 491.0. HPLC (max plot) 98.76%; Rt 2.96 min.

Example 238

1-[4-(Morpholin-4-ylmethyl)phenyl]-1,4-dihydrothiochromeno[4,3-c]pyrazole-3-carboxylic acid 5,5-dioxide

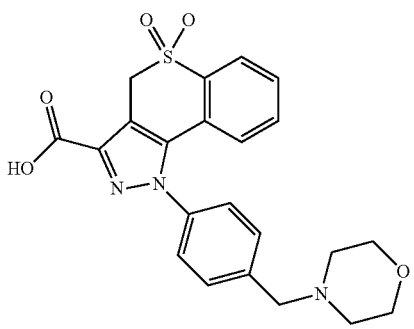

To a suspension of 1-[4-(hydroxymethyl)phenyl]-1,4-dihydrothiochromeno[4,3-c]pyrazole-3-carboxylic acid 5,5-dioxide (30 mg; 0.08 mmol; 1 eq.) in DCE (2 ml) at 0° C. is added thionyl chloride (15 µl; 0.2 mmol; 2.5 eq.). The reaction mixture is stirred for 15 min, the solvent is removed then a solution of morpholine (300 µl; 10 V) in DCE (2 mL) is added. After overnight stirring, the solvent is removed and the crude residue is purified by Autoprep to afford the title compound as a white fluffy solid. $^1$H NMR (DMSO-$d_6$) δ 8.02 (dd, J=1.3, 7.7 Hz, 1H), 7.69-7.41 (m, 5H), 6.93-6.72 (m, 1H), 4.97 (s, 2H), 3.76-3.53 (m, 5H), 3.32-3.30 (m, 2H), 2.46-2.32 (m, 3H). HPLC (max plot) 91.4%; Rt 2.26 min. MS (ESI+): 439.98.

Example 212

N-Methyl-3-(morpholin-4-ylcarbonyl)-1-phenyl-1,4-dihydrothiochromeno[4,3-c]pyrazol-6-amine 5,5-dioxide

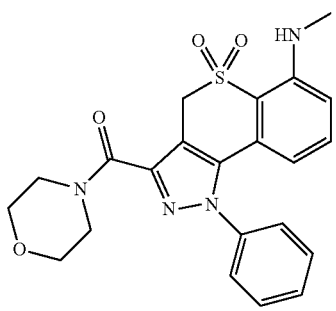

To a solution of N-methyl-3-(morpholin-4-ylcarbonyl)-1-phenyl-1,4-dihydrothiochromeno[4,3-c]pyrazol-6-amine (90 mg, 0.22 mmol) in THF: H$_2$O (1:1, 10 mL) is added oxone (545 mg, 0.88 mmol) and the reaction mixture is stirred at RT for 3 h. After this time, EtOAc is added to the reaction mixture that is washed with water. The organic layer is separated, dried over Na$_2$SO$_4$, concentrated under reduced pressure. The solid residue is purified by silica gel flash chromatography (40% EtOAc in pet.ether) the title compound as a white solid. $^1$H NMR (DMSO-$d_6$, 400 MHz): δ 7.59-7.56 (m, 3H), 7.47-7.44 (m, 2H), 7.26-7.22 (t, J=8.1 Hz,1H), 6.80-6.74 (m, 2H), 5.98-5.96 (d, J=7.6 Hz,1H), 4.87 (s, 2H), 3.95-3.94 (m, 2H), 3.65 (m, 4H), 3.61-3.59 (m, 2H), 2.83-2.82 (d, J=4.7 Hz, 3H). MS (ESI+): 439.0. HPLC (max plot) 95.63%; Rt 4.39 min.

Example 440

Enantiomer B of 1-(2-{3-[3-(morpholin-4-ylcarbonyl)-5,5-dioxidothiochromeno[4,3-c]pyrazol-1(4H)-yl]piperidin-1-yl}ethyl)pyrrolidin-2-one

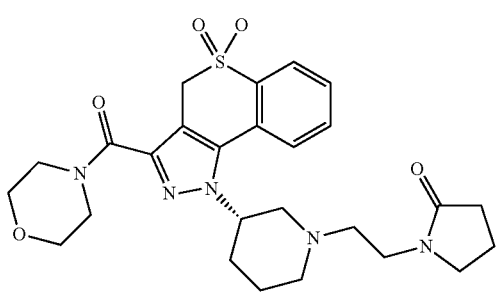

A solution of 2-pyrrolidone (35 mg; 0.42 mmol; 2 eq.) with NaH (10 mg; 0.42 mmol; 2 eq.) in ACN at 0° C. is added to a solution of enantiomer B of 1-[1-(2-chloroethyl)piperidin-3-yl]-3-(morpholin-4-ylcarbonyl)-1,4-dihydrothiochromeno[4,3-c]pyrazole 5,5-dioxide (100 mg; 0.21 mmol; 1 eq.) and NaI (31 mg; 0.21 mmol; 1 eq.) in ACN (2 mL). Reaction mixture is heated to 60° C. for 18 h after which DCM is added and organic phase is washed with water and brine. It is dried over MgSO$_4$ then purified by MD-Autoprep to give 11 mg (9%) of the title compound as a white solid. $^1$H NMR (DMSO-d$_6$, 300 MHz): δ 8.05 (d, J=7.7 Hz, 1H), 8.00-7.82 (m, 2H), 7.81-7.67 (m, 1H), 4.89-4.64 (m, 3H), 4.00-3.83 (m, 2H), 3.83-3.56 (m, 8H), 3.22-3.12 (m, 1H), 2.99-2.82 (m, 1H), 2.67-2.34 (m, 4H), 2.29-2.15 (m, 2H), 2.15-1.54 (m, 8H). MS (ESI+): 528.5. HPLC (max plot) 97.6%; Rt 1.86 min.

Example 454

Enantiomer B of 1-(1-{2-1-[(1-methylpiperidin-4-yl)oxy]ethyl}piperidin-3-yl)-3-(morpholin-4-ylcarbonyl)-1,4-dihydrothiochromeno[4,3-c]pyrazole 5,5-dioxide

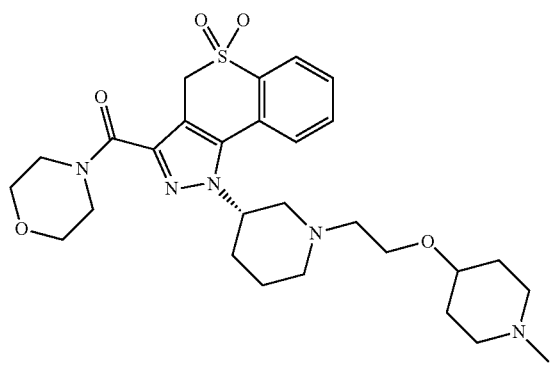

A solution of enantiomer B of 1-[1-(2-chloroethyl)piperidin-3-yl]-3-(morpholin-4-ylcarbonyl)-1,4-dihydrothiochromeno[4,3-c]pyrazole 5,5-dioxide (100 mg; 0.21 mmol; 1 eq.) and NaH (18 mg; 0.42 mmol; 2 eq.) in acetonitril (2 mL) at 0° C. is added to a solution of 1-methyl-4-piperidinol (49 µl; 0.42 mmol; 2 eq.) and NaI (31 mg; 0.21 mmol; 1 eq.) in ACN (2 mL). Reaction mixture is heated to 60° C. for 18 h after which DCM is added and organic phase is washed with water and brine. It is dried over MgSO$_4$ then purified by MD-Autoprep to give the title compound as a yellow oil. $^1$H NMR (DMSO-d$_6$, 300 MHz): δ 8.06 (d, J=7.9 Hz, 1H), 7.98-7.87 (m, 1H), 7.86-7.70 (m, 2H), 4.87-4.70 (m, 3H), 3.97-3.84 (m, 2H), 3.84-3.76 (m, 1H), 3.76-3.56 (m, 6H), 3.55-3.47 (m, 2H), 3.37-3.16 (m, 3H), 3.15-2.93 (m, 4H), 2.91-2.70 (m, 3H), 2.63-2.54 (m, 1H), 2.30-1.59 (m, 10H). MS (ESI+): 558.3. HPLC (max plot) 75.1%; Rt 1.74 min

Example 452

Enantiomer B of 2-{3-[3-(morpholin-4-ylcarbonyl)-5,5-dioxidothiochromeno[4,3-c]pyrazol-1(4H)-yl]piperidin-1-yl}ethanamine

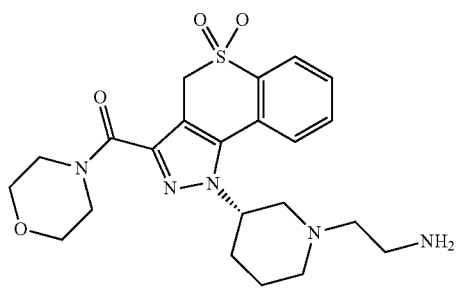

To a solution of enantiomer B of 1-[1-(2-chloroethyl)piperidin-3-yl]-3-(morpholin-4-ylcarbonyl)-1,4-dihydrothiochromeno[4,3-c]pyrazole 5,5-dioxide (90 mg; 0.19 mmol; 1.00 eq.) in CH3CN (0.90 ml) is added aq ammonia (181.88 µl; 2.82 mmol; 15.00 eq.) and the reaction is stirred at 135° C. for 15 min under microwave irradiation which after purification by MD-Autoprep affords the title compound as a white solid. $^1$H NMR (DMSO-d$_6$, 300 MHz): δ 8.05 (d, J=7.8 Hz, 1H), 7.96 (t, J=7.1 Hz, 1H), 7.87 (d, J=7.6 Hz, 1H), 7.75 (t, J=7.4 Hz, 1H), 4.79 (q, J=16.2 Hz, 3H), 3.90 (s, 2H), 3.66 (s, 6H), 3.15 (d, J=9.7 Hz, 2H), 2.90 (q, J=13.0 Hz, 3H), 2.73-2.53 (m, 2H), 2.27-2.02 (m, 2H), 2.00-1.59 (m, 3H). MS (ESI+): 460.3. HPLC (max plot) 55.4%; Rt 2.09 min.

Procedure AY

Example 487

4-(Methoxymethyl)-3-(morpholin-4-ylcarbonyl)-1-phenyl-1,4-dihydropyrazolo[4,3-c][1,2]benzothiazine 5,5-dioxide

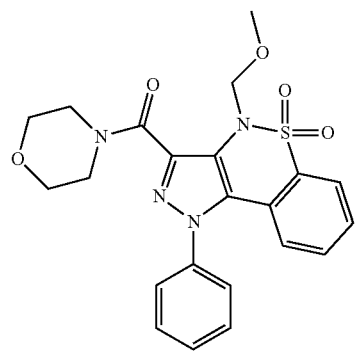 [SMILES: COCN1c2c(C(=O)N3CCOCC3)nn(-c3ccccc3)c2-c2ccccc2S1(=O)=O]

A mixture of 2-bromo-N-(methoxymethyl)-N-[3(morpholin-4-ylcarbonyl)-1-phenyl-1H-pyrazol-4-yl] benzenesulfonamide (240 mg; 0.45 mmol; 1.00 eq.), palladium acetate (20 mg; 0.09 mmol; 0.20 eq.), triphenylphosphine (94 mg; 0.36 mmol; 0.80 eq.) and Cs$_2$CO$_3$ (584 mg; 1.79 mmol; 4.00 eq.) is flushed with N2 for 10 minutes. Toluene (50 mL) is added and the resulting mixture is stirred at reflux for 2 hours. After this time, reaction mixture is filtered through a short plug of celite, ished with ethyl acetate. Combined organic phase are ished with NaHCO$_3$ then brine, dried over sodium sulfate and concentrated in vacuo and purified by flash chromatography to give the title compound as a white solid. $^1$H NMR (300 MHz, DMSO-d$_6$): δ 8.03 (dd, J=1.3, 7.5 Hz, 1H), 7.88-7.46 (m, 7H), 7.04-6.94 (m, 1H), 5.15 (s, 2H), 3.69 (s, 6H), 3.64-3.54 (m, 2H), 2.89 (s, 3H). HPLC (max plot) 83.4%; Rt 3.71 min. MS (ESI+) 423.2.

Example 488

4-Methyl-3-(morpholin-4-ylcarbonyl)-1-phenyl-1,4-dihydropyrazolo[4,3-c][1,2]benzothiazine 5,5-dioxide

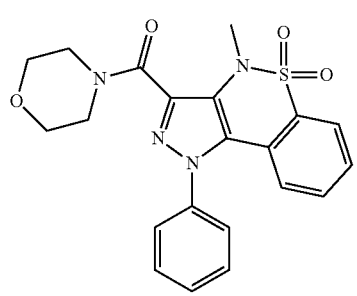 [SMILES: CN1c2c(C(=O)N3CCOCC3)nn(-c3ccccc3)c2-c2ccccc2S1(=O)=O]

Following protocol outlined in procedure AY, 4-methyl-3-(morpholin-4-ylcarbonyl)-1-phenyl-1,4-dihydropyrazolo[4,3-c][1,2]benzothiazine 5,5-dioxide is obtained from 2-bromo-N-methyl-N-[3-(morpholin-4-ylcarbonyl)-1-phenyl-1H-pyrazol-4-yl]benzenesulfonamide to give 4 mg (19%) of the title compound as a white solid. 1H NMR (300 MHz, DMSO-d6): δ 8.04-7.98 (m, 1H), 7.76-7.55 (m, 7H), 7.00-6.92 (m, 1H), 3.80-3.66 (m, 6H), 3.66-3.57 (m, 2H), 3.16 (s, 3H), HPLC (max plot) 100.0%; Rt 3.45 min. MS (ESI+) 425.3.

Example 489

3-(Morpholin-4-ylcarbonyl)-1-phenyl-1,4-dihydropyrazolo[4,3-c][1,2]benzothiazine 5,5-dioxide

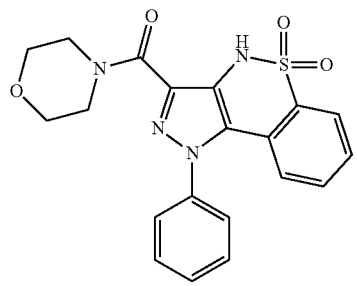 [SMILES: O=C(c1nn(-c2ccccc2)c2c1NS(=O)(=O)c1ccccc1-2)N1CCOCC1]

To a solution of 4-(methoxymethyl)-3-(morpholin-4-ylcarbonyl)-1-phenyl-1,4-dihydropyrazolo[4,3-c][1,2]benzothiazine 5,5-dioxide (85 mg; 0.19 mmol; 1.00 eq.) in 1,4-dioxane (3 mL) is added HCl (0.75 mL; 1 M; 0.75 mmol; 4.00 eq.) after which reaction mixture is stirred at 100° C. for 90 min under microwave irradiation (*2). DCM is added to the reaction mixture that is neutralized to pH 6 with NaHCO$_3$, extracted with DCM, dried over MgSO$_4$ and purified by MD-Autoprep to give 8 mg (10%) of the title compound as an off white solid. 1H NMR (300 MHz, DMSO-d6): δ 10.94 (s, 1H), 8.00-7.91 (m, 1H), 7.71-7.50 (m, 7H), 6.99-6.86 (m, 1H), 3.83-3.55 (m, 8H). HPLC (max plot) 97.4%; Rt 3.27 min. MS (ESI+) 411.2.

Example 486

3-(Morpholin-4-ylcarbonyl)-1-phenyl-4H-imidazo[5,1-c][1,4]benzothiazine 5,5-dioxide

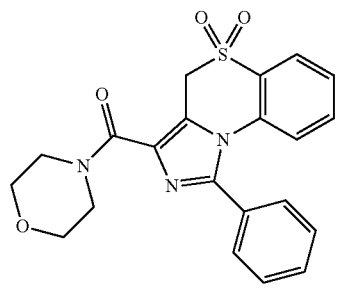 [SMILES: O=C(c1nc(-c2ccccc2)n2c1CS(=O)(=O)c1ccccc1-2)N1CCOCC1]

Following protocol outlines in procedure Q 3-(Morpholin-4-ylcarbonyl)-1-phenyl-4H-imidazo[5,1-c][1,4]benzothiazine 5,5-dioxide is obtained from 3-(morpholin-4-ylcarbonyl)-1-phenyl-4H-imidazo[5,1-c][1, 4]benzothiazine to give 16 mg (73%) of the title compound. 1H NMR (DMSO-d6, 400 MHz) δ 8.04-8.02 (m,1H), 7.61-7.58 (m, 2H), 7.55-7.52 (m, 3H), 7.50-7.43 (m, 2H), 6.99-6.97 (m, 1H), 5.24 (s, 2H), 4.15 (m, 2H), 3.63 (m, 6H). MS (ESI+): 410.0, HPLC (max plot) 94.7%; Rt 3.73 min.

Example 600

Biological Assays

Pi3K Alpha

The efficacy of compounds of the invention in inhibiting the PI3K induced-lipid phosphorylation may be tested in the following binding assay. The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin. To a 384 wells MTP containing 5 μl of the test compound of Formula (I) (solubilized in 2% DMSO; to yield a final concentration of 20, 5, 1.25, 0.3125, 0.0781, 0.0195, 0.0049, 0.0012, 0.0003 and 0.00075 μM of the test compound), the following assay components are added: 1) 5 μL of lipid micelles 2) 5 μL of Kinase buffer ([$^{33}$P]γATP 30 μM/200 nCi, MgCl$_2$ 10 mM, DTT 1 mM, Na$_3$VO$_4$ 100 μM, Cholic acid sodium salt 0.1%, beta Glycerophosphate 1 mM in Hepes 40 mM, pH 7.4) and 3) 5 µL (30 ng) of Human recombinant GST-PI3K (in Hepes 40 mM, pH 7.4). After incubation at 30° C. for 120 minutes, with gentle agitation, the reaction is stopped by addition of 60 µL of a solution containing 75 µg of neomycin-coated PVT SPA beads, ATP 5 mM and EDTA 5 mM in PBS. The assay is further incubated 30° C. for 60 minutes with gentle agitation to allow binding of phospholipids to neomycin-SPA beads. After precipitation of the neomycin-coated PVT SPA beads for 5 hours, radioactive PtdIns(3)P is quantified by scintillation counting in a Wallac MicroBeta™ plate counter.

Pi3K Beta

The efficacy of compounds of the invention in inhibiting the PI3K induced-lipid phosphorylation may be tested in the following binding assay. The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3H$, $^{125}I$, $^{33}P$). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin. To a 384 wells MTP containing 5 µl of the test compound of Formula (I) (solubilized in 2% DMSO; to yield a final concentration of 20, 5, 1.25, 0.3125, 0.0781, 0.0195, 0.0049, 0.0012, 0.0003 and 0.00075 µM of the test compound), the following assay components are added: 1) 5 µL of lipid micelles 2) 5 µL of Kinase buffer ([$^{33}P$]γATP 70 µM/300 nCi, MgCl$_2$ 4 mM, DTT 1 mM, Na$_3$VO$_4$ 0.1 µM, Cholic acid sodium salt 0.2% in Hepes 40 mM, pH 7.4) and 3) 5 µL (12 ng) of Human recombinant GST-PI3K (in Hepes 40 mM, pH 7.4). After incubation at 30° C. for 120 minutes, with gentle agitation, the reaction is stopped by addition of 60 µL of a solution containing 75 µg of neomycin-coated PVT SPA beads, ATP 5 mM and EDTA 5 mM in PBS. The assay is further incubated at 30° C. for 60 minutes with gentle agitation to allow binding of phospholipids to neomycin-SPA beads. After precipitation of the neomycin-coated PVT SPA beads for 5 hours, radioactive PtdIns(3)P is quantified by scintillation counting in a Wallac MicroBeta™ plate counter.

Pi3K Delta The efficacy of compounds of the invention in inhibiting the PI3K induced-lipid phosphorylation may be tested in the following binding assay. The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3H$, $^{125}I$, $^{33}P$). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin. To a 384 wells MTP containing 5 µl of the test compound of Formula (I) (solubilized in 2% DMSO; to yield a final concentration of 20, 5, 1.25, 0.3125, 0.0781, 0.0195, 0.0049, 0.0012, 0.0003 and 0.00075 µM of the test compound), the following assay components are added: 1) 5 µL of lipid micelles 2) 5 µL of Kinase buffer ([$^{33}P$]γATP260 µM/300 nCi, MgCl$_2$ 4 mM, DTT 4 mM, Na$_3$VO$_4$ 0.4 µM in Hepes 40 mM, pH 7.4) and 3) 5 µL (50 ng) of Human recombinant GST-PI3K (in Hepes 40 mM, pH 7.4). After incubation at room temperature for 120 minutes, with gentle agitation, the reaction is stopped by addition of 60 µL of a solution containing 75 µg of neomycin-coated PVT SPA beads, ATP 6.5 mM and EDTA 6.5 mM in PBS. The assay is further incubated at room temperature for 60 minutes with gentle agitation to allow binding of phospholipids to neomycin-SPA beads. After precipitation of the neomycin-coated PVT SPA beads for 5 hours, radioactive PtdIns(3)P is quantified by scintillation counting in a Wallac MicroBeta™ plate counter.

Pi3K Gamma

The efficacy of compounds of the invention in inhibiting the PI3K induced-lipid phosphorylation may be tested in the following binding assay. The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3H$, $^{125}I$, $^{33}P$). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin. To a 384 wells MTP containing 5 µl of the test compound of Formula (I) (solubilized in 2% DMSO; to yield a final concentration of 20, 5, 1.25, 0.3125, 0.0781, 0.0195, 0.0049, 0.0012, 0.0003 and 0.00075 µM of the test compound), the following assay components are added: 1) 5 µL of lipid micelles 2) 5 µL of Kinase buffer ([$^{33}P$]γATP 30 µM/200 nCi, MgCl$_2$ 10 mM, DTT 1 mM, Na$_3$VO$_4$ 100 µM, Cholic acid sodium salt 0.1%, beta Glycerophosphate 1 mM in Hepes 40 mM, pH 7.4) and 3) 5 µL (30 ng) of Human recombinant GST-PI3K (in Hepes 40 mM, pH 7.4). After incubation at 30° C. for 120 minutes, with gentle agitation, the reaction is stopped by addition of 60 µL of a solution containing 75 µg of neomycin-coated PVT SPA beads, ATP 5 mM and EDTA 5 mM in PBS. The assay is further incubated 30° C. for 60 minutes with gentle agitation to allow binding of phospholipids to neomycin-SPA beads. After precipitation of the neomycin-coated PVT SPA beads for 5 hours, radioactive PtdIns(3)P is quantified by scintillation counting in a Wallac MicroBeta™ plate counter.

The values indicated in Table I below refer to the best IC$_{50}$ (µM) obtained with the four above described isoforms of PI3K, i.e. the amount necessary to achieve 50% inhibition of said target.

Example 512

Mechanistic-On Target Cell Assay

The cellular activity of the examples was measured by Flow Cytometry assay format using a Ramos B-lymphocyte cell line (ATCC #CRL-1923). These cells were incubated overnight in 5% serum and next day serum-starved to reduce background of AKT phosphorylation, pre-incubated with test compounds for 20 min and then stimulated with anti-human IGM antibody (JacksonImmunoResearch #109 006 129) (10 ug/ml final) for 15 minutes. The reaction was stopped by fixing the cells with Paraformaldehyde 4% (final) for 10 minutes at room temperature. Cells were washed once with Phosphate Buffer Saline (PBS), permabilized in PBS-Triton X-100 0.2% for 15 minutes at room temperature washed twice with PBS and once with PBS-4% serum. The cells were incubated anti p-AKT (Ser 473) (Cell Signalling #4058L) (1/70 dilution) in PBS-4% serum for one hour at room temperature. After two washes in PBS-4% serum, cells were stained with a mixture of Mouse anti-human IgM-APC (BD Pharmingen #551062) (1:50), anti rabbit IgG-Alexa 488 (Invitrogen Ref. A-45558A) (1:200) and Goat IgG (5mg/ml, 10 mg) (Zymed #02-6202) (1:200) for 30 minutes at 4° C. Cells were washed twice in PBS and resuspended in PBS. The cell suspension was passed on a FC500 flow cytometer (Beckman Coulter), gating on the IGM positive cells and measuring the AKT phosphorylation.

Examples of inhibitory activities for compounds according to the invention are set out in Table I below.

TABLE I

| EX. | Formula | Best potency measured on the 4 PI3K isoforms (nM) | Cell Assay: Ramos (nM) |
| --- | --- | --- | --- |
| 1 | | 459 | 570 |
| 2 | | 1730 | — |
| 3 | | 2881 | — |
| 4 | | 422 | — |
| 5 | | 349 | — |

TABLE I-continued

| EX. | Formula | Best potency measured on the 4 PI3K isoforms (nM) | Cell Assay: Ramos (nM) |
|---|---|---|---|
| 6 | | 926 | — |
| 7 | | 690 | 976 |
| 8 | | 4195 | — |
| 9 | | 1320 | — |

TABLE I-continued

| EX. | Formula | Best potency measured on the 4 PI3K isoforms (nM) | Cell Assay: Ramos (nM) |
|---|---|---|---|
| 10 | | 749 | — |
| 11 | | 1595 | — |
| 12 | | 136 | 167 |
| 13 | | 1090 | — |
| 14 | | 687 | — |

TABLE I-continued

| EX. | Formula | Best potency measured on the 4 PI3K isoforms (nM) | Cell Assay: Ramos (nM) |
|---|---|---|---|
| 15 | | 424 | 364 |
| 16 | | 2215 | — |
| 17 | | 987 | — |
| 18 | | 494 | — |
| 19 | | 2285 | — |

TABLE I-continued

| EX. | Formula | Best potency measured on the 4 PI3K isoforms (nM) | Cell Assay: Ramos (nM) |
|---|---|---|---|
| 20 | | 5500 | — |
| 21 | | 2000 | — |
| 22 | | 4020 | — |
| 23 | | 670 | — |
| 24 | | 662 | — |

TABLE I-continued

| EX. | Formula | Best potency measured on the 4 PI3K isoforms (nM) | Cell Assay: Ramos (nM) |
|---|---|---|---|
| 25 | | 616 | — |
| 26 | | 440 | — |
| 27 | | 1123 | — |
| 28 | | 373 | — |

TABLE I-continued

| EX. | Formula | Best potency measured on the 4 PI3K isoforms (nM) | Cell Assay: Ramos (nM) |
|---|---|---|---|
| 29 | | 895 | — |
| 30 | | 1472 | — |
| 31 | | 4045 | — |
| 32 | | 223 | — |

TABLE I-continued

| EX. | Formula | Best potency measured on the 4 PI3K isoforms (nM) | Cell Assay: Ramos (nM) |
|---|---|---|---|
| 33 | | 244 | 706 |
| 34 | | 1753 | 1800 (high SD) |
| 35 | | 2770 | — |
| 36 | | 1830 | — |
| 37 | | 601 | 493 |

TABLE I-continued

| EX. | Formula | Best potency measured on the 4 PI3K isoforms (nM) | Cell Assay: Ramos (nM) |
|---|---|---|---|
| 38 | | 459 | 942 |
| 39 | | 641 | 388 |
| 40 | | 1189 | — |
| 41 | | 1440 | — |

TABLE I-continued

| EX. | Formula | Best potency measured on the 4 PI3K isoforms (nM) | Cell Assay: Ramos (nM) |
|---|---|---|---|
| 42 | | 1505 | — |
| 43 | | 495 | 534 |
| 44 | | 907 | — |
| 45 | | 1560 | — |

TABLE I-continued

| EX. | Formula | Best potency measured on the 4 PI3K isoforms (nM) | Cell Assay: Ramos (nM) |
|---|---|---|---|
| 46 | | 661 | 680 |
| 47 | | 3955 | — |
| 48 | | 377 | — |
| 49 | | 247 | — |

TABLE I-continued
| EX. | Formula | Best potency measured on the 4 PI3K isoforms (nM) | Cell Assay: Ramos (nM) |
| --- | --- | --- | --- |
| 50 | 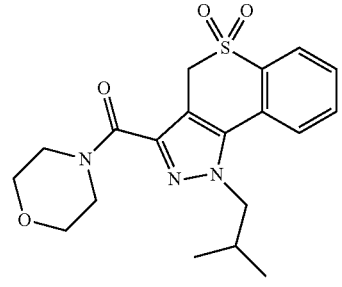 [SMILES: CC(C)Cn1nc(C(=O)N2CCOCC2)c2c1-c1ccccc1S(=O)(=O)C2] | 960 | — |
| 51 | 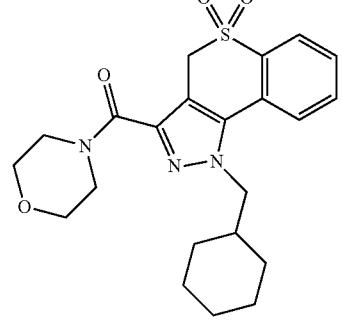 | 509 | — |
| 52 | 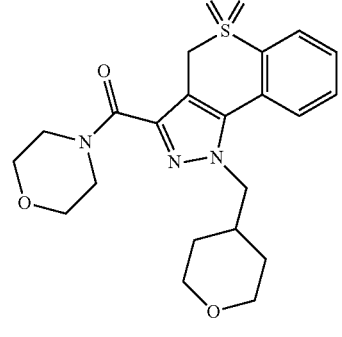 | 789 | — |
| 53 | 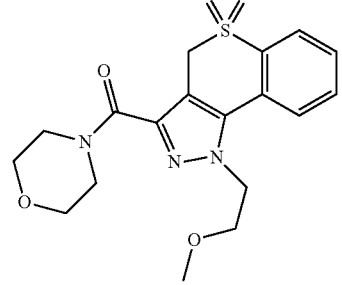 | 1290 | — |

TABLE I-continued

| EX. | Formula | Best potency measured on the 4 PI3K isoforms (nM) | Cell Assay: Ramos (nM) |
|---|---|---|---|
| 54 | | 2250 | — |
| 55 | | 1915 | — |
| 56 | | 531 | 8150 |
| 57 | | 2475 | — |

TABLE I-continued

| EX. | Formula | Best potency measured on the 4 PI3K isoforms (nM) | Cell Assay: Ramos (nM) |
|---|---|---|---|
| 58 | | 3900 | — |
| 59 | | 2470 | — |
| 60 | | 52% in @20 μM | — |
| 61 | | 73 | — |

TABLE I-continued

| EX. | Formula | Best potency measured on the 4 PI3K isoforms (nM) | Cell Assay: Ramos (nM) |
|-----|---------|---------------------------------------------------|------------------------|
| 62  |         | 957                                               | —                      |
| 63  |         | 1044                                              | —                      |
| 64  |         | 1298                                              | —                      |
| 65  |         | 368                                               | 251                    |

TABLE I-continued

| EX. | Formula | Best potency measured on the 4 PI3K isoforms (nM) | Cell Assay: Ramos (nM) |
|---|---|---|---|
| 66 | | 421 | 942 |
| 67 | | 54% inh @20 µM | — |
| 68 | | 376 | — |
| 69 | | 3114 | — |

TABLE I-continued

| EX. | Formula | Best potency measured on the 4 PI3K isoforms (nM) | Cell Assay: Ramos (nM) |
|---|---|---|---|
| 70 | | 6051 | — |
| 71 | | 1233 | — |
| 72 | | 795 | — |
| 73 | | 205 | 317 |

TABLE I-continued

| EX. | Formula | Best potency measured on the 4 PI3K isoforms (nM) | Cell Assay: Ramos (nM) |
|---|---|---|---|
| 74 | | 1515 | — |
| 75 | | 3008 | — |
| 76 | | — | — |
| 77 | | 772 | — |
| 78 | | 469 | — |

TABLE I-continued

| EX. | Formula | Best potency measured on the 4 PI3K isoforms (nM) | Cell Assay: Ramos (nM) |
|---|---|---|---|
| 79 | | 437 | 492 |
| 80 | | — | — |
| 81 | | — | — |
| 82 | | 1900 | — |
| 83 | | — | — |

TABLE I-continued

| EX. | Formula | Best potency measured on the 4 PI3K isoforms (nM) | Cell Assay: Ramos (nM) |
|---|---|---|---|
| 84 | | 4640 | — |
| 85 | | — | — |
| 86 | | — | — |
| 87 | | — | — |
| 88 | | 1130 | — |

TABLE I-continued

| EX. | Formula | Best potency measured on the 4 PI3K isoforms (nM) | Cell Assay: Ramos (nM) |
|---|---|---|---|
| 89 | | 1390 | — |
| 90 | | — | — |
| 91 | | — | — |
| 92 | | — | — |

TABLE I-continued
| EX. | Formula | Best potency measured on the 4 PI3K isoforms (nM) | Cell Assay: Ramos (nM) |
|---|---|---|---|
| 93 | 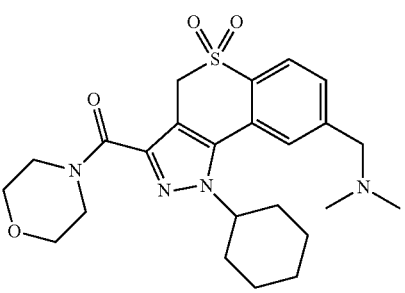 [SMILES: CN(C)Cc1ccc2c(c1)-c1c(c(C(=O)N3CCOCC3)nn1C1CCCCC1)CS2(=O)=O] | — | — |
| 94 | 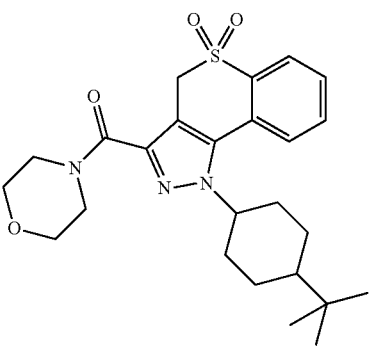 [SMILES: CC(C)(C)C1CCC(n2nc(C(=O)N3CCOCC3)c3c2-c2ccccc2S(=O)(=O)C3)CC1] | 4120 | — |
| 95 | 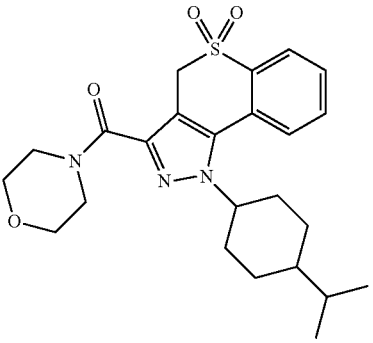 [SMILES: CC(C)C1CCC(n2nc(C(=O)N3CCOCC3)c3c2-c2ccccc2S(=O)(=O)C3)CC1] | — | — |
| 96 | 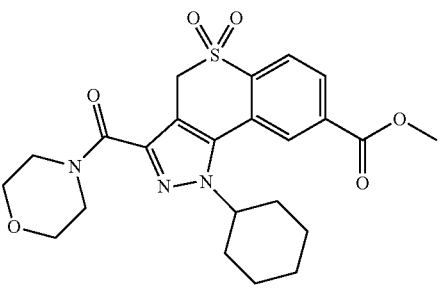 [SMILES: COC(=O)c1ccc2c(c1)-c1c(c(C(=O)N3CCOCC3)nn1C1CCCCC1)CS2(=O)=O] | — | — |

TABLE I-continued

| EX. | Formula | Best potency measured on the 4 PI3K isoforms (nM) | Cell Assay: Ramos (nM) |
| --- | --- | --- | --- |
| 97 | | — | — |
| 98 | | 512 | — |
| 99 | | 326 | — |
| 100 | | 876 | — |

TABLE I-continued

| EX. | Formula | Best potency measured on the 4 PI3K isoforms (nM) | Cell Assay: Ramos (nM) |
|---|---|---|---|
| 101 | | 1920 | — |
| 102 | | — | — |
| 103 | | — | — |
| 104 | | — | — |

TABLE I-continued

| EX. | Formula | Best potency measured on the 4 PI3K isoforms (nM) | Cell Assay: Ramos (nM) |
|---|---|---|---|
| 105 | | — | — |
| 106 | | — | — |
| 107 | | — | — |
| 108 | | — | — |

TABLE I-continued

| EX. | Formula | Best potency measured on the 4 PI3K isoforms (nM) | Cell Assay: Ramos (nM) |
|---|---|---|---|
| 109 | | — | — |
| 110 | | — | — |
| 111 | | 5270 | — |
| 112 | | 5070 | — |

TABLE I-continued

| EX. | Formula | Best potency measured on the 4 PI3K isoforms (nM) | Cell Assay: Ramos (nM) |
|---|---|---|---|
| 113 | | 3350 | — |
| 114 | | 4275 | — |
| 115 | | 3728 | — |
| 116 | | 3030 | — |
| 117 | | 3412 | — |

TABLE I-continued
| EX. | Formula | Best potency measured on the 4 PI3K isoforms (nM) | Cell Assay: Ramos (nM) |
|---|---|---|---|
| 118 | 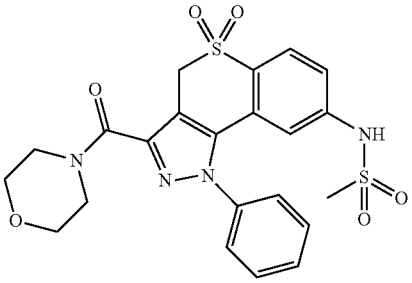 | 1312 | — |
| 119 | 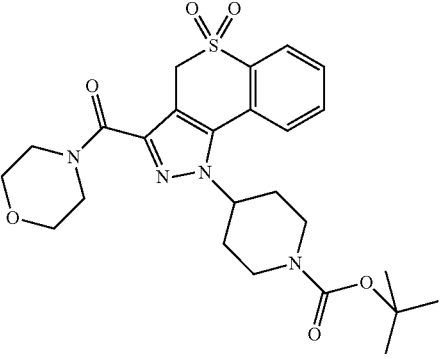 [SMILES: CC(C)(C)OC(=O)N1CCC(n2nc(C(=O)N3CCOCC3)c3c2-c2ccccc2S(=O)(=O)C3)CC1] | 808 | — |
| 120 | 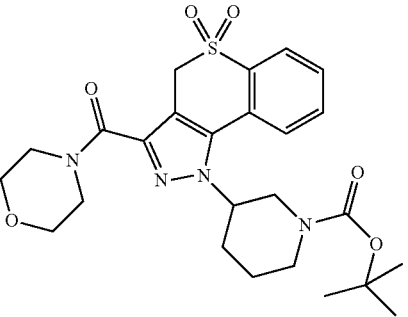 [SMILES: CC(C)(C)OC(=O)N1CCCC(n2nc(C(=O)N3CCOCC3)c3c2-c2ccccc2S(=O)(=O)C3)C1] | 1544 | — |
| 121 | 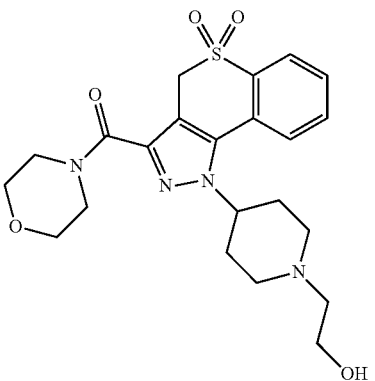 [SMILES: O=C(c1nn(C2CCN(CCO)CC2)c2c1CS(=O)(=O)c1ccccc1-2)N1CCOCC1] | 1755 | — |

TABLE I-continued

| EX. | Formula | Best potency measured on the 4 PI3K isoforms (nM) | Cell Assay: Ramos (nM) |
|---|---|---|---|
| 122 | | 904 | — |
| 123 | | 2100 | — |
| 124 | | 253 | — |
| 125 | | 182 | — |

TABLE I-continued

| EX. | Formula | Best potency measured on the 4 PI3K isoforms (nM) | Cell Assay: Ramos (nM) |
|---|---|---|---|
| 126 | | 1112 | — |
| 127 | | 426 | — |
| 128 | | 691 | — |
| 129 | | 1500 | — |

TABLE I-continued
| EX. | Formula | Best potency measured on the 4 PI3K isoforms (nM) | Cell Assay: Ramos (nM) |
|---|---|---|---|
| 130 | 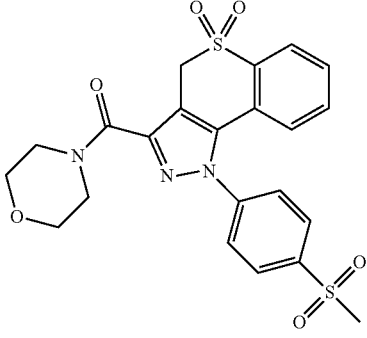 [SMILES: CS(=O)(=O)c1ccc(-n2nc(C(=O)N3CCOCC3)c3c2-c2ccccc2S(=O)(=O)C3)cc1] | 4520 | — |
| 131 | 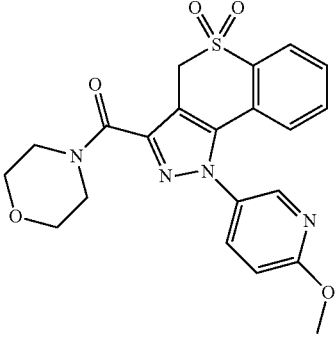 | 2200 | — |
| 132 | 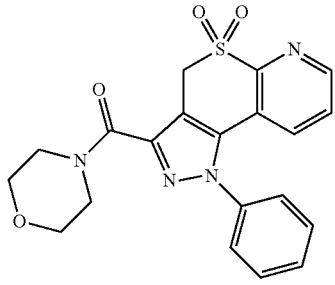 | 530 | — |
| 133 | 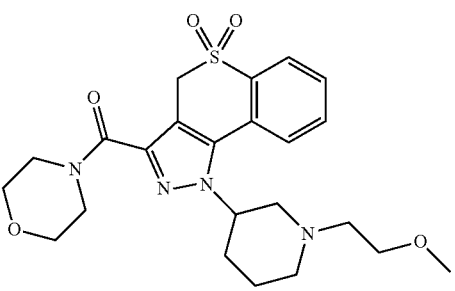 | 188 | — |

TABLE I-continued

| EX. | Formula | Best potency measured on the 4 PI3K isoforms (nM) | Cell Assay: Ramos (nM) |
|---|---|---|---|
| 134 | | 815 | — |
| 135 | | 994 | — |
| 136 | | 1300 | — |
| 137 | | 170 | 300 |

TABLE I-continued

| EX. | Formula | Best potency measured on the 4 PI3K isoforms (nM) | Cell Assay: Ramos (nM) |
|---|---|---|---|
| 138 | | 2564 | — |
| 139 | | 1843 | — |
| 140 | | 4524 | — |
| 141 | | 2252 | — |

TABLE I-continued

| EX. | Formula | Best potency measured on the 4 PI3K isoforms (nM) | Cell Assay: Ramos (nM) |
|---|---|---|---|
| 142 | | 302 | — |
| 143 | | 371 | — |
| 144 | | 348 | — |

TABLE I-continued

| EX. | Formula | Best potency measured on the 4 PI3K isoforms (nM) | Cell Assay: Ramos (nM) |
|---|---|---|---|
| 145 | | 502 | — |
| 146 | | 319 | — |
| 147 | | 274 | — |

TABLE I-continued
| EX. | Formula | Best potency measured on the 4 PI3K isoforms (nM) | Cell Assay: Ramos (nM) |
|---|---|---|---|
| 148 | 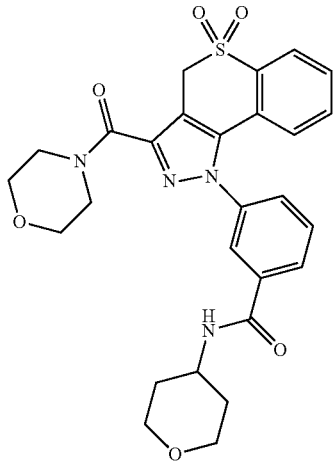 [SMILES: O=C(NC1CCOCC1)c1cccc(-n2nc(C(=O)N3CCOCC3)c3c2-c2ccccc2S(=O)(=O)C3)c1] | 1258 | — |
| 149 | 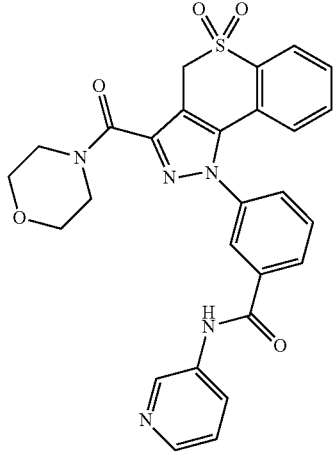 [SMILES: O=C(Nc1cccnc1)c1cccc(-n2nc(C(=O)N3CCOCC3)c3c2-c2ccccc2S(=O)(=O)C3)c1] | 926 | — |
| 150 | 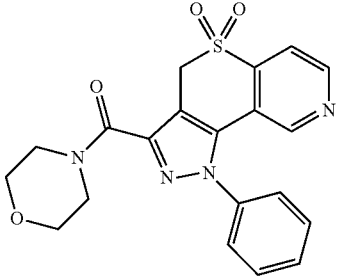 [SMILES: O=C(c1nn(-c2ccccc2)c2c1CS(=O)(=O)c1ccncc1-2)N1CCOCC1] | 3050 | — |

TABLE I-continued

| EX. | Formula | Best potency measured on the 4 PI3K isoforms (nM) | Cell Assay: Ramos (nM) |
|---|---|---|---|
| 151 | | 238 | — |
| 152 | | 5020 | — |
| 153 | | 1064 | — |
| 154 | | 673 | — |

TABLE I-continued

| EX. | Formula | Best potency measured on the 4 PI3K isoforms (nM) | Cell Assay: Ramos (nM) |
|---|---|---|---|
| 155 | | 3943 | — |
| 156 | | 902 | — |
| 157 | | 764 | — |
| 158 | | 3059 | — |

TABLE I-continued

| EX. | Formula | Best potency measured on the 4 PI3K isoforms (nM) | Cell Assay: Ramos (nM) |
|---|---|---|---|
| 159 | | 246 | — |
| 160 | | 1075 | — |
| 161 | | 6468 | — |
| 162 | | 1620 | — |

TABLE I-continued

| EX. | Formula | Best potency measured on the 4 PI3K isoforms (nM) | Cell Assay: Ramos (nM) |
|---|---|---|---|
| 163 | | 2158 | — |
| 164 | | 1940 | — |
| 165 | | 1128 | — |
| 166 | | 2695 | — |

TABLE I-continued

| EX. | Formula | Best potency measured on the 4 PI3K isoforms (nM) | Cell Assay: Ramos (nM) |
|---|---|---|---|
| 167 | | 247 | — |
| 168 | | 249 | — |
| 169 | | 110 | — |
| 170 | | 386 | — |

TABLE I-continued

| EX. | Formula | Best potency measured on the 4 PI3K isoforms (nM) | Cell Assay: Ramos (nM) |
|---|---|---|---|
| 171 | | 498 | — |
| 172 | | 140 | — |
| 173 | | 138 | — |
| 174 | | 540 | — |
| 175 | | 122 | — |

TABLE I-continued

| EX. | Formula | Best potency measured on the 4 PI3K isoforms (nM) | Cell Assay: Ramos (nM) |
|---|---|---|---|
| 176 | | 739 | — |
| 177 | | 4720 | — |
| 178 | | 394 | — |
| 179 | | 1112 | — |

TABLE I-continued
| EX. | Formula | Best potency measured on the 4 PI3K isoforms (nM) | Cell Assay: Ramos (nM) |
|---|---|---|---|
| 180 | 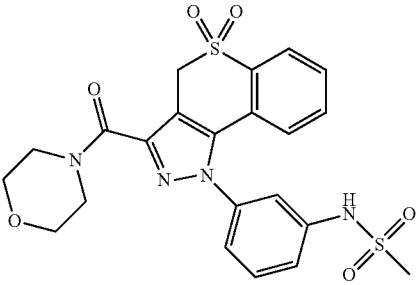 | 1780 | — |
| 181 | 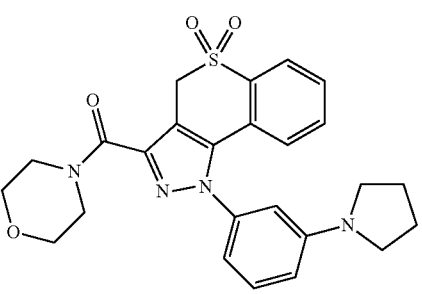 [SMILES: O=C(c1nn(-c2cccc(N3CCCC3)c2)c2c1CS(=O)(=O)c1ccccc1-2)N1CCOCC1] | 4949 | — |
| 182 | 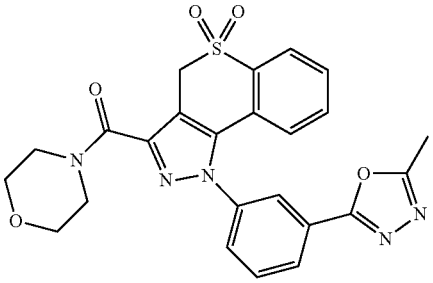 | 1201 | — |
| 183 | 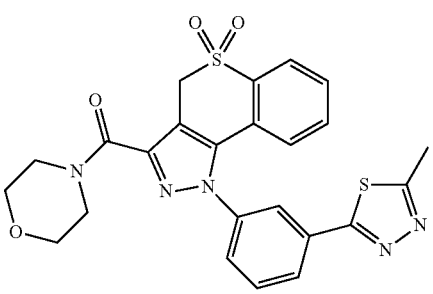 | 661 | — |
| 184 | 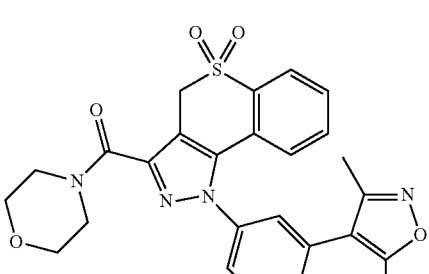 | 300 | — |

TABLE I-continued

| EX. | Formula | Best potency measured on the 4 PI3K isoforms (nM) | Cell Assay: Ramos (nM) |
|---|---|---|---|
| 185 | | 184 | — |
| 186 | | 454 | — |
| 187 | | 193 | — |
| 188 | | 338 | — |

TABLE I-continued

| EX. | Formula | Best potency measured on the 4 PI3K isoforms (nM) | Cell Assay: Ramos (nM) |
| --- | --- | --- | --- |
| 189 | | 4219 | — |
| 190 | | 681 | — |
| 191 | | 2825 | — |
| 192 | | 1699 | — |

TABLE I-continued

| EX. | Formula | Best potency measured on the 4 PI3K isoforms (nM) | Cell Assay: Ramos (nM) |
|---|---|---|---|
| 193 | | 362 | — |
| 194 | | 420 | — |
| 195 | | 2694 | — |
| 196 | | 2694 | — |

TABLE I-continued

| EX. | Formula | Best potency measured on the 4 PI3K isoforms (nM) | Cell Assay: Ramos (nM) |
|---|---|---|---|
| 197 | | 826 | — |
| 198 | | 280 | — |
| 199 | | 2588 | — |
| 200 | | 4862 | — |
| 201 | | 302 | — |

TABLE I-continued

| EX. | Formula | Best potency measured on the 4 PI3K isoforms (nM) | Cell Assay: Ramos (nM) |
|---|---|---|---|
| 202 | | 1737 | — |
| 203 | | 1636 | — |
| 204 | | 2077 | — |
| 205 | | 643 | — |

TABLE I-continued
| EX. | Formula | Best potency measured on the 4 PI3K isoforms (nM) | Cell Assay: Ramos (nM) |
|---|---|---|---|
| 206 | 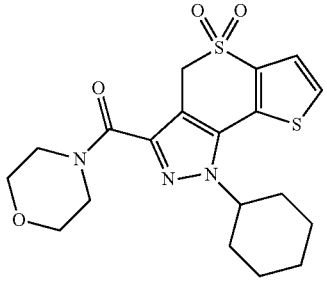 [SMILES: O=C(c1nn(C2CCCCC2)c2c1CS(=O)(=O)c1ccsc1-2)N1CCOCC1] | 212 | — |
| 207 | 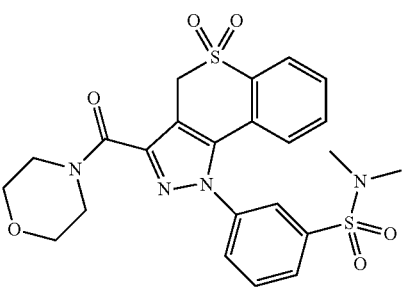 [SMILES: CN(C)S(=O)(=O)c1cccc(-n2nc(C(=O)N3CCOCC3)c3c2-c2ccccc2S(=O)(=O)C3)c1] | 641 | — |
| 208 | 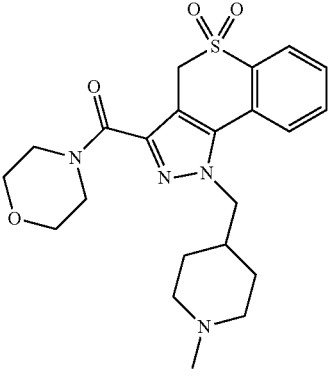 [SMILES: CN1CCC(Cn2nc(C(=O)N3CCOCC3)c3c2-c2ccccc2S(=O)(=O)C3)CC1] | 2651 | — |
| 209 | 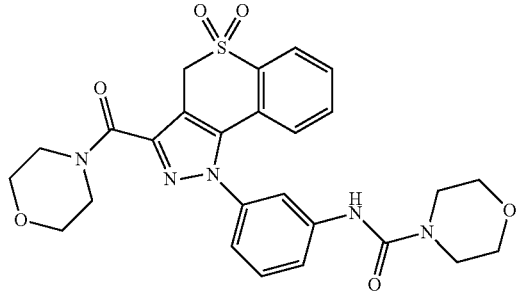 | 3587 | — |

TABLE I-continued

| EX. | Formula | Best potency measured on the 4 PI3K isoforms (nM) | Cell Assay: Ramos (nM) |
|---|---|---|---|
| 210 | | 2946 | — |
| 211 | | 400 | — |
| 212 | | 3510 | — |
| 213 | | 2980 | — |

TABLE I-continued
| EX. | Formula | Best potency measured on the 4 PI3K isoforms (nM) | Cell Assay: Ramos (nM) |
|---|---|---|---|
| 214 | 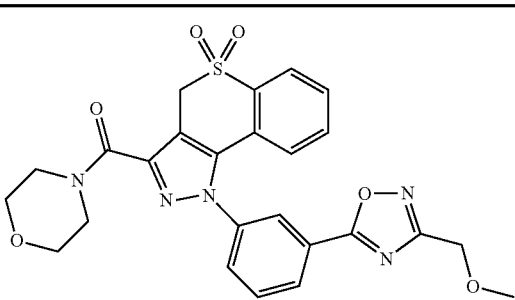 | 4190 | — |
| 215 | 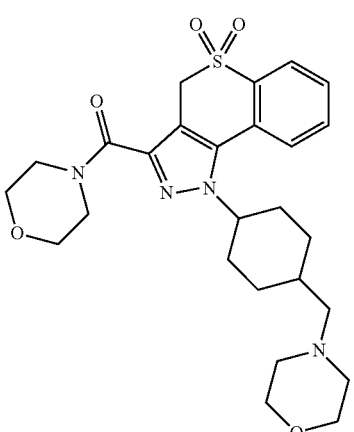 | 912 | — |
| 216 | 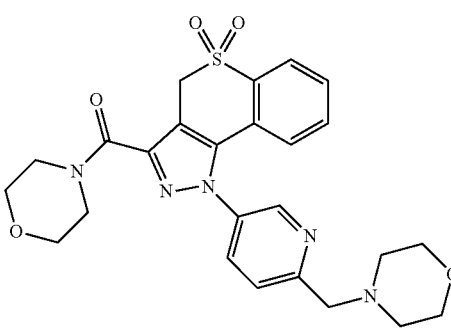 | 614 | — |
| 217 | 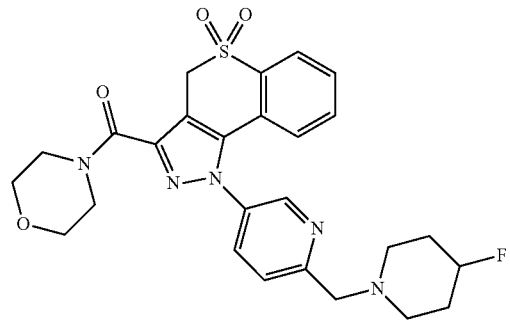 [SMILES: O=C(c1nn(-c2ccc(CN3CCC(F)CC3)nc2)c2c1CS(=O)(=O)c1ccccc1-2)N1CCOCC1] | 1200 | — |

TABLE I-continued

| EX. | Formula | Best potency measured on the 4 PI3K isoforms (nM) | Cell Assay: Ramos (nM) |
|---|---|---|---|
| 218 | | 468 | — |
| 219 | | 711 | — |
| 220 | | 587 | — |
| 221 | | 320 | — |
| 222 | | 149 | — |

TABLE I-continued

| EX. | Formula | Best potency measured on the 4 PI3K isoforms (nM) | Cell Assay: Ramos (nM) |
|---|---|---|---|
| 223 | | 679 | — |
| 224 | | 54 | — |
| 225 | | 635 | — |
| 226 | | 43 | 492 |

TABLE I-continued

| EX. | Formula | Best potency measured on the 4 PI3K isoforms (nM) | Cell Assay: Ramos (nM) |
|---|---|---|---|
| 227 | | 859 | — |
| 228 | | 285 | — |
| 229 | | 920 | — |

TABLE I-continued

| EX. | Formula | Best potency measured on the 4 PI3K isoforms (nM) | Cell Assay: Ramos (nM) |
|-----|---------|---------------------------------------------------|------------------------|
| 230 | | 1920 | — |
| 231 | | 431 | — |
| 232 | | 1170 | — |

TABLE I-continued

| EX. | Formula | Best potency measured on the 4 PI3K isoforms (nM) | Cell Assay: Ramos (nM) |
|---|---|---|---|
| 233 | | 167 | — |
| 234 | | 240 | — |
| 235 | | 389 | — |

TABLE I-continued
| EX. | Formula | Best potency measured on the 4 PI3K isoforms (nM) | Cell Assay: Ramos (nM) |
|---|---|---|---|
| 236 | 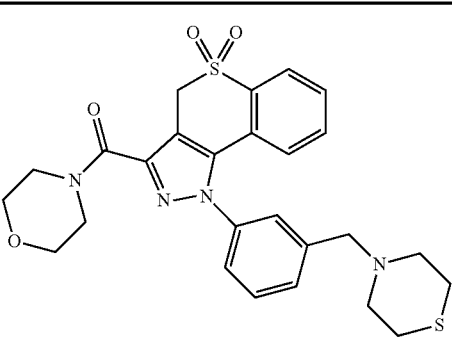 | 232 | — |
| 237 | 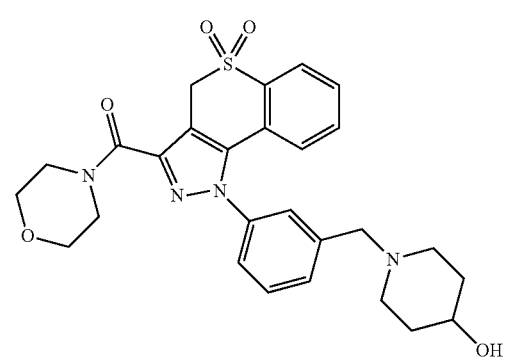 [SMILES: O=C(c1nn(-c2cccc(CN3CCC(O)CC3)c2)c2c1CS(=O)(=O)c1ccccc1-2)N1CCOCC1] | 573 | — |
| 238 | 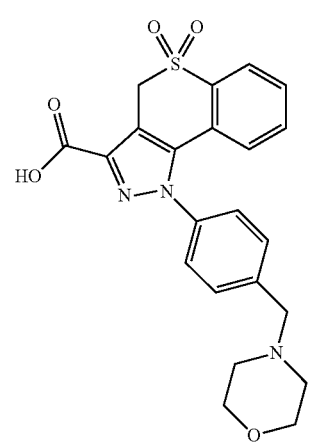 | 4040 | — |

TABLE I-continued

| EX. | Formula | Best potency measured on the 4 PI3K isoforms (nM) | Cell Assay: Ramos (nM) |
|-----|---------|---------------------------------------------------|------------------------|
| 239 | | 1490 | — |
| 240 | | 624 | — |
| 242 | | 437 | — |
| 243 | | 464 | — |

TABLE I-continued

| EX. | Formula | Best potency measured on the 4 PI3K isoforms (nM) | Cell Assay: Ramos (nM) |
|---|---|---|---|
| 244 | | 1543 | — |
| 245 | | 516 | — |
| 246 | | 824 | — |
| 247 | | 639 | — |

TABLE I-continued

| EX. | Formula | Best potency measured on the 4 PI3K isoforms (nM) | Cell Assay: Ramos (nM) |
| --- | --- | --- | --- |
| 248 | | 997 | — |
| 249 | | 1030 | — |
| 250 | | 7897 | — |
| 251 | | 370 | — |

TABLE I-continued

| EX. | Formula | Best potency measured on the 4 PI3K isoforms (nM) | Cell Assay: Ramos (nM) |
|---|---|---|---|
| 252 | | 335 | — |
| 253 | | 72 | — |
| 254 | | 1200 | — |
| 255 | | 1480 | — |

TABLE I-continued

| EX. | Formula | Best potency measured on the 4 PI3K isoforms (nM) | Cell Assay: Ramos (nM) |
|---|---|---|---|
| 256 | | 923 | — |
| 257 | | 824 | — |
| 258 | | 438 | — |
| 259 | | 478 | — |

TABLE I-continued

| EX. | Formula | Best potency measured on the 4 PI3K isoforms (nM) | Cell Assay: Ramos (nM) |
|---|---|---|---|
| 260 | | 560 | — |
| 261 | | 643 | — |
| 262 | | 277 | — |
| 263 | | 169 | — |

TABLE I-continued

| EX. | Formula | Best potency measured on the 4 PI3K isoforms (nM) | Cell Assay: Ramos (nM) |
|---|---|---|---|
| 264 | | 673 | — |
| 265 | | 98 | — |
| 266 | | 350 | — |
| 267 | | 59 | — |

TABLE I-continued

| EX. | Formula | Best potency measured on the 4 PI3K isoforms (nM) | Cell Assay: Ramos (nM) |
| --- | --- | --- | --- |
| 268 | | 230 | — |
| 269 | | 355 | — |
| 270 | | 280 | — |
| 271 | | 395 | — |

TABLE I-continued

| EX. | Formula | Best potency measured on the 4 PI3K isoforms (nM) | Cell Assay: Ramos (nM) |
| --- | --- | --- | --- |
| 272 | | 165 | — |
| 273 | | 36 | — |
| 274 | | 305 | — |
| 275 | | 192 | — |

TABLE I-continued

| EX. | Formula | Best potency measured on the 4 PI3K isoforms (nM) | Cell Assay: Ramos (nM) |
|---|---|---|---|
| 276 | | 875 | — |
| 277 | | 149 | — |
| 278 | | 667 | — |

TABLE I-continued

| EX. | Formula | Best potency measured on the 4 PI3K isoforms (nM) | Cell Assay: Ramos (nM) |
|---|---|---|---|
| 279 | | 711 | — |
| 280 | | 22 | — |
| 281 | | 34 | — |
| 282 | | 72 | — |

TABLE I-continued

| EX. | Formula | Best potency measured on the 4 PI3K isoforms (nM) | Cell Assay: Ramos (nM) |
|---|---|---|---|
| 283 | | 34 | — |
| 284 | | 83 | — |
| 285 | | 692 | — |
| 286 | | 257 | — |

TABLE I-continued

| EX. | Formula | Best potency measured on the 4 PI3K isoforms (nM) | Cell Assay: Ramos (nM) |
|---|---|---|---|
| 287 | | 733 | — |
| 288 | | 166 | — |
| 289 | | 284 | — |
| 290 | | 369 | — |

TABLE I-continued
| EX. | Formula | Best potency measured on the 4 PI3K isoforms (nM) | Cell Assay: Ramos (nM) |
|---|---|---|---|
| 291 | 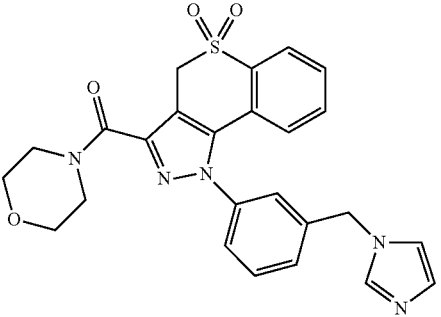 [SMILES: O=C(c1nn(-c2cccc(Cn3ccnc3)c2)c2c1CS(=O)(=O)c1ccccc1-2)N1CCOCC1] | 673 | — |
| 292 | 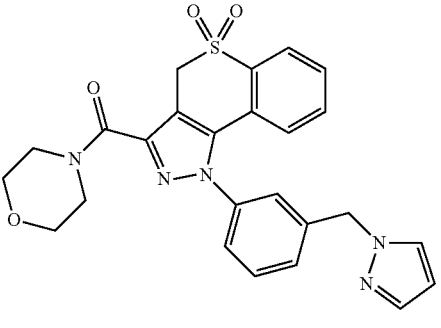 [SMILES: O=C(c1nn(-c2cccc(Cn3cccn3)c2)c2c1CS(=O)(=O)c1ccccc1-2)N1CCOCC1] | 488 | — |
| 293 | 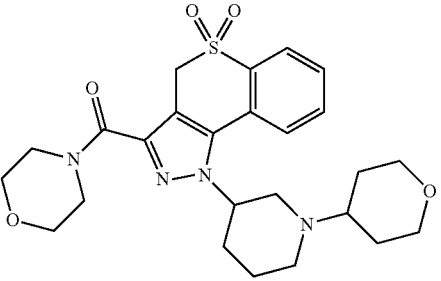 | 254 | — |
| 294 | 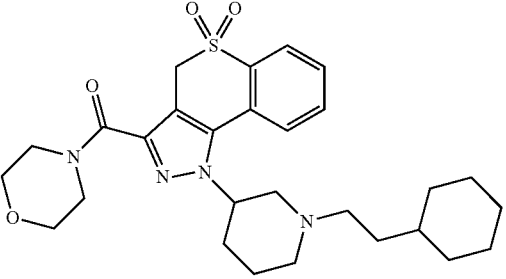 | 155 | — |

TABLE I-continued

| EX. | Formula | Best potency measured on the 4 PI3K isoforms (nM) | Cell Assay: Ramos (nM) |
|---|---|---|---|
| 295 | | 134 | — |
| 296 | | 90 | — |
| 297 | | 52 | — |
| 298 | | 29 | — |

TABLE I-continued

| EX. | Formula | Best potency measured on the 4 PI3K isoforms (nM) | Cell Assay: Ramos (nM) |
|-----|---------|---------------------------------------------------|------------------------|
| 299 | | 871 | — |
| 300 | | 77 | — |
| 301 | | 38 | — |
| 302 | | 21 | — |

TABLE I-continued

| EX. | Formula | Best potency measured on the 4 PI3K isoforms (nM) | Cell Assay: Ramos (nM) |
|---|---|---|---|
| 303 | | 353 | — |
| 304 | | 57 | — |
| 305 | | 11 | — |
| 306 | | 34 | — |

TABLE I-continued

| EX. | Formula | Best potency measured on the 4 PI3K isoforms (nM) | Cell Assay: Ramos (nM) |
|---|---|---|---|
| 307 | | 2200 | — |
| 308 | | 120 | — |
| 309 | | 120 | — |
| 310 | | 192 | — |

TABLE I-continued
| EX. | Formula | Best potency measured on the 4 PI3K isoforms (nM) | Cell Assay: Ramos (nM) |
|---|---|---|---|
| 311 | 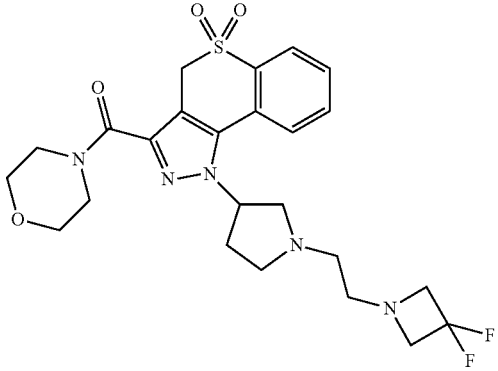 [SMILES: O=C(c1nn(C2CCN(CCN3CC(F)(F)C3)C2)c2c1CS(=O)(=O)c1ccccc1-2)N1CCOCC1] | 156 | — |
| 312 | 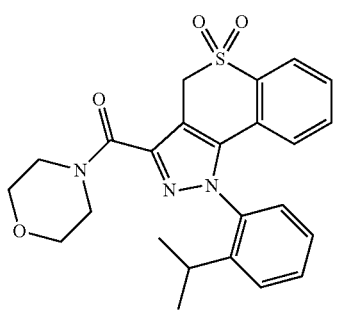 [SMILES: CC(C)c1ccccc1-n1nc(C(=O)N2CCOCC2)c2c1-c1ccccc1S(=O)(=O)C2] | 47% inh @20 μM | — |
| 313 | 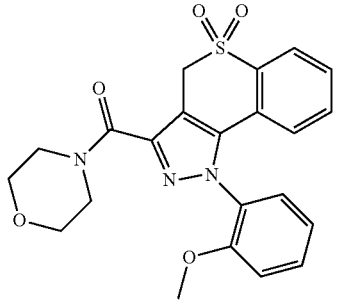 [SMILES: COc1ccccc1-n1nc(C(=O)N2CCOCC2)c2c1-c1ccccc1S(=O)(=O)C2] | 14850 | — |
| 314 | 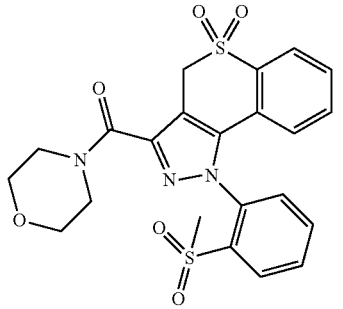 [SMILES: CS(=O)(=O)c1ccccc1-n1nc(C(=O)N2CCOCC2)c2c1-c1ccccc1S(=O)(=O)C2] | 45% inh @20 μM | — |

TABLE I-continued

| EX. | Formula | Best potency measured on the 4 PI3K isoforms (nM) | Cell Assay: Ramos (nM) |
|---|---|---|---|
| 315 | | 10745 | — |
| 316 | | 9798 | — |
| 317 | | 14457 | — |
| 318 | | 10% inh @20 μM | — |

TABLE I-continued

| EX. | Formula | Best potency measured on the 4 PI3K isoforms (nM) | Cell Assay: Ramos (nM) |
|---|---|---|---|
| 319 | | 33% inh @20 μM | — |
| 320 | | 32% inh @20 μM | — |
| 321 | | 7960 | — |
| 322 | | 9880 | — |

TABLE I-continued

| EX. | Formula | Best potency measured on the 4 PI3K isoforms (nM) | Cell Assay: Ramos (nM) |
| --- | --- | --- | --- |
| 323 | | 17880 | — |
| 324 | | 6690 | — |
| 325 | | 19% inh @20 μM | — |
| 326 | | 9791 | — |

TABLE I-continued
| EX. | Formula | Best potency measured on the 4 PI3K isoforms (nM) | Cell Assay: Ramos (nM) |
| --- | --- | --- | --- |
| 327 | 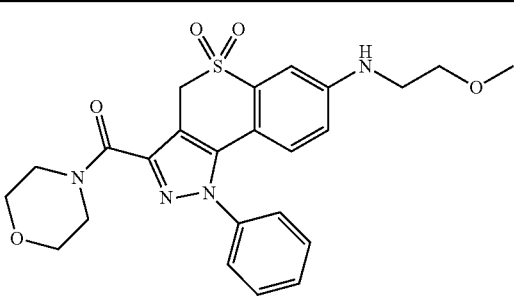 | 6610 | — |
| 328 | 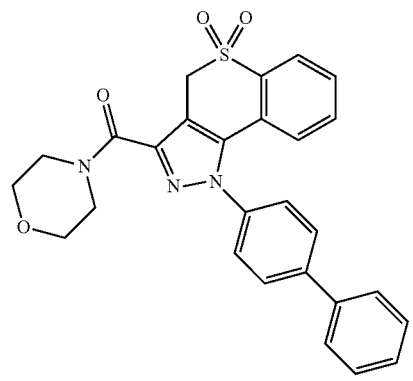 [SMILES: O=C(c1nn(-c2ccc(-c3ccccc3)cc2)c2c1CS(=O)(=O)c1ccccc1-2)N1CCOCC1] | 10293 | — |
| 329 | 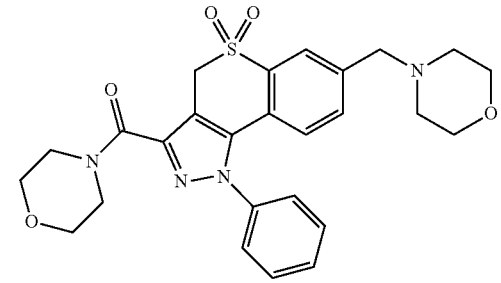 [SMILES: O=C(c1nn(-c2ccccc2)c2c1CS(=O)(=O)c1cc(CN3CCOCC3)ccc1-2)N1CCOCC1] | 23% inh @20 μM | — |
| 330 | 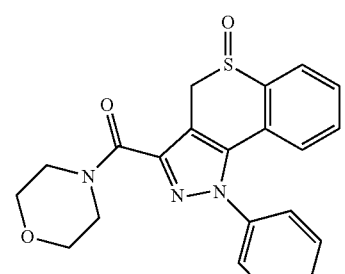 | 18% inh @20 μM | — |

TABLE I-continued

| EX. | Formula | Best potency measured on the 4 PI3K isoforms (nM) | Cell Assay: Ramos (nM) |
|---|---|---|---|
| 331 | | — | — |
| 332 | | 15% inh @20 μM | — |
| 333 | | 6530 | — |
| 334 | | 9069 | — |
| 335 | | 13% inh @20 μM | — |

TABLE I-continued

| EX. | Formula | Best potency measured on the 4 PI3K isoforms (nM) | Cell Assay: Ramos (nM) |
|---|---|---|---|
| 336 | | — | — |
| 337 | | 11% inh @20 μM | — |
| 338 | | 13851 | — |
| 339 | | 347 | 133 |

TABLE I-continued

| EX. | Formula | Best potency measured on the 4 PI3K isoforms (nM) | Cell Assay: Ramos (nM) |
|---|---|---|---|
| 340 | | 445 | — |
| 341 | | 726 | — |
| 342 | | 890 | — |
| 343 | | 1920 | — |

TABLE I-continued

| EX. | Formula | Best potency measured on the 4 PI3K isoforms (nM) | Cell Assay: Ramos (nM) |
|---|---|---|---|
| 344 | | 6 | — |
| 345 | | 16 | 68 |
| 346 | | 40 | 128 |
| 347 | | 3550 | — |
| 348 | | 1280 | — |

TABLE I-continued

| EX. | Formula | Best potency measured on the 4 PI3K isoforms (nM) | Cell Assay: Ramos (nM) |
|---|---|---|---|
| 349 | | — | — |
| 350 | | 16 | 40 |
| 353 | | 2040 | — |
| 354 | | 92 | — |

TABLE I-continued

| EX. | Formula | Best potency measured on the 4 PI3K isoforms (nM) | Cell Assay: Ramos (nM) |
|-----|---------|---------------------------------------------------|------------------------|
| 355 | | 52 | 94 |
| 356 | | 1690 | — |
| 357 | | 180 | — |
| 358 | | 3000 | — |

TABLE I-continued

| EX. | Formula | Best potency measured on the 4 PI3K isoforms (nM) | Cell Assay: Ramos (nM) |
|---|---|---|---|
| 359 | | 1060 | — |
| 360 | | 179 | — |
| 361 | | 25 | — |
| 362 | | 17 | — |

TABLE I-continued
| EX. | Formula | Best potency measured on the 4 PI3K isoforms (nM) | Cell Assay: Ramos (nM) |
|---|---|---|---|
| 363 | 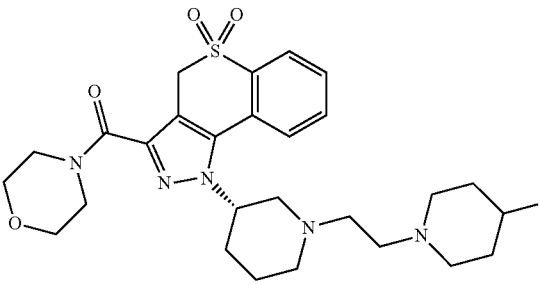 | 25 | — |
| 364 | 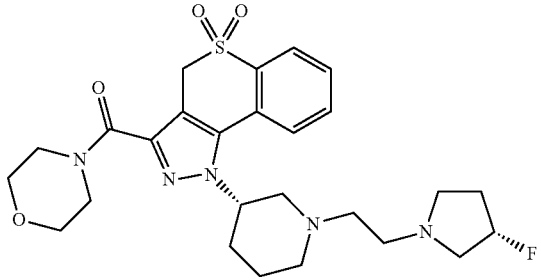 | 14 | — |
| 365 | 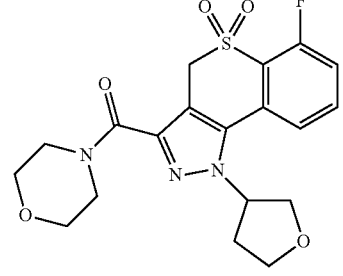 | 353 | — |
| 366 | 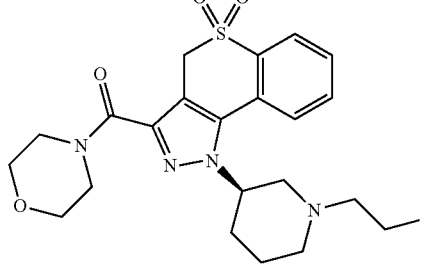 | 7970 | — |
| 367 | 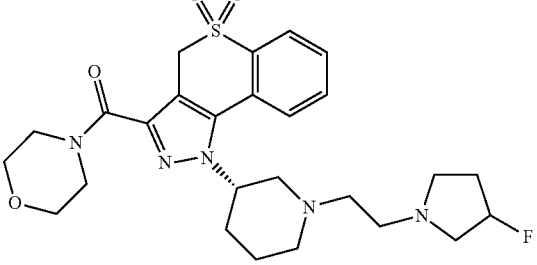 | 32 | — |

TABLE I-continued

| EX. | Formula | Best potency measured on the 4 PI3K isoforms (nM) | Cell Assay: Ramos (nM) |
|---|---|---|---|
| 368 | | — | — |
| 369 | | 27 | — |
| 370 | | 73 | — |
| 371 | | 830 | — |

TABLE I-continued
| EX. | Formula | Best potency measured on the 4 PI3K isoforms (nM) | Cell Assay: Ramos (nM) |
|---|---|---|---|
| 372 | 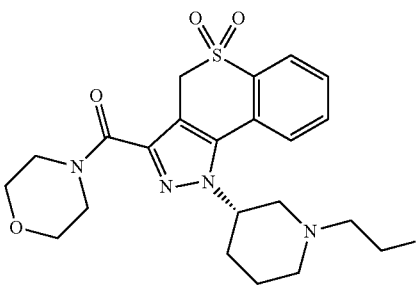 | 200 | — |
| 373 | 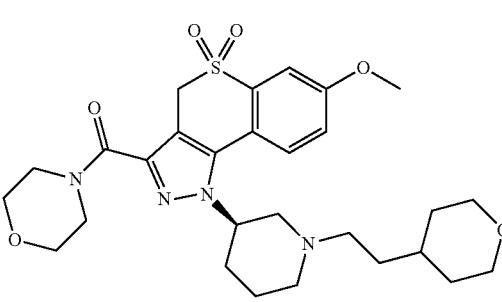 | 10300 | — |
| 374 | 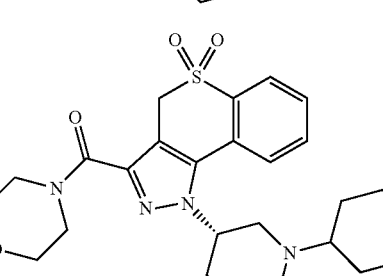 | 80 | — |
| 375 | 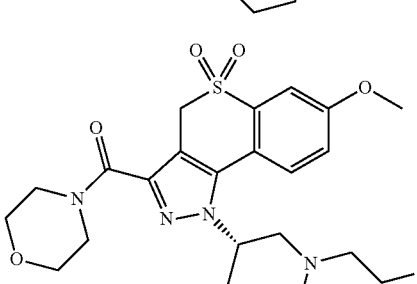 | — | — |
| 376 | 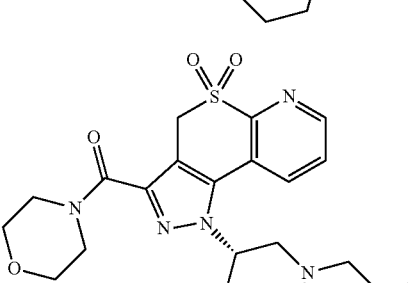 | 13 | — |

TABLE I-continued

| EX. | Formula | Best potency measured on the 4 PI3K isoforms (nM) | Cell Assay: Ramos (nM) |
|---|---|---|---|
| 377 | | 101 | — |
| 378 | | 65 | — |
| 379 | | 2930 | — |
| 380 | | — | 320 |
| 381 | | 36 | — |

TABLE I-continued

| EX. | Formula | Best potency measured on the 4 PI3K isoforms (nM) | Cell Assay: Ramos (nM) |
|---|---|---|---|
| 382 | | 15 | — |
| 383 | | 24 | — |
| 384 | | 19 | — |
| 385 | | 29 | — |
| 386 | | 30 | — |

TABLE I-continued

| EX. | Formula | Best potency measured on the 4 PI3K isoforms (nM) | Cell Assay: Ramos (nM) |
| --- | --- | --- | --- |
| 387 | | 5230 | — |
| 388 | | — | — |
| 389 | | 24 | — |
| 390 | | 250 | — |

TABLE I-continued

| EX. | Formula | Best potency measured on the 4 PI3K isoforms (nM) | Cell Assay: Ramos (nM) |
|---|---|---|---|
| 391 | | 202 | — |
| 392 | | 555 | — |
| 393 | | 10200 | — |
| 394 | | 93 | — |

TABLE I-continued

| EX. | Formula | Best potency measured on the 4 PI3K isoforms (nM) | Cell Assay: Ramos (nM) |
| --- | --- | --- | --- |
| 395 | | 44 | — |
| 396 | | 750 | — |
| 397 | | 1500 | — |
| 398 | | 345 | — |

TABLE I-continued

| EX. | Formula | Best potency measured on the 4 PI3K isoforms (nM) | Cell Assay: Ramos (nM) |
|---|---|---|---|
| 399 | | 735 | — |
| 400 | | 104 | 888 |
| 401 | | 340 | 3630 |
| 402 | | 1440 | — |

TABLE I-continued

| EX. | Formula | Best potency measured on the 4 PI3K isoforms (nM) | Cell Assay: Ramos (nM) |
|---|---|---|---|
| 403 | | 45 | 214 |
| 404 | | 21 | — |
| 405 | | 95 | — |
| 406 | | 80 | — |

TABLE I-continued

| EX. | Formula | Best potency measured on the 4 PI3K isoforms (nM) | Cell Assay: Ramos (nM) |
|---|---|---|---|
| 407 | | 236 | — |
| 408 | | 61 | — |
| 409 | | 55 | — |
| 410 | | 3690 | — |

TABLE I-continued

| EX. | Formula | Best potency measured on the 4 PI3K isoforms (nM) | Cell Assay: Ramos (nM) |
|---|---|---|---|
| 411 | | 444 | — |
| 412 | | 5600 | — |
| 413 | | 16 | — |
| 414 | | 38 | — |
| 415 | | 67 | — |

TABLE I-continued

| EX. | Formula | Best potency measured on the 4 PI3K isoforms (nM) | Cell Assay: Ramos (nM) |
|---|---|---|---|
| 422 | | 16 | — |
| 423 | | 99 | — |
| 424 | | 59 | — |
| 425 | | 25 | — |

TABLE I-continued

| EX. | Formula | Best potency measured on the 4 PI3K isoforms (nM) | Cell Assay: Ramos (nM) |
|---|---|---|---|
| 426 | | 113 | — |
| 427 | | 13 | — |
| 428 | | 128 | — |
| 429 | | 39 | — |

TABLE I-continued

| EX. | Formula | Best potency measured on the 4 PI3K isoforms (nM) | Cell Assay: Ramos (nM) |
|---|---|---|---|
| 430 | | 229 | — |
| 431 | | 164 | — |
| 432 | | 105 | — |

TABLE I-continued

| EX. | Formula | Best potency measured on the 4 PI3K isoforms (nM) | Cell Assay: Ramos (nM) |
|---|---|---|---|
| 433 | | 48 | — |
| 434 | | 31 | — |
| 435 | | 57 | — |
| 436 | | 107 | — |

TABLE I-continued
| EX. | Formula | Best potency measured on the 4 PI3K isoforms (nM) | Cell Assay: Ramos (nM) |
|---|---|---|---|
| 437 | 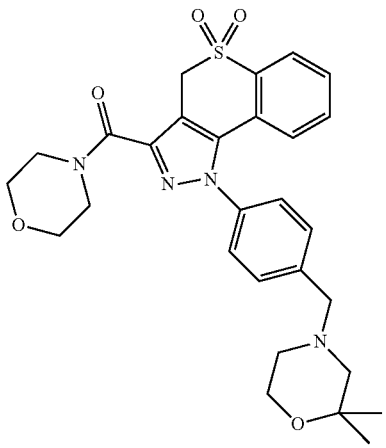 [SMILES: CC1(C)CN(Cc2ccc(-n3nc(C(=O)N4CCOCC4)c4c3-c3ccccc3S(=O)(=O)C4)cc2)CCO1] | 120 | — |
| 438 | 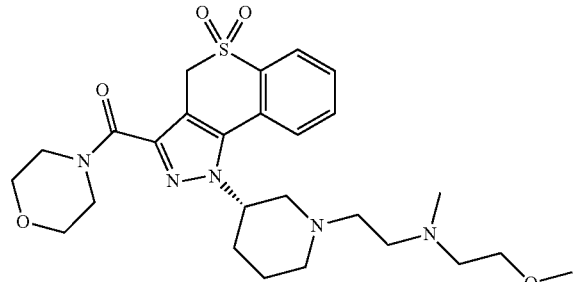 | 45 | — |
| 439 | 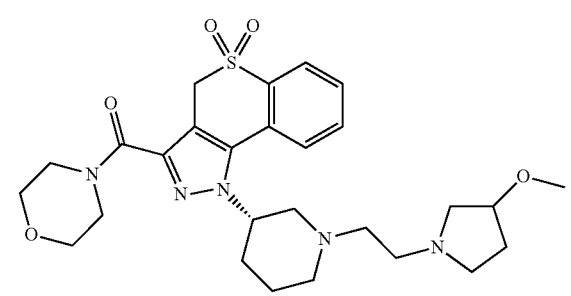 [SMILES: COC1CCN(CCN2CCC[C@H](n3nc(C(=O)N4CCOCC4)c4c3-c3ccccc3S(=O)(=O)C4)C2)C1] | 25 | — |
| 440 | 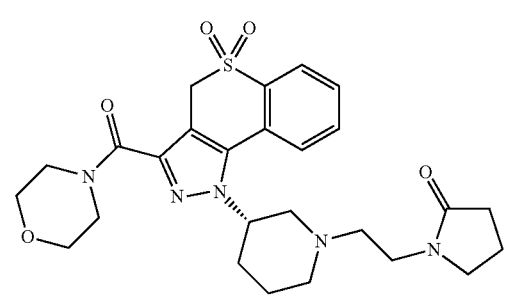 [SMILES: O=C1CCCN1CCN1CCC[C@H](n2nc(C(=O)N3CCOCC3)c3c2-c2ccccc2S(=O)(=O)C3)C1] | 80 | — |

TABLE I-continued

| EX. | Formula | Best potency measured on the 4 PI3K isoforms (nM) | Cell Assay: Ramos (nM) |
|---|---|---|---|
| 441 | | 41 | — |
| 442 | | 40 | — |
| 443 | | 62 | — |
| 444 | | 105 | — |

TABLE I-continued

| EX. | Formula | Best potency measured on the 4 PI3K isoforms (nM) | Cell Assay: Ramos (nM) |
|---|---|---|---|
| 445 | | 34 | — |
| 446 | | 20 | — |
| 447 | | 261 | — |
| 448 | | 113 | — |

TABLE I-continued

| EX. | Formula | Best potency measured on the 4 PI3K isoforms (nM) | Cell Assay: Ramos (nM) |
|---|---|---|---|
| 449 | | 226 | — |
| 450 | | 7 | — |
| 451 | | 28 | — |
| 452 | | 73 | — |

TABLE I-continued
| EX. | Formula | Best potency measured on the 4 PI3K isoforms (nM) | Cell Assay: Ramos (nM) |
|---|---|---|---|
| 453 | 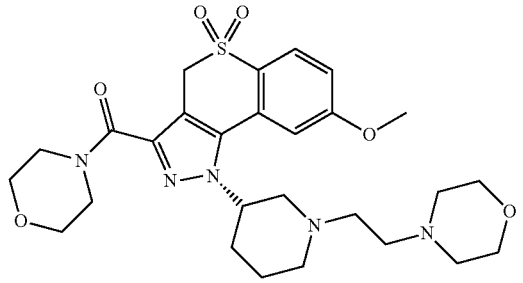 | 28 | — |
| 454 | 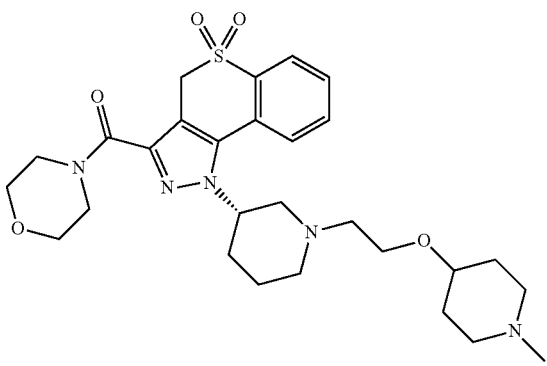 | 20 | — |
| 455 | 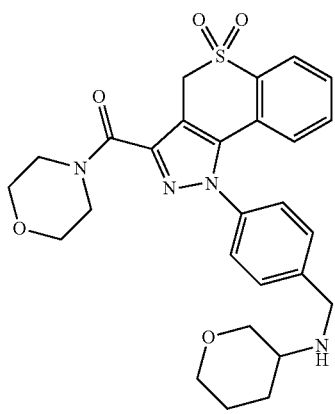 | 224 | — |
| 456 | 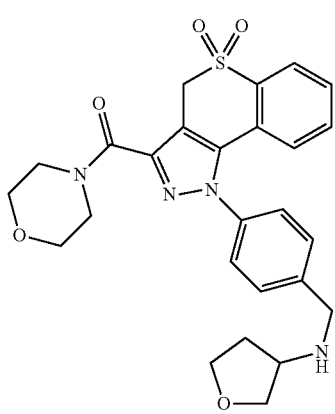 [SMILES: O=C(c1nn(-c2ccc(CNC3CCOC3)cc2)c2c1CS(=O)(=O)c1ccccc1-2)N1CCOCC1] | 156 | — |

TABLE I-continued
| EX. | Formula | Best potency measured on the 4 PI3K isoforms (nM) | Cell Assay: Ramos (nM) |
|---|---|---|---|
| 457 | 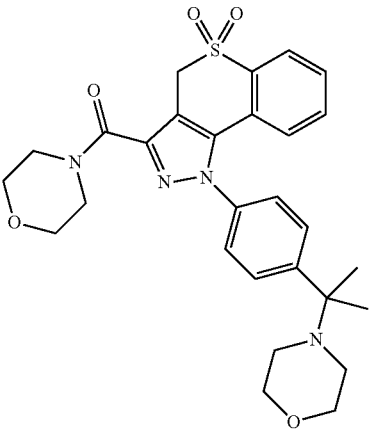 [SMILES: CC(C)(c1ccc(-n2nc(C(=O)N3CCOCC3)c3c2-c2ccccc2S(=O)(=O)C3)cc1)N1CCOCC1] | 584 | — |
| 458 | 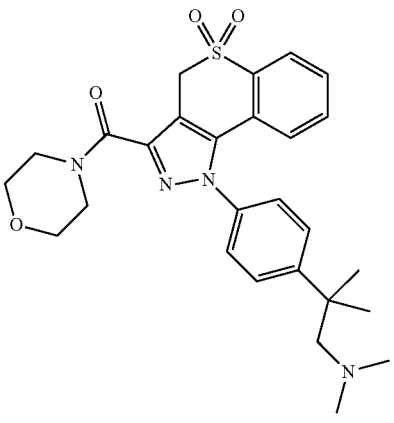 [SMILES: CN(C)CC(C)(C)c1ccc(-n2nc(C(=O)N3CCOCC3)c3c2-c2ccccc2S(=O)(=O)C3)cc1] | 159 | — |
| 459 | 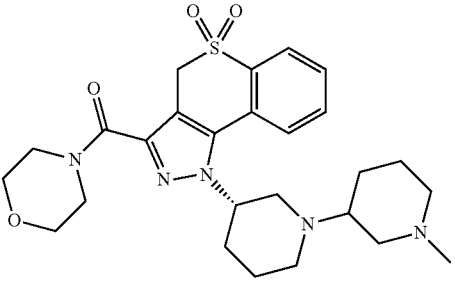 [SMILES: CN1CCCC(N2CCC[C@H](n3nc(C(=O)N4CCOCC4)c4c3-c3ccccc3S(=O)(=O)C4)C2)C1] | 18 | — |
| 460 | 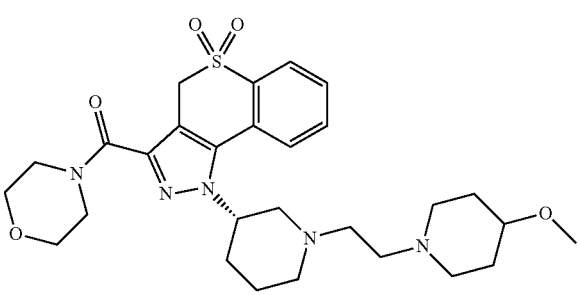 [SMILES: COC1CCN(CCN2CCC[C@H](n3nc(C(=O)N4CCOCC4)c4c3-c3ccccc3S(=O)(=O)C4)C2)CC1] | 21 | — |

TABLE I-continued

| EX. | Formula | Best potency measured on the 4 PI3K isoforms (nM) | Cell Assay: Ramos (nM) |
|---|---|---|---|
| 461 | | 341 | — |
| 462 | | 995 | — |
| 463 | | 18 | — |
| 464 | | 22 | — |

TABLE I-continued
| EX. | Formula | Best potency measured on the 4 PI3K isoforms (nM) | Cell Assay: Ramos (nM) |
|---|---|---|---|
| 465 | 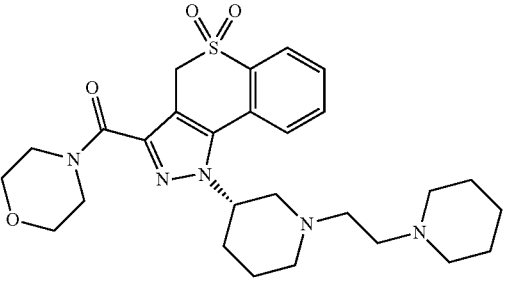 | 15 | — |
| 466 | 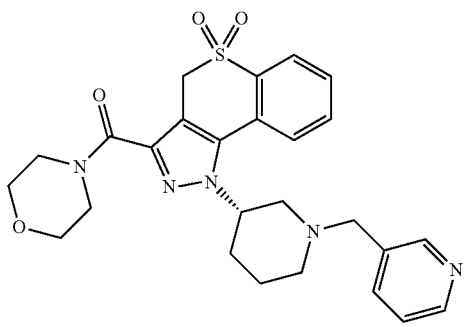 | 85 | — |
| 467 | 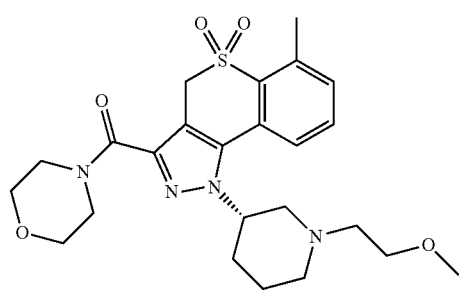 [SMILES: COCCN1CCC[C@H](n2nc(C(=O)N3CCOCC3)c3c2-c2cccc(C)c2S(=O)(=O)C3)C1] | 96 | — |
| 468 | 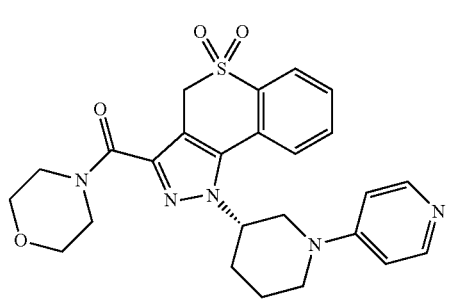 [SMILES: O=C(c1nn([C@H]2CCCN(c3ccncc3)C2)c2c1CS(=O)(=O)c1ccccc1-2)N1CCOCC1] | 133 | — |
| 469 | 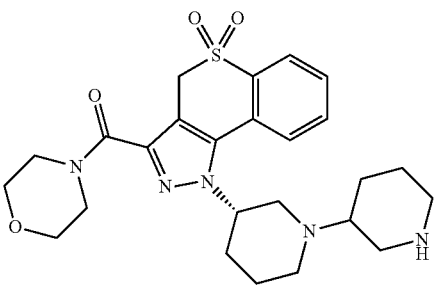 [SMILES: O=C(c1nn([C@H]2CCCN(C3CCCNC3)C2)c2c1CS(=O)(=O)c1ccccc1-2)N1CCOCC1] | 25 | — |

TABLE I-continued

| EX. | Formula | Best potency measured on the 4 PI3K isoforms (nM) | Cell Assay: Ramos (nM) |
|---|---|---|---|
| 470 | | 349 | — |
| 471 | | 49 | — |
| 472 | | 14 | 45 |
| 473 | | 45 | — |

TABLE I-continued

| EX. | Formula | Best potency measured on the 4 PI3K isoforms (nM) | Cell Assay: Ramos (nM) |
|---|---|---|---|
| 474 | | 13 | — |
| 481 | | 10500 | — |
| 484 | | 48 | — |
| 485 | | 477 | — |
| 486 | | 2740 | — |

TABLE I-continued

| EX. | Formula | Best potency measured on the 4 PI3K isoforms (nM) | Cell Assay: Ramos (nM) |
|---|---|---|---|
| 487 | | 11700 | — |
| 488 | | 3460 | — |
| 489 | | 5500 | — |

Example 511

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of Formula (I*):

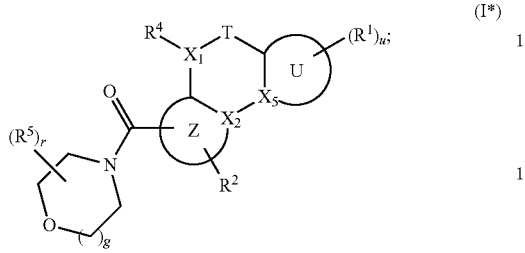

wherein:
$X_1$ denotes a nitrogen atom or $CR^3$;
$X_2$, $X_5$ are independently from one another nitrogen or carbon atoms;
U denotes an aromatic 6-membered ring having optionally 1, 2 or 3 nitrogen atoms, including $X_5$, or an unsaturated or aromatic 5-membered ring having 1 to 3 heteroatoms selected from N, S or O, including the meaning of $X_5$;
Z denotes an unsaturated or aromatic 5-membered heterocyclic ring having 2 nitrogen atoms, including the meaning of $X_2$;
T denotes SO or $SO_2$;
$R^1$ denotes H, A, Hal, CN, $NO_2$, $N(R^6)_2$, $OR^6$, Ar, Het, Y, —$NR^6COR^6$, $CON(R^6)_2$, —$NR^6COAr$, $NR^6COHet$, COHet, —$NR^6SO_2R^6$, or $CO_2R^6$, including $CO_2Y$;
$R^2$ denotes H, Ar, Het, A, or Cyc;
$R^3$ denotes H or Y;
$R^4$ denotes H, Y, $(CH_2)_nAr$, $(CH_2)_nCyc$, $(CH_2)_nHet$, $(CH_2)_nOY$, $(CH_2)_nNHY$, or $(CH_2)_nNH_2$, or if $X_1$ is $CR^3$, $R^4$ denotes H, Y, $(CH_2)_nAr$, $(CH_2)_nCyc$, $(CH_2)_nHet$, $(CH_2)_nOY$, $(CH_2)_nNHY$, $(CH_2)_nNH_2$ or Hal;
$R^5$ denotes H, Y or Ar, when $R^5$ is Y and r is 2, two $R^5$ groups may be linked together to provide with the morpholine group to which they are linked, a bridged system;
$R^6$ is H, A, Cyc or Ar;
u is 0, 1, 2, 3, or 4;
r is 0, 1 or 2;
g is 1 or 2;
Ar denotes a monocyclic or fused bicyclic, unsaturated or aromatic carbocyclic ring having 6 to 14 carbon atoms, which is unsubstituted or monosubstituted, disubstituted or trisubstituted by Hal, $OCF_3$, $NO_2$, CN, perfluoroalkyl, A, $OR^6$, $N(R^6)_2$, $COR^6$, —$CO_2R^6$, $CON(R^6)_2$, COHet, —$NHCOR^6$, —$NHSO_2A$, —$NHSO_2Ar$, —$NHSO_2$—$N(R^6)_2$, $N(H)_{1-q}A_qCOR^6$, $N(H)_{1-q}A_qSO_2$—$N(H)_{2-m}(A)_m$, —$N(H)_{1-q}A_qCON(H)_{2-m(A)m}$, —$SO_2A$, —$SO_2Ar$, —$SO_2N(H)_{2-m}(A)_m$, —$SO_2Het$, —$(CH_2)_n$—$N(R^6)_2$, —$(CH_2)_n$—$OR^6$, —$(CH_2)_n$—$N(R^6)SO_2A$, —$(CH_2)_n$—$N(R^6)SO_2R^6$, $Het^2$, —$(CH_2)_n$—$Het^2$, or —$(CHY)_n$—$Het^2$;

Het denotes a monocyclic or bicyclic saturated, unsaturated or aromatic heterocyclic ring having 1, 2, 3 or 4 N, O and/or S atoms and eventually comprising a $SO_2$ or a CO group, which is unsubstituted or monosubstituted, disubstituted or trisubstituted by Hal, $OCF_3$, $NO_2$, CN, perfluoroalkyl, A, $OR^6$, $N(R^6)_2$, $COR^6$, —$CO_2R^6$, $CON(R^6)_2$, —$NHCOR^6$, —$NHSO_2A$, —$NHSO_2R^6$, —$NHSO_2$—$N(H)_{2-m}(A)_m$, $N(H)_{1-q}A_qCOR^6$, $N(H)_{1-q}A_qSO_2$—$N(H)_{2-m}(A)_m$, —$N(H)_{1-q}A_qCON(H)_{2-m}(A)_m$, —$SO_2A$, —$SO_2Ar$, —$SO_2N(H)_{2-m}(A)_m$, COHet, —$SO_2Het$, —$(CH_2)_n$—$N(H)_{2-m}(A)_m$, —$(CH_2)_n$—$OR^6$, —$(CH_2)_n$—$N(R^6)SO_2A$, —$(CH_2)_n$—$N(R^6)SO_2R^6$, $Het^2$, —$(CH_2)_n$—$Het^2$; or —$(CHY)_n$—$Het^2$;

$Het^2$ denotes

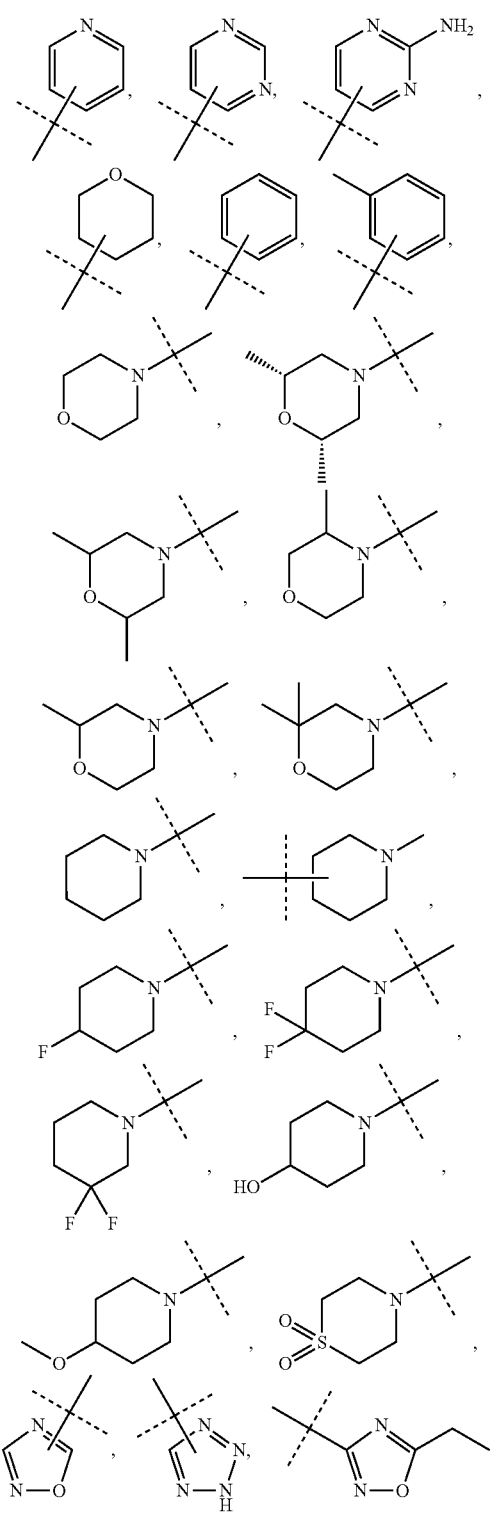

1023
-continued

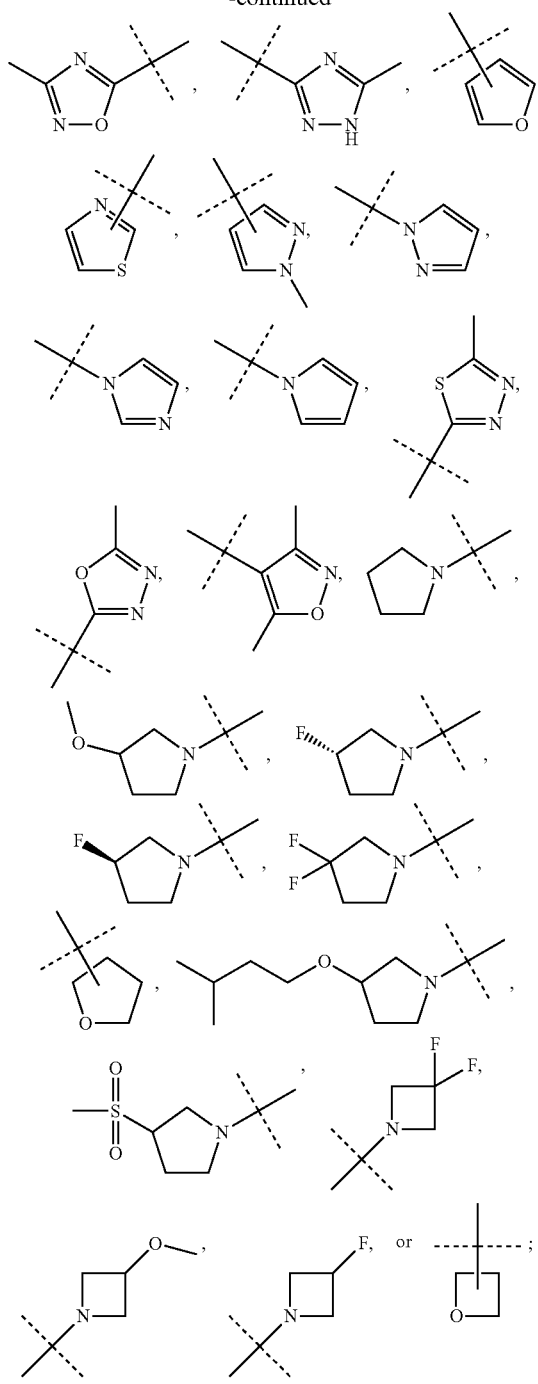

Cyc denotes a saturated or unsaturated carbocyclic ring having 3 to 8 carbon atoms, which is unsubstituted, mono-substituted, di-substituted or tri-substituted by Hal, $OCF_3$, $NO_2$, CN, perfluoroalkyl, A, $OR^6$, $N(R^6)_2$, $COR^6$, $CON(R^6)_2$, —$NHCOR^6$, —$NHSO_2A$, —$NHSO_2R^6$, —$NHSO_2$—$N(H)_{2-m}(A)_m$, $N(H)_{1-q}A_q$-$COR^6$, $N(H)_{1-q}A_q$ $SO_2$—$N(H)_{2-m}(A)_m$, —$N(H)_{1-q}A_q$-$CON(H)_{2-m}(A)_m$, —$COOR^6$, —$SO_2A$, —$SO_2Ar$, —$SO_2N(H)_{2-m}(A)_m$, —$SO_2Het$, —$(CH_2)_p$—$N(H)_{2-m}(A)_m$, —$(CH_2)_n$—$OR^6$, —$(CH_2)_n$—$N(R^6)SO_2A$, —$(CH_2)_n$—$N(R^6)SO_2R^6$, $Het^2$, —$(CH_2)_n$—$Het^2$; or —$(CHY)_n$—$Het^2$;

1024

A is a branched or linear alkyl having 1 to 12 C-atoms, wherein one or more H-atoms may be replaced by Hal, Ar, Het, Cyc, $OR^6$, —CN, —$CO_2Y$, $CO_2H$ or $N(R^6)_2$ and wherein one or more non-adjacent $CH_2$-groups may be replaced by O, $NR^6$, CO, $CONR^6$, $NR^6CO$, OCO, - and/or by —CH=CH- or —C≡C- groups, or denotes cycloalkyl or cycloalkylalkylene having 3-7 ring C atoms;

Y denotes a branched or linear alkyl having 1 to 8 carbon atoms;

Hal denotes F, Cl, Br or I;

q is 0 or 1;

m is 0, 1 or 2;

n is 1, 2, 3, or 4;

and pharmaceutically acceptable, solvates, tautomers, salts, hydrates and stereoisomers thereof, including mixtures thereof in all ratios, with the proviso that compound of formula (B1) is excluded:

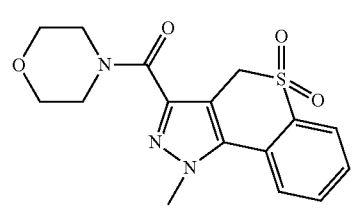

B1

2. A compound of Formula (I*) according to claim 1, wherein the moiety

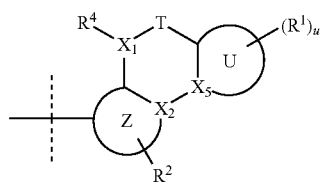

in Formula (I*) is selected from the following groups:

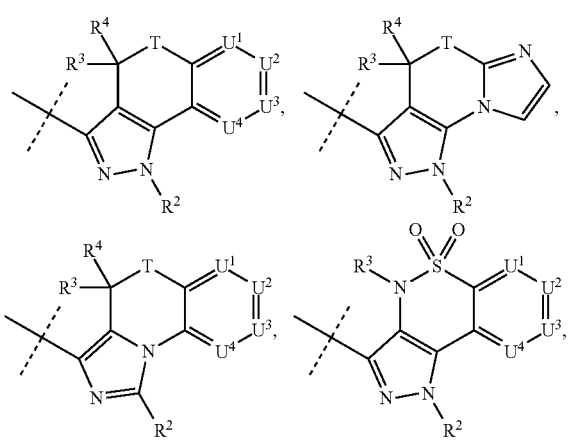

-continued

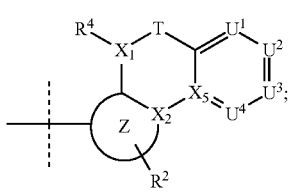

wherein R¹, R², R³, R⁴, and T, are as defined in claim 1; and wherein:
U¹, U², U³, and U⁴ denote CR¹ or one or two of U¹, U², U³ and U⁴ are independently N, and the remaining are CR¹, or one of U¹ and U⁴ is S, U²—U³ form together a group CR¹ and the remaining is CR¹, or one of U¹ and U⁴ is S, U²—U³ form together a group CR¹ and the remaining is N;
or denotes the following group:

wherein U¹ denotes N, U²—U³ form together a group CR¹, U⁴ is CR¹, X₅ is N, and Z, X¹, X², R², T, are as above defined.

3. The compound of Formula (I*) according to claim 1, wherein R² is selected from H, a branched or linear $C_1$—$C_6$-alkyl or one of the following groups:

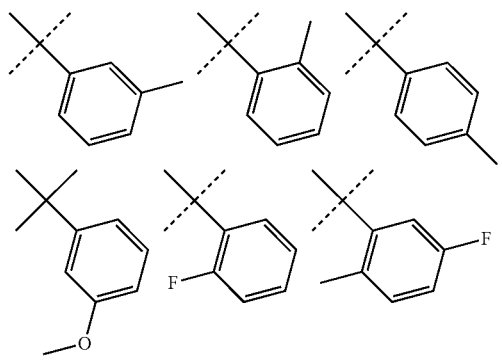

1027
-continued
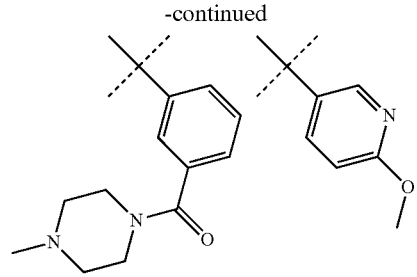
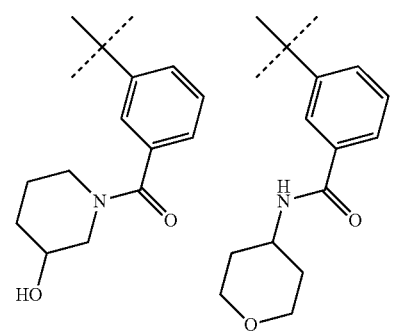
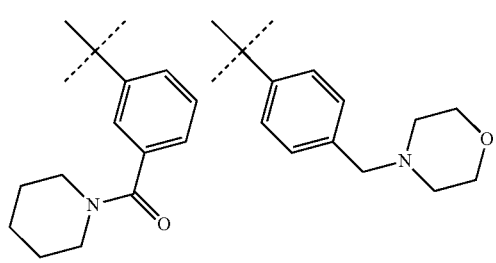
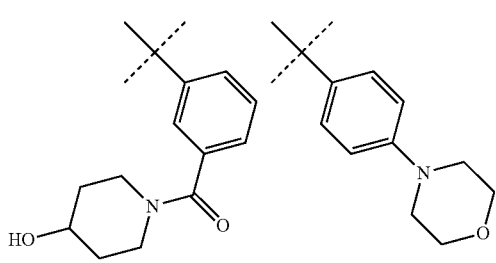
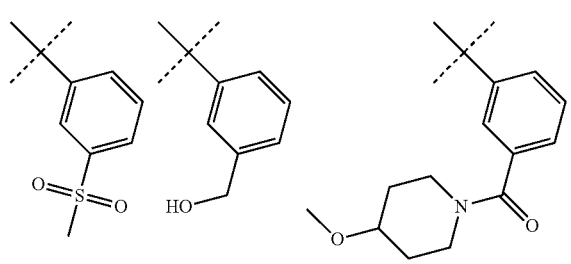
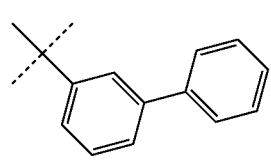
1028
-continued
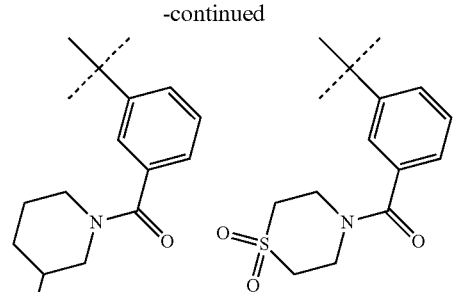
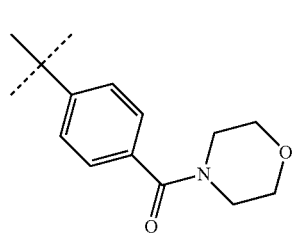
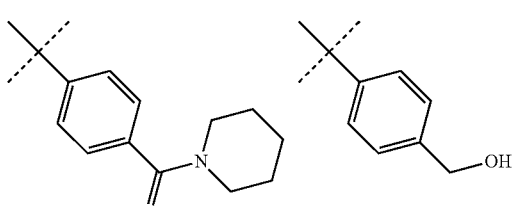
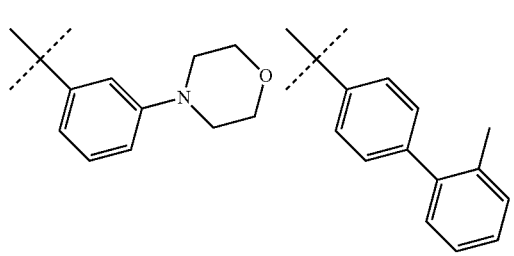
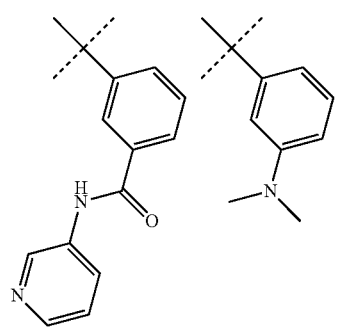
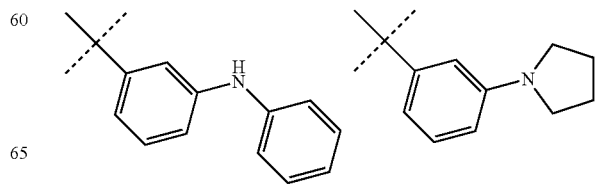

1029
-continued
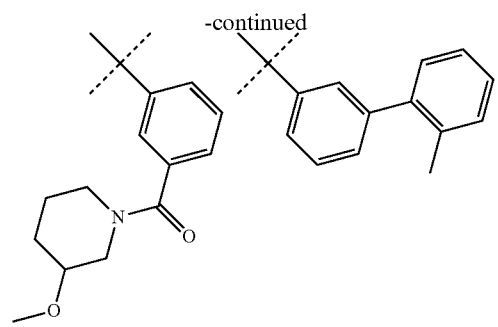
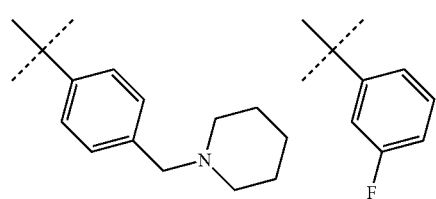
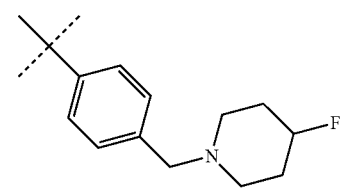
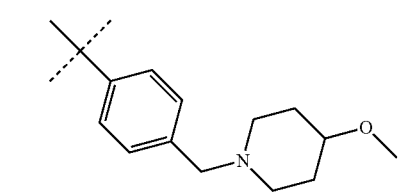
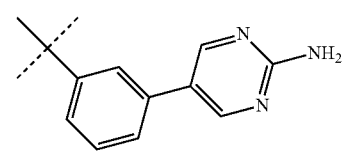
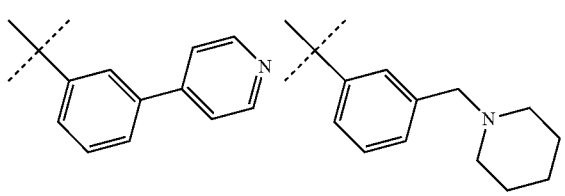
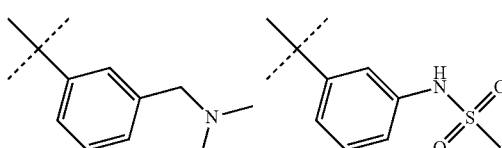
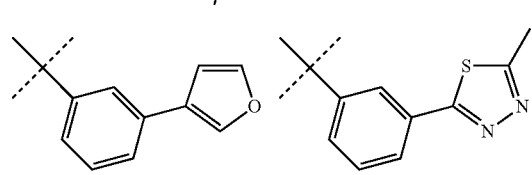
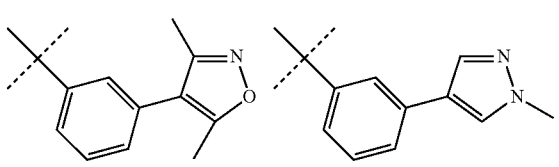
1030
-continued
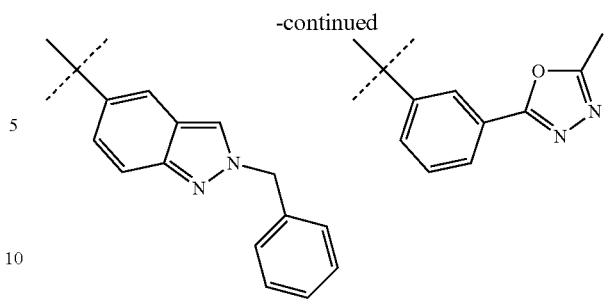
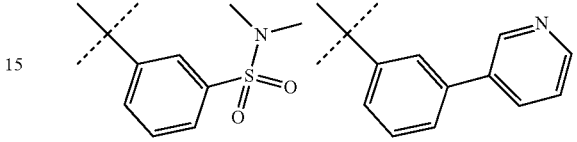
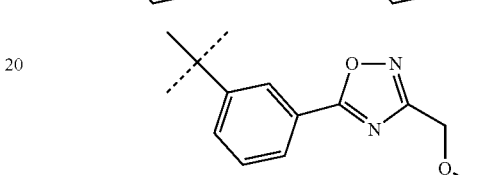
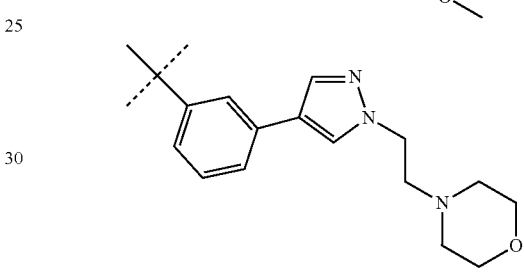
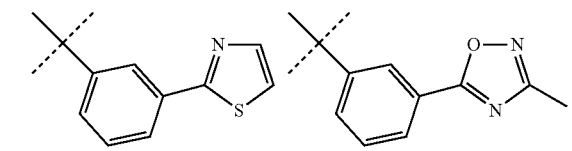
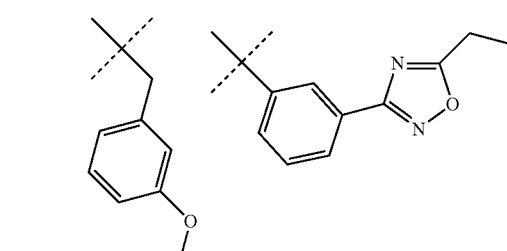
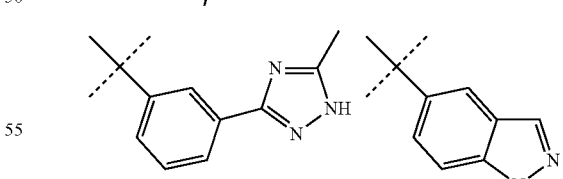
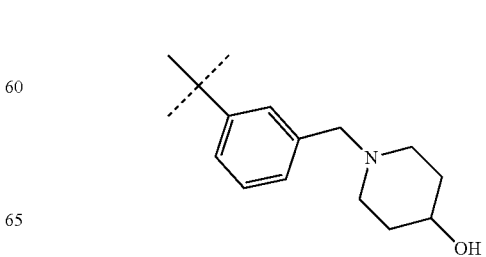

US 9,073,940 B2
1031
-continued
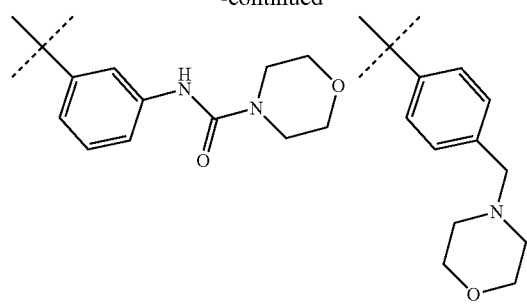
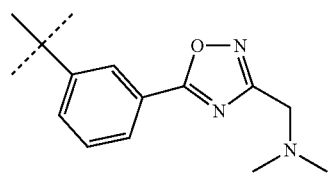
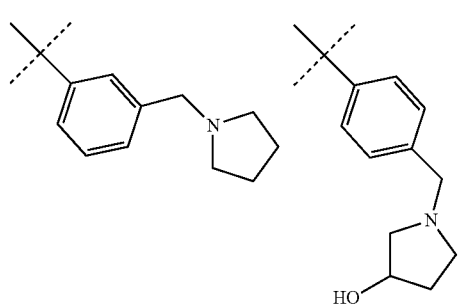
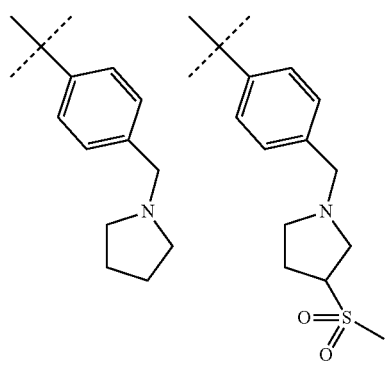
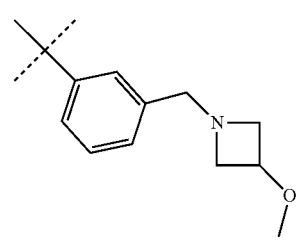
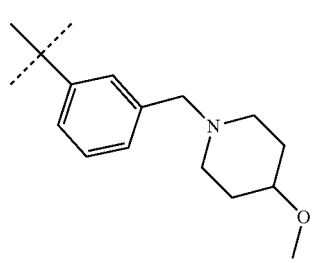
1032
-continued
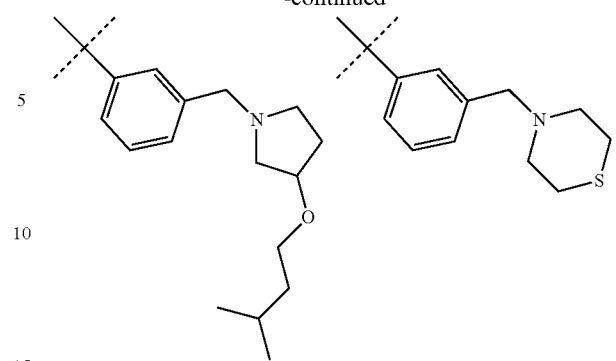
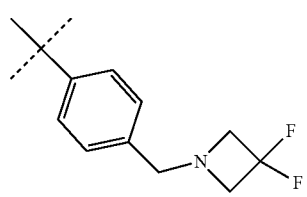
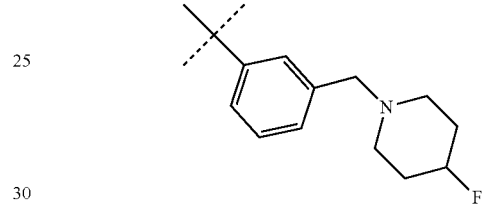
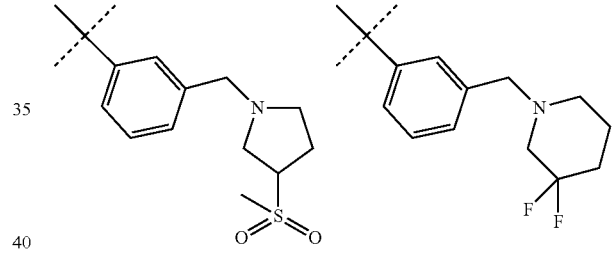
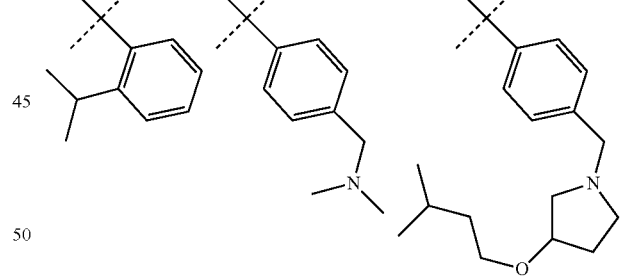
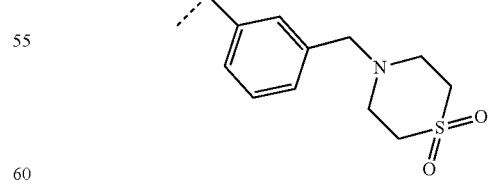
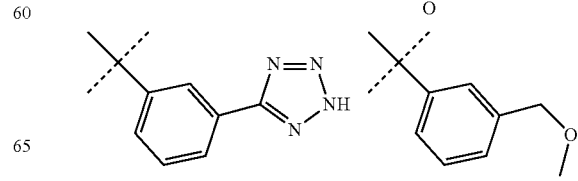

1033
-continued
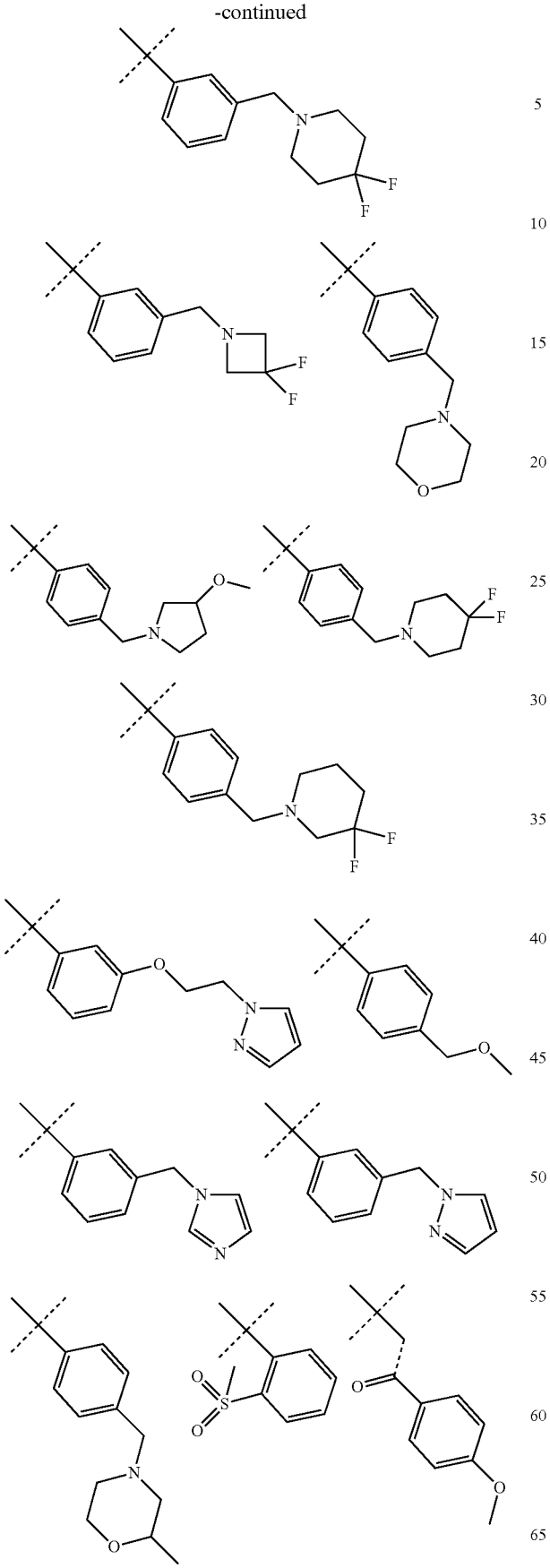
1034
-continued
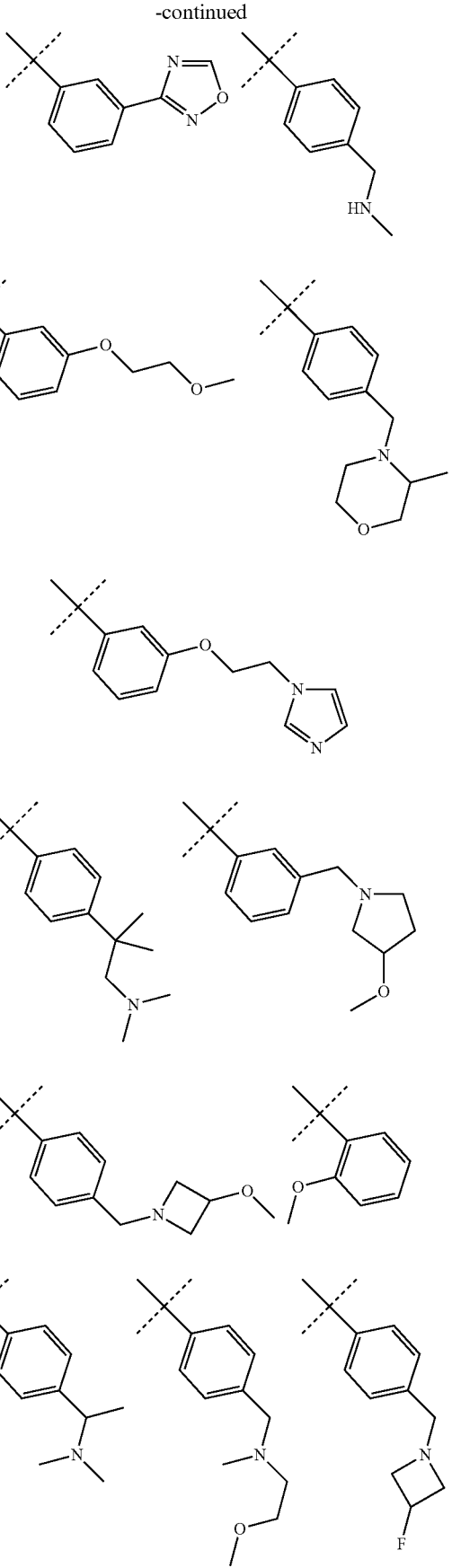

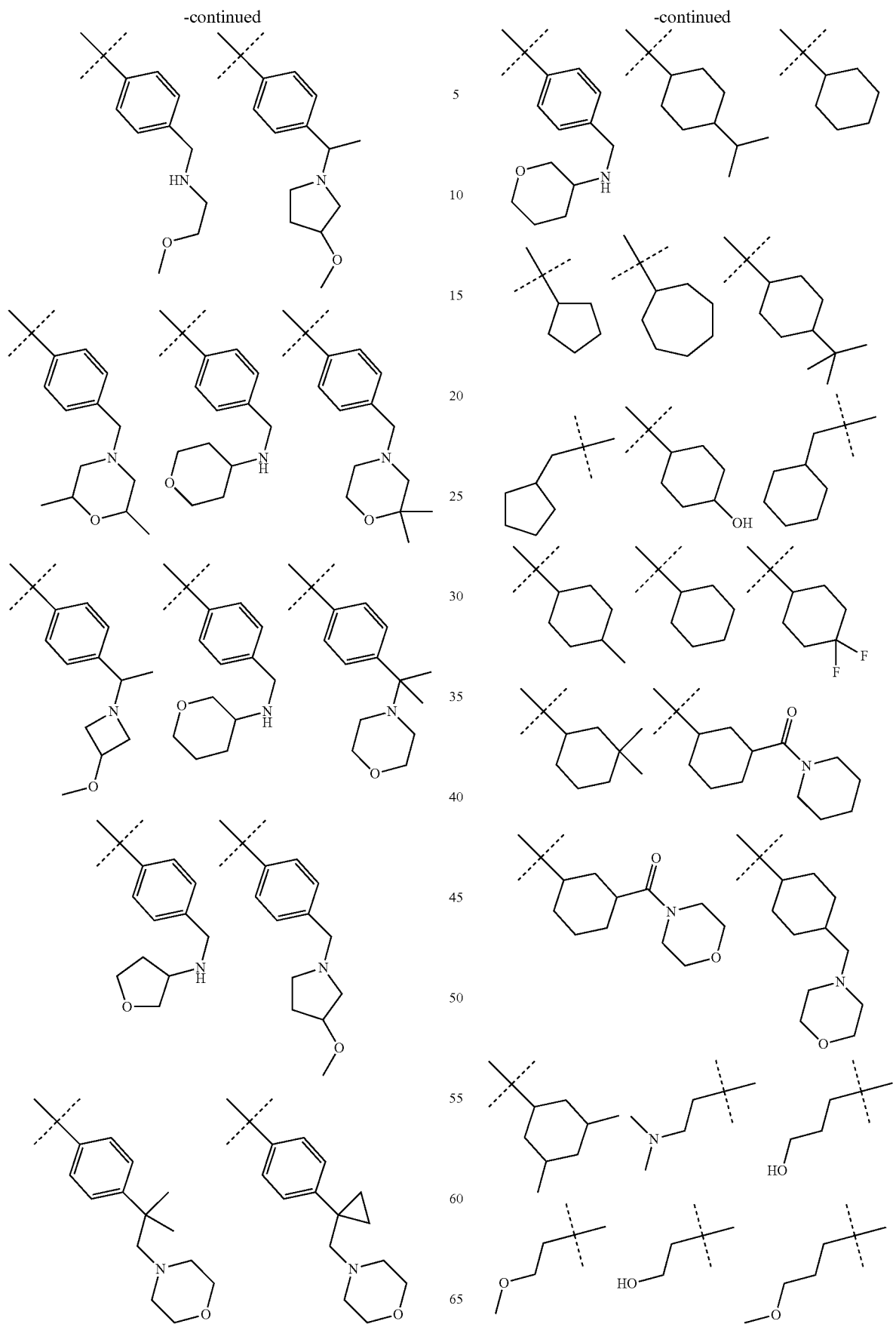

1037
-continued
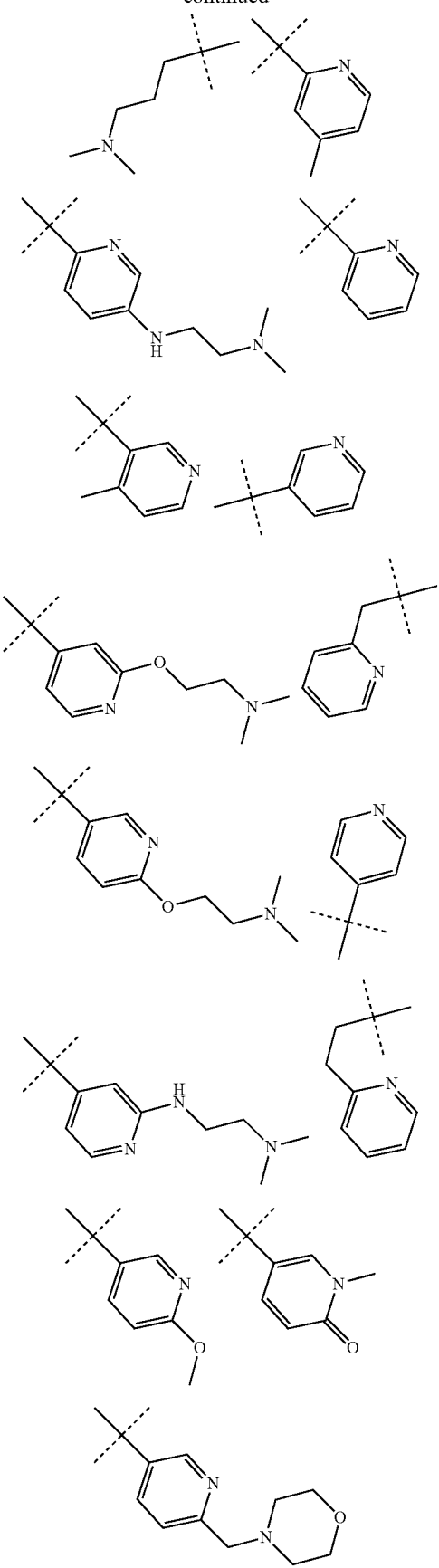
1038
-continued
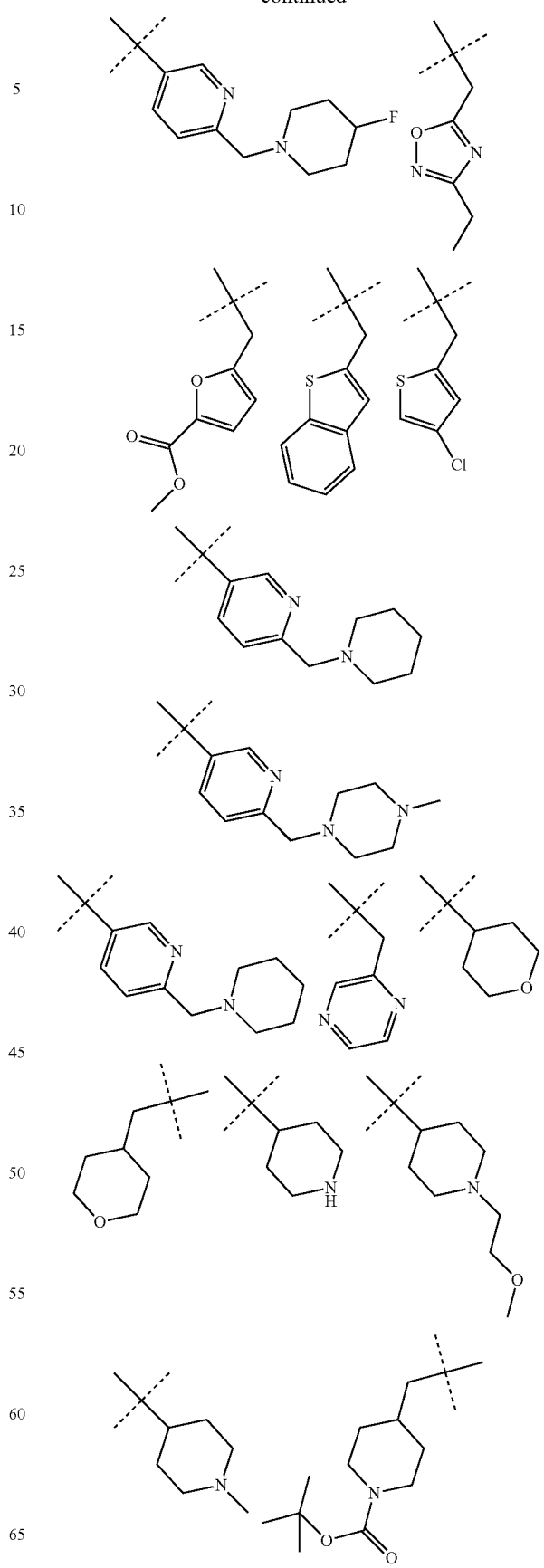

1039
-continued
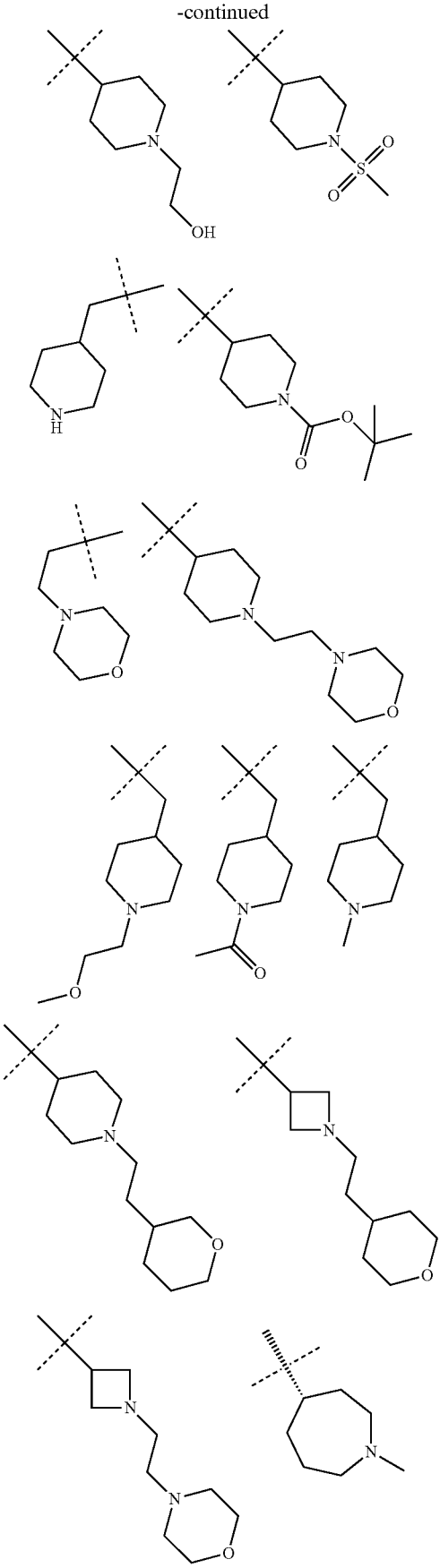
1040
-continued
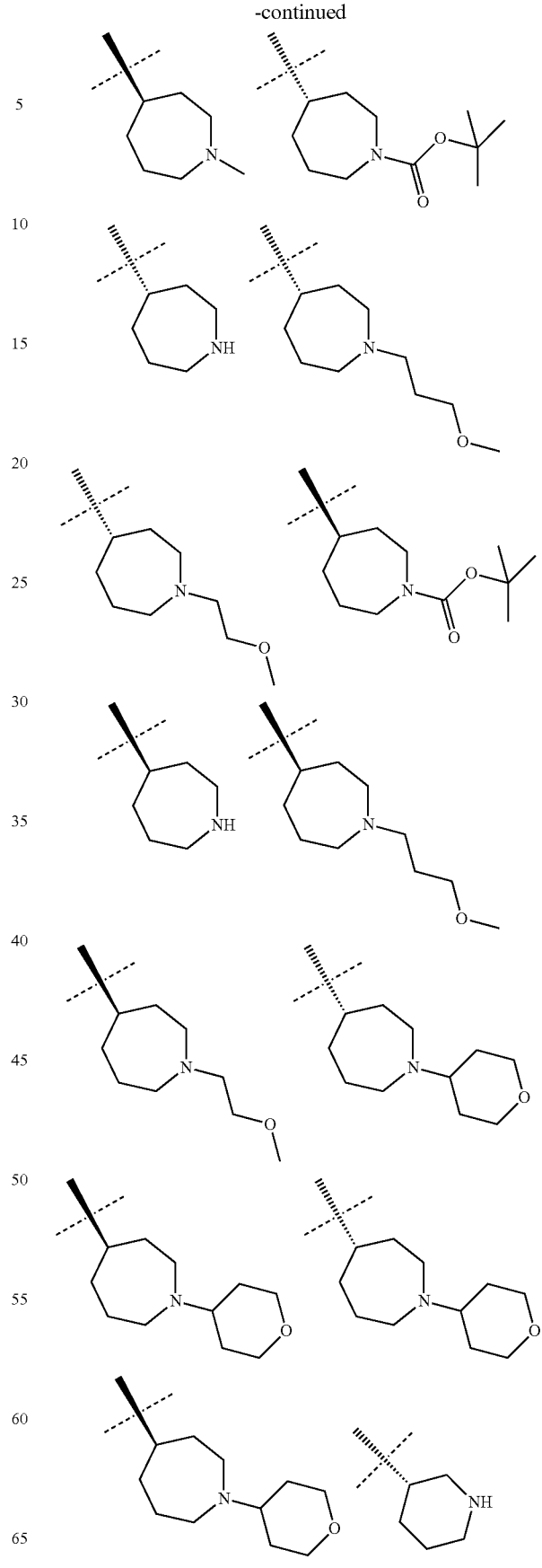

1041
-continued
1042
-continued
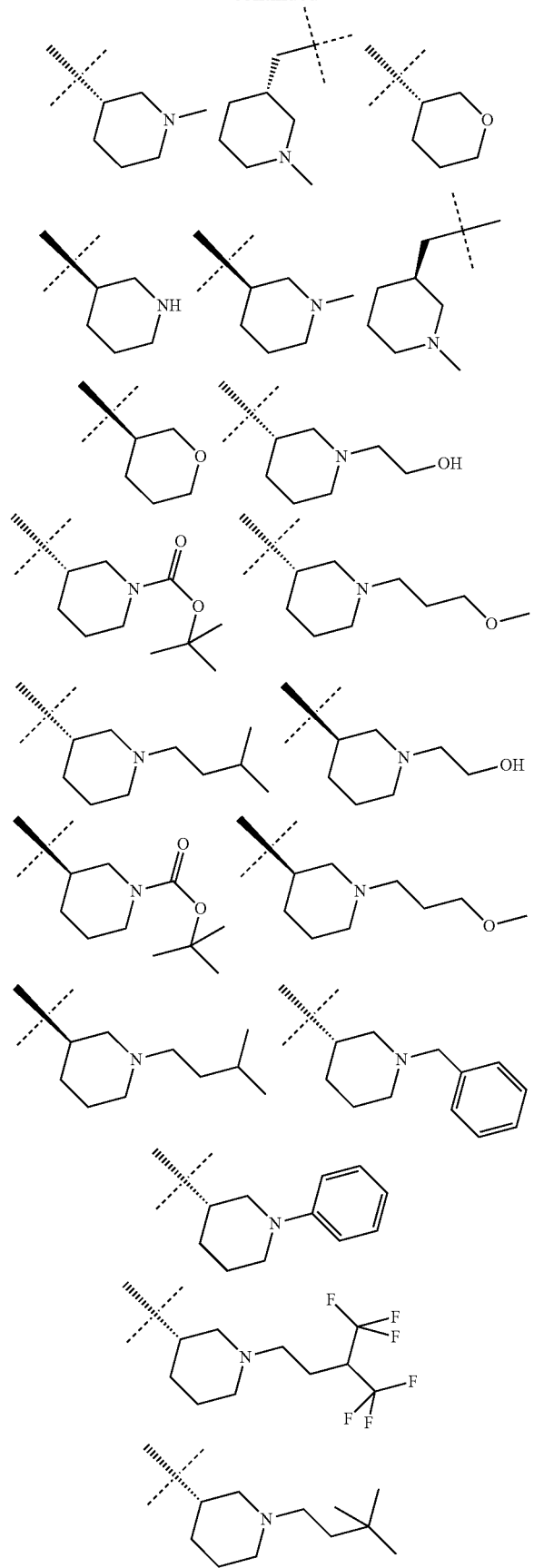
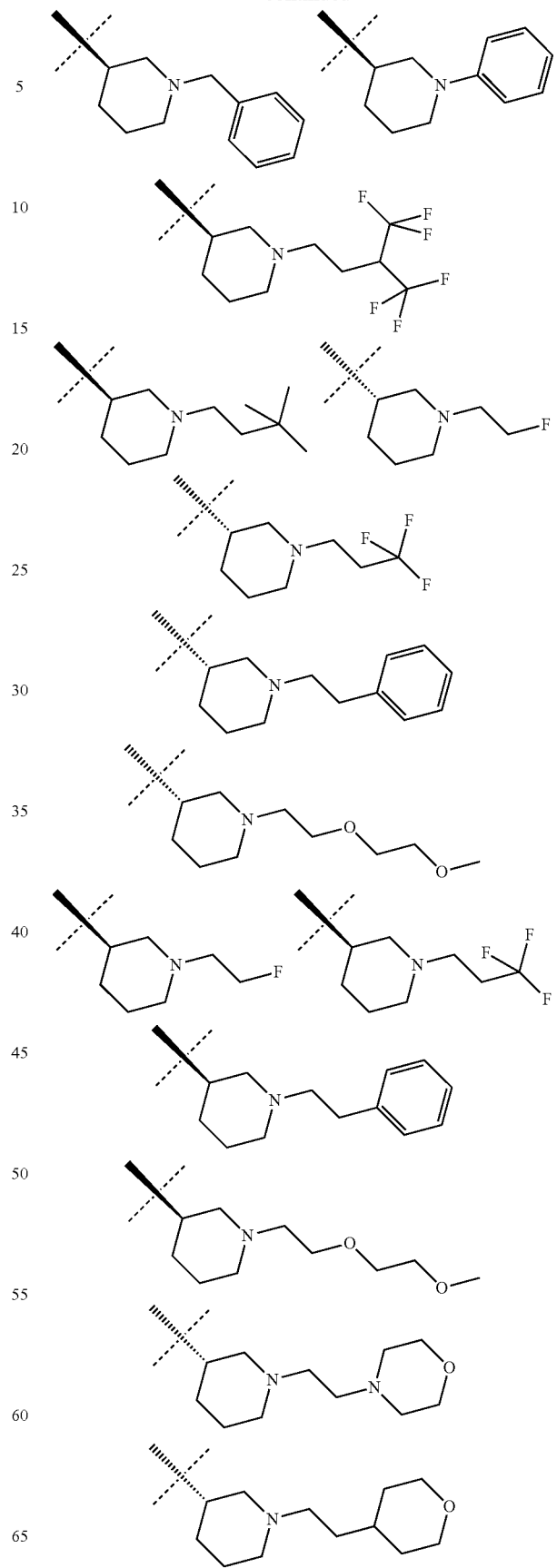

1043
-continued
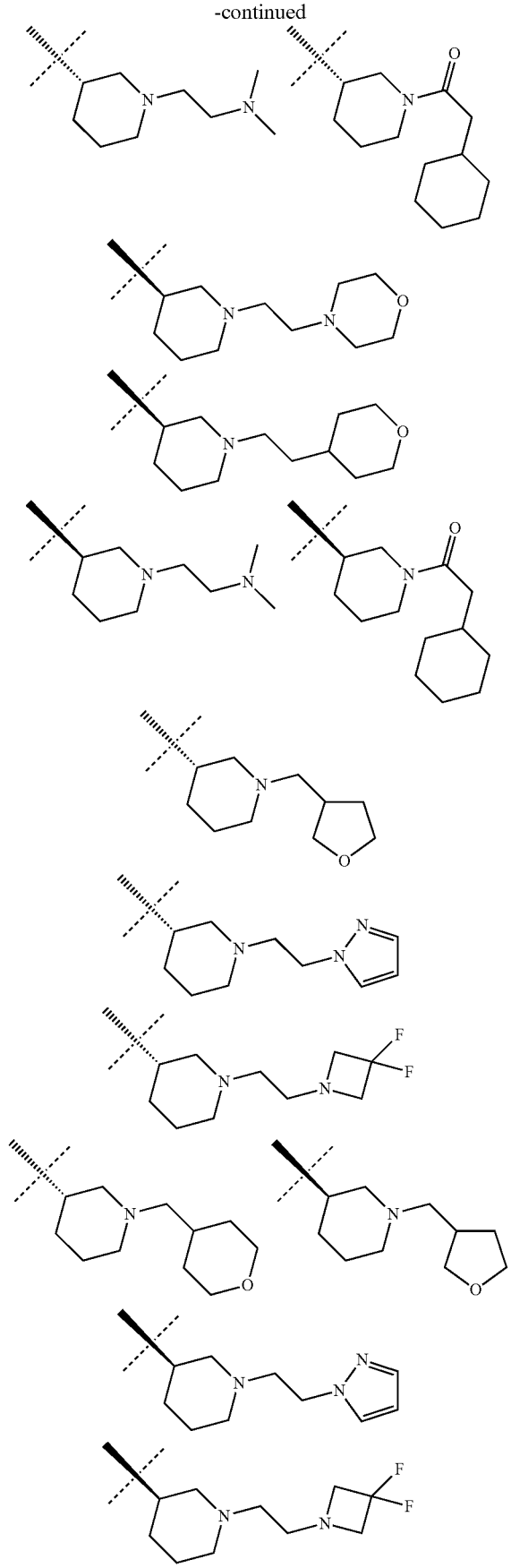
1044
-continued
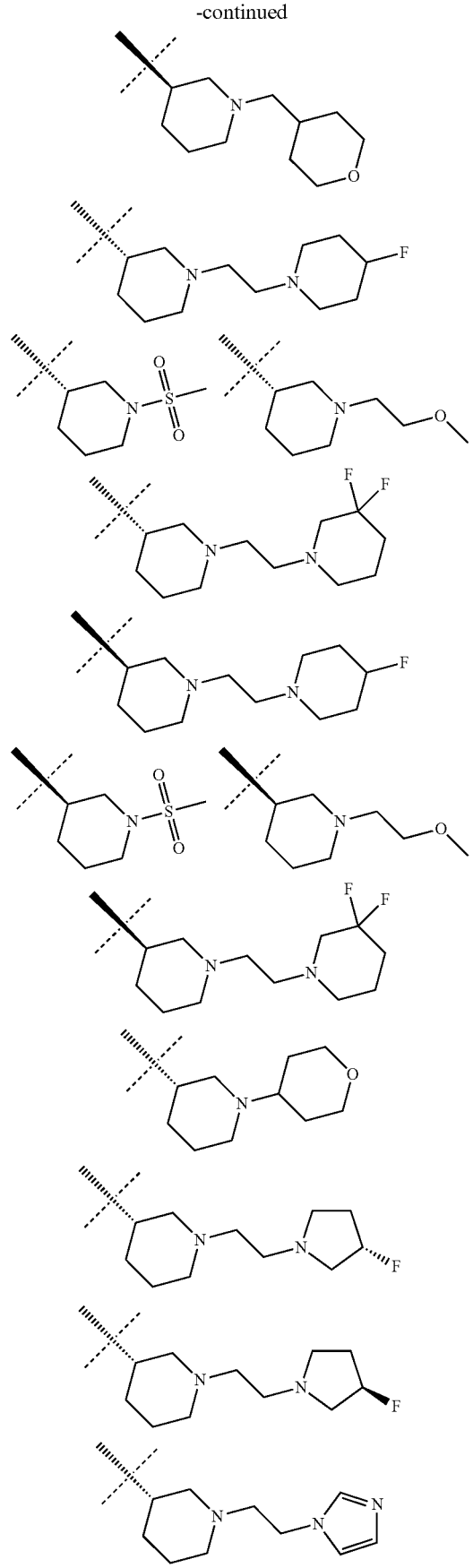

1045
-continued
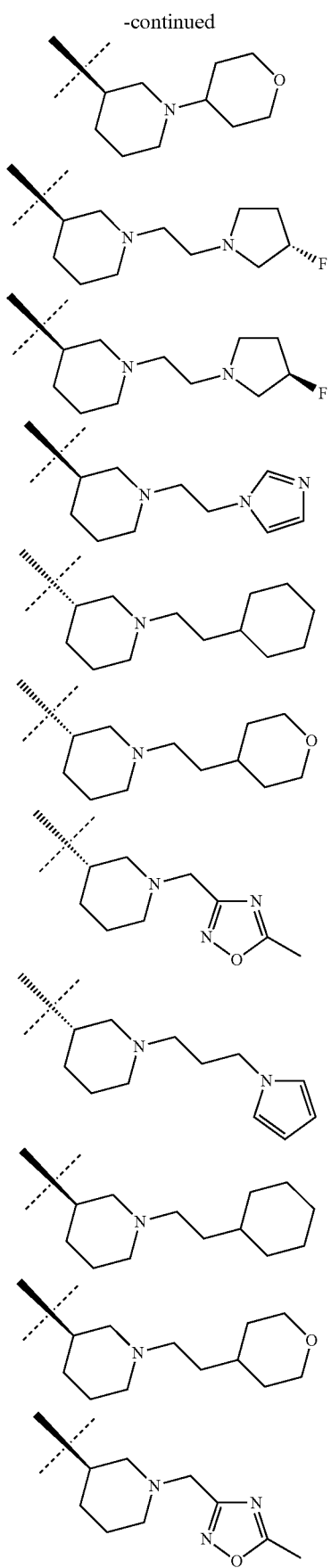
1046
-continued
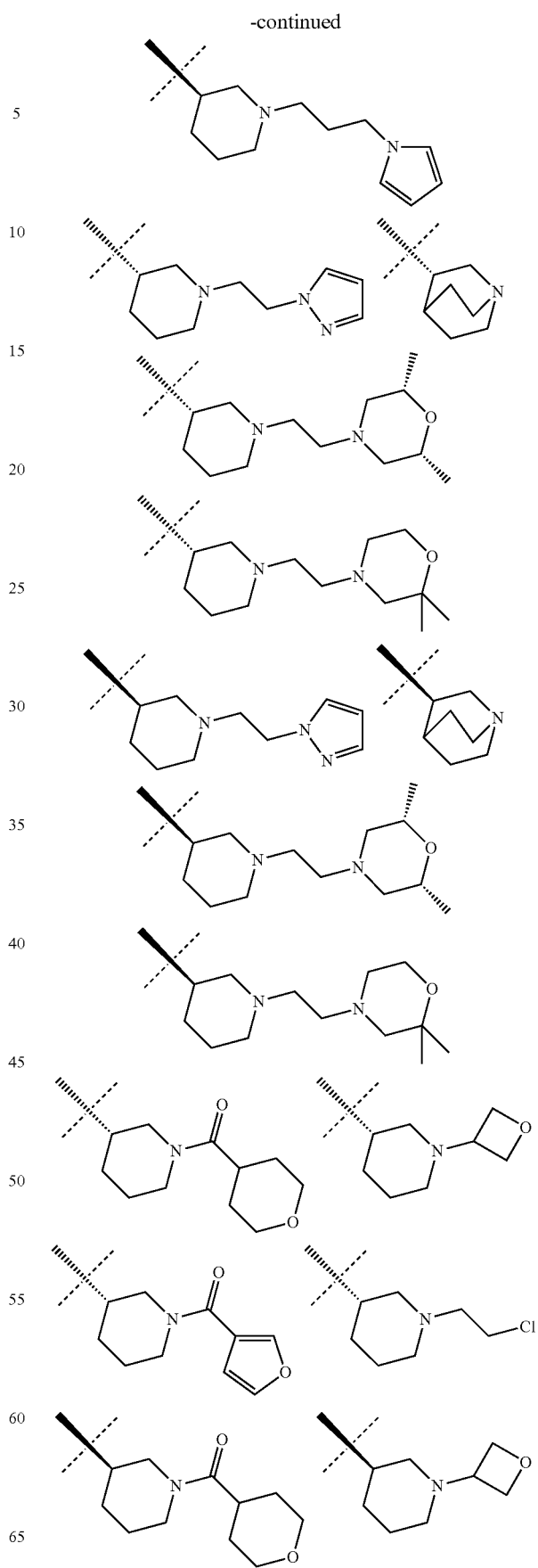

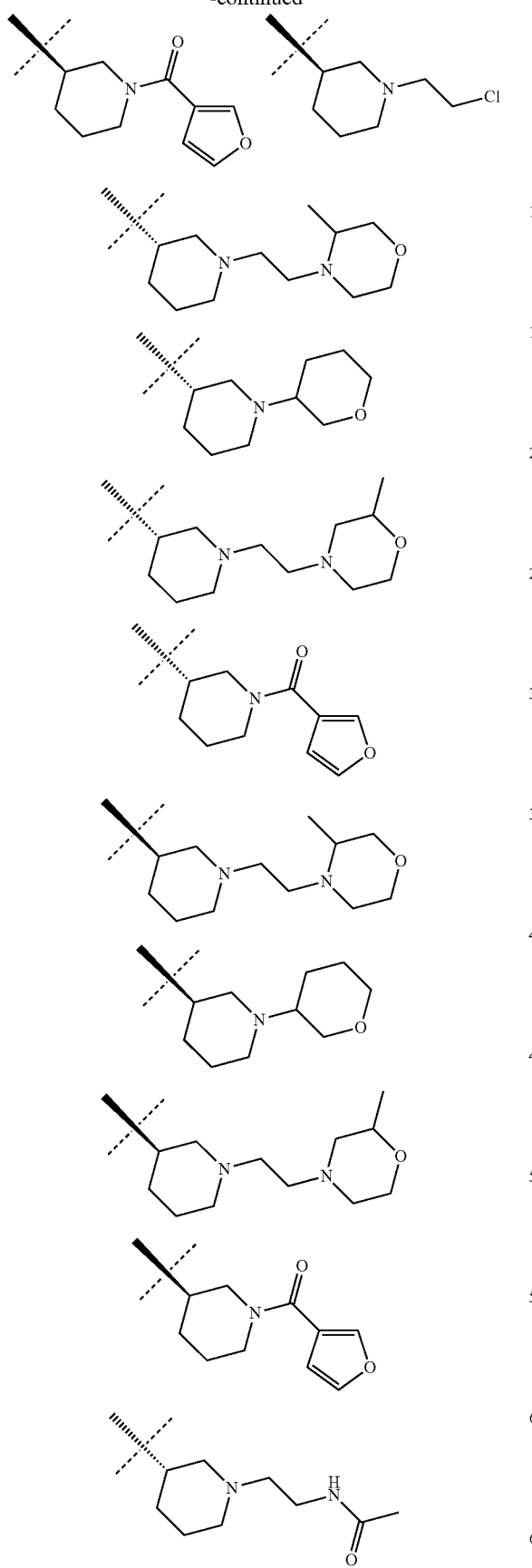
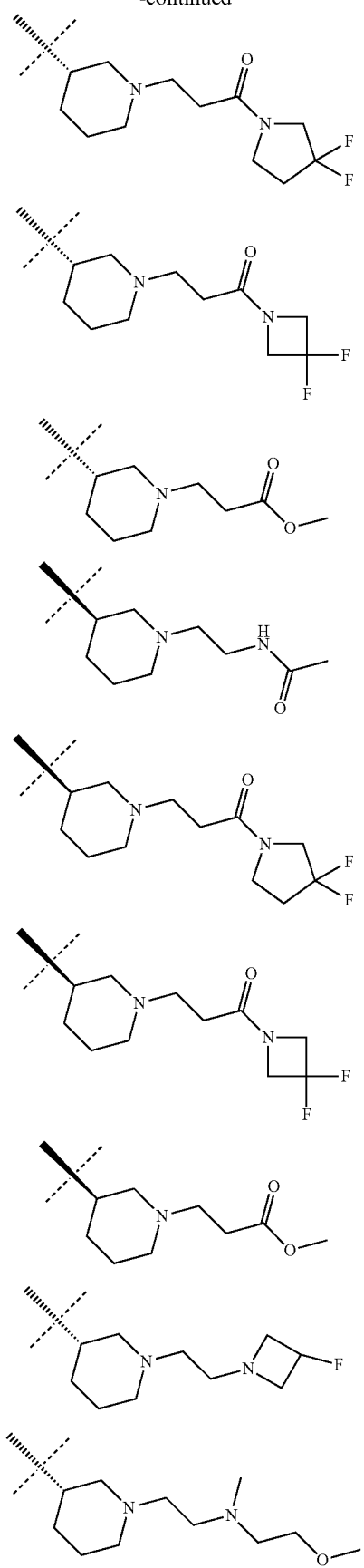

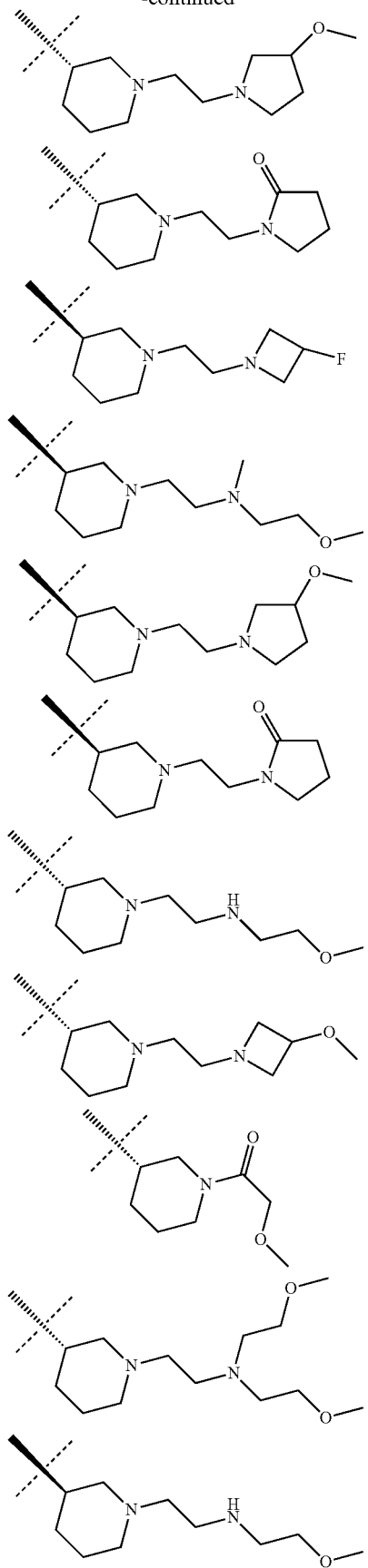
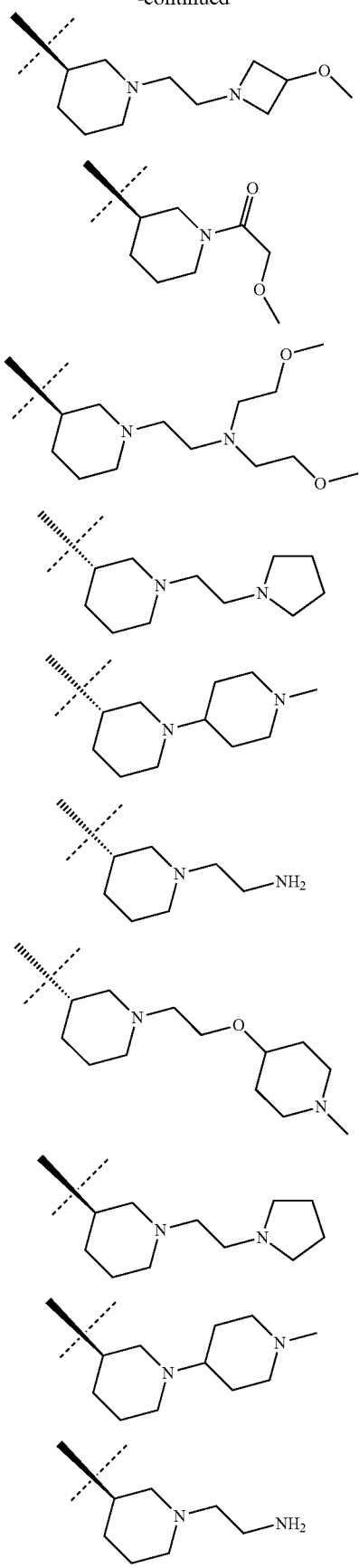

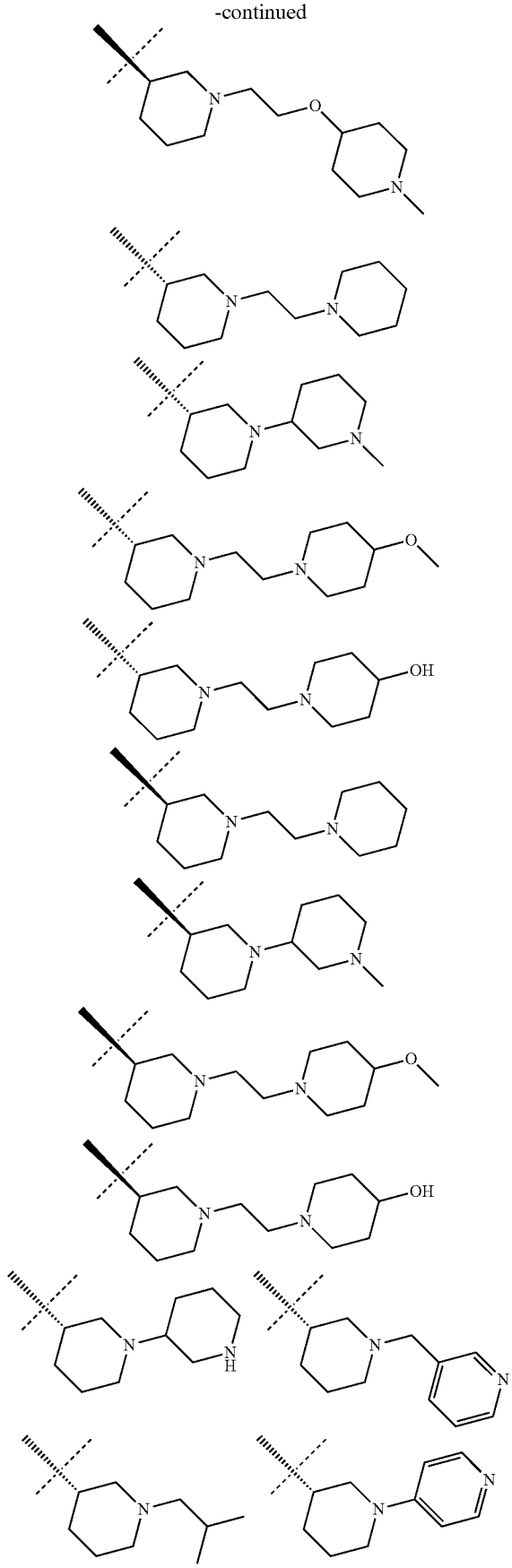
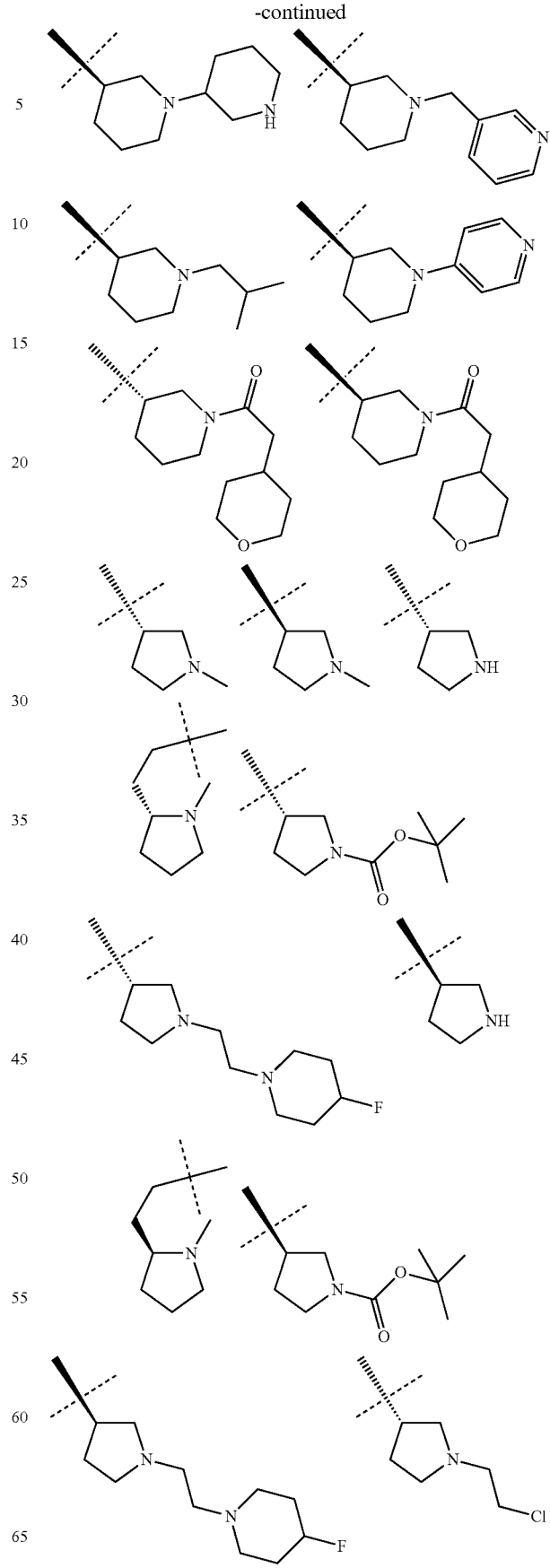

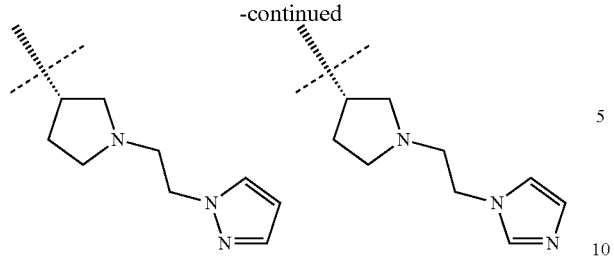
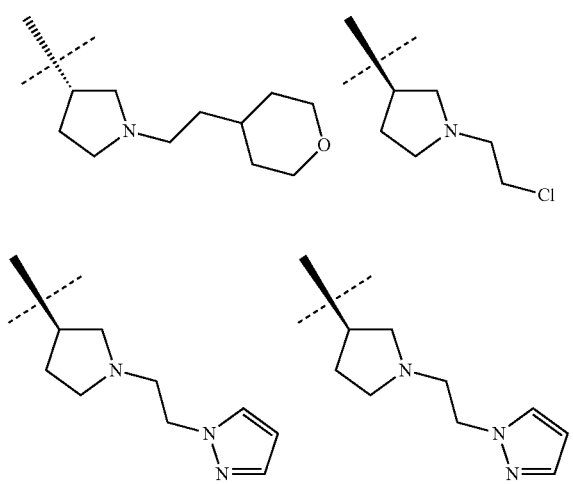
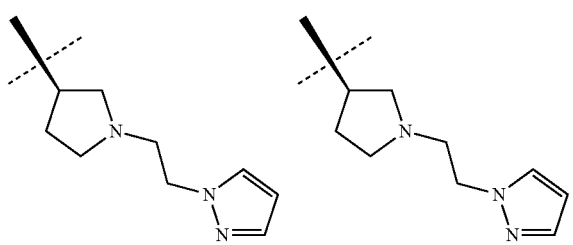
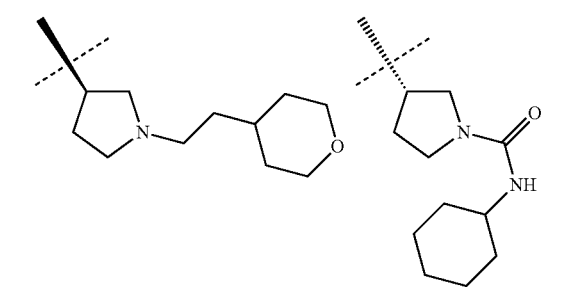
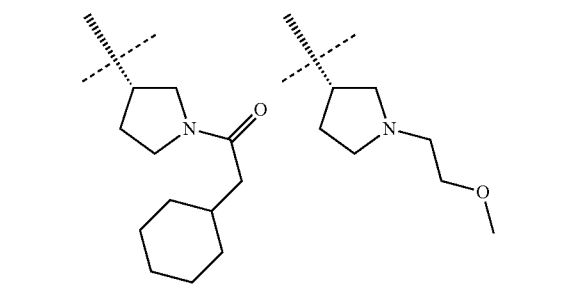
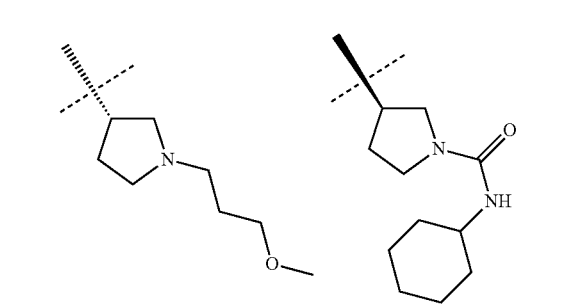
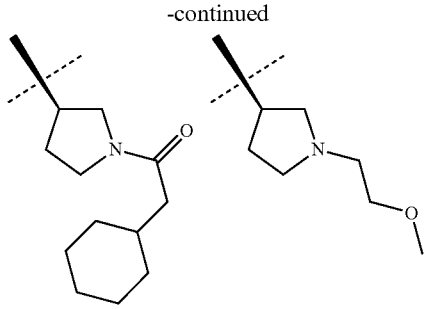
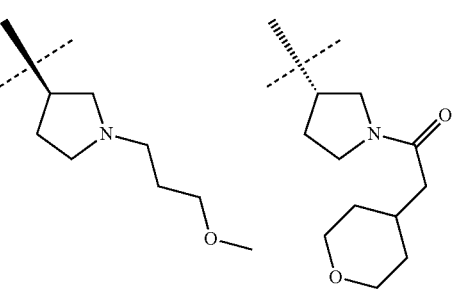
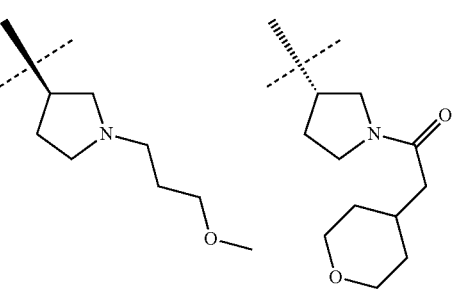
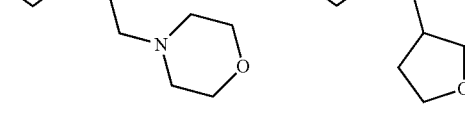
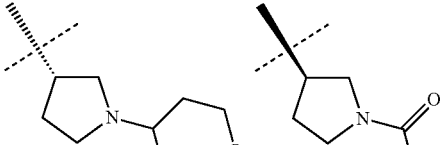
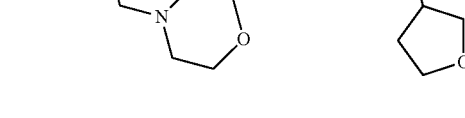
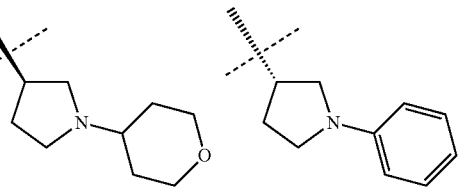

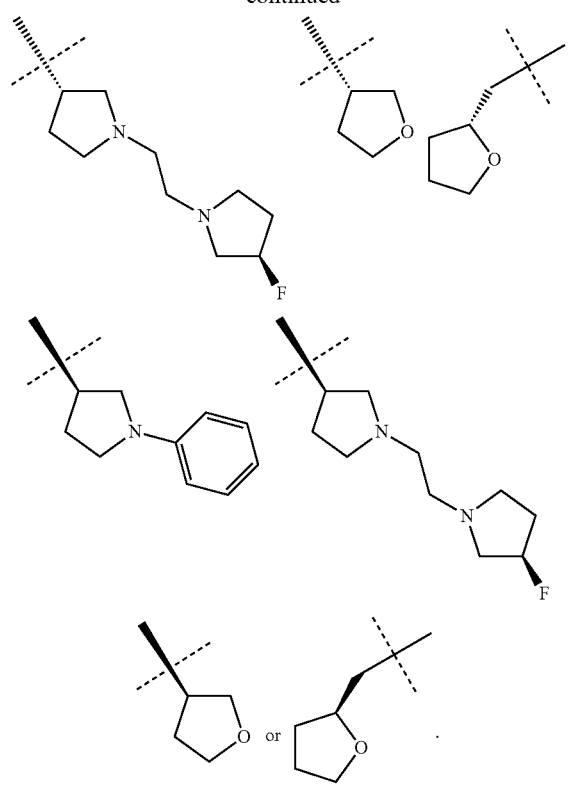
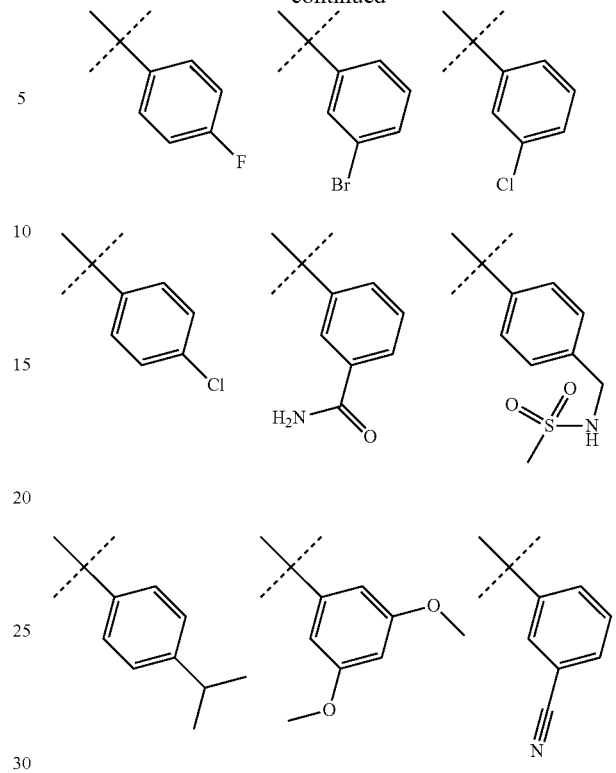
4. The compound of Formula (I*) according to claim 2, wherein $R^2$ is selected from H, a branched or linear $C_1$-$C_6$-alkyl or one of the following groups:
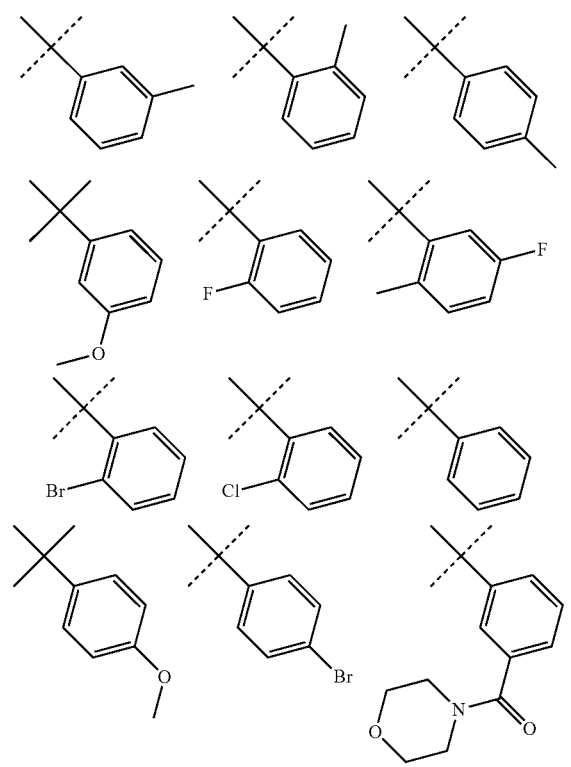
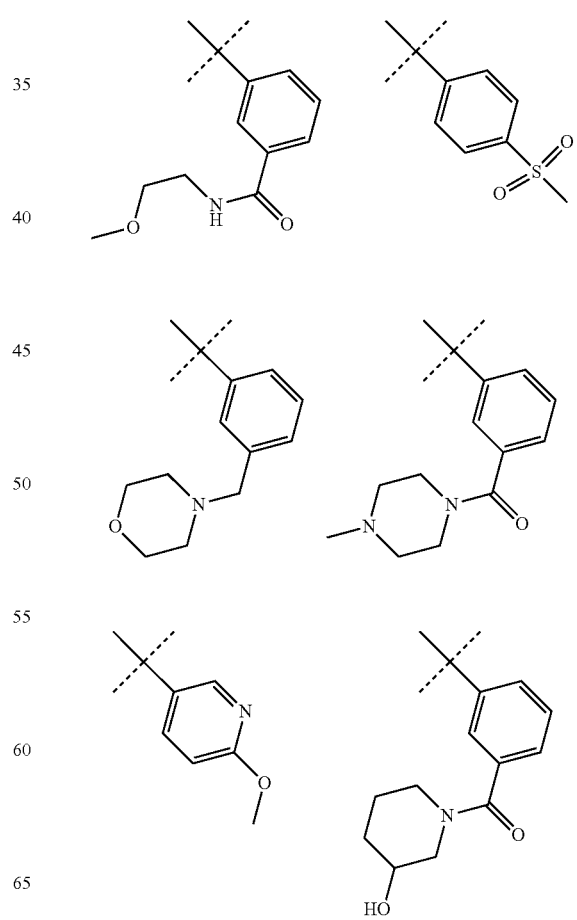

1057
-continued
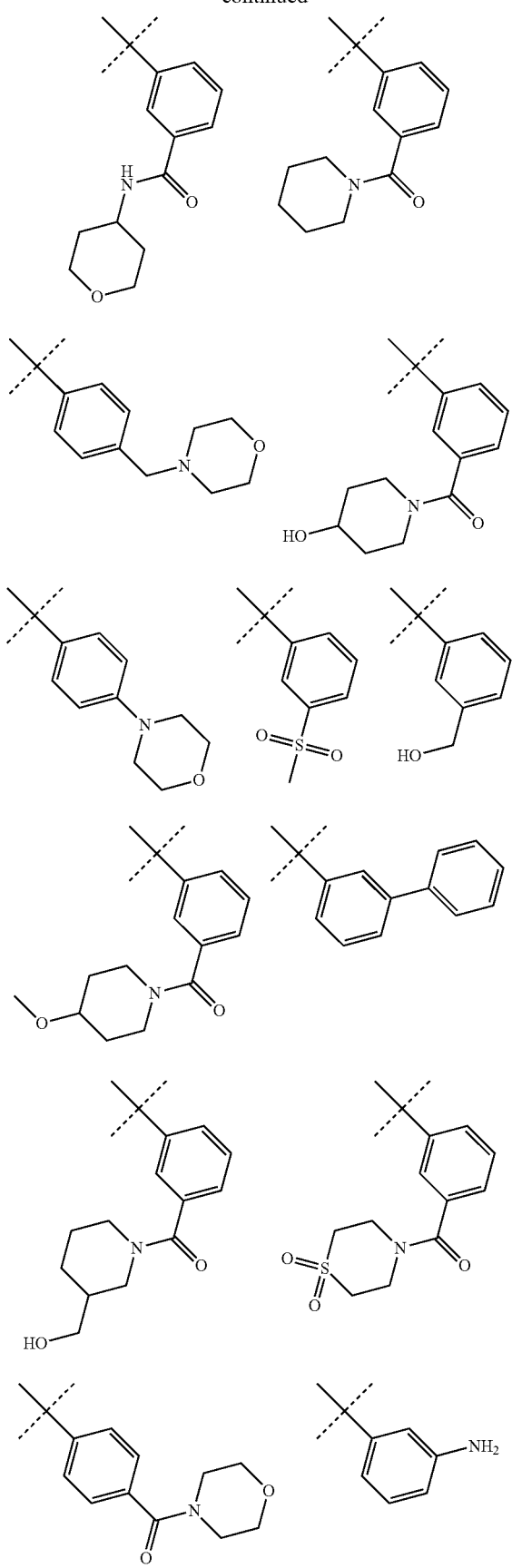
1058
-continued
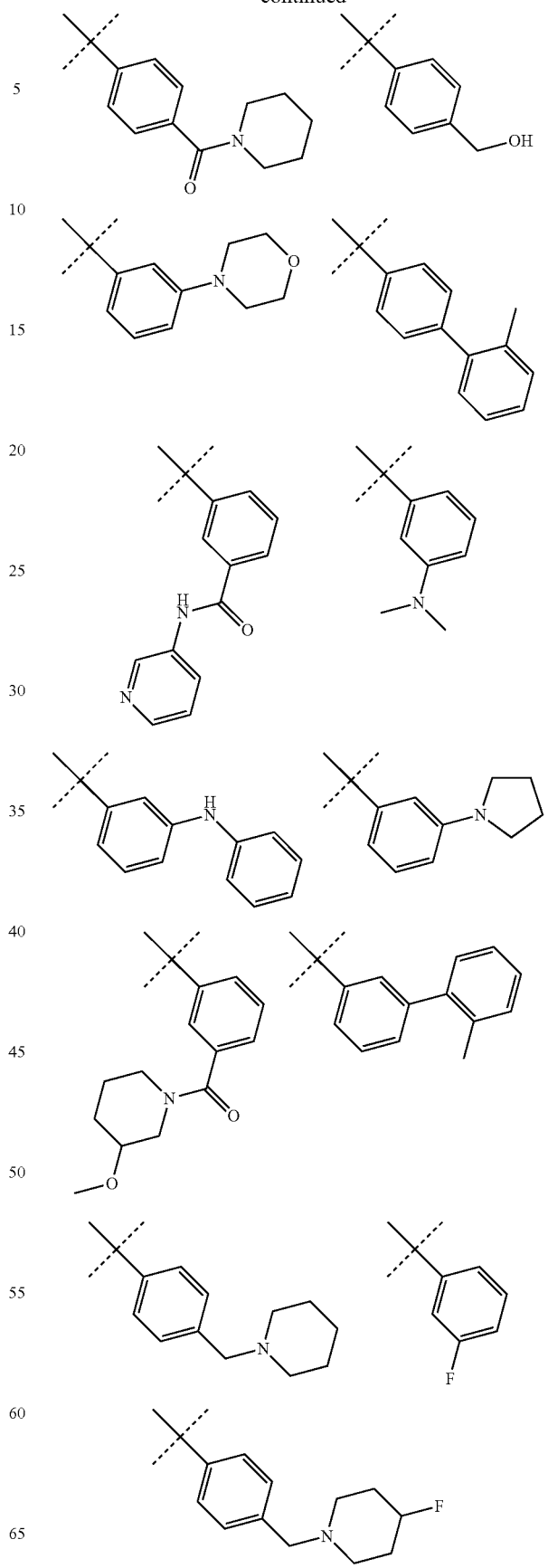

1059
-continued
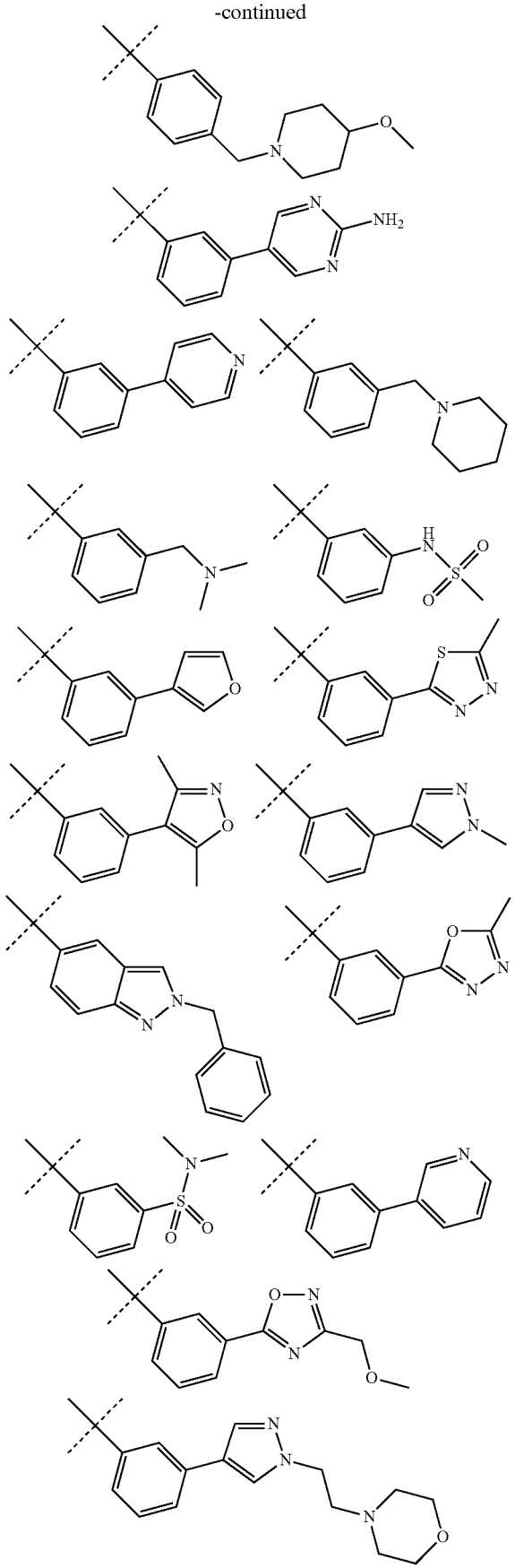
1060
-continued
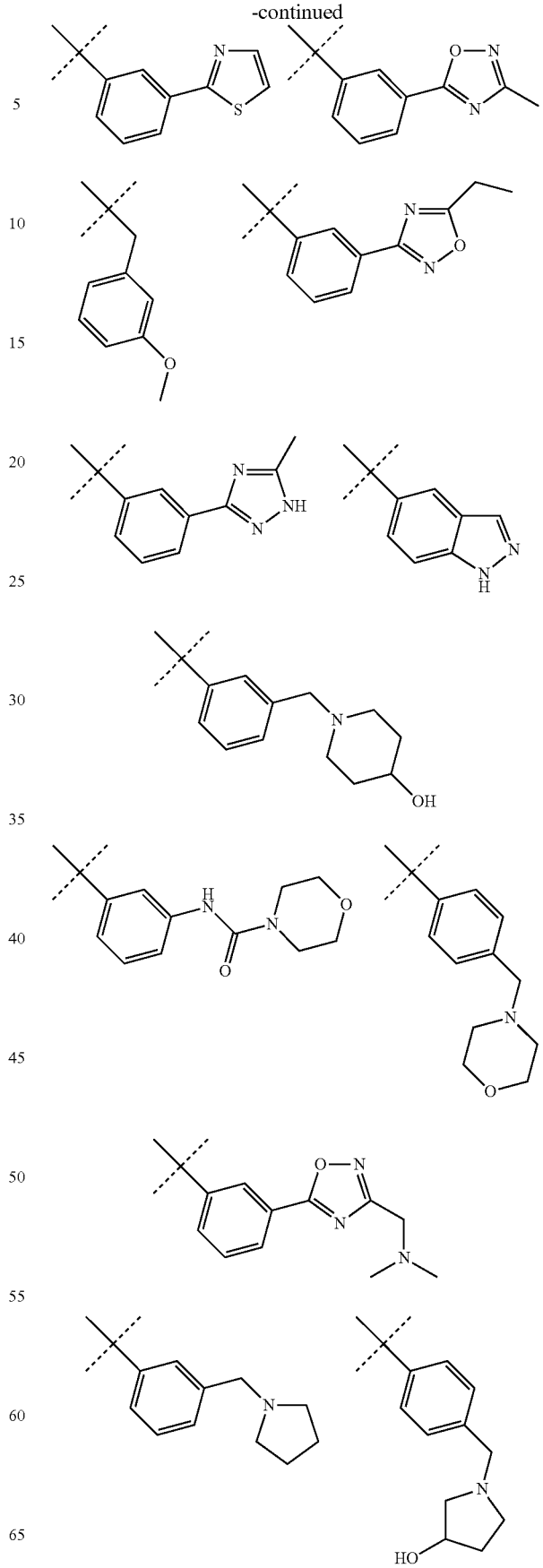

1061
-continued
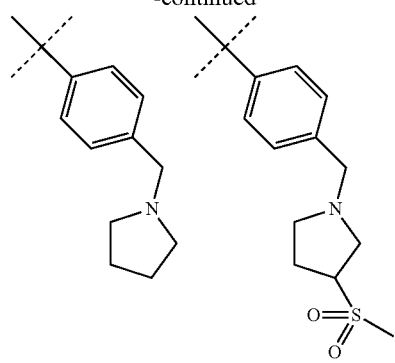
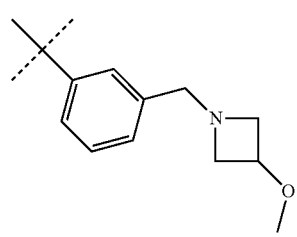
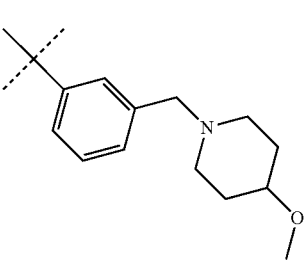
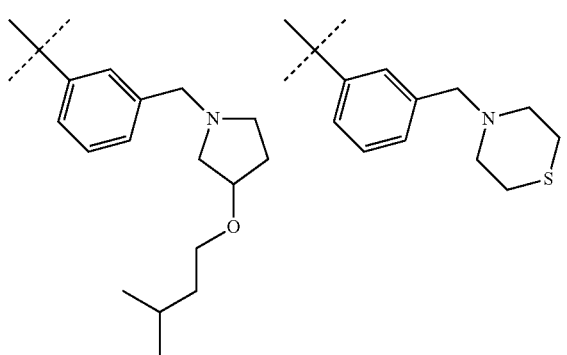
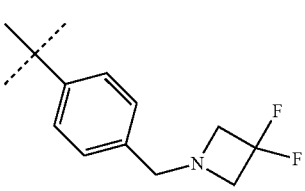
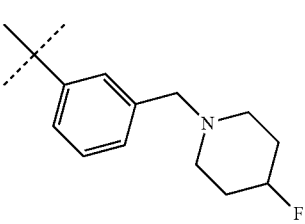
1062
-continued
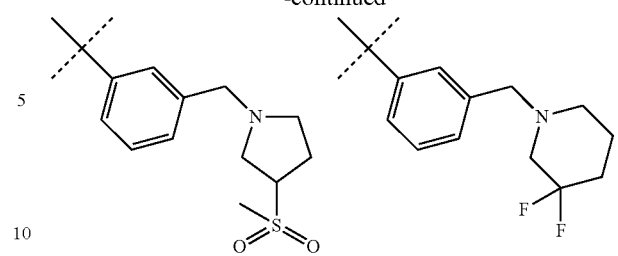
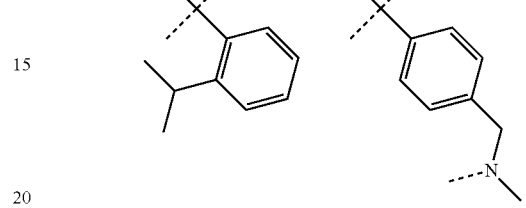
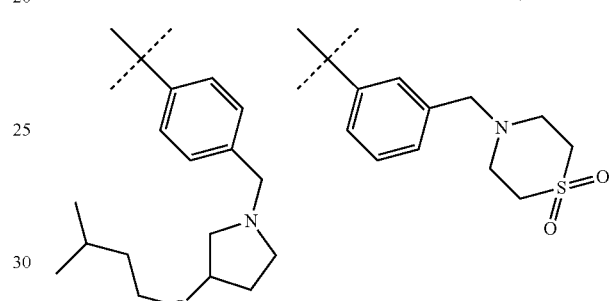
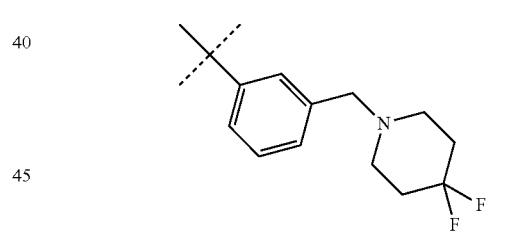
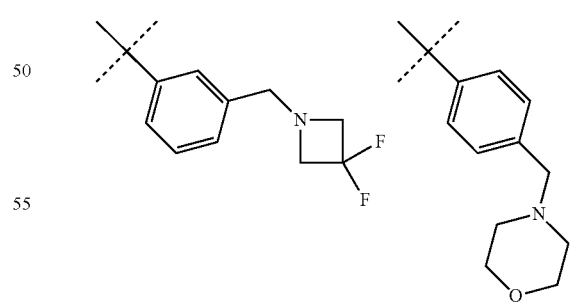
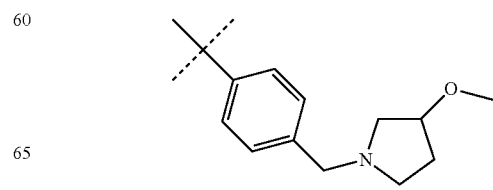

1063
-continued
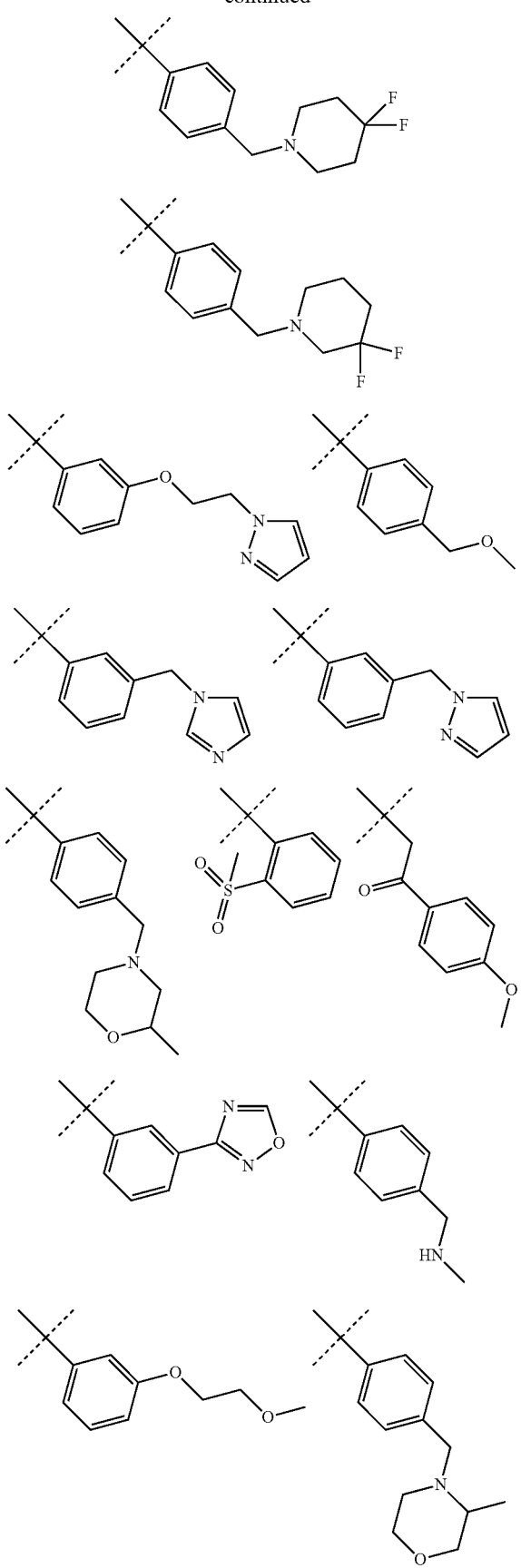
1064
-continued
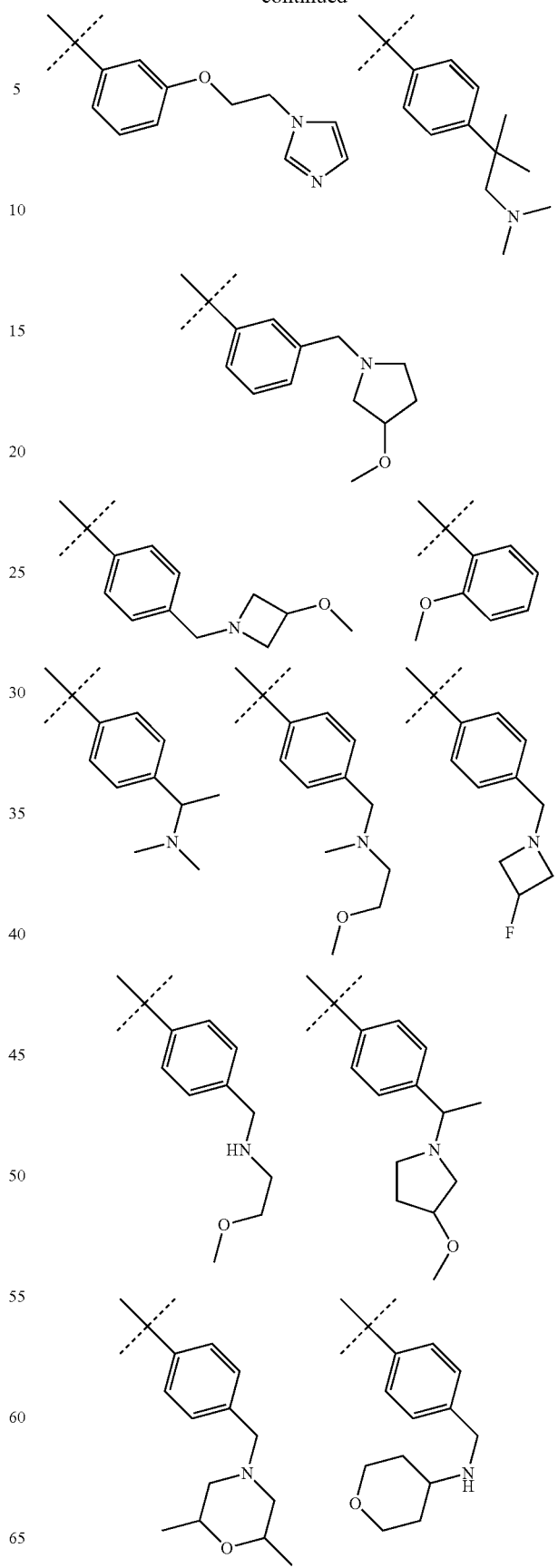

1065
-continued
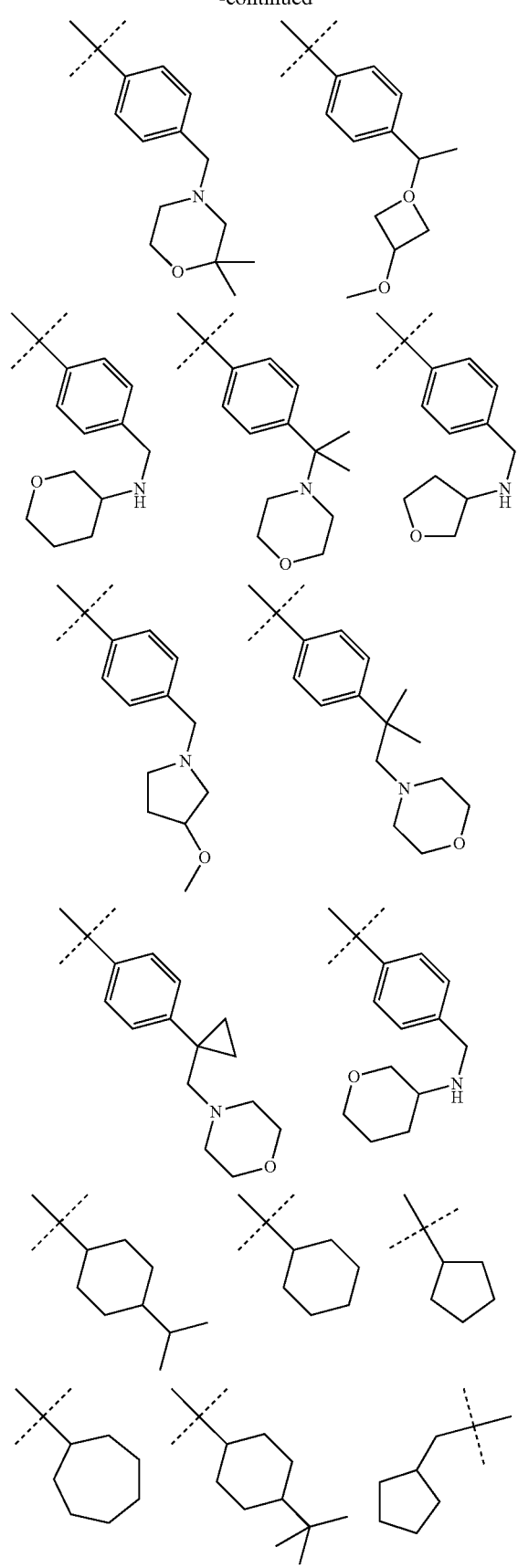
1066
-continued
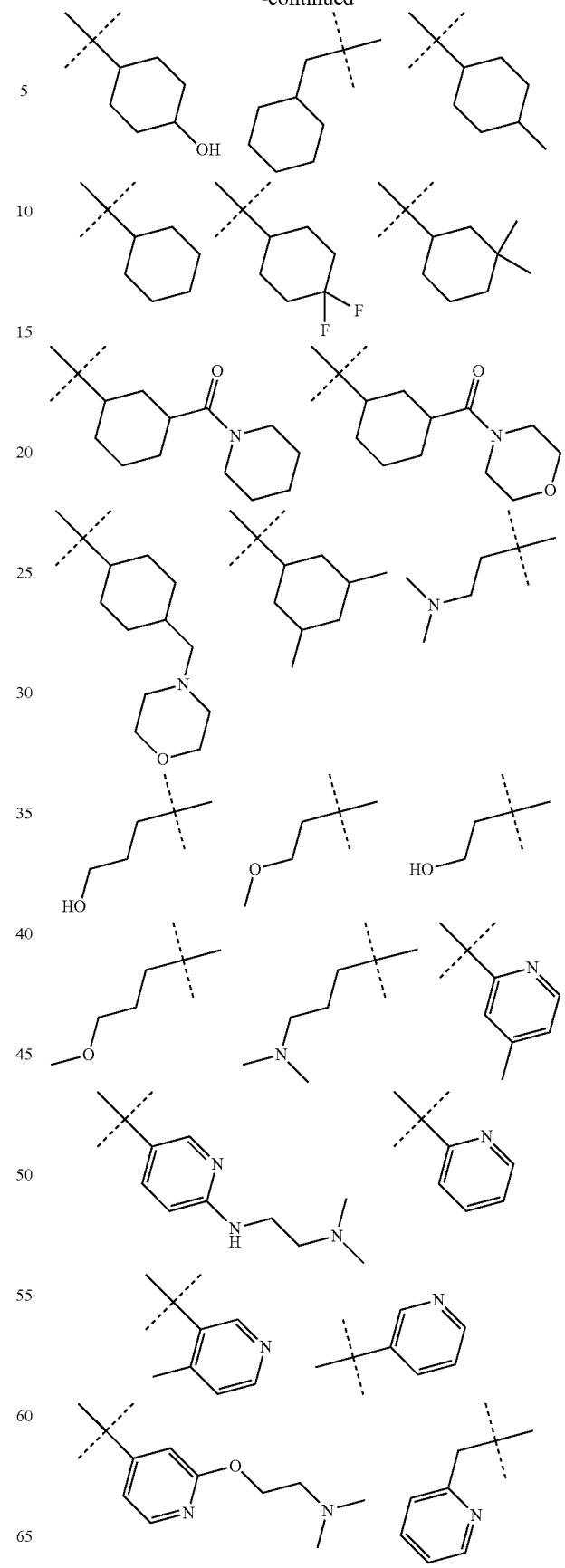

1067
-continued
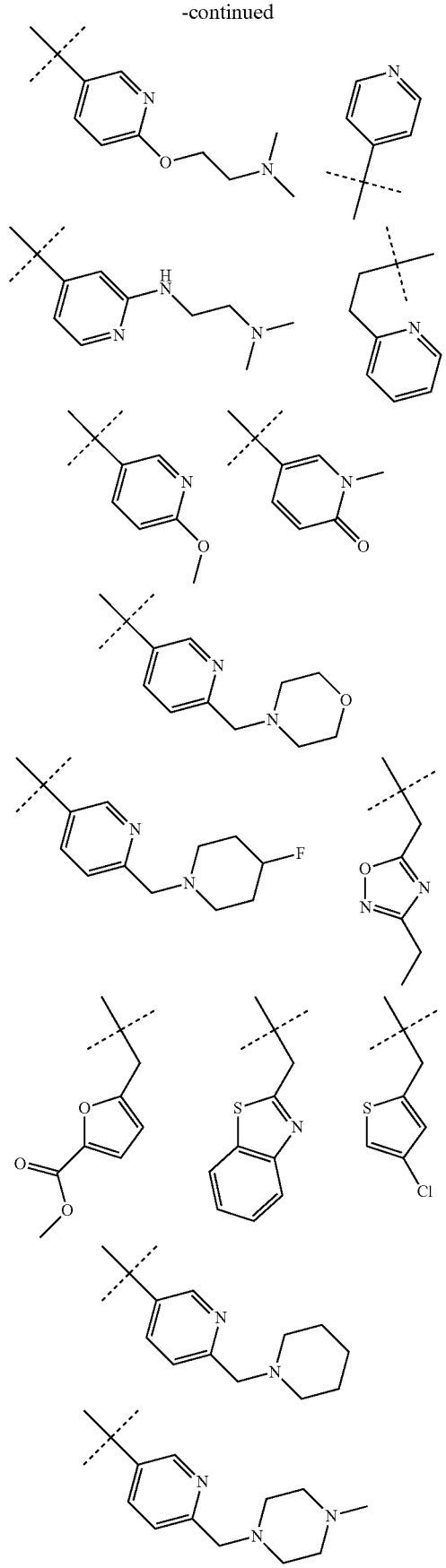
1068
-continued
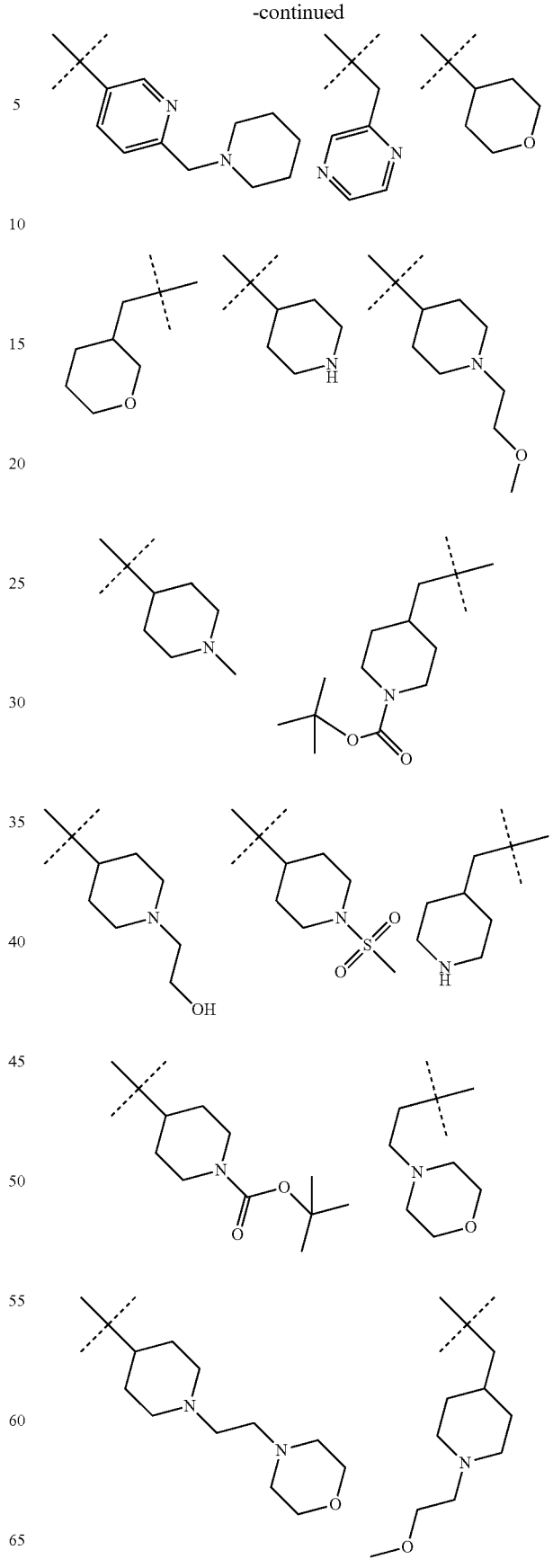

1069
-continued
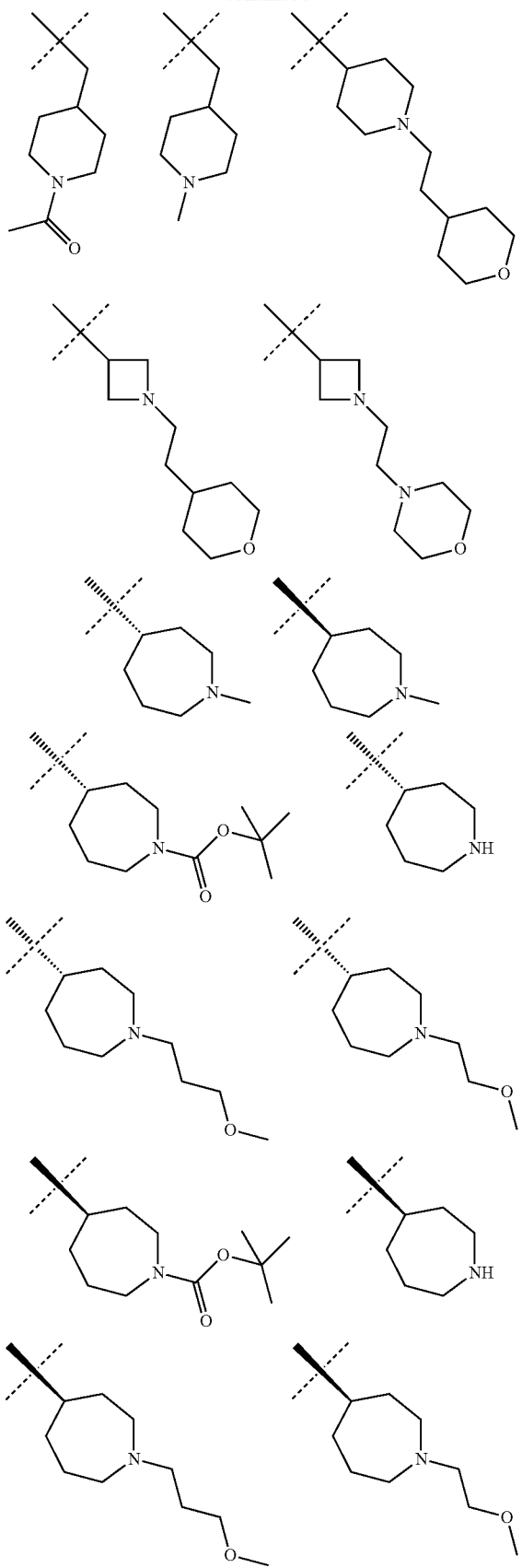
1070
-continued
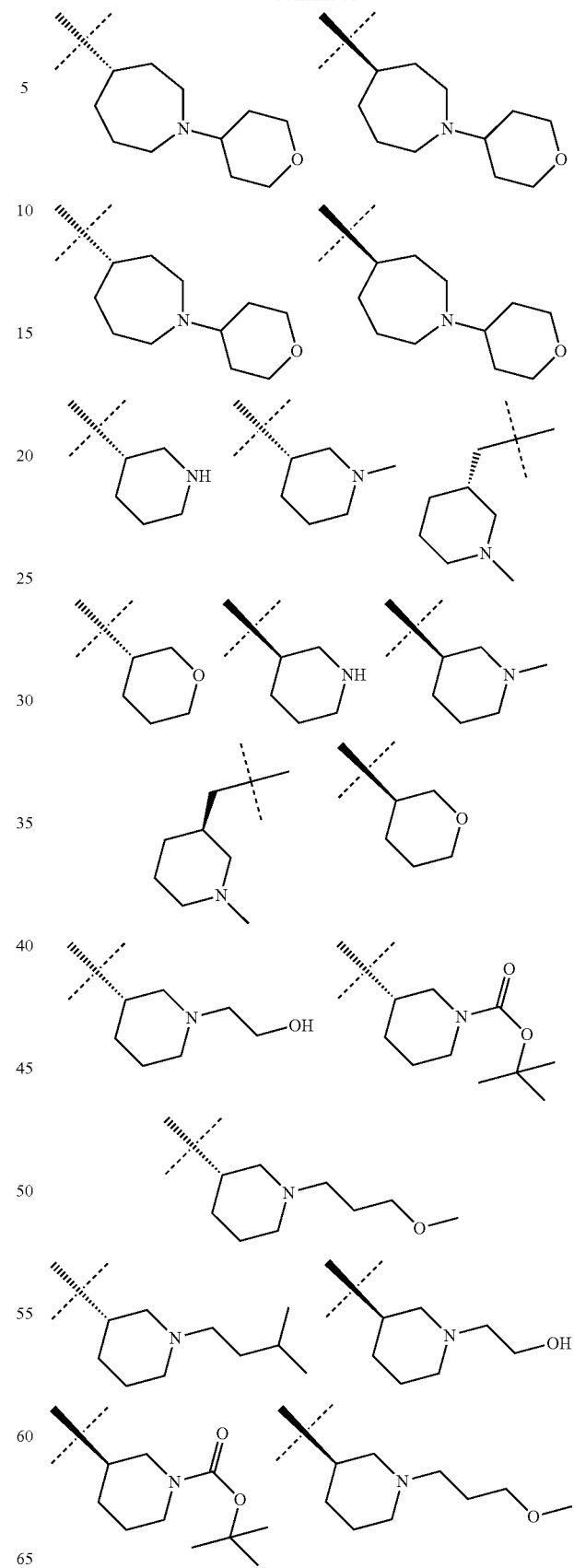

1071
-continued
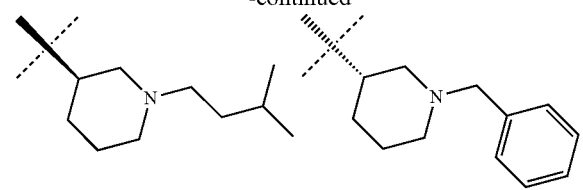
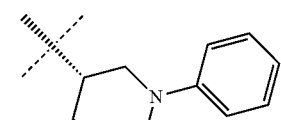
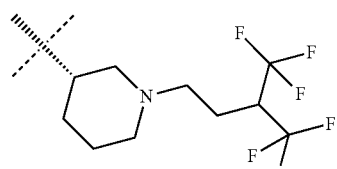
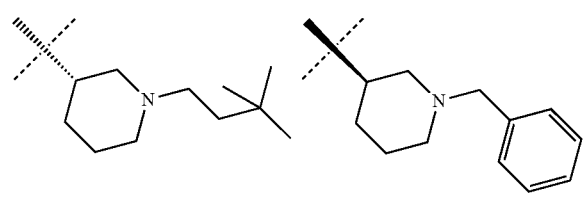
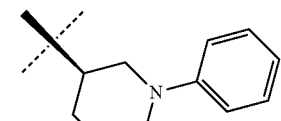
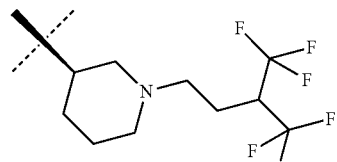
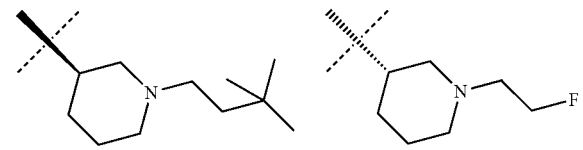
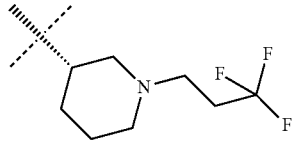
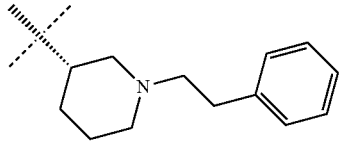
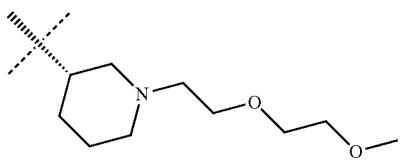
1072
-continued
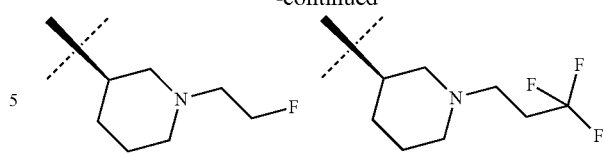
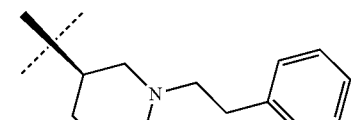
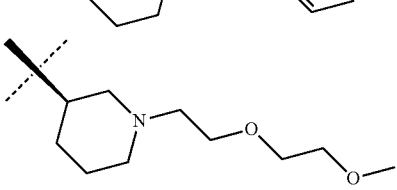
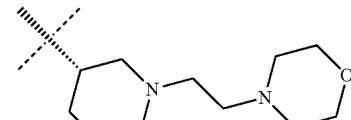
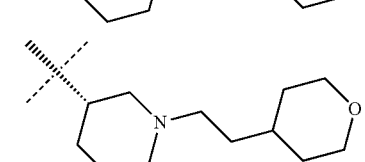
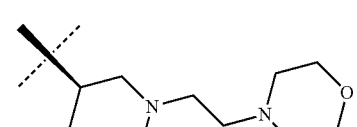
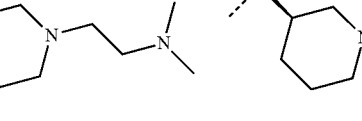
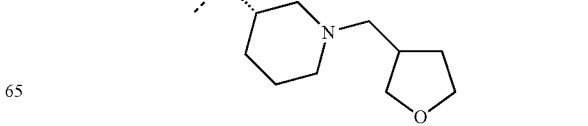

1073
-continued
1074
-continued
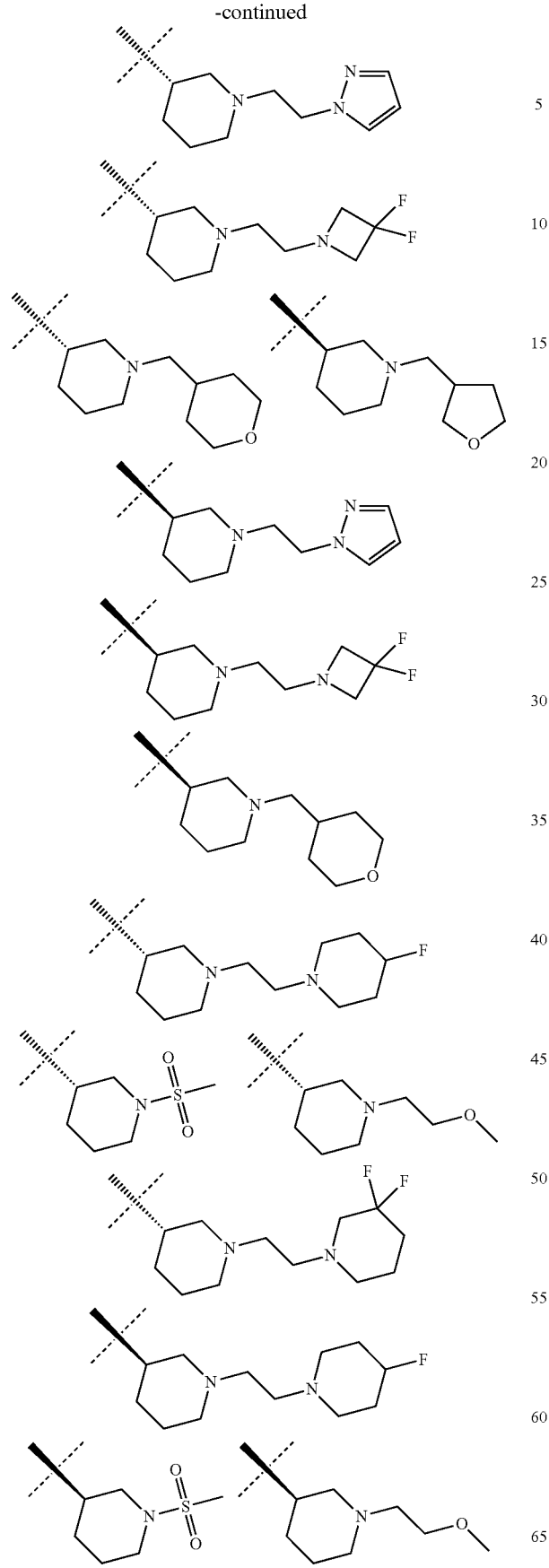
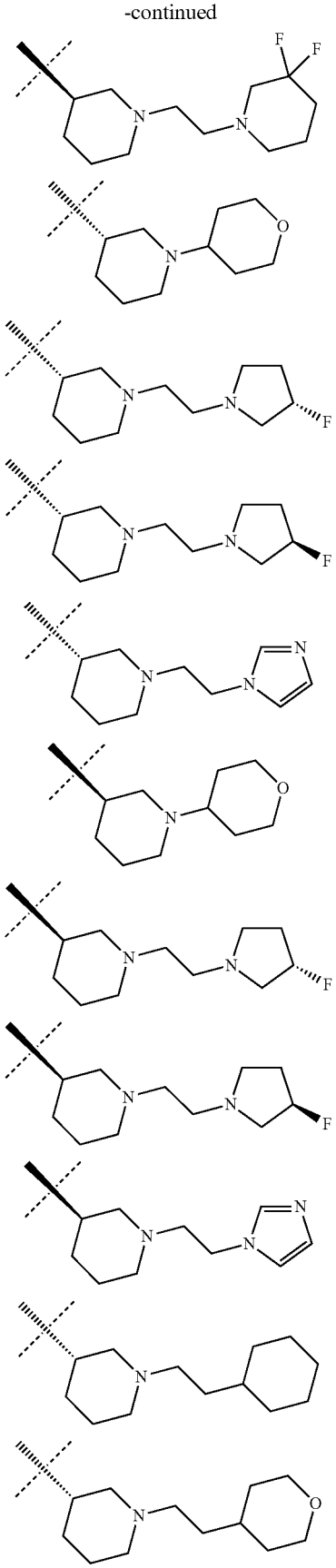

1075
-continued
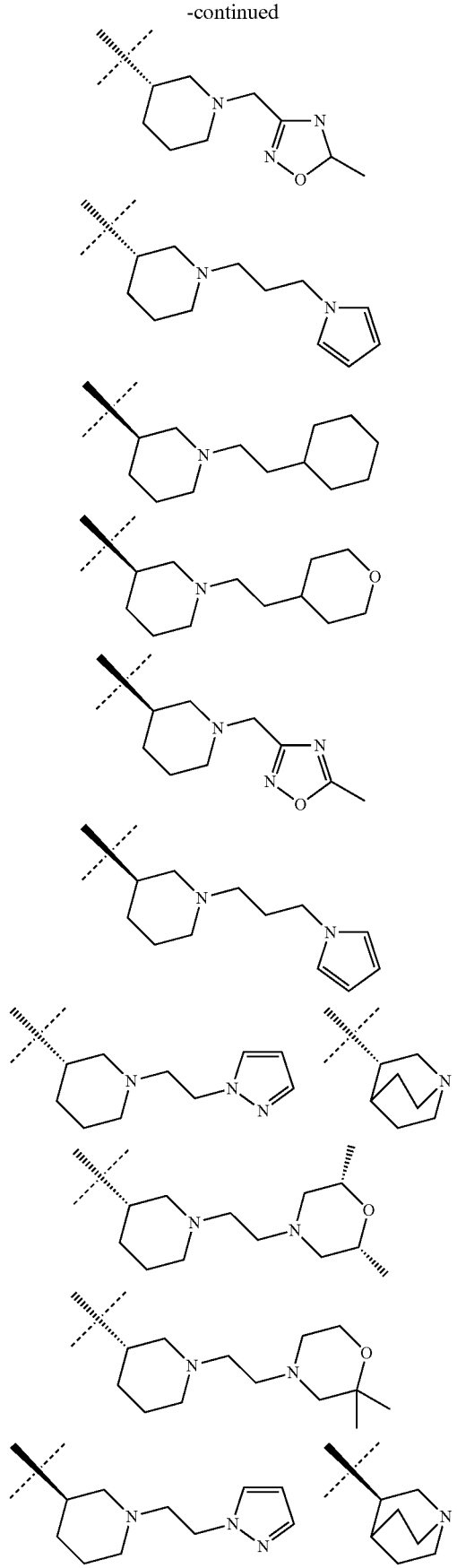
1076
-continued
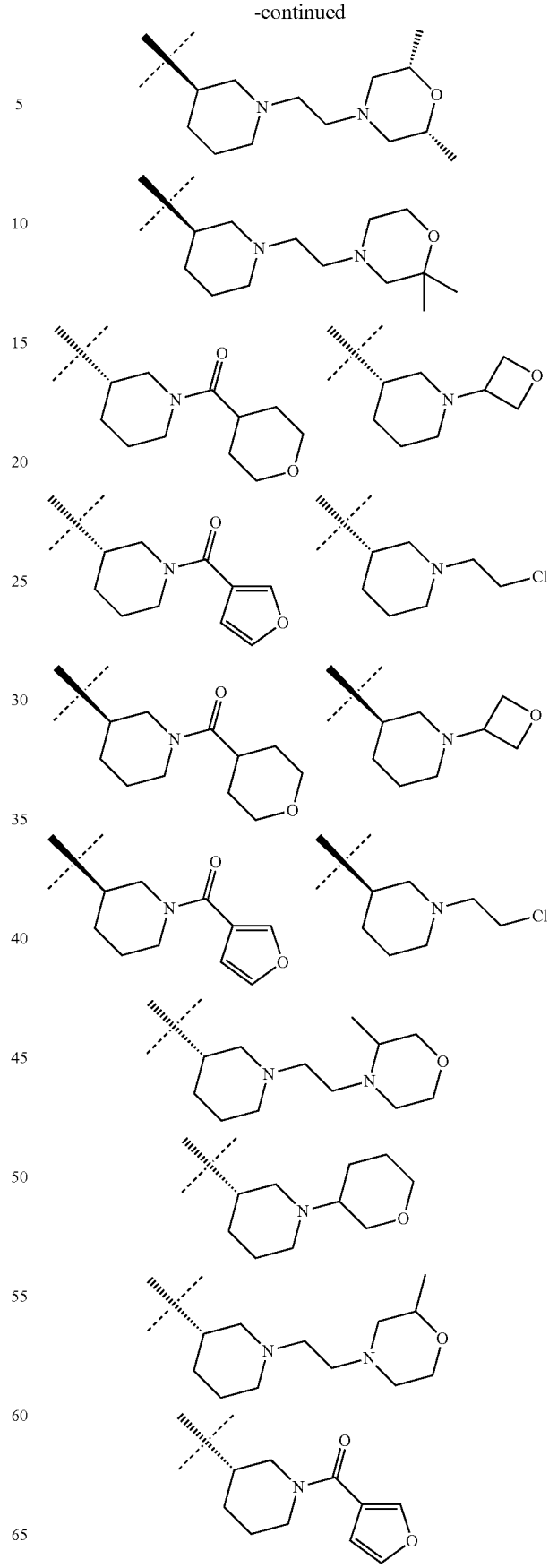

1077
-continued
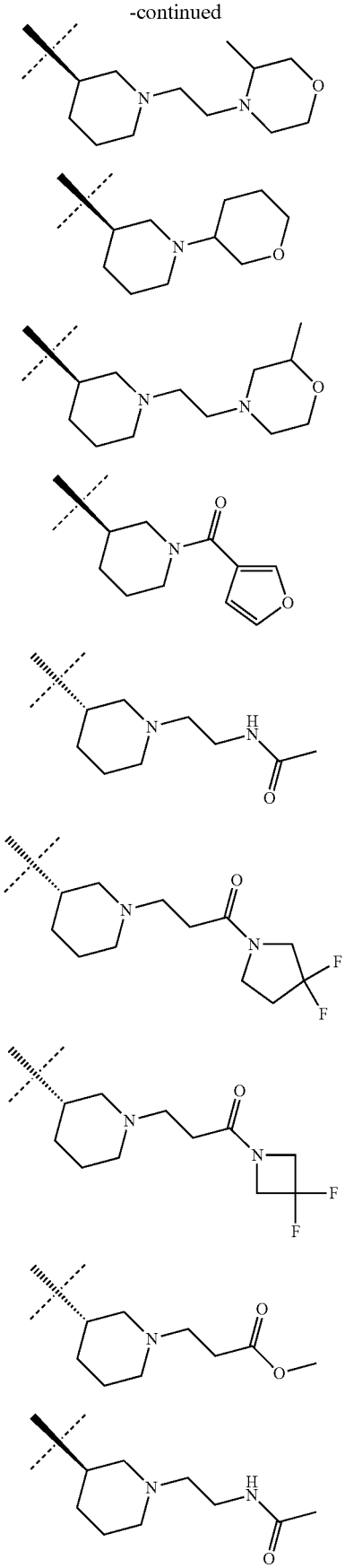
1078
-continued
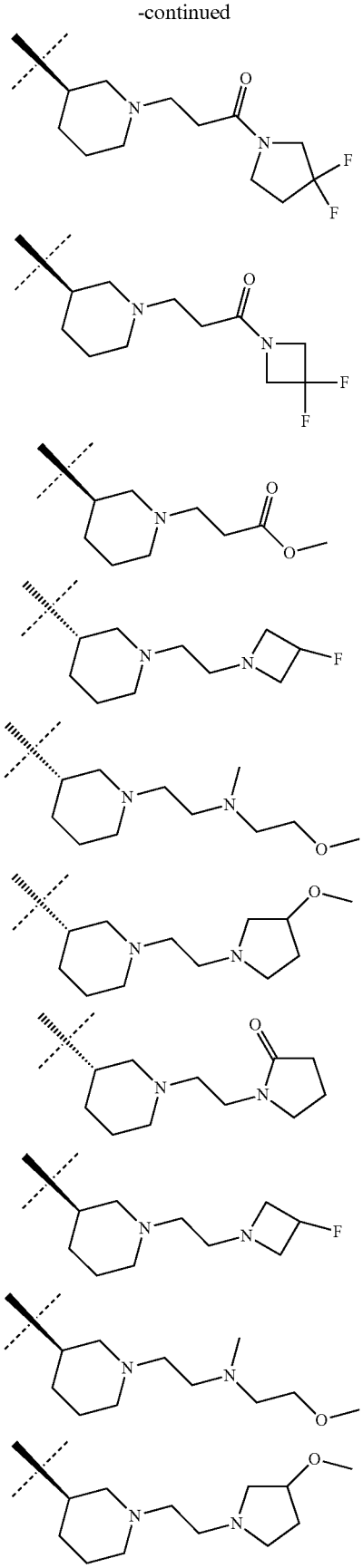

1079
-continued
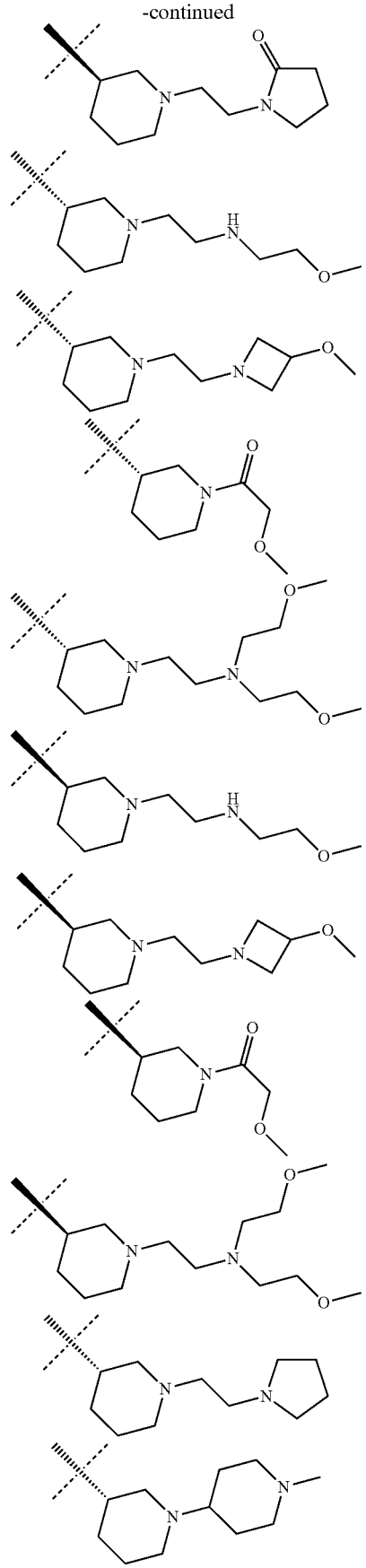
1080
-continued
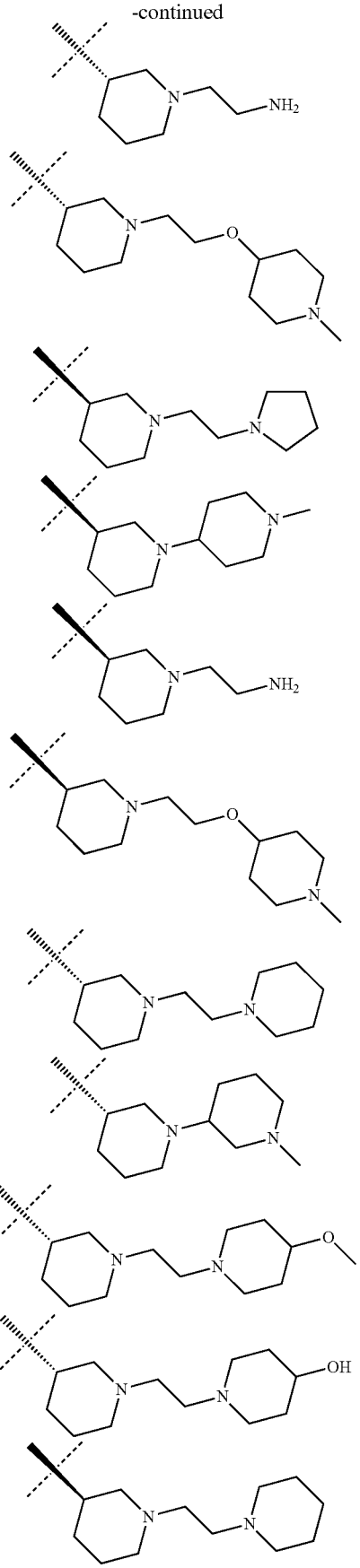

1081
-continued
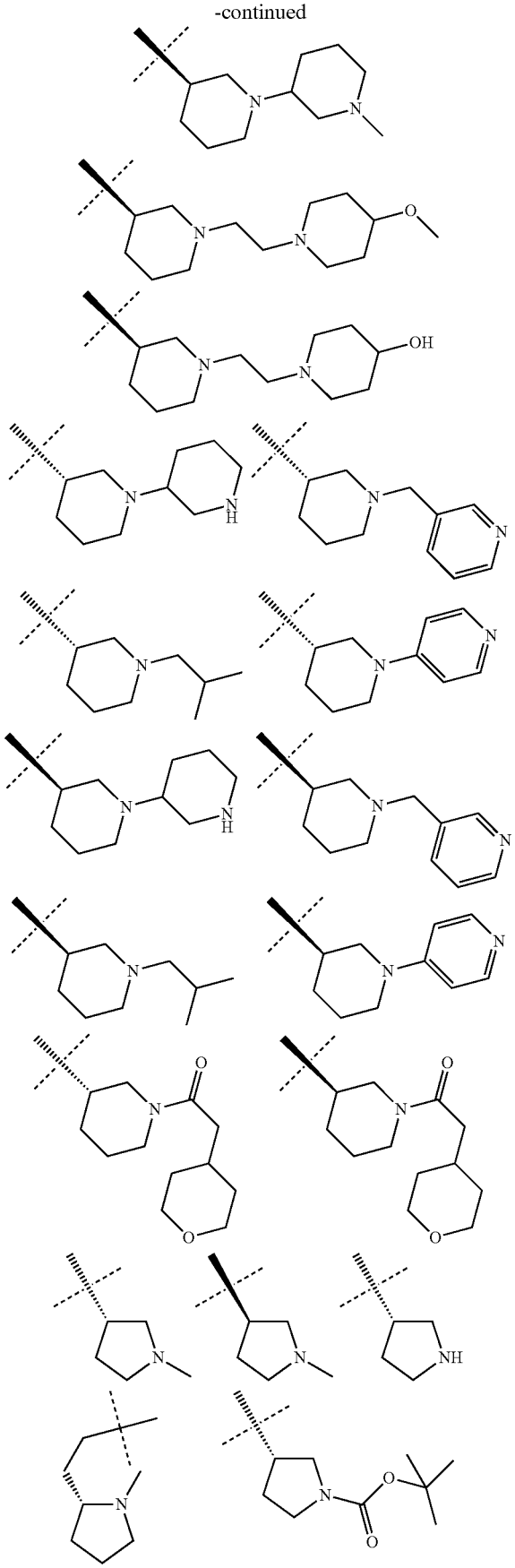
1082
-continued
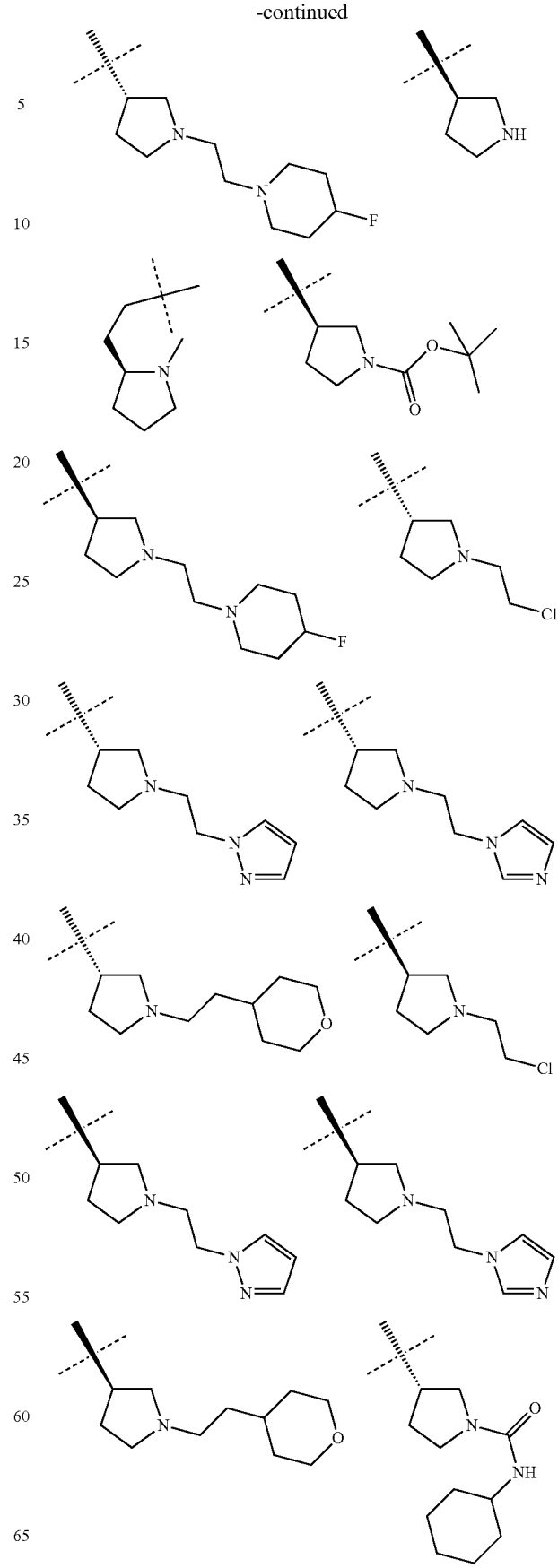

-continued
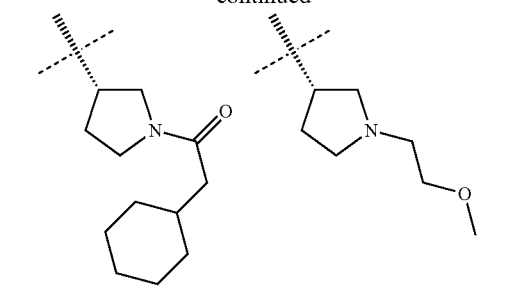
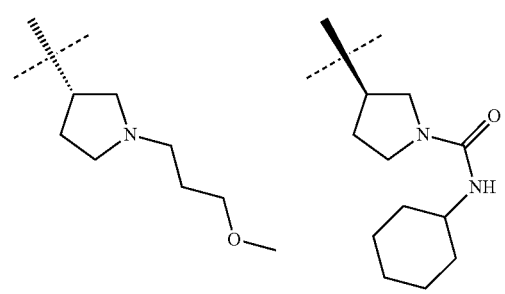
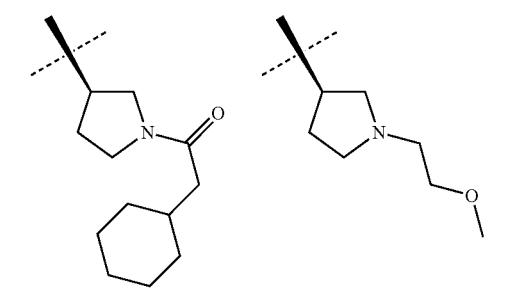
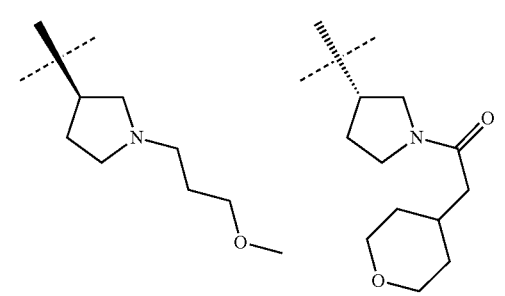
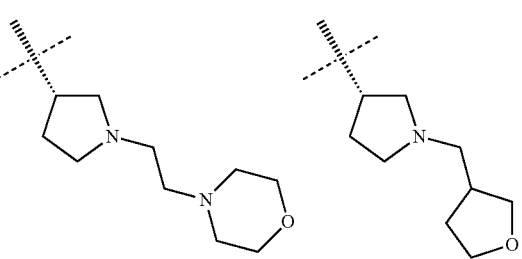
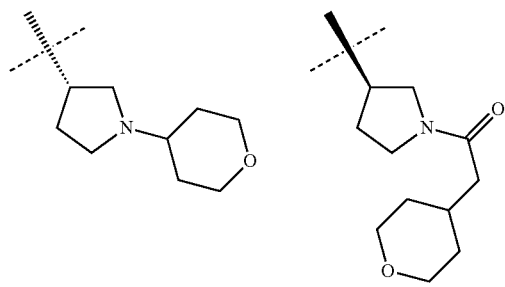
-continued
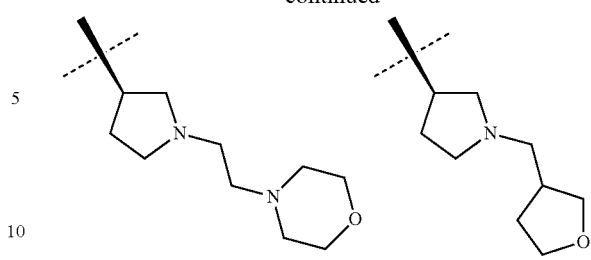
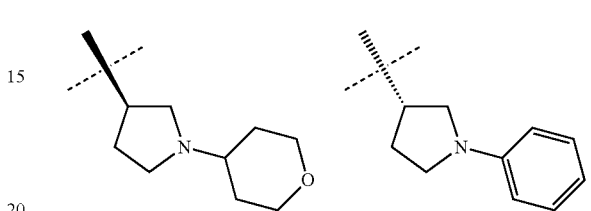
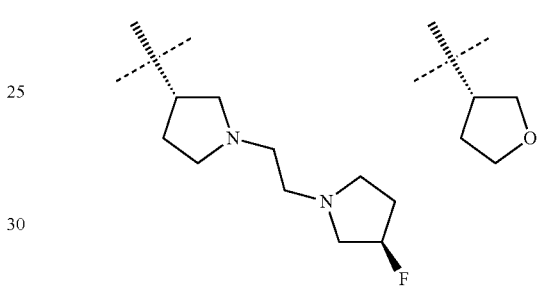
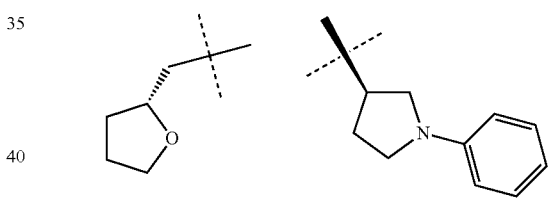
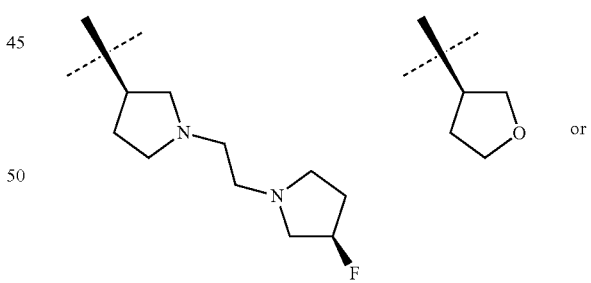
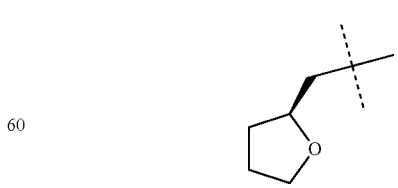
5. The compound of Formula (I*) according to claim 1, wherein the compound is of Formula (I):

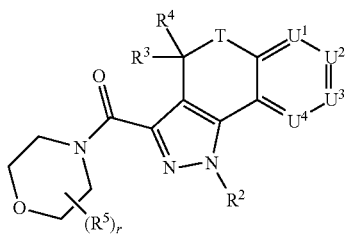

(I)

wherein:

$R^2$ denotes H, Ar, Het, A, or Cyc;

$R^3$ denotes H or Y;

$R^4$ H, Y, $(CH_2)_n Ar$, $(CH_2)_n Cyc$, or $(CH_2)_n Het$;

$R^5$ denotes H, Y or Ar;

$U^1$, $U^2$, $U^3$, and $U^4$ denote $CR^1$ or one or two of $U^1$, $U^2$, $U^3$ and $U^4$ are independently N, and the remaining are $CR^1$;

$R^1$ denotes H, A, Hal, CN, $NO_2$, $N(R^6)_2$, $OR^6$, Ar, Het, Y, $-NR^6COR^6$, or $CON(R^6)_2$;

T denotes SO or $SO_2$;

r denotes 0, 1 or 2;

Ar denotes a monocyclic or fused bicyclic, unsaturated or aromatic carbocyclic ring having 6 to 14 carbon atoms, which is unsubstituted or monosubstituted, disubstituted or trisubstituted by Hal, $OCF_3$, $NO_2$, CN, perfluoroalkyl, A, $OR^6$, $N(R^6)_2$, $COR^6$, $-CO_2R^6$, $CON(R^6)_2$, COHet, $-NHCOR^6$, $-NHSO_2A$, $-NHSO_2Ar$, $-NHSO_2-N(R^6)_2$, $N(H)_{1-q}A_qCOR^6$, $N(H)_{1-q}A_qSO_2-N(H)_{2-m}(A)_m$, $-N(H)_{1-q}A_qCON(H)_{2-m}(A)_m$, $-SO_2A$, $-SO_2Ar$, $-SO_2N(H)_{2-m}(A)_m$, $-SO_2Het$, $-(CH_2)_n-N(R^6)_2$, $-(CH_2)_n-OR^6$, $-(CH_2)_n-N(R^6)SO_2A$, $-(CH_2)_n-N(R^6)SO_2R^6$, $Het^2$, $-(CH_2)_n-Het^2$; or $-(CHY)_n-Het^2$;

Het denotes a monocyclic or bicyclic saturated, unsaturated or aromatic heterocyclic ring having 1, 2, 3 or 4 N, O and/or S atoms which is unsubstituted or monosubstituted, disubstituted or trisubstituted by Hal, $OCF_3$, $NO_2$, CN, perfluoroalkyl, A, $OR^6$, $N(R^6)_2$, $COR^6$, $-CO_2R^6$, $CON(R^6)_2$, $-NHCOR^6$, $-NHSO_2A$, $-NHSO_2R^6$, $-NHSO_2-N(H)_{2-m}(A)_m$, $N(H)_{1-q}A_qCOR^6$, $N(H)_{1-q}A_qSO_2-N(H)_{2-m}(A)_m$, $-N(H)_{1-q}A_qCON(H)_{2-m}(A)_m$, $-SO_2A$, $-SO_2Ar$, $-SO_2N(H)_{2-m}(A)_m$, COHet, $-SO_2Het$, $-(CH_2)_n-N(H)_{2-m}(A)_m$, $-(CH_2)_n-OR^6$, $-(CH_2)_n-N(R^6)SO_2A$, $-(CH_2)_n-N(R^6)SO_2R^6$, $Het^2$, $-(CH_2)_n-Het^2$; or $-(CHY)_n-Het^2$;

Cyc denotes a saturated carbocyclic ring having 1 to 8 carbon atoms, which is unsubstituted, mono-substituted, di-substituted or tri-substituted by Hal, $OCF_3$, $NO_2$, CN, perfluoroalkyl, A, $OR^6$, $N(R^6)_2$, $COR^6$, $CON(R^6)_2$, $-NHCOR^6$, $-NHSO_2A$, $-NHSO_2R^6$, $-NHSO_2-N(H)_{2-m}(A)_m$, $N(H)_{1-q}A_qCOR^6$, $N(H)_{1-q}A_qSO_2-N(H)_{2-m}(A)_m$, $-N(H)_{1-q}A_qCON(H)_{2-m}(A)_m$, $-COOR^6$, $-SO_2A$, $-SO_2Ar$, $-SO_2N(H)_{2-m}(A)_m$, $-SO_2Het$, $-(CH_2)_p-N(H)_{2-m}(A)_m$, $-(CH_2)_n-OR^6$, $-(CH_2)_n-N(R^6)SO_2A$, $-(CH_2)_n-N(R^6)SO_2R^6$, $Het^2$, $-(CH_2)_n-Het^2$; or $-(CHY)_n-Het^2$;

A is a branched or linear alkyl having 1 to 12 C-atoms, wherein one or more H-atoms may be replaced by Hal, Ar, Het, Cyc, $OR^6$, $-CN$, $-CO_2Y$ or $N(R^6)_2$ and wherein one or more non-adjacent $CH_2$-groups may be replaced by O, $NR^6$, $CONR^6$- and/or by $-CH=CH$- or $-C\equiv C$- groups, or denotes cycloalkyl or cycloalkylene having 3-7 ring C atoms;

Y denotes a branched or linear alkyl having 1 to 8 carbon atoms;

$R^6$ is H, A, Cyc, or Ar;

Hal denotes F, Cl, Br or I;

q is 0 or 1;

m is 0, 1 or 2;

n is 1, 2, 3, or 4;

and pharmaceutically acceptable solvates, tautomers, salts, hydrates and stereoisomers thereof, including mixtures thereof in all ratios with the proviso that compound of formula (B1) is excluded:

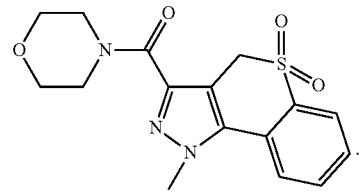

B1

6. The compound of Formula (I*) according to claim 1, wherein the compound is selected from:

| Example No | Structures | Example No | Structures |
|---|---|---|---|
| 1 | 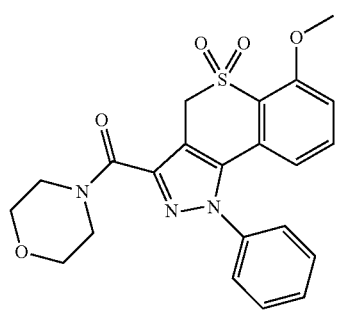 [SMILES: COc1cccc2c1S(=O)(=O)Cc1c(C(=O)N3CCOCC3)nn(-c3ccccc3)c1-2] | 2 | 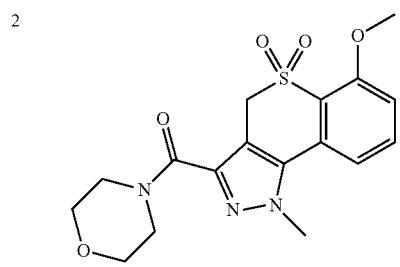 |

-continued
| Example No | Structures | Example No | Structures |
|---|---|---|---|
| 3 | 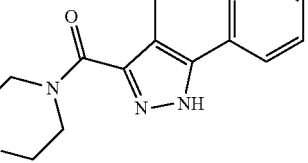 | 4 | 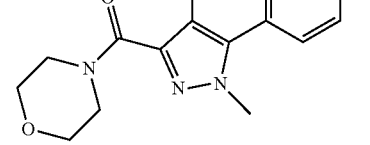 |
| 5 | 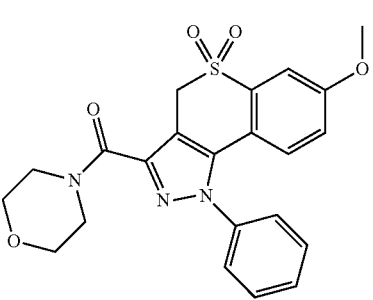 [SMILES: COc1ccc2c(c1)S(=O)(=O)Cc1c(C(=O)N3CCOCC3)nn(-c3ccccc3)c1-2] | 6 | 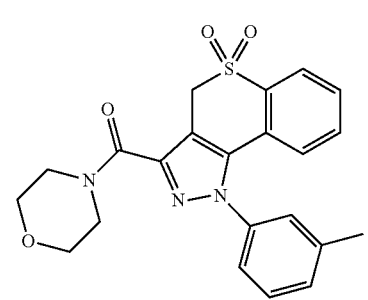 [SMILES: Cc1cccc(-n2nc(C(=O)N3CCOCC3)c3c2-c2ccccc2S(=O)(=O)C3)c1] |
| 7 | 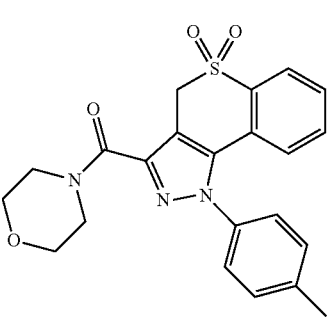 [SMILES: Cc1ccc(-n2nc(C(=O)N3CCOCC3)c3c2-c2ccccc2S(=O)(=O)C3)cc1] | 8 | 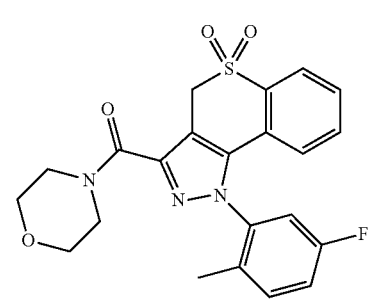 [SMILES: Cc1ccc(F)cc1-n1nc(C(=O)N2CCOCC2)c2c1-c1ccccc1S(=O)(=O)C2] |
| 9 | 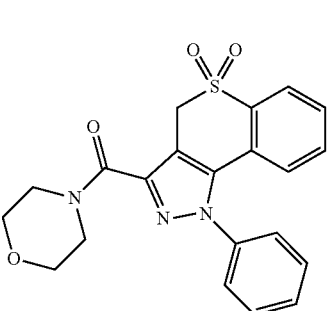 | 10 | 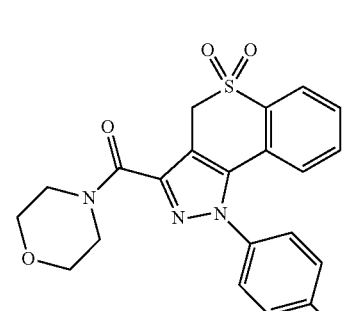 |
| 11 | 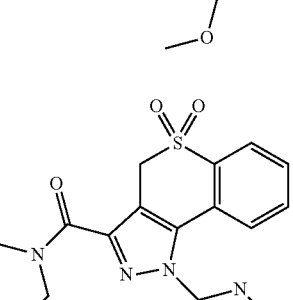 | 12 | 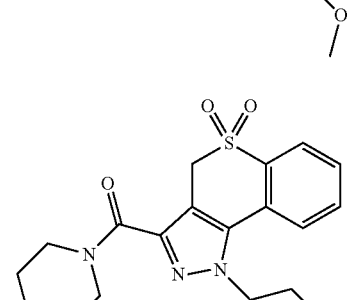 |

-continued

| Example No | Structures | Example No | Structures |
|---|---|---|---|
| 13 | 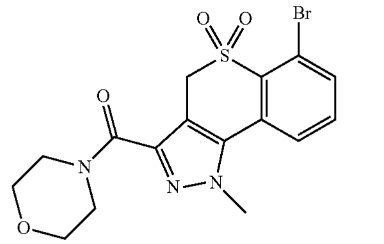 | 14 | 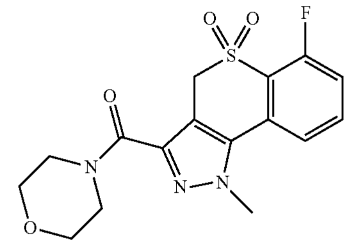 [SMILES: Cn1nc(C(=O)N2CCOCC2)c2c1-c1cccc(F)c1S(=O)(=O)C2] |
| 15 | 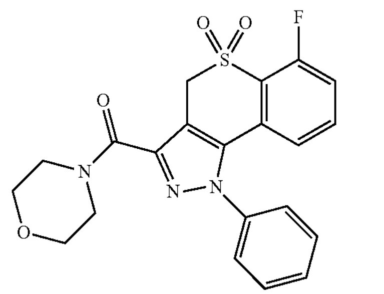 [SMILES: O=C(c1nn(-c2ccccc2)c2c1CS(=O)(=O)c1c(F)cccc1-2)N1CCOCC1] | 16 | 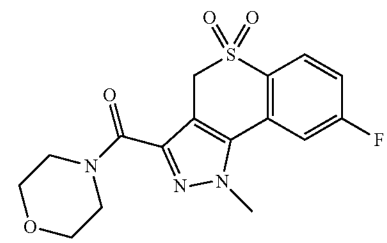 [SMILES: Cn1nc(C(=O)N2CCOCC2)c2c1-c1cc(F)ccc1S(=O)(=O)C2] |
| 17 | 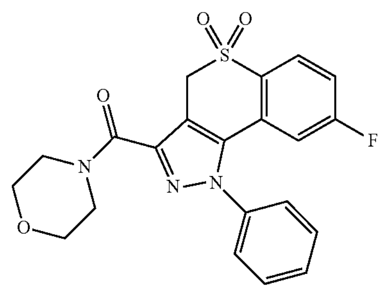 [SMILES: O=C(c1nn(-c2ccccc2)c2c1CS(=O)(=O)c1ccc(F)cc1-2)N1CCOCC1] | 18 | 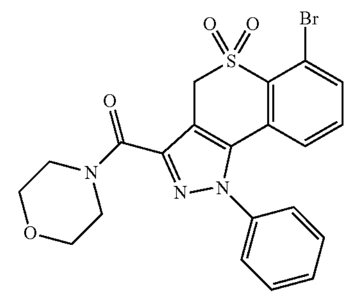 [SMILES: O=C(c1nn(-c2ccccc2)c2c1CS(=O)(=O)c1c(Br)cccc1-2)N1CCOCC1] |
| 19 | 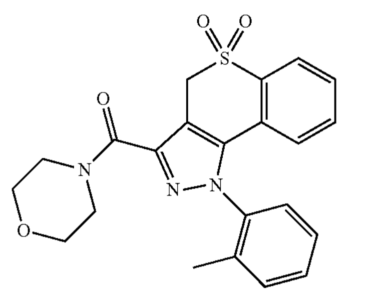 [SMILES: Cc1ccccc1-n1nc(C(=O)N2CCOCC2)c2c1-c1ccccc1S(=O)(=O)C2] | 20 | 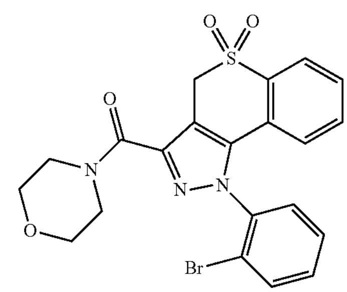 [SMILES: O=C(c1nn(-c2ccccc2Br)c2c1CS(=O)(=O)c1ccccc1-2)N1CCOCC1] |
| 21 | 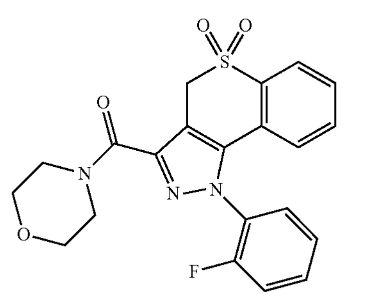 | 22 | 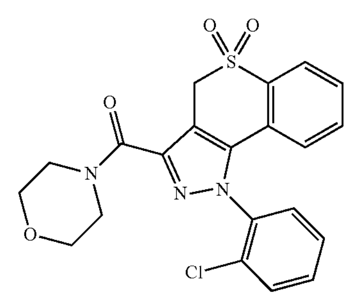 [SMILES: O=C(c1nn(-c2ccccc2Cl)c2c1CS(=O)(=O)c1ccccc1-2)N1CCOCC1] |

-continued

| Example No | Structures | Example No | Structures |
|---|---|---|---|
| 23 | 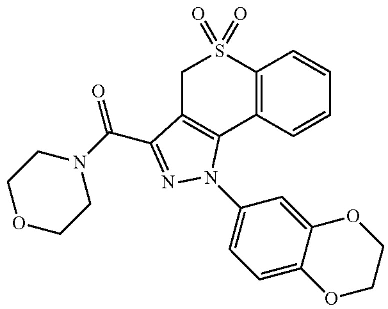 [SMILES: O=C(c1nn(-c2ccc3c(c2)OCCO3)c2c1CS(=O)(=O)c1ccccc1-2)N1CCOCC1] | 24 | 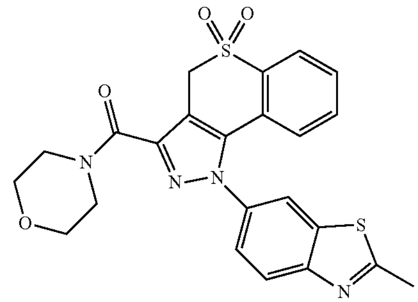 [SMILES: Cc1nc2ccc(-n3nc(C(=O)N4CCOCC4)c4c3-c3ccccc3S(=O)(=O)C4)cc2s1] |
| 25 | 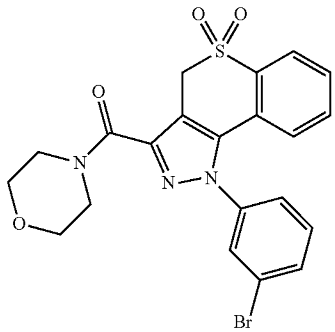 | 26 | 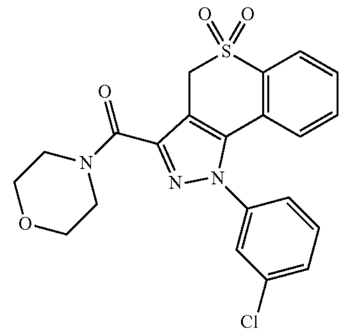 [SMILES: O=C(c1nn(-c2cccc(Cl)c2)c2c1CS(=O)(=O)c1ccccc1-2)N1CCOCC1] |
| 27 | 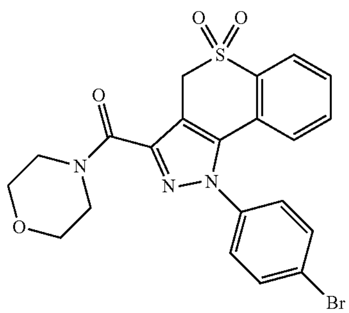 [SMILES: O=C(c1nn(-c2ccc(Br)cc2)c2c1CS(=O)(=O)c1ccccc1-2)N1CCOCC1] | 28 | 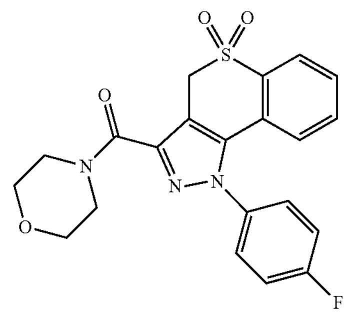 [SMILES: O=C(c1nn(-c2ccc(F)cc2)c2c1CS(=O)(=O)c1ccccc1-2)N1CCOCC1] |
| 29 | 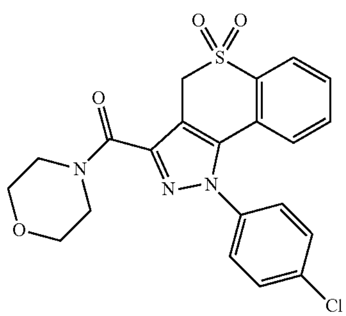 [SMILES: O=C(c1nn(-c2ccc(Cl)cc2)c2c1CS(=O)(=O)c1ccccc1-2)N1CCOCC1] | 30 | 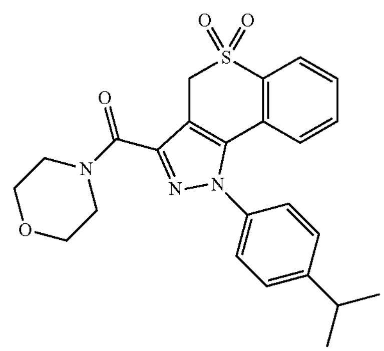 [SMILES: CC(C)c1ccc(-n2nc(C(=O)N3CCOCC3)c3c2-c2ccccc2S(=O)(=O)C3)cc1] |
| 31 | 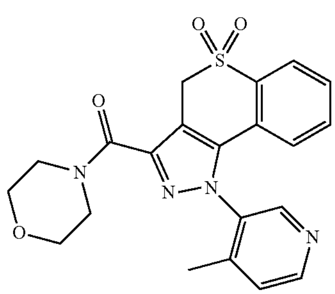 | 32 | 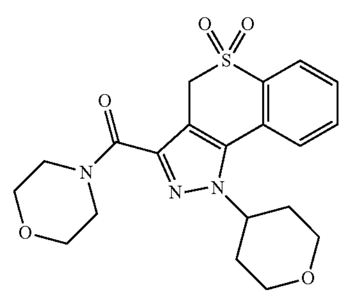 [SMILES: O=C(c1nn(C2CCOCC2)c2c1CS(=O)(=O)c1ccccc1-2)N1CCOCC1] |

-continued
| Example No | Structures | Example No | Structures |
|---|---|---|---|
| 33 | 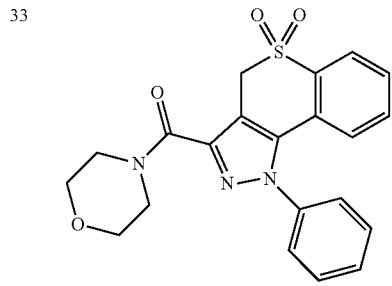 | | |
| 35 | 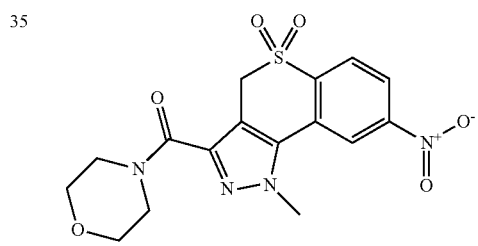 | 36 | 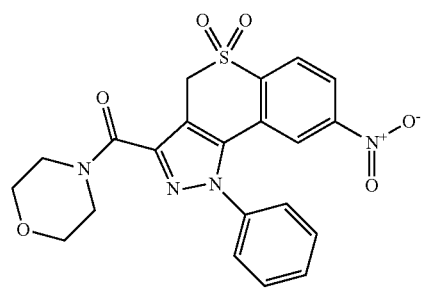 [SMILES: O=C(c1nn(-c2ccccc2)c2c1CS(=O)(=O)c1ccc([N+](=O)[O-])cc1-2)N1CCOCC1] |
| 37 | 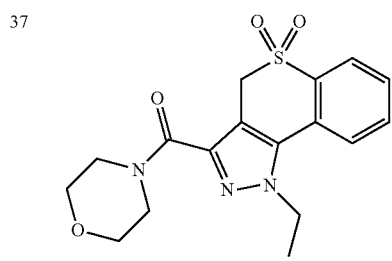 | 38 | 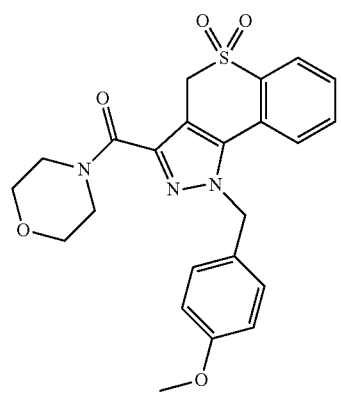 [SMILES: COc1ccc(Cn2nc(C(=O)N3CCOCC3)c3c2-c2ccccc2S(=O)(=O)C3)cc1] |
| 39 | 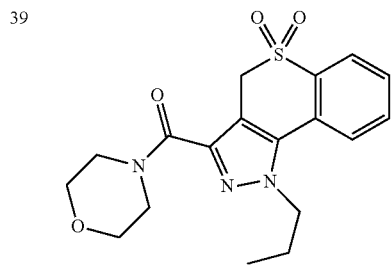 | 40 | 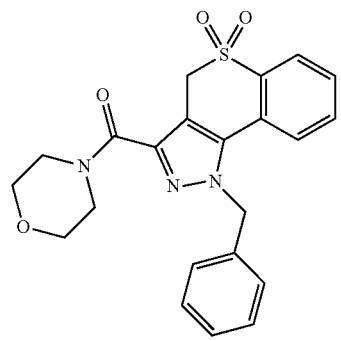 |

-continued

| Example No | Structures | Example No | Structures |
|---|---|---|---|
| 41 | 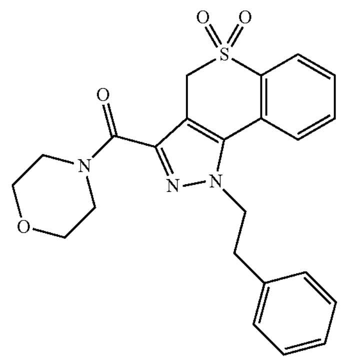 [SMILES: O=C(c1nn(CCc2ccccc2)c2c1CS(=O)(=O)c1ccccc1-2)N1CCOCC1] | 42 | 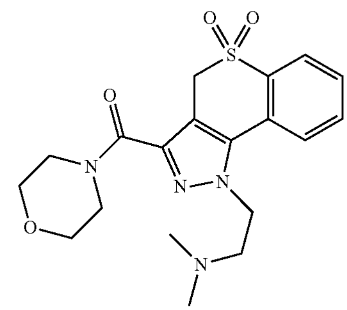 [SMILES: CN(C)CCn1nc(C(=O)N2CCOCC2)c2c1-c1ccccc1S(=O)(=O)C2] |
| 43 | 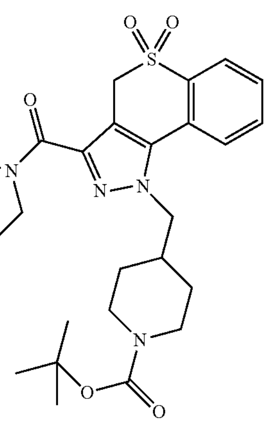 | 44 | 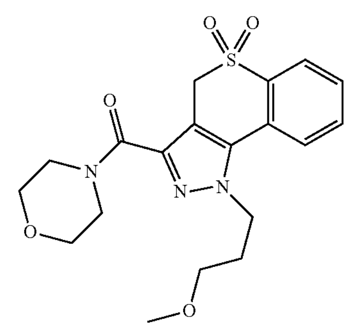 [SMILES: COCCCn1nc(C(=O)N2CCOCC2)c2c1-c1ccccc1S(=O)(=O)C2] |
| 45 | 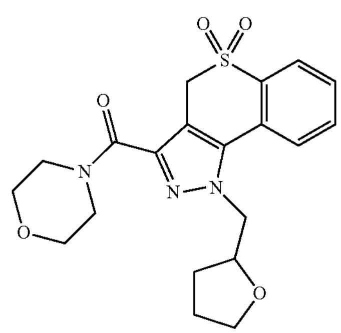 | 46 | 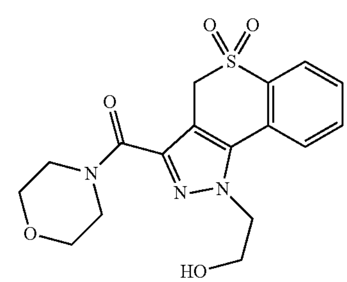 [SMILES: O=C(c1nn(CCO)c2c1CS(=O)(=O)c1ccccc1-2)N1CCOCC1] |
| 47 | 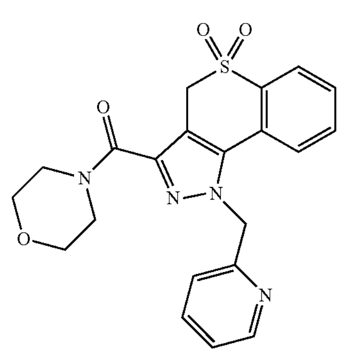 | 48 | 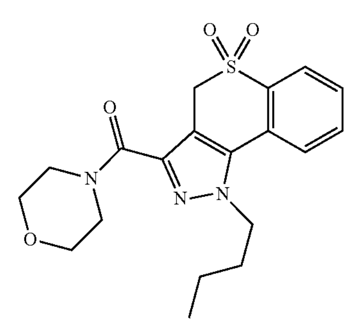 [SMILES: CCCCn1nc(C(=O)N2CCOCC2)c2c1-c1ccccc1S(=O)(=O)C2] |

-continued
| Example No | Structures | Example No | Structures |
|---|---|---|---|
| 49 | 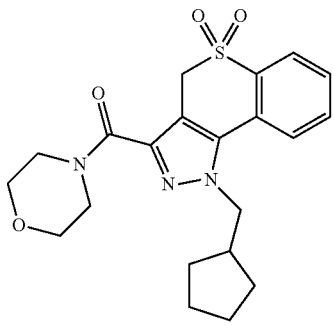 [SMILES: O=C(c1nn(CC2CCCC2)c2c1CS(=O)(=O)c1ccccc1-2)N1CCOCC1] | 50 | 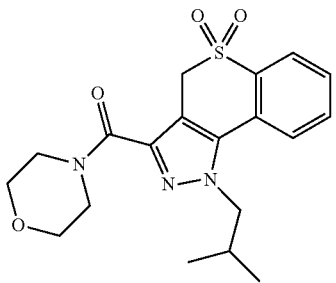 [SMILES: CC(C)Cn1nc(C(=O)N2CCOCC2)c2c1-c1ccccc1S(=O)(=O)C2] |
| 51 | 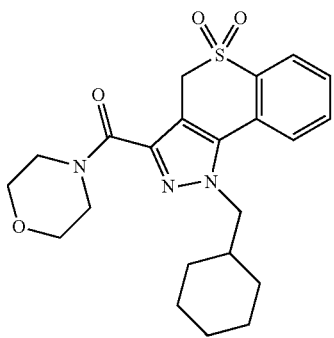 [SMILES: O=C(c1nn(CC2CCCCC2)c2c1CS(=O)(=O)c1ccccc1-2)N1CCOCC1] | 52 | 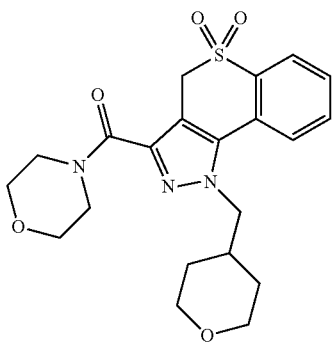 [SMILES: O=C(c1nn(CC2CCOCC2)c2c1CS(=O)(=O)c1ccccc1-2)N1CCOCC1] |
| 53 | 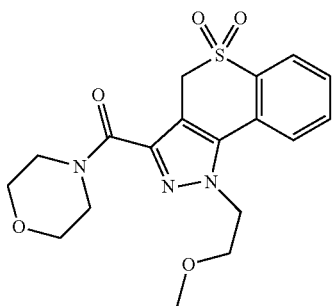 [SMILES: COCCn1nc(C(=O)N2CCOCC2)c2c1-c1ccccc1S(=O)(=O)C2] | 54 | 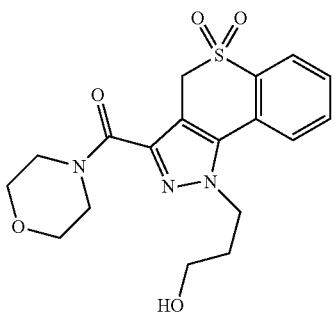 [SMILES: O=C(c1nn(CCCO)c2c1CS(=O)(=O)c1ccccc1-2)N1CCOCC1] |
| 55 | 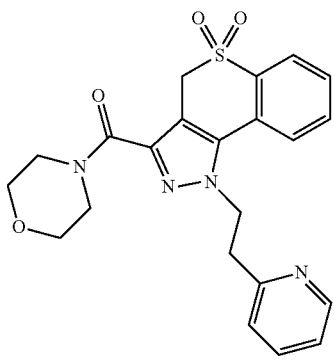 [SMILES: O=C(c1nn(CCc2ccccn2)c2c1CS(=O)(=O)c1ccccc1-2)N1CCOCC1] | 56 | 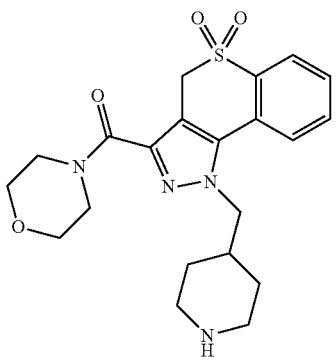 [SMILES: O=C(c1nn(CC2CCNCC2)c2c1CS(=O)(=O)c1ccccc1-2)N1CCOCC1] |

-continued
| Example No | Structures | Example No | Structures |
|---|---|---|---|
| 57 | 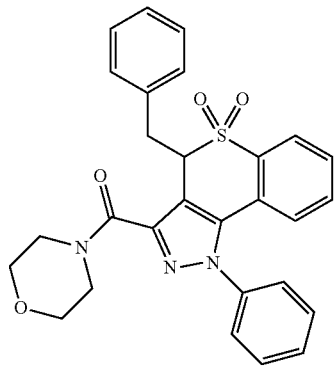 [SMILES: O=C(c1nn(-c2ccccc2)c2c1C(Cc1ccccc1)S(=O)(=O)c1ccccc1-2)N1CCOCC1] | 58 | 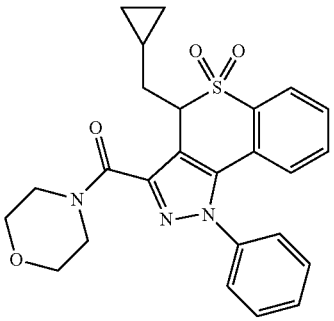 [SMILES: O=C(c1nn(-c2ccccc2)c2c1C(CC1CC1)S(=O)(=O)c1ccccc1-2)N1CCOCC1] |
| 59 | 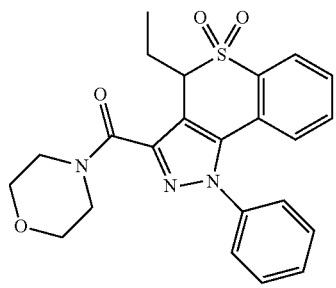 [SMILES: CCC1c2c(C(=O)N3CCOCC3)nn(-c3ccccc3)c2-c2ccccc2S1(=O)=O] | 60 | 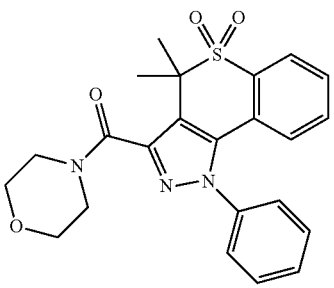 [SMILES: CC1(C)c2c(C(=O)N3CCOCC3)nn(-c3ccccc3)c2-c2ccccc2S1(=O)=O] |
| 61 | 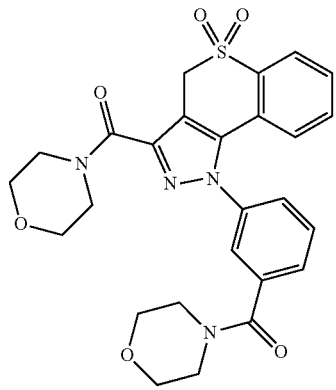 [SMILES: O=C(c1cccc(-n2nc(C(=O)N3CCOCC3)c3c2-c2ccccc2S(=O)(=O)C3)c1)N1CCOCC1] | 62 | 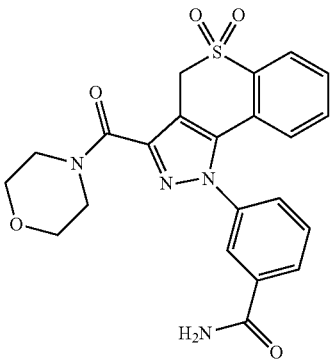 [SMILES: NC(=O)c1cccc(-n2nc(C(=O)N3CCOCC3)c3c2-c2ccccc2S(=O)(=O)C3)c1] |
| 63 | 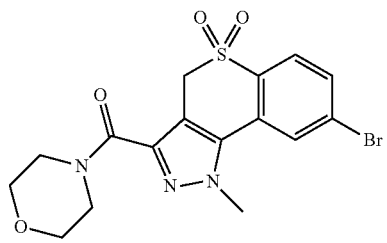 [SMILES: Cn1nc(C(=O)N2CCOCC2)c2c1-c1cc(Br)ccc1S(=O)(=O)C2] | 64 | 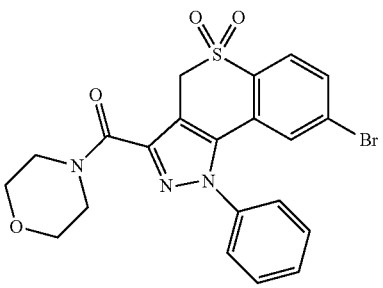 [SMILES: O=C(c1nn(-c2ccccc2)c2c1CS(=O)(=O)c1ccc(Br)cc1-2)N1CCOCC1] |

-continued
| Example No | Structures | Example No | Structures |
|---|---|---|---|
| 65 | 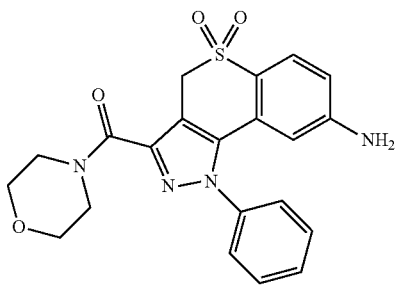 | 66 | 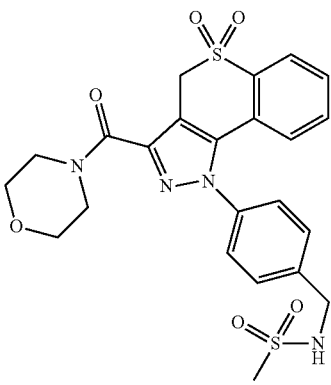 [SMILES: CS(=O)(=O)NCc1ccc(-n2nc(C(=O)N3CCOCC3)c3c2-c2ccccc2S(=O)(=O)C3)cc1] |
| 67 | 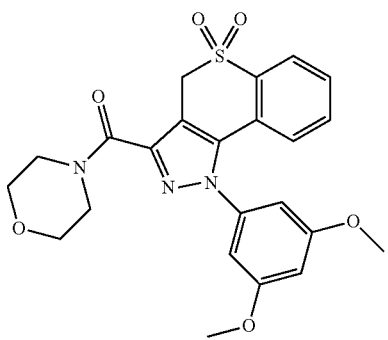 [SMILES: COc1cc(OC)cc(-n2nc(C(=O)N3CCOCC3)c3c2-c2ccccc2S(=O)(=O)C3)c1] | 68 | 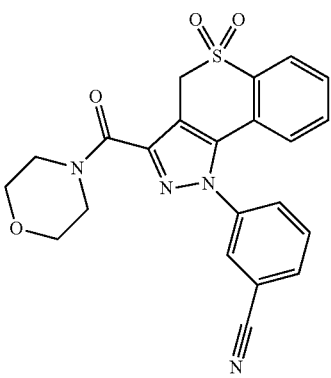 [SMILES: N#Cc1cccc(-n2nc(C(=O)N3CCOCC3)c3c2-c2ccccc2S(=O)(=O)C3)c1] |
| 69 | 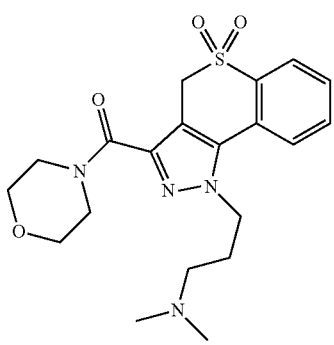 [SMILES: CN(C)CCCn1nc(C(=O)N2CCOCC2)c2c1-c1ccccc1S(=O)(=O)C2] | 70 | 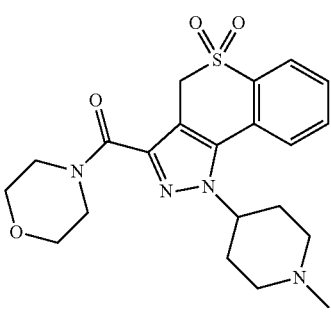 |
| 71 | 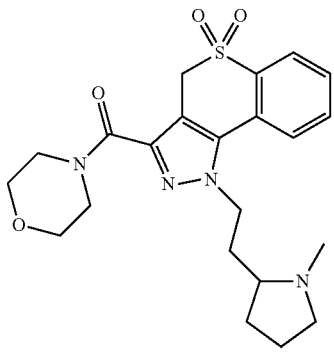 [SMILES: CN1CCCC1CCn1nc(C(=O)N2CCOCC2)c2c1-c1ccccc1S(=O)(=O)C2] | 72 | 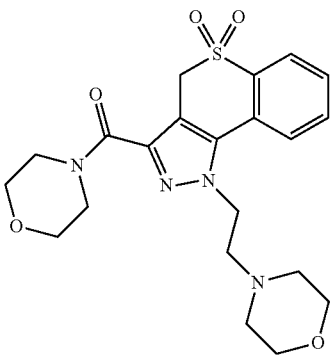 |

-continued
| Example No | Structures | Example No | Structures |
|---|---|---|---|
| 73 | 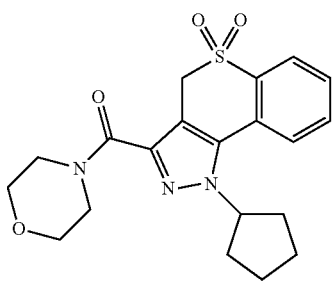 [SMILES: O=C(c1nn(C2CCCC2)c2c1CS(=O)(=O)c1ccccc1-2)N1CCOCC1] | 74 | 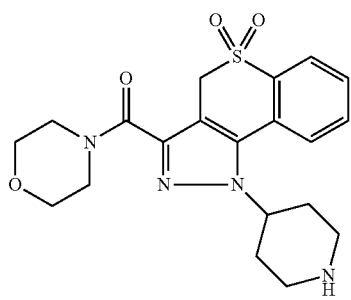 [SMILES: O=C(c1nn(C2CCNCC2)c2c1CS(=O)(=O)c1ccccc1-2)N1CCOCC1] |
| 75 | 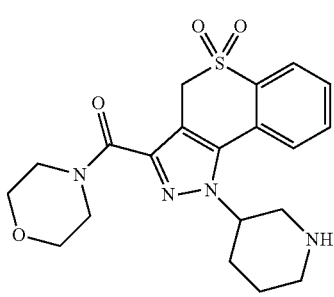 [SMILES: O=C(c1nn(C2CCCNC2)c2c1CS(=O)(=O)c1ccccc1-2)N1CCOCC1] | 76 | 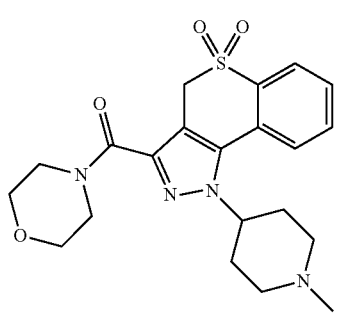 [SMILES: CN1CCC(n2nc(C(=O)N3CCOCC3)c3c2-c2ccccc2S(=O)(=O)C3)CC1] |
| 77 | 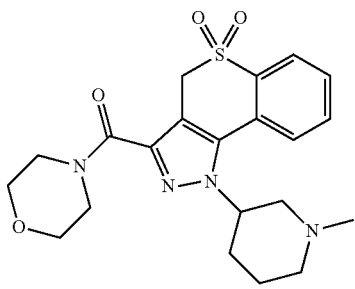 [SMILES: CN1CCCC(n2nc(C(=O)N3CCOCC3)c3c2-c2ccccc2S(=O)(=O)C3)C1] | 78 | 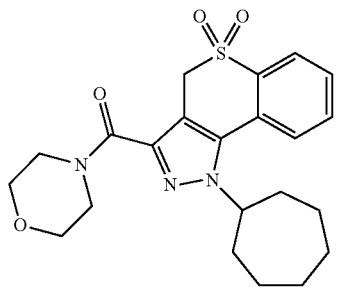 [SMILES: O=C(c1nn(C2CCCCCC2)c2c1CS(=O)(=O)c1ccccc1-2)N1CCOCC1] |
| 79 | 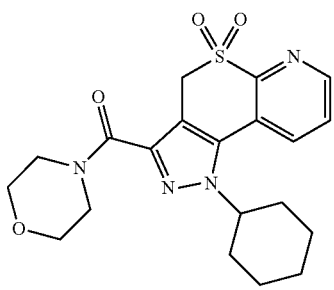 [SMILES: O=C(c1nn(C2CCCCC2)c2c1CS(=O)(=O)c1ncccc1-2)N1CCOCC1] | 80 | 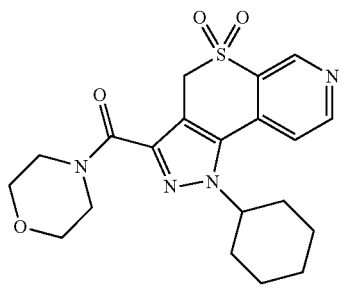 |
| 81 | 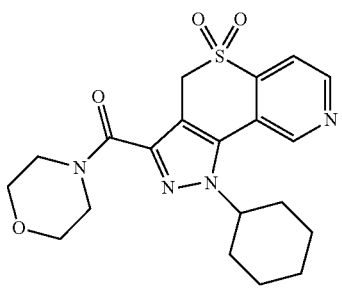 [SMILES: O=C(c1nn(C2CCCCC2)c2c1CS(=O)(=O)c1ccncc1-2)N1CCOCC1] | 82 | 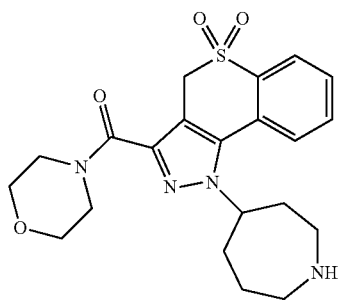 [SMILES: O=C(c1nn(C2CCCNCC2)c2c1CS(=O)(=O)c1ccccc1-2)N1CCOCC1] |

-continued
| Example No | Structures | Example No | Structures |
|---|---|---|---|
| 83 | 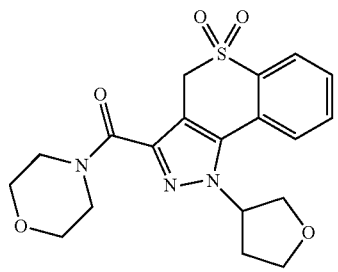 [SMILES: O=C(c1nn(C2CCOC2)c2c1CS(=O)(=O)c1ccccc1-2)N1CCOCC1] | 84 | 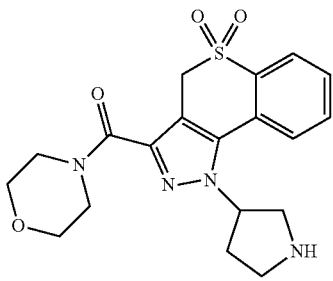 [SMILES: O=C(c1nn(C2CCNC2)c2c1CS(=O)(=O)c1ccccc1-2)N1CCOCC1] |
| 85 | 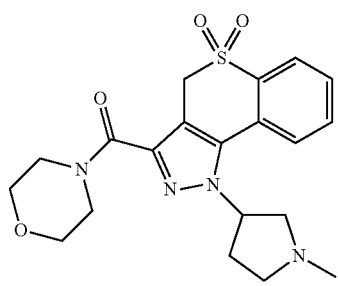 [SMILES: CN1CCC(n2nc(C(=O)N3CCOCC3)c3c2-c2ccccc2S(=O)(=O)C3)C1] | 86 | 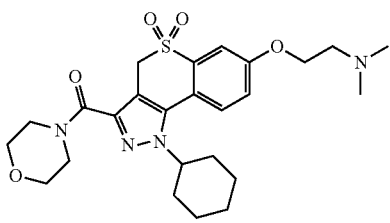 [SMILES: CN(C)CCOc1ccc2c(c1)S(=O)(=O)Cc1c(C(=O)N3CCOCC3)nn(C3CCCCC3)c1-2] |
| 87 | 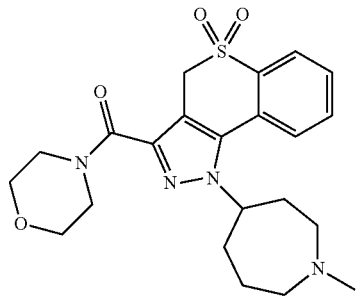 [SMILES: CN1CCCC(n2nc(C(=O)N3CCOCC3)c3c2-c2ccccc2S(=O)(=O)C3)CC1] | 88 | 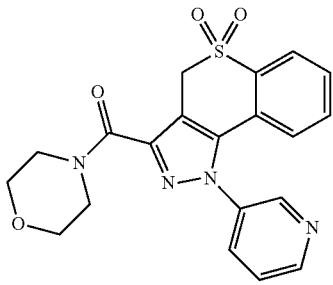 [SMILES: O=C(c1nn(-c2cccnc2)c2c1CS(=O)(=O)c1ccccc1-2)N1CCOCC1] |
| 89 | 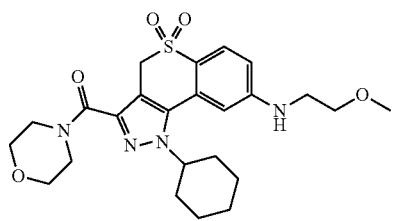 [SMILES: COCCNc1ccc2c(c1)-c1c(c(C(=O)N3CCOCC3)nn1C1CCCCC1)CS2(=O)=O] | 90 | 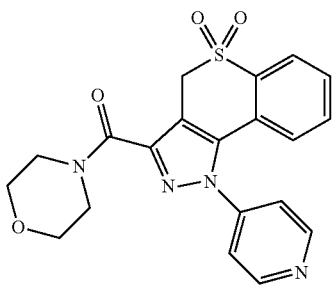 [SMILES: O=C(c1nn(-c2ccncc2)c2c1CS(=O)(=O)c1ccccc1-2)N1CCOCC1] |
| 91 | 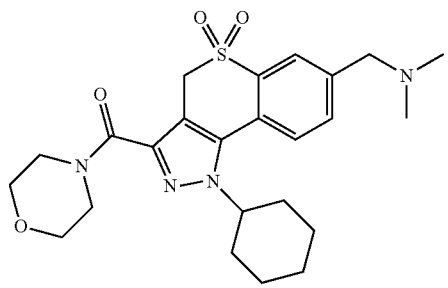 [SMILES: CN(C)Cc1ccc2c(c1)S(=O)(=O)Cc1c(C(=O)N3CCOCC3)nn(C3CCCCC3)c1-2] | 92 | 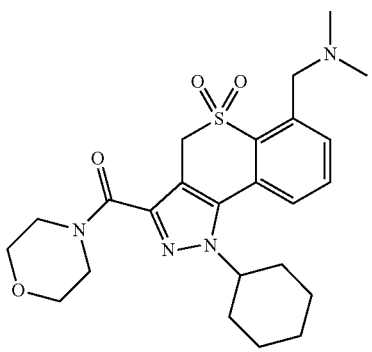 [SMILES: CN(C)Cc1cccc2c1S(=O)(=O)Cc1c(C(=O)N3CCOCC3)nn(C3CCCCC3)c1-2] |

-continued
| Example No | Structures | Example No | Structures |
|---|---|---|---|
| 93 | 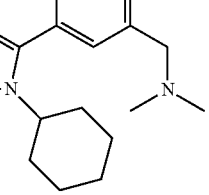 | 94 | 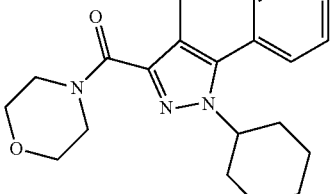 |
| 95 | 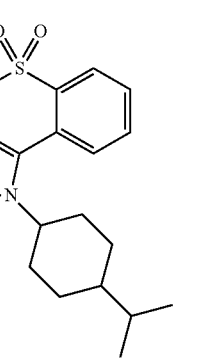 | 96 | 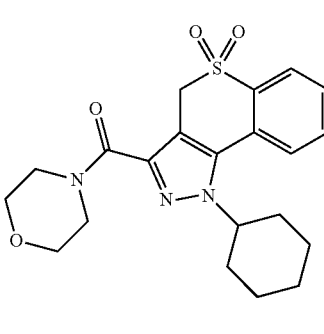 |
| 97 | 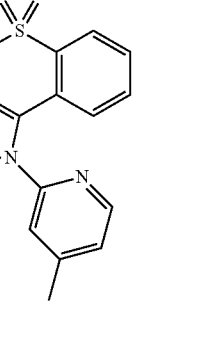 | 98 | 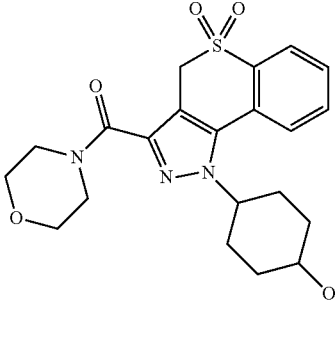 |
| 99 | 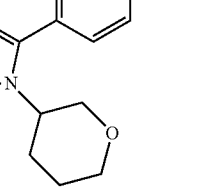 | 100 | 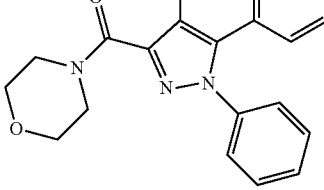 |

-continued
| Example No | Structures | Example No | Structures |
|---|---|---|---|
| 101 | 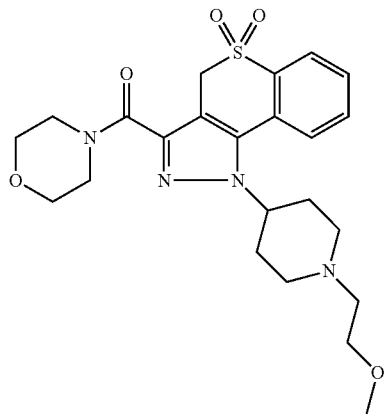 [SMILES: COCCN1CCC(n2nc(C(=O)N3CCOCC3)c3c2-c2ccccc2S(=O)(=O)C3)CC1] | 102 | 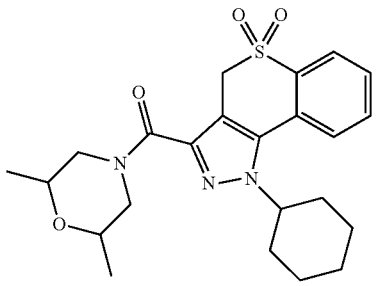 [SMILES: CC1CN(C(=O)c2nn(C3CCCCC3)c3c2CS(=O)(=O)c2ccccc2-3)CC(C)O1] |
| 103 | 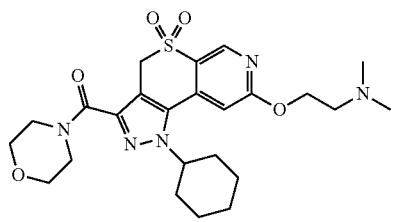 [SMILES: CN(C)CCOc1cc2c(cn1)S(=O)(=O)Cc1c(C(=O)N3CCOCC3)nn(C3CCCCC3)c1-2] | 104 | 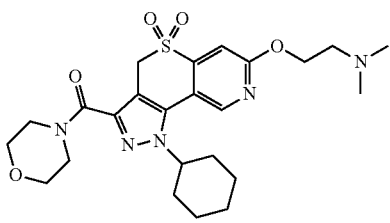 [SMILES: CN(C)CCOc1cc2c(cn1)-c1c(c(C(=O)N3CCOCC3)nn1C1CCCCC1)CS2(=O)=O] |
| 105 | 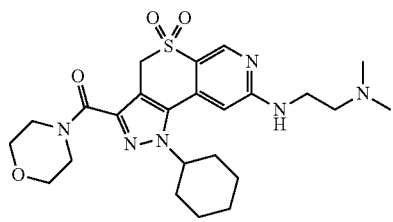 [SMILES: CN(C)CCNc1cc2c(cn1)S(=O)(=O)Cc1c(C(=O)N3CCOCC3)nn(C3CCCCC3)c1-2] | 106 | 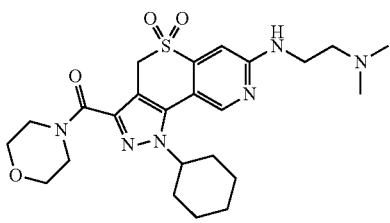 [SMILES: CN(C)CCNc1cc2c(cn1)-c1c(c(C(=O)N3CCOCC3)nn1C1CCCCC1)CS2(=O)=O] |
| 107 | 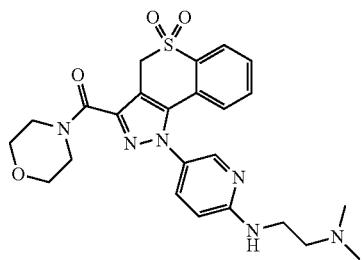 [SMILES: CN(C)CCNc1ccc(-n2nc(C(=O)N3CCOCC3)c3c2-c2ccccc2S(=O)(=O)C3)cn1] | 108 | 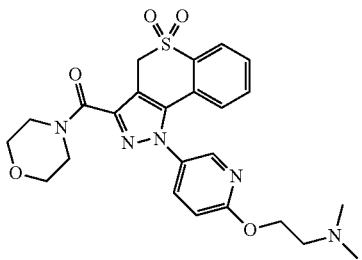 [SMILES: CN(C)CCOc1ccc(-n2nc(C(=O)N3CCOCC3)c3c2-c2ccccc2S(=O)(=O)C3)cn1] |
| 109 | 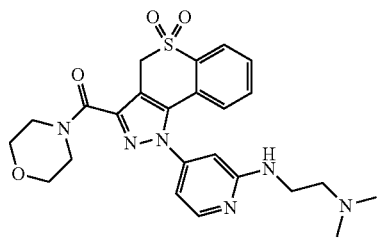 [SMILES: CN(C)CCNc1cc(-n2nc(C(=O)N3CCOCC3)c3c2-c2ccccc2S(=O)(=O)C3)ccn1] | 110 | 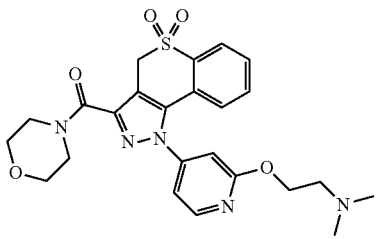 [SMILES: CN(C)CCOc1cc(-n2nc(C(=O)N3CCOCC3)c3c2-c2ccccc2S(=O)(=O)C3)ccn1] |

-continued
| Example No | Structures | Example No | Structures |
|---|---|---|---|
| 111 | 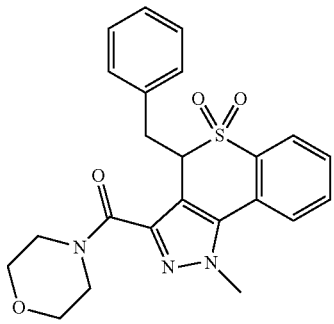 [SMILES: Cn1nc(C(=O)N2CCOCC2)c2c1-c1ccccc1S(=O)(=O)C2Cc1ccccc1] | 112 | 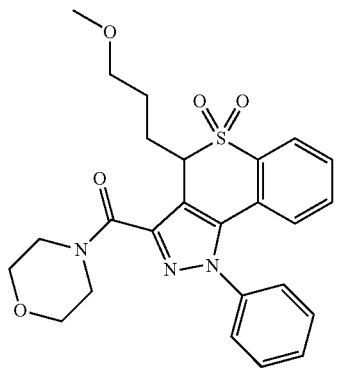 [SMILES: COCCCC1c2c(C(=O)N3CCOCC3)nn(-c3ccccc3)c2-c2ccccc2S1(=O)=O] |
| 113 | 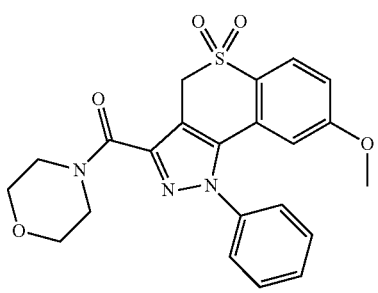 [SMILES: COc1ccc2c(c1)-c1c(c(C(=O)N3CCOCC3)nn1-c1ccccc1)CS2(=O)=O] | 114 | 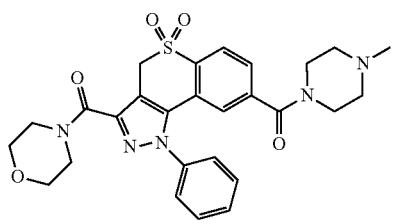 [SMILES: CN1CCN(C(=O)c2ccc3c(c2)-c2c(c(C(=O)N4CCOCC4)nn2-c2ccccc2)CS3(=O)=O)CC1] |
| 115 | 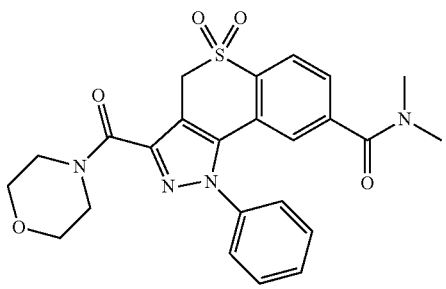 [SMILES: CN(C)C(=O)c1ccc2c(c1)-c1c(c(C(=O)N3CCOCC3)nn1-c1ccccc1)CS2(=O)=O] | 116 | 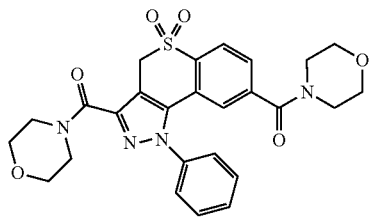 [SMILES: O=C(c1ccc2c(c1)-c1c(c(C(=O)N3CCOCC3)nn1-c1ccccc1)CS2(=O)=O)N1CCOCC1] |
| 117 | 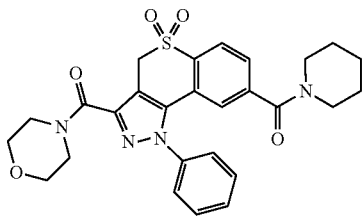 [SMILES: O=C(c1ccc2c(c1)-c1c(c(C(=O)N3CCOCC3)nn1-c1ccccc1)CS2(=O)=O)N1CCCCC1] | 118 | 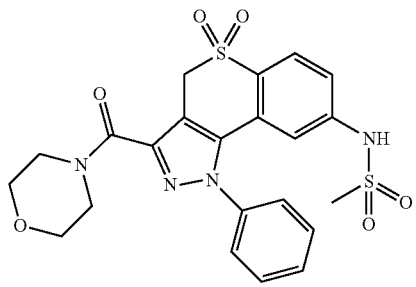 [SMILES: CS(=O)(=O)Nc1ccc2c(c1)-c1c(c(C(=O)N3CCOCC3)nn1-c1ccccc1)CS2(=O)=O] |

-continued
| Example No | Structures | Example No | Structures |
|---|---|---|---|
| 119 | 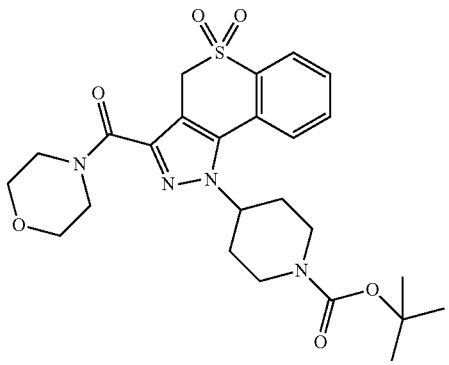 [SMILES: CC(C)(C)OC(=O)N1CCC(n2nc(C(=O)N3CCOCC3)c3c2-c2ccccc2S(=O)(=O)C3)CC1] | 120 | 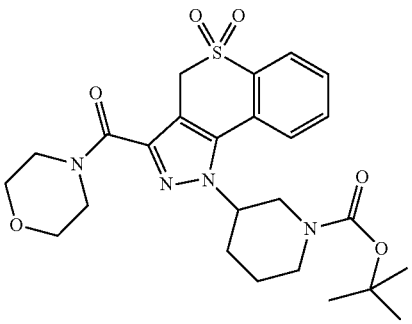 [SMILES: CC(C)(C)OC(=O)N1CCCC(n2nc(C(=O)N3CCOCC3)c3c2-c2ccccc2S(=O)(=O)C3)C1] |
| 121 | 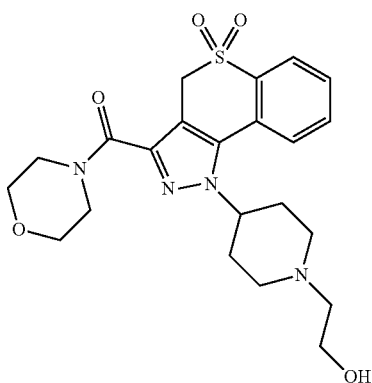 [SMILES: O=C(c1nn(C2CCN(CCO)CC2)c2c1CS(=O)(=O)c1ccccc1-2)N1CCOCC1] | 122 | 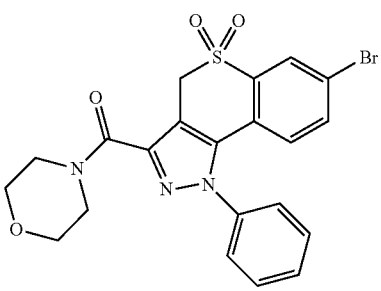 [SMILES: O=C(c1nn(-c2ccccc2)c2c1CS(=O)(=O)c1cc(Br)ccc1-2)N1CCOCC1] |
| 123 | 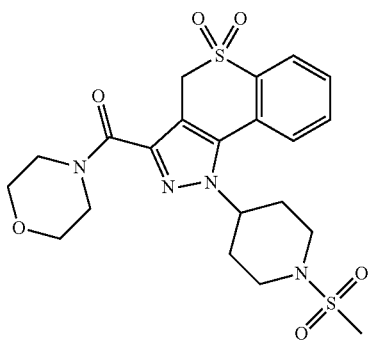 [SMILES: CS(=O)(=O)N1CCC(n2nc(C(=O)N3CCOCC3)c3c2-c2ccccc2S(=O)(=O)C3)CC1] | 124 | 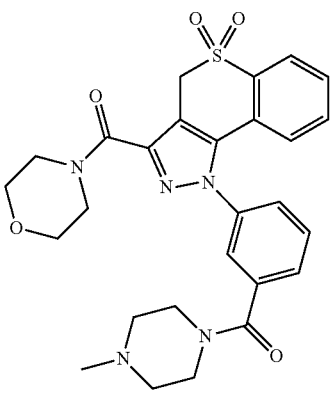 [SMILES: CN1CCN(C(=O)c2cccc(-n3nc(C(=O)N4CCOCC4)c4c3-c3ccccc3S(=O)(=O)C4)c2)CC1] |
| 125 | 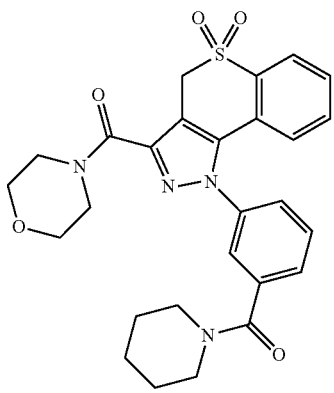 [SMILES: O=C(c1cccc(-n2nc(C(=O)N3CCOCC3)c3c2-c2ccccc2S(=O)(=O)C3)c1)N1CCCCC1] | 126 | 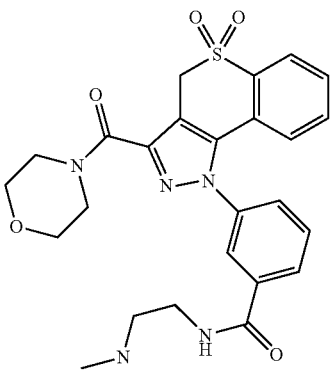 |

| Example No | Structures | Example No | Structures |
|---|---|---|---|
| 127 | 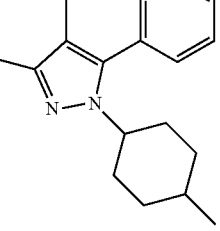 | 128 | 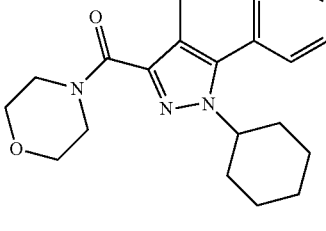 |
| 129 | 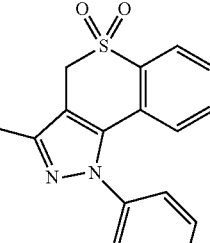 | 130 | 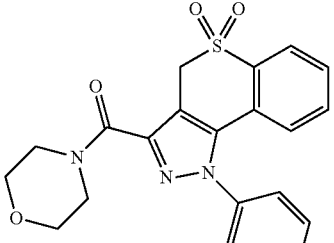 |
| 131 | 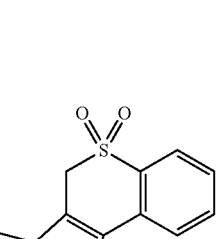 | 132 | 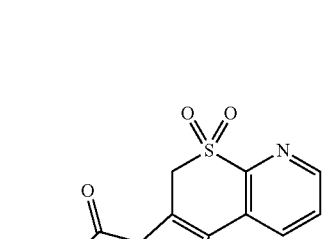 |
| 133 | 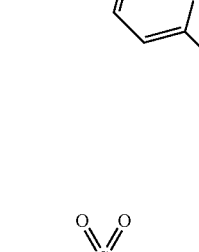 | 134 | 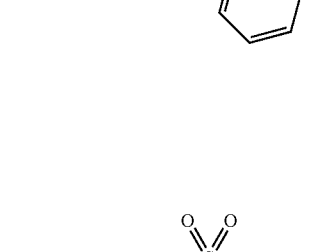 |

-continued
| Example No | Structures | Example No | Structures |
|---|---|---|---|
| 135 | 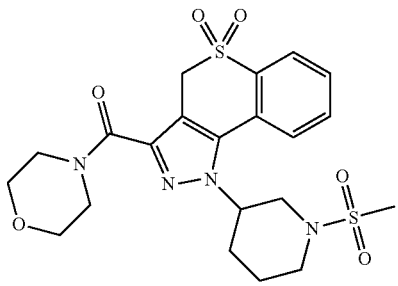 [SMILES: CS(=O)(=O)N1CCCC(n2nc(C(=O)N3CCOCC3)c3c2-c2ccccc2S(=O)(=O)C3)C1] | 136 | 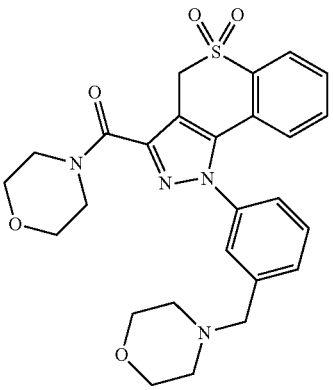 [SMILES: O=C(c1nn(-c2cccc(CN3CCOCC3)c2)c2c1CS(=O)(=O)c1ccccc1-2)N1CCOCC1] |
| 137 | 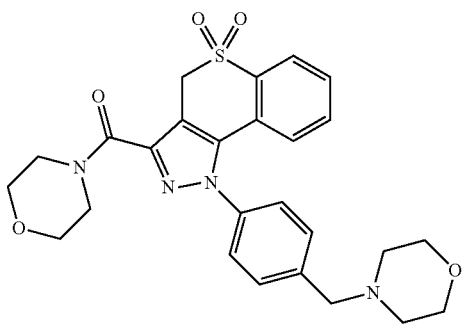 [SMILES: O=C(c1nn(-c2ccc(CN3CCOCC3)cc2)c2c1CS(=O)(=O)c1ccccc1-2)N1CCOCC1] | 138 | 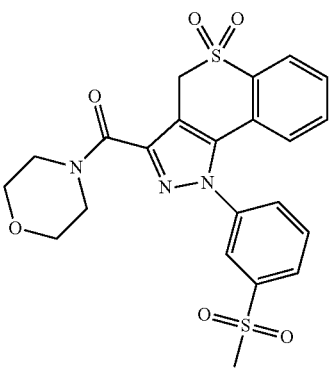 [SMILES: CS(=O)(=O)c1cccc(-n2nc(C(=O)N3CCOCC3)c3c2-c2ccccc2S(=O)(=O)C3)c1] |
| 139 | 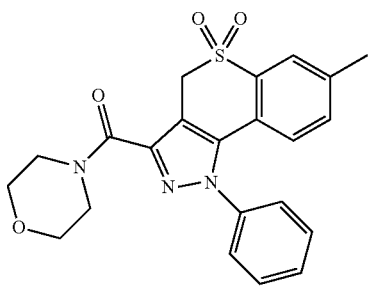 [SMILES: Cc1ccc2c(c1)S(=O)(=O)Cc1c(C(=O)N3CCOCC3)nn(-c3ccccc3)c1-2] | 140 | 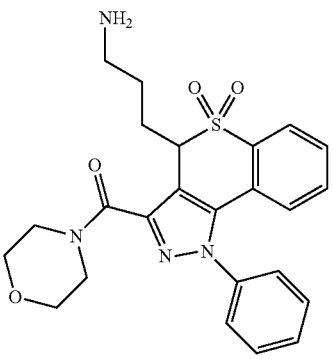 [SMILES: NCCCC1c2c(C(=O)N3CCOCC3)nn(-c3ccccc3)c2-c2ccccc2S1(=O)=O] |
| 141 | 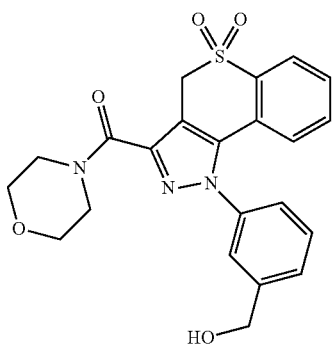 [SMILES: O=C(c1nn(-c2cccc(CO)c2)c2c1CS(=O)(=O)c1ccccc1-2)N1CCOCC1] | 142 | 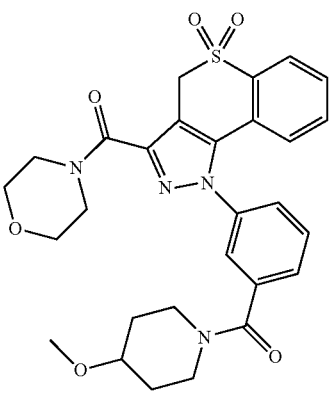 [SMILES: COC1CCN(C(=O)c2cccc(-n3nc(C(=O)N4CCOCC4)c4c3-c3ccccc3S(=O)(=O)C4)c2)CC1] |

-continued
| Example No | Structures | Example No | Structures |
|---|---|---|---|
| 143 | 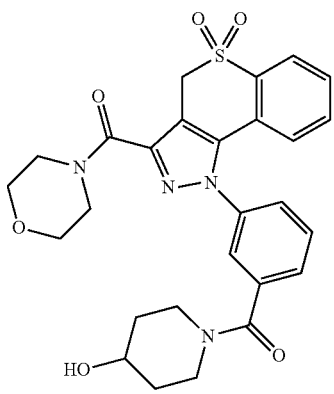 [SMILES: O=C(c1cccc(-n2nc(C(=O)N3CCOCC3)c3c2-c2ccccc2S(=O)(=O)C3)c1)N1CCC(O)CC1] | 144 | 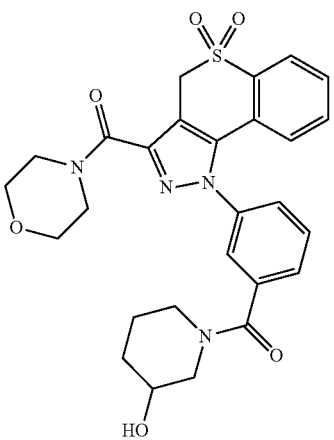 [SMILES: O=C(c1cccc(-n2nc(C(=O)N3CCOCC3)c3c2-c2ccccc2S(=O)(=O)C3)c1)N1CCCC(O)C1] |
| 145 | 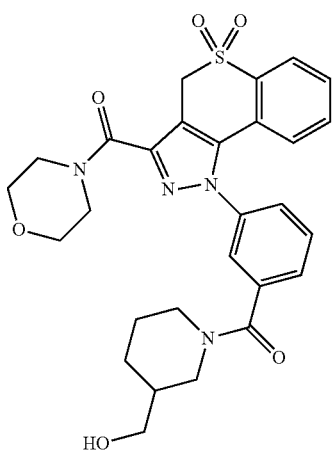 [SMILES: O=C(c1cccc(-n2nc(C(=O)N3CCOCC3)c3c2-c2ccccc2S(=O)(=O)C3)c1)N1CCCC(CO)C1] | 146 | 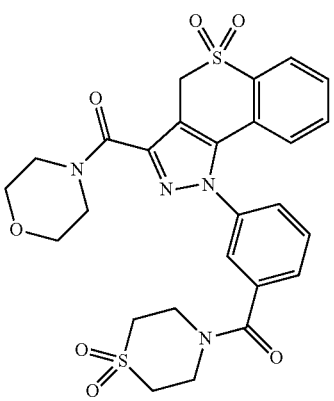 [SMILES: O=C(c1cccc(-n2nc(C(=O)N3CCOCC3)c3c2-c2ccccc2S(=O)(=O)C3)c1)N1CCS(=O)(=O)CC1] |
| 147 | 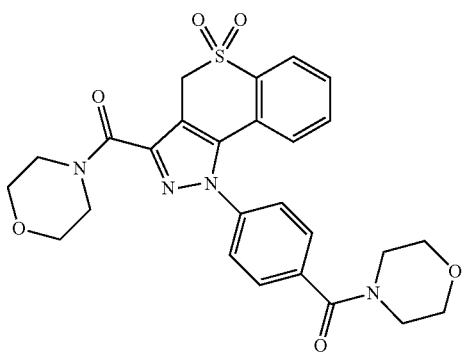 [SMILES: O=C(c1ccc(-n2nc(C(=O)N3CCOCC3)c3c2-c2ccccc2S(=O)(=O)C3)cc1)N1CCOCC1] | 148 | 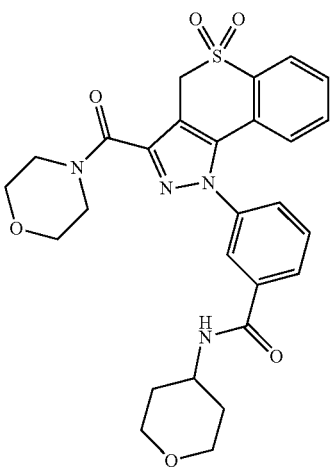 [SMILES: O=C(NC1CCOCC1)c1cccc(-n2nc(C(=O)N3CCOCC3)c3c2-c2ccccc2S(=O)(=O)C3)c1] |

1121

-continued

| Example No | Structures |
|---|---|
| 149 | (structure) |
| 151 | (structure) |
| 153 | (structure) |
| 155 | (structure) |

1122

| Example No | Structures |
|---|---|
| 150 | (structure) |
| 152 | (structure) |
| 154 | (structure) |
| 156 | (structure) |

| Example No | Structures | Example No | Structures |
|---|---|---|---|
| 157 | 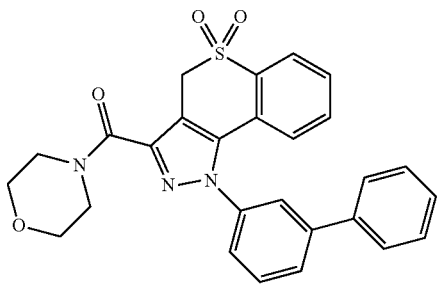 [SMILES: O=C(c1nn(-c2cccc(-c3ccccc3)c2)c2c1CS(=O)(=O)c1ccccc1-2)N1CCOCC1] | 158 | 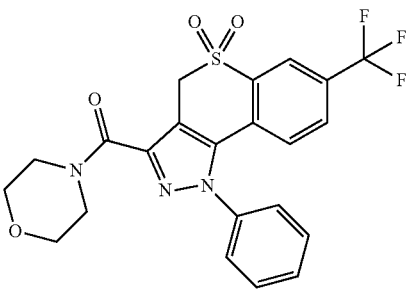 [SMILES: O=C(c1nn(-c2ccccc2)c2c1CS(=O)(=O)c1cc(C(F)(F)F)ccc1-2)N1CCOCC1] |
| 159 | 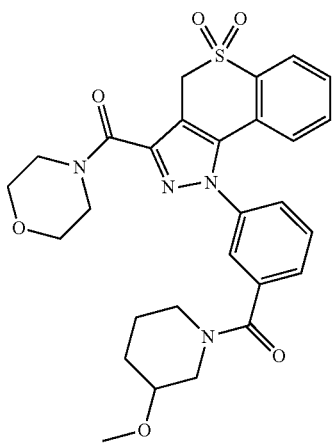 [SMILES: COC1CCCN(C(=O)c2cccc(-n3nc(C(=O)N4CCOCC4)c4c3-c3ccccc3S(=O)(=O)C4)c2)C1] | 160 | 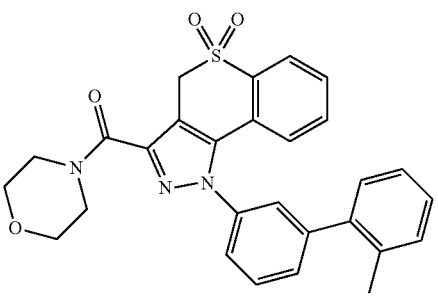 [SMILES: Cc1ccccc1-c1cccc(-n2nc(C(=O)N3CCOCC3)c3c2-c2ccccc2S(=O)(=O)C3)c1] |
| 161 | 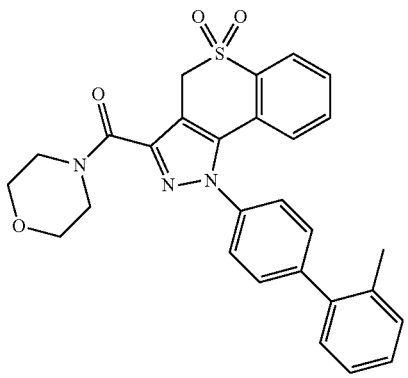 [SMILES: Cc1ccccc1-c1ccc(-n2nc(C(=O)N3CCOCC3)c3c2-c2ccccc2S(=O)(=O)C3)cc1] | 162 | 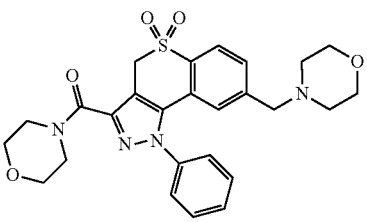 [SMILES: O=C(c1nn(-c2ccccc2)c2c1CS(=O)(=O)c1ccc(CN3CCOCC3)cc1-2)N1CCOCC1] |
| 163 | 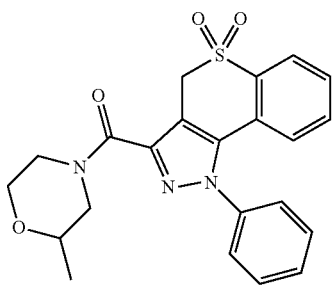 [SMILES: CC1CN(C(=O)c2nn(-c3ccccc3)c3c2CS(=O)(=O)c2ccccc2-3)CCO1] | 164 | 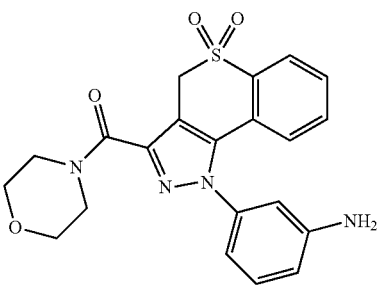 [SMILES: Nc1cccc(-n2nc(C(=O)N3CCOCC3)c3c2-c2ccccc2S(=O)(=O)C3)c1] |

-continued
| Example No | Structures | Example No | Structures |
|---|---|---|---|
| 165 | 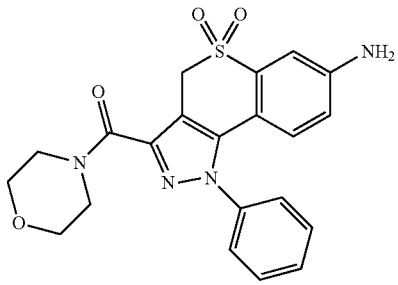 [SMILES: Nc1ccc2c(c1)S(=O)(=O)Cc1c(C(=O)N3CCOCC3)nn(-c3ccccc3)c1-2] | 166 | 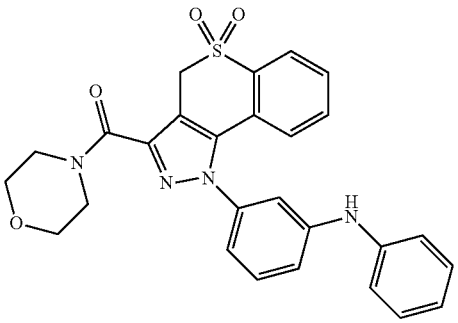 [SMILES: O=C(c1nn(-c2cccc(Nc3ccccc3)c2)c2c1CS(=O)(=O)c1ccccc1-2)N1CCOCC1] |
| 167 | 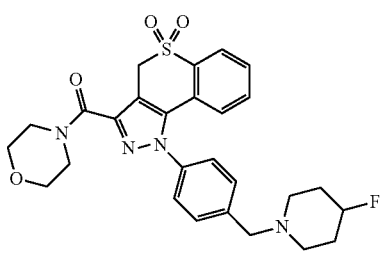 [SMILES: O=C(c1nn(-c2ccc(CN3CCC(F)CC3)cc2)c2c1CS(=O)(=O)c1ccccc1-2)N1CCOCC1] | 168 | 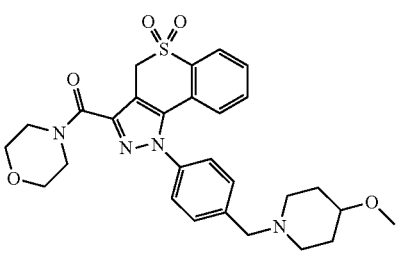 [SMILES: COC1CCN(Cc2ccc(-n3nc(C(=O)N4CCOCC4)c4c3-c3ccccc3S(=O)(=O)C4)cc2)CC1] |
| 169 | 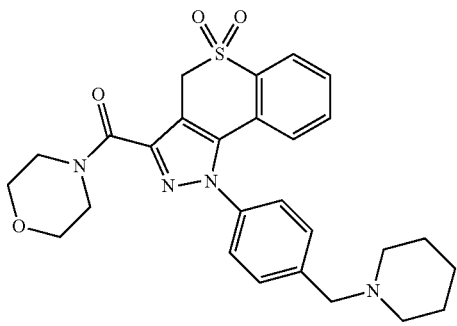 [SMILES: O=C(c1nn(-c2ccc(CN3CCCCC3)cc2)c2c1CS(=O)(=O)c1ccccc1-2)N1CCOCC1] | 170 | 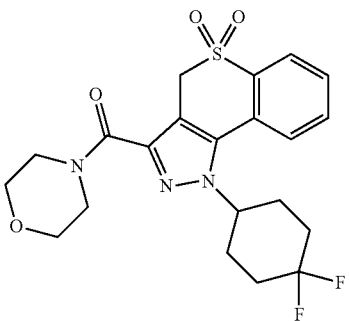 [SMILES: O=C(c1nn(C2CCC(F)(F)CC2)c2c1CS(=O)(=O)c1ccccc1-2)N1CCOCC1] |
| 171 | 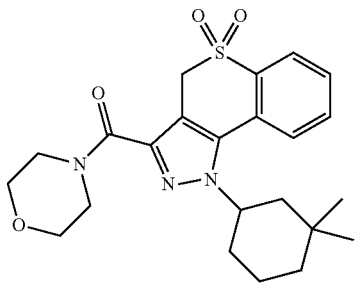 [SMILES: CC1(C)CCCC(n2nc(C(=O)N3CCOCC3)c3c2-c2ccccc2S(=O)(=O)C3)C1] | 172 | 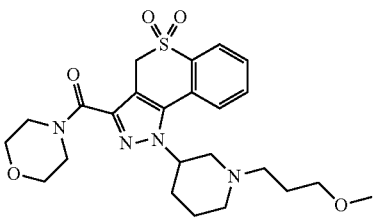 [SMILES: COCCCN1CCCC(n2nc(C(=O)N3CCOCC3)c3c2-c2ccccc2S(=O)(=O)C3)C1] |
| 173 | 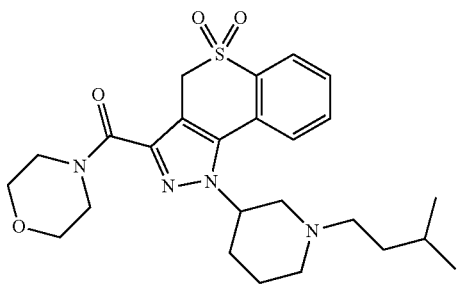 [SMILES: CC(C)CCN1CCCC(n2nc(C(=O)N3CCOCC3)c3c2-c2ccccc2S(=O)(=O)C3)C1] | 174 | 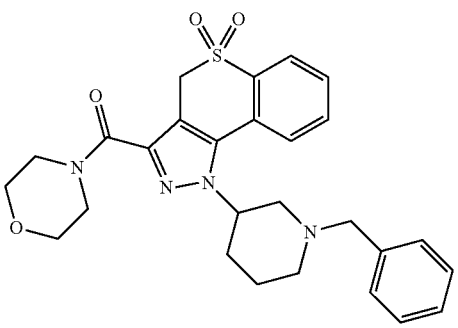 [SMILES: O=C(c1nn(C2CCCN(Cc3ccccc3)C2)c2c1CS(=O)(=O)c1ccccc1-2)N1CCOCC1] |

-continued
| Example No | Structures | Example No | Structures |
|---|---|---|---|
| 175 | 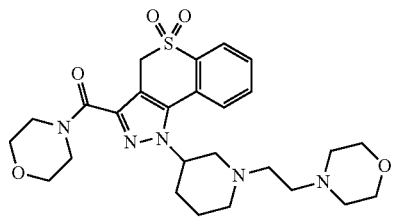 [SMILES: O=C(c1nn(C2CCCN(CCN3CCOCC3)C2)c2c1CS(=O)(=O)c1ccccc1-2)N1CCOCC1] | 176 | 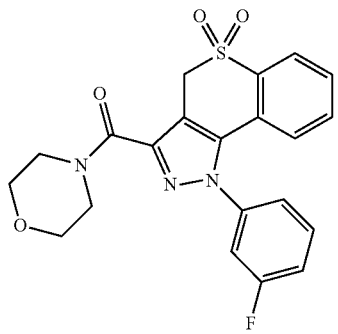 [SMILES: O=C(c1nn(-c2cccc(F)c2)c2c1CS(=O)(=O)c1ccccc1-2)N1CCOCC1] |
| 177 | 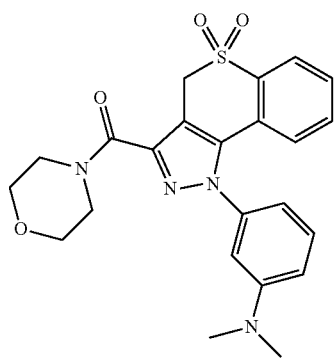 [SMILES: CN(C)c1cccc(-n2nc(C(=O)N3CCOCC3)c3c2-c2ccccc2S(=O)(=O)C3)c1] | 178 | 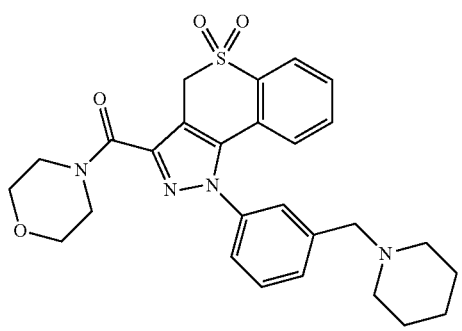 |
| 179 | 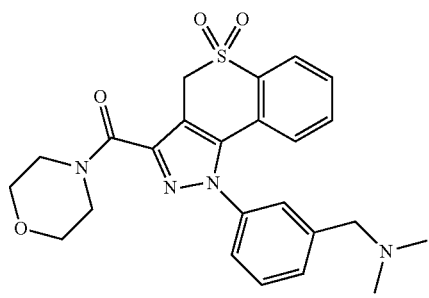 [SMILES: CN(C)Cc1cccc(-n2nc(C(=O)N3CCOCC3)c3c2-c2ccccc2S(=O)(=O)C3)c1] | 180 | 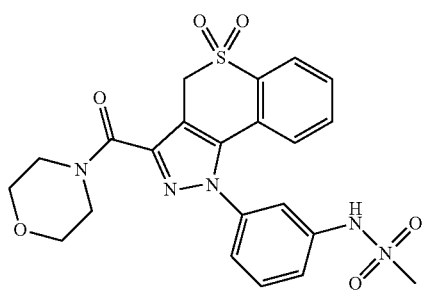 |
| 181 | 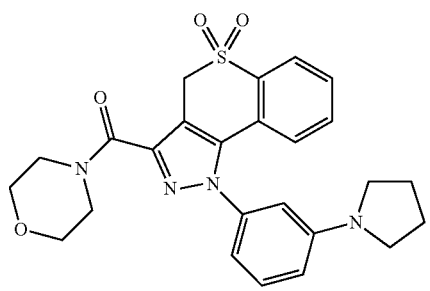 [SMILES: O=C(c1nn(-c2cccc(N3CCCC3)c2)c2c1CS(=O)(=O)c1ccccc1-2)N1CCOCC1] | 182 | 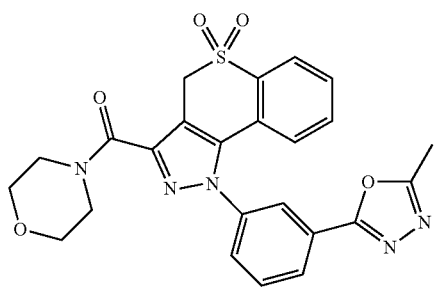 [SMILES: Cc1nnc(-c2cccc(-n3nc(C(=O)N4CCOCC4)c4c3-c3ccccc3S(=O)(=O)C4)c2)o1] |
| 183 | 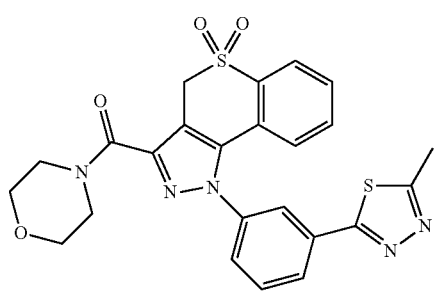 [SMILES: Cc1nnc(-c2cccc(-n3nc(C(=O)N4CCOCC4)c4c3-c3ccccc3S(=O)(=O)C4)c2)s1] | 184 | 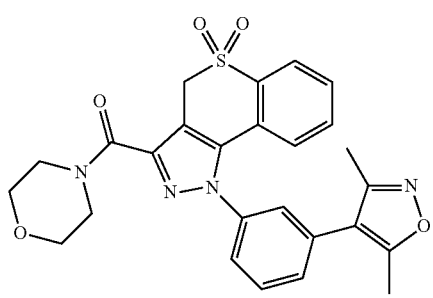 [SMILES: Cc1noc(C)c1-c1cccc(-n2nc(C(=O)N3CCOCC3)c3c2-c2ccccc2S(=O)(=O)C3)c1] |

-continued
| Example No | Structures | Example No | Structures |
|---|---|---|---|
| 185 | 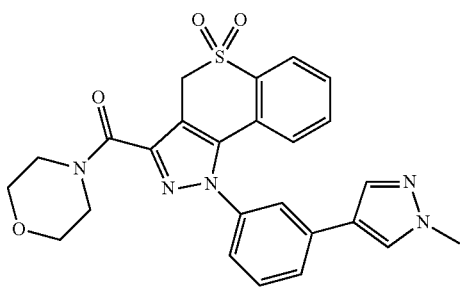 [SMILES: Cn1cc(-c2cccc(-n3nc(C(=O)N4CCOCC4)c4c3-c3ccccc3S(=O)(=O)C4)c2)cn1] | 186 | 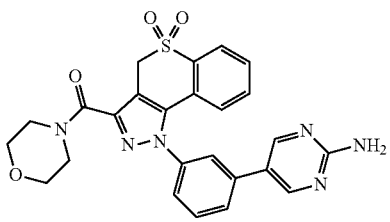 [SMILES: Nc1ncc(-c2cccc(-n3nc(C(=O)N4CCOCC4)c4c3-c3ccccc3S(=O)(=O)C4)c2)cn1] |
| 187 | 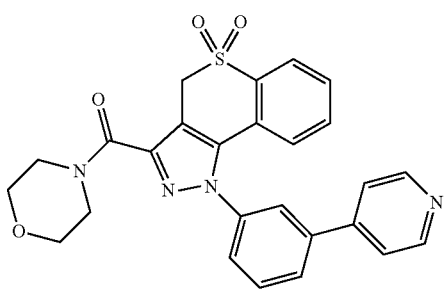 [SMILES: O=C(c1nn(-c2cccc(-c3ccncc3)c2)c2c1CS(=O)(=O)c1ccccc1-2)N1CCOCC1] | 188 | 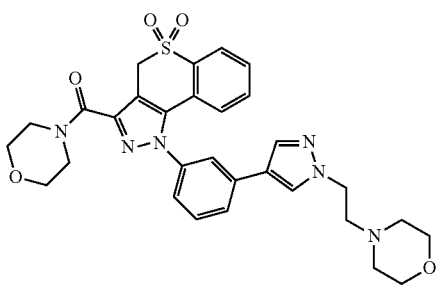 [SMILES: O=C(c1nn(-c2cccc(-c3cnn(CCN4CCOCC4)c3)c2)c2c1CS(=O)(=O)c1ccccc1-2)N1CCOCC1] |
| 189 | 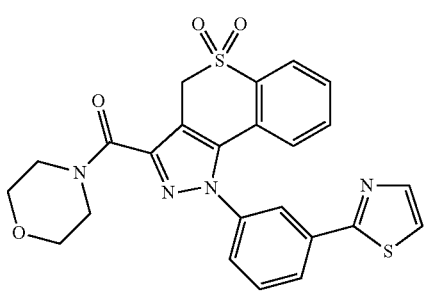 [SMILES: O=C(c1nn(-c2cccc(-c3nccs3)c2)c2c1CS(=O)(=O)c1ccccc1-2)N1CCOCC1] | 190 | 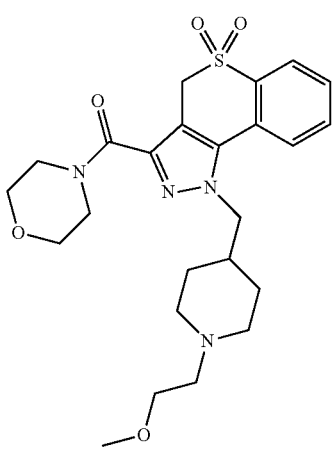 [SMILES: COCCN1CCC(Cn2nc(C(=O)N3CCOCC3)c3c2-c2ccccc2S(=O)(=O)C3)CC1] |
| 191 | 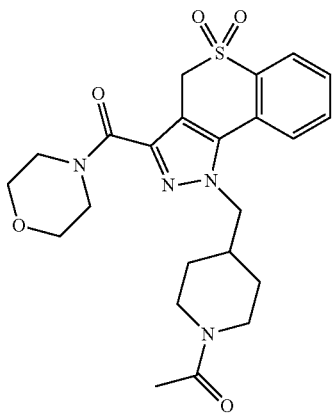 [SMILES: CC(=O)N1CCC(Cn2nc(C(=O)N3CCOCC3)c3c2-c2ccccc2S(=O)(=O)C3)CC1] | 192 | 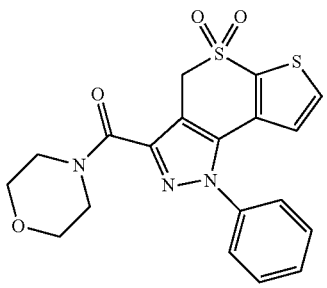 [SMILES: O=C(c1nn(-c2ccccc2)c2c1CS(=O)(=O)c1sccc1-2)N1CCOCC1] |

-continued
| Example No | Structures | Example No | Structures |
|---|---|---|---|
| 193 | 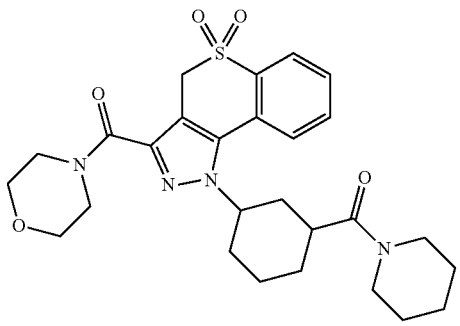 [SMILES: O=C(c1nn(C2CCCC(C(=O)N3CCCCC3)C2)c2c1CS(=O)(=O)c1ccccc1-2)N1CCOCC1] | 194 | 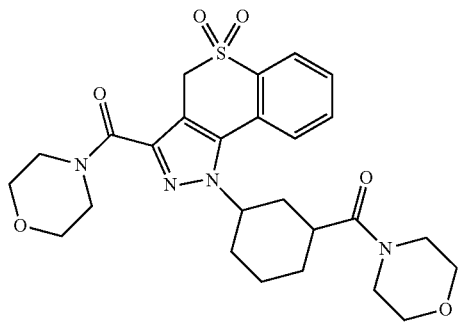 |
| 195 | 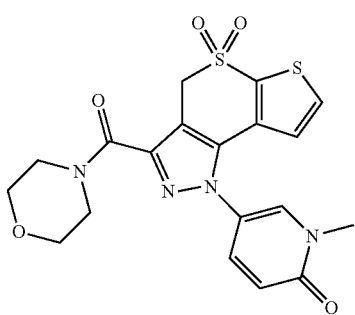 [SMILES: Cn1cc(-n2nc(C(=O)N3CCOCC3)c3c2-c2ccsc2S(=O)(=O)C3)ccc1=O] | 196 | 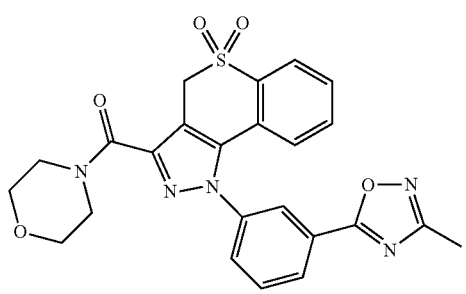 [SMILES: Cc1noc(-c2cccc(-n3nc(C(=O)N4CCOCC4)c4c3-c3ccccc3S(=O)(=O)C4)c2)n1] |
| 197 | 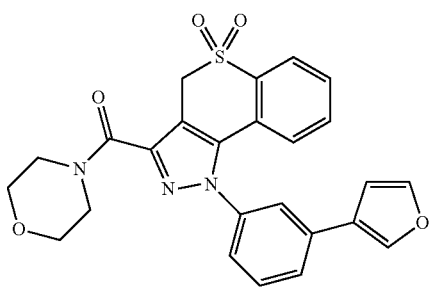 [SMILES: O=C(c1nn(-c2cccc(-c3ccoc3)c2)c2c1CS(=O)(=O)c1ccccc1-2)N1CCOCC1] | 198 | 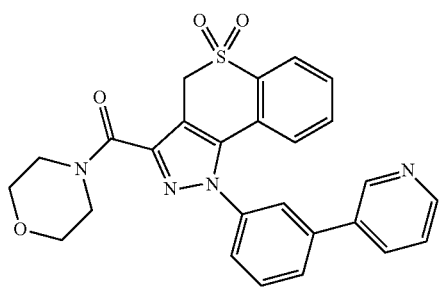 |
| 199 | 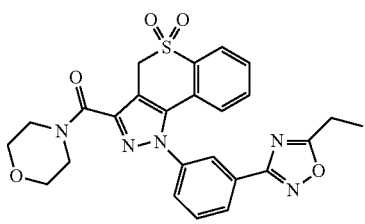 [SMILES: CCc1nc(-c2cccc(-n3nc(C(=O)N4CCOCC4)c4c3-c3ccccc3S(=O)(=O)C4)c2)no1] | 200 | 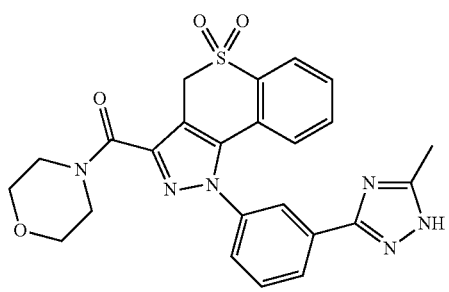 [SMILES: Cc1nc(-c2cccc(-n3nc(C(=O)N4CCOCC4)c4c3-c3ccccc3S(=O)(=O)C4)c2)n[nH]1] |
| 201 | 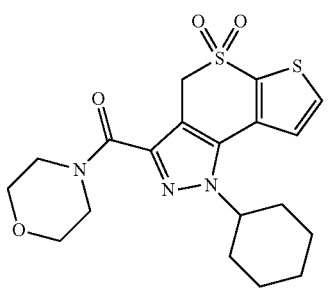 | 202 | 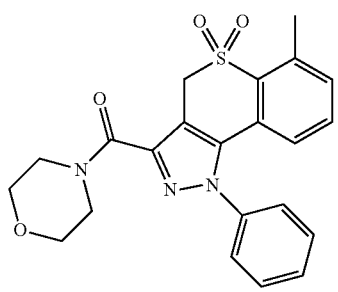 |

-continued
| Example No | Structures | Example No | Structures |
|---|---|---|---|
| 203 | 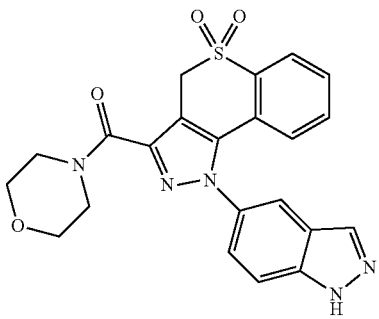 [SMILES: O=C(c1nn(-c2ccc3[nH]ncc3c2)c2c1CS(=O)(=O)c1ccccc1-2)N1CCOCC1] | 204 | 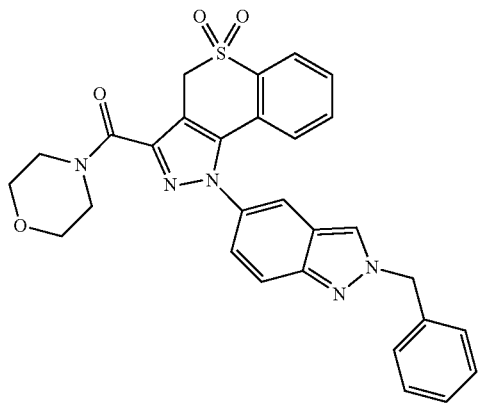 [SMILES: O=C(c1nn(-c2ccc3nn(Cc4ccccc4)cc3c2)c2c1CS(=O)(=O)c1ccccc1-2)N1CCOCC1] |
| 205 | 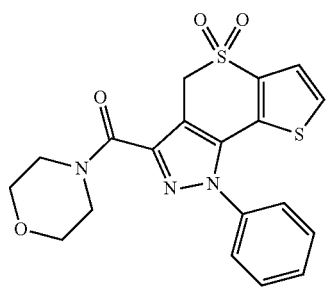 [SMILES: O=C(c1nn(-c2ccccc2)c2c1CS(=O)(=O)c1ccsc1-2)N1CCOCC1] | 206 | 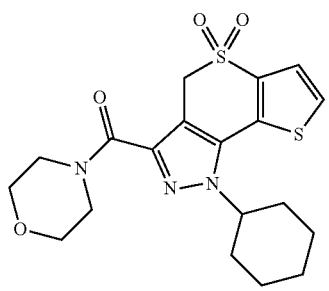 [SMILES: O=C(c1nn(C2CCCCC2)c2c1CS(=O)(=O)c1ccsc1-2)N1CCOCC1] |
| 207 | 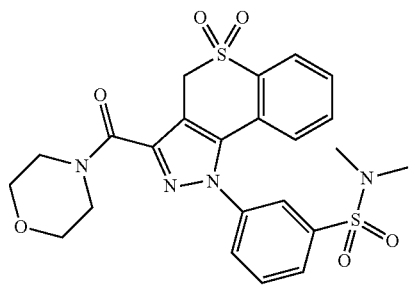 [SMILES: CN(C)S(=O)(=O)c1cccc(-n2nc(C(=O)N3CCOCC3)c3c2-c2ccccc2S(=O)(=O)C3)c1] | 208 | 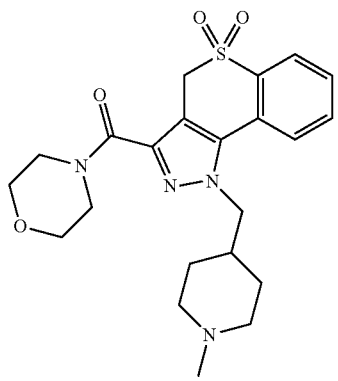 [SMILES: CN1CCC(Cn2nc(C(=O)N3CCOCC3)c3c2-c2ccccc2S(=O)(=O)C3)CC1] |
| 209 | 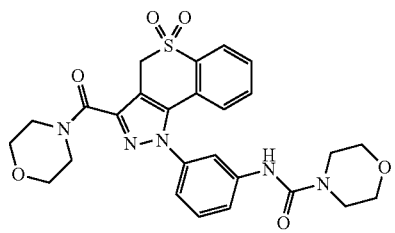 [SMILES: O=C(Nc1cccc(-n2nc(C(=O)N3CCOCC3)c3c2-c2ccccc2S(=O)(=O)C3)c1)N1CCOCC1] | 210 | 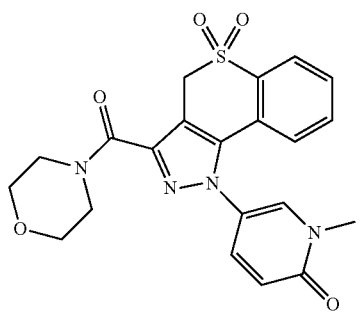 [SMILES: Cn1cc(-n2nc(C(=O)N3CCOCC3)c3c2-c2ccccc2S(=O)(=O)C3)ccc1=O] |

-continued
| Example No | Structures | Example No | Structures |
|---|---|---|---|
| 211 | 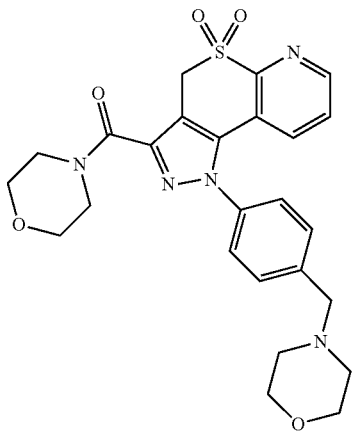 [SMILES: O=C(c1nn(-c2ccc(CN3CCOCC3)cc2)c2c1CS(=O)(=O)c1ncccc1-2)N1CCOCC1] | 212 | 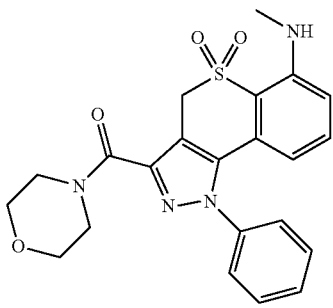 [SMILES: CNc1cccc2c1S(=O)(=O)Cc1c(C(=O)N3CCOCC3)nn(-c3ccccc3)c1-2] |
| 213 | 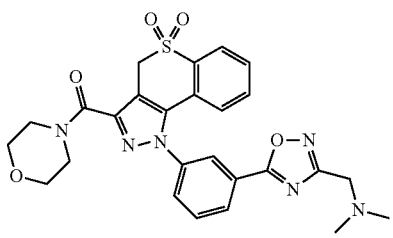 [SMILES: CN(C)Cc1noc(-c2cccc(-n3nc(C(=O)N4CCOCC4)c4c3-c3ccccc3S(=O)(=O)C4)c2)n1] | 214 | 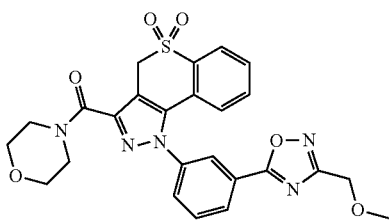 [SMILES: COCc1noc(-c2cccc(-n3nc(C(=O)N4CCOCC4)c4c3-c3ccccc3S(=O)(=O)C4)c2)n1] |
| 215 | 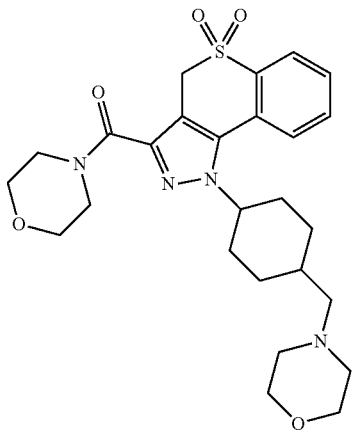 [SMILES: O=C(c1nn(C2CCC(CN3CCOCC3)CC2)c2c1CS(=O)(=O)c1ccccc1-2)N1CCOCC1] | 216 | 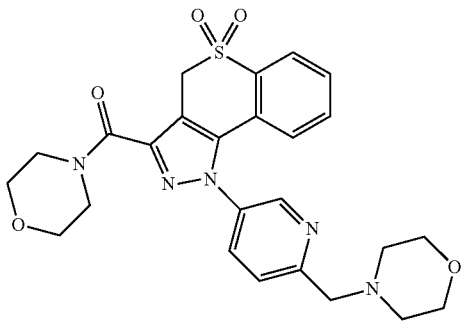 |
| 217 | 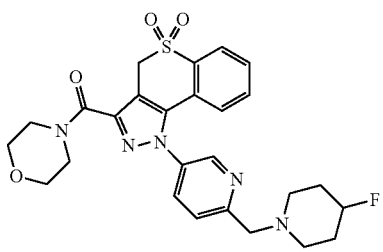 [SMILES: O=C(c1nn(-c2ccc(CN3CCC(F)CC3)nc2)c2c1CS(=O)(=O)c1ccccc1-2)N1CCOCC1] | 218 | 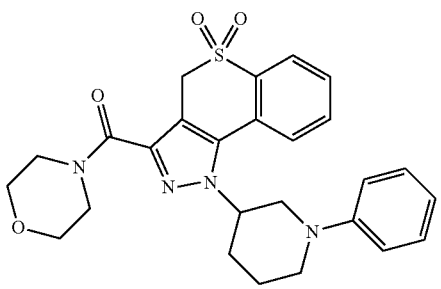 [SMILES: O=C(c1nn(C2CCCN(c3ccccc3)C2)c2c1CS(=O)(=O)c1ccccc1-2)N1CCOCC1] |

-continued

| Example No | Structures | Example No | Structures |
|---|---|---|---|
| 219 | 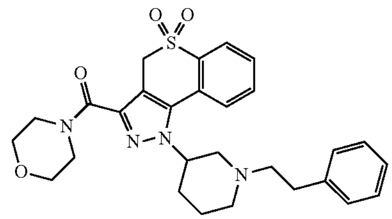 [SMILES: O=C(c1nn(C2CCCN(CCc3ccccc3)C2)c2c1CS(=O)(=O)c1ccccc1-2)N1CCOCC1] | 220 | 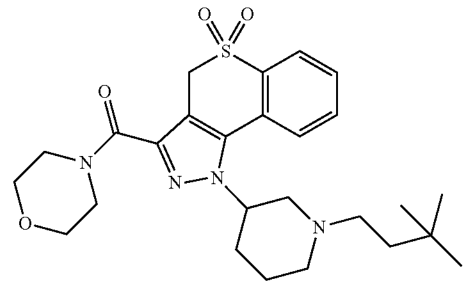 [SMILES: CC(C)(C)CCN1CCCC(n2nc(C(=O)N3CCOCC3)c3c2-c2ccccc2S(=O)(=O)C3)C1] |
| 221 | 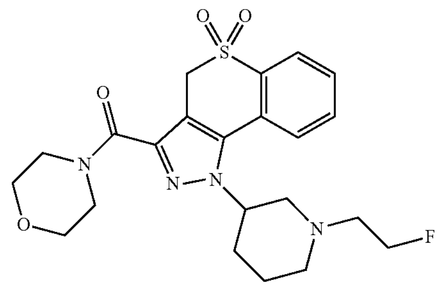 | 222 | 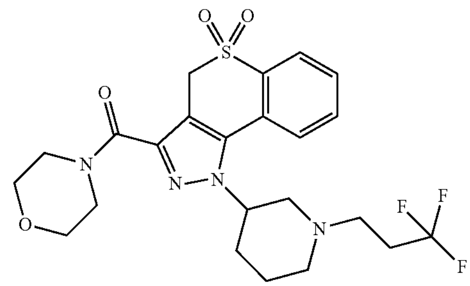 [SMILES: O=C(c1nn(C2CCCN(CCC(F)(F)F)C2)c2c1CS(=O)(=O)c1ccccc1-2)N1CCOCC1] |
| 223 | 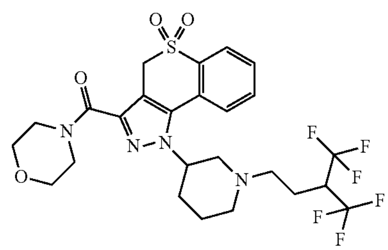 [SMILES: O=C(c1nn(C2CCCN(CCC(C(F)(F)F)C(F)(F)F)C2)c2c1CS(=O)(=O)c1ccccc1-2)N1CCOCC1] | 224 | 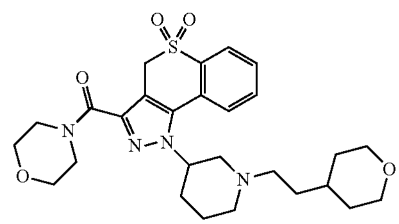 [SMILES: O=C(c1nn(C2CCCN(CCC3CCOCC3)C2)c2c1CS(=O)(=O)c1ccccc1-2)N1CCOCC1] |
| 225 | 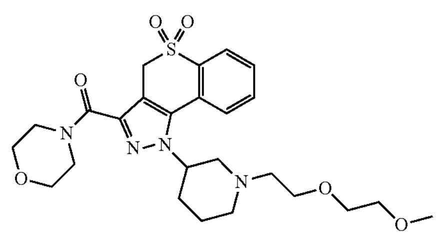 [SMILES: COCCOCCN1CCCC(n2nc(C(=O)N3CCOCC3)c3c2-c2ccccc2S(=O)(=O)C3)C1] | 226 | 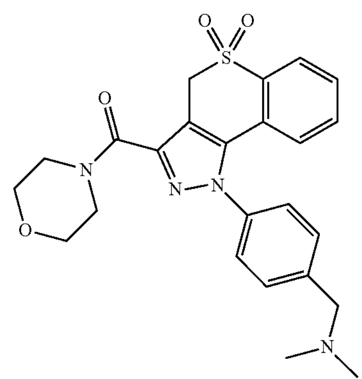 [SMILES: CN(C)Cc1ccc(-n2nc(C(=O)N3CCOCC3)c3c2-c2ccccc2S(=O)(=O)C3)cc1] |

-continued
| Example No | Structures | Example No | Structures |
|---|---|---|---|
| 227 | 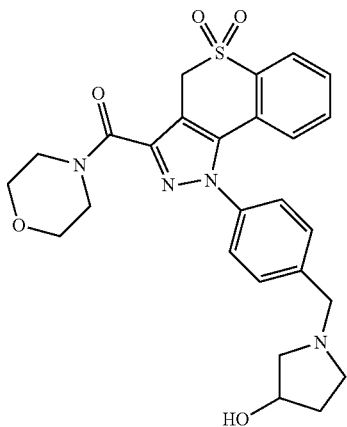 [SMILES: O=C(c1nn(-c2ccc(CN3CCC(O)C3)cc2)c2c1CS(=O)(=O)c1ccccc1-2)N1CCOCC1] | 228 | 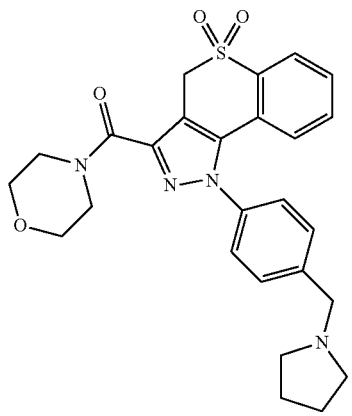 [SMILES: O=C(c1nn(-c2ccc(CN3CCCC3)cc2)c2c1CS(=O)(=O)c1ccccc1-2)N1CCOCC1] |
| 229 | 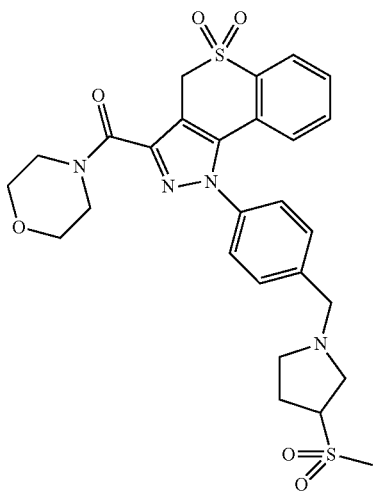 [SMILES: CS(=O)(=O)C1CCN(Cc2ccc(-n3nc(C(=O)N4CCOCC4)c4c3-c3ccccc3S(=O)(=O)C4)cc2)C1] | 230 | 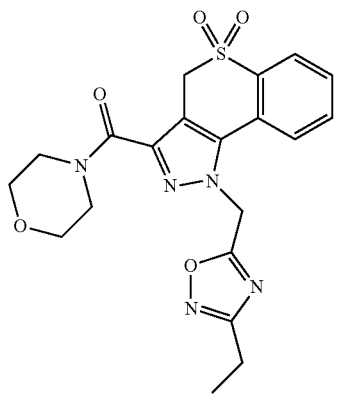 [SMILES: CCc1noc(Cn2nc(C(=O)N3CCOCC3)c3c2-c2ccccc2S(=O)(=O)C3)n1] |
| 231 | 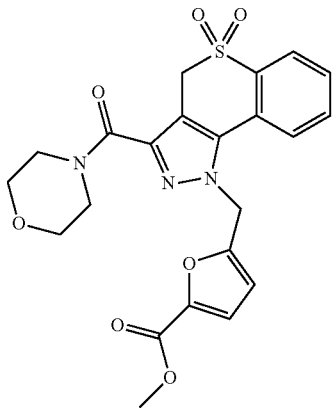 [SMILES: COC(=O)c1ccc(Cn2nc(C(=O)N3CCOCC3)c3c2-c2ccccc2S(=O)(=O)C3)o1] | 232 | 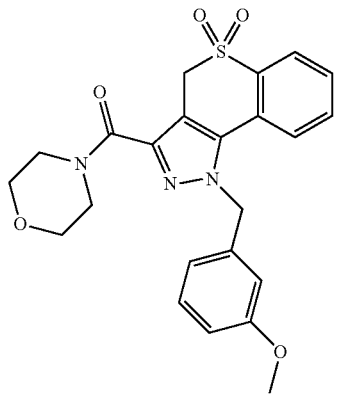 [SMILES: COc1cccc(Cn2nc(C(=O)N3CCOCC3)c3c2-c2ccccc2S(=O)(=O)C3)c1] |

1141                                                                  1142
-continued
| Example No | Structures | Example No | Structures |
|---|---|---|---|
| 233 | 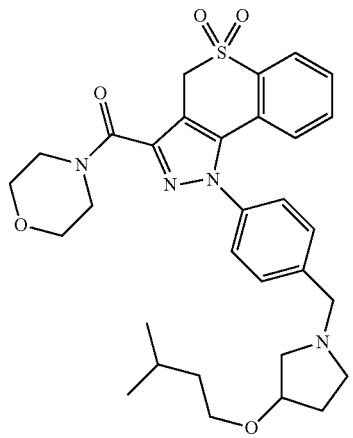 [SMILES: CC(C)CCOC1CCN(Cc2ccc(-n3nc(C(=O)N4CCOCC4)c4c3-c3ccccc3S(=O)(=O)C4)cc2)C1] | 234 | 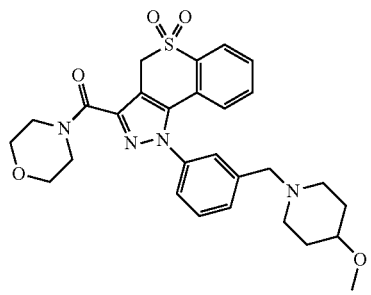 [SMILES: COC1CCN(Cc2cccc(-n3nc(C(=O)N4CCOCC4)c4c3-c3ccccc3S(=O)(=O)C4)c2)CC1] |
| 235 | 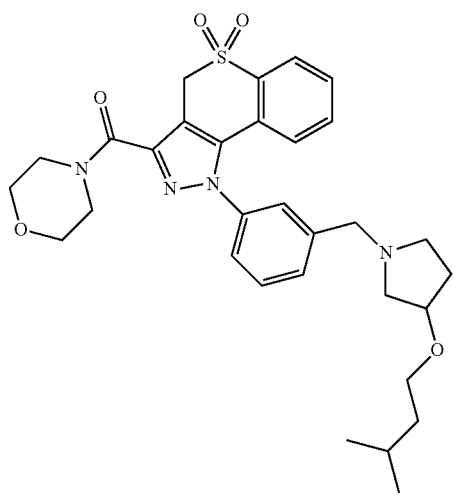 [SMILES: CC(C)CCOC1CCN(Cc2cccc(-n3nc(C(=O)N4CCOCC4)c4c3-c3ccccc3S(=O)(=O)C4)c2)C1] | 236 | 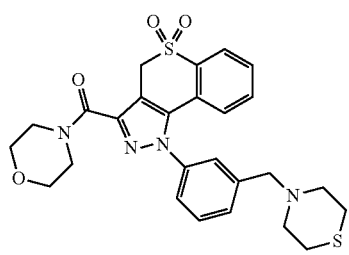 [SMILES: O=C(c1nn(-c2cccc(CN3CCSCC3)c2)c2c1CS(=O)(=O)c1ccccc1-2)N1CCOCC1] |
| 237 | 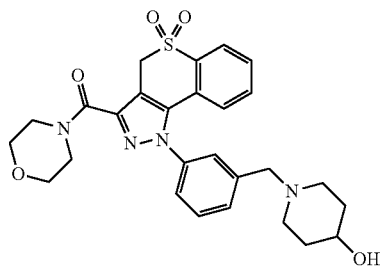 [SMILES: O=C(c1nn(-c2cccc(CN3CCC(O)CC3)c2)c2c1CS(=O)(=O)c1ccccc1-2)N1CCOCC1] | 238 | 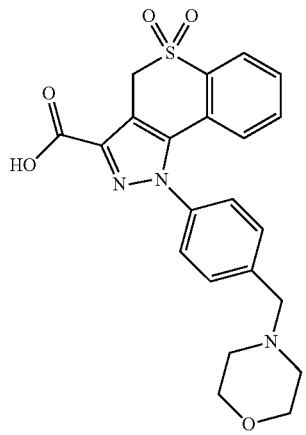 [SMILES: O=C(O)c1nn(-c2ccc(CN3CCOCC3)cc2)c2c1CS(=O)(=O)c1ccccc1-2] |

| Example No | Structures | Example No | Structures |
|---|---|---|---|
| 239 | 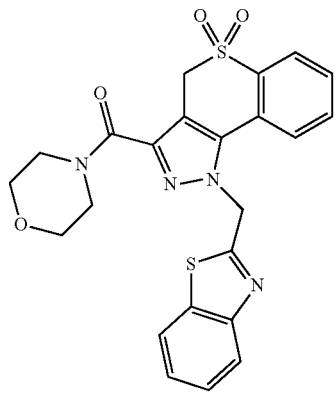 [SMILES: O=C(c1nn(Cc2nc3ccccc3s2)c2c1CS(=O)(=O)c1ccccc1-2)N1CCOCC1] | 240 | 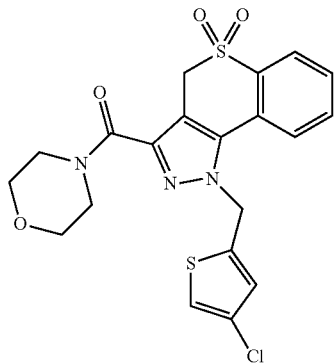 [SMILES: O=C(c1nn(Cc2cc(Cl)cs2)c2c1CS(=O)(=O)c1ccccc1-2)N1CCOCC1] |
| 242 | 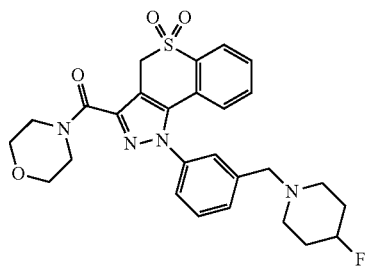 [SMILES: O=C(c1nn(-c2cccc(CN3CCC(F)CC3)c2)c2c1CS(=O)(=O)c1ccccc1-2)N1CCOCC1] | 243 | 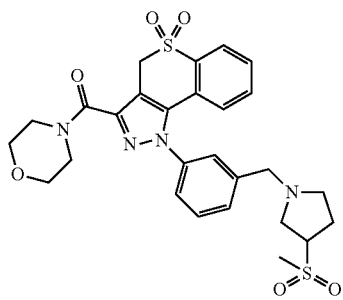 [SMILES: CS(=O)(=O)C1CCN(Cc2cccc(-n3nc(C(=O)N4CCOCC4)c4c3-c3ccccc3S(=O)(=O)C4)c2)C1] |
| 244 | 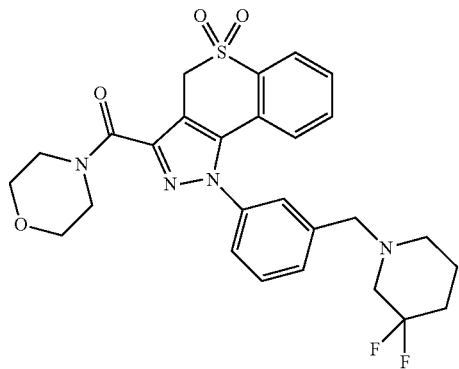 [SMILES: O=C(c1nn(-c2cccc(CN3CCCC(F)(F)C3)c2)c2c1CS(=O)(=O)c1ccccc1-2)N1CCOCC1] | 245 | 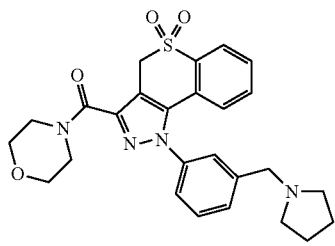 [SMILES: O=C(c1nn(-c2cccc(CN3CCCC3)c2)c2c1CS(=O)(=O)c1ccccc1-2)N1CCOCC1] |
| 246 | 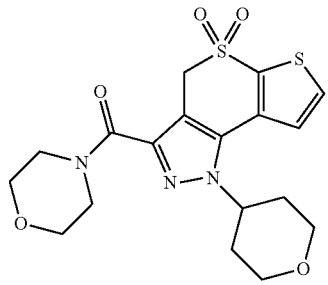 [SMILES: O=C(c1nn(C2CCOCC2)c2c1CS(=O)(=O)c1sccc1-2)N1CCOCC1] | 247 | 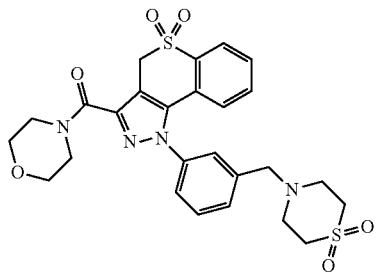 [SMILES: O=C(c1nn(-c2cccc(CN3CCS(=O)(=O)CC3)c2)c2c1CS(=O)(=O)c1ccccc1-2)N1CCOCC1] |

-continued

| Example No | Structures | Example No | Structures |
|---|---|---|---|
| 248 | 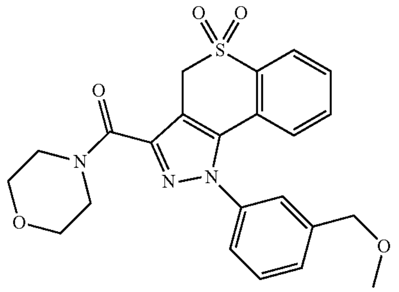 [SMILES: COCc1cccc(-n2nc(C(=O)N3CCOCC3)c3c2-c2ccccc2S(=O)(=O)C3)c1] | 249 | 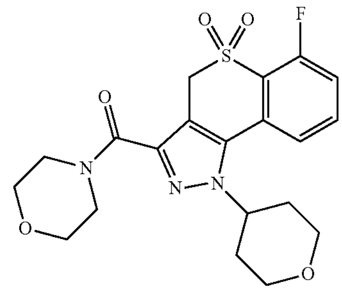 [SMILES: O=C(c1nn(C2CCOCC2)c2c1CS(=O)(=O)c1c(F)cccc1-2)N1CCOCC1] |
| 250 | 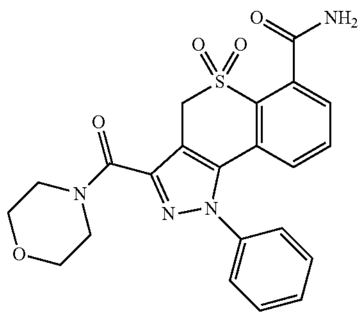 [SMILES: NC(=O)c1cccc2c1S(=O)(=O)Cc1c(C(=O)N3CCOCC3)nn(-c3ccccc3)c1-2] | 251 | 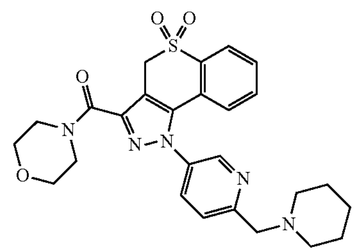 [SMILES: O=C(c1nn(-c2ccc(CN3CCCCC3)nc2)c2c1CS(=O)(=O)c1ccccc1-2)N1CCOCC1] |
| 252 | 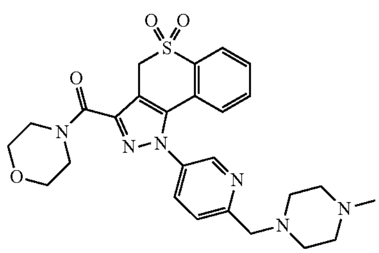 [SMILES: CN1CCN(Cc2ccc(-n3nc(C(=O)N4CCOCC4)c4c3-c3ccccc3S(=O)(=O)C4)cn2)CC1] | 253 | 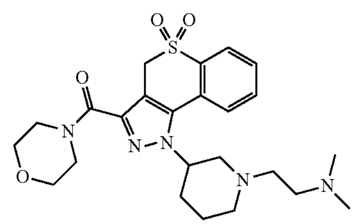 [SMILES: CN(C)CCN1CCCC(n2nc(C(=O)N3CCOCC3)c3c2-c2ccccc2S(=O)(=O)C3)C1] |
| 254 | 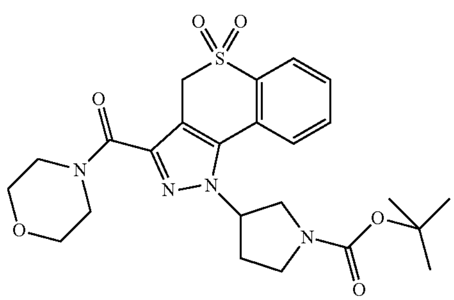 [SMILES: CC(C)(C)OC(=O)N1CCC(n2nc(C(=O)N3CCOCC3)c3c2-c2ccccc2S(=O)(=O)C3)C1] | 255 | 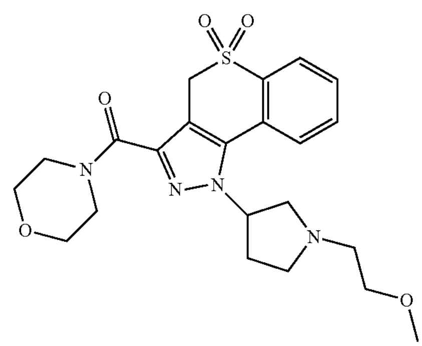 [SMILES: COCCN1CCC(n2nc(C(=O)N3CCOCC3)c3c2-c2ccccc2S(=O)(=O)C3)C1] |
| 256 | 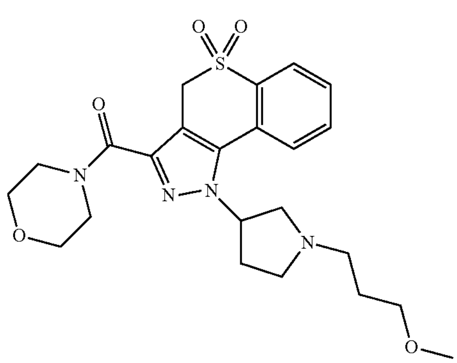 [SMILES: COCCCN1CCC(n2nc(C(=O)N3CCOCC3)c3c2-c2ccccc2S(=O)(=O)C3)C1] | 257 | 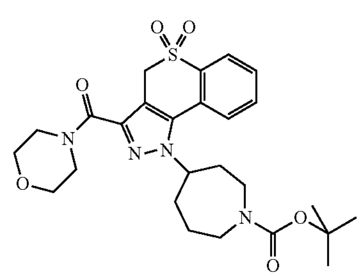 [SMILES: CC(C)(C)OC(=O)N1CCCC(n2nc(C(=O)N3CCOCC3)c3c2-c2ccccc2S(=O)(=O)C3)CC1] |

-continued

| Example No | Structures | Example No | Structures |
|---|---|---|---|
| 258 | 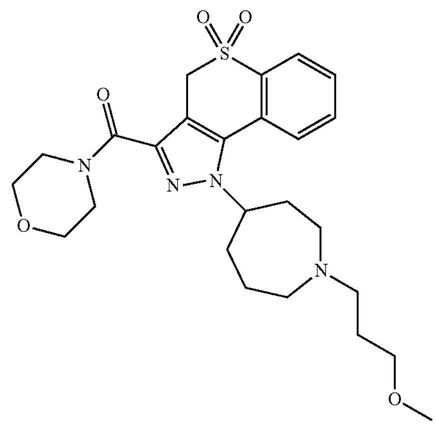 [SMILES: COCCCN1CCCC(n2nc(C(=O)N3CCOCC3)c3c2-c2ccccc2S(=O)(=O)C3)CC1] | 259 | 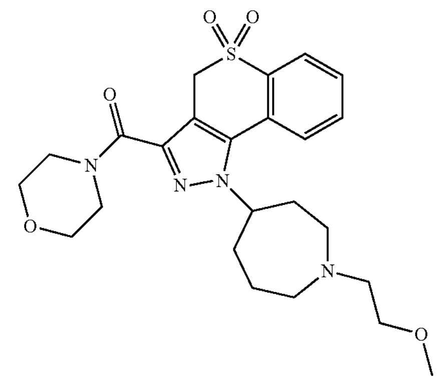 [SMILES: COCCN1CCCC(n2nc(C(=O)N3CCOCC3)c3c2-c2ccccc2S(=O)(=O)C3)CC1] |
| 260 | 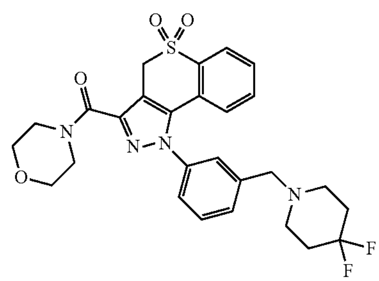 [SMILES: O=C(c1nn(-c2cccc(CN3CCC(F)(F)CC3)c2)c2c1CS(=O)(=O)c1ccccc1-2)N1CCOCC1] | 261 | 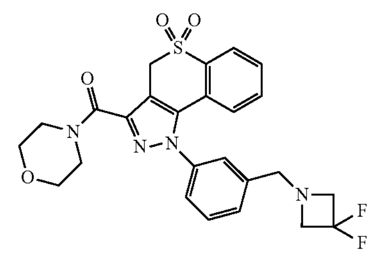 [SMILES: O=C(c1nn(-c2cccc(CN3CC(F)(F)C3)c2)c2c1CS(=O)(=O)c1ccccc1-2)N1CCOCC1] |
| 262 | 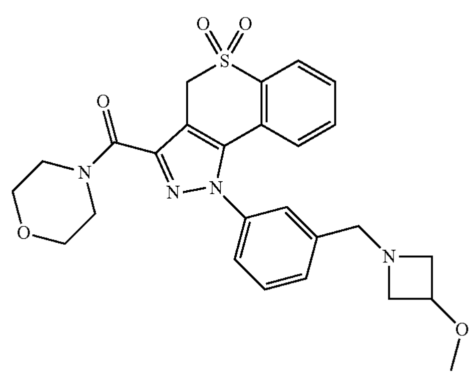 | 263 | 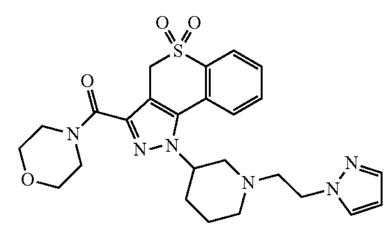 [SMILES: O=C(c1nn(C2CCCN(CCn3cccn3)C2)c2c1CS(=O)(=O)c1ccccc1-2)N1CCOCC1] |
| 264 | 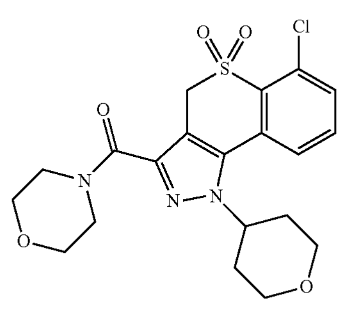 | 265 | 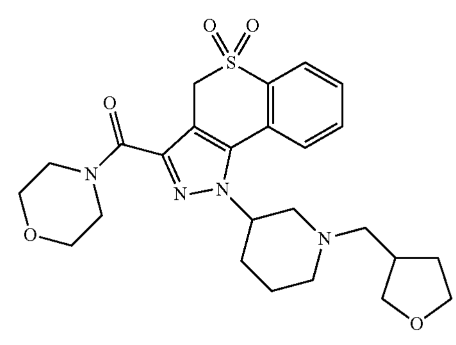 [SMILES: O=C(c1nn(C2CCCN(CC3CCOC3)C2)c2c1CS(=O)(=O)c1ccccc1-2)N1CCOCC1] |

-continued

| Example No | Structures | Example No | Structures |
|---|---|---|---|
| 266 | 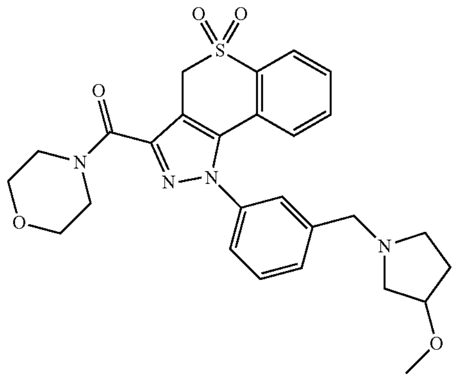 [SMILES: COC1CCN(Cc2cccc(-n3nc(C(=O)N4CCOCC4)c4c3-c3ccccc3S(=O)(=O)C4)c2)C1] | 267 | 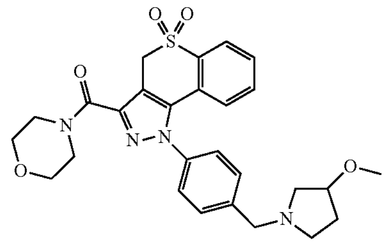 [SMILES: COC1CCN(Cc2ccc(-n3nc(C(=O)N4CCOCC4)c4c3-c3ccccc3S(=O)(=O)C4)cc2)C1] |
| 268 | 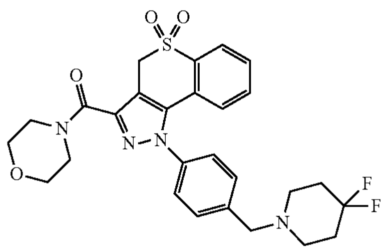 [SMILES: O=C(c1nn(-c2ccc(CN3CCC(F)(F)CC3)cc2)c2c1CS(=O)(=O)c1ccccc1-2)N1CCOCC1] | 269 | 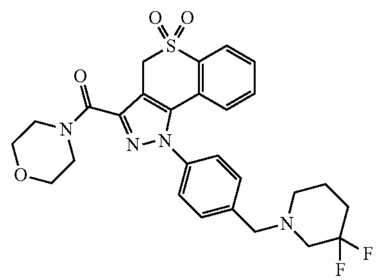 [SMILES: O=C(c1nn(-c2ccc(CN3CCCC(F)(F)C3)cc2)c2c1CS(=O)(=O)c1ccccc1-2)N1CCOCC1] |
| 270 | 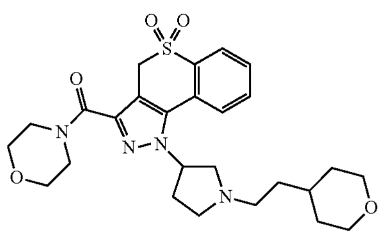 [SMILES: O=C(c1nn(C2CCN(CCC3CCOCC3)C2)c2c1CS(=O)(=O)c1ccccc1-2)N1CCOCC1] | 271 | 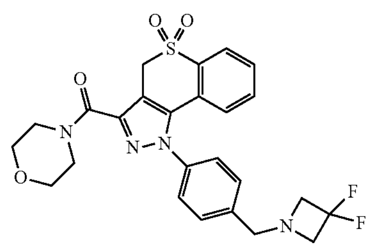 [SMILES: O=C(c1nn(-c2ccc(CN3CC(F)(F)C3)cc2)c2c1CS(=O)(=O)c1ccccc1-2)N1CCOCC1] |
| 272 | 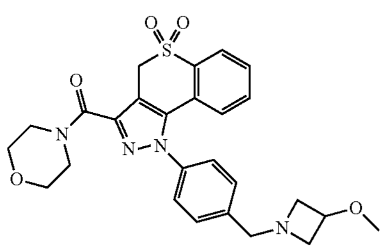 [SMILES: COC1CN(Cc2ccc(-n3nc(C(=O)N4CCOCC4)c4c3-c3ccccc3S(=O)(=O)C4)cc2)C1] | 273 | 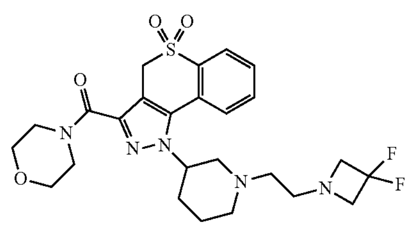 [SMILES: O=C(c1nn(C2CCCN(CCN3CC(F)(F)C3)C2)c2c1CS(=O)(=O)c1ccccc1-2)N1CCOCC1] |
| 274 | 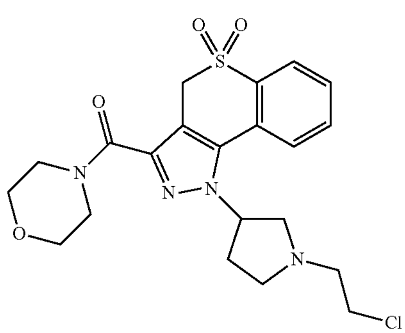 [SMILES: O=C(c1nn(C2CCN(CCCl)C2)c2c1CS(=O)(=O)c1ccccc1-2)N1CCOCC1] | 275 | 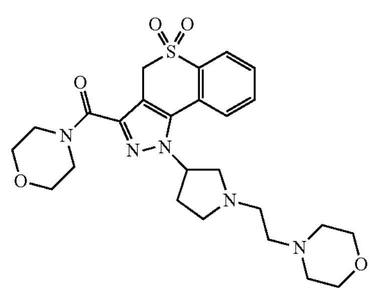 [SMILES: O=C(c1nn(C2CCN(CCN3CCOCC3)C2)c2c1CS(=O)(=O)c1ccccc1-2)N1CCOCC1] |

-continued
| Example No | Structures | Example No | Structures |
|---|---|---|---|
| 276 | 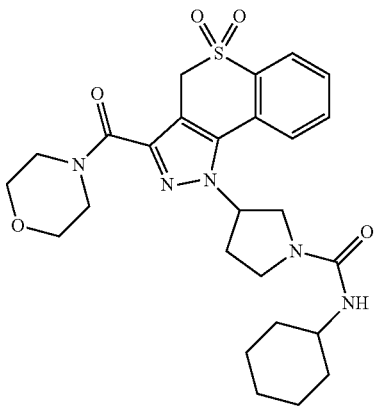 | 277 | 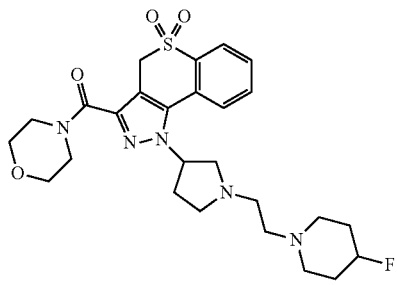 [SMILES: O=C(c1nn(C2CCN(CCN3CCC(F)CC3)C2)c2c1CS(=O)(=O)c1ccccc1-2)N1CCOCC1] |
| 278 | 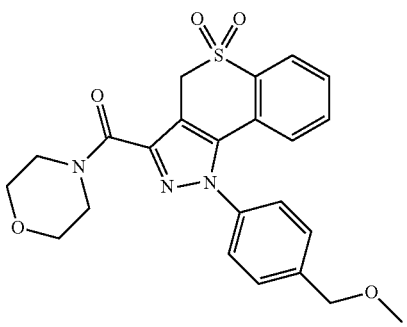 [SMILES: COCc1ccc(-n2nc(C(=O)N3CCOCC3)c3c2-c2ccccc2S(=O)(=O)C3)cc1] | 279 | 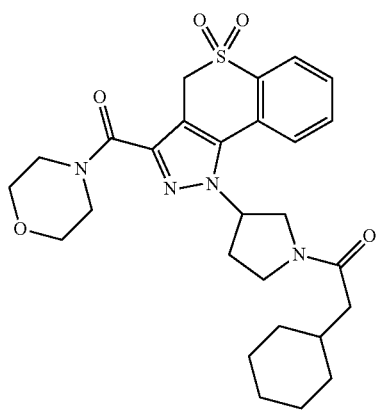 |
| 280 | 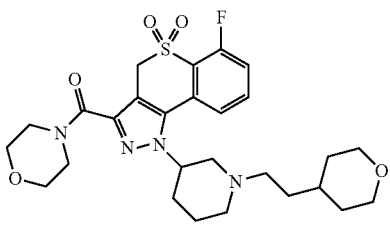 | 281 | 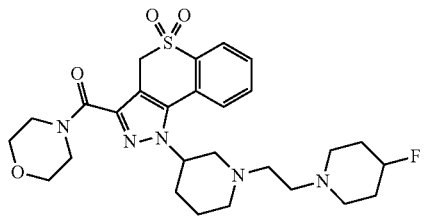 [SMILES: O=C(c1nn(C2CCCN(CCN3CCC(F)CC3)C2)c2c1CS(=O)(=O)c1ccccc1-2)N1CCOCC1] |
| 282 | 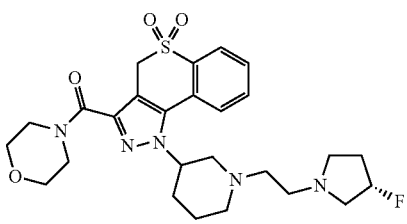 [SMILES: O=C(c1nn(C2CCCN(CCN3CC[C@H](F)C3)C2)c2c1CS(=O)(=O)c1ccccc1-2)N1CCOCC1] | 283 | 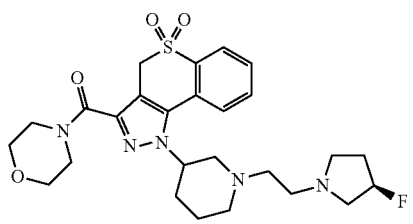 [SMILES: O=C(c1nn(C2CCCN(CCN3CC[C@@H](F)C3)C2)c2c1CS(=O)(=O)c1ccccc1-2)N1CCOCC1] |

-continued
| Example No | Structures | Example No | Structures |
|---|---|---|---|
| 284 | 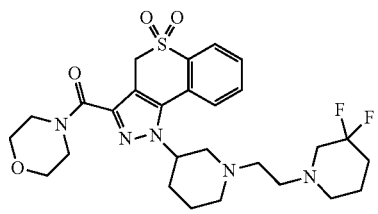 [SMILES: O=C(c1nn(C2CCCN(CCN3CCCC(F)(F)C3)C2)c2c1CS(=O)(=O)c1ccccc1-2)N1CCOCC1] | 285 | 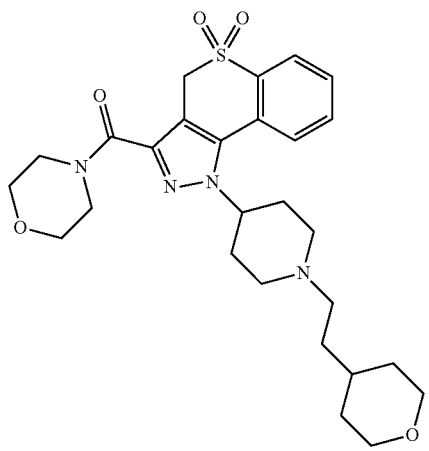 [SMILES: O=C(c1nn(C2CCN(CCC3CCOCC3)CC2)c2c1CS(=O)(=O)c1ccccc1-2)N1CCOCC1] |
| 286 | 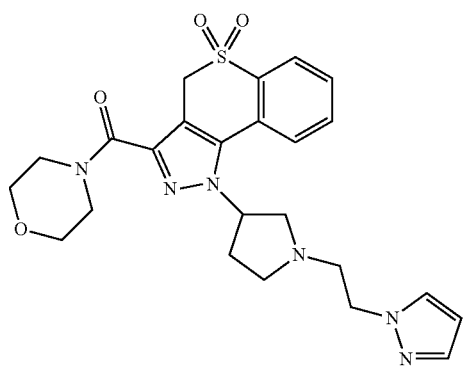 [SMILES: O=C(c1nn(C2CCN(CCn3cccn3)C2)c2c1CS(=O)(=O)c1ccccc1-2)N1CCOCC1] | 287 | 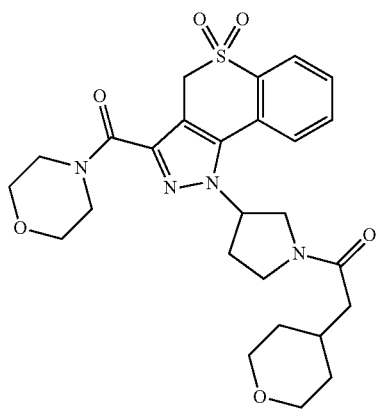 |
| 288 | 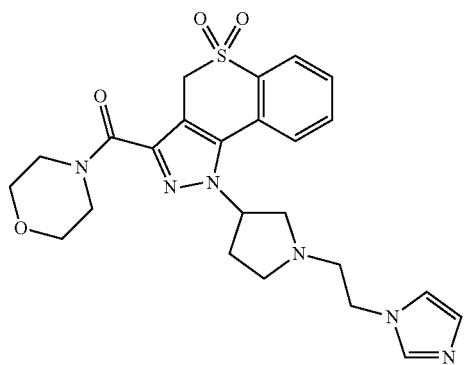 | 289 | 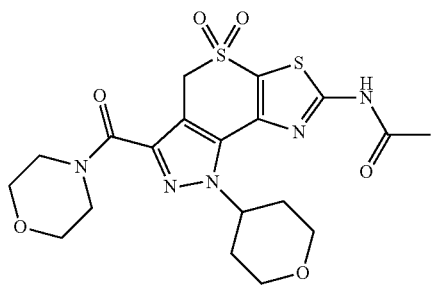 [SMILES: CC(=O)Nc1nc2c(s1)S(=O)(=O)Cc1c(C(=O)N3CCOCC3)nn(C3CCOCC3)c1-2] |

-continued
| Example No | Structures | Example No | Structures |
|---|---|---|---|
| 290 | 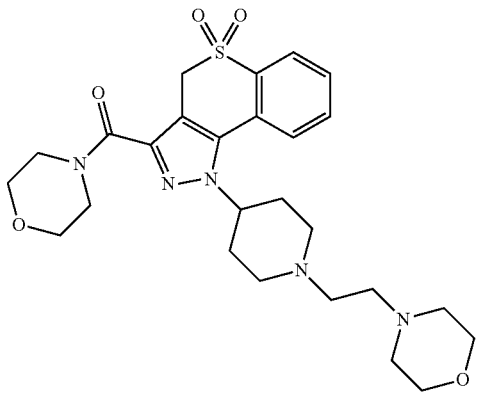 [SMILES: O=C(c1nn(C2CCN(CCN3CCOCC3)CC2)c2c1CS(=O)(=O)c1ccccc1-2)N1CCOCC1] | 291 | 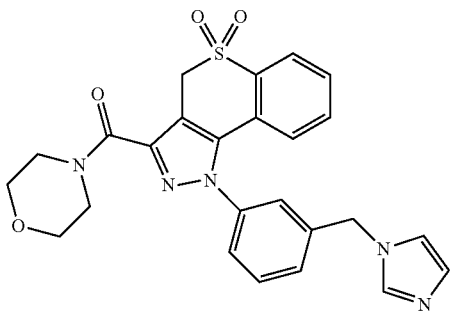 [SMILES: O=C(c1nn(-c2cccc(Cn3ccnc3)c2)c2c1CS(=O)(=O)c1ccccc1-2)N1CCOCC1] |
| 292 | 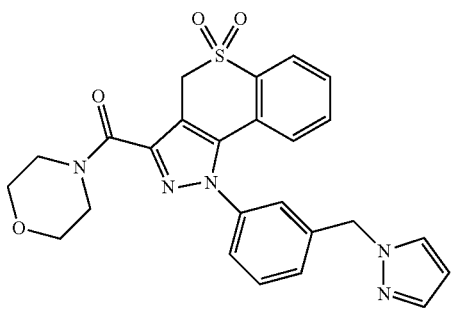 [SMILES: O=C(c1nn(-c2cccc(Cn3cccn3)c2)c2c1CS(=O)(=O)c1ccccc1-2)N1CCOCC1] | 293 | 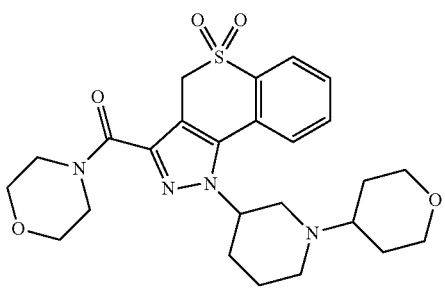 |
| 294 | 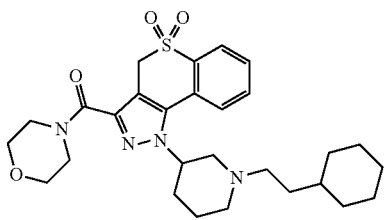 [SMILES: O=C(c1nn(C2CCCN(CCC3CCCCC3)C2)c2c1CS(=O)(=O)c1ccccc1-2)N1CCOCC1] | 295 | 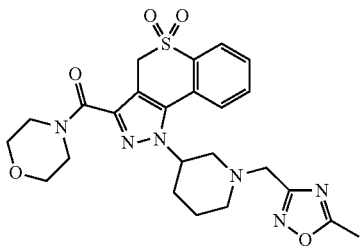 [SMILES: Cc1nc(CN2CCCC(n3nc(C(=O)N4CCOCC4)c4c3-c3ccccc3S(=O)(=O)C4)C2)no1] |
| 296 | 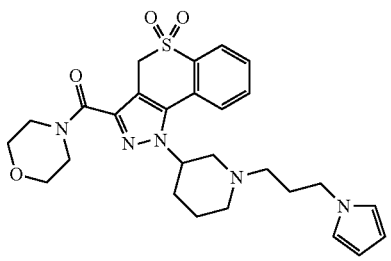 [SMILES: O=C(c1nn(C2CCCN(CCCn3cccc3)C2)c2c1CS(=O)(=O)c1ccccc1-2)N1CCOCC1] | 297 | 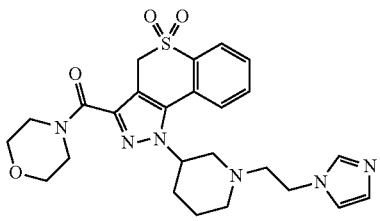 [SMILES: O=C(c1nn(C2CCCN(CCn3ccnc3)C2)c2c1CS(=O)(=O)c1ccccc1-2)N1CCOCC1] |

-continued

| Example No | Structures | Example No | Structures |
|---|---|---|---|
| 298 | | 299 | |
| 300 | | 301 | |
| 302 | | 303 | |
| 304 | | 305 | |

-continued
| Example No | Structures | Example No | Structures |
|---|---|---|---|
| 306 | 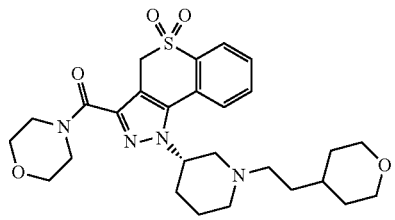 | 307 | 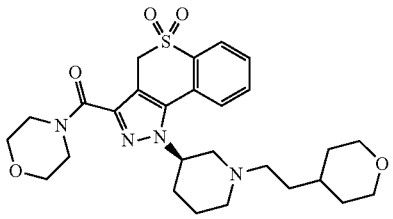 [SMILES: O=C(c1nn([C@@H]2CCCN(CCC3CCOCC3)C2)c2c1CS(=O)(=O)c1ccccc1-2)N1CCOCC1] |
| 308 | 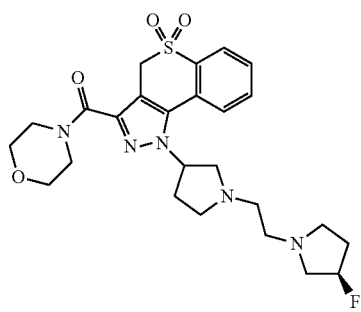 [SMILES: O=C(c1nn(C2CCN(CCN3CC[C@@H](F)C3)C2)c2c1CS(=O)(=O)c1ccccc1-2)N1CCOCC1] | 309 | 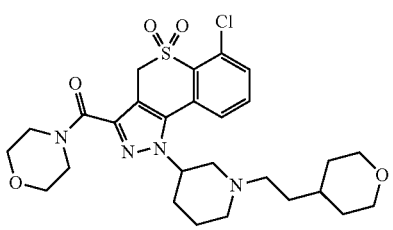 |
| 310 | 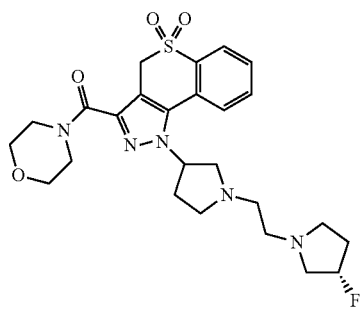 [SMILES: O=C(c1nn(C2CCN(CCN3CC[C@H](F)C3)C2)c2c1CS(=O)(=O)c1ccccc1-2)N1CCOCC1] | 311 | 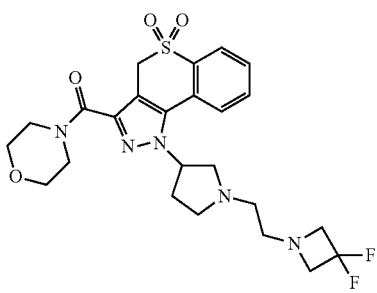 [SMILES: O=C(c1nn(C2CCN(CCN3CC(F)(F)C3)C2)c2c1CS(=O)(=O)c1ccccc1-2)N1CCOCC1] |
| 312 | 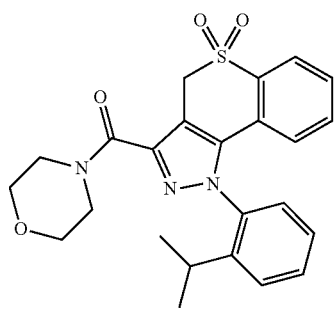 [SMILES: CC(C)c1ccccc1-n1nc(C(=O)N2CCOCC2)c2c1-c1ccccc1S(=O)(=O)C2] | 313 | 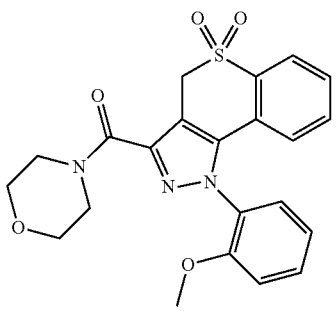 [SMILES: COc1ccccc1-n1nc(C(=O)N2CCOCC2)c2c1-c1ccccc1S(=O)(=O)C2] |
| 314 | 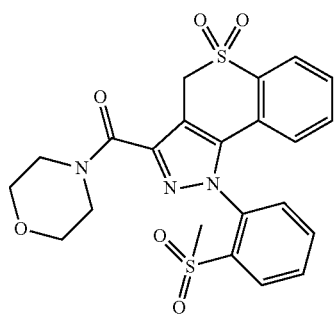 [SMILES: CS(=O)(=O)c1ccccc1-n1nc(C(=O)N2CCOCC2)c2c1-c1ccccc1S(=O)(=O)C2] | 315 | 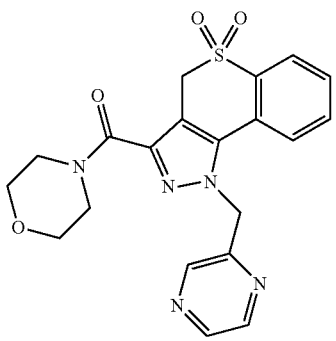 [SMILES: O=C(c1nn(Cc2cnccn2)c2c1CS(=O)(=O)c1ccccc1-2)N1CCOCC1] |

-continued

| Example No | Structures | Example No | Structures |
|---|---|---|---|
| 316 | 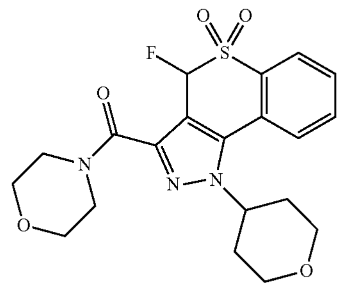 [SMILES: O=C(c1nn(C2CCOCC2)c2c1C(F)S(=O)(=O)c1ccccc1-2)N1CCOCC1] | 317 | 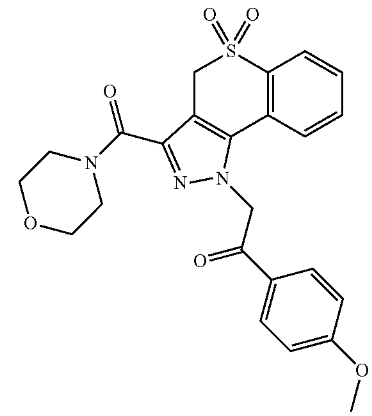 [SMILES: COc1ccc(C(=O)Cn2nc(C(=O)N3CCOCC3)c3c2-c2ccccc2S(=O)(=O)C3)cc1] |
| 318 | 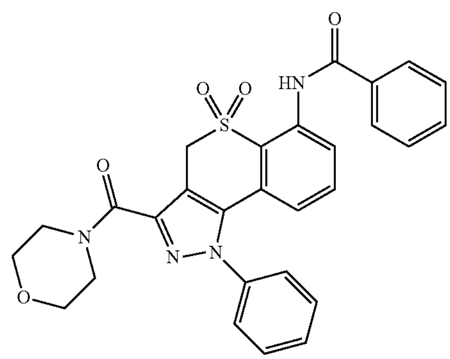 [SMILES: O=C(Nc1cccc2c1S(=O)(=O)Cc1c(C(=O)N3CCOCC3)nn(-c3ccccc3)c1-2)c1ccccc1] | 319 | 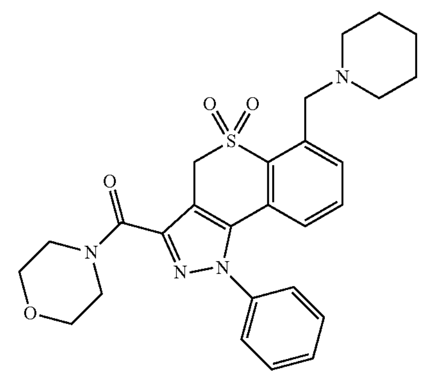 [SMILES: O=C(c1nn(-c2ccccc2)c2c1CS(=O)(=O)c1c(CN3CCCCC3)cccc1-2)N1CCOCC1] |
| 320 | 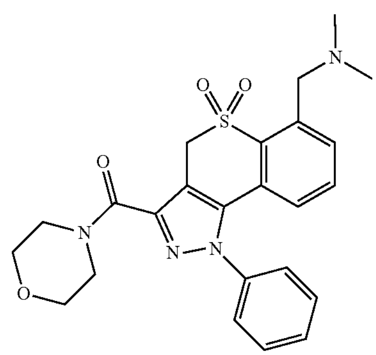 [SMILES: CN(C)Cc1cccc2c1S(=O)(=O)Cc1c(C(=O)N3CCOCC3)nn(-c3ccccc3)c1-2] | 321 | 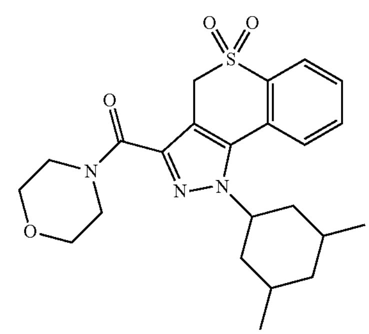 [SMILES: CC1CC(C)CC(n2nc(C(=O)N3CCOCC3)c3c2-c2ccccc2S(=O)(=O)C3)C1] |
| 322 | 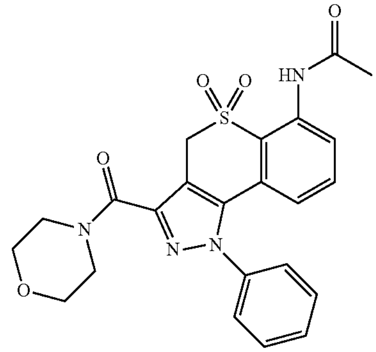 [SMILES: CC(=O)Nc1cccc2c1S(=O)(=O)Cc1c(C(=O)N3CCOCC3)nn(-c3ccccc3)c1-2] | 323 | 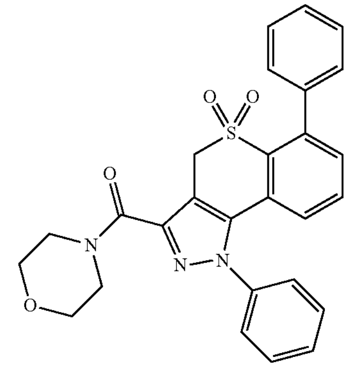 [SMILES: O=C(c1nn(-c2ccccc2)c2c1CS(=O)(=O)c1c(-c3ccccc3)cccc1-2)N1CCOCC1] |

-continued
| Example No | Structures | Example No | Structures |
|---|---|---|---|
| 324 | 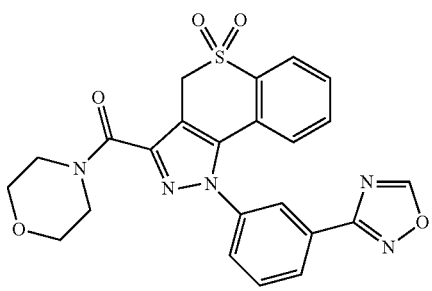 [SMILES: O=C(c1nn(-c2cccc(-c3ncon3)c2)c2c1CS(=O)(=O)c1ccccc1-2)N1CCOCC1] | 325 | 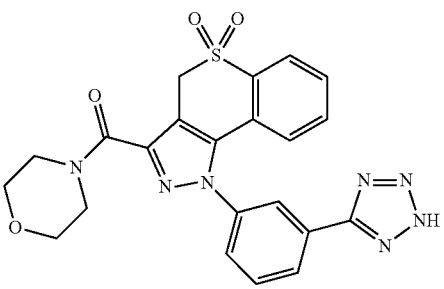 [SMILES: O=C(c1nn(-c2cccc(-c3nn[nH]n3)c2)c2c1CS(=O)(=O)c1ccccc1-2)N1CCOCC1] |
| 326 | 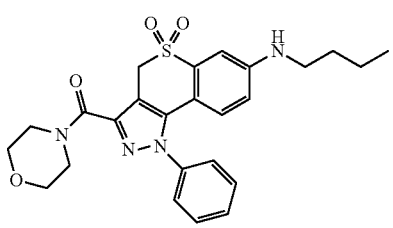 | 327 | 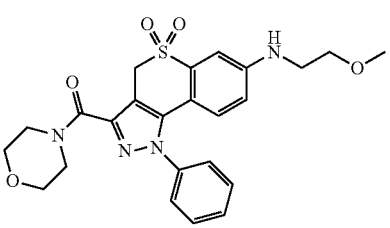 [SMILES: CCCCNc1ccc2c(c1)S(=O)(=O)Cc1c(C(=O)N3CCOCC3)nn(-c3ccccc3)c1-2] |
| 328 | 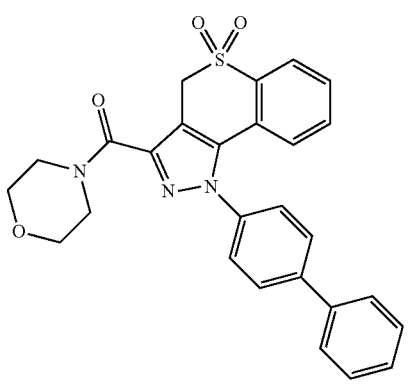 [SMILES: O=C(c1nn(-c2ccc(-c3ccccc3)cc2)c2c1CS(=O)(=O)c1ccccc1-2)N1CCOCC1] | 329 | 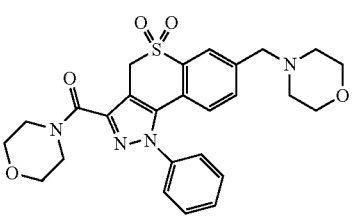 [SMILES: O=C(c1nn(-c2ccccc2)c2c1CS(=O)(=O)c1cc(CN3CCOCC3)ccc1-2)N1CCOCC1] |
| 330 | 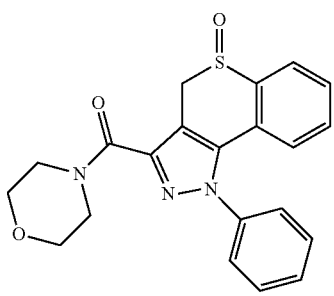 [SMILES: O=C(c1nn(-c2ccccc2)c2c1CS(=O)c1ccccc1-2)N1CCOCC1] | 331 | 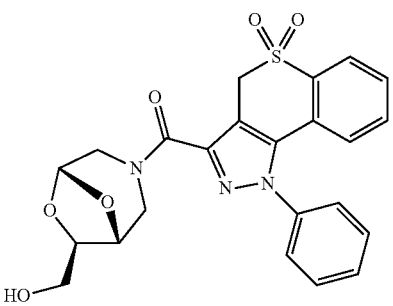 [SMILES: O=C(c1nn(-c2ccccc2)c2c1CS(=O)(=O)c1ccccc1-2)N1C[C@H]2O[C@H](CO)[C@@H](C1)O2] |
| 332 | 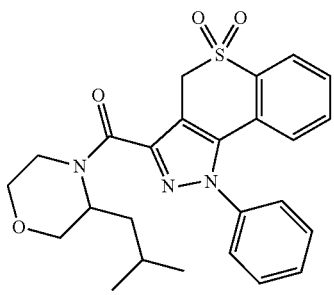 [SMILES: CC(C)CC1COCCN1C(=O)c1nn(-c2ccccc2)c2c1CS(=O)(=O)c1ccccc1-2] | 333 | 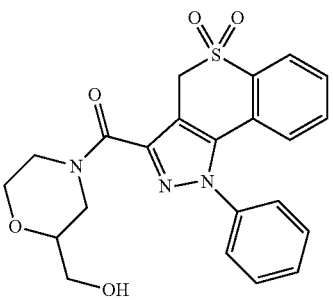 [SMILES: O=C(c1nn(-c2ccccc2)c2c1CS(=O)(=O)c1ccccc1-2)N1CCOC(CO)C1] |

-continued

| Example No | Structures | Example No | Structures |
|---|---|---|---|
| 334 | 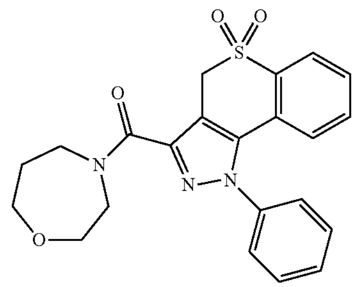 [SMILES: O=C(c1nn(-c2ccccc2)c2c1CS(=O)(=O)c1ccccc1-2)N1CCCOCC1] | 335 | 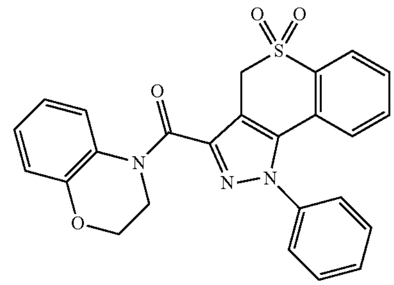 [SMILES: O=C(c1nn(-c2ccccc2)c2c1CS(=O)(=O)c1ccccc1-2)N1CCOc2ccccc21] |
| 336 | 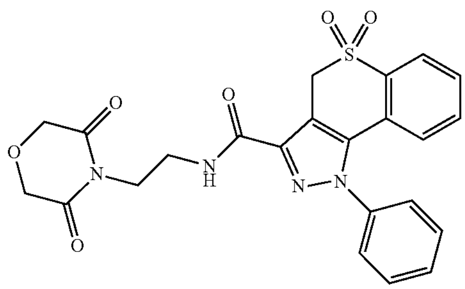 [SMILES: O=C(NCCN1C(=O)COCC1=O)c1nn(-c2ccccc2)c2c1CS(=O)(=O)c1ccccc1-2] | 337 | 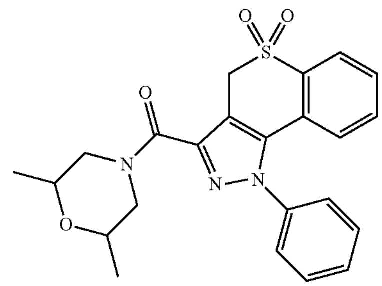 [SMILES: CC1CN(C(=O)c2nn(-c3ccccc3)c3c2CS(=O)(=O)c2ccccc2-3)CC(C)O1] |
| 338 | 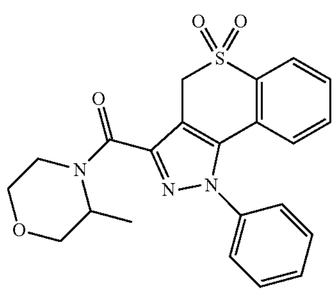 [SMILES: CC1COCCN1C(=O)c1nn(-c2ccccc2)c2c1CS(=O)(=O)c1ccccc1-2] | 339 | 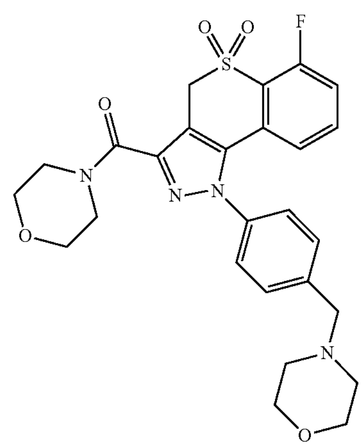 [SMILES: O=C(c1nn(-c2ccc(CN3CCOCC3)cc2)c2c1CS(=O)(=O)c1c(F)cccc1-2)N1CCOCC1] |
| 340 | 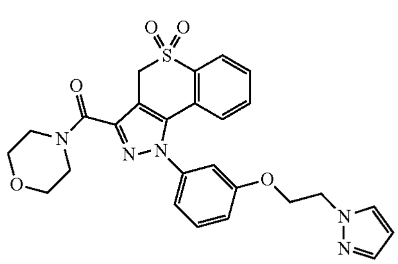 [SMILES: O=C(c1nn(-c2cccc(OCCn3cccn3)c2)c2c1CS(=O)(=O)c1ccccc1-2)N1CCOCC1] | 341 | 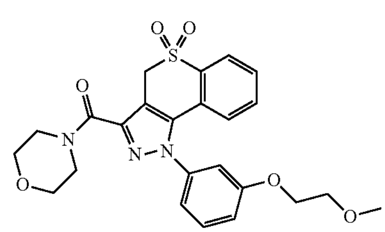 [SMILES: COCCOc1cccc(-n2nc(C(=O)N3CCOCC3)c3c2-c2ccccc2S(=O)(=O)C3)c1] |
| 342 | 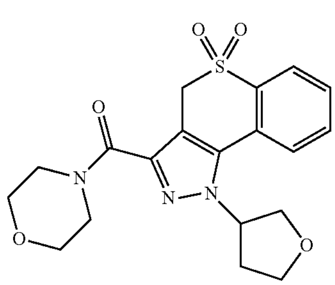 [SMILES: O=C(c1nn(C2CCOC2)c2c1CS(=O)(=O)c1ccccc1-2)N1CCOCC1] | 343 | 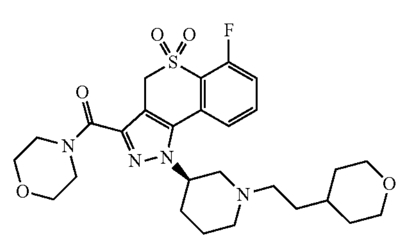 [SMILES: O=C(c1nn([C@@H]2CCCN(CCC3CCOCC3)C2)c2c1CS(=O)(=O)c1c(F)cccc1-2)N1CCOCC1] |

-continued
| Example No | Structures | Example No | Structures |
|---|---|---|---|
| 344 | 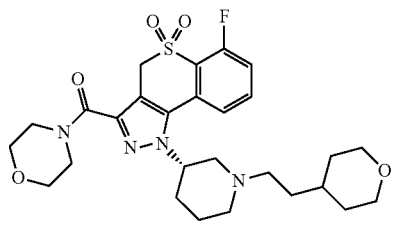 | 345 | 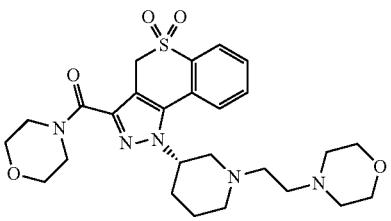 [SMILES: O=C(c1nn([C@H]2CCCN(CCN3CCOCC3)C2)c2c1CS(=O)(=O)c1ccccc1-2)N1CCOCC1] |
| 346 | 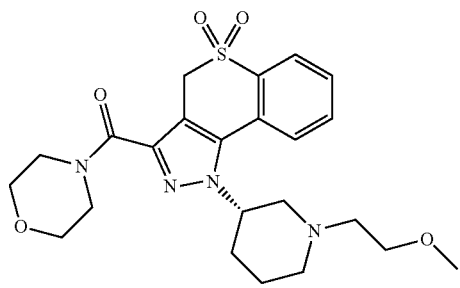 [SMILES: COCCN1CCC[C@H](n2nc(C(=O)N3CCOCC3)c3c2-c2ccccc2S(=O)(=O)C3)C1] | 347 | 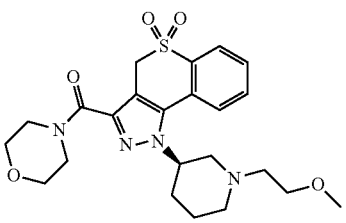 [SMILES: COCCN1CCC[C@@H](n2nc(C(=O)N3CCOCC3)c3c2-c2ccccc2S(=O)(=O)C3)C1] |
| 348 | 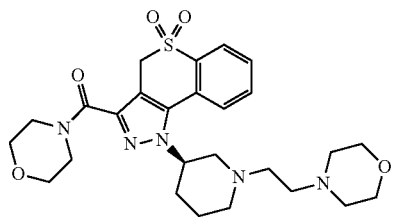 [SMILES: O=C(c1nn([C@@H]2CCCN(CCN3CCOCC3)C2)c2c1CS(=O)(=O)c1ccccc1-2)N1CCOCC1] | 349 | 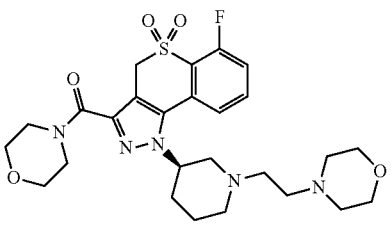 [SMILES: O=C(c1nn([C@@H]2CCCN(CCN3CCOCC3)C2)c2c1CS(=O)(=O)c1c(F)cccc1-2)N1CCOCC1] |
| 350 | 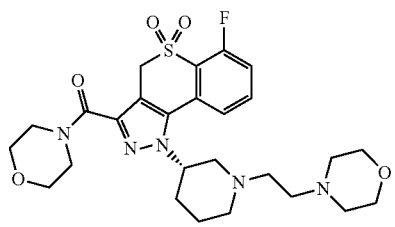 | 353 | 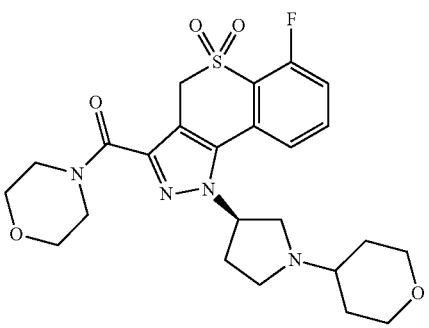 [SMILES: O=C(c1nn([C@@H]2CCN(C3CCOCC3)C2)c2c1CS(=O)(=O)c1c(F)cccc1-2)N1CCOCC1] |
| 354 | 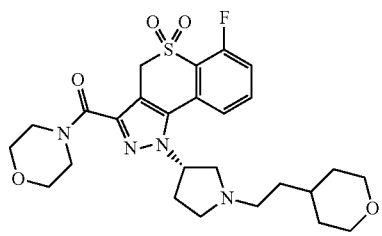 [SMILES: O=C(c1nn([C@H]2CCN(CCC3CCOCC3)C2)c2c1CS(=O)(=O)c1c(F)cccc1-2)N1CCOCC1] | 355 | 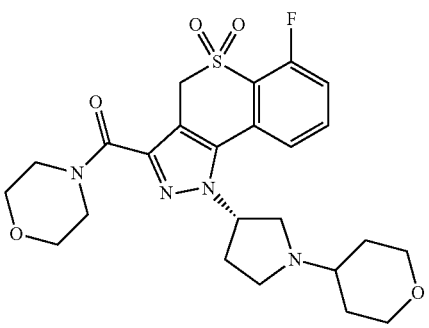 |

-continued

| Example No | Structures | Example No | Structures |
|---|---|---|---|
| 356 | 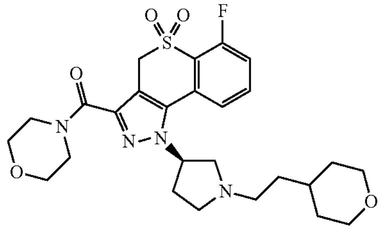 [SMILES: O=C(c1nn([C@@H]2CCN(CCC3CCOCC3)C2)c2c1CS(=O)(=O)c1c(F)cccc1-2)N1CCOCC1] | 357 | 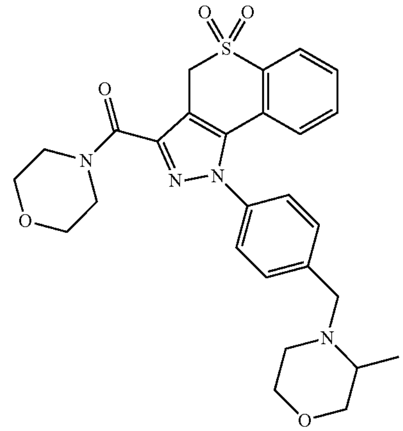 [SMILES: CC1COCCN1Cc1ccc(-n2nc(C(=O)N3CCOCC3)c3c2-c2ccccc2S(=O)(=O)C3)cc1] |
| 358 | 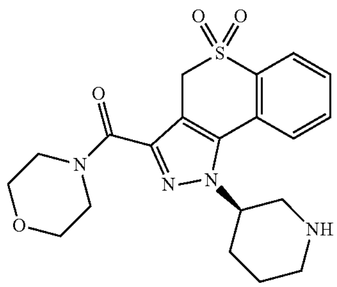 [SMILES: O=C(c1nn([C@@H]2CCCNC2)c2c1CS(=O)(=O)c1ccccc1-2)N1CCOCC1] | 359 | 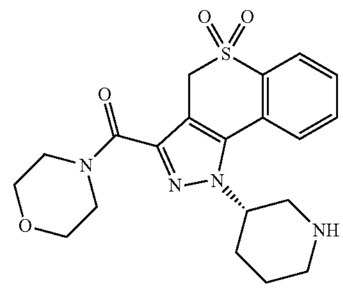 [SMILES: O=C(c1nn([C@H]2CCCNC2)c2c1CS(=O)(=O)c1ccccc1-2)N1CCOCC1] |
| 360 | 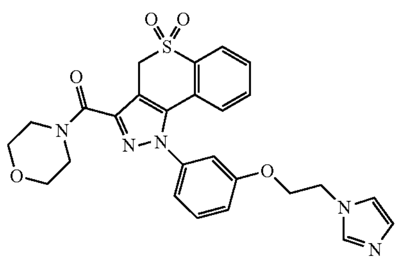 [SMILES: O=C(c1nn(-c2cccc(OCCn3ccnc3)c2)c2c1CS(=O)(=O)c1ccccc1-2)N1CCOCC1] | 361 | 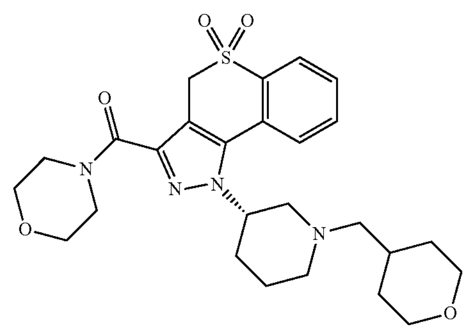 [SMILES: O=C(c1nn([C@H]2CCCN(CC3CCOCC3)C2)c2c1CS(=O)(=O)c1ccccc1-2)N1CCOCC1] |
| 362 | 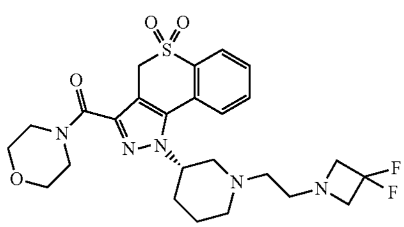 [SMILES: O=C(c1nn([C@H]2CCCN(CCN3CC(F)(F)C3)C2)c2c1CS(=O)(=O)c1ccccc1-2)N1CCOCC1] | 363 | 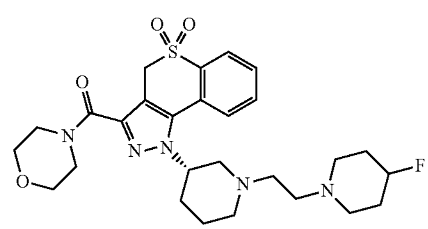 [SMILES: O=C(c1nn([C@H]2CCCN(CCN3CCC(F)CC3)C2)c2c1CS(=O)(=O)c1ccccc1-2)N1CCOCC1] |
| 364 | 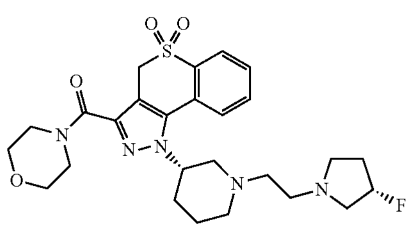 [SMILES: O=C(c1nn([C@H]2CCCN(CCN3CC[C@H](F)C3)C2)c2c1CS(=O)(=O)c1ccccc1-2)N1CCOCC1] | 365 | 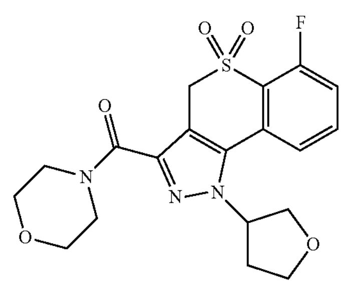 [SMILES: O=C(c1nn(C2CCOC2)c2c1CS(=O)(=O)c1c(F)cccc1-2)N1CCOCC1] |

-continued

| Example No | Structures | Example No | Structures |
|---|---|---|---|
| 366 | 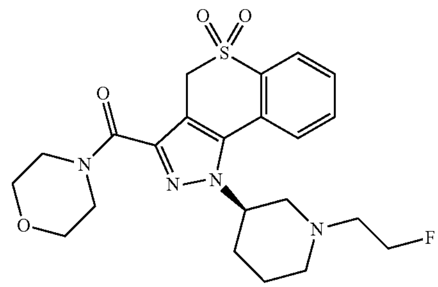 [SMILES: O=C(c1nn([C@@H]2CCCN(CCF)C2)c2c1CS(=O)(=O)c1ccccc1-2)N1CCOCC1] | 367 | 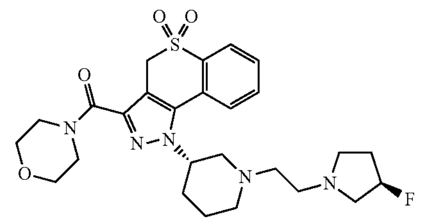 [SMILES: O=C(c1nn([C@H]2CCCN(CCN3CC[C@@H](F)C3)C2)c2c1CS(=O)(=O)c1ccccc1-2)N1CCOCC1] |
| 368 | 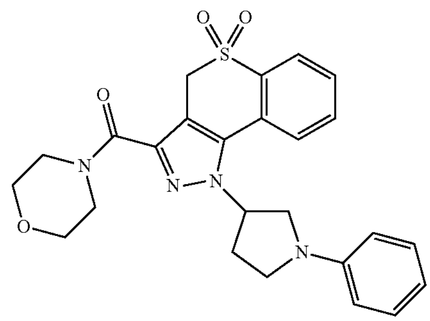 [SMILES: O=C(c1nn(C2CCN(c3ccccc3)C2)c2c1CS(=O)(=O)c1ccccc1-2)N1CCOCC1] | 369 | 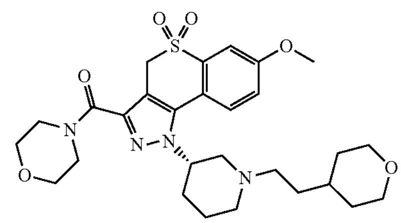 [SMILES: COc1ccc2c(c1)S(=O)(=O)Cc1c(C(=O)N3CCOCC3)nn([C@H]3CCCN(CCC4CCOCC4)C3)c1-2] |
| 370 | 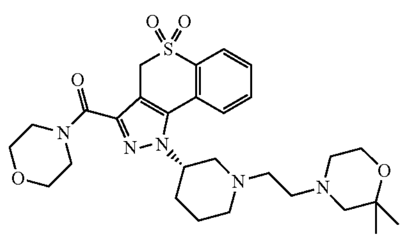 [SMILES: CC1(C)CN(CCN2CCC[C@H](n3nc(C(=O)N4CCOCC4)c4c3-c3ccccc3S(=O)(=O)C4)C2)CCO1] | 371 | 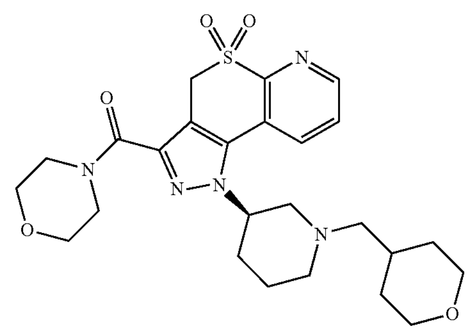 [SMILES: O=C(c1nn([C@@H]2CCCN(CC3CCOCC3)C2)c2c1CS(=O)(=O)c1ncccc1-2)N1CCOCC1] |
| 372 | 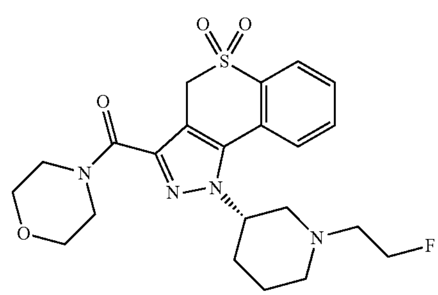 | 373 | 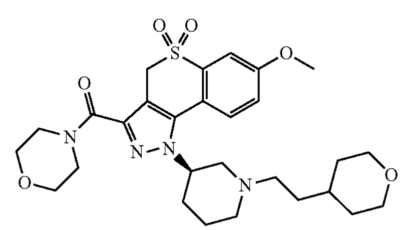 [SMILES: COc1ccc2c(c1)S(=O)(=O)Cc1c(C(=O)N3CCOCC3)nn([C@@H]3CCCN(CCC4CCOCC4)C3)c1-2] |
| 374 | 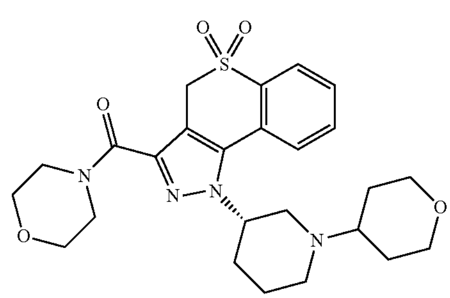 [SMILES: O=C(c1nn([C@H]2CCCN(C3CCOCC3)C2)c2c1CS(=O)(=O)c1ccccc1-2)N1CCOCC1] | 375 | 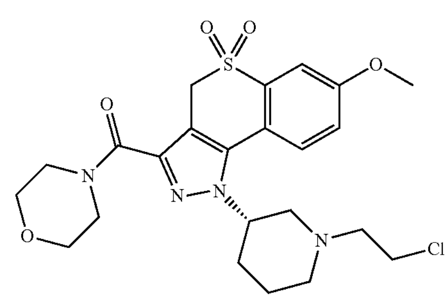 [SMILES: COc1ccc2c(c1)S(=O)(=O)Cc1c(C(=O)N3CCOCC3)nn([C@H]3CCCN(CCCl)C3)c1-2] |

-continued

| Example No | Structures | Example No | Structures |
|---|---|---|---|
| 376 | 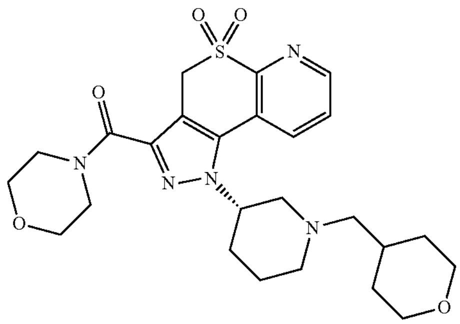 | 377 | 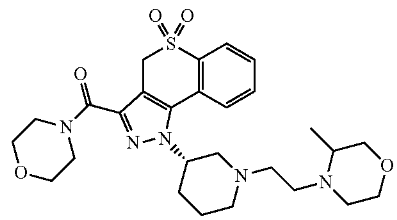 [SMILES: CC1COCCN1CCN1CCC[C@H](n2nc(C(=O)N3CCOCC3)c3c2-c2ccccc2S(=O)(=O)C3)C1] |
| 378 | 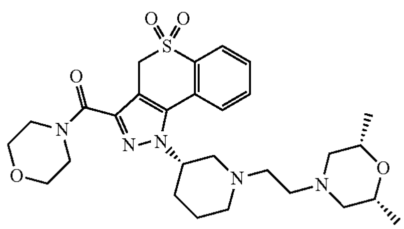 [SMILES: C[C@@H]1CN(CCN2CCC[C@H](n3nc(C(=O)N4CCOCC4)c4c3-c3ccccc3S(=O)(=O)C4)C2)C[C@H](C)O1] | 379 | 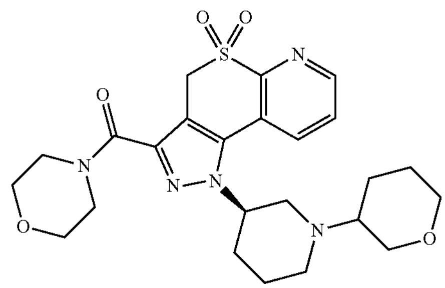 [SMILES: O=C(c1nn([C@@H]2CCCN(C3CCCOC3)C2)c2c1CS(=O)(=O)c1ncccc1-2)N1CCOCC1] |
| 380 | 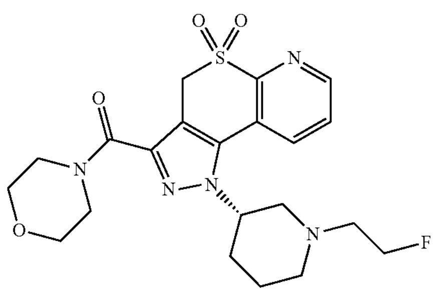 [SMILES: O=C(c1nn([C@H]2CCCN(CCF)C2)c2c1CS(=O)(=O)c1ncccc1-2)N1CCOCC1] | 381 | 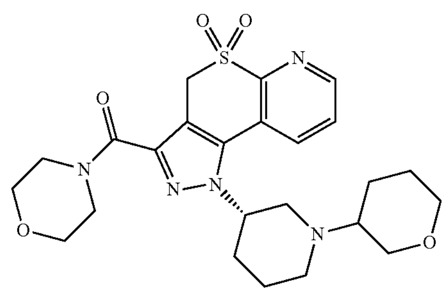 [SMILES: O=C(c1nn([C@H]2CCCN(C3CCCOC3)C2)c2c1CS(=O)(=O)c1ncccc1-2)N1CCOCC1] |
| 382 | 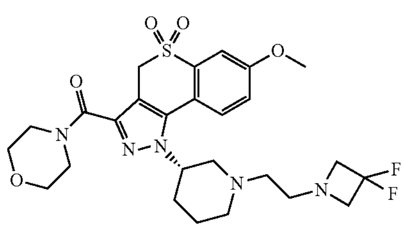 [SMILES: COc1ccc2c(c1)S(=O)(=O)Cc1c(C(=O)N3CCOCC3)nn([C@H]3CCCN(CCN4CC(F)(F)C4)C3)c1-2] | 383 | 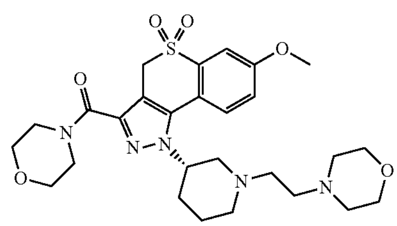 |
| 384 | 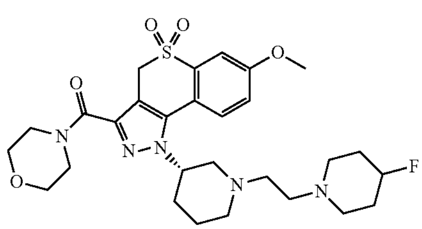 [SMILES: COc1ccc2c(c1)S(=O)(=O)Cc1c(C(=O)N3CCOCC3)nn([C@H]3CCCN(CCN4CCC(F)CC4)C3)c1-2] | 385 | 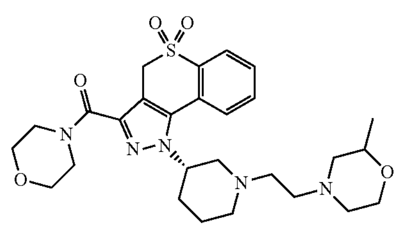 [SMILES: CC1CN(CCN2CCC[C@H](n3nc(C(=O)N4CCOCC4)c4c3-c3ccccc3S(=O)(=O)C4)C2)CCO1] |
| 386 | 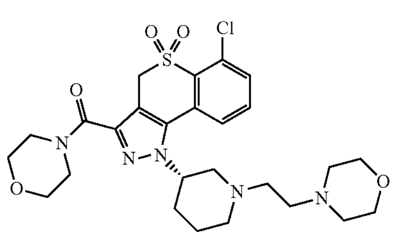 [SMILES: O=C(c1nn([C@H]2CCCN(CCN3CCOCC3)C2)c2c1CS(=O)(=O)c1c(Cl)cccc1-2)N1CCOCC1] | 387 | 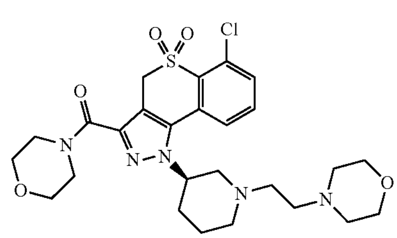 [SMILES: O=C(c1nn([C@@H]2CCCN(CCN3CCOCC3)C2)c2c1CS(=O)(=O)c1c(Cl)cccc1-2)N1CCOCC1] |

-continued
| Example No | Structures | Example No | Structures |
|---|---|---|---|
| 388 | 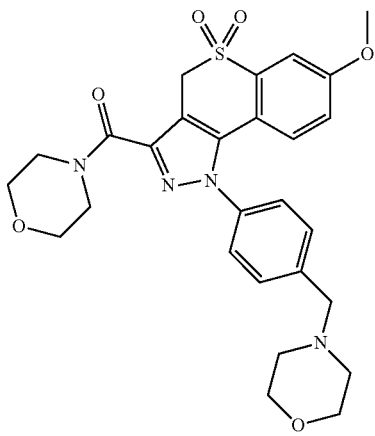 [SMILES: COc1ccc2c(c1)S(=O)(=O)Cc1c(C(=O)N3CCOCC3)nn(-c3ccc(CN4CCOCC4)cc3)c1-2] | 389 | 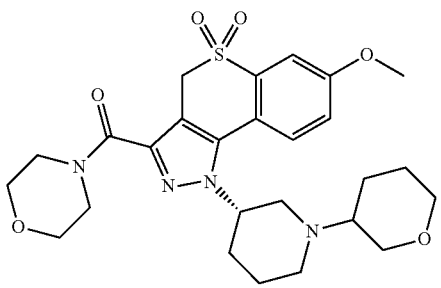 [SMILES: COc1ccc2c(c1)S(=O)(=O)Cc1c(C(=O)N3CCOCC3)nn([C@H]3CCCN(C4CCCOC4)C3)c1-2] |
| 390 | 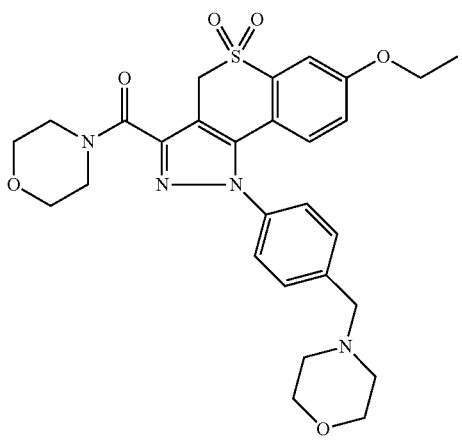 [SMILES: CCOc1ccc2c(c1)S(=O)(=O)Cc1c(C(=O)N3CCOCC3)nn(-c3ccc(CN4CCOCC4)cc3)c1-2] | 391 | 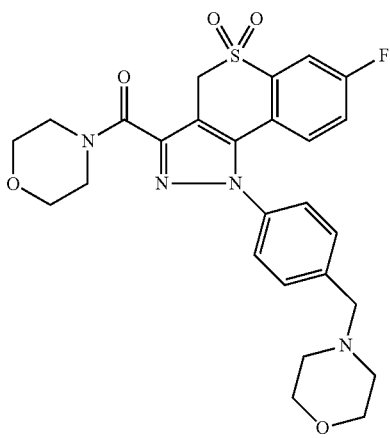 [SMILES: O=C(c1nn(-c2ccc(CN3CCOCC3)cc2)c2c1CS(=O)(=O)c1cc(F)ccc1-2)N1CCOCC1] |
| 392 | 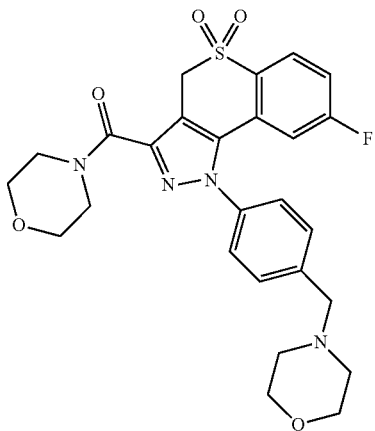 [SMILES: O=C(c1nn(-c2ccc(CN3CCOCC3)cc2)c2c1CS(=O)(=O)c1ccc(F)cc1-2)N1CCOCC1] | 393 | 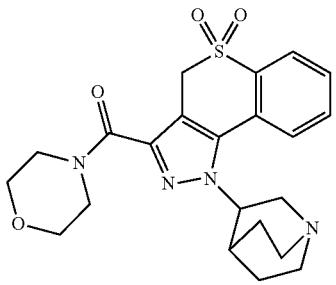 [SMILES: O=C(c1nn(C2CN3CCC2CC3)c2c1CS(=O)(=O)c1ccccc1-2)N1CCOCC1] |

-continued
| Example No | Structures | Example No | Structures |
|---|---|---|---|
| 394 | 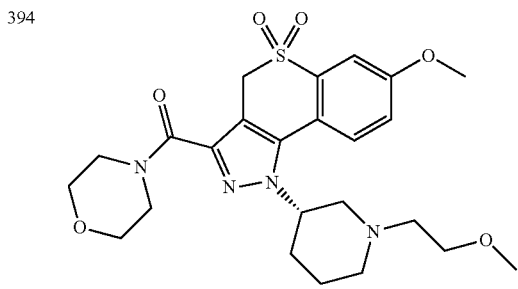 | 395 | 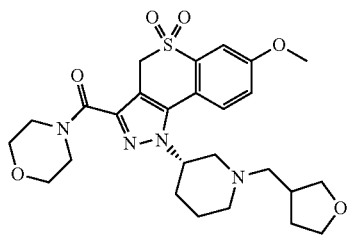 [SMILES: COc1ccc2c(c1)S(=O)(=O)Cc1c(C(=O)N3CCOCC3)nn([C@H]3CCCN(CC4CCOC4)C3)c1-2] |
| 396 | 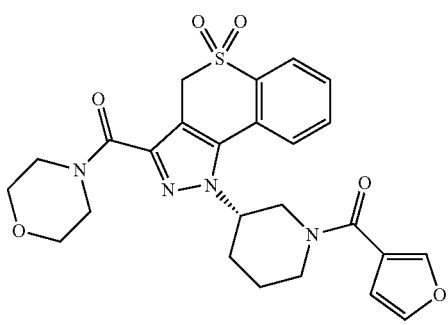 | 397 | 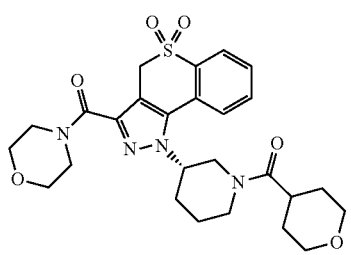 [SMILES: O=C(c1nn([C@H]2CCCN(C(=O)C3CCOCC3)C2)c2c1CS(=O)(=O)c1ccccc1-2)N1CCOCC1] |
| 398 | 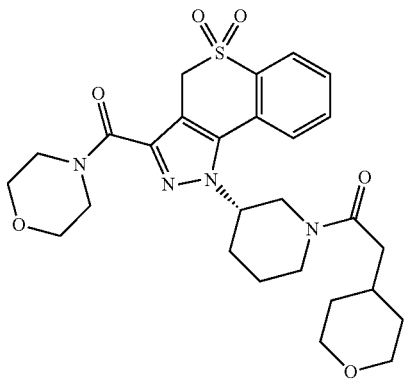 [SMILES: O=C(CC1CCOCC1)N1CCC[C@H](n2nc(C(=O)N3CCOCC3)c3c2-c2ccccc2S(=O)(=O)C3)C1] | 399 | 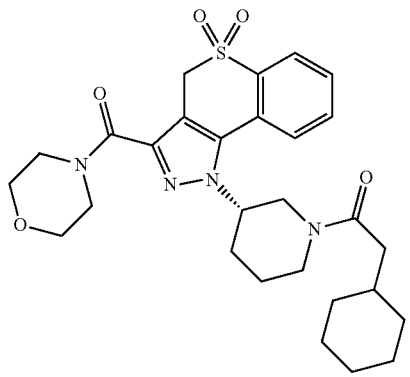 [SMILES: O=C(CC1CCCCC1)N1CCC[C@H](n2nc(C(=O)N3CCOCC3)c3c2-c2ccccc2S(=O)(=O)C3)C1] |
| 400 | 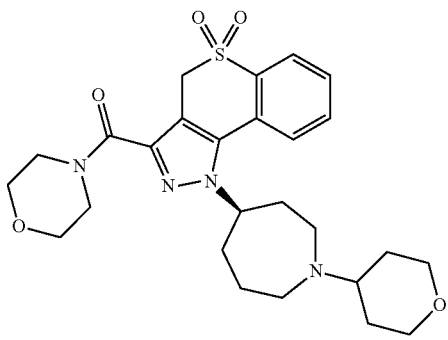 [SMILES: O=C(c1nn([C@@H]2CCCN(C3CCOCC3)CC2)c2c1CS(=O)(=O)c1ccccc1-2)N1CCOCC1] | 401 | 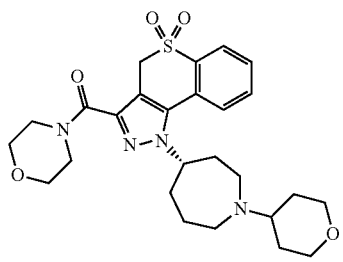 [SMILES: O=C(c1nn([C@H]2CCCN(C3CCOCC3)CC2)c2c1CS(=O)(=O)c1ccccc1-2)N1CCOCC1] |

-continued
| Example No | Structures | Example No | Structures |
|---|---|---|---|
| 402 | 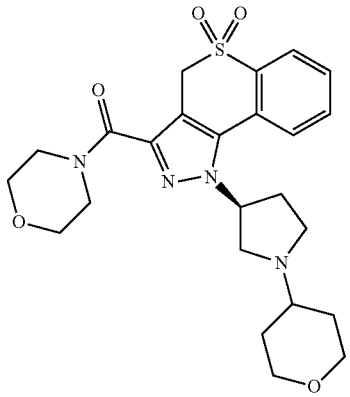 [SMILES: O=C(c1nn([C@H]2CCN(C3CCOCC3)C2)c2c1CS(=O)(=O)c1ccccc1-2)N1CCOCC1] | 403 | 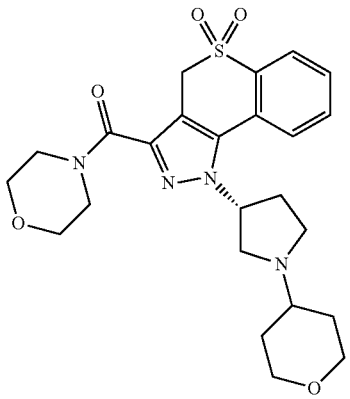 [SMILES: O=C(c1nn([C@@H]2CCN(C3CCOCC3)C2)c2c1CS(=O)(=O)c1ccccc1-2)N1CCOCC1] |
| 404 | 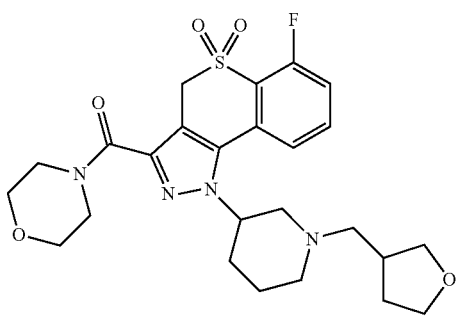 [SMILES: O=C(c1nn(C2CCCN(CC3CCOC3)C2)c2c1CS(=O)(=O)c1c(F)cccc1-2)N1CCOCC1] | 405 | 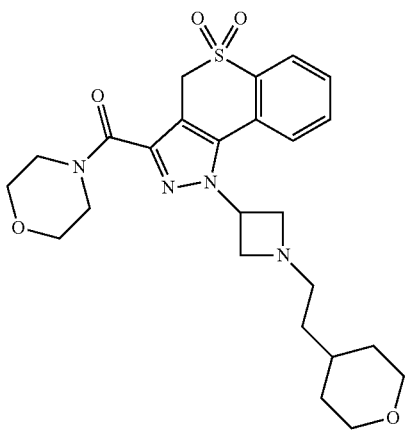 |
| 406 | 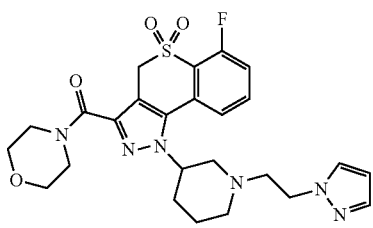 [SMILES: O=C(c1nn(C2CCCN(CCn3cccn3)C2)c2c1CS(=O)(=O)c1c(F)cccc1-2)N1CCOCC1] | 407 | 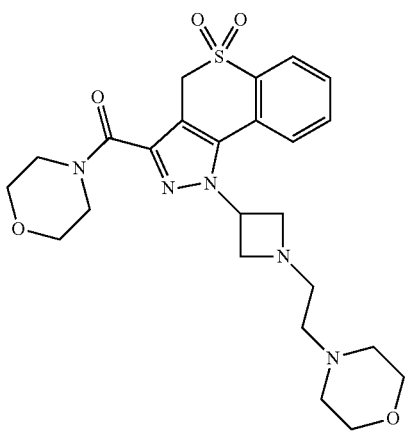 [SMILES: O=C(c1nn(C2CN(CCN3CCOCC3)C2)c2c1CS(=O)(=O)c1ccccc1-2)N1CCOCC1] |
| 408 | 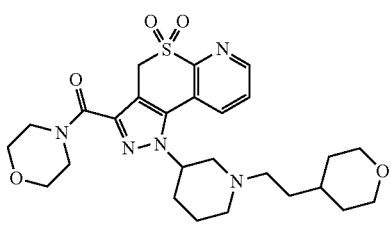 [SMILES: O=C(c1nn(C2CCCN(CCC3CCOCC3)C2)c2c1CS(=O)(=O)c1ncccc1-2)N1CCOCC1] | 409 | 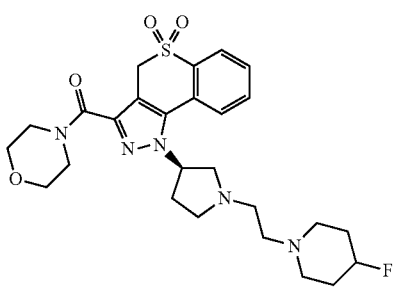 [SMILES: O=C(c1nn([C@@H]2CCN(CCN3CCC(F)CC3)C2)c2c1CS(=O)(=O)c1ccccc1-2)N1CCOCC1] |

| Example No | Structures | Example No | Structures |
|---|---|---|---|
| 410 | 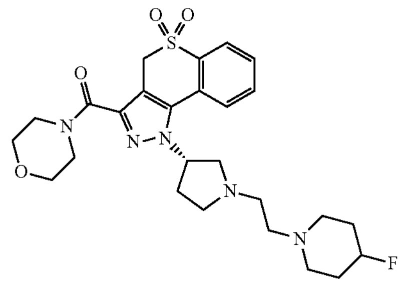 [SMILES: O=C(c1nn([C@H]2CCN(CCN3CCC(F)CC3)C2)c2c1CS(=O)(=O)c1ccccc1-2)N1CCOCC1] | 411 | 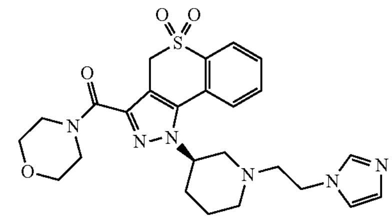 [SMILES: O=C(c1nn([C@@H]2CCCN(CCn3ccnc3)C2)c2c1CS(=O)(=O)c1ccccc1-2)N1CCOCC1] |
| 412 | 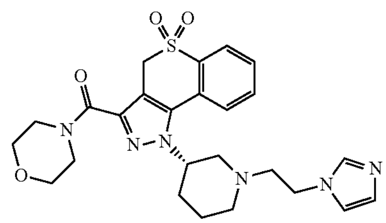 | 413 | 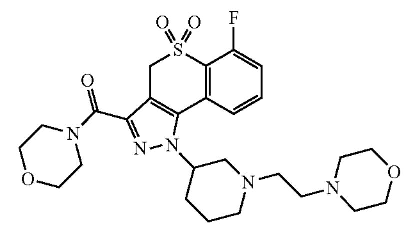 [SMILES: O=C(c1nn(C2CCCN(CCN3CCOCC3)C2)c2c1CS(=O)(=O)c1c(F)cccc1-2)N1CCOCC1] |
| 414 | 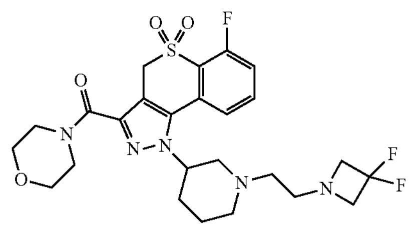 [SMILES: O=C(c1nn(C2CCCN(CCN3CC(F)(F)C3)C2)c2c1CS(=O)(=O)c1c(F)cccc1-2)N1CCOCC1] | 415 | 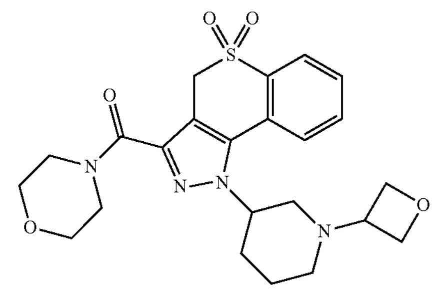 [SMILES: O=C(c1nn(C2CCCN(C3COC3)C2)c2c1CS(=O)(=O)c1ccccc1-2)N1CCOCC1] |
| 422 | 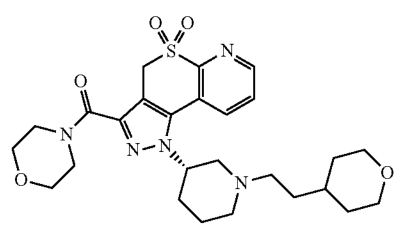 [SMILES: O=C(c1nn([C@H]2CCCN(CCC3CCOCC3)C2)c2c1CS(=O)(=O)c1ncccc1-2)N1CCOCC1] | 423 | 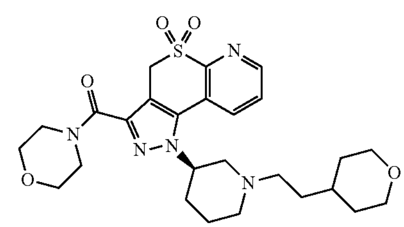 [SMILES: O=C(c1nn([C@@H]2CCCN(CCC3CCOCC3)C2)c2c1CS(=O)(=O)c1ncccc1-2)N1CCOCC1] |
| 424 | 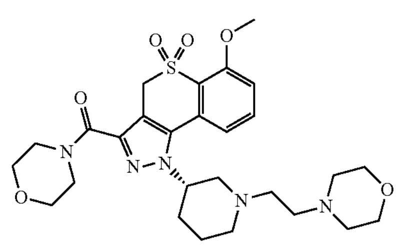 [SMILES: COc1cccc2c1S(=O)(=O)Cc1c(C(=O)N3CCOCC3)nn([C@H]3CCCN(CCN4CCOCC4)C3)c1-2] | 425 | 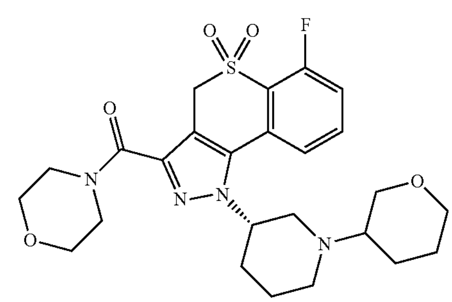 [SMILES: O=C(c1nn([C@H]2CCCN(C3CCCOC3)C2)c2c1CS(=O)(=O)c1c(F)cccc1-2)N1CCOCC1] |

-continued
| Example No | Structures | Example No | Structures |
|---|---|---|---|
| 426 | 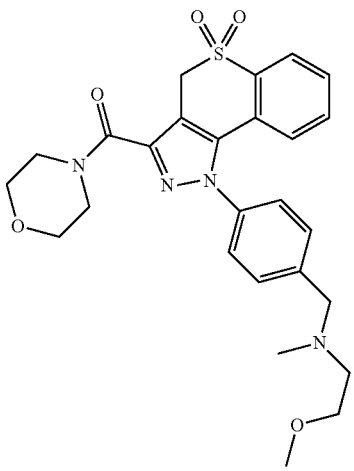 [SMILES: COCCN(C)Cc1ccc(-n2nc(C(=O)N3CCOCC3)c3c2-c2ccccc2S(=O)(=O)C3)cc1] | 427 | 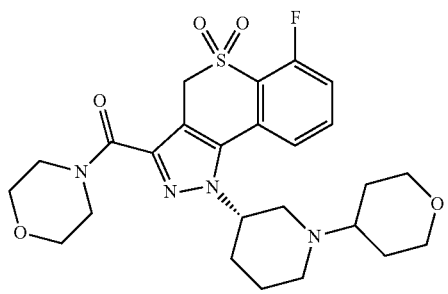 [SMILES: O=C(c1nn([C@H]2CCCN(C3CCOCC3)C2)c2c1CS(=O)(=O)c1c(F)cccc1-2)N1CCOCC1] |
| 428 | 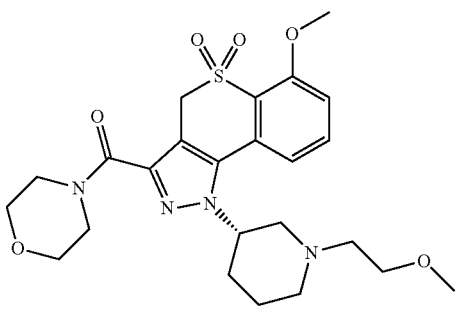 [SMILES: COCCN1CCC[C@H](n2nc(C(=O)N3CCOCC3)c3c2-c2cccc(OC)c2S(=O)(=O)C3)C1] | 429 | 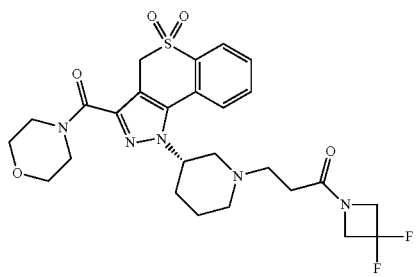 |
| 430 | 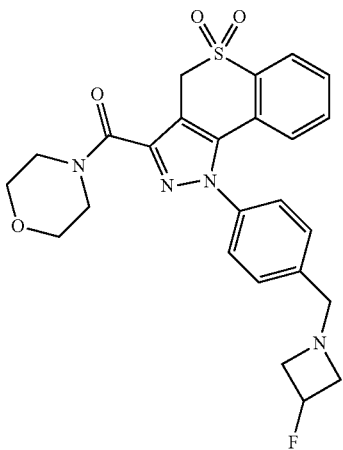 [SMILES: O=C(c1nn(-c2ccc(CN3CC(F)C3)cc2)c2c1CS(=O)(=O)c1ccccc1-2)N1CCOCC1] | 431 | 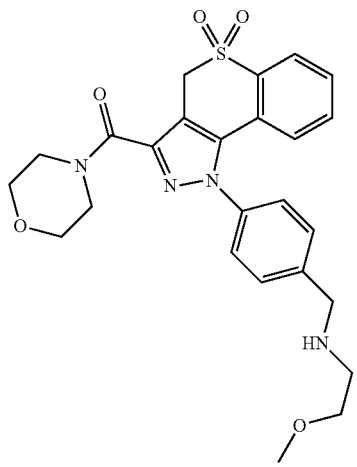 [SMILES: COCCNCc1ccc(-n2nc(C(=O)N3CCOCC3)c3c2-c2ccccc2S(=O)(=O)C3)cc1] |

US 9,073,940 B2
-continued
| Example No | Structures | Example No | Structures |
|---|---|---|---|
| 432 | 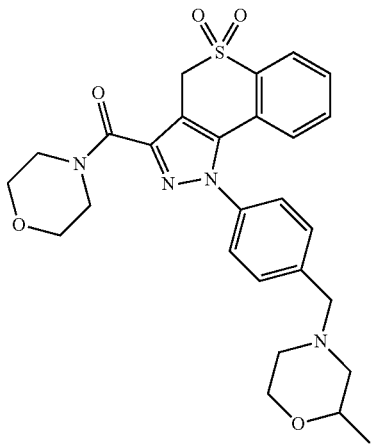 [SMILES: CC1CN(Cc2ccc(-n3nc(C(=O)N4CCOCC4)c4c3-c3ccccc3S(=O)(=O)C4)cc2)CCO1] | 433 | 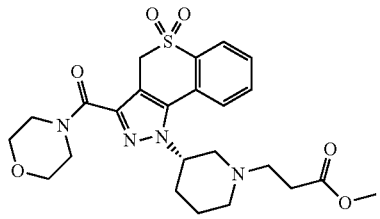 [SMILES: COC(=O)CCN1CCC[C@H](n2nc(C(=O)N3CCOCC3)c3c2-c2ccccc2S(=O)(=O)C3)C1] |
| 434 | 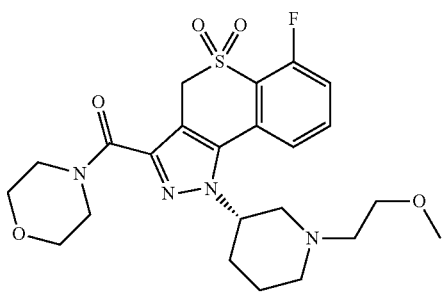 [SMILES: COCCN1CCC[C@H](n2nc(C(=O)N3CCOCC3)c3c2-c2cccc(F)c2S(=O)(=O)C3)C1] | 435 | 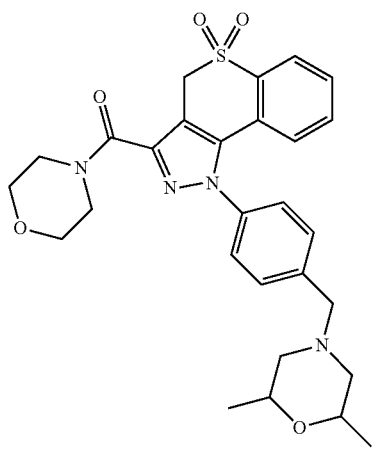 [SMILES: CC1CN(Cc2ccc(-n3nc(C(=O)N4CCOCC4)c4c3-c3ccccc3S(=O)(=O)C4)cc2)CC(C)O1] |
| 436 | 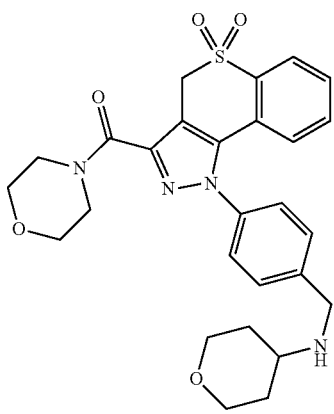 | 437 | 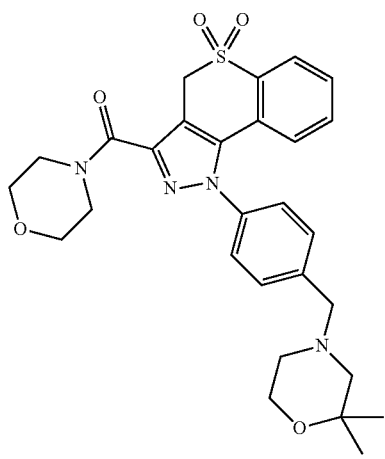 [SMILES: CC1(C)CN(Cc2ccc(-n3nc(C(=O)N4CCOCC4)c4c3-c3ccccc3S(=O)(=O)C4)cc2)CCO1] |
| 438 | 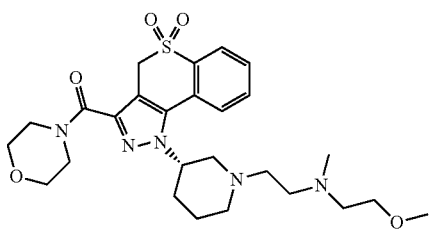 [SMILES: COCCN(C)CCN1CCC[C@H](n2nc(C(=O)N3CCOCC3)c3c2-c2ccccc2S(=O)(=O)C3)C1] | 439 | 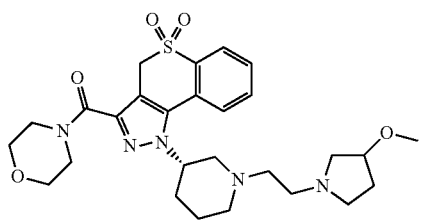 [SMILES: COC1CCN(CCN2CCC[C@H](n3nc(C(=O)N4CCOCC4)c4c3-c3ccccc3S(=O)(=O)C4)C2)C1] |

-continued
| Example No | Structures | Example No | Structures |
|---|---|---|---|
| 440 | 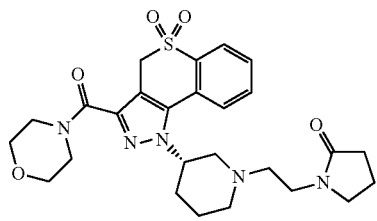 [SMILES: O=C1CCCN1CCN1CCC[C@H](n2nc(C(=O)N3CCOCC3)c3c2-c2ccccc2S(=O)(=O)C3)C1] | 441 | 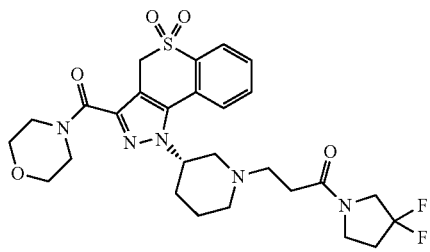 [SMILES: O=C(CCN1CCC[C@H](n2nc(C(=O)N3CCOCC3)c3c2-c2ccccc2S(=O)(=O)C3)C1)N1CCC(F)(F)C1] |
| 442 | 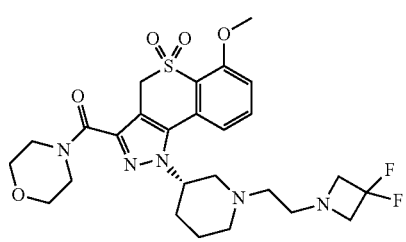 [SMILES: COc1cccc2c1S(=O)(=O)Cc1c(C(=O)N3CCOCC3)nn([C@H]3CCCN(CCN4CC(F)(F)C4)C3)c1-2] | 443 | 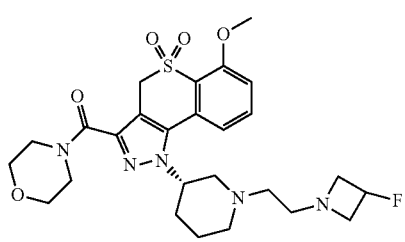 [SMILES: COc1cccc2c1S(=O)(=O)Cc1c(C(=O)N3CCOCC3)nn([C@H]3CCCN(CCN4CC(F)C4)C3)c1-2] |
| 444 | 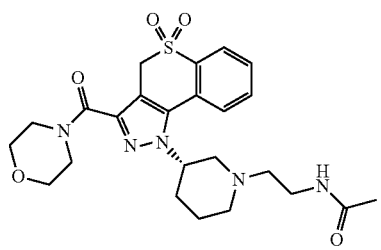 [SMILES: CC(=O)NCCN1CCC[C@H](n2nc(C(=O)N3CCOCC3)c3c2-c2ccccc2S(=O)(=O)C3)C1] | 445 | 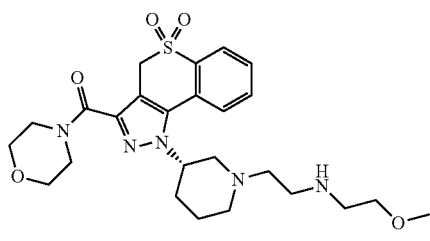 [SMILES: COCCNCCN1CCC[C@H](n2nc(C(=O)N3CCOCC3)c3c2-c2ccccc2S(=O)(=O)C3)C1] |
| 446 | 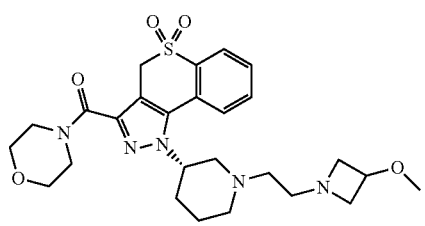 [SMILES: COC1CN(CCN2CCC[C@H](n3nc(C(=O)N4CCOCC4)c4c3-c3ccccc3S(=O)(=O)C4)C2)C1] | 447 | 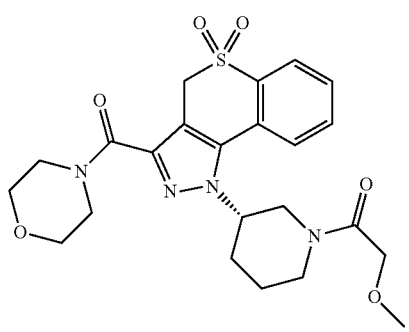 [SMILES: COCC(=O)N1CCC[C@H](n2nc(C(=O)N3CCOCC3)c3c2-c2ccccc2S(=O)(=O)C3)C1] |
| 448 | 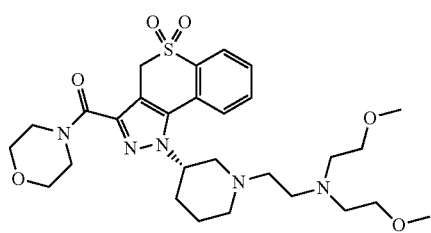 [SMILES: COCCN(CCOC)CCN1CCC[C@H](n2nc(C(=O)N3CCOCC3)c3c2-c2ccccc2S(=O)(=O)C3)C1] | 449 | 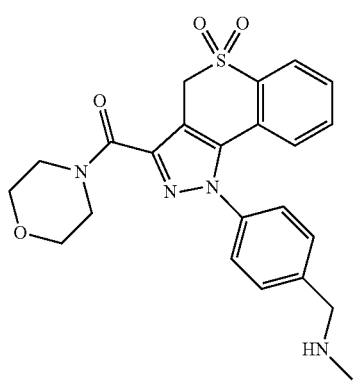 [SMILES: CNCc1ccc(-n2nc(C(=O)N3CCOCC3)c3c2-c2ccccc2S(=O)(=O)C3)cc1] |

-continued
| Example No | Structures | Example No | Structures |
|---|---|---|---|
| 450 | 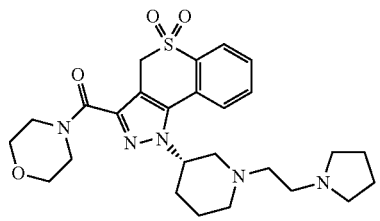 [SMILES: O=C(c1nn([C@H]2CCCN(CCN3CCCC3)C2)c2c1CS(=O)(=O)c1ccccc1-2)N1CCOCC1] | 451 | 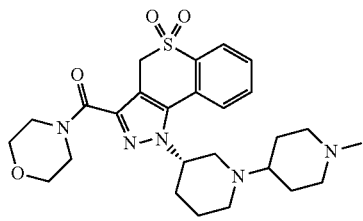 [SMILES: CN1CCC(N2CCC[C@H](n3nc(C(=O)N4CCOCC4)c4c3-c3ccccc3S(=O)(=O)C4)C2)CC1] |
| 452 | 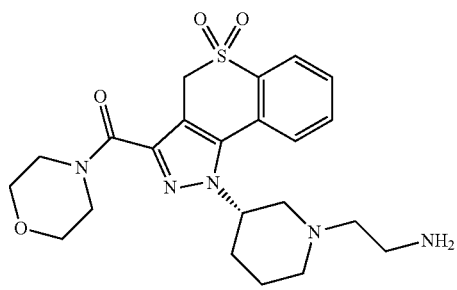 [SMILES: NCCN1CCC[C@H](n2nc(C(=O)N3CCOCC3)c3c2-c2ccccc2S(=O)(=O)C3)C1] | 453 | 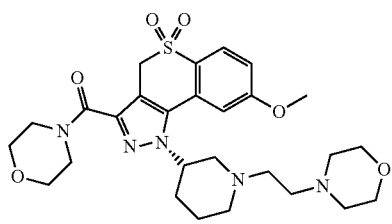 |
| 454 | 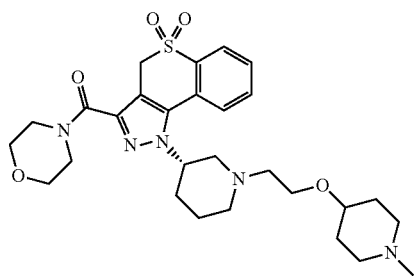 [SMILES: CN1CCC(OCCN2CCC[C@H](n3nc(C(=O)N4CCOCC4)c4c3-c3ccccc3S(=O)(=O)C4)C2)CC1] | 455 | 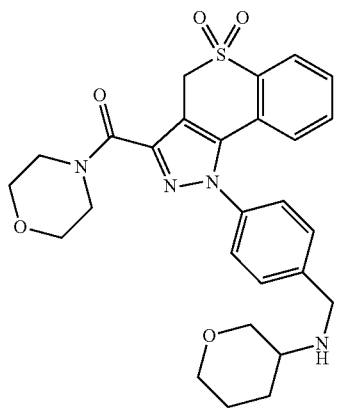 [SMILES: O=C(c1nn(-c2ccc(CNC3CCCOC3)cc2)c2c1CS(=O)(=O)c1ccccc1-2)N1CCOCC1] |
| 456 | 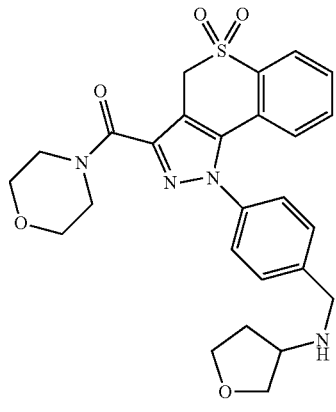 [SMILES: O=C(c1nn(-c2ccc(CNC3CCOC3)cc2)c2c1CS(=O)(=O)c1ccccc1-2)N1CCOCC1] | 457 | 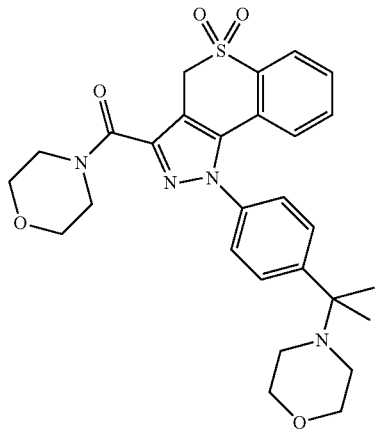 [SMILES: CC(C)(c1ccc(-n2nc(C(=O)N3CCOCC3)c3c2-c2ccccc2S(=O)(=O)C3)cc1)N1CCOCC1] |

-continued

| Example No | Structures | Example No | Structures |
|---|---|---|---|
| 458 | 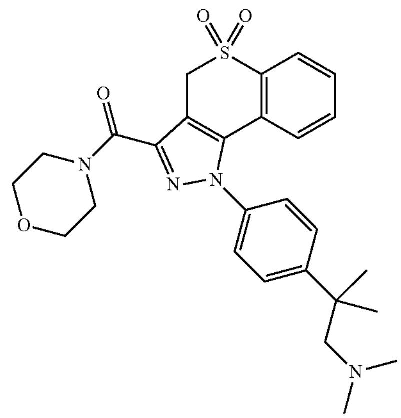 [SMILES: CN(C)CC(C)(C)c1ccc(-n2nc(C(=O)N3CCOCC3)c3c2-c2ccccc2S(=O)(=O)C3)cc1] | 459 | 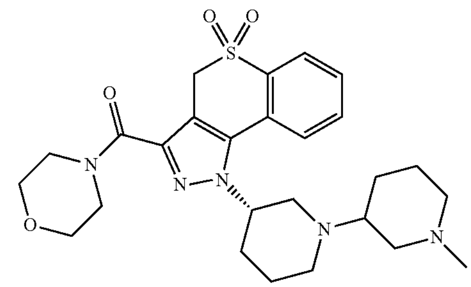 [SMILES: CN1CCCC(N2CCC[C@H](n3nc(C(=O)N4CCOCC4)c4c3-c3ccccc3S(=O)(=O)C4)C2)C1] |
| 460 | 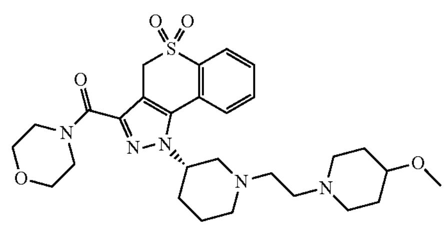 [SMILES: COC1CCN(CCN2CCC[C@H](n3nc(C(=O)N4CCOCC4)c4c3-c3ccccc3S(=O)(=O)C4)C2)CC1] | 461 | 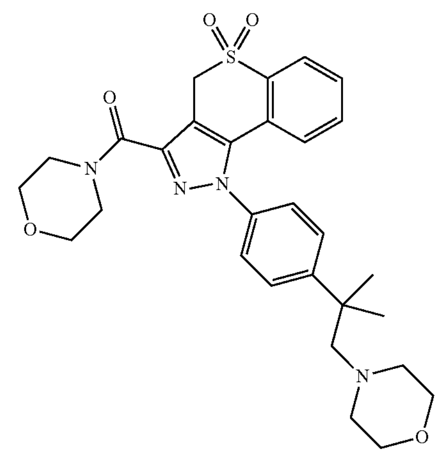 [SMILES: CC(C)(CN1CCOCC1)c1ccc(-n2nc(C(=O)N3CCOCC3)c3c2-c2ccccc2S(=O)(=O)C3)cc1] |
| 462 | 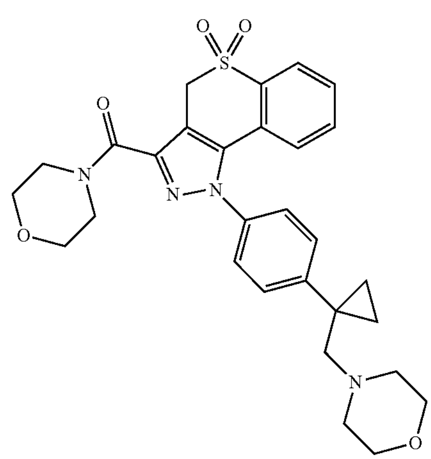 [SMILES: O=C(c1nn(-c2ccc(C3(CN4CCOCC4)CC3)cc2)c2c1CS(=O)(=O)c1ccccc1-2)N1CCOCC1] | 463 | 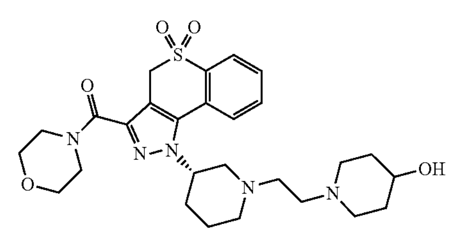 [SMILES: O=C(c1nn([C@H]2CCCN(CCN3CCC(O)CC3)C2)c2c1CS(=O)(=O)c1ccccc1-2)N1CCOCC1] |
| 464 | 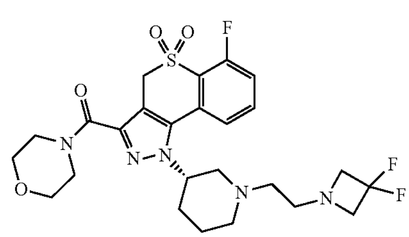 [SMILES: O=C(c1nn([C@H]2CCCN(CCN3CC(F)(F)C3)C2)c2c1CS(=O)(=O)c1c(F)cccc1-2)N1CCOCC1] | 465 | 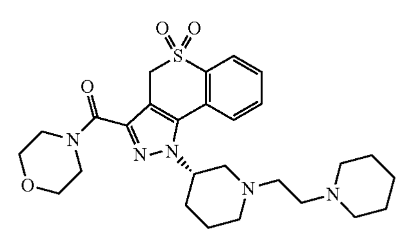 [SMILES: O=C(c1nn([C@H]2CCCN(CCN3CCCCC3)C2)c2c1CS(=O)(=O)c1ccccc1-2)N1CCOCC1] |

| Example No | Structures | Example No | Structures |
|---|---|---|---|
| 466 | 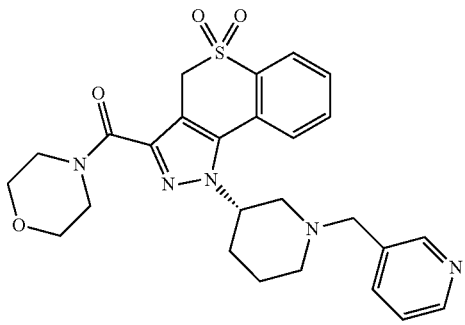 [SMILES: O=C(c1nn([C@H]2CCCN(Cc3cccnc3)C2)c2c1CS(=O)(=O)c1ccccc1-2)N1CCOCC1] | 467 | 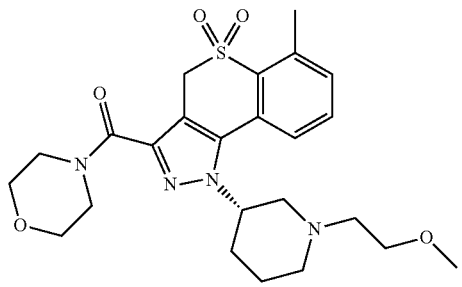 [SMILES: COCCN1CCC[C@H](n2nc(C(=O)N3CCOCC3)c3c2-c2cccc(C)c2S(=O)(=O)C3)C1] |
| 468 | 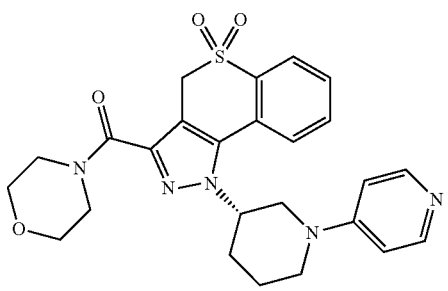 [SMILES: O=C(c1nn([C@H]2CCCN(c3ccncc3)C2)c2c1CS(=O)(=O)c1ccccc1-2)N1CCOCC1] | 469 | 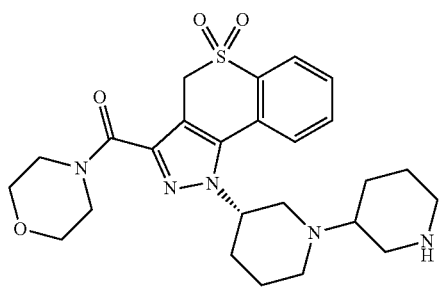 [SMILES: O=C(c1nn([C@H]2CCCN(C3CCCNC3)C2)c2c1CS(=O)(=O)c1ccccc1-2)N1CCOCC1] |
| 470 | 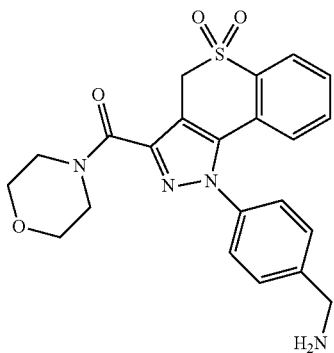 [SMILES: NCc1ccc(-n2nc(C(=O)N3CCOCC3)c3c2-c2ccccc2S(=O)(=O)C3)cc1] | 471 | 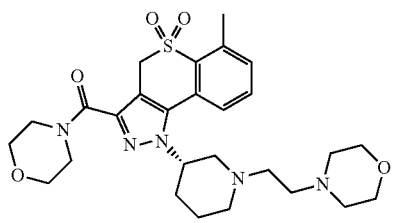 |
| 472 | 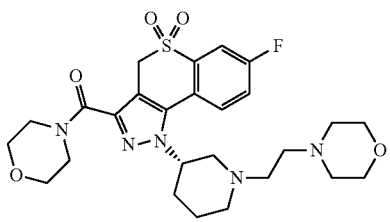 [SMILES: O=C(c1nn([C@H]2CCCN(CCN3CCOCC3)C2)c2c1CS(=O)(=O)c1cc(F)ccc1-2)N1CCOCC1] | 473 | 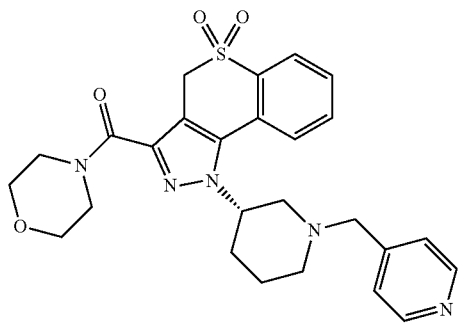 |

-continued
| Example No | Structures | Example No | Structures |
|---|---|---|---|
| 474 | 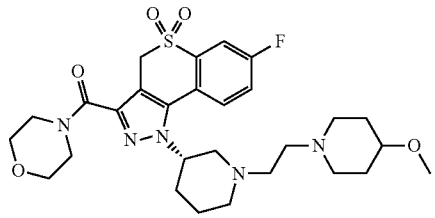 [SMILES: COC1CCN(CCN2CCC[C@H](n3nc(C(=O)N4CCOCC4)c4c3-c3ccc(F)cc3S(=O)(=O)C4)C2)CC1] | 481 | 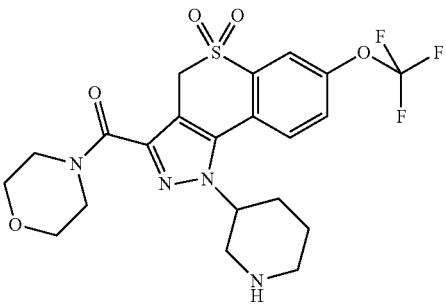 [SMILES: O=C(c1nn(C2CCCNC2)c2c1CS(=O)(=O)c1cc(OC(F)(F)F)ccc1-2)N1CCOCC1] |
| 485 | 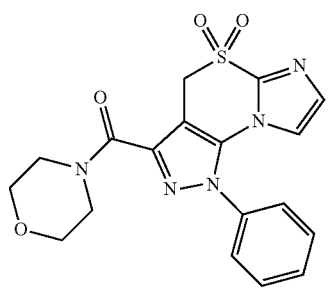 [SMILES: O=C(c1nn(-c2ccccc2)c2c1CS(=O)(=O)c1nccn1-2)N1CCOCC1] | 486 | 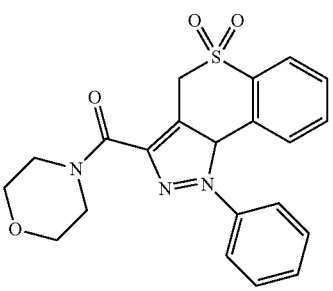 |
| 487 | 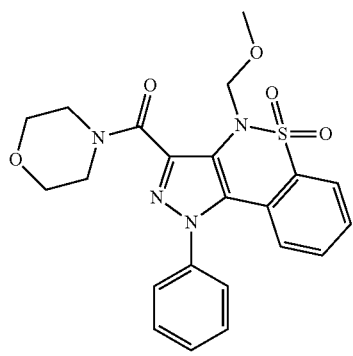 [SMILES: COCN1c2c(C(=O)N3CCOCC3)nn(-c3ccccc3)c2-c2ccccc2S1(=O)=O] | 488 | 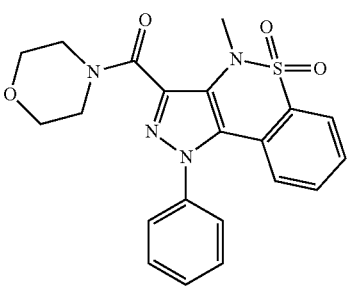 [SMILES: CN1c2c(C(=O)N3CCOCC3)nn(-c3ccccc3)c2-c2ccccc2S1(=O)=O] |
| 489 | 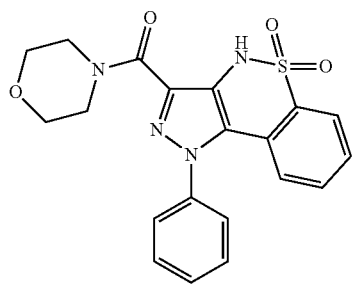 [SMILES: O=C(c1nn(-c2ccccc2)c2c1NS(=O)(=O)c1ccccc1-2)N1CCOCC1] | 490 | 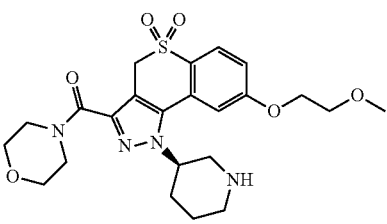 [SMILES: COCCOc1ccc2c(c1)-c1c(c(C(=O)N3CCOCC3)nn1[C@@H]1CCCNC1)CS2(=O)=O] |

-continued
| Example No | Structures | Example No | Structures |
|---|---|---|---|
| 491 | 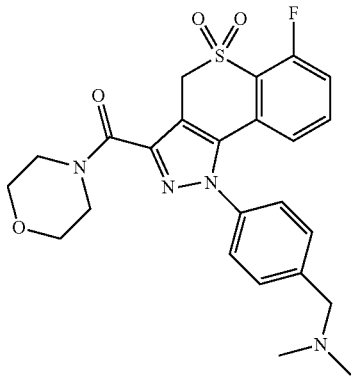 [SMILES: CN(C)Cc1ccc(-n2nc(C(=O)N3CCOCC3)c3c2-c2cccc(F)c2S(=O)(=O)C3)cc1] | 492 | 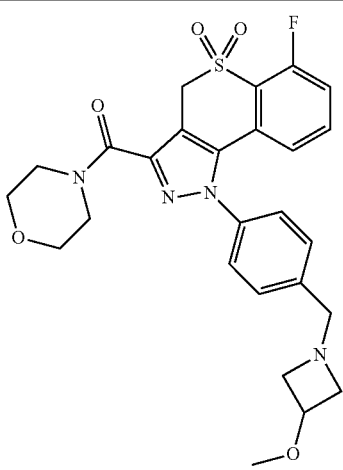 |
| 493 | 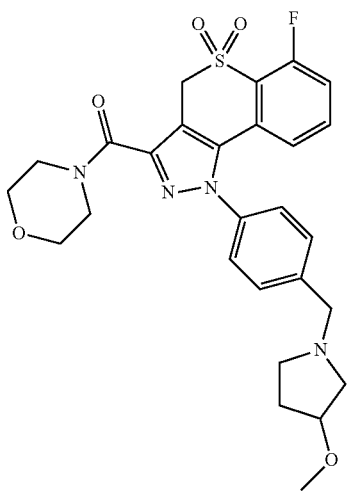 [SMILES: COC1CCN(Cc2ccc(-n3nc(C(=O)N4CCOCC4)c4c3-c3cccc(F)c3S(=O)(=O)C4)cc2)C1] | 494 | 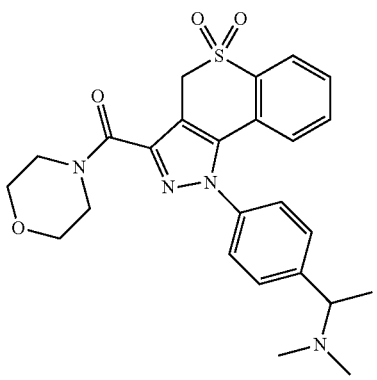 [SMILES: CC(c1ccc(-n2nc(C(=O)N3CCOCC3)c3c2-c2ccccc2S(=O)(=O)C3)cc1)N(C)C] |
| 495 | 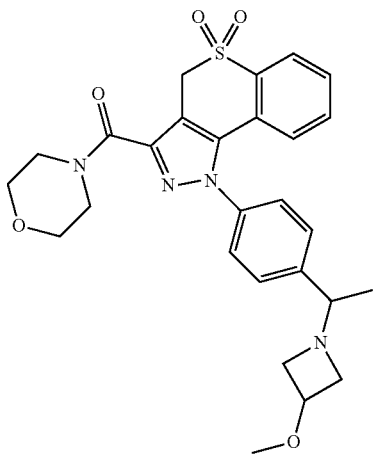 [SMILES: COC1CN(C(C)c2ccc(-n3nc(C(=O)N4CCOCC4)c4c3-c3ccccc3S(=O)(=O)C4)cc2)C1] | 496 | 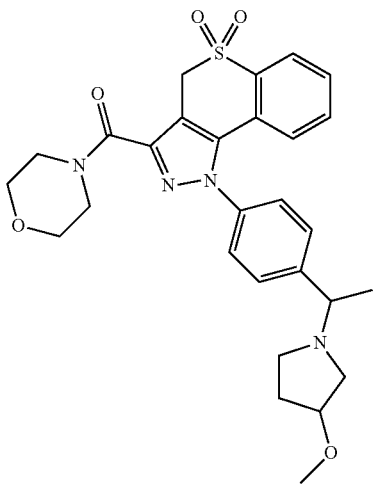 [SMILES: COC1CCN(C(C)c2ccc(-n3nc(C(=O)N4CCOCC4)c4c3-c3ccccc3S(=O)(=O)C4)cc2)C1] |

-continued

| Example No | Structures | Example No | Structures |
|---|---|---|---|
| 497 | 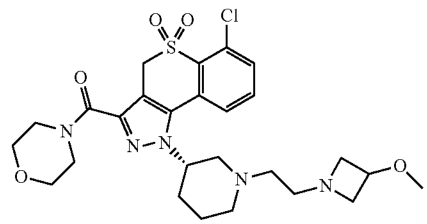 [SMILES: COC1CN(CCN2CCC[C@H](n3nc(C(=O)N4CCOCC4)c4c3-c3cccc(Cl)c3S(=O)(=O)C4)C2)C1] | 498 | 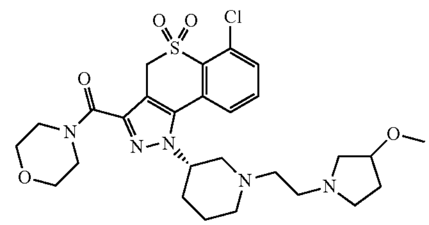 [SMILES: COC1CCN(CCN2CCC[C@H](n3nc(C(=O)N4CCOCC4)c4c3-c3cccc(Cl)c3S(=O)(=O)C4)C2)C1] |
| 499 | 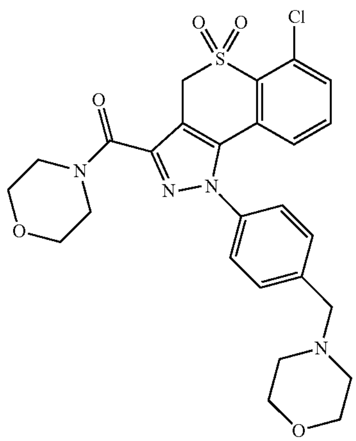 | 500 | 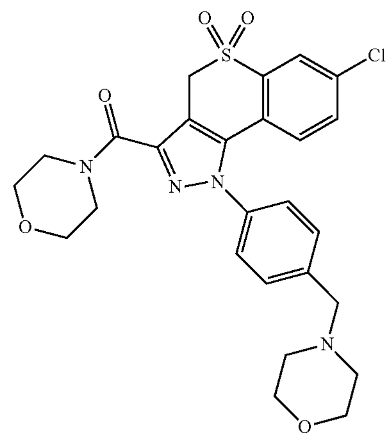 [SMILES: O=C(c1nn(-c2ccc(CN3CCOCC3)cc2)c2c1CS(=O)(=O)c1cc(Cl)ccc1-2)N1CCOCC1] |
| 501 | 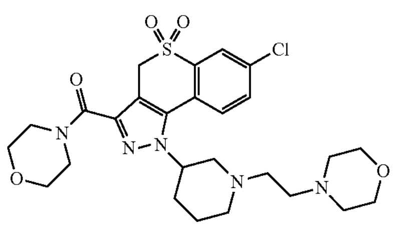 [SMILES: O=C(c1nn(C2CCCN(CCN3CCOCC3)C2)c2c1CS(=O)(=O)c1cc(Cl)ccc1-2)N1CCOCC1] | 502 | 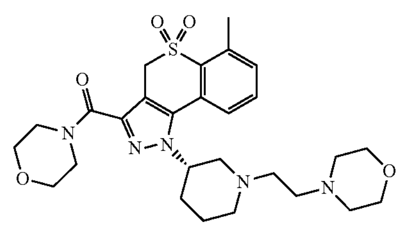 [SMILES: Cc1cccc2c1S(=O)(=O)Cc1c(C(=O)N3CCOCC3)nn([C@H]3CCCN(CCN4CCOCC4)C3)c1-2] |
| 503 | 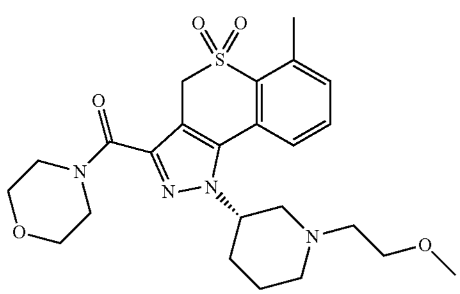 [SMILES: COCCN1CCC[C@H](n2nc(C(=O)N3CCOCC3)c3c2-c2cccc(C)c2S(=O)(=O)C3)C1] | 504 | 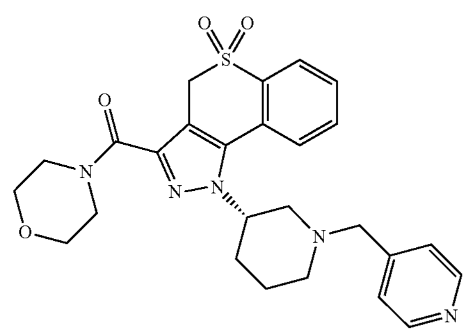 [SMILES: O=C(c1nn([C@H]2CCCN(Cc3ccncc3)C2)c2c1CS(=O)(=O)c1ccccc1-2)N1CCOCC1] |
| 505 | 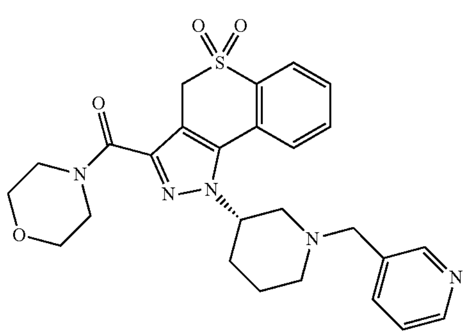 [SMILES: O=C(c1nn([C@H]2CCCN(Cc3cccnc3)C2)c2c1CS(=O)(=O)c1ccccc1-2)N1CCOCC1] | 506 | 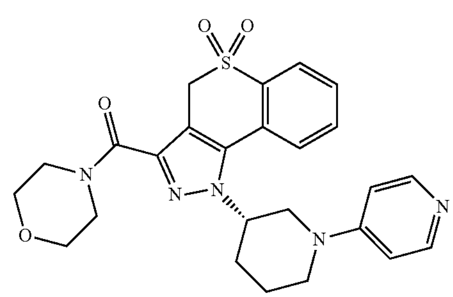 [SMILES: O=C(c1nn([C@H]2CCCN(c3ccncc3)C2)c2c1CS(=O)(=O)c1ccccc1-2)N1CCOCC1] |

| Example No | Structures | Example No | Structures |
|---|---|---|---|
| 507 | 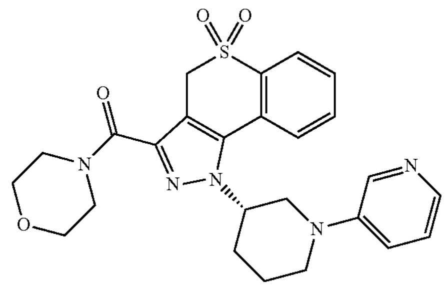 [SMILES: O=C(c1nn([C@H]2CCCN(c3cccnc3)C2)c2c1CS(=O)(=O)c1ccccc1-2)N1CCOCC1] | 508 | 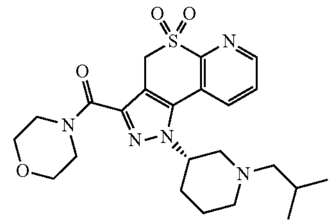 [SMILES: CC(C)CN1CCC[C@H](n2nc(C(=O)N3CCOCC3)c3c2-c2cccnc2S(=O)(=O)C3)C1] |
| 509 | 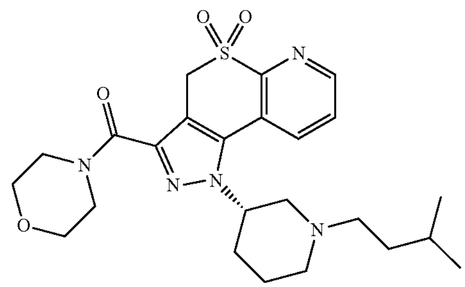 [SMILES: CC(C)CCN1CCC[C@H](n2nc(C(=O)N3CCOCC3)c3c2-c2cccnc2S(=O)(=O)C3)C1] | or 510 | 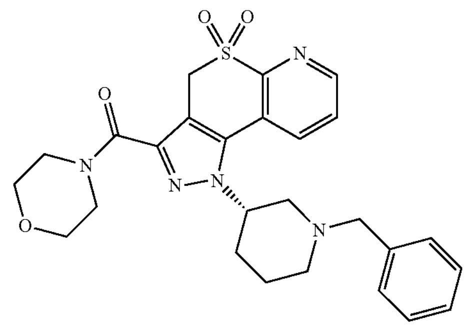 |

7. A method of making a pharmaceutical composition comprising combining an excipient and a compound of Formula (I*):

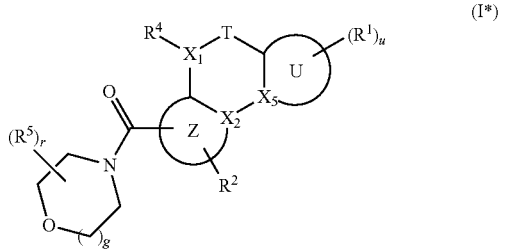

wherein:
X₁ denotes a nitrogen atom or CR³;
X₂, X₅ are independently from one another nitrogen or carbon atoms;
U denotes aromatic 6-membered ring having optionally 1, 2 or 3 nitrogen atoms, including X₅, or an unsaturated or aromatic 5-membered ring having 1 to 3 heteroatoms selected from N, S or O, including the meaning of X₅;
Z denotes an unsaturated or aromatic 5-membered heterocyclic ring having 2 nitrogen atoms, including the meaning of X₂;
T denotes SO Or SO₂;
R¹ denotes H, A, Hal, CN, NO₂, N(R⁶)₂, OR⁶, Ar, Het, Y, —NR⁶COR⁶, CON(R⁶)₂, —NR⁶COAr, NR⁶COHet, COHet, —NR⁶SO₂R⁶, including CO₂Y;
R² denotes H, Ar, Het, A, or Cyc;
R³ denotes H or Y;
R⁴ denotes H, Y, (CH₂)ₙAr, (CH₂)ₙCyc, (CH₂)ₙHet, (CH₂)ₙOY, (CH₂)ₙNHY, or (CH₂)ₙNH₂, or if X₁ is CR³, R⁴ denotes H, Y, (CH₂)ₙAR, (CH₂)ₙCyc, (CH₂)ₙHet, (CH₂)ₙOY, (CH₂)ₙNHY, (CH₂)ₙNH₂ or Hal;

R⁵ denotes H, Y, or Ar, when R⁵ is Y and r is 2, two R⁵ groups may be linked together to provide with the morpholine group to which they are linked, a bridged system;
R⁶ is H, A, Cyc or Ar;
u is 0, 1, 2, 3, or 4:
r is 0, 1, or 2;
g is 1 or 2;
Ar denotes a monocyclic or fused bicyclic, unsaturated or aromatic carbocyclic ring having 6 to 14 carbon atoms, which is unsubstituted or monosubstituted, disubstituted or trisubstituted by Hal, OCF₃, NO₂, CN, purfluoroalkyl, A, OR⁶, N(R⁶)₂, COR⁶, —CO₂R⁶, CON(R⁶)₂, COHet, —NHCOR⁶, —NHSO₂A, —NHSO₂Ar, —NHSO₂—N(R⁶)₂, N(H)₁₋qAqCOR⁶, N(H)₁₋qAqSO₂—N(H)₂₋ₘ(A)ₘ, —N(H)₁₋qAqCON(H)₂₋ₘ(A)ₘ, —SO₂A, —SO₂Ar, —SO₂N(H)₂₋ₘ(A)ₘ, —SO₂Het, —(CH₂)ₙ—N(R⁶)₂, —(CH₂)ₙOR⁶, —(CH₂)ₙ—N(R⁶)SO₂A, —(CH₂)ₙ—N(R⁶)SO₂R⁶, Het², —(CH₂)ₙ—Het², or —(CHY)ₙ—Het²;
Het denotes a monocyclic or bicyclic saturated, unsaturated or aromatic heterocyclic ring having 1, 2, 3 or 4 N, O and/or S atoms and eventually comprising a SO₂ or a CO group, which is unsubstituted or monosubstituted, disubstituted or trisubstituted by Hal, OCF₃, NO₂, CN, perfluoroalkyl, A, OR⁶, N(R⁶)₂, COR⁶, —CO₂R⁶, CON(R⁶)₂, —NHCOR⁶, —NHSO₂A, —NHSO₂R⁶, —NHSO₂—N(H)₂₋ₘ(A)ₘ, N(H)₁₋qAqCOR⁶, N(H)₁₋qAqSO₂—N(H)₂₋ₘ(A)ₘ, —N(H)₁₋qAqCON(H)₂₋ₘ(A)ₘ, —SO₂A, —SO₂Ar, —SO₂N(H)₂₋ₘ(A)ₘ, COHet, —SO₂Het, —(CH₂)ₙ—N(H)₂₋ₘ(A)ₘ, —(CH₂)ₙ—OR⁶, —(CH₂)ₙ—N(R⁶)SO₂A, —(CH₂)ₙ—N(R⁶)SO₂R⁶, Het², —(CH₂)ₙ—Het²; or —(CHY)ₙ—Het²;

Het² denotes

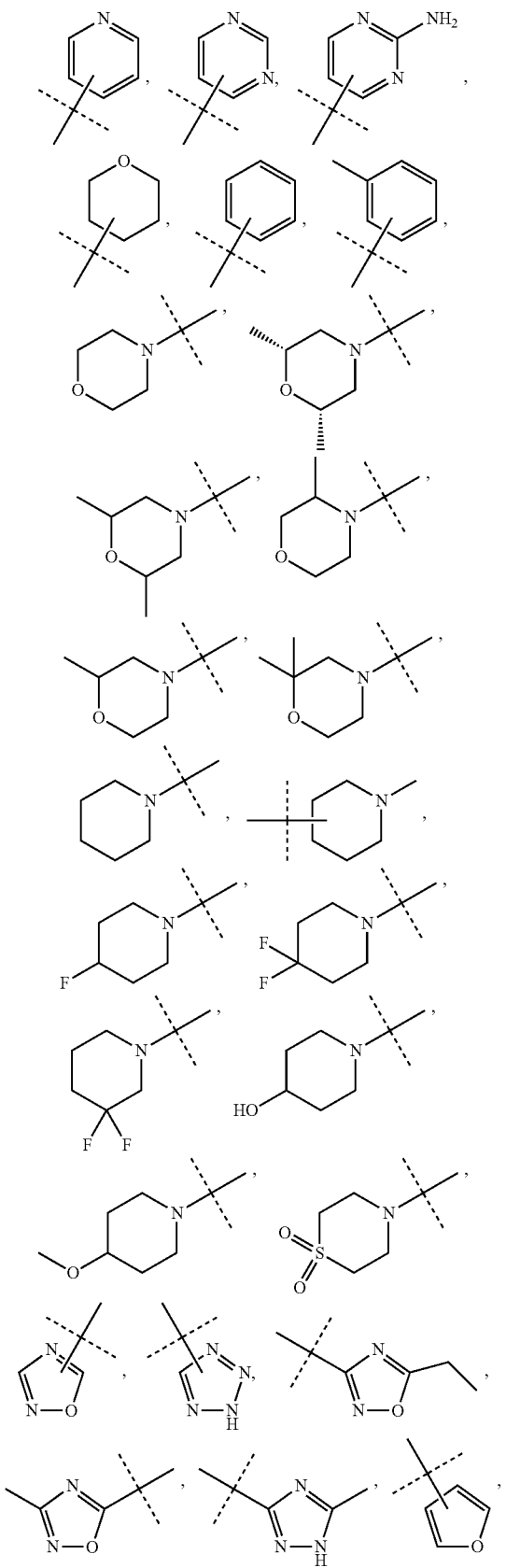

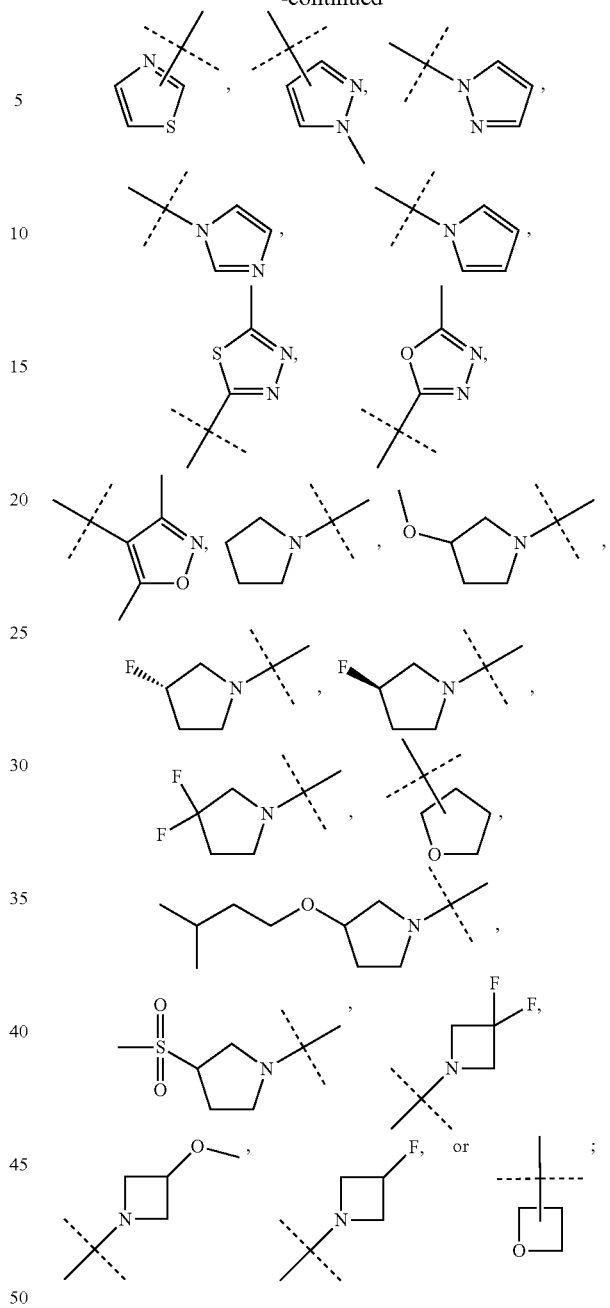

Cyc denotes a saturated or unsaturated carbocyclic ring having 3 to 8 carbon atoms, which is unsubstituted, mono-substituted, di-substituted or tri-substituted by Hal, $OCF_3$, $NO_2$, CN, perfluoroalkyl, A, $OR^6$, $N(R^6)_2$, $COR^6$, $CON(R^6)_2$, $-NHCOR^6$, $-NHSO_2A$, $-NHSO_2R^6$, $-NHSO_2-N(H)_{2-m}(A)_m$, $N(H)_{1-q}A_q-COR^6$, $N(H)_{1-q}A_qSO_2-N(H)_{2-m}(A)_m$, $-N(H)_{1-q}A_q-CON(H)_{2-m}(A)_m$, $-COOR^6$, $-SO_2A$, $-SO_2Ar$, $-SO_2N(H)_{2-m}(A)_m$, $-SO_2Het$, $-(CH_2)_p-N(H)_{2-m}(A)_m$, $-(CH_2)_n-OR^6$, $-(CH_2)_n-N(R^6)SO_2A$, $-(CH_2)_n-N(R^6)SO_2R^6$, $Het^2$, $-(CH_2)_n-Het^2$; or $-(CHY)_n-Het^2$;

A is a branched or linear alkyl having 1 to 12 C-atoms, wherein one or more H-atoms may be replace by Hal, Ar, Het, Cyc, $OR^6$, $-CN$, $-CO_2Y$, $CO_2H$ or $N(R^6)_2$ and wherein one or more non-adjacent $CH_2$-groups may be replaced by O, NR⁶, CO, CONR⁶, NR⁶CO, OCO, - and/or by —CH=CH- or —C≡C- groups, or denotes cycloalkyl or cycloalkylkylene having 3-7 ring C atoms;

Y denotes a branched or linear alkyl having 1 to 8 carbon atoms;

Hal denotes F, Cl, Br or I;

q is 0 or 1;

m is 0, 1 or 2;

n is 1, 2, 3, or 4;

and pharmaceutically acceptable, solvate, tautomers, salts, hydrates and stereoisomers thereof, including mixtures thereof in all ratios, with the proviso that compound of formula (B1) is excluded:

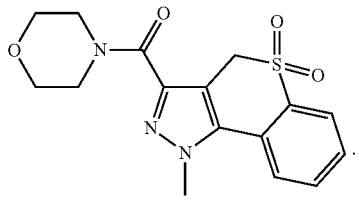

8. A method of treating an inflammatory disease, autoimmune disorder, cancer or multiple sclerosis wherein the inflammatory disease, autoimmune disorder, cancer or multiple sclerosis is related to phosphoinositide 3-kinase delta comprising the administration of a therapeutically effective amount of a compound according to claim 1 to an individual having an inflammatory disease, autoimmune disorder, cancer or multiple sclerosis.

9. The method according to claim 8, wherein said autoimmune disease is selected from the group consisting of Asthma, Rheumatoid arthritis, Acute disseminated encephalomyelitis (ADEM), Addison's disease, Alopecia areata, Ankylosing spondylitis, Antiphospholipid antibody syndrome (APS), Autoimmune hemolytic anemia, Autoimmune hepatitis, Autoimmune inner ear disease, Bullous pemphigoid, Behcet's disease, Coeliac disease, Anti-transglutaminase, Chagas disease, Chronic obstructive pulmonary disease, Crohn's Disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Multiple sclerosis (MS), Myasthenia gravis, Narcolepsy, Neuromyotonia, Pemphigus vulgaris, Pernicious anaemia, Psoriasis, Psoriatic Arthritis, Polymyositis, Primary biliary cirrhosis, Schizophrenia, Scleroderma, Sjogren's syndrome, Stiff person syndrome, Temporal arteritis, Ulcerative Colitis, Vasculitis, Vitiligo, or Wegener's granulomatosis.

10. A kit consisting of separate packs of:
a) an effective amount of a compound according to claim 1; and/or pharmaceutically acceptable solvates, salts, hydrates and stereoisomers thereof, including mixtures thereof in all ratios; and
b) an effective amount of an active ingredient other than a compound according to claim 1 and/or pharmaceutically acceptable solvates, salts, hydrates and stereoisomers thereof, including mixtures thereof in all ratios.

11. A pharmaceutical composition comprising a compound according to claim 1.

12. The pharmaceutical composition according to claim 11, wherein said composition comprises an active ingredient for the treatment of inflammatory diseases or immune disorders.

13. The pharmaceutical composition according to claim 12, wherein said composition also comprises at least one immunomodulating agent.

14. A process for producing compounds of Formula (I*) according to claim 1, said method comprising the reaction of a compound of Formula (II*) wherein $X_1, X_2, X_5, R^1, R^2, R^4$, T, U, Z and u are as defined in claim 1 and V is H or Y,

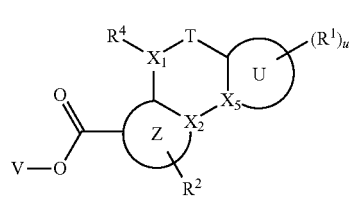

with compound D*:

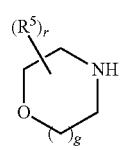

wherein $R^5$, g and r are as defined in claim 1.

15. A process for producing compounds of Formula (I*) wherein T is $SO_2$ comprising the oxidation of compounds of Formula (I*) wherein T is S:

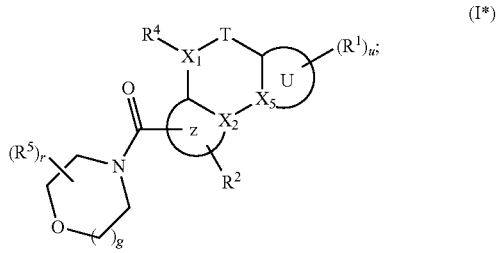

$X_1$ denotes a nitrogen or $CR^3$;

$X_2, X_5$ are independently from one another nitrogen or carbon atoms;

U denotes an aromatic 6-membered ring having optionally 1, 2 or 3 nitrogen atoms, including $X_5$, or an unsaturated or aromatic 5-membered ring having 1 to 3 heteroatoms selected form N, S or O, including the meaning of $X_5$;

Z denotes an unsaturated or aromatic 5-membered heterocyclic ring having 2 nitrogen atoms, including the meaning of $X_2$;

$R^1$ denotes H, A, hal, CN, $NO_2$, $N(R^6)_2$, $OR^6$, Ar, Het, Y, —$NR^6COR^6$, $CON(R^6)_2$, —$NR^6COAr$, $NR^6COHet$, COHet, —$NR^6SO_2R^6$, or $CO_2R^6$, including $CO_2Y$;

$R^2$ denotes H, Ar, Het, A, or Cyc;

$R^3$ denotes H or Y;

$R^4$ denotes H, Y, $(CH_2)_nAr$, $(CH_2)_nCyc$, $(CH_2)_nHet$, $(CH_2)_nOY$, $(CH_2)_nNHY$, or $(CH_2)_nNH_2$, or if $X_1$ is $CR^3$, $R^4$ denotes H, Y, (CH$_2$)$_n$Ar, (CH$_2$)$_n$Cyc, (CH$_2$)$_n$Het, (CH$_2$)$_n$OY, (CH$_2$)$_n$NHY, (CH$_2$)$_n$NH$_2$ or Hal;

$R^5$ denotes H, Y or Ar, when $R^3$ is Y and r is 2, two $R^5$ groups may be linked together to provide with the morpholine group to which they are linked, a bridged system;

$R^6$ is H, A, Cyc or Ar;
u is 0, 1, 2, 3, or 4;
r is 0, 1, or 2;
g is 1 or 2;

Ar denotes a monocyclic or fused bicyclic, unsaturated or aromatic carbocyclic ring having 6 to 14 carbon atoms, which is unsubstituted or monosubstituted, disubstituted or trisubstituted by Hal, OCF$_3$, NO$_2$, CN, perfluoroalkyl, A, OR$^6$, N(R$^6$)$_2$, COR$^6$, —CO$_2$R$^6$, CON(R$^6$)$_2$, COHet, —NHCOR$^6$, —NHSO$_2$A, —NHSO$_2$Ar, —NHSO$_2$—N(R$^6$)$_2$, N(H)$_{1-q}$A$_q$COR$^6$, N(H)$_{1-q}$A$_q$SO$^2$—N(H)$_{2-m}$(A)$_m$, —N(H)$_{1-q}$A$_q$CON(H)$^{2-m}$(A)$_m$, —SO$_2$A, —SO$_2$Ar, —SO$_2$N(H)$_{2-m}$(A)$_m$, —SO$_2$Het, —(CH$_2$)$_n$—N(R$^6$)$_2$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$—Het$^2$, or —(CHY)$_n$Het$^2$;

Het denotes a monocyclic or bicyclic saturated, unsaturated or aromatic heterocyclic ring having 1, 2, 3, or 4 N, O and/or S atoms and eventually comprising a SO$_2$ or a CO group, which is unsubstituted or mono substituted, disubstituted or trisubstituted by Hal, OCF$_3$, NO$_2$, CN, perfluoroalkyl, A, OR$^6$, N(R$^6$)$_2$, COR$^5$, —CO$_2$R$^6$, CON(R$^6$)$_2$, —NHCOR$^6$, —NHSO$_2$A, —NHSO$_2$R$^6$, —NHSO$_2$—N(H)$_{2-m}$(A)$_m$, N(H)$_{1-q}$A$_q$COR$^6$, N(H)$_{1-q}$A$_q$SO$_2$—N(H)$_{2-m}$A$_m$, —N(H)$_{1-q}$A$_q$CON(H)$_{2-m}$(A)$_m$, —SO$_2$A, —SO$_2$Ar, —SO$_2$N(H)$_{2-m}$(A)$_m$, COHet, —SO$_2$Het, —(CH$_2$)$_n$—N(H)$_{2-m}$(A)$_m$, —(CH$_2$)$_n$—OR$^6$, —(CH$_2$)$_n$—N(R$^6$)SO$_2$A, —(CH$_2$)$_n$—N(R$^6$)SO$_2$R$^6$, Het$^2$, —(CH$_2$)$_n$Het$^2$; or —(CHY)$_n$—Het$^2$;

Het$^2$ denotes

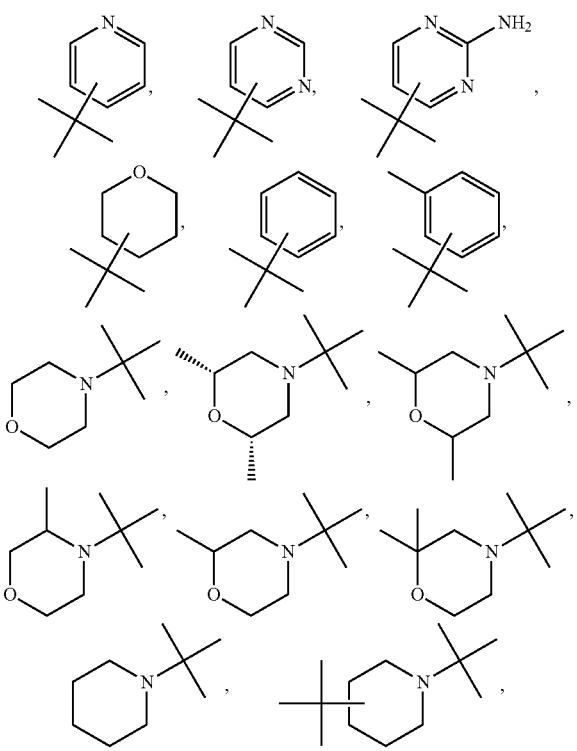

-continued

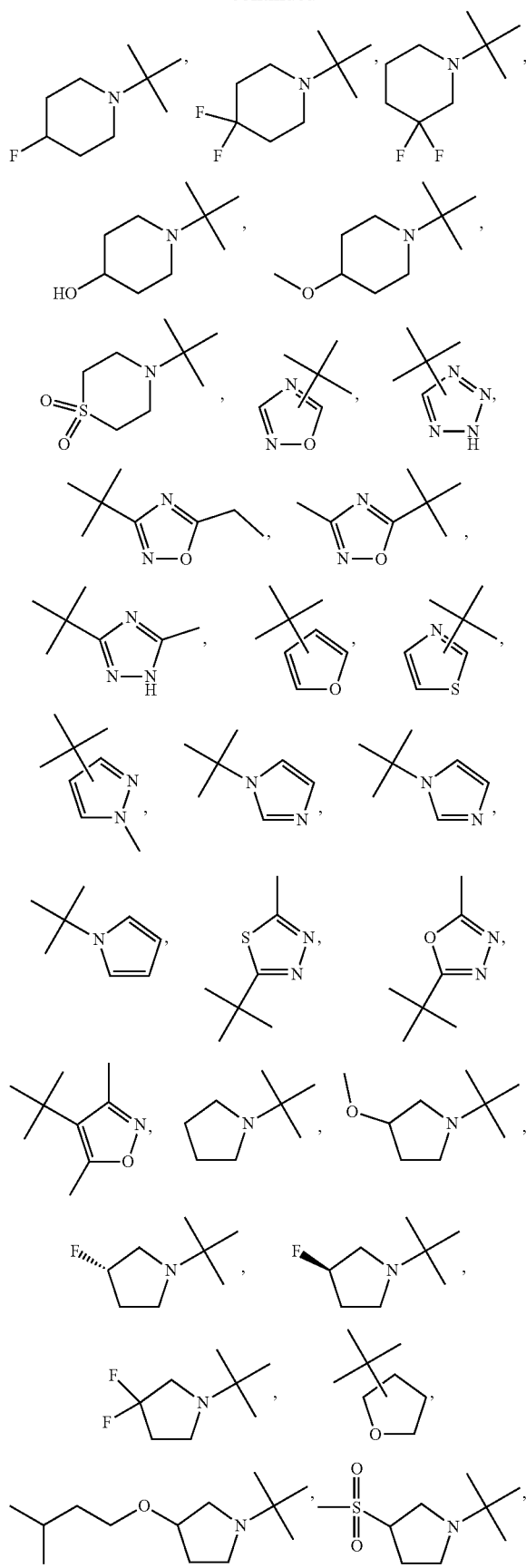

-continued

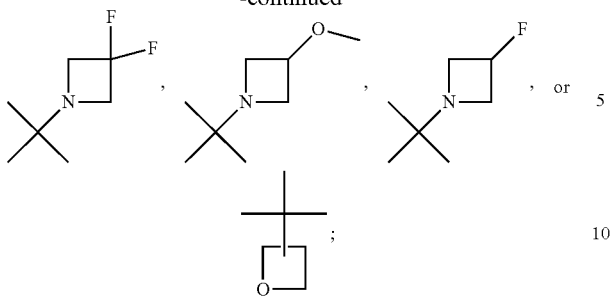

Cyc denotes a saturated or unsaturated carbocyclic ring having 3 to 8 carbon atoms, which is unsubstituted, mono-substituted, di-substituted or tri-substituted by Hal, $OCF_3$, $NO_2$, CN, perfluoroalkyl, A, $OR^5$, $N(R^6)_2$, $COR^6$, $CON(R^6)_2$, $-NHCOR^6$, $-NHSO_2A$, $-NHSO_2R^6$, $-NHSO_2-N(H)_{2-m}(A)_m$, $N(H)_{1-q}A_q-COR^6$, $N(H)_{1-q}A_qSO_2-N(H)_{2-m}A_m$, $-N(H)_{1-q}A_q-CON(H)_{2-m}(A)_m$, $-COOR^6$, $-SO_2A$, $-SO_2Ar$, $-SO_2N(H)_{2-m}(A)_m$, $-SO_2Het$, $-(CH_2)_p-N(H)_{2-m}(A)_m$, $-(CH_2)_nOR^6$, $-(CH_2)_n-N(R^6)SO_2A$, $-(CH_2)_n-N(R^6)SO_2R^6$, $Het^2$, $-(CH_2)_n-Het^2$; or $-(CHY)_n-Het^2$;

A is a brached or linear alkyl ahving 1 to 12 C-atoms, wherein one or more H-atoms may be replace by Hal, Ar, Het, Cyc, $OR^6$, $-CN$, $-CO_2Y$, $CO_2H$ or $N(R^6)_2$ and wherein one or more non-adjacent $CH_2$-groups may be replace by O, $NR^6$, CO, $CONR^6$, $NR^6CO$, OCO, - and/or by $-CH=CH-$ or $-C\equiv C-$ groups, or denotes cycloalkyl or cycloalkylalkylene having 3-7 ring C atoms;

Y denotes a brached or linear alkyl having 1 to 8 carbon atoms;

Hal dentoes F, Cl, Br, or 1;

q is 0 or 1;

m is 0, 1 or 2;

n is 1, 2, 3, or 4;

with the proviso that compound of formula (B1) is excluded:

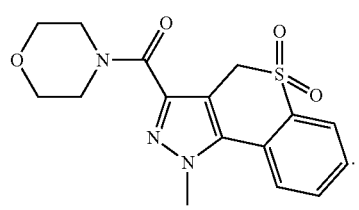

B1

* * * * *